(12) United States Patent
Yang et al.

(10) Patent No.: US 11,555,036 B2
(45) Date of Patent: *Jan. 17, 2023

(54) FGFR4 INHIBITOR, PREPARATION METHOD THEREFOR AND PHARMACEUTICAL USE THEREOF

(71) Applicant: Abbisko Therapeutics Co., Ltd., Shanghai (CN)

(72) Inventors: Fei Yang, Shanghai (CN); Haibing Deng, Pudong New Area Shanghai (CN); Haiyan Ying, Pudong New Area Shanghai (CN); Hongping Yu, Shanghai (CN); Zhui Chen, Shanghai (CN); Yaochang Xu, Shanghai (CN)

(73) Assignee: ABBISKO THERAPEUTICS CO., LTD., Pudong New Area Shanghai (CN)

(*) Notice: Subject to any disclaimer, the term of this patent is extended or adjusted under 35 U.S.C. 154(b) by 136 days.

This patent is subject to a terminal disclaimer.

(21) Appl. No.: 17/139,552

(22) Filed: Dec. 31, 2020

(65) Prior Publication Data

US 2022/0348573 A1    Nov. 3, 2022

Related U.S. Application Data

(63) Continuation of application No. 16/348,957, filed as application No. PCT/CN2017/116186 on Dec. 14, 2017, now Pat. No. 10,968,220.

(30) Foreign Application Priority Data

Dec. 19, 2016  (CN) .......................... 201611177188.2
Jun. 15, 2017   (CN) .......................... 201710453749.5

(51) Int. Cl.
| | |
|---|---|
| *A61P 35/00* | (2006.01) |
| *C07D 471/04* | (2006.01) |
| *C07D 491/052* | (2006.01) |
| *C07D 495/04* | (2006.01) |
| *C07D 513/04* | (2006.01) |
| *A61K 31/505* | (2006.01) |
| *C07D 239/84* | (2006.01) |
| *A61K 31/517* | (2006.01) |
| *A61K 31/506* | (2006.01) |
| *A61K 31/519* | (2006.01) |
| *C07D 475/00* | (2006.01) |
| *A61K 31/437* | (2006.01) |

(52) U.S. Cl.
CPC .......... *C07D 471/04* (2013.01); *A61K 31/437* (2013.01); *A61K 31/505* (2013.01); *A61K 31/506* (2013.01); *A61K 31/517* (2013.01); *A61K 31/519* (2013.01); *A61P 35/00* (2018.01); *C07D 239/84* (2013.01); *C07D 475/00* (2013.01); *C07D 491/052* (2013.01); *C07D 495/04* (2013.01); *C07D 513/04* (2013.01); *Y02P 20/55* (2015.11)

(58) Field of Classification Search
CPC ...................................................... A61P 35/00
See application file for complete search history.

(56) References Cited

U.S. PATENT DOCUMENTS

| | | |
|---|---|---|
| 2005/0009849 A1 | 1/2005 | Veach et al. |
| 2015/0197519 A1 | 7/2015 | Bifulco, Jr. et al. |

FOREIGN PATENT DOCUMENTS

| | | |
|---|---|---|
| CN | 104540809 A | 4/2015 |
| CN | 105307657 A | 2/2016 |
| CN | 105658642 A | 6/2016 |
| WO | 2004063195 A1 | 7/2004 |
| WO | 2015108992 A1 | 7/2015 |
| WO | 2016115412 A1 | 7/2016 |

OTHER PUBLICATIONS

Chesi et al, "Activated fibroblast growth factor receptor 3 is an oncogene that contributes to tumor progression in multiple myeloma," Blood, vol. 97, No. 3, pp. 729-736 (2001).

(Continued)

*Primary Examiner* — Bruck Kifle

(74) *Attorney, Agent, or Firm* — Panitch Schwarze Belisario & Nadel LLP

(57) ABSTRACT

Provided are an FGFR4 inhibitor having the structure of formula (I), and a preparation method therefor and the use thereof. The compound has a very strong inhibitory effect on FGFR4 kinase activity and has a very high selectivity, and can be widely used in the preparation of a drug for treating cancers, especially prostate cancer, liver cancer, pancreatic cancer, esophageal carcinomas, gastric cancer, lung cancer, breast cancer, ovarian carcinomas, colon cancer, skin cancer, glioblastomas or rhabdomyosarcomas, and is expected to be developed into a new generation of FGFR4 inhibitor drugs.

3 Claims, No Drawings

(56) References Cited

OTHER PUBLICATIONS

Eswarakumar et al, "Cellular signaling by fibroblast growth factor receptors," Cytokine & Growth Factor Reviews, vol. 16, pp. 139-149(2005).
Extended European Search Report dated Mar. 25, 2020 in EP Application No. 17883905.6.
Fawdar et al., "Targeted genetic dependency screen facilitates identification of actionable mutations in FGFR4, MAP3K9, and PAK5 in lung cancer," Proceedings of the National Academy of Sciences of the United States of America, vol. 110, No. 30, pp. 12426-12431 (2013).
Gowardhan et al., "Evaluation of the fibroblast growth factor system as a potential target for therapy in human prostate cancer," British Journal of Cancer, vol. 92, pp. 320-327 (2005).
Int'l Search Report dated Feb. 26, 2018 in Int'l Application No. PCT/CN2017/116186.
Jaakkola et al., "Amplification of FGFR4 Gene in Human Breast and Gynecological Cancers," International Journal of Cancer, vol. 54, pp. 378-382 (1993).
Jang et al., "Mutations in Fibroblast Growth Factor Receptor 2 and Fibroblast Growth Factor Receptor 3 Genes Associated with Human Gastric and Colorectal Cancers," Cancer Research, vol. 61, pp. 3541-3543 (2001).
Office Action dated Jun. 9, 2020 in JP Application No. 2019525831.
Office Action dated Jul. 13, 2020 in U.S. Appl. No. 16/348,957 by Yang.
Ornitz et al, "Fibroblast growth factors," Genome Biology, vol. 2, No. 3, pp. reviews3005.1-reviews3005.12 (2001).
Powers et al., "Fibroblast growth factors, their receptors and signaling," Endocrine-Related Cancer, vol. 7, pp. 165-197 (2000).
RN 1025884-41-6 Registry, Database Registry [Online], SciFinder, 3 pages, Retrieved from STN (2008).
Shariff et al., "Hepatocellular carcinoma: current trends in woridwide epidemiology, risk factors, diagnosis and therapeutics," Expert Review of Gastroenterology & Hepatology, vol. 3, No. 4, pp. 353-367 (2009).
Ullrich et al., "Signal Transduction by Receptors with Tyrosine Kinase Activity," Cell, vol. 61, pp. 203-212 (1990).
Xu et al., "FGFR4 Gly388Arg polymorphism contributes to prostate cancer development and progression: A meta-analysis of 2618 cases and 2305 controls," BMC Cancer, vol. 11, No. 84 (2011).
Ye at al, "Fibroblast Growth Factor Receptor 4 Regulates Proliferation and Antiapoptosis During Gastric Cancer Progression," Cancer, vol. 117, pp. 5304-5313 (2011).
Zhang et al., "Design, Synthesis and Anti-Proliferative Activities of 2,6-Substituted Thieno[3,2-d]pyrimidine Derivatives Containing Electrophilic Warheads," Molecules, vol. 22, No. 5, pp. 1-16 (2017).
Hagel et al., "First Selective Small Molecule Inhibitor of FGFR4 for the Treatment of Hepatocellular Carcinomas with an Activated FGFR4 Signaling Pathway," American Association for Cancer Research, Cancer Discovery, 5 (4), pp. 425-437 (2015).
Tolcher et al., "A Phase I, first in human study of FP-1039 (GSK3052230), a novel FGF ligand trap, in patients with advanced solid tumors," Annals of Oncology, pp. 1-7 (2016).
Zaid et al., "Identification of FGFR4 as a Potential Therapeutic Target for Advanced-Stage, High-Grade Serous Ovarian Cancer," American Association for Cancer Research, Clinical Cancer Research; vol. 19, No. 4, pp. 809-820 (2013).
Ye et al., "Silencing of FGFR4 could influence the biological features of gastric cancer cells and its therapeutic value in gastric cancer", Tumor Biol., 11 pages (2015).
Shimada et al., "Role of fibroblast growth factor receptors in esophageal squamous cell carcinoma," Esophagus, 12 pages (2015).
Heinzle et al., "Is Fibroblast Growth Factor Receptor 4 a Suitable Target of Cancer Therapy?," Current Pharmaceutical Design, vol. 20, No. 00, pp. 1-18 (2014).
Repana et al., "Targeting FGF19/FGFR4 Pathway: A Novel Therapetutic Strategy for Hepatocellular Carcinoma," Diseases, pp. 294-305 (2015).

FGFR4 INHIBITOR, PREPARATION METHOD THEREFOR AND PHARMACEUTICAL USE THEREOF

CROSS-REFERENCE TO RELATED APPLICATION

This application is a Continuation of U.S. patent application Ser. No. 16/348,957, filed May 10, 2019, which is a Section 371 of International Application No. PCT/CN2017/116186, filed Dec. 14, 2017, which was published in the Chinese language on Jun. 28, 2018 under International Publication No. WO 2018/113584 A1, which claims priority under 35 U.S.C. § 119(b) to Chinese Application No. 201611177188.2, filed Dec. 19, 2016, and Chinese Application No. 201710453749.5, filed Jun. 15, 2017, and the disclosures of which are incorporated herein by reference.

TECHNICAL FIELD

The present invention belongs to the field of medicament synthesis, and in particular relates to an FGFR4 inhibitor, preparation method and pharmaceutical use thereof.

TECHNICAL BACKGROUND

Fibroblast growth factor (FGF) is a family of 22 structurally related polypeptides with diverse biological activities that can regulate cell proliferation, differentiation and migration, and play a major role in the process of limb development, angiogenesis, tissue repair, tumor formation and the like. (Eswarakumar et al., 2005 Cytokine Growth Factor Rev 16: 139-149 Ornitz and Itoh 2001 Genome Bio 12: Reviews 3005).

The receptors for FGF (FGFR) belong to a family of RPTK of receptor tyrosine kinases. Four FGFRs, FGFR1, FGFR2, FGFR3 and FGFR4, have been identified to date (Ullrich and Schlessinger, 1990 Cell 61:203). The interaction between receptors and the corresponding ligands FGF leads to receptor dimerization and autophosphorylation, thereby initiating multiple downstream signaling cascades including MAPK and AKT (Powers et al., 2000 Endocr Relat Cancer 7: 165-197).

FGFR1-3 has been found to be overexpressed, mutated or translocated in a variety of tumors (including myeloma, breast cancer, stomach cancer, colon cancer, bladder cancer, pancreatic cancer, and hepatocellular carcinoma), and considered to be driver gene in cancer (Chesi et al., 2001 Blood 97:729-726; Gowardhan et al., 2005 Br J Cancer 92: 320-327; Jaakkola et al., 1993 Int J Cancer 54:378-282; Jang et al., 2001 Cancer Res 61: 3541-3543). Some FGFR inhibitors have also been developed in the clinical and preclinical development process. However, previous studies have shown that FGFR1 can regulate the level of phosphate, so pan-FGFR inhibitors may pose safety concerns.

Hepatocellular carcinoma (CC) is one of the leading causes of cancer-related deaths in China and is one of the fastest growing cancers every year (Shariff et al., 2009 Expert Rev Gastroenterol Hepato 13: 353-367). Currently, the first-line treatment option is sorafenib, there are no approved second-line treatment, and there is still a need for targeted therapy with anti-tumor agents.

Overexpression of FGF19 is present in 5-10% of hepatocellular carcinoma patients, whereas FGFR4 is a dominant FGFR present in human hepatocytes, and its high expression in hepatocytes is found to be associated with the aggressiveness of hepatocellular tumors. Therefore, FGFR4 plays a very important role in liver cancer. In addition, the interaction of FGF19 and FGFR4 is also considered to be related to the aggressiveness of other cancers (such as gastric cancer, prostate cancer, lung cancer, colorectal cancer, pancreatic cancer, and ovarian cancer) (Ye et al, 2011 Cancer 5304-5313; Xu et al, 2011 BMC Cancer 11:84; Fawdar et al, 2013 PNAS 110:12426-12431).

At present, some FGFR inhibitors have entered into the clinical research stage as anti-tumor drugs, but mostly inhibitors against FGFR1, 2 and 3, with weaker inhibition of FGFR4 activity. The inhibition of FGFR1-3 has on-target side effects such as hyperphosphatenia. Highly selective inhibitor of FGFR4 can effectively treat cancer caused by abnormal FGFR4 signaling, and can avoid the side effects caused by FGFR1-3 inhibition such as hyperphosphatemia. Highly selective small molecule inhibitors against FGFR4 have significant application prospects in the field of anti-tumor targeted therapy. Therefore, the development of a novel anti-tumor agent that can selectively target FGFR4 as a good drug candidate will meet the needs of domestic liver cancer and other anti-tumor target therapy, and have the advantages of better safety and higher selectivity.

SUMMARY OF THE INVENTION

An object of the present invention is to provide an FGFR4 inhibitor, preparation method and pharmaceutical use thereof.

The first aspect of the invention provides a compound of formula (I), a stereoisomer or a pharmaceutically acceptable salt thereof:

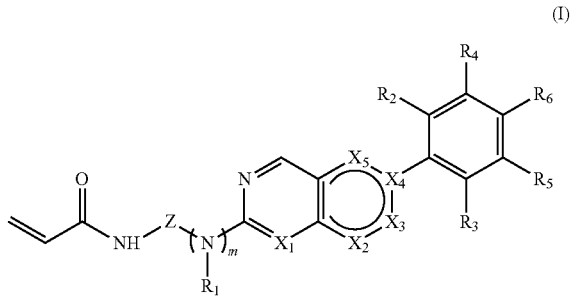

(I)

wherein, $X_1$ is —$C(R_7)$— or N;

$X_2$, $X_3$, and $X_5$ are each independently selected from the group consisting of —$(CR_8)_n$—, —C(O)—, —$N(R_9)$—, N and S;

$X_4$ is C or N;

Z is selected from the group consisting of $C_{1-8}$ alkylene, $C_{2-8}$ alkenylene, $C_{2-8}$ alkynylene, $C_{3-8}$ cycloalkyl, 3-10 membered heterocyclyl, $C_{5-10}$ aryl and 5-10 membered heteroaryl, above groups are further optionally substituted by one or more substituents selected from the group consisting of deuterium, halogen, cyano, nitro, azido, $C_{1-8}$ alky, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—OC(O)R$_{12}$, —$C_{0-8}$—NR$_{13}$R$_{14}$, —$C_{0-8}$—C(O)NR$_{13}$R$^{14}$, —$C_{0-8}$—N(R$_{13}$)—C(O)R$_{12}$ and —$C_{0-8}$—N(R$_{13}$)—C(O)OR$_{11}$, above groups are further more optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—OC(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$;

R$_1$ is selected from the group consisting of H, deuterium, $C_{1-8}$ alkyl, $C_{1-8}$ alkoxy$C_{1-8}$ alkyl, $C_{3-8}$ cycloalkyloxy$C_{1-8}$ alkyl, $C_{3-8}$ cycloalkyl$C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl and $C_{1-8}$ alkanoyl;

R$_2$, R$_3$, R$_4$, R$_5$, R$_6$ and R$_7$ are each independently selected from the group consisting of H, deuterium, halogen, cyano, nitro, azido, $C_{1-8}$ alkyl, $C_{2-8}$ alkenyl, $C_{2-8}$ alkynyl, $C_{3-8}$ cycloalkyl, 3-10 membered heterocyclyl, —$C_{0-8}$—S(O)$_r$R$_{10}$, —$C_{0-8}$—S(O)(NR$_9$)R$_{10}$, —$C_{0-8}$—P(O)(R$_{10}$)$_2$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$, or R$_2$ and R$_4$, R$_3$ and R$_5$, R$_4$ and R$_6$, R$_5$ and R$_6$ are taken together with the directly attached carbon atoms to form a $C_{5-10}$ cycloalkyl, 5-10 membered heterocyclyl, 5-10 membered aryl or 5-10 membered heteroaryl, above groups are further optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$;

R$_8$ is selected from the group consisting of H, deuterium, halogen, cyano, nitro, azido, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—S(O)(NR$_9$)R$_{10}$, —$C_{0-8}$—P(O)(R$_{10}$)$_2$, —$C_{0-8}$—O—R$_{11}$, —$C_{0-8}$—C(O)R$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$, above groups are further optionally substituted by one or more substituents selected from the group consisting of deuterium, halogen, cyano, nitro, azido $C_{1-8}$ alkyl, $C_{2-8}$ alkenyl, $C_{2-8}$ alkynyl, $C_{1-8}$ haloalkyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$, above groups are further more optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$;

R$_9$ is selected from the group consisting of H, deuterium, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl and $C_{1-8}$ alkanoyl, above groups are further optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$;

R$_{10}$ is selected from the group consisting of H, deuterium, $C_{1-8}$ alkyl, $C_{2-8}$ alkenyl, $C_{3-8}$ cycloalkyl, 3-10 membered heterocyclyl, $C_{1-8}$ haloalkyl, $C_{5-10}$ aryl, 5-10 membered heteroaryl, amino, mono-$C_{1-8}$ alkylamino, di-$C_{1-8}$ alkylamino and $C_{1-8}$ alkanoylamino;

R$_{11}$ is selected from the group consisting of H, deuterium, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl and 5-10 membered heteroaryl, above groups are further optionally substituted by one or more substituents selected from the group consisting of deuterium, halogen, cyano, $C_{1-8}$ alkyl, $C_{1-8}$ alkoxy, $C_{1-8}$ alkylthio, $C_{3-8}$ cycloalkyl, 3-10 membered heterocyclyl, $C_{5-10}$ aryl, 5-10 membered heteroaryl, $C_{1-8}$ alkylsulfonyl, $C_{1-8}$ alkylsulfonylamino, amino, mono-$C_{1-8}$ alkylamino, di-$C_{1-8}$ alkylamino, =O or hydroxyl;

R$_{12}$ is selected from the group consisting of H, deuterium, $C_{1-8}$ alkyl, $C_{2-8}$ alkenyl, $C_{2-8}$ alkynyl, $C_{1-8}$ alkoxy, $C_{3-8}$ cycloalkyl, $C_{3-8}$ cycloalkyloxy, 3-10 membered heterocyclyl, 3-10 membered heterocyclyloxy, $C_{5-10}$ aryl, 5-10 membered heteroaryl, $C_{5-10}$ aryloxy and 5-10 membered heteroaryloxy, above groups are further optionally substituted by one or more substituents selected from the group consisting of deuterium, halogen, cyano, $C_{1-8}$ alkyl, $C_{1-8}$ alkoxy, $C_{1-8}$ alkylthio, $C_{3-8}$ cycloalkyl, 3-10 membered heterocyclyl, $C_{5-10}$ aryl, 5-10 membered heteroaryl, $C_{1-8}$ alkylsulfonyl, $C_{1-8}$ alkylsulfonylamino, amino, mono-$C_{1-8}$ alkylamino, di-$C_{1-8}$ alkylamino, =O or hydroxyl;

R$_{13}$ and R$_{14}$ are each independently selected from the group consisting of H, deuterium, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, $C_{1-8}$ alkylsulfonyl and $C_{1-8}$ alkanoyl, or R$_{13}$ and R$_{14}$ are taken together with the directly attached nitrogen atom to form a 4-10 membered heterocyclyl, above groups are further optionally substituted by one or more substituents selected from the group consisting of deuterium, halogen, $C_{1-8}$ alkyl, $C_{1-8}$ alkoxy, $C_{1-8}$ alkylthio, $C_{3-8}$ cycloalkyl, 3-10 membered heterocyclyl, $C_{5-10}$ aryl, 5-10 membered heteroaryl, $C_{1-8}$ alkysulfonyl, $C_{1-8}$ alkylsulfonylamino, amino, mono-C-s alkylamino, di-C-s alkylamino, =O or hydroxyl;

m is 0 or 1;

n is 0, 1 or 2;

r is 0, 1 or 2;

provided that, when X$_3$ is —(CR$_8$)$_n$—, X$_2$ is —C(O)—, X$_4$ is C, X$_5$ is selected from the group consisting of —N(R$_9$)— N, O and S; when X$_3$ is —C(O)—, X$_2$ is —N(R$_9$)—, and Z is selected from the group consisting of $C_{1-8}$ alkyl, $C_{2-8}$ alkenyl, $C_{2-8}$ alkynyl and phenyl.

In a further preferred embodiment, in the compound of formula (I), the stereoisomer or pharmaceutically acceptable salt thereof, Z is selected from the group consisting of $C_{1-4}$ alkylene, $C_{2-4}$ alkenylene, $C_{2-4}$ alkynylene, $C_{3-6}$ cycloalkyl, 3-8 membered heterocyclyl, $C_{5-8}$ aryl and 5-8 membered heteroaryl, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-6}$ cycloalkyl, 3-8 membered heterocyclyl, $C_{5-8}$ aryl, 5-8 membered heteroaryl, —$C_{0-4}$—S(O)$_r$R$_{10}$, —$C_{0-4}$—O—R$_{11}$, —$C_{0-4}$—C(O)OR$_{11}$, —$C_{0-4}$—C(O)R$_{12}$, —$C_{0-4}$—O—C(O)R$_{12}$, —$C_{0-4}$—NR$_{13}$R$_{14}$, —$C_{0-4}$—C(O)NR$_{13}$R$_{14}$—, —$C_{0-4}$—N(R$_{13}$)—C(O)R$_{12}$ and —$C_{0-4}$—N(R$_{13}$)—C(O)OR$_{11}$, above groups are further more optionally substituted by one or more substituents selected from the group consisting of deuterium halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-10}$ aryl, 5-8 membered heteroaryl, $—C_{0-4}—S(O)_rR_{10}$, $—C_{0-4}—O—R_{11}$, $—C_{0-4}—C(O)OR_{11}$, $—C_{0-4}—C(O)R_{11}$, $—C_{0-4}—O—C(O)R_{12}$, $—C_{0-4}—NR_{13}R_{14}$, $—C_{0-4}—C(O)NR_{13}R_{14}$, $—C_{0-4}—N(R_{13})—C(O)R_{12}$ and $—C_{0-4}—N(R_{13})—C(O)OR_{11}$;

$R_1$ is selected from the group consisting of H, deuterium, $C_{1-4}$ alkyl, $C_{1-4}$ alkoxy$C_{1-4}$ alkyl, $C_{3-6}$ cycloalkyloxy$C_{1-4}$ alkyl, $C_{3-6}$ cycloalkyl$C_{1-4}$ alkyl, $C_{2-4}$ alkenyl, $C_{2-4}$ alkynyl, $C_{3-6}$ cycloalkyl, 3-8 membered heterocyclyl, $C_{5-8}$ aryl, 5-8 membered heteroaryl and $C_{1-4}$ alkanoyl;

$R_2$, $R_3$, $R_4$, $R_5$, $R_6$ and $R_7$ are each independently selected from the group consisting of H, deuterium, halogen, cyano, nitro, azido, $C_{1-4}$ alkyl, $C_{1-4}$ alkenyl. $C_{2-4}$ alkynyl, $C_{3-6}$ cycloalkyl, 3-8 membered heterocyclyl, $—C_{0-4}—S(O)_rR_{10}$, $—C_{0-4}—S(O)(NR_9)R_{10}$, $—C_{0-4}—P(O)(R_{10})_2$, $—C_{0-4}—O—R_{11}$, $—C_{0-4}—C(O)OR_{11}$, $—C_{0-4}—C(O)R_{12}$, $—C_{0-4}—O—C(O)R_{12}$, $—C_{0-4}—NR_{13}R_{14}$, $—C_{0-4}—C(O)NR_{13}R_{14}$, $—C_{0-4}—N(R_{13})—C(O)R_{12}$ and $—C_{0-4}—N(R_{13})—C(O)OR_{11}$, or $R_2$ and $R_4$, $R_3$ and $R_5$, $R_4$ and $R_6$, $R_5$ and $R_6$ are taken together with the directly attached carbon atoms to form a $C_{5-8}$ cycloalkyl, 5-8 membered heterocyclyl, 5-8 membered aryl or 5-8 membered heteroaryl, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-4}$ cycloalkyl, 3-8 membered heterocyclyl, $C_{5-8}$ aryl, 5-8 membered heteroaryl, $—C_{0-4}—S(O)_rR_{10}$, $—C_{0-4}—O—R_{11}$, $—C_{0-4}—C(O)OR_{11}$, $—C_{0-4}—C(O)R_{12}$, $—C_{0-4}—O—C(O)R_{12}$, $—C_{0-4}—NR_{13}R_{14}$, $—C_{0-4}—C(O)NR_{13}R_{14}$, $—C_{0-4}—N(R_{13})—C(O)R_{12}$ and $—C_{0-4}—N(R_{13})—C(O)OR_{11}$.

In a further preferred embodiment, in the compound of formula (I), the stereoisomer or pharmaceutically acceptable salt thereof, Z is selected from the group consisting of $C_{1-2}$ alkylene and the following structures:

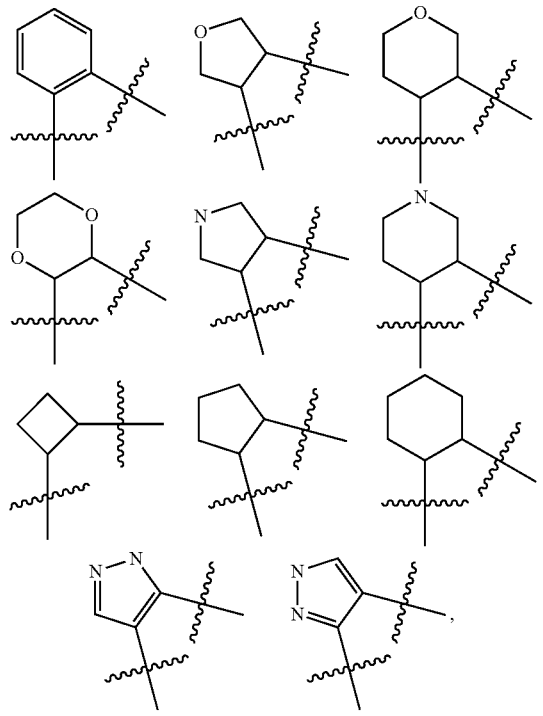

above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-6}$ cycloalkyl, 3-8 membered heterocyclyl, $C_{5-8}$ aryl, 5-8 membered heteroaryl, $—C_{0-4}—S(O)_rR_{10}$, $—C_{0-4}—O—R_{11}$, $—C_{0-4}—C(O)OR_{11}$, $—C_{0-4}—C(O)R_{12}$, $—C_{0-4}—O—C(O)R_{12}$, $—C_{0-4}—NR_{13}R_{14}$, $—C_{0-4}—C(O)NR_{13}R_{14}$, $—C_{0-4}—N(R_{13})—C(O)R_{12}$ and $—C_{0-4}—N(R_{13})—C(O)OR_{11}$, above groups are further more optionally substituted by one or more substituents selected from the group consisting of deuterium, halogen, cyano, nitro, azido. $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, $—C_{0-4}—S(O)_rR_{10}$, $—C_{0-4}—O—R_{11}$, $—C_{0-4}—C(O)OR_{11}$, $—C_{0-4}—C(O)R_{12}$, $—C_{0-4}—O—C(O)R_{12}$, $—C_{0-4}—NR_{13}R_{14}$, $—C_{0-4}—C(O)NR_{13}R_{14}$, $—C_{0-4}—N(R_{13})—C(O)R_{12}$ and $—C_{0-4}—N(R_{13})—C(O)OR_{11}$.

In a further preferred embodiment, in the compound of formula (I), the stereoisomer or pharmaceutically acceptable salt thereof, $R_1$ is selected from the group consisting of H, deuterium, methyl, isopropyl, methoxyethyl, cyclopropyloxymethyl, cyclopropylmethyl, allyl, cyclopropyl and acetyl;

$R_2$, $R_3$, $R_4$ and $R_5$ are each independently selected from the group consisting of H, deuterium, halogen, $C_{1-4}$ alkyl, $C_{2-4}$ alkenyl, $C_{2-4}$ alkynyl, $C_{3-6}$ cycloalkyl, 3-8 membered heterocyclyl, $—C_{0-4}—O—R_{11}$ and $—C_{0-4}—NR_{13}R_{14}$, or $R_2$ and $R_4$, $R_3$ and $R_5$ are taken together with the directly attached carbon atoms to form a $C_{5-8}$ cycloalkyl, 5-8 membered heterocyclyl, 5-8 membered aryl or 5-8 membered heteroaryl, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-4}$ cycloalkyl, 3-8 membered heterocyclyl, $C_{5-8}$ aryl, 5-8 membered heteroaryl, $—C_{0-4}—S(O)_rR_{10}$, $—C_{0-4}—O—R_{11}$, $—C_{0-4}—C(O)OR_{11}$, $—C_{0-4}—C(O)R_{12}$, $—C_{0-4}—O—C(O)R_{12}$, $—C_{0-4}—NR_{13}R_{14}$, $—C_{0-4}—C(O)NR_{13}R_{14}$, $—C_{0-4}—N(R_{13})—C(O)R_{12}$ and $—C_{0-4}—N(R_{13})—C(O)OR_{11}$;

$R_6$ is H or deuterium.

In a further preferred embodiment, in the compound of formula (I), the stereoisomer or pharmaceutically acceptable salt thereof, $R_1$ is selected from the group consisting of H, deuterium, methyl and cyclopropylmethyl;

$R_2$, $R_3$, $R_4$ and $R_5$ are each independently selected from the group consisting of H, deuterium, F, Cl, methyl, isopropyl, allyl, ethynyl, cyclopropyl, 3-oxacyclobutyl, trifluoromethyl, trideuteromethyl, $—C_{0-4}—O—R_{11}$ and $—C_{0-4}—NR_{13}R_{14}$, or $R_2$ and $R_4$, $R_3$ and $R_5$ are taken together with the directly attached carbon atoms to form a 5-8 membered heterocyclyl, the heteroatom is O or N, the 5-8 membered heterocyclyl is optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-4}$ cycloalkyl, 3-8 membered heterocyclyl, $C_{5-8}$ aryl, 5-8 membered heteroaryl, $—C_{0-4}—S(O)_rR_{10}$, $—C_{0-4}—O—R_{11}$, $—C_{0-4}—C(O)OR_{11}$, $—C_{0-4}—C(O)R_{12}$, $—C_{0-4}—O—C(O)R_{12}$, $—C_{0-4}—NR_{13}R_{14}$, $—C_{0-4}—C(O)NR_{13}R_{14}$, $—C_{0-4}—N(R_{13})—C(O)R_{12}$ and $—C_{0-4}—N(R_{13})—C(O)OR_{11}$;

$R_6$ is H or deuterium.

In a further preferred embodiment, the compound of formula (I), the stereoisomer or pharmaceutically acceptable salt thereof is the compound of the following formula (IIa):

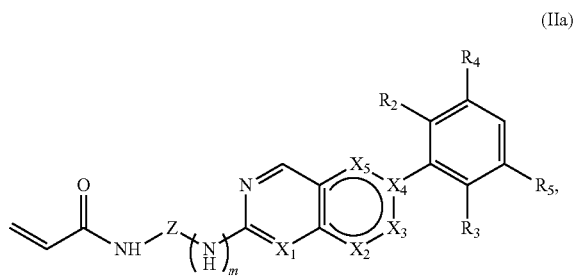

wherein $X_3$ is selected from the group consisting of —N($R_9$)—, N, O and S;

Z is selected from the group consisting of $C_{1-2}$ alkylene and the following structures:

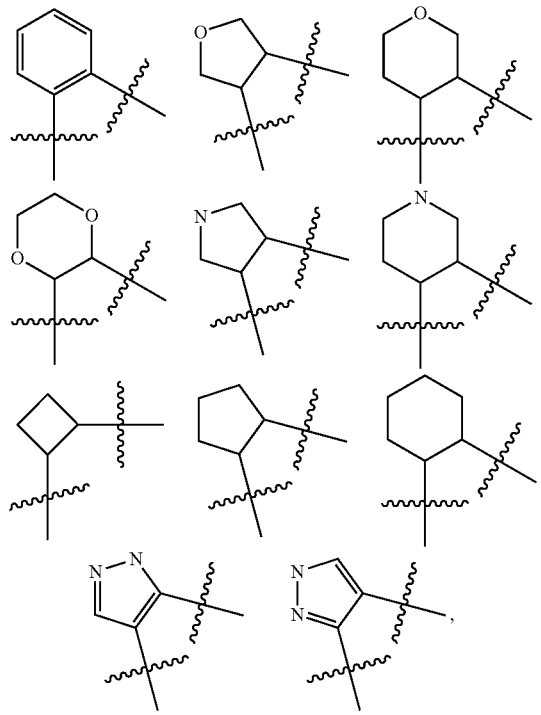

above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-4}$ cycloalkyl, 3-8 membered heterocyclyl, $C_{5-8}$ aryl, 5-8 membered heteroaryl, —$C_{0-4}$—S(O)$_r$$R_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-4}$—C(O)N$R_{13}R_{14}$, —$C_{0-4}$—N($R_{13}$)—C(O)$R_{12}$ and —$C_{0-4}$—N($R_{13}$)—C(O)O$R_{11}$, above groups are further more optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—S(O)$_r$$R_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-4}$—C(O)N$R_{13}R_{14}$, —$C_{0-4}$—N($R_{13}$)—C(O)$R_{12}$ and —$C_{0-4}$—N($R_{13}$)—C(O)O$R_{11}$;

$R_2$, $R_3$, $R_4$ and $R_5$ are each independently selected from the group consisting of H, deuterium, F, Cl, methyl, isopropyl, allyl, ethynyl, cyclopropyl, 3-oxacyclobutyl, trifluoromethyl, trideuteromethyl, —$C_{0-4}$—O—$R_{11}$ and —$C_{0-4}$—N$R_{13}R_{14}$, or $R_2$ and $R_4$, $R_3$ and $R_5$ are taken together with the directly attached carbon atoms to form a 5-8 membered heterocyclyl, the heteroatom is O or N, the 5-8 membered heterocyclyl is optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-4}$ cycloalkyl, 3-8 membered heterocyclyl, $C_{5-8}$ aryl, 5-8 membered heteroaryl, —$C_{0-4}$—S(O)$_r$$R_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-4}$—C(O)N$R_{13}R_{14}$, —$C_{0-4}$—N($R_{13}$)—C(O)$R_{12}$ and —$C_{0-4}$—N($R_{13}$)—C(O)O$R_{11}$;

$R_7$ is selected from the group consisting of H, deuterium, Cl, F, hydroxyl, allyl, ethynyl, cyclopropyl, 3-oxacyclobutyl, trifluoromethyl, trideuteromethyl, —$C_{0-4}$—O—$R_{11}$ and —$C_{0-4}$—N$R_{13}R_{14}$;

$R_9$ is selected from the group consisting of H, deuterium, $C_{1-4}$ alkyl, $C_{3-6}$ cycloalkyl and 3-8 membered heterocyclyl, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{1-4}$ aryl, 5-8 membered heteroaryl, —$C_{0-4}$—S(O)$_r$$R_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-4}$—C(O)N$R_{13}R_{14}$, —$C_{0-4}$—N($R_{13}$)—C(O)$R_{12}$ and —$C_{0-4}$—N($R_{13}$)—C(O)O$R_{11}$;

$X_1$, $X_2$, $X_5$, $R_8$, $R_{10}$, $R_{11}$, $R_{12}$, $R_{13}$, $R_{14}$, m, n, and r are as described above.

In a further preferred embodiment, the compound of formula (I), the stereoisomer or pharmaceutically acceptable salt thereof is selected from the group consisting of the following compounds of formula (IIIa-1), (IIIa-2), (IIIa-3) and (IIIa-4):

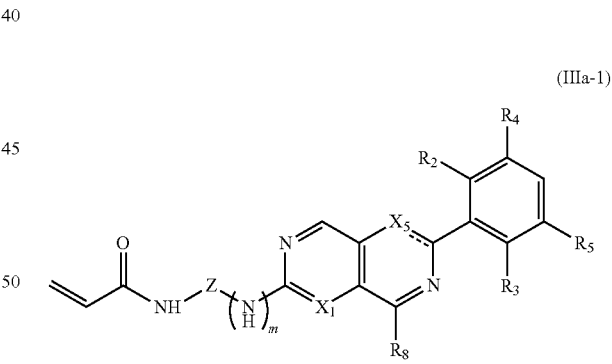

(IIIa-1)

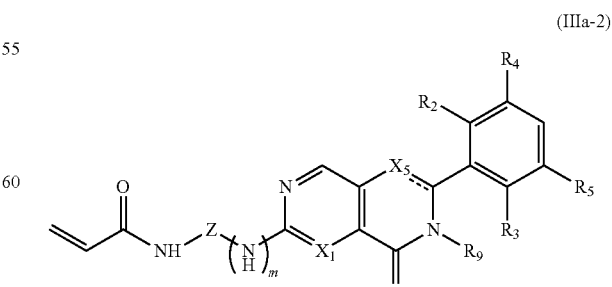

(IIIa-2)

-continued

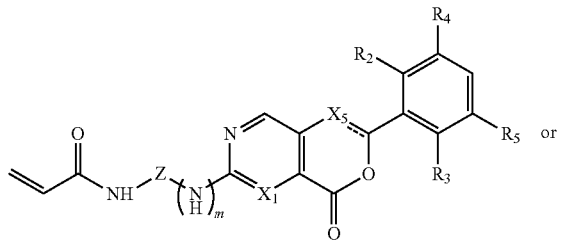

(IIIa-3)

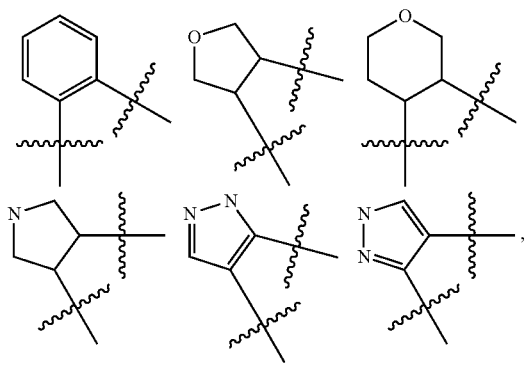

(IIIa-4)

wherein Z is selected from the group consisting of $C_{1-2}$ alkylene and the following structures.

above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-4}$ cycloalkyl, 3-8 membered heterocyclyl, $C_{5-8}$ aryl, 5-8 membered heteroaryl, —$C_{0-4}$—S(O)$_r$R$_{10}$, —$C_{0-4}$—O—R$_{11}$, —$C_{0-4}$—C(O)OR$_{11}$, —$C_{0-4}$—C(O)R$_{12}$, —$C_{0-4}$—O—C(O)R$_{12}$, —$C_{0-4}$—NR$_{13}$R$_{14}$, —$C_{0-4}$—C(O)NR$_{13}$R$_{14}$, —$C_{0-4}$—N(R$_{13}$)—C(O)R$_{12}$ and —$C_{0-4}$—N(R$_{13}$)—C(O)OR$_{11}$, above groups are further more optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—S(O)$_r$R$_{10}$, —$C_{0-4}$—O—R$_{11}$, —$C_{0-4}$—C(O)OR$_{11}$, —$C_{0-4}$—C(O)R$_{12}$, —$C_{0-4}$—O—C(O)R$_{12}$, —$C_{0-4}$—NR$_{13}$R$_{14}$, —$C_{0-4}$—C(O)NR$_{13}$R$_{14}$, —$C_{0-4}$—N(R$_{13}$)—C(O)R$_{12}$ and —$C_{0-4}$—N(R$_{13}$)—C(O)OR$_{11}$;

$R_2$, $R_3$, $R_4$ and $R_5$ are each independently selected from the group consisting of H, deuterium, Cl, F, hydroxyl, methyl, isopropyl, cyclopropyl, 3-oxacyclobutyl, trifluoromethyl, trideuteromethyl and —O—R$_{11}$, or $R_2$ and $R_4$, $R_3$ and $R_5$ are taken together with the directly attached carbon atoms to form a 5-8 membered heterocyclyl, the heteroatom is N or O;

$R_7$ is selected from the group consisting of H, deuterium, Cl, F, hydroxyl, cyclopropyl and —O—R$_{11}$;

$R_9$ is selected from the group consisting of H, deuterium, $C_{1-4}$ alkyl, $C_{3-6}$ cycloalkyl and 3-8 membered heterocyclyl, above groups are further optionally substituted by one or more substituents selected from the group consisting of deuterium, halogen, $C_{1-4}$ alkyl, $C_{1-4}$ haloalkyl, $C_{3-6}$ cycloalkyl, 3-8 membered heterocyclyl, —$C_{0-4}$—O—R$_{11}$, —$C_{0-4}$—NR$_{13}$R$_{14}$ and —$C_{0-4}$—C(O)NR$_{13}$R$_{14}$;

$X_1$, $X_5$, $R_8$, $R_{10}$, $R_{11}$, $R_{12}$, $R_{13}$, $R_{14}$, m, n and r are described in claim 1.

In a further preferred embodiment, the compound of formula (I), the stereoisomer or pharmaceutically acceptable salt thereof is selected from the compound of the formula (IVa-1):

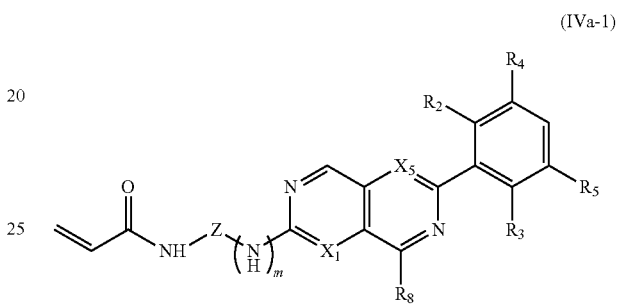

(IVa-1)

wherein $X_5$ is —CH— or N:

Z is selected from the group consisting of $C_{1-2}$ alkylene and the following structures:

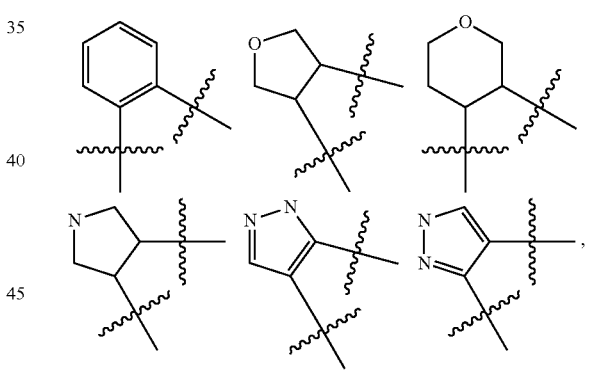

above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-6}$ cycloalkyl, 3-8 membered heterocyclyl, $C_{5-8}$ aryl, 5-8 membered heteroaryl. —$C_{0-4}$—S(O)$_r$R$_{10}$, —$C_{0-4}$—O—R$_{11}$, —$C_{0-4}$—C(O)OR$_{11}$, —$C_{0-4}$—C(O)R$_{12}$, —$C_{0-4}$—O—C(O)R$_{12}$, —$C_{0-4}$—NR$_{13}$R$_{14}$, —$C_{0-4}$—C(O)NR$_{13}$R$_{14}$, —$C_{0-4}$—N(R$_{13}$)—C(O)R$_{12}$ and —$C_{0-4}$—N(R$_{13}$)—C(O)OR$_{11}$, above groups are further more optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—S(O)$_r$R$_{10}$, —$C_{0-4}$—O—R$_{11}$, —$C_{0-4}$—C(O)OR$_{11}$, —$C_{0-4}$—C(O)R$_{12}$, —$C_{0-4}$—O—C(O)R$_{12}$, —$C_{0-4}$—NR$_{13}$R$_{14}$. —$C_{0-4}$—C(O)NR$_{13}$R$_{14}$, —$C_{0-4}$—N(R$_{13}$)—C(O)R$_{12}$ and —$C_{0-4}$—N(R$_{13}$)—C(O)OR$_{11}$;

$R_2$, $R_3$, $R_4$ and $R_5$ are each independently selected from the group consisting of H, deuterium, Cl, F, hydroxyl, methyl, isopropyl, cyclopropyl, 3-oxacyclobutyl, trifluoromethyl, trideuteromethyl and —O—$R_{11}$, or $R_2$ and $R_4$, $R_3$ and $R_5$ are taken together with the directly attached carbon atoms to form a 5-8 membered heterocyclyl, the heteroatom is N or O;

$R_7$ is selected from the group consisting of H, deuterium, Cl, F, hydroxyl, cyclopropyl and —O—$R_{11}$;

$R_8$ is selected from the group consisting of H, deuterium, halogen, cyano, nitro, azido, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—$S(O)_rR_{10}$, —$C_{0-8}$—$S(O)(NR_9)R_{10}$, —$C_{0-8}$—$P(O)(R_{10})_2$, —$C_{0-8}$—O—$R_{11}$, —$C_{0-8}$—$C(O)OR_{11}$, —$C_{0-8}$—$C(O)R_{12}$, —$C_{0-8}$—O—C(O)$R_{12}$, —$C_{0-8}$—$NR_{13}R_{14}$, —$C_{0-8}$—$C(O)NR_{13}R_{14}$, —$C_{0-8}$—N($R_{13}$)—C(O)$R_{12}$ and —$C_{0-8}$—N($R_{13}$)—C(O)O$R_{11}$, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—$S(O)_rR_{10}$, —$C_{0-4}$—O—$R_{11}$, —$C_{0-4}$—$C(O)OR_{11}$, —$C_{0-4}$—$C(O)R_{12}$, —$C_{0-4}$—O—C(O)$R_{12}$, —$C_{0-4}$—$NR_{13}R_{14}$, —$C_{0-4}$—$C(O)NR_{13}R_{14}$, —$C_{0-4}$—N($R_{13}$)—C(O)$R_{12}$ and —$C_{0-4}$—N($R_{13}$)—C(O)O$R_{11}$, above groups are further more optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—$S(O)_rR_{10}$, —$C_{0-4}$—O—$R_{11}$, —$C_{0-4}$—$C(O)OR_{11}$, —$C_{0-4}$—$C(O)R_{12}$, —$C_{0-4}$—O—C(O)$R_{12}$, —$C_{0-4}$—$NR_{13}R_{14}$, —$C_{0-4}$—$C(O)NR_{13}R_{14}$, —$C_{0-4}$—N($R_{13}$)—C(O)$R_{12}$ and —$C_{0-4}$—N($R_{13}$)—C(O)O$R_{11}$;

$X_1$, $R_{10}$, $R_{11}$, $R_{12}$, $R_{13}$, $R_{14}$, m, n and r are as described above.

In a further preferred embodiment, in the compound of formula (I), the stereoisomer or pharmaceutically acceptable salt thereof, $R_8$ is selected from the group consisting of H, deuterium, halogen, cyano, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—O—$R_{11}$, —$C_{0-8}$—$NR_{13}R_{14}$, —$C_{0-8}$—N($R_{13}$)—C(O)$R_{12}$ and —$C_{0-8}$—N($R_{13}$)—C(O)O$R_{11}$, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—$S(O)_rR_{10}$, —$C_{0-4}$—O—$R_{11}$, —$C_{0-4}$—$C(O)OR_{11}$, —$C_{0-4}$—$C(O)R_{12}$, —$C_{0-4}$—O—C(O)$R_{12}$, —$C_{0-4}$—$NR_{13}R_{14}$, —$C_{0-4}$—$C(O)NR_{13}R_{14}$, —$C_{0-4}$—N($R_{13}$)—C(O)$R_{12}$ and —$C_{0-4}$—N($R_{13}$)—C(O)O$R_{11}$, above groups are further more optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—$S(O)_rR_{10}$, —$C_{0-4}$—O—$R_{11}$, —$C_{0-4}$—$C(O)OR_{11}$, —$C_{0-4}$—$C(O)R_{12}$, —$C_{0-4}$—O—C(O)$R_{12}$, —$C_{0-4}$—$NR_{13}R_{14}$, —$C_{0-4}$—$C(O)NR_{13}R_{14}$, —$C_{0-4}$—N($R_{13}$)—C(O)$R_{12}$ and —$C_{0-4}$—N($R_{13}$)—C(O)O$R_{11}$.

In a further preferred embodiment, the compound of formula (I), the stereoisomer or pharmaceutically acceptable salt thereof is selected from the compound of the formula (IIb):

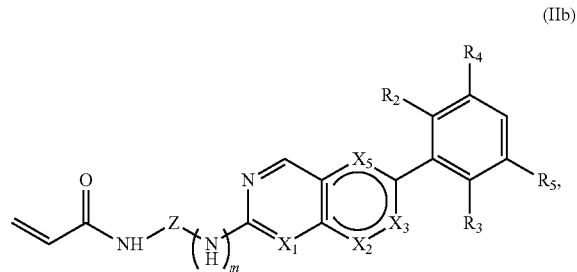

(IIb)

wherein $X_3$ is —(CR$_8$)$_n$— or —C(O)—;

Z is selected from the group consisting of $C_{1-2}$ alkylene and the following structures:

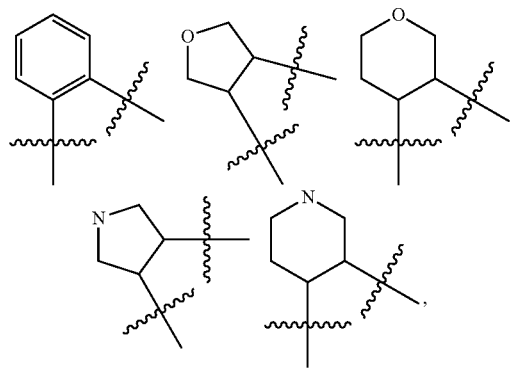

above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-6}$ cycloalkyl, 3-8 membered heterocyclyl, $C_{5-8}$ aryl, 5-8 membered heteroaryl, —$C_{0-4}$—$S(O)_rR_{10}$, —$C_{0-4}$—O—$R_{11}$, —$C_{0-4}$—$C(O)OR_{11}$, —$C_{0-4}$—C(O)$R_{12}$, —$C_{0-4}$—O—C(O)$R_{12}$, —$C_{0-4}$—$NR_{13}R_{14}$, —$C_{0-4}$—$C(O)NR_{13}R_{14}$, —$C_{0-4}$—N($R_{13}$)—C(O)$R_{12}$ and —$C_{0-4}$—N($R_{13}$)—C(O)O$R_{11}$;

$R_2$, $R_3$, $R_4$ and $R_5$ are each independently selected from the group consisting of H, deuterium, F, Cl, methyl, isopropyl, allyl, ethynyl, cyclopropyl, 3-oxacyclobutyl, trifluoromethyl, trideuteromethyl, —$C_{0-4}$—O—$R_{11}$ and —$C_{0-4}$—$NR_{13}R_{14}$, or $R_2$ and $R_4$, $R_3$ and $R_5$ are taken together with the directly attached carbon atoms to form a 5-8 membered heterocyclyl, the heteroatom is N or O, the 5-8 membered heterocyclyl optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-4}$ cycloalkyl, 3-8 membered heterocyclyl, $C_{5-8}$ aryl, 5-8 membered heteroaryl, —$C_{0-4}$—$S(O)_rR_{10}$, —$C_{0-4}$—O—$R_{11}$, —$C_{0-4}$—$C(O)OR_{11}$, —$C_{0-4}$—C(O)$R_{12}$, —$C_{0-4}$—O—C(O)$R_{12}$, —$C_{0-4}$—$NR_{13}R_{14}$, —$C_{0-4}$—$C(O)NR_{13}R_{14}$, —$C_{0-4}$—N($R_{13}$)—C(O)$R_{12}$ and —$C_{0-4}$—N($R_{13}$)—C(O)O$R_{11}$;

$R_7$ is selected from the group consisting of H, deuterium, Cl, F, hydroxyl, allyl, ethynyl, cyclopropyl, 3-oxacyclobutyl, trifluoromethyl, trideuteromethyl, —$C_{0-4}$—O—$R_{11}$ and —$C_{0-4}$—$NR_{13}R_{14}$;

$R_9$ is selected from the group consisting of H, deuterium, $C_{1-4}$ alkyl, $C_{3-6}$ cycloalkyl and 3-8 membered heterocyclyl, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—$S(O)_rR_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-4}$—C(O)N$R_{13}R_{14}$, —$C_{0-4}$—N($R_{13}$)—C(O)$R_{12}$ and —$C_{0-4}$—N($R_{13}$)—C(O)O$R_{11}$;

$X_1$, $X_2$, $X_5$, $R_8$, $R_{10}$, $R_{11}$, $R_{12}$, $R_{13}$, $R_{14}$, m, n and r are as described above;

provided that, when $X_3$ is —(C$R_8$)$_n$—, $X_2$ is —C(O)—, $X_5$ is —N($R_9$)—, N, O or S; when $X_3$ is —C(O)—, $X_2$ is —N($R_9$)—, and Z is a $C_{1-4}$ alkyl or phenyl.

In a further preferred embodiment, the compound of formula (I), the stereoisomer or pharmaceutically acceptable salt thereof is selected from the group consisting of the following compounds of the formula (IIIb-1) and (IIIb-2):

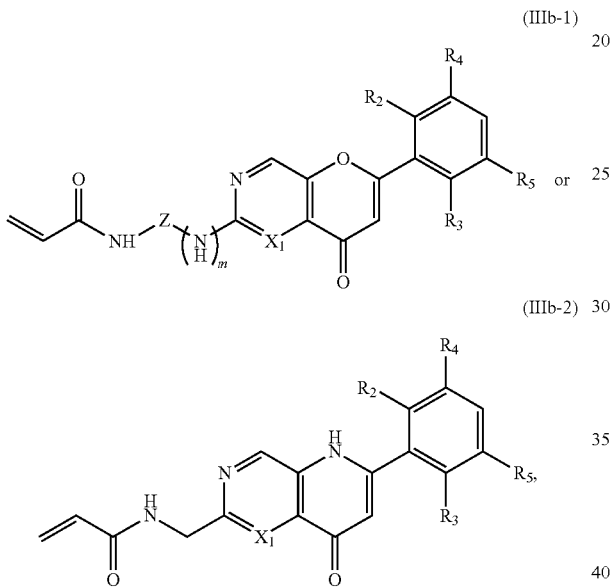

(IIIb-1)

(IIIb-2)

wherein Z is selected from the group consisting of $C_{1-2}$ alkylene and the following structures

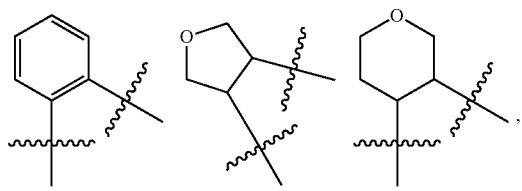 [SMILES: *c1ccccc1* ; *C1COCC1* ; *C1CCOCC1*]

above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-6}$ cycloalkyl, 3-8 membered heterocyclyl, $C_{5-8}$ aryl, 5-8 membered heteroaryl, —$C_{0-4}$—S(O)$_rR_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-4}$—C(O)N$R_{13}R_{14}$, —$C_{0-4}$—N($R_{13}$)—C(O)$R_{12}$ and —$C_{0-4}$—N($R_{13}$)—C(O)O$R_{11}$;

$R_2$, $R_3$, $R_4$ and $R_5$ are each independently selected from the group consisting of H, deuterium Cl, F, hydroxyl, methyl, isopropyl, cyclopropyl, 3-oxacyclobutyl, trifluoromethyl, trideuteromethyl and —O—$R_{11}$, or $R_2$ and $R_4$, $R_3$ and $R_5$ are taken together with the directly attached carbon atoms to form a 5-8 membered heterocyclyl, the heteroatom is N or O;

$R_7$ is selected from the group consisting of H, deuterium Cl, F hydroxyl, cyclopropyl and —O—$R_{11}$;

$X_1$, $R_{10}$, $R_{11}$, $R_{12}$, $R_{13}$, $R_{14}$, m and r are as described above.

In a further preferred embodiment, the compound of formula (I), the stereoisomer or pharmaceutically acceptable salt thereof is selected from the compound of formula (IIIb-3):

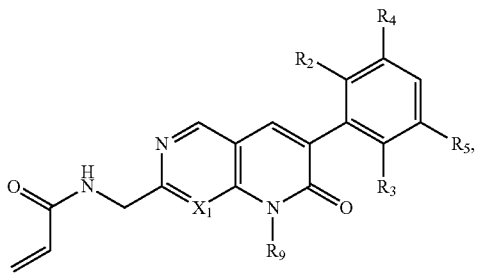

(IIIb-3)

wherein $R_2$, $R_3$, $R_4$ and $R_5$ are each independently selected from the group consisting of H, deuterium, Cl, F hydroxyl, methyl, isopropyl, cyclopropyl, 3-oxacyclobutyl, trifluoromethyl, trideuteromethyl and —O—$R_{11}$, or $R_2$ and $R_4$, $R_3$ and $R_5$ are taken together with the directly attached carbon atoms to form a 5-8 membered heterocyclyl, the heteroatom is N or O;

$R_7$ is selected from the group consisting of H, deuterium, Cl, F, hydroxyl, cyclopropyl and —O—$R_{11}$;

$R_9$ is selected from the group consisting of H, deuterium, $C_{1-4}$ alkyl, $C_{3-6}$ cycloalkyl or 3-8 membered heterocyclyl, above groups are further optionally substituted by one or more substituents selected from the group consisting of deuterium, halogen, $C_{1-4}$ alkyl, $C_{1-4}$ haloalkyl, $C_{3-6}$ cycloalkyl 3-8 membered heterocycyl, —$C_{0-4}$—O—$R_{11}$, —$C_{0-4}$—N$R_{13}R_{14}$ and —$C_{0-4}$—C(O)N$R_{13}R_{14}$; $X_1$, $R_8$, $R_{10}$, $R_{11}$, $R_{13}$, $R_{14}$ and n are as described above.

In the most preferred embodiment, the compound of formula (I), the stereoisomer or pharmaceutically acceptable salt thereof includes, but is not limited to, the following compounds:

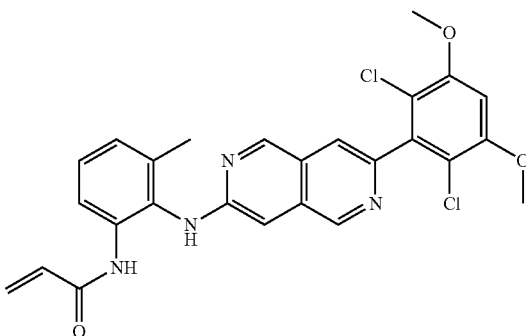

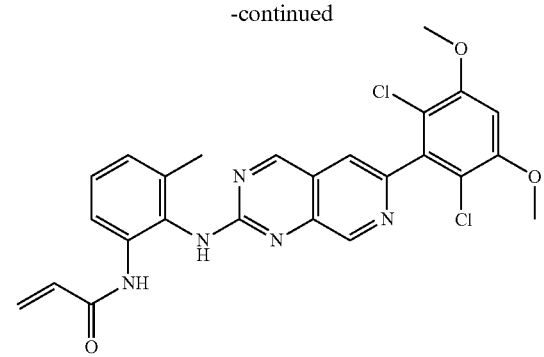
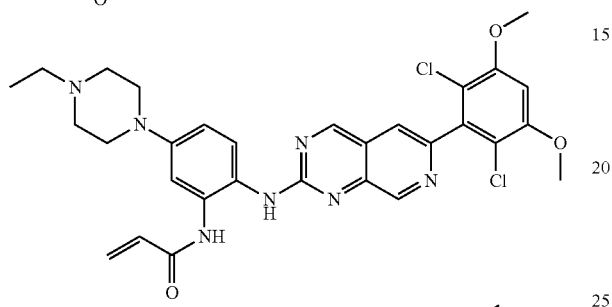
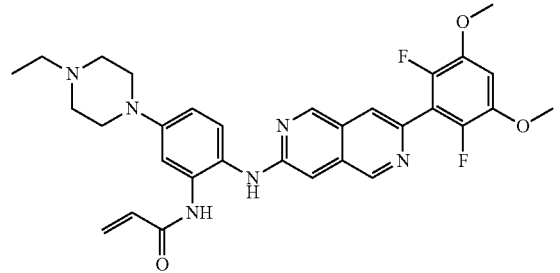
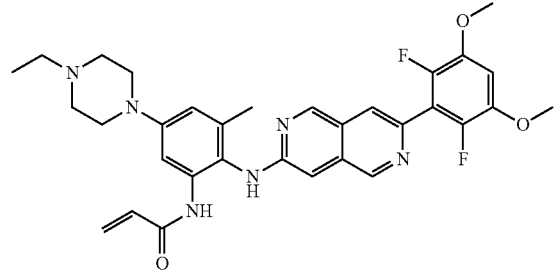
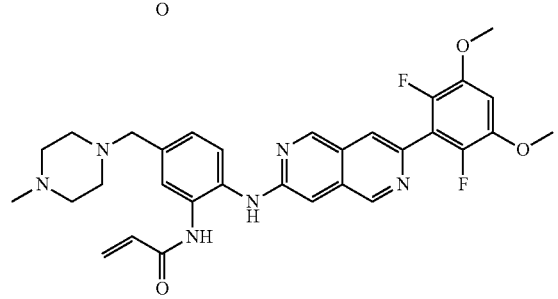
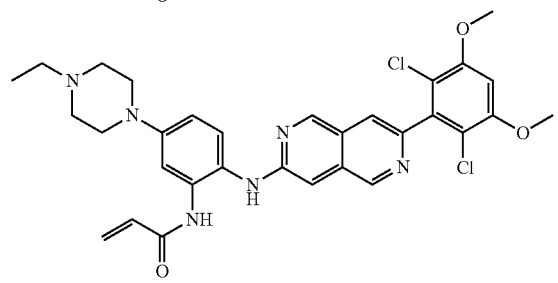
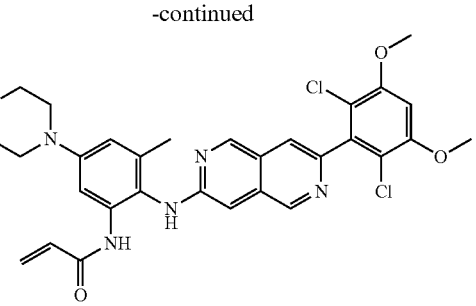
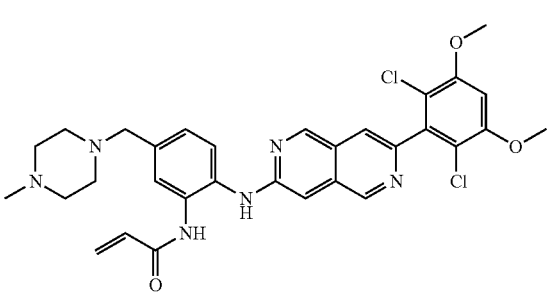
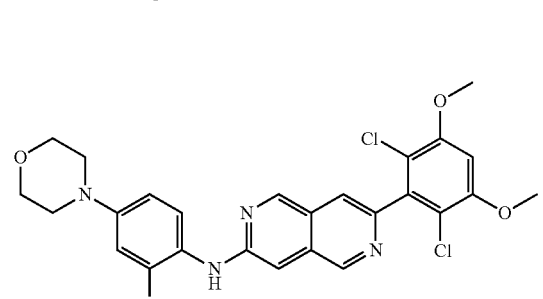
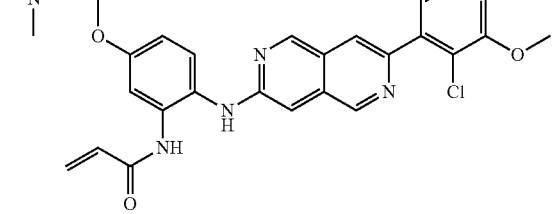
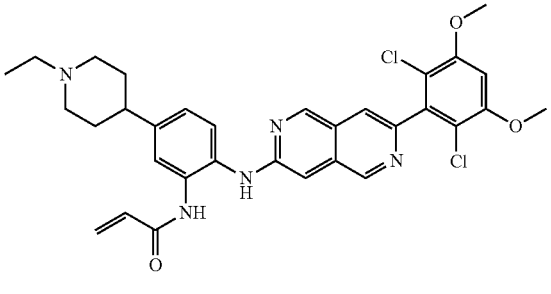

-continued
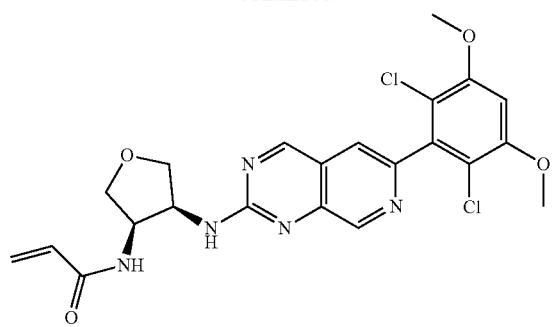
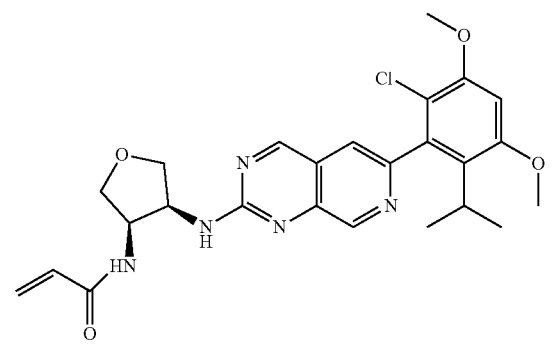
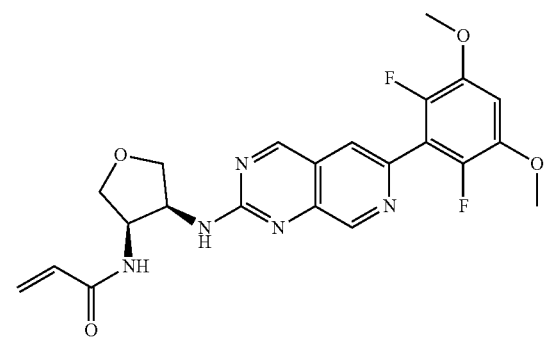
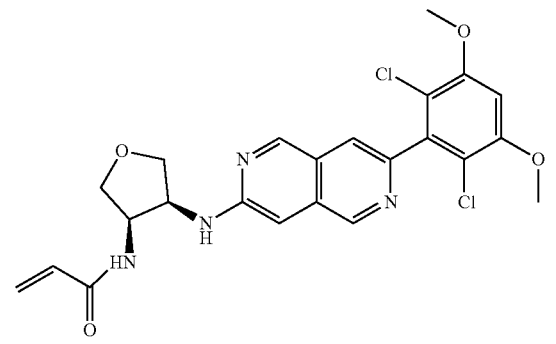
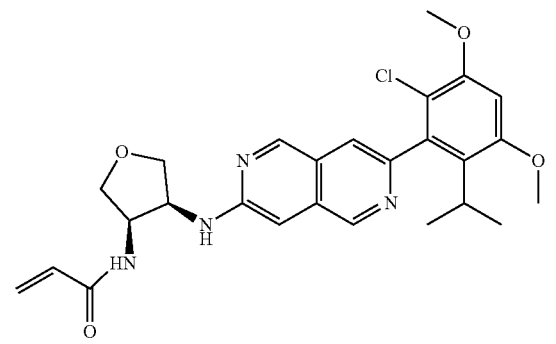
-continued
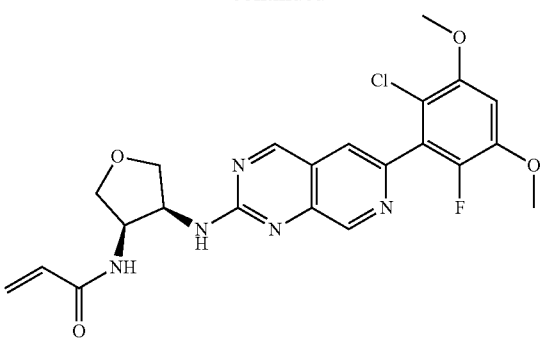
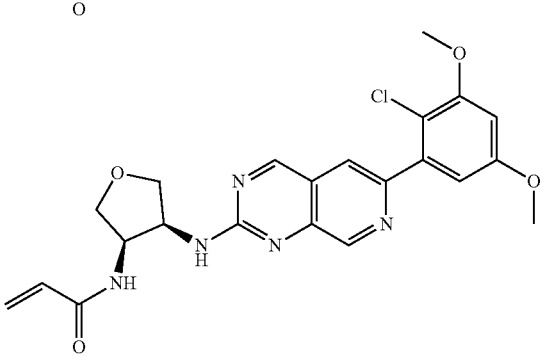
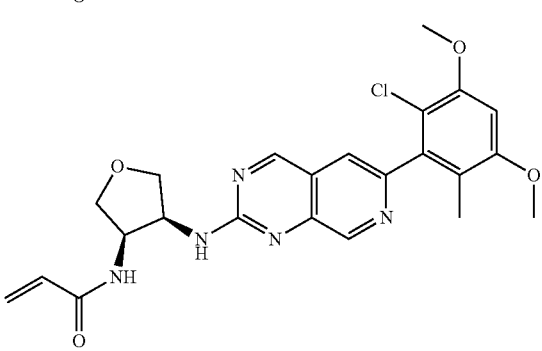
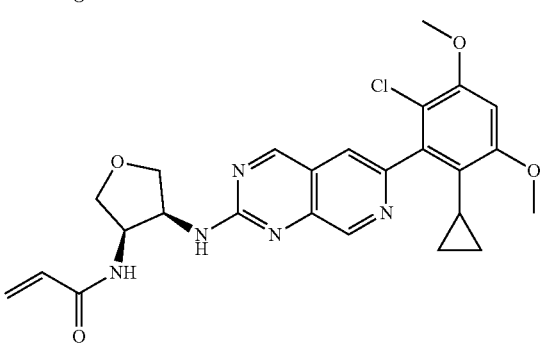
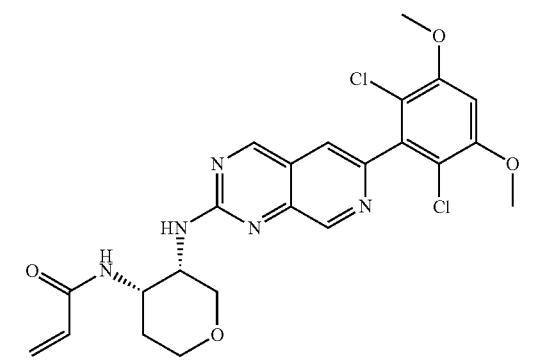

19
-continued
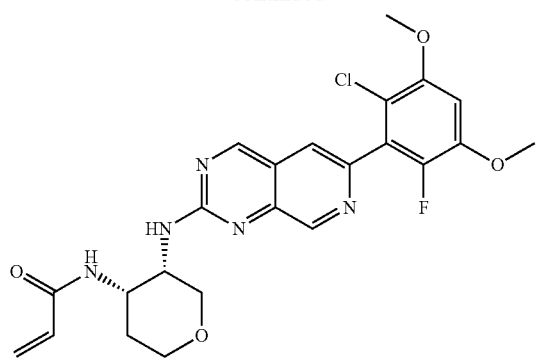
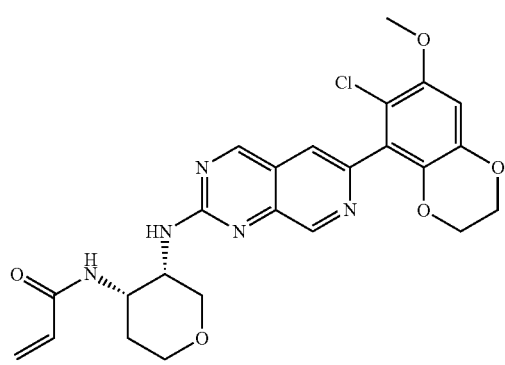
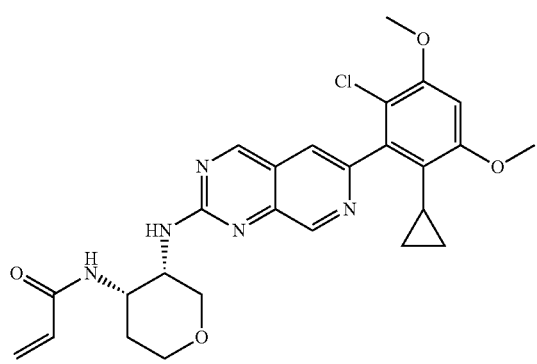
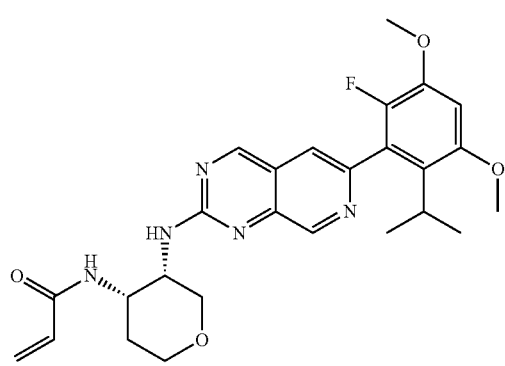
20
-continued
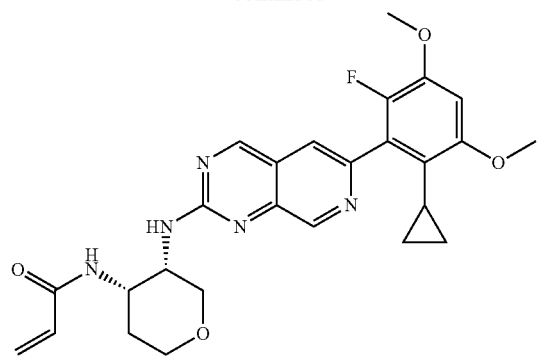
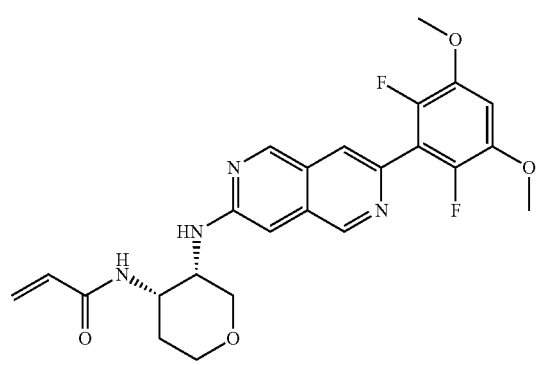
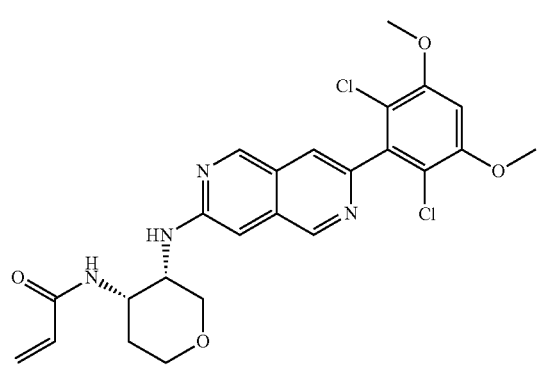

21
-continued
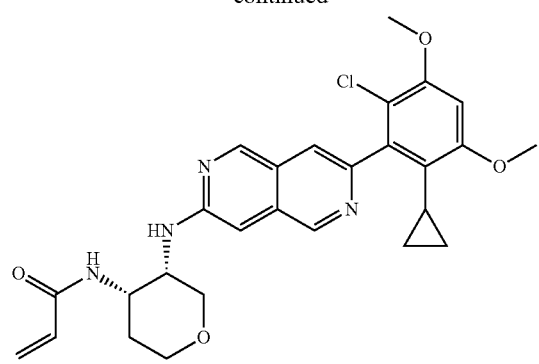
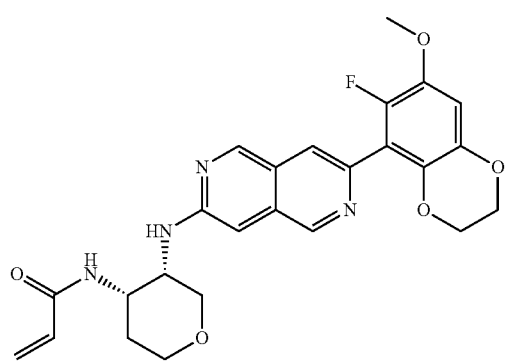
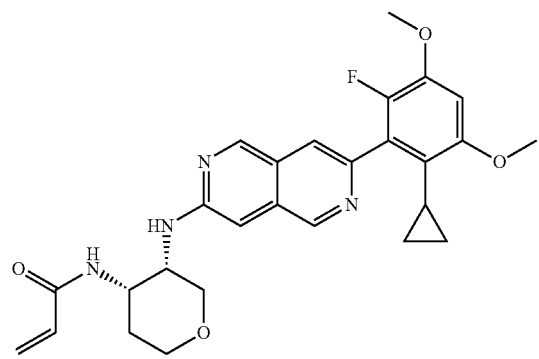
22
-continued
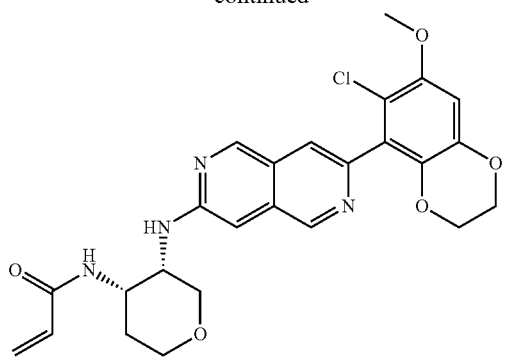
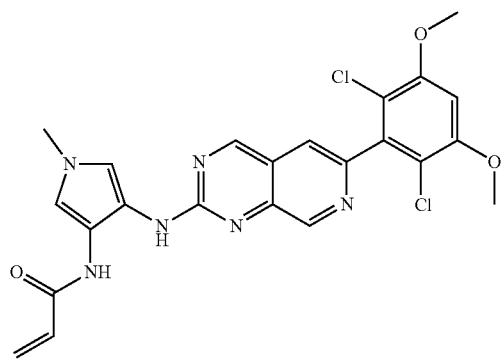
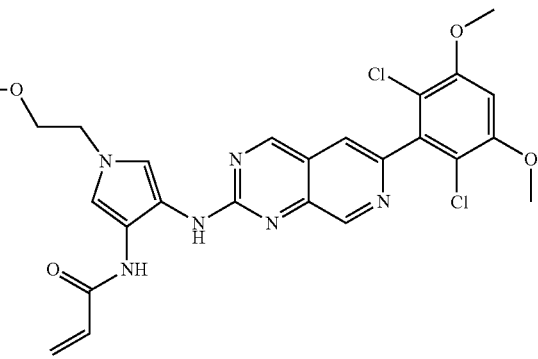

23
-continued
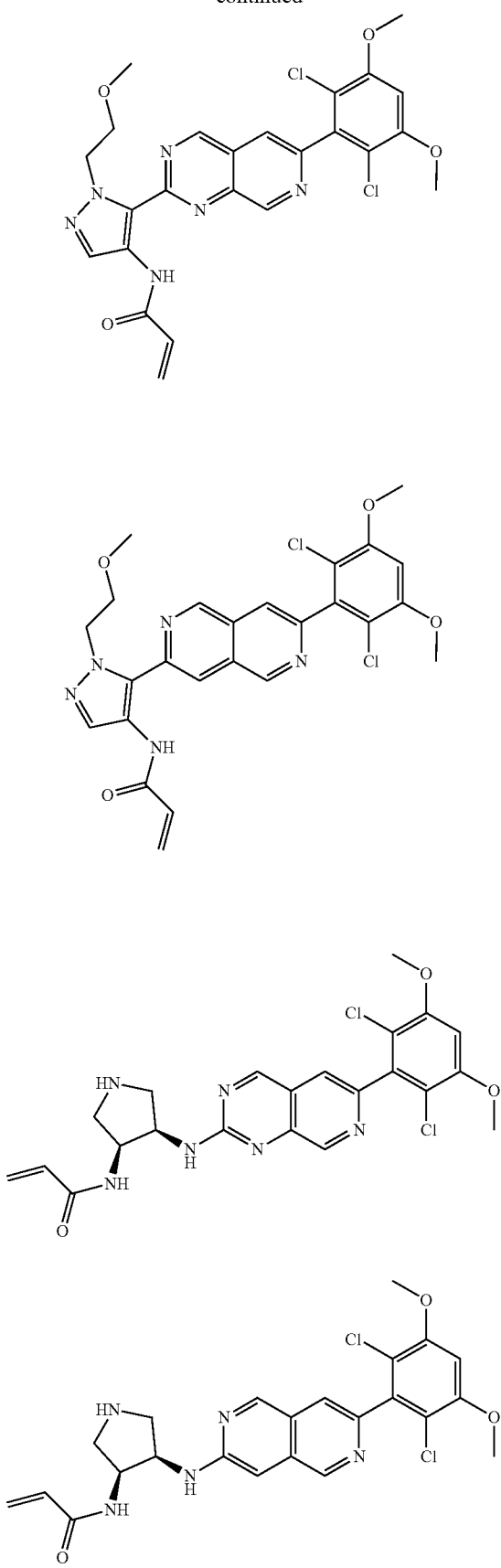
24
-continued
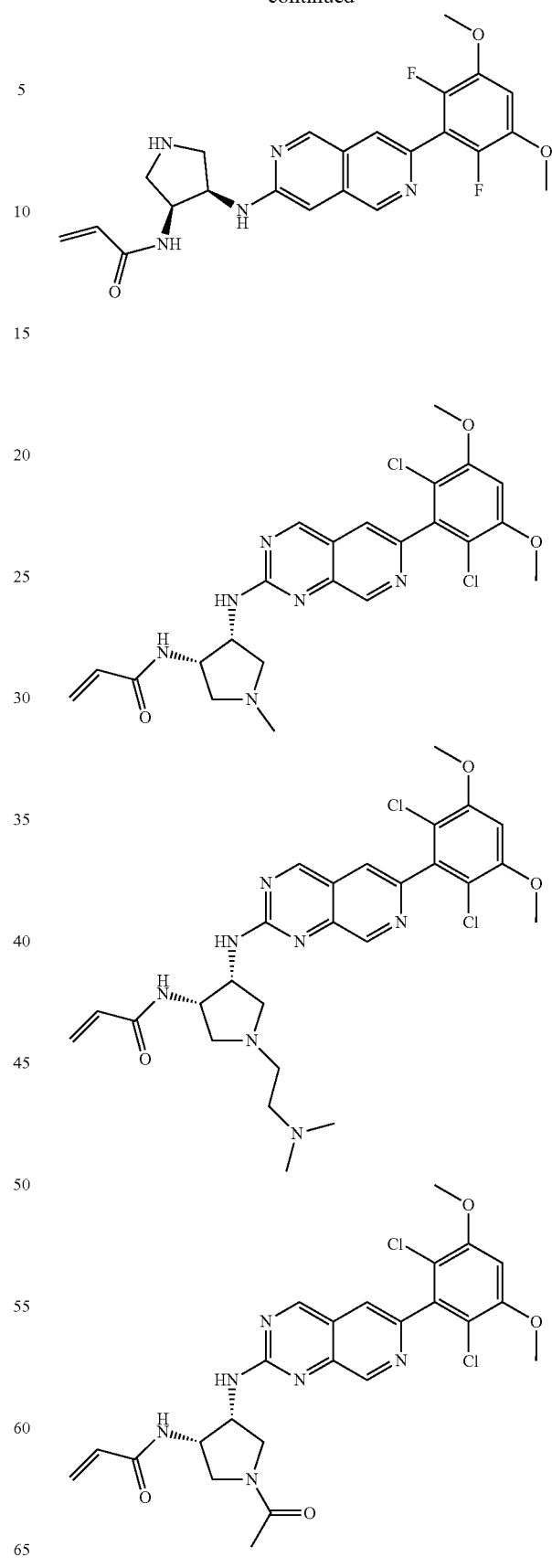

25
-continued
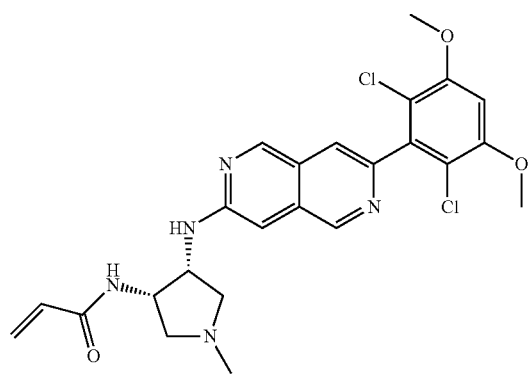
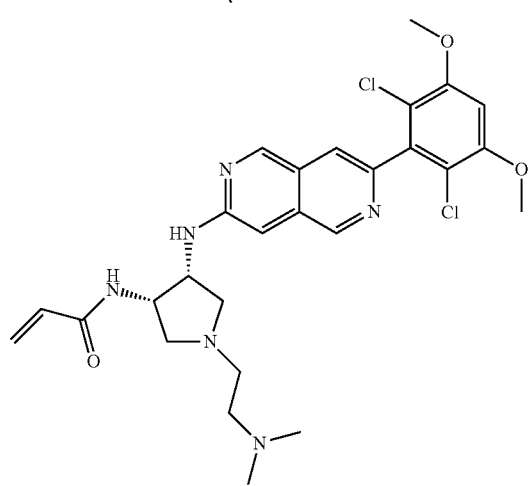
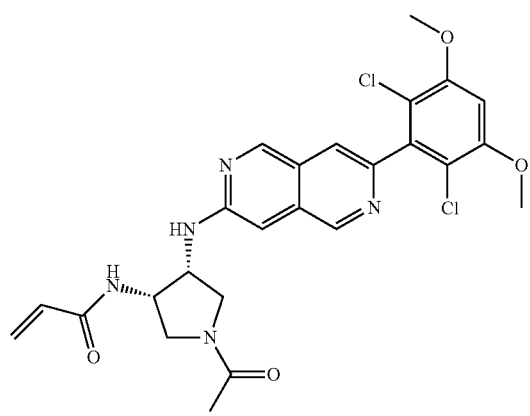
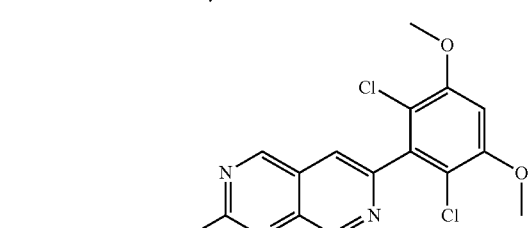
26
-continued
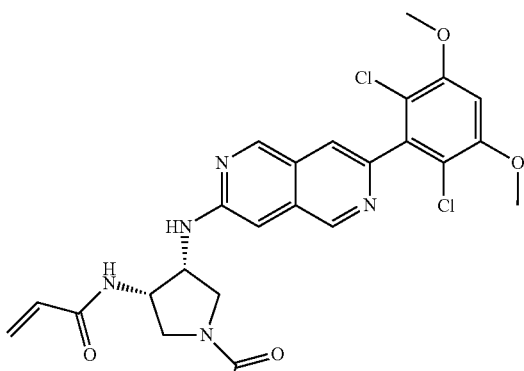
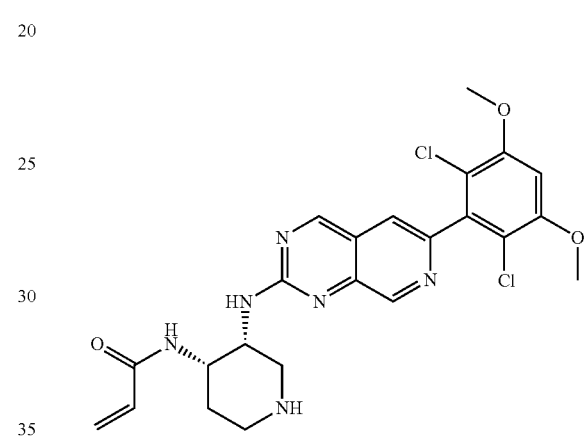
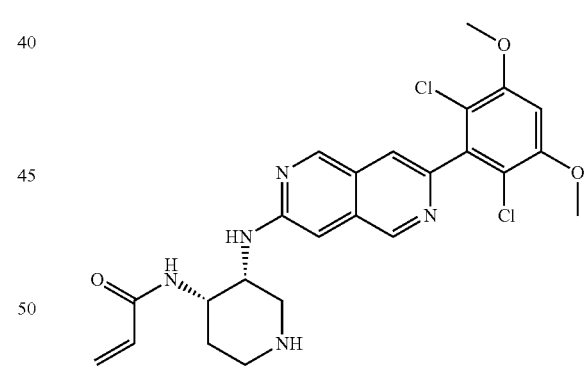
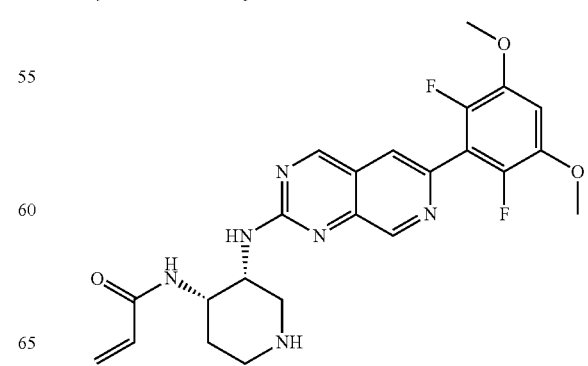

27
-continued
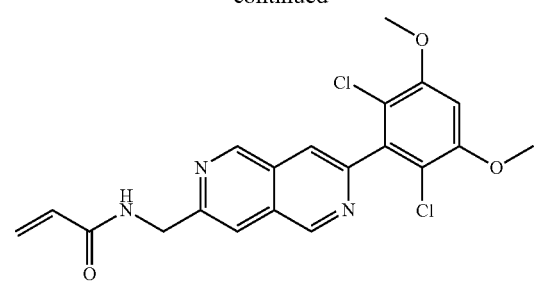
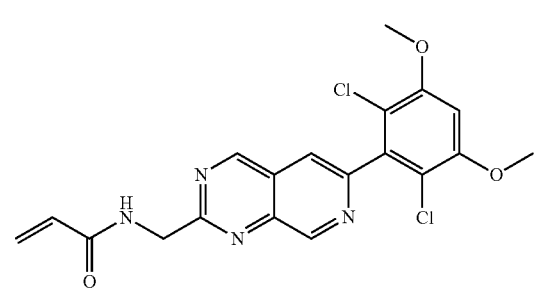
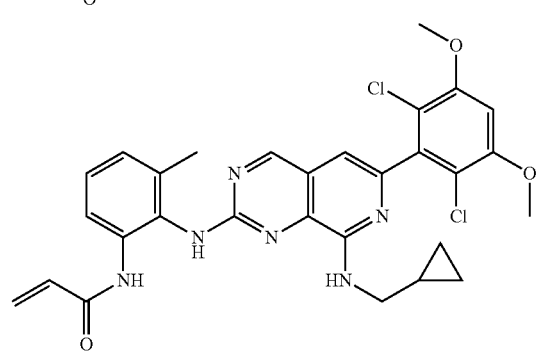
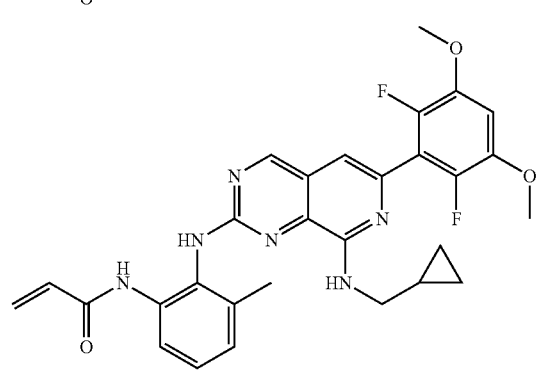
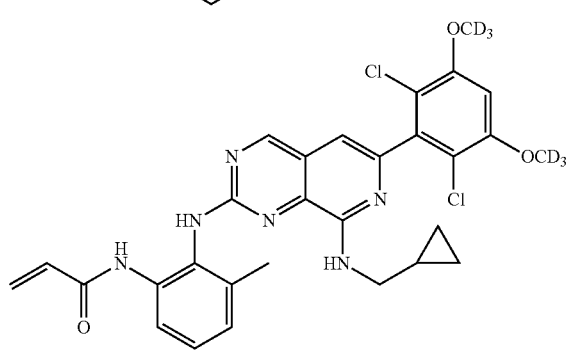
28
-continued
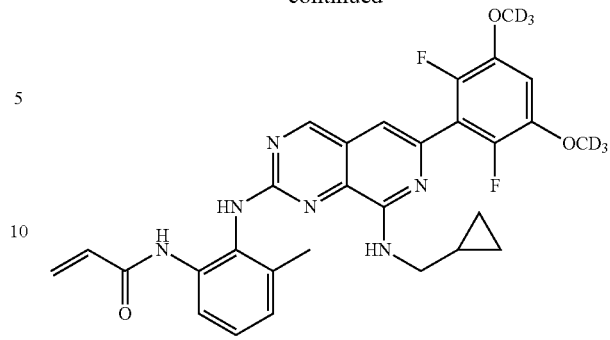
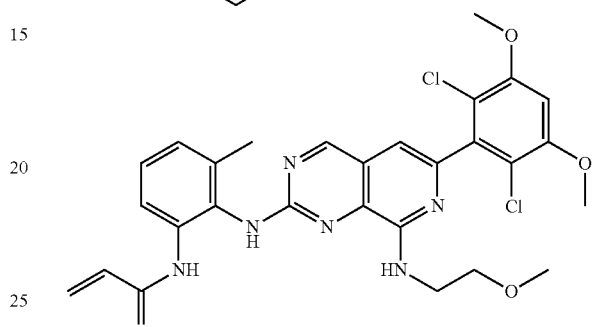
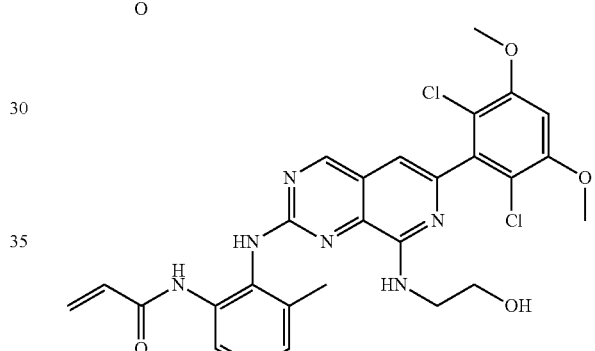
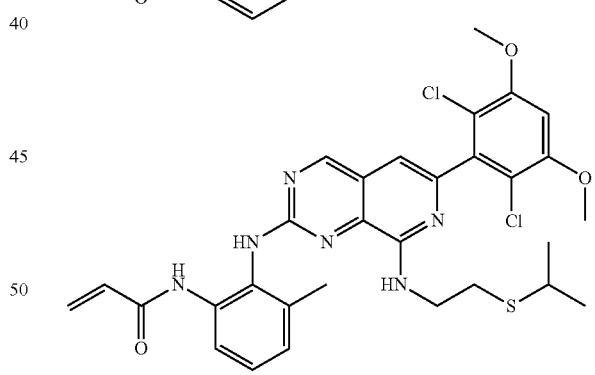
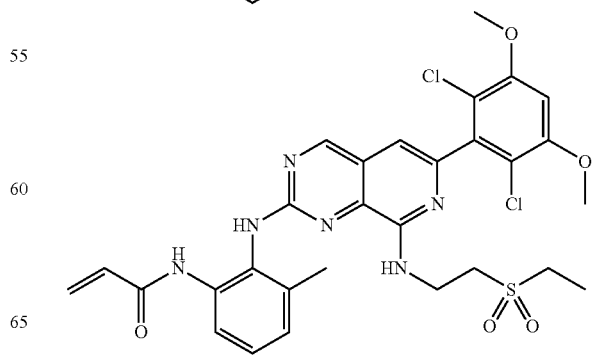

29
-continued
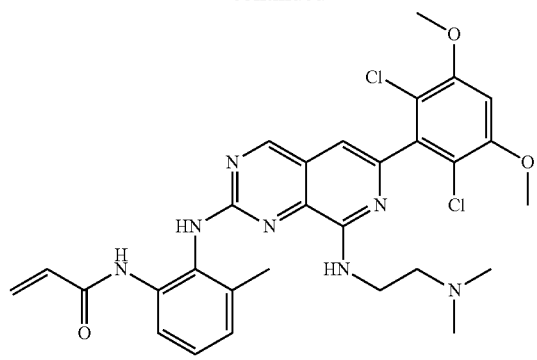
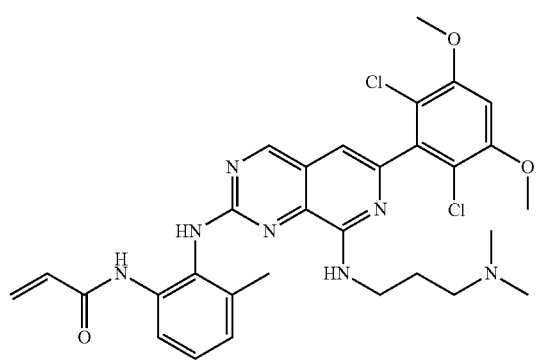
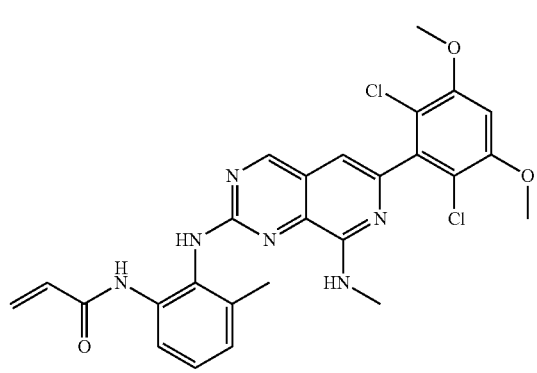
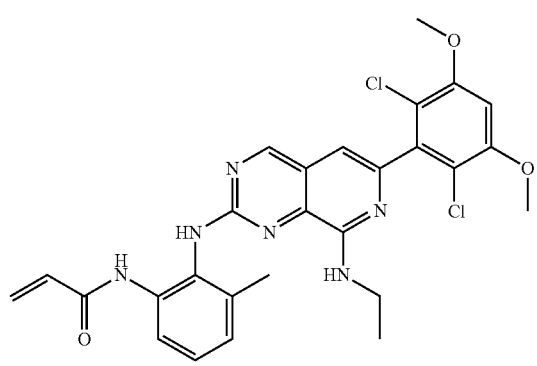
30
-continued
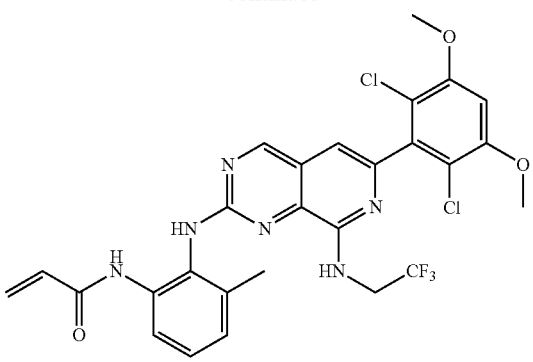
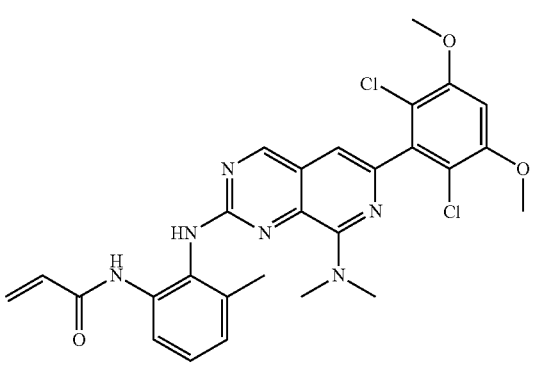
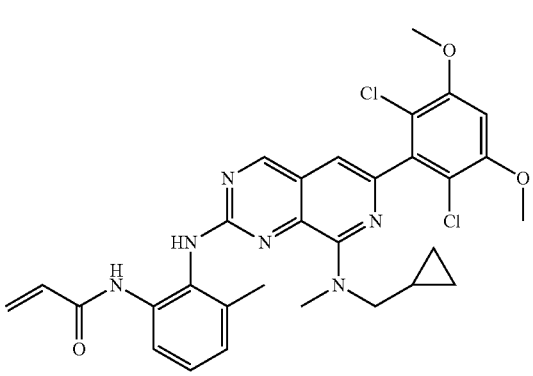
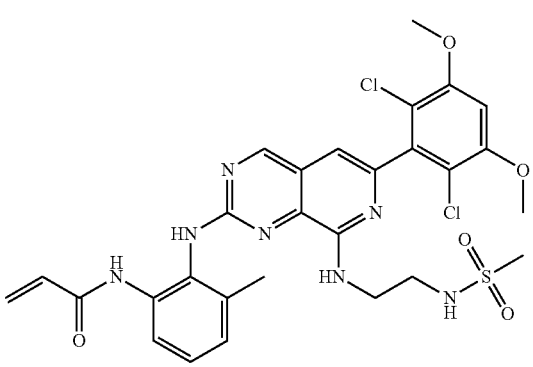

-continued
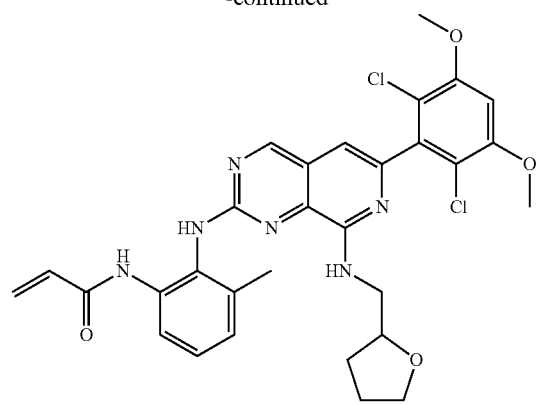
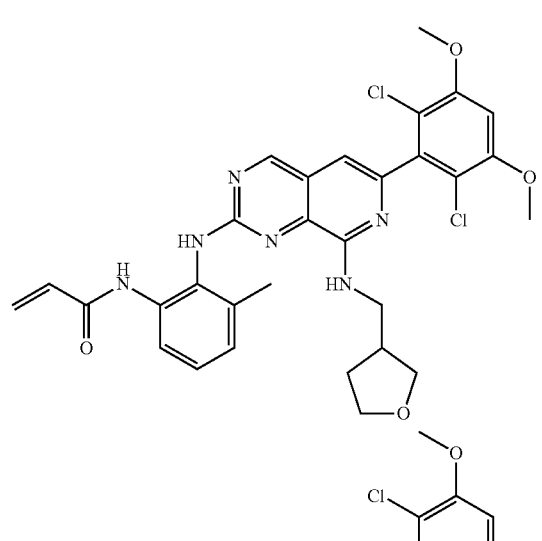
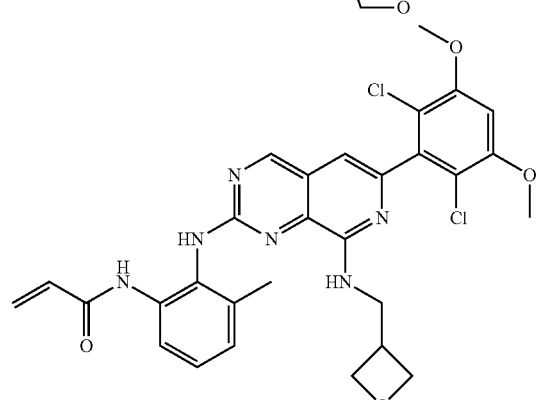
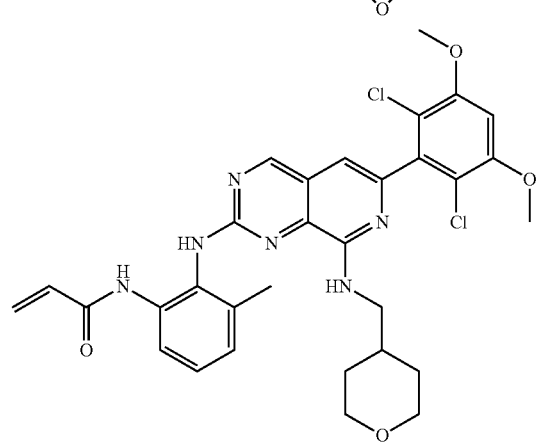
-continued
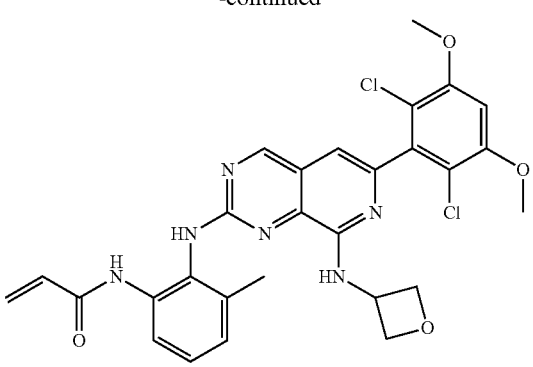
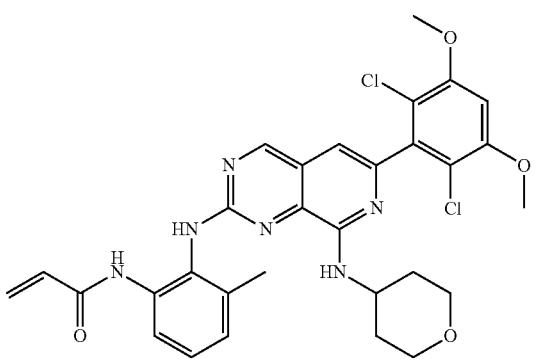
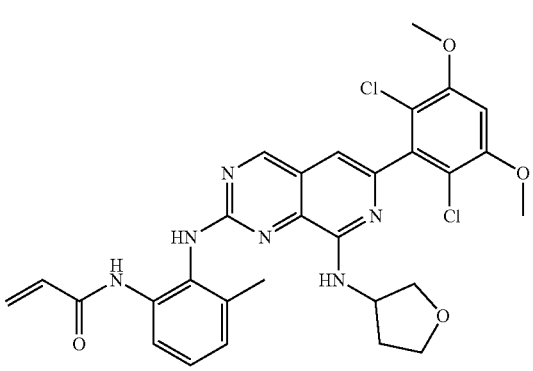
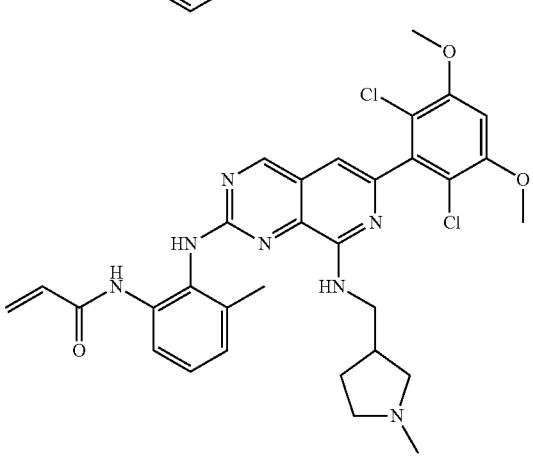

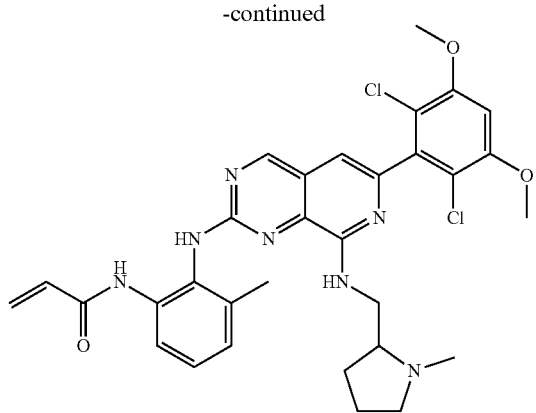
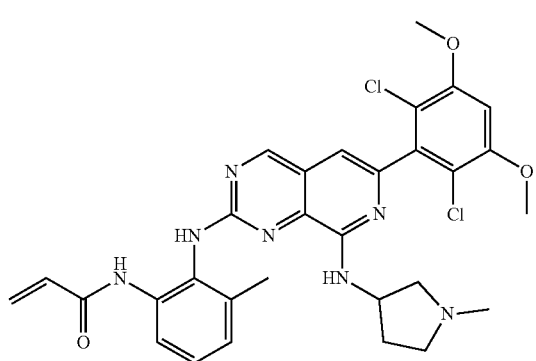
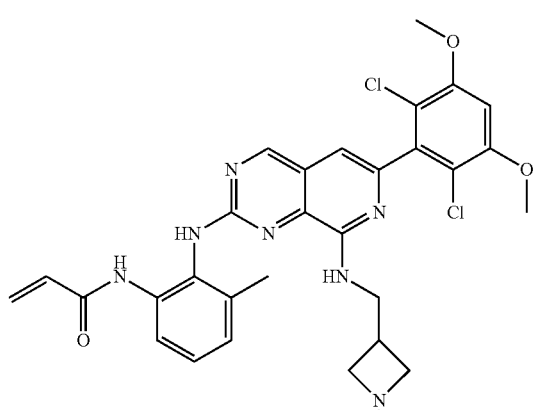
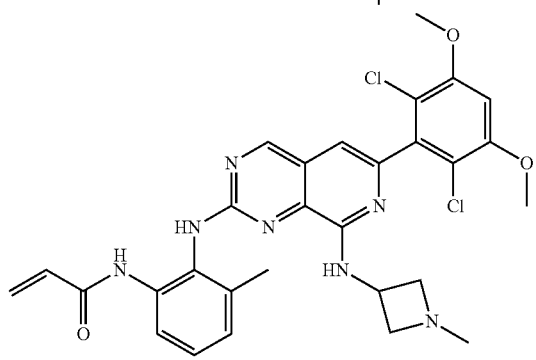
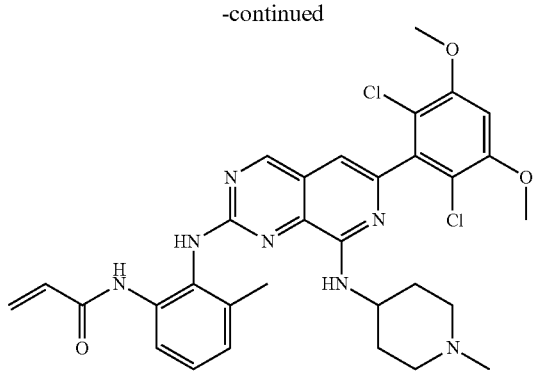
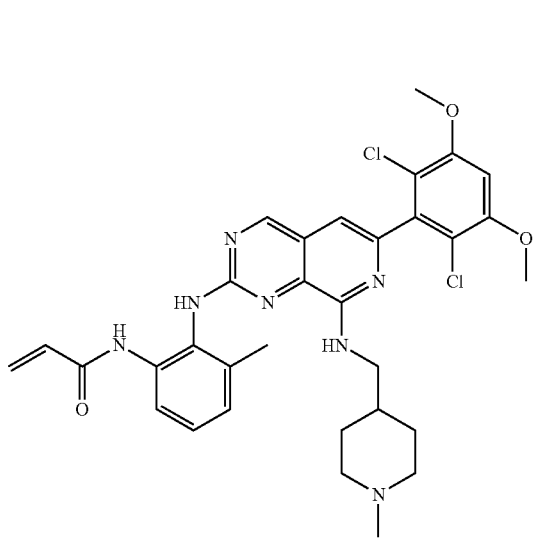
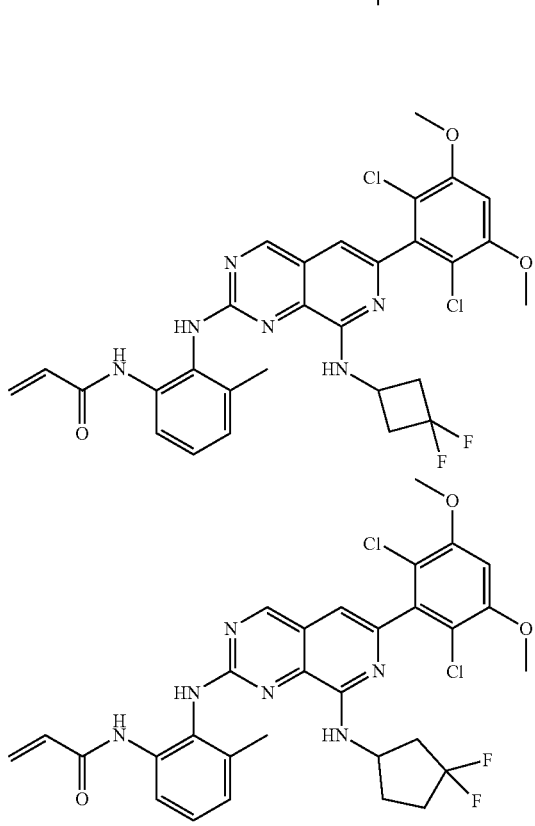
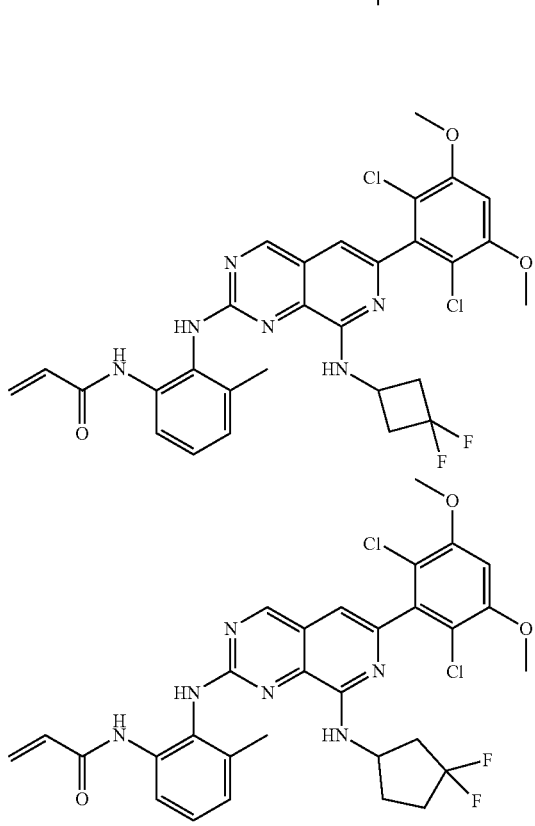

35
-continued
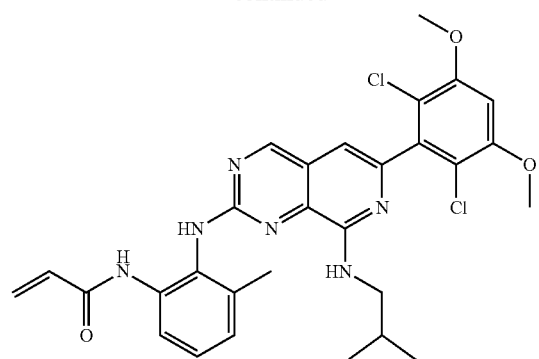
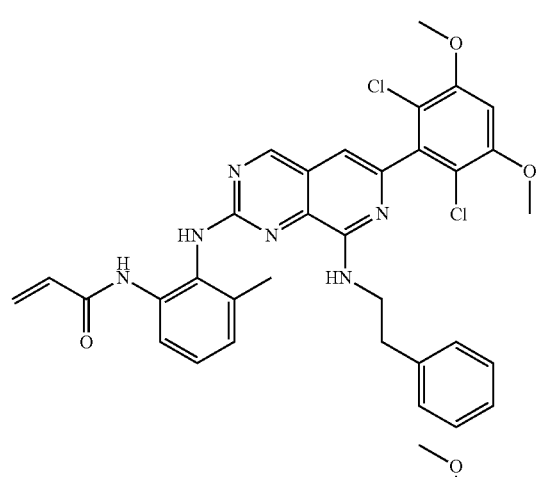
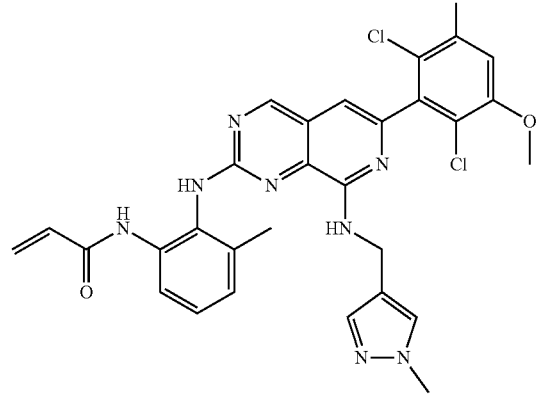
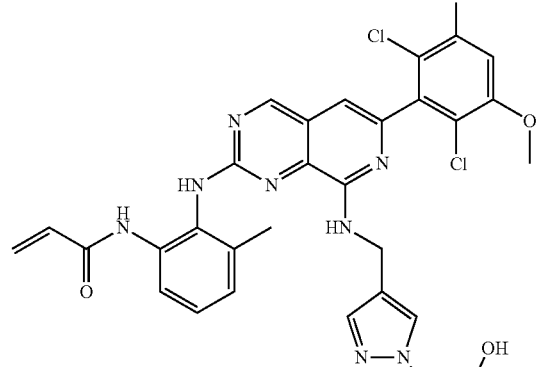
36
-continued
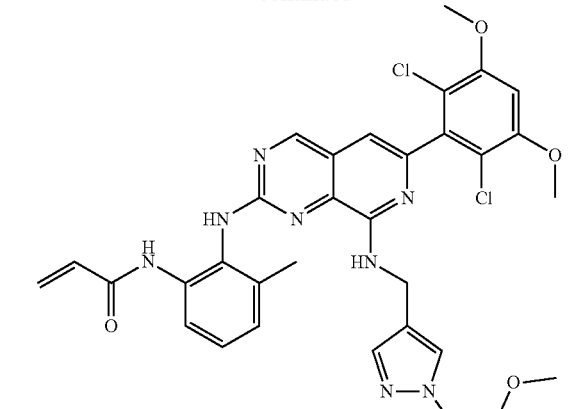
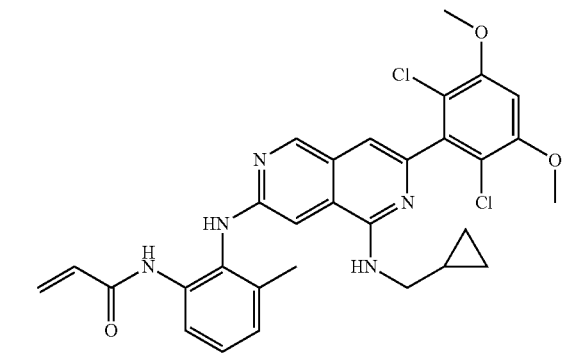
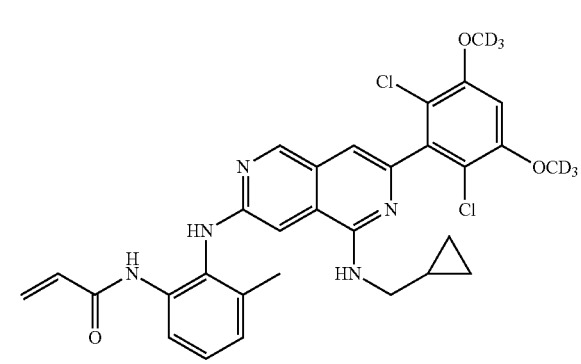
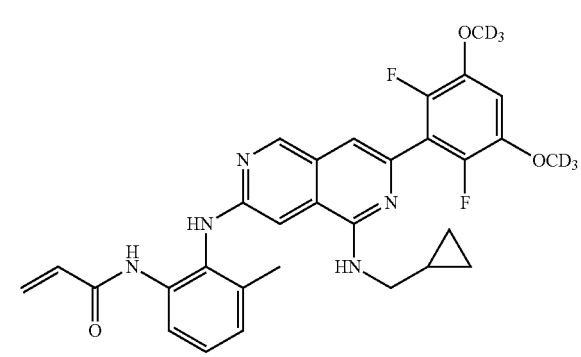

-continued
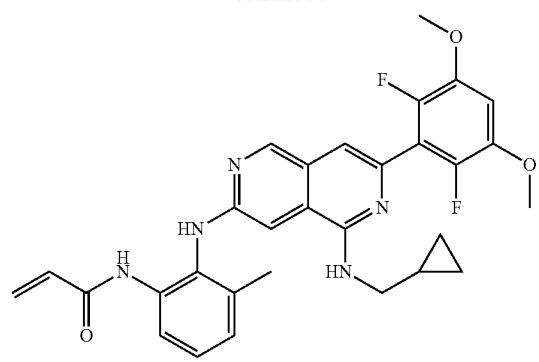
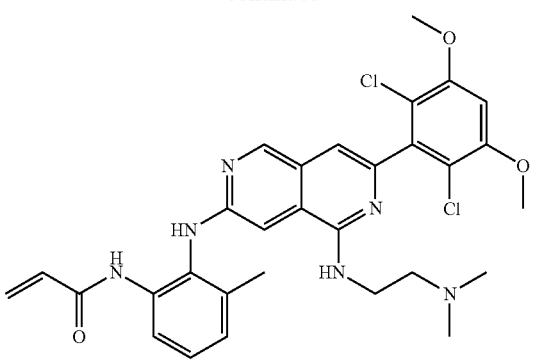 [SMILES: C=CC(=O)Nc1cccc(C)c1Nc1cc2c(NCCN(C)C)nc(-c3c(Cl)c(OC)cc(OC)c3Cl)cc2cn1]
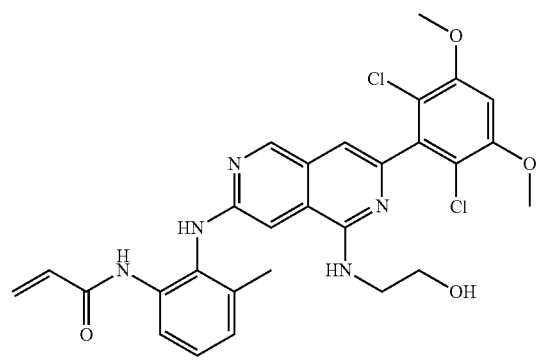
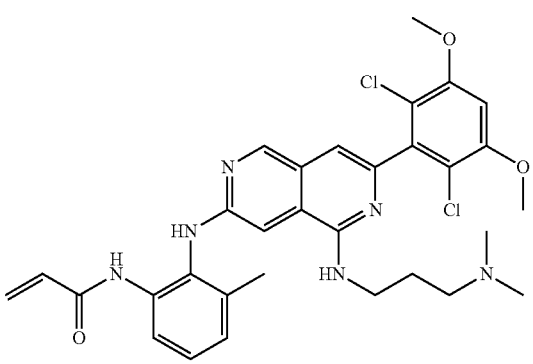
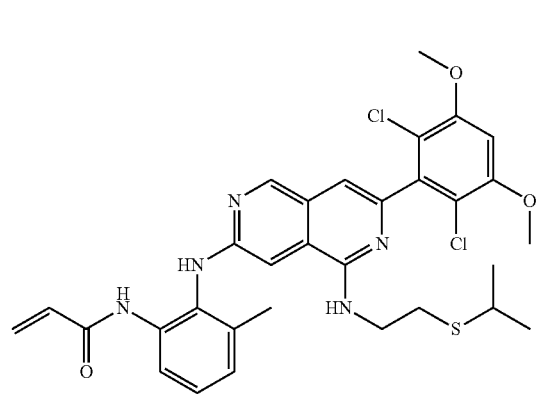
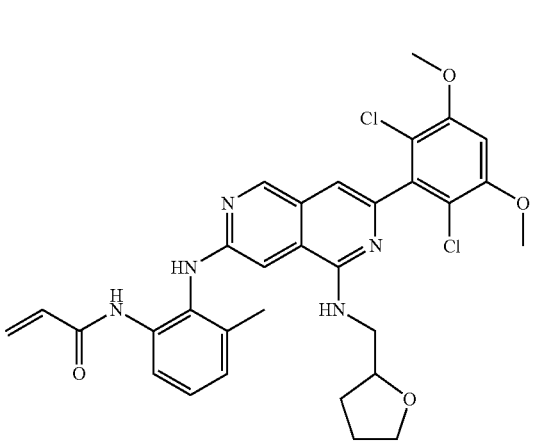
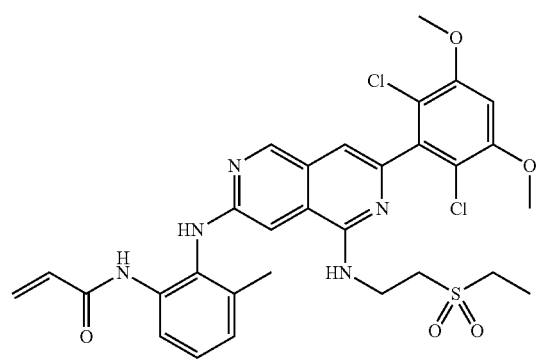
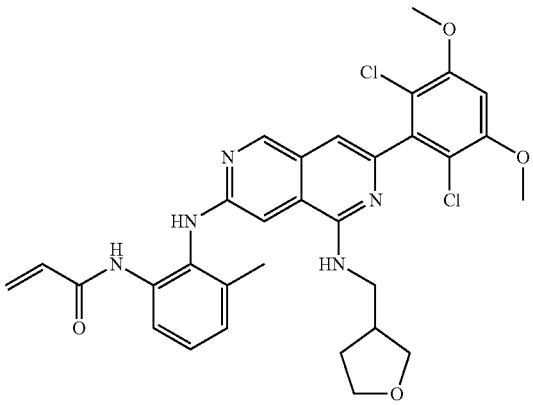

-continued
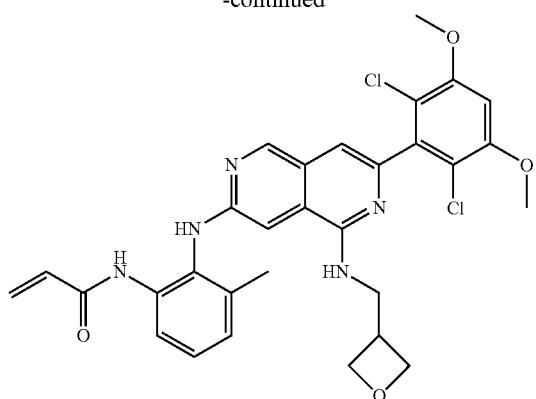
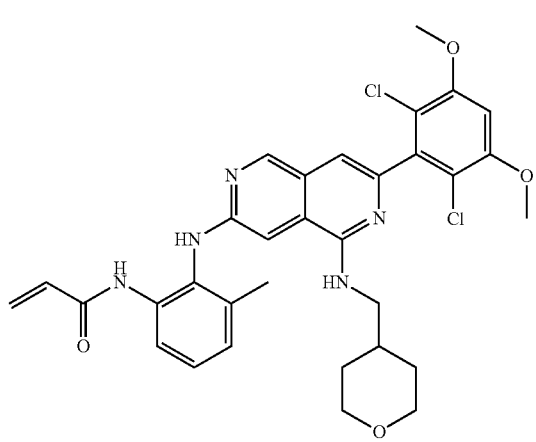
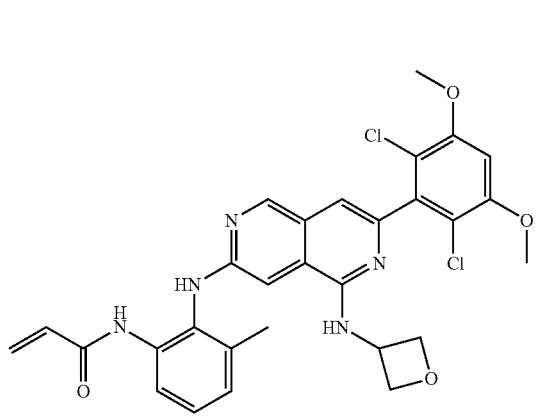
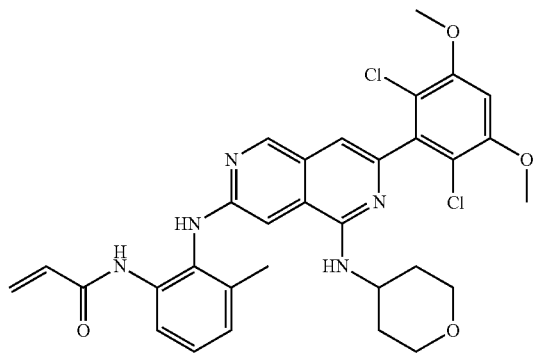
-continued
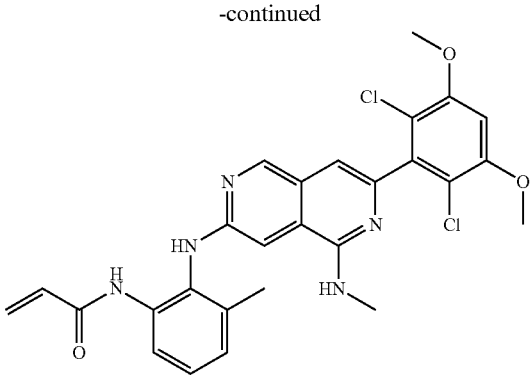
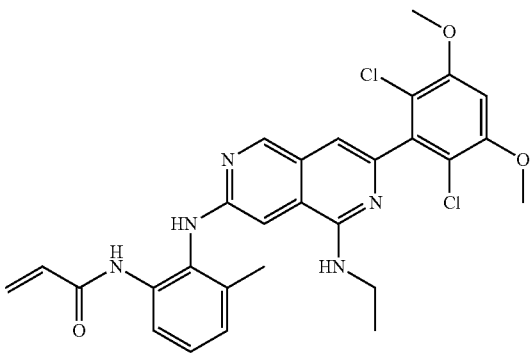
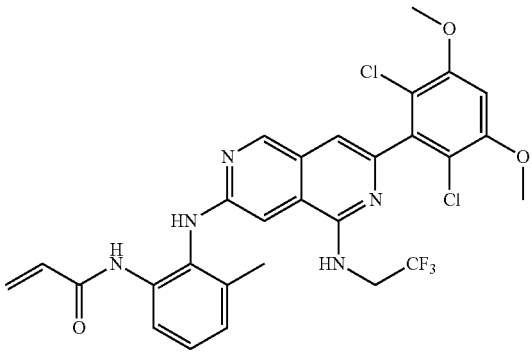
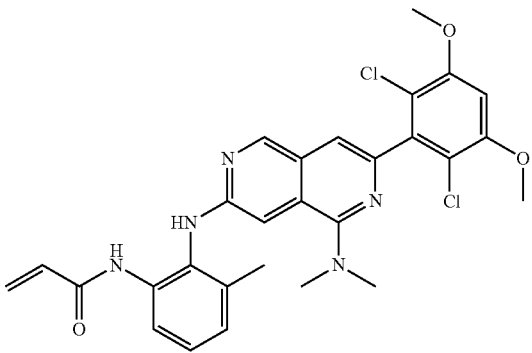

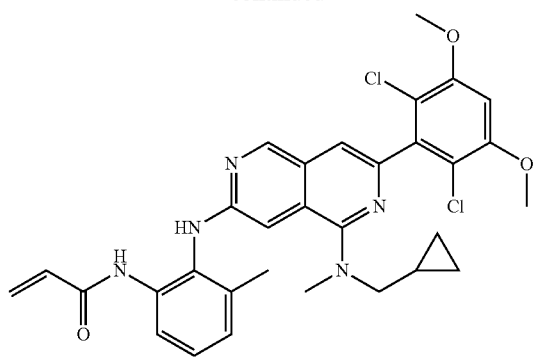
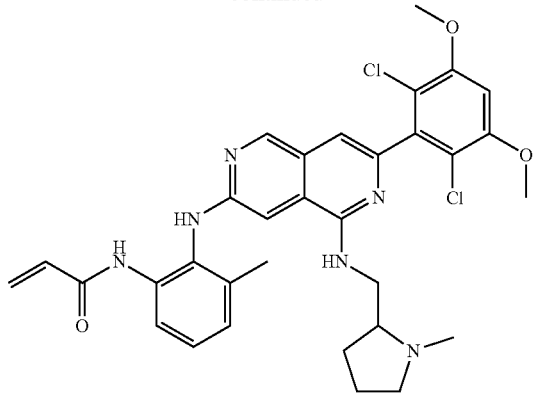
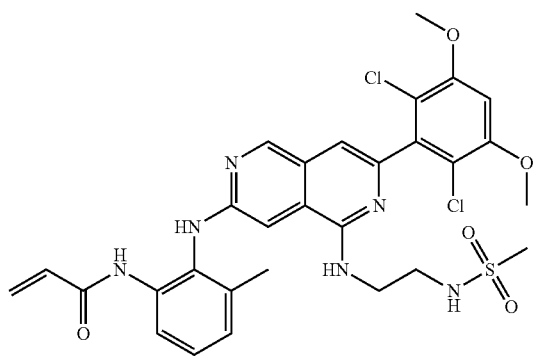
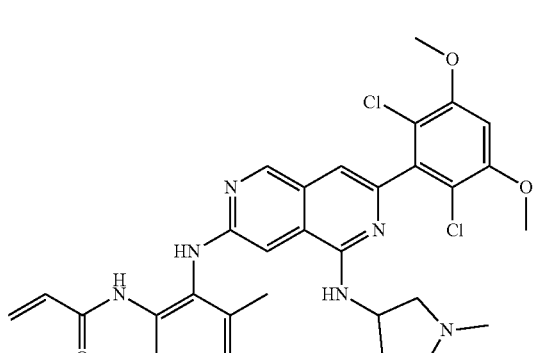
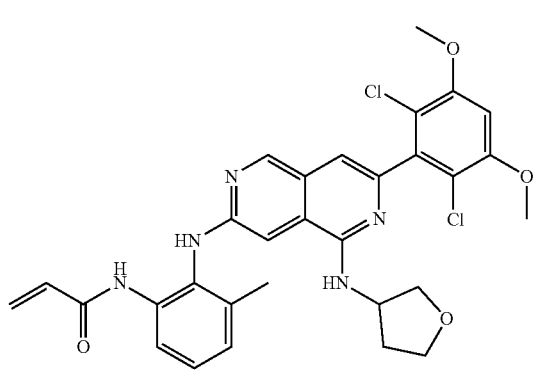
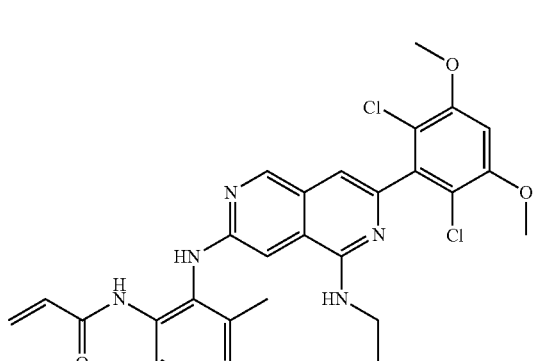
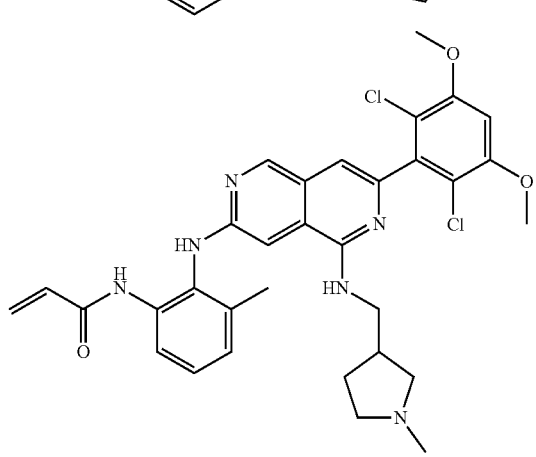
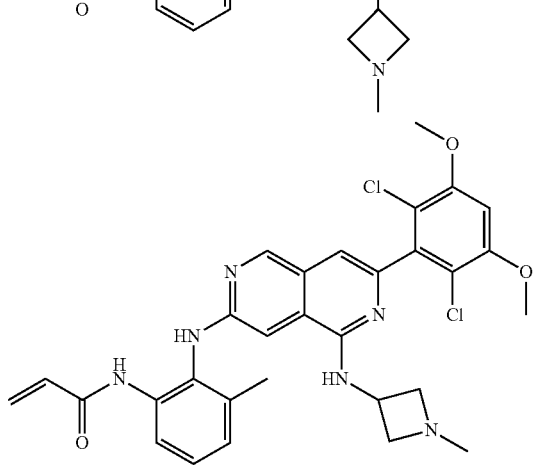

43
-continued
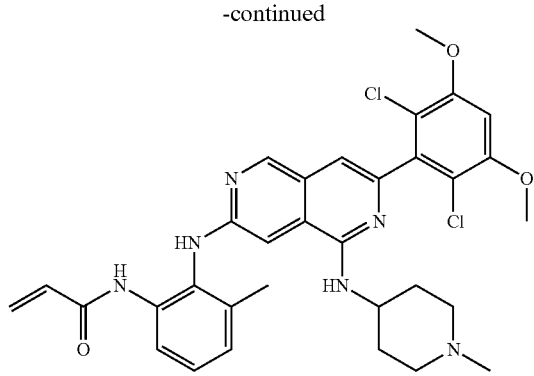
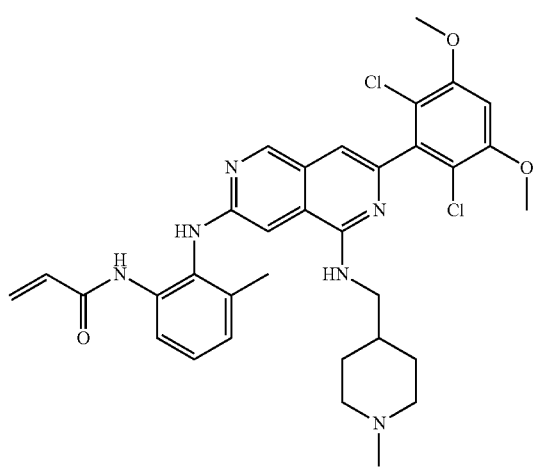
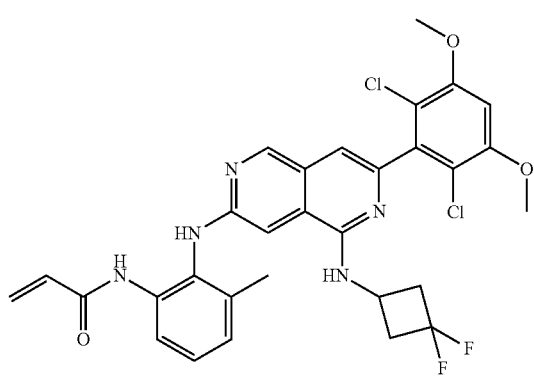
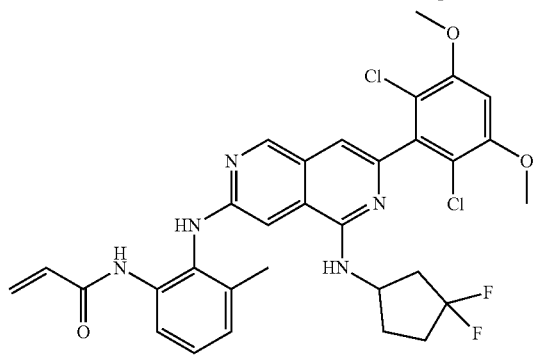
44
-continued
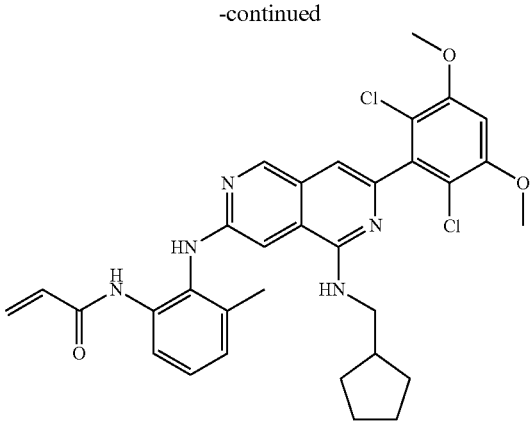
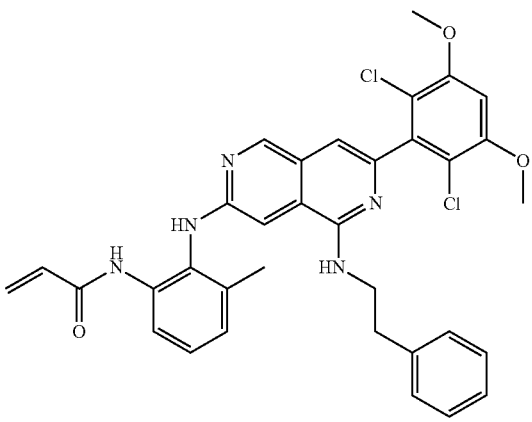
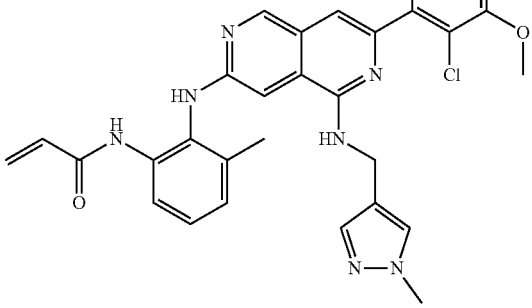
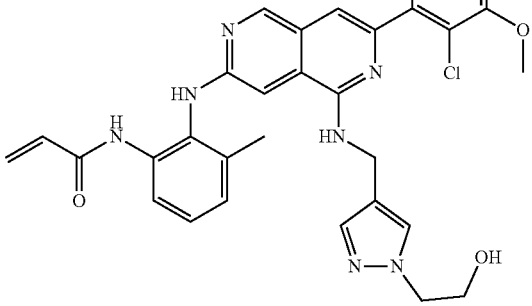

45
-continued
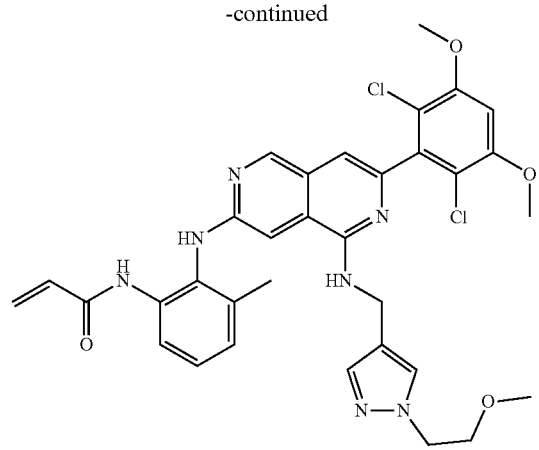
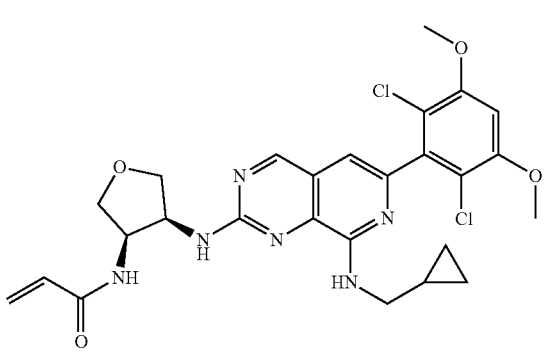
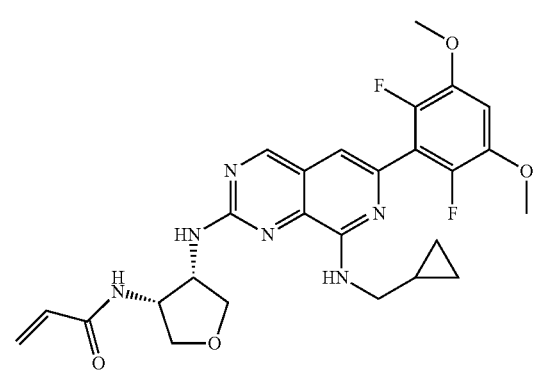
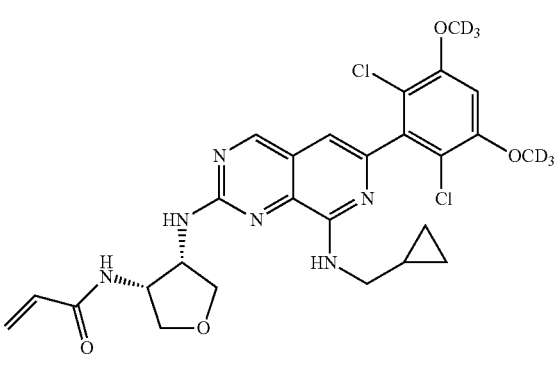
46
-continued
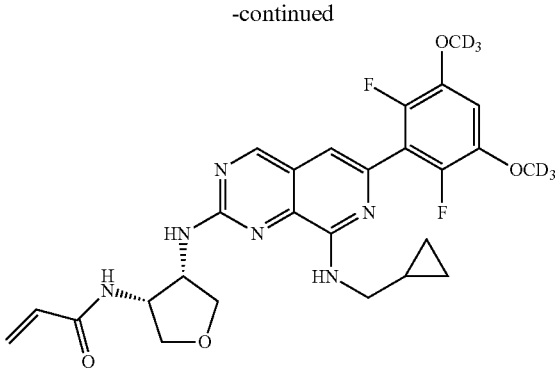
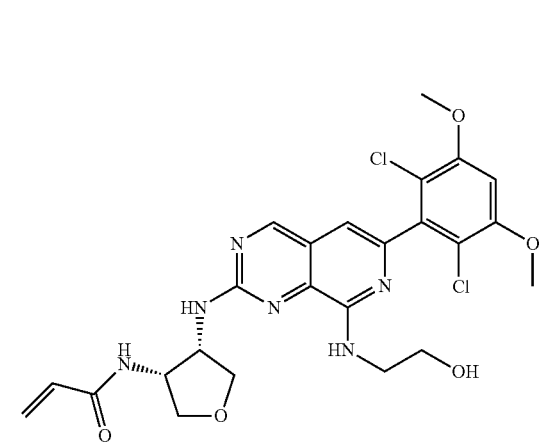
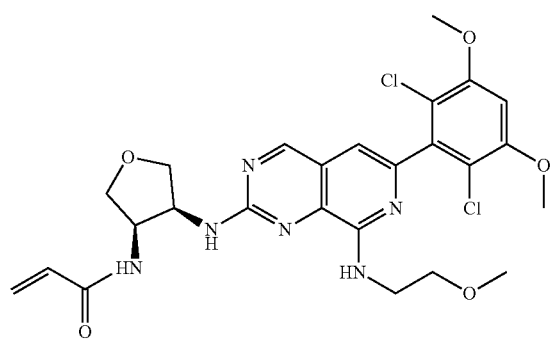
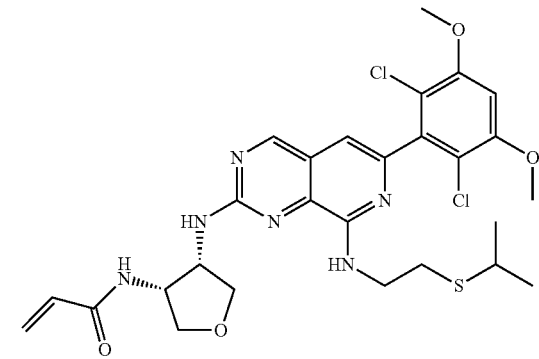

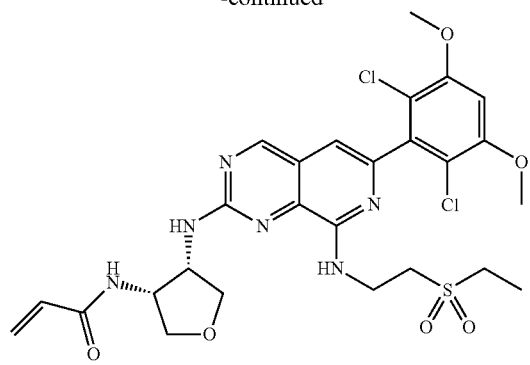
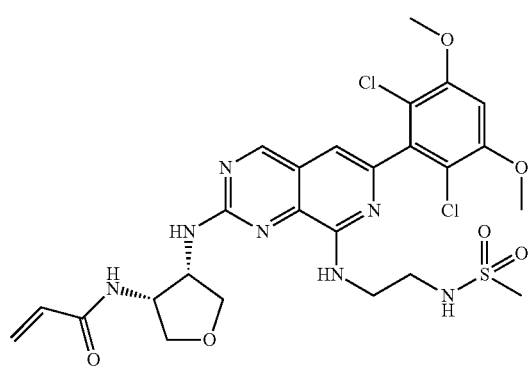
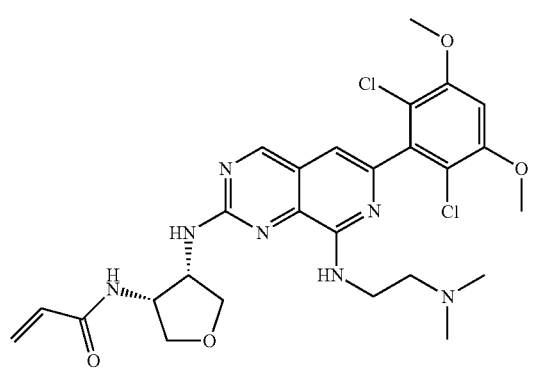
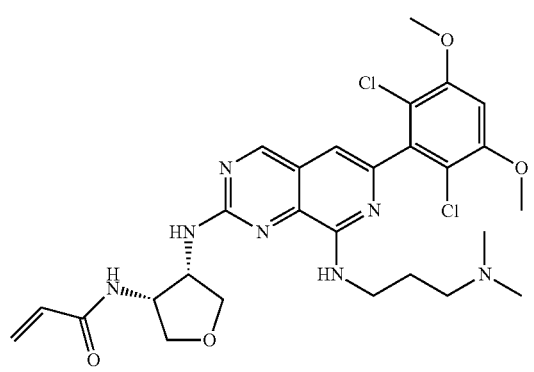
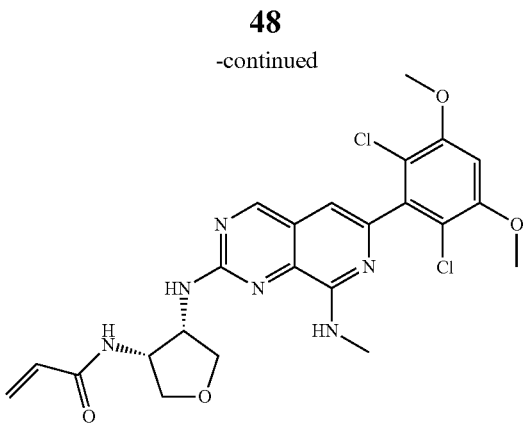
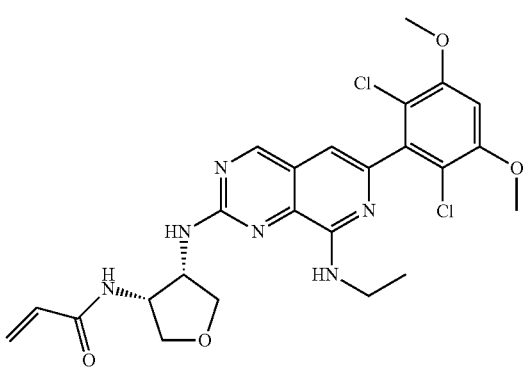
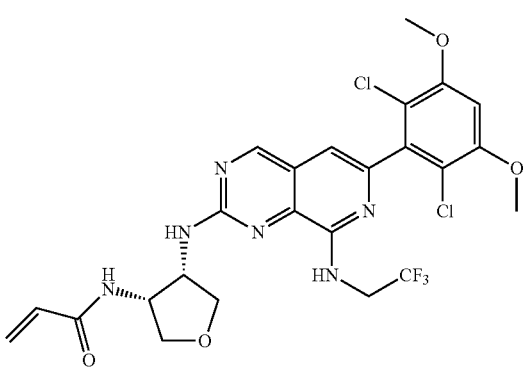
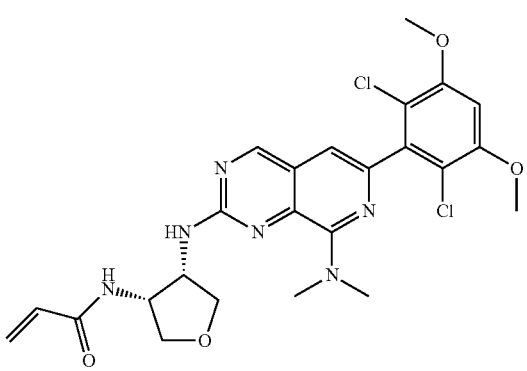

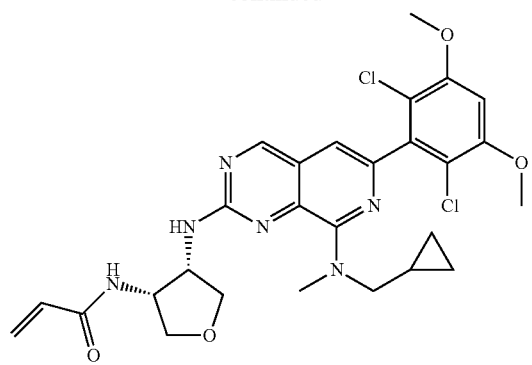
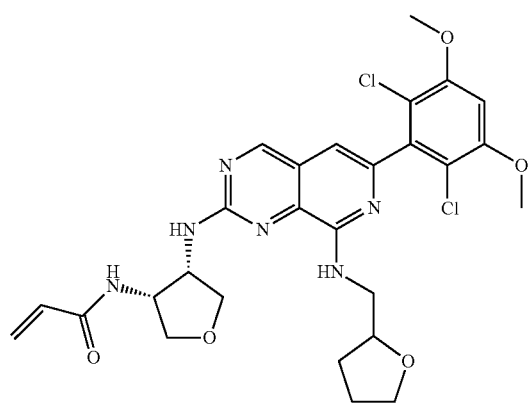
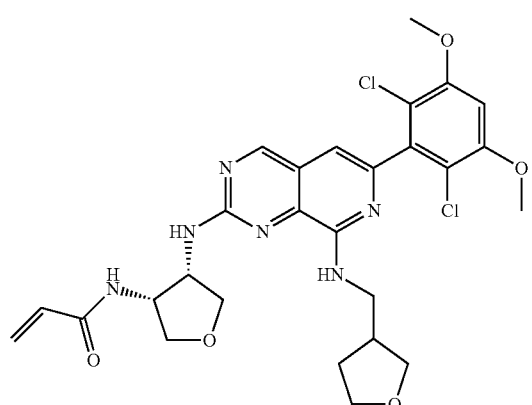
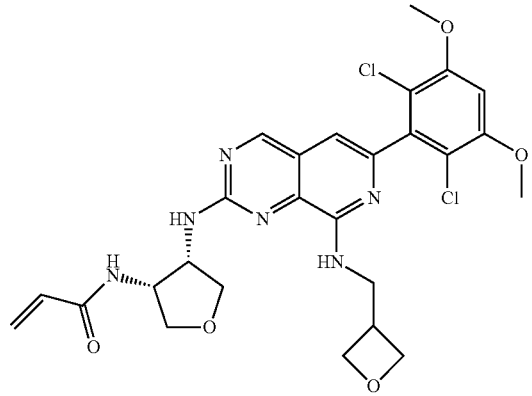
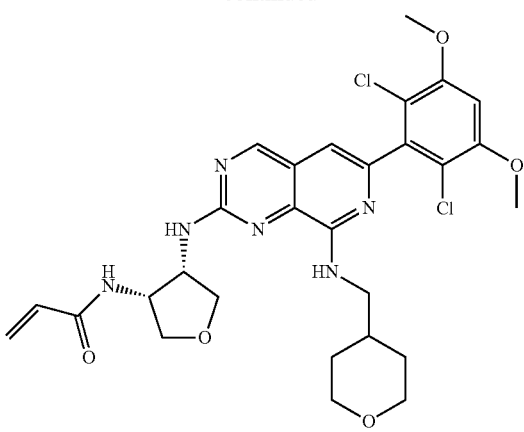
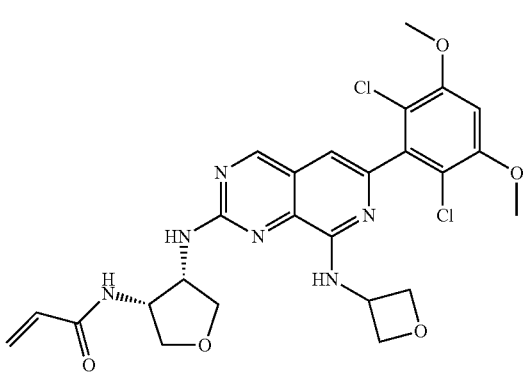
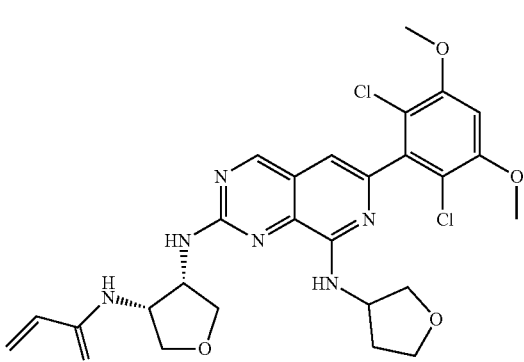
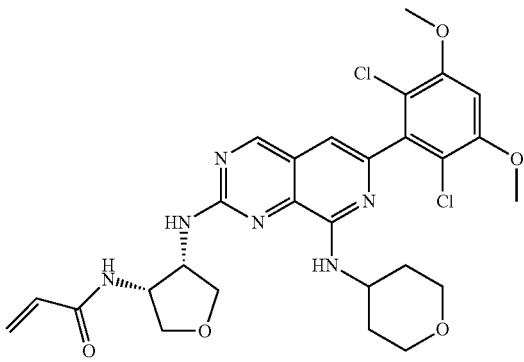

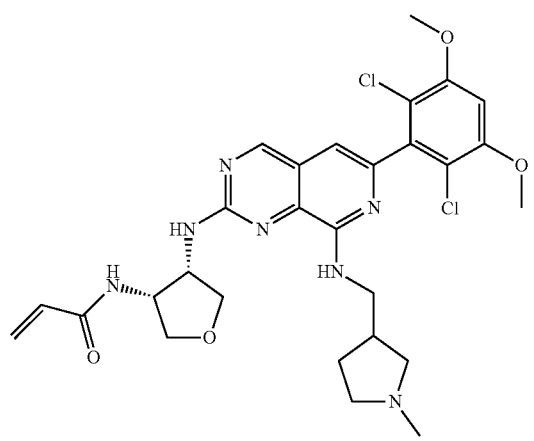
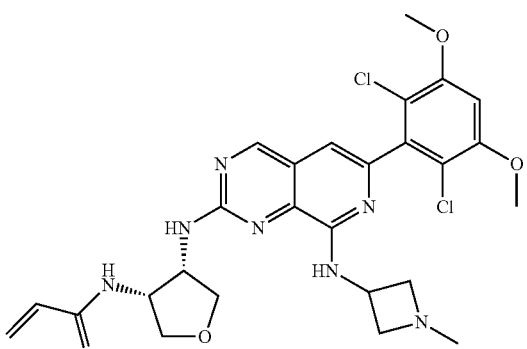
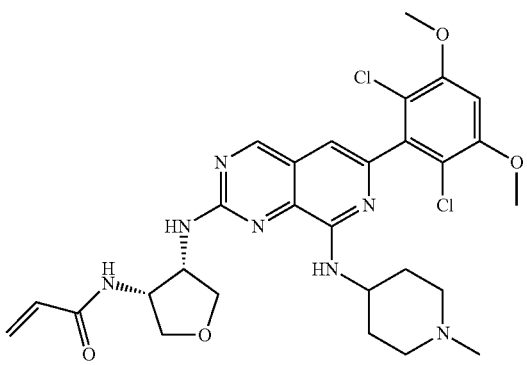
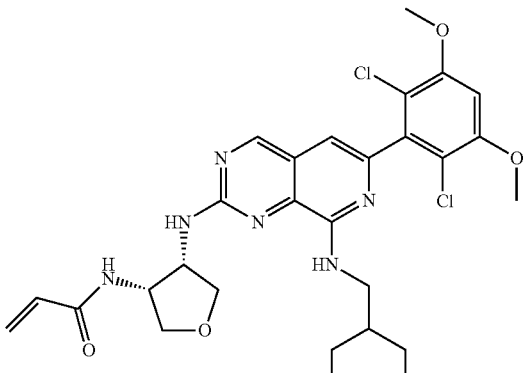
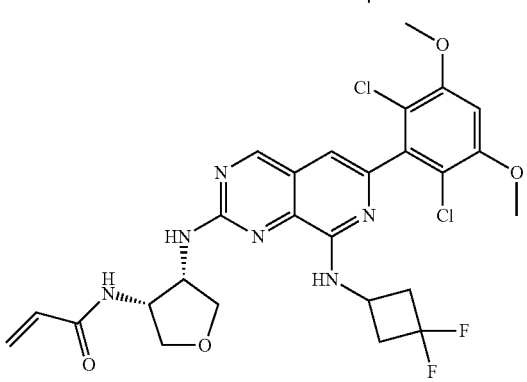

53
-continued
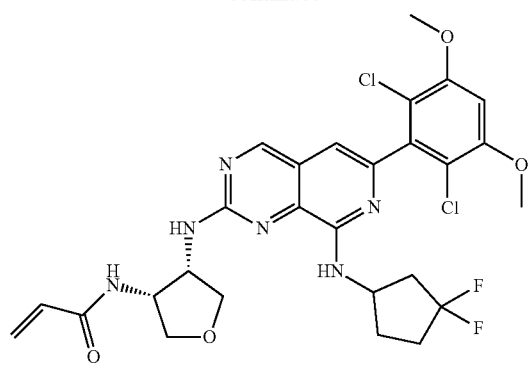
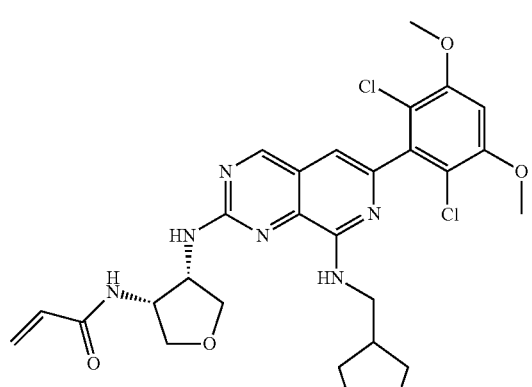
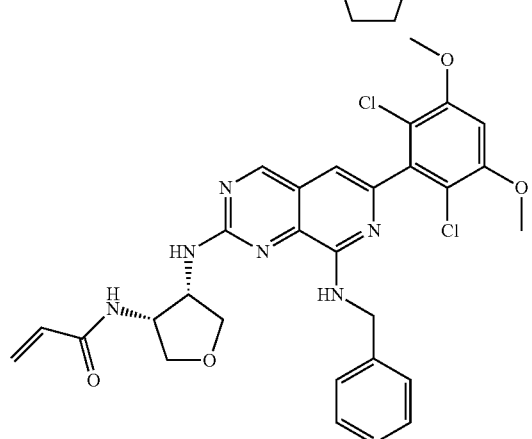
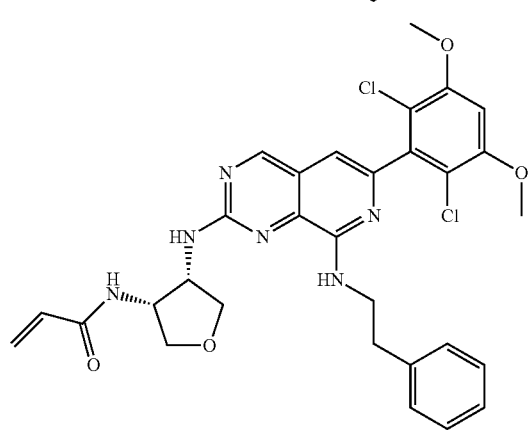
54
-continued
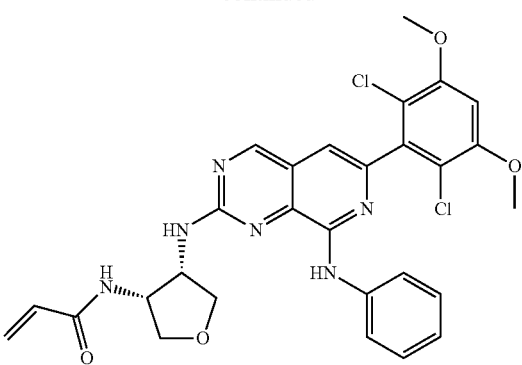
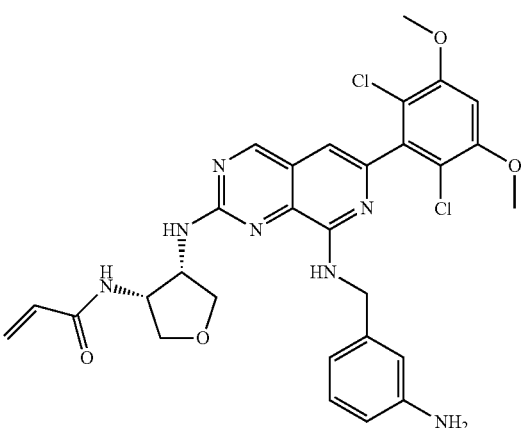
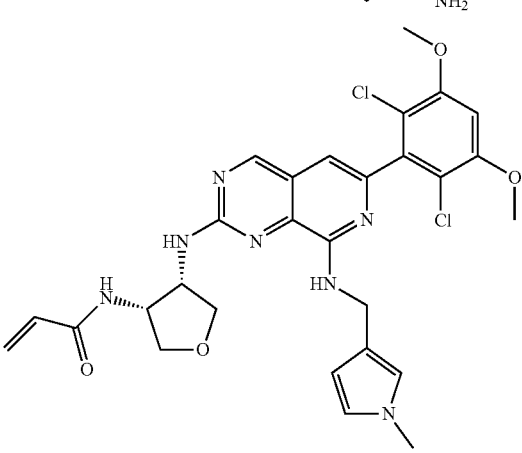
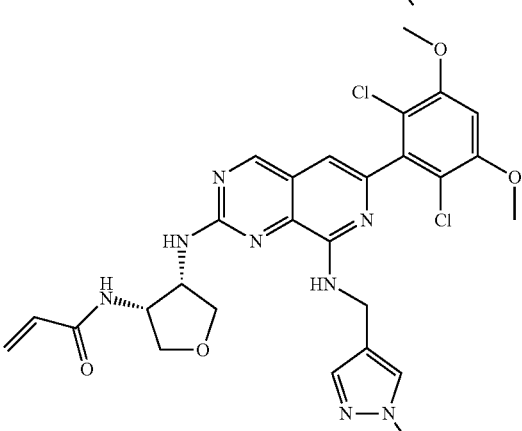

-continued
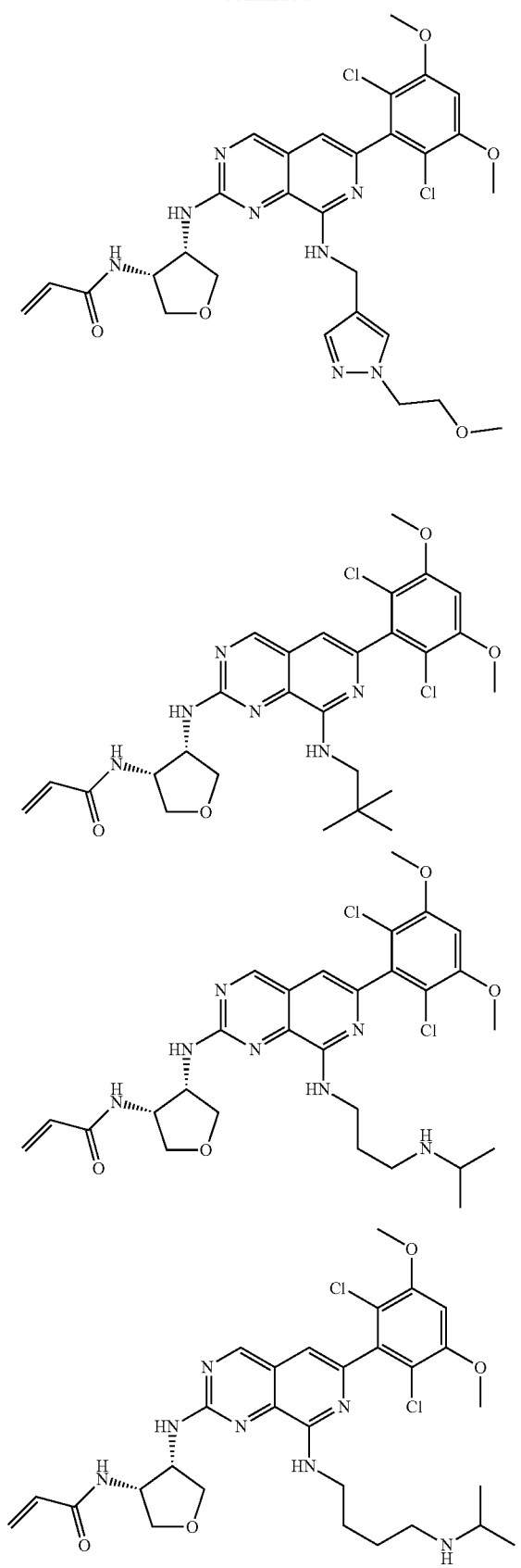
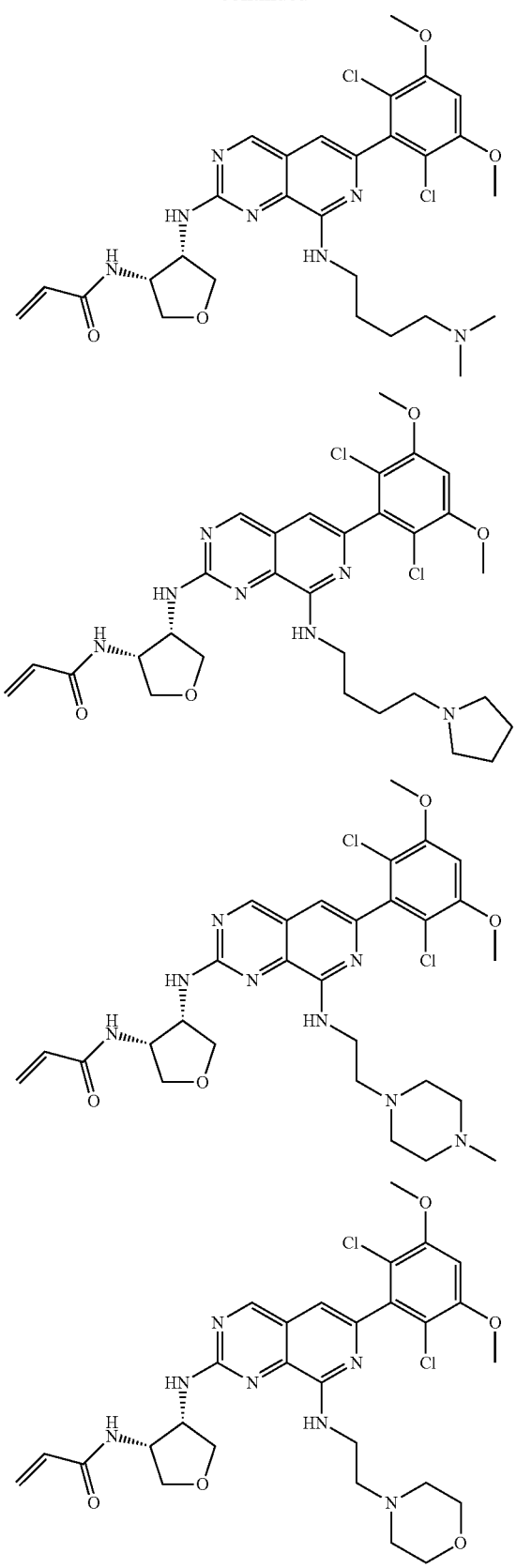

57
-continued
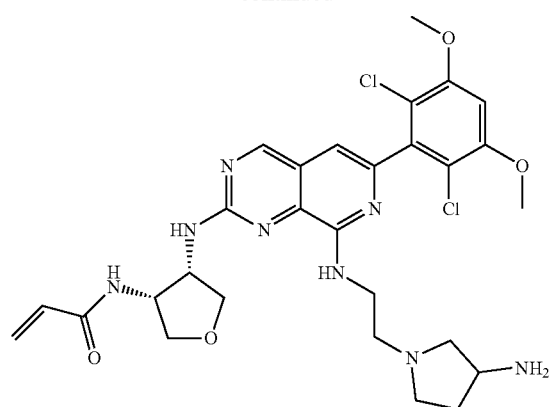
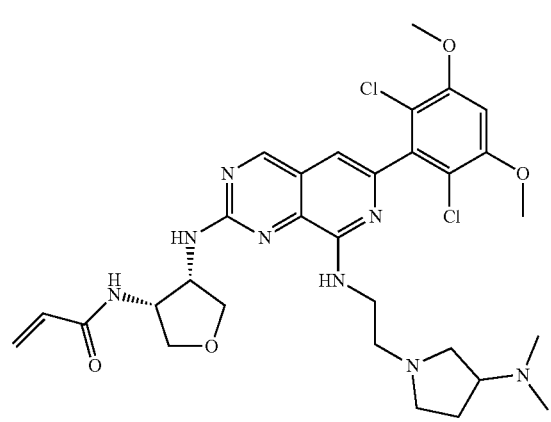
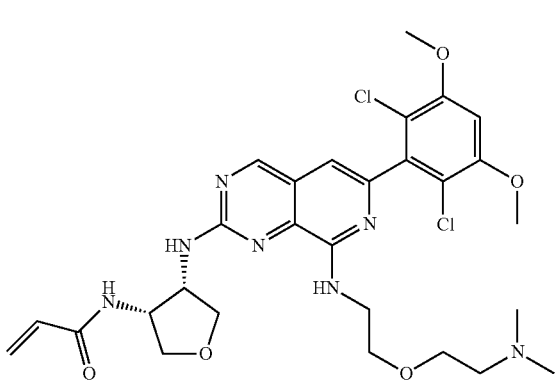
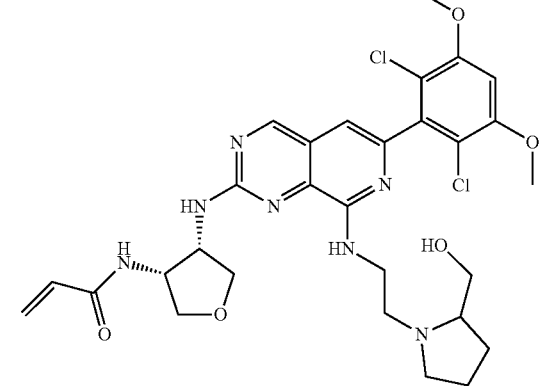
58
-continued
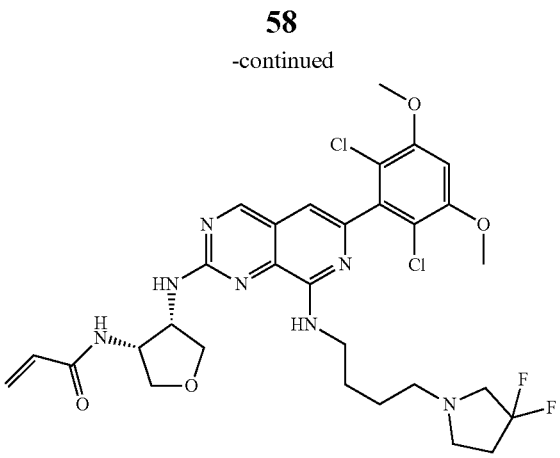
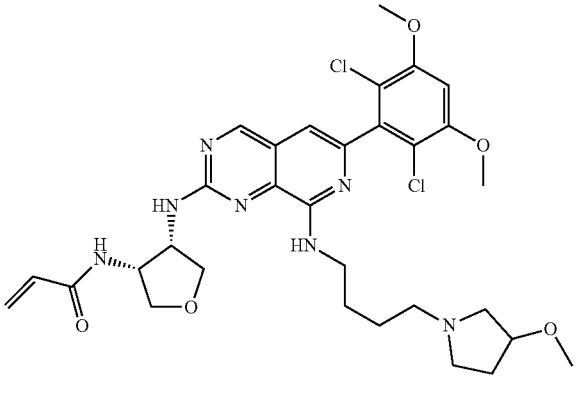
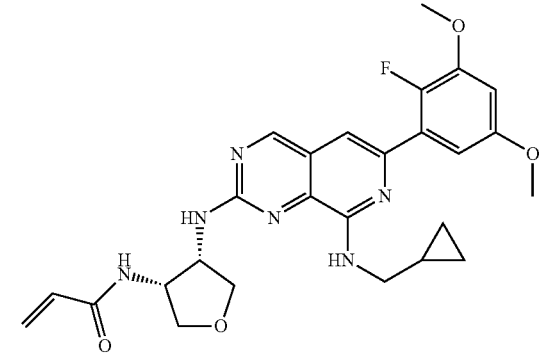
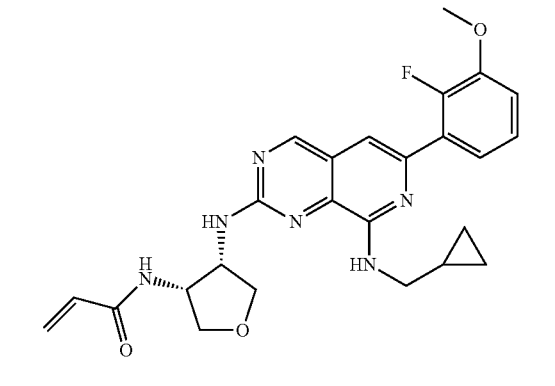

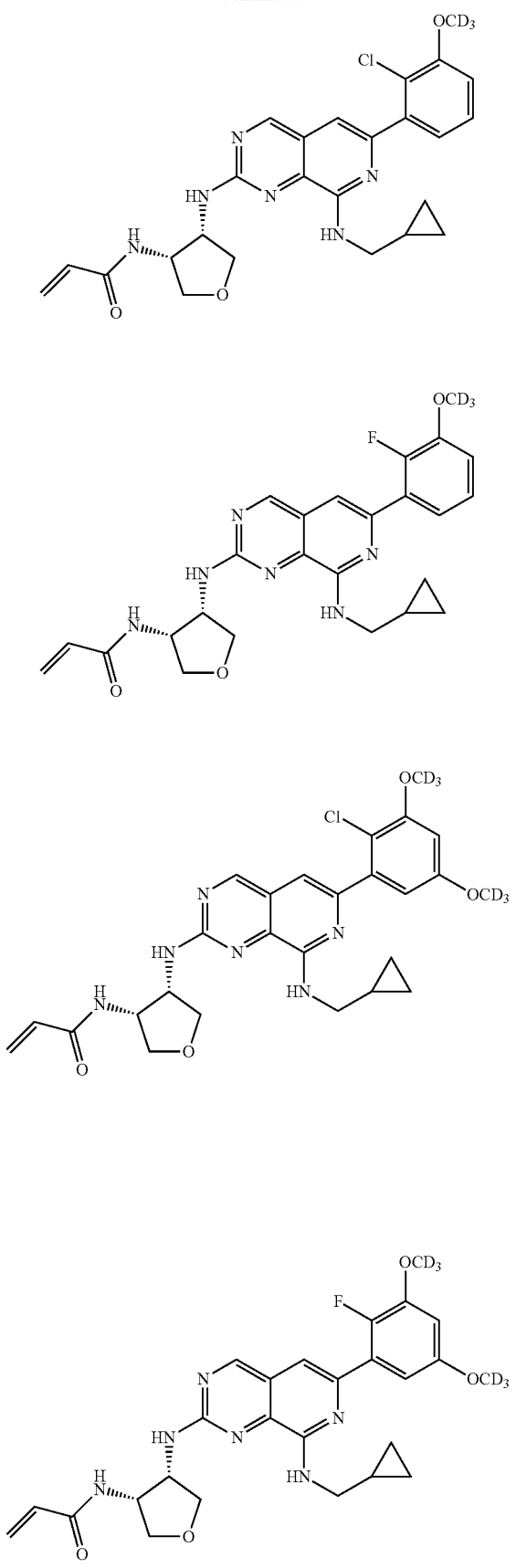
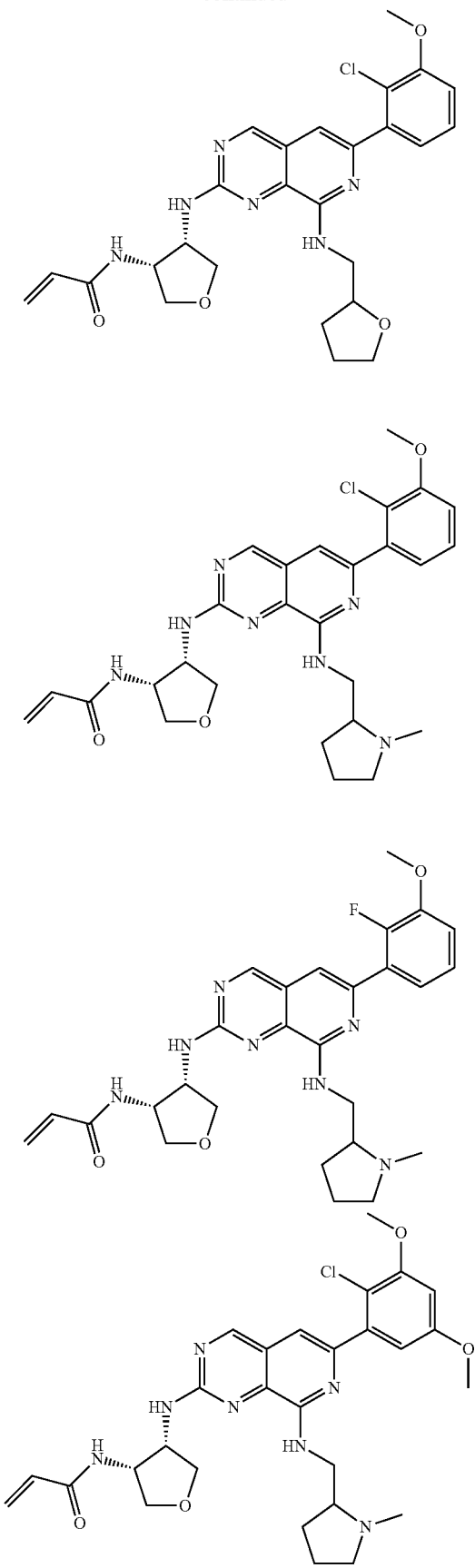

61
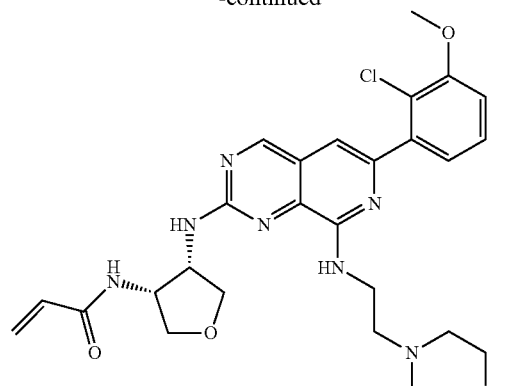
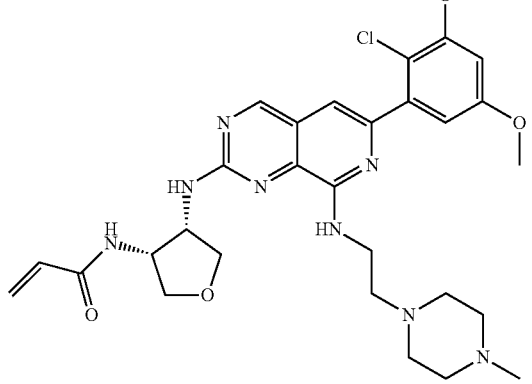
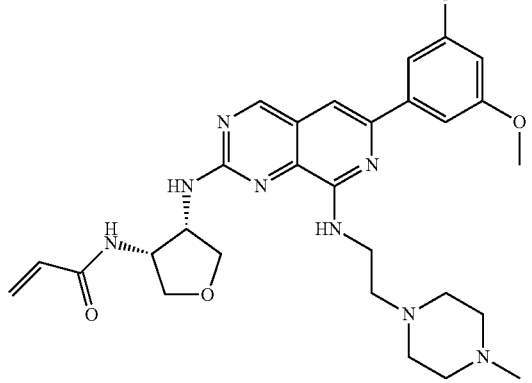
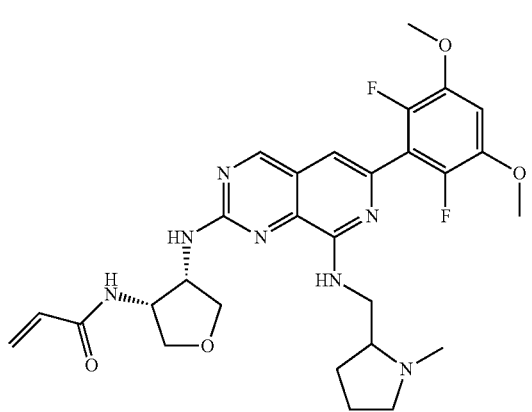
62
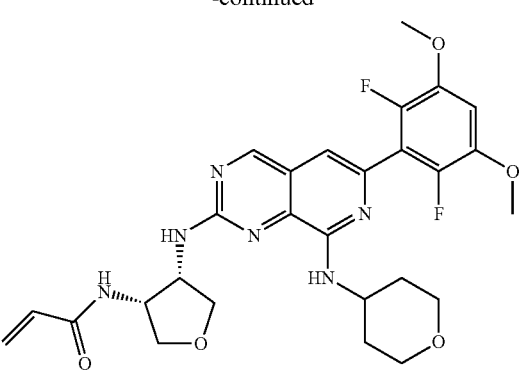
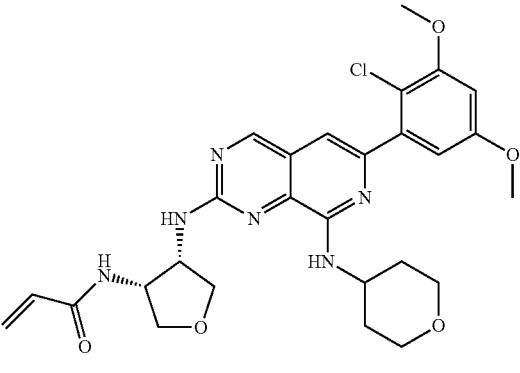
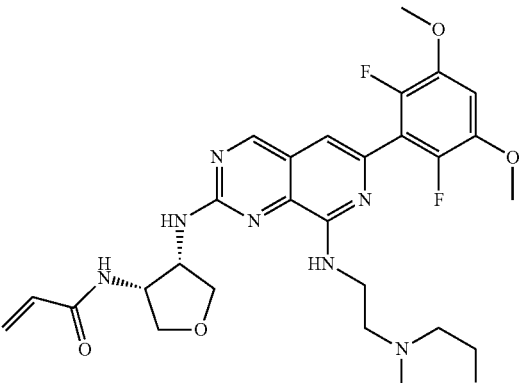
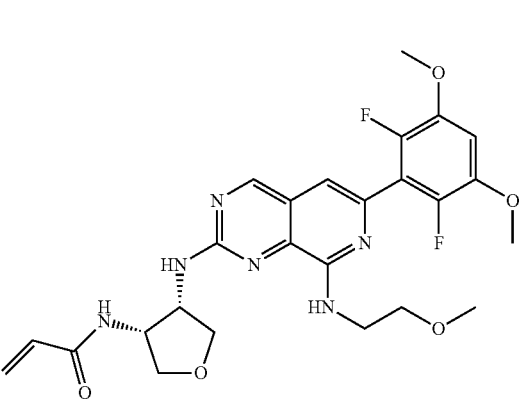

63
-continued
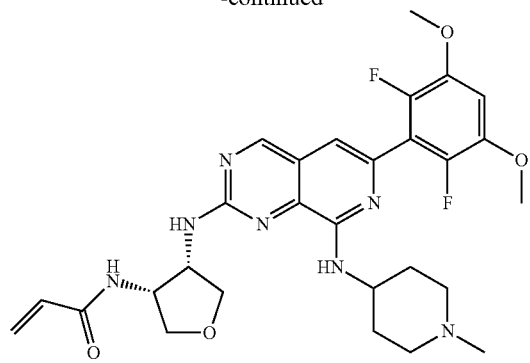
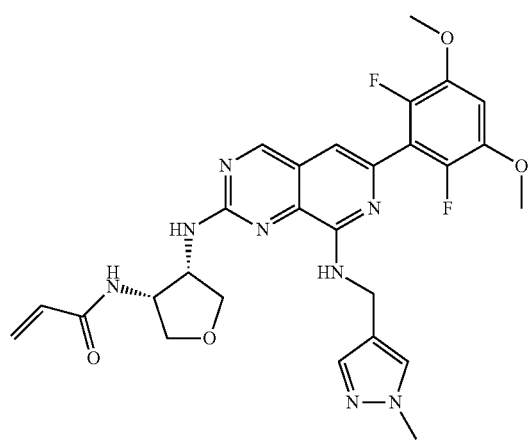
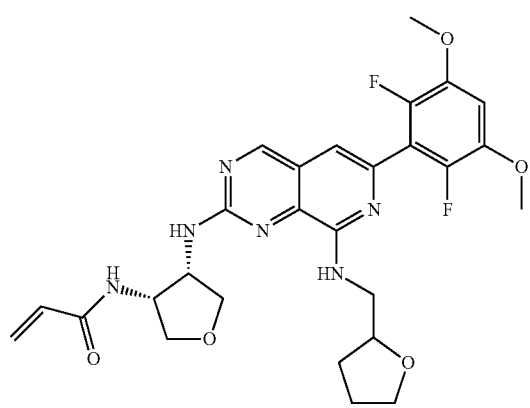
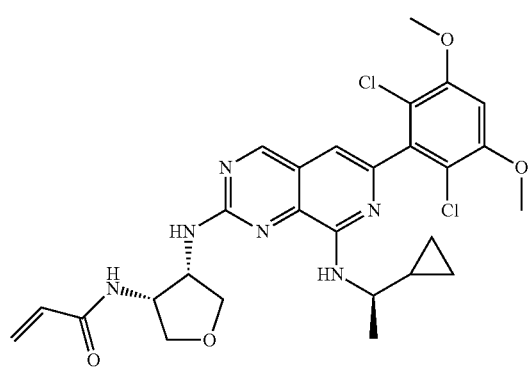
64
-continued

65
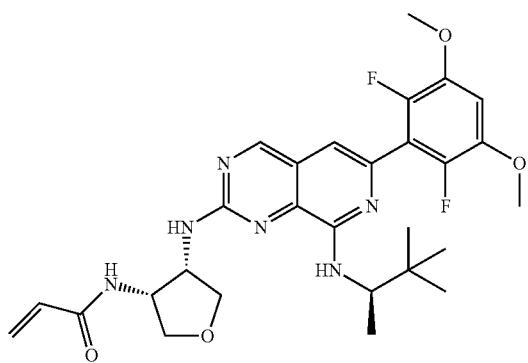
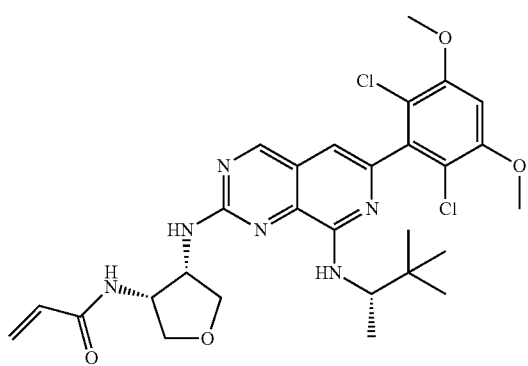
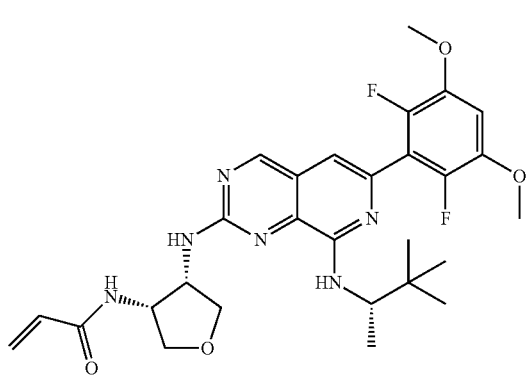
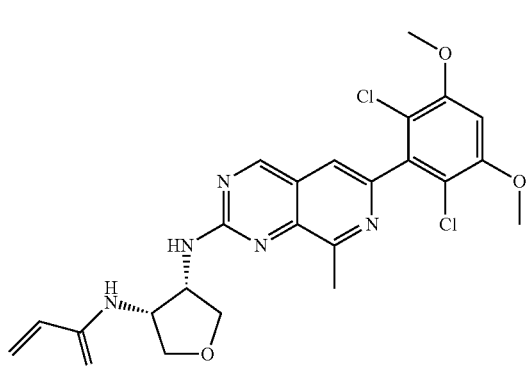
66
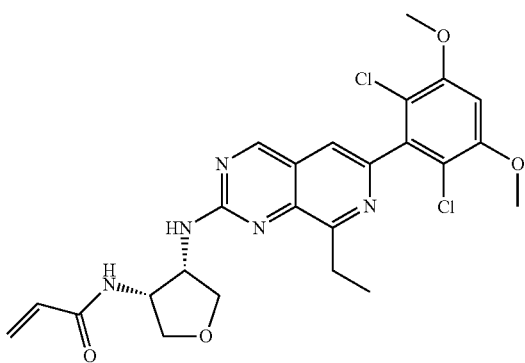
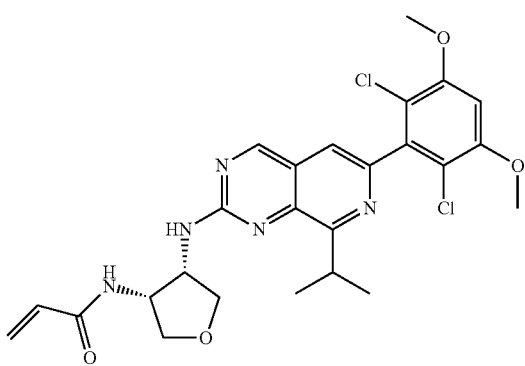
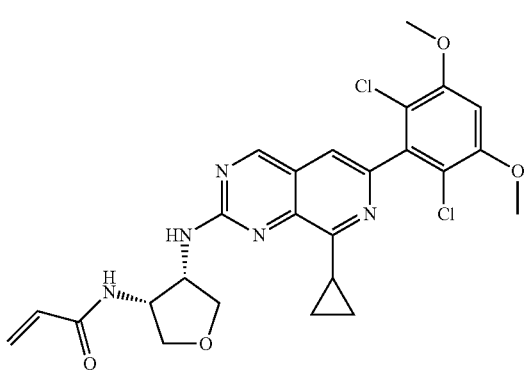
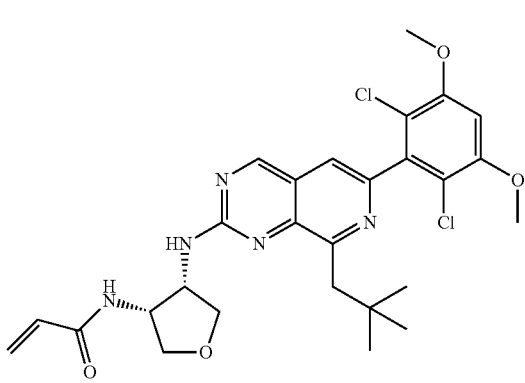

67
-continued
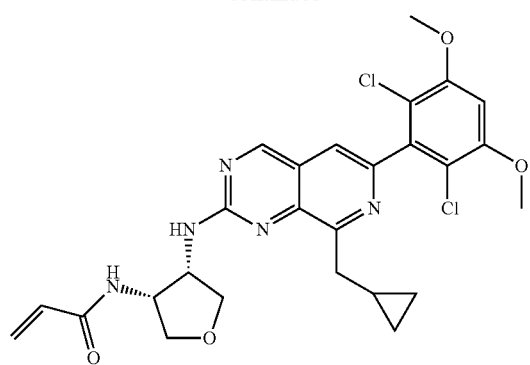
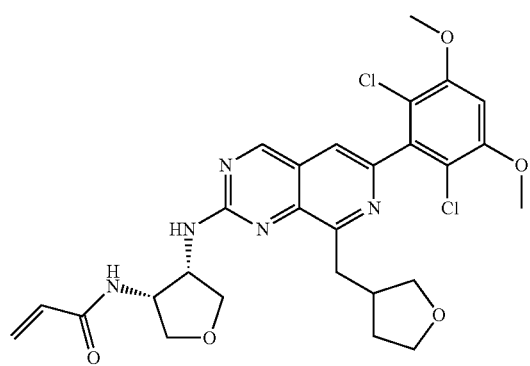
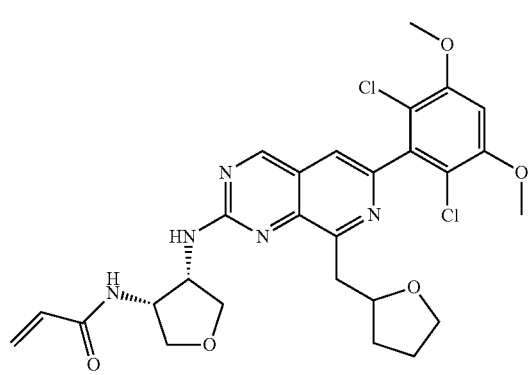
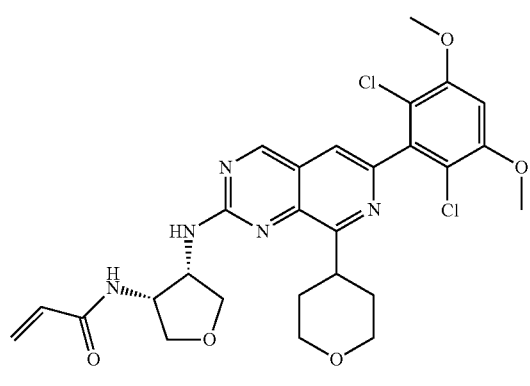
68
-continued
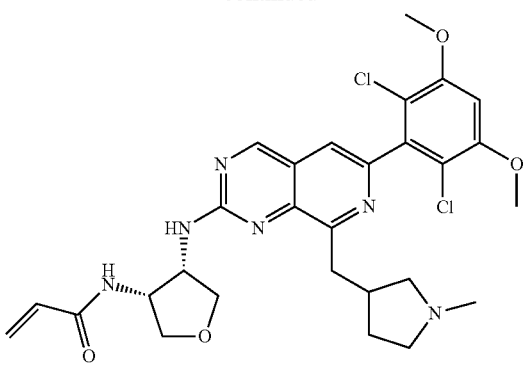

69
-continued
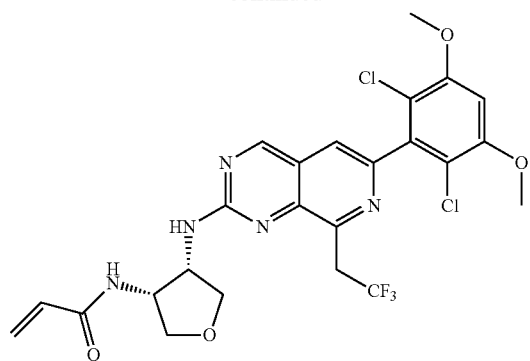
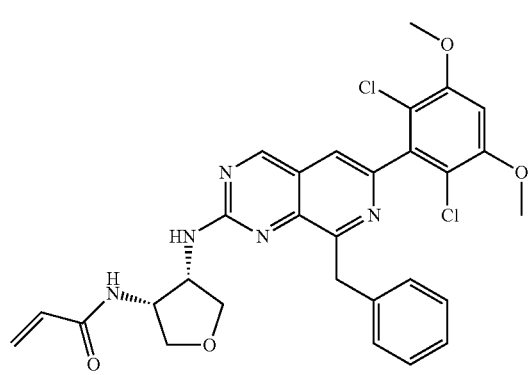
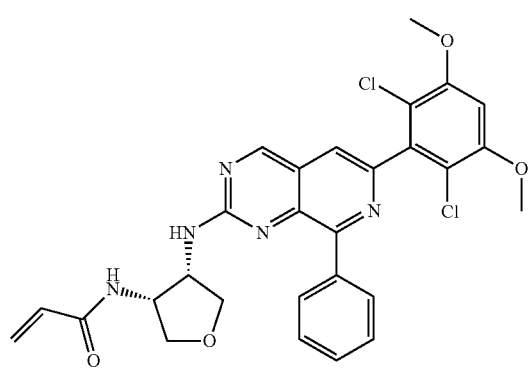
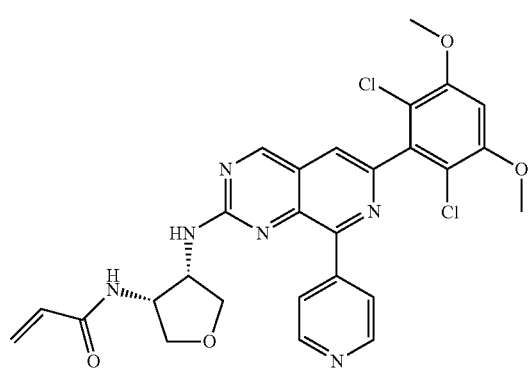
70
-continued
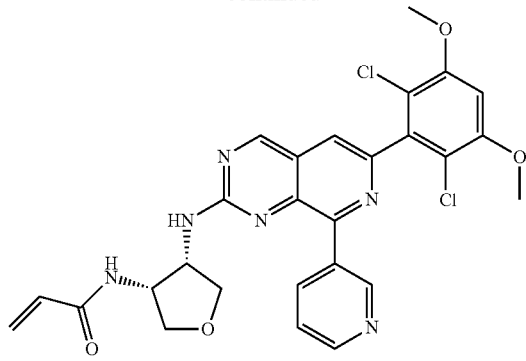
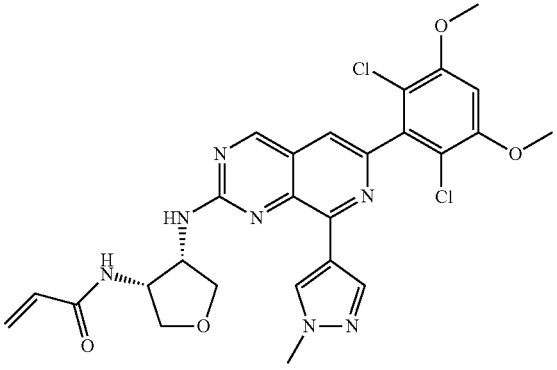
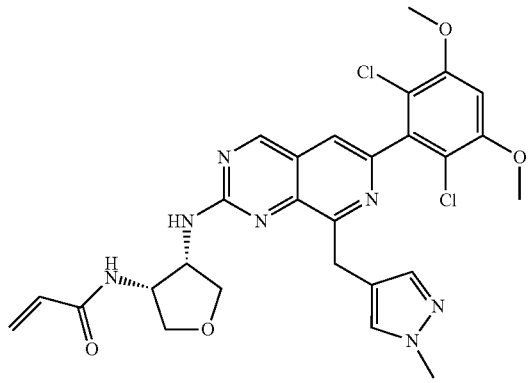
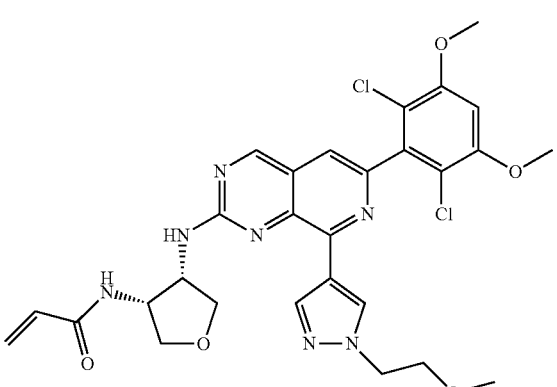

71
-continued
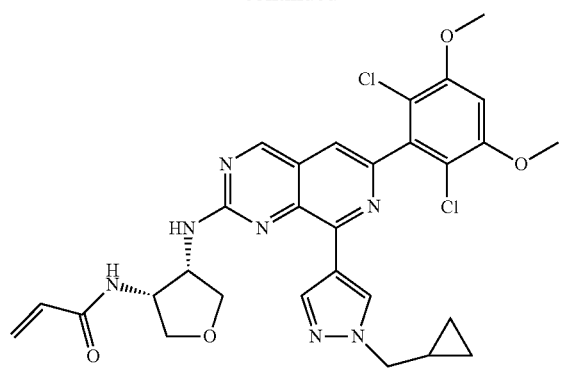
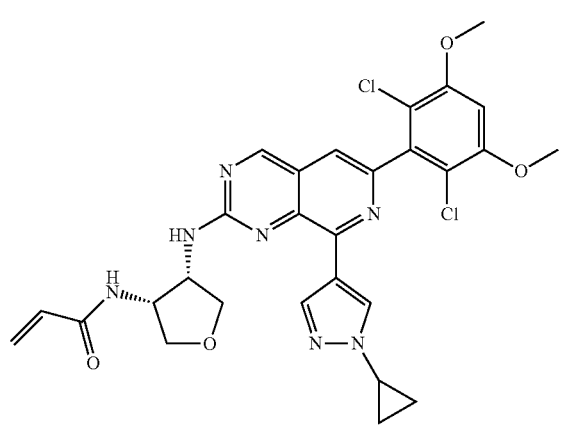
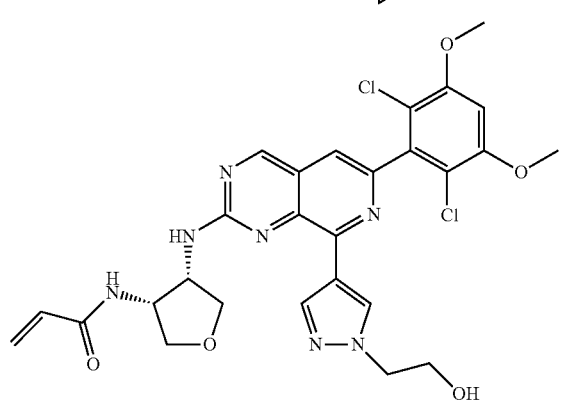
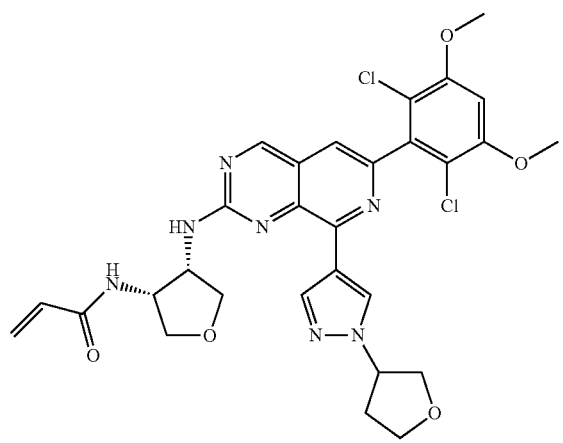
72
-continued
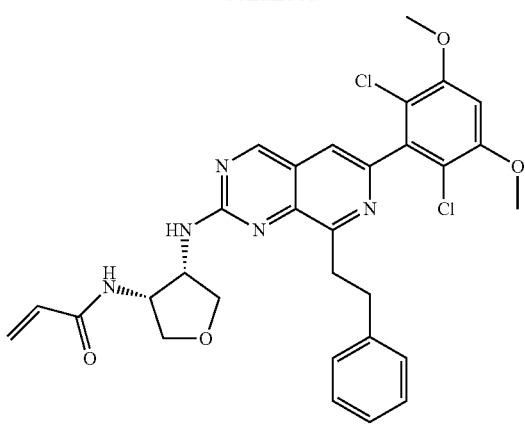
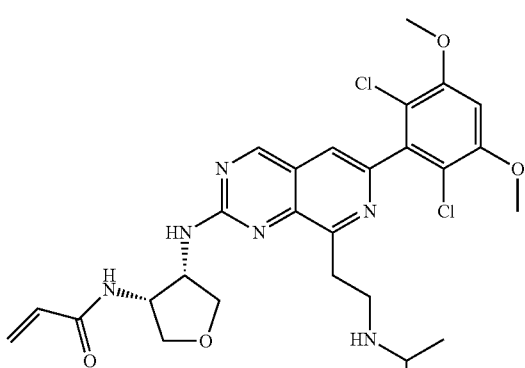
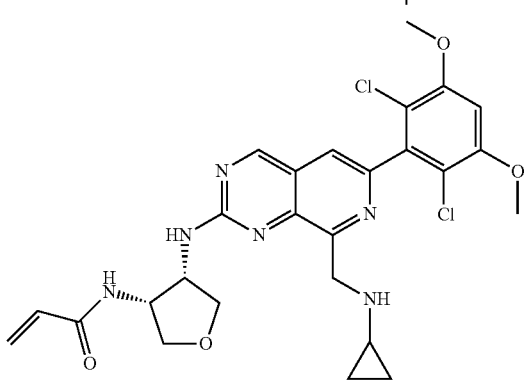
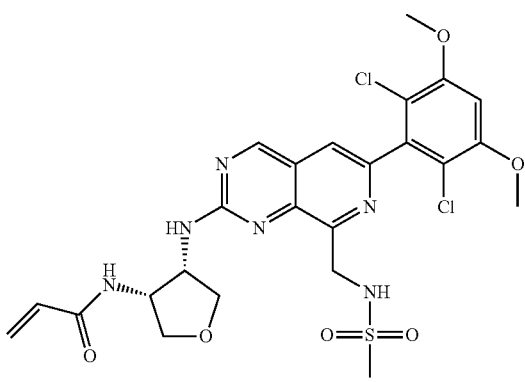

73
-continued
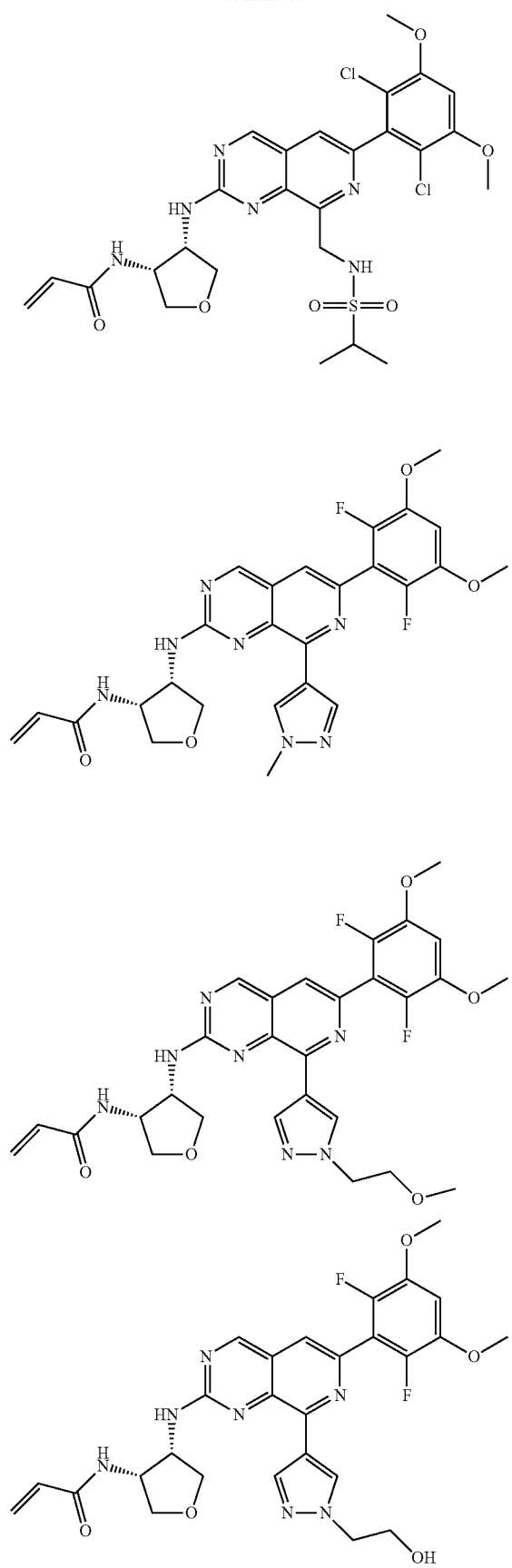
74
-continued
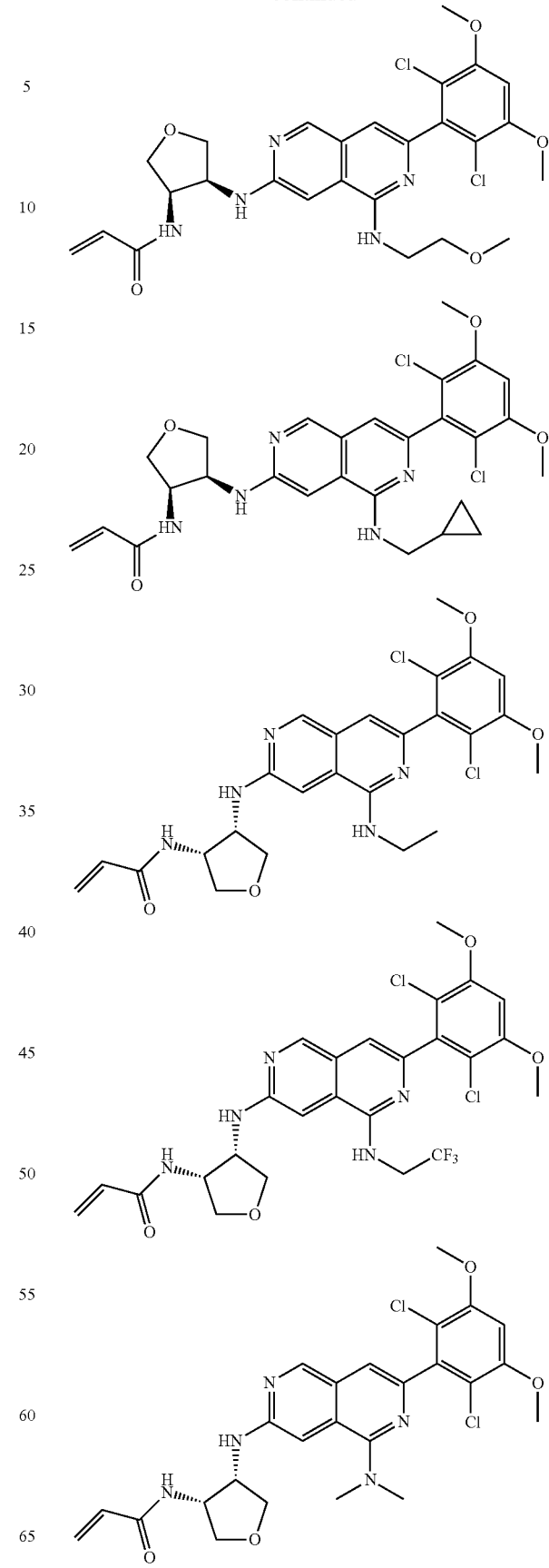

75
-continued
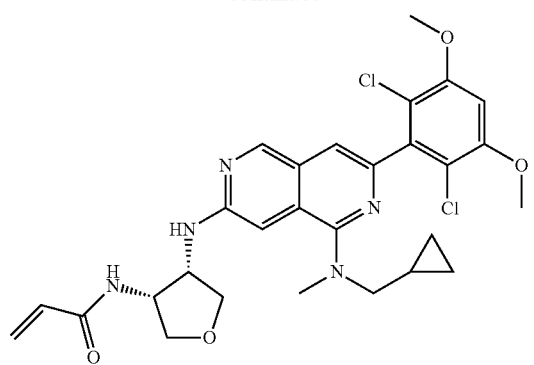
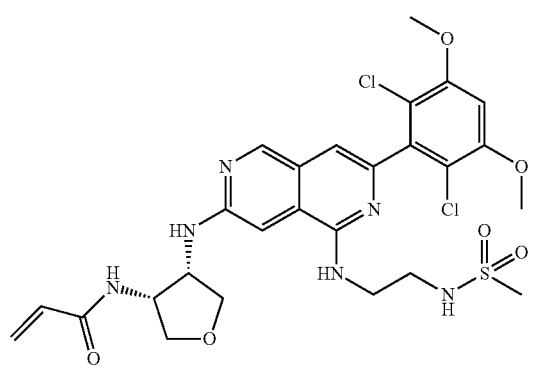
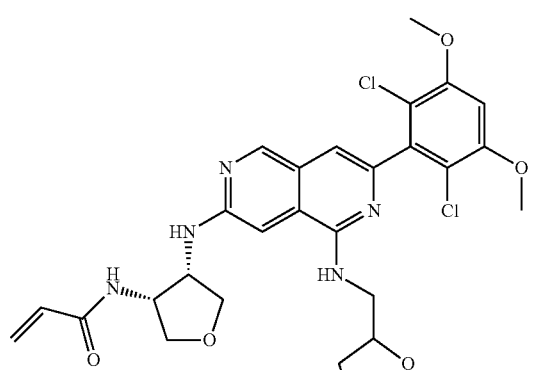
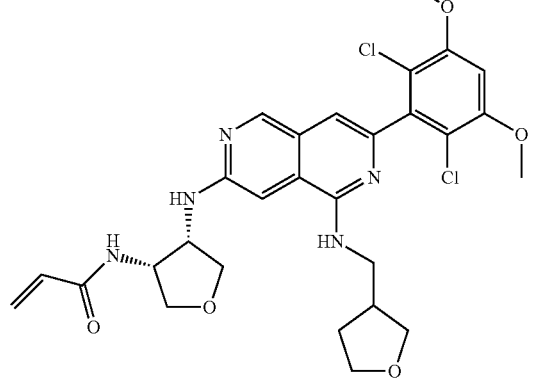
76
-continued
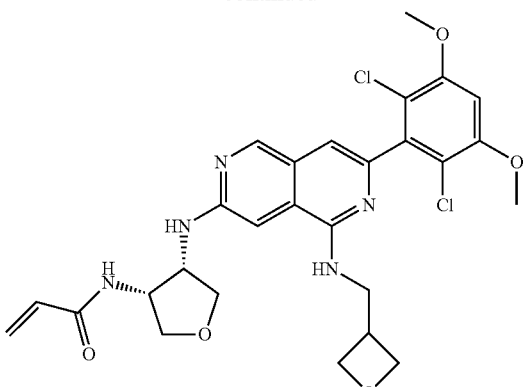
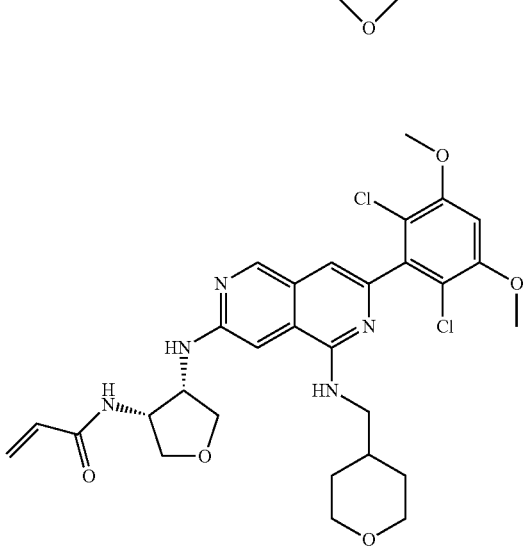

77
-continued
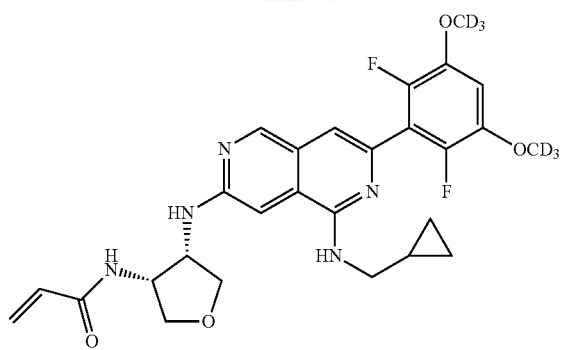
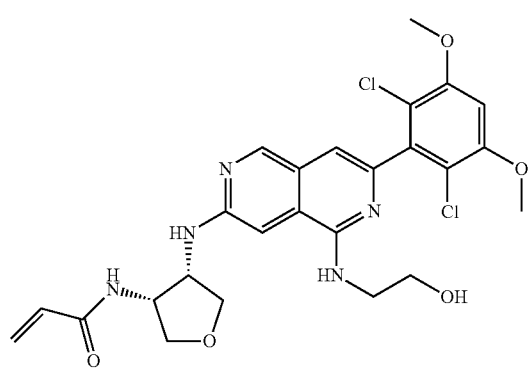
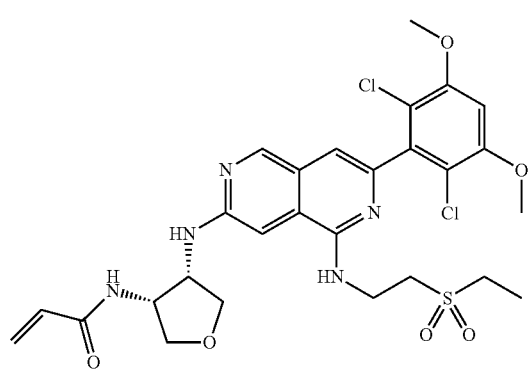
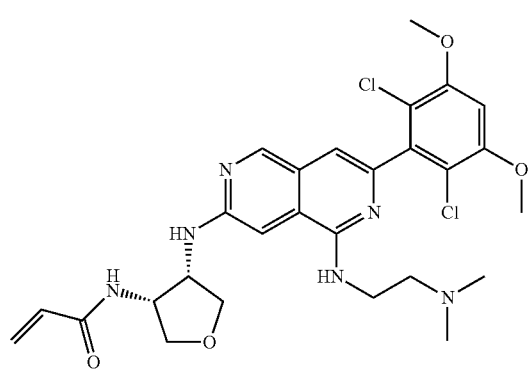
78
-continued
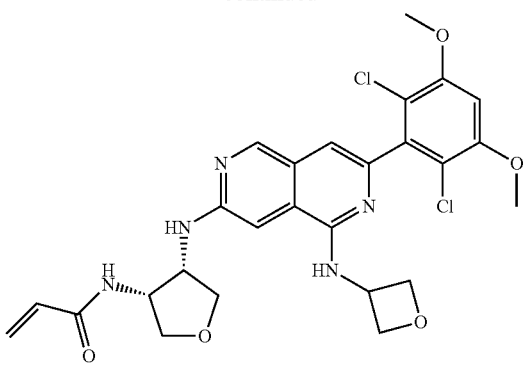
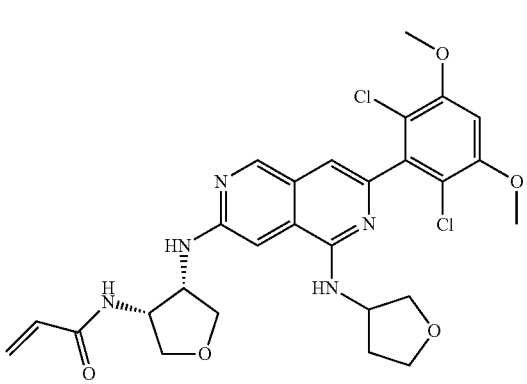
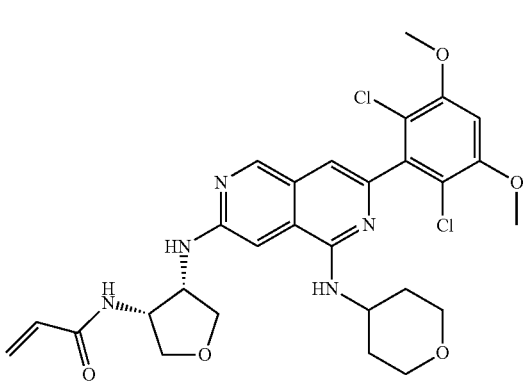
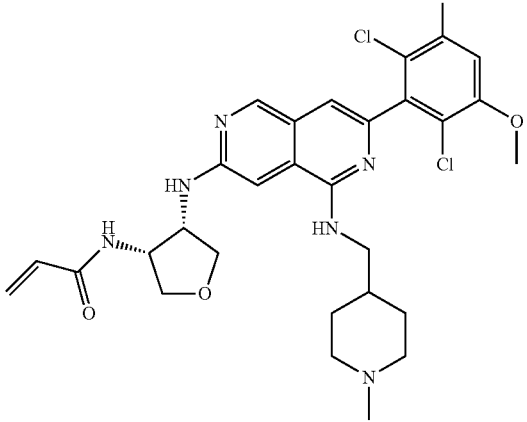

79
-continued
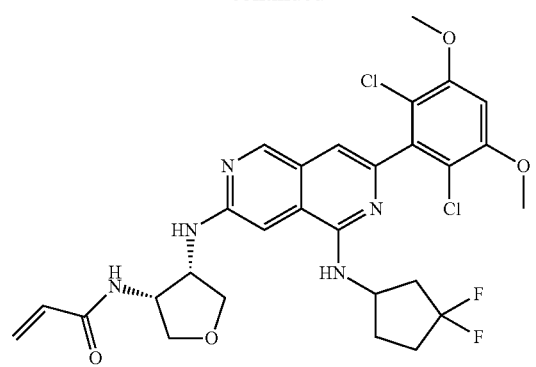
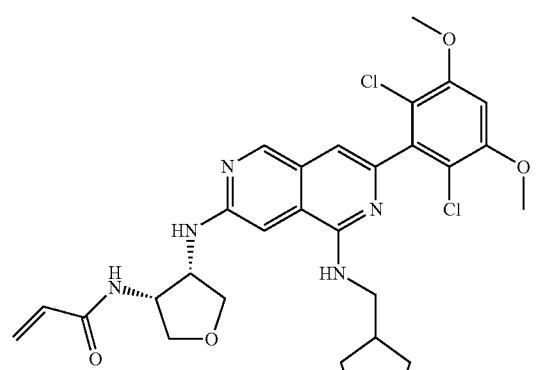
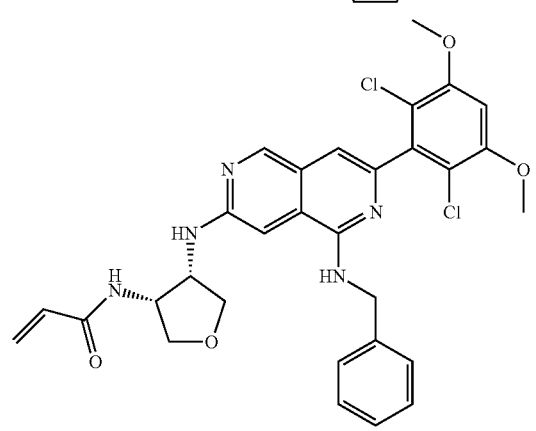
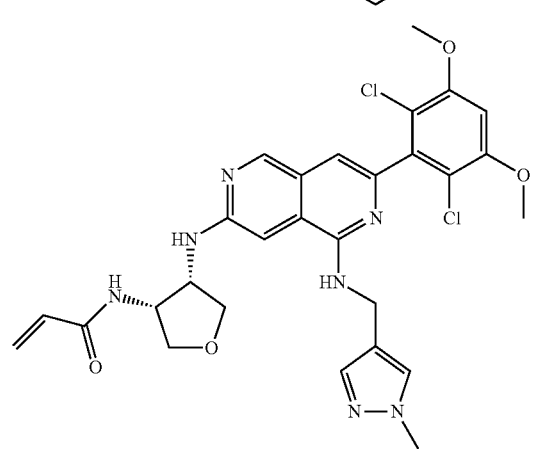
80
-continued
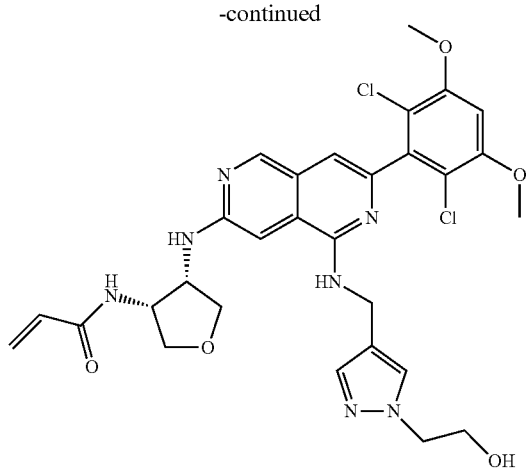
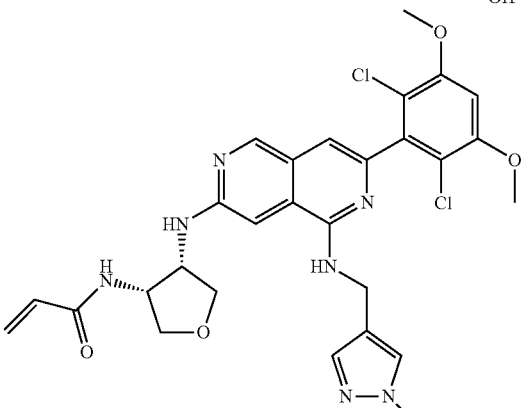
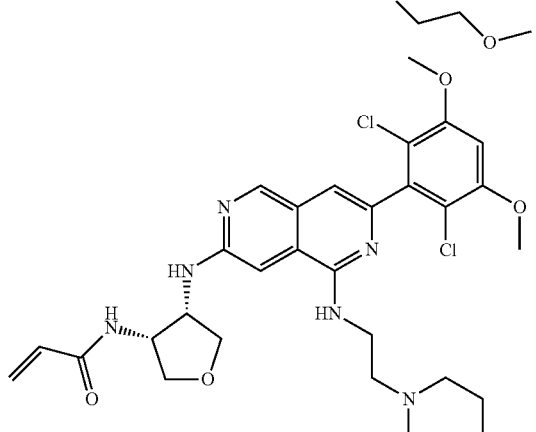
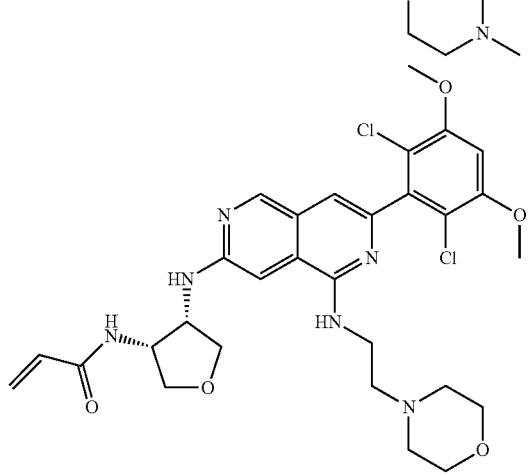

81
-continued
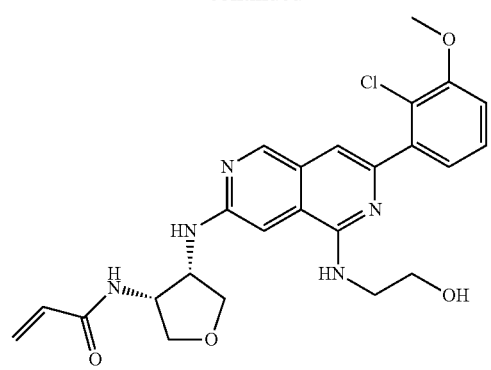
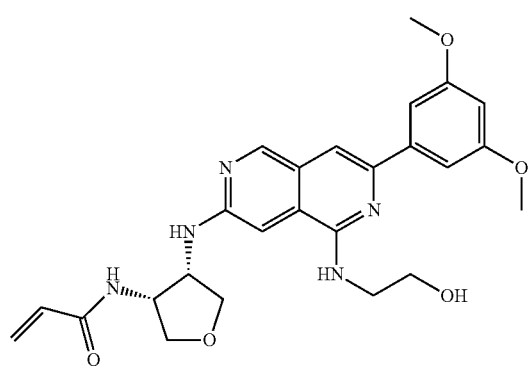
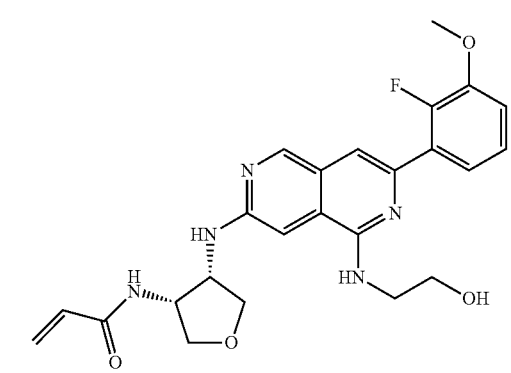
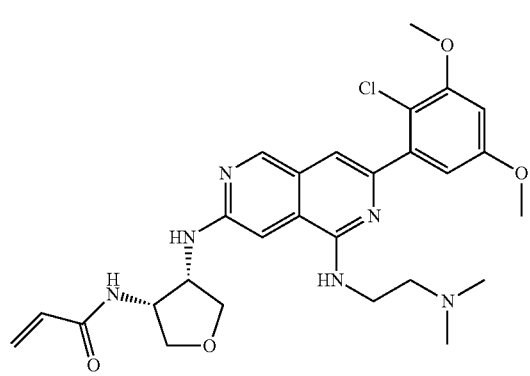
82
-continued
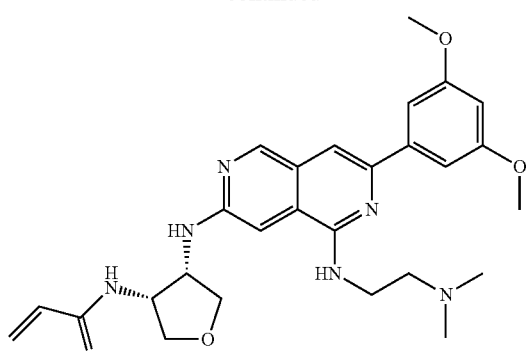
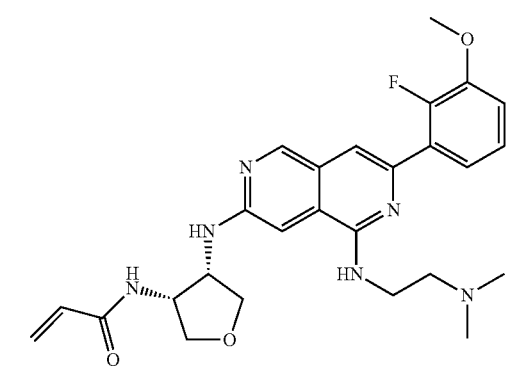
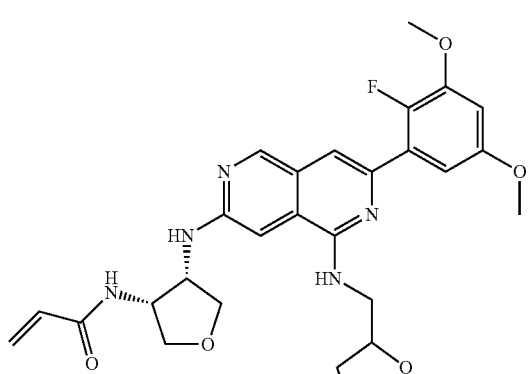
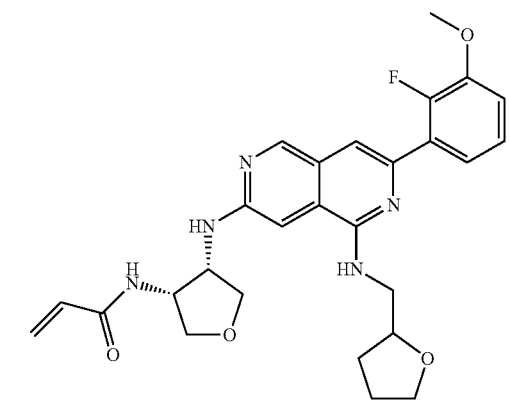

83
-continued
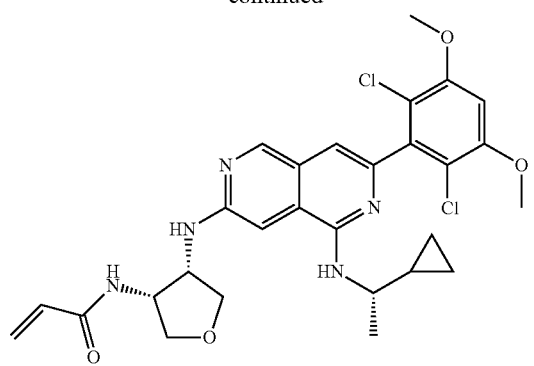
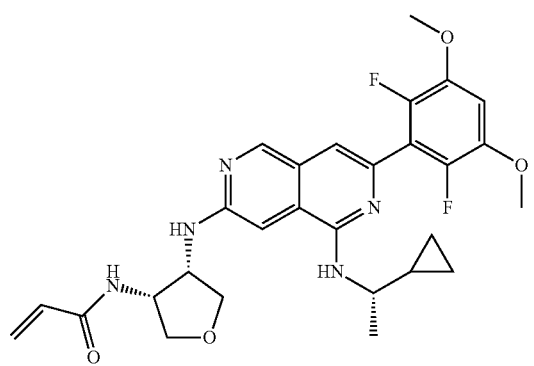
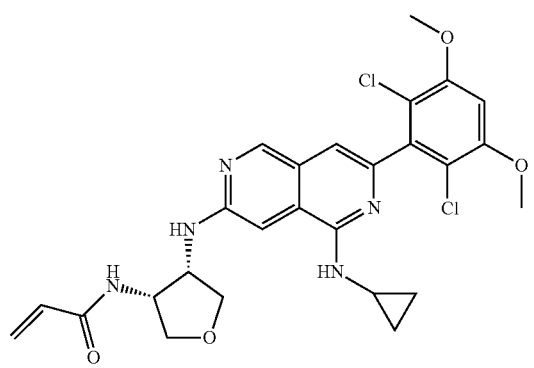

84
-continued
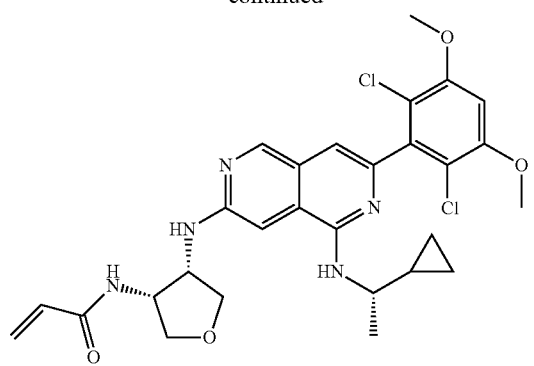

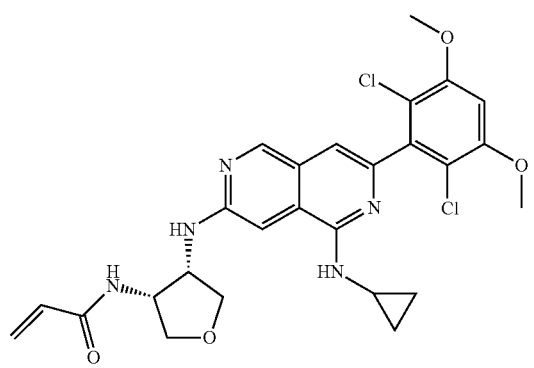
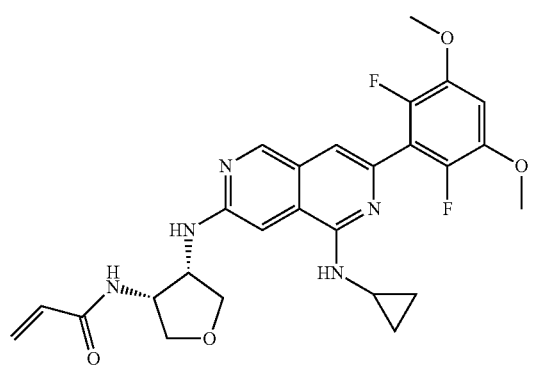

85
-continued
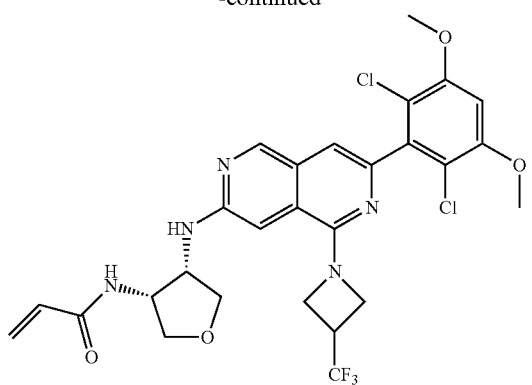
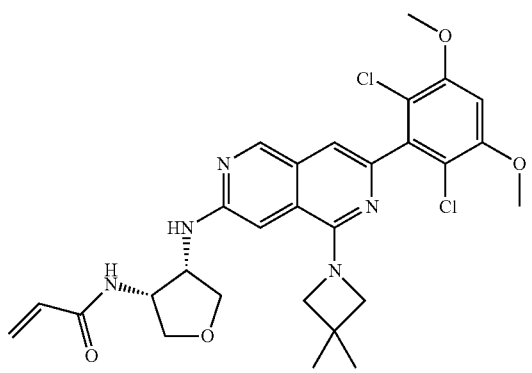
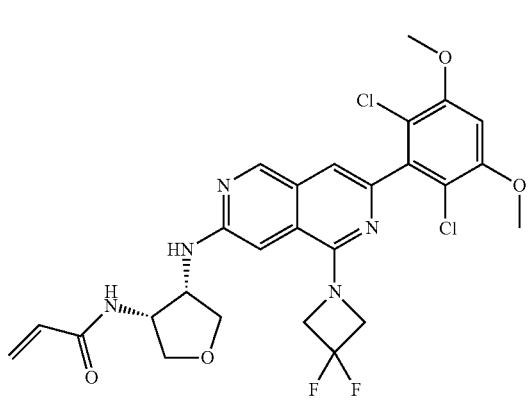
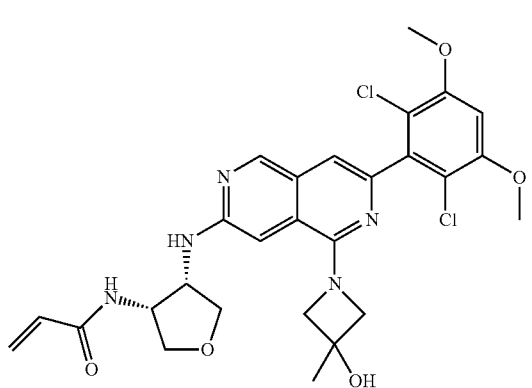
86
-continued
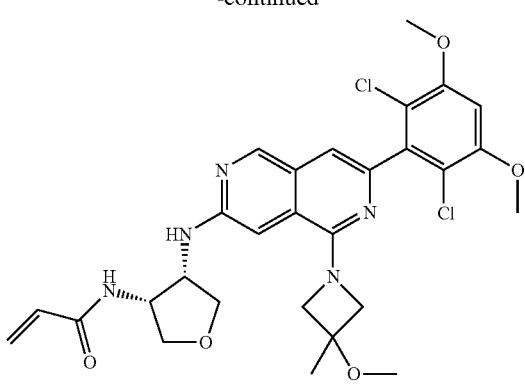
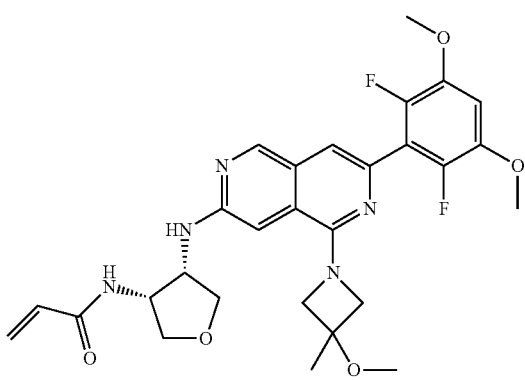
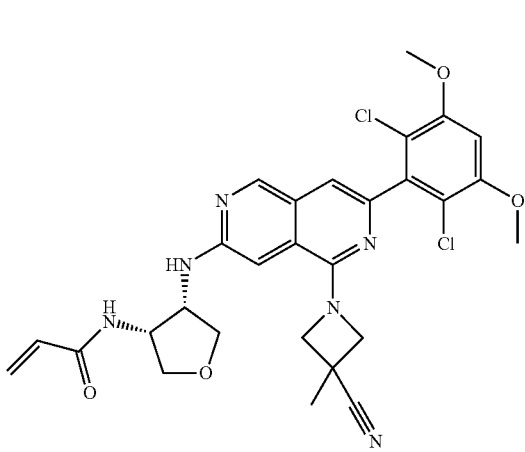
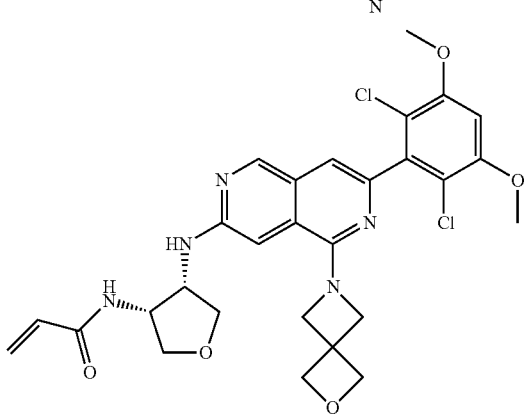

87
-continued
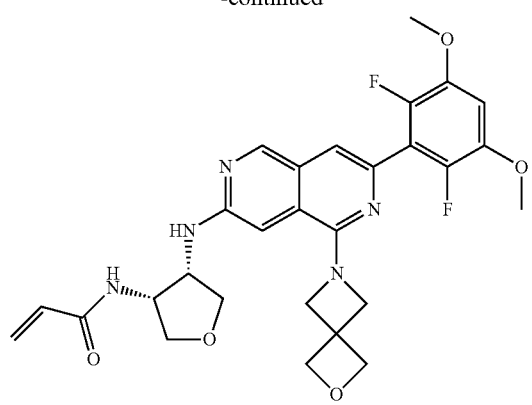
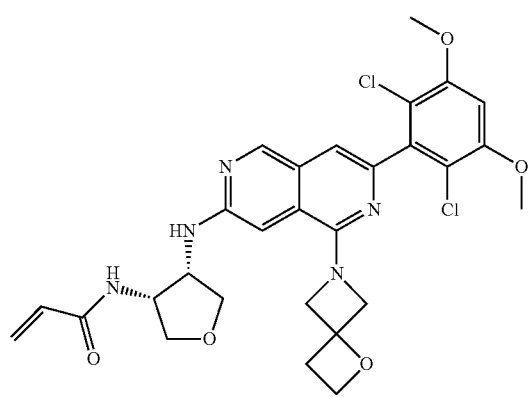
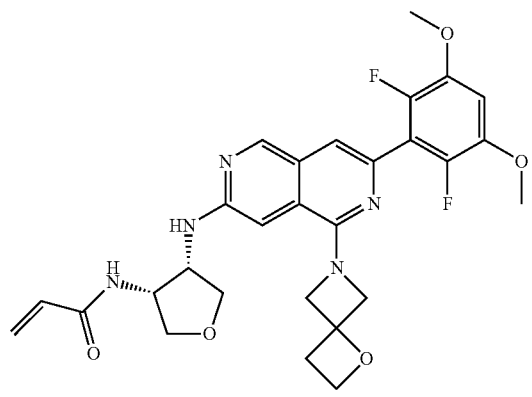
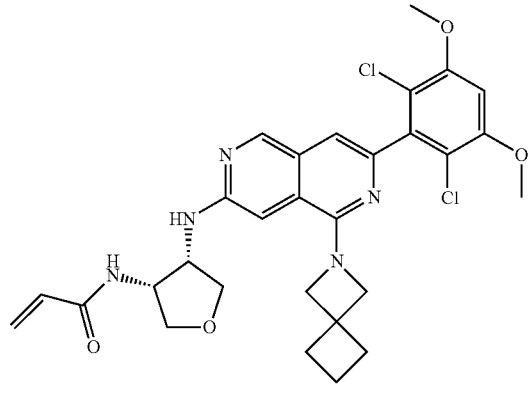
88
-continued
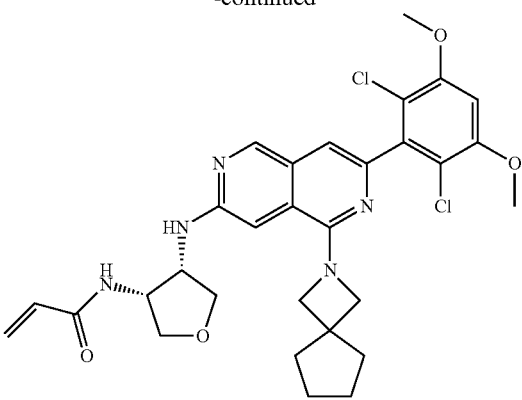
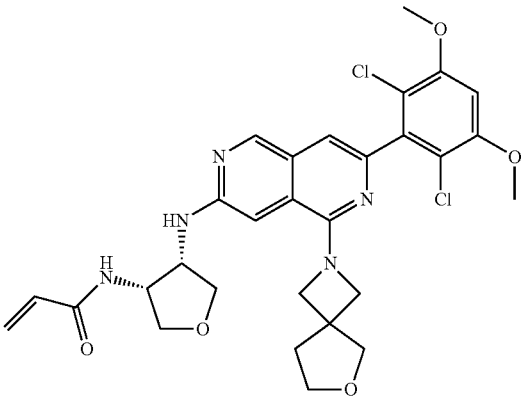
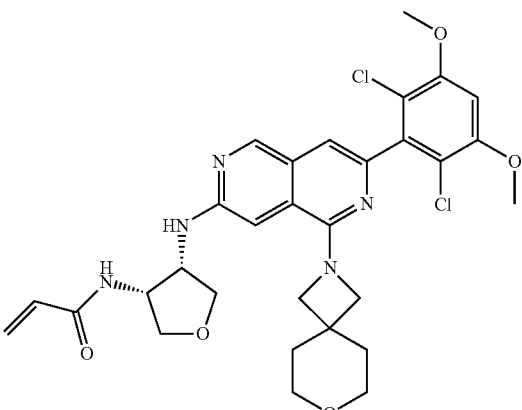
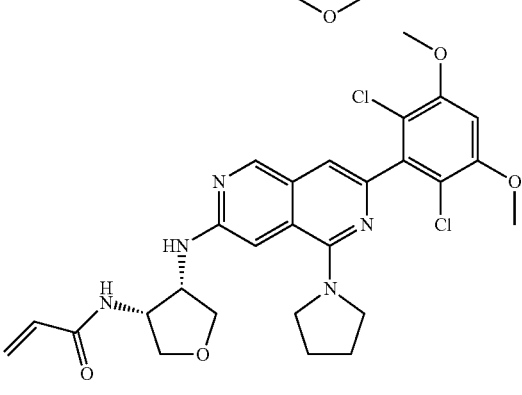

89
-continued
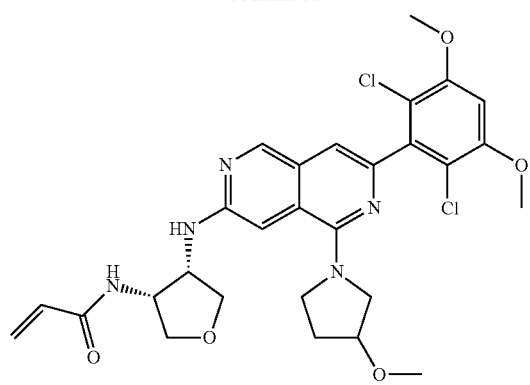
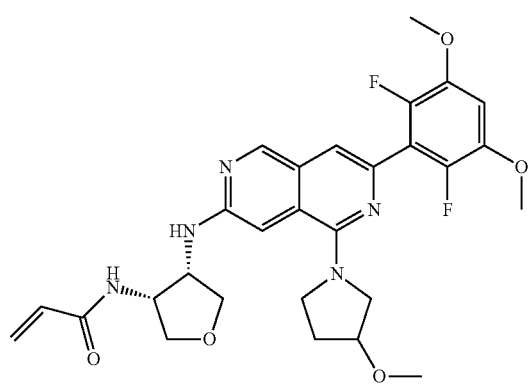
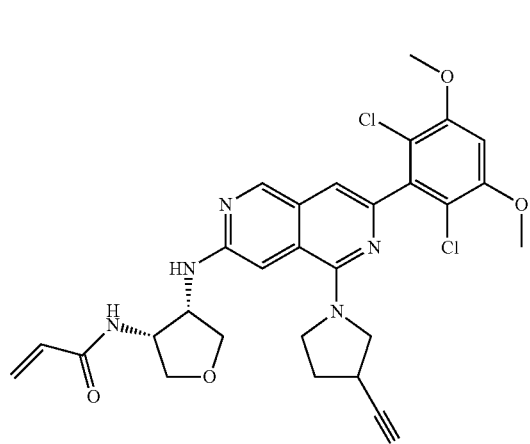
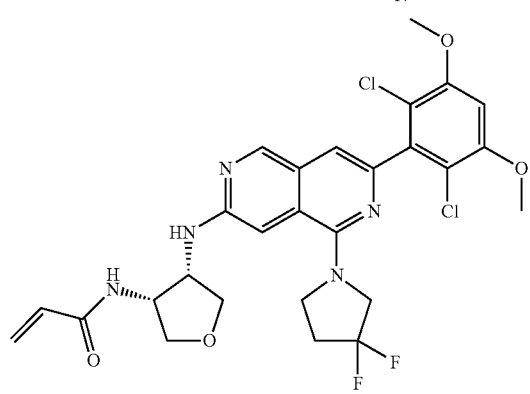
90
-continued
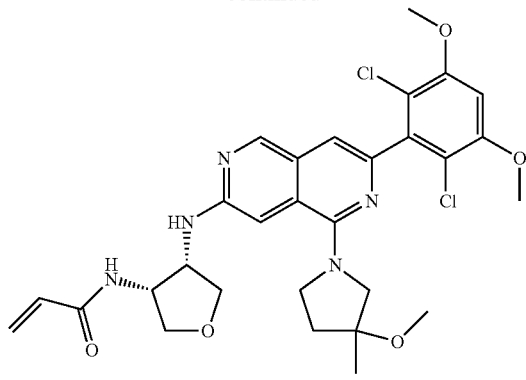
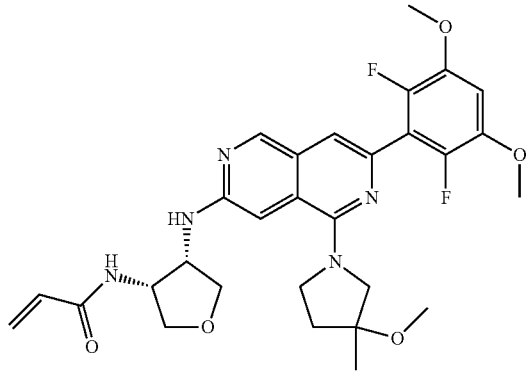
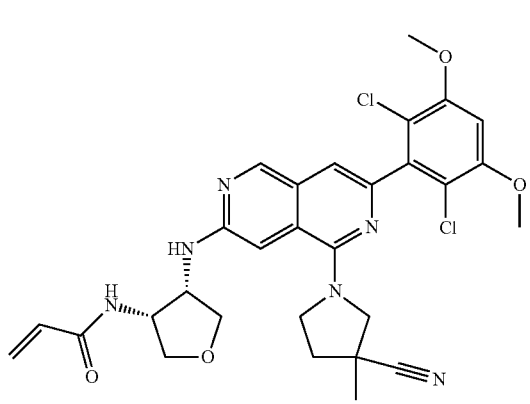
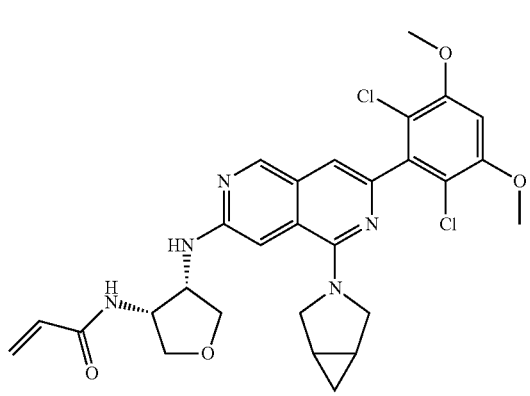

91
-continued
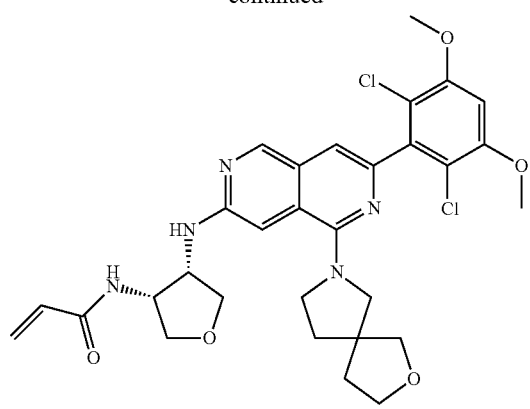
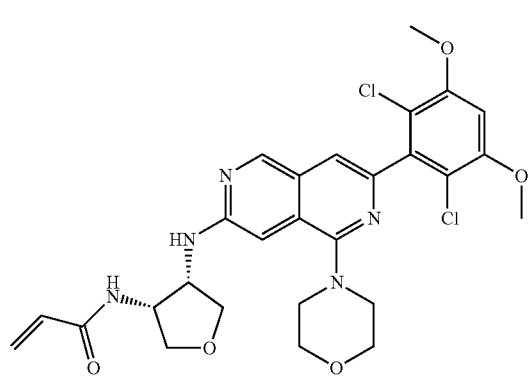
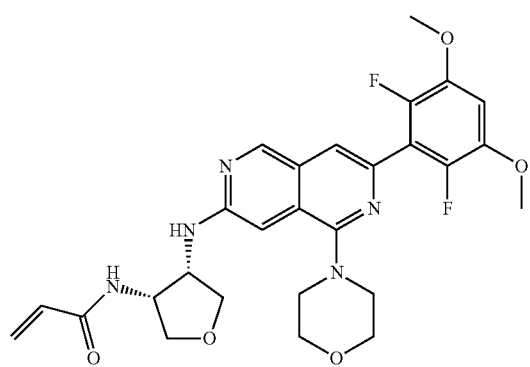
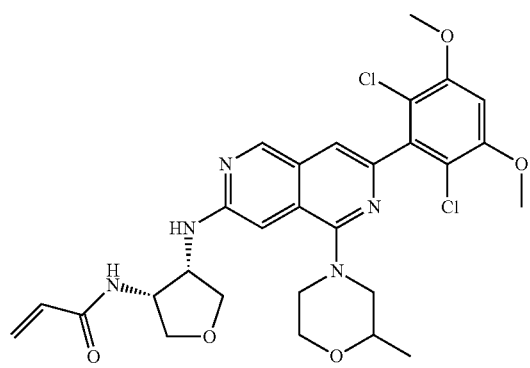
92
-continued
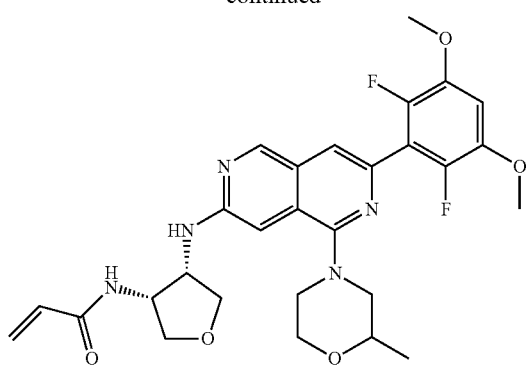
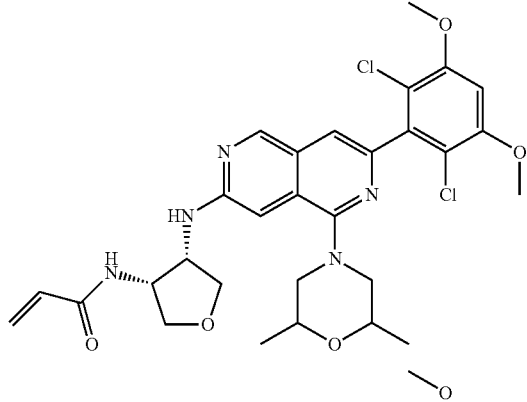
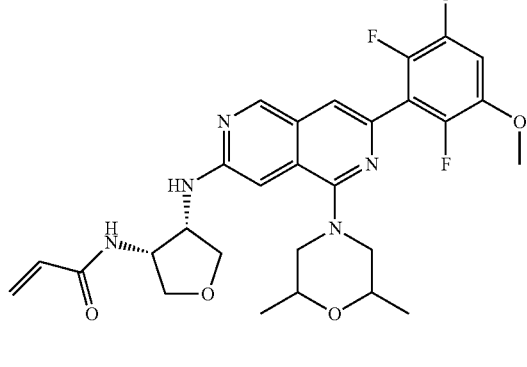
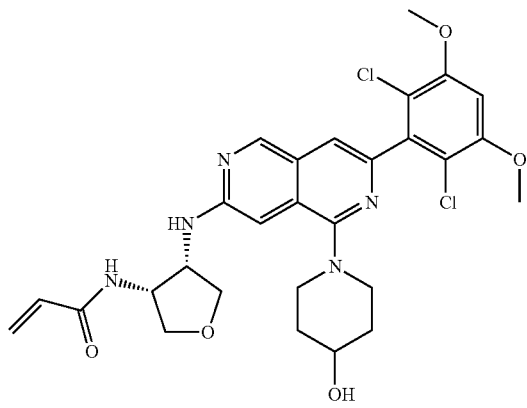

93
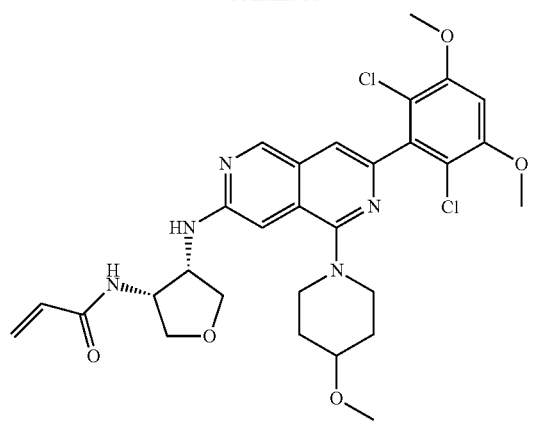
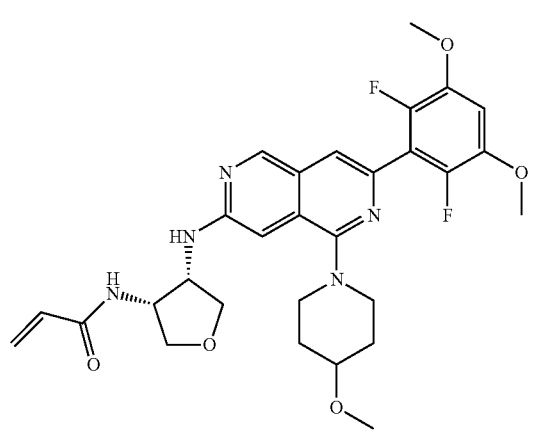
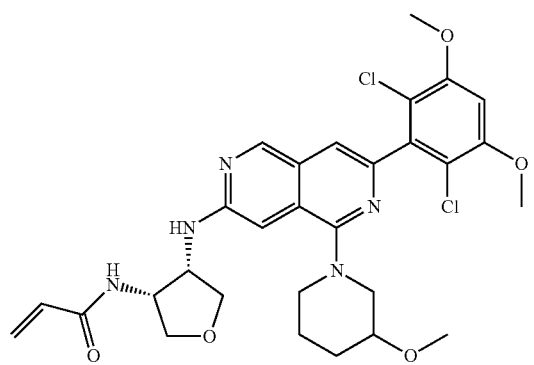
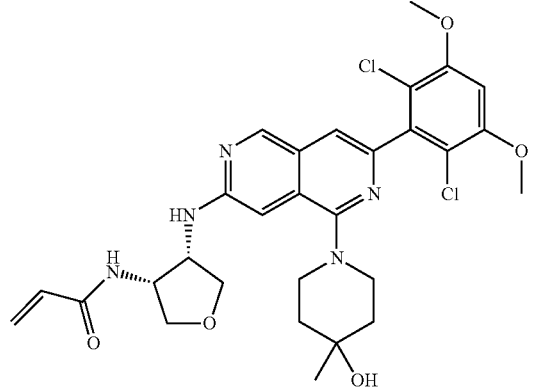
94
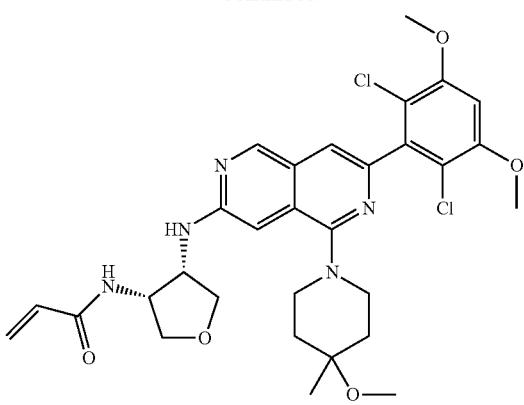
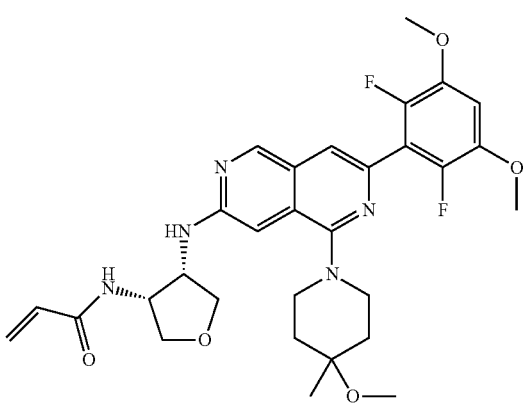
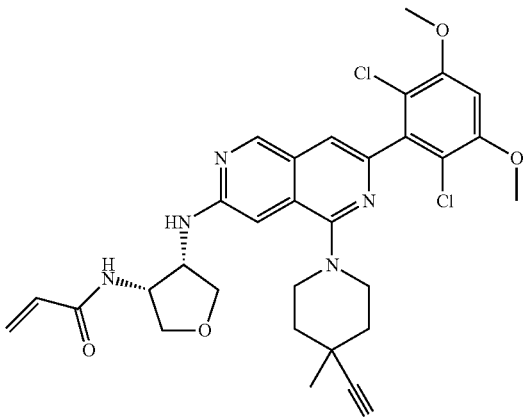
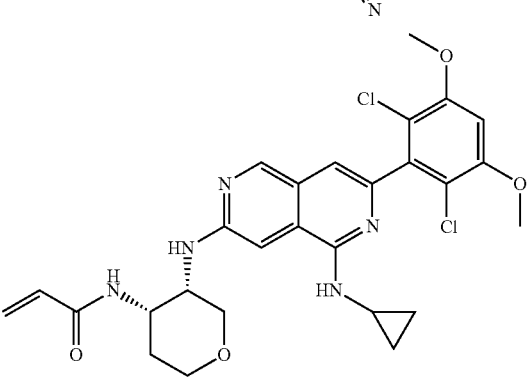

95
-continued
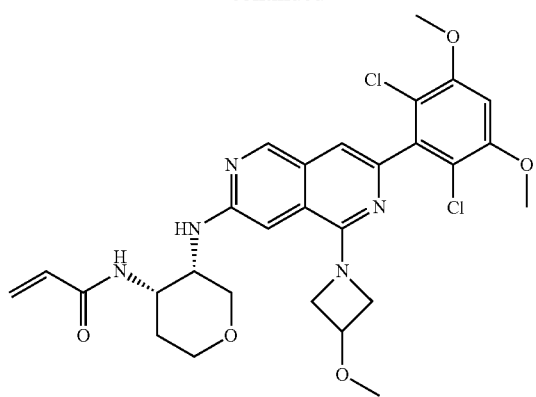
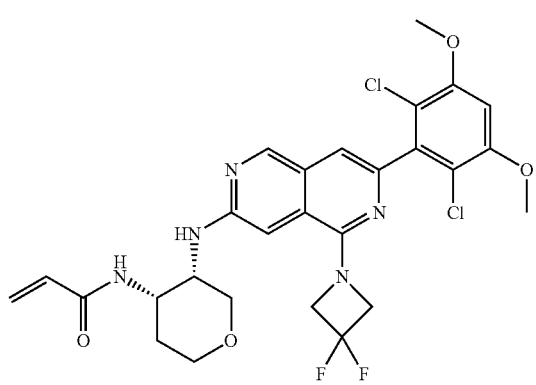
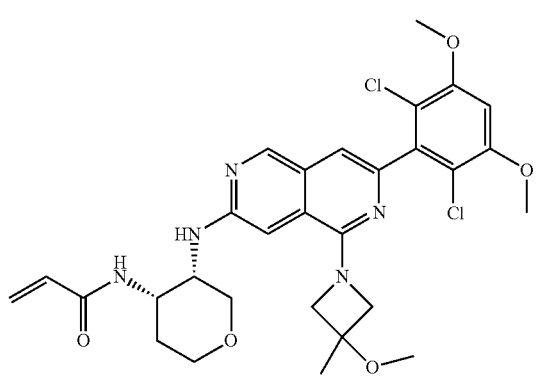
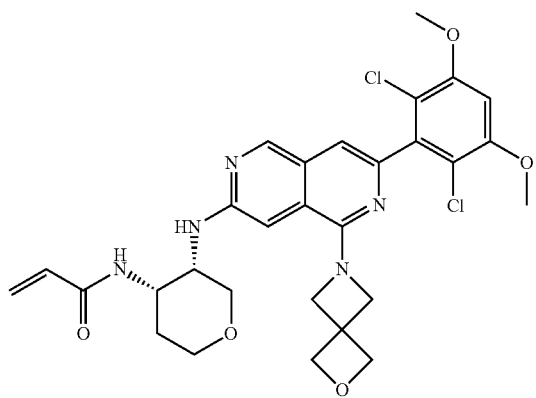
96
-continued
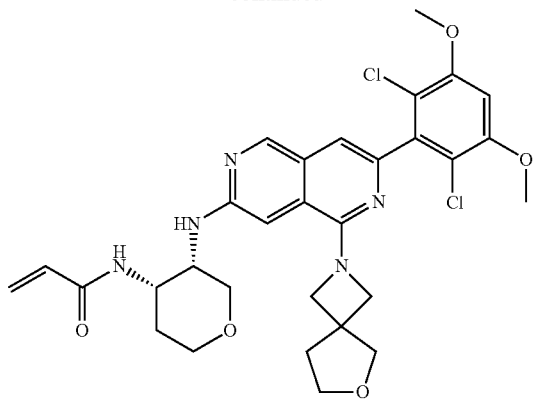
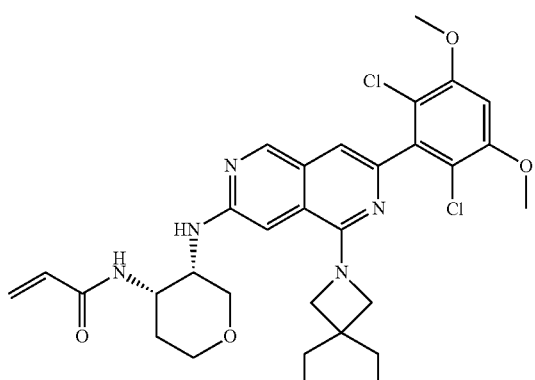
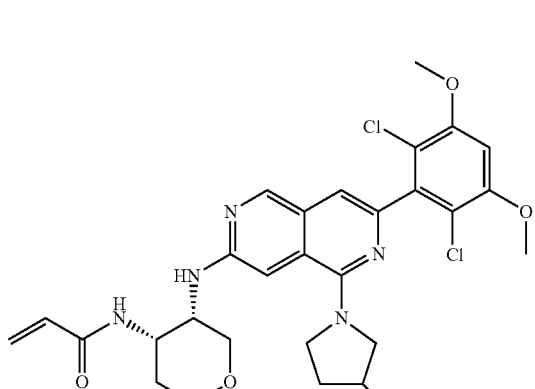
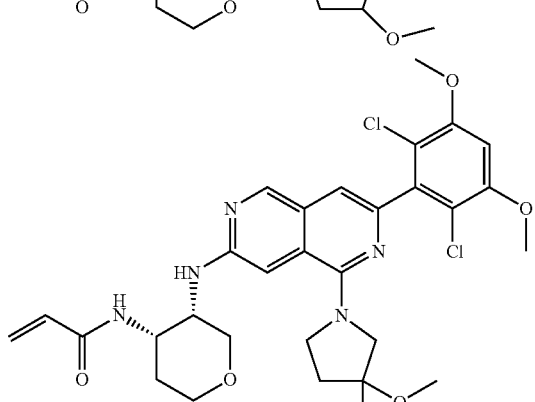

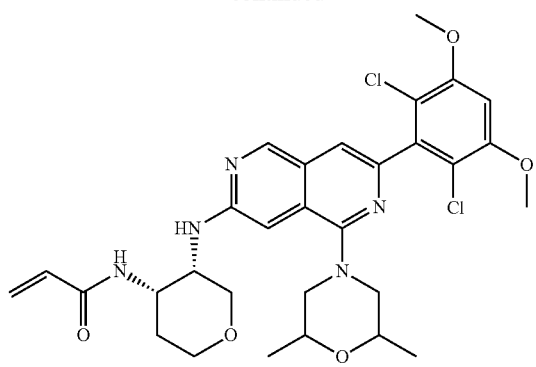
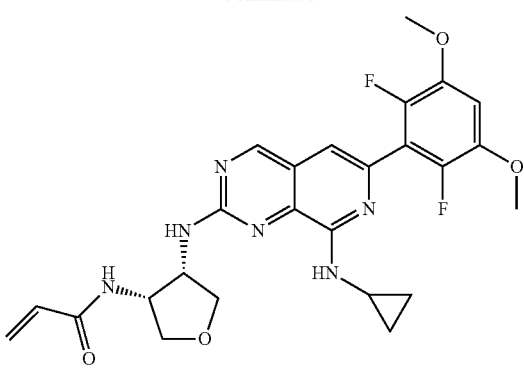
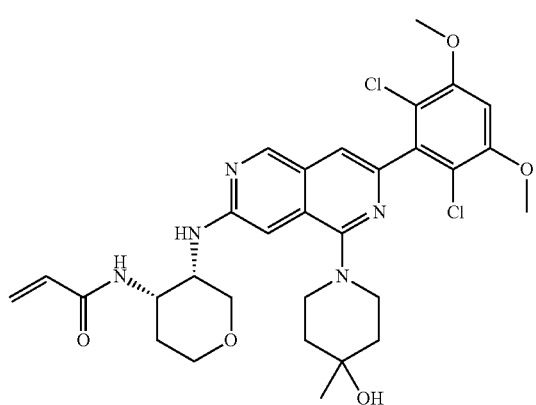
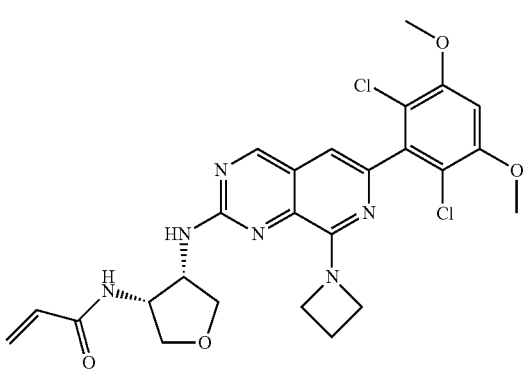
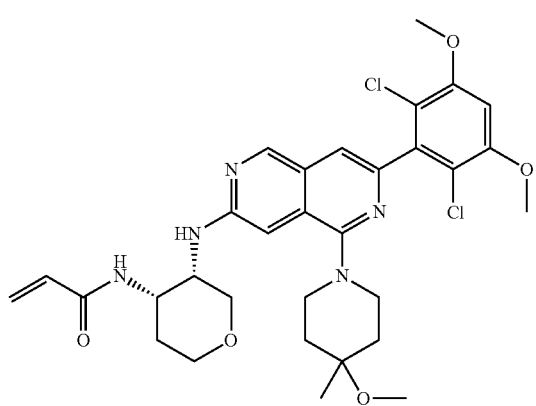
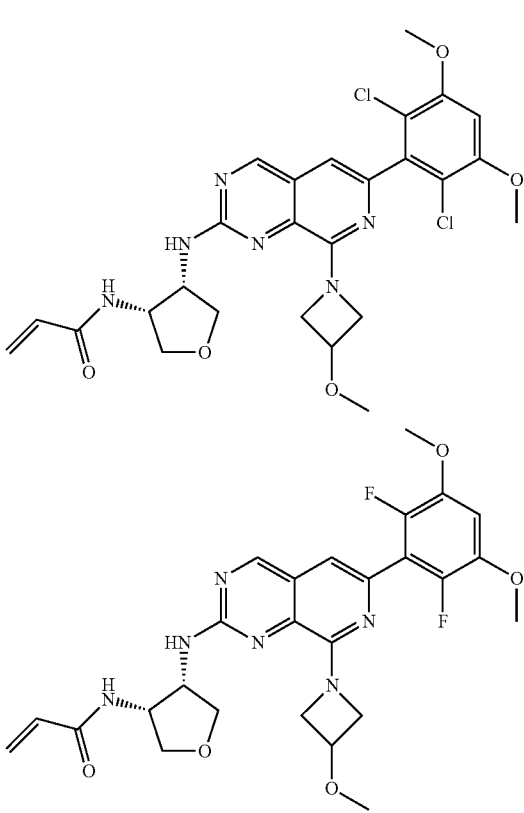

99
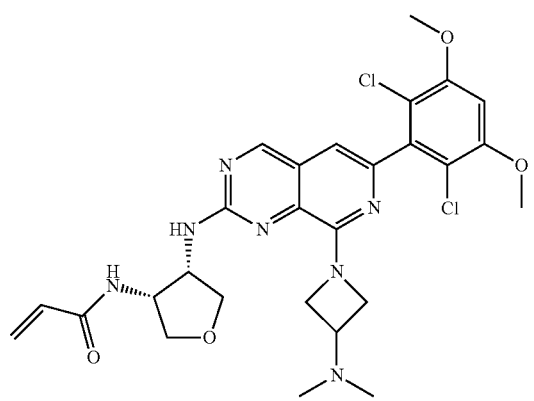
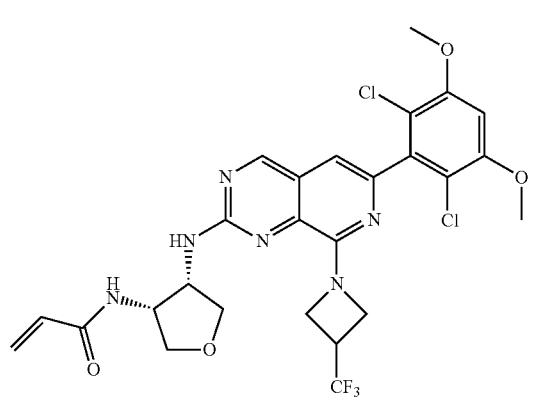
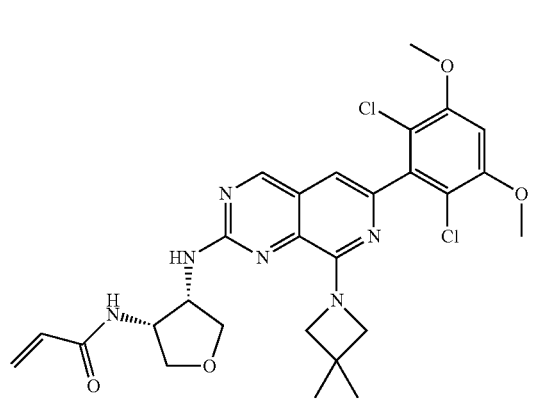
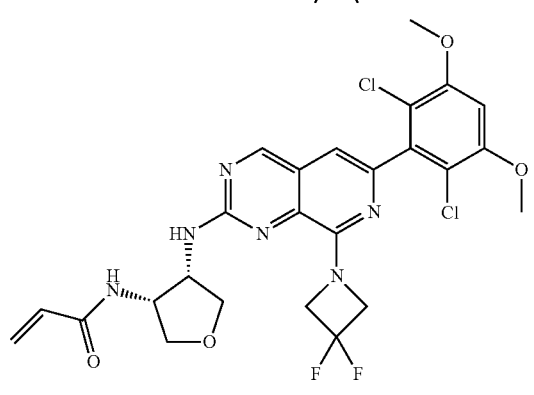
100
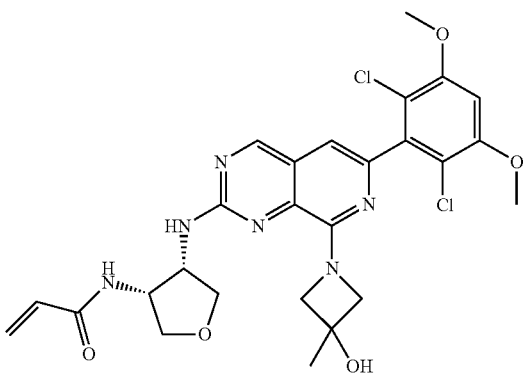
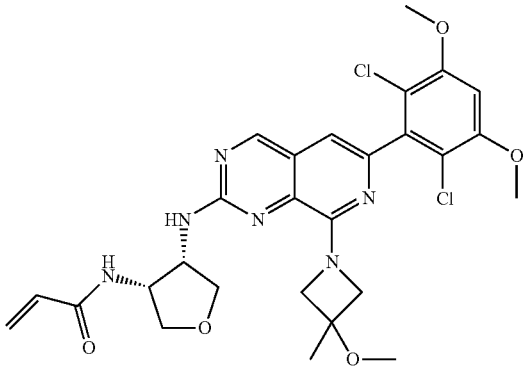
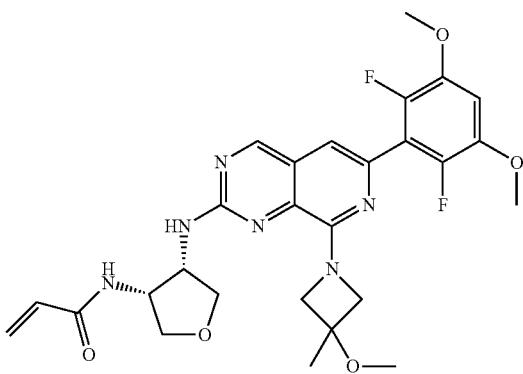
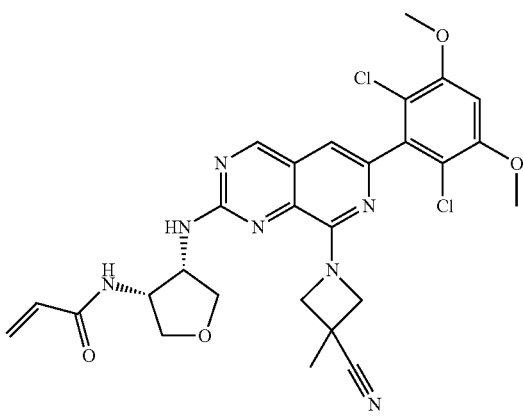

101
-continued
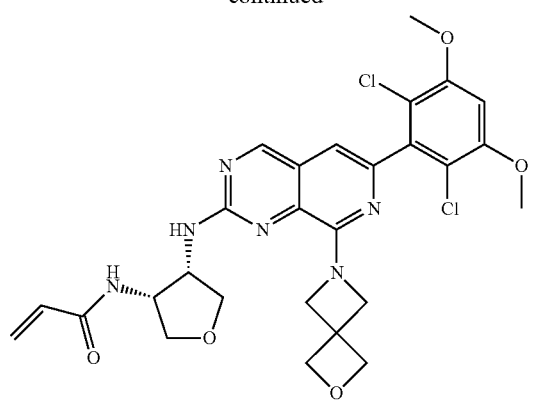
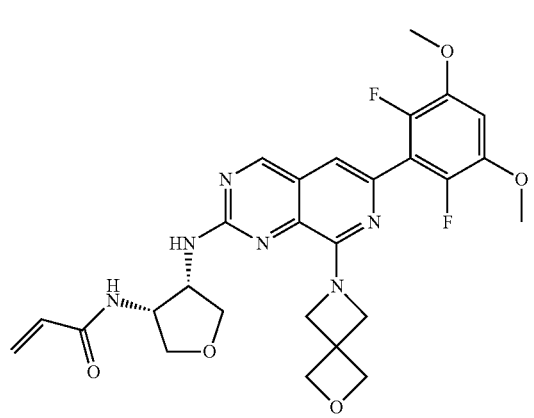
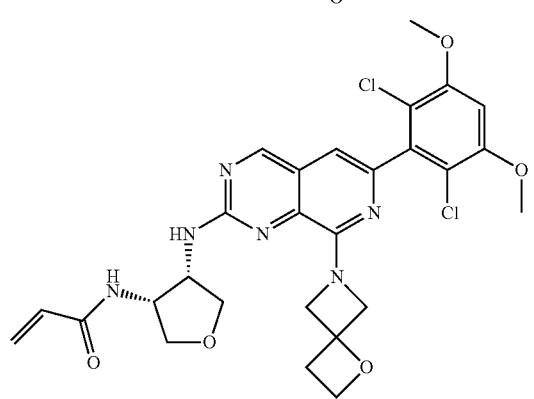
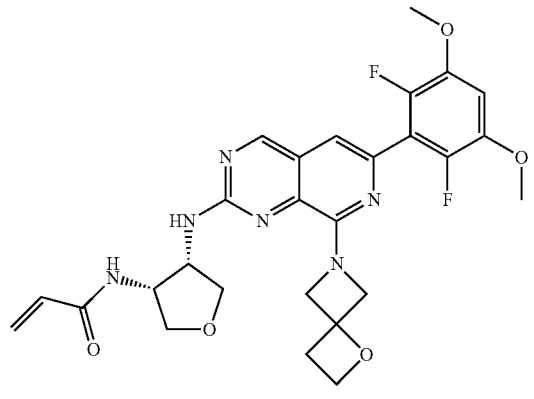
102
-continued
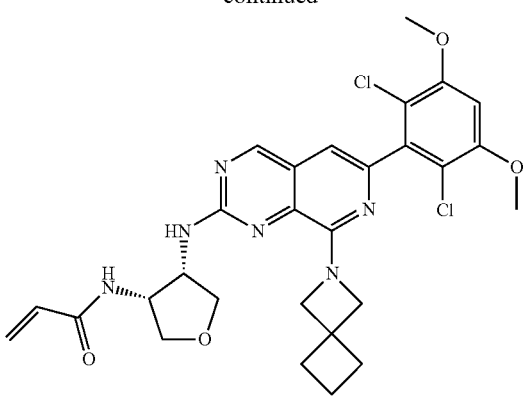
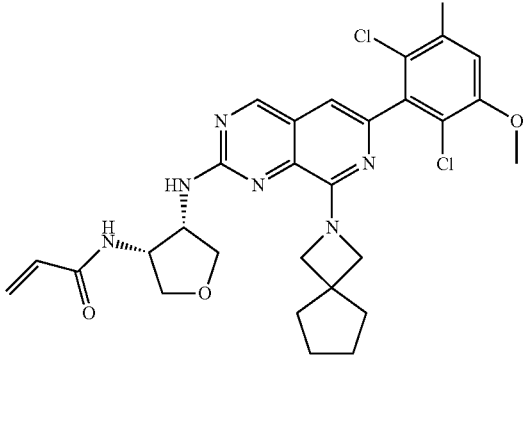
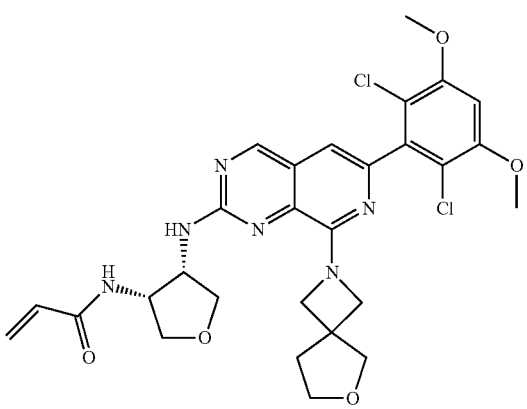
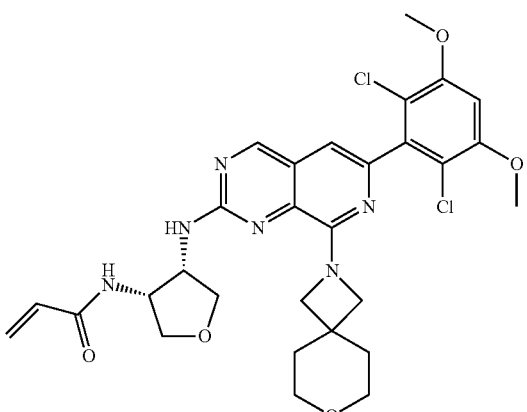

103
-continued
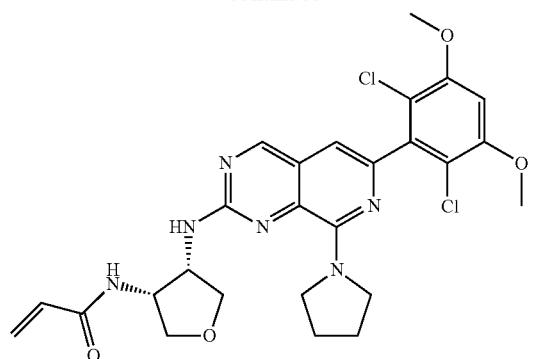
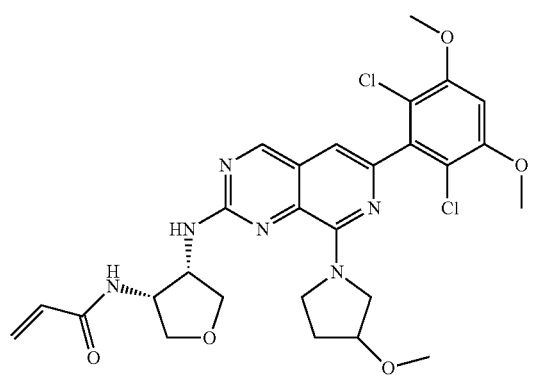
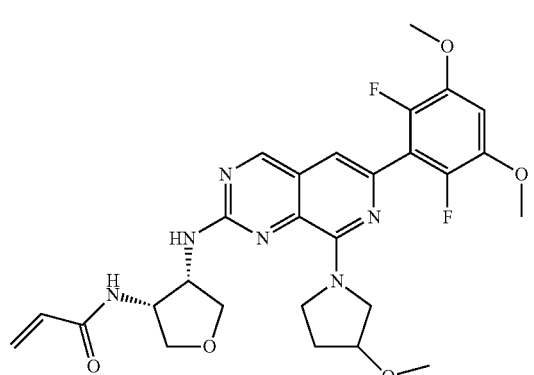
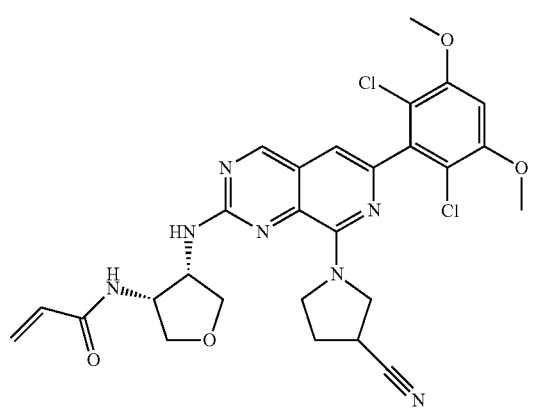
104
-continued
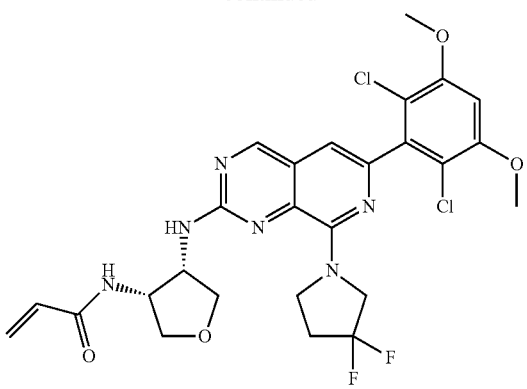
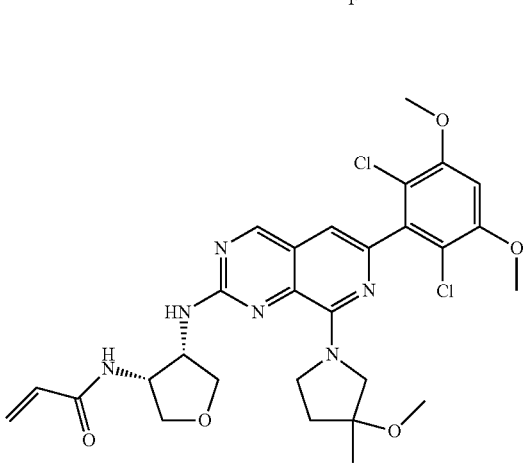
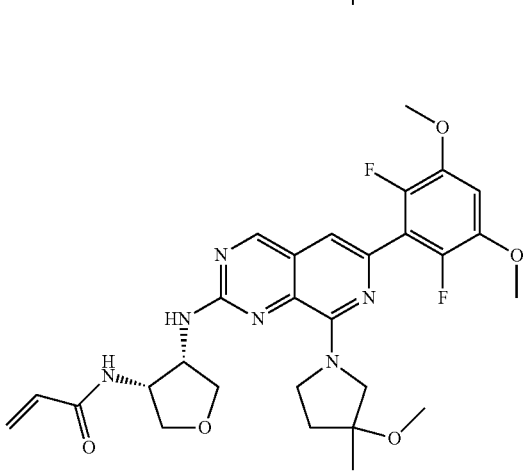
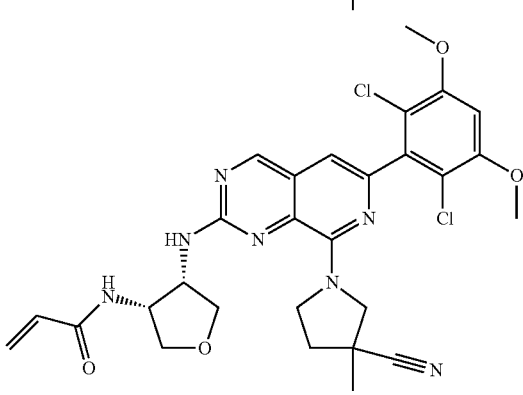

105
-continued

106
-continued

107
-continued
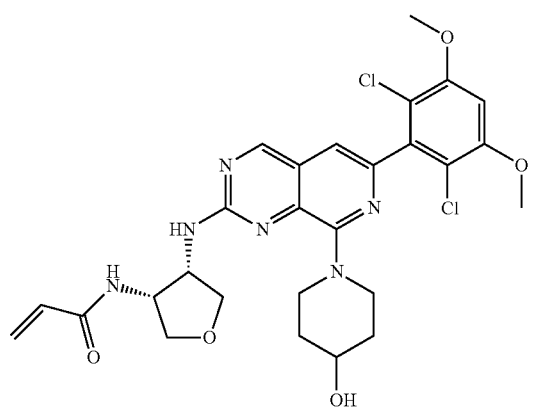
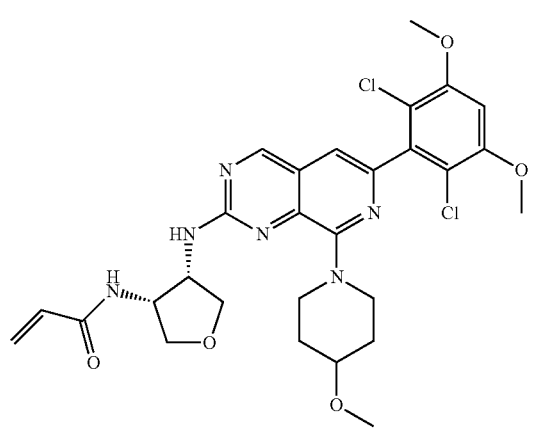
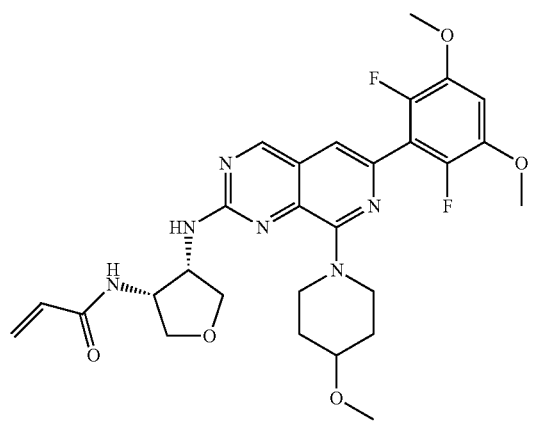
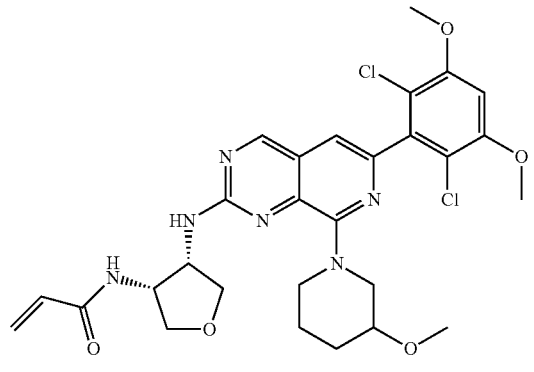
108
-continued
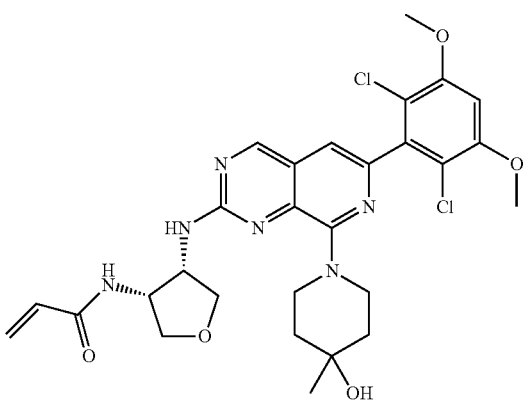
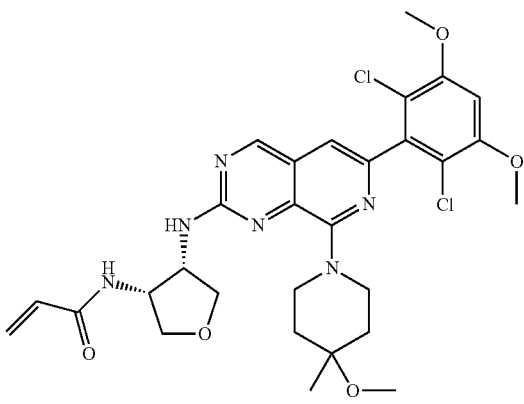
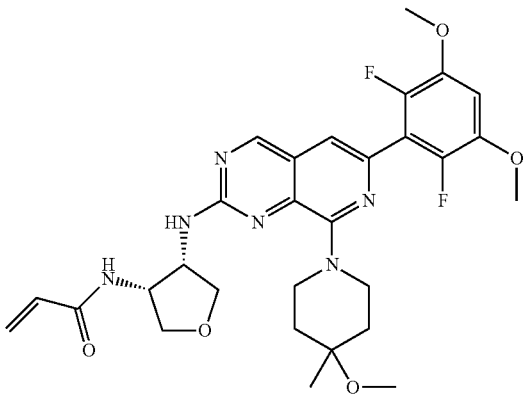
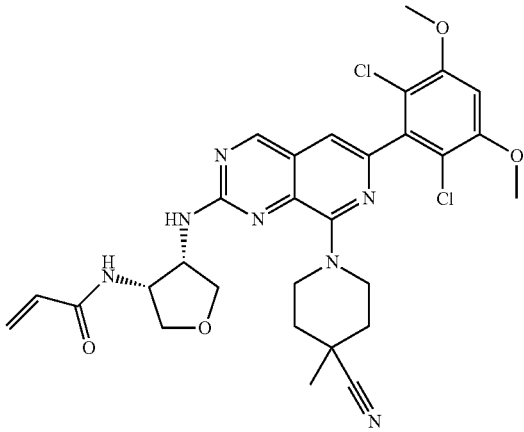

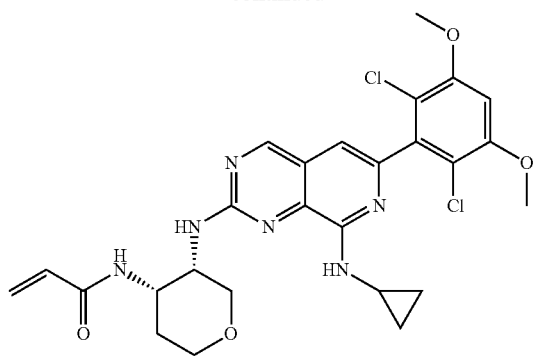
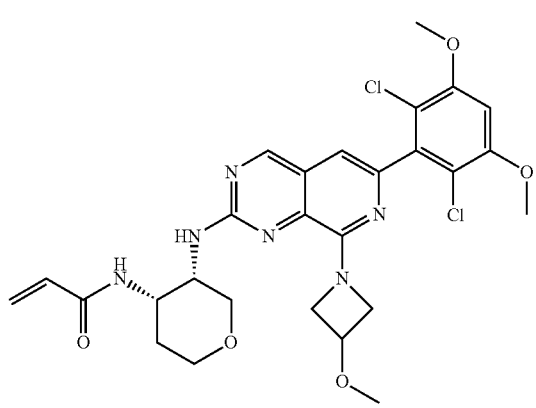
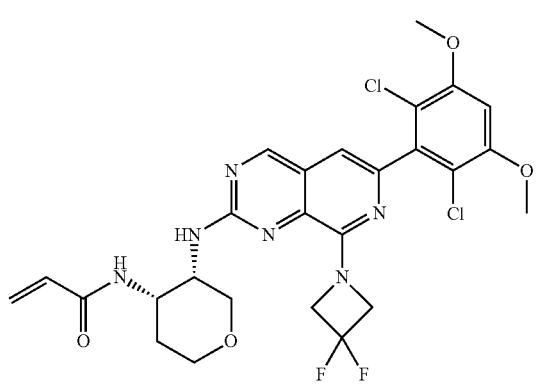
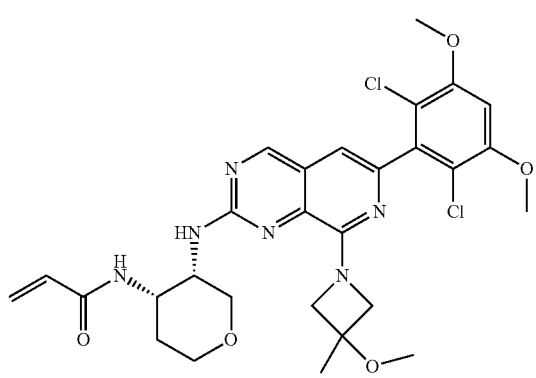
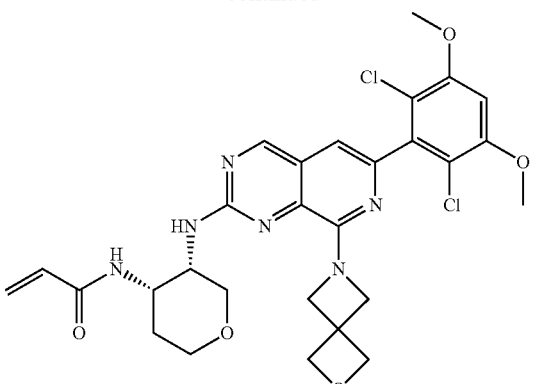
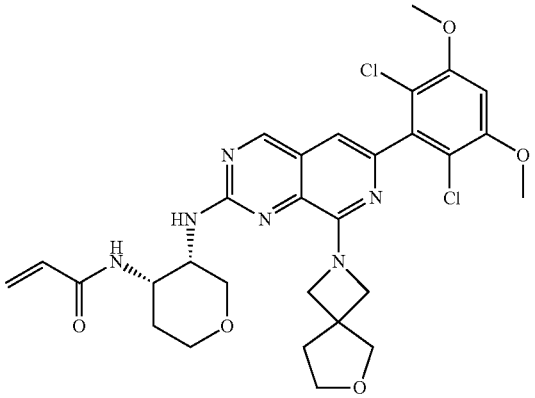
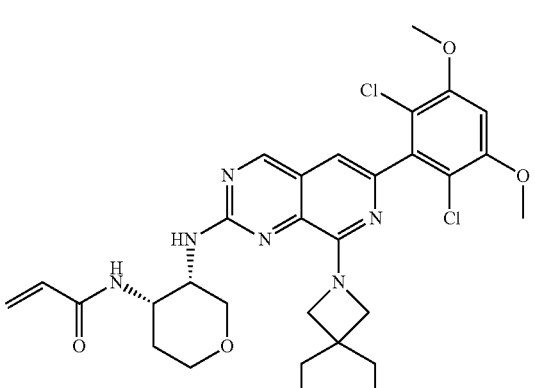
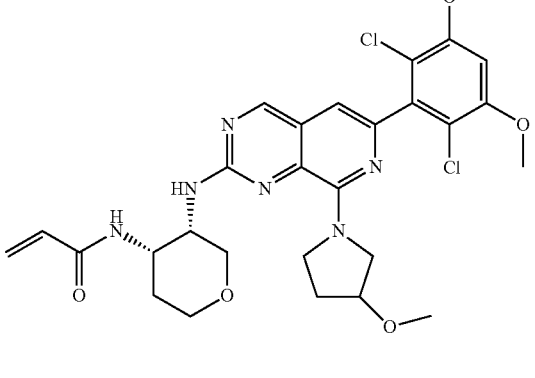

111
-continued
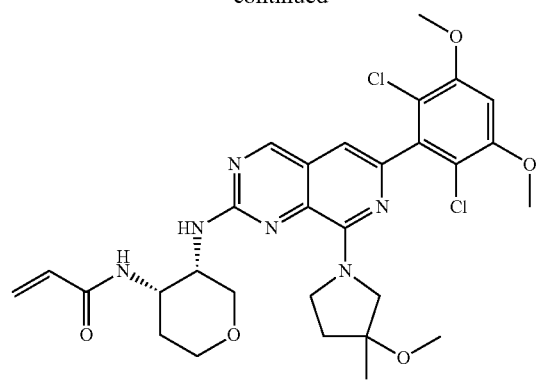
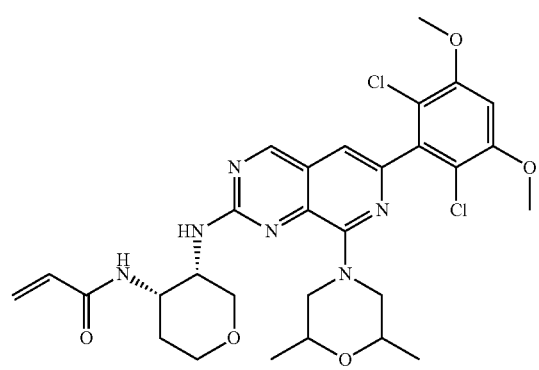
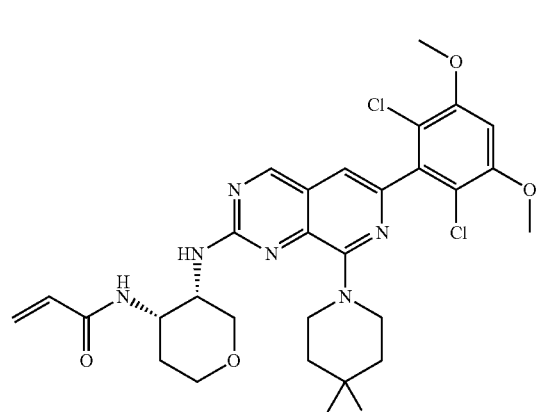
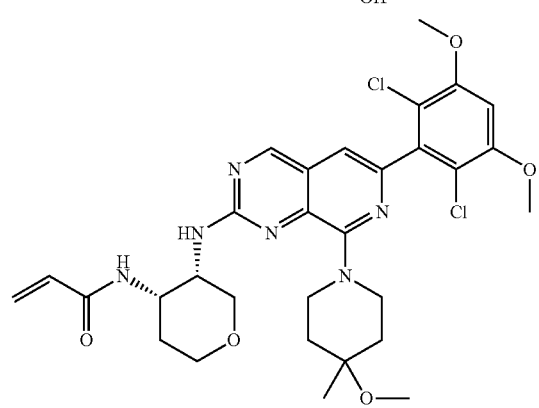
112
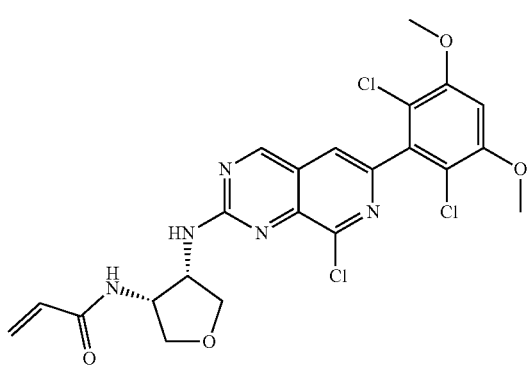
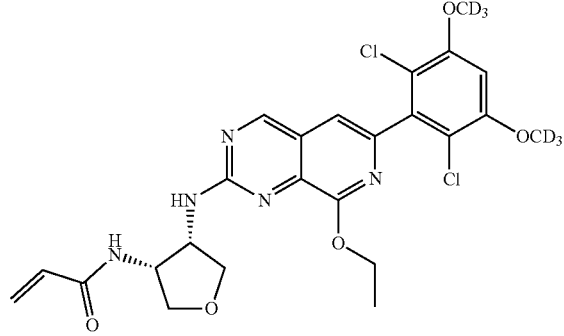
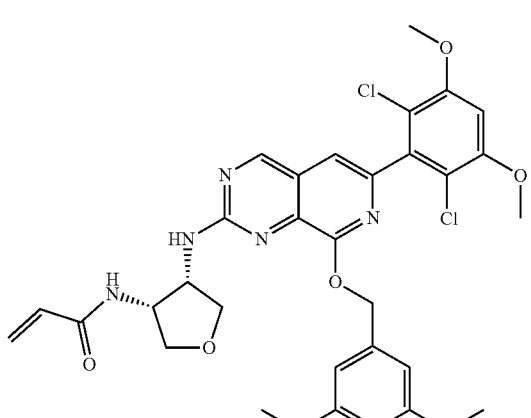
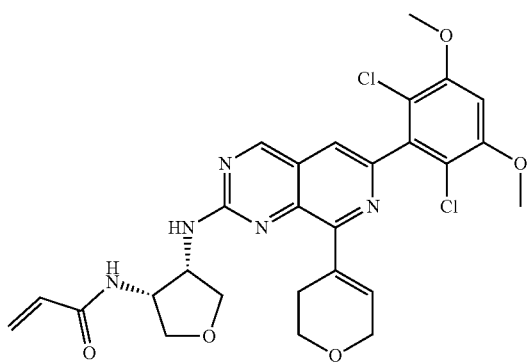

113
-continued
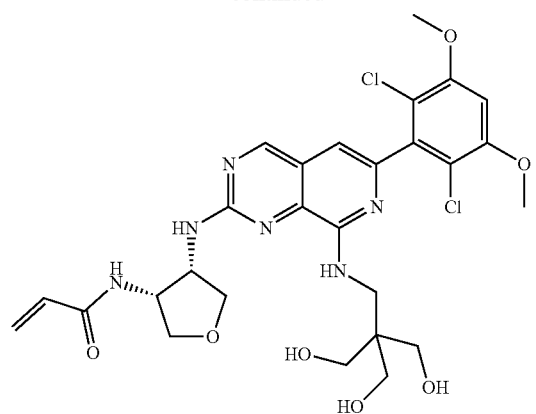
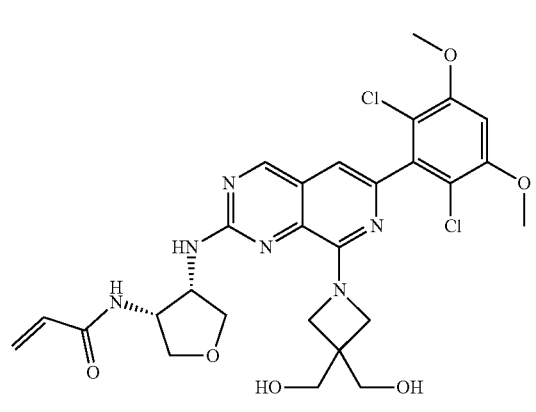
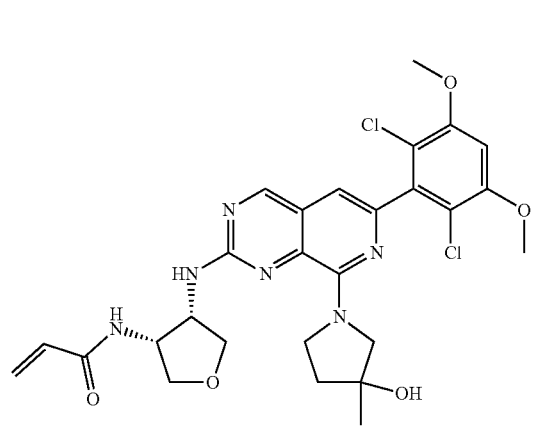
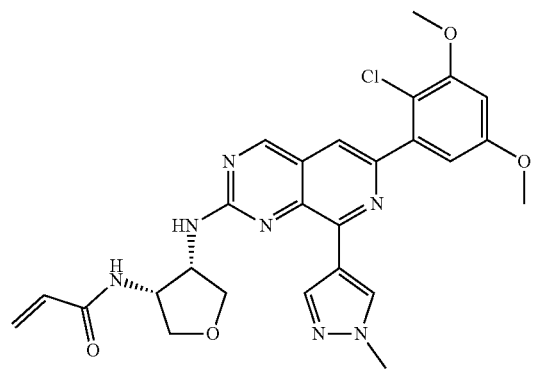
114
-continued
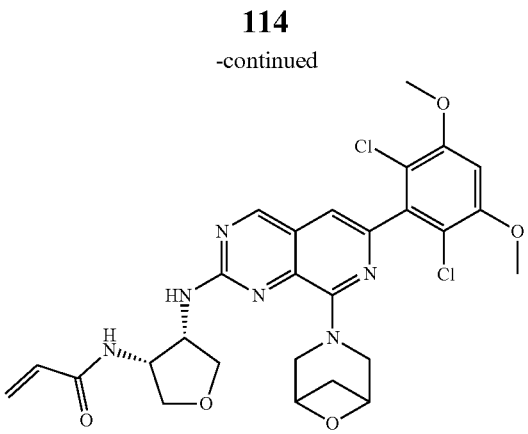
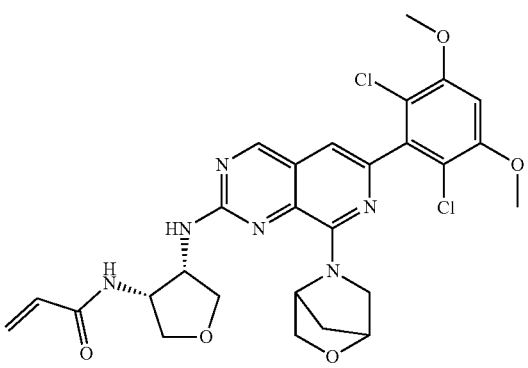
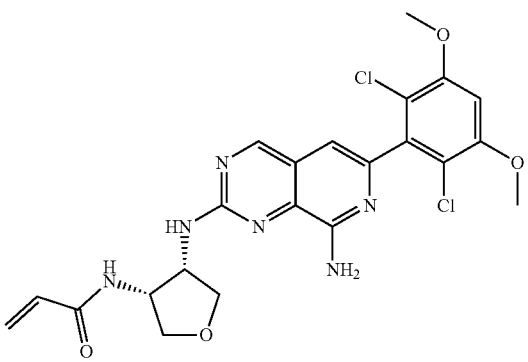
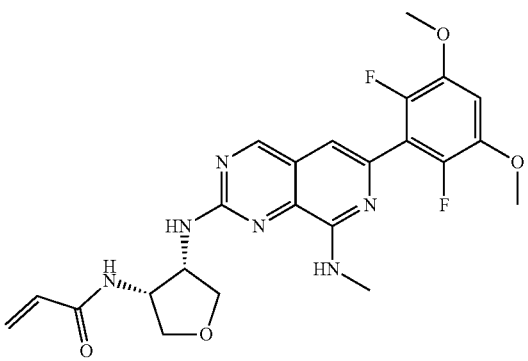

115
-continued
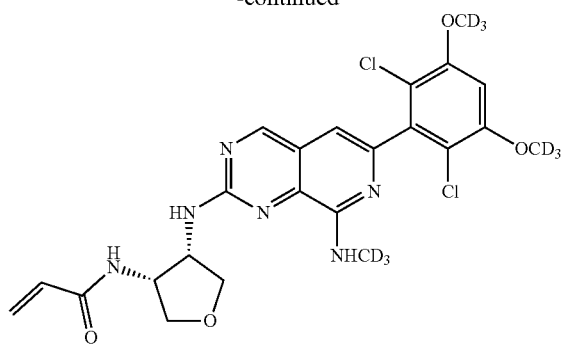
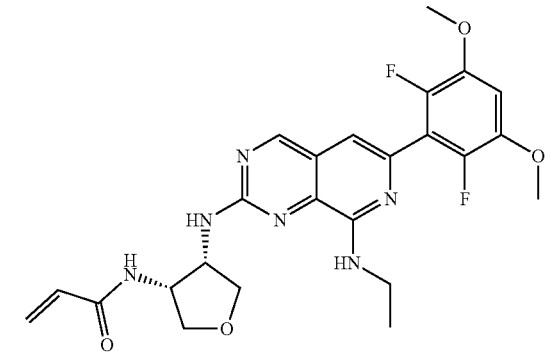
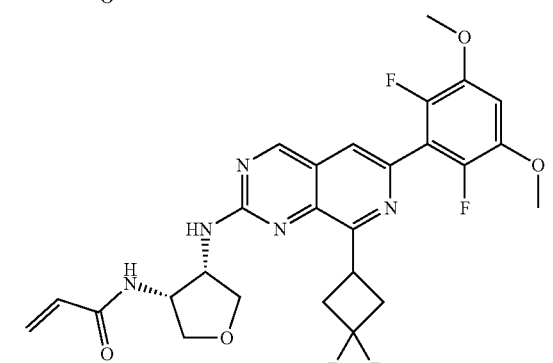
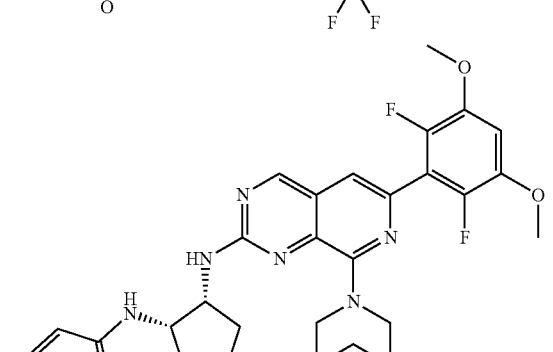
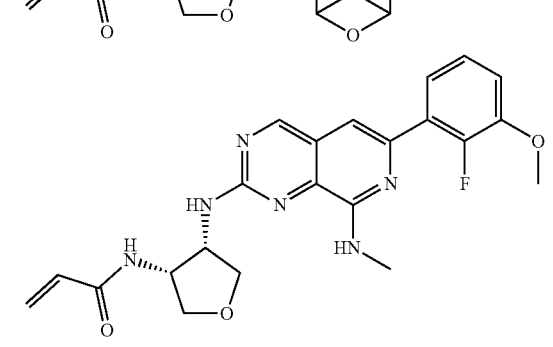
116
-continued
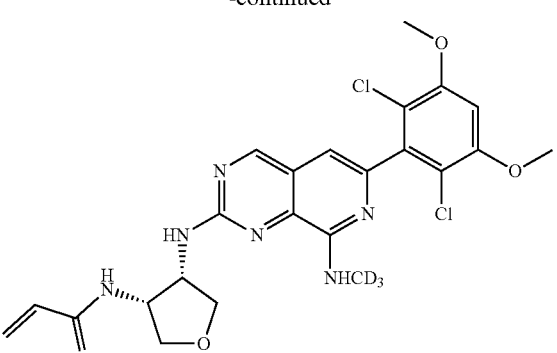
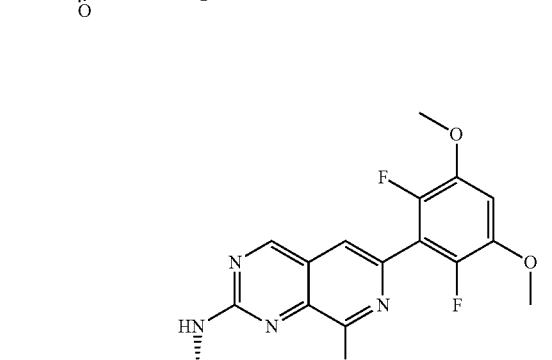
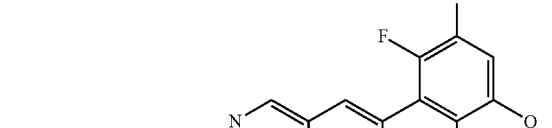
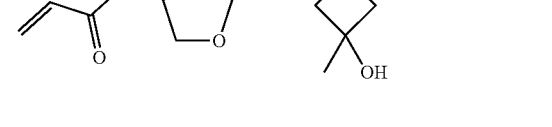
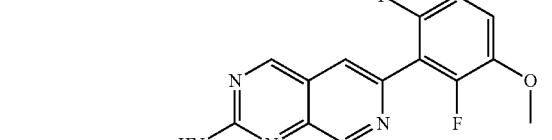

117
-continued
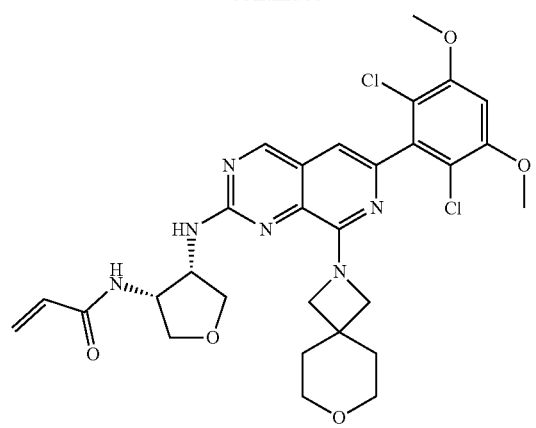
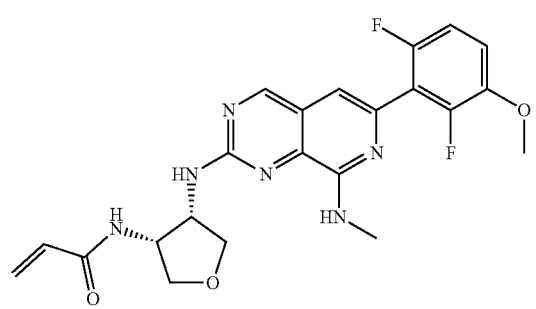
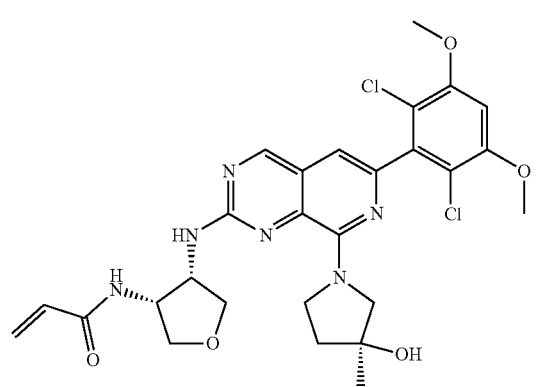
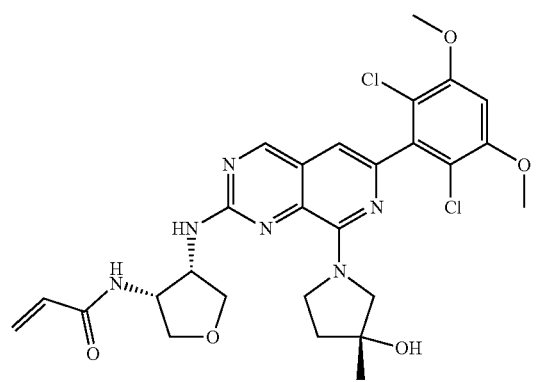
118
-continued
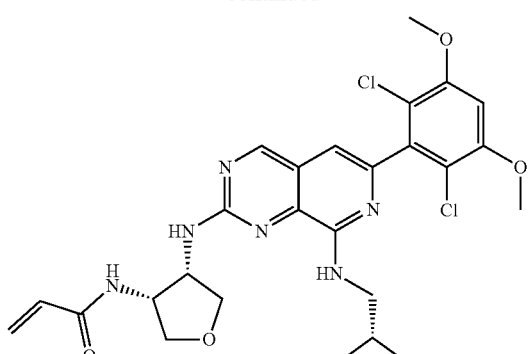
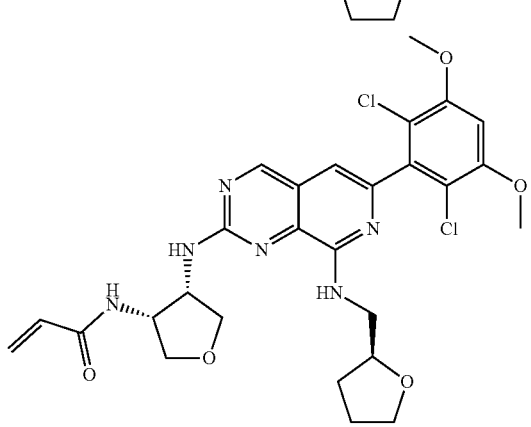
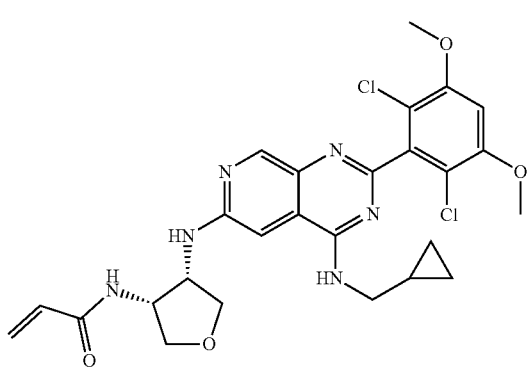
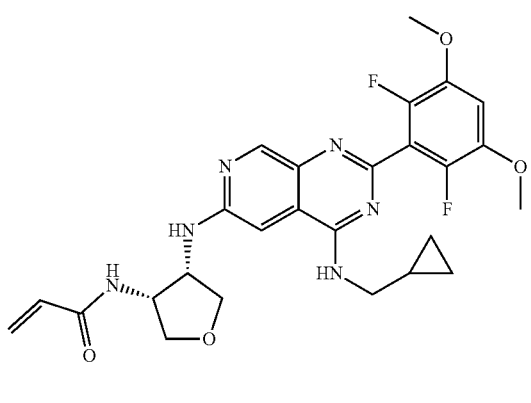

119
-continued
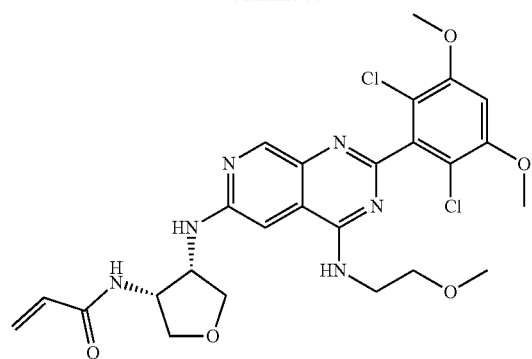
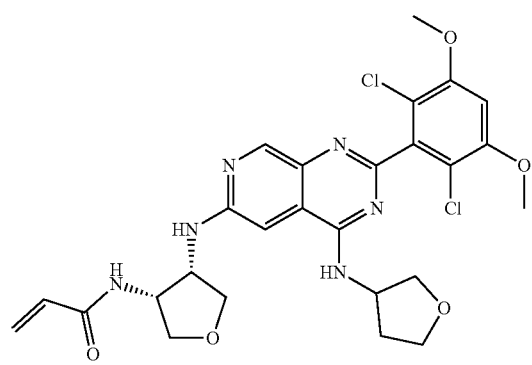
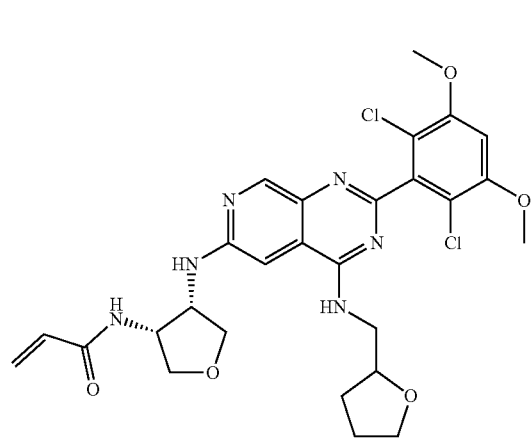
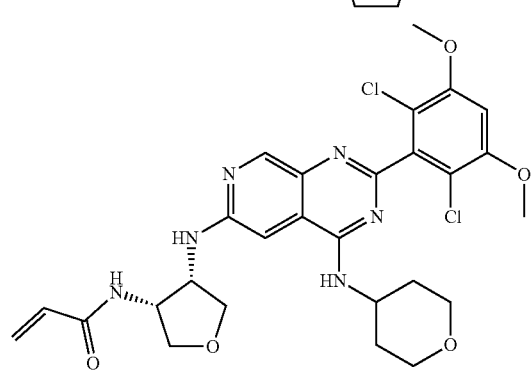
120
-continued
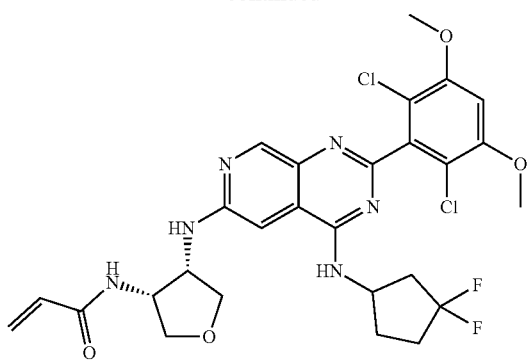
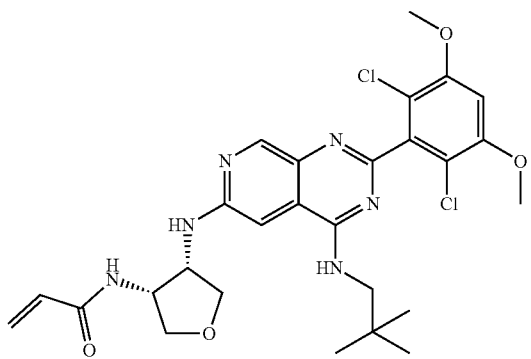
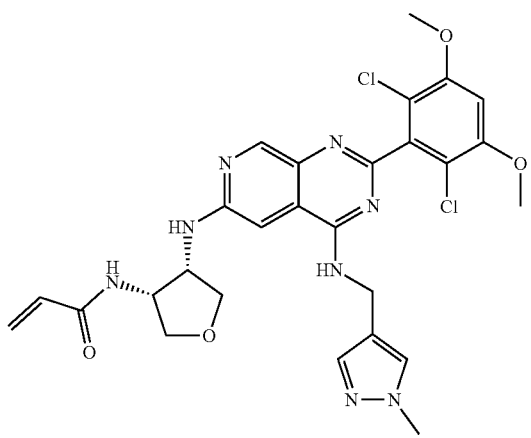
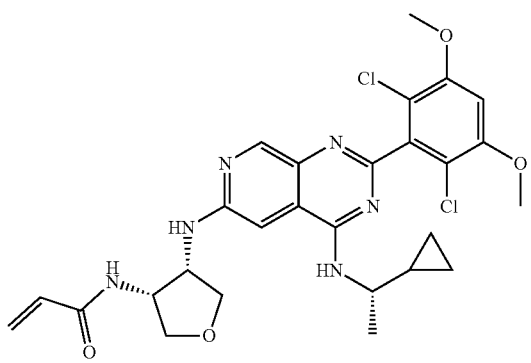

121
-continued
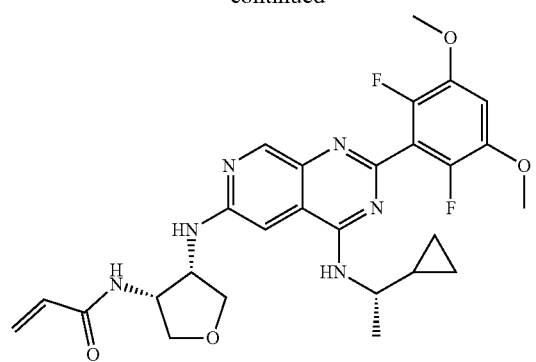
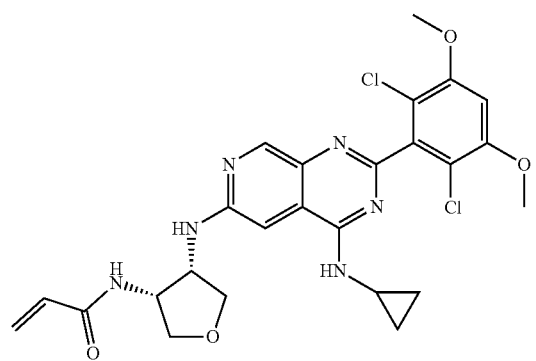
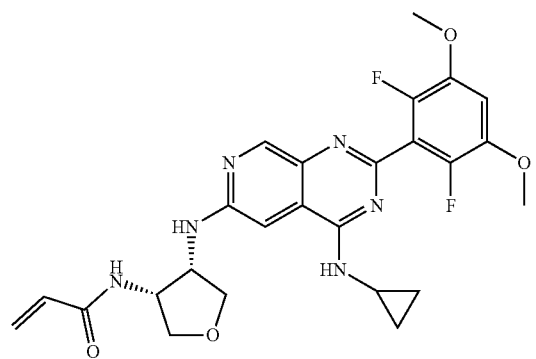
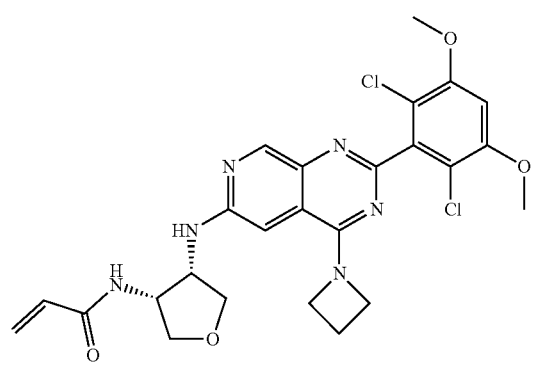
122
-continued
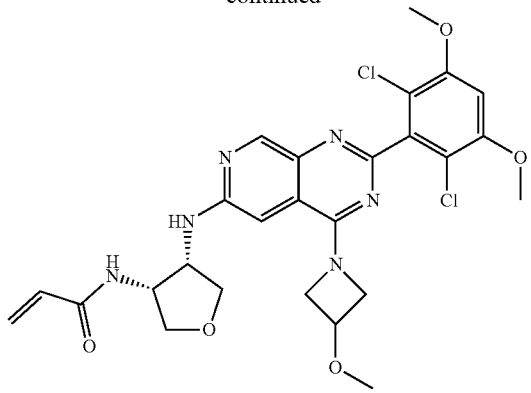
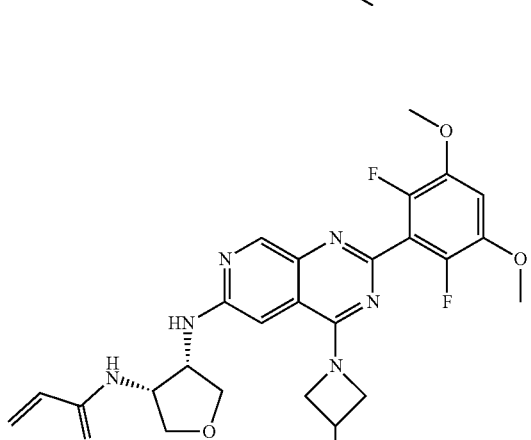
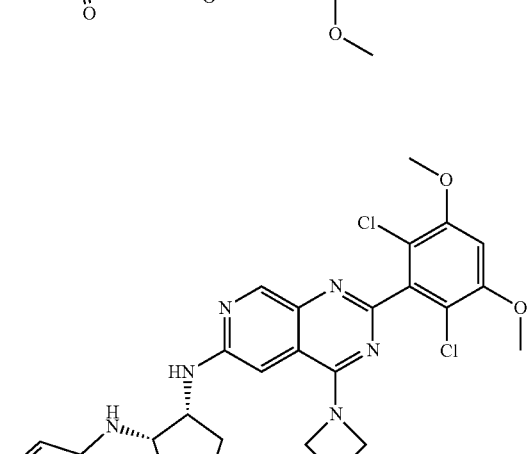
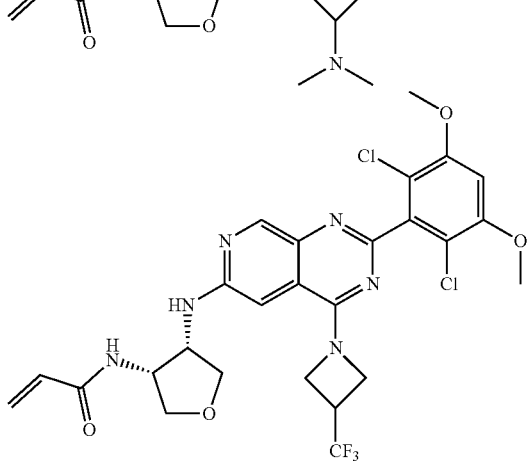

123
-continued
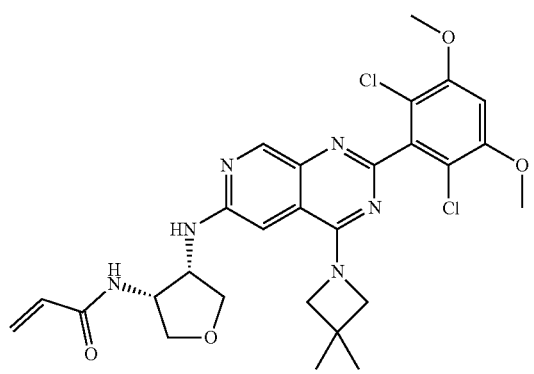
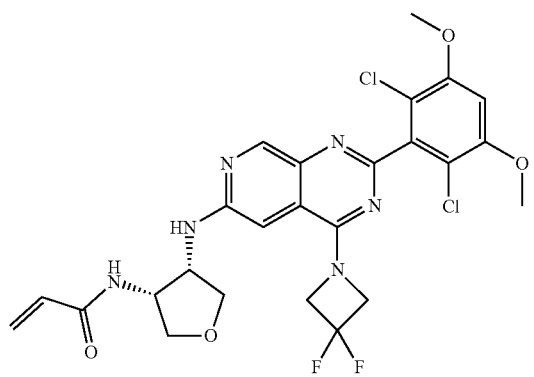
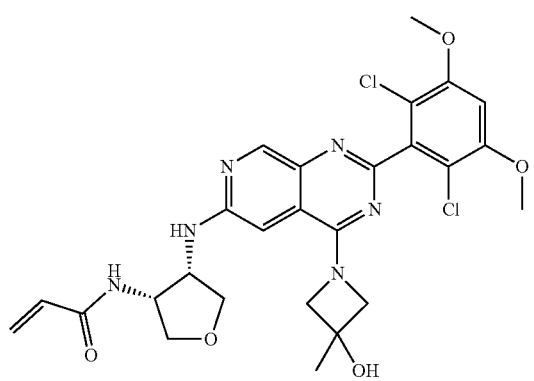
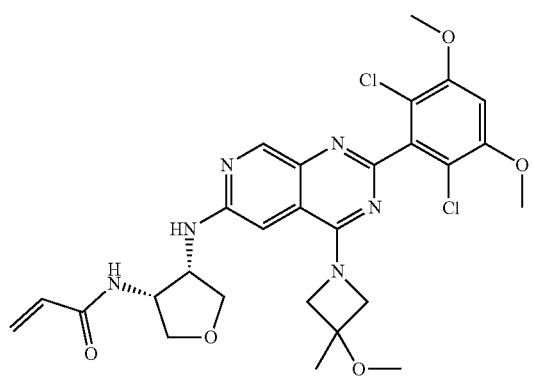
124
-continued
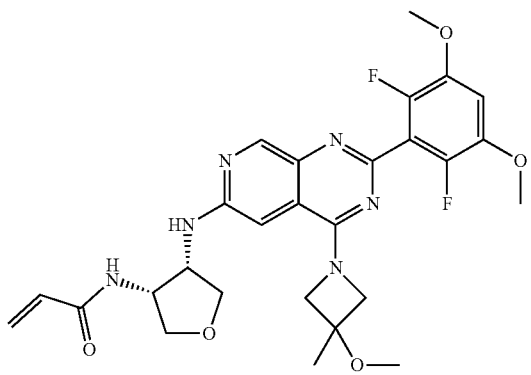
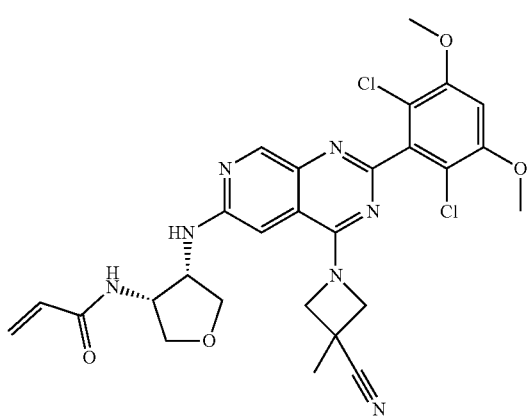
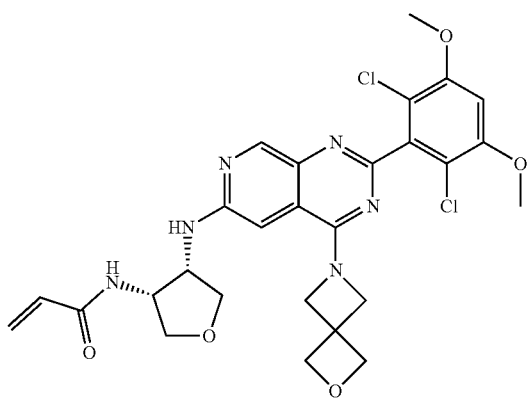
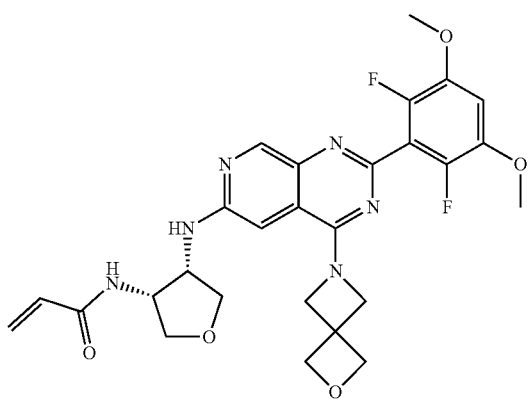

125
-continued
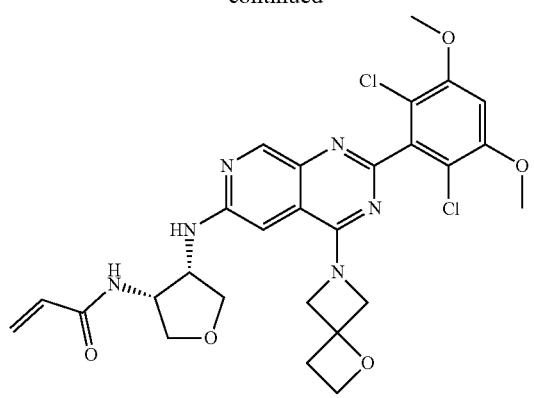
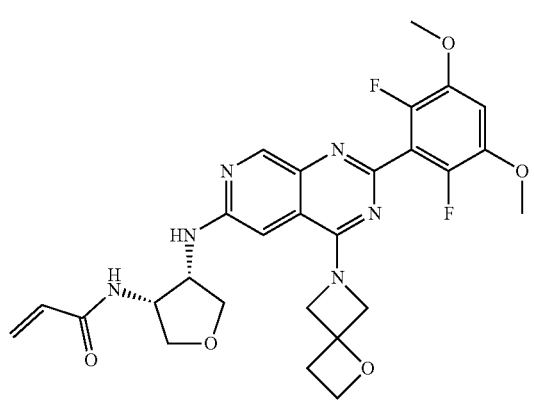
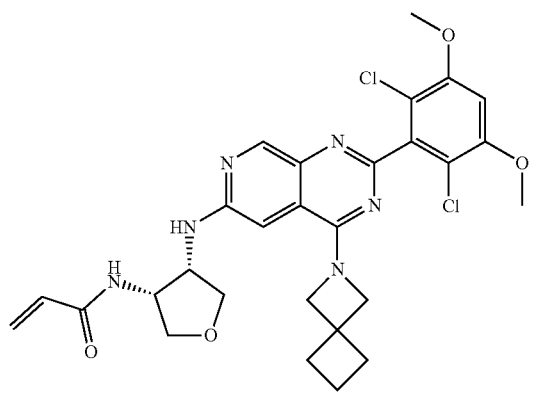
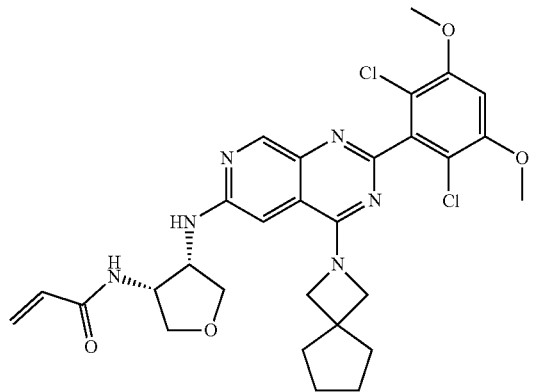
126
-continued
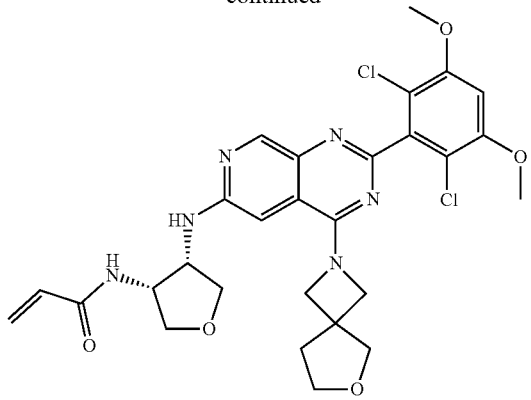
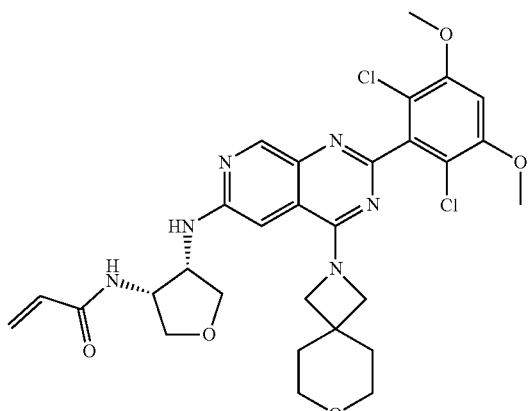
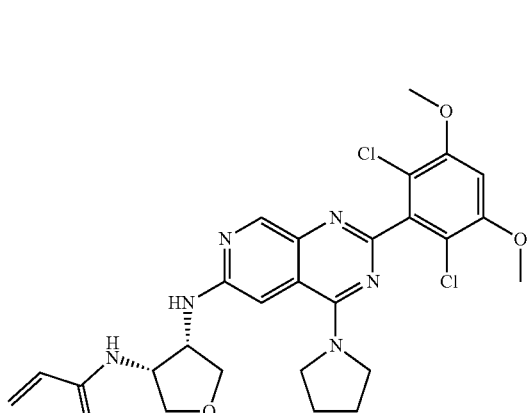
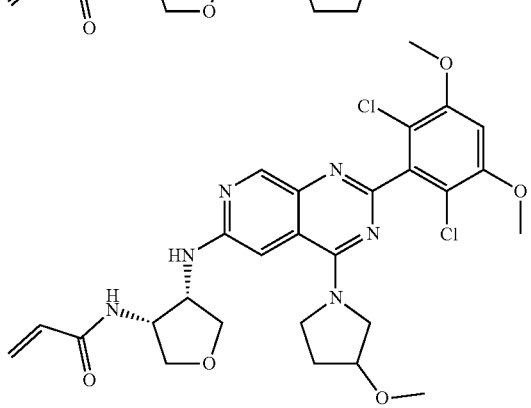

127
-continued
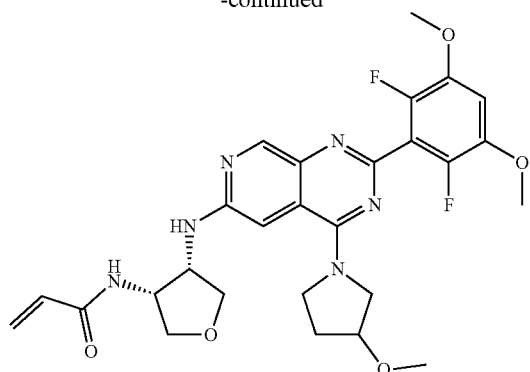
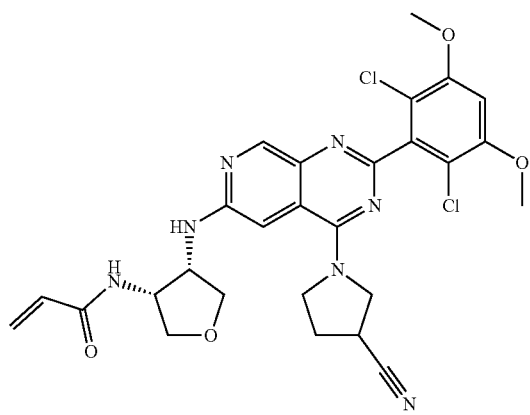
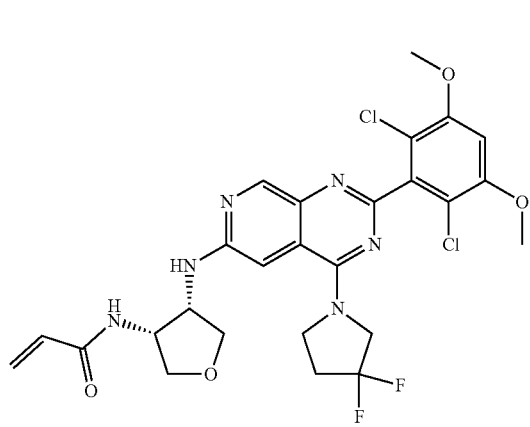
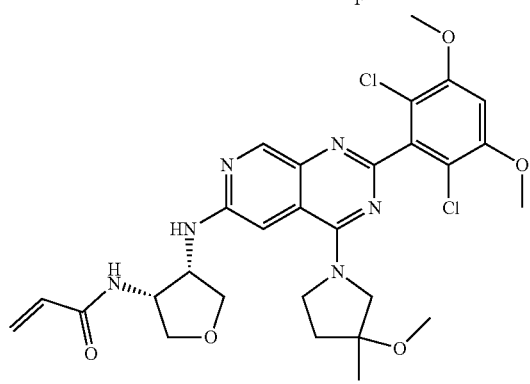
128
-continued
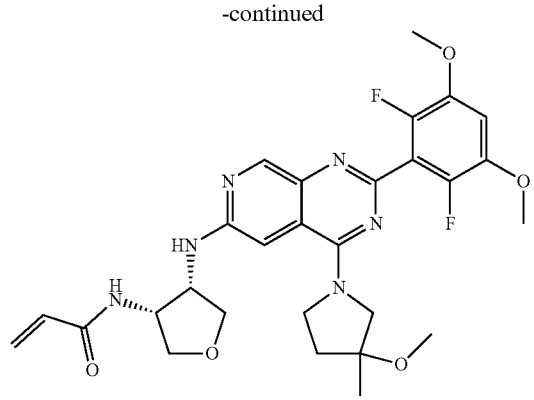
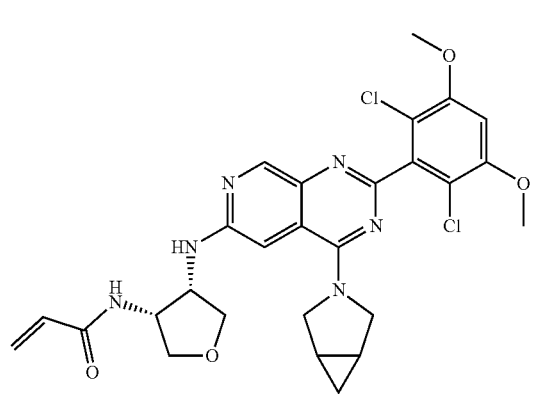
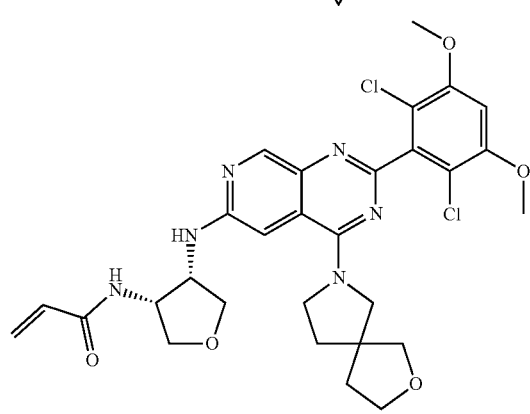

129
-continued
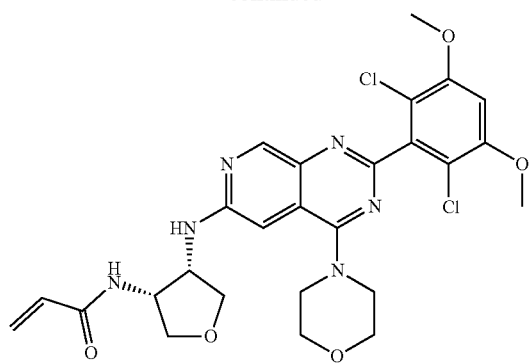
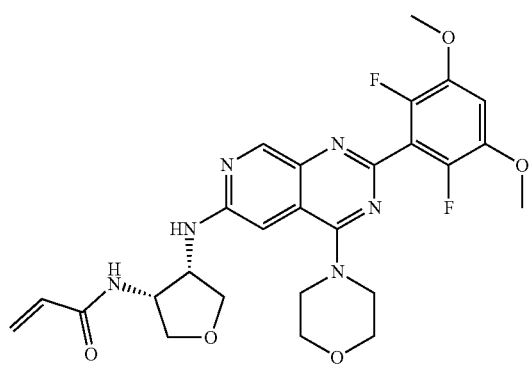
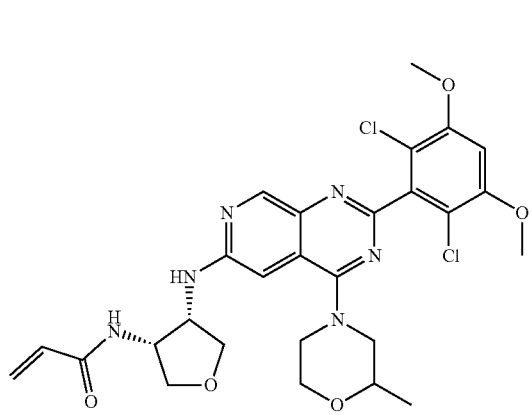
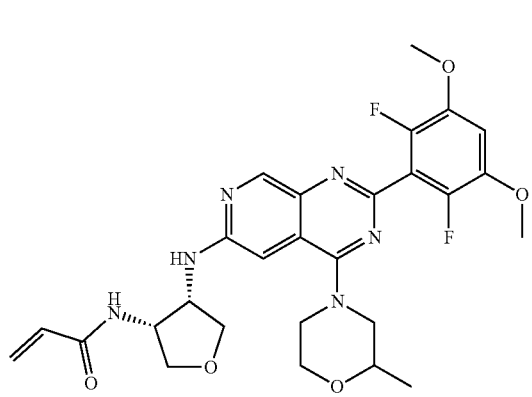
130
-continued
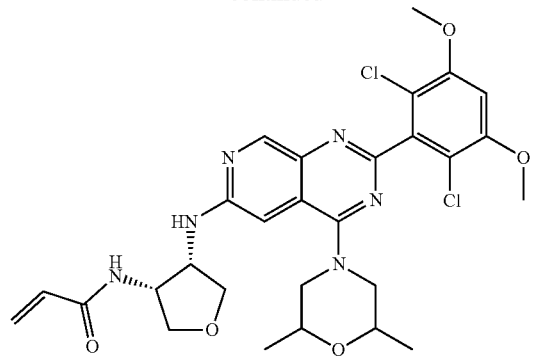
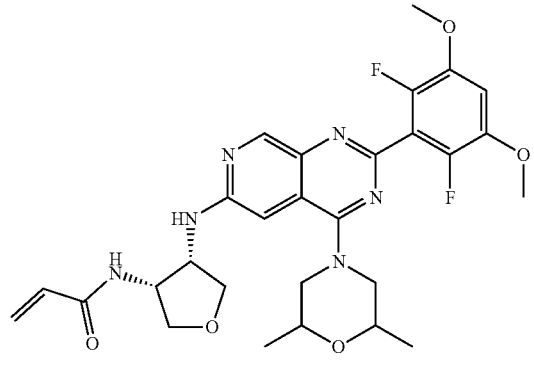
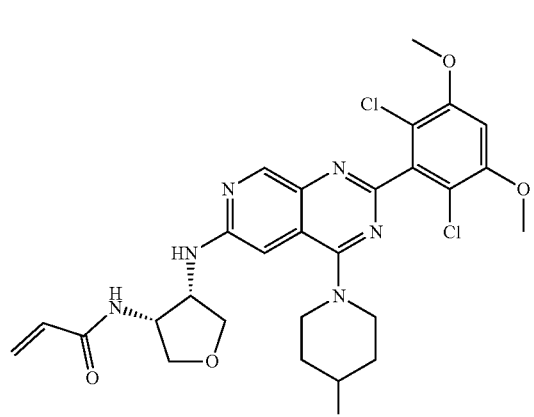
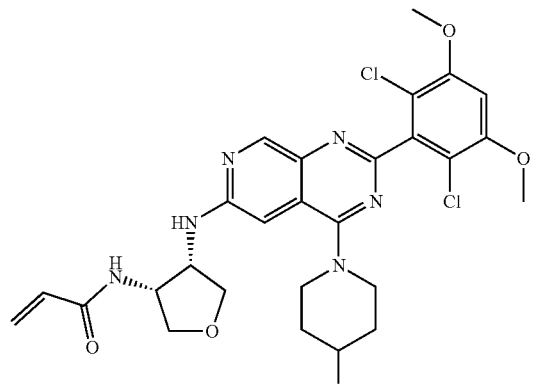

131
-continued
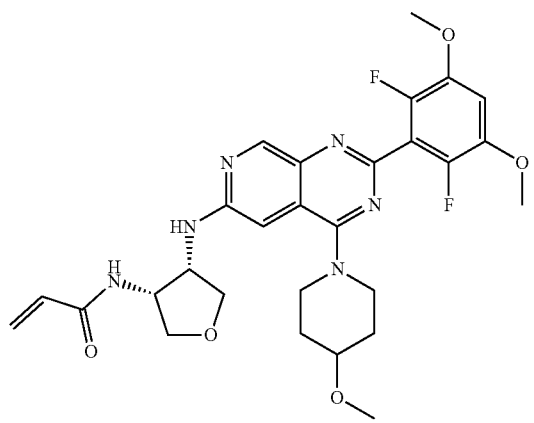
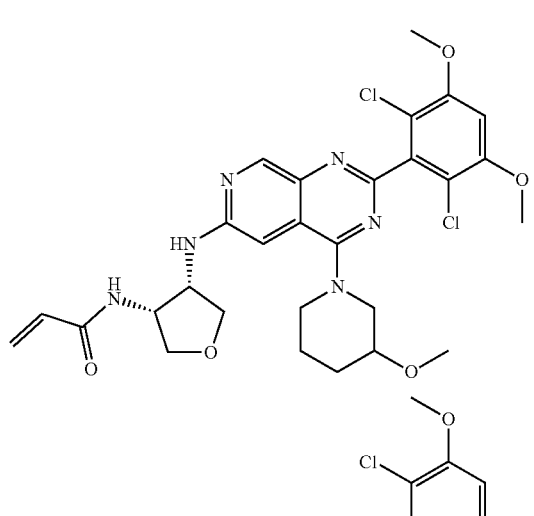
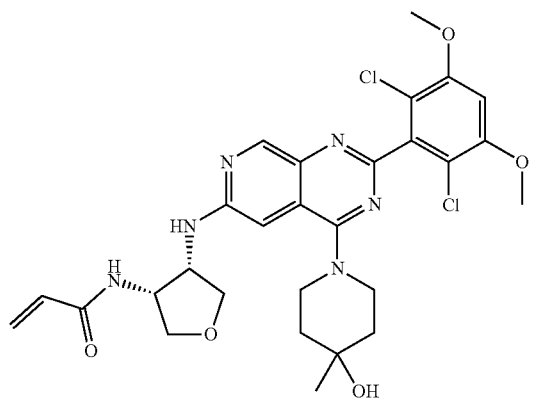
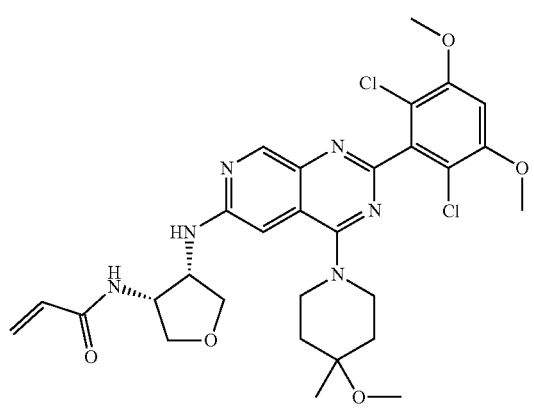
132
-continued
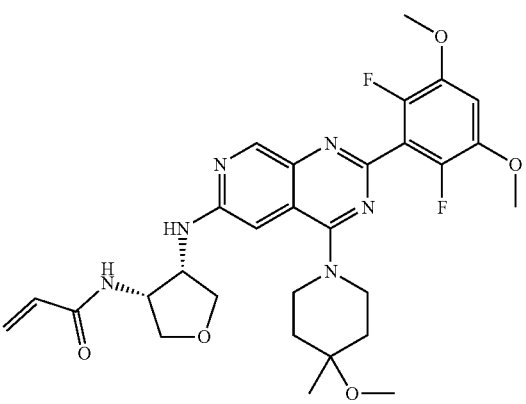
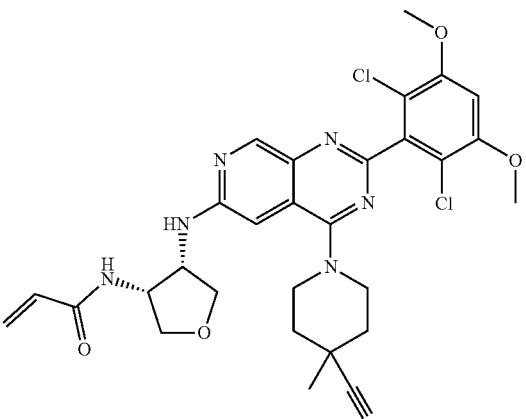
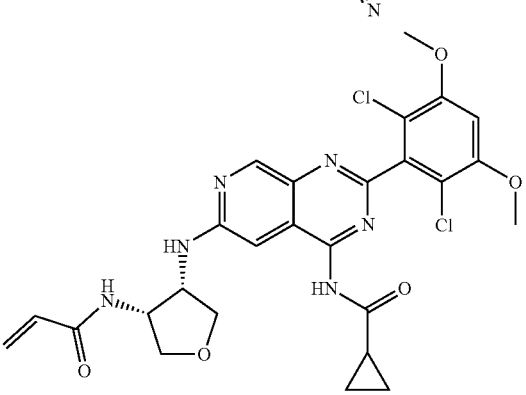
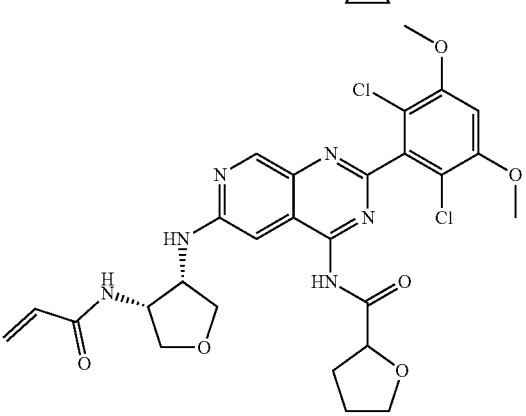

133
-continued
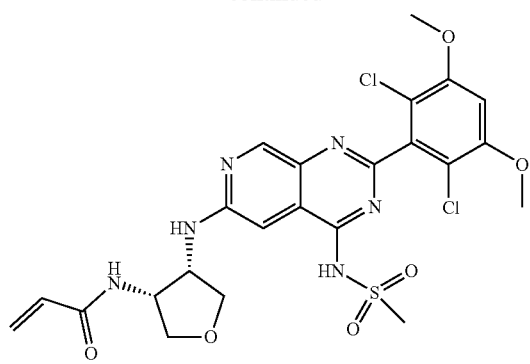
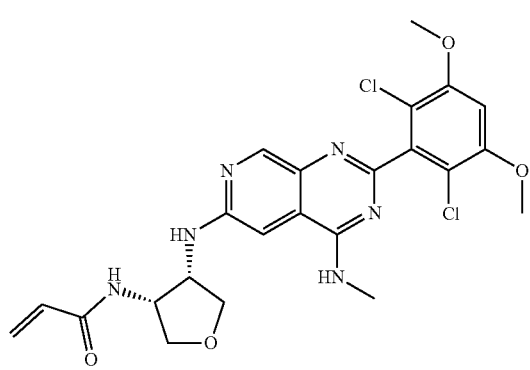
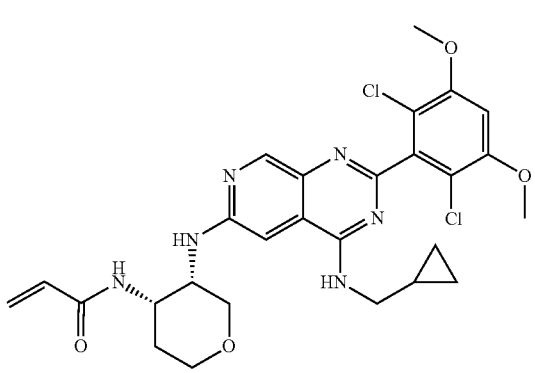
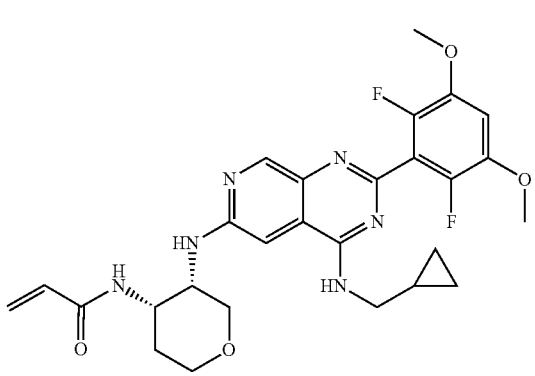
134
-continued
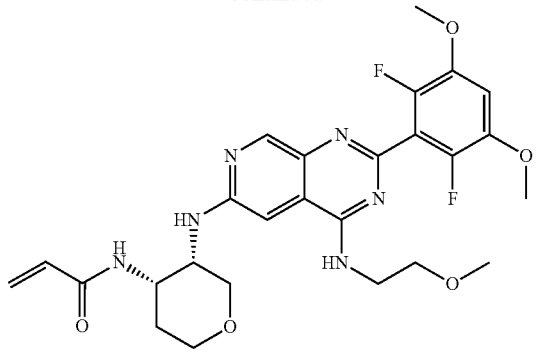
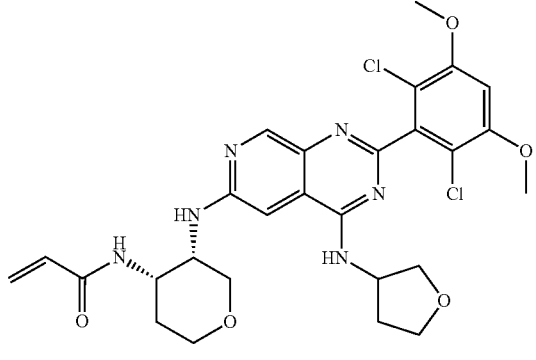
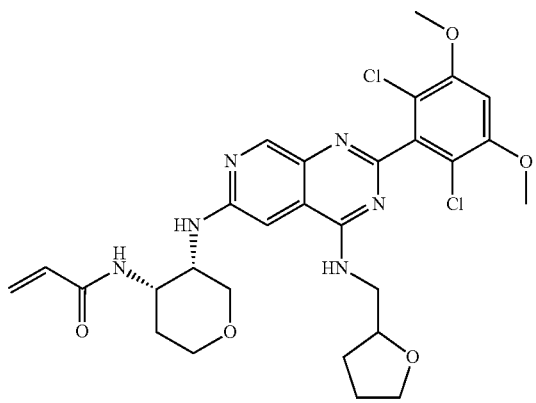
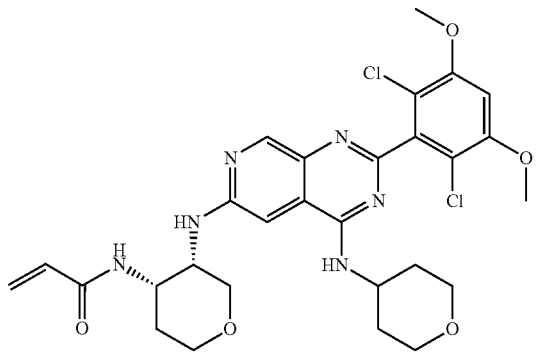

135
-continued
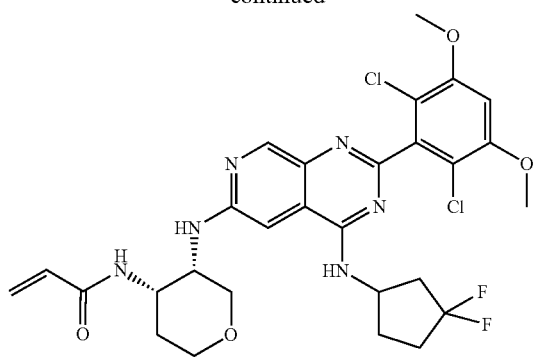
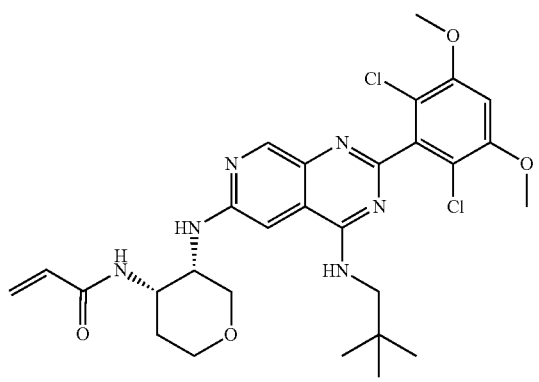
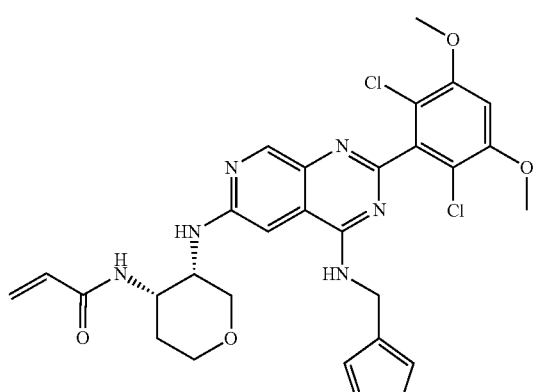
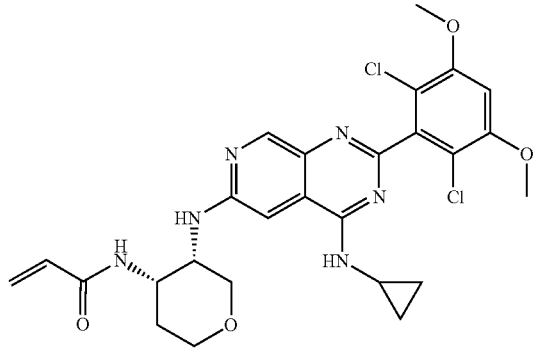
136
-continued
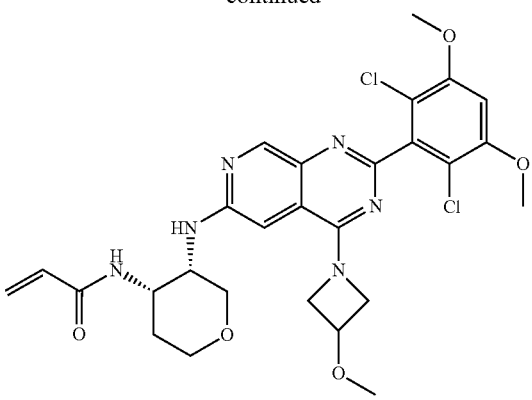
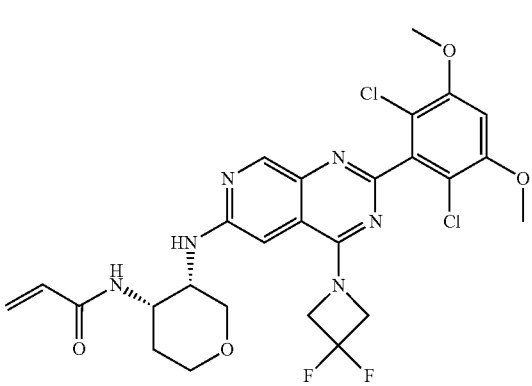
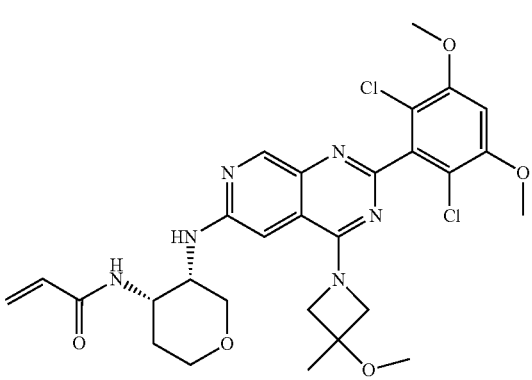

137
-continued
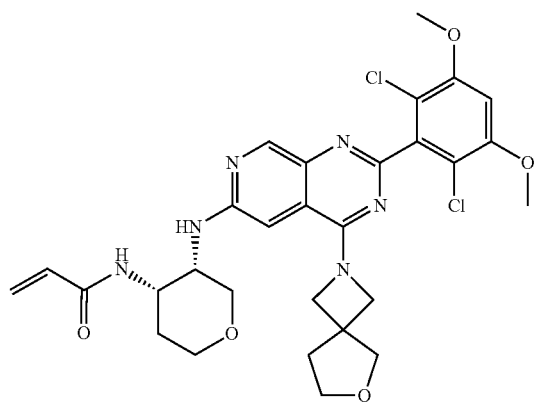
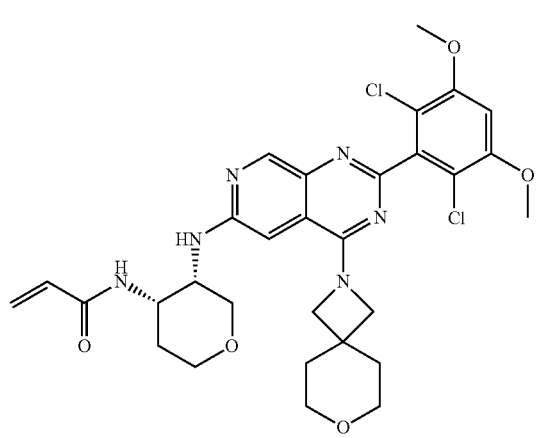
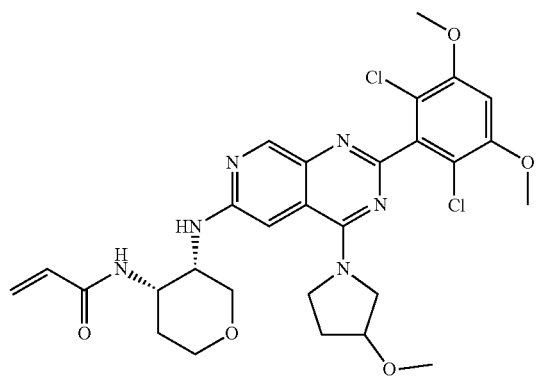
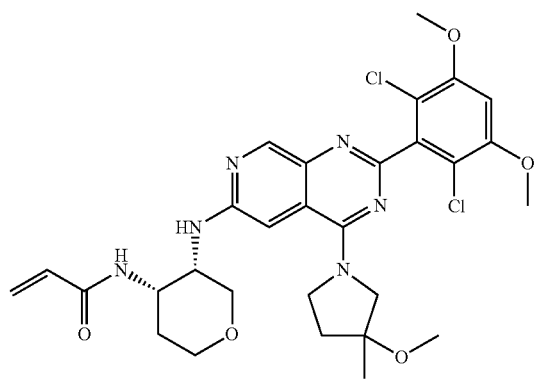
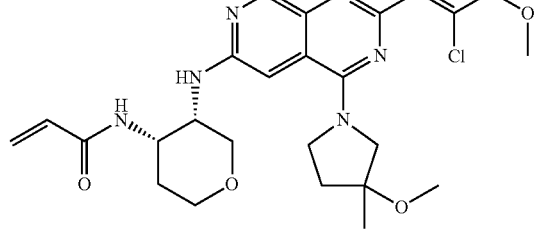
138
-continued
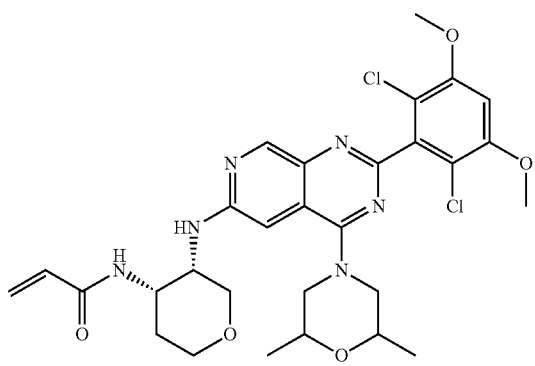
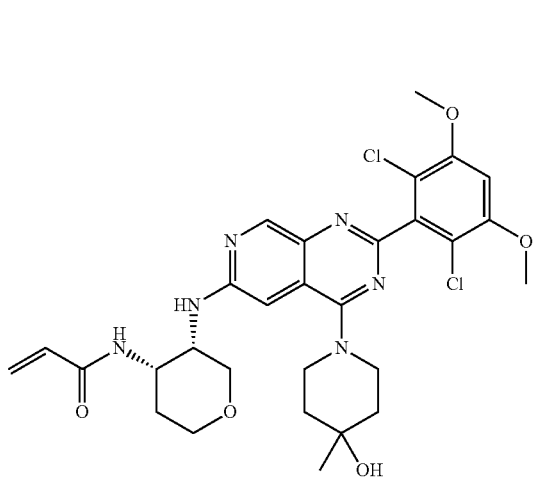
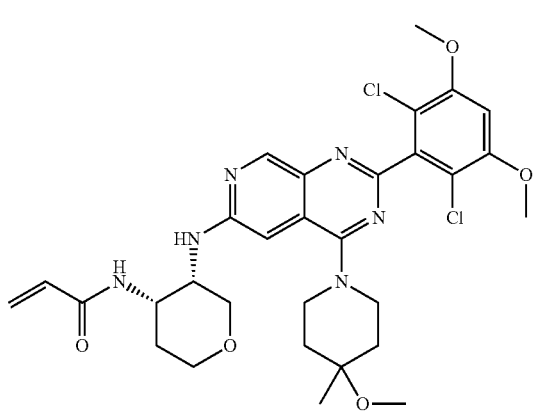
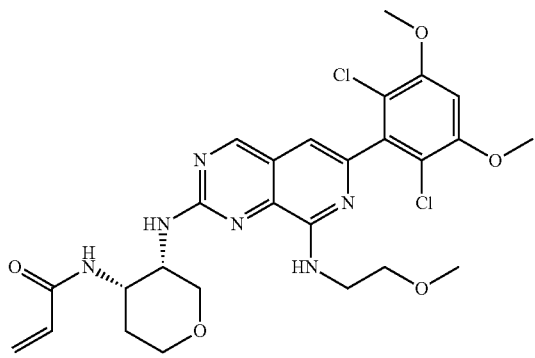

139
-continued

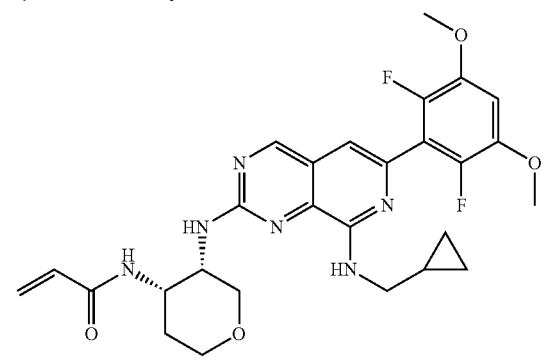
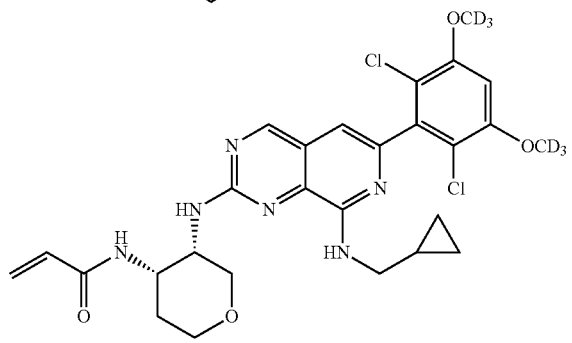
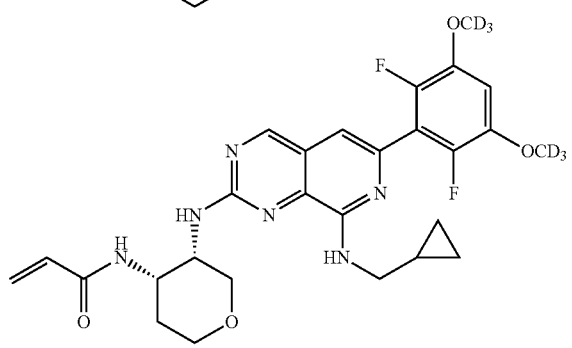
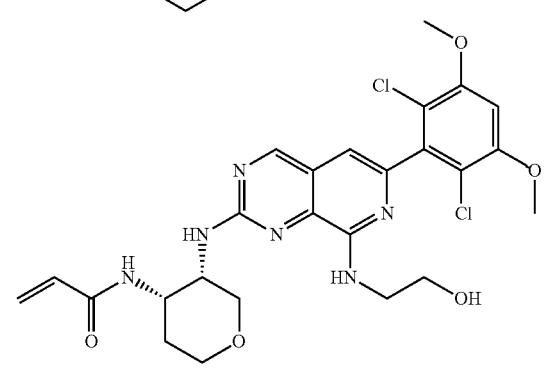
140
-continued

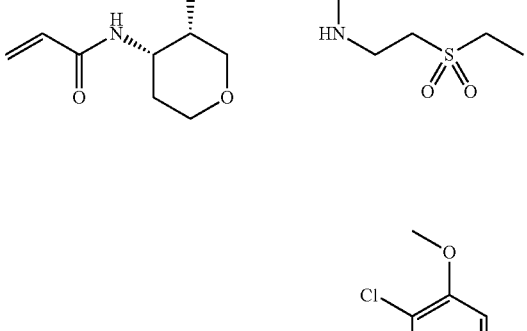
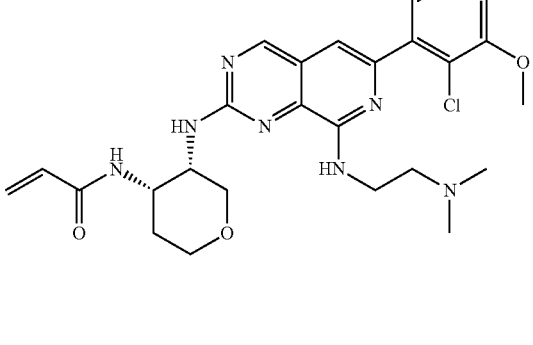
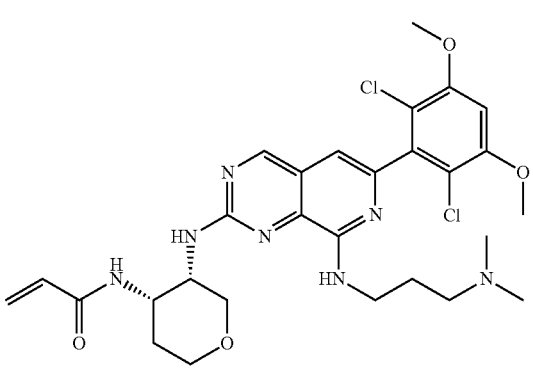

141
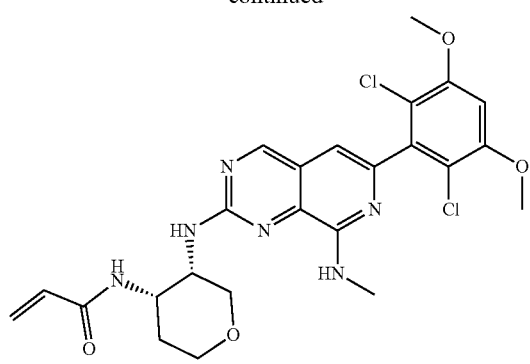
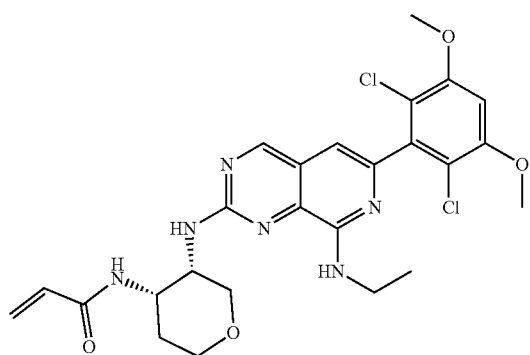
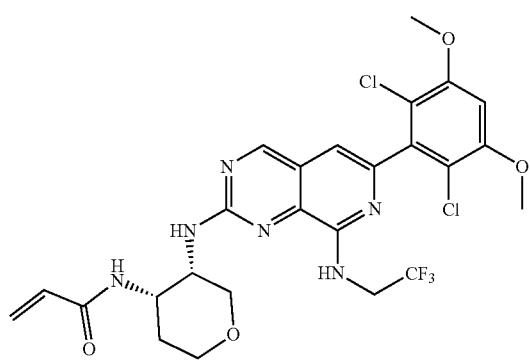
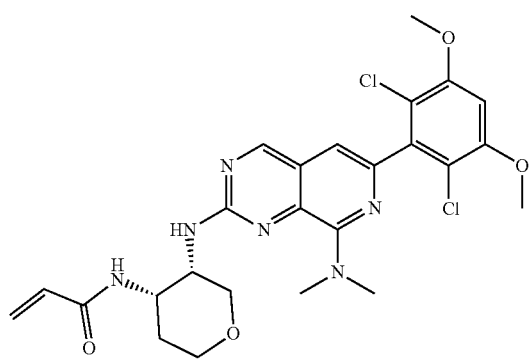
142
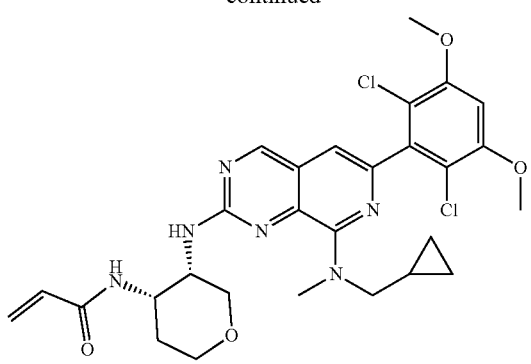
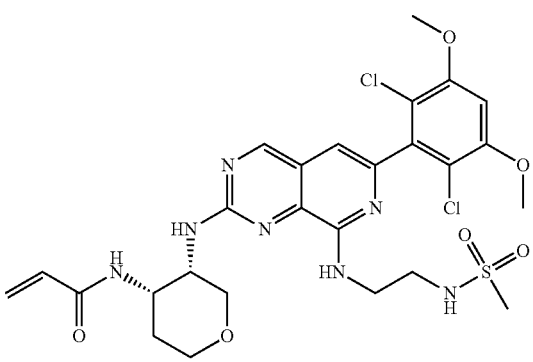
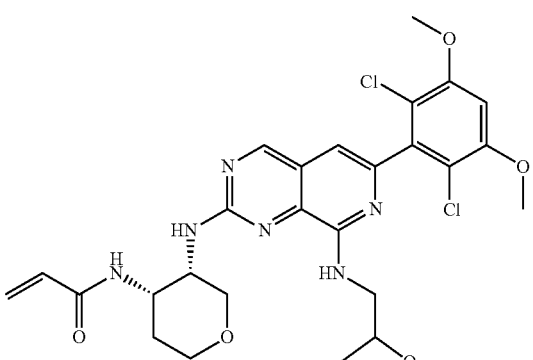
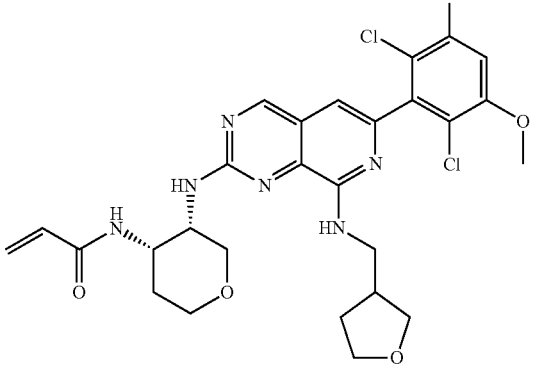

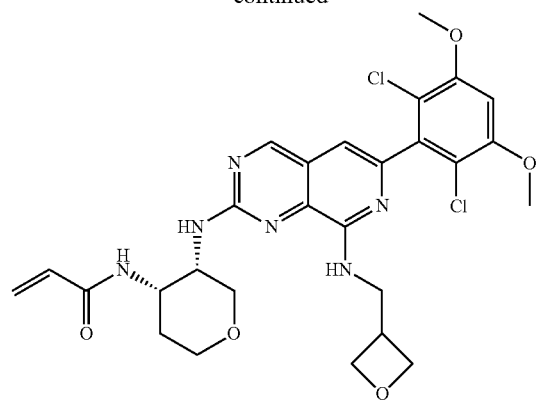
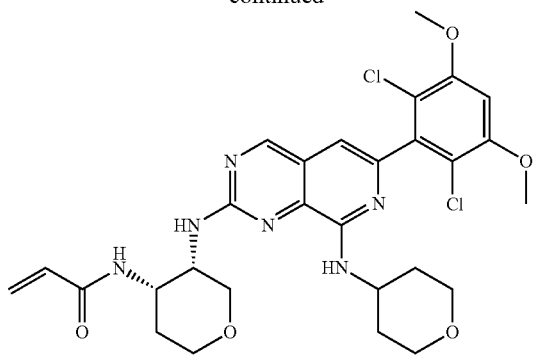
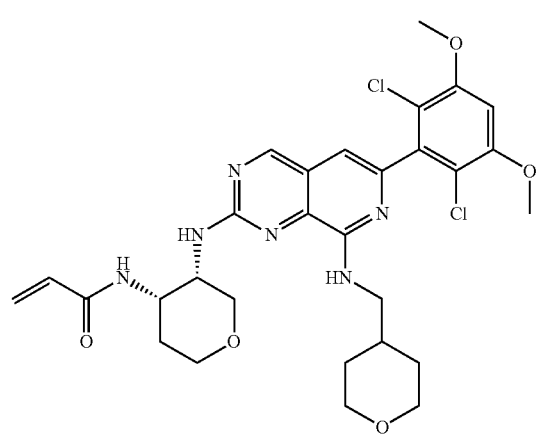
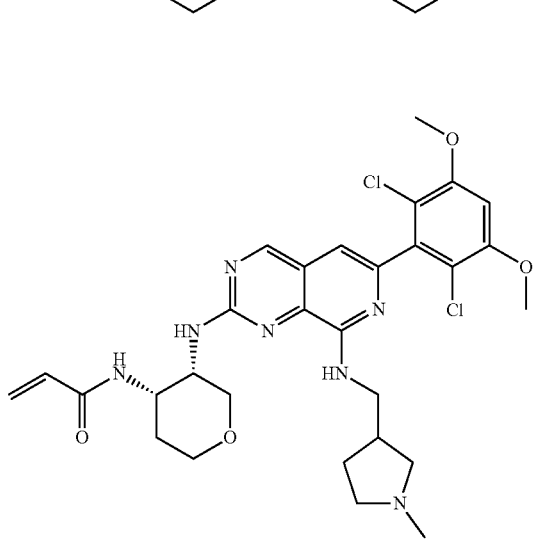
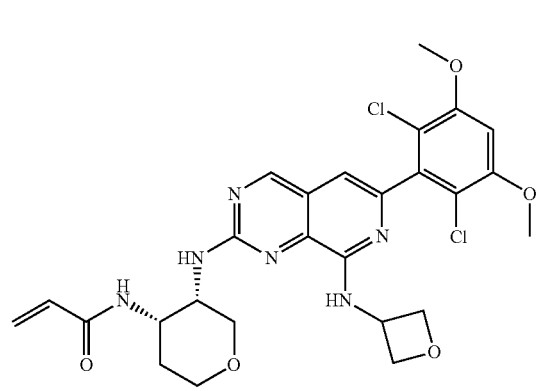
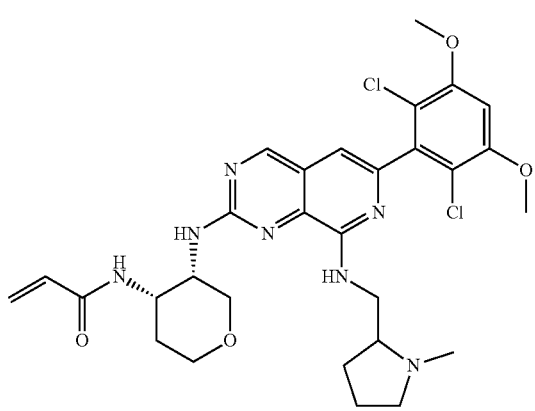
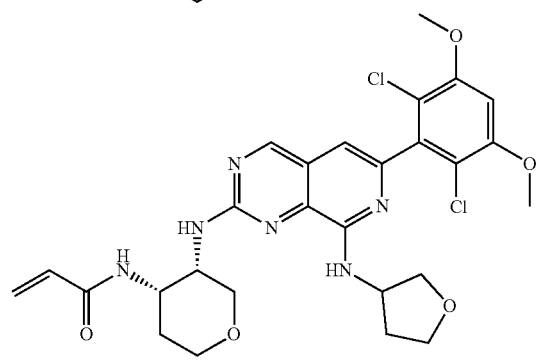
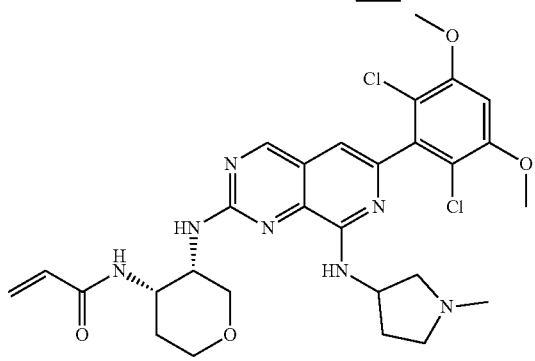

145
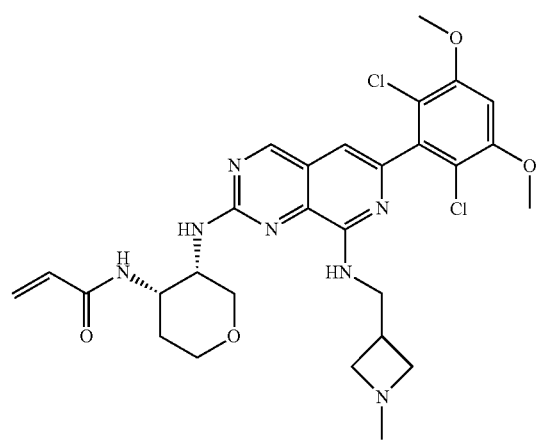
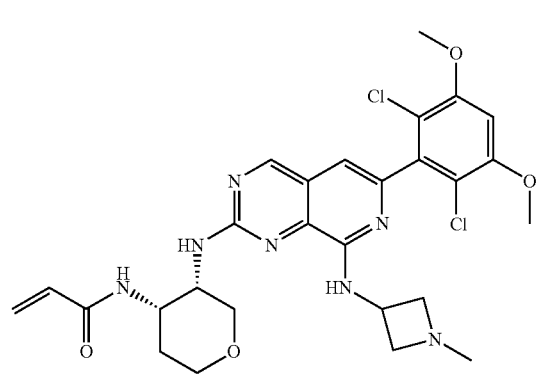
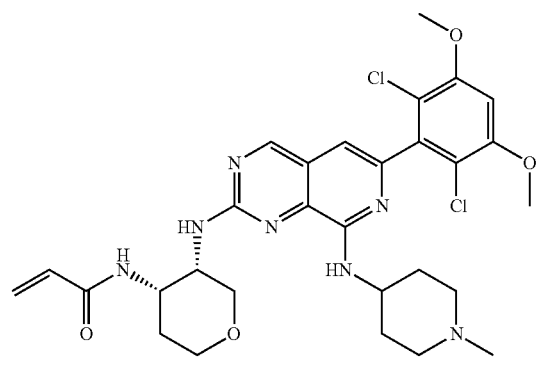
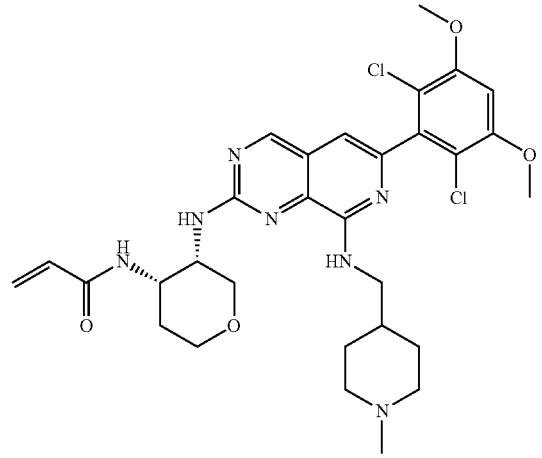
146
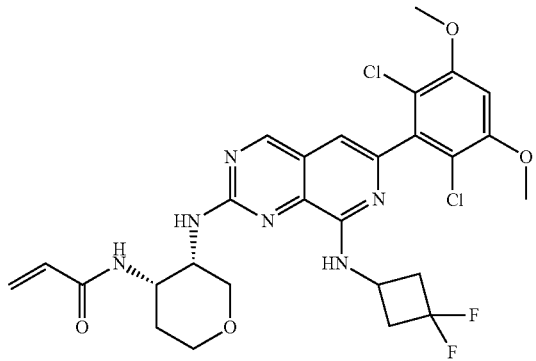
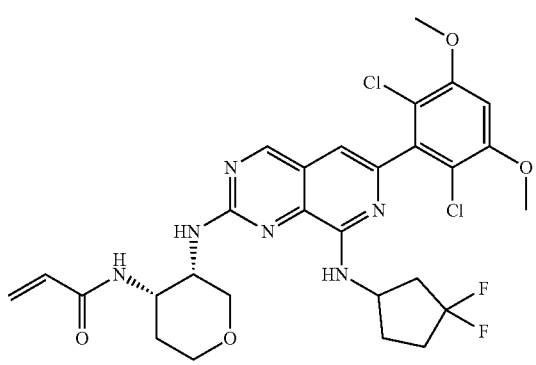
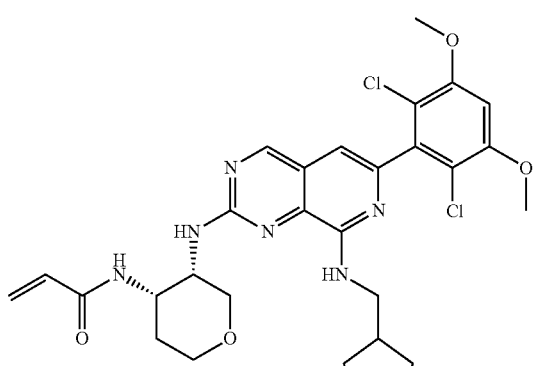
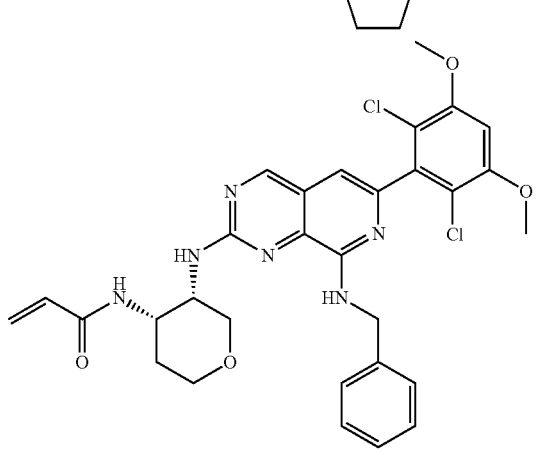

147
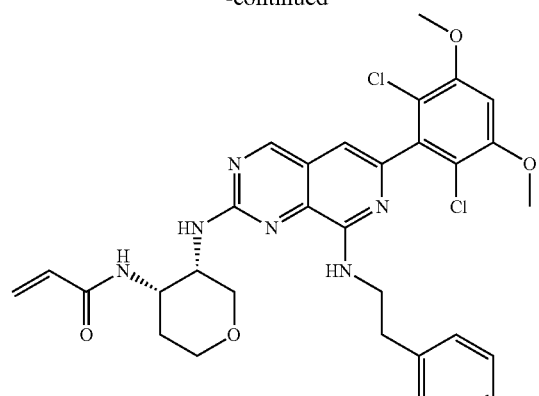
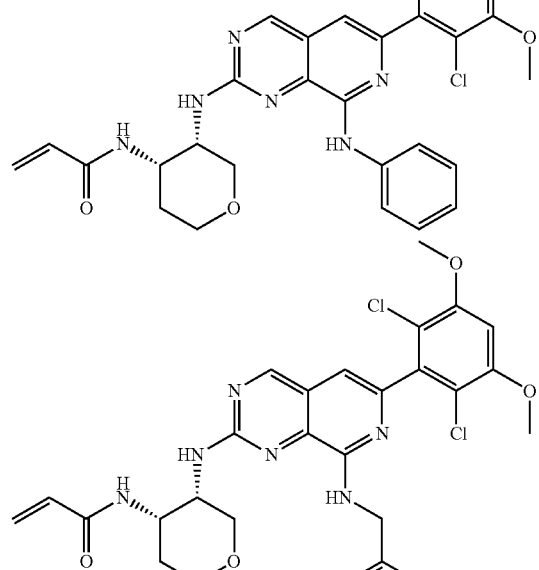
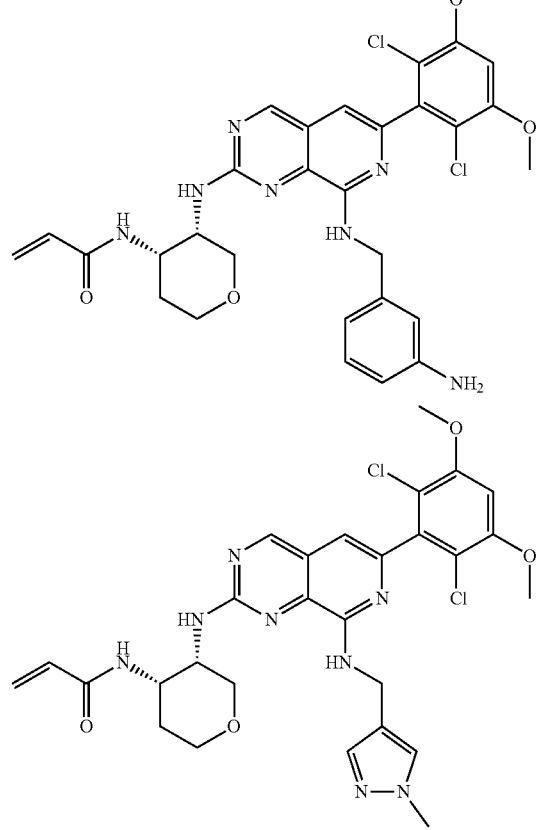
148
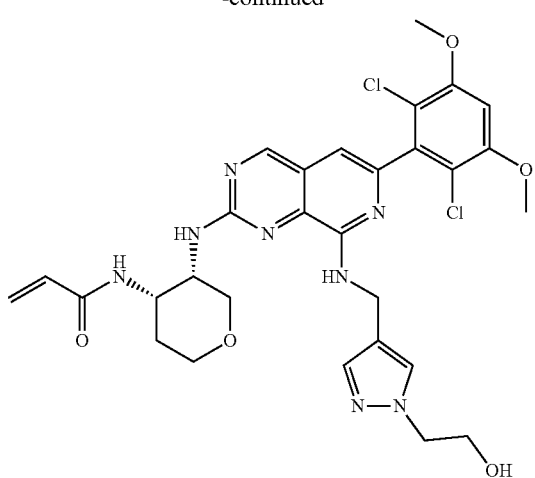
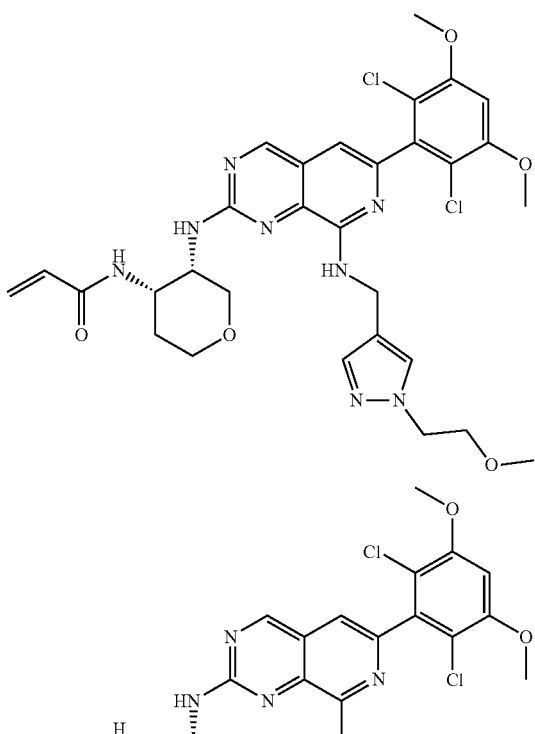
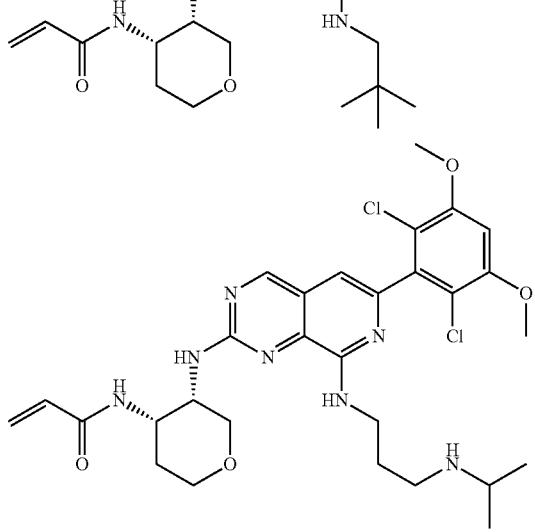
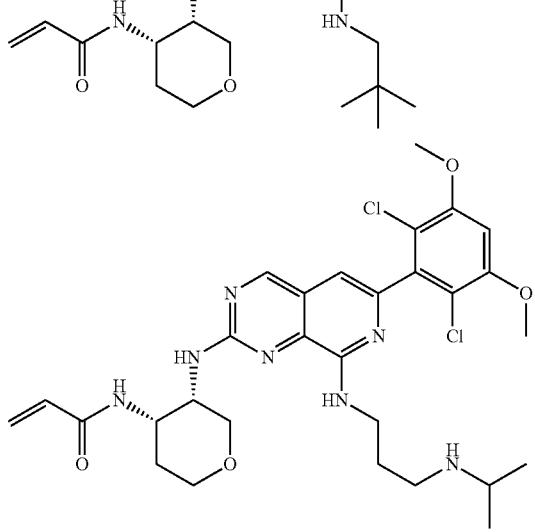
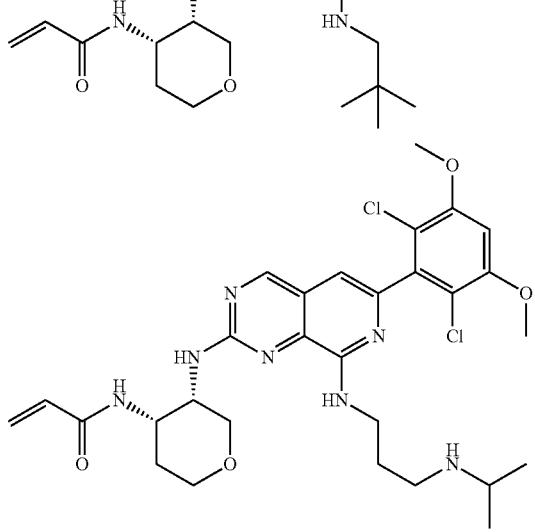

149
-continued
150
-continued
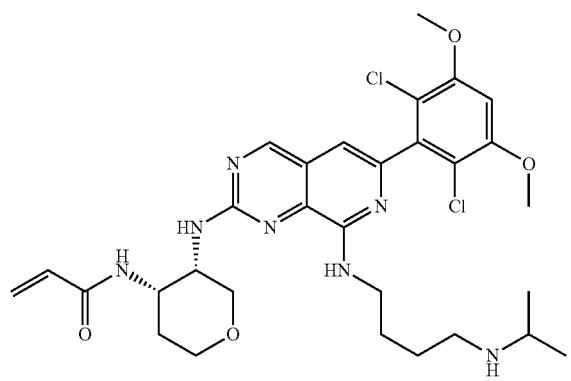
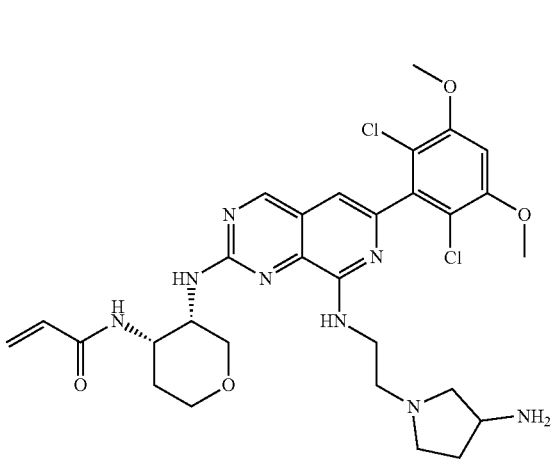
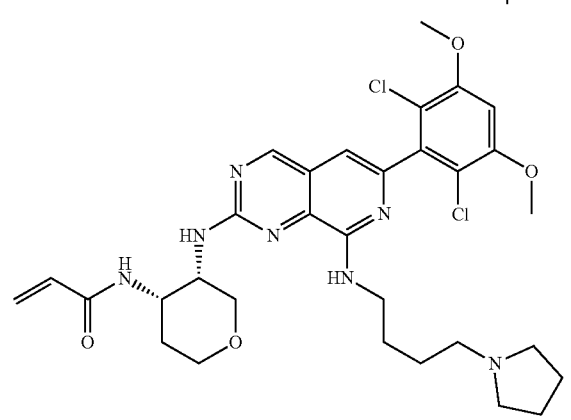
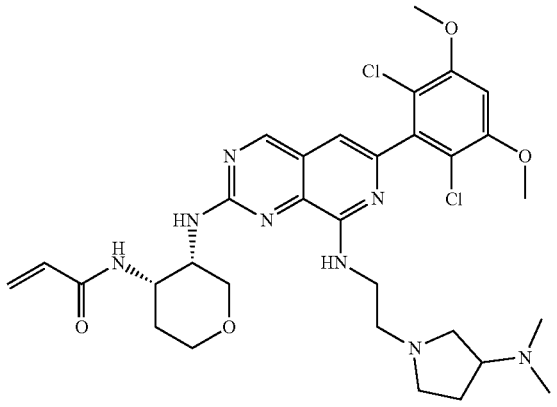
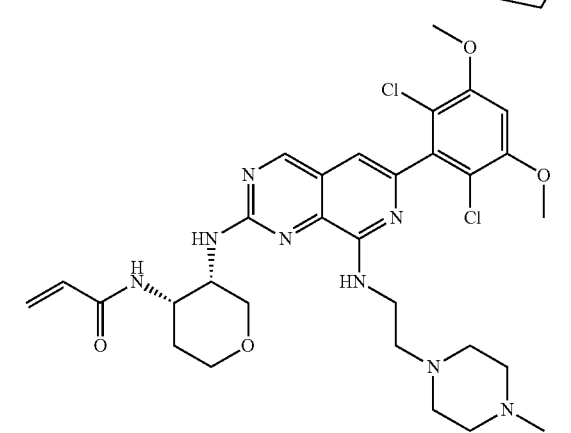

151
-continued
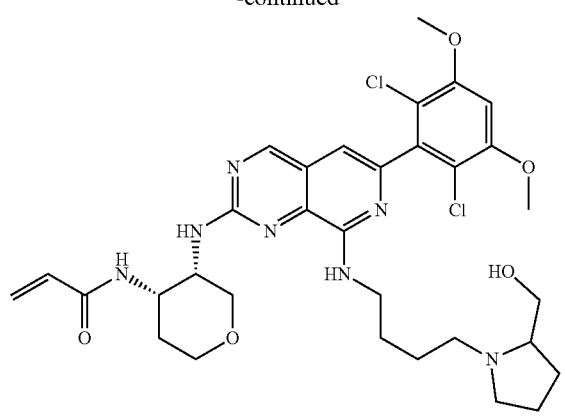
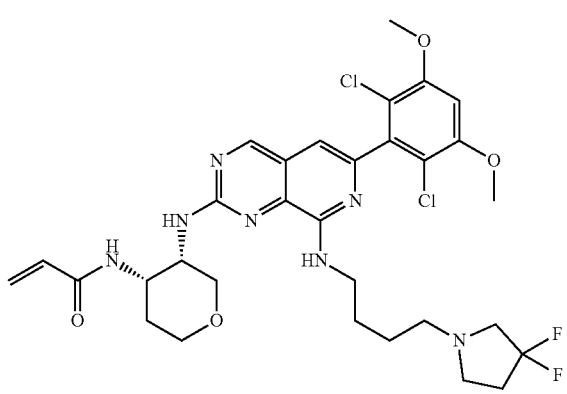
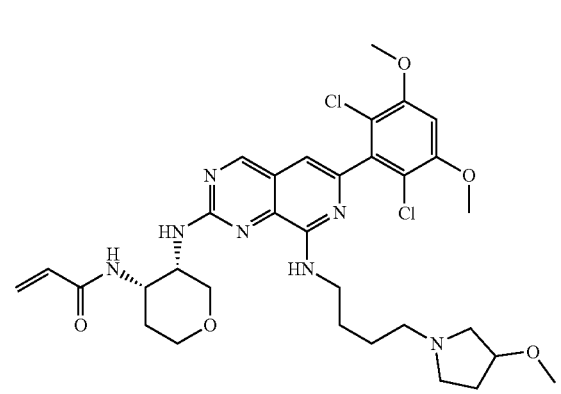
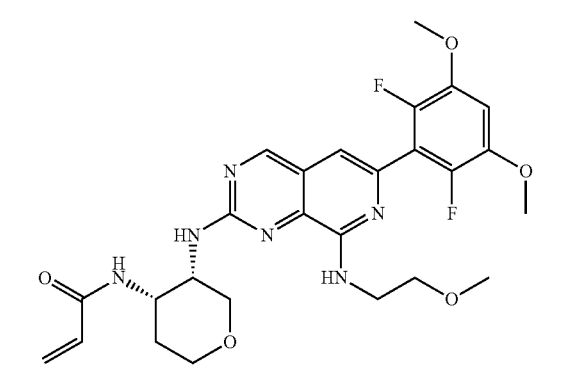
152
-continued
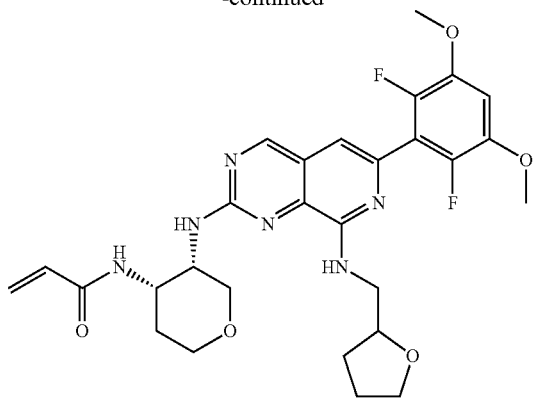

153
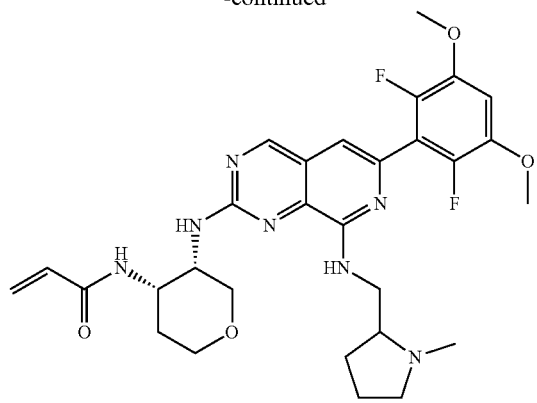
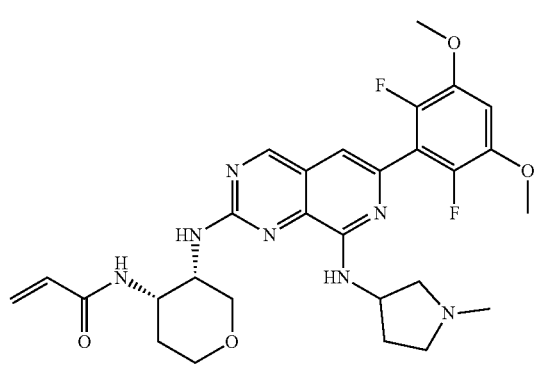
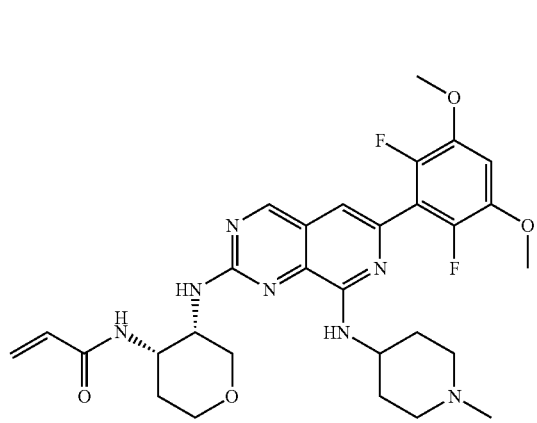
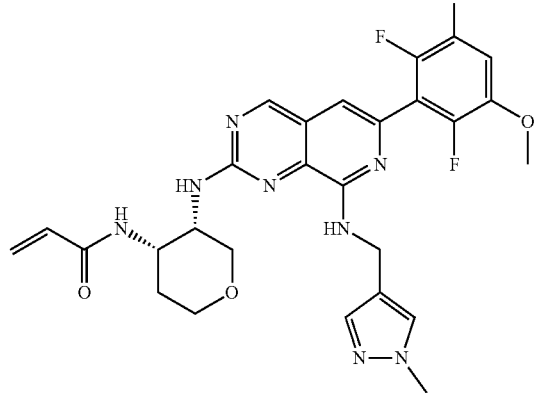
154
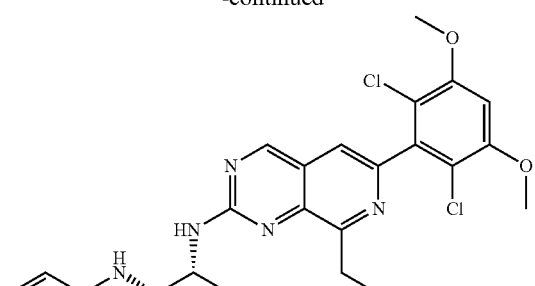

155
-continued
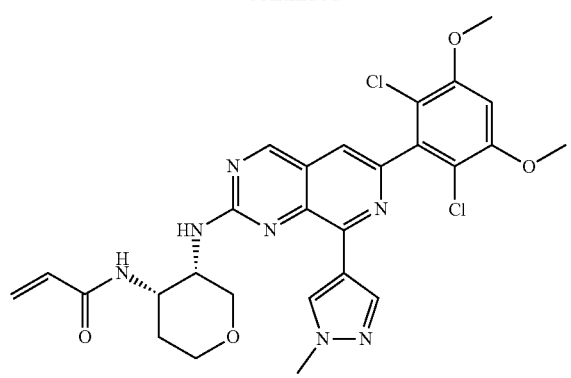
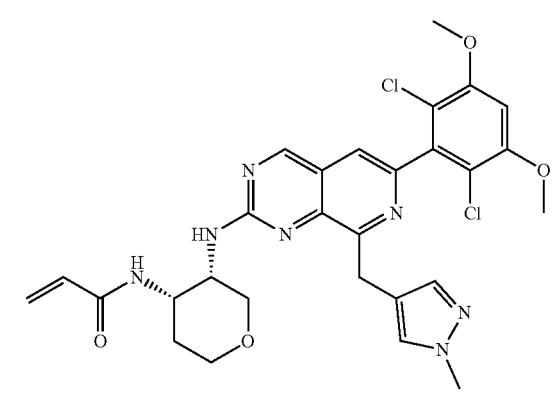
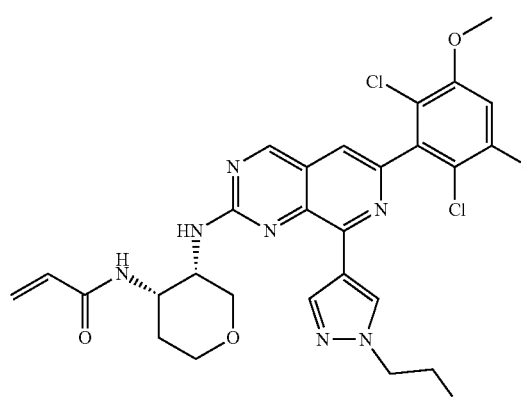
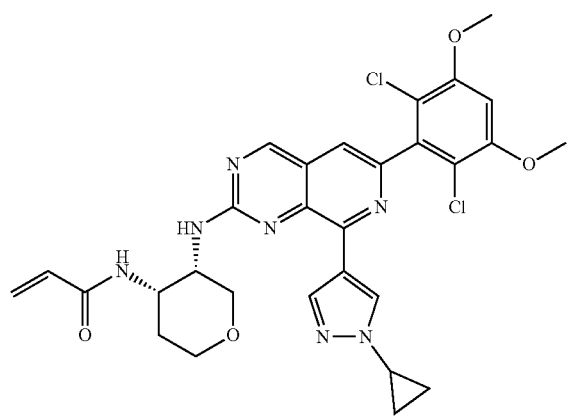
156
-continued
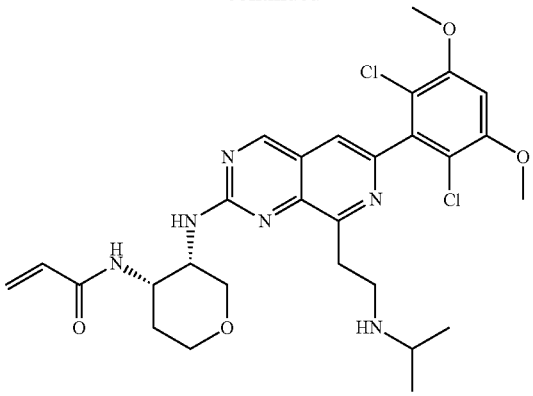
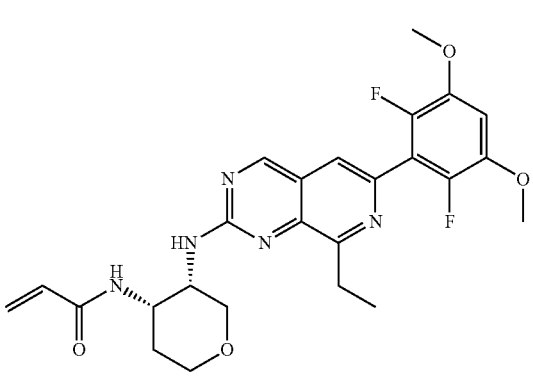
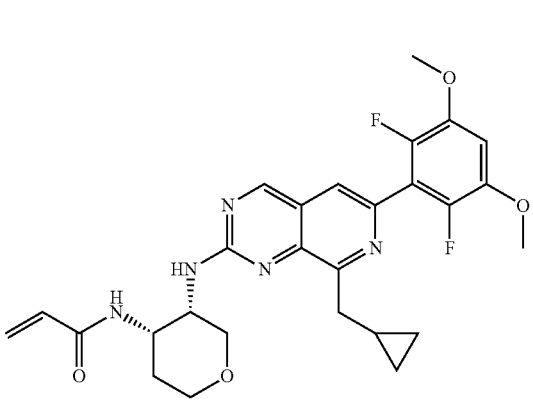
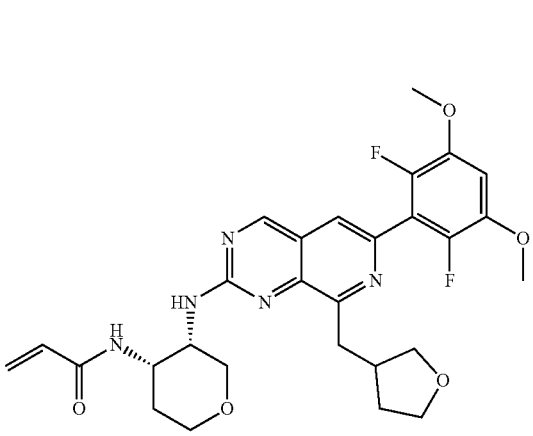

157
-continued
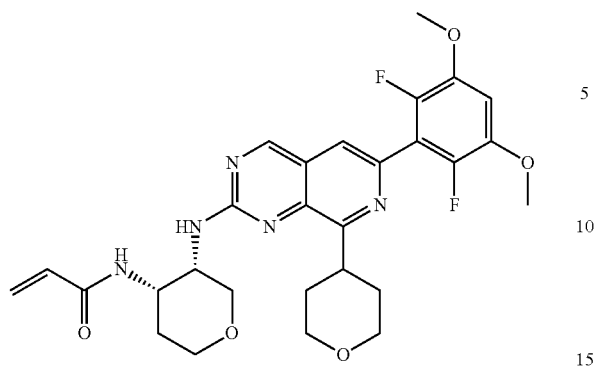
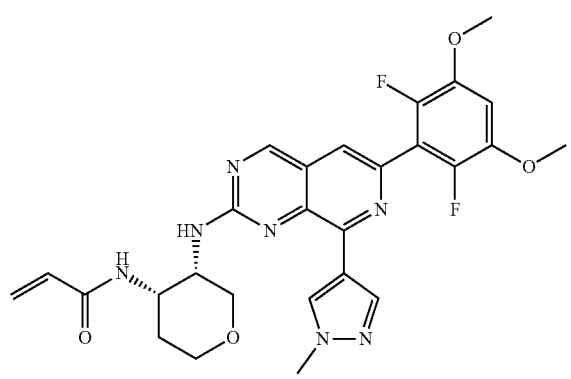
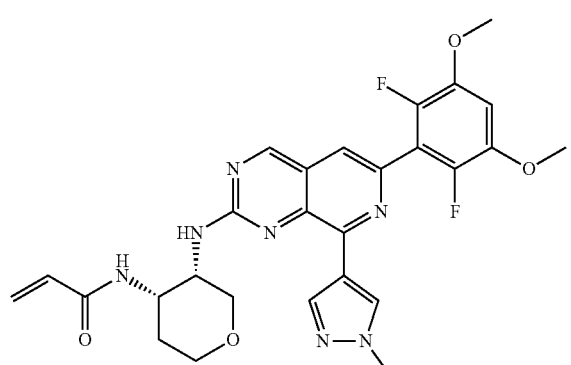
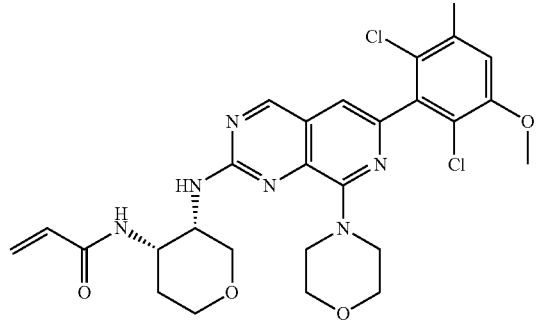
158
-continued
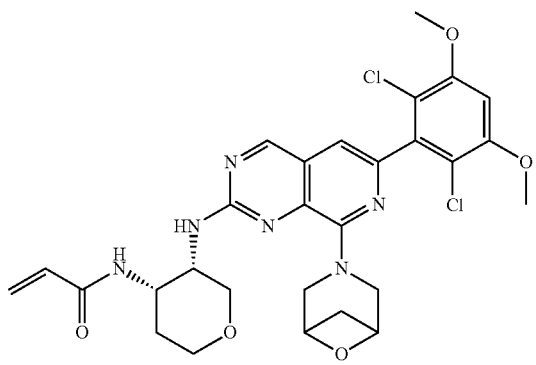
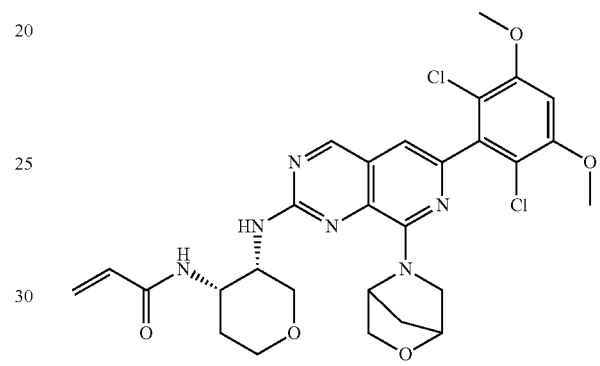
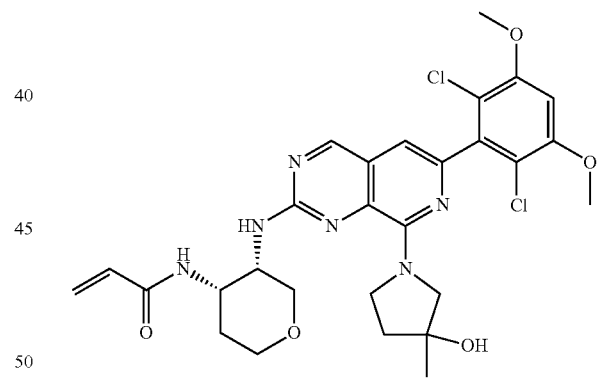
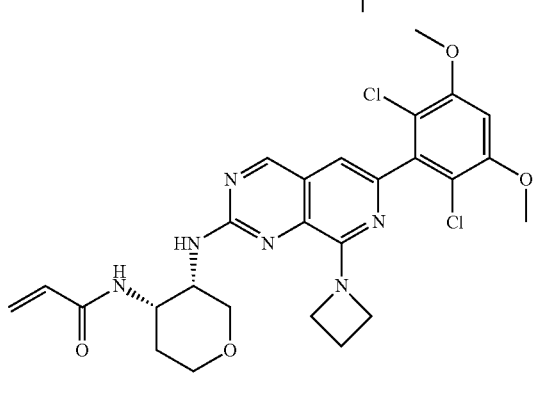

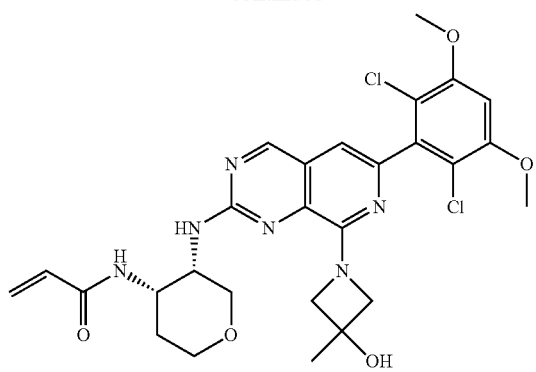
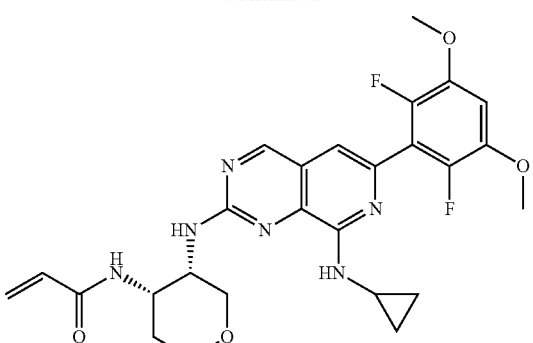

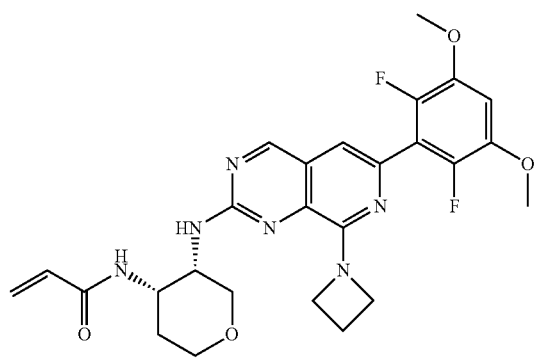
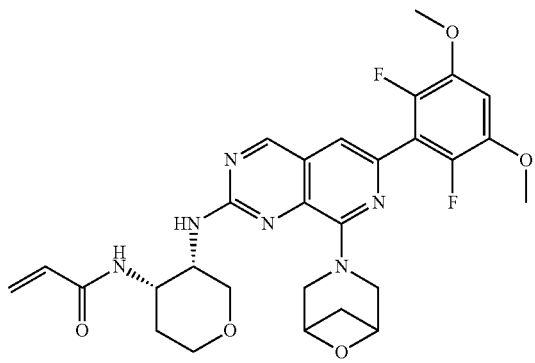
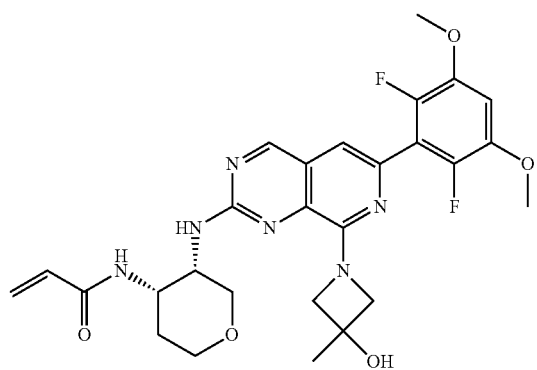

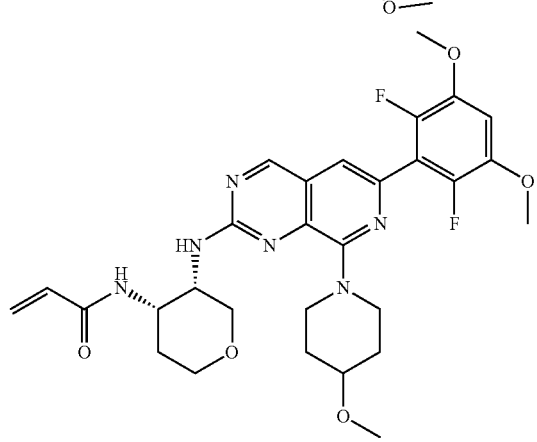
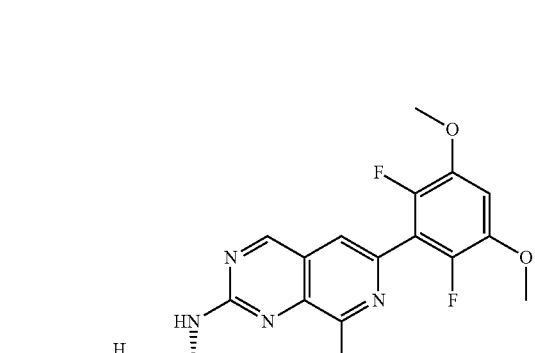
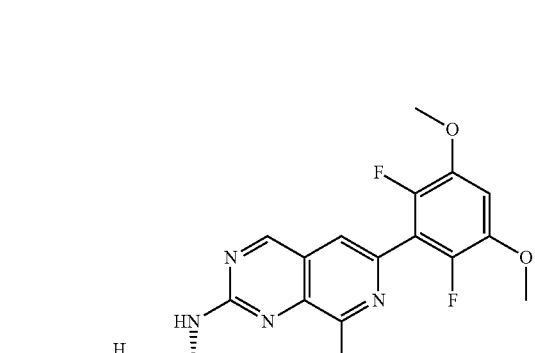
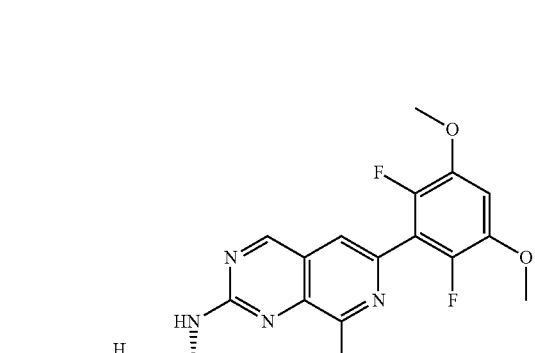

163
-continued
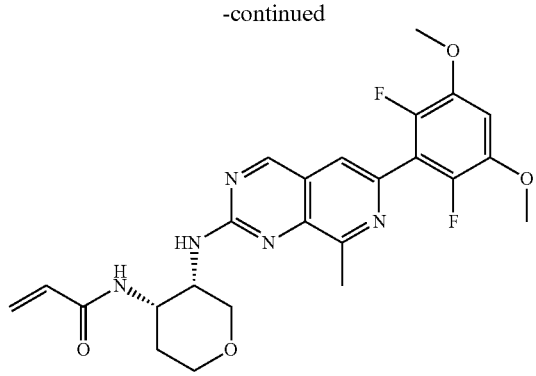
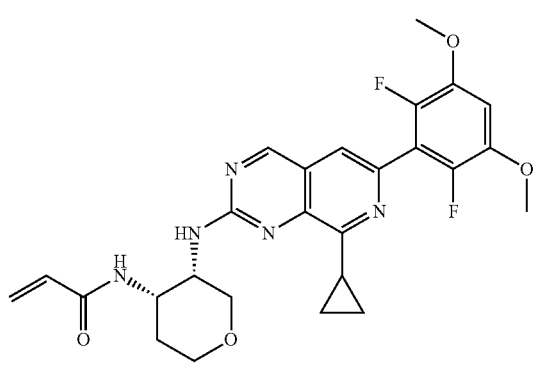
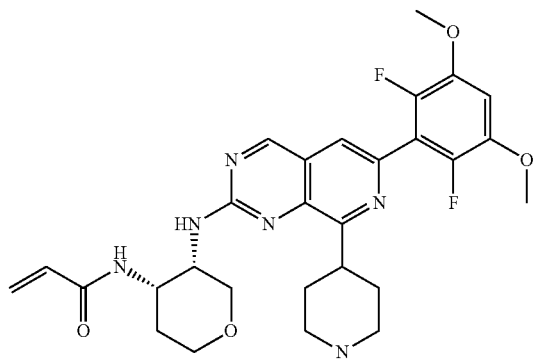
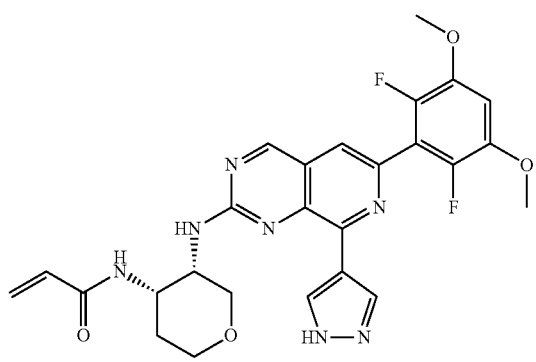
164
-continued
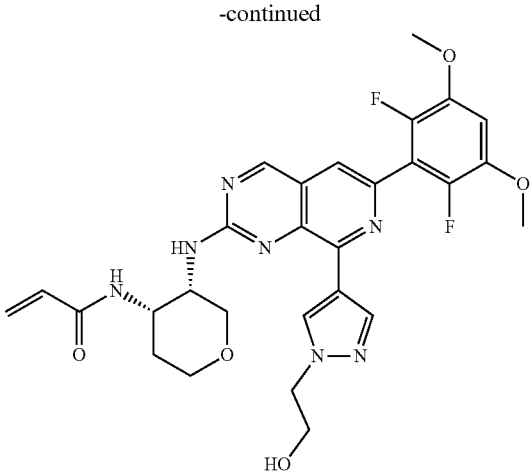
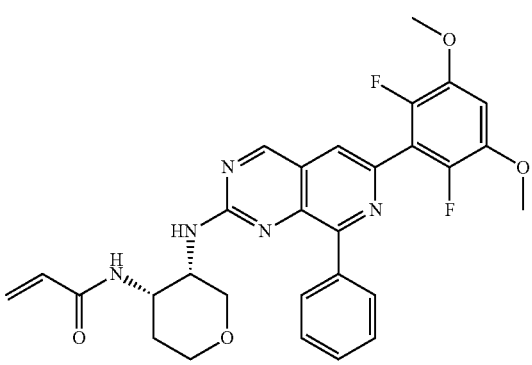
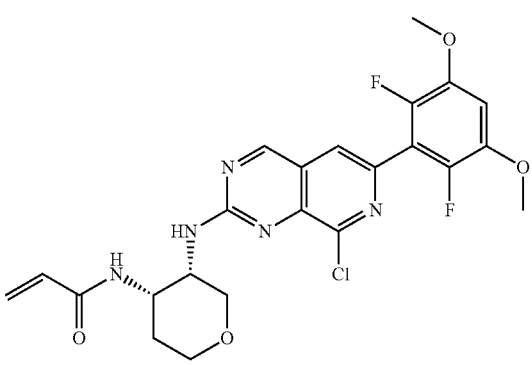
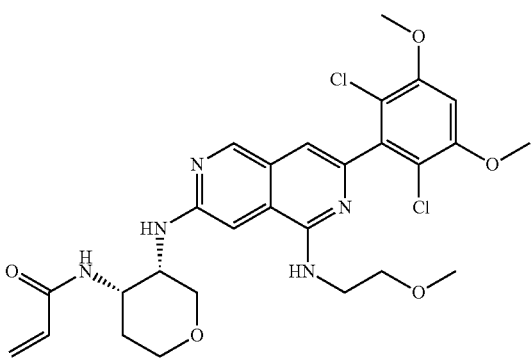

165
-continued
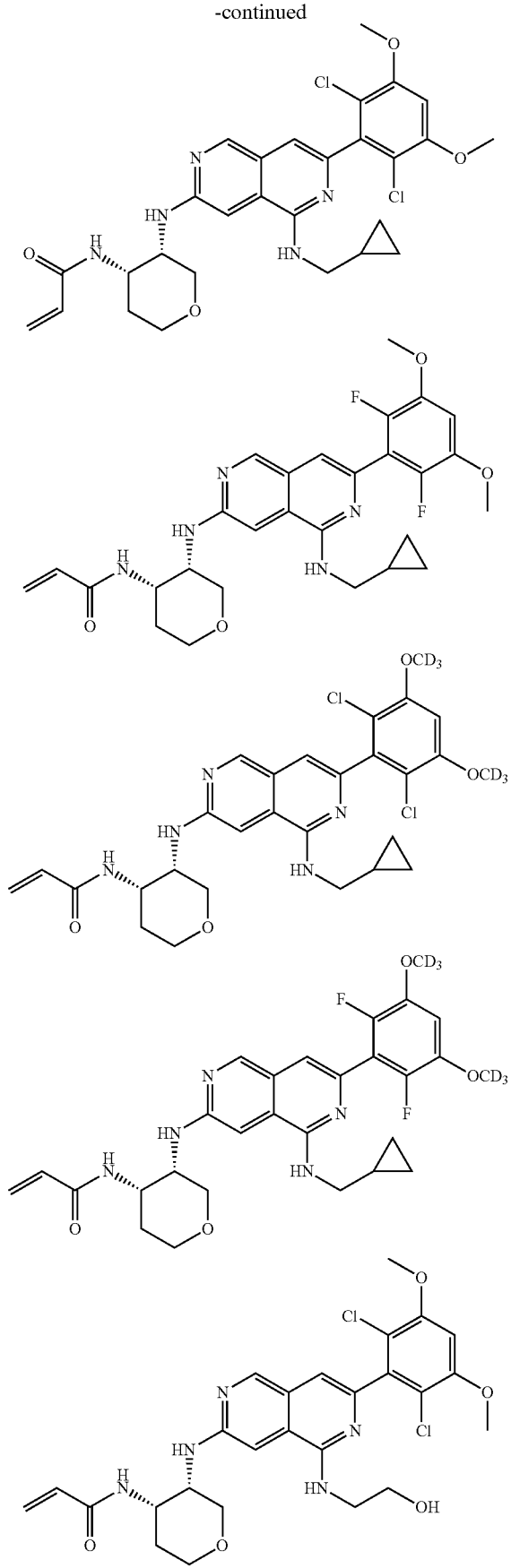
166
-continued
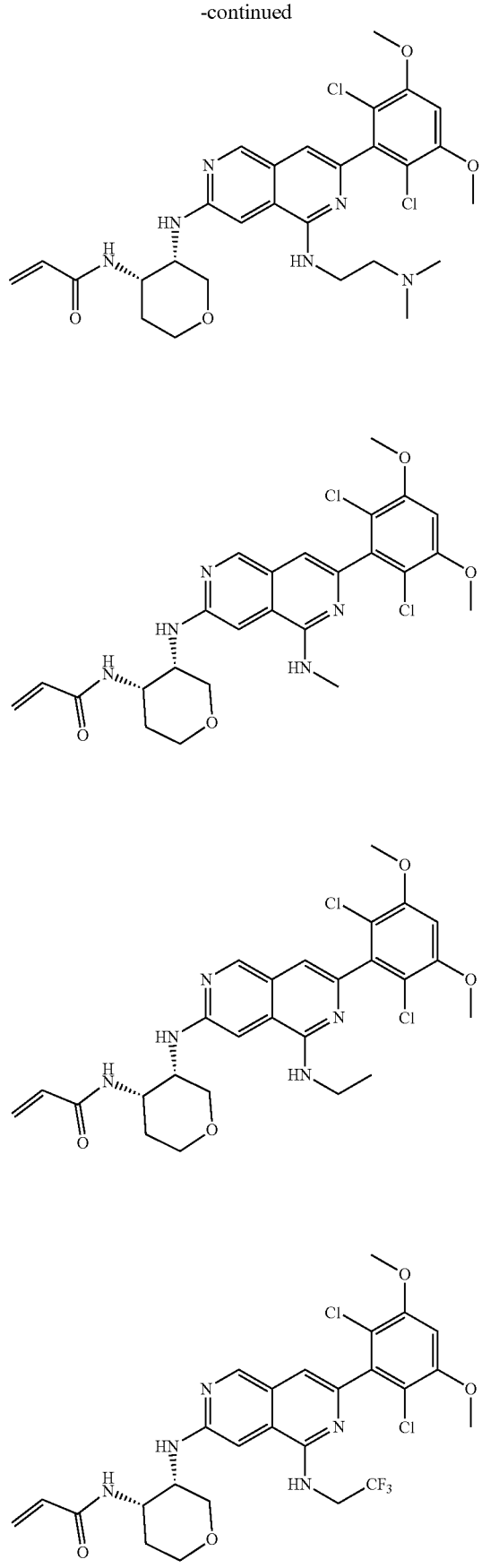

167
-continued
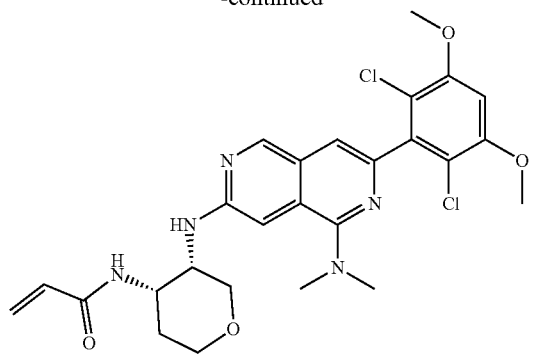
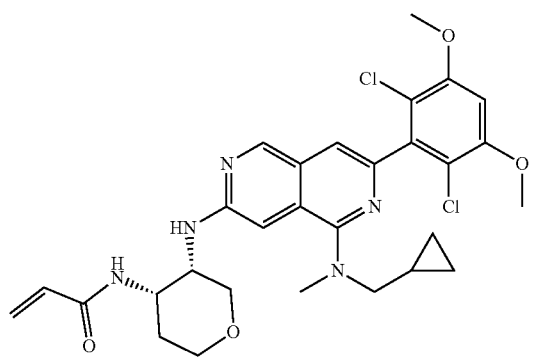
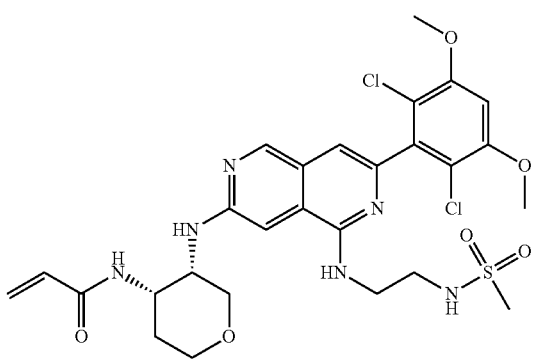
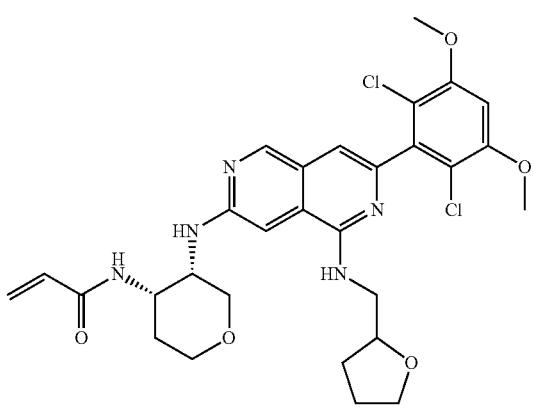
168
-continued
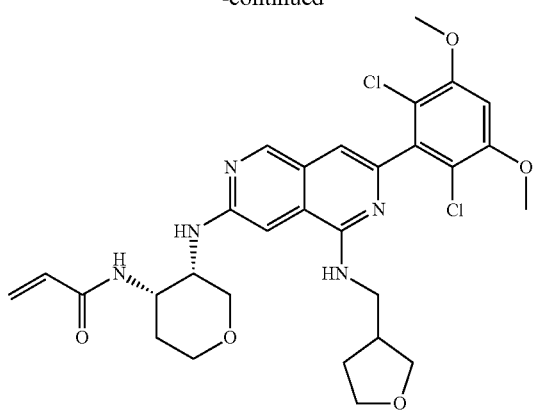
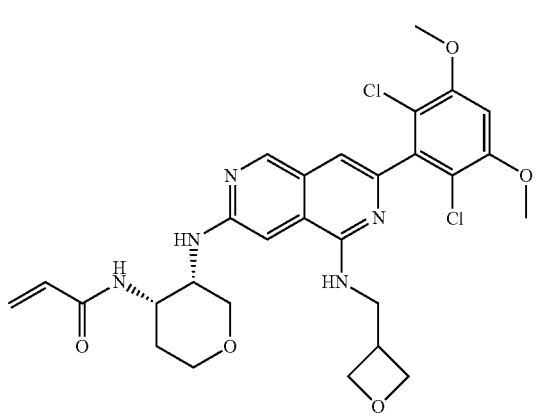
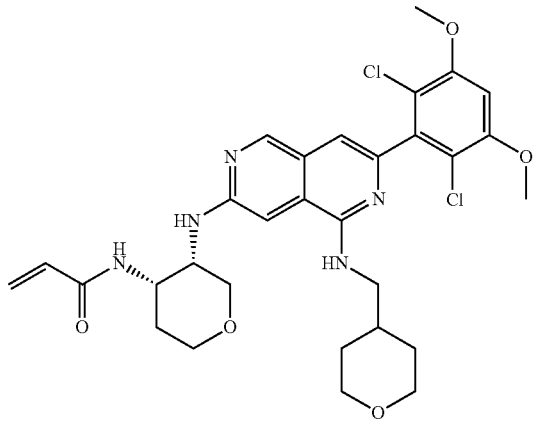
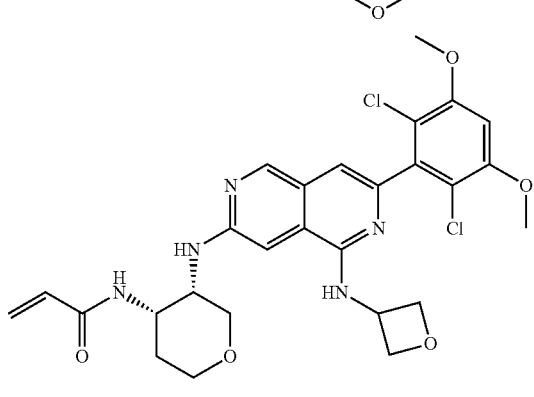

169
-continued
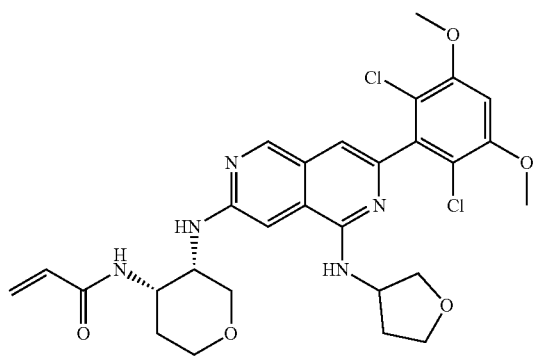
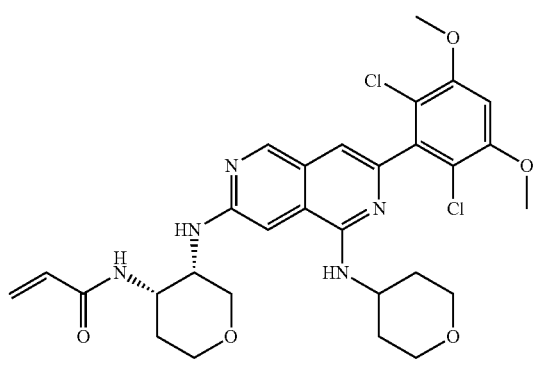
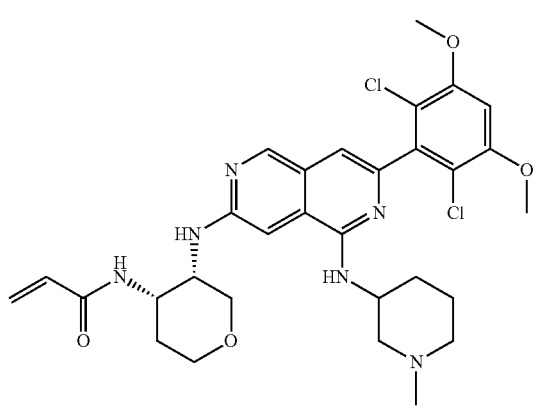
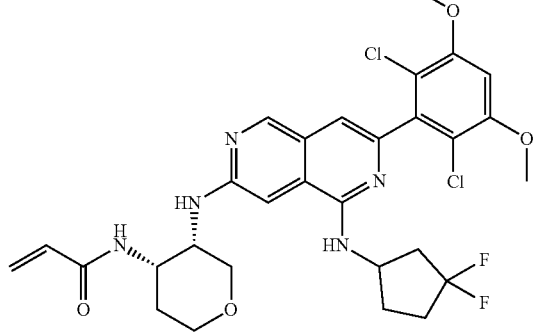
170
-continued
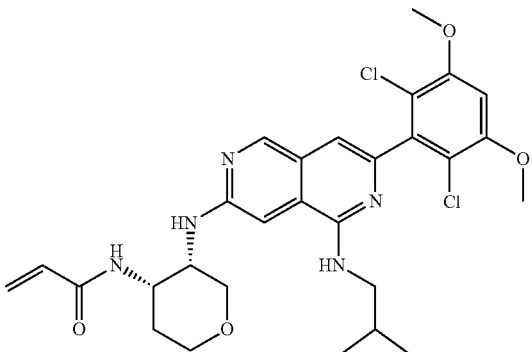
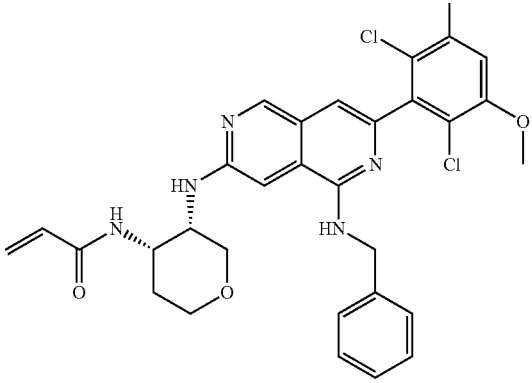
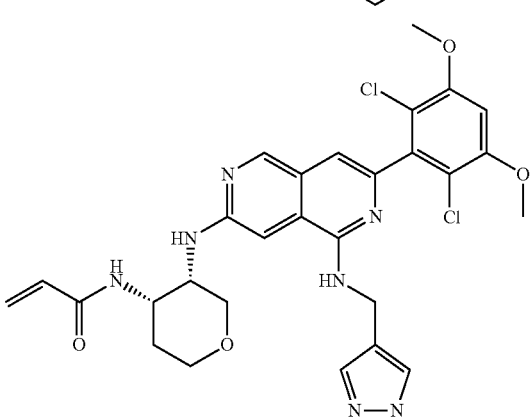
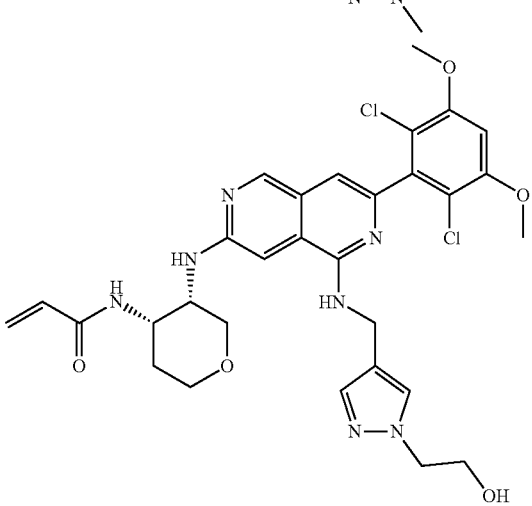

171
-continued
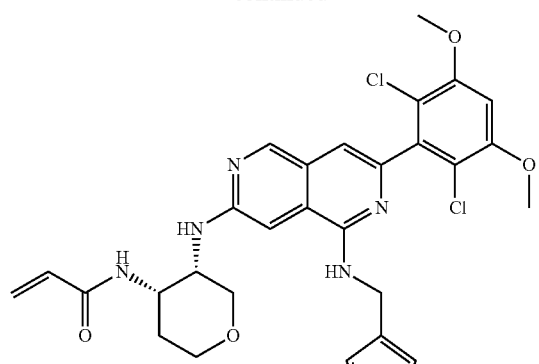
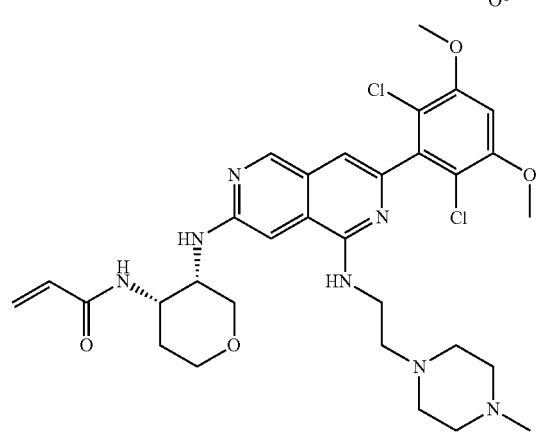
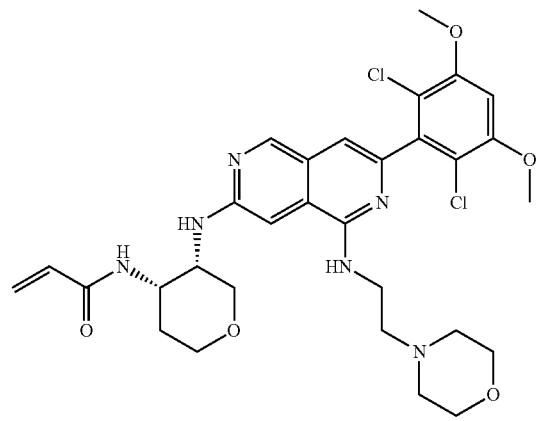
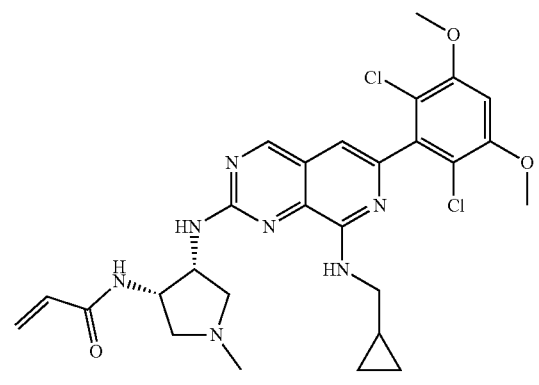
172
-continued
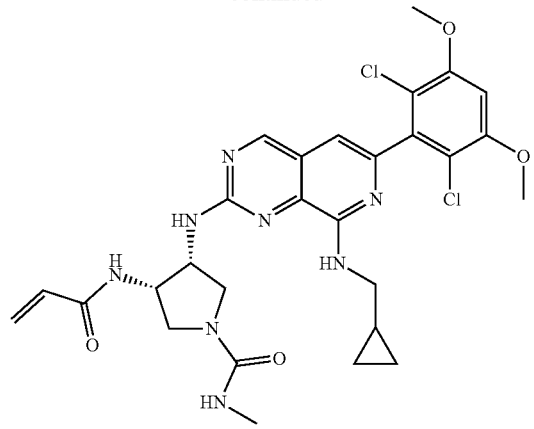
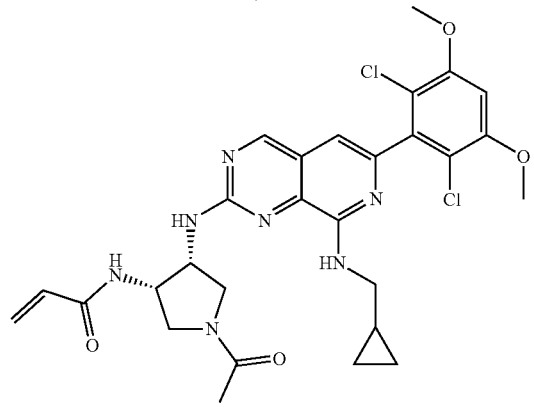
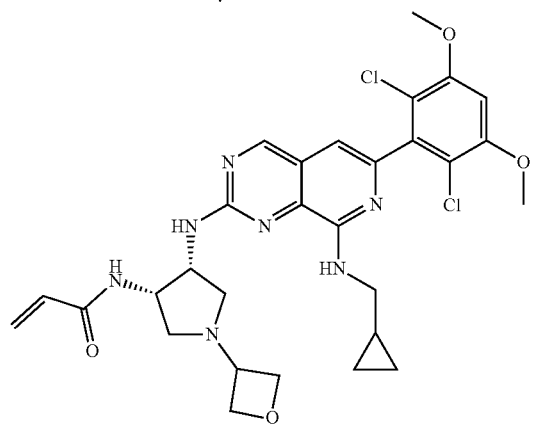
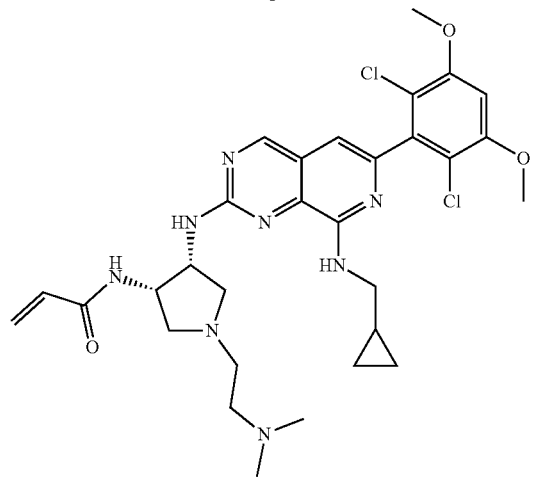

173
-continued
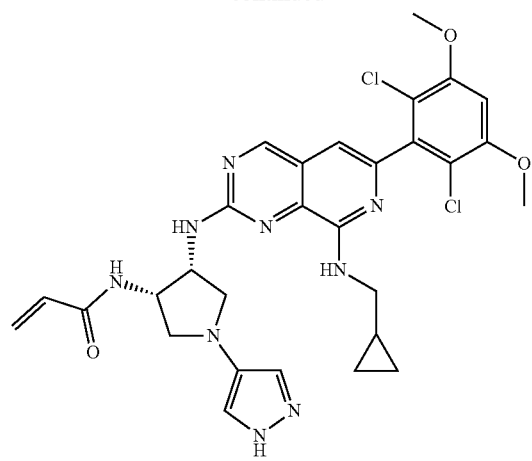
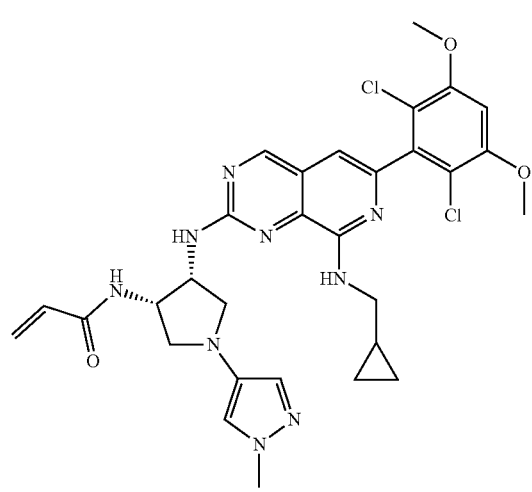
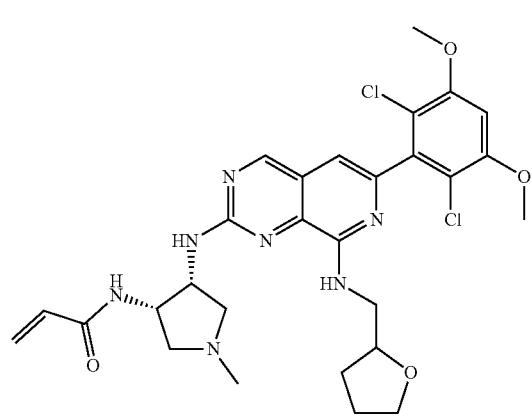
174
-continued
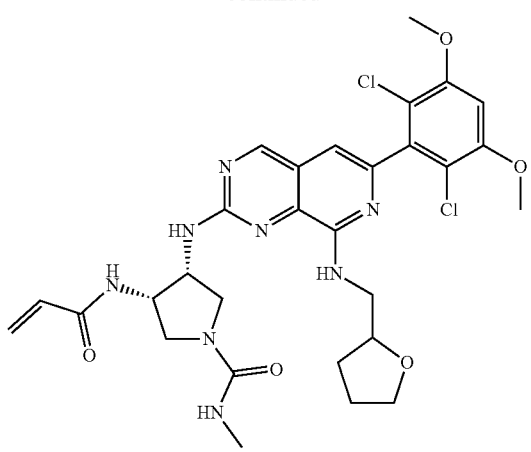

175
-continued
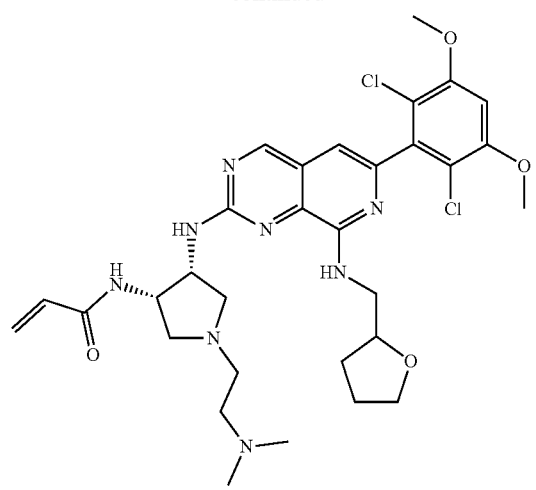
176
-continued
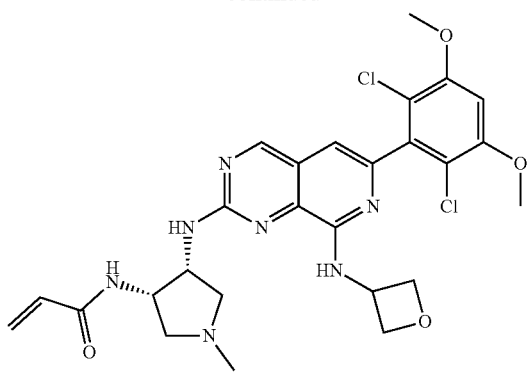
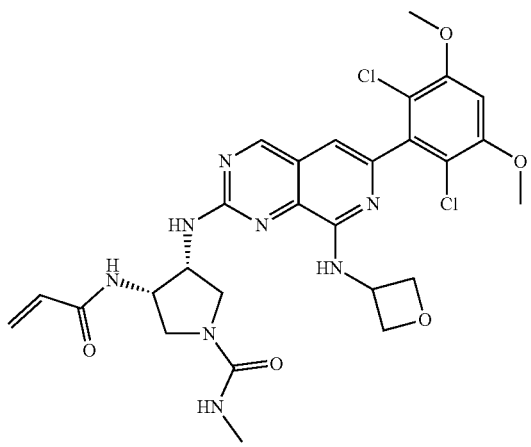
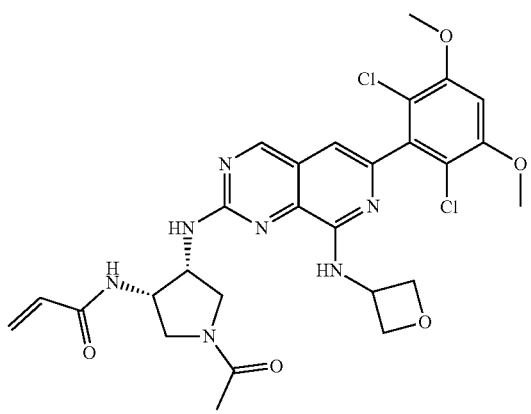
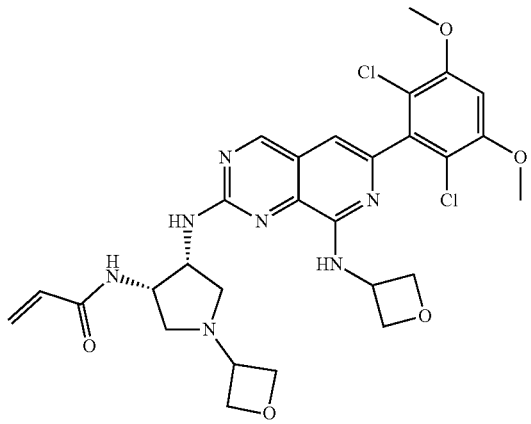

177 178
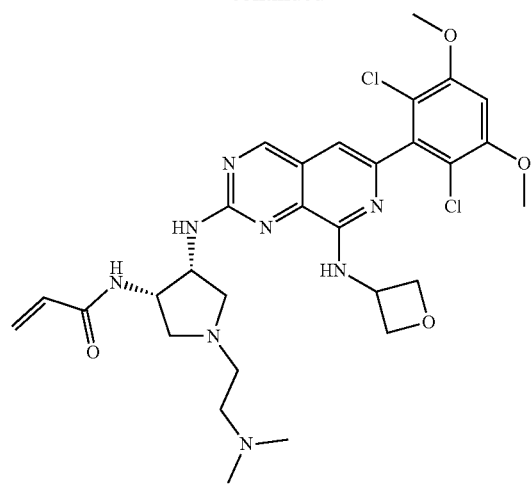
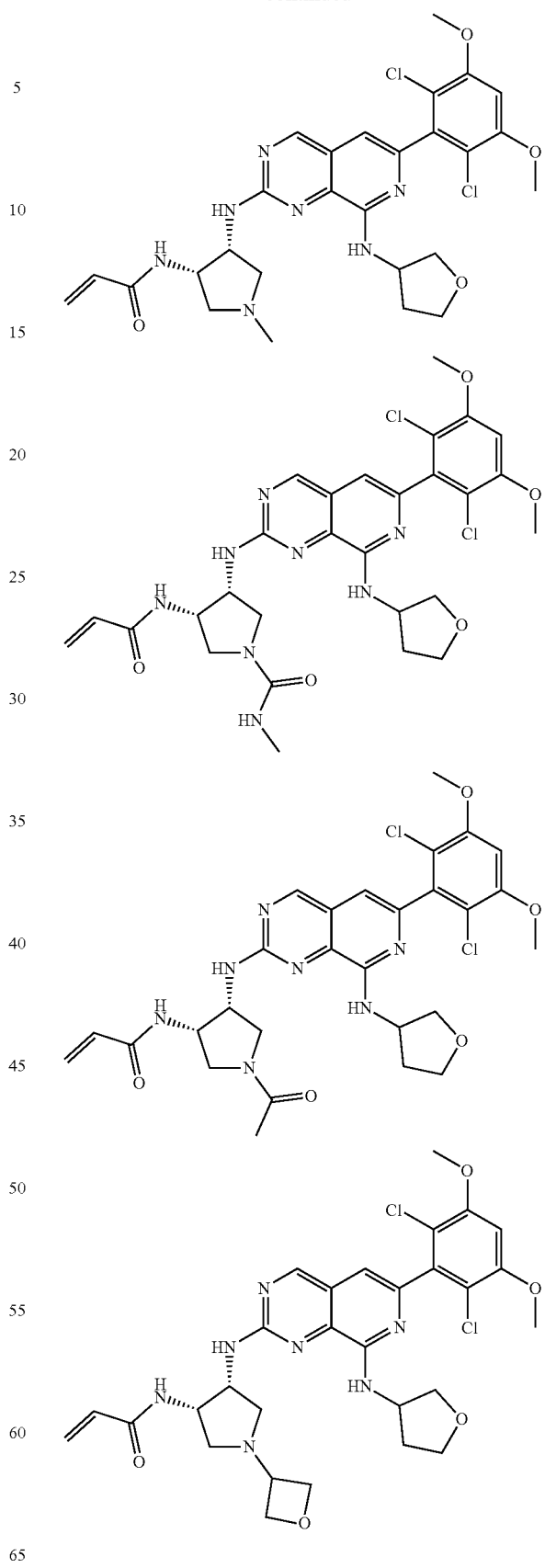

179
-continued
180
-continued
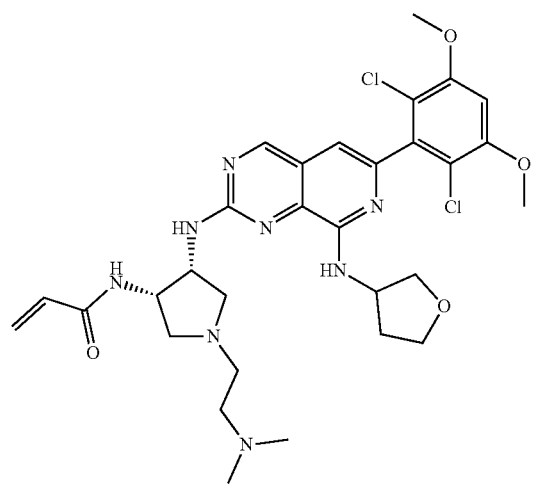
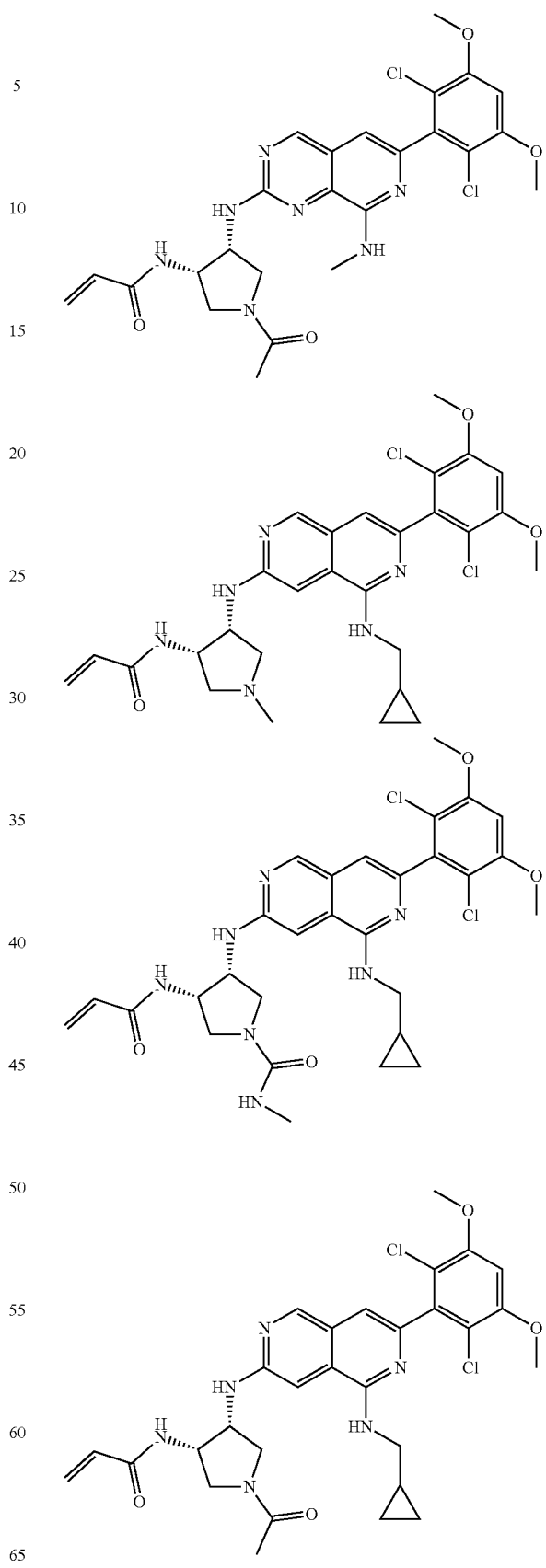

181
-continued

182
-continued
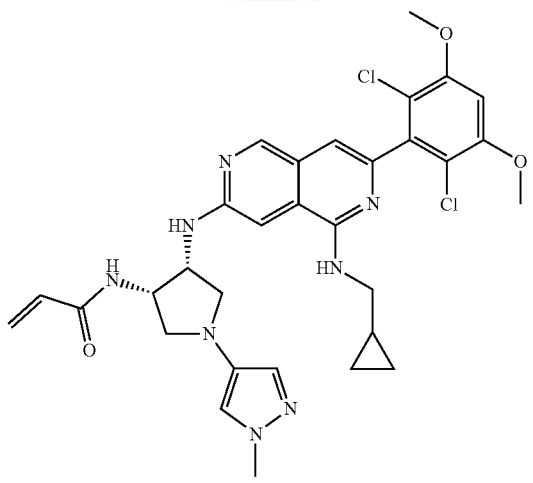
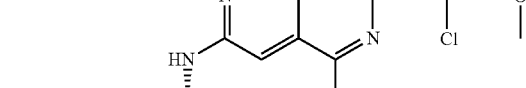

183
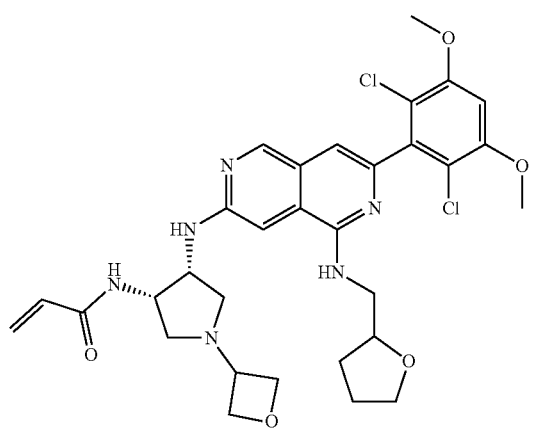
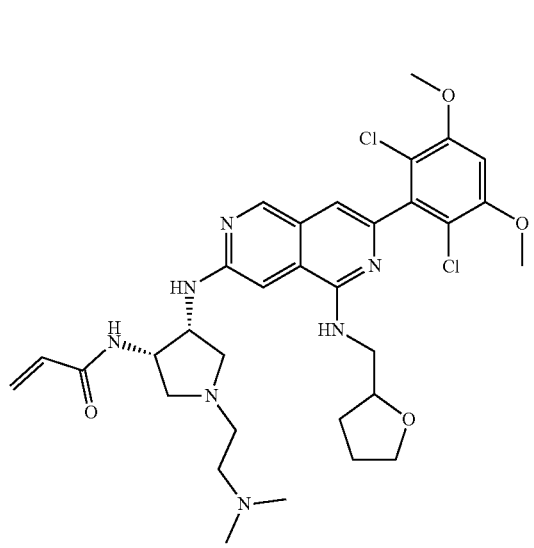
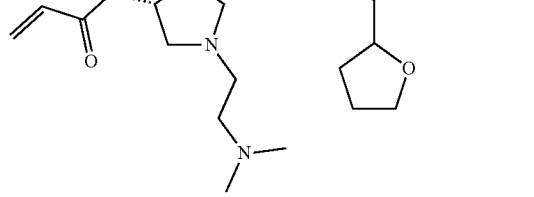
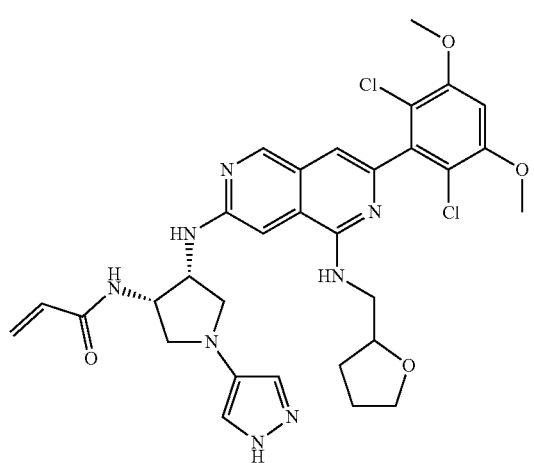
184
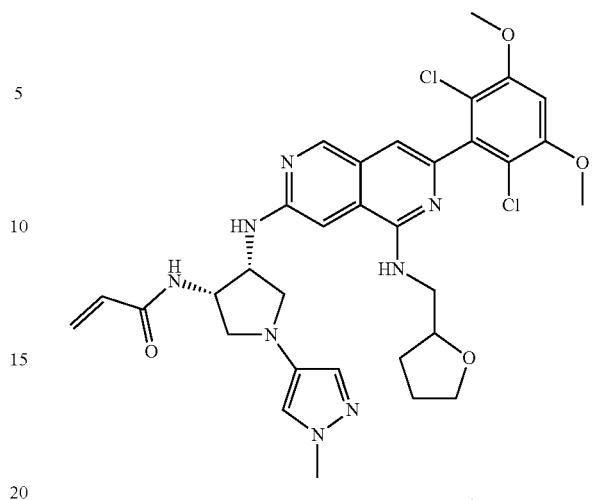
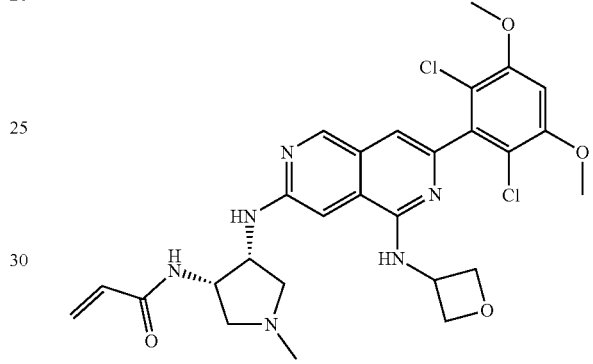
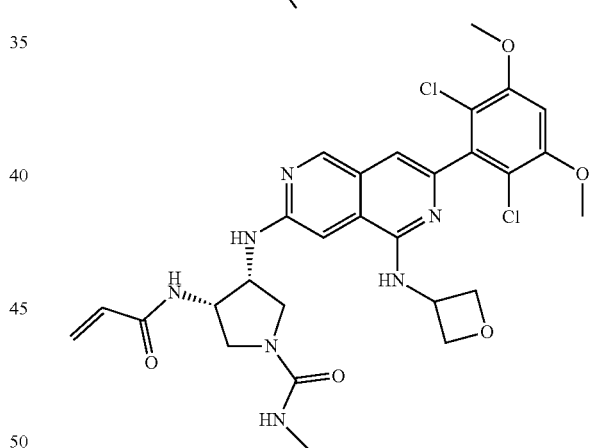
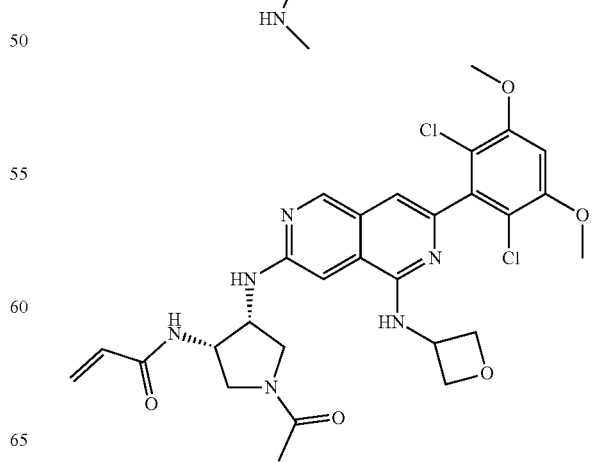

185
-continued
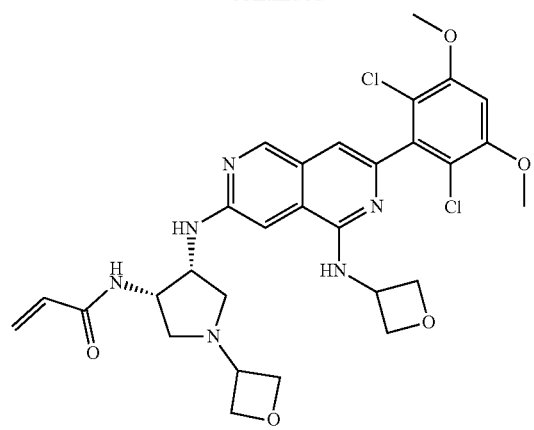
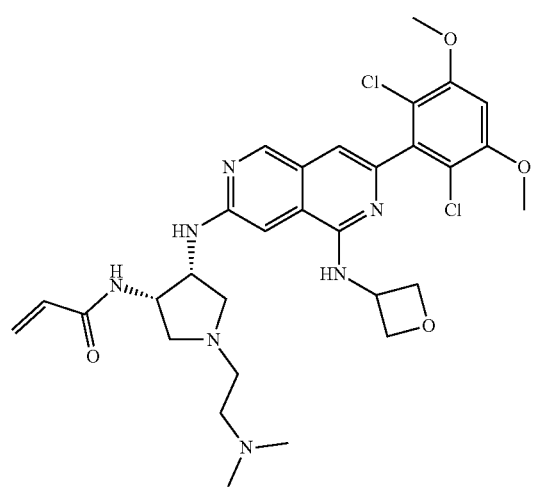
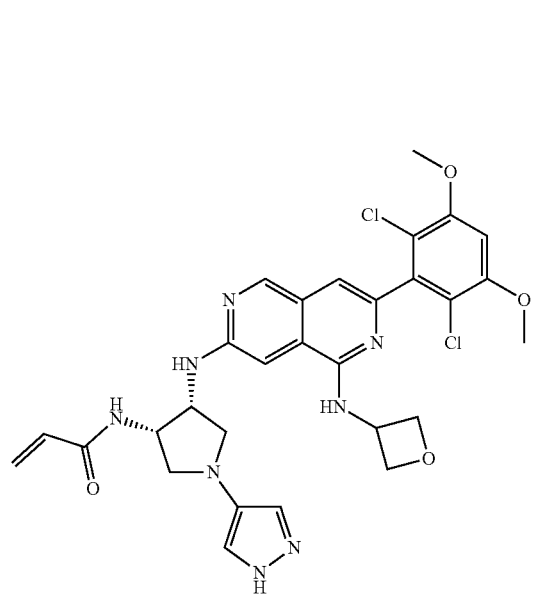
186
-continued
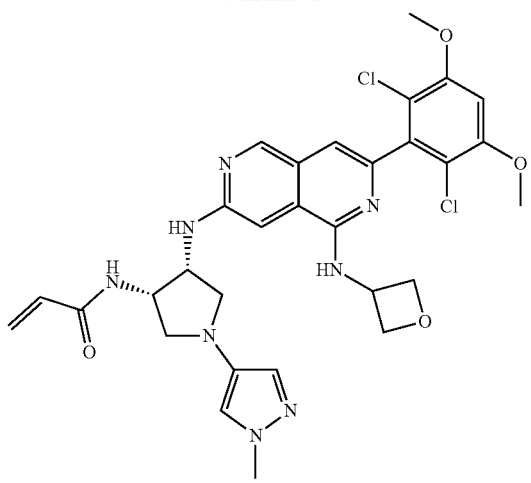
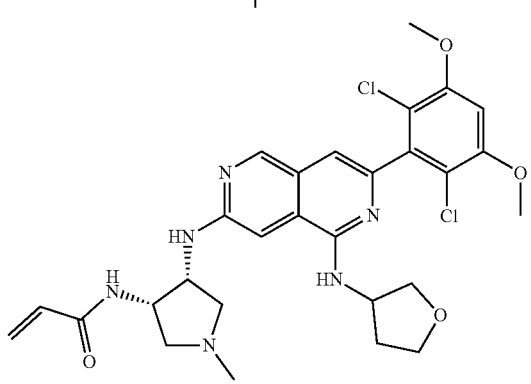
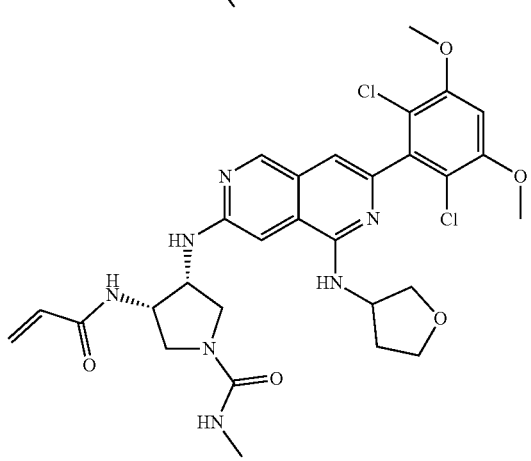
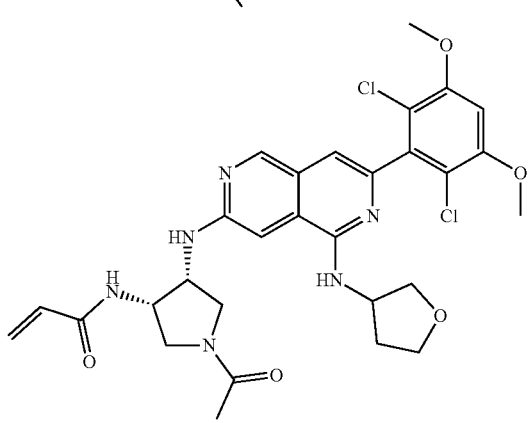

187
-continued
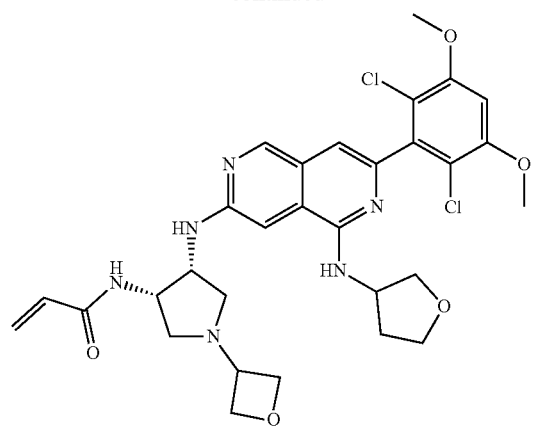
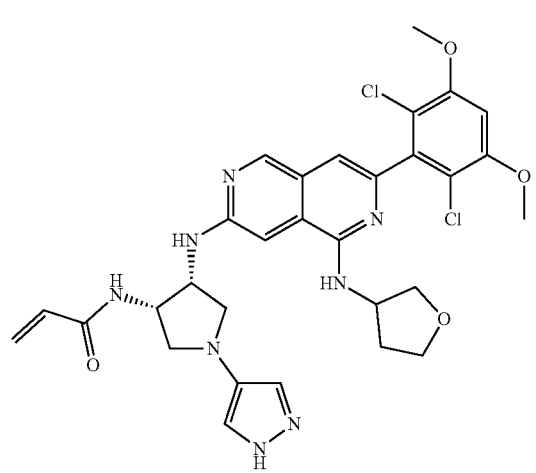
188
-continued
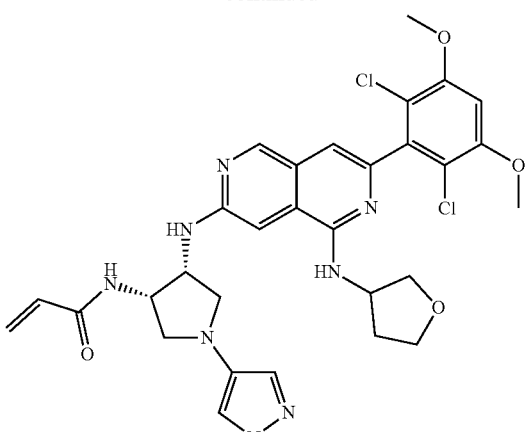
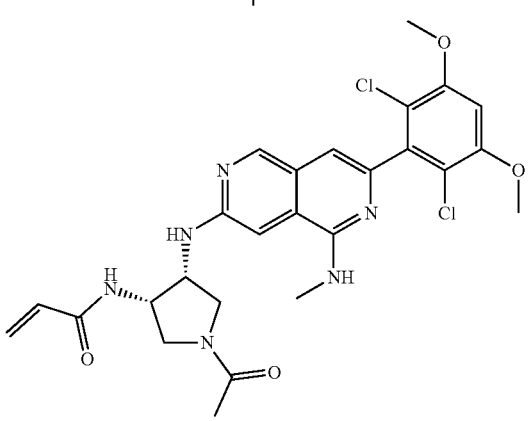
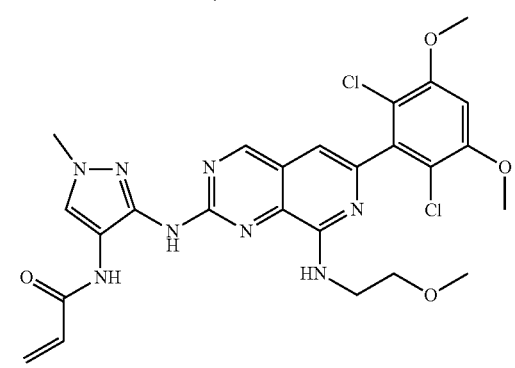

189
-continued
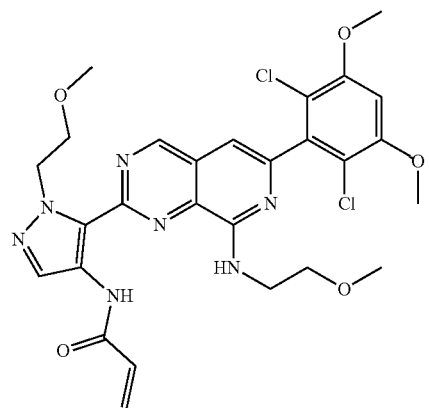
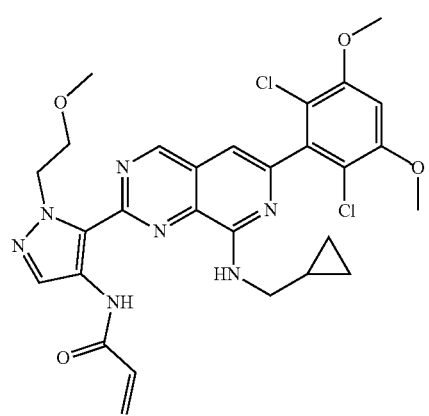
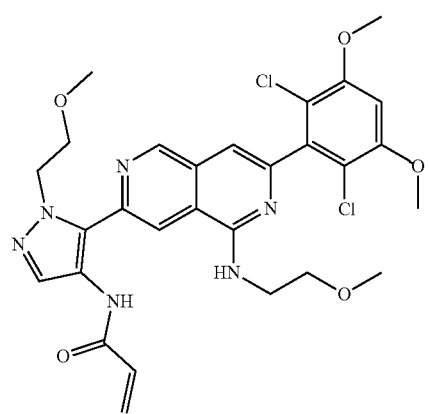
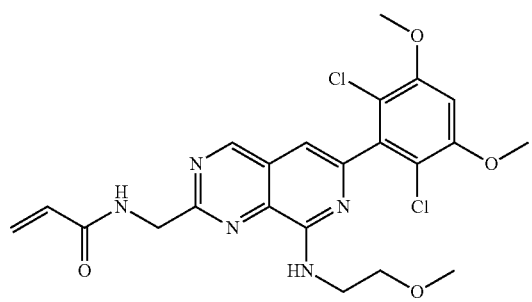
190
-continued
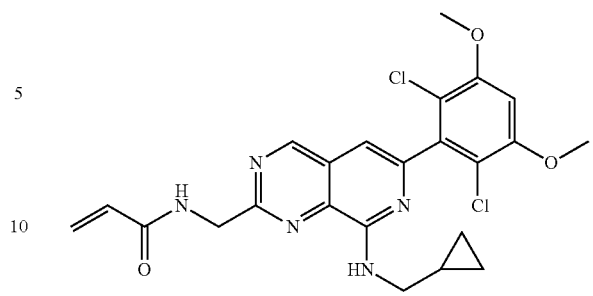
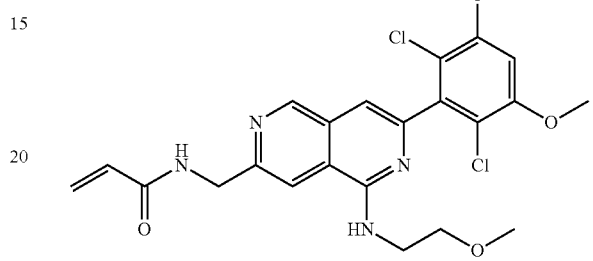

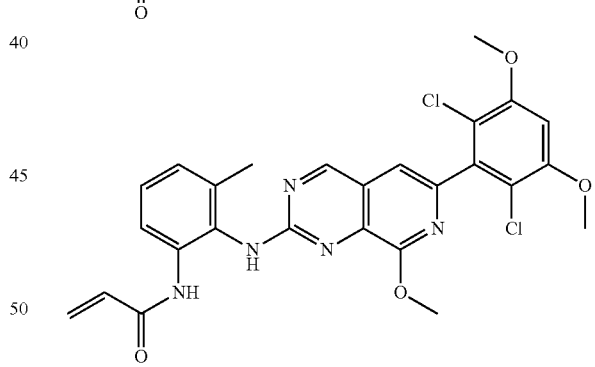
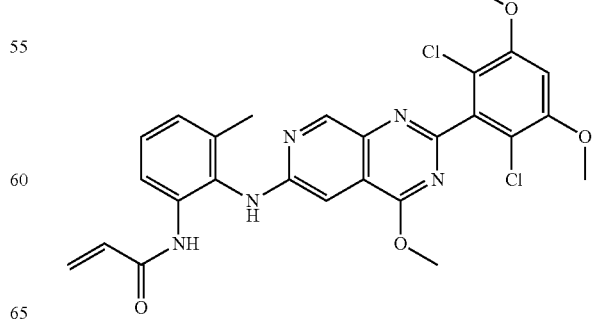

191
-continued
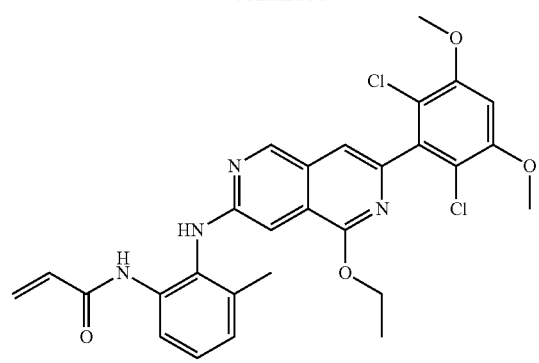
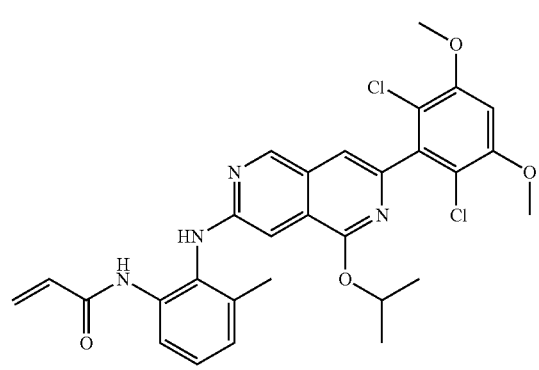
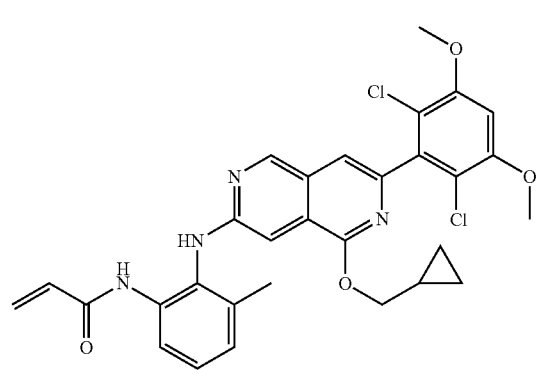
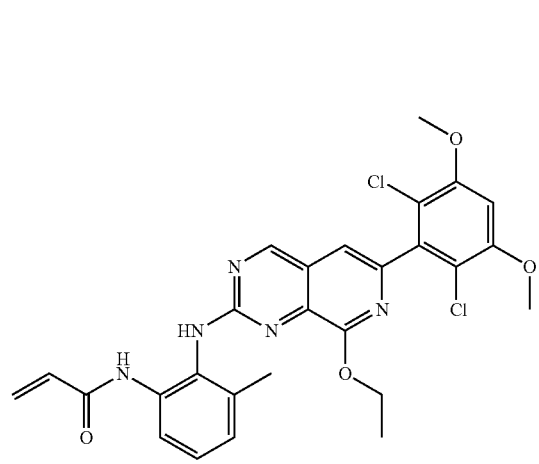
192
-continued
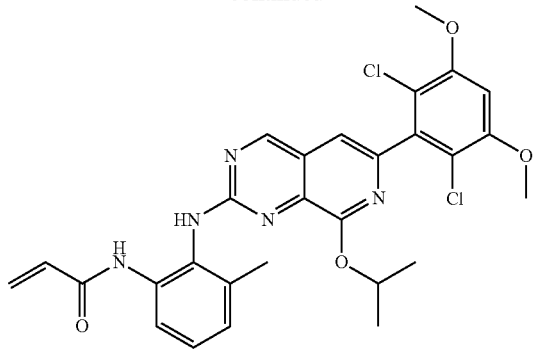
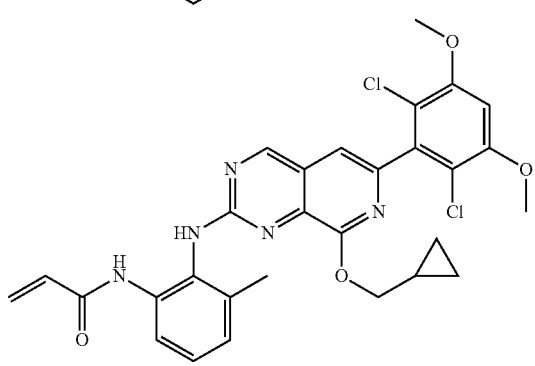
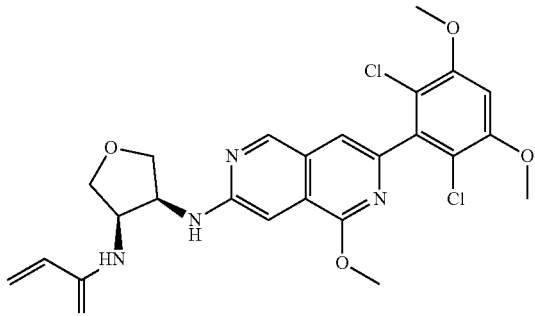
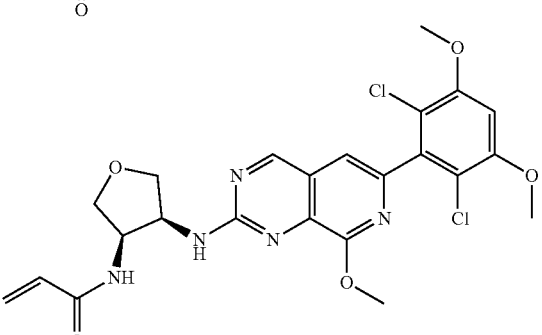
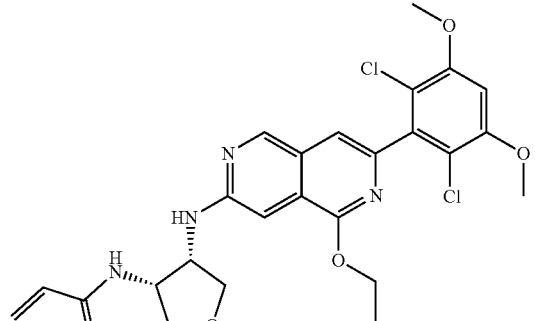

193
-continued
194
-continued
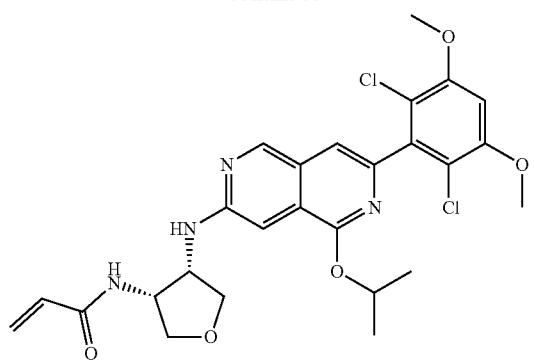
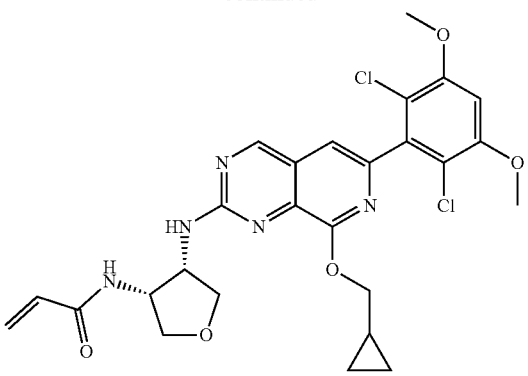

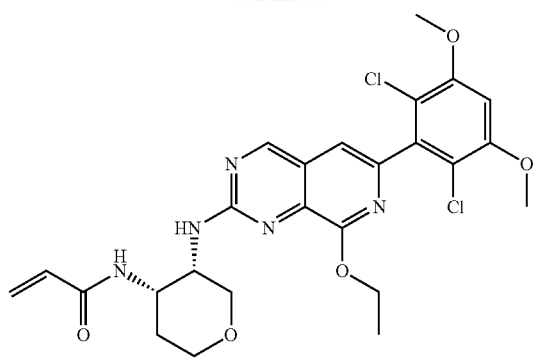
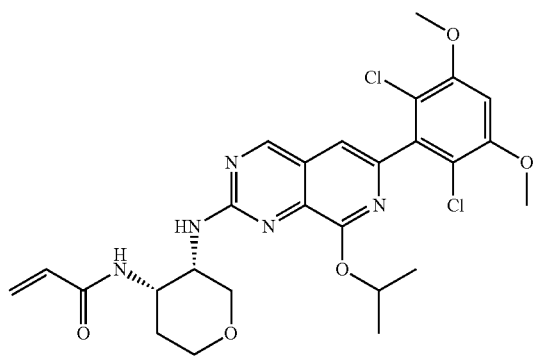
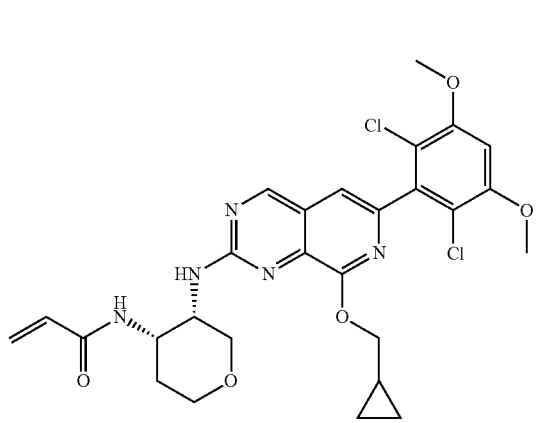
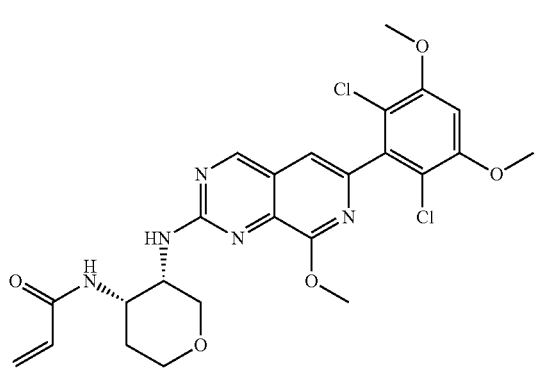
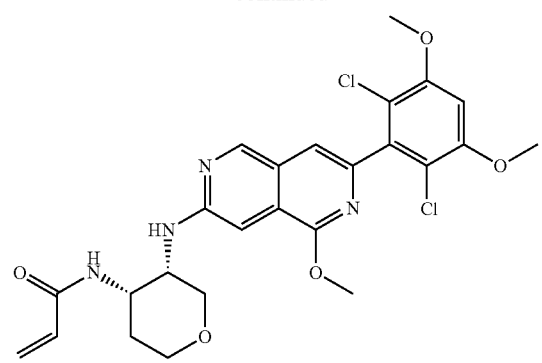
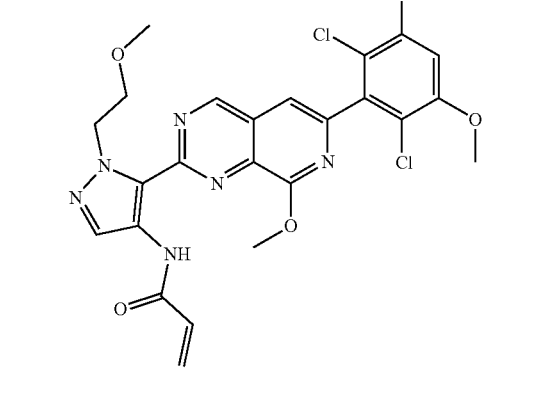
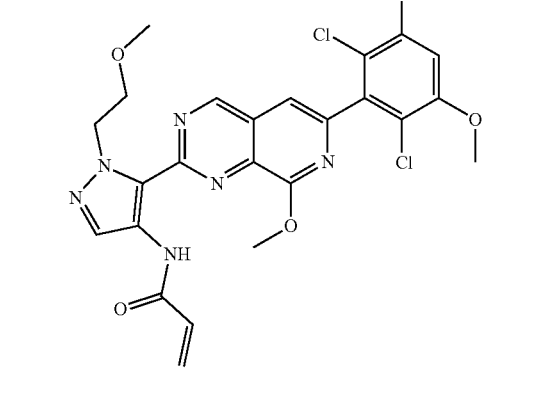
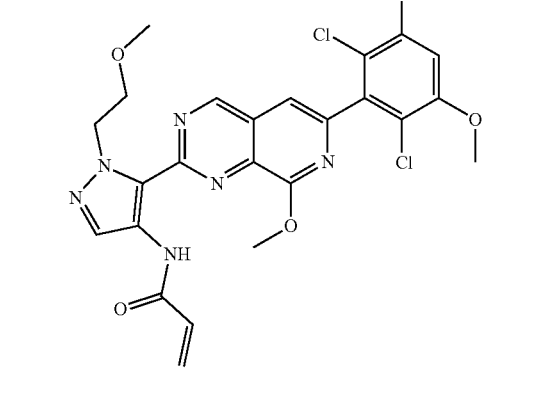

197
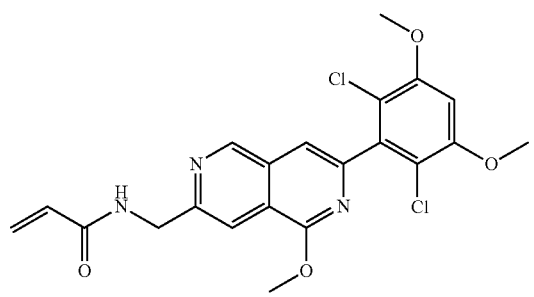
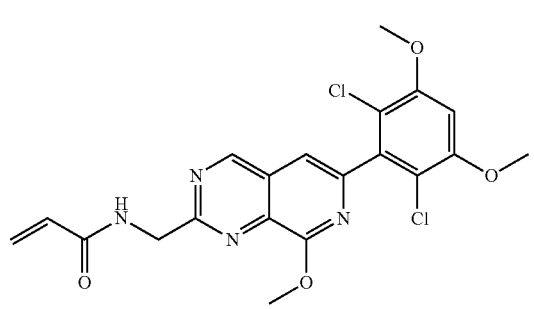
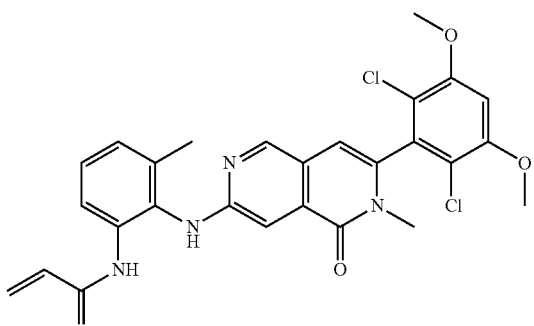
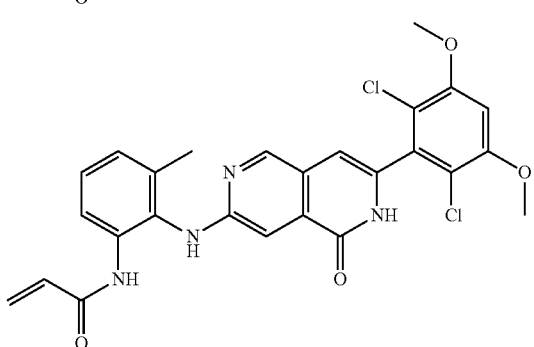
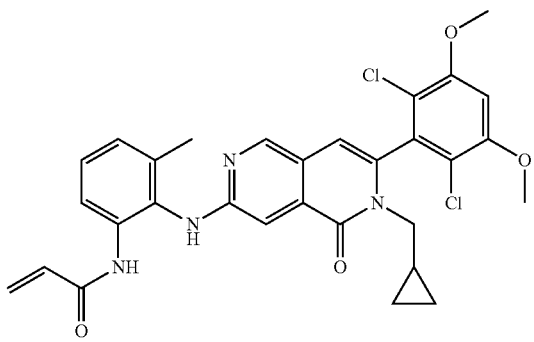
198
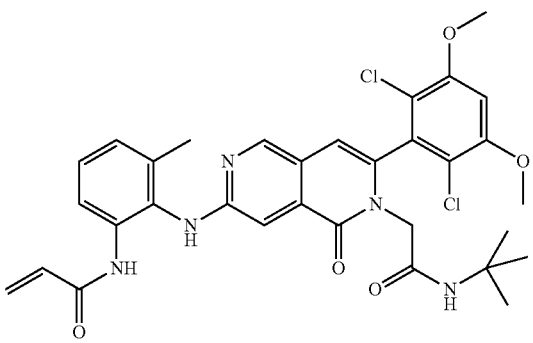
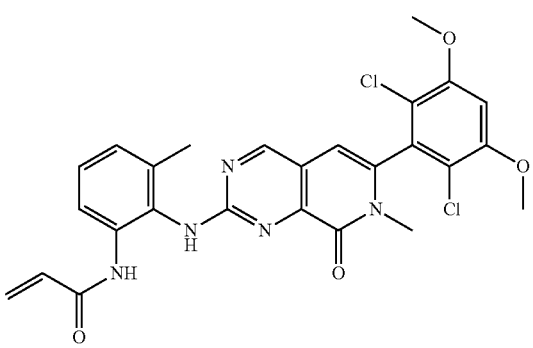
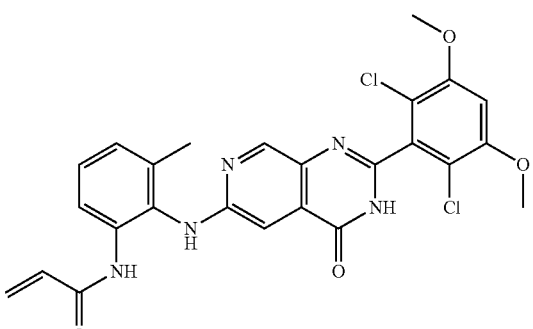
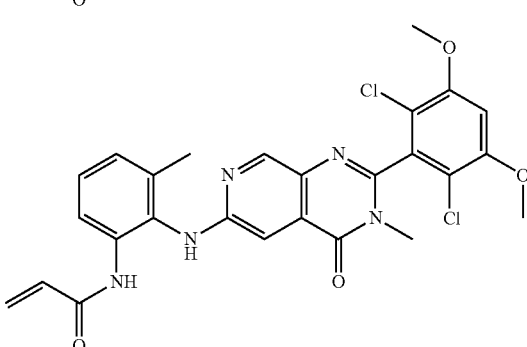
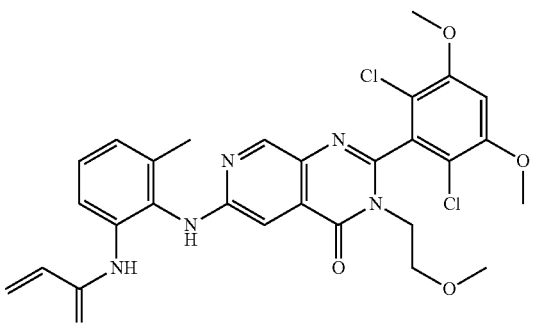

199
-continued
200
-continued
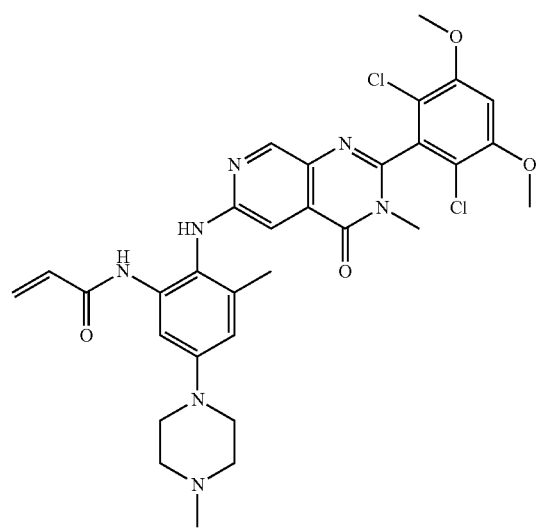
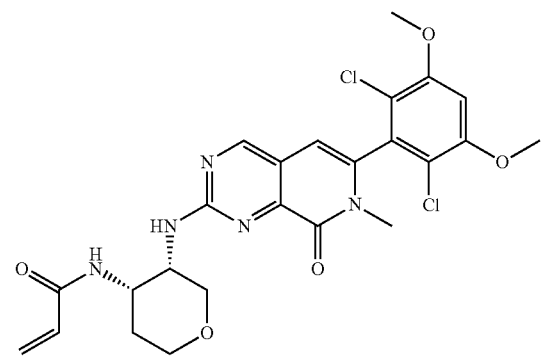
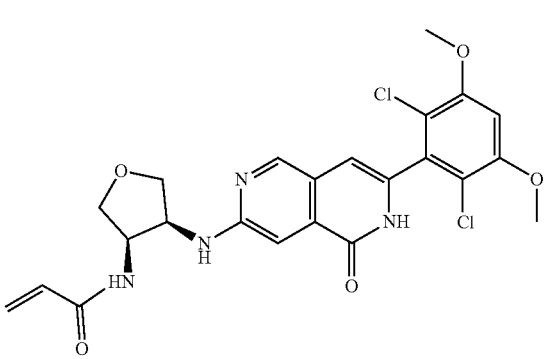
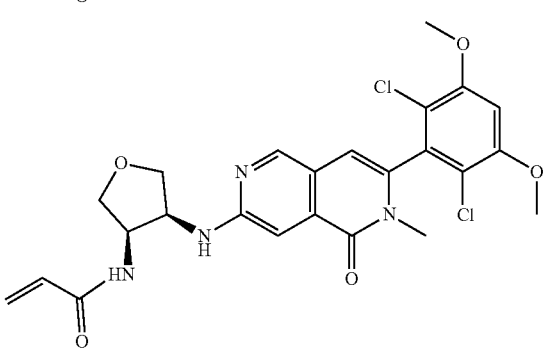
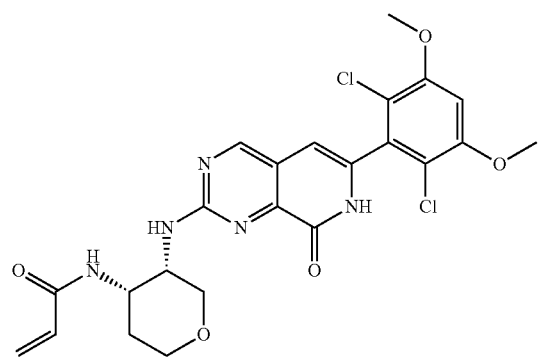

201
-continued
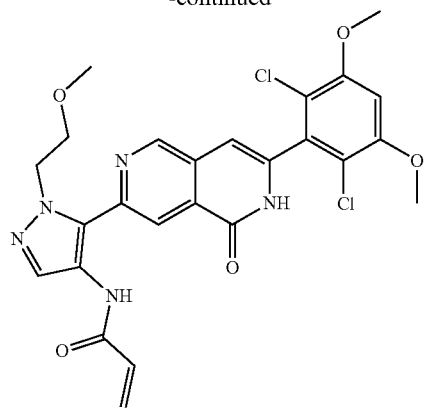
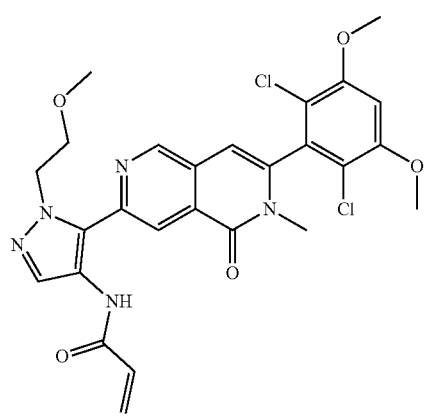
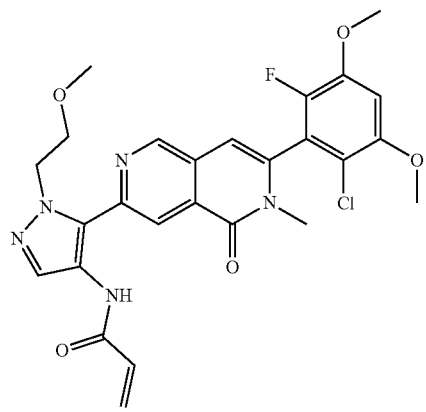
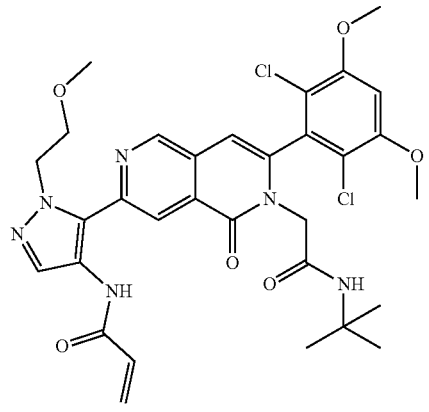
202
-continued
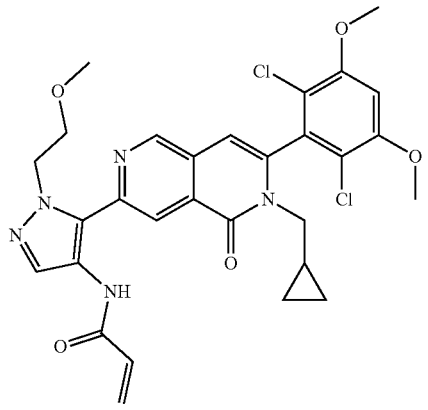
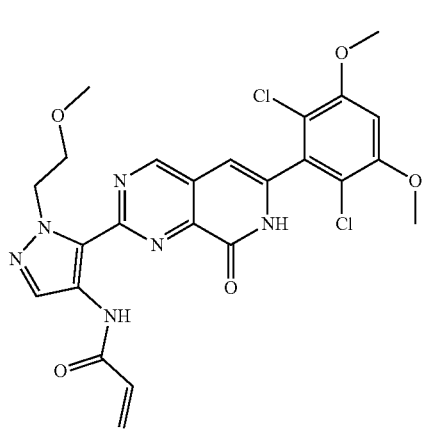
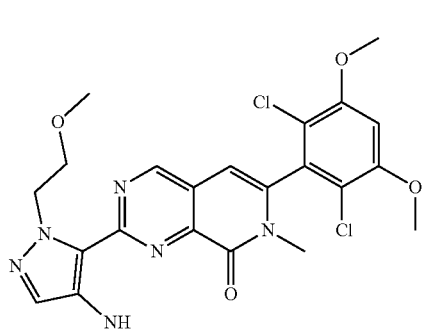
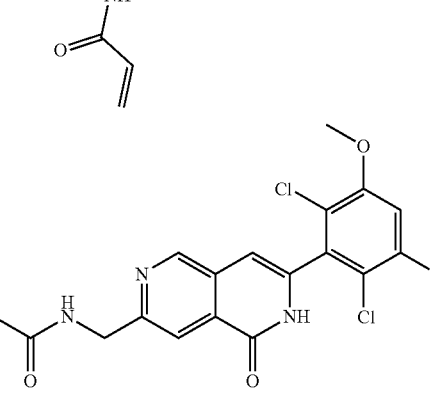

-continued
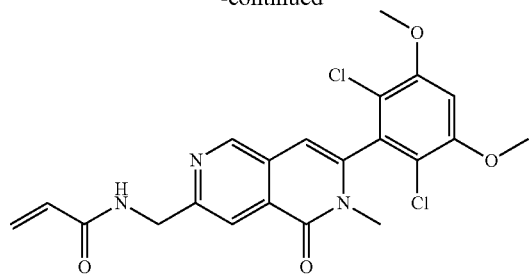
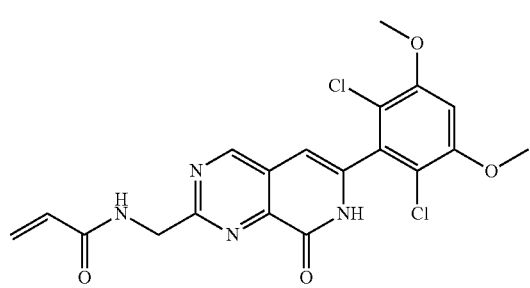
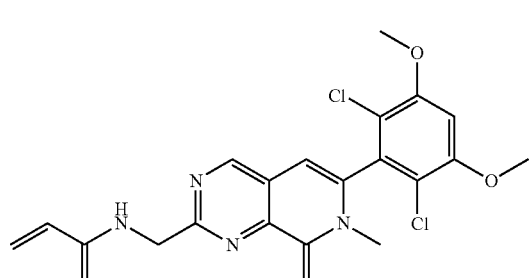
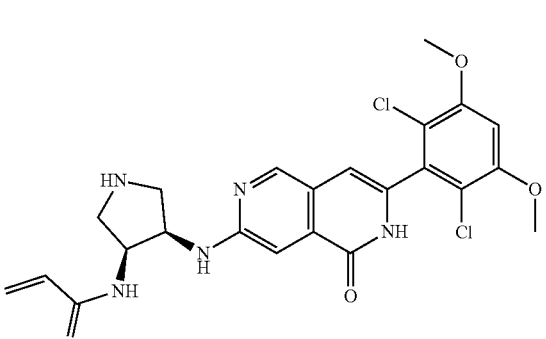
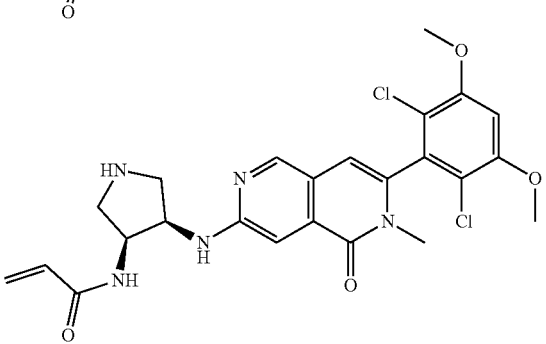
-continued
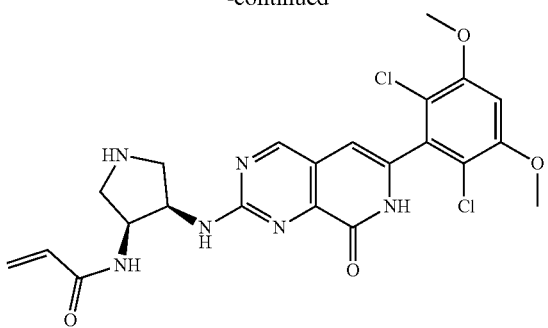
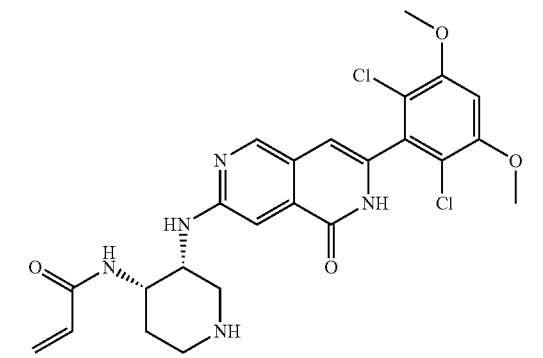
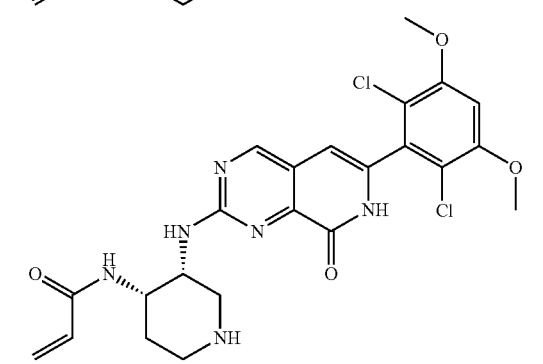
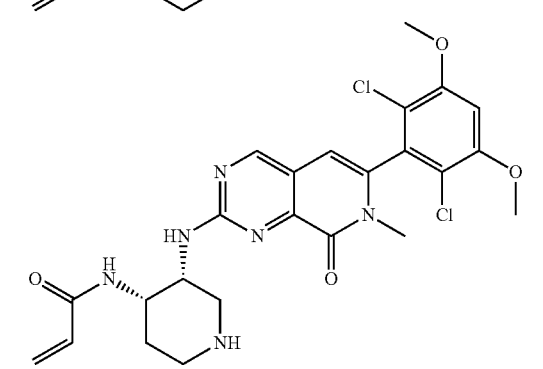
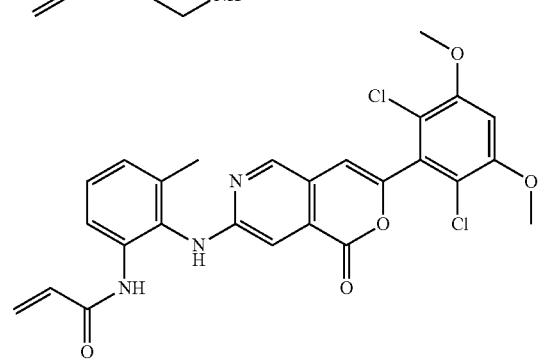

-continued
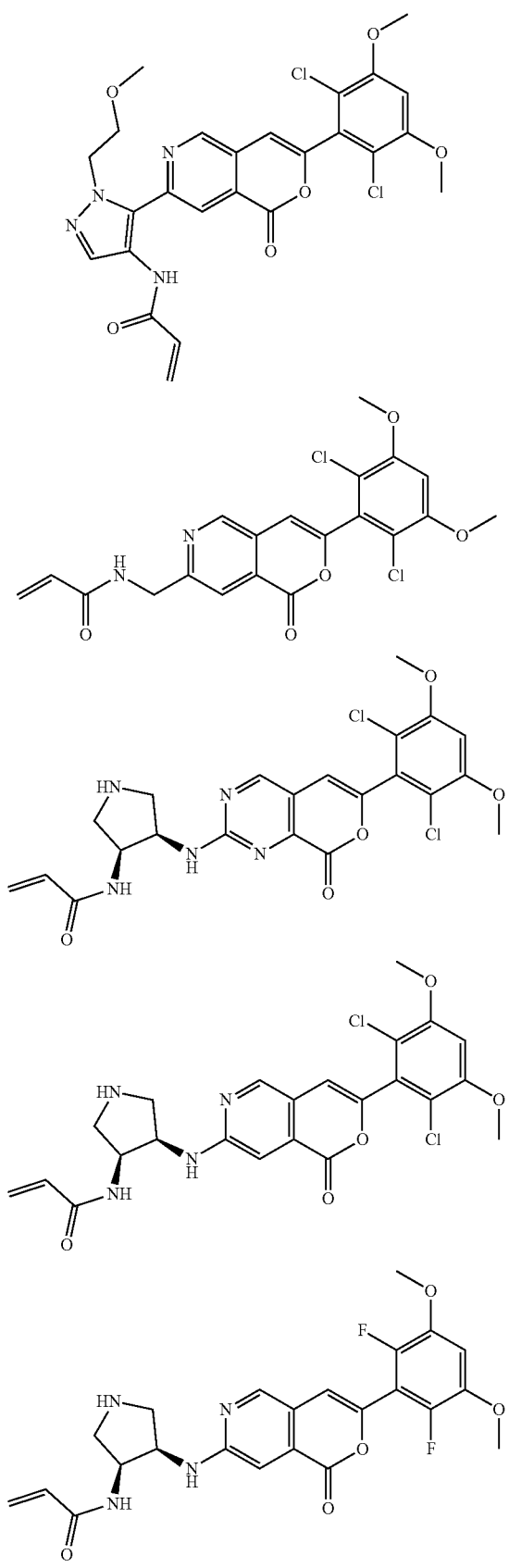
-continued
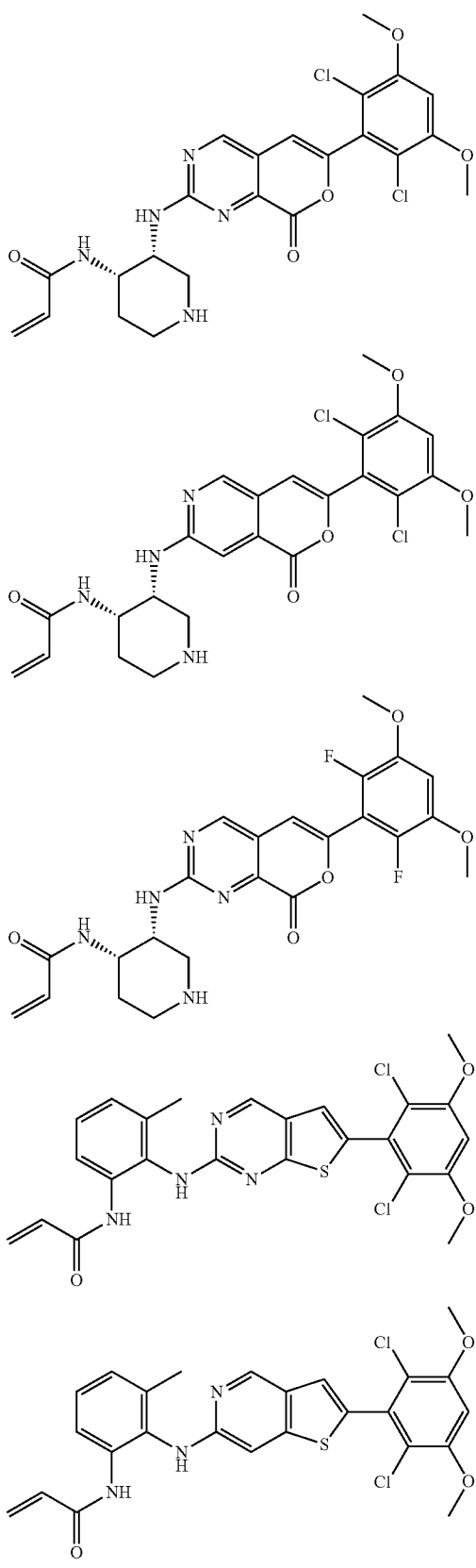

207
-continued
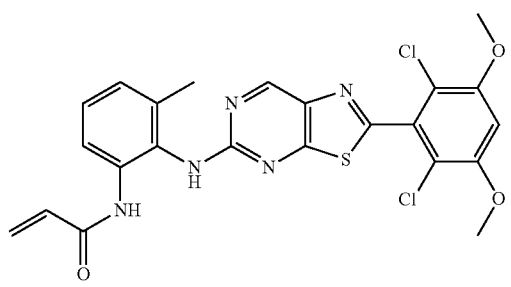
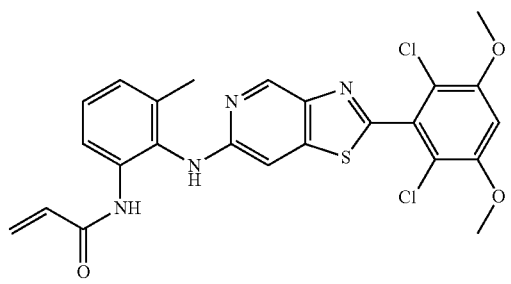
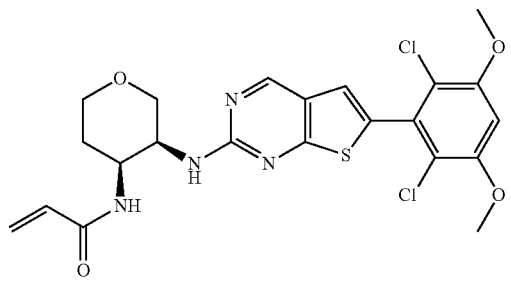
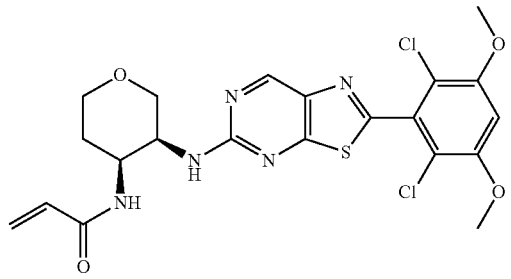
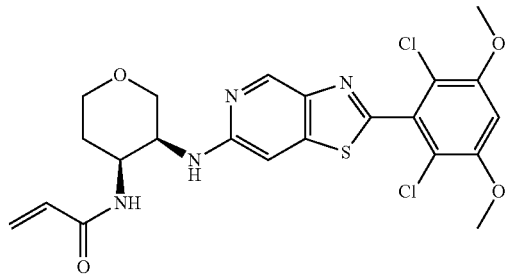
208
-continued
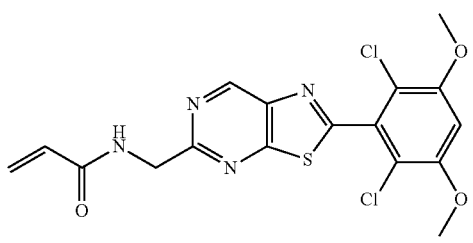

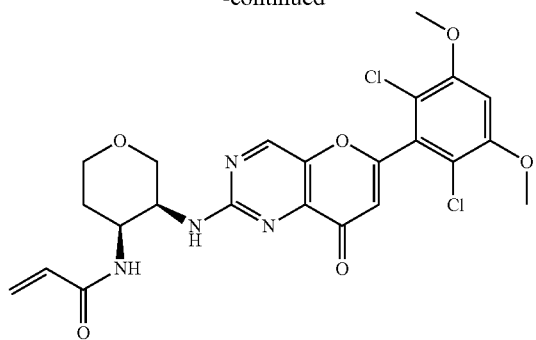
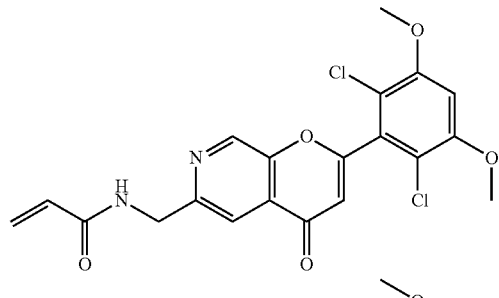
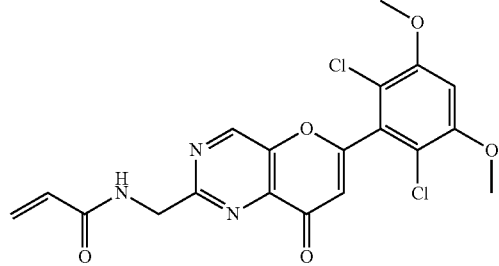
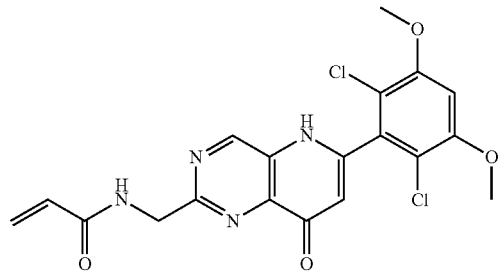
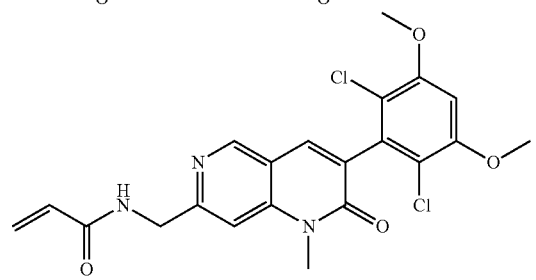
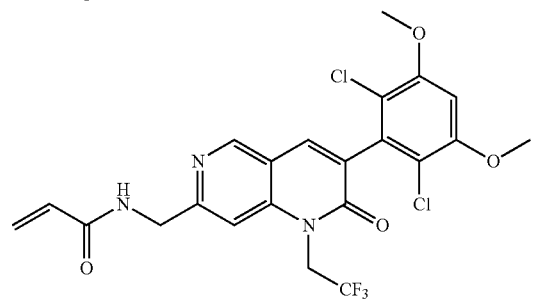
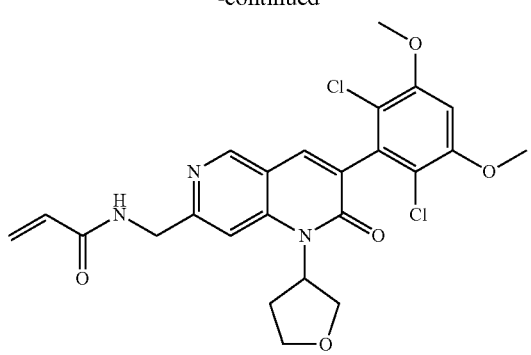
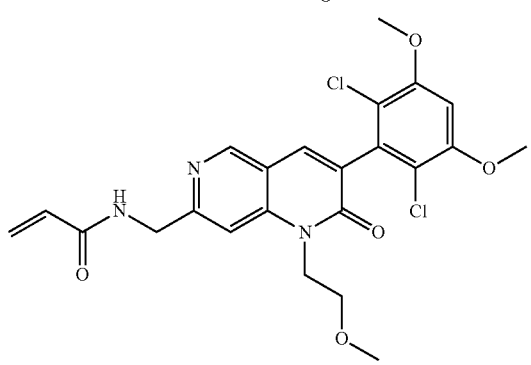
The second aspect of the invention provides a process for preparing the above compound of formula (I), the stereoisomer or pharmaceutically acceptable salt thereof, which is carried out by the following way according to the reaction steps of the allylamide group, when m=1:
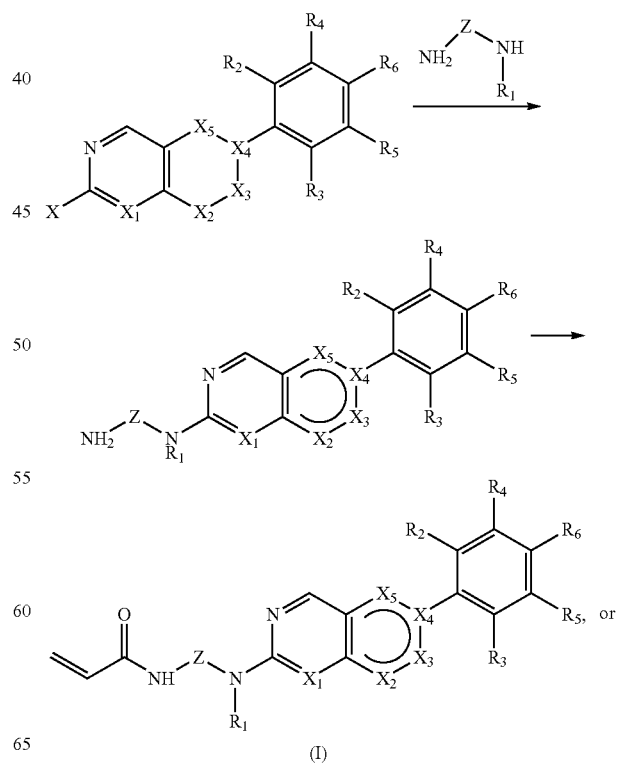

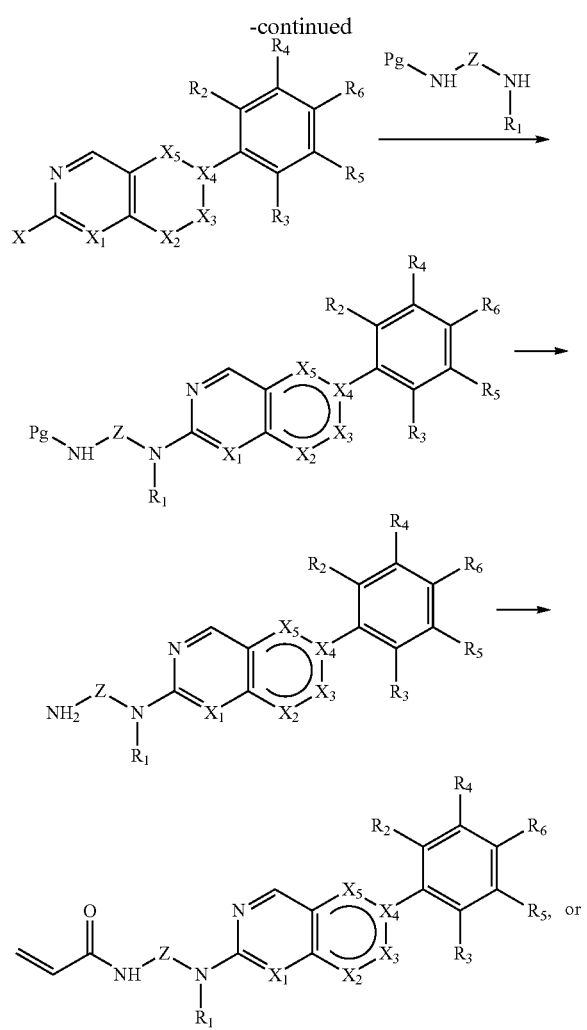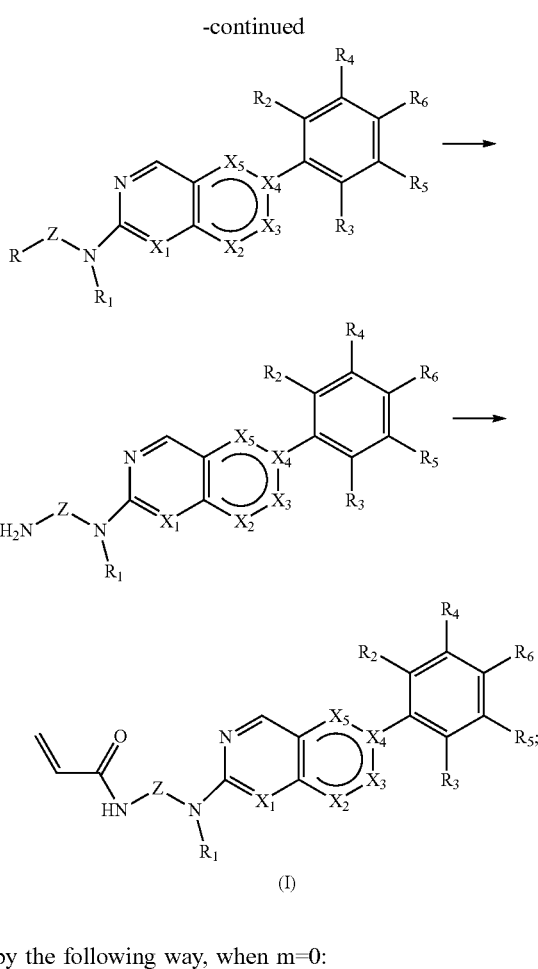
or by the following way, when m=0:
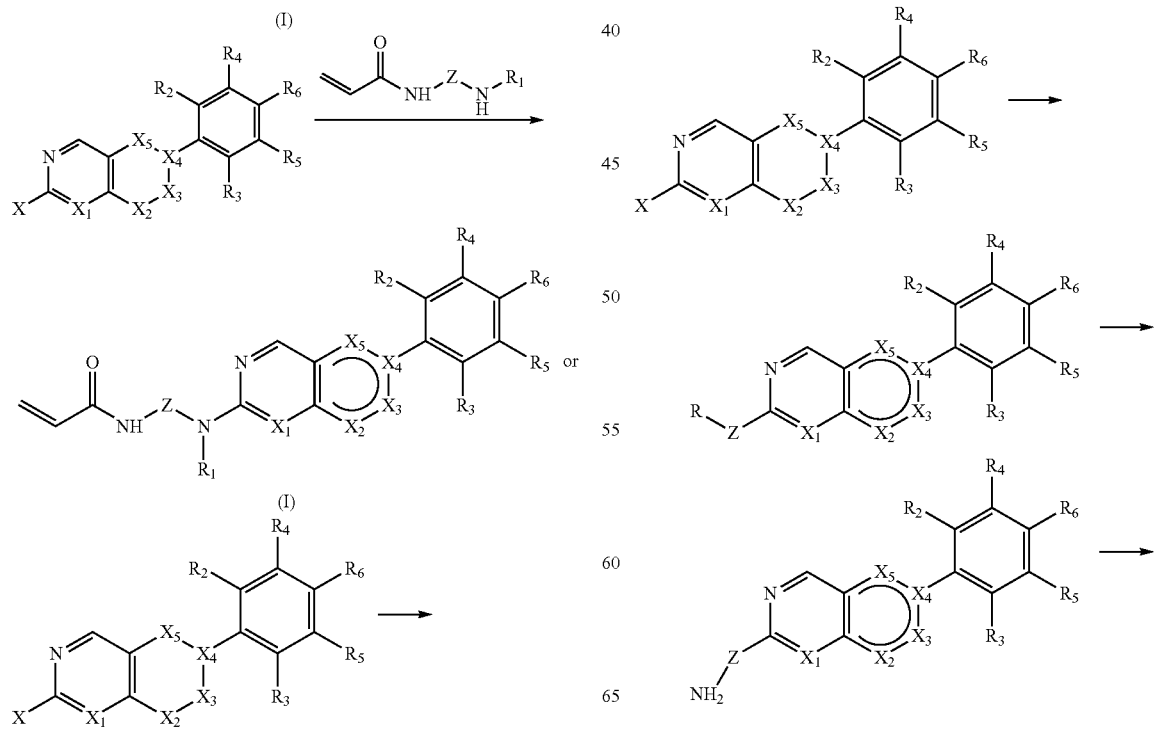

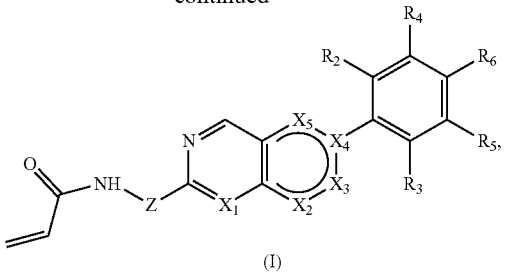

(I)

optionally, a conversion reaction is further carried out between the different substituents according to the different substituent;

wherein, X is a leaving group, and is preferably selected from the group consisting of Cl, Br, methylthio, methylsulfonyl and methoxy; R is selected from the group consisting of nitro, cyano and azido; Pg is an amino protecting group, and is preferably selected from the group consisting of tert-butyloxycarbonyl, benzyloxycarbonyl, 2-biphenyl-2-propoxy carbonyl and p-toluenesulfonyl; and $X_1$, $X_2$, $X_3$, $X_4$, $X_5$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, m, n and r are as described above.

In a further preferred embodiment, when X is methylsulfonyl, the corresponding compound can be produced by an oxidation reaction of the methylthio when R is with an oxidizing agent such as m-CPBA (m-chloroperoxybenzoic acid).

In a further preferred embodiment, the conversion reaction between the different substituents according to the different substituent means that, if necessary, the conversion of substituents can be carried out by the conventional experiment in the art under the conditions meeting chemical synthesis principle according to the different definitions of $X_1$, $X_2$, $X_3$, $X_4$, $X_5$, $R_1$, $R_2$, $R_3$, $R_4$, $R_5$, $R_6$, $R^7$, $R_8$, $R_9$, $R_{10}$, $R_{11}$, $R_{12}$, $R_{13}$, and $R_{14}$, after the condensation reaction.

The third aspect of the present invention provides a pharmaceutical composition comprising a therapeutically effective amount of the above compound of formula (I), stereoisomer or a pharmaceutically acceptable salt thereof, and pharmaceutically acceptable carrier.

The fourth aspect of the present invention provides use of the above compound of formula (I), the stereoisomer or pharmaceutically acceptable salt thereof or the aforementioned pharmaceutical composition for preparing a medicament as an FGFR4 inhibitor.

The fifth aspect of the present invention provides use of the above compound of formula (I), the stereoisomer or pharmaceutically acceptable salt thereof or the aforementioned pharmaceutical composition for preparing a medicament for treating cancer.

Preferably, the cancer is prostate cancer, liver cancer, pancreatic cancer, esophageal cancer, gastric cancer, lung cancer, breast cancer, ovarian cancer, colon cancer, skin cancer, glioblastoma or rhabdomyosarcoma.

The sixth aspect of the invention provides the above compound of formula (I), the stereoisomer or pharmaceutically acceptable salt thereof or the aforementioned pharmaceutical composition for use as an FGFR4 inhibitor.

The seventh aspect of the invention provides the above compound of formula (I), the stereoisomer or pharmaceutically acceptable salt thereof or the aforementioned pharmaceutical composition for use in the treatment of cancer.

Preferably, the cancer is prostate cancer, liver cancer, pancreatic cancer, esophageal cancer, gastric cancer, lung cancer, breast cancer, ovarian cancer, colon cancer, skin cancer, glioblastoma or rhabdomyosarcoma.

The eighth aspect of the invention provides a method for inhibiting FGFR4, which comprises administering to a patient in need thereof a therapeutically effective amount of the above compound of formula (I), the stereoisomer or pharmaceutically acceptable salt thereof, or the aforementioned pharmaceutical composition.

The ninth aspect of the invention provides a method for treating cancer, which comprises administering to a patient in need thereof treatment a therapeutically effective amount of the above compound of formula (T), the stereoisomer or pharmaceutically acceptable salt thereof, or the aforementioned pharmaceutical composition.

Preferably, the cancer is prostate cancer, liver cancer, pancreatic cancer, esophageal cancer, gastric cancer, lung cancer, breast cancer, ovarian cancer, colon cancer, skin cancer, glioblastoma or rhabdomyosarcoma.

The series of compounds developed by the present invention have strong inhibitory effects on FGFR4 kinase activity and very high selectivity, and can be widely used for preparing a medicament for treating cancer, especially prostate cancer, liver cancer, pancreatic cancer, esophageal cancer, stomach cancer, lung cancer, breast cancer, ovarian cancer, colon cancer, skin cancer, glioblastoma or rhabdomyosarcoma. The compounds are expected to be developed into a new generation medicaments of FGFR4 inhibitor.

It is to be understood that within the scope of the present invention, the above various technical features of the present invention and the technical features specifically described hereinafter (as in the examples) may be combined with each other to constitute a new or preferred technical solution. Due to space limitations, they will not be described one by one.

DETAILED DESCRIPTION OF THE INVENTION

Based on a long-term and in-depth study, the inventors have developed for the first time an FGFR4 inhibitor with a structure of the formula (I), the series of compounds have very strong inhibitory effects on FGFR4 kinase activity and very high selectivity, and could be widely used for preparing a medicament for treating cancer, especially prostate cancer, liver cancer, pancreatic cancer, esophageal cancer, stomach cancer, lung cancer, breast cancer, ovarian cancer, colon cancer, skin cancer, glioblastoma or rhabdomyosarcoma. These compounds will be expected to be developed into a new generation medicaments of FGFR4 inhibitor. On such basis, the present invention has been completed.

Detailed description: Unless otherwise stated, the following terms used in the specification and claims have the following meanings.

"Alkyl" means a straight or branched saturated aliphatic hydrocarbon group, for example, "$C_{1-8}$ alkyl" means a straight or branched alkyl having 1 to 8 carbon atoms, including but is not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl 4-ethylhexyl, 2-methyl-2-ethylpentyl, 2-methyl-3-ethylpentyl or various branched isomers thereof and so on.

Alkyl can be optionally substituted or unsubstituted, and when substituted, the substituent is preferably one or more of the following groups, independently selected from the group consisting of deuterium halogen, cyano, nitro, azido $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, $—C_{0-8}—S(O)_rR_{10}$, $—C_{0-8}—O—R_{11}$, $—C_{0-8}—C(O)OR_{11}$, $—C_{0-8}—C(O)R_{12}$, $—C_{0-8}—O—C(O)R_{12}$, $—C_{0-8}—NR_{13}R_{14}$, $—C_{0-8}—C(O)NR_{13}R_{14}$, $—C_{0-8}—N(R_{13})—C(O)R_{12}$ and $—C_{0-8}—N(R_{13})—C(O)OR_{11}$.

"Cycloalkyl" means a saturated or partially unsaturated monocyclic or polycyclic hydrocarbon substituent, for example, "$C_{3-8}$ cycloalkyl" refers to a cycloalkyl having 3-8 carbon atoms, which may be a monocyclic cycloalkyl and a polycyclic cycloalkyl, wherein, monocyclic cycloalkyl includes, but is not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl and the like; and polycyclic cycloalkyl includes spiro, fused, and bridged cycloalkyls.

"Spirocycloalkyl" refers to a polycyclic group that shares a carbon atom (called a spiro atom) between the monocyclic rings. These groups may contain one or more double bonds, but none of the rings have a fully conjugated π-electron system. The spirocycloalkyl may be a monospirocycloalkyl, a bispirocycloalkyl or a polyspirocycloalkyl according to the number of common spiro atoms between the rings, spirocycloalkyl includes, but is not limited to:

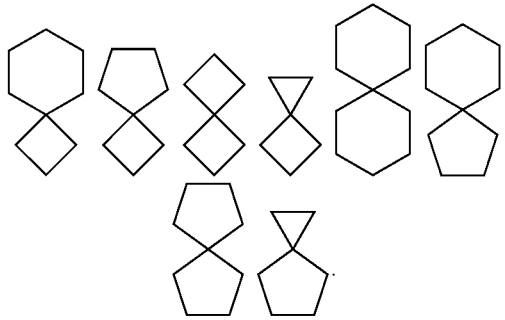

"Fused cycloalkyl" means an all-carbon polycyclic group in which each ring shares an adjacent pair of carbon atoms with other rings in the system, wherein one or more of the rings may contain one or more double bonds, but none of the rings have a fully conjugated π-electron system. Depending on the number of rings, it may be bicyclic, tricyclic, tetracyclic or polycyclic, fused cycloalkyl includes but is not limited to:

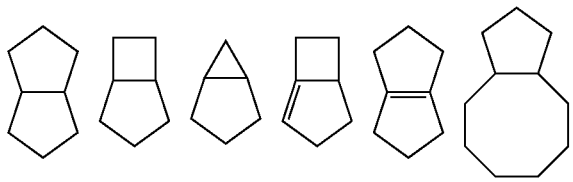

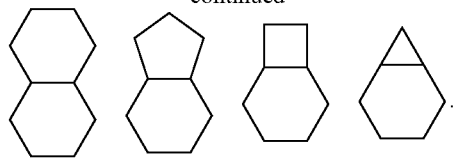

"Bridged cycloalkyl" refers to an all-carbon polycyclic group in which any two rings share two carbon atoms that are not directly bonded, which may contain one or more double bonds, but none of the rings have a fully conjugated pi-electron system. Depending on the number of rings, it may be bicyclic, tricyclic, tetracyclic or polycyclic, bridged cycloalkyl includes but is not limited to:

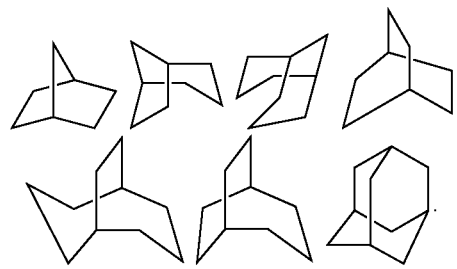

The ring of the cycloalkyl may be fused to a ring of aryl, heteroaryl or heterocycloalkyl, wherein the ring attached to the parent structure is a cycloalkyl, includes, but is not limited to indanyl, tetrahydronaphthyl, benzocycloheptyl and the likes.

The cycloalkyl can be optionally substituted or unsubstituted, and when substituted, the substituent is preferably one or more of the following groups, and independently selected from the group consisting of deuterium, halogen, cyano, nitro, azido, $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, $—C_{0-8}—S(O)_rR_{10}$, $—C_{0-8}—O—R_{11}$, $—C_{0-8}—C(O)OR_{11}$, $—C_{0-8}—C(O)R_{12}$, $—C_{0-8}—O—C(O)R_{12}$, $—C_{0-8}—NR_{13}R_{14}$, $—C_{0-8}—C(O)NR_{13}R_{14}$, $—C_{0-8}—N(R_{13})—C(O)R_{12}$ and $—C_{0-8}—N(R_{13})—C(O)OR_{11}$.

"Heterocyclyl" means a saturated or partially unsaturated monocyclic or polycyclic cyclic hydrocarbon substituent wherein one or more of the ring atoms are heteroatoms selected from nitrogen, oxygen or S(O)$_r$ (wherein r is an integer of 0, 1, 2), but excluding ring moiety of —O—O—, —O—S— or —S—S—, and the remaining ring atoms are carbon atoms. For example, "5-10 membered heterocyclyl" means a cyclic group containing 5 to 10 ring atoms, and "3-10 membered heterocyclyl" means a cyclic group containing 3 to 10 ring atoms.

Monocyclic heterocyclyl includes, but is not limited to pyrrolidinyl, piperidinyl, piperazinyl, morpholinyl, thiomorpholinyl, homopiperazinyl and the likes.

Polycyclic heterocyclyl includes a spiro, fused, and bridged heterocyclyl. "Spiroheterocyclyl" refers to a polycyclic heterocyclyl that shares a carbon atom (called a spiro atom) between the monocyclic rings, wherein one or more of the ring atoms are heteroatoms selected from nitrogen, oxygen or S(O)$_r$ (wherein r is an integer of 0, 1, 2), and the remaining ring atoms are carbon atoms. These groups may contain one or more double bonds, but none of the rings have a fully conjugated π-electron system. The spiro heterocyclyl may be a monospiroheterocyclyl, a bispiroheterocyclyl or a polyspiroheterocyclyl according to the number of common spiro atoms between the rings, spiroheterocyclyl includes, but is not limited to:

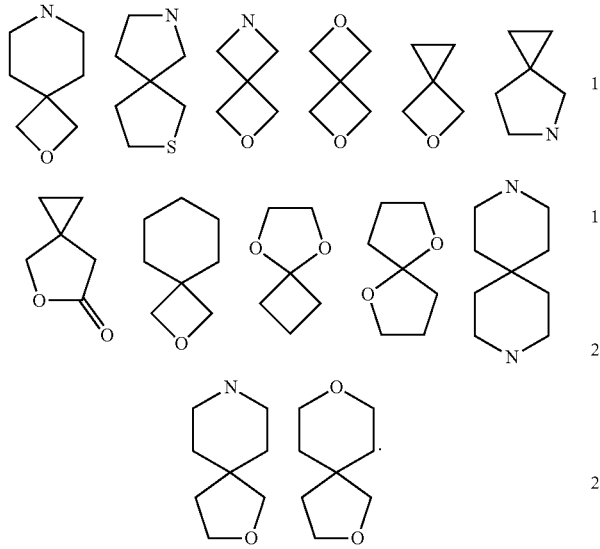

"Fused heterocyclyl" means a polycyclic heterocyclyl in which each ring shares an adjacent pair of carbon atoms with other rings in the system, wherein one or more of the rings may contain one or more double bonds, but none of the rings have a fully conjugated π-electron system, wherein one or more of the ring atoms are heteroatoms selected from nitrogen, oxygen or $S(O)_r$ (wherein r is an integer of 0, 1, 2), and the remaining ring atoms are carbon atoms. Depending on the number of rings, it may be bicyclic, tricyclic, tetracyclic or polycyclic, fused heterocyclyl includes, but is not limited to:

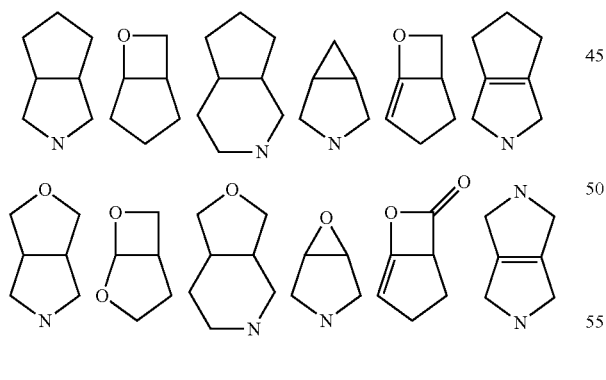

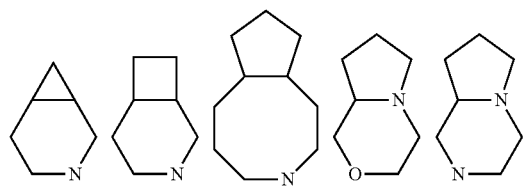

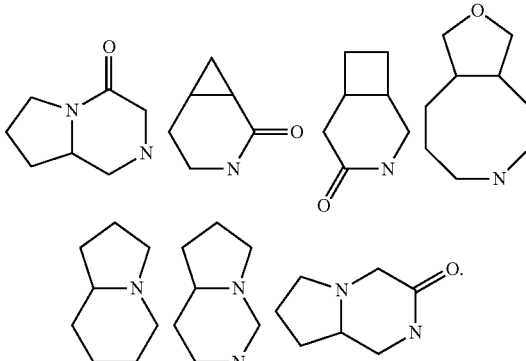

"Bridged heterocyclyl" refers to a polycyclic heterocyclyl in which any two rings share two carbon atoms that are not directly bonded, which may contain one or more double bonds, but none of the rings have a fully conjugated pi-electron system wherein one or more of the ring atoms are heteroatoms selected from nitrogen, oxygen or $S(O)_r$ (wherein r is an integer of 0, 1, 2), and the remaining ring atoms are carbon atoms. Depending on the number of rings, it may be bicyclic, tricyclic, tetracyclic or polycyclic, bridged heterocyclyl includes, but is not limited to:

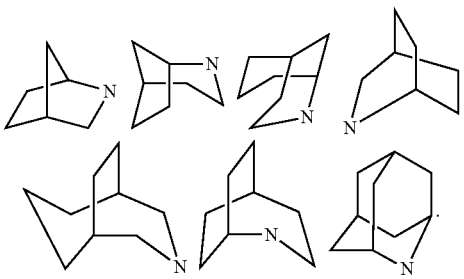

The ring of the heterocycyl may be fused to a ring of aryl heteroaryl or cycloalkyl wherein the ring attached to the parent structure is a heterocyclyl, includes but is not limited to:

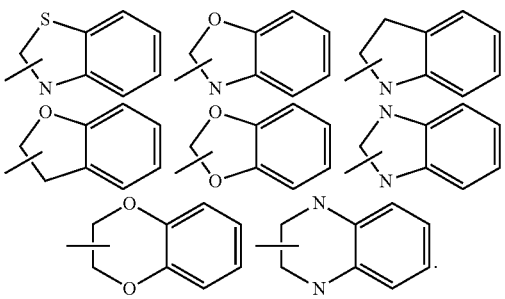

The heterocycyl can be optionally substituted or unsubstituted, and when substituted, the substituent is preferably one or more of the following groups and independently selected from the group consisting of deuterium, halogen, cyano, nitro, azido, $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, $-C_{0-8}-S(O)_rR_{10}$, $-C_{0-8}-O-R_{11}$, $-C_{0-8}-C(O)OR_{11}$, $-C_{0-8}-C(O)R_{12}$, —$C_{0-8}$—O—C(O)$R_{12}$, —$C_{0-8}$—$NR_{13}R_{14}$, —$C_{0-8}$—C(O)$NR_{13}R_{14}$, —$C_{0-8}$—N($R_{13}$)—C(O)$R_{12}$ and —$C_{0-8}$—N($R_{13}$)—C(O)O$R_{11}$.

"Aryl" means an all-carbon monocyclic or fused polycyclic (ie, a ring that shares a pair of adjacent carbon atoms) group, and a polycyclic group having a conjugated π-electron system (i.e., a ring with adjacent pairs of carbon atoms), for example, "$C_{5-10}$ aryl" means an all-carbon aryl having 5-10 carbons, and "5-10 membered aryl" means an all-carbon aryl having 5-10 carbons, including but not limited to phenyl and naphthyl. The aryl ring may be fused to a ring of heteroaryl, heterocyclyl or cycloalkyl, wherein the ring attached to the parent structure is an aryl ring, includes, but is not limited to:

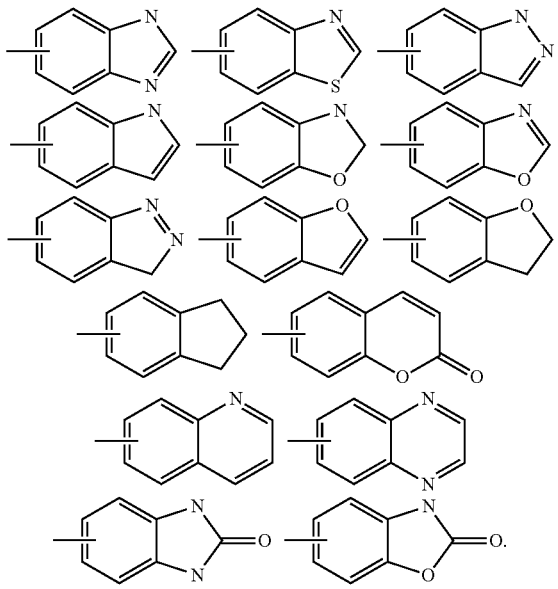

The aryl group can be optionally substituted or unsubstituted, and when substituted, the substituent is preferably one or more of the following groups, and independently selected from the group consisting of halogen, cyano, nitro, azido, $C_{1-8}$ alkyl, $C_{2-8}$ alkenyl, $C_{2-8}$ alkynyl, $C_{1-8}$ haloalkyl, $C_{3-8}$ cycloalkyl, 3-10 membered heterocyclyl, $C_{5-10}$ aryl, 5-10 membered heteroaryl, —$C_{0-8}$—S(O)$_r$$R_{10}$, —$C_{0-8}$—O—$R_{11}$, —$C_{0-8}$—C(O)O$R_{11}$, —$C_{0-8}$—C(O)$R_{12}$, —$C_{0-8}$—O—C(O)$R_{12}$, —$C_{0-8}$—$NR_{13}R_{14}$, —$C_{0-8}$—C(O)$NR_{13}R_{14}$, —$C_{0-8}$—N($R_{13}$)—C(O)$R_{12}$ and —$C_{0-8}$—N($R_{13}$)—C(O)O$R_{11}$.

"Heteroaryl" refers to a heteroaromatic system containing 1 to 4 heteroatoms including a hetero atom selected from nitrogen, oxygen or S(O)r (wherein r is an integer of 0, 1, 2), for example, 5-7 membered heteroaryl refers to a heteroaromatic system containing 5 to 7 ring atoms, and 5-10 membered heteroaryl refers to a heteroaromatic system containing 5 to 10 ring atoms, including but not limited to furyl, thiophenyl, pyridyl, pyrrolyl, N-alkylpyrrolyl, pyrimidinyl, pyrazinyl, imidazolyl, tetrazolyl group or the like. The heteroaryl ring may be fused to a ring of aryl, heterocyclyl or cycloalkyl wherein the ring attached to the parent structure is a heteroaryl ring, includes, but is not limited to

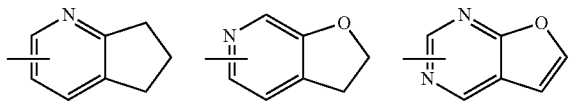

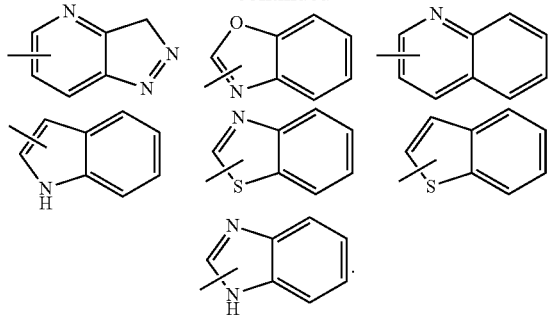

The heteroaryl can be optionally substituted or unsubstituted, and when substituted, the substituent is preferably one or more of the following groups and independently selected from the group consisting of deuterium, halogen, cyano, nitro, azido, $C_{1-8}$ alkyl, $C_{1-8}$ haloalkyl, $C_{2-8}$ alkenyl, $C_{2-8}$ alkynyl $C_{3-8}$ cycloalkyl, 3-10 membered heterocyclyl, $C_{5-10}$ aryl, 5-10 membered heteroaryl, —$C_{0-8}$—S(O)$_r$$R_{10}$, —$C_{0-8}$—O—$R_{11}$, —$C_{0-8}$—C(O)O$R_{11}$, —$C_{0-8}$—C(O)$R_{12}$, —$C_{0-8}$—O—C(O)$R_{12}$, —$C_{0-8}$—$NR_{13}R_{14}$, —$C_{0-8}$—C(O)$NR_{13}R_{14}$, —$C_{0-8}$—N($R_{13}$)—C(O)$R_{12}$ and —$C_{0-8}$—N($R_{13}$)—C(O)O$R_{11}$.

"Alkenyl" refers to an alkyl group as defined above consisting of at least two carbon atoms and at least one carbon-carbon double bond, for example, $C_{2-8}$ alkenyl refers to a straight or branched alkenyl containing 2 to 8 carbons. Alkenyl includes, but is not limited to vinyl, 1-propenyl, 2-propenyl, 1-, 2- or 3-butenyl, and the likes.

The alkenyl group can be substituted or unsubstituted, and when substituted, the substituent is preferably one or more of the following groups, and independently selected from the group consisting of deuterium, halogen, cyano, nitro, azido, $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—S(O)$_r$$R_{10}$, —$C_{0-8}$—O—$R_{13}$, —$C_{0-8}$—C(O)O$R_{11}$, —$C_{0-8}$—C(O)$R_{12}$, —$C_{0-8}$—O—C(O)$R_{12}$, —$C_{0-8}$—$NR_{13}R_{14}$, —$C_{0-8}$—C(O)$NR_{13}R_{14}$, —$C_{0-8}$—N($R_{13}$)—C(O)$R_{12}$ and —$C_{0-8}$—N($R_{13}$)—C(O)O$R_{11}$.

"Alkynyl" refers to an alkyl group as defined above consisting of at least two carbon atoms and at least one carbon-carbon triple bond, for example, $C_{2-8}$ alkynyl refers to a straight or branched alkynyl containing 2 to 8 carbons. Alkynyl includes, but is not limited to ethynyl, 1-propynyl, 2-propynyl, 1-, 2- or 3-butynyl, and the likes.

The alkynyl can be substituted or unsubstituted, and when substituted, the substituent is preferably one or more of the following groups, and independently selected from the group consisting of deuterium halogen, cyano, nitro, azido, $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—S(O)$_r$$R_{10}$, —$C_{0-8}$—O—$R_{11}$, —$C_{0-8}$—C(O)O$R_{11}$, —$C_{0-8}$—C(O)$R_{12}$, —$C_{0-8}$—O—C(O)$R_{12}$, —$C_{0-8}$—$NR_{13}R_{14}$, —$C_{0-8}$—C(O)$NR_{13}R_{14}$, —$C_{0-8}$—N($R_{13}$)—C(O)$R_{12}$ and —$C_{0-8}$—N($R_{13}$)—C(O)O$R_{11}$.

"Alkoxy" means —O-(alkyl), wherein alkyl is as defined above, for example, "$C_{1-8}$ alkoxy" refers to an alkyloxy containing 1 to 8 carbons. Alkoxy includes, but is not limited to methoxy, ethoxy, propoxy, butoxy, and the likes.

The alkoxy can be substituted or unsubstituted, and when substituted, the substituent is preferably one or more of the following groups, and independently selected from the group consisting of deuterium halogen, cyano, nitro, azido, $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$^{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$.

"Cycloalkyloxy" means —O-(unsubstituted cycloalkyl), wherein cycloalkyl is as defined above, for example, "$C_{3-8}$ cycloalkyloxy" refers to a cycloalkyoxy containing 3 to 8 carbon atoms. Cycloalkyloxy includes, but is not limited to, cyclopropyloxy, cyclobutyloxy, cyclopentyloxy, cyclohexyloxy and the likes.

The cycloalkyloxy can be substituted or unsubstituted, and when substituted, the substituent is preferably one or more of the following groups, and independently selected from the group consisting of deuterium, halogen, cyano, nitro, azido, $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocycyl-, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$.

"3-10 membered heterocyclyloxy" means —O-(unsubstituted 3-10 membered heterocyclyl), wherein 3-10 membered heterocyclyl is as defined above, 3-10 membered heterocyclyloxy can be substituted or unsubstituted, and when substituted, the substituent is preferably one or more of the following groups, and independently selected from the group consisting of deuterium, halogen, cyano, nitro, azido, $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$.

"$C_{5-10}$ aryloxy" means —O-(unsubstituted $C_{5-10}$ aryl), wherein $C_{5-10}$ aryl is as defined above, $C_{5-10}$ aryloxy can be substituted or unsubstituted, and when substituted, the substituent is preferably one or more of the following groups, and independently selected from the group consisting of deuterium, halogen, cyano, nitro, azido, $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$.

"5-10 membered heteroaryloxy" means —O-(unsubstituted 5-10 membered heteroaryl), wherein 5-10 membered heteroaryl is as defined above, 5-10 membered heteroaryloxy can be substituted or unsubstituted, and when substituted, the substituent is preferably one or more of the following groups, and independently selected from the group consisting of deuterium, halogen, cyano, nitro, azido, $C_{1-8}$ alkyl, $C_{1-8}$ haloalkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(O)NR$_{13}$R$_{14}$, —$C_{0-8}$—N(R$_{13}$)—C(O)R$_{12}$ and —$C_{0-8}$—N(R$_{13}$)—C(O)OR$_{11}$.

"$C_{1-8}$ alkanoyl" refers to a monovalent group obtained by removing hydroxyl from C-s alkyl acid, is also generally referred to as "$C_{0-7}$—C(O)—", for example, "$C_1$—C(O)—" refers to acetyl; "$C_2$—C(O)—" refers to propionyl; and "$C_3$—C(O)—" refers to butyryl or isobutyryl.

"—$C_{0-8}$—S(O)$_r$R$_{10}$" means that the sulfur atom in —S(O)$_r$R$_{10}$ is bonded to $C_{0-8}$ alkyl, wherein $C_0$ alkyl means a bond, and $C_{1-8}$ alkyl is as defined above.

"—$C_{0-8}$—O—R$_{11}$" means that the oxygen atom in —O—R$_{11}$ is bonded to $C_{0-8}$ alkyl, wherein $C_0$ alkyl means a bond, and $C_{1-8}$ alkyl is as defined above.

"—$C_{0-8}$—C(O)OR$_{11}$" means that the carbonyl group in —C(O)OR$_{11}$ is bonded to $C_{0-8}$ alkyl, wherein $C_0$ alkyl means a bond, and $C_{1-8}$ alkyl is as defined above.

"—$C_{0-8}$—C(O)R$_{12}$" means that the carbonyl group in —C(O)R$_{12}$ is bonded to $C_{0-8}$ alkyl, wherein $C_0$ alkyl means a bond, and $C_{1-8}$ alkyl is as defined above.

"—$C_{0-8}$—O—C(O)R$_{12}$" means that the oxygen atom in —O—C(O)R$_{12}$ is bonded to $C_{0-8}$ alkyl, wherein $C_0$ alkyl means a bond, and C-s alkyl is as defined above.

"—$C_{0-8}$—NR$_{13}$R$_{14}$" means that the nitrogen atom in —NR$_{13}$R$_{14}$ is bonded to $C_{0-8}$ alkyl, wherein $C_0$ alkyl means a bond, and $C_{1-8}$ alkyl is as defined above.

"—$C_{0-8}$—C(O)NR$_{13}$R$_{14}$" means that the carbonyl in —C(O)NR$_{13}$R$_{14}$ is bonded to $C_{0-8}$ alkyl, wherein $C_0$ alkyl means a bond, and $C_{1-8}$ alkyl is as defined above.

"—$C_{0-8}$—N(R$_{13}$)—C(O)R$_{12}$" means that the nitrogen atom in —N(R$_{13}$)—C(O)R$_{11}$ is bonded to $C_{0-8}$ alkyl, wherein $C_0$ alkyl means a bond, and $C_{1-8}$ alkyl is as defined above.

"—$C_{0-8}$—N(R$_{13}$)—C(O)OR$_{11}$" means that the nitrogen atom in —N(R$_{13}$)—C(O)OR$_{11}$ is bonded to $C_{0-8}$ alkyl, wherein $C_0$ alkyl means a bond, and $C_{1-8}$ alkyl is as defined above.

"$C_{1-8}$ haloalkyl" means a alkyl group having 1 to 8 carbon atoms, wherein any hydrogen atom on which is optionally substituted with F, Cl, Br or I, and includes, but is not limited to difluoromethyl, dichloromethyl, dibromomethyl, trifluoromethyl, trichloromethyl, tribromomethyl, and the likes.

"$C_{1-8}$ haloalkoxy" means an alkoxy having 1 to 8 carbon atoms, wherein any hydrogen atom on which is optionally substituted with F, Cl, Br or I, and includes, but is not limited to difluoromethoxy, dichloromethoxy, dibromomethoxy, trifluoromethoxy, trichloromethoxy, tribromomethoxy, and the likes.

"Halogen" means F. Cl, Br or I. "THF" refers to tetrahydrofuran. "EA/EtOAc" refers to ethyl acetate. "MeOH" means methanol. "EtOH" refers to ethanol. "PivOH" refers to trimethylacetic acid. "DMSO" refers to dimethyl sulfoxide. "DIMF" means N,N-dimethylformamide. "DIPEA" refers to diisopropylethylamine. "CH$_3$CN" means acetonitrile. "PE" means petroleum ether. "DCM/CH$_2$Cl$_2$" means dichloromethane. "DCE" refers to dichloroethane. "DMA" refers to dimethylacetamide. "Et$_3$N" refers to triethylamine. "NH$_4$Cl" means ammonium chloride. "NMP" refers to N-methylpyrrolidone. "HOAc" refers to acetic acid. "TFA" refers to trifluoroacetic acid. "MeI" means methyl iodide. "K" means potassium iodide. "MsC" refers to methylsulfonyl chloride. "SO$_2$Cl$_2$" means sulfonyl chloride. "POCl$_3$" refers to phosphorus oxychloride. "MeONa" means sodium methoxide. "NaHCO$_3$" refers to sodium bicarbonate. "Na$_2$SO$_4$" means sodium sulfate. "K$_2$CO$_3$" means potassium carbonate. "NaN$_3$" refers to sodium azide. "NaH" refers to sodium hydride. "CuI" refers to cuprous iodide. "PPA" refers to polyphosphoric acid. "m-CPBA" refers to m-chloroperoxybenzoic acid. "MnO$_2$" means manganese dioxide. "LiAlH$_4$" means lithium aluminum hydride. "LiOH" refers to lithium hydroxide. "NaOAc" refers to sodium acetate. "NaNO$_2$" refers to sodium nitrite. "AgNO$_3$" means silver nitrate. "Boc$_2$O" refers to di-tert-butyl dicarbonate. "LiCl" means lithium chloride. "Zn(CN)$_2$" refers to zinc cyanide. "IBX" means 2-iodoxybenzoic acid. "Pd/C"

means palladium carbon. "Pd(OAc)$_2$" means palladium acetate. "PPh$_3$" means triphenylphosphine. "Pd(PPh$_3$)$_2$Cl$_2$" means palladium bis(triphenylphosphine) dichloride. "Pd$_2$(dba)$_3$" means tris(dibenzylideneacetone) dipalladium. "Pd(dppf)Cl$_2$" means [1,1'-bis(diphenylphosphino)ferrocene] palladium dichloride. "Pd(PPh$_3$)$_4$" means tetrakis (triphenylphosphine) palladium. "brett-phos" refers to dicyclohexyl[3,6-dimethoxy-2',4"-triisopropyl[1,1'-biphenyl]-2-yl] phosphine.

"Optional" or "optionally" means that the event or environment subsequently described may, but need not, occur, including where the event or environment occurs or does not occur. For example, "heterocyclyl optionally substituted by alkyl" means that an alkyl group may be, but is not necessarily, present, and the description includes the case where the heterocyclyl is substituted with an alkyl and the case where the heterocyclyl is not substituted with an alkyl.

"Substituted" means that one or more hydrogen atoms in a group are each independently substituted with a corresponding number of substituents. It goes without saying that a substituent is only in its possible chemical position, and those skilled in the art will be able to determine (by experiment or theory) possible or impossible substitution without undue efforts. For example, it may be unstable that an amino group or a hydroxyl group having a free hydrogen is attached with a carbon atom having an unsaturated bond (such as an olefin).

"Pharmaceutical composition" means a mixture comprising one or more of the compounds described herein, or a physiologically/pharmaceutically acceptable salt or prodrug thereof, and other chemical components, for example physiological/pharmaceutically acceptable carriers and excipients. The purpose of the pharmaceutical composition is to promote the administration to an organism, which facilitates the absorption of the active ingredient thereby exerting biological activities.

The Present Invention Will be Further Described in Detail Below in Conjunction with the Embodiments which is not Intended to Limit the Present Invention. The Present Invention is Also not Limited to the Contents of the Embodiments.

The structure of the compound of the present invention is determined by nuclear magnetic resonance (NMR) or/and liquid chromatography-mass spectrometry (LC-MS). The NMR chemical shift (δ) is given in parts per million (ppm). The NMR is measured by a Bruker AVANCE-400 nuclear magnetic apparatus, and the solvent is deuterated dimethyl sulfoxide (DMSO-d$_6$), deuterated methanol (CD$_3$OD) and deuterated chloroform (CDCl$_3$), and the internal standard is tetramethylsilane (TMS).

The measurement of LC-MS is performed by using an Agilent 6120 mass spectrometer. The measurement of HPLC is performed by using an Agilent 1200 DAD high pressure liquid chromatograph (Sunfire C18 150×4.6 mm column) and a Waters 2695-2996 high pressure liquid chromatograph (Gimini C18 150×4.6 mm column).

The thin layer chromatography silica gel plate is Yantai Yellow Sea HSGF254 or Qingdao GF254 silica gel plate. The specification of TLC is 0.15 mm-0.20 mm, and the specification for thin layer chromatography separation and purification is 0.4 mm-0.5 mm. 200-300 mesh silica gel (Yantai Huanghai silica gel) as a carrier is generally used in column chromatography.

The starting materials in the examples of the present invention are known and commercially available or can be synthesized according to methods known in the art.

Unless otherwise stated, all reactions of the present invention are carried out under continuous magnetic stirring under a dry nitrogen or argon atmosphere, the solvent is a dry solvent, and the unit of the reaction temperature is degrees Celsius.

Preparation of Intermediates

Intermediate 1: Preparation of 7-chloro-3-(2,6-dichloro-3,5-dimethoxyphenyl)-2H-pyrano [3,2-c] pyridin-2-one

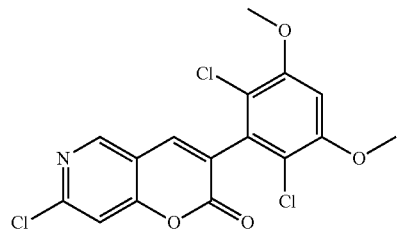 [SMILES: COc1cc(OC)c(Cl)c(-c2cc3cnc(Cl)cc3oc2=O)c1Cl]

Step 1: Preparation of Ethyl 6-chloro-4-methoxynicotinate

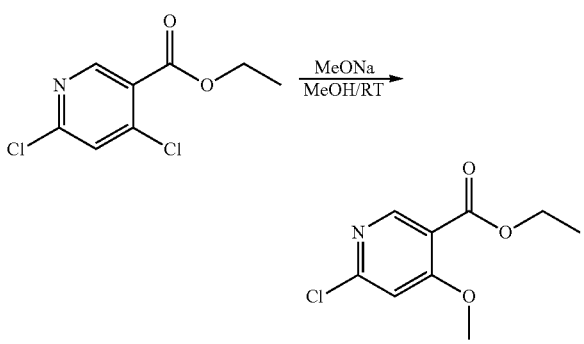

Ethyl 4,6-dichloronicotinate (10.0 g, 45.4 mmol) was added to anhydrous THF (100 mL), and cooled to 0° C. with ice water, then MeONa (2.8 g, 51.8 mmol) was added. After the addition was completed, the mixture was stirred at room temperature overnight. After the reaction as completed, the mixture was concentrated to remove THF. The crude product was dissolved in ethyl acetate (100 mL), washed twice with water and dried over anhydrous Na$_2$SO$_4$ filtrated and concentrated to obtain ethyl 6-chloro-4-methoxynicotinate (8.2 g, yield: 84%). MS (ESI): m/z 216.3 [M+1]$^+$.

Step 2: Preparation of (6-chloro-4-methoxypyridin-3-yl)methano

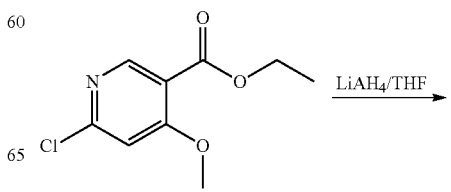

-continued

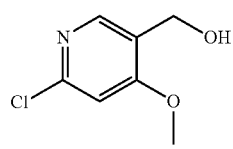

Ethyl 6-chloro-4-methoxynicotinate (8.2 g, 38.1 mmol) was dissolved in anhydrous THF (200 mL), then LiAH₄ (3.0, 81.1 mmol) was added under ice-water bath. After the addition was completed, the mixture, was stirred at room temperature for 2 h. After the reaction was completed, 2N aqueous NaOH (25 mL) was added for extraction. The solid residue was removed by filtration, and the filtrate was concentrated to obtain compound (6-chloro-4-methoxypyridin-3-yl)methanol (6.0 g, yield: 91%). MS (ESI): m/z 2174.2 [M+1]⁺.

Step 3: Preparation of 6-chloro-4-methoxynicotinaldehyde

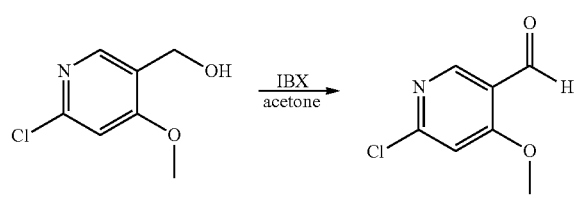

(6-chloro-4-methoxypyridin-3-yl)methanol (6.0 g, 34.6 mmol) was dissolved in acetone (100 mL), then IBX (12.0 g, 42.9 mmol) was added. The mixture was heated to reflux for 18 h. After the reaction was completed, the mixture was filtered and concentrated to obtain compound 6-chloro-4-methoxynicotinaldehyde (4.2 g, yield: 71%). MS (ESI): m/z 172.2 [M+1]⁺.

Step 4: Preparation of 6-chloro-4-hydroxyinicotinaldehyde

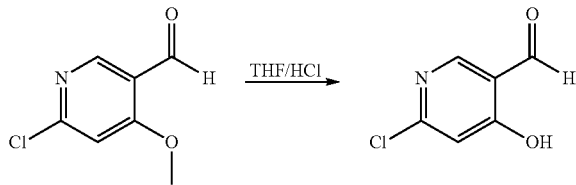

6-chloro-4-methoxynicotinaldehyde (4.2 g, 24.5 mmol) was dissolved in 1,4-dioxane (30 ml), then concentrated hydrochloric acid (10 n) was added. The mixture was heated to 90° for 16 h. After the reaction was completed, the mixture was concentrated. The crude product was separated by silica gel column chromatography to obtain compound 6-chloro-4-hydroxylnicotinaldehyde (1.5 g, yield: 39%).

¹H NMR (400 MHz, CDCl₃): δ ppm 11.37 (s, 1H), 9.99 (s, 1H), 8.57 (s, 1H), 6.99 (s, 1H).

Step 5: Preparation of 7-chloro-3-(3,5-dimethoxyphenyl)-2H-pyrano[3,2-c]pyridin-2-one

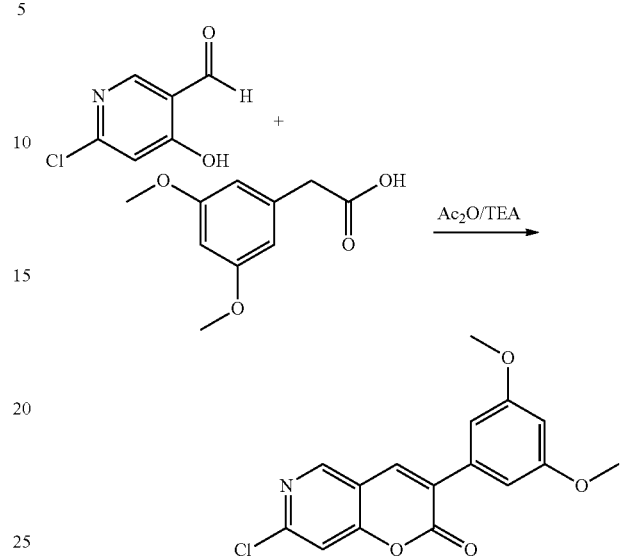

6-chloro-4-hydroxylnicotinaldehyde (0.60 g, 3.82 mmol) was added to acetic anhydride (10 mL), then 2-(3,5-dimethoxyphenyl)acetic acid (0.80 g, 4.08 mmol) and triethylamine (1.5 g, 107 mmol) were added, the mixture was heated to 110° C. for 40 min. After the reaction was completed, the mixture was cooled to room temperature and concentrated. The obtained solids were washed with petroleum ether/ethyl acetate (3:1) to obtain compoundd 7-chloro-3-(3,5-dimethoxyphenyl)-2H-pyrano[3,2-c]pyridin-2-one (0.35 g, yield: 29%). MS (ESI): m/z 318.3 [M+1]⁺.

Step 6: Preparation of 7-chloro-3-(2,6-dichloro-3,5-dimethoxyphenyl)-2H-pyrano[3,2-c]pyridin-2-one

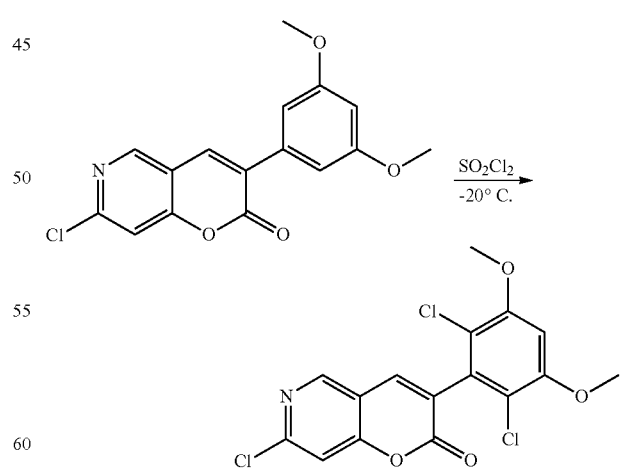

7-chloro-3-(3,5-dimethoxyphenyl)-2H-pyrano[3,2-c] pyridin-2-one (0.35 g, 1.1 mmol) was dissolved in anhydrous acetonitrile (10 mL), the mixture was cooled to −30° C., then SO₂Cl₂ (1.0 g, 7.4 mmol) was added dropwise, the mixture was stirred at this temperature for 1 h. A saturated aqueous solution of NaHCO₃ was added to quench the reaction, and then acetonitrile was removed by concentration. After filtration, the solids were washed with water and then petroleum ether/ethyl acetate (3:1) to obtain 7-chloro-3-(2,6-dichloro-3,5-dimethoxyphenyl)-2H-pyrano[3,2-c]pyridin-2-one (0.21 g, yield: 49%). MS (ESI): m/z 3863 [M+1]⁺.

Intermediate 2: Preparation of 2-chloro-6-(2,6-dichloro-3,5-dimethoxyphenyl)pyrido[3,4-d]pyrimidine

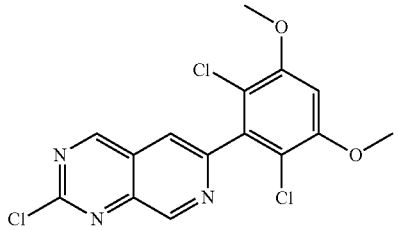 [SMILES: COc1cc(OC)c(Cl)c(-c2cc3cnc(Cl)nc3cn2)c1Cl]

Step 1 Preparation of 2-Chloro-5-Nitroisonicotinic Acid

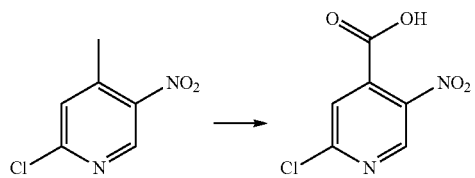

Chromium trioxide (40.0 g, 40 mmol) was added to a solution of 2-chloro-4-methyl-5-nitropyridine (20.0 g, 11.6 mmol) in sulfuric acid (200 mL) at 0°. After the addition was completed, the mixture was stirred at 0° C. for 1 h, then slowly warmed to room temperature and stirred overnight, and then poured into ice water (1 L) and filtrated to obtain 2-chloro-5-nitroisonicotinic acid (18 g, yield: 77%). MS (ESI): m/z 201.1 [M−1]⁻.

Step 2: Preparation of Methyl 2-Chloro-5-Nitroisonicotinate

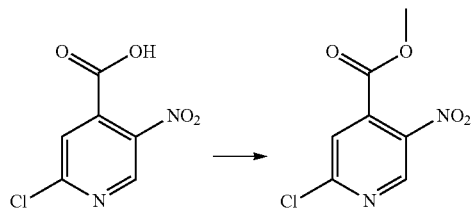

Oxalyl chloride (12.7 g, 100 mmol) was added to a suspension of 2-chloro-5-nitroisonicotinic acid (16 g, 80 mmol) in dichloromethane (150 mL) at 0°. After the addition was completed, the mixture was stirred at room temperature for 3 h. Methanol (100 mL) was added, the reaction mixture was stirred at room temperature for another 4 h and then concentrated. The crude product was dissolved in dichloromethane (200 ml), the mixture was washed with sodium bicarbonate solution (100 mL*2), dried over anhydrous sodium sulfate and concentrated to obtain methyl 2-chloro-5-nitroisonicotinate (17.2 g, yield: 98%).

Step 3: Preparation of Methyl 2-(3,5-dimethoxyphenyl)-5-nitroisonicotinate

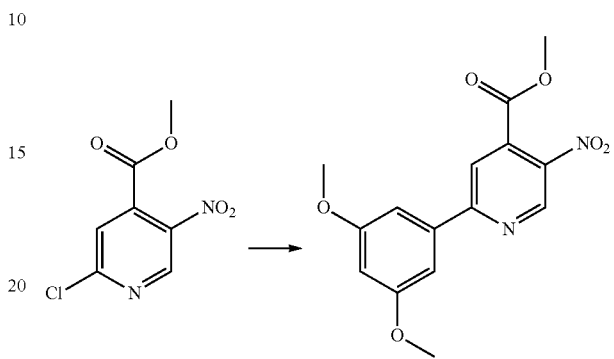

3,5-dimethoxyphenylboronic acid (8.47 g 46 mmol), tetrakis(triphenylphosphine)palladium (5 g, 4.6 mmol) and sodium carbonate (5 g 16 mmol) were added to a solution of methyl 2-chloro-5-nitroisonicotinate (10.0 g, 46.0 mmol) in the mixture of dioxane (200 mL) and water (50 mL). After the addition was completed, the mixture was stirred under N2 at 110° C. until the reaction of the starting materials was completed. The reaction solution was concentrated and separated by column chromatography (eluent: CH₂Cl₂/PE 20:1) to obtain compound methyl 2-(3,5-dimethoxyphenyl)-5-nitroisonicotinate (6 g, yield: 41%). MS (ESI): m/z 2318.9 [M+1]⁺.

Step 4: Preparation of Methyl 5-amino-2-(3,5-dimethoxyphenyl)isonicotinate

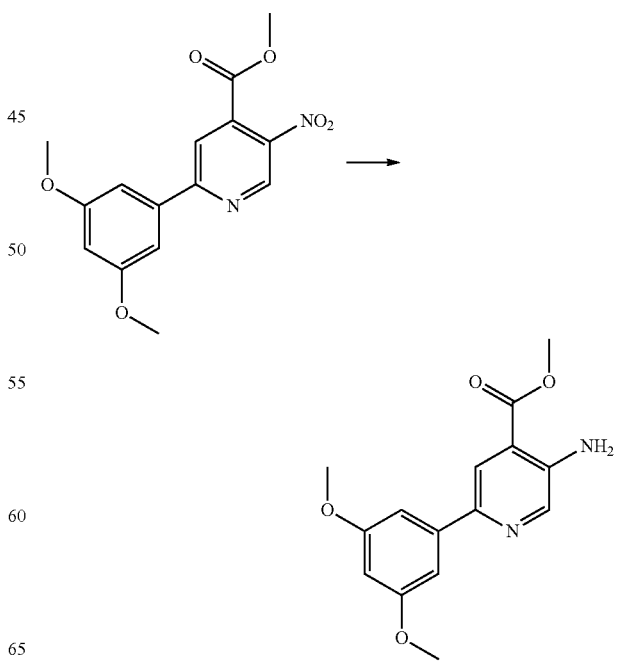

Palladium carbon (10%, 500 mg) was added to a solution of methyl 2-(3,5-dimethoxyphenyl)-5-nitroisonicotinate (6 g, 18.8 mmol) in methanol (100 mL). Then the mixture was stirred under a hydrogen atmosphere at room temperature for 4 h, filtrated and concentrated to obtain methyl 5-amino-2-(3,5-dimethoxyphenyl)nitroisonicotinate (5 g, yield: 92.3%). MS (ESI): m/z 289.3[M+1]⁺.

Step 5: Preparation of 6-(3,5-dimethoxyphenyl)pyrido[3,4-d]pyrimidine-2,4(1H,3H)-dione

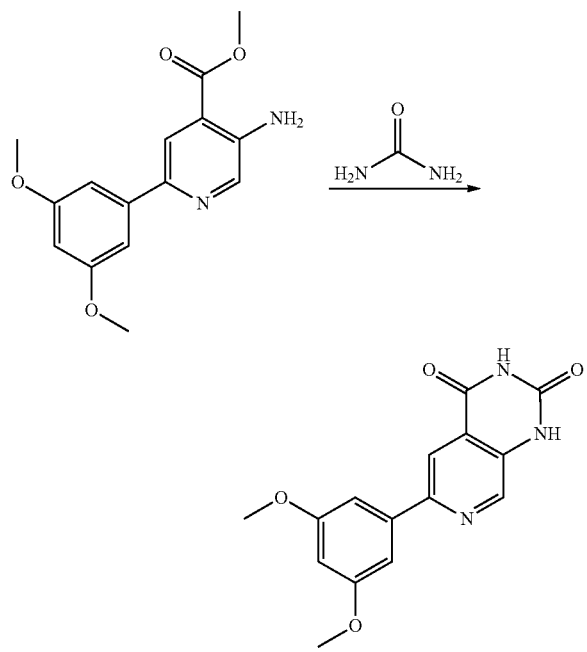

A mixture of methyl 5-amino-2-(3,5-dimethoxyphenyl)isonicotinate (5 g, 17.4 mmol) and urea (12 g, 200 mmol) was heated to 160° C. and stirred for 4 h. Then the mixture was poured into ice water (100 mL) and filtered to obtain 6-(3,5-dimethoxyphenyl)pyrido[3,4-d]pyrimidine-2,4(1H, 3H)-dione (6 g, yield: 99%). MS (ESI): m/z 300.3 [M+1]⁺.

Step 6: Preparation of 2,4-dichloro-6-(3,5-dimethoxyphenyl)pyrido[3,4-d]pyrimidine

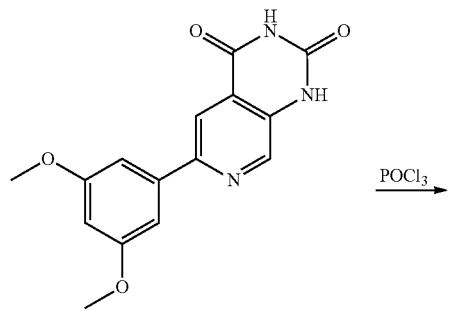

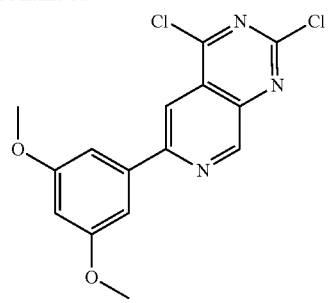

N,N-diethylaniline (3 mL) was added to a suspension of 6-(3,5-dimethoxyphenyl)pyrido[3,4-d]pyrimidine-2,4(1H, 3H)-dione (5.0 g, 16.7 mmol) in phosphorus oxychloride (50 mL). The mixture was then stirred at 110° C. overnight. The solvent was evaporated, ice water (200 mL) was added, and pH was adjusted to 7 with aqueous sodium bicarbonate solution. The aqueous solution was extracted for three times with EtOAc (50 mL). The organic phase was dried over anhydrous sodium sulfate, filtered, concentrated and separated by column chromatography [eluent: (EA:PE=1:5)] to obtain compound 2,4-dichloro-6-(3,5-dimethoxyphenyl)pyrido[3,4-d]pyrimidine (2.5 g, yield: 44.5%). MS (ESI): m/z 336.2 [M+1]⁺.

Step 7: Preparation of 2-chloro-6-(3,5-dimethoxyphenyl)pyrido[3,4-d]pyrimidine-4-amine

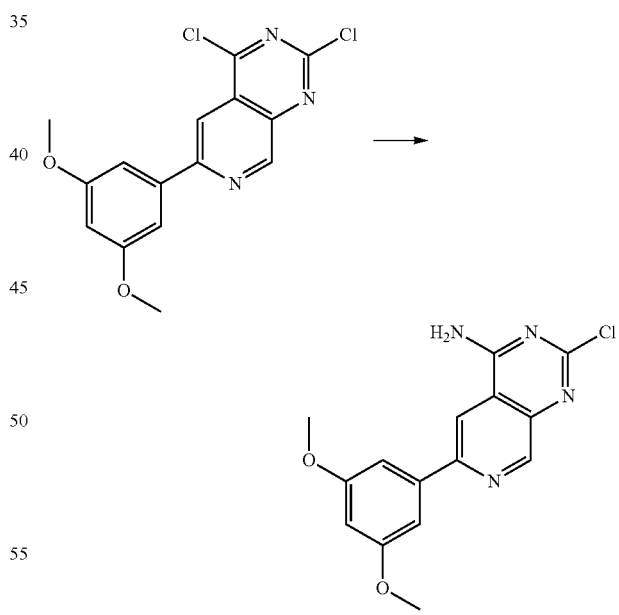

A concentrated aqueous ammonia (2 g) was added to a solution of 2,4-dichloro-6-(3,5-dimethoxyphenyl)pyrido[3, 4-d]pyrimidine (5 g, 7.5 mmol) in methanol (100 mL). The mixture was then stirred at 25° C. for 4 h. The pH was adjusted to 7 with hydrochloric acid (1N), then methanol is removed under vacuum, 2-chloro-6-(3,5-dimethoxyphenyl)pyrido[3,4-d]pyrimidine-4-amine (2 g, yield: 84%) was obtained after filtration. MS (ESI): m/z 317.1 [M+1]⁺.

Step 8: Preparation of 2-chloro-6-(3,5-dimethoxy-phenyl)pyrido[3,4-d]pyrimidine

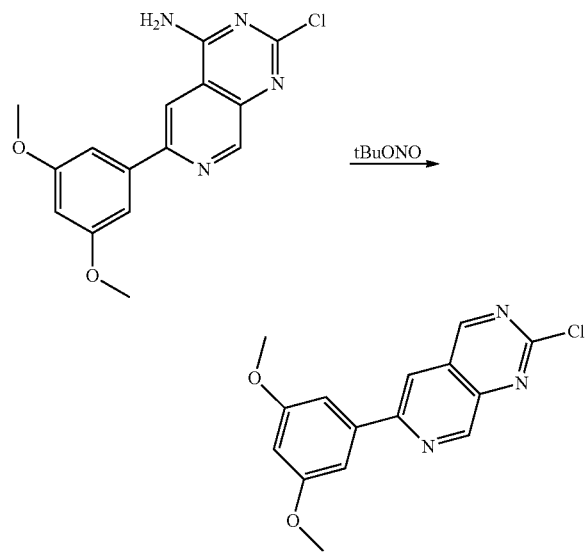

Tert-butyl nitrite (720 mg, 6.2 mmol) was added to a solution of 2-chloro-6-(3,5-dimethoxyphenyl)pyrido[3,4-d]pyrimidine-4-amine (I g, 3.1 mmol) in tetrahydrofuran (100 mL). The mixture was then heated to reflux and stirred for 48 h. The reaction mixture was concentrated and separated by column chromatography [eluent: (EA:PE=1: 5-1:2)] to obtain compound 2-chlor-6-(3,5-dimethoxyphenyl)pyrido[3,4-d]pyrimidine (400 mg, yield: 41%).

$^1$H NMR (400 MHz, DMSO-$d_6$: δ 9.7 (s, 1H) 9.53 (s, 1H), 8.74 (s, 1H), 7.4 (s, 2H), 6.64 (s, 1H), 3.88 (S, 61H);

MS (ESI): m/z 302.0 [M+1]$^+$.

Step 9: Preparation of 2-chloro-6-(2,6-dichloro-3,5-dimethoxyphenyl)pyrido[3,4-d]pyrimidine

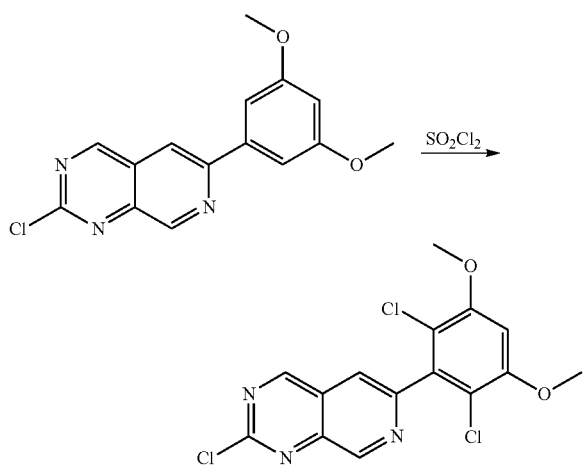

The compound was prepared referring to the synthesis method of step 6 of intermediate 1.

Intermediate 3 and Intermediate 4: Preparation of 2-chloro-6-(2,6-difluoro-3,5-dimethoxyphenyl)pyrido[3,4-d]pyrimidine and 2-chloro-6-(2-fluoro-3,5-dimethoxyphenyl)pyrido[3,4-d]pyrimidine

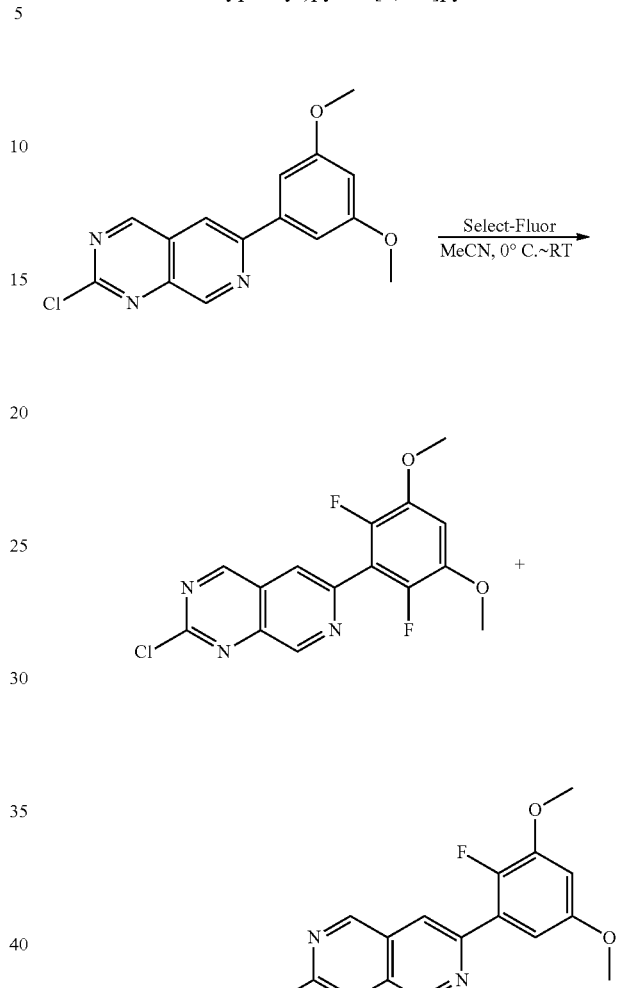

2-chloro-6-(3,5-dimethoxyphenyl)pyrido[3,4-d]pyrimidine (120 mg, 0.4 mmol) was dissolved in anhydrous acetonitrile (20 mL) then the mixture was cooled to 0° C. with ice-water bath. 1-chloromethyl-4-fluoro-1,4-diazonibicyclo[2.2.2]octane bis(tetrafluoroborate) (select-fluor, 283 mg, 0.8 mmol) was added dropwise. After the addition was completed, the reaction solution was warmed to room temperature for 6 h. The reaction was completed monitored by TLC. A saturated aqueous NaHCO$_3$ solution was added to quench the reaction, and then majority of acetonitrile was removed. The mixture was extracted with ethyl acetate, concentrated, and separated by silica gel column chromatography (PE/EA=10/11, adjusted by adding 10% DCM) to obtain 2-chloro-6-(2,6-difluoro-3,5-dimethoxyphenyl)pyrido[3,4-d]pyrimidine(20 mg, yield: 15%), MS m/z (ESI): 338 [M+H]+. At the same time, 2-chloro-6-(2-fluoro-3,5-dimethoxyphenyl)pyrido[3,4-d]pyrimidine(70 mg, yield: 55%) was also obtained, MS m/z (ESI): 320 [M+H]$^+$.

Intermediates 5-10 were prepared referring to the the synthesis method of intermediate 2.

| Intermediate No. | Compound structure | Compound name | MS: m/z [M + 1]+ |
|---|---|---|---|
| 5 | 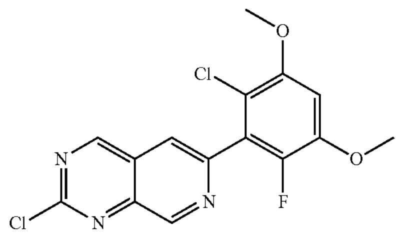 [SMILES: COc1cc(OC)c(Cl)c(-c2cc3cnc(Cl)nc3cn2)c1F] | 2-chloro-6-(2-chloro-6-fluoro-3,5-dimethoxyphenyl)pyrido[3,4-d]pyrimidine | 355 |
| 6 | 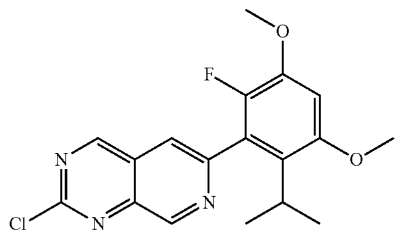 [SMILES: COc1cc(OC)c(C(C)C)c(-c2cc3cnc(Cl)nc3cn2)c1F] | 2-chloro-6-(2-fluoro-6-isopropyl-3,5-dimethoxyphenyl)pyrido[3,4-d]pyrimidine | 362 |
| 7 | 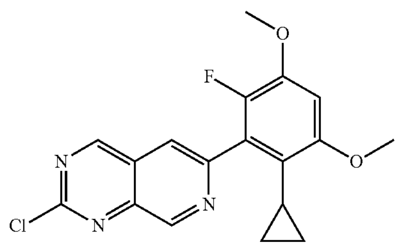 [SMILES: COc1cc(OC)c(C2CC2)c(-c2cc3cnc(Cl)nc3cn2)c1F] | 2-chloro-6-(2-cyclopropyl-6-fluoro-3,5-dimethoxyphenyl)pyrido[3,4-d]pyrimidine | 360 |
| 8 | 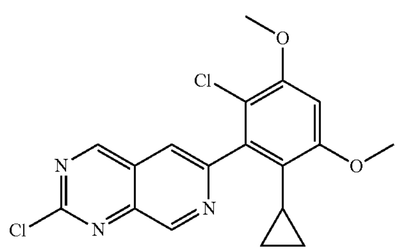 [SMILES: COc1cc(OC)c(C2CC2)c(-c2cc3cnc(Cl)nc3cn2)c1Cl] | 2-chloro-6-(2-chloro-6-cyclopropyl-3,5-dimethoxyphenyl)pyrido[3,4-d]pyrimidine | 377 |
| 9 | 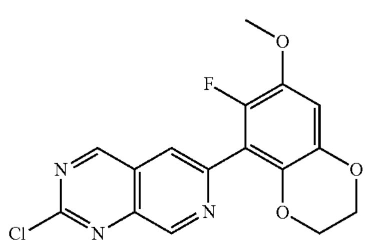 | 2-chloro-6-(6-fluoro-7-methoxy-2,3-dihydrobenzo[b][1,4]dioxin-5-yl)pyrido[3,4-d]pyrimidine | 348 |
| 10 | 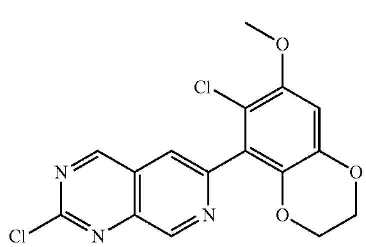 [SMILES: COc1cc2c(c(-c3cc4cnc(Cl)nc4cn3)c1Cl)OCCO2] | 2-chloro-6-(6-chloro-7-methoxy-2,3-dihydrobenzo[b][1,4]dioxin-5-yl)pyrido[3,4-d]pyrimidine | 365 |

Intermediate 11: Preparation of 7-chloro-3-(2,6-dichloro-3,5-dimethoxyphenyl)-1H-pyrano[4,3-c]pyridin-1-one

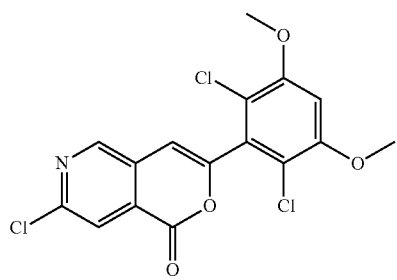 [SMILES: COc1cc(OC)c(Cl)c(-c2cc3cnc(Cl)cc3c(=O)o2)c1Cl]

Step 1: Preparation of Methyl 5-bromo-2-chloroisonicotinate

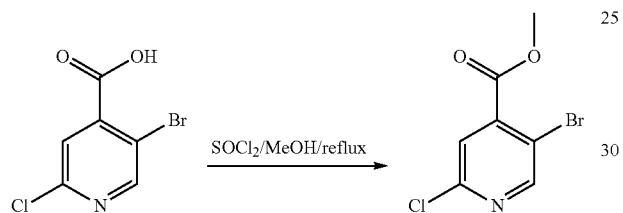

5-bromo-2-chloroisonicotinic acid (30.0 g 12.6 mmol) was dissolved in methanol (300 mL), then SOCl$_2$ (18.0 g, 15 mmol) was added, the mixture was heated to 75° C. for 8 h. The reaction was completed monitored by LCMS. The mixture was cooled to room temperature and concentrated by reduced pressure, and then EtOAc (300 mL) was added to the residue. The mixture was washed with a saturated aqueous solution of NaHCO$_3$ dried over anhydrous Na$_2$SO$_4$, filtered and concentrated to obtain methyl 5-bromo-2-chloroisonicotinate (32.0 g, yield: 99%). MS (ESI): m/z 251.9 [M+1]$^+$.

Step 2: Preparation of Methyl 2-chloro-5-((3,5-dimethoxyphenyl)ethynyl)isonicotinate

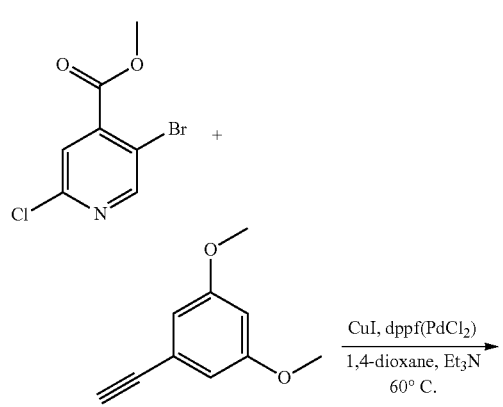

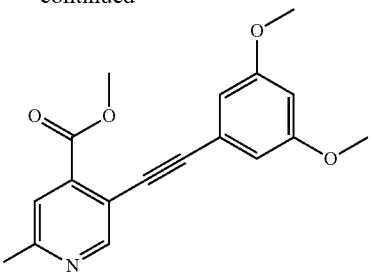

Methyl 5-bromo-2-chloro isonicotinate 30 g, 120 mmol) was dissolved in 1,4-dioxane (300 mL), and 3,5-dimethoxyphenylacetylene (20.4 g, 120 mmol), CuI (2.28 g, 12 mmol), Pd(dppf)Cl$_2$ (4.2 g, 6 mmol) and Et$_3$N (12.0 g, 120 mmol) were added, and the mixture was heated to 60° C. under N2 for 6 h. The reaction was complete, and the mixture was filtered and concentrated. The crude product was separated by silica gel column chromatography (DCM:PE=20:1) to obtain compound methyl 2-chloro-5-((3,5-dimethoxyphenyl)ethynyl)isonicotinate (22 g, yield: 55%). MS (ESI): m/z 332.1 [M+1]$^+$.

Step 3: Preparation of 7-chloro-3-(3,5-dimethoxyphenyl)-1H-pyrano[4,3-c]pyridin-1-one

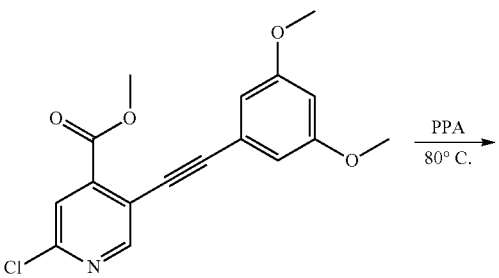

Methyl 2-chloro-5-((3,5-dimethoxyphenyl)ethynyl)isonicotinate (21.0 g 63 mmol) was added to PPA (200 mL), and the mixture was heated to 80° for 8 h. The reaction was completed monitored by LCMS. The reaction mixture was poured into ice water (1000 mL), and then filtered to obtain solid compound 7-choro-3-(3,5-dimethoxyphenyl)-1H-pyrano[4,3-c]pyridin-1-one (15.0 g, yield: 75%). MS (ESI): m/z 318.2 [M+1]$^+$.

Step 4: Preparation of 7-chloro-3-(2,6-dichloro-3,5-dimethoxyphenyl)-1H-pyrano[4,3-c]pyridin-1-one

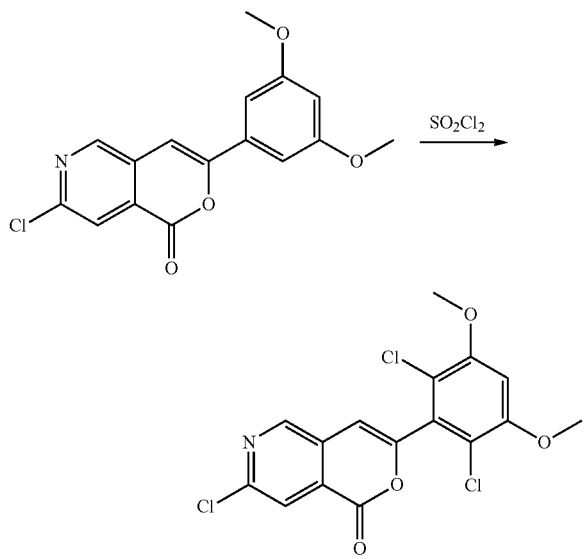

The compound was prepared referring to the synthetic method of step 6 of Intermediate 1.

Intermediate 12: Preparation of 7-chloro-3-(2,6-dichloro-3,5-dimethoxyphenyl)-2-methyl-2,6-naphthyridin-1(2H)-one

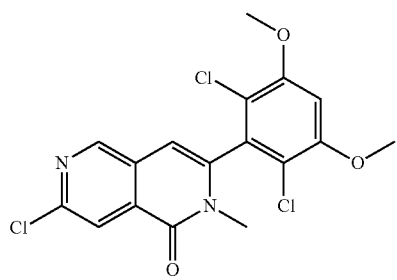 [SMILES: COc1cc(OC)c(Cl)c(-c2cc3cnc(Cl)cc3c(=O)n2C)c1Cl]

Step 1: Preparation of 7-chloro-3-(3,5-dimethoxyphenyl)-2,6-naphthyridin-1(2H)-one

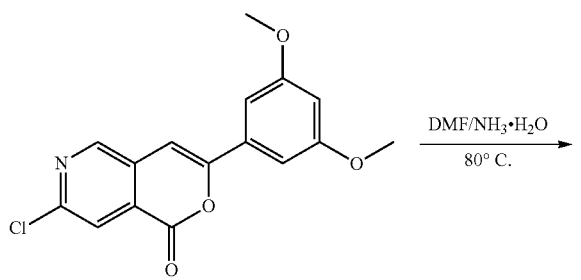

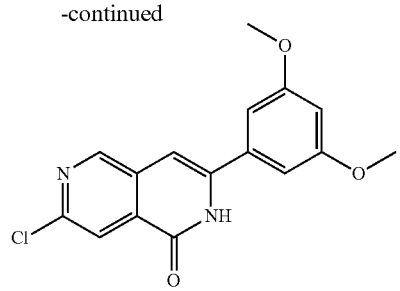

7-chloro-3-(3,5-dimethoxyphenyl)-1H-pyrano[4,3-c]pyridin-1-one (15 g, 47.3 mmol) was dissolved in DMF (200 mL), then concentrated aqueous ammonia (150 mL) was added. The reaction mixture was heated to 80° C. for 48 h. The reaction was completed monitored by LCMS, and then filtered to obtain solid compound 7-chloro-3-(3,5-dimethoxyphenyl)-2,6-naphthyridin-1(2H)-one (7.5 g, yield: 50.5%).

$^1$H NMR (400 MHz, DMSO-d6): δ ppm 11.7 (m, 1H), 8.97 (s, 1-), 8.01 (s, 1-), 7.14 (s, 1H), 6.97 (s, 21), 6.61 (s, 1H), 3.86 (s, 611).

MS (ESI): m/z 317.2 [M+1]$^+$.

Step 2: Preparation of 7-chloro-3-(3,5-dimethoxyphenyl)-2-methyl-2,6-naphthyridin-1(2H)-one

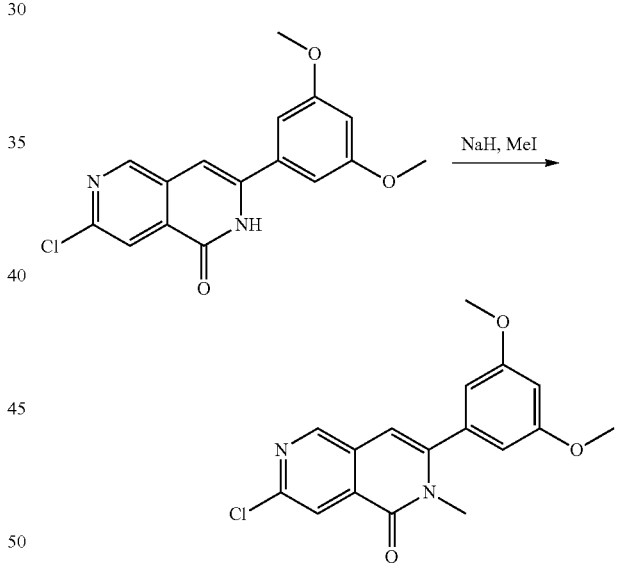

7-chloro-3-(3,5-dimethoxyphenyl)-2,6-naphthyridin-(2H)-one (2 g, 6.32 mmol) was dissolved in DMF (30 mL), and Na (758 mg, 18.95 mmol) was added under ice water bath. The mixture was stirred at 0° C. for 15 minutes, then MeI (8,967 g, 63.151 mmol) was added dropwise, the mixture was stirred at room temperature for 1 h. After the reaction was completed, it was quenched with water. The mixture was extracted for three times with ethyl acetate, and the organic phases were combined and washed with water, saturated brine, dried over anhydrous sodium sulfate, filtrated, concentrated and separated by column chromatography (Eluent: PE/EtOAc=2:1) to obtain compound 7-chloro-3-(3,5-dimethoxyphenyl)-2-methyl-2,6-naphthyridin-1(2H)-one (1.35 g, yield: 65%).

MS m/z (ESI): 331.0 [M+H]$^+$.

Step 3: Preparation of 7-chloro-3-(2,6-dichloro-3,5-dimethoxyphenyl)-2-methyl-2,6-naphthyridin-1(2H)-one

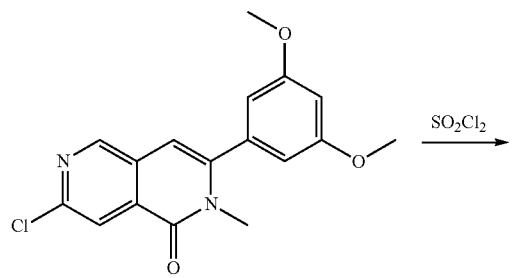

SO$_2$Cl$_2$ →

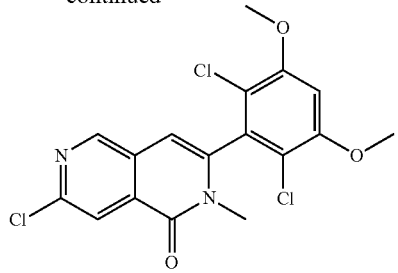

The compound was prepared referring to the synthetic method of step 6 of Intermediate 1 MS m/z (ESI): 399.2 [M+H]$^+$.

Intermediate 13-19 were prepared referring to the synthesis method of Intermediate 12.

| Intermediate No. | Compound structure | Compound name | MS: m/z [M + 1]$^+$ |
|---|---|---|---|
| 13 | 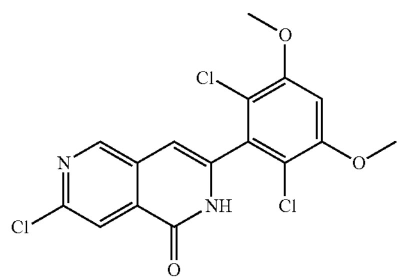 [SMILES: COc1cc(OC)c(Cl)c(-c2cc3cnc(Cl)cc3c(=O)[nH]2)c1Cl] | 7-chloro-3-(2,6-dichloro-3,5-dimethoxyphenyl)-2,6-naphthyridin-1(2H)-one | 385 |
| 14 | 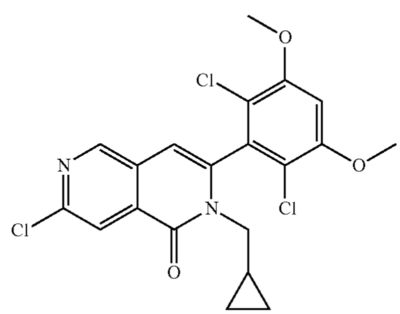 [SMILES: COc1cc(OC)c(Cl)c(-c2cc3cnc(Cl)cc3c(=O)n2CC2CC2)c1Cl] | 7-chloro-2-(cyclopropylmethyl)-3-(2,6-dichloro-3,5-dimethoxyphenyl)-2,6-naphthyridin-1(2H)-one | 440 |
| 15 | 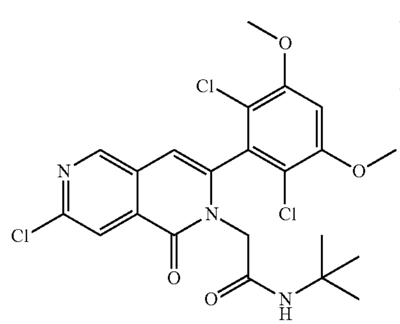 | N-(tert-butyl)-2-(7-chloro-3-(2,6-dichloro-3,5-dimethoxyphenyl)-1-oxo-2,6-naphthyridin-2(1H)-yl)acetamide | 499 |

-continued

| Intermediate No. | Compound structure | Compound name | MS: m/z [M + 1]+ |
|---|---|---|---|
| 16 | 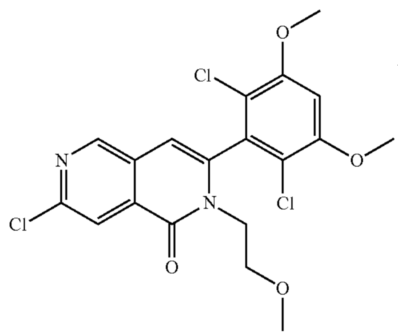 | 7-chloro-3-(2,6-dichloro-3,5-dimethoxyphenyl)-2-(2-methoxyethyl)-2,6-naphthyridin-1(2H)-one | 444 |
| 17 | 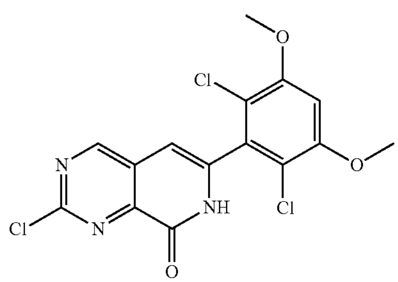 [SMILES: COc1cc(OC)c(Cl)c(-c2cc3cnc(Cl)nc3c(=O)[nH]2)c1Cl] | 2-chloro-6-(2,6-dichloro-3,5-dimethoxyphenyl)pyrido[3,4-d]pyrimidin-8(7H)-one | 387 |
| 18 | 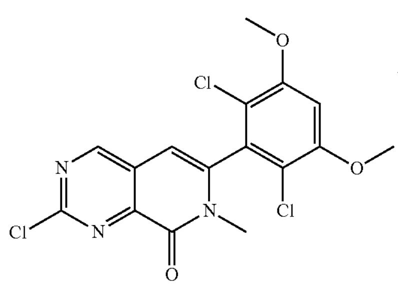 | 2-chloro-6-(2,6-dichloro-3,5-dimethoxyphenyl)-7-methylpyrido[3,4-d]pyrimidin-8(7H)-one | 401 |
| 19 | 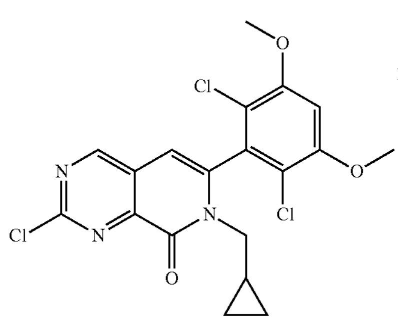 | 2-chloro-7-(cyclopropylmethyl)-6-(2,6-dichloro-3,5-dimethoxyphenyl)pyrido[3,4-d]pyrimidin-8(7H)-one | 441 |

Intermediate 20: Preparation of 6-chloro-2-(2,6-dichloro-3,5-dimethoxyphenyl)pyrido[3,4-d]pyrimidine-4(3H)-one

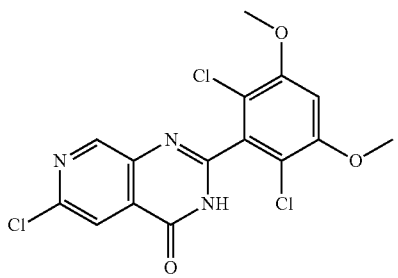 [SMILES: COc1cc(OC)c(Cl)c(-c2nc3cnc(Cl)cc3c(=O)[nH]2)c1Cl]

Step-1: Preparation of 5-amino-2-chloroisonicotinamide

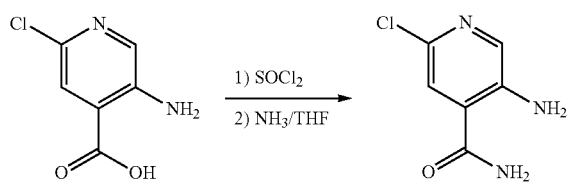 [SMILES: Nc1cnc(Cl)cc1C(=O)O ; NC(=O)c1cc(Cl)ncc1N]

5-amino-2-chloroisonicotinic acid (4.0 g, 23 mmol) was added to SOCl₂ (50 mL), the mixture was heated to 80° C. for 4 h. After the reaction was completed, the mixture was cooled to room temperature and concentrated. The residue was dissolved in anhydrous THF (20 mL), and then the mixture was cooled under ice water bath, a concentrated aqueous ammonia (100 mL) was added. The reaction was completed, and the mixture was extracted for five times with CH₂Cl₂ (100 mL). The organic phases were combined, dried over anhydrous sodium sulfate, filtrated and concentrated to obtain compound 5-amino-2-chloroisonicotinamide (3.5 g yield: 88%).

Step 2: Preparation of 6-chloro-2-(3,5-dimethoxyphenyl)pyrido[3,4-d]pyrimidine-4(3H)-one

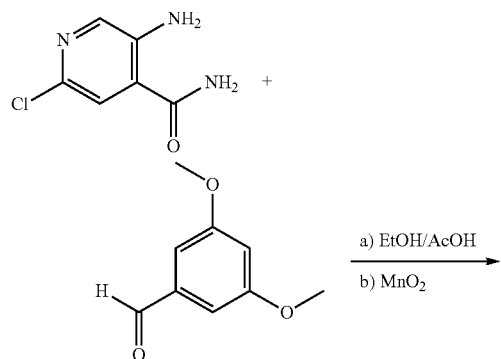

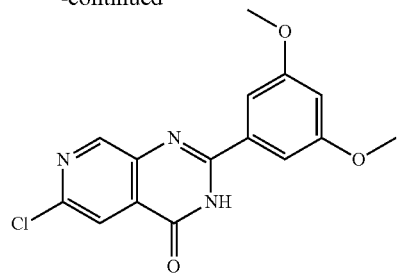

5-amino-2-chloroisonicotinamide (3.5 g, 20.4 mmol) and 3,5-dimethoxybenzaldehyde (3.7 g, 22.3 mmol) were dissolved in EtOH (50 mL) then HOAc (10 mL) was added, the mixture was heated to 80° C. for 2 days. The reaction liquid was concentrated, the residue was dissolved in the mixture of CH₂Cl₂ (100 mL) and THF (100 mL). Then MnO₂ (17.0 g, 87.0 mmol) was added, and the mixture was stirred at room temperature for 4 days. The reaction was completed, the mixture was filtered and concentrated. The residue was added to EtOAc (100 mL), stirred and filtrated to obtain compound 6-chloro-2-(3,5-dimethoxyphenyl)pyrido[3,4-d]pyrimidin-4(3H)-one (4.0 g, yield: 63%).

¹H NMR (400 MHz, DMSO-d6): δ ppm 12.78 (s, 1H), 8.91 (s, 1H), 7.95 (s, 1H), 7.44 (s, 1H), 7.43 (s, 1H), 3.84 (s, 6H).

Step 3: Preparation of 6-chloro-2-(2,6-dichloro-3,5-dimethoxyphenyl)pyrido[3,4-d]pyrimidine-4(3H)-one

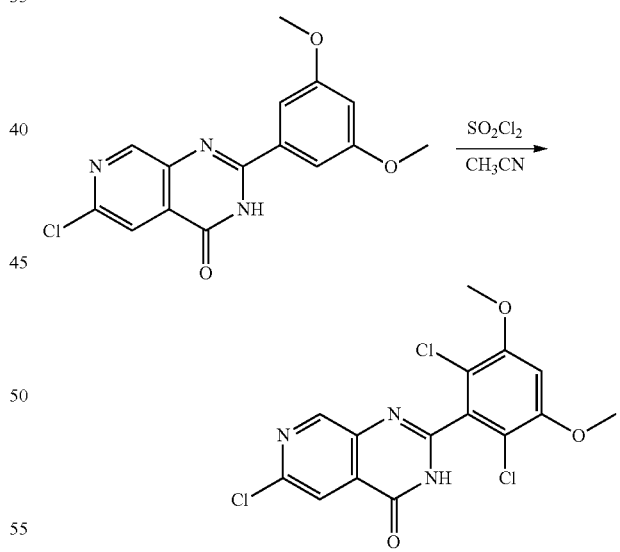

6-chloro-2-(3,5-dimethoxyphenyl)pyrido[3,4-d]pyrimidine-4(3H)-one (1.0 g, 3.2 mmol) was dissolved in CH₃CN (50 mL), then the mixture was cooled to −20° C., SO₂Cl₂ (0.85 g, 6.3 mmol) was added, the mixture was reacted at this temperature for 3 h. After the reaction was completed, a saturated aqueous solution of NaHCO₃ was added to quench the reaction, and the mixture was filtrated to obtain compound 6-chloro-2-(2,6-dichloro-3,5-dimethoxyphenyl)pyrido[3,4-d]pyrimidin-4(3H)-one (1.1 g, 92%). MS (ESI): m/z 386 [M+H]⁺.

Intermediate 21: Preparation of 6-chloro-2-(2,6-dichloro-3,5-dimethoxyphenyl)-3-methylpyrido[3,4-d]pyrimidine-4(3H)-one

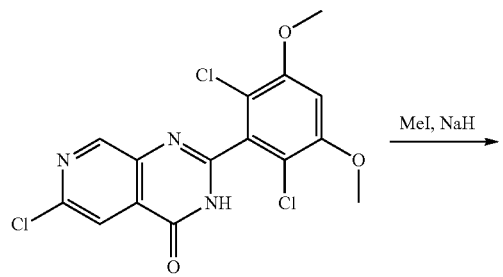

6-chloro-2-(2,6-dichloro-3,5-dimethoxyphenyl)pyrido[34-d]pyrimidine-4(3H)-one (0.65 g, 1.68 mmol) was dissolved in DMF (20 mL), then the mixture was cooled to 0° under ice water bath, NaH (134 mg, 3.36 mmol) was added, the mixture was stirred at room temperature for 2 h. The reaction was completed, water (50 mL) was added to quench the reaction. The mixture was filtrated, washed with water and dried to obtain compound 6-chloro-2-(2,6-dichloro-3,5-dimethoxyphenyl)-3-methylpyrido[3,4-d]pyrimidin-4(3H)-one (0.65 g, yield:96%) MS n/z (ESI): 400 [M+H]⁺.

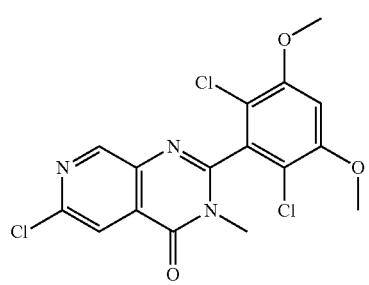

Intermediate 22: Preparation of 7-chloro-3-(2,6-dichloro-3,5-dimethoxyphenyl)-1-(2,2,2-trifluoroethyl)-1,6-naphthyridin-2(1H)-one

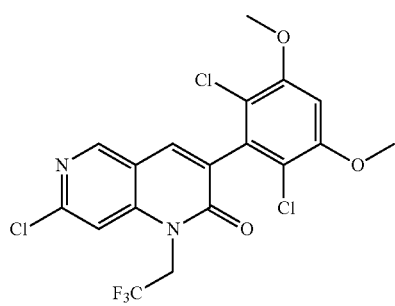 [SMILES: COc1cc(OC)c(Cl)c(-c2cc3cnc(Cl)cc3n(CC(F)(F)F)c2=O)c1Cl]

Step 1: Preparation of Ethyl 6-chloro-4-((2,2,2-trifluoroethyl)amino)nicotinate

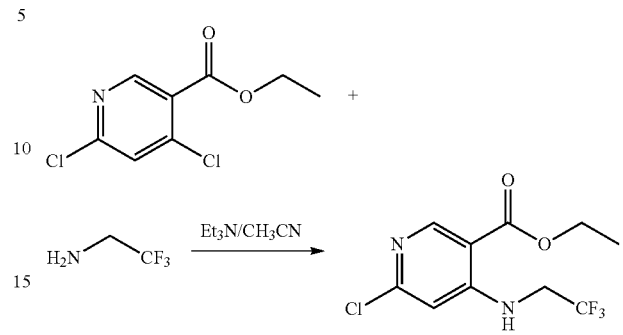

Ethyl 4,6-dichloronicotinate (4.0 g, 18.18 mmol) and trifluoroethylamine (2.7 g, 27.27 mmol) were dissolved in DMSO (50 mL) then Et$_3$N (5.5 g, 54.55 mmol) was added, the mixture was heated to 120° C. for 12 h. The reaction was completed, the mixture was cooled to room temperature, water (200 ml) was added, and then the mixture was extracted for three times with EtOAc (50 mL). The organic phase was dried over anhydrous sodium sulfate, filtrated and concentrated. The crude product was separated by silica gel column chromatography (PE:EA=3:1) to obtain compound ethyl 6-chloro-4-((2,2,2-trifluoroethyl)amino)nicotinate (1.5 g, yield: 29.1%). MS (ESI): m/z 283.0 [M+1]⁺.

Step 2: Preparation of (6-chloro-4-((2,2,2-trifluoroethyl)amino)pyridin-3-yl)methanol

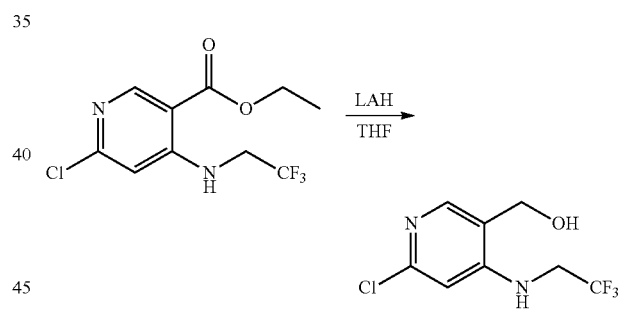

Ethyl 6-chloro-4-((2,2,2-trifluoroethyl)amino)nicotinate (1.5 g, 5.32 mmol) was dissolved in dried T-IF (30 mL) then the mixture was cooled under ice water bath LiAlH$_4$ (0.39 g, 10.64 mmol) was slowly added, and the mixture was stirred at 0° C. for 2 h. The reaction was completed, Na$_2$SO$_4$.10H$_2$O was added to quench the reaction. The mixture was filtrated, and the filtrate was concentrated to obtain compound (6-chloro-4-((2,2,2-trifluoroethyl)amino)pyridin-3-yl)methanol (1.1 g, yield: 86%).

Step 3: Preparation of 6-chloro-4-((2,2,2-trifluoroethyl)amino)nicotinaldehyde

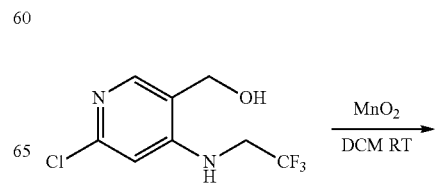

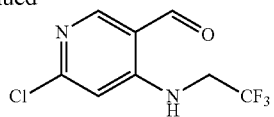

(6-chloro-4-((2,2-trifluoroethyl)amino)pyridin-3-yl)methanol (1.1 g, 4.58 mmol) was dissolved in the mixture of CH₂Cl₂ and THF (30 mL/10 mL), then MnO₂ (4.78 g, 54.9 mmol) was added, and the mixture was stirred at room temperature for 12 h. The reaction was completed, filtrated, and the filtrate was concentrated to obtain crude product 6-chloro-4-((2,2-trifluoroethyl)amino)nicotinaldehyde (0.86, yield: 79%).

Step 4: Preparation of 7-chloro-3-(3,5-dimethoxyphenyl)-1-(2,2,2-trifluoroethyl)-1,6-naphthyridin-2(1H)-one

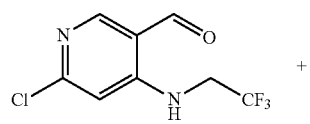

+

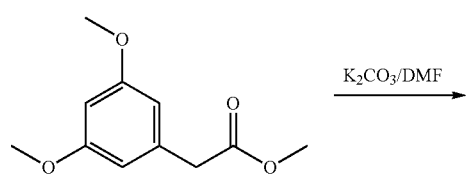

K₂CO₃/DMF →

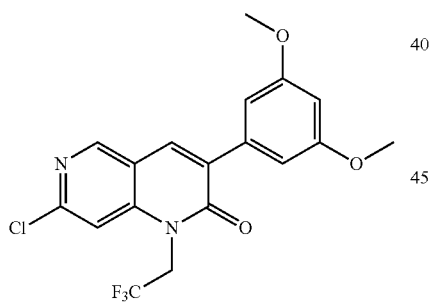

6-chloro-4-((2,2-trifluoroethyl)amino)nicotinaldehyde (0.86 g, 3.61 mmol) was dissolved in DMF (20 mL), then methyl 3,5-dimethoxyphenylacetate (760 mg, 3.61 mmol) and K₂CO₃ (1.5 g, 10.84 mmol) were added, the mixture was heated to 110° C. for 3 h. After the reaction was completed, the mixture was concentrated and separated by silica gel column chromatography (PE:EA=10:1) to obtain 7-chloro-3-(3,5-dimethoxyphenyl)-1-(2,2,2-trifluoroethyl)-1,6-naphthyridin-2(1H)-one (960 mg, yield: 67%). MS (ESI): m/z 399.0 [M+1]⁺.

Step 5: Preparation of 7-chloro-3-(2,6-dichloro-3,5-dimethoxyphenyl)-1-(2,2,2-trifluoroethyl)-1,6-naphthyridin-2(1H)-one

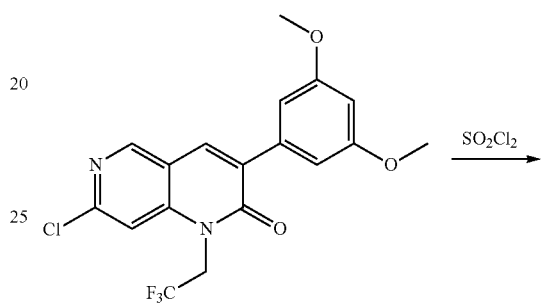

The compound was prepared referring to the synthetic method of step 6 of Intermediate 1.

Intermediates 23-25 were prepared according to the synthesis method of Intermediate 22.

| Intermediate No. | Compound structure | Compound name | MS: m/z [M + 1]⁺ |
|---|---|---|---|
| 23 | 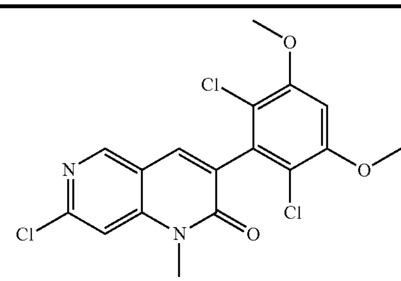 | 7-chloro-3-(2,6-dichloro-3,5-dimethoxyphenyl)-1-methyl-1,6-naphthyridin-2(1H)-one | 400 |

-continued

| Intermediate No. | Compound structure | Compound name | MS: m/z [M + 1]+ |
|---|---|---|---|
| 24 | 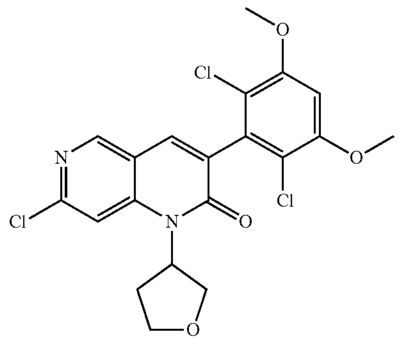 [SMILES: COc1cc(OC)c(Cl)c(-c2cc3cnc(Cl)cc3n(C3CCOC3)c2=O)c1Cl] | 7-chloro-3-(2,6-dichloro-3,5-dimethoxyphenyl)-1-(tetrahydrofuran-3-yl)-1,6-naphthyridin-2(1H)-one | 456 |
| 25 | 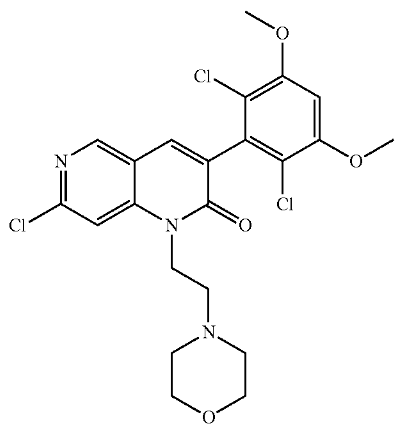 [SMILES: COc1cc(OC)c(Cl)c(-c2cc3cnc(Cl)cc3n(CCN3CCOCC3)c2=O)c1Cl] | 7-chloro-3-(2,6-dichloro-3,5-dimethoxyphenyl)-1-(2-morpholinoethyl)-1,6-naphthyridin-2(1H)-one | 499 |

Intermediate 26: Preparation of 3-chloro-7-(2,6-dichloro-3,5-dimethoxyphenyl)-2,6-naphthyridine

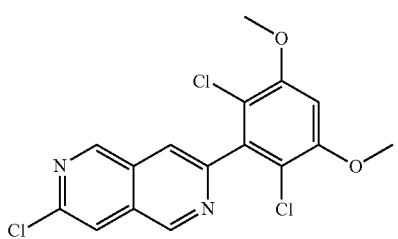

Step 1: Preparation of 5-bromo-2-chloroisonicotinaldehyde

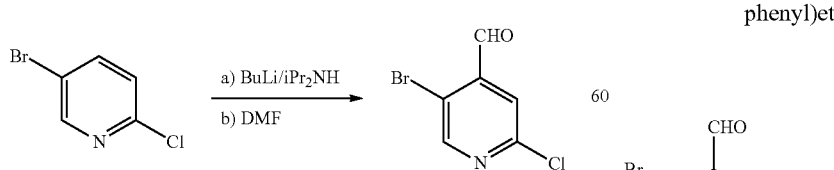

Diisopropylamine (8.95 g, 88 mmol) was dissolved in dried THF (100 mL) under N2, then the mixture was cooled to −78° C. N-butyllithium (50 ml, 78 mmol) was added dropwise, and then the mixture was stirred at 0° C. for 10 min. The mixture was cooled to −78° C., then 2-chloro-5-bromopyridine (10.0 g, 52 mmol) was added, the mixture was stirred at −78° C. for 1 h then dried DMF (11.4 g, 0.16 mol) was added dropwise, the mixture was stirred at this temperature for another 1 h. A ammonium chloride solution was added to quench the reaction, and the mixture was diluted with EtOAc (300 mL), washed for three times with water (50 mL), washed with saturated brine (100 mL), dried over anhydrous sodium sulfate, filtrated, concentrated and separated by column chromatography (Eluent: PE/EtOAc 9:1) to obtain compound 5-bromo-2-chloroisonicotinaldehyde (7.0 g, yield: 61%).

$^1$H NMR (400 MHz, CDCl3): δ 10.3 (s, 1H), 8.69 (s, 1H), 7.73 (s, 1H).

MS m/z (ESI): 252.0, 254.0, 256.0 [M+MeOH+H]+.

Step 2: Preparation of 2-chloro-5-((3,5-dimethoxyphenyl)ethynyl)isonicotinaldehyde

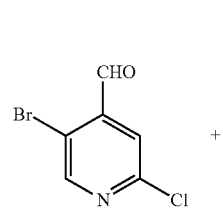

+

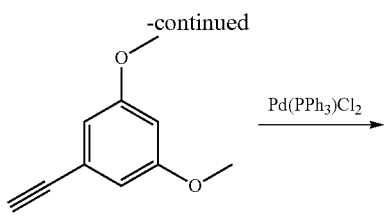

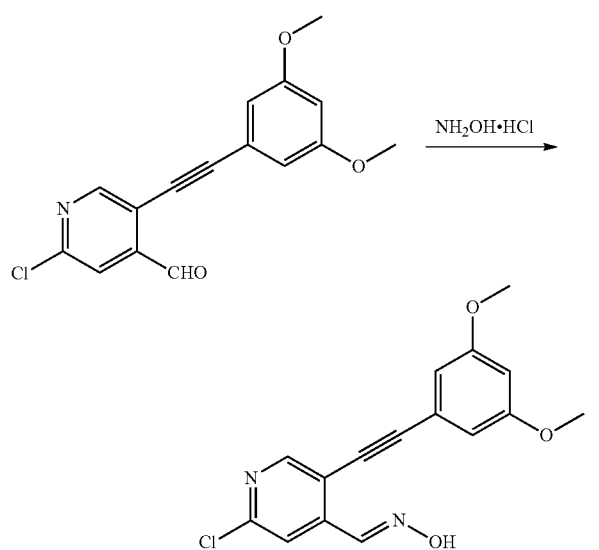

5-bromo-2-chloroisonicotinaldehyde (2.5 g, 11.3 mmol), 1-ethynyl-3,5-dimethoxybenzene (1.93 g, 11.9 mmol), DIPEA (3.66 g, 28.4 mmol), CuI (108 mg, 0.6 mmol) and Pd(PPh$_3$)$_2$Cl$_2$ (398 mg, 0.6 mmol) were added to 1,4-dioxane (50 mL) under N2, the mixture was heated to 50° C. for 1 h. After the reaction was completed, the mixture was diluted with EtOAc (300 mL), washed successively with water (50 mL×3) and saturated brine (100 mL), concentrated and separated by column chromatography (Eluent: PE/EtOAc 9:1) to obtain compound 2-chloro-5-((3,5-dimethoxyphenyl)ethynyl)isonicotinaldehyde (3.0 g, yield: 75%). MS m/z (ESI): 302.2, 3042 [M+H]$^+$.

Step 3: Preparation of 2-chloro-5-((3,5-dimethoxyphenyl)ethynyl)isonicotinaldehydeoxime 2-chloro-5-((3,5-dimethoxyphenyl)ethynyl)isonicotinaldehyde (0.6 g, 2 mmol), NaOAc (245 mg, 3.0 mmol) and hydroxylamine hydrochloride (207 mg, 3.0 mol) were dissolved in the mixture of ethanol and 1,2-dichloroethane (20 ml/1.2 mL) under N2, the mixture was heated to 50° C. for 50 min. After the reaction was completed, the mixture was diluted with EtOAc (200 mL) washed successively with water (50 mL×2) and saturated brine (80 mL), dried over anhydrous sodium sulfate, filtrated and concentrated to obtain compound 2-chloro-5-((3,5-dimethoxyphenyl)ethynyl)isonicotinaldehydeoxime (612 mg, yield: 100%).

Step 4: Preparation of 7-chloro-3-(3,5-dimethoxyphenyl)-2,6-naphthyridin-2-oxide

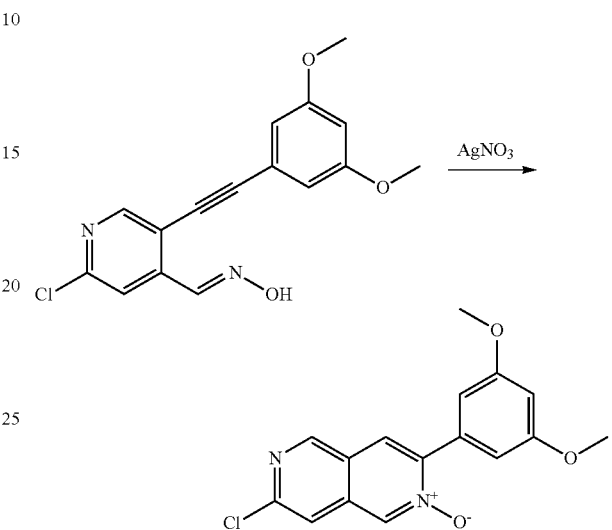

2-chloro-5-((3,5-dimethoxyphenyl)ethynyl)isonicotinaldehydeoxime (612 mg, 1.9 mmol) and AgNO$_3$ (66 mg 0.38 mmol) were added to chloroform (20 mL), the mixture was heated to 60° C. for 1 h. After the reaction was completed, the mixture was concentrated and separated by column chromatography (Eluent: CH$_2$Cl$_2$/MeOH 35:1) to obtain compound 7-chloro-3-(3,5-dimethoxyphenyl)-2,6-naphthyridin-2-oxide (580 mg, yield: 95%).

MS m/z (ESI): 317.2, 319.2 [M+H]$^+$.

Step 5: Preparation of 3-chloro-7-(3,5-dimethoxyphenyl)-2,6-naphthyridine

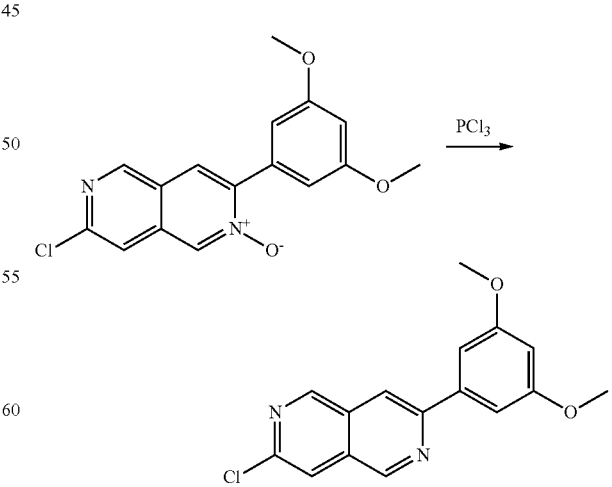

7-chloro-3-(3,5-dimethoxyphenyl)-2,6-naphthyridin-2-oxide (200 ng, 0.63 mmol) was dissolved in dichloromethane (10 mL) tinder ice water bath, then phosphorus trichloride (0.7 mL, 1.4 mmol) was added, the mixture was stirred at room temperature overnight. The reaction was completed, the mixture was washed successively with a saturated aqueous solution of NaHCO$_3$ (20 ml), DCM (80 mL), saturated brine (50 ml), dried over anhydrous sodium sulfate, filtrated, concentrated and separated by column chromatography (Eluent: CH$_2$Cl$_2$/MeOH 50:1) to obtain compound 3-chloro-7-(3,5-dimethoxyphenyl)-2,6-naphthyridine (60 mg, yield: 32%). MS m/z (ESI): 301.1303.2 [M+H]+.

Step 6: Preparation of 3-chloro-7-(2,6-dichloro-3,5-dimethoxyphenyl)-2,6-naphthyridine

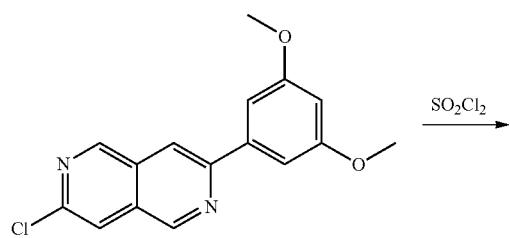

$\xrightarrow{SO_2Cl_2}$

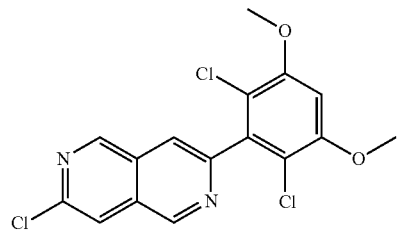 [SMILES: COc1cc(OC)c(Cl)c(-c2cc3cnc(Cl)cc3cn2)c1Cl]

The compound was prepared referring to the synthesis method of Intermediate 1.

Intermediates 27-32 were prepared referring to the synthesis method of Intermediate 26.

| Intermediate No. | Compound structure | Compound name | MS: m/z [M + 1]+ |
|---|---|---|---|
| 27 | 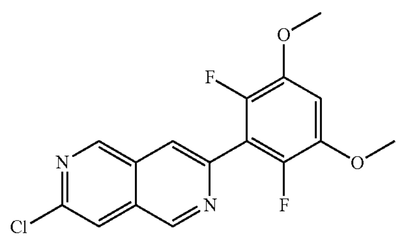 [SMILES: COc1cc(OC)c(F)c(-c2cc3cnc(Cl)cc3cn2)c1F] | 3-chloro-7-(2,6-difluoro-3,5-dimethoxyphenyl)-2,6-naphthyridine | 337 |
| 28 | 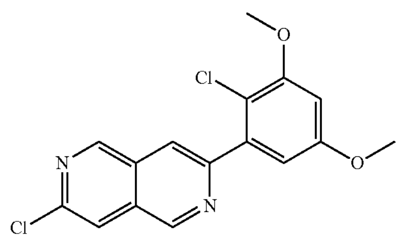 [SMILES: COc1cc(OC)c(Cl)c(-c2cc3cnc(Cl)cc3cn2)c1] | 3-chloro-7-(2-chloro-3,5-dimethoxyphenyl)-2,6-naphthyridine | 336 |
| 29 | 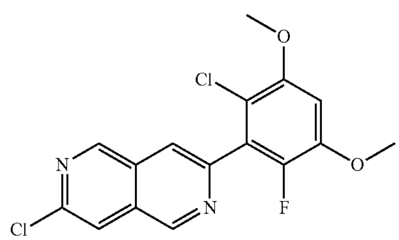 [SMILES: COc1cc(OC)c(Cl)c(-c2cc3cnc(Cl)cc3cn2)c1F] | 3-chloro-7-(2-chloro-6-fluoro-3,5-dimethoxyphenyl)-2,6-naphthyridine | 354 |
| 30 | 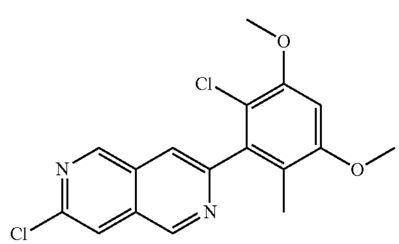 [SMILES: COc1cc(OC)c(Cl)c(-c2cc3cnc(Cl)cc3cn2)c1C] | 3-chloro-7-(2-chloro-3,5-dimethoxy-6-methylphenyl)-2,6-naphthyridine | 350 |

-continued

| Intermediate No. | Compound structure | Compound name | MS: m/z [M + 1]+ |
|---|---|---|---|
| 31 | 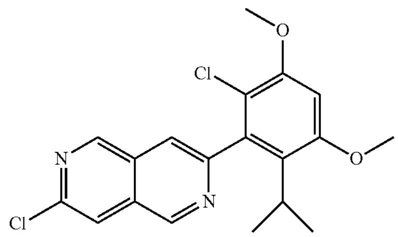 [SMILES: COc1cc(OC)c(C(C)C)c(-c2cc3cnc(Cl)cc3cn2)c1Cl] | 3-chloro-7-(2-chloro-6-isopropyl-3,5-dimethoxyphenyl)-2,6-naphthyridine | 378 |
| 32 | 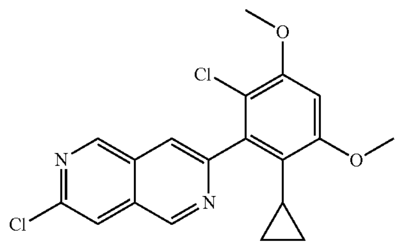 [SMILES: COc1cc(OC)c(C2CC2)c(-c2cc3cnc(Cl)cc3cn2)c1Cl] | 3-chloro-7-(2-chloro-6-cyclopropyl-3,5-dimethoxyphenyl)-2,6-naphthyridine | 376 |

Intermediate 33: Preparation of 7-chloro-N-(cyclopropylmethyl)-3-(2,6-dichloro-3,5-dimethoxyphenyl)-2,6-naphthyridine-1-amine

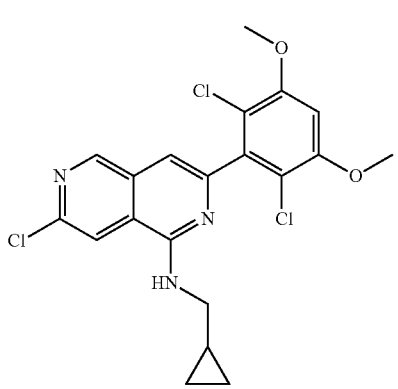 [SMILES: COc1cc(OC)c(Cl)c(-c2cc3cnc(Cl)cc3c(NCC3CC3)n2)c1Cl]

Step 1: Preparation of 7-chloro-1-((cyclopropylmethyl)amino)-3-(3,5-dimethoxyphenyl)-2,6-naphthyridine 2-oxide

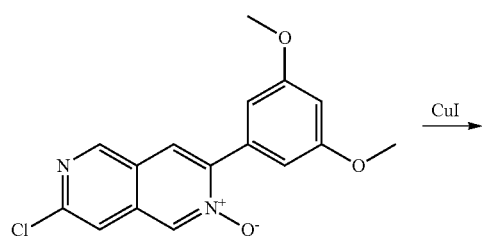

-continued

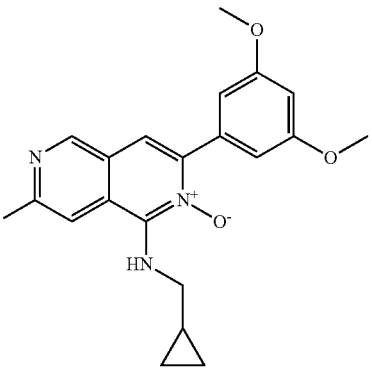

7-chloro-3-(3,5-dimethoxyphenyl)-2,6-naphthyridine 2-oxide (4.0 g, 12.6 mmc) was dissolved in toluene (80 mL), cyclopropylmethylamine (7.19 g, 0.1 mol) and CuI (241 mg, 1.26 mmol) were added successively, the mixture was heated to 50 T overnight under an oxygen atmosphere. After the reaction was completed, the reaction liquid was filtrated and concentrated. The residue was separated by column chromatography (Eluent: dichloromethane/methanol 25:1) to obtain compound 7-choro-1-((cyclopropylmethyl)amino)-3-(3,5-dimethoxyphenyl)-2,6-naphthyridine 2-oxide (2.8 g, 57%).

MS m/z (ESI): 386.4 [M+H]+.

257

Step 2: Preparation of 7-chloro-N-(cyclopropylmethyl)-3-(3,5-dimethoxyphenyl)-2,6-naphthyridine-1-amine

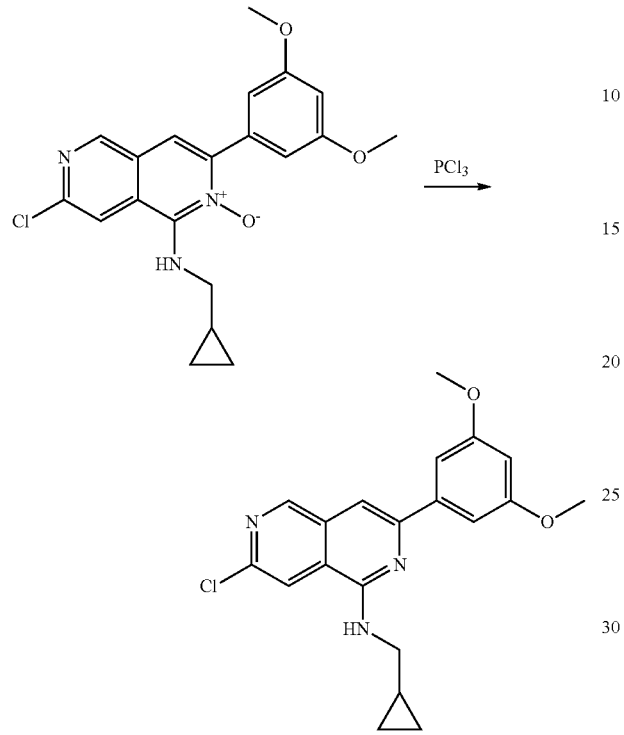

7-chloro-1-((cyclopropylmethyl)amino)-3-(3,5-dimethoxyphenyl)-2,6-naphthridine 2-oxide (2.8 g, 5.1 mmol) was dissolved in dichloromethane (40 mL), PCl₃ (3 mL, 6.1 mmol) was added dropwise under ice water bath, the mixture was stirred at room temperature for 1 h. A saturated solution of sodium hydrogencarbonate (50 mL) was added, then the mixture was extracted with dichloromethane (100 mL×3), the organic phases were combined, dried over anhydrous sodium sulfate, concentrated and separated by column chromatography (Eluent: dichloromethane/methanol 50:1) to obtain compound 7-chloro-N-(cyclopropylmethyl)-3-(3,5-dimethoxyphenyl)-2,6-naphthyridine-1-amine (570 mg, 21%).

MS m/z (ESI): 370.4 [M+H]⁺.

258

Step 3: Preparation of 7-chloro-N-(cyclopropylmethyl)-3-(2,6-dichloro-3,5-dimethoxyphenyl)-2,6-naphthyridine-1-amine

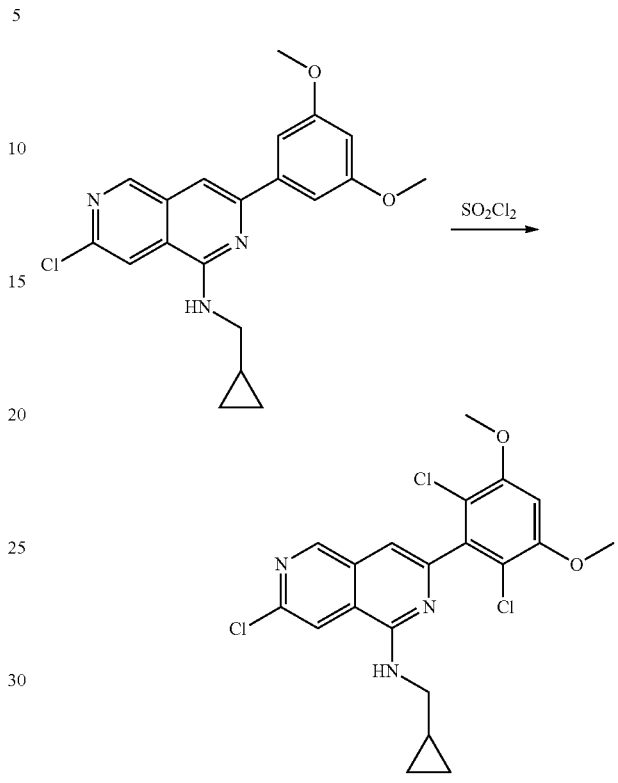

7-chloro-N-(cyclopropylmethyl)-3-(3,5-dimethoxyphenyl)-2,6-naphthyridine-1-amine (550 mg, 0.27 mmol) was added to acetonitrile (20 mL), then sulfonyl chloride (73 mg, 0.54 mmol) was added dropwise at −30° C., the mixture was stirred at this temperature for 1 h. A saturated solution of sodium hydrogencarbonate (30 mL) was added, then the mixture was extracted with ethyl acetate (50 mL×3), the organic phases were combined, dried over anhydrous sodium sulfate, filtrated, concentrated and separated by column chromatography (Eluent: petroleum ether/ethyl acetate 10:1) to obtain compound 7-chloro-N-(cyclopropyl methyl)-3-(2,6-dichloro-3,5-dimethoxyphenyl)-2,6-naphthyridine-1-amine (337 mg, 52%).

MS m/z (ESI+APCI): 438.2/440.2 [M+H]⁺.

Intermediates 34-131 were prepared referring to the synthesis method of Intermediate 33.

| Intermediate No. | Compound structure | Compound name | MS: m/z [M + 1]⁺ |
|---|---|---|---|
| 34 | (structure) | 7-chloro-N-(cyclopropylmethyl)-3-(2,6-dichloro-3,5-dimethoxyphenyl)-2,6-naphthyridine-1-amine | 438 |

-continued

| Intermediate No. | Compound structure | Compound name | MS: m/z [M + 1]+ |
|---|---|---|---|
| 35 | 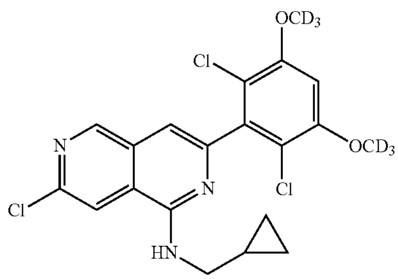 | 7-chloro-N-(cyclopropylmethyl)-3-(2,6-dichloro-3,5-di(methoxy-d₃)phenyl)-2,6-naphthyridine-1-amine | 444 |
| 36 | 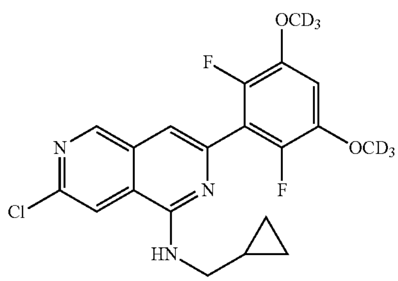 | 7-chloro-N-(cyclopropylmethyl)-3-(2,6-difluoro-3,5-di(methoxy-d₃)phenyl)-2,6-naphthyridine-1-amine | 412 |
| 37 | 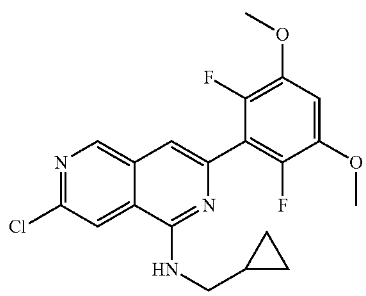 [SMILES: COc1cc(OC)c(F)c(-c2cc3cnc(Cl)cc3c(NCC3CC3)n2)c1F] | 7-chloro-N-(cyclopropylmethyl)-3-(2,6-difluoro-3,5-dimethoxyphenyl)-2,6-naphthyridine-1-amine | 406 |
| 38 | 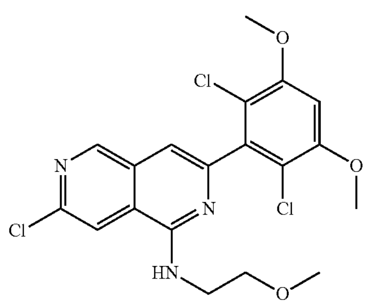 [SMILES: COCCNc1nc(-c2c(Cl)c(OC)cc(OC)c2Cl)cc2cnc(Cl)cc12] | 7-chloro-3-(2,6-dichloro-3,5-dimethoxyphenyl)-N-(2-methoxyethyl)-2,6-naphthyridine-1-amine | 442 |
| 39 | 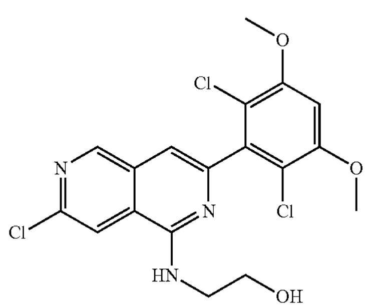 [SMILES: COc1cc(OC)c(Cl)c(-c2cc3cnc(Cl)cc3c(NCCO)n2)c1Cl] | 2-((7-chloro-3-(2,6-dichloro-3,5-dimethoxyphenyl)-2,6-naphthyridin-1-yl)amino)ethan-1-ol | 428 |

-continued

| Intermediate No. | Compound structure | Compound name | MS: m/z [M + 1]⁺ |
|---|---|---|---|
| 40 | 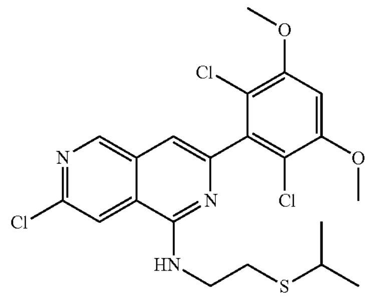 [SMILES: COc1cc(OC)c(Cl)c(-c2cc3cnc(Cl)cc3c(NCCSC(C)C)n2)c1Cl] | 7-chloro-3-(2,6-dichloro-3,5-dimethoxyphenyl)-N-(2-(isopropylthio)ethyl)-2,6-naphthyridine-1-amine | 486 |
| 41 | 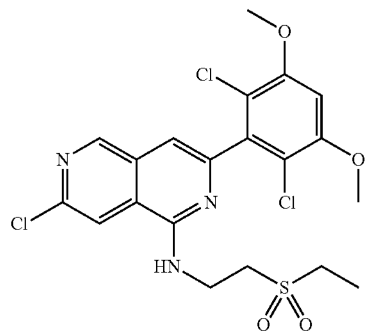 [SMILES: CCS(=O)(=O)CCNc1nc(-c2c(Cl)c(OC)cc(OC)c2Cl)cc2cnc(Cl)cc12] | 7-chloro-3-(2,6-dichloro-3,5-dimethoxyphenyl)-N-(2-(ethylsulfonyl)ethyl)-2,6-naphthyridine-1-amine | 504 |
| 42 | 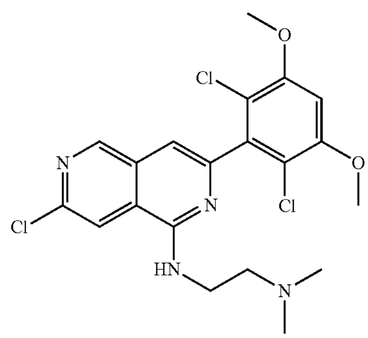 [SMILES: COc1cc(OC)c(Cl)c(-c2cc3cnc(Cl)cc3c(NCCN(C)C)n2)c1Cl] | $N^1$-(7-chloro-3-(2,6-dichloro-3,5-dimethoxyphenyl)-2,6-naphthyridin-1-yl)-$N^2$,$N^2$-dimethylethane-1,2-diamine | 455 |
| 43 | 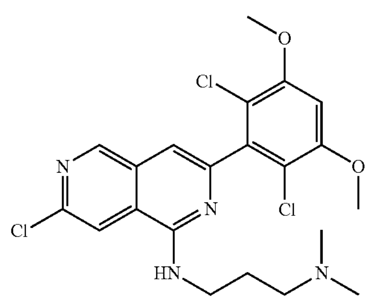 [SMILES: COc1cc(OC)c(Cl)c(-c2cc3cnc(Cl)cc3c(NCCCN(C)C)n2)c1Cl] | $N^1$-(7-chloro-3-(2,6-dichloro-3,5-dimethoxyphenyl)-2,6-naphthyridin-1-yl)-$N^3$,$N^3$-dimethylpropane-1,3-diamine | 469 |
| 44 | 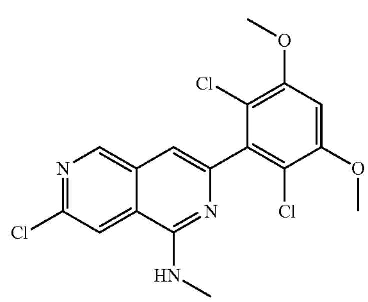 [SMILES: CNc1nc(-c2c(Cl)c(OC)cc(OC)c2Cl)cc2cnc(Cl)cc12] | 7-chloro-3-(2,6-dichloro-3,5-dimethoxyphenyl)-N-methyl-2,6-naphthyridine-1-amine | 398 |

-continued

| Intermediate No. | Compound structure | Compound name | MS: m/z [M + 1]⁺ |
|---|---|---|---|
| 45 | 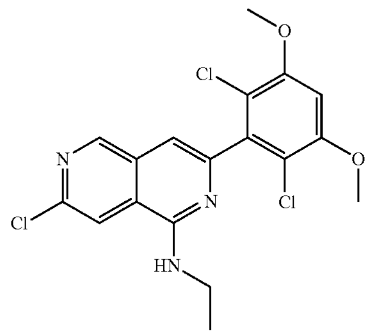 [SMILES: CCNc1nc(-c2c(Cl)c(OC)cc(OC)c2Cl)cc2cnc(Cl)cc12] | 7-chloro-3-(2,6-dichloro-3,5-dimethoxyphenyl)-N-ethyl-2,6-naphthyridine-1-amine | 412 |
| 46 | 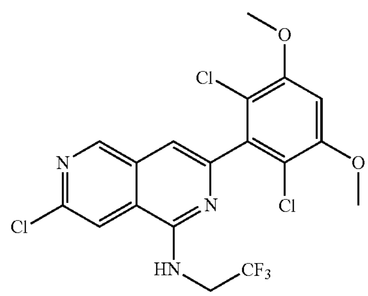 [SMILES: COc1cc(OC)c(Cl)c(-c2cc3cnc(Cl)cc3c(NCC(F)(F)F)n2)c1Cl] | 7-chloro-3-(2,6-dichloro-3,5-dimethoxyphenyl)-N-(2,2,2-trifluoroethyl)-2,6-naphthyridine-1-amine | 466 |
| 47 | 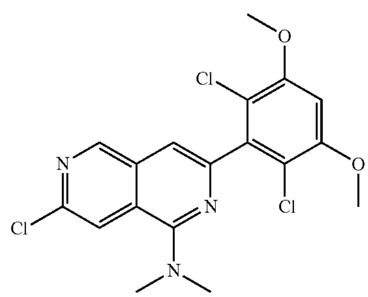 [SMILES: COc1cc(OC)c(Cl)c(-c2cc3cnc(Cl)cc3c(N(C)C)n2)c1Cl] | 7-chloro-3-(2,6-dichloro-3,5-dimethoxyphenyl)-N,N-dimethyl-2,6-naphthyridine-1-amine | 412 |
| 48 | 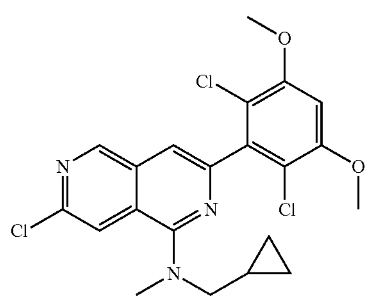 [SMILES: COc1cc(OC)c(Cl)c(-c2cc3cnc(Cl)cc3c(N(C)CC3CC3)n2)c1Cl] | 7-chloro-N-(cyclopropylmethyl)-3-(2,6-dichloro-3,5-dimethoxyphenyl)-N-methyl-2,6-naphthyridine-1-amine | 452 |
| 49 | 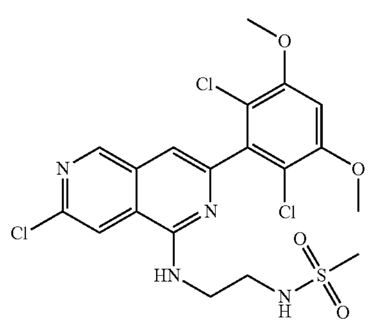 [SMILES: COc1cc(OC)c(Cl)c(-c2cc3cnc(Cl)cc3c(NCCNS(C)(=O)=O)n2)c1Cl] | N-(2-((7-chloro-3-(2,6-dichloro-3,5-dimethoxyphenyl)-2,6-naphthyridin-1-yl)amino)ethyl)methanesulfonamide | 505 |

-continued
| Intermediate No. | Compound structure | Compound name | MS: m/z [M + 1]+ |
|---|---|---|---|
| 50 | 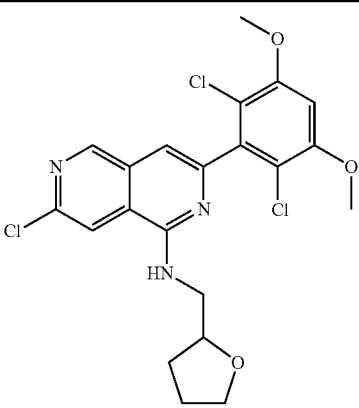 | 7-chloro-3-(2,6-dichloro-3,5-dimethoxyphenyl)-N-((tetrahydrofuran2-yl)methyl)-2,6-naphthyridine-1-amine | 468 |
| 51 | 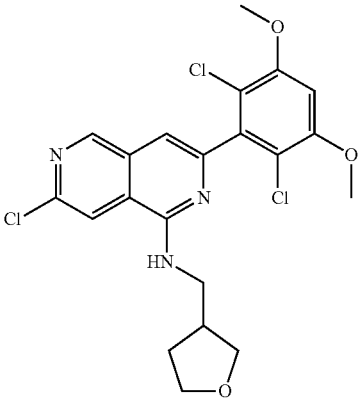 [SMILES: COc1cc(OC)c(Cl)c(-c2cc3cnc(Cl)cc3c(NCC3CCOC3)n2)c1Cl] | 7-chloro-3-(2,6-dichloro-3,5-dimethoxyphenyl)-N-((tetrahydrofuran-3-yl)methyl)-2,6-naphthyridine-1-amine | 468 |
| 52 | 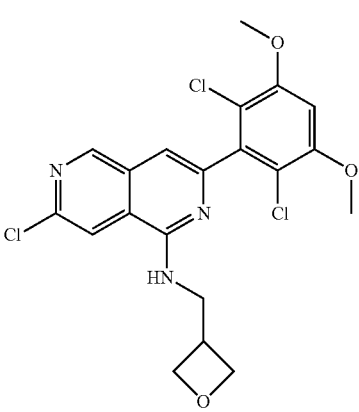 [SMILES: COc1cc(OC)c(Cl)c(-c2cc3cnc(Cl)cc3c(NCC3COC3)n2)c1Cl] | 7-chloro-3-(2,6-dichloro-3,5-dimethoxyphenyl)-N-(oxetan-3-ylmethyl)-2,6-naphthyridine-1-amine | 454 |

-continued

| Intermediate No. | Compound structure | Compound name | MS: m/z [M + 1]+ |
|---|---|---|---|
| 53 | 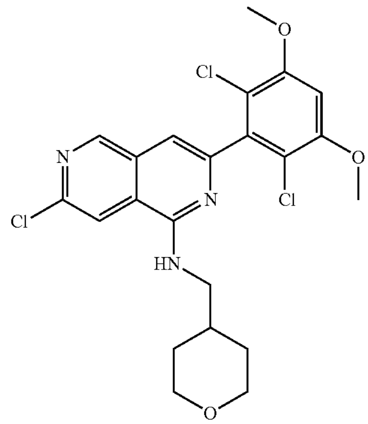 [SMILES: COc1cc(OC)c(Cl)c(-c2cc3cnc(Cl)cc3c(NCC3CCOCC3)n2)c1Cl] | 7-chloro-3-(2,6-dichloro-3,5-dimethoxyphenyl)-N-((tetrahydro-2H-pyran-4-yl)methyl)-2,6-naphthyridine-1-amine | 482 |
| 54 | 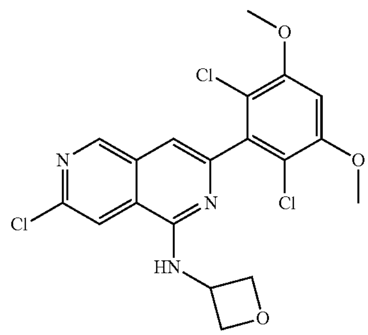 [SMILES: COc1cc(OC)c(Cl)c(-c2cc3cnc(Cl)cc3c(NC3COC3)n2)c1Cl] | 7-chloro-3-(2,6-dichloro-3,5-dimethoxyphenyl)-N-(oxetan-3-yl)-2,6-naphthyridine-1-amine | 440 |
| 55 | 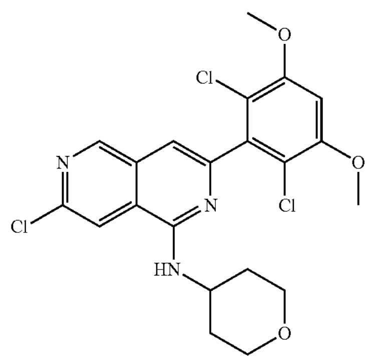 [SMILES: COc1cc(OC)c(Cl)c(-c2cc3cnc(Cl)cc3c(NC3CCOCC3)n2)c1Cl] | 7-chloro-3-(2,6-dichloro-3,5-dimethoxyphenyl)-N-(tetrahydro-2H-pyran-4-yl)-2,6-naphthyridine-1-amine | 468 |
| 56 | 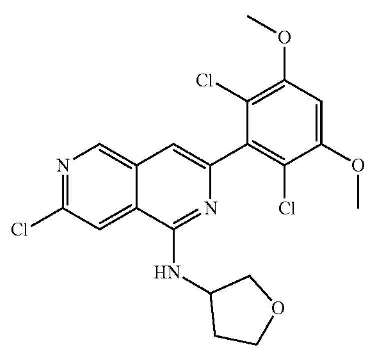 [SMILES: COc1cc(OC)c(Cl)c(-c2cc3cnc(Cl)cc3c(NC3CCOC3)n2)c1Cl] | 7-chloro-3-(2,6-dichloro-3,5-dimethoxyphenyl)-N-(tetrahydrofuran-3-yl)-2,6-naphthyridine-1-amine | 454 |

-continued

| Intermediate No. | Compound structure | Compound name | MS: m/z [M + 1]+ |
|---|---|---|---|
| 57 | 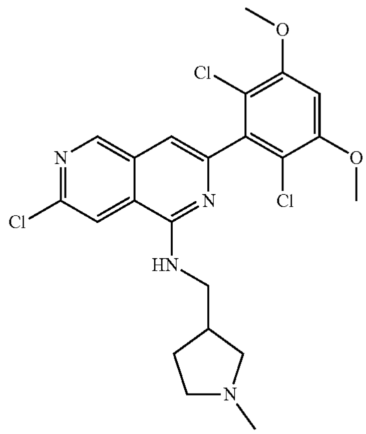 [SMILES: COc1cc(OC)c(Cl)c(-c2cc3cnc(Cl)cc3c(NCC3CCN(C)C3)n2)c1Cl] | 7-chloro-3-(2,6-dichloro-3,5-dimethoxyphenyl)-N-((1-methylpyrrolidin-3-yl)methyl)-2,6-naphthyridine-1-amine | 481 |
| 58 | 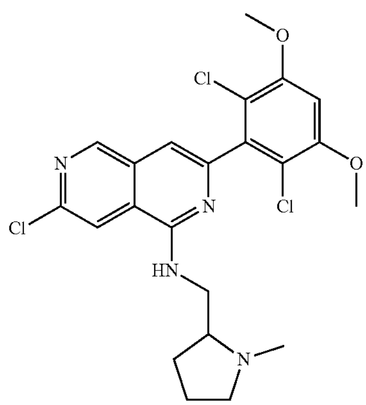 [SMILES: COc1cc(OC)c(Cl)c(-c2cc3cnc(Cl)cc3c(NCC3CCCN3C)n2)c1Cl] | 7-chloro-3-(2,6-dichloro-3,5-dimethoxyphenyl)-N-((1-methylpyrrolidin-2-yl)methyl)-2,6-naphthyridine-1-amine | 481 |
| 59 | 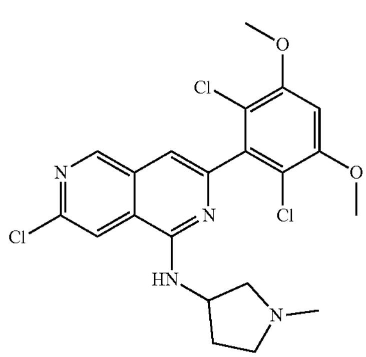 [SMILES: COc1cc(OC)c(Cl)c(-c2cc3cnc(Cl)cc3c(NC3CCN(C)C3)n2)c1Cl] | 7-chloro-3-(2,6-dichloro-3,5-dimethoxyphenyl)-N-(1-methylpyrrolidin-3-yl)-2,6-naphthyridine-1-amine | 467 |

-continued

| Intermediate No. | Compound structure | Compound name | MS: m/z [M + 1]+ |
|---|---|---|---|
| 60 | 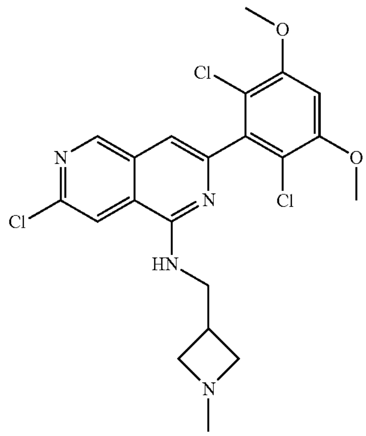 [SMILES: COc1cc(OC)c(Cl)c(-c2cc3cnc(Cl)cc3c(NCC3CN(C)C3)n2)c1Cl] | 7-chloro-3-(2,6-dichloro-3,5-dimethoxyphenyl)-N-((1-methylazetidin-3-yl)methyl)-2,6-naphthyridine-1-amine | 467 |
| 61 | 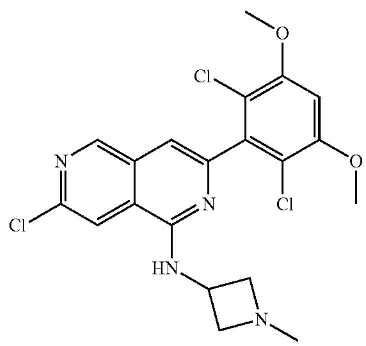 [SMILES: COc1cc(OC)c(Cl)c(-c2cc3cnc(Cl)cc3c(NC3CN(C)C3)n2)c1Cl] | 7-chloro-3-(2,6-dichloro-3,5-dimethoxyphenyl)-N-(1-methylazetidin-3-yl)-2,6-naphthyridine-1-amine | 453 |
| 62 | 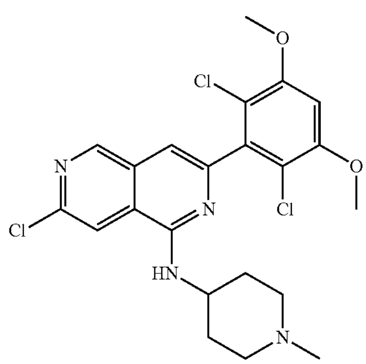 [SMILES: COc1cc(OC)c(Cl)c(-c2cc3cnc(Cl)cc3c(NC3CCN(C)CC3)n2)c1Cl] | 7-chloro-3-(2,6-dichloro-3,5-dimethoxyphenyl)-N-(1-methylpiperidin-4-yl)-2,6-naphthyridine-1-amine | 481 |
| 63 | 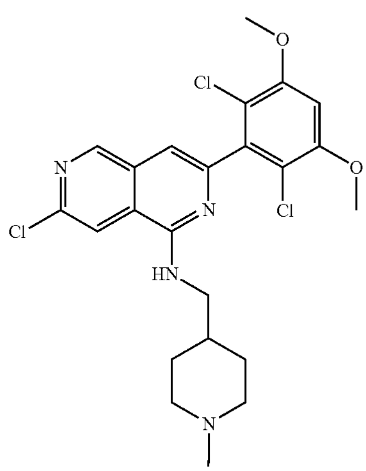 [SMILES: COc1cc(OC)c(Cl)c(-c2cc3cnc(Cl)cc3c(NCC3CCN(C)CC3)n2)c1Cl] | 7-chloro-3-(2,6-dichloro-3,5-dimethoxyphenyl)-N-((1-methylpiperidin-4-yl)methyl)-2,6-naphthyridine-1-amine | 495 |

| Intermediate No. | Compound structure | Compound name | MS: m/z [M + 1]+ |
|---|---|---|---|
| 64 | 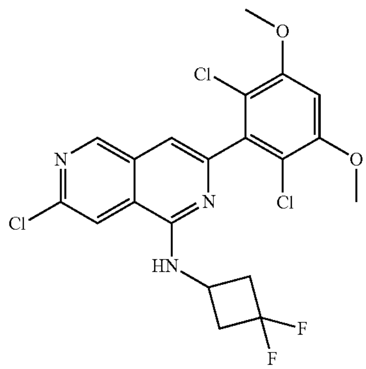 [SMILES: COc1cc(OC)c(Cl)c(-c2cc3cnc(Cl)cc3c(NC3CC(F)(F)C3)n2)c1Cl] | 7-chloro-3-(2,6-dichloro-3,5-dimethoxyphenyl)-N-(3,3-difluorocyclobutyl)-2,6-naphthyridine-1-amine | 474 |
| 65 | 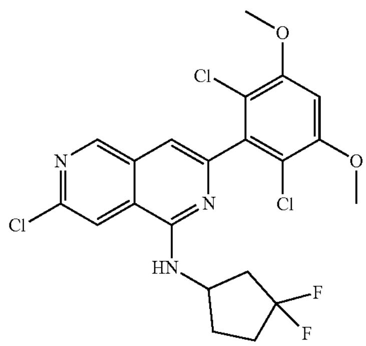 [SMILES: COc1cc(OC)c(Cl)c(-c2cc3cnc(Cl)cc3c(NC3CCC(F)(F)C3)n2)c1Cl] | 7-chloro-3-(2,6-dichloro-3,5-dimethoxyphenyl)-N-(3,3-difluorocyclopentyl)-2,6-naphthyridine-1-amine | 488 |
| 66 | 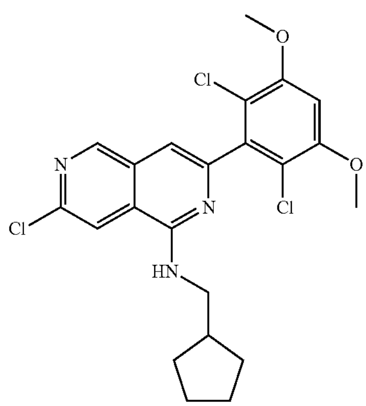 [SMILES: COc1cc(OC)c(Cl)c(-c2cc3cnc(Cl)cc3c(NCC3CCCC3)n2)c1Cl] | 7-chloro-N-(cyclopentylmethyl)-3-(2,6-dichloro-3,5-dimethoxyphenyl)-2,6-naphthyridine-1-amine | 466 |
| 67 | 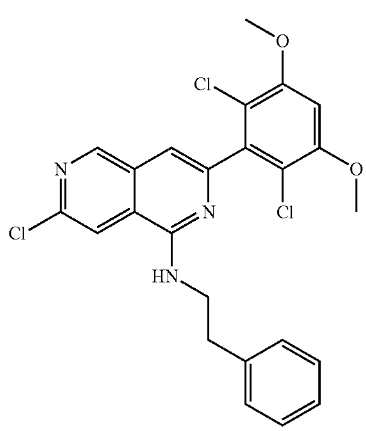 [SMILES: COc1cc(OC)c(Cl)c(-c2cc3cnc(Cl)cc3c(NCCc3ccccc3)n2)c1Cl] | 7-chloro-3-(2,6-dichloro-3,5-dimethoxyphenyl)-N-phenethyl-2,6-naphthyridine-1-amine | 488 |

-continued

| Intermediate No. | Compound structure | Compound name | MS: m/z [M + 1]+ |
|---|---|---|---|
| 68 | 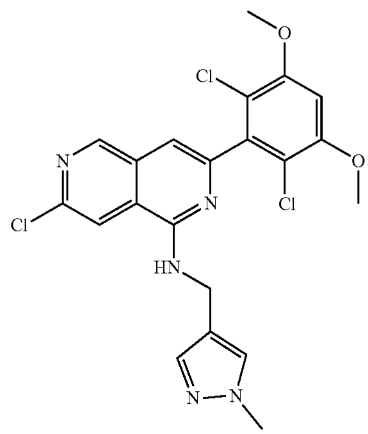 [SMILES: COc1cc(OC)c(Cl)c(-c2cc3cnc(Cl)cc3c(NCc3cnn(C)c3)n2)c1Cl] | 7-chloro-3-(2,6-dichloro-3,5-dimethoxyphenyl)-N-((1-methyl-1H-pyrazol-4-yl)methyl)-2,6-naphthyridine-1-amine | 478 |
| 69 | 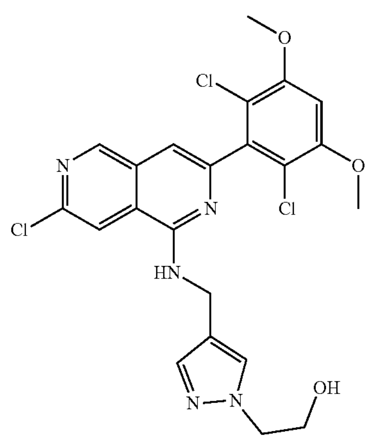 [SMILES: COc1cc(OC)c(Cl)c(-c2cc3cnc(Cl)cc3c(NCc3cnn(CCO)c3)n2)c1Cl] | 2-(4-(((7-chloro-3-(2,6-dichloro-3,5-dimethoxyphenyl)-2,6-naphthyridin-1-yl)amino)methyl)-1H-pyrazol-1-yl)ethan-1-ol | 508 |
| 70 | 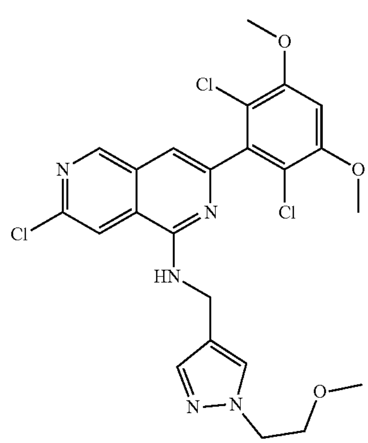 [SMILES: COCCn1cc(CNc2nc(-c3c(Cl)c(OC)cc(OC)c3Cl)cc3cnc(Cl)cc23)cn1] | 7-chloro-3-(2,6-dichloro-3,5-dimethoxyphenyl)-N-((1-(2-methoxyethyl)-1H-pyrazol-4-yl)methyl)-2,6-naphthyridine-1-amine | 522 |

| Intermediate No. | Compound structure | Compound name | MS: m/z [M + 1]+ |
|---|---|---|---|
| 71 | 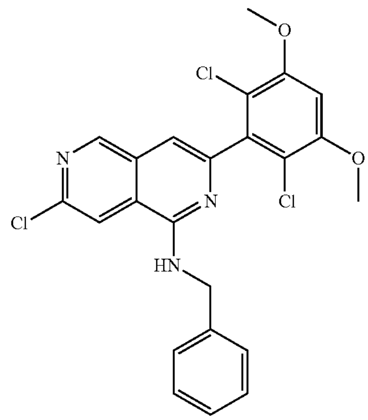 [SMILES: COc1cc(OC)c(Cl)c(-c2cc3cnc(Cl)cc3c(NCc3ccccc3)n2)c1Cl] | N-benzyl-7-chloro-3-(2,6-dichloro-3,5-dimethoxyphenyl)-2,6-naphthyridine-1-amine | 474 |
| 72 | 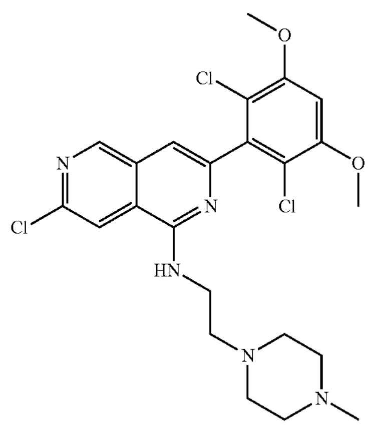 [SMILES: COc1cc(OC)c(Cl)c(-c2cc3cnc(Cl)cc3c(NCCN3CCN(C)CC3)n2)c1Cl] | 7-chloro-3-(2,6-dichloro-3,5-dimethoxyphenyl)-N-(2-(4-methylpiperazin-1-yl)ethyl)-2,6-naphthyridine-1-amine | 510 |
| 73 | 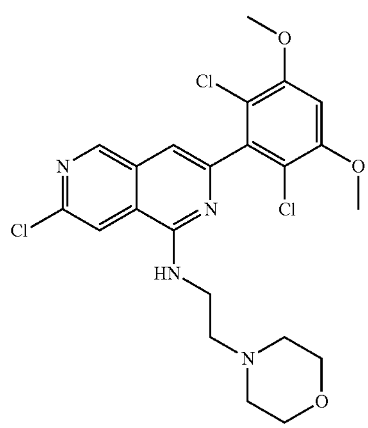 [SMILES: COc1cc(OC)c(Cl)c(-c2cc3cnc(Cl)cc3c(NCCN3CCOCC3)n2)c1Cl] | 7-chloro-3-(2,6-dichloro-3,5-dimethoxyphenyl)-N-(2-morpholinoethyl)-2,6-naphthyridine-1-amine | 497 |
| 74 | 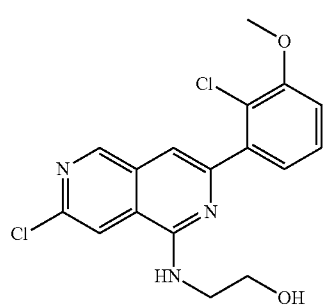 [SMILES: COc1cccc(-c2cc3cnc(Cl)cc3c(NCCO)n2)c1Cl] | 2-((7-chloro-3-(2-chloro-3-methoxyphenyl)-2,6-naphthyridin-1-yl)amino)ethan-1-ol | 364 |

| Intermediate No. | Compound structure | Compound name | MS: m/z [M + 1]+ |
|---|---|---|---|
| 75 | 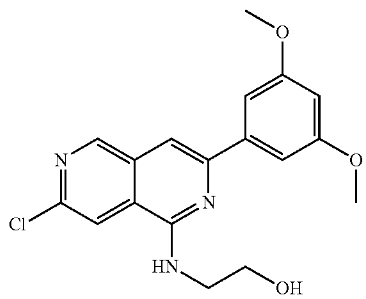 [SMILES: COc1cc(OC)cc(-c2cc3cnc(Cl)cc3c(NCCO)n2)c1] | 2-((7-chloro-3-(3,5-dimethoxyphenyl)-2,6-naphthyridin-1-yl)amino)ethan-1-ol | 360 |
| 76 | 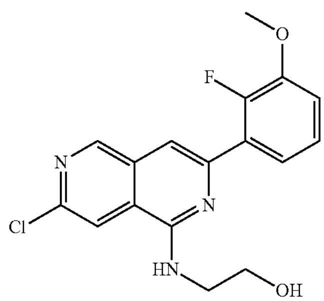 [SMILES: COc1cccc(-c2cc3cnc(Cl)cc3c(NCCO)n2)c1F] | 2-((7-chloro-3-(2-fluoro-3-methoxyphenyl)-2,6-naphthyridin-1-yl)amino)ethan-1-ol | 348 |
| 77 | 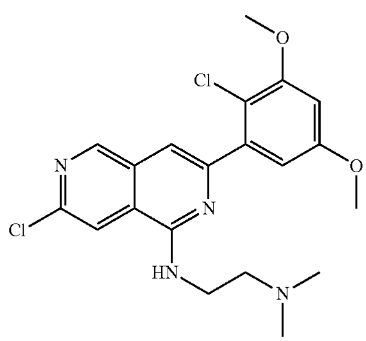 [SMILES: COc1cc(OC)c(Cl)c(-c2cc3cnc(Cl)cc3c(NCCN(C)C)n2)c1] | $N^1$-(7-chloro-3-(2-chloro-3,5-dimethoxyphenyl)-2,6-naphthyridin-1-yl)-$N^2$,$N^2$-dimethylethane-1,2-diamine | 421 |
| 78 | 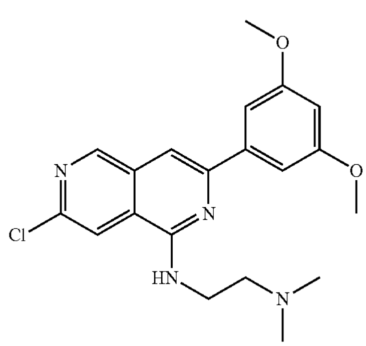 [SMILES: COc1cc(OC)cc(-c2cc3cnc(Cl)cc3c(NCCN(C)C)n2)c1] | $N^1$-(7-chloro-3-(3,5-dimethoxyphenyl)-2,6-naphthyridin-1-yl)-$N^2$,$N^2$-dimethylethane-1,2-diamine | 387 |

-continued

| Intermediate No. | Compound structure | Compound name | MS: m/z [M + 1]+ |
|---|---|---|---|
| 79 | 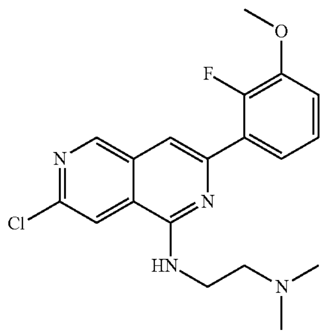 [SMILES: COc1cccc(-c2cc3cnc(Cl)cc3c(NCCN(C)C)n2)c1F] | N1-(7-chloro-3-(2-fluoro-3-methoxyphenyl)-2,6-naphthyridin-1-yl)-N2,N2-dimethylethane-1,2-diamine | 375 |
| 80 | 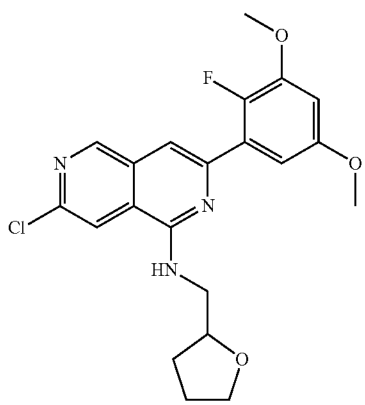 [SMILES: COc1cc(OC)c(F)c(-c2cc3cnc(Cl)cc3c(NCC3CCCO3)n2)c1] | 7-chloro-3-(2-fluoro-3,5-dimethoxyphenyl)-N-((tetrahydrofuran2-yl)methyl)-2,6-naphthyridine-1-amine | 418 |
| 81 | 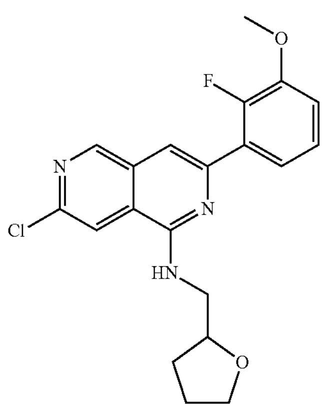 [SMILES: COc1cccc(-c2cc3cnc(Cl)cc3c(NCC3CCCO3)n2)c1F] | 7-chloro-3-(2-fluoro-3-methoxyphenyl)-N-((tetrahydrofuran2-yl)methyl)-2,6-naphthyridine-1-amine | 388 |
| 82 | 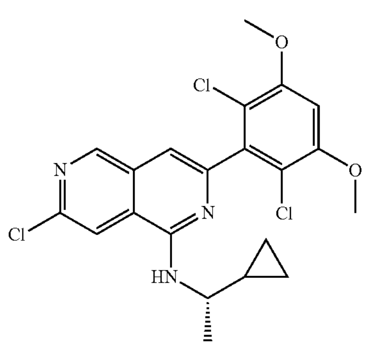 [SMILES: COc1cc(OC)c(Cl)c(-c2cc3cnc(Cl)cc3c(N[C@@H](C)C3CC3)n2)c1Cl] | (S)-7-chloro-N-(1-cyclopropylethyl)-3-(2,6-dichloro-3,5-dimethoxyphenyl)-2,6-naphthyridine-1-amine | 452 |

-continued

| Intermediate No. | Compound structure | Compound name | MS: m/z [M + 1]⁺ |
|---|---|---|---|
| 83 | 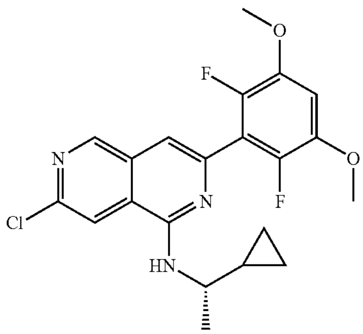 [SMILES: COc1cc(OC)c(F)c(-c2cc3cnc(Cl)cc3c(N[C@@H](C)C3CC3)n2)c1F] | (S)-7-chloro-N-(1-cyclopropylethyl)-3-(2,6-difluoro-3,5-dimethoxyphenyl)-2,6-naphthyridine-1-amine | 420 |
| 84 | 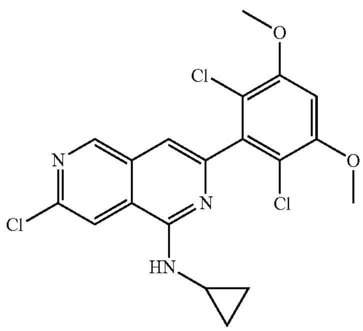 [SMILES: COc1cc(OC)c(Cl)c(-c2cc3cnc(Cl)cc3c(NC3CC3)n2)c1Cl] | 7-chloro-N-cyclopropyl-3-(2,6-dichloro-3,5-dimethoxyphenyl)-2,6-naphthyridine-1-amine | 424 |
| 85 | 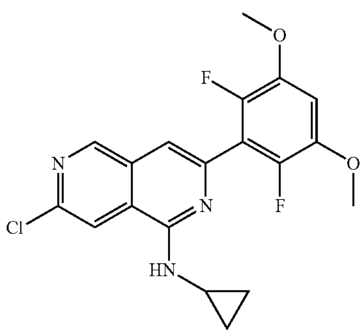 [SMILES: COc1cc(OC)c(F)c(-c2cc3cnc(Cl)cc3c(NC3CC3)n2)c1F] | 7-chloro-N-cyclopropyl-3-(2,6-difluoro-3,5-dimethoxyphenyl)-2,6-naphthyridine-1-amine | 392 |
| 86 | 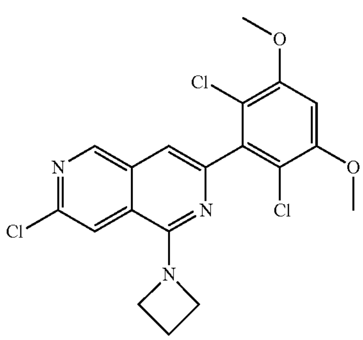 [SMILES: COc1cc(OC)c(Cl)c(-c2cc3cnc(Cl)cc3c(N3CCC3)n2)c1Cl] | 1-(azetidin-1-yl)-7-chloro-3-(2,6-dichloro-3,5-dimethoxyphenyl)-2,6-naphthyridine | 424 |

-continued

| Intermediate No. | Compound structure | Compound name | MS: m/z [M + 1]+ |
|---|---|---|---|
| 87 | 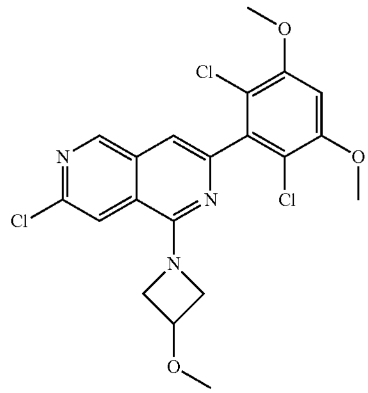 [SMILES: COc1cc(OC)c(Cl)c(-c2cc3cnc(Cl)cc3c(N3CC(OC)C3)n2)c1Cl] | 7-chloro-3-(2,6-dichloro-3,5-dimethoxyphenyl)-1-(3-methoxyazetidin-1-yl)-2,6-naphthyridine | 454 |
| 88 | 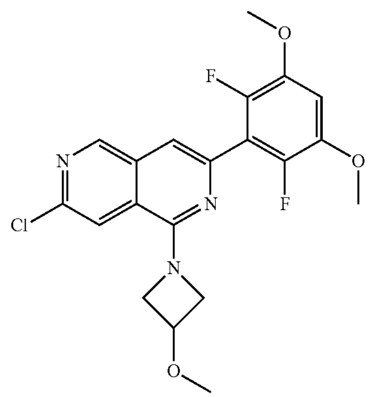 [SMILES: COc1cc(OC)c(F)c(-c2cc3cnc(Cl)cc3c(N3CC(OC)C3)n2)c1F] | 7-chloro-3-(2,6-difluoro-3,5-dimethoxyphenyl)-1-(3-methoxyazetidin-1-yl)-2,6-naphthyridine | 422 |
| 89 | 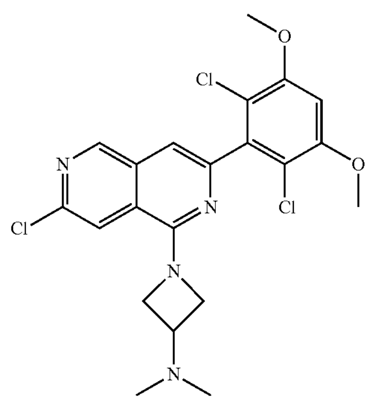 [SMILES: COc1cc(OC)c(Cl)c(-c2cc3cnc(Cl)cc3c(N3CC(N(C)C)C3)n2)c1Cl] | 1-(7-chloro-3-(2,6-dichloro-3,5-dimethoxyphenyl)-2,6-naphthyridin-1-yl)-N,N-dimethylazetidin-3-amine | 467 |
| 90 | 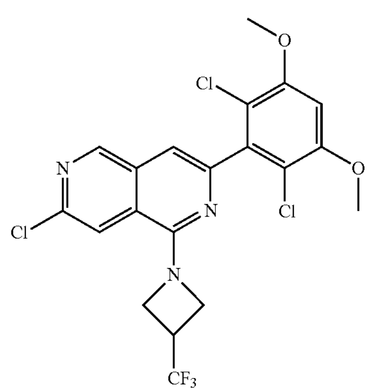 [SMILES: COc1cc(OC)c(Cl)c(-c2cc3cnc(Cl)cc3c(N3CC(C(F)(F)F)C3)n2)c1Cl] | 7-chloro-3-(2,6-dichloro-3,5-dimethoxyphenyl)-1-(3-(trifluoromethyl)azetidin-1-yl)-2,6-naphthyridine | 492 |

| Intermediate No. | Compound structure | Compound name | MS: m/z [M + 1]+ |
|---|---|---|---|
| 91 | 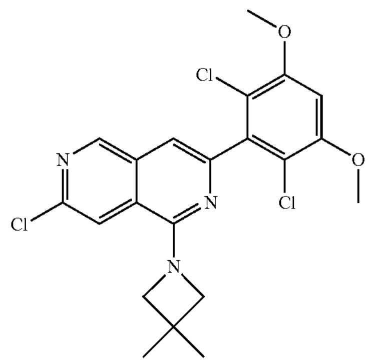 [SMILES: COc1cc(OC)c(Cl)c(-c2cc3cnc(Cl)cc3c(N3CC(C)(C)C3)n2)c1Cl] | 7-chloro-3-(2,6-dichloro-3,5-dimethoxyphenyl)-1-(3,3-dimethylazetidin-1-yl)-2,6-naphthyridine | 452 |
| 92 | 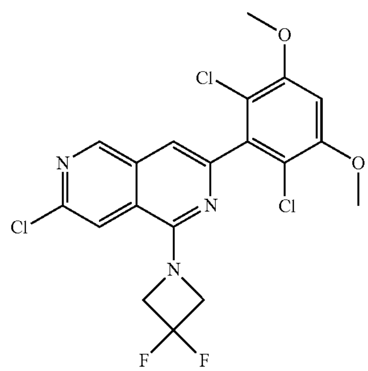 [SMILES: COc1cc(OC)c(Cl)c(-c2cc3cnc(Cl)cc3c(N3CC(F)(F)C3)n2)c1Cl] | 7-chloro-3-(2,6-dichloro-3,5-dimethoxyphenyl)-1-(3,3-difluoroazetidin-1-yl)-2,6-naphthyridine | 460 |
| 93 | 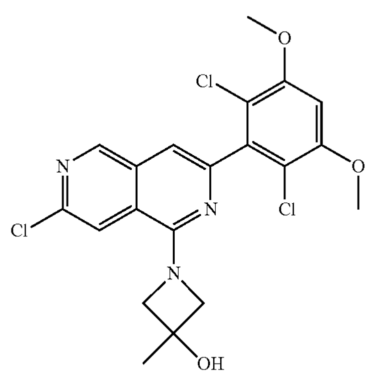 [SMILES: COc1cc(OC)c(Cl)c(-c2cc3cnc(Cl)cc3c(N3CC(C)(O)C3)n2)c1Cl] | 1-(7-chloro-3-(2,6-dichloro-3,5-dimethoxyphenyl)-2,6-naphthyridin-1-yl)-3-methylazetidin-3-ol | 454 |
| 94 | 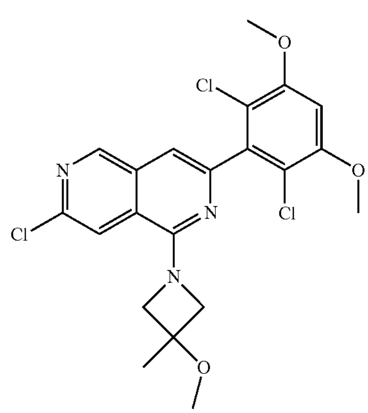 [SMILES: COc1cc(OC)c(Cl)c(-c2cc3cnc(Cl)cc3c(N3CC(C)(OC)C3)n2)c1Cl] | 7-chloro-3-(2,6-dichloro-3,5-dimethoxyphenyl)-1-(3-methoxy-3-methylazetidin-1-yl)-2,6-naphthyridine | 468 |

| Intermediate No. | Compound structure | Compound name | MS: m/z [M + 1]⁺ |
|---|---|---|---|
| 95 | 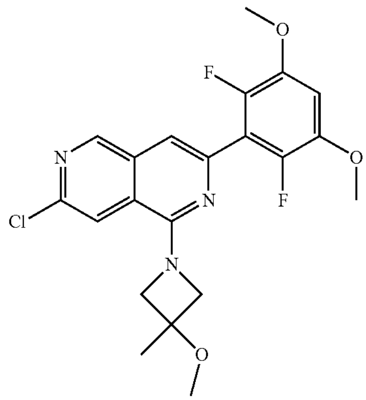 [SMILES: COc1cc(OC)c(F)c(-c2cc3cnc(Cl)cc3c(N3CC(C)(OC)C3)n2)c1F] | 7-chloro-3-(2,6-difluoro-3,5-dimethoxyphenyl)-1-(3-methoxy-3-methylazetidin-1-yl)-2,6-naphthyridine | 436 |
| 96 | 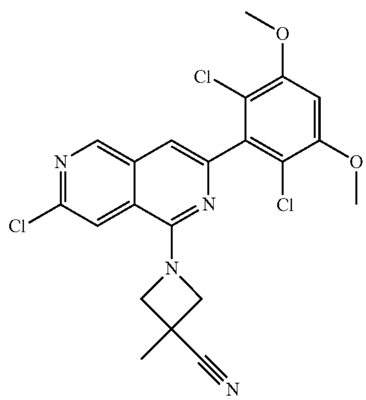 [SMILES: COc1cc(OC)c(Cl)c(-c2cc3cnc(Cl)cc3c(N3CC(C)(C#N)C3)n2)c1Cl] | 1-(7-chloro-3-(2,6-dichloro-3,5-dimethoxyphenyl)-2,6-naphthyridin-1-yl)-3-methylazetidin-3-carbonitrile | 463 |
| 97 | 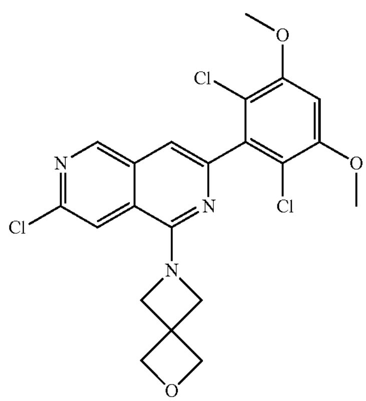 [SMILES: COc1cc(OC)c(Cl)c(-c2cc3cnc(Cl)cc3c(N3CC4(COC4)C3)n2)c1Cl] | 6-(7-chloro-3-(2,6-dichloro-3,5-dimethoxyphenyl)-2,6-naphthyridin-1-yl)-2-oxa-6-azaspiro[3.3]heptane | 466 |
| 98 | 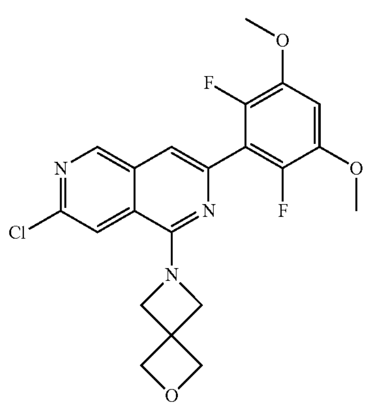 [SMILES: COc1cc(OC)c(F)c(-c2cc3cnc(Cl)cc3c(N3CC4(COC4)C3)n2)c1F] | 6-(7-chloro-3-(2,6-difluoro-3,5-dimethoxyphenyl)-2,6-naphthyridin-1-yl)-2-oxa-6-azaspiro[3.3]heptane | 434 |

| Intermediate No. | Compound structure | Compound name | MS: m/z [M + 1]+ |
|---|---|---|---|
| 99 | 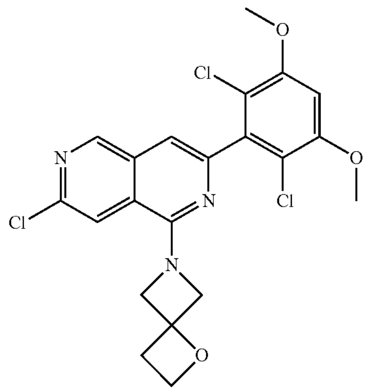 [SMILES: COc1cc(OC)c(Cl)c(-c2cc3cnc(Cl)cc3c(N3CC4(CCO4)C3)n2)c1Cl] | 6-(7-chloro-3-(2,6-dichloro-3,5-dimethoxyphenyl)-2,6-naphthyridin-1-yl)-1-oxa-6-azaspiro[3.3]heptane | 466 |
| 100 | 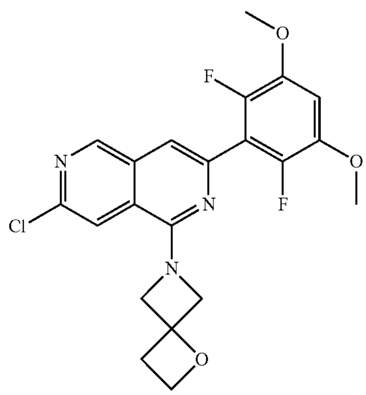 [SMILES: COc1cc(OC)c(F)c(-c2cc3cnc(Cl)cc3c(N3CC4(CCO4)C3)n2)c1F] | 6-(7-chloro-3-(2,6-difluoro-3,5-dimethoxyphenyl)-2,6-naphthyridin-1-yl)-1-oxa-6-azaspiro[3.3]heptane | 434 |
| 101 | 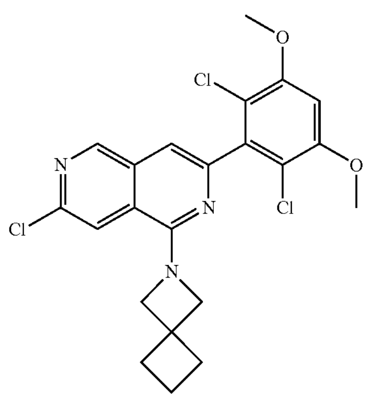 [SMILES: COc1cc(OC)c(Cl)c(-c2cc3cnc(Cl)cc3c(N3CC4(CCC4)C3)n2)c1Cl] | 7-chloro-3-(2,6-dichloro-3,5-dimethoxyphenyl)-1-(2-azaspiro[3.3]hept-2-yl)-2,6-naphthyridine | 464 |
| 102 | 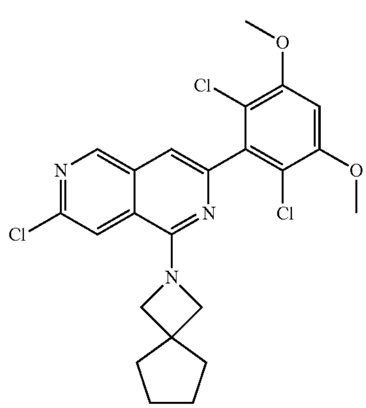 [SMILES: COc1cc(OC)c(Cl)c(-c2cc3cnc(Cl)cc3c(N3CC4(CCCC4)C3)n2)c1Cl] | 7-chloro-3-(2,6-dichloro-3,5-dimethoxyphenyl)-1-(2-azaspiro[3.4]oct-2-yl)-2,6-naphthyridine | 478 |

| Intermediate No. | Compound structure | Compound name | MS: m/z [M + 1]+ |
|---|---|---|---|
| 103 | 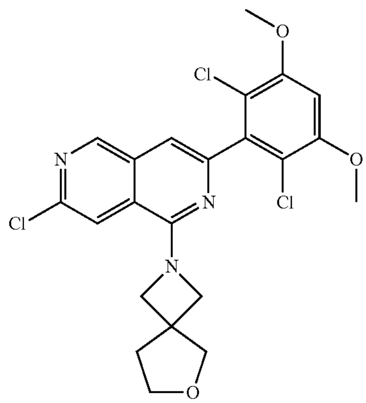 [SMILES: COc1cc(OC)c(Cl)c(-c2cc3cnc(Cl)cc3c(N3CC4(CCOC4)C3)n2)c1Cl] | 2-(7-chloro-3-(2,6-dichloro-3,5-dimethoxyphenyl)-2,6-naphthyridin-1-yl)-6-oxa-2-azaspiro[3.4]octane | 480 |
| 104 | 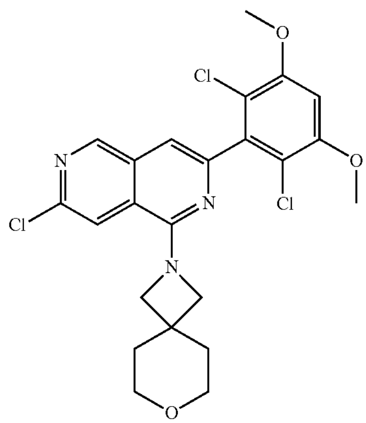 [SMILES: COc1cc(OC)c(Cl)c(-c2cc3cnc(Cl)cc3c(N3CC4(CCOCC4)C3)n2)c1Cl] | 2-(7-chloro-3-(2,6-dichloro-3,5-dimethoxyphenyl)-2,6-naphthyridin-1-yl)-7-oxa-2-azaspiro[3.5]nonane | 494 |
| 105 | 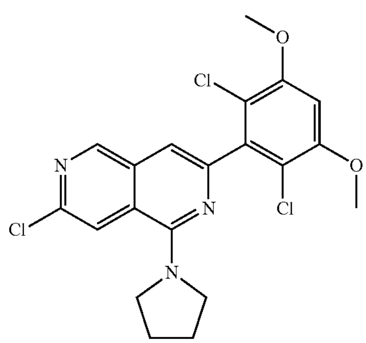 [SMILES: COc1cc(OC)c(Cl)c(-c2cc3cnc(Cl)cc3c(N3CCCC3)n2)c1Cl] | 7-chloro-3-(2,6-dichloro-3,5-dimethoxyphenyl)-1-(pyrrolidin-1-yl)-2,6-naphthyridine | 438 |
| 106 | 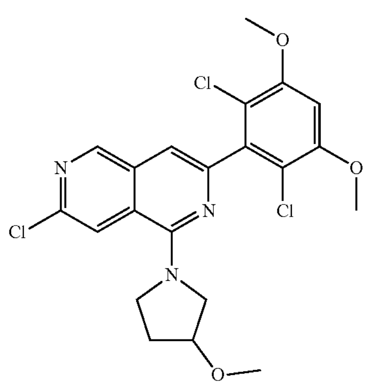 [SMILES: COc1cc(OC)c(Cl)c(-c2cc3cnc(Cl)cc3c(N3CCC(OC)C3)n2)c1Cl] | 7-chloro-3-(2,6-dichloro-3,5-dimethoxyphenyl)-1-(3-methoxypyrrolidin-1-yl)-2,6-naphthyridine | 468 |

-continued

| Intermediate No. | Compound structure | Compound name | MS: m/z [M + 1]⁺ |
|---|---|---|---|
| 107 | 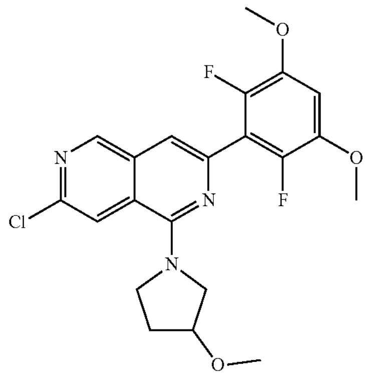 [SMILES: COc1cc(OC)c(F)c(-c2cc3cnc(Cl)cc3c(N3CCC(OC)C3)n2)c1F] | 7-chloro-3-(2,6-difluoro-3,5-dimethoxyphenyl)-1-(3-methoxypyrrolidin-1-yl)-2,6-naphthyridine | 436 |
| 108 | 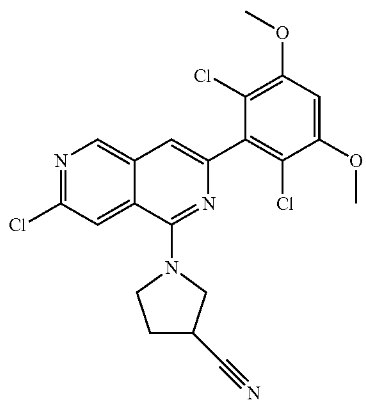 [SMILES: COc1cc(OC)c(Cl)c(-c2cc3cnc(Cl)cc3c(N3CCC(C#N)C3)n2)c1Cl] | 1-(7-chloro-3-(2,6-dichloro-3,5-dimethoxyphenyl)-2,6-naphthyridin-1-yl)pyrrolidine-3-carbonitrile | 463 |
| 109 | 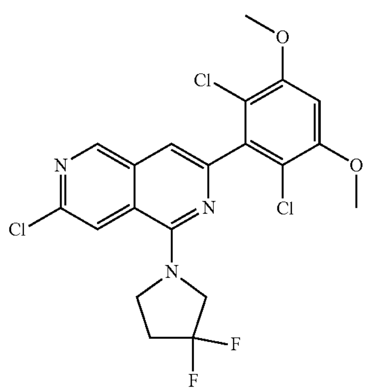 [SMILES: COc1cc(OC)c(Cl)c(-c2cc3cnc(Cl)cc3c(N3CCC(F)(F)C3)n2)c1Cl] | 7-chloro-3-(2,6-dichloro-3,5-dimethoxyphenyl)-1-(3,3-difluoropyrrolidin-1-yl)-2,6-naphthyridine | 474 |
| 110 | 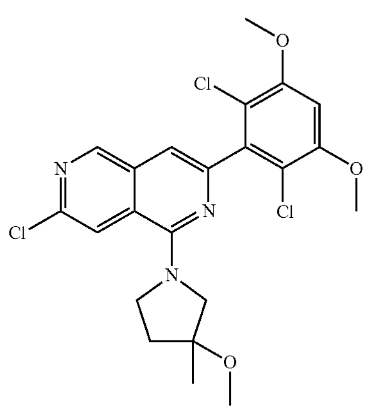 [SMILES: COc1cc(OC)c(Cl)c(-c2cc3cnc(Cl)cc3c(N3CCC(C)(OC)C3)n2)c1Cl] | 7-chloro-3-(2,6-dichloro-3,5-dimethoxyphenyl)-1-(3-methoxy-3-methylpyrrolidin-1-yl)-2,6-naphthyridine | 482 |

-continued

| Intermediate No. | Compound structure | Compound name | MS: m/z [M + 1]+ |
|---|---|---|---|
| 111 | 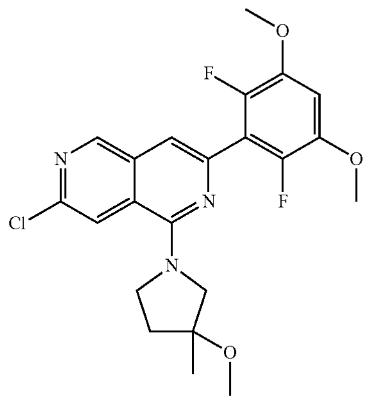 [SMILES: COc1cc(OC)c(F)c(-c2cc3cnc(Cl)cc3c(N3CCC(C)(OC)C3)n2)c1F] | 7-chloro-3-(2,6-difluoro-3,5-dimethoxyphenyl)-1-(3-methoxy-3-methylpyrrolidin-1-yl)-2,6-naphthyridine | 450 |
| 112 | 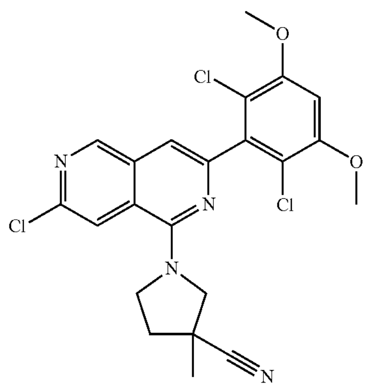 [SMILES: COc1cc(OC)c(Cl)c(-c2cc3cnc(Cl)cc3c(N3CCC(C)(C#N)C3)n2)c1Cl] | 1-(7-chloro-3-(2,6-dichloro-3,5-dimethoxyphenyl)-2,6-naphthyridin-1-yl)-3-methylpyrrolidine-3-carbonitrile | 477 |
| 113 | 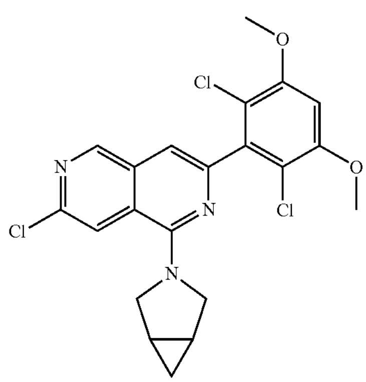 [SMILES: COc1cc(OC)c(Cl)c(-c2cc3cnc(Cl)cc3c(N3CC4CC4C3)n2)c1Cl] | 1-(3-azabicyclo[3.1.0]hex-3-yl)-7-chloro-3-(2,6-dichloro-3,5-dimethoxyphenyl)-2,6-naphthyridine | 450 |
| 114 | 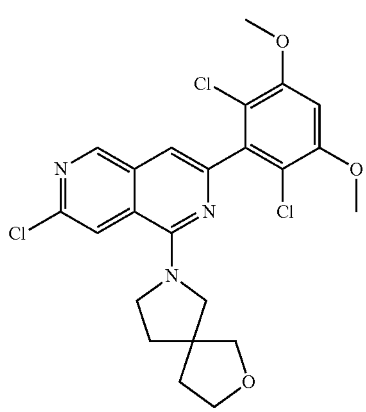 [SMILES: COc1cc(OC)c(Cl)c(-c2cc3cnc(Cl)cc3c(N3CCC4(CCOC4)C3)n2)c1Cl] | 7-(7-chloro-3-(2,6-dichloro-3,5-dimethoxyphenyl)-2,6-naphthyridin-1-yl)-2-oxa-7-azaspiro[34.4]nonane | 494 |

| Intermediate No. | Compound structure | Compound name | MS: m/z [M + 1]⁺ |
|---|---|---|---|
| 115 | 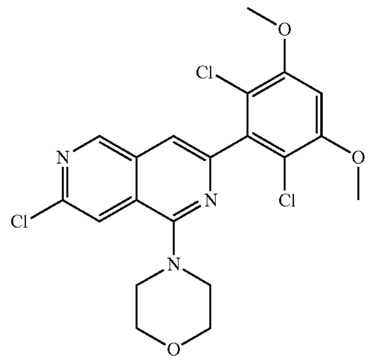 [SMILES: COc1cc(OC)c(Cl)c(-c2cc3cnc(Cl)cc3c(N3CCOCC3)n2)c1Cl] | 4-(7-chloro-3-(2,6-dichloro-3,5-dimethoxyphenyl)-2,6-naphthyridin-1-yl)morpholine | 454 |
| 116 | 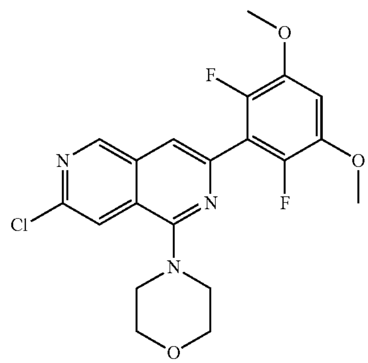 [SMILES: COc1cc(OC)c(F)c(-c2cc3cnc(Cl)cc3c(N3CCOCC3)n2)c1F] | 4-(7-chloro-3-(2,6-difluoro-3,5-dimethoxyphenyl)-2,6-naphthyridin-1-yl)morpholine | 422 |
| 117 | 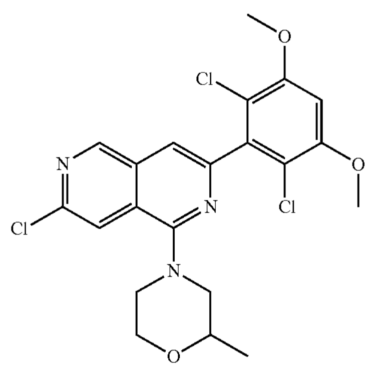 [SMILES: COc1cc(OC)c(Cl)c(-c2cc3cnc(Cl)cc3c(N3CCOC(C)C3)n2)c1Cl] | 4-(7-chloro-3-(2,6-dichloro-3,5-dimethoxyphenyl)-2,6-naphthyridin-1-yl)-2-methylmorpholine | 468 |
| 118 | 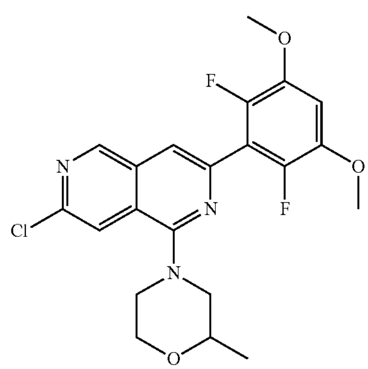 [SMILES: COc1cc(OC)c(F)c(-c2cc3cnc(Cl)cc3c(N3CCOC(C)C3)n2)c1F] | 4-(7-chloro-3-(2,6-difluoro-3,5-dimethoxyphenyl)-2,6-naphthyridin-1-yl)-2-methylmorpholine | 436 |

-continued

| Intermediate No. | Compound structure | Compound name | MS: m/z [M + 1]+ |
|---|---|---|---|
| 119 | 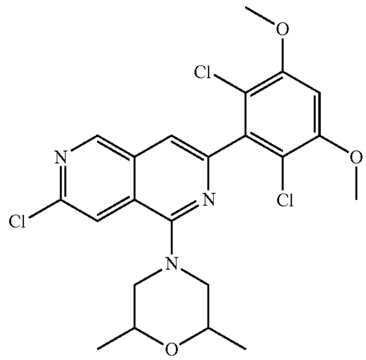 [SMILES: COc1cc(OC)c(Cl)c(-c2cc3cnc(Cl)cc3c(N3CC(C)OC(C)C3)n2)c1Cl] | 4-(7-chloro-3-(2,6-dichloro-3,5-dimethoxyphenyl)-2,6-naphthyridin-1-yl)-2,6-dimethylmorpholine | 482 |
| 120 | 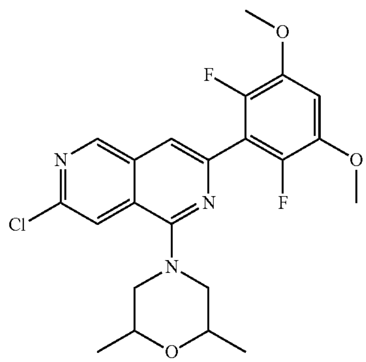 [SMILES: COc1cc(OC)c(F)c(-c2cc3cnc(Cl)cc3c(N3CC(C)OC(C)C3)n2)c1F] | 4-(7-chloro-3-(2,6-difluoro-3,5-dimethoxyphenyl)-2,6-naphthyridin-1-yl)-2,6-dimethylmorpholine | 450 |
| 121 | 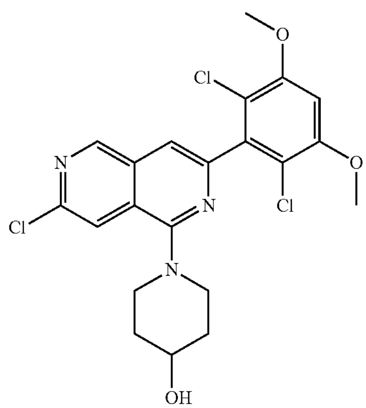 [SMILES: COc1cc(OC)c(Cl)c(-c2cc3cnc(Cl)cc3c(N3CCC(O)CC3)n2)c1Cl] | 1-(7-chloro-3-(2,6-dichloro-3,5-dimethoxyphenyl)-2,6-naphthyridin-1-yl)piperidin-4-ol | 468 |
| 122 | 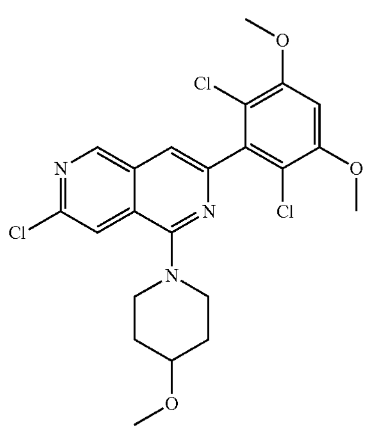 [SMILES: COc1cc(OC)c(Cl)c(-c2cc3cnc(Cl)cc3c(N3CCC(OC)CC3)n2)c1Cl] | 7-chloro-3-(2,6-dichloro-3,5-dimethoxyphenyl)-1-(4-methoxypiperidin-1-yl)-2,6-naphthyridine | 482 |

-continued

| Intermediate No. | Compound structure | Compound name | MS: m/z [M + 1]⁺ |
|---|---|---|---|
| 123 | 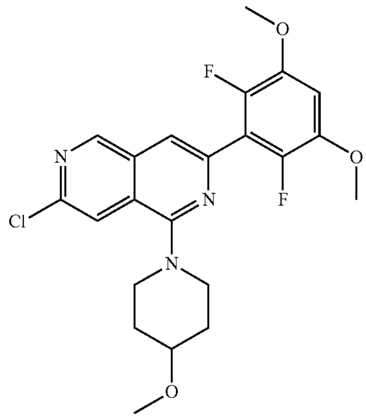 [SMILES: COc1cc(OC)c(F)c(-c2cc3cnc(Cl)cc3c(N3CCC(OC)CC3)n2)c1F] | 7-chloro-3-(2,6-difluoro-3,5-dimethoxyphenyl)-1-(4-methoxypiperidin-1-yl)-2,6-naphthyridine | 450 |
| 124 | 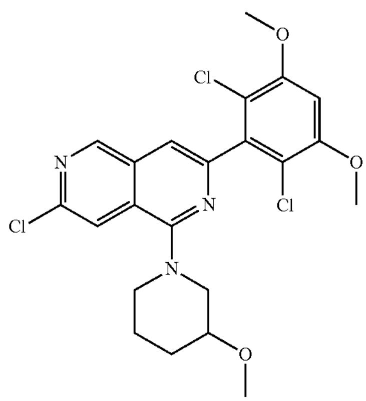 [SMILES: COc1cc(OC)c(Cl)c(-c2cc3cnc(Cl)cc3c(N3CCCC(OC)C3)n2)c1Cl] | 7-chloro-3-(2,6-dichloro-3,5-dimethoxyphenyl)-1-(3-methoxypiperidin-1-yl)-2,6-naphthyridine | 482 |
| 125 | 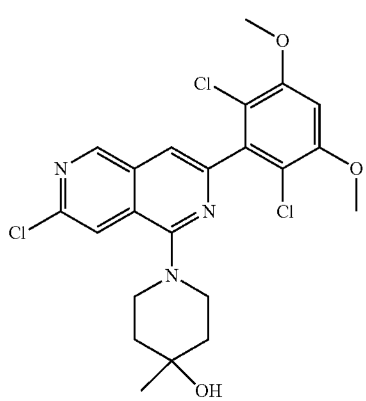 [SMILES: COc1cc(OC)c(Cl)c(-c2cc3cnc(Cl)cc3c(N3CCC(C)(O)CC3)n2)c1Cl] | 1-(7-chloro-3-(2,6-dichloro-3,5-dimethoxyphenyl)-2,6-naphthyridin-1-yl)-4-methylpiperidin-4-ol | 482 |

-continued

| Intermediate No. | Compound structure | Compound name | MS: m/z [M + 1]⁺ |
|---|---|---|---|
| 126 | 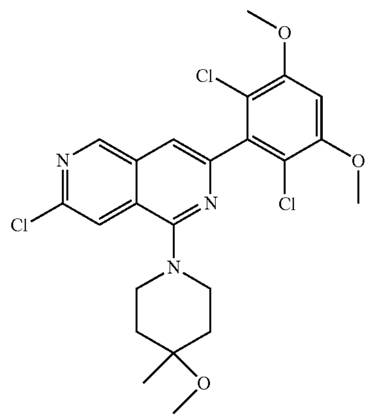 [SMILES: COc1cc(OC)c(Cl)c(-c2cc3cnc(Cl)cc3c(N3CCC(C)(OC)CC3)n2)c1Cl] | 7-chloro-3-(2,6-dichloro-3,5-dimethoxyphenyl)-1-(4-methoxy-4-methylpiperidin-1-yl)-2,6-naphthyridine | 496 |
| 127 | 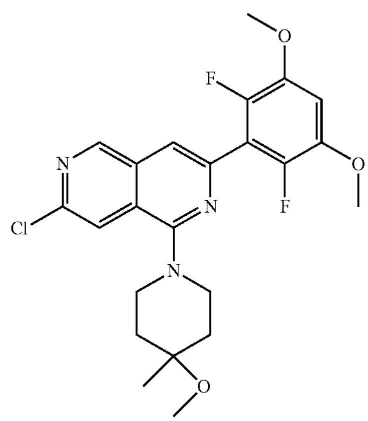 [SMILES: COc1cc(OC)c(F)c(-c2cc3cnc(Cl)cc3c(N3CCC(C)(OC)CC3)n2)c1F] | 7-chloro-3-(2,6-difluoro-3,5-dimethoxyphenyl)-1-(4-methoxy-4-methylpiperidin-1-yl)-2,6-naphthyridine | 464 |
| 128 | 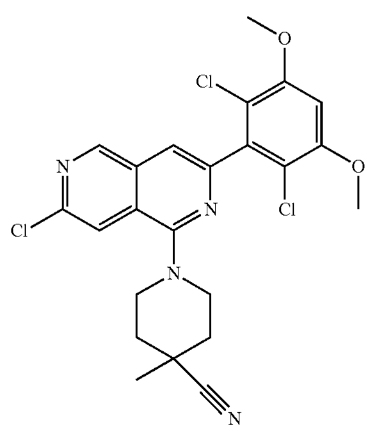 [SMILES: COc1cc(OC)c(Cl)c(-c2cc3cnc(Cl)cc3c(N3CCC(C)(C#N)CC3)n2)c1Cl] | 1-(7-chloro-3-(2,6-dichloro-3,5-dimethoxyphenyl)-2,6-naphthyridin-1-yl)-4-methylpiperidine-4-carbonitrile | 491 |

| Intermediate No. | Compound structure | Compound name | MS: m/z [M + 1]+ |
|---|---|---|---|
| 129 | 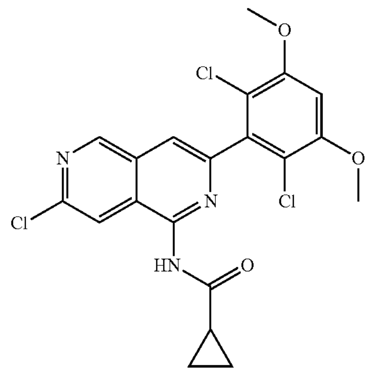 [SMILES: COc1cc(OC)c(Cl)c(-c2cc3cnc(Cl)cc3c(NC(=O)C3CC3)n2)c1Cl] | N-(7-chloro-3-(2,6-dichloro-3,5-dimethoxyphenyl)-2,6-naphthyridin-1-yl)cyclopropyl carboxamide | 452 |
| 130 | 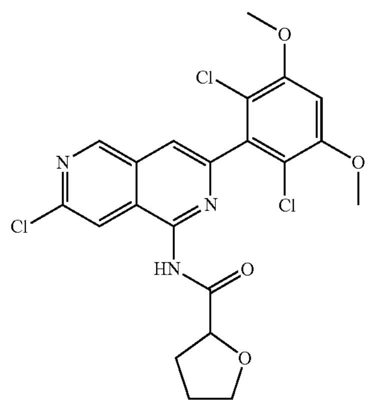 [SMILES: COc1cc(OC)c(Cl)c(-c2cc3cnc(Cl)cc3c(NC(=O)C3CCCO3)n2)c1Cl] | N-(7-chloro-3-(2,6-dichloro-3,5-dimethoxyphenyl)-2,6-naphthyridin-1-yl)tetrahydrofuran 2-carboxamide | 482 |
| 131 | 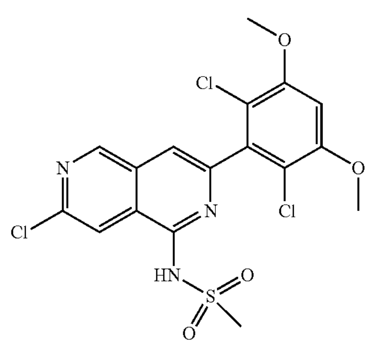 [SMILES: COc1cc(OC)c(Cl)c(-c2cc3cnc(Cl)cc3c(NS(C)(=O)=O)n2)c1Cl] | N-(7-chloro-3-(2,6-dichloro-3,5-dimethoxyphenyl)-2,6-naphthyridin-1-yl)sulfonamide | 462 |

Intermediate 132: Preparation of 6-(2,6-dichloro-3,5-dimethoxyphenyl)-8-methoxy-2-(methylthio)pyrido[3,4-d]pyrimidine

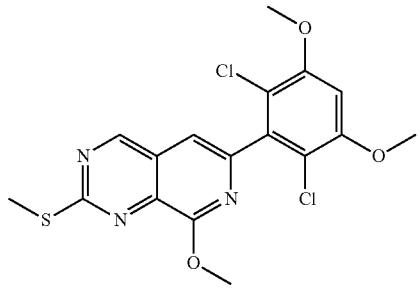

Step 1: Preparation of Methyl 5-((3,5-dimethoxyphenyl)ethynyl)-2-methylthio)pyrimidine-4-carboxylate

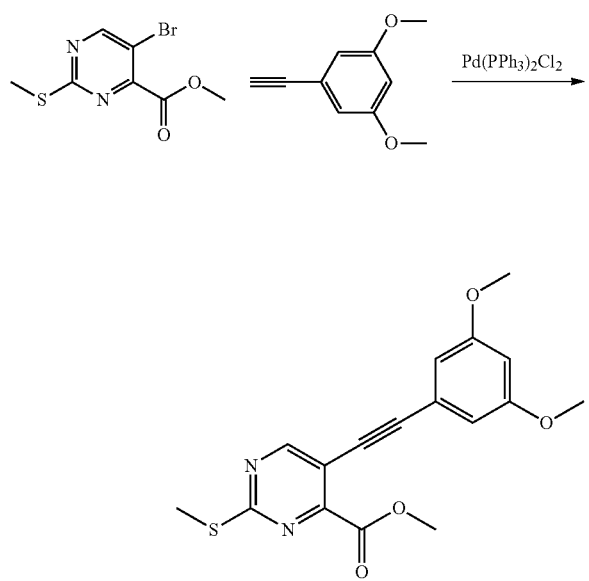

Methyl 5-bromo-2-(methylthio)pyrimidine-4-carboxylate (2631 mg, 10.0 mmol) and 1-ethynyl-3,5-dimethoxybenzene (1622 mg, 10.0 mmol) were dissolved in dried THF (50 mL). The gas was exchanged with $N_2$, $Et_3N$ (2.8 mL, 20.0 mmol), $Pd(PPh_3)_2Cl_2$ (702 mg, 1.0 mmol), $PPh_3$ (525 mg, 2.0 mmol) and CuI (190 mg, 1.0 mmol) were added successively under $N_2$, the mixture was heated to 90° C. and stirred overnight. After the reaction was completed, the mixture was cooled to room temperature, added with a saturated aqueous solution of $NaHCO_3$ (100 mL), extracted tice with EtOAc (100 mL), the organic phase was washed with saturated brine, dried over anhydrous sodium sulfate, filtrated, concentrated, and separated by silica gel column chromatography (PE:EA 4:1) to obtain compound methyl 5-((3,5-dimethoxyphenyl)ethynyl)-2-(methylthio)pyrimidine-4-carboxylate (2.5 g, yield: 73%). MS m/z (ESI): 345.2 [M+H]$^+$.

Step 2: Preparation of 5-((3,5-dimethoxyphenyl)ethynyl)-2-(methylthio)pyrimidine-4-carboxylic Acid

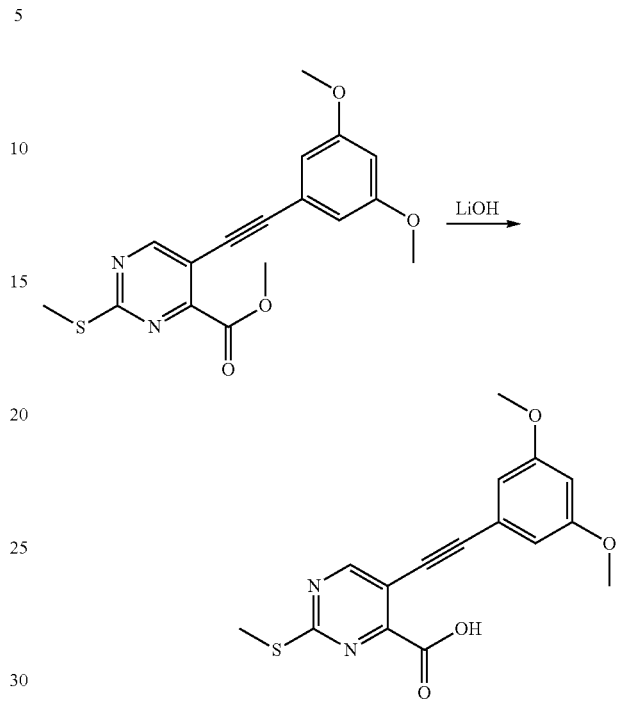

Methyl 5-((3,5-dimethoxyphenyl)ethynyl)-2-(methylthio)pyrimidine-4-carboxylate (600 m g, 1.742 mmol) was dissolved in methanol (15 mL), and then an aqueous lithium hydroxide monohydrate (366 mg, 8.711 mmol) in water (5 mL) was added, and the mixture was stirred at room temperature overnight. The reaction was completed. The organic solvent was evaporated by reduced pressure, EtOAc (30 mL) was added to the residue, and the pH was adjusted with 1 N hydrochloric acid solution to 34. The organic phase was separated, washed with saturated brine, dried over anhydrous sodium sulfate, filtrated, and concentrated to obtain compound 5-((3,5-dimethoxyphenyl)ethynyl)-2-(methylthio)pyrimidine-4-carboxylic acid (584 mg, quantitative yield). MS m/z (ESI): 331.2 [M+H]+.

Step 3: Preparation of 6-(3,5-dimethoxyphenyl)-2-(methylthio)-8H-pyrano[3,4-d]pyrimidine-8-one

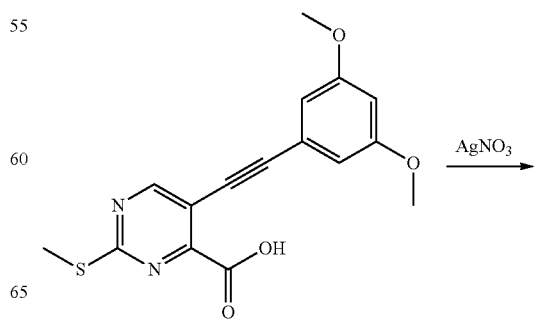

-continued

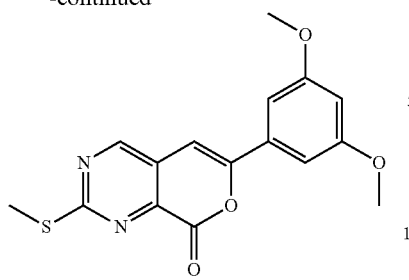

5-((3,5-dimethoxyphenyl)ethynyl)-2-(methylthio)pyrimidine-4-carboxylic acid (584 mg, 1.768 mmol) was suspended in acetone (25 mL), and AgNO₃ (180 mg, 1.059 mmol) was added to the suspension. The mixture was stirred at room temperature for 4 h, and green solid was precipitated, filtered to obtain 6-(3,5-dimethoxyphenyl)-2-(methylthio)-8H-pyrano[3,4-d]pyrimidine-8-one (600 mg, the crude product) MS m/z (ESI): 331.2 [M+H]⁺.

Step 4: Preparation of 6-(3,5-dimethoxyphenyl)-2-(methylthio)pyrido[3,4-d]pyrimidine-8(7H)-one

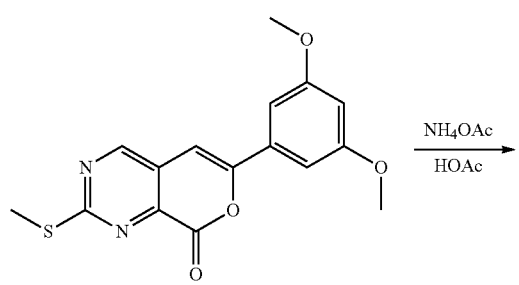

6-(3,5-dimethoxyphenyl)-2-(methylthio)-8H-pyrano[3,4-d]pyrimidine-8-one (600 mg, the crude product) was added to glacial acetic acid (50 mL), then ammonium acetate (2.1 g, 27.243 mmol) was added, the mixture was heated to 115° C. for 16 h. The reaction was completed, the mixture was cooled to room temperature, poured slowly into a saturated aqueous sodium bicarbonate solution, and extracted with EtOAc (100 mL). The organic phase was separated, and washed with saturated brine, dried over anhydrous sodium sulfate, filtrated, concentrated and separated by column chromatography (Eluent: CH₂Cl₂/MeOH 0~6%) to obtain compound 6-(3,5-dimethoxyphenyl)-2-(methylthio)pyrido[3,4-d]pyrimidine-8(7H)-one (298 mg, two-step yield: 50%). MS m/z (ESI): 330.2 [M+H]⁺.

Step 5: Preparation of 6-(3,5-dimethoxyphenyl)-8-methoxy-2-(methylthio)pyrido[3,4-d]pyrimidine

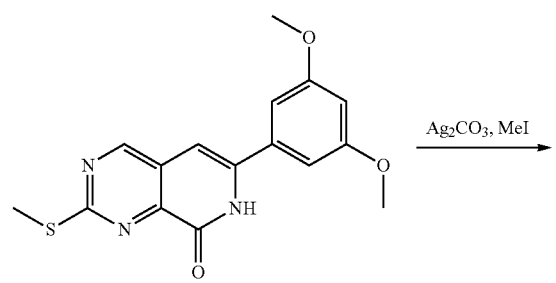

6-(3,5-dimethoxyphenyl)-2-(methylthio)pyrido[3,4-d]pyrimidine-8(7H)-one (100 mg, 0.304 mmol) and silver carbonate (109 mg, 0.395 mmol) were suspended in toluene (3 mL), then methyl iodide (431 mg, 3.036 mmol) was added. The mixture was heated to 100° C. in a sealed tube for 3 h. The reaction was completed, the mixture was cooled to room temperature, diluted with EtOA, and filtrated to remove salt. The filtrate was concentrated and separated by column chromatography (Eluent: PE/EtOAc 10-80%) to obtain compound 6-(3,5-dimethoxyphenyl)-8-methoxy-2-(methylthio)pyrido[3,4-d]pyrimidine (47 mg, yield: 4 5%). MS m/z (ESI):344.3 [M+H]⁺.

Step 6: Preparation of 6-(2,6-dichloro-3,5-dimethoxyphenyl)-8-methoxy-2-(methylthio) pyrido[3,4-d]pyrimidine

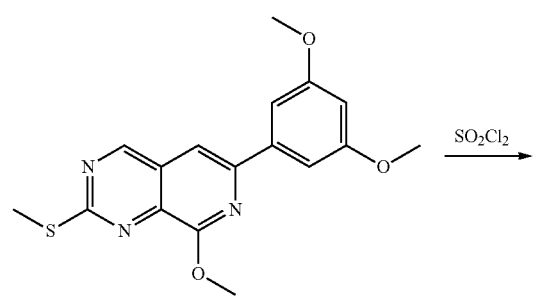

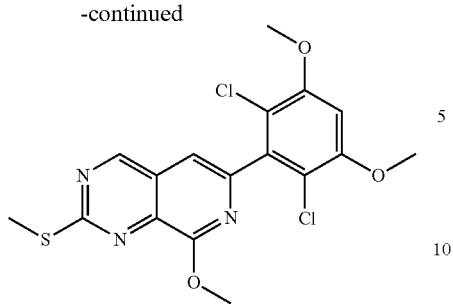

The compound was prepared referring to the synthesis method of Intermediate 1.

Intermediates 133-134 were prepared by referring, to the synthesis method of example 1.2.

| Intermediate No. | Compound structure | Compound name | MS: m/z [M + 1]⁺ |
|---|---|---|---|
| 133 | 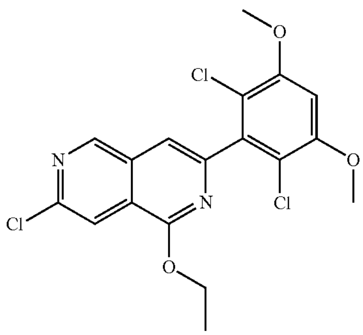 [SMILES: CCOc1nc(-c2c(Cl)c(OC)cc(OC)c2Cl)cc2cnc(Cl)cc12] | 7-chloro-3-(2,6-dichloro-3,5-dimethoxyphenyl)-1-ethoxy-2,6-naphthyridine | 413 |
| 134 | 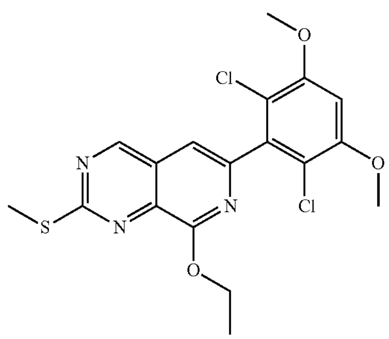 | 6-(2,6-dichloro-3,5-dimethoxyphenyl)-8-ethoxy-2-(methylthio)pyrido[3,4-d]pyrimidine | 426 |

Intermediate 135: Preparation of 6-(2,6-dichloro-3,5-dimethoxyphenyl)-N-(2-methoxyethyl)-2-(methylthio)pyrido[3,4-d]pyrimidine-8-amine Step 1: Preparation of 8-chloro-6-(3,5-dimethoxyphenyl)-2-(methylthio)pyrido[3,4-d]pyrimidine

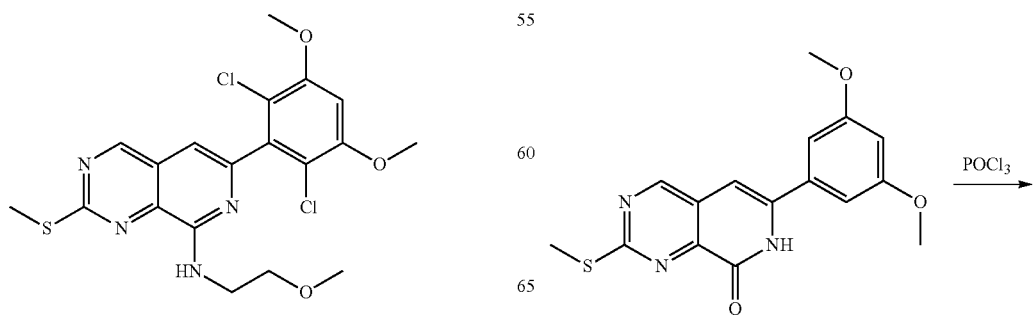

-continued

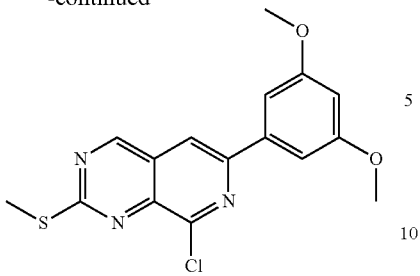

6-(3,5-dimethoxyphenyl)-2-(methylthio)pyrido[3,4-d]pyrimidine-8(7H)-one (20.0 mg, 0.06 1 mmol) and N,N-diisopropylethylamine (78 mg, 0.610 mmol) were added to acetonitrile (2 mL), then POCl₃ (0.8 mL) was added, the mixture was heated to 90° C. and stirred overnight. The solvent was removed by reduced pressure. The residue was diluted with EtOAc (10 mL) and washed with a saturated sodium bicarbonate solution. The organic phase was separated, washed with saturated brine, dried over anhydrous sodium sulfate, filtrated, concentrated and separated by column chromatography (Eluent: PE/EtOAc 040%) to obtain compound 8-chloro-6-(3,5-dimethoxyphenyl)-2-(methylthio)pyrido[3,4-d]pyrimidine (6 mg, yield: 28%).

MS m/z (ESI): 348.2 [M+H]⁺.

Step 2: Preparation of 6-(3,5-dimethoxyphenyl)-N-(2-methoxyethyl)-2-(methylthio)pyrido[3,4-d]pyrimidine-8-amine

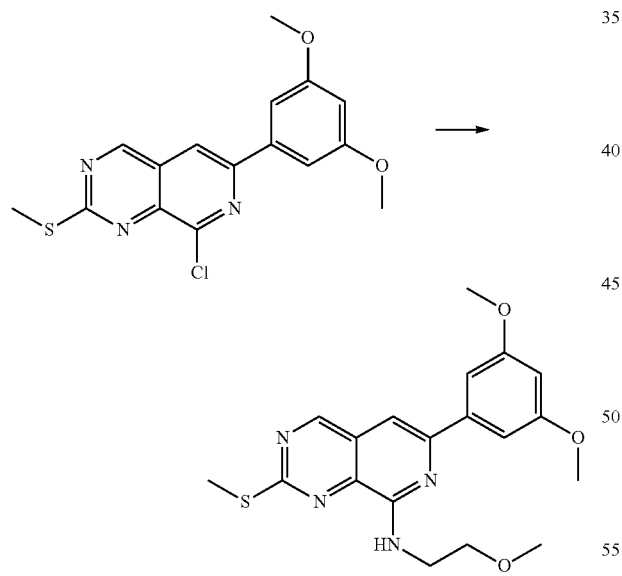

8-chloro-6-(3,5-dimethoxyphenyl)-2-(methylthio)pyrido[3,4-d]pyrimidine (6 mg, 0.017 mmol) and N,N-diisopropylethylamine (6.5 mg, 0.052 mmol) were dissolved in acetonitrile (1.5 mL), then 2-methoxyethyl-1-amine (4 mg, 0.052 mmol) was added, the mixture was heated to 90° C. and stirred overnight. The reaction was completed, the mixture was cooled to room temperature, diluted with EtOAc (5 mL), washed with saturated brine, dried over anhydrous sodium sulfate, filtrated, concentrated and separated by column chromatography (Eluent: PE/EtOAc 0-50%) to obtain compound 6-(3,5-dimethoxyphenyl)-N-(2-methoxyethyl)-2-(methylthio)pyrido[3,4-d]pyrimidine-8-amine (4 mg, yield: 61%).

MS m/z (ESI): 387.4 [M+H]⁺.

Step 3: Preparation of 6-(2,6-dichloro-3,5-dimethoxyphenyl)-N-(2-methoxyethyl)-2-(methylthio)pyrido[3,4-d]pyrimidine-8-amine

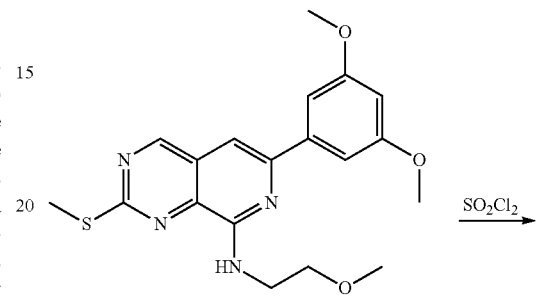

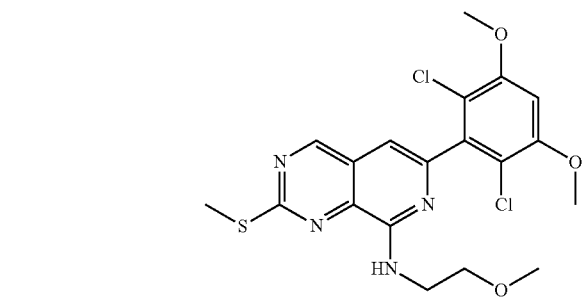

The compound was prepared referring to the synthesis method of Intermediate 1.

Intermediate 139: Preparation of 4-(6-(2,6-difluoro-3,5-dimethoxyphenyl)-2-(methylthio)pyrido[3,4-d]pyrimidin-8-yl)morpholine

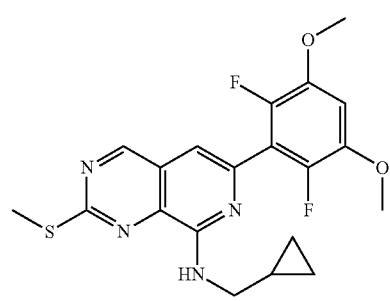

Step 1: Preparation of 2,4-difluoro-3-iodo-1,5-dimethoxybenzene

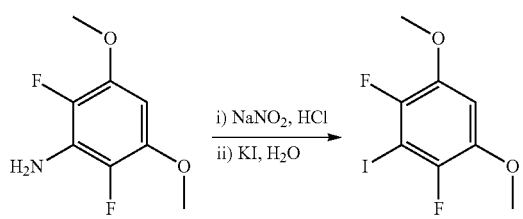

2,6-difluoro-3,5-dimethoxyaniline (27.0 g, 143 mmol) was added to 6.0 M hydrochloric acid solution (240 mL), and NaNO₂ aqueous solution (10.35 g, 150 mmol, 30 mL water) was slowly added dropwise under ice water for cooling within 25 min. After the addition was completed, the mixture was reacted for another 15 min to obtain an orange-red suspension, and then added to an aqueous KI solution (94.9 g, 570 mmol, 150 mL water), the mixture was heated to room temperature and stirred for 30 min to precipitate a solid. The mixture was filtrated and washed with water to obtain a crude product. MeOH (60 mL) was added to the crude product, then the mixture was stirred at room temperature for 30 min, filtrated, and dried to obtain 2,4-difluoro-3-iodo-1,5-dimethoxybenzene (29.3 g, yield: 68%).

Step 2: Preparation of (2,6-difluoro-3,5-dimethoxyphenylacetylene)trimethylsilane

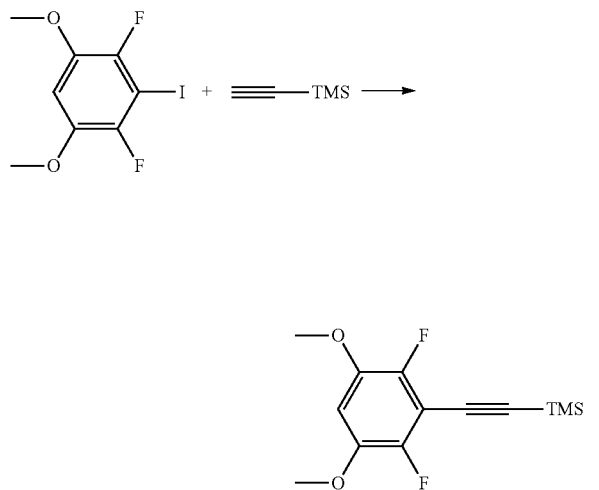

2,4-difluoro-3-iodo-1,5-dimethoxybenzene (25.8 g, 86.0 mmol), trimethylsilylacetylene (36.5 mL, 258 mmol), CuI (817 mg, 4.3 mmol) and triethylamine (35.8 mL, 258 mmol) were added to DMF (250 mL) under N2, then Pd(PPh₃)₂Cl₂ (3.15 g, 4.3 mmol) was added, and the mixture was heated to 50° C. for 2 h. The reaction was completed, a saturated aqueous NH₄Cl solution was added to quench the reaction, the mixture was extracted for three times with dichloromethane, and the organic phases were combined, dried over Na₂SO₄, filtrated and concentrated to obtain a crude product (27.0 g) which was used directly in the next step.

Step 3: Preparation of 3-ethynyl-2,4-difluoro-1,5-dimethoxybenzene

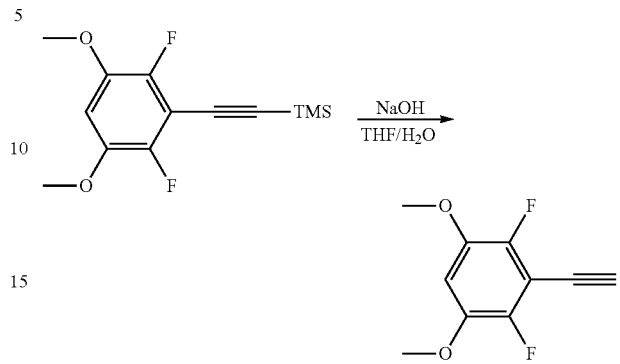

(2,6-difluoro-3,5-dimethoxyphenylacetylene)trimethylsilane (27.0 g, a crude product) was added to the mixture of THF and MeOH (200/200 mL), then aqueous NaOH solution (8.6 mL, 8.6 mmol, 1.0 N) was added, and the mixture was stirred at room temperature for 15 mm. The reaction was completed, a saturated aqueous NH₄Cl solution was added to quench the reaction, and the mixture was extracted for three times with dichloromethane, and the organic phases were combined, dried over anhydrous sodium sulfate, filtrated and concentrated. MeOH (50 mL) was added to the crude product, and then the mixture was stirred at room temperature for 30 min, filtered to obtain the target product (15.0 g, two-step yield: 88%).

Step 4: Preparation of Methyl 5-((2,6-difluoro-3,5-dimethoxyphenyl)ethynyl)-2-(methylthio)pyrimidine-4-carboxylate

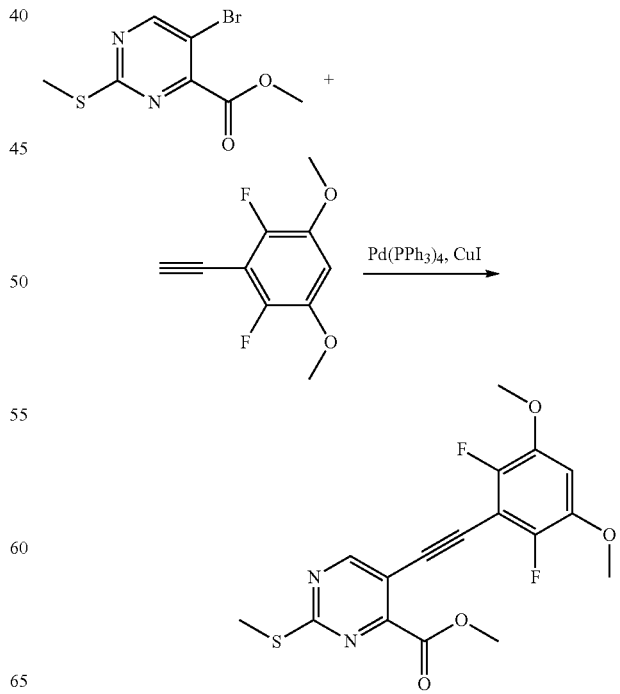

3-ethynyl-2,4-difluoro-1,5-dimethoxybenzene (10.0 g, 50.5 mmol) and methyl 5-bromo-2-methylthio-pyrimidine-4-carboxylate (13.0 g, 49.5 mmol) were dissolved in DMF (100 mL), then CuI (479 mg, 2.52 mmol), Pd(PPh$_3$)$_4$ (2.91 g, 2.52 mmol) and Et$_3$N (35.0 mL, 252.5 mmol) were added, the mixture was heated to 100° C. for 1.5 h under N2. The reaction was completed, the mixture was cooled to room temperature, a saturated aqueous NH$_4$Cl solution was added to quench the reaction, then the mixture was extracted for three times with dichloromethane, and the organic phases were combined, dried over anhydrous sodium sulfate, filtrated and concentrated to obtain a crude product, then the crude product was separated by silica gel column chromatography (PE:EA:DCM=10:2:1) to obtain the target product (15.4 g, yield: 82%). $^1$H NMR (400 MHz, CDCl$_3$) δ 8.82 (s, 1H), 6.69 (t, J=8.0 Hz, 1H), 4.03 (s, 3H), 3.90 (s, 6H), 2.63 (s, 3H).

Step 5: Preparation of 5-((2,6-difluoro-3,5-dimethoxyphenyl)ethynyl)-2-(methylthio)pyrimidine-4-carboxylic Acid

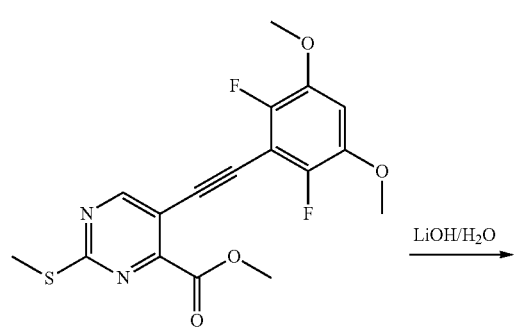

LiOH/H$_2$O

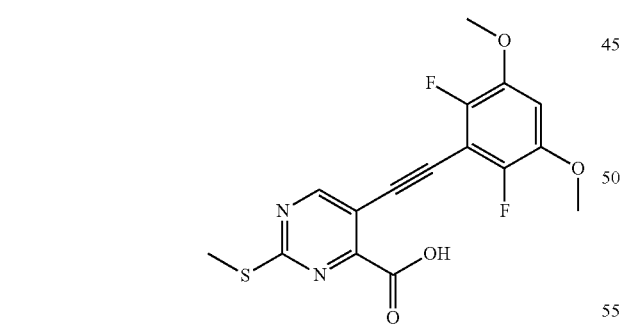

Methyl 5-((2,6-difluoro-3,5-dimethoxyphenyl)ethynyl)-2-(methylthio)pyrimidine-4-carboxylate (30.0 g, 78.9 mmol) was dissolved in THF (300 mL), then LiOH/H$_2$O (236.8 mL, 236.8 mmol, 1 M) was added, the mixture was stirred at room temperature for 2 h. The reaction was completed, the mixture was concentrated to remove THF, then acidified to pH 3 with diluted hydrochloric acid to precipitate a solid. The mixture was filtrated, washed with water, and dried to obtain the target product (28.5 g, yield: 99%).

Step 6: Preparation of 6-(2,6-difluoro-3,5-dimethoxyphenyl)-2-(methylthio)-8H-pyrano[3,4-d]pyrimidine-8-one

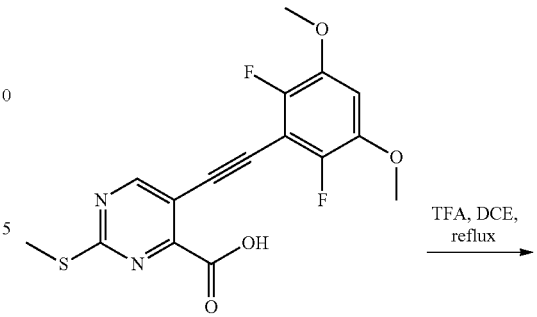

TFA, DCE, reflux 5-((2,6-difluoro-3,5-dimethoxyphenyl)ethynyl)-2-(methylthio)pyrimidine-4-carboxylic acid (2.5 g, 6.83 mmol) was dissolved in DCE (50 mL), then TFA (0.5 mL) was added, the mixture was heated to reflux overnight. The reaction was completed, the mixture was concentrated, MeOH (50 mL) was added, then the mixture was stirred at room temperature for 30 min. The mixture was filtrated, and the solid was washed with MeOH (10 mL) to obtain the target product (2.0 g, yield: 80%). $^1$H NMR (400 MHz, DMSO-d$_6$) δ 9.23 (s, 1H), 7.22 (t, J=8.4 Hz, 1H), 7.17 (s, 1H), 3.93 (s, 6H), 2.63 (s, 3H).

Step 7: Preparation of 6-(2,6-difluoro-3,5-dimethoxyphenyl)-2-(methylthio)pyrido[3,4-d]pyrimidine-8(7H)-one

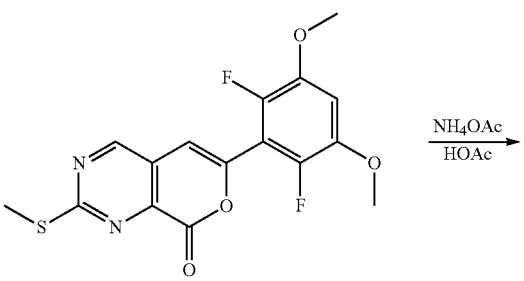

NH$_4$OAc
HOAc

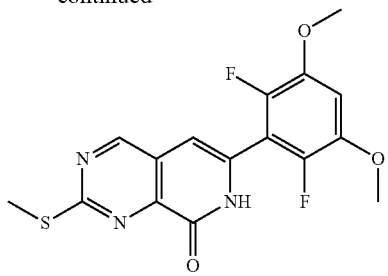

The compound was prepared referring to the synthesis method of step 4 of Intermediate 132.

Step 8: Preparation of 8-chloro-6-(2,6-difluoro-3,5-dimethoxyphenyl)-2-(methylthio)pyrido[3,4-d]pyrimidine

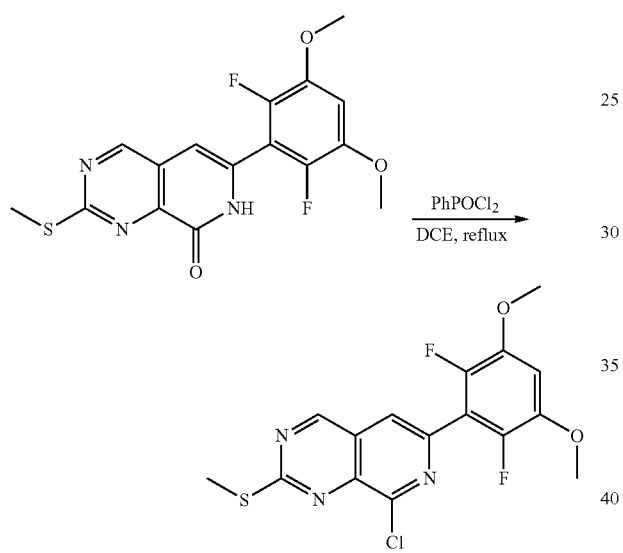

6-(2,6-difluoro-3,5-dimethoxyphenyl)-2-(methylthio)pyrido[3,4-d]pyrimidine-8(7H)-one (1 g, 2.74 mmol) was dissolved in DCE (80 mL), the mixture was heated to 90° C., then phenylphosphonic dichloride (3.0 mL, 21.92 mmol) was added, the mixture was heated and stirred for 16 h, and then cooled. pH was adjusted to neutral under ice bath. The mixture was extracted with DCM, and then separated by silica gel column chromatography (MeOH/DCM 1/20) to obtain compound 8-chloro-6-(2,6-difluoro-3,5-dimethoxyphenyl)-2-(methylthio)pyrido[3,4-d]pyrimidine (930 mg, yield:88%). MS m/z (ESI): 384 [M+H]+.

Step 9: Preparation of N-(cyclopropylmethyl)-6-(2,6-difluoro-3,5-dimethoxyphenyl)-2-(methylthio)pyrido[3,4-d]pyrimidine-8-amine

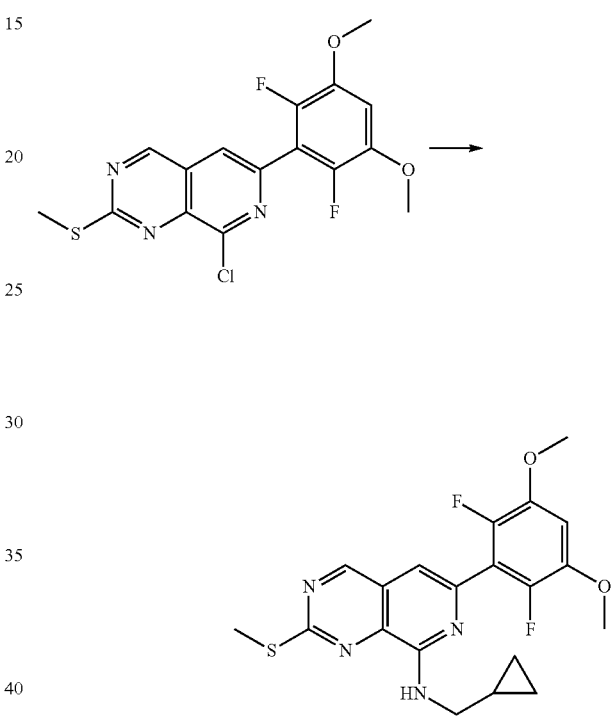

The compound was prepared referring to the synthesis method of step 2 of Intermediate 135.

Intermediates 136-330 were prepared referring to the synthesis method of Intermediate 135 or 139.

| Intermediate No. | Compound structure | Compound name | MS: m/z [M + 1]+ |
|---|---|---|---|
| 136 | 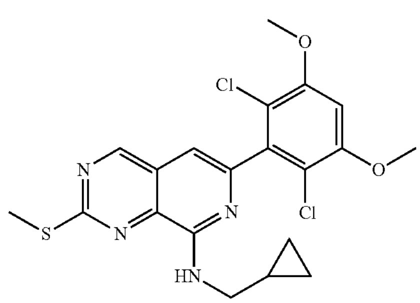 | N-(cyclopropylmethyl)-6-(2,6-dichloro-3,5-dimethoxyphenyl)-2-(methylthio)pyrido[3,4-d]pyrimidine-8-amine | 451 |

| Intermediate No. | Compound structure | Compound name | MS: m/z [M + 1]+ |
|---|---|---|---|
| 137 | 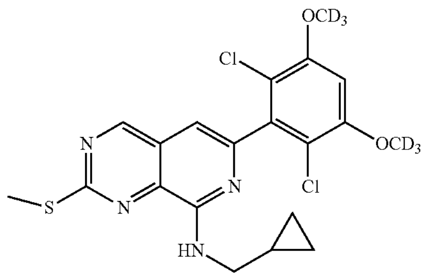 | N-(cyclopropylmethyl)-6-(2,6-dichloro-3,5-di(methoxy-d₃)phenyl)-2-(methylthio)pyrido[3,4-d]pyrimidine-8-amine | 457 |
| 138 | 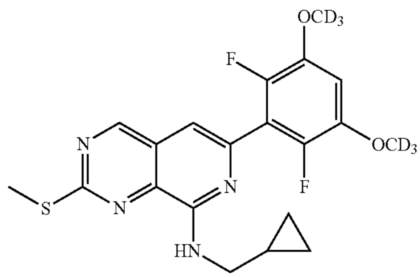 | N-(cyclopropylmethyl)-6-(2,6-difluoro-3,5-di(methoxy-d₃)phenyl)-2-(methylthio)pyrido[3,4-d]pyrimidine-8-amine | 425 |
| 140 | 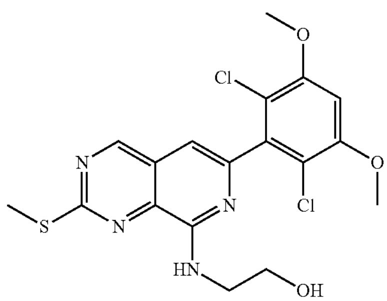 | 2-((6-(2,6-dichloro-3,5-dimethoxyphenyl)-2-(methylthio)pyrido[3,4-d]pyrimidin-8-yl)amino)ethan-1-ol | 441 |
| 141 | 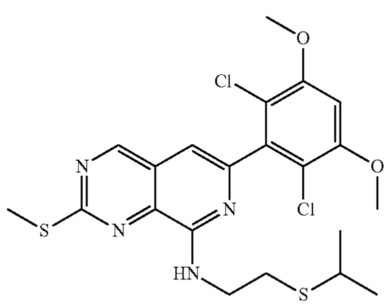 | 6-(2,6-dichloro-3,5-dimethoxyphenyl)-N-(2-(isopropylthio)ethyl)-2-(methylthio)pyrido[3,4-d]pyrimidine-8-amine | 499 |
| 142 | 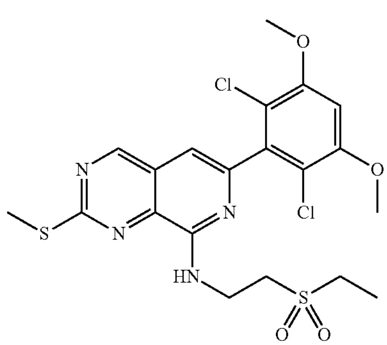 | 6-(2,6-dichloro-3,5-dimethoxyphenyl)-N-(2-(ethylsulfonyl)ethyl)-2-(methylthio)pyrido[3,4-d]pyrimidine-8-amine | 518 |

| Intermediate No. | Compound name | MS: m/z [M + 1]+ |
|---|---|---|
| 143 | 6-(2,6-dichloro-3,5-dimethoxyphenyl)-N-methyl-2-(methylthio)pyrido[3,4-d]pyrimidine-8-amine | 411 |
| 144 | 6-(2,6-dichloro-3,5-dimethoxyphenyl)-N-ethyl-2-(methylthio)pyrido[3,4-d]pyrimidine-8-amine | 425 |
| 145 | 6-(2,6-dichloro-3,5-dimethoxyphenyl)-N,N-dimethyl-2-(methylthio)pyrido[3,4-d]pyrimidine-8-amine | 425 |
| 146 | 6-(2,6-dichloro-3,5-dimethoxyphenyl)-2-(methylthio)-N-(2,2,2-trifluoroethyl)pyrido[3,4-d]pyrimidine-8-amine | 479 |
| 147 | N-(cyclopropylmethyl)-6-(2,6-dichloro-3,5-dimethoxyphenyl)-N-methyl-2-(methylthio)pyrido[3,4-d]pyrimidine-8-amine | 465 |

-continued

| Intermediate No. | Compound structure | Compound name | MS: m/z [M + 1]+ |
|---|---|---|---|
| 148 | 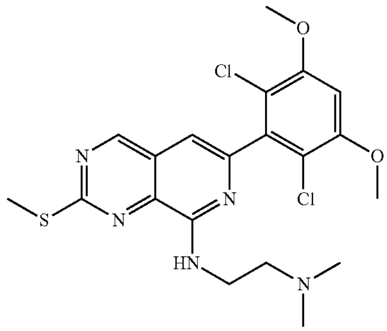 | $N^1$-(6-(2,6-dichloro-3,5-dimethoxyphenyl)-2-(methylthio)pyrido[3,4-d]pyrimidin-8-yl)-$N^2$,$N^2$-dimethylethane-1,2-diamine | 468 |
| 149 | 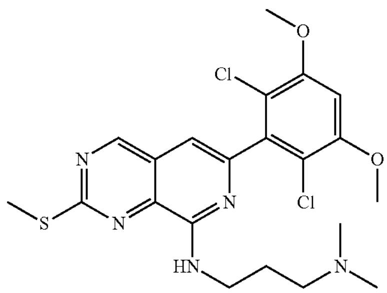 | $N^1$-(6-(2,6-dichloro-3,5-dimethoxyphenyl)-2-(methylthio)pyrido[3,4-d]pyrimidin-8-yl)-$N^3$,$N^3$-dimethylpropane-1,3-diamine | 482 |
| 150 | 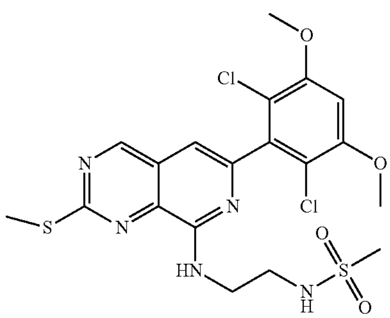 | N-(2-((6-(2,6-dichloro-3,5-dimethoxyphenyl)-2-(methylthio)pyrido[3,4-d]pyrimidin-8-yl)amino)ethyl)sulfonamide | 518 |
| 151 | 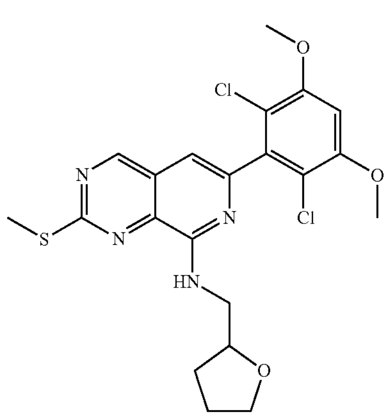 | 6-(2,6-dichloro-3,5-dimethoxyphenyl)-2-(methylthio)-N-((tetrahydrofuran2-yl)methyl)pyrido[3,4-d]pyrimidine-8-amine | 481 |

| Intermediate No. | Compound structure | Compound name | MS: m/z [M + 1]+ |
|---|---|---|---|
| 152 | 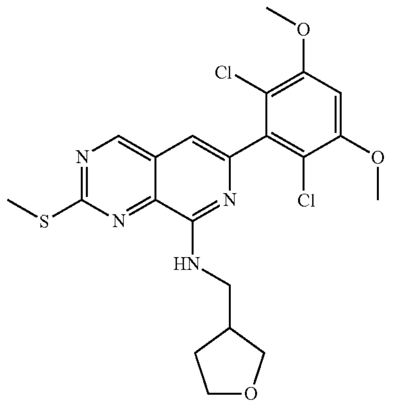 | 6-(2,6-dichloro-3,5-dimethoxyphenyl)-2-(methylthio)-N-((tetrahydrofuran-3-yl)methyl)pyrido[3,4-d]pyrimidine-8-amine | 481 |
| 153 | 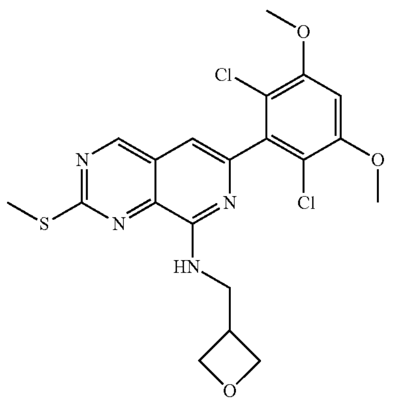 | 6-(2,6-dichloro-3,5-dimethoxyphenyl)-2-(methylthio)-N-(oxetan-3-ylmethyl)pyrido[3,4-d]pyrimidine-8-amine | 467 |
| 154 | 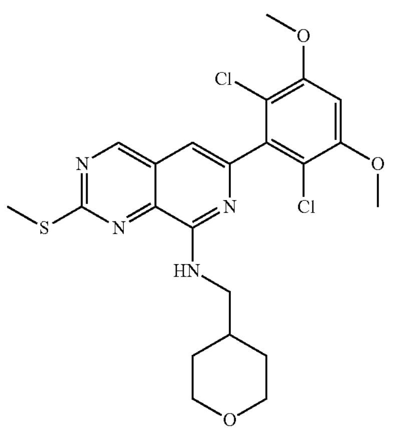 | 6-(2,6-dichloro-3,5-dimethoxyphenyl)-2-(methylthio)-N-((tetrahydro-2H-pyran-4-yl)methyl)pyrido[3,4-d]pyrimidine-8-amine | 495 |
| 155 | 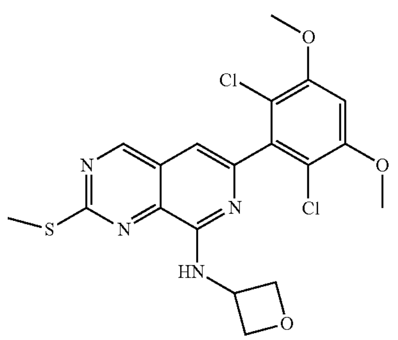 | 6-(2,6-dichloro-3,5-dimethoxyphenyl)-2-(methylthio)-N-(oxetan-3-yl)pyrido[3,4-d]pyrimidine-8-amine | 453 |

| Intermediate No. | Compound structure | Compound name | MS: m/z [M + 1]+ |
|---|---|---|---|
| 156 | 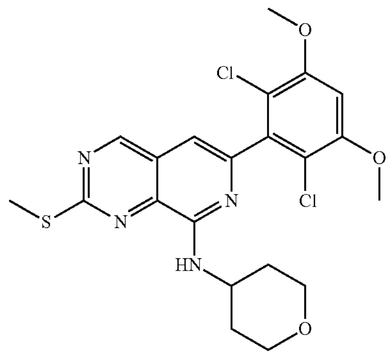 | 6-(2,6-dichloro-3,5-dimethoxyphenyl)-2-(methylthio)-N-(tetrahydro-2H-pyran-4-yl)pyrido[3,4-d]pyrimidine-8-amine | 481 |
| 157 | 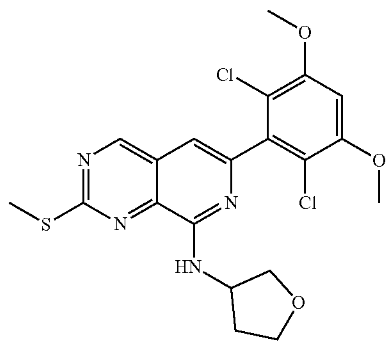 | 6-(2,6-dichloro-3,5-dimethoxyphenyl)-2-(methylthio)-N-(tetrahydrofuran-3-yl)pyrido[3,4-d]pyrimidine-8-amine | 467 |
| 158 | 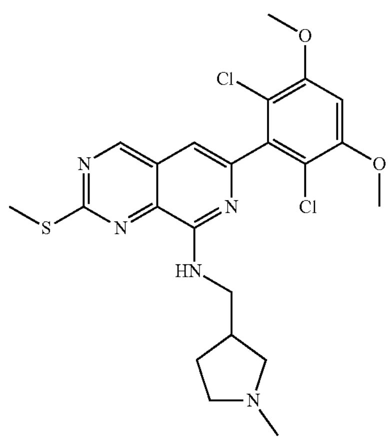 | 6-(2,6-dichloro-3,5-dimethoxyphenyl)-N-((1-methylpyrrolidin-3-yl)methyl)-2-(methylthio)pyrido[3,4-d]pyrimidine-8-amine | 494 |
| 159 | 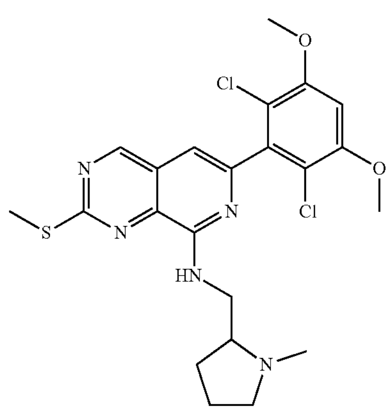 | 6-(2,6-dichloro-3,5-dimethoxyphenyl)-N-((1-methylpyrrolidin-2-yl)methyl)-2-(methylthio)pyrido[3,4-d]pyrimidine-8-amine | 494 |

-continued

| Intermediate No. | Compound structure | Compound name | MS: m/z [M + 1]+ |
|---|---|---|---|
| 160 | 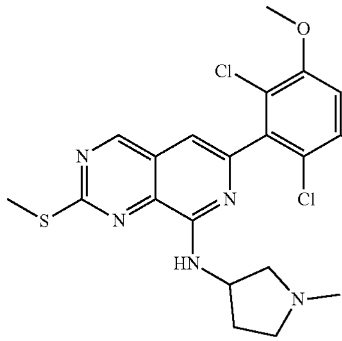 | 6-(2,6-dichloro-3,5-dimethoxyphenyl)-N-(1-methylpyrrolidin-3-yl)-2-(methylthio)pyrido[3,4-d]pyrimidine-8-amine | 480 |
| 161 | 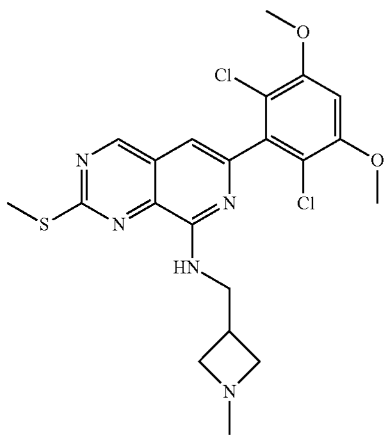 | 6-(2,6-dichloro-3,5-dimethoxyphenyl)-N-((1-methylazetidin-3-yl)methyl)-2-(methylthio)pyrido[3,4-d]pyrimidine-8-amine | 480 |
| 162 | 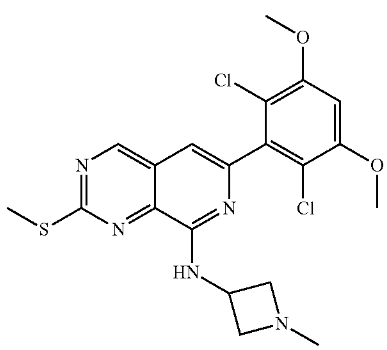 | 6-(2,6-dichloro-3,5-dimethoxyphenyl)-N-(1-methylazetidin-3-yl)-2-(methylthio)pyrido[3,4-d]pyrimidine-8-amine | 466 |
| 163 | 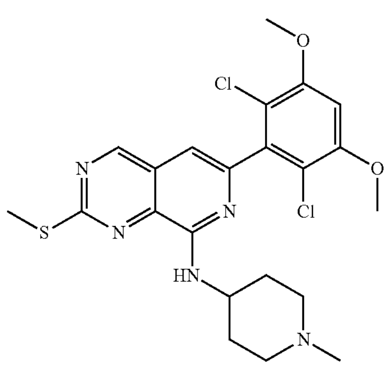 | 6-(2,6-dichloro-3,5-dimethoxyphenyl)-N-(1-methylpiperidin-4-yl)-2-(methylthio)pyrido[3,4-d]pyrimidine-8-amine | 494 |

-continued

| Intermediate No. | Compound structure | Compound name | MS: m/z [M + 1]⁺ |
|---|---|---|---|
| 164 | 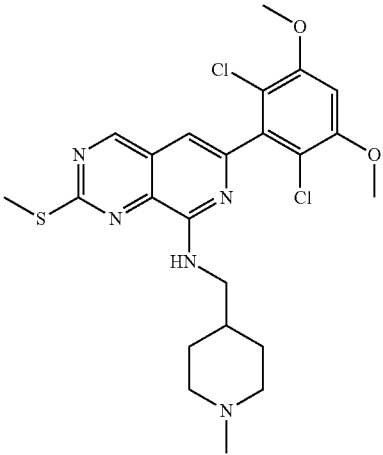 | 6-(2,6-dichloro-3,5-dimethoxyphenyl)-N-((1-methylpiperidin-4-yl)methyl)-2-(methylthio)pyrido[3,4-d]pyrimidine-8-amine | 508 |
| 165 | 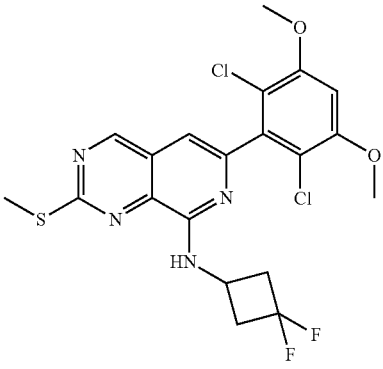 | 6-(2,6-dichloro-3,5-dimethoxyphenyl)-N-(3,3-difluorocyclobutyl)-2-(methylthio)pyrido[3,4-d]pyrimidine-8-amine | 487 |
| 166 | 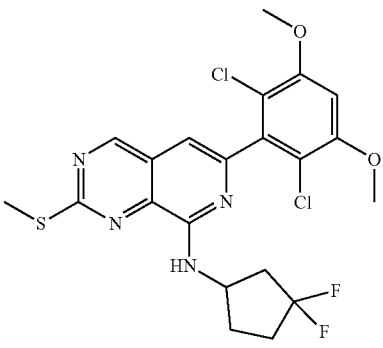 | 6-(2,6-dichloro-3,5-dimethoxyphenyl)-N-(3,3-difluorocyclopentyl)-2-(methylthio)pyrido[3,4-d]pyrimidine-8-amine | 501 |
| 167 | 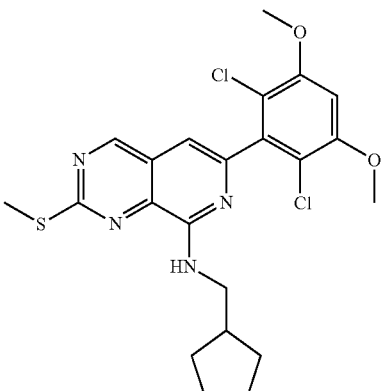 | N-(cyclopentylmethyl)-6-(2,6-dichloro-3,5-dimethoxyphenyl)-2-(methylthio)pyrido[3,4-d]pyrimidine-8-amine | 479 |

-continued

| Intermediate No. | Compound structure | Compound name | MS: m/z [M + 1]+ |
|---|---|---|---|
| 168 | 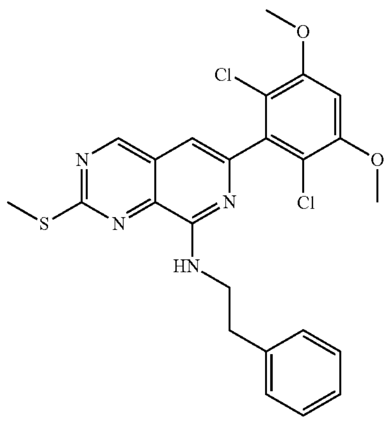 | 6-(2,6-dichloro-3,5-dimethoxyphenyl)-2-(methylthio)-N-phenethylpyrido[3,4-d]pyrimidine-8-amine | 501 |
| 169 | 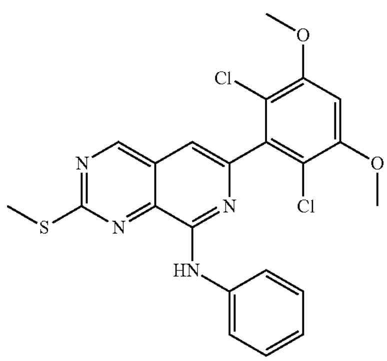 | 6-(2,6-dichloro-3,5-dimethoxyphenyl)-2-(methylthio)-N-phenylpyrido[3,4-d]pyrimidine-8-amine | 473 |
| 170 | 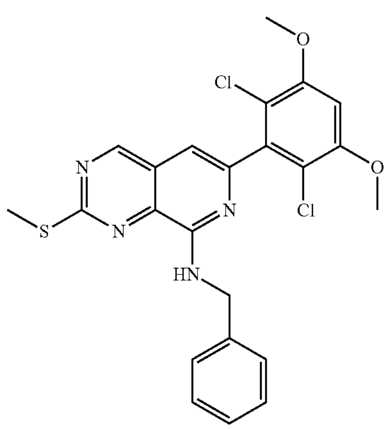 | N-benzyl-6-(2,6-dichloro-3,5-dimethoxyphenyl)-2-(methylthio)pyrido[3,4-d]pyrimidine-8-amine | 487 |

-continued

| Intermediate No. | Compound structure | Compound name | MS: m/z $[M + 1]^+$ |
|---|---|---|---|
| 171 | 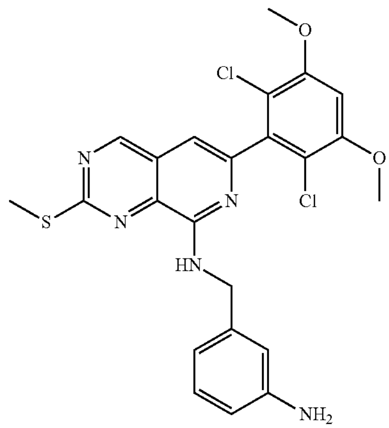 | N-(3-aminobenzyl)-6-(2,6-dichloro-3,5-dimethoxyphenyl)-2-(methylthio)pyrido[3,4-d]pyrimidine-8-amine | 502 |
| 172 | 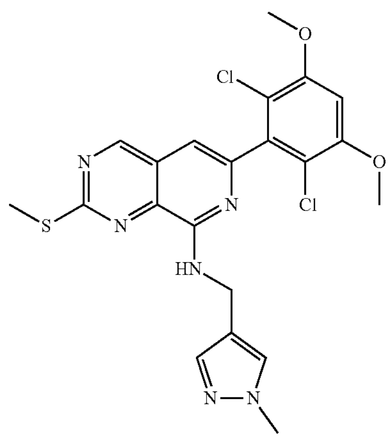 | 6-(2,6-dichloro-3,5-dimethoxyphenyl)-N-((1-methyl-1H-pyrazol-4-yl)methyl)-2-(methylthio)pyrido[3,4-d]pyrimidine-8-amine | 491 |
| 173 | 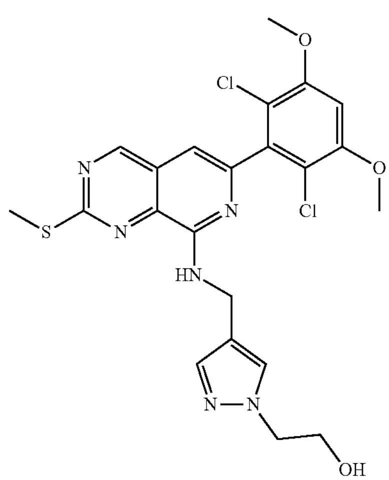 | 2-(4-(((6-(2,6-dichloro-3,5-dimethoxyphenyl)-2-(methylthio)pyrido[3,4-d]pyrimidin-8-yl)amino)methyl)-1H-pyrazol-1-yl)ethan-1-ol | 521 |

| Intermediate No. | Compound structure | Compound name | MS: m/z [M + 1]+ |
|---|---|---|---|
| 174 | 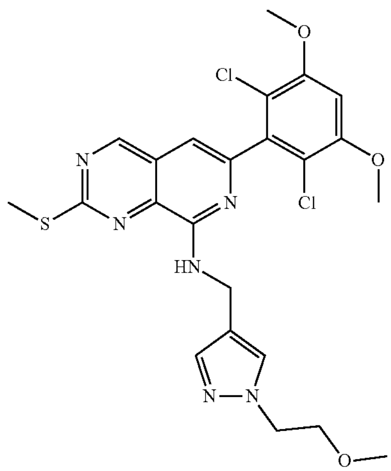 | 6-(2,6-dichloro-3,5-dimethoxyphenyl)-N-((1-(2-methoxyethyl)-1H-pyrazol-4-yl)methyl)-2-(methylthio)pyrido[3,4-d]pyrimidine-8-amine | 535 |
| 175 | 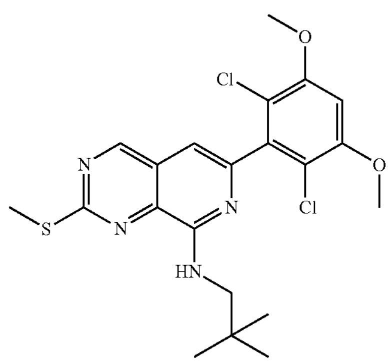 | 6-(2,6-dichloro-3,5-dimethoxyphenyl)-2-(methylthio)-N-neopentylpyrido[3,4-d]pyrimidine-8-amine | 467 |
| 176 | 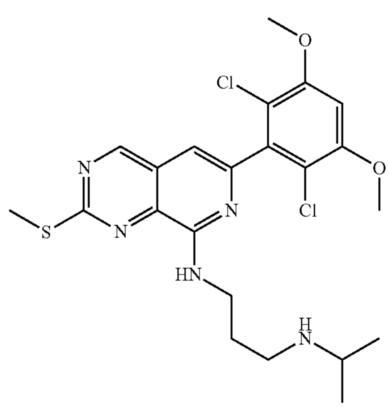 [SMILES: COc1cc(OC)c(Cl)c(-c2cc3cnc(SC)nc3c(NCCCNC(C)C)n2)c1Cl] | $N^1$-(6-(2,6-dichloro-3,5-dimethoxyphenyl)-2-(methylthio)pyrido[3,4-d]pyrimidin-8-yl)-$N^3$-isopropylpropane-1,3-diamine | 496 |

-continued

| Intermediate No. | Compound structure | Compound name | MS: m/z [M + 1]+ |
|---|---|---|---|
| 177 | 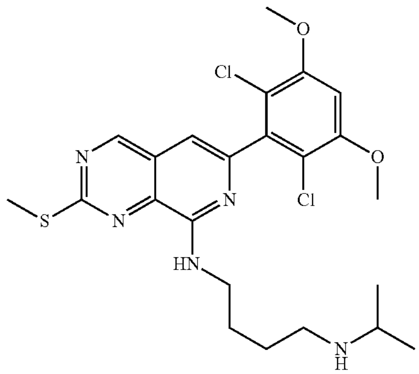 [SMILES: COc1cc(OC)c(Cl)c(-c2cc3cnc(SC)nc3c(NCCCCNC(C)C)n2)c1Cl] | $N^1$-(6-(2,6-dichloro-3,5-dimethoxyphenyl)-2-(methylthio)pyrido[3,4-d]pyrimidin-8-yl)-$N^4$-isopropylbutane-1,4-diamine | 510 |
| 178 | 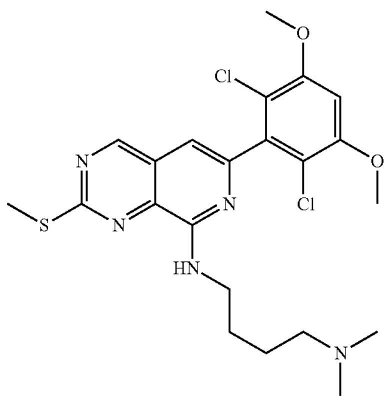 | $N^1$-(6-(2,6-dichloro-3,5-dimethoxyphenyl)-2-(methylthio)pyrido[3,4-d]pyrimidin-8-yl)-$N^4,N^4$-dimethylbutane-1,4-diamine | 496 |
| 179 | 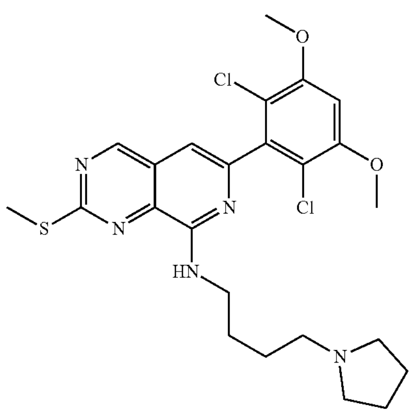 [SMILES: COc1cc(OC)c(Cl)c(-c2cc3cnc(SC)nc3c(NCCCCN3CCCC3)n2)c1Cl] | 6-(2,6-dichloro-3,5-dimethoxyphenyl)-2-(methylthio)-N-(4-(pyrrolidin-1-yl)butyl)pyrido[3,4-d]pyrimidine-8-amine | 522 |
| 180 | 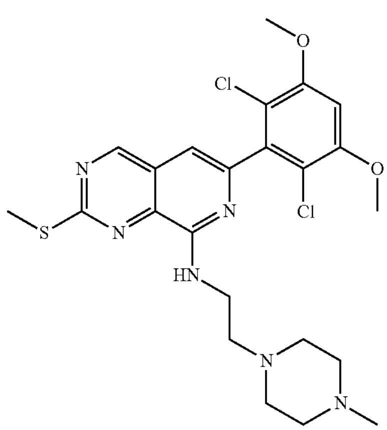 | 6-(2,6-dichloro-3,5-dimethoxyphenyl)-N-(2-(4-methylpiperazin-1-yl)ethyl)-2-(methylthio)pyrido[3,4-d]pyrimidine-8-amine | 523 |

-continued
| Intermediate No. | Compound structure | Compound name | MS: m/z [M + 1]+ |
|---|---|---|---|
| 181 | 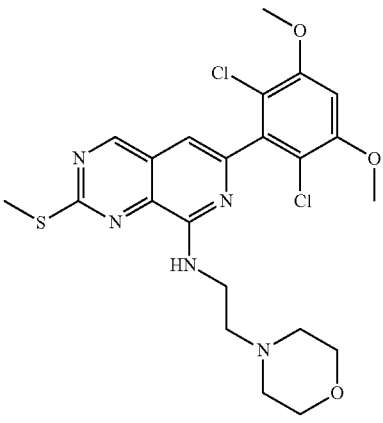 | 6-(2,6-dichloro-3,5-dimethoxyphenyl)-2-(methylthio)-N-(2-morpholinoethyl)pyrido[3,4-d]pyrimidine-8-amine | 510 |
| 182 | 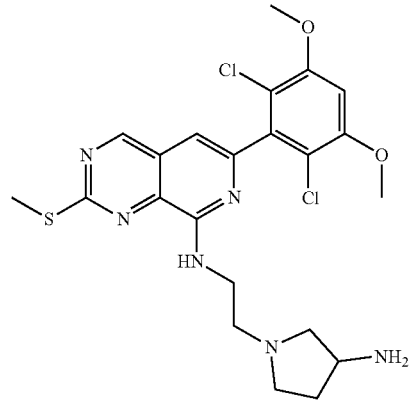 | N-(2-(3-aminopyrrolidin-1-yl)ethyl)-6-(2,6-dichloro-3,5-dimethoxyphenyl)-2-(methylthio)pyrido[3,4-d]pyrimidine-8-amine | 509 |
| 183 | 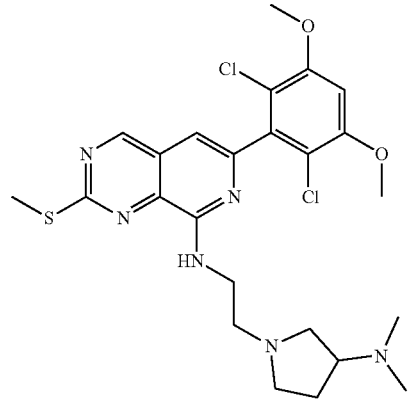 | 6-(2,6-dichloro-3,5-dimethoxyphenyl)-N-(2-(3-(dimethylamino)pyrrolidin-1-yl)ethyl)-2-(methylthio)pyrido[3,4-d]pyrimidine-8-amine | 537 |

| Intermediate No. | Compound structure | Compound name | MS: m/z [M + 1]+ |
|---|---|---|---|
| 184 | 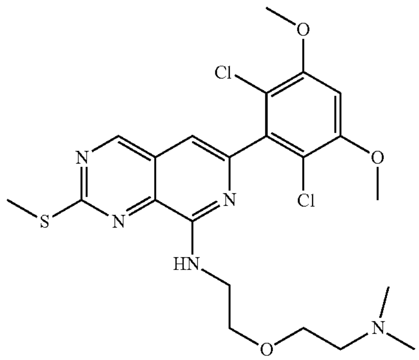 | 6-(2,6-dichloro-3,5-dimethoxyphenyl)-N-(2-(2-(dimethylamino)ethoxy)ethyl)-2-(methylthio)pyrido[3,4-d]pyrimidine-8-amine | 512 |
| 185 | 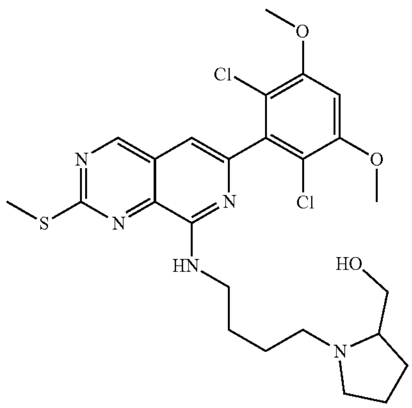 [SMILES: COc1cc(OC)c(Cl)c(-c2cc3cnc(SC)nc3c(NCCCCN3CCCC3CO)n2)c1Cl] | (1-(4-((6-(2,6-dichloro-3,5-dimethoxyphenyl)-2-(methylthio)pyrido[3,4-d]pyrimidin-8-yl)amino)butyl)pyrrolidin-2-yl)methanol | 552 |
| 186 | 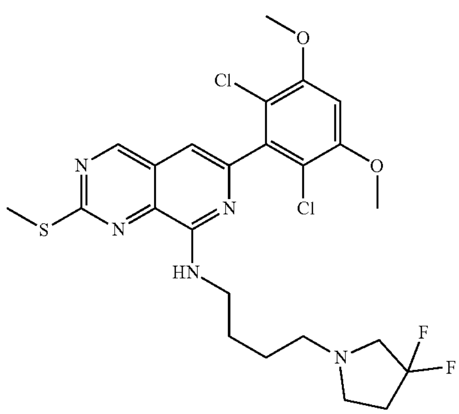 [SMILES: COc1cc(OC)c(Cl)c(-c2cc3cnc(SC)nc3c(NCCCCN3CCC(F)(F)C3)n2)c1Cl] | 6-(2,6-dichloro-3,5-dimethoxyphenyl)-N-(4-(3,3-difluoropyrrolidin-1-yl)butyl)-2-(methylthio)pyrido[3,4-d]pyrimidine-8-amine | 558 |
| 187 | 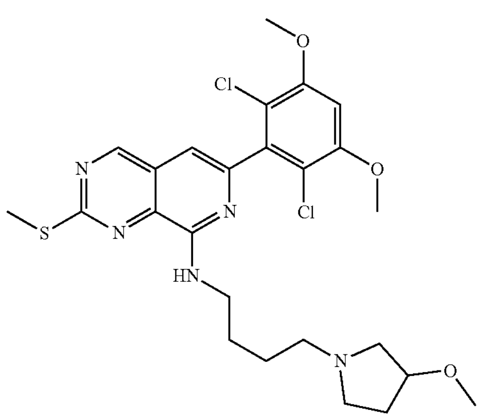 | 6-(2,6-dichloro-3,5-dimethoxyphenyl)-N-(4-(3-methoxypyrrolidin-1-yl)butyl)-2-(methylthio)pyrido[3,4-d]pyrimidine-8-amine | 552 |

-continued

| Intermediate No. | Compound name | MS: m/z [M + 1]+ |
|---|---|---|
| 188 | N-(cyclopropylmethyl)-6-(2-fluoro-3,5-dimethoxyphenyl)-2-(methylthio)pyrido[3,4-d]pyrimidine-8-amine | 401 |
| 189 | N-(cyclopropylmethyl)-6-(2-fluoro-3-methoxyphenyl)-2-(methylthio)pyrido[3,4-d]pyrimidine-8-amine | 371 |
| 190 | 6-(2-chloro-3-(methoxy-$d_3$)phenyl)-N-(cyclopropylmethyl)-2-(methylthio)pyrido[3,4-d]pyrimidine-8-amine | 390 |
| 191 | N-(cyclopropylmethyl)-6-(2-fluoro-3-(methoxy-$d_3$)phenyl)-2-(methylthio)pyrido[3,4-d]pyrimidine-8-amine | 374 |
| 192 | 6-(2-chloro-3,5-di(methoxy-$d_3$)phenyl)-N-(cyclopropylmethyl)-2-(methylthio)pyrido[3,4-d]pyrimidine-8-amine | 423 |

-continued

| Intermediate No. | Compound structure | Compound name | MS: m/z [M + 1]+ |
|---|---|---|---|
| 193 | 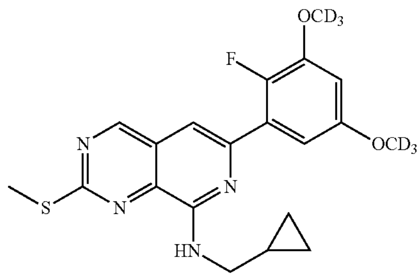 | N-(cyclopropylmethyl)-6-(2-fluoro-3,5-di(methoxy-d₃)phenyl)-2-(methylthio)pyrido[3,4-d]pyrimidine-8-amine | 407 |
| 194 | 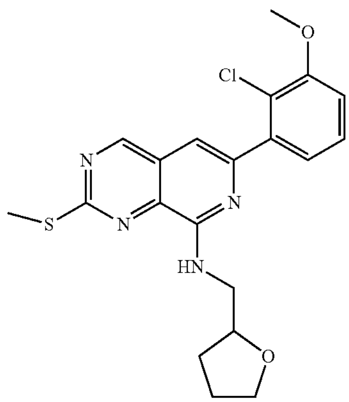 [SMILES: COc1cccc(-c2cc3cnc(SC)nc3c(NCC3CCCO3)n2)c1Cl] | 6-(2-chloro-3-methoxyphenyl)-2-(methylthio)-N-((tetrahydrofuran2-yl)methyl)pyrido[3,4-d]pyrimidine-8-amine | 417 |
| 195 | 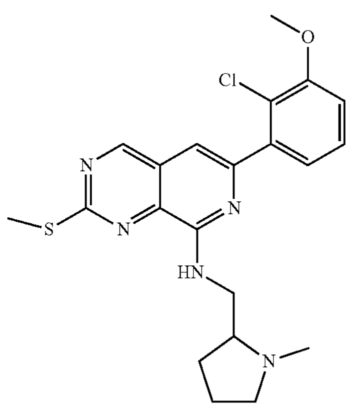 [SMILES: COc1cccc(-c2cc3cnc(SC)nc3c(NCC3CCCN3C)n2)c1Cl] | 6-(2-chloro-3-methoxyphenyl)-N-((1-methylpyrrolidin-2-yl)methyl)-2-(methylthio)pyrido[3,4-d]pyrimidine-8-amine | 430 |
| 196 | 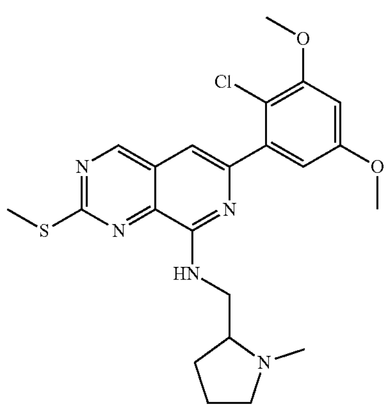 | 6-(2-chloro-3,5-dimethoxyphenyl)-N-((1-methylpyrrolidin-2-yl)methyl)-2-(methylthio)pyrido[3,4-d]pyrimidine-8-amine | 460 |

-continued

| Intermediate No. | Compound structure | Compound name | MS: m/z [M + 1]+ |
|---|---|---|---|
| 197 | 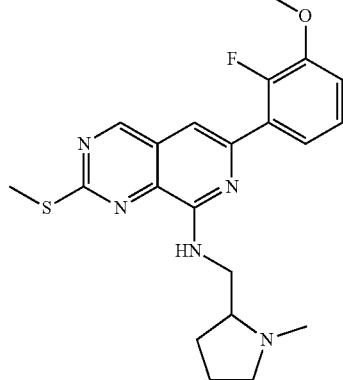 | 6-(2-fluoro-3-methoxyphenyl)-N-((1-methylpyrrolidin-2-yl)methyl)-2-(methylthio)pyrido[3,4-d]pyrimidine-8-amine | 414 |
| 198 | 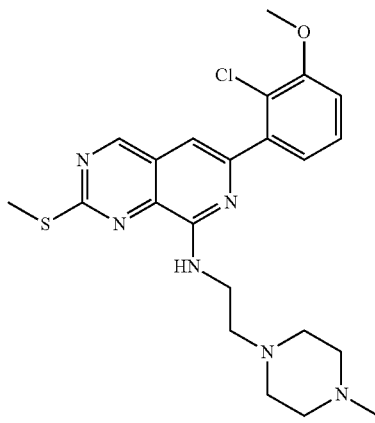 | 6-(2-chloro-3-methoxyphenyl)-N-(2-(4-methylpiperazin-1-yl)ethyl)-2-(methylthio)pyrido[3,4-d]pyrimidine-8-amine | 459 |
| 199 | 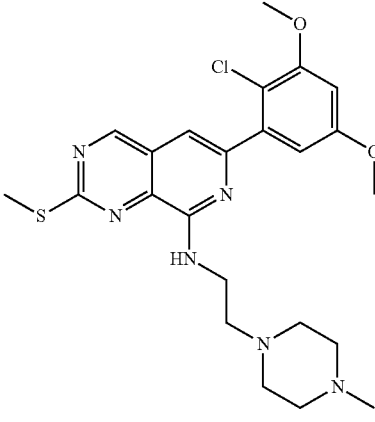 | 6-(2-chloro-3,5-dimethoxyphenyl)-N-(2-(4-methylpiperazin-1-yl)ethyl)-2-(methylthio)pyrido[3,4-d]pyrimidine-8-amine | 489 |
| 200 | 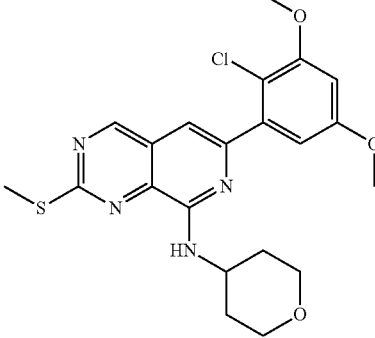 | 6-(2-chloro-3,5-dimethoxyphenyl)-2-(methylthio)-N-(tetrahydro-2H-pyran-4-yl)pyrido[3,4-d]pyrimidine-8-amine | 447 |

| Intermediate No. | Compound structure | Compound name | MS: m/z [M + 1]+ |
|---|---|---|---|
| 201 | 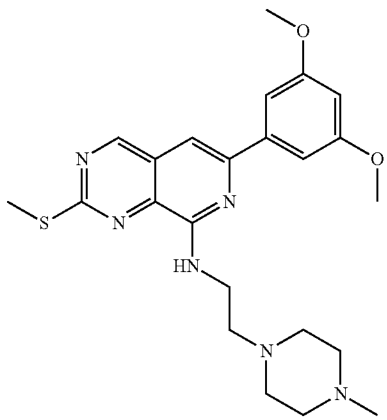 | 6-(3,5-dimethoxyphenyl)-N-(2-(4-methylpiperazin-1-yl)ethyl)-2-(methylthio)pyrido[3,4-d]pyrimidine-8-amine | 455 |
| 202 | 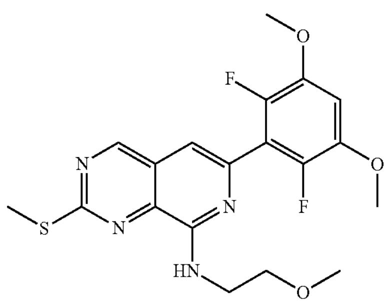 | 6-(2,6-difluoro-3,5-dimethoxyphenyl)-N-(2-methoxyethyl)-2-(methylthio)pyrido[3,4-d]pyrimidine-8-amine | 423 |
| 203 | 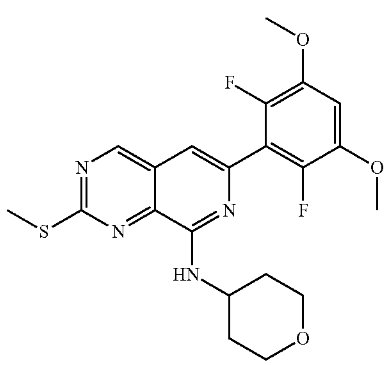 [SMILES: COc1cc(OC)c(F)c(-c2cc3cnc(SC)nc3c(NC3CCOCC3)n2)c1F] | 6-(2,6-difluoro-3,5-dimethoxyphenyl)-2-(methylthio)-N-(tetrahydro-2H-pyran-4-yl)pyrido[3,4-d]pyrimidine-8-amine | 449 |
| 204 | 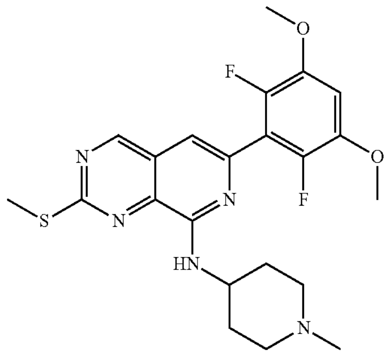 [SMILES: COc1cc(OC)c(F)c(-c2cc3cnc(SC)nc3c(NC3CCN(C)CC3)n2)c1F] | 6-(2,6-difluoro-3,5-dimethoxyphenyl)-N-(1-methylpiperidin-4-yl)-2-(methylthio)pyrido[3,4-d]pyrimidine-8-amine | 462 |

-continued

| Intermediate No. | Compound structure | Compound name | MS: m/z [M + 1]+ |
|---|---|---|---|
| 205 | 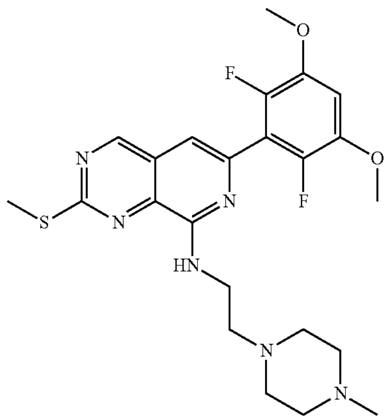 | 6-(2,6-difluoro-3,5-dimethoxyphenyl)-N-(2-(4-methylpiperazin-1-yl)ethyl)-2-(methylthio)pyrido[3,4-d]pyrimidine-8-amine | 491 |
| 206 | 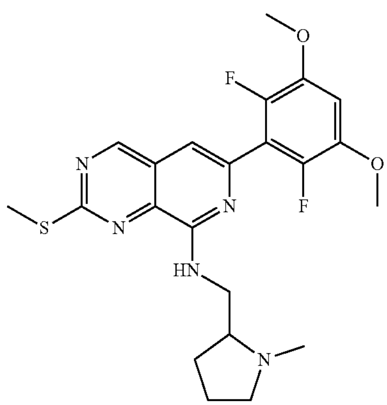 [SMILES: COc1cc(OC)c(F)c(-c2cc3cnc(SC)nc3c(NCC3CCCN3C)n2)c1F] | 6-(2,6-difluoro-3,5-dimethoxyphenyl)-N-((1-methylpyrrolidin-2-yl)methyl)-2-(methylthio)pyrido[3,4-d]pyrimidine-8-amine | 462 |
| 207 | 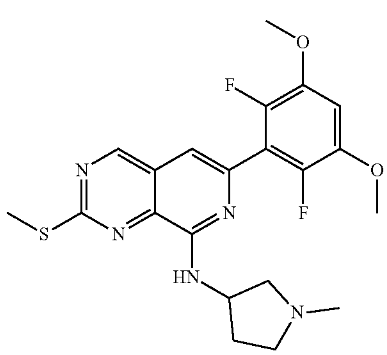 [SMILES: COc1cc(OC)c(F)c(-c2cc3cnc(SC)nc3c(NC3CCN(C)C3)n2)c1F] | 6-(2,6-difluoro-3,5-dimethoxyphenyl)-N-(1-methylpyrrolidin-3-yl)-2-(methylthio)pyrido[3,4-d]pyrimidine-8-amine | 448 |

| Intermediate No. | Compound structure | Compound name | MS: m/z [M + 1]+ |
|---|---|---|---|
| 208 | 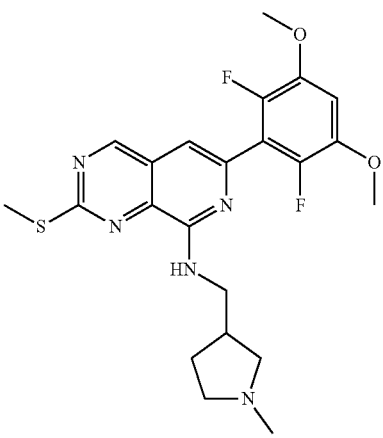 [SMILES: COc1cc(OC)c(F)c(-c2cc3cnc(SC)nc3c(NCC3CCN(C)C3)n2)c1F] | 6-(2,6-difluoro-3,5-dimethoxyphenyl)-N-((1-methylpyrrolidin-3-yl)methyl)-2-(methylthio)pyrido[3,4-d]pyrimidine-8-amine | 462 |
| 209 | 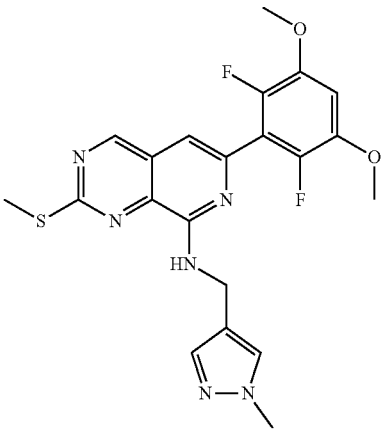 [SMILES: COc1cc(OC)c(F)c(-c2cc3cnc(SC)nc3c(NCc3cnn(C)c3)n2)c1F] | 6-(2,6-difluoro-3,5-dimethoxyphenyl)-N-((1-methyl-1H-pyrazol-4-yl)methyl)-2-(methylthio)pyrido[3,4-d]pyrimidine-8-amine | 459 |
| 210 | 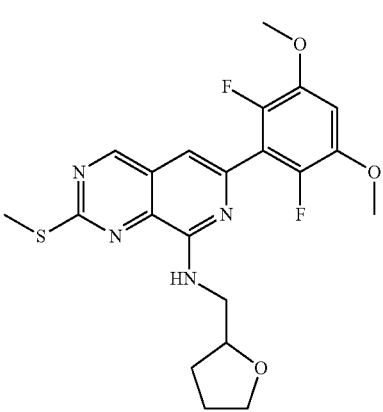 [SMILES: COc1cc(OC)c(F)c(-c2cc3cnc(SC)nc3c(NCC3CCCO3)n2)c1F] | 6-(2,6-difluoro-3,5-dimethoxyphenyl)-2-(methylthio)-N-((tetrahydrofuran2-yl)methyl)pyrido[3,4-d]pyrimidine-8-amine | 449 |

| Intermediate No. | Compound structure | Compound name | MS: m/z [M + 1]⁺ |
|---|---|---|---|
| 211 | 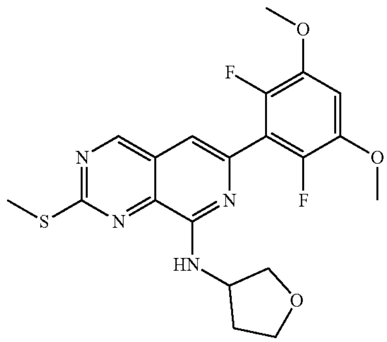 [SMILES: COc1cc(OC)c(F)c(-c2cc3cnc(SC)nc3c(NC3CCOC3)n2)c1F] | 6-(2,6-difluoro-3,5-dimethoxyphenyl)-2-(methylthio)-N-(tetrahydrofuran-3-yl)pyrido[3,4-d]pyrimidine-8-amine | 435 |
| 212 | 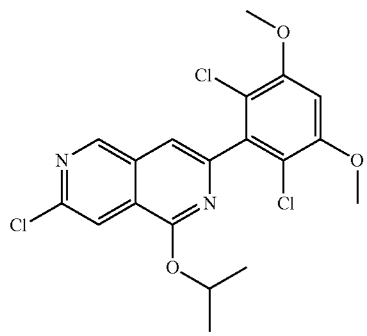 [SMILES: COc1cc(OC)c(Cl)c(-c2cc3cnc(Cl)cc3c(OC(C)C)n2)c1Cl] | 7-chloro-3-(2,6-dichloro-3,5-dimethoxyphenyl)-1-isopropyoxy-2,6-naphthyridine | 427 |
| 213 | 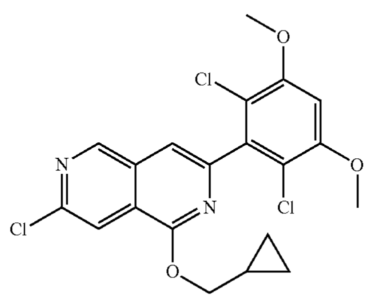 [SMILES: COc1cc(OC)c(Cl)c(-c2cc3cnc(Cl)cc3c(OCC3CC3)n2)c1Cl] | 7-chloro-1-(cyclopropylmethoxy)-3-(2,6-dichloro-3,5-dimethoxyphenyl)-2,6-naphthyridine | 439 |
| 214 | 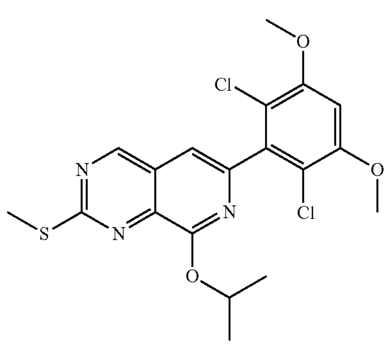 | 6-(2,6-dichloro-3,5-dimethoxyphenyl)-8-isopropyoxy-2-(methylthio)pyrido[3,4-d]pyrimidine | 440 |

-continued

| Intermediate No. | Compound structure | Compound name | MS: m/z [M + 1]+ |
|---|---|---|---|
| 215 | 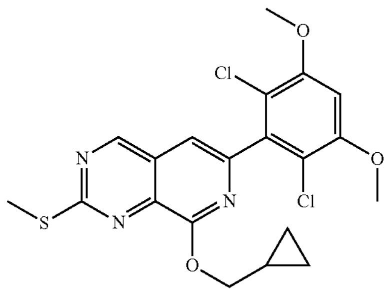 [SMILES: COc1cc(OC)c(Cl)c(-c2cc3cnc(SC)nc3c(OCC3CC3)n2)c1Cl] | 8-(cyclopropylmethoxy)-6-(2,6-dichloro-3,5-dimethoxyphenyl)-2-(methylthio)pyrido[3,4-d]pyrimidine | 452 |
| 216 | 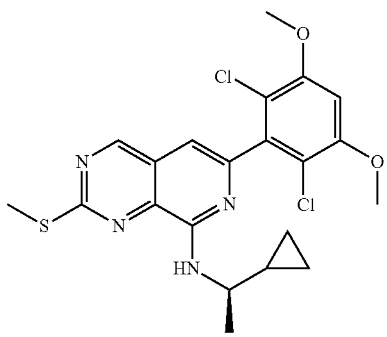 [SMILES: COc1cc(OC)c(Cl)c(-c2cc3cnc(SC)nc3c(N[C@H](C)C3CC3)n2)c1Cl] | (R)-N-(1-cyclopropylethyl)-6-(2,6-dichloro-3,5-dimethoxyphenyl)-2-(methylthio)pyrido[3,4-d]pyrimidine-8-amine | 465 |
| 217 | 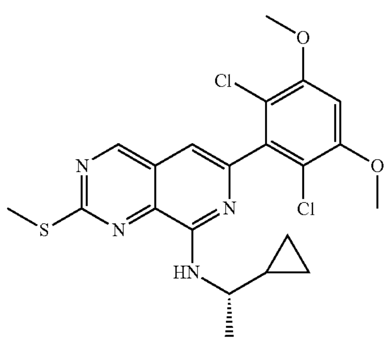 [SMILES: COc1cc(OC)c(Cl)c(-c2cc3cnc(SC)nc3c(N[C@@H](C)C3CC3)n2)c1Cl] | (S)-N-(1-cyclopropylethyl)-6-(2,6-dichloro-3,5-dimethoxyphenyl)-2-(methylthio)pyrido[3,4-d]pyrimidine-8-amine | 465 |
| 218 | 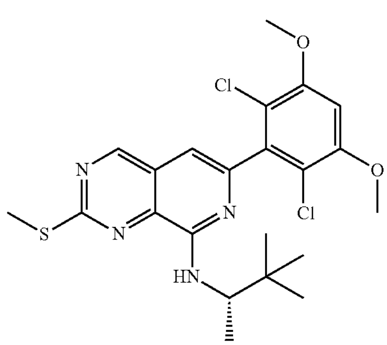 [SMILES: COc1cc(OC)c(Cl)c(-c2cc3cnc(SC)nc3c(N[C@@H](C)C(C)(C)C)n2)c1Cl] | (S)-6-(2,6-dichloro-3,5-dimethoxyphenyl)-N-(3,3-dimethylbut-2-yl)-2-(methylthio)pyrido[3,4-d]pyrimidine-8-amine | 481 |

-continued

| Intermediate No. | Compound structure | Compound name | MS: m/z [M + 1]+ |
|---|---|---|---|
| 219 | 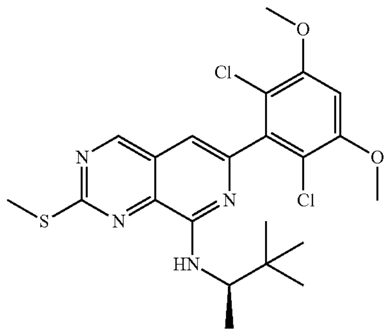 [SMILES: COc1cc(OC)c(Cl)c(-c2cc3cnc(SC)nc3c(N[C@H](C)C(C)(C)C)n2)c1Cl] | (R)-6-(2,6-dichloro-3,5-dimethoxyphenyl)-N-(3,3-dimethylbut-2-yl)-2-(methylthio)pyrido[3,4-d]pyrimidine-8-amine | 481 |
| 220 | 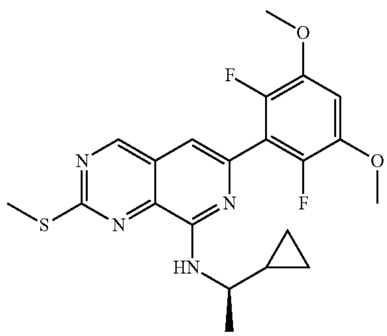 [SMILES: COc1cc(OC)c(F)c(-c2cc3cnc(SC)nc3c(N[C@H](C)C3CC3)n2)c1F] | (R)-N-(1-cyclopropylethyl)-6-(2,6-difluoro-3,5-dimethoxyphenyl)-2-(methylthio)pyrido[3,4-d]pyrimidine-8-amine | 433 |
| 221 | 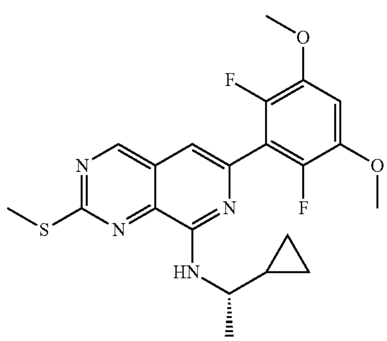 [SMILES: COc1cc(OC)c(F)c(-c2cc3cnc(SC)nc3c(N[C@@H](C)C3CC3)n2)c1F] | (S)-N-(1-cyclopropylethyl)-6-(2,6-difluoro-3,5-dimethoxyphenyl)-2-(methylthio)pyrido[3,4-d]pyrimidine-8-amine | 433 |
| 222 | 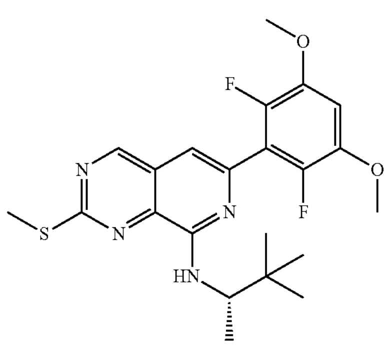 [SMILES: COc1cc(OC)c(F)c(-c2cc3cnc(SC)nc3c(N[C@@H](C)C(C)(C)C)n2)c1F] | (S)-6-(2,6-difluoro-3,5-dimethoxyphenyl)-N-(3,3-dimethylbut-2-yl)-2-(methylthio)pyrido[3,4-d]pyrimidine-8-amine | 449 |

-continued

| Intermediate No. | Compound structure | Compound name | MS: m/z [M + 1]+ |
|---|---|---|---|
| 223 | 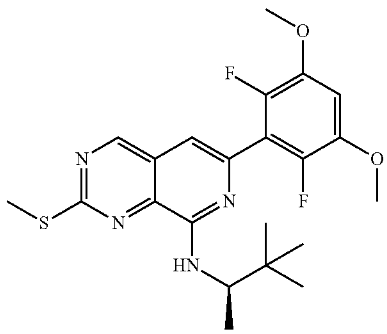 [SMILES: COc1cc(OC)c(F)c(-c2cc3cnc(SC)nc3c(N[C@H](C)C(C)(C)C)n2)c1F] | (R)-6-(2,6-difluoro-3,5-dimethoxyphenyl)-N-(3,3-dimethylbut-2-yl)-2-(methylthio)pyrido[3,4-d]pyrimidine-8-amine | 449 |
| 224 | 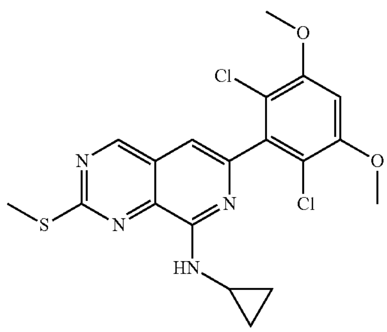 | N-cyclopropyl-6-(2,6-dichloro-3,5-dimethoxyphenyl)-2-(methylthio)pyrido[3,4-d]pyrimidine-8-amine | 437 |
| 225 | 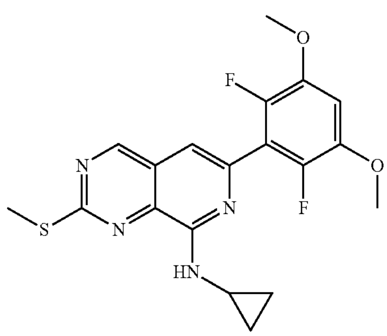 [SMILES: COc1cc(OC)c(F)c(-c2cc3cnc(SC)nc3c(NC3CC3)n2)c1F] | N-cyclopropyl-6-(2,6-difluoro-3,5-dimethoxyphenyl)-2-(methylthio)pyrido[3,4-d]pyrimidine-8-amine | 405 |
| 226 | 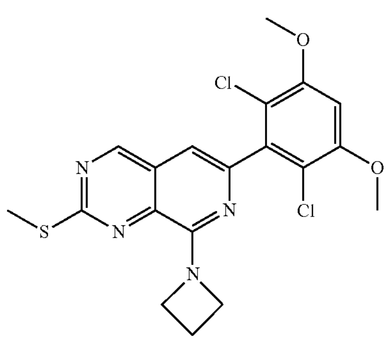 [SMILES: COc1cc(OC)c(Cl)c(-c2cc3cnc(SC)nc3c(N3CCC3)n2)c1Cl] | 8-(azetidin-1-yl)-6-(2,6-dichloro-3,5-dimethoxyphenyl)-2-(methylthio)pyrido[3,4-d]pyrimidine | 437 |

-continued

| Intermediate No. | Compound structure | Compound name | MS: m/z [M + 1]+ |
|---|---|---|---|
| 227 | 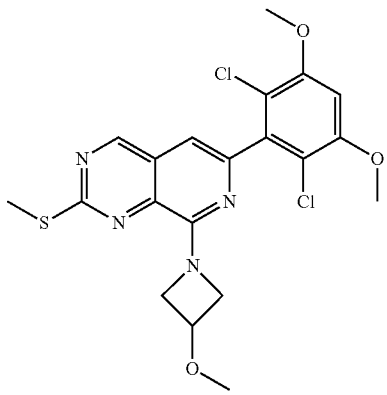 [SMILES: COc1cc(OC)c(Cl)c(-c2cc3cnc(SC)nc3c(N3CC(OC)C3)n2)c1Cl] | 6-(2,6-dichloro-3,5-dimethoxyphenyl)-8-(3-methoxyazetidin-1-yl)-2-(methylthio)pyrido[3,4-d]pyrimidine | 467 |
| 228 | 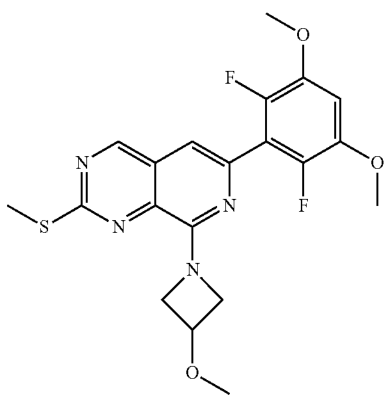 [SMILES: COc1cc(OC)c(F)c(-c2cc3cnc(SC)nc3c(N3CC(OC)C3)n2)c1F] | 6-(2,6-difluoro-3,5-dimethoxyphenyl)-8-(3-methoxyazetidin-1-yl)-2-(methylsulfanyl)pyrido[3,4-d]pyrimidine | 435 |
| 229 | 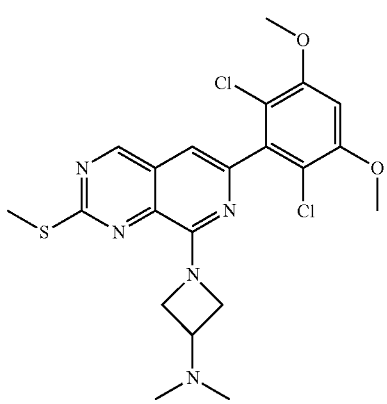 [SMILES: COc1cc(OC)c(Cl)c(-c2cc3cnc(SC)nc3c(N3CC(N(C)C)C3)n2)c1Cl] | 1-(6-(2,6-dichloro-3,5-dimethoxyphenyl)-2-(methylthio)pyrido[3,4-d]pyrimidin-8-yl)-N,N-dimethylazetidin-3-amine | 480 |
| 230 | 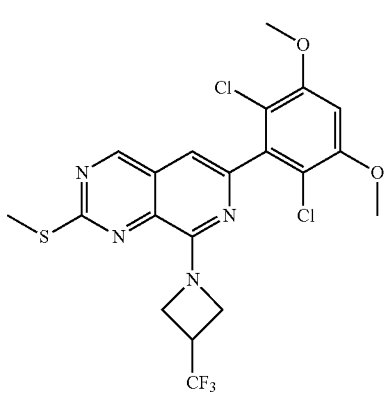 [SMILES: COc1cc(OC)c(Cl)c(-c2cc3cnc(SC)nc3c(N3CC(C(F)(F)F)C3)n2)c1Cl] | 6-(2,6-dichloro-3,5-dimethoxyphenyl)-2-(methylthio)-8-(3-(trifluoromethyl)azetidin-1-yl)pyrido[3,4-d]pyrimidine | 505 |

| Intermediate No. | Compound name | MS: m/z [M + 1]+ |
|---|---|---|
| 231 | 6-(2,6-dichloro-3,5-dimethoxyphenyl)-8-(3,3-dimethylazetidin-1-yl)-2-(methylthio)pyrido[3,4-d]pyrimidine | 465 |
| 232 | 6-(2,6-dichloro-3,5-dimethoxyphenyl)-8-(3,3-difluoroazetidin-1-yl)-2-(methylthio)pyrido[3,4-d]pyrimidine | 473 |
| 233 | 1-(6-(2,6-dichloro-3,5-dimethoxyphenyl)-2-(methylthio)pyrido[3,4-d]pyrimidin-8-yl)-3-methylazetidin-3-ol | 467 |
| 234 | 6-(2,6-dichloro-3,5-dimethoxyphenyl)-8-(3-methoxy-3-methylazetidin-1-yl)-2-(methylthio)pyrido[3,4-d]pyrimidine | 481 |

| Intermediate No. | Compound structure | Compound name | MS: m/z [M + 1]+ |
|---|---|---|---|
| 235 | 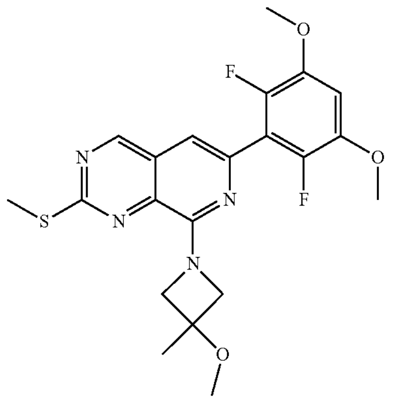 [SMILES: COc1cc(OC)c(F)c(-c2cc3cnc(SC)nc3c(N3CC(C)(OC)C3)n2)c1F] | 6-(2,6-difluoro-3,5-dimethoxyphenyl)-8-(3-methoxy-3-methylazetidin-1-yl)-2-(methylthio)pyrido[3,4-d]pyrimidine | 449 |
| 236 | 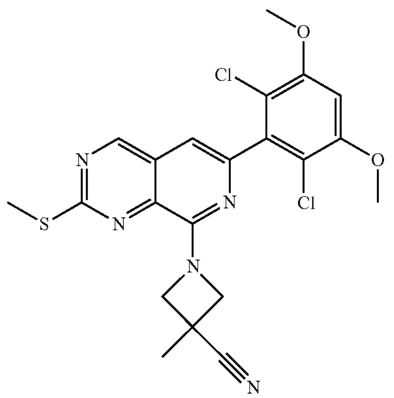 [SMILES: COc1cc(OC)c(Cl)c(-c2cc3cnc(SC)nc3c(N3CC(C)(C#N)C3)n2)c1Cl] | 1-(6-(2,6-dichloro-3,5-dimethoxyphenyl)-2-(methylthio)pyrido[3,4-d]pyrimidin-8-yl)-3-methylazetidin-3-carbonitrile | 476 |
| 237 | 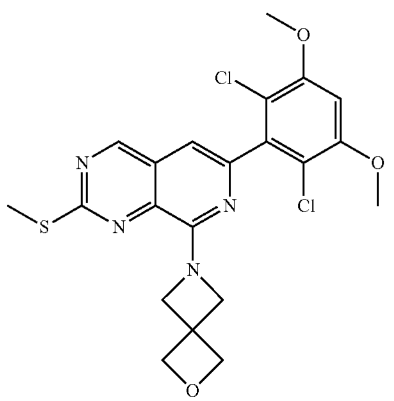 [SMILES: COc1cc(OC)c(Cl)c(-c2cc3cnc(SC)nc3c(N3CC4(COC4)C3)n2)c1Cl] | 6-(6-(2,6-dichloro-3,5-dimethoxyphenyl)-2-(methylthio)pyrido[3,4-d]pyrimidin-8-yl)-2-oxa-6-azaspiro[3.3]heptane | 479 |
| 238 | 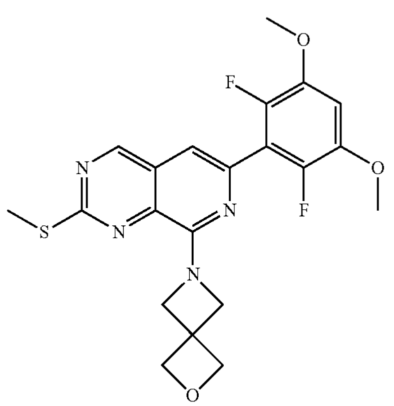 [SMILES: COc1cc(OC)c(F)c(-c2cc3cnc(SC)nc3c(N3CC4(COC4)C3)n2)c1F] | 6-(6-(2,6-difluoro-3,5-dimethoxyphenyl)-2-(methylthio)pyrido[3,4-d]pyrimidin-8-yl)-2-oxa-6-azaspiro[3.3]heptane | 447 |

-continued

| Intermediate No. | Compound structure | Compound name | MS: m/z [M + 1]+ |
|---|---|---|---|
| 239 | 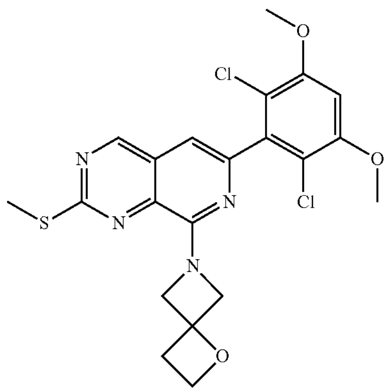 [SMILES: COc1cc(OC)c(Cl)c(-c2cc3cnc(SC)nc3c(N3CC4(CCO4)C3)n2)c1Cl] | 6-(6-(2,6-dichloro-3,5-dimethoxyphenyl)-2-(methylthio)pyrido[3,4-d]pyrimidin-8-yl)-1-oxa-6-azaspiro[3.3]heptane | 479 |
| 240 | 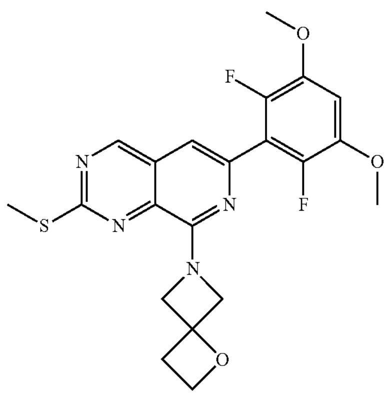 [SMILES: COc1cc(OC)c(F)c(-c2cc3cnc(SC)nc3c(N3CC4(CCO4)C3)n2)c1F] | 6-(6-(2,6-difluoro-3,5-dimethoxyphenyl)-2-(methylthio)pyrido[3,4-d]pyrimidin-8-yl)-1-oxa-6-azaspiro[3.3]heptane | 447 |
| 241 | 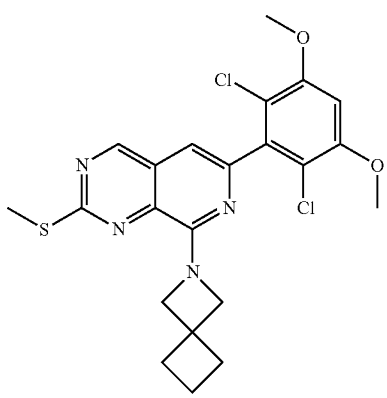 [SMILES: COc1cc(OC)c(Cl)c(-c2cc3cnc(SC)nc3c(N3CC4(CCC4)C3)n2)c1Cl] | 6-(2,6-dichloro-3,5-dimethoxyphenyl)-2-(methylthio)-8-(2-azaspiro[3.3]hept-2-yl)pyrido[3,4-d]pyrimidine | 477 |
| 242 | 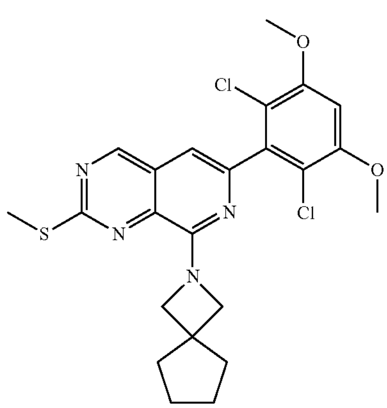 [SMILES: COc1cc(OC)c(Cl)c(-c2cc3cnc(SC)nc3c(N3CC4(CCCC4)C3)n2)c1Cl] | 6-(2,6-dichloro-3,5-dimethoxyphenyl)-2-(methylthio)-8-(2-azaspiro[3.4]oct-2-yl)pyrido[3,4-d]pyrimidine | 491 |

-continued

| Intermediate No. | Compound structure | Compound name | MS: m/z [M + 1]+ |
|---|---|---|---|
| 243 | 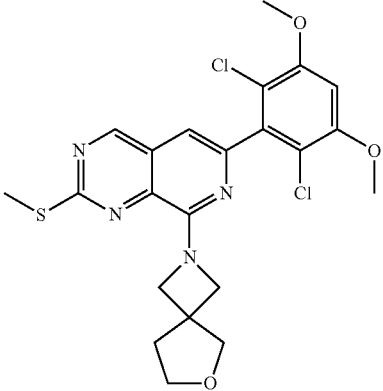 [SMILES: COc1cc(OC)c(Cl)c(-c2cc3cnc(SC)nc3c(N3CC4(CCOC4)C3)n2)c1Cl] | 2-(6-(2,6-dichloro-3,5-dimethoxyphenyl)-2-(methylthio)pyrido[3,4-d]pyrimidin-8-yl)-6-oxa-2-azaspiro[3.4]octane | 493 |
| 244 | 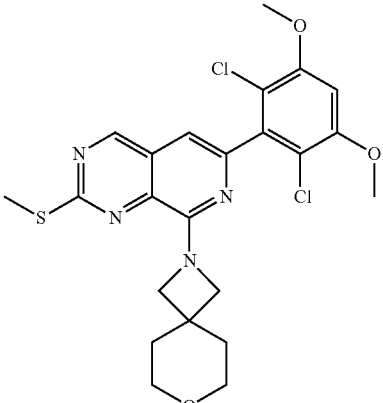 | 2-(6-(2,6-dichloro-3,5-dimethoxyphenyl)-2-(methylthio)pyrido[3,4-d]pyrimidin-8-yl)-7-oxa-2-azaspiro[3.5]nonane | 507 |
| 245 | 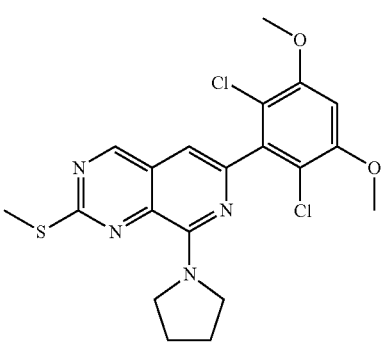 [SMILES: COc1cc(OC)c(Cl)c(-c2cc3cnc(SC)nc3c(N3CCCC3)n2)c1Cl] | 6-(2,6-dichloro-3,5-dimethoxyphenyl)-2-(methylthio)-8-(pyrrolidin-1-yl)pyrido[3,4-d]pyrimidine | 451 |
| 246 | 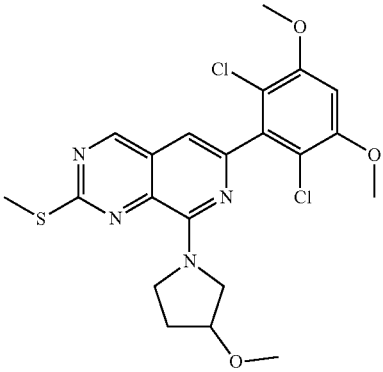 [SMILES: COc1cc(OC)c(Cl)c(-c2cc3cnc(SC)nc3c(N3CCC(OC)C3)n2)c1Cl] | 6-(2,6-dichloro-3,5-dimethoxyphenyl)-8-(3-methoxypyrrolidin-1-yl)-2-(methylthio)pyrido[3,4-d]pyrimidine | 481 |

| Intermediate No. | Compound structure | Compound name | MS: m/z [M + 1]+ |
|---|---|---|---|
| 247 | 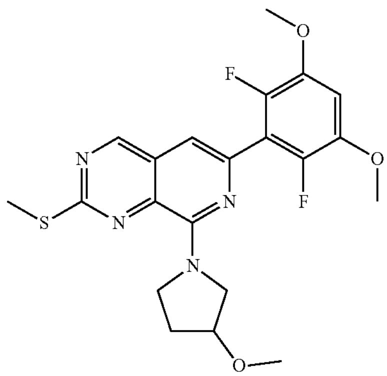 [SMILES: COc1cc(OC)c(F)c(-c2cc3cnc(SC)nc3c(N3CCC(OC)C3)n2)c1F] | 6-(2,6-difluoro-3,5-dimethoxyphenyl)-8-(3-methoxypyrrolidin-1-yl)-2-(methylthio)pyrido[3,4-d]pyrimidine | 449 |
| 248 | 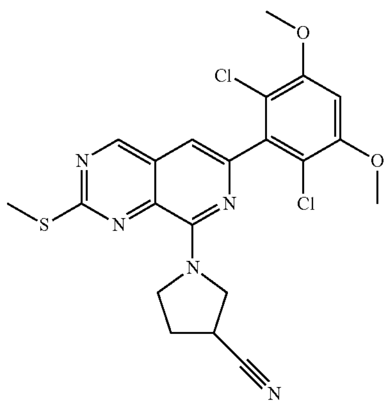 [SMILES: COc1cc(OC)c(Cl)c(-c2cc3cnc(SC)nc3c(N3CCC(C#N)C3)n2)c1Cl] | 1-(6-(2,6-dichloro-3,5-dimethoxyphenyl)-2-(methylthio)pyrido[3,4-d]pyrimidin-8-yl)pyrrolidine-3-carbonitrile | 476 |
| 249 | 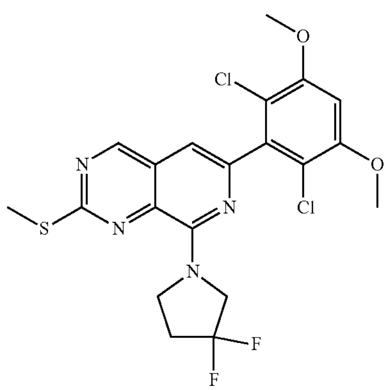 [SMILES: COc1cc(OC)c(Cl)c(-c2cc3cnc(SC)nc3c(N3CCC(F)(F)C3)n2)c1Cl] | 6-(2,6-dichloro-3,5-dimethoxyphenyl)-8-(3,3-difluoropyrrolidin-1-yl)-2-(methylthio)pyrido[3,4-d]pyrimidine | 487 |
| 250 | 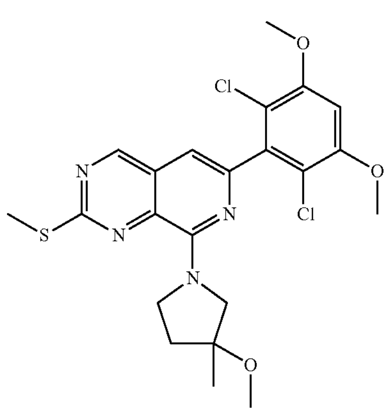 [SMILES: COc1cc(OC)c(Cl)c(-c2cc3cnc(SC)nc3c(N3CCC(C)(OC)C3)n2)c1Cl] | 6-(2,6-dichloro-3,5-dimethoxyphenyl)-8-(3-methoxy-3-methylpyrrolidin-1-yl)-2-(methylthio)pyrido[3,4-d]pyrimidine | 495 |

| Intermediate No. | Compound structure | Compound name | MS: m/z [M + 1]+ |
| --- | --- | --- | --- |
| 251 | 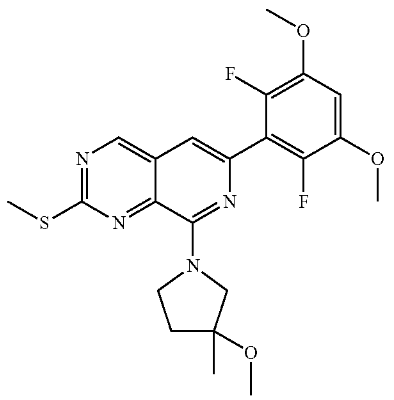 [SMILES: COc1cc(OC)c(F)c(-c2cc3cnc(SC)nc3c(N3CCC(C)(OC)C3)n2)c1F] | 6-(2,6-difluoro-3,5-dimethoxyphenyl)-8-(3-methoxy-3-methylpyrrolidin-1-yl)-2-(methylthio)pyrido[3,4-d]pyrimidine | 463 |
| 252 | 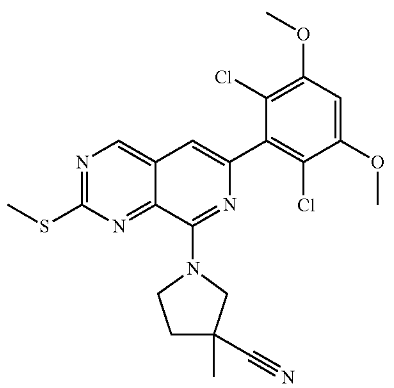 [SMILES: COc1cc(OC)c(Cl)c(-c2cc3cnc(SC)nc3c(N3CCC(C)(C#N)C3)n2)c1Cl] | 1-(6-(2,6-dichloro-3,5-dimethoxyphenyl)-2-(methylthio)pyrido[3,4-d]pyrimidin-8-yl)-3-methylpyrrolidine-3-carbonitrile | 490 |
| 253 | 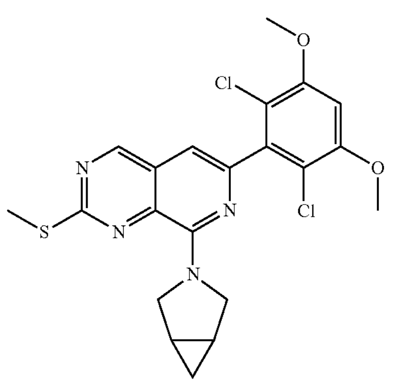 [SMILES: COc1cc(OC)c(Cl)c(-c2cc3cnc(SC)nc3c(N3CC4CC4C3)n2)c1Cl] | 8-(3-azabicyclo[3.1.0]hex-3-yl)-6-(2,6-dichloro-3,5-dimethoxyphenyl)-2-(methylthio)pyrido[3,4-d]pyrimidine | 463 |
| 254 | 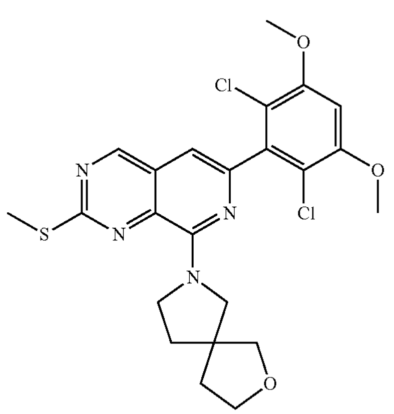 [SMILES: COc1cc(OC)c(Cl)c(-c2cc3cnc(SC)nc3c(N3CCC4(CCOC4)C3)n2)c1Cl] | 7-(6-(2,6-dichloro-3,5-dimethoxyphenyl)-2-(methylthio)pyrido[3,4-d]pyrimidin-8-yl)-2-oxa-7-azaspiro[34.4]nonane | 507 |

| Intermediate No. | Compound structure | Compound name | MS: m/z [M + 1]+ |
|---|---|---|---|
| 255 | 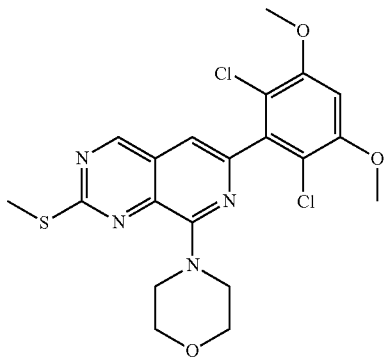 | 4-(6-(2,6-dichloro-3,5-dimethoxyphenyl)-2-(methylthio)pyrido[3,4-d]pyrimidin-8-yl)morpholine | 467 |
| 256 | 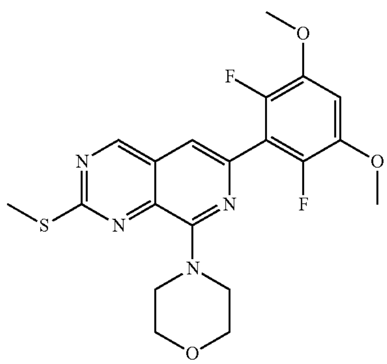 | 4-(6-(2,6-difluoro-3,5-dimethoxyphenyl)-2-(methylthio)pyrido[3,4-d]pyrimidin-8-yl)morpholine | 435 |
| 257 | 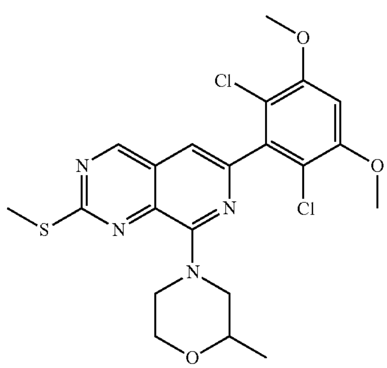 | 4-(6-(2,6-dichloro-3,5-dimethoxyphenyl)-2-(methylsulfanyl)pyrido[3,4-d]pyrimidin-8-yl)-2-methylmorpholine | 481 |
| 258 | 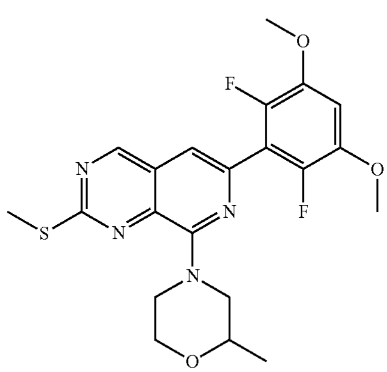 [SMILES: COc1cc(OC)c(F)c(-c2cc3cnc(SC)nc3c(N3CCOC(C)C3)n2)c1F] | 4-(6-(2,6-difluoro-3,5-dimethoxyphenyl)-2-(methylthio)pyrido[3,4-d]pyrimidin-8-yl)-2-methylmorpholine | 449 |

-continued

| Intermediate No. | Compound structure | Compound name | MS: m/z [M + 1]+ |
|---|---|---|---|
| 259 | 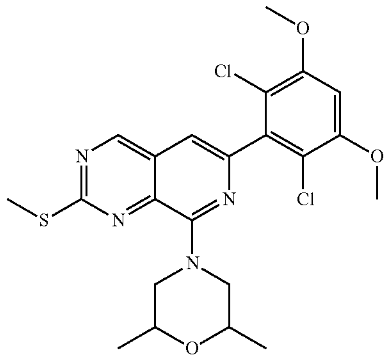 [SMILES: COc1cc(OC)c(Cl)c(-c2cc3cnc(SC)nc3c(N3CC(C)OC(C)C3)n2)c1Cl] | 4-(6-(2,6-dichloro-3,5-dimethoxyphenyl)-2-(methylthio)pyrido[3,4-d]pyrimidin-8-yl)-2,6-dimethylmorpholine | 495 |
| 260 | 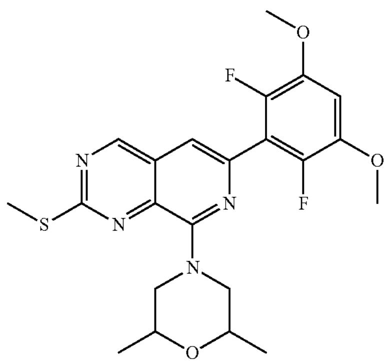 [SMILES: COc1cc(OC)c(F)c(-c2cc3cnc(SC)nc3c(N3CC(C)OC(C)C3)n2)c1F] | 4-(6-(2,6-difluoro-3,5-dimethoxyphenyl)-2-(methylthio)pyrido[3,4-d]pyrimidin-8-yl)-2,6-dimethylmorpholine | 463 |
| 261 | 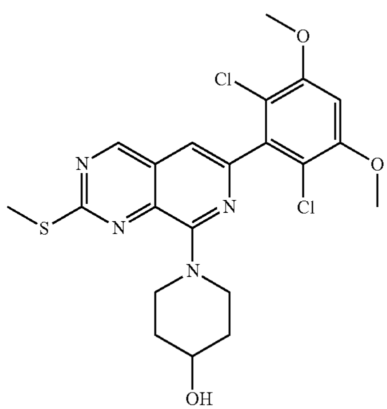 [SMILES: COc1cc(OC)c(Cl)c(-c2cc3cnc(SC)nc3c(N3CCC(O)CC3)n2)c1Cl] | 1-(6-(2,6-dichloro-3,5-dimethoxyphenyl)-2-(methylthio)pyrido[3,4-d]pyrimidin-8-yl)piperidin-4-ol | 481 |
| 262 | 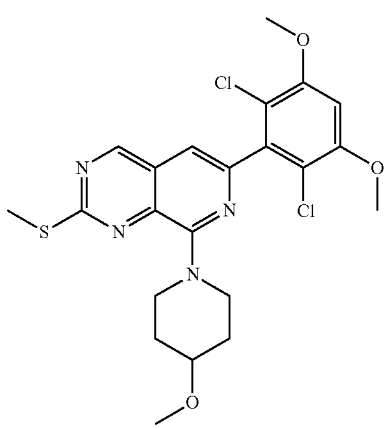 [SMILES: COc1cc(OC)c(Cl)c(-c2cc3cnc(SC)nc3c(N3CCC(OC)CC3)n2)c1Cl] | 6-(2,6-dichloro-3,5-dimethoxyphenyl)-8-(4-methoxypiperidin-1-yl)-2-(methylthio)pyrido[3,4-d]pyrimidine | 495 |

-continued

| Intermediate No. | Compound structure | Compound name | MS: m/z [M + 1]+ |
| --- | --- | --- | --- |
| 263 | 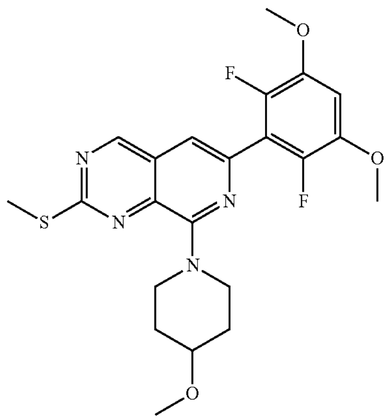 [SMILES: COc1cc(OC)c(F)c(-c2cc3cnc(SC)nc3c(N3CCC(OC)CC3)n2)c1F] | 6-(2,6-difluoro-3,5-dimethoxyphenyl)-8-(4-methoxypiperidin-1-yl)-2-(methylthio)pyrido[3,4-d]pyrimidine | 463 |
| 264 | 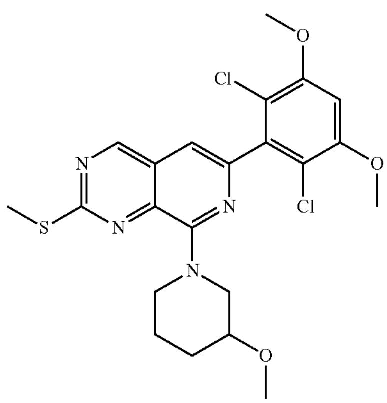 [SMILES: COc1cc(OC)c(Cl)c(-c2cc3cnc(SC)nc3c(N3CCCC(OC)C3)n2)c1Cl] | 6-(2,6-dichloro-3,5-dimethoxyphenyl)-8-(3-methoxypiperidin-1-yl)-2-(methylthio)pyrido[3,4-d]pyrimidine | 495 |
| 265 | 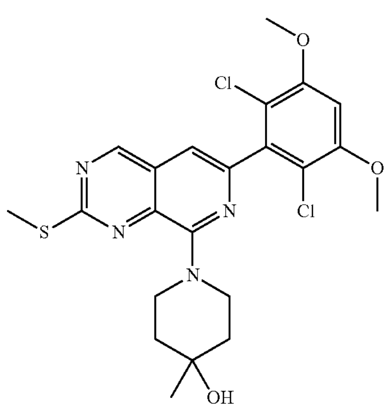 [SMILES: COc1cc(OC)c(Cl)c(-c2cc3cnc(SC)nc3c(N3CCC(C)(O)CC3)n2)c1Cl] | 1-(6-(2,6-dichloro-3,5-dimethoxyphenyl)-2-(methylthio)pyrido[3,4-d]pyrimidin-8-yl)-4-methylpiperidin-4-ol | 495 |

-continued

| Intermediate No. | Compound structure | Compound name | MS: m/z [M + 1]+ |
|---|---|---|---|
| 266 | 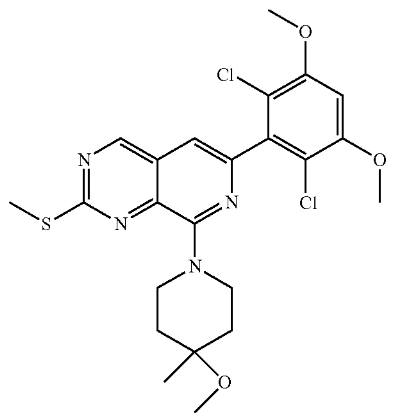 [SMILES: COc1cc(OC)c(Cl)c(-c2cc3cnc(SC)nc3c(N3CCC(C)(OC)CC3)n2)c1Cl] | 6-(2,6-dichloro-3,5-dimethoxyphenyl)-8-(4-methoxy-4-methylpiperidin-1-yl)-2-(methylthio)pyrido[3,4-d]pyrimidine | 509 |
| 267 | 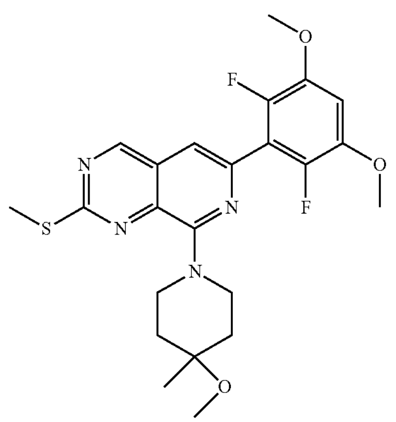 [SMILES: COc1cc(OC)c(F)c(-c2cc3cnc(SC)nc3c(N3CCC(C)(OC)CC3)n2)c1F] | 6-(2,6-difluoro-3,5-dimethoxyphenyl)-8-(4-methoxy-4-methylpiperidin-1-yl)-2-(methylthio)pyrido[3,4-d]pyrimidine | 477 |
| 268 | 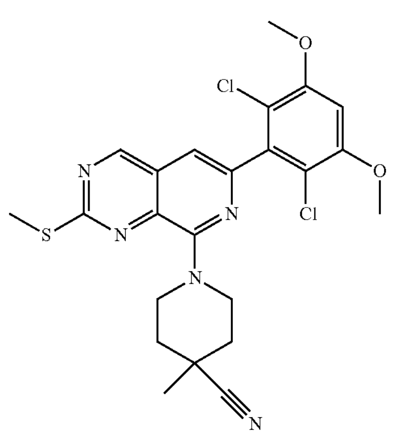 [SMILES: COc1cc(OC)c(Cl)c(-c2cc3cnc(SC)nc3c(N3CCC(C)(C#N)CC3)n2)c1Cl] | 1-(6-(2,6-dichloro-3,5-dimethoxyphenyl)-2-(methylthio)pyrido[3,4-d]pyrimidin-8-yl)-4-methylpiperidine-4-carbonitrile | 504 |

-continued

| Intermediate No. | Compound structure | Compound name | MS: m/z [M + 1]+ |
|---|---|---|---|
| 269 | 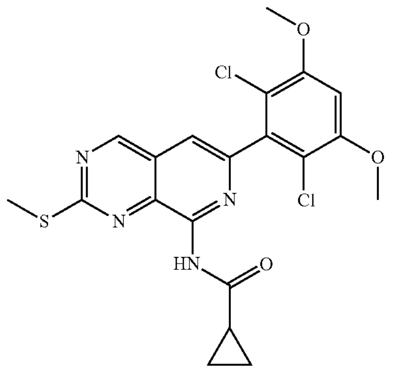 [SMILES: COc1cc(OC)c(Cl)c(-c2cc3cnc(SC)nc3c(NC(=O)C3CC3)n2)c1Cl] | N-(6-(2,6-dichloro-3,5-dimethoxyphenyl)-2-(methylthio)pyrido[3,4-d]pyrimidin-8-yl)cyclopropyl carboxamide | 465 |
| 270 | 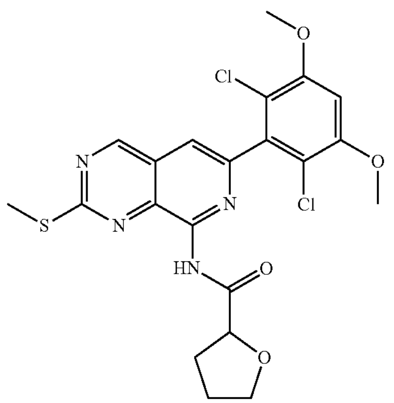 [SMILES: COc1cc(OC)c(Cl)c(-c2cc3cnc(SC)nc3c(NC(=O)C3CCCO3)n2)c1Cl] | N-(6-(2,6-dichloro-3,5-dimethoxyphenyl)-2-(methylthio)pyrido[3,4-d]pyrimidin-8-yl)tetrahydrofuran2-carboxamide | 495 |
| 271 | 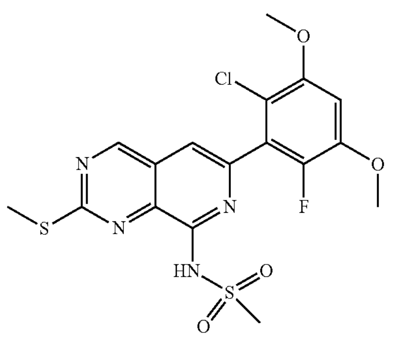 [SMILES: COc1cc(OC)c(Cl)c(-c2cc3cnc(SC)nc3c(NS(C)(=O)=O)n2)c1F] | N-(6-(2,6-dichloro-3,5-dimethoxyphenyl)-2-(methylthio)pyrido[3,4-d]pyrimidin-8-yl)sulfonamide | 475 |
| 272 | 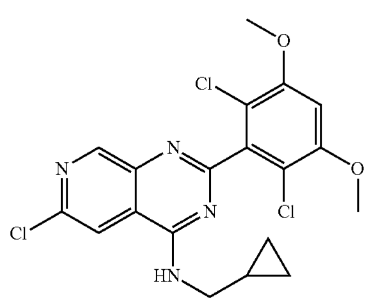 | 6-chloro-N-(cyclopropylmethyl)-2-(2,6-dichloro-3,5-dimethoxyphenyl)pyrido[3,4-d]pyrimidine-4-amine | 439 |

-continued

| Intermediate No. | Compound structure | Compound name | MS: m/z [M + 1]+ |
|---|---|---|---|
| 273 | 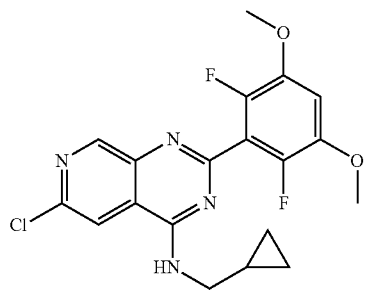 [SMILES: COc1cc(OC)c(F)c(-c2nc(NCC3CC3)c3cc(Cl)ncc3n2)c1F] | 6-chloro-N-(cyclopropylmethyl)-2-(2,6-difluoro-3,5-dimethoxyphenyl)pyrido[3,4-d]pyrimidine-4-amine | 407 |
| 274 | 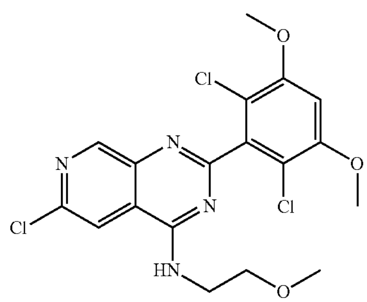 [SMILES: COCCNc1nc(-c2c(Cl)c(OC)cc(OC)c2Cl)nc2cnc(Cl)cc12] | 6-chloro-2-(2,6-dichloro-3,5-dimethoxyphenyl)-N-(2-methoxyethyl)pyrido[3,4-d]pyrimidine-4-amine | 443 |
| 275 | 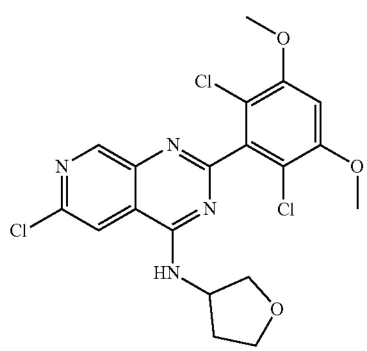 [SMILES: COc1cc(OC)c(Cl)c(-c2nc(NC3CCOC3)c3cc(Cl)ncc3n2)c1Cl] | 6-chloro-2-(2,6-dichloro-3,5-dimethoxyphenyl)-N-(tetrahydrofuran-3-yl)pyrido[3,4-d]pyrimidine-4-amine | 455 |
| 276 | 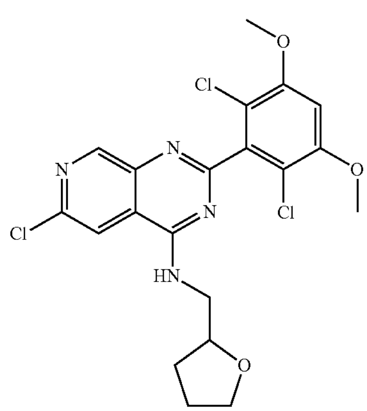 [SMILES: COc1cc(OC)c(Cl)c(-c2nc(NCC3CCCO3)c3cc(Cl)ncc3n2)c1Cl] | 6-chloro-2-(2,6-dichloro-3,5-dimethoxyphenyl)-N-((tetrahydrofuran-2-yl)methyl)pyrido[3,4-d]pyrimidine-4-amine | 469 |

-continued

| Intermediate No. | Compound structure | Compound name | MS: m/z [M + 1]+ |
|---|---|---|---|
| 277 | 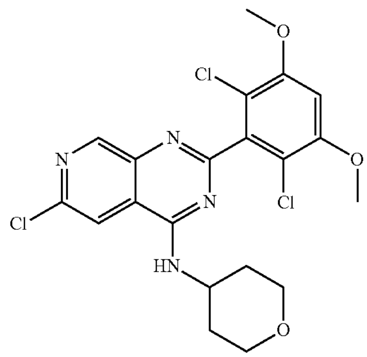 [SMILES: COc1cc(OC)c(Cl)c(-c2nc(NC3CCOCC3)c3cc(Cl)ncc3n2)c1Cl] | 6-chloro-2-(2,6-dichloro-3,5-dimethoxyphenyl)-N-(tetrahydro-2H-pyran-4-yl)pyrido[3,4-d]pyrimidine-4-amine | 469 |
| 278 | 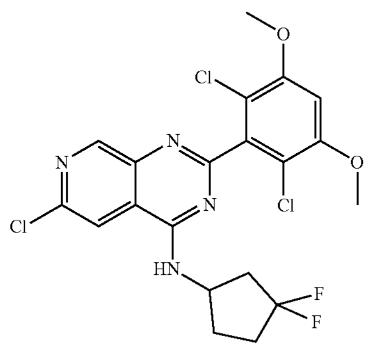 [SMILES: COc1cc(OC)c(Cl)c(-c2nc(NC3CCC(F)(F)C3)c3cc(Cl)ncc3n2)c1Cl] | 6-chloro-2-(2,6-dichloro-3,5-dimethoxyphenyl)-N-(3,3-difluorocyclopentyl)pyrido[3,4-d]pyrimidine-4-amine | 489 |
| 279 | 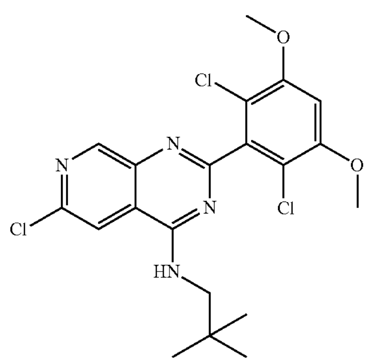 [SMILES: COc1cc(OC)c(Cl)c(-c2nc(NCC(C)(C)C)c3cc(Cl)ncc3n2)c1Cl] | 6-chloro-2-(2,6-dichloro-3,5-dimethoxyphenyl)-N-neopentylpyrido[3,4-d]pyrimidine-4-amine | 455 |
| 280 | 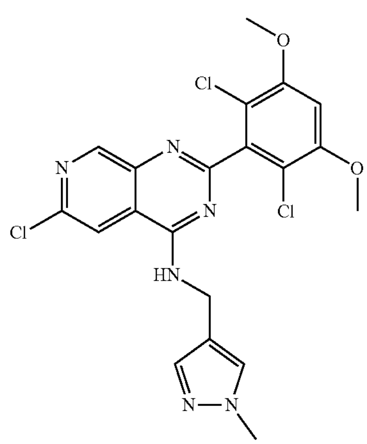 [SMILES: COc1cc(OC)c(Cl)c(-c2nc(NCc3cnn(C)c3)c3cc(Cl)ncc3n2)c1Cl] | 6-chloro-2-(2,6-dichloro-3,5-dimethoxyphenyl)-N-((1-methyl-1H-pyrazol-4-yl)methyl)pyrido[3,4-d]pyrimidine-4-amine | 479 |

-continued

| Intermediate No. | Compound structure | Compound name | MS: m/z [M + 1]+ |
| --- | --- | --- | --- |
| 281 | 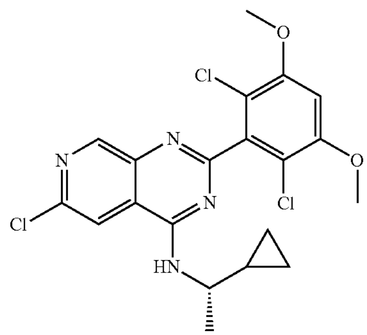 | (S)-6-chloro-N-(1-cyclopropylethyl)-2-(2,6-dichloro-3,5-dimethoxyphenyl)pyrido[3,4-d]pyrimidine-4-amine | 453 |
| 282 | 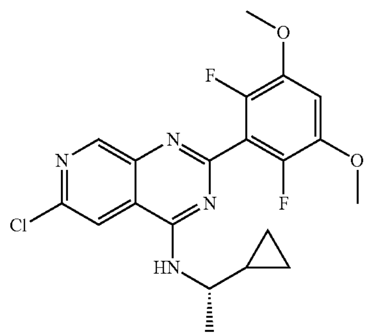 | (S)-6-chloro-N-(1-cyclopropylethyl)-2-(2,6-difluoro-3,5-dimethoxyphenyl)pyrido[3,4-d]pyrimidine-4-amine | 421 |
| 283 | 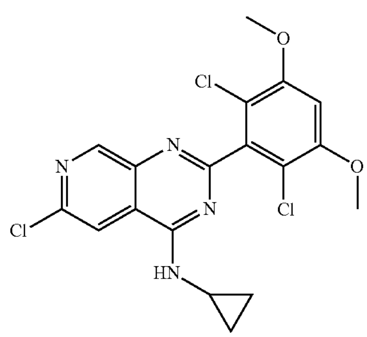 [SMILES: COc1cc(OC)c(Cl)c(-c2nc(NC3CC3)c3cc(Cl)ncc3n2)c1Cl] | 6-chloro-N-cyclopropyl-2-(2,6-dichloro-3,5-dimethoxyphenyl)pyrido[3,4-d]pyrimidine-4-amine | 425 |
| 284 | 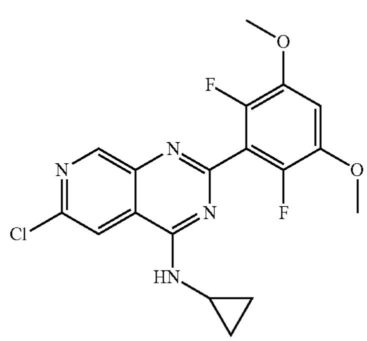 [SMILES: COc1cc(OC)c(F)c(-c2nc(NC3CC3)c3cc(Cl)ncc3n2)c1F] | 6-chloro-N-cyclopropyl-2-(2,6-difluoro-3,5-dimethoxyphenyl)pyrido[3,4-d]pyrimidine-4-amine | 393 |

| Intermediate No. | Compound structure | Compound name | MS: m/z [M + 1]+ |
|---|---|---|---|
| 285 | 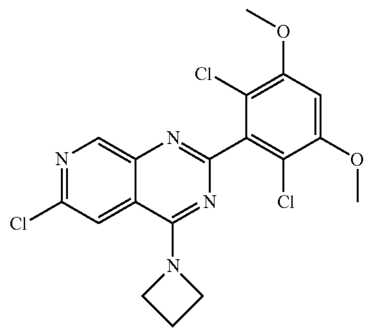 [SMILES: COc1cc(OC)c(Cl)c(-c2nc(N3CCC3)c3cc(Cl)ncc3n2)c1Cl] | 4-(azetidin-1-yl)-6-chloro-2-(2,6-dichloro-3,5-dimethoxyphenyl)pyrido[3,4-d]pyrimidine | 425 |
| 286 | 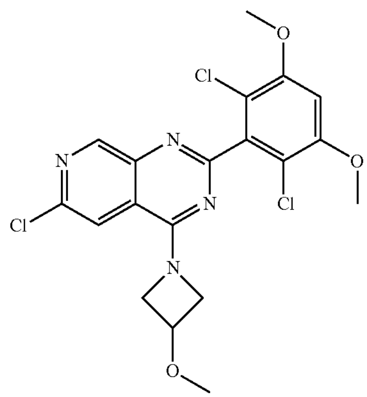 [SMILES: COc1cc(OC)c(Cl)c(-c2nc(N3CC(OC)C3)c3cc(Cl)ncc3n2)c1Cl] | 6-chloro-2-(2,6-dichloro-3,5-dimethoxyphenyl)-4-(3-methoxyazetidin-1-yl)pyrido[3,4-d]pyrimidine | 455 |
| 287 | 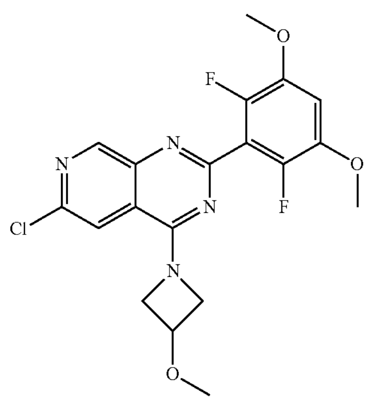 [SMILES: COc1cc(OC)c(F)c(-c2nc(N3CC(OC)C3)c3cc(Cl)ncc3n2)c1F] | 6-chloro-2-(2,6-difluoro-3,5-dimethoxyphenyl)-4-(3-methoxyazetidin-1-yl)pyrido[3,4-d]pyrimidine | 423 |
| 288 | 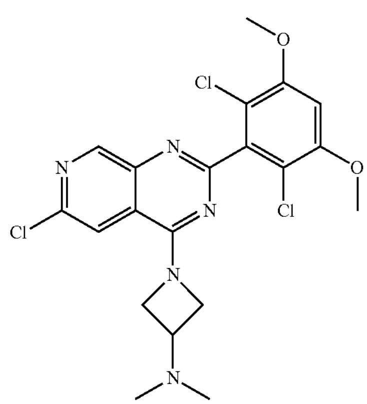 [SMILES: COc1cc(OC)c(Cl)c(-c2nc(N3CC(N(C)C)C3)c3cc(Cl)ncc3n2)c1Cl] | 1-(6-chloro-2-(2,6-dichloro-3,5-dimethoxyphenyl)pyrido[3,4-d]pyrimidin-4-yl)-N,N-dimethylazetidin-3-amine | 468 |

-continued

| Intermediate No. | Compound structure | Compound name | MS: m/z [M + 1]+ |
|---|---|---|---|
| 289 | 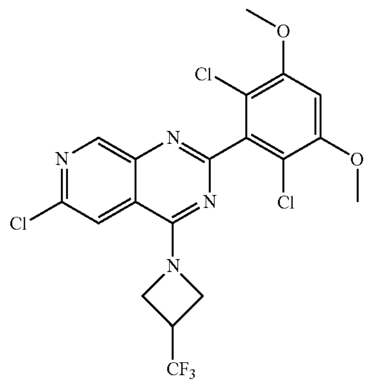 [SMILES: COc1cc(OC)c(Cl)c(-c2nc(N3CC(C(F)(F)F)C3)c3cc(Cl)ncc3n2)c1Cl] | 6-chloro-2-(2,6-dichloro-3,5-dimethoxyphenyl)-4-(3-(trifluoromethyl)azetidin-1-yl)pyrido[3,4-d]pyrimidine | 493 |
| 290 | 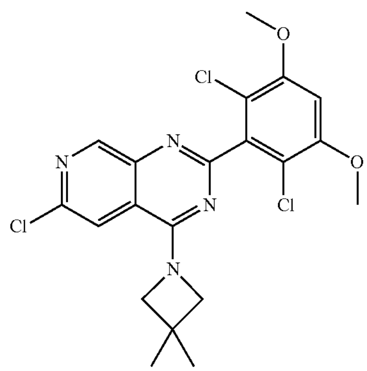 [SMILES: COc1cc(OC)c(Cl)c(-c2nc(N3CC(C)(C)C3)c3cc(Cl)ncc3n2)c1Cl] | 6-chloro-2-(2,6-dichloro-3,5-dimethoxyphenyl)-4-(3,3-dimethylazetidin-1-yl)pyrido[3,4-d]pyrimidine | 453 |
| 291 | 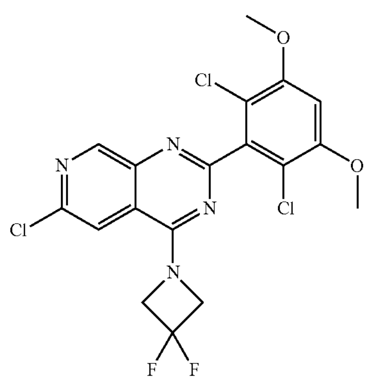 [SMILES: COc1cc(OC)c(Cl)c(-c2nc(N3CC(F)(F)C3)c3cc(Cl)ncc3n2)c1Cl] | 6-chloro-2-(2,6-dichloro-3,5-dimethoxyphenyl)-4-(3,3-difluoroazetidin-1-yl)pyrido[3,4-d]pyrimidine | 461 |
| 292 | 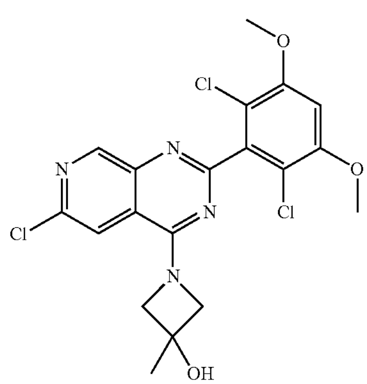 [SMILES: COc1cc(OC)c(Cl)c(-c2nc(N3CC(C)(O)C3)c3cc(Cl)ncc3n2)c1Cl] | 1-(6-chloro-2-(2,6-dichloro-3,5-dimethoxyphenyl)pyrido[3,4-d]pyrimidin-4-yl)-3-methylazetidin-3-ol | 455 |

-continued

| Intermediate No. | Compound structure | Compound name | MS: m/z [M + 1]+ |
|---|---|---|---|
| 293 | 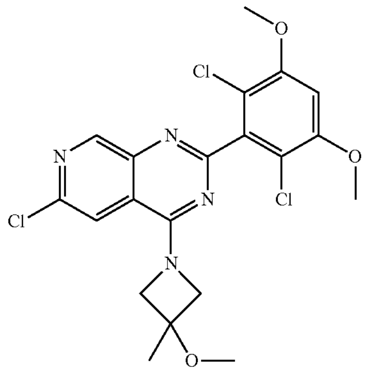 [SMILES: COc1cc(OC)c(Cl)c(-c2nc(N3CC(C)(OC)C3)c3cc(Cl)ncc3n2)c1Cl] | 6-chloro-2-(2,6-dichloro-3,5-dimethoxyphenyl)-4-(3-methoxy-3-methylazetidin-1-yl)pyrido[3,4-d]pyrimidine | 469 |
| 294 | 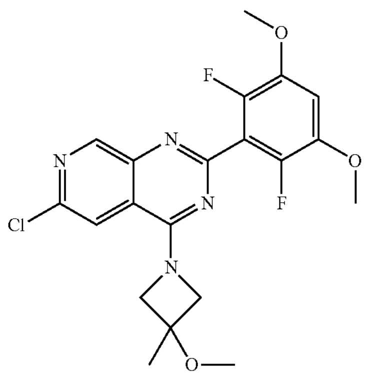 [SMILES: COc1cc(OC)c(F)c(-c2nc(N3CC(C)(OC)C3)c3cc(Cl)ncc3n2)c1F] | 6-chloro-2-(2,6-difluoro-3,5-dimethoxyphenyl)-4-(3-methoxy-3-methylazetidin-1-yl)pyrido[3,4-d]pyrimidine | 437 |
| 295 | 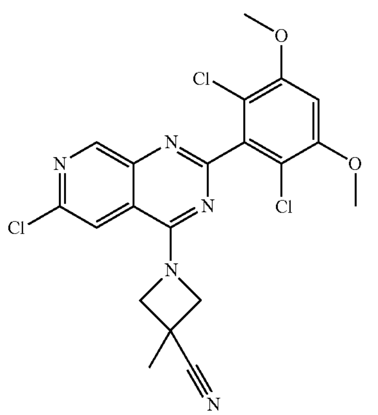 [SMILES: COc1cc(OC)c(Cl)c(-c2nc(N3CC(C)(C#N)C3)c3cc(Cl)ncc3n2)c1Cl] | 1-(6-chloro-2-(2,6-dichloro-3,5-dimethoxyphenyl)pyrido[3,4-d]pyrimidin-4-yl)-3-methylazetidin-3-carbonitrile | 464 |
| 296 | 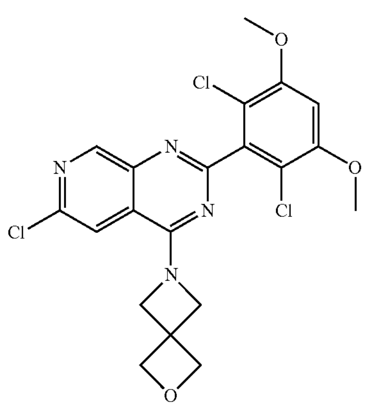 [SMILES: COc1cc(OC)c(Cl)c(-c2nc(N3CC4(COC4)C3)c3cc(Cl)ncc3n2)c1Cl] | 6-(6-chloro-2-(2,6-dichloro-3,5-dimethoxyphenyl)pyrido[3,4-d]pyrimidin-4-yl)-2-oxa-6-azaspiro[3.3]heptane | 467 |

-continued

| Intermediate No. | Compound name | MS: m/z [M + 1]+ |
|---|---|---|
| 297 | 6-(6-chloro-2-(2,6-difluoro-3,5-dimethoxyphenyl)pyrido[3,4-d]pyrimidin-4-yl)-2-oxa-6-azaspiro[3.3]heptane | 435 |
| 298 | 6-(6-chloro-2-(2,6-dichloro-3,5-dimethoxyphenyl)pyrido[3,4-d]pyrimidin-4-yl)-1-oxa-6-azaspiro[3.3]heptane | 467 |
| 299 | 6-(6-chloro-2-(2,6-difluoro-3,5-dimethoxyphenyl)pyrido[3,4-d]pyrimidin-4-yl)-1-oxa-6-azaspiro[3.3]heptane | 435 |
| 300 | 6-chloro-2-(2,6-dichloro-3,5-dimethoxyphenyl)-4-(2-azaspiro[3.3]hept-2-yl)pyrido[3,4-d]pyrimidine | 465 |

-continued

| Intermediate No. | Compound structure | Compound name | MS: m/z [M + 1]+ |
|---|---|---|---|
| 301 | 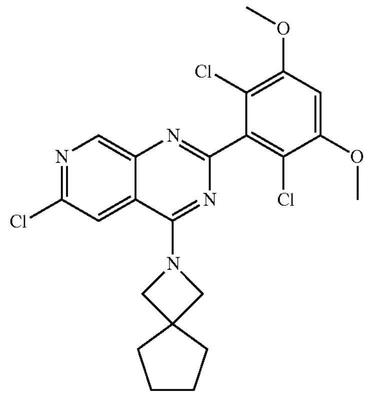 [SMILES: COc1cc(OC)c(Cl)c(-c2nc(N3CC4(CCCC4)C3)c3cc(Cl)ncc3n2)c1Cl] | 6-chloro-2-(2,6-dichloro-3,5-dimethoxyphenyl)-4-(2-azaspiro[3.4]oct-2-yl)pyrido[3,4-d]pyrimidine | 479 |
| 302 | 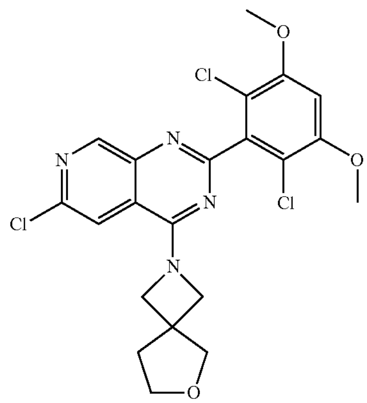 [SMILES: COc1cc(OC)c(Cl)c(-c2nc(N3CC4(CCOC4)C3)c3cc(Cl)ncc3n2)c1Cl] | 2-(6-chloro-2-(2,6-dichloro-3,5-dimethoxyphenyl)pyrido[3,4-d]pyrimidin-4-yl)-6-oxa-2-azaspiro[3.4]octane | 481 |
| 303 | 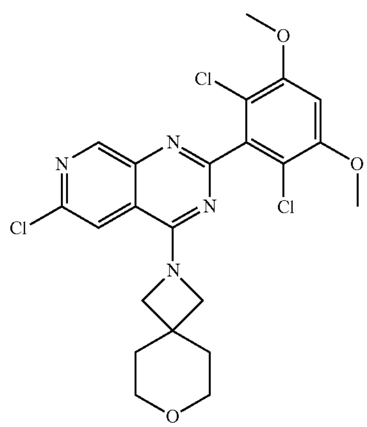 [SMILES: COc1cc(OC)c(Cl)c(-c2nc(N3CC4(CCOCC4)C3)c3cc(Cl)ncc3n2)c1Cl] | 2-(6-chloro-2-(2,6-dichloro-3,5-dimethoxyphenyl)pyrido[3,4-d]pyrimidin-4-yl)-7-oxa-2-azaspiro[3.5]nonane | 495 |
| 304 | 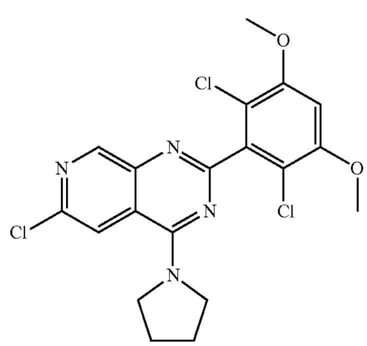 [SMILES: COc1cc(OC)c(Cl)c(-c2nc(N3CCCC3)c3cc(Cl)ncc3n2)c1Cl] | 6-chloro-2-(2,6-dichloro-3,5-dimethoxyphenyl)-4-(pyrrolidin-1-yl)pyrido[3,4-d]pyrimidine | 439 |

-continued

| Intermediate No. | Compound structure | Compound name | MS: m/z [M + 1]+ |
|---|---|---|---|
| 305 | 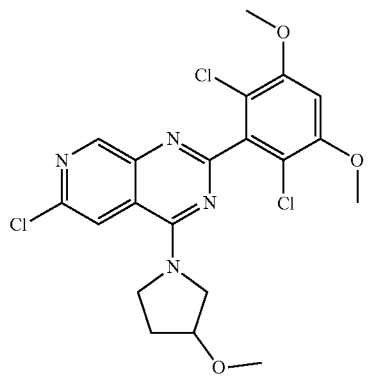 [SMILES: COc1cc(OC)c(Cl)c(-c2nc(N3CCC(OC)C3)c3cc(Cl)ncc3n2)c1Cl] | 6-chloro-2-(2,6-dichloro-3,5-dimethoxyphenyl)-4-(3-methoxypyrrolidin-1-yl)pyrido[3,4-d]pyrimidine | 469 |
| 306 | 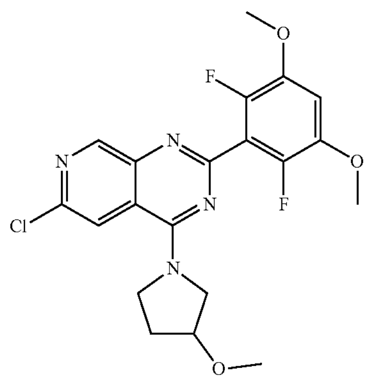 [SMILES: COc1cc(OC)c(F)c(-c2nc(N3CCC(OC)C3)c3cc(Cl)ncc3n2)c1F] | 6-chloro-2-(2,6-difluoro-3,5-dimethoxyphenyl)-4-(3-methoxypyrrolidin-1-yl)pyrido[3,4-d]pyrimidine | 437 |
| 307 | 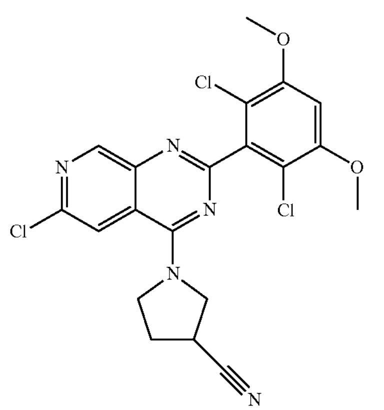 [SMILES: COc1cc(OC)c(Cl)c(-c2nc(N3CCC(C#N)C3)c3cc(Cl)ncc3n2)c1Cl] | 1-(6-chloro-2-(2,6-dichloro-3,5-dimethoxyphenyl)pyrido[3,4-d]pyrimidin-4-yl)pyrrolidine-3-carbonitrile | 464 |
| 308 | 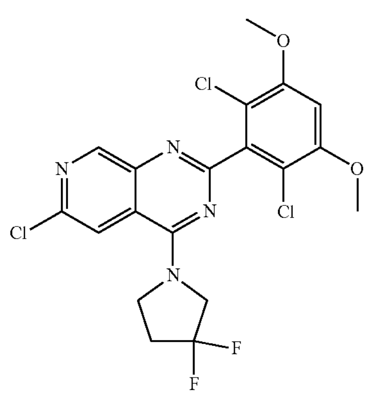 [SMILES: COc1cc(OC)c(Cl)c(-c2nc(N3CCC(F)(F)C3)c3cc(Cl)ncc3n2)c1Cl] | 6-chloro-2-(2,6-dichloro-3,5-dimethoxyphenyl)-4-(3,3-difluoropyrrolidin-1-yl)pyrido[3,4-d]pyrimidine | 475 |

| Intermediate No. | Compound structure | Compound name | MS: m/z [M + 1]⁺ |
|---|---|---|---|
| 309 | 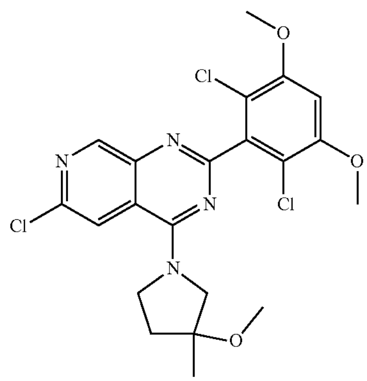 [SMILES: COc1cc(OC)c(Cl)c(-c2nc(N3CCC(C)(OC)C3)c3cc(Cl)ncc3n2)c1Cl] | 6-chloro-2-(2,6-dichloro-3,5-dimethoxyphenyl)-4-(3-methoxy-3-methylpyrrolidin-1-yl)pyrido[3,4-d]pyrimidine | 483 |
| 310 | 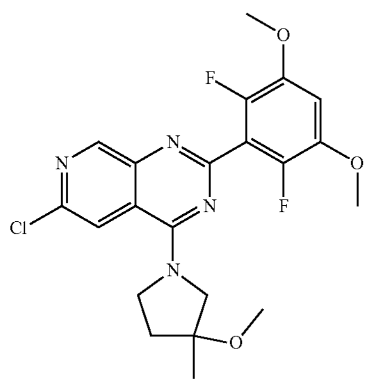 [SMILES: COc1cc(OC)c(F)c(-c2nc(N3CCC(C)(OC)C3)c3cc(Cl)ncc3n2)c1F] | 6-chloro-2-(2,6-difluoro-3,5-dimethoxyphenyl)-4-(3-methoxy-3-methylpyrrolidin-1-yl)pyrido[3,4-d]pyrimidine | 451 |
| 311 | 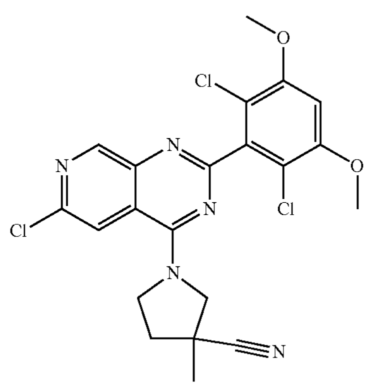 [SMILES: COc1cc(OC)c(Cl)c(-c2nc(N3CCC(C)(C#N)C3)c3cc(Cl)ncc3n2)c1Cl] | 1-(6-chloro-2-(2,6-dichloro-3,5-dimethoxyphenyl)pyrido[3,4-d]pyrimidin-4-yl)-3-methylpyrrolidine-3-carbonitrile | 478 |
| 312 | 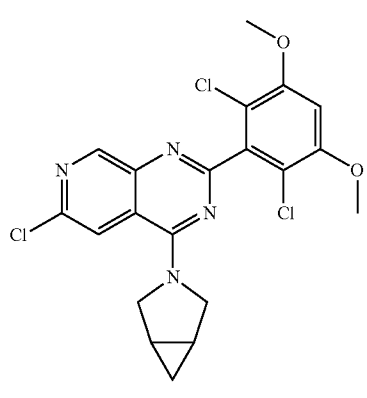 [SMILES: COc1cc(OC)c(Cl)c(-c2nc(N3CC4CC4C3)c3cc(Cl)ncc3n2)c1Cl] | 4-(3-azabicyclo[3.1.0]hex-3-yl)-6-chloro-2-(2,6-dichloro-3,5-dimethoxyphenyl)pyrido[3,4-d]pyrimidine | 451 |

| Intermediate No. | Compound structure | Compound name | MS: m/z [M + 1]+ |
|---|---|---|---|
| 313 | 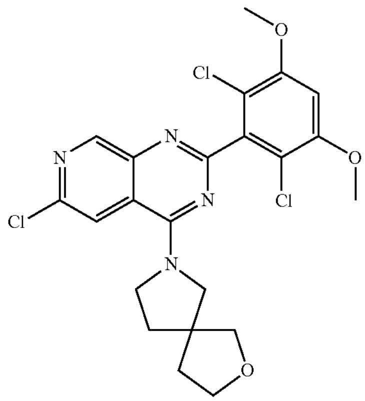 [SMILES: COc1cc(OC)c(Cl)c(-c2nc(N3CCC4(CCOC4)C3)c3cc(Cl)ncc3n2)c1Cl] | 7-(6-chloro-2-(2,6-dichloro-3,5-dimethoxyphenyl)pyrido[3,4-d]pyrimidin-4-yl)-2-oxa-7-azaspiro[4.4]nonane | 495 |
| 314 | 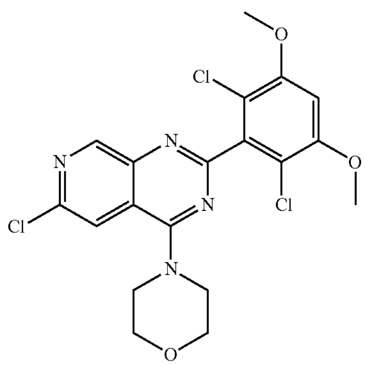 [SMILES: COc1cc(OC)c(Cl)c(-c2nc(N3CCOCC3)c3cc(Cl)ncc3n2)c1Cl] | 4-(6-chloro-2-(2,6-dichloro-3,5-dimethoxyphenyl)pyrido[3,4-d]pyrimidin-4-yl)morpholine | 455 |
| 315 | 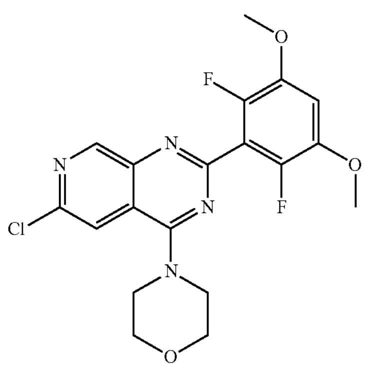 [SMILES: COc1cc(OC)c(F)c(-c2nc(N3CCOCC3)c3cc(Cl)ncc3n2)c1F] | 4-(6-chloro-2-(2,6-difluoro-3,5-dimethoxyphenyl)pyrido[3,4-d]pyrimidin-4-yl)morpholine | 423 |
| 316 | 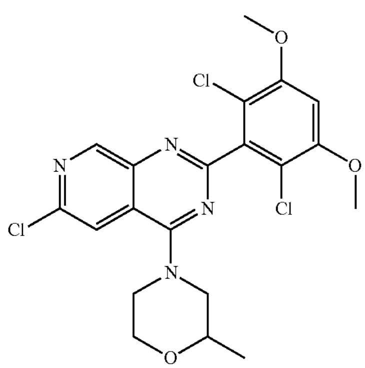 [SMILES: COc1cc(OC)c(Cl)c(-c2nc(N3CCOC(C)C3)c3cc(Cl)ncc3n2)c1Cl] | 4-(6-chloro-2-(2,6-dichloro-3,5-dimethoxyphenyl)pyrido[3,4-d]pyrimidin-4-yl)-2-methylmorpholine | 469 |

| Intermediate No. | Compound structure | Compound name | MS: m/z [M + 1]⁺ |
|---|---|---|---|
| 317 | 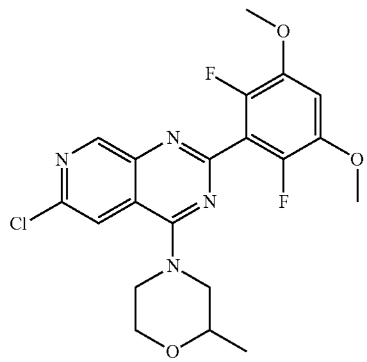 [SMILES: COc1cc(OC)c(F)c(-c2nc(N3CCOC(C)C3)c3cc(Cl)ncc3n2)c1F] | 4-(6-chloro-2-(2,6-difluoro-3,5-dimethoxyphenyl)pyrido[3,4-d]pyrimidin-4-yl)-2-methylmorpholine | 437 |
| 318 | 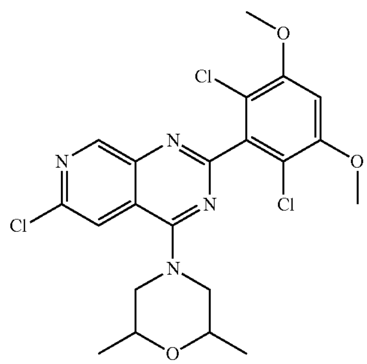 [SMILES: COc1cc(OC)c(Cl)c(-c2nc(N3CC(C)OC(C)C3)c3cc(Cl)ncc3n2)c1Cl] | 4-(6-chloro-2-(2,6-dichloro-3,5-dimethoxyphenyl)pyrido[3,4-d]pyrimidin-4-yl)-2,6-dimethylmorpholine | 483 |
| 319 | 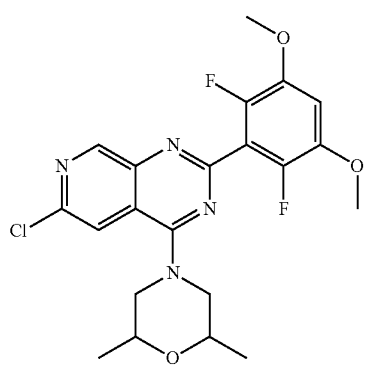 [SMILES: COc1cc(OC)c(F)c(-c2nc(N3CC(C)OC(C)C3)c3cc(Cl)ncc3n2)c1F] | 4-(6-chloro-2-(2,6-difluoro-3,5-dimethoxyphenyl)pyrido[3,4-d]pyrimidin-4-yl)-2,6-dimethylmorpholine | 451 |
| 320 | 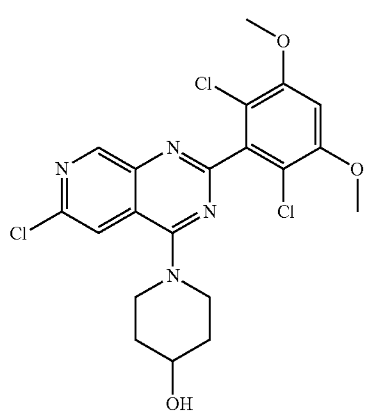 [SMILES: COc1cc(OC)c(Cl)c(-c2nc(N3CCC(O)CC3)c3cc(Cl)ncc3n2)c1Cl] | 1-(6-chloro-2-(2,6-dichloro-3,5-dimethoxyphenyl)pyrido[3,4-d]pyrimidin-4-yl)piperidin-4-ol | 469 |

| Intermediate No. | Compound structure | Compound name | MS: m/z [M + 1]⁺ |
|---|---|---|---|
| 321 | 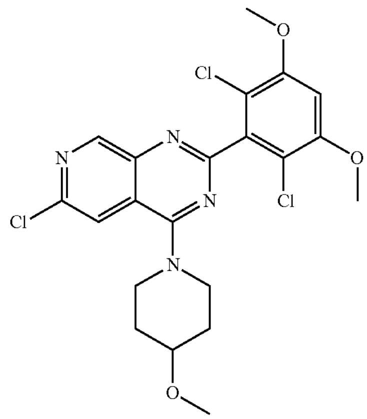 [SMILES: COc1cc(OC)c(Cl)c(-c2nc(N3CCC(OC)CC3)c3cc(Cl)ncc3n2)c1Cl] | 6-chloro-2-(2,6-dichloro-3,5-dimethoxyphenyl)-4-(4-methoxypiperidin-1-yl)pyrido[3,4-d]pyrimidine | 483 |
| 322 | 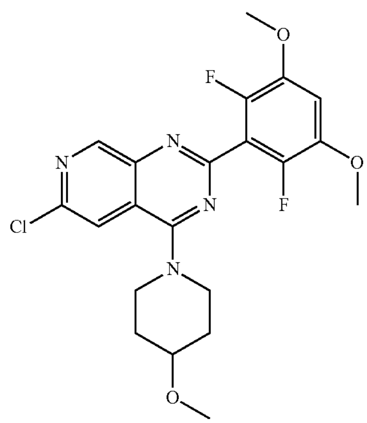 [SMILES: COc1cc(OC)c(F)c(-c2nc(N3CCC(OC)CC3)c3cc(Cl)ncc3n2)c1F] | 6-chloro-2-(2,6-difluoro-3,5-dimethoxyphenyl)-4-(4-methoxypiperidin-1-yl)pyrido[3,4-d]pyrimidine | 451 |
| 323 | 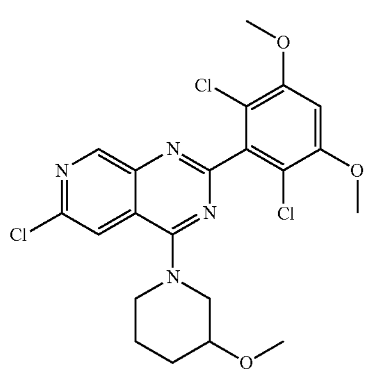 [SMILES: COc1cc(OC)c(Cl)c(-c2nc(N3CCCC(OC)C3)c3cc(Cl)ncc3n2)c1Cl] | 6-chloro-2-(2,6-dichloro-3,5-dimethoxyphenyl)-4-(3-methoxypiperidin-1-yl)pyrido[3,4-d]pyrimidine | 483 |

-continued

| Intermediate No. | Compound structure | Compound name | MS: m/z [M + 1]+ |
|---|---|---|---|
| 324 | 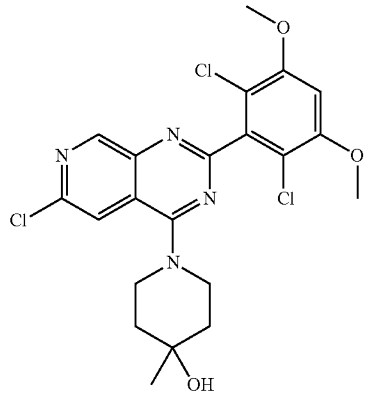 [SMILES: COc1cc(OC)c(Cl)c(-c2nc(N3CCC(C)(O)CC3)c3cc(Cl)ncc3n2)c1Cl] | 1-(6-chloro-2-(2,6-dichloro-3,5-dimethoxyphenyl)pyrido[3,4-d]pyrimidin-4-yl)-4-methylpiperidin-4-ol | 483 |
| 325 | 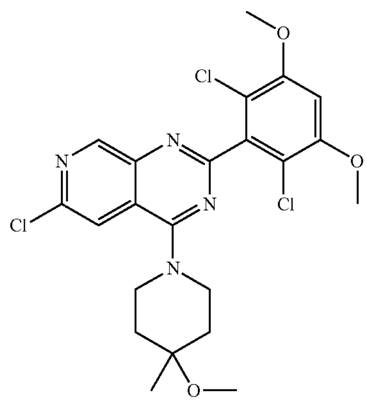 [SMILES: COc1cc(OC)c(Cl)c(-c2nc(N3CCC(C)(OC)CC3)c3cc(Cl)ncc3n2)c1Cl] | 6-chloro-2-(2,6-dichloro-3,5-dimethoxyphenyl)-4-(4-methoxy-4-methylpiperidin-1-yl)pyrido[3,4-d]pyrimidine | 497 |
| 326 | 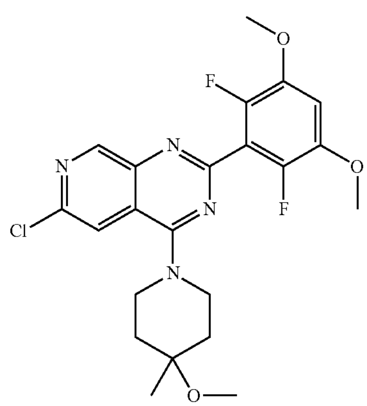 [SMILES: COc1cc(OC)c(F)c(-c2nc(N3CCC(C)(OC)CC3)c3cc(Cl)ncc3n2)c1F] | 6-chloro-2-(2,6-difluoro-3,5-dimethoxyphenyl)-4-(4-methoxy-4-methylpiperidin-1-yl)pyrido[3,4-d]pyrimidine | 465 |

| Intermediate No. | Compound structure | Compound name | MS: m/z [M + 1]⁺ |
|---|---|---|---|
| 327 | 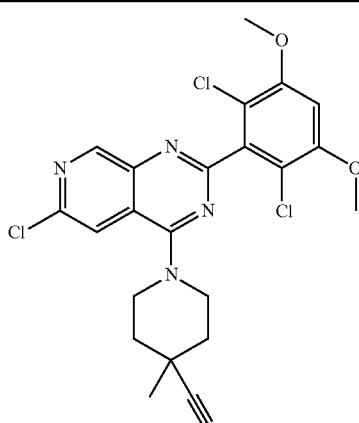 | 1-(6-chloro-2-(2,6-dichloro-3,5-dimethoxyphenyl)pyrido[3,4-d]pyrimidin-4-yl)-4-methylpiperidine-4-carbonitrile | 492 |
| 328 | 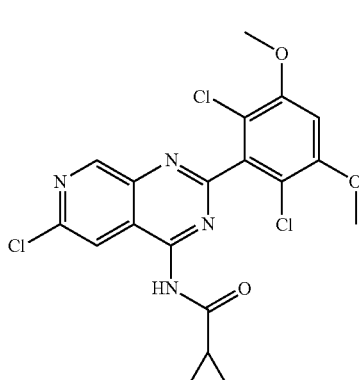 | N-(6-chloro-2-(2,6-dichloro-3,5-dimethoxyphenyl)pyrido[3,4-d]pyrimidin-4-yl)cyclopropyl carboxamide | 453 |
| 329 | 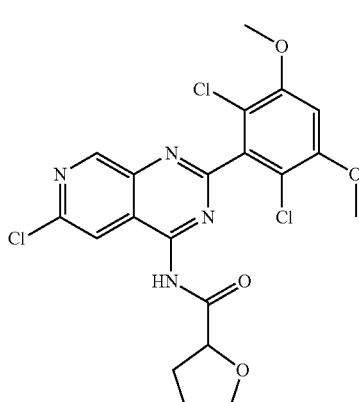 | N-(6-chloro-2-(2,6-dichloro-3,5-dimethoxyphenyl)pyrido[3,4-d]pyrimidin-4-yl)tetrahydrofuran2-carboxamide | 483 |
| 330 | 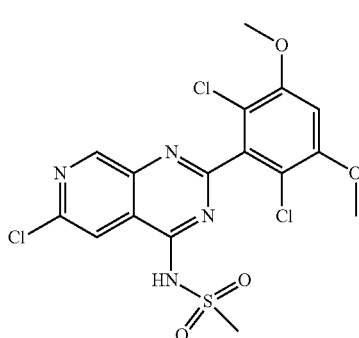 | N-(6-chloro-2-(2,6-dichloro-3,5-dimethoxyphenyl)pyrido[3,4-d]pyrimidin-4-yl)sulfonamide | 463 |

Intermediate 331: Preparation of 8-cyclopropyl-6-(2,6-dichloro-3,5-dimethoxyphenyl)-2-(methylthio) pyrido[3,4-d]pyrimidine

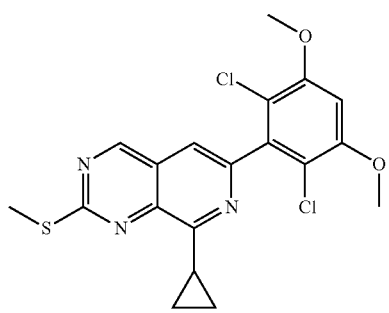

Step 1: Preparation of 8-chloro-6-(2,6-dichloro-3,5-dimethoxyphenyl)-2-(methylthio) pyrido[3,4-d]pyrimidine

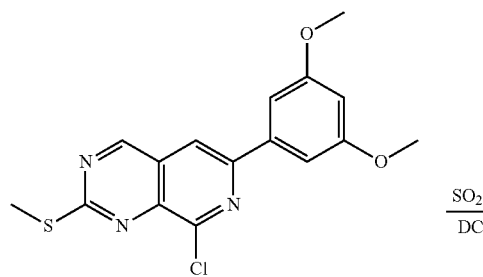

8-chloro-6-(3,5-dimethoxyphenyl)-2-(methylthio)pyrido[3,4-d]pyrimidine (500 mg, 1.43 mmol) was added to dichloromethane (30 mL), then the mixture was cooled to −30° C. $SO_2Cl_2$ (0.35 mL, 4.31 mmol) was dissolved in dichloromethane (30 mL), and slowly added dropwise to the above reaction liquid with stirring. After the addition, the mixture was stirred for another 0.5 h. The reaction was completed, then quenched with a saturated aqueous sodium bicarbonate solution (50 mL). The mixture was extracted, washed with water and then saturated brine, dried over anhydrous sodium sulfate, filtrated, concentrated and separated by column chromatography to obtain 8-chloro-6-(2,6-dichloro-3,5-dimethoxyphenyl)-2-(methylthio)pyrido[3,4-d]pyrimidine (620 mg, 88%). MS m/z (ESI): 416.2 [M+H]$^+$.

Step 2: Preparation of 8-cyclopropyl-6-(2,6-dichloro-3,5-dimethoxyphenyl)-2-(methyl thio)pyrido [3,4-d]pyrimidine

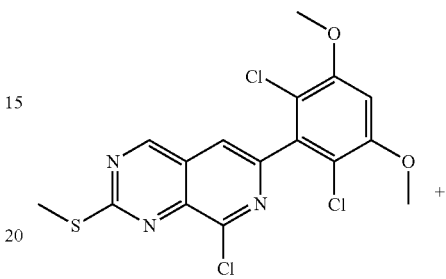

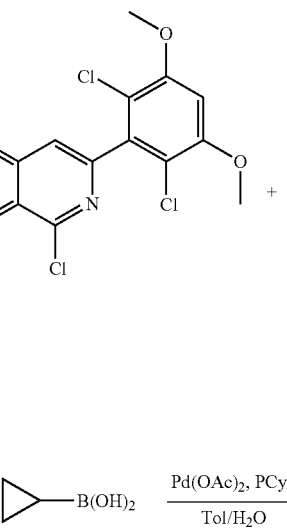

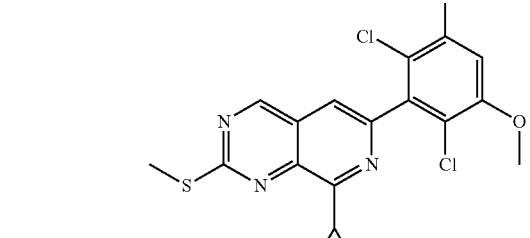

8-chloro-6-(2,6-dichloro-3,5-dimethoxyphenyl)-2-(methylthio)pyrido[3,4-d]pyrimidine (83 mg, 0.20 mmol), cyclopropyl boronic acid (26 mg, 0.30 mmol), Pd(OAc)$_2$ (5 mg, 0.02 mmol), PCy$_3$ (11 mg, 0.04 mmol) and K$_3$PO$_4$ (127 mg, 0.60 mmol) were added to the mixture of toluene and water (6:1, 5 mL), the mixture was heated to 100° C. and stirred over night. The reaction was completed, then the mixture was cooled to room temperature, diluted with EtOAc, washed with saturated brine, dried over anhydrous sodium sulfate, filtrated, concentrated and separated by column chromatography to obtain 8-cyclopropyl-6-(2,6-dichloro-3,5-dimethoxyphenyl)-2-(methylthio)pyrido[3,4-d]pyrimidine (60 mg, 71%). MS m/z (ESI): 422.2 [M+H]$^+$.

Intermediates 332-364 were prepared referring to the synthesis method of 331.

| Intermediate No. | Compound structure | Compound name | MS: m/z [M + 1]+ |
|---|---|---|---|
| 332 | 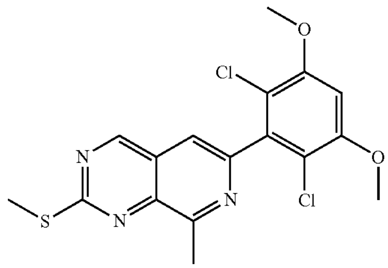 | 6-(2,6-dichloro-3,5-dimethoxyphenyl)-8-methyl-2-(methylthio)pyrido[3,4-d]pyrimidine | 396 |
| 333 | 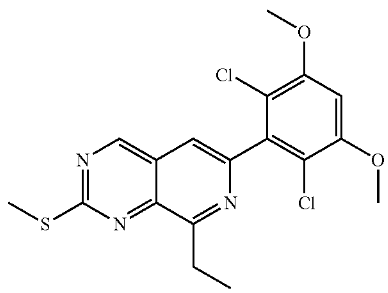 | 6-(2,6-dichloro-3,5-dimethoxyphenyl)-8-ethyl-2-(methylthio)pyrido[3,4-d]pyrimidine | 410 |
| 334 | 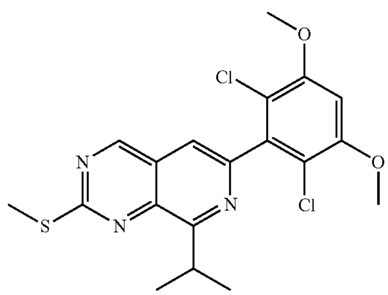 | 6-(2,6-dichloro-3,5-dimethoxyphenyl)-8-isopropyl-2-(methylthio)pyrido[3,4-d]pyrimidine | 424 |
| 335 | 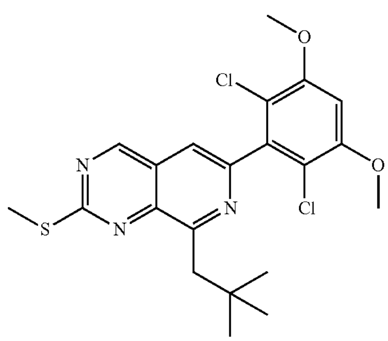 | 6-(2,6-dichloro-3,5-dimethoxyphenyl)-2-(methylthio)-8-neopentylpyrido[3,4-d]pyrimidine | 452 |
| 336 | 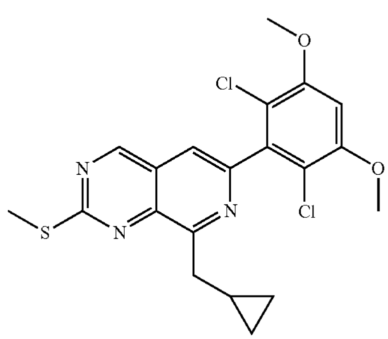 | 8-(cyclopropylmethyl)-6-(2,6-dichloro-3,5-dimethoxyphenyl)-2-(methylthio)pyrido[3,4-d]pyrimidine | 436 |

| Intermediate No. | Compound structure | Compound name | MS: m/z [M + 1]+ |
|---|---|---|---|
| 337 | 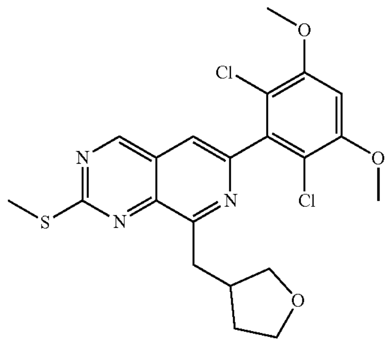 | 6-(2,6-dichloro-3,5-dimethoxyphenyl)-2-(methylthio)-8-((tetrahydrofuran-3-yl)methyl)pyrido[3,4-d]pyrimidine | 466 |
| 338 | 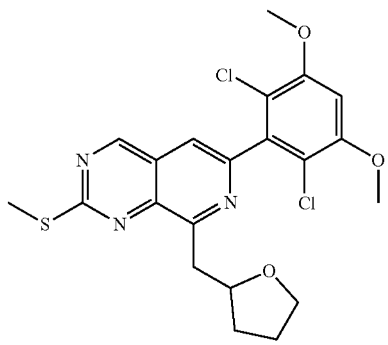 | 6-(2,6-dichloro-3,5-dimethoxyphenyl)-2-(methylthio)-8-((tetrahydrofuran2-yl)methyl)pyrido[3,4-d]pyrimidine | 466 |
| 339 | 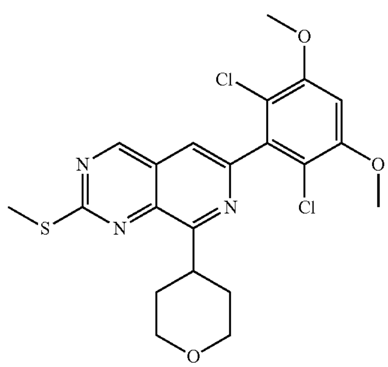 | 6-(2,6-dichloro-3,5-dimethoxyphenyl)-2-(methylthio)-8-(tetrahydro-2H-pyran-4-yl)pyrido[3,4-d]pyrimidine | 466 |
| 340 | 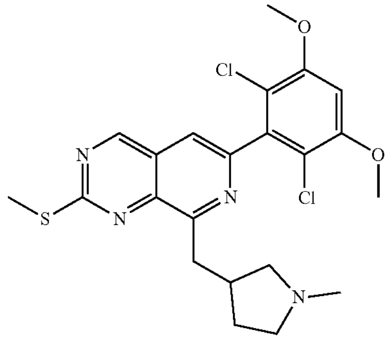 | 6-(2,6-dichloro-3,5-dimethoxyphenyl)-8-((1-methylpyrrolidin-3-yl)methyl)-2-(methylthio)pyrido[3,4-d]pyrimidine | 479 |

| Intermediate No. | Compound structure | Compound name | MS: m/z [M + 1]+ |
|---|---|---|---|
| 341 | 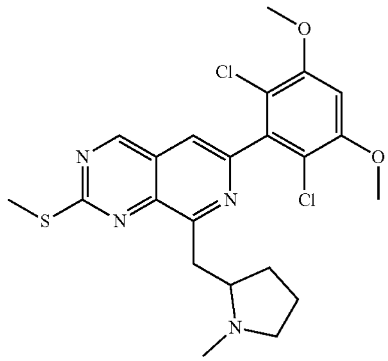 | 6-(2,6-dichloro-3,5-dimethoxyphenyl)-8-((1-methylpyrrolidin-2-yl)methyl)-2-(methylthio)pyrido[3,4-d]pyrimidine | 479 |
| 342 | 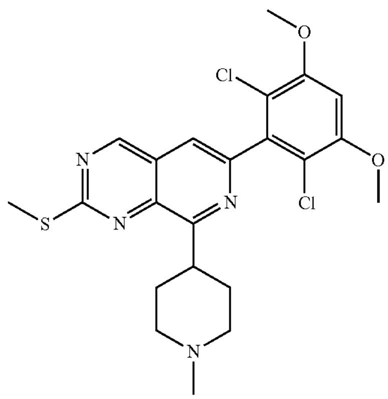 | 6-(2,6-dichloro-3,5-dimethoxyphenyl)-8-(1-methylpiperidin-4-yl)-2-(methylthio)pyrido[3,4-d]pyrimidine | 479 |
| 343 | 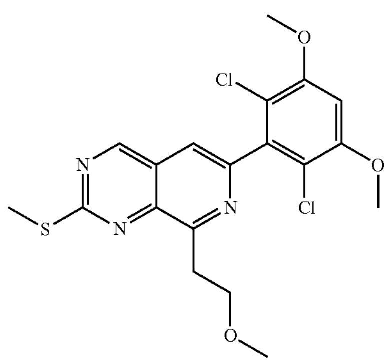 | 6-(2,6-dichloro-3,5-dimethoxyphenyl)-8-(2-methoxyethyl)-2-(methylthio)pyrido[3,4-d]pyrimidine | 440 |
| 344 | 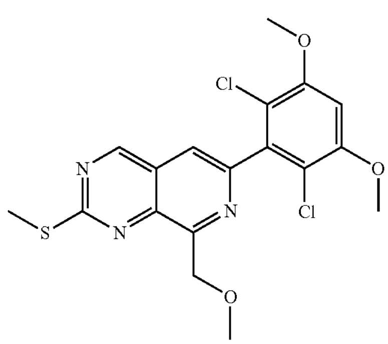 | 6-(2,6-dichloro-3,5-dimethoxyphenyl)-8-(methoxymethyl)-2-(methylthio)pyrido[3,4-d]pyrimidine | 426 |

-continued

| Intermediate No. | Compound structure | Compound name | MS: m/z [M + 1]⁺ |
|---|---|---|---|
| 345 | 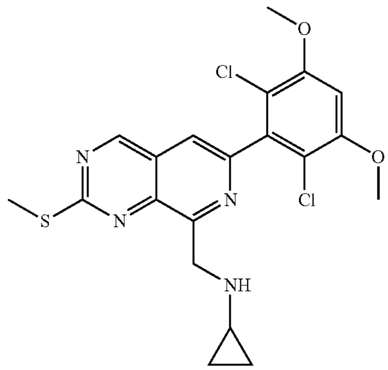 | N-((6-(2,6-dichloro-3,5-dimethoxyphenyl)-2-(methylthio)pyrido[3,4-d]pyrimidin-8-yl)methyl)cyclopropylamine | 451 |
| 346 | 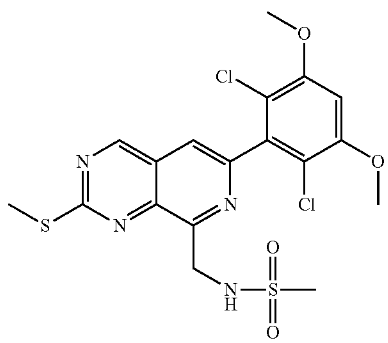 | N-((6-(2,6-dichloro-3,5-dimethoxyphenyl)-2-(methylthio)pyrido[3,4-d]pyrimidin-8-yl)methyl)sulfonamide | 489 |
| 347 | 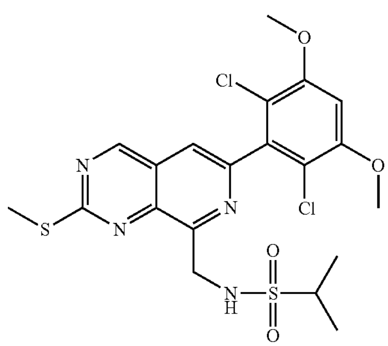 | N-((6-(2,6-dichloro-3,5-dimethoxyphenyl)-2-(methylthio)pyrido[3,4-d]pyrimidin-8-yl)methyl)propane-2-sulfonamide | 517 |
| 348 | 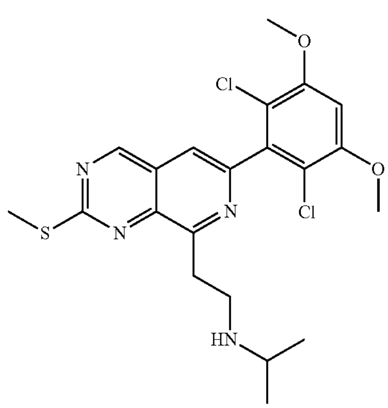 | N-(2-(6-(2,6-dichloro-3,5-dimethoxyphenyl)-2-(methylthio)pyrido[3,4-d]pyrimidin-8-yl)ethyl)propane-2-amine | 467 |

| Intermediate No. | Compound structure | Compound name | MS: m/z [M + 1]+ |
|---|---|---|---|
| 349 | 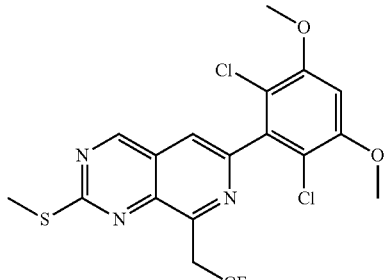 | 6-(2,6-dichloro-3,5-dimethoxyphenyl)-2-(methylthio)-8-(2,2,2-trifluoroethyl)pyrido[3,4-d]pyrimidine | 464 |
| 350 | 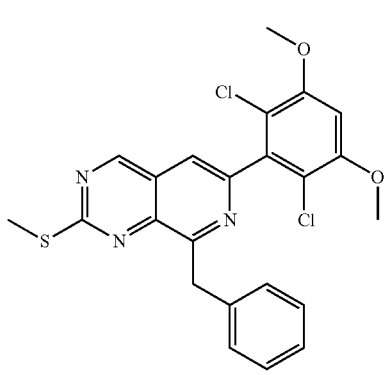 | 8-benzyl-6-(2,6-dichloro-3,5-dimethoxyphenyl)-2-(methylthio)pyrido[3,4-d]pyrimidine | 472 |
| 351 | 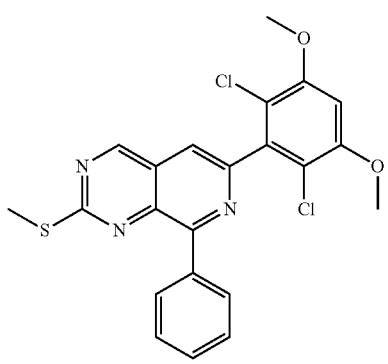 | 6-(2,6-dichloro-3,5-dimethoxyphenyl)-2-(methylthio)-8-phenylpyrido[3,4-d]pyrimidine | 458 |
| 352 | 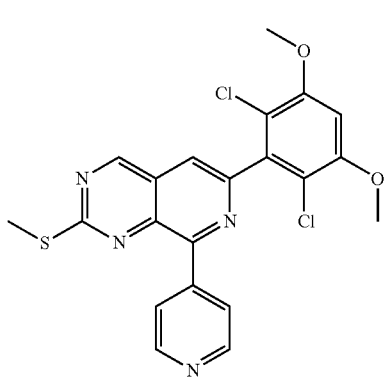 | 6-(2,6-dichloro-3,5-dimethoxyphenyl)-2-(methylthio)-8-(pyridin-4-yl)pyrido[3,4-d]pyrimidine | 459 |

-continued

| Intermediate No. | Compound structure | Compound name | MS: m/z [M + 1]+ |
|---|---|---|---|
| 353 | 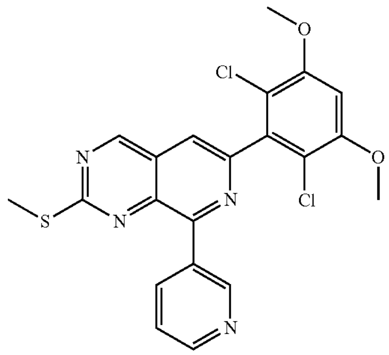 | 6-(2,6-dichloro-3,5-dimethoxyphenyl)-2-(methylthio)-8-(pyridin-3-yl)pyrido[3,4-d]pyrimidine | 459 |
| 354 | 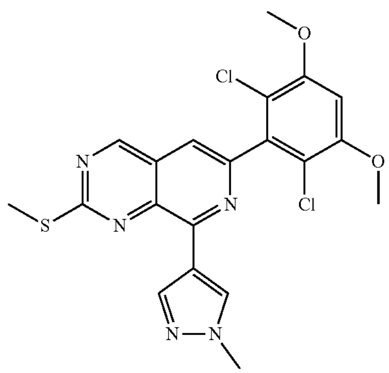 | 6-(2,6-dichloro-3,5-dimethoxyphenyl)-8-(1-methyl-1H-pyrazol-4-yl)-2-(methylthio)pyrido[3,4-d]pyrimidine | 462 |
| 355 | 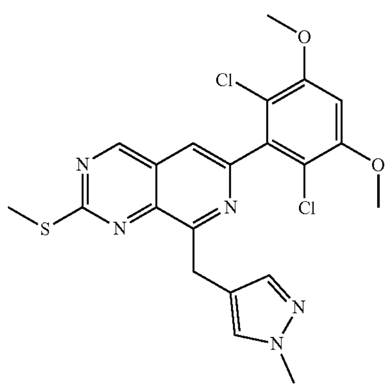 | 6-(2,6-dichloro-3,5-dimethoxyphenyl)-8-((1-methyl-1H-pyrazol-4-yl)methyl)-2-(methylthio)pyrido[3,4-d]pyrimidine | 476 |
| 356 | 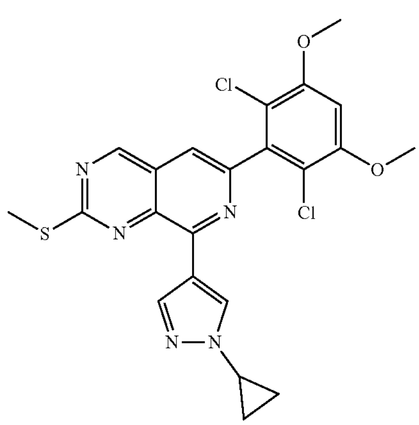 | 8-(1-cyclopropyl-1H-pyrazol-4-yl)-6-(2,6-dichloro-3,5-dimethoxyphenyl)-2-(methylthio)pyrido[3,4-d]pyrimidine | 488 |

| Intermediate No. | Compound structure | Compound name | MS: m/z [M + 1]+ |
|---|---|---|---|
| 357 | 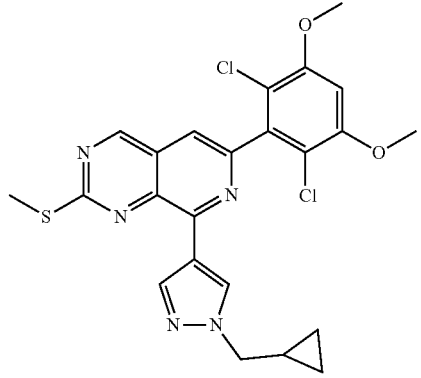 | 8-(1-(cyclopropylmethyl)-1H-pyrazol-4-yl)-6-(2,6-dichloro-3,5-dimethoxyphenyl)-2-(methylthio)pyrido[3,4-d]pyrimidine | 502 |
| 358 | 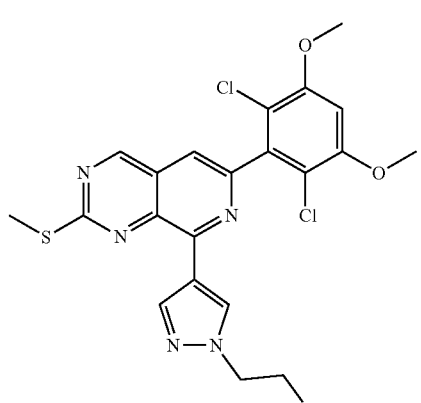 | 6-(2,6-dichloro-3,5-dimethoxyphenyl)-8-(1-(2-methoxyethyl)-1H-pyrazol-4-yl)-2-(methylthio)pyrido[3,4-d]pyrimidine | 506 |
| 359 | 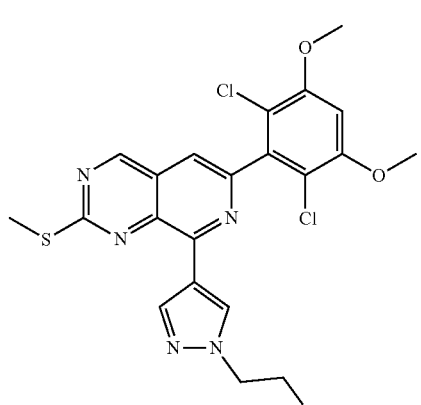 | 2-(4-(6-(2,6-dichloro-3,5-dimethoxyphenyl)-2-(methylthio)pyrido[3,4-d]pyrimidin-8-yl)-1H-pyrazol-1-yl)ethan-1-ol | 492 |

-continued

| Intermediate No. | Compound structure | Compound name | MS: m/z [M + 1]+ |
|---|---|---|---|
| 360 | 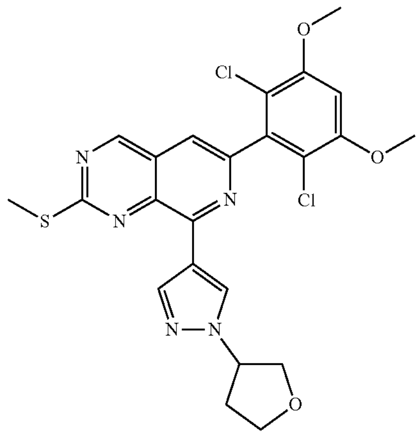 | 6-(2,6-dichloro-3,5-dimethoxyphenyl)-2-(methylthio)-8-(1-(tetrahydrofuran-3-yl)-1H-pyrazol-4-yl)pyrido[3,4-d]pyrimidine | 518 |
| 361 | 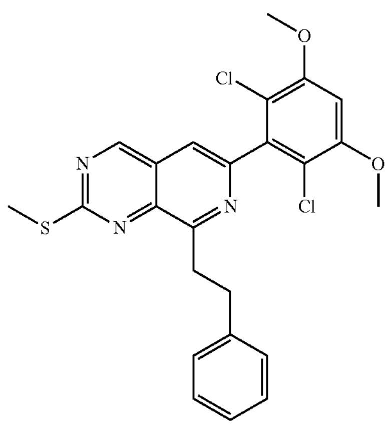 | 6-(2,6-dichloro-3,5-dimethoxyphenyl)-2-(methylthio)-8-phenethylpyrido[3,4-d]pyrimidine | 486 |
| 362 | 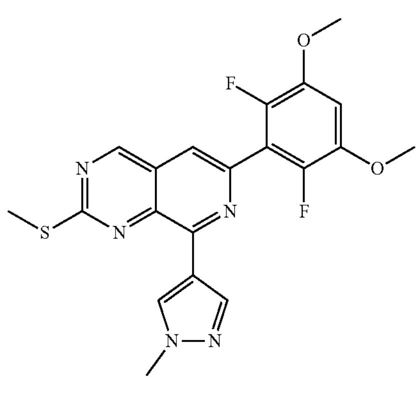 | 6-(2,6-difluoro-3,5-dimethoxyphenyl)-8-(1-methyl-1H-pyrazol-4-yl)-2-(methylthio)pyrido[3,4-d]pyrimidine | 430 |

| Intermediate No. | Compound structure | Compound name | MS: m/z [M + 1]+ |
|---|---|---|---|
| 363 | 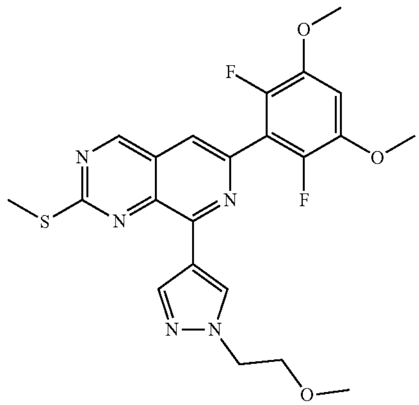 | 6-(2,6-difluoro-3,5-dimethoxyphenyl)-8-(1-(2-methoxyethyl)-1H-pyrazol-4-yl)-2-(methylthio)pyrido[3,4-d]pyrimidine | 474 |
| 364 | 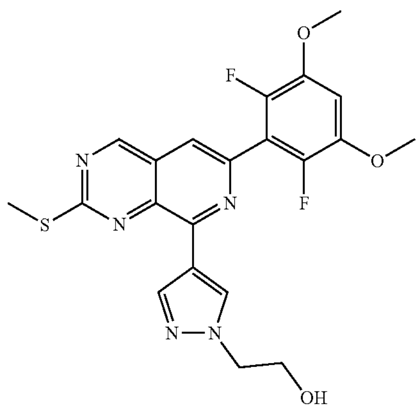 | 2-(4-(6-(2,6-difluoro-3,5-dimethoxyphenyl)-2-(methylthio)pyrido[3,4-d]pyrimidin-8-yl)-1H-pyrazol-1-yl)ethan-1-ol | 460 |

Intermediate 365: Preparation of (3S,4S)-4-azidotetrahydro-2H-pyran-3-amine Hydrochloride

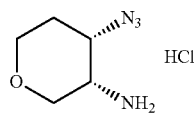

Step 1: Preparation of Tert-Butyl ((3S,4S)-4-hydroxyltetrahydro-2H-pyran-3-yl)carbamate

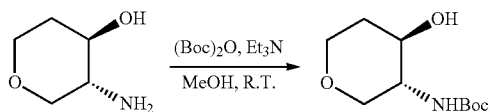

(3R,4R)-3-aminotetrahydro-2H-pyran-4-ol (5.00 g, 42.7 mmol) was dissolved in MeOH (100 mL), and then Et₃N (4.75 g, 47.0 mmol) and Boc₂O (10.25 g, 47.0 mmol) were successively added, the mixture was stirred at room temperature overnight. The reaction was completed monitored by LCMS. The mixture was concentrated to remove methanol, and the crude product was washed with petroleum ether (100 mL), and then filtrated to obtain tert-butyl ((3S,4S)-4-hydroxyltetrahydro-2H-pyran-3-yl)carbamate (8.50 g, yield: 92%).

¹H NMR (400 MHz, CDCl₃): δ ppm 4.68 (m, 1H), 4.03 (m, 1H), 3.93 (m, 1H), 3.63 (m, 1H), 3.45 (m, 2H), 3.19 (m, 1H), 2.81 (m, 1H), 2.04 (m, 1H), 1.68 (m, 1H), 1.61 (s, 9H).

Step 2: Preparation of (3R,4R)-3-((tert-butoxycarbonyl)amino)tetrahydro-2H-pyran-4-yl Methanesulfonate

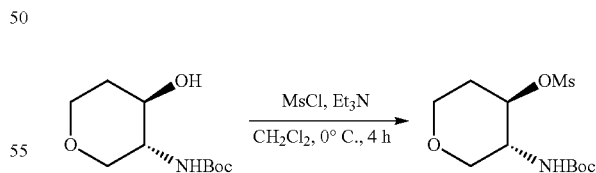

Tert-butyl ((3S,4S)-4-hydroxytetrahydro-2H-pyran-3-yl)carbamate (8.5 g, 39.2 mmol) was dissolved in CH₂Cl₂ (100 ML), the mixture was cooled under ice water bath, and then Et₃N (4.30 g, 43.0 mmol) and MsCl (4.98 g, 43.0 mmol) were successively added, the mixture was stirred at 0° C. for 6 h. The reaction was completed, the mixture was washed with water (20 mL), then the organic phase was dried over anhydrous sodium sulfate, filtrated, and concentrated to obtain (3R,4R)-3-((tert-butoxycarbonyl)amino)tetrahydro-2H-pyran-4-yl methanesulfonate (10.2 g, yield: 88%).

¹H NMR (400 MHz, CDCl₃): δ ppm 4.90 (m, 1H), 4.76 (m, 1H), 4.03 (m, 1H), 3.98 (m, 1H), 3.67 (m, 2H), 3.47 (m, 1H), 3.14 (s, 3H), 2.18 (m, 1H), 1.92 (m, 1H), 1.44 (s, 9H).

Step 3: Preparation of Tert-butyl ((3S,4S)-4-azido-tetrahydro-2H-pyran-3-yl)carbamate

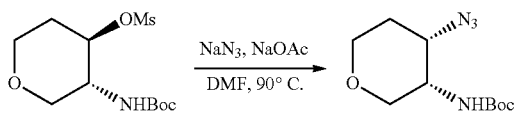 [SMILES: CC(C)(C)OC(=O)N[C@@H]1COCC[C@H]1OS(C)(=O)=O ; CC(C)(C)OC(=O)N[C@@H]1COCC[C@@H]1N=[N+]=[N-]]

(3R,4R)-3-((tert-butoxycarbonyl)amino)tetrahydro-2H-pyran-4-yl methanesulfonate (10.2 g, 34.6 mmol) was dissolved in dried DMF (100 mL), NaOAc (9.38 g, 69.0 mmol) and NaN₃ (4.49 g, 69.0 mmol) were successively added, the mixture was heated at 90° C. overnight. The reaction was completed, then the reaction solution was poured into water (200 mL) and extracted twice with EtOAc (50 mL), the organic phases were combined, washed twice with aqueous LiCl solution (50 mL), dried over anhydrous sodium sulfate, filtered and concentrated to obtain compound tert-butyl ((3S,4S)-4-azidotetrahydro-2H-pyran-3-yl)carbamate (6.8 g, yield: 81%).
¹H NMR (400 MHz, CDCl₃): δ ppm 4.85 (m, 1H), 3.89 (m, 2H), 3.77 (m, 1H), 3.63 (m, 2H), 3.51 (m, 1H), 1.93 (m, 2H), 1.45 (s, 9H).

Step 4: Preparation of (3S,4S)-4-azidotetrahydro-2H-pyran-3-amine Hydrochloride

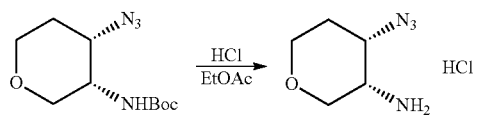 [SMILES: "EtOAc" ; CC(C)(C)OC(=O)N[C@@H]1COCC[C@@H]1N=[N+]=[N-] ; Cl ; [N-]=[N+]=N[C@H]1CCOC[C@H]1N ; Cl]

Tert-butyl ((3S,4S)-4-azidotetrahydro-2H-pyran-3-yl)carbamate (6.8 g, 28.0 mmol) was added to the mixture of HCl and EtOAc (100 mL), the mixture was stirred at room temperature for 8 h. The reaction was completed monitored by LCMS. The mixture was concentrated to obtain compound (3S,4S)-4-azidotetrahydro-2H-pyran-3-amine hydrochloride (4.0 g, yield: 80%).
¹H NMR (400 MHz, DMSO-d6): δ ppm 8.47 (m, 3H), 4.36 (m, 1H), 3.80 (m, 2H), 3.63 (m, 3H), 2.0 (m, 2H).

Intermediate 366: Preparation of (3S,4R)-4-azidotetrahydrofuran-3-amine Hydrochloride

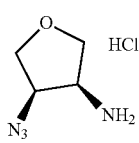

Intermediate 366 was prepared referring to the synthesis method of Intermediate 365 from (3S,4R)-4-aminotetrahydro furan-3-ol.

Intermediate 367: Preparation of Tert-Butyl ((3R,4S)-4-aminotetrahydrofuran-3-yl)carbamate

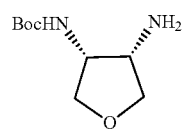 [SMILES: CC(C)(C)OC(=O)N[C@H]1COC[C@H]1N]

Step 1: Preparation of Tert-Butyl ((3S,4R)-4-hydroxyltetrahydrofuran-3-yl)carbamate

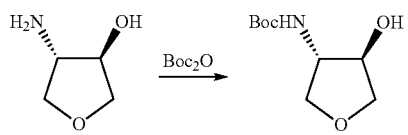 [SMILES: "Boc2O" ; N[C@H]1COC[C@@H]1O ; CC(C)(C)OC(=O)N[C@H]1COC[C@@H]1O]

(3R,4S)-4-aminotetrahydrofuran-3-ol (5.00 g, 48.487 mmol) was dissolved in methanol (100 mL), then triethylamine (12.24 g, 121.2 mmol) was added, the mixture was cooled under ice water bath, then Boc₂O (11.64 g, 53.34 mmol) was added. After the addition, the mixture was stirred at room temperature for 24 h. The reaction was completed, the organic phase was concentrated to remove the majority solvent. Water (100 mL) was added, and the mixture was stirred to precipitate a large amount of white solids. The mixture was filtrated and washed with water to obtain compound tert-butyl ((3S,4R)-4-hydroxyltetrahydrofuran-3-yl)carbamate (8.00 g, yield: 81%).
¹H NMR (400 MHz, Chloroform-d) δ 4.72 (s, 1H), 4.29 (m, 1H), 4.09 (m, 1H), 4.08-4.02 (m, 1H), 3.95 (s, 1H), 3.69 (m, 1H), 3.61 (m, 1H), 1.45 (s, 9H).

Step 2: Preparation of Tert-Butyl ((3R,4S)-4-(1,3-dicarbonylisoindolin-2-yl)tetrahydrofuran-3-yl)carbamate

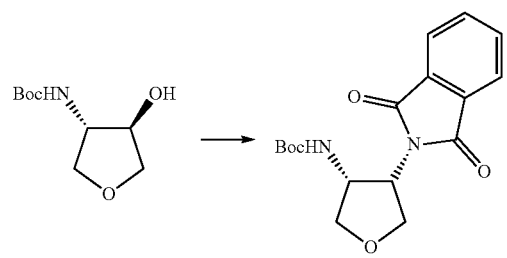

Tert-butyl ((3S,4R)-4-hydroxyltetrahydrofuran-3-yl)carbamate (200 mg, 0.984 mmol), triphenylphosphine (620 mg, 2.364 mmol) and isoindoline-1,3-dione (173 mg, 1.181 mmol) were dissolved in tetrahydrofuran (10 mL), the mixture was cooled under ice water bath, then diisopropyl azodicarboxylate (717 mg, 3.546 mmol) was slowly added dropwise. After addition, the mixture was stirred under ice water bath for 1 h. The reaction liquid was directly concentrated and separated by column chromatography (Eluent: PE/EA 15-30%) to obtain a crude product compound tert-butyl ((3R,4S)-4-(1,3-dicarbonylisoindolin-2-yl)tetrahydrofuran-3-yl)carbamate (950 mg).

¹H NMR (400 MHz, Chloroform-d) δ 7.87 (m, 2H), 7.75 (m, 2H), 4.84 (d, J=9.5 Hz, 1H), 4.51 (t, J=8.0 Hz, 1H), 4.37 (t, J=8.3 Hz, 1H), 4.21-4.15 (m, 1H), 4.09 (t, J=8.8 Hz, 1H), 3.85 (m, J=9.2, 6.4 Hz, 1H), 1.11 (s, 9H).
MS m/z (ESI): 559.5 [M+H]⁺.

Step 3: Preparation of Tert-Butyl ((3R,4S)-4-aminotetrahydrofuran-3-yl)carbamate

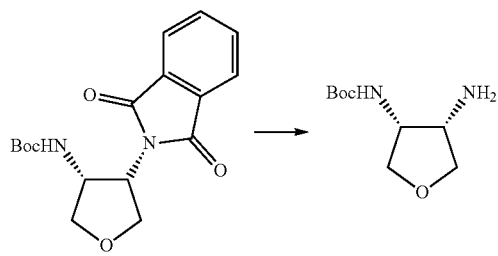

Tert-buty ((3R,4S)-4-(1,3-dicarbonylisoindolin-2-yl)tetrahydrofuran-3-yl)carbamate (950 mg, 21%, 0.600 mmol) was dissolved in ethanol (6 mL), then hydrazine hydrate (45 mg, 0.900 mmol) was added, the mixture was heated to 75° C. and stirred for 2 h. The react ion was completed, then the mixture was concentrated and separated by column chromatography (Eluent: DCM/MeOH 0-5%) to obtain compound tert-butyl ((3R,4S)-4-aminotetrahydrofuran-3-yl)carbamate (120 mg, two-step yield: 60/).

¹H NMR (400 MHz, Chloroform-d) δ 5.24 (s, 1H), 4.11 (s, 1H), 4.05 (m, 1H), 4.00 (m, 1H), 3.63-3.52 (m, 2H), 3.49 (m, 1H), 1.46 (s, 9H).

Intermediates 368-375 were prepared referring to the synthesis method of Intermediate 367.

| Intermediate No. | Compound structure | Compound name | MS: m/z [M + 1]⁺ |
|---|---|---|---|
| 368 | TeocHN⋯⟨pyrrolidine⟩⋯NH₂, N-Boc | tert-butyl (3R,4S)-3-amino-4-(((2,2,2-trichloroethoxy)carbonyl)amino)pyrrolidine-1-carboxylate | 377 |
| 369 | TeocHN⋯⟨pyrrolidine⟩⋯NH₂, N-Me | 2,2,2-trichloroethyl ((3S,4R)-4-amino-1-methylpyrrolidin-3-yl) carbamate | 291 |
| 370 | TeocHN⋯⟨pyrrolidine⟩⋯NH₂, N-acetyl | 2,2,2-trichloroethyl ((3S,4R)-1-acetyl-4-aminopyrrolidin-3-yl) carbamate | 319 |
| 371 | TeocHN⋯⟨pyrrolidine⟩⋯NH₂, N-CH₂CH₂N(CH₃)₂ | 2,2,2-trichloroethyl ((3S,4R)-4-amino-1-(2-(dimethylamino)ethyl)pyrrolidin-3-yl)carbamate | 348 |

-continued

| Intermediate No. | Compound structure | Compound name | MS: m/z [M + 1]+ |
|---|---|---|---|
| 372 | 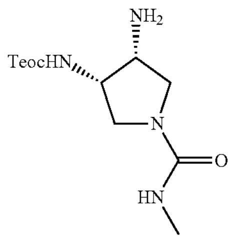 | 2,2,2-trichloroethyl ((3S,4R)-4-amino-1-(methylaminoformyl)pyrrolidin-3-yl)carbamate | 334 |
| 373 | 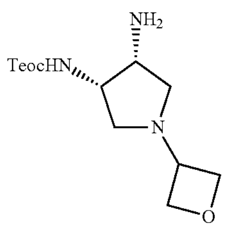 | 2,2,2-trichloroethyl ((3S,4R)-4-amino-1-(oxetan-3-yl)pyrrolidin-3-yl)carbamate | 333 |
| 374 | 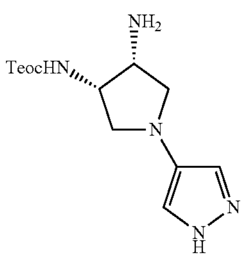 | 2,2,2-trichloroethyl ((3S,4R)-4-amino-1-(1H-pyrazol-4-yl)pyrrolidin-3-yl)carbamate | 343 |
| 375 | 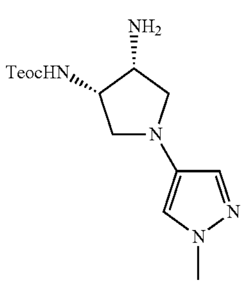 | 2,2,2-trichloroethyl ((3S,4R)-4-amino-1-(1-methyl-1H-pyrazol-4-yl)pyrrolidin-3-yl)carbamate | 357 |

Preparation of Specific Examples

Example 1 Preparation of N-(2-((7-(2,6-dichloro-3,5-dimethoxyphenyl)-6-methyl-5-oxo-5,6-dihydro-2,6-naphthyridin-3-yl)amino)-3-methylphenyl)acrylamide

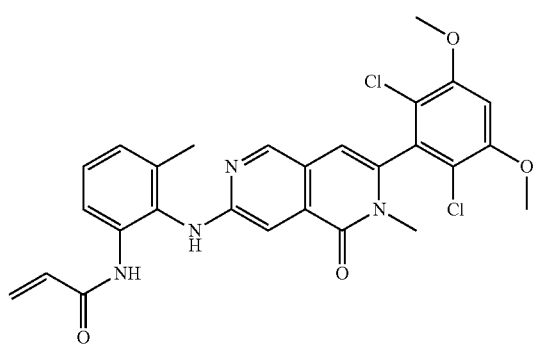 [SMILES: C=CC(=O)Nc1cccc(C)c1Nc1cc2c(=O)n(C)c(-c3c(Cl)c(OC)cc(OC)c3Cl)cc2cn1]

Step 1: Preparation of 3-(2,6-dichloro-3,5-dimethoxyphenyl)-2-methyl-7-((2-methyl-6-nitrophenyl)amino)-2,6-naphthyridin-1(2H)-one

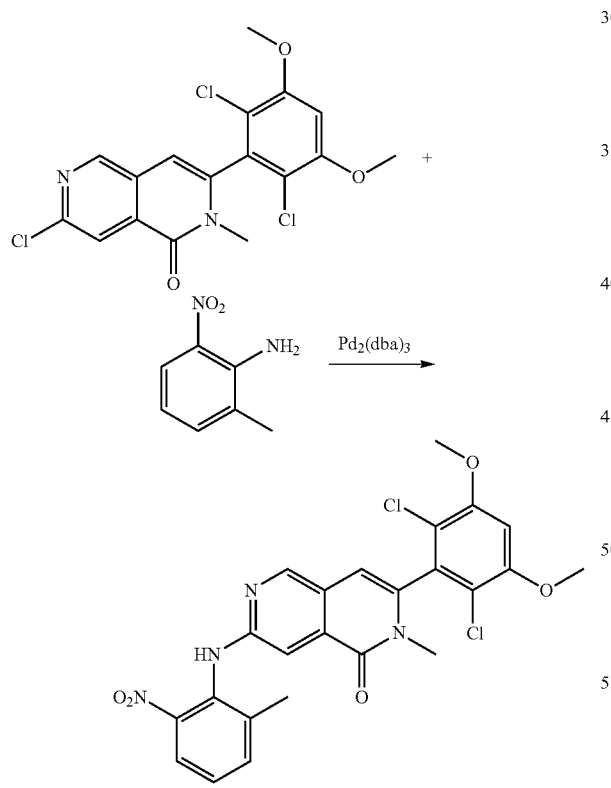

7-chloro-3-(2,6-dichloro-3,5-dimethoxyphenyl)-2-methyl-2,6-naphthyridin-1(2H)-one (150 mg, 0.375 mmol) was dissolved in 14-dioxane (20 mL), then 2-methyl-6-nitroaniline (114 mg, 0.751 mmol), cesium carbonate (367 mg, 1.126 mmol), brett-phos (161 mg, 0.3 m mol) and Pd$_2$(dba)$_3$ (172 mg, 0.188 mmol) were added. The gas was exchanged with N2, and the mixture was heated to 120° C. for 2 h. The reaction was completed, and the mixture was concentrated and separated by silica gel column chromatography (Eluent: PE/EtOAc =2:1) to obtain compound 3-(2,6-dichloro-3,5-dimethoxyphenyl)-2-methy-7-((2-methyl-6-nitrophenyl)amino)-2,6-naphthyridin-1(2H)-one (40 mg, yield: 21%). MS m/z (ESI): 516 [M+H]$^+$.

Step 2: Preparation of 7-((2-amino-6-methylphenyl)amino)-3-(2,6-dichloro-3,5-dimethoxyphenyl)-2-methyl-2,6-naphthyridin-1(2H)-one

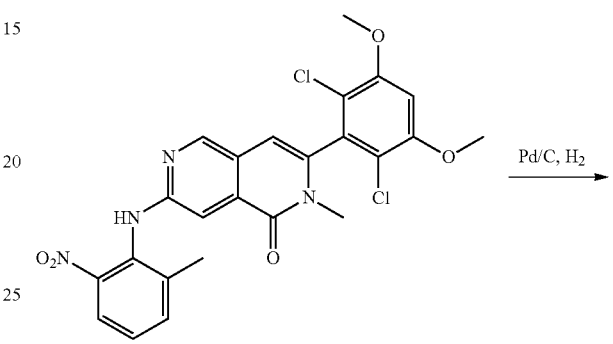

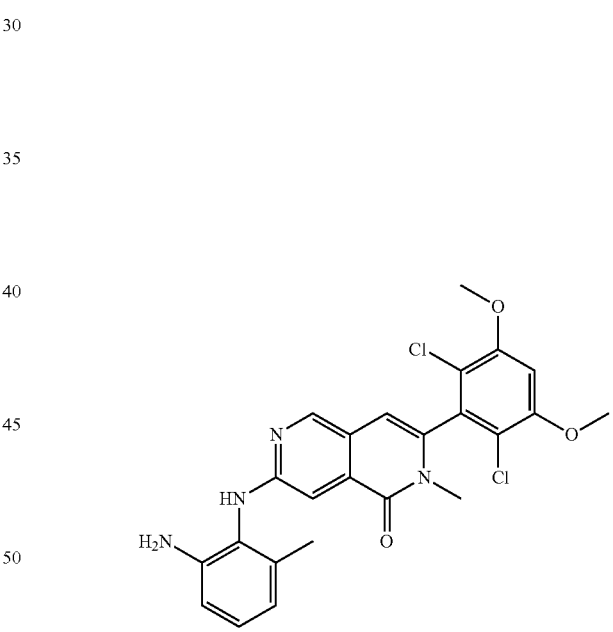

3-(2,6-dichloro-3,5-dimethoxyphenyl)-2-methyl-7-((2-methyl-6-nitrophenyl)amino)-2,6-naphthyridin-1(2H)-one (40 mg, 0.078 mmol) was dissolved in 10 mL of methanol, then 10 mg of Pd—C was added. The mixture was stirred at room temperature under H$_2$ for 30 min. The reaction was completed, and the mixture was concentrated and separated by silica gel column chromatography (Eluent: CH$_2$Cl$_2$/MeOH=10:1) to obtain compound 7-((2-amino-6-methylphenyl)amino)-3-(2,6-dichloro-3,5-dimethoxyphenyl)-2-methyl-2,6-naphthyridin-1(2H)-one (9.5 mg, yield:25%).

MS m/z (ESI): 486.4 [M+H]$^+$.

Step 3: Preparation of N-(2-((7-(2,6-dichloro-3,5-dimethoxyphenyl)-6-methyl-5-oxo-5,6-dihydro-2,6-naphthyridin-3-yl)amino)-3-methylphenyl)acrylamide

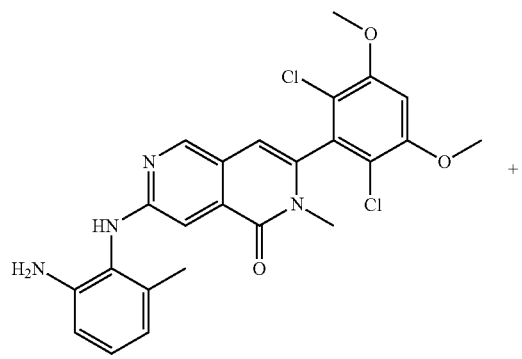

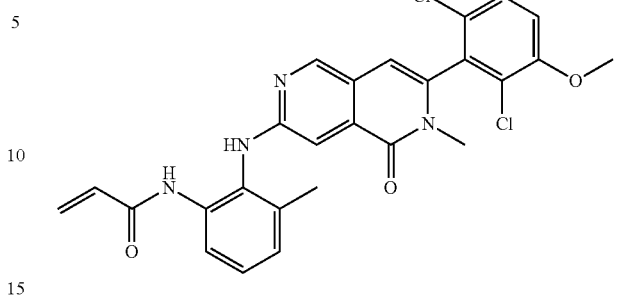

7-((2-amino-6-methylphenyl)amino)-3-(2,6-dichloro-3,5-dimethoxyphenyl)-2-methyl-2,6-naphthyridin-1(2H)-one (9.5 mg, 0.02 mmol) was dissolved in the mixture of THF and H$_2$O (4 mL/1 mL), then sodium bicarbonate (9 mg, 0.104 mmol) was added, the mixture was cooled with ice water bath, and the solution of acryloyl chloride in THF (2 mg/2 mL, 0.02 mmol) was added dropwise. The mixture was stirred at 0° C. for 10 min. After the reaction was completed, the mixture was extracted for three times with dichloromethane. The organic phases were combined, washed with a saturated aqueous solution of sodium chloride, dried over anhydrous sodium sulfate, filtrated and concentrated. The crude product was separated by silica gel column chromatography, to obtain compound N-(2-((7-(2,6-dichloro-3,5-dimethoxyphenyl)-6-methyl-5-oxo-5,6-dihydro-2,6-naphthyridin-3-yl)amino)-3-methylphenyl)acrylamide (1 mg, yield: 9%).

$^1$H NMR (400 MHz, CDCl$_3$) δ 8.60 (s, 1H), 8.30 (d, J=8.1 Hz, 1H), 7.31 (s, 1H), 7.10-7.05 (m, 2H), 6.68 (s, 1H), 6.52-6.48 (m, 1H), 6.44 (s, 1H), 6.39 (s, 1H), 6.33 (d, J=1.4 Hz, 1H), 6.19 (d, J=10.2 Hz, 1H), 5.68 (dd. J=10.2, 1.4 Hz, 1H), 3.99 (s, 6H), 3.25 (s, 3H), 2.21 (s, 3H).

MS m/z (ESI): 541.4 [M+H]$^+$.

Examples 2-75 were prepared referring to the synthesis method of Example 1.

| Example No. | Compound structure | Compound name | MS: m/z [M + 1]$^+$ |
|---|---|---|---|
| 2 | 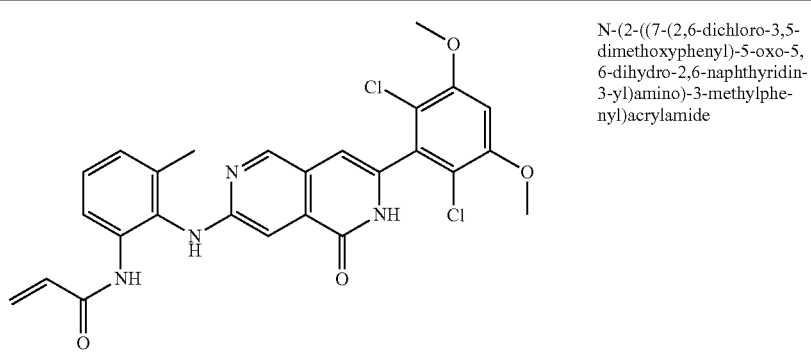 | N-(2-((7-(2,6-dichloro-3,5-dimethoxyphenyl)-5-oxo-5,6-dihydro-2,6-naphthyridin-3-yl)amino)-3-methylphenyl)acrylamide | 525 |

-continued

| Example No. | Compound structure | Compound name | MS: m/z [M + 1]+ |
|---|---|---|---|
| 3 | 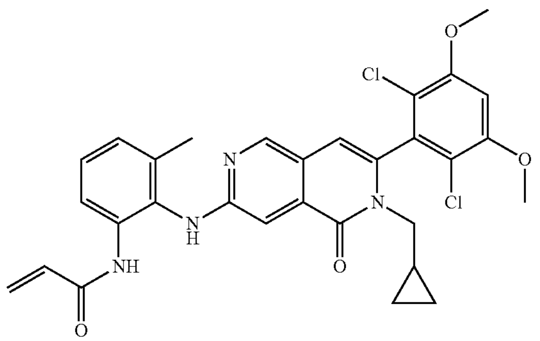 [SMILES: C=CC(=O)Nc1cccc(C)c1Nc1cc2c(=O)n(CC3CC3)c(-c3c(Cl)c(OC)cc(OC)c3Cl)cc2cn1] | N-(2-((6-(cyclopropylmethyl)-7-(2,6-dichloro-3,5-dimethoxyphenyl)-5-oxo-5,6-dihydro-2,6-naphthyridin-3-yl)amino)-3-methylphenyl)acrylamide | 579 |
| 4 | 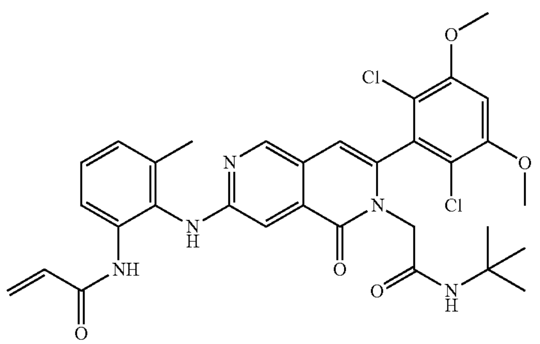 [SMILES: C=CC(=O)Nc1cccc(C)c1Nc1cc2c(=O)n(CC(=O)NC(C)(C)C)c(-c3c(Cl)c(OC)cc(OC)c3Cl)cc2cn1] | N-(2-((6-(2-(tert-butylamino)-2-oxoethyl)-7-(2,6-dichloro-3,5-dimethoxyphenyl)-5-oxo-5,6-dihydro-2,6-naphthyridin-3-yl)amino)-3-methylphenyl)acrylamide | 638 |
| 5 | 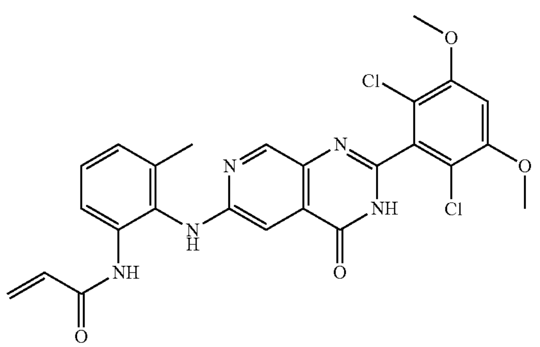 [SMILES: C=CC(=O)Nc1cccc(C)c1Nc1cc2c(=O)[nH]c(-c3c(Cl)c(OC)cc(OC)c3Cl)nc2cn1] | N-(2-((2-(2,6-dichloro-3,5-dimethoxyphenyl)-4-oxo-3,4-dihydropyrido[3,4-d]pyrimidin-6-yl)amino)-3-methylphenyl)acrylamide | 526 |
| 6 | 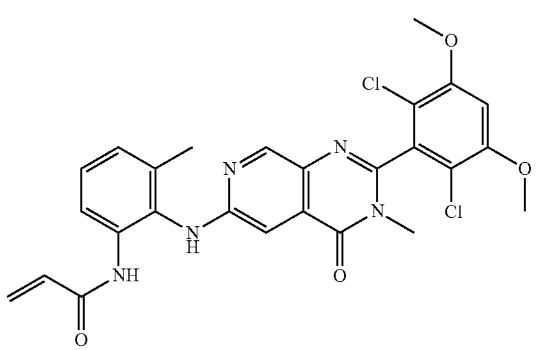 | N-(2-((2-(2,6-dichloro-3,5-dimethoxyphenyl)-3-methyl-4-oxo-3,4-dihydropyrido[3,4-d]pyrimidin-6-yl)amino)-3-methylphenyl)acrylamide | 540 |

-continued

| Example No. | Compound structure | Compound name | MS: m/z [M + 1]+ |
|---|---|---|---|
| 7 | 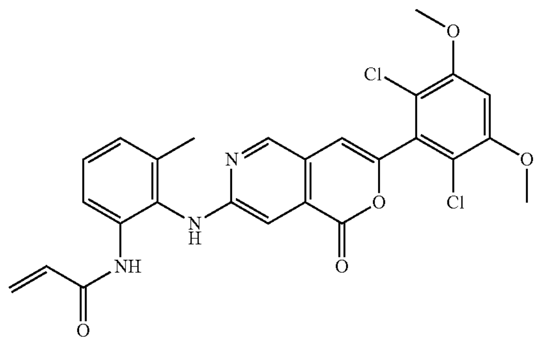 [SMILES: C=CC(=O)Nc1cccc(C)c1Nc1cc2c(=O)oc(-c3c(Cl)c(OC)cc(OC)c3Cl)cc2cn1] | N-(2-((3-(2,6-dichloro-3,5-dimethoxyphenyl)-1-oxo-1H-pyrano[4,3-c]pyridin-7-yl)amino)-3-methylphenyl)acrylamide | 526 |
| 8 | 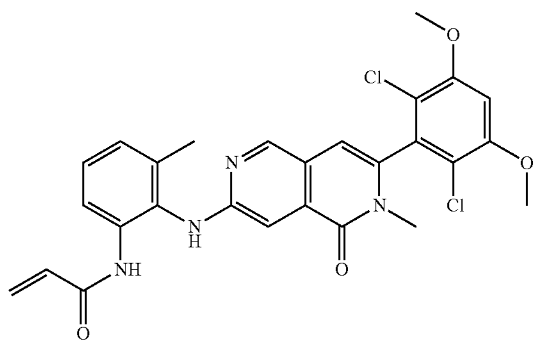 [SMILES: C=CC(=O)Nc1cccc(C)c1Nc1cc2c(=O)n(C)c(-c3c(Cl)c(OC)cc(OC)c3Cl)cc2cn1] | N-(2-((6-(2,6-dichloro-3,5-dimethoxyphenyl)-7-methyl-8-oxo-7,8-dihydropyrido[3,4-d]pyrimidin-2-yl)amino)-3-methylphenyl)acrylamide | 540 |
| 9 | 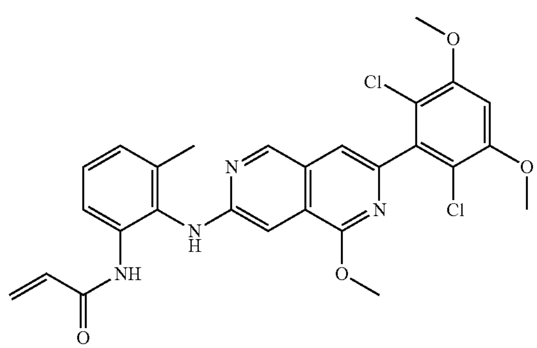 [SMILES: C=CC(=O)Nc1cccc(C)c1Nc1cc2c(OC)nc(-c3c(Cl)c(OC)cc(OC)c3Cl)cc2cn1] | N-(2-((7-(2,6-dichloro-3,5-dimethoxyphenyl)-5-dimethoxy-2,6-naphthyridin-3-yl)amino)-3-methylphenyl)acrylamide | 539 |
| 10 | 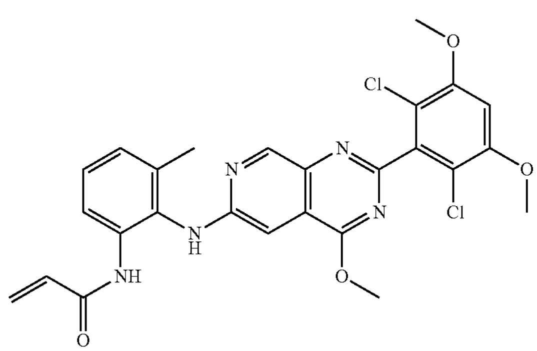 [SMILES: C=CC(=O)Nc1cccc(C)c1Nc1cc2c(OC)nc(-c3c(Cl)c(OC)cc(OC)c3Cl)nc2cn1] | N-(2-((2-(2,6-dichloro-3,5-dimethoxyphenyl)-4-methoxypyrido[3,4-d]pyrimidin-6-yl)amino)-3-methylphenyl)acrylamide | 540 |

-continued

| Example No. | Compound structure | Compound name | MS: m/z [M + 1]+ |
|---|---|---|---|
| 11 | 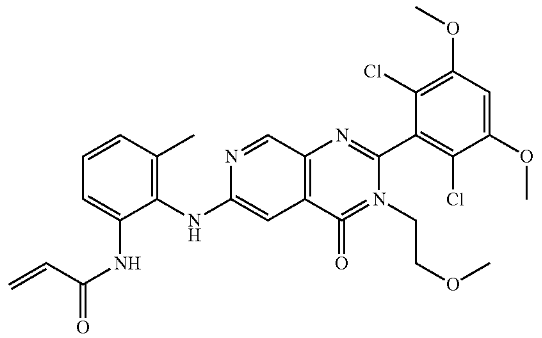 | N-(2-((2-(2,6-dichloro-3,5-dimethoxyphenyl)-3-(2-methoxyethyl)-4-oxo-3,4-dihydropyrido[3,4-d]pyrimidin-6-yl)amino)-3-methylphenyl) acrylamide | 584 |
| 13 | 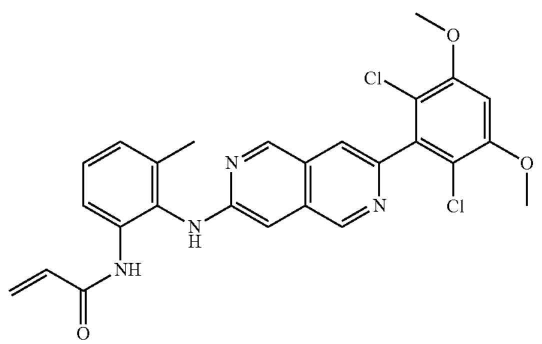 [SMILES: C=CC(=O)Nc1cccc(C)c1Nc1cc2cnc(-c3c(Cl)c(OC)cc(OC)c3Cl)cc2cn1] | N-(-2-((7-(2,6-dichloro-3,5-dimethoxyphenyl)-2,6-naphthyridin-3-yl)amino)-3-methylphenyl)acrylamide | 509 |
| 14 | 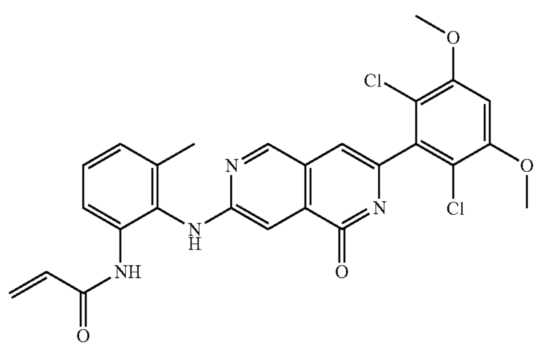 | N-(2-((6-(2,6-dichloro-3,5-dimethoxyphenyl)pyrido[3,4-d]pyrimidin-2-yl)amino)-3-methylphenyl)acrylamide | 510 |
| 15 | 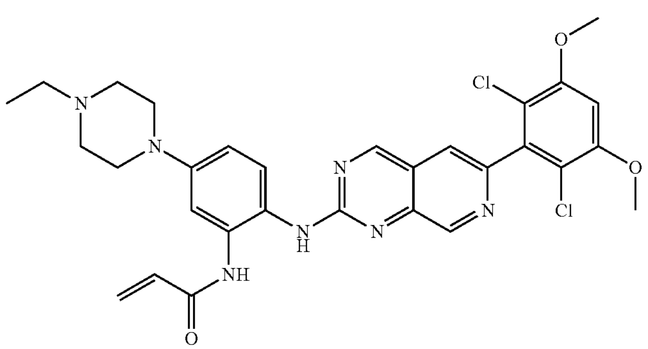 [SMILES: C=CC(=O)Nc1cc(N2CCN(CC)CC2)ccc1Nc1ncc2cc(-c3c(Cl)c(OC)cc(OC)c3Cl)ncc2n1] | N-(2-((6-(2,6-dichloro-3,5-dimethoxyphenyl)pyrido[3,4-d]pyrimidin-2-yl)amino)-5-(4-ethylpiperazin-1-yl)phenyl)acrylamide | 608 |

-continued
| Example No. | Compound structure | Compound name | MS: m/z [M + 1]+ |
|---|---|---|---|
| 16 | 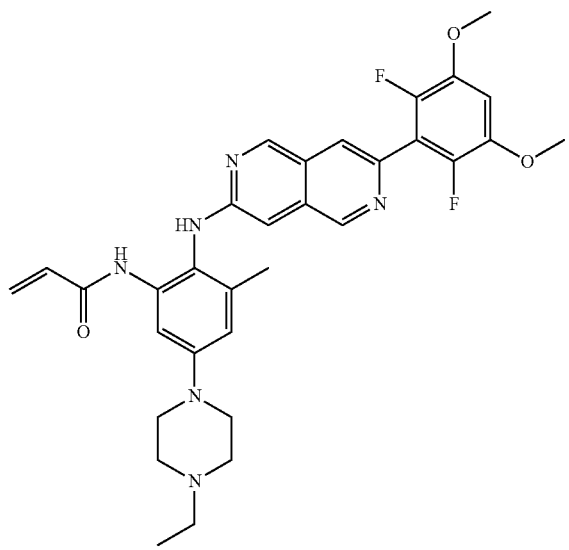 [SMILES: C=CC(=O)Nc1cc(N2CCN(CC)CC2)cc(C)c1Nc1cc2cnc(-c3c(F)c(OC)cc(OC)c3F)cc2cn1] | N-(2-((7-(2,6-difluoro-3,5-dimethoxyphenyl)-2,6-naphthyridin-3-yl)amino)-5-(4-ethylpiperazin-1-yl)-3-methylphenyl)acrylamide | 589 |
| 17 | 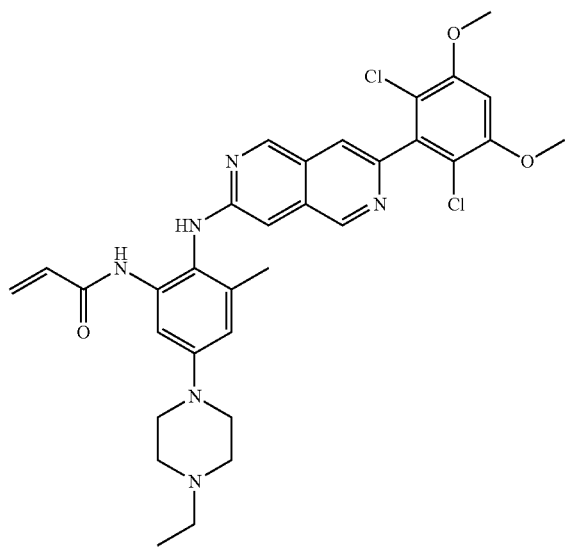 [SMILES: C=CC(=O)Nc1cc(N2CCN(CC)CC2)cc(C)c1Nc1cc2cnc(-c3c(Cl)c(OC)cc(OC)c3Cl)cc2cn1] | N-(2-((7-(2,6-dichloro-3,5-dimethoxyphenyl)-2,6-naphthyridin-3-yl)amino)-5-(4-ethylpiperazin-1-yl)-3-methylphenyl)acrylamide | 621 |

-continued

| Example No. | Compound structure | Compound name | MS: m/z [M + 1]+ |
|---|---|---|---|
| 18 | 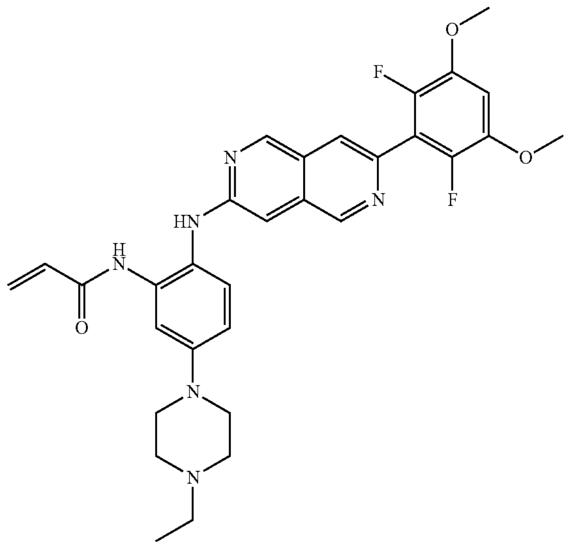 [SMILES: C=CC(=O)Nc1cc(N2CCN(CC)CC2)ccc1Nc1cc2cnc(-c3c(F)c(OC)cc(OC)c3F)cc2cn1] | N-(2-((7-(2,6-difluoro-3,5-dimethoxyphenyl)-2,6-naphthyridin-3-yl)amino)-5-(4-ethylpiperazin-1-yl)phenyl)acrylamide | 575 |
| 19 | 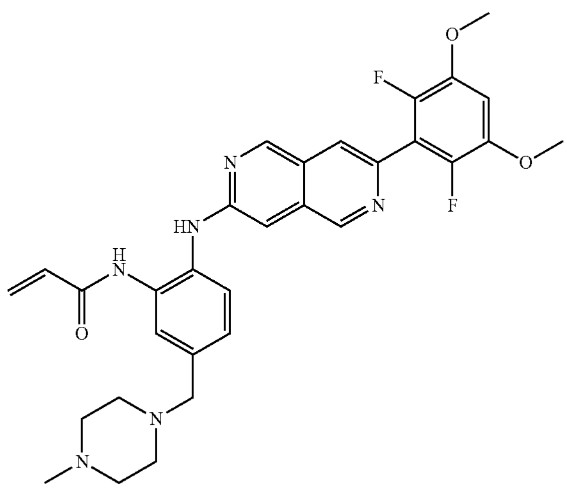 [SMILES: C=CC(=O)Nc1cc(CN2CCN(C)CC2)ccc1Nc1cc2cnc(-c3c(F)c(OC)cc(OC)c3F)cc2cn1] | N-(2-((7-(2,6-difluoro-3,5-dimethoxyphenyl)-2,6-naphthyridin-3-yl)amino)-5-((4-methylpiperazin-1-yl)methyl)phenyl)acrylamide | 575 |
| 20 | 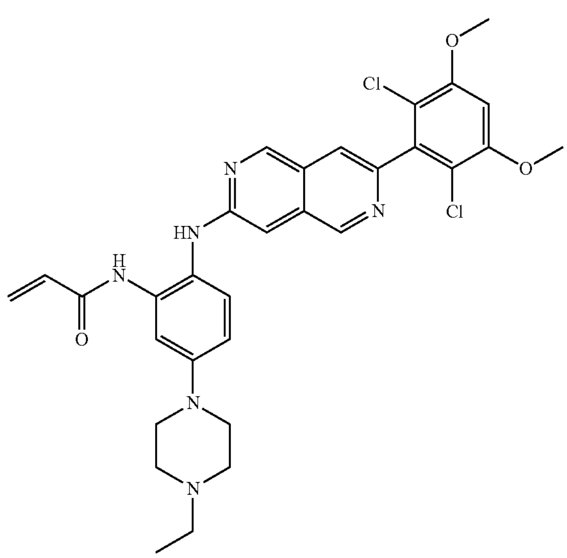 [SMILES: C=CC(=O)Nc1cc(N2CCN(CC)CC2)ccc1Nc1cc2cnc(-c3c(Cl)c(OC)cc(OC)c3Cl)cc2cn1] | N-(2-((7-(2,6-dichloro-3,5-dimethoxyphenyl)-2,6-naphthyridin-3-yl)amino)-5-(4-ethylpiperazin-1-yl)phenyl)acrylamide | 607 |

| Example No. | Compound structure | Compound name | MS: m/z [M + 1]+ |
|---|---|---|---|
| 21 | 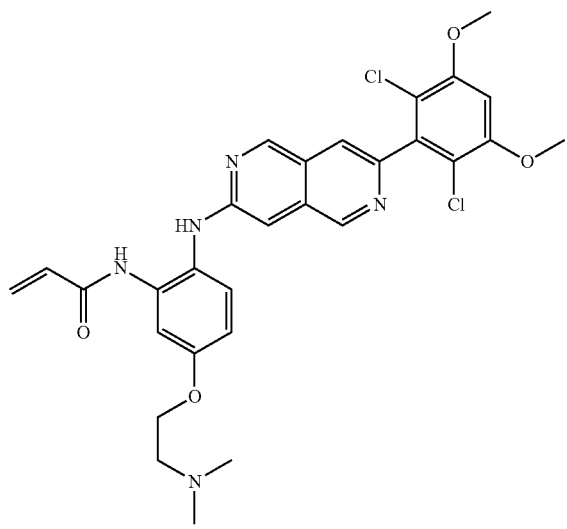 [SMILES: C=CC(=O)Nc1cc(OCCN(C)C)ccc1Nc1cc2cnc(-c3c(Cl)c(OC)cc(OC)c3Cl)cc2cn1] | N-(2-((7-(2,6-dichloro-3,5-dimethoxyphenyl)-2,6-naphthyridin-3-yl)amino)-5-(2-dimethylamino)dimethoxy)phenyl)acrylamide | 582 |
| 22 | 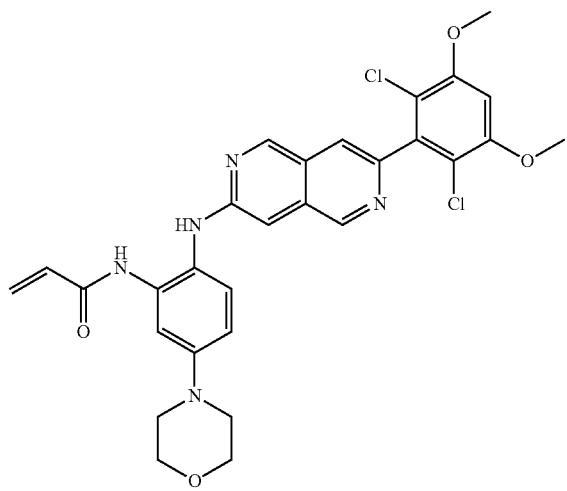 [SMILES: C=CC(=O)Nc1cc(N2CCOCC2)ccc1Nc1cc2cnc(-c3c(Cl)c(OC)cc(OC)c3Cl)cc2cn1] | N-(2-((7-(2,6-dichloro-3,5-dimethoxyphenyl)-2,6-naphthyridin-3-yl)amino)-5-morpholinophenyl)acrylamide | 580 |
| 23 | 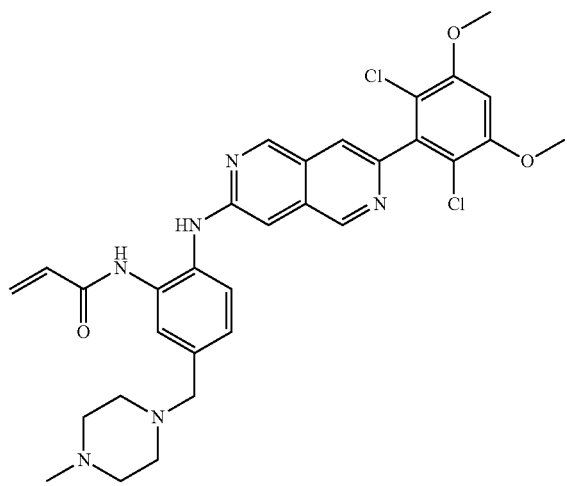 [SMILES: C=CC(=O)Nc1cc(CN2CCN(C)CC2)ccc1Nc1cc2cnc(-c3c(Cl)c(OC)cc(OC)c3Cl)cc2cn1] | N-(2-((7-(2,6-dichloro-3,5-dimethoxyphenyl)-2,6-naphthyridin-3-yl))amino)-5-((4-methylpiperazin-1-yl)methyl)phenyl)acrylamide | 607 |

-continued

| Example No. | Compound structure | Compound name | MS: m/z [M + 1]+ |
|---|---|---|---|
| 24 | 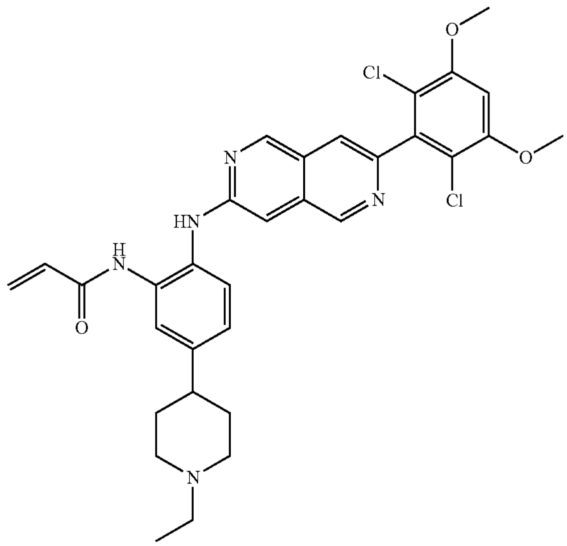 [SMILES: C=CC(=O)Nc1cc(C2CCN(CC)CC2)ccc1Nc1cc2cnc(-c3c(Cl)c(OC)cc(OC)c3Cl)cc2cn1] | N-(2-((7-(2,6-dichloro-3,5-dimethoxyphenyl)-2,6-naphthyridin-3-yl)amino)-5-(1-ethylpiperidin-4-yl)phenyl)acrylamide | 606 |
| 25 | 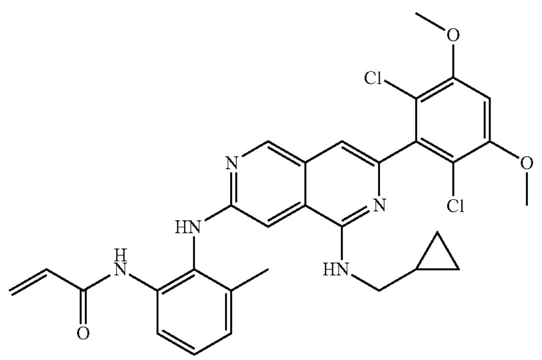 [SMILES: C=CC(=O)Nc1cccc(C)c1Nc1cc2c(NCC3CC3)nc(-c3c(Cl)c(OC)cc(OC)c3Cl)cc2cn1] | N-(2-((5-((cyclopropylmethyl)amino)-7-(2,6-dichloro-3,5-dimethoxyphenyl)-2,6-naphthyridin-3-yl)amino)-3-methylphenyl)acrylamide | 578 |
| 26 | 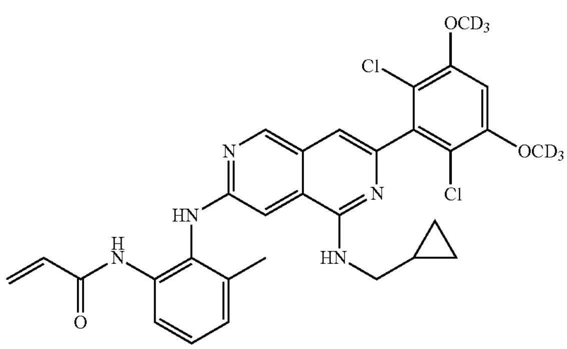 | N-(2-((5-((cyclopropylmethyl)amino)-7-(2,6-dichloro-3,5-bis(dimethoxy-$d_3$)phenyl)-2,6-naphthyridin-3-yl)amino)-3-methylphenyl)acrylamide | 584 |
| 27 | 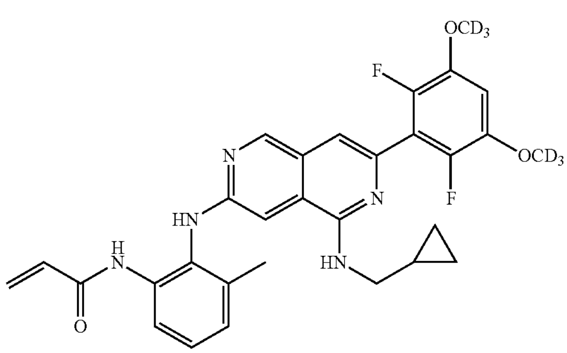 | N-(2-((5-((cyclopropylmethyl)amino)-7-(2,6-difluoro-3,5-bis(dimethoxy-$d_3$)phenyl)-2,6-naphthyridin-3-yl)amino)-3-methylphenyl)acrylamide | 552 |

| Example No. | Compound structure | Compound name | MS: m/z [M + 1]+ |
|---|---|---|---|
| 28 | 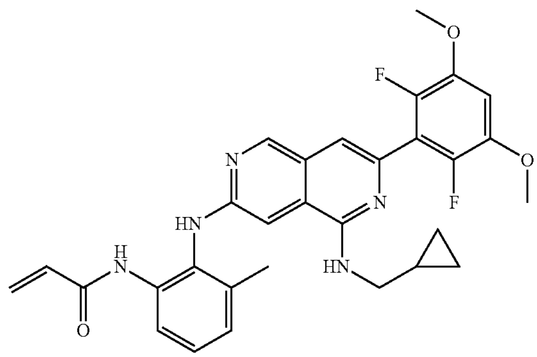 [SMILES: C=CC(=O)Nc1cccc(C)c1Nc1cc2c(NCC3CC3)nc(-c3c(F)c(OC)cc(OC)c3F)cc2cn1] | N-(2-((5-((cyclopropylmethyl)amino)-7-(2,6-difluoro-3,5-dimethoxyphenyl)-2,6-naphthyridin-3-yl)amino)-3-methylphenyl)acrylamide | 546 |
| 29 | 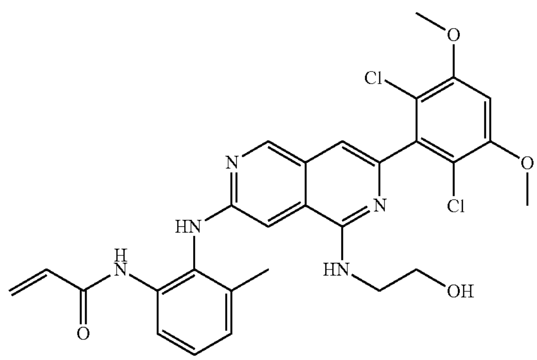 [SMILES: C=CC(=O)Nc1cccc(C)c1Nc1cc2c(NCCO)nc(-c3c(Cl)c(OC)cc(OC)c3Cl)cc2cn1] | N-(2-((7-(2,6-dichloro-3,5-dimethoxyphenyl)-5-((2-hydroxyethyl)amino)-2,6-naphthyridin-3-yl)amino)-3-methylphenyl)acrylamide | 568 |
| 30 | 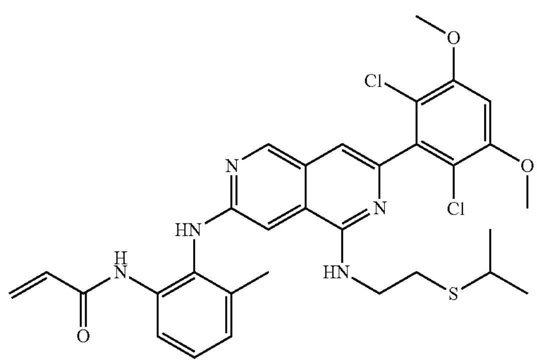 [SMILES: C=CC(=O)Nc1cccc(C)c1Nc1cc2c(NCCSC(C)C)nc(-c3c(Cl)c(OC)cc(OC)c3Cl)cc2cn1] | N-(2-((7-(2,6-dichloro-3,5-dimethoxyphenyl)-5-((2-isopropylthio)ethyl)amino)-2,6-naphthyridin-3-yl)amino)-3-methylphenyl)acrylamide | 626 |
| 31 | 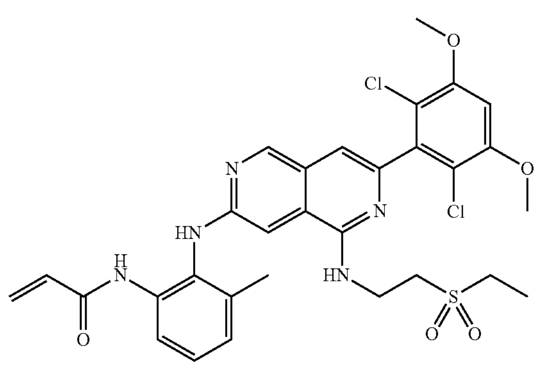 [SMILES: C=CC(=O)Nc1cccc(C)c1Nc1cc2c(NCCS(=O)(=O)CC)nc(-c3c(Cl)c(OC)cc(OC)c3Cl)cc2cn1] | N-(2-((7-(2,6-dichloro-3,5-dimethoxyphenyl)-5-((2-(ethylsulfonyl)ethyl)amino)-2,6-naphthyridin-3-yl)amino)-3-methylphenyl)acrylamide | 644 |

| Example No. | Compound structure | Compound name | MS: m/z [M + 1]+ |
|---|---|---|---|
| 32 | 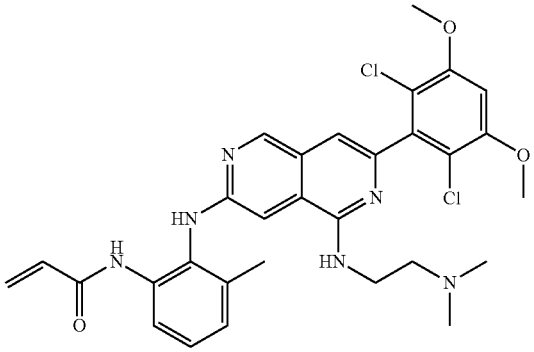 [SMILES: C=CC(=O)Nc1cccc(C)c1Nc1cc2c(NCCN(C)C)nc(-c3c(Cl)c(OC)cc(OC)c3Cl)cc2cn1] | N-(2-((7-(2,6-dichloro-3,5-dimethoxyphenyl)-5-((2-(dimethylamino)ethyl)amino)-2,6-naphthyridin-3-yl)amino)-3-methylphenyl)acrylamide | 595 |
| 33 | 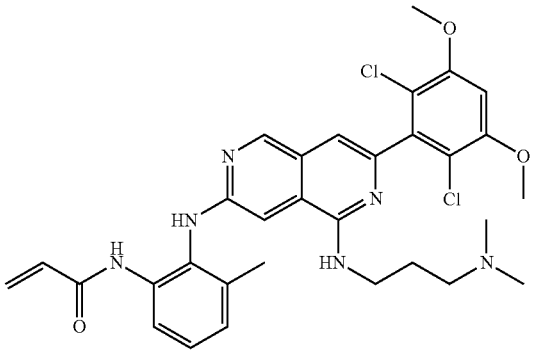 [SMILES: C=CC(=O)Nc1cccc(C)c1Nc1cc2c(NCCCN(C)C)nc(-c3c(Cl)c(OC)cc(OC)c3Cl)cc2cn1] | N-(2-((7-(2,6-dichloro-3,5-dimethoxyphenyl)-5-((3-(dimethylamino)propyl)amino)-2,6-naphthyridin-3-yl)amino)-3-methylphenyl)acrylamide | 609 |
| 34 | 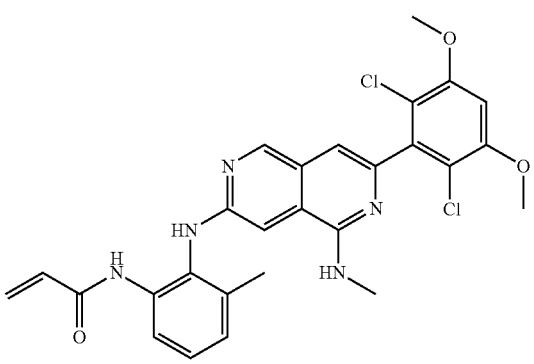 [SMILES: C=CC(=O)Nc1cccc(C)c1Nc1cc2c(NC)nc(-c3c(Cl)c(OC)cc(OC)c3Cl)cc2cn1] | N-(2-((7-(2,6-dichloro-3,5-dimethoxyphenyl)-5-(methylamino)-2,6-naphthyridin-3-yl)amino)-3-methylphenyl)acrylamide | 538 |
| 35 | 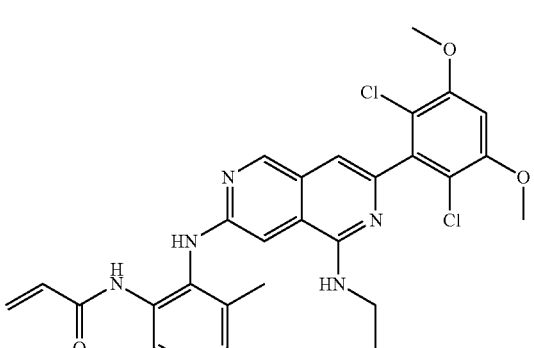 | N-(2-((7-(2,6-dichloro-3,5-dimethoxyphenyl)-5-(ethylamino)-2,6-naphthyridin-3-yl)amino)-3-methylphenyl)acrylamide | 552 |

-continued

| Example No. | Compound structure | Compound name | MS: m/z [M + 1]⁺ |
|---|---|---|---|
| 36 | 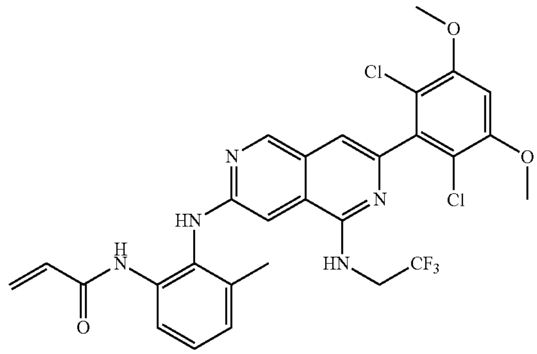 [SMILES: C=CC(=O)Nc1cccc(C)c1Nc1cc2c(NCC(F)(F)F)nc(-c3c(Cl)c(OC)cc(OC)c3Cl)cc2cn1] | N-(2-((7-(2,6-dichloro-3,5-dimethoxyphenyl)-5-((2,2,2-trifluoroethyl)amino)-2,6-naphthyridin-3-yl)amino)-3-methylphenyl)acrylamide | 606 |
| 37 | 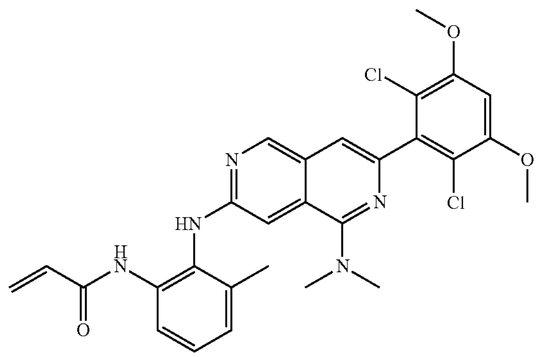 [SMILES: C=CC(=O)Nc1cccc(C)c1Nc1cc2c(N(C)C)nc(-c3c(Cl)c(OC)cc(OC)c3Cl)cc2cn1] | N-(2-((7-(2,6-dichloro-3,5-dimethoxyphenyl)-5-(dimethylamino)-2,6-naphthyridin-3-yl)amino)-3-methylphenyl)acrylamide | 552 |
| 38 | 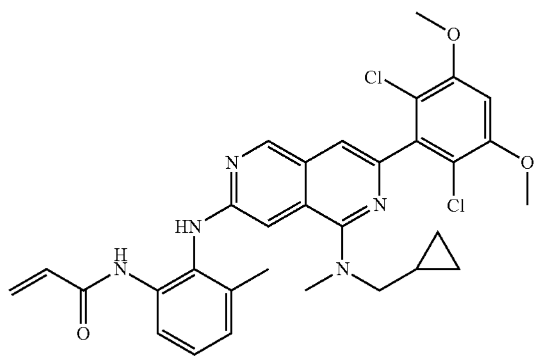 [SMILES: C=CC(=O)Nc1cccc(C)c1Nc1cc2c(N(C)CC3CC3)nc(-c3c(Cl)c(OC)cc(OC)c3Cl)cc2cn1] | N-(2-((5-((cyclopropylmethyl)(methyl)amino)-7-(2,6-dichloro-3,5-dimethoxyphenyl)-2,6-naphthyridin-3-yl)amino)-3-methylphenyl)acrylamide | 592 |
| 39 | 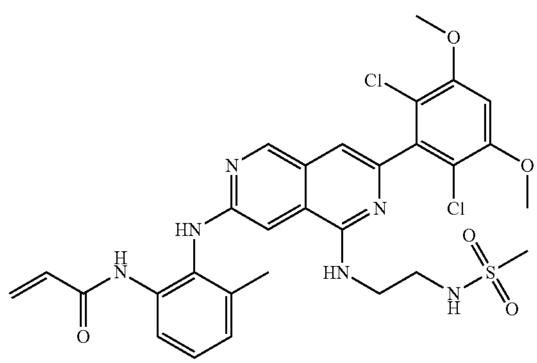 [SMILES: C=CC(=O)Nc1cccc(C)c1Nc1cc2c(NCCNS(C)(=O)=O)nc(-c3c(Cl)c(OC)cc(OC)c3Cl)cc2cn1] | N-(2-((7-(2,6-dichloro-3,5-dimethoxyphenyl)-5-((2-(methylsulfonamido)ethyl)amino)-2,6-naphthyridin-3-yl)amino)-3-methylphenyl)acrylamide | 645 |

| Example No. | Compound structure | Compound name | MS: m/z [M + 1]+ |
|---|---|---|---|
| 40 | 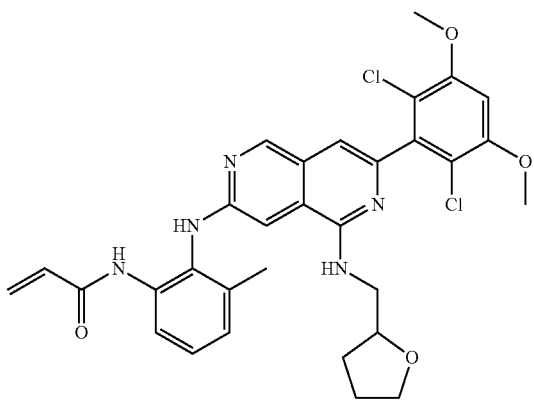 [SMILES: C=CC(=O)Nc1cccc(C)c1Nc1cc2c(NCC3CCCO3)nc(-c3c(Cl)c(OC)cc(OC)c3Cl)cc2cn1] | N-(2-((7-(2,6-dichloro-3,5-dimethoxyphenyl)-5-(((tetrahydrofuran-2-yl)methyl)amino)-2,6-naphthyridin-3-yl)amino)-3-methylphenyl)acrylamide | 608 |
| 41 | 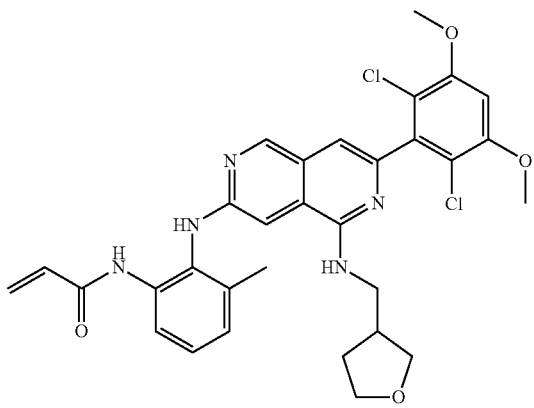 [SMILES: C=CC(=O)Nc1cccc(C)c1Nc1cc2c(NCC3CCOC3)nc(-c3c(Cl)c(OC)cc(OC)c3Cl)cc2cn1] | N-(2-((7-(2,6-dichloro-3,5-dimethoxyphenyl)-5-(((tetrahydrofuran-3-yl)methyl)amino)-2,6-naphthyridin-3-yl)amino)-3-methylphenyl)acrylamide | 608 |
| 42 | 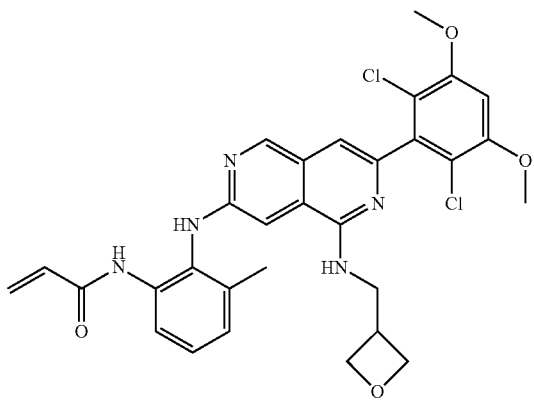 [SMILES: C=CC(=O)Nc1cccc(C)c1Nc1cc2c(NCC3COC3)nc(-c3c(Cl)c(OC)cc(OC)c3Cl)cc2cn1] | N-(2-((7-(2,6-dichloro-3,5-dimethoxyphenyl)-5-((oxetan-3-ylmethyl)amino)-2,6-naphthyridin-3-yl)amino)-3-methylphenyl)acrylamide | 594 |

-continued

| Example No. | Compound structure | Compound name | MS: m/z [M + 1]+ |
|---|---|---|---|
| 43 | 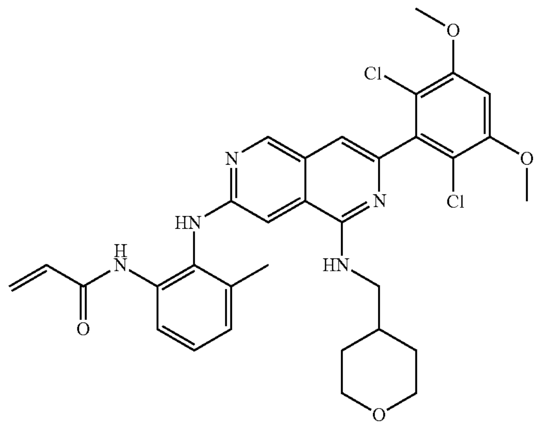 [SMILES: C=CC(=O)Nc1cccc(C)c1Nc1cc2c(NCC3CCOCC3)nc(-c3c(Cl)c(OC)cc(OC)c3Cl)cc2cn1] | N-(2-((7-(2,6-dichloro-3,5-dimethoxyphenyl)-5-(((tetrahydro-2H-pyran-4-yl)methylamino)-2,6-naphthyridin-3-yl)amino)-3-methylphenyl)acrylamide | 622 |
| 44 | 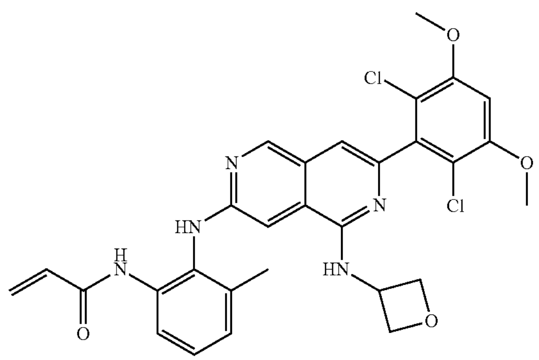 [SMILES: C=CC(=O)Nc1cccc(C)c1Nc1cc2c(NC3COC3)nc(-c3c(Cl)c(OC)cc(OC)c3Cl)cc2cn1] | N-(2-((7-(2,6-dichloro-3,5-dimethoxyphenyl)-5-(oxetan-3-ylamino)-2,6-naphthyridin-3-yl))amino)-3-methylphenyl)acrylamide | 580 |
| 45 | 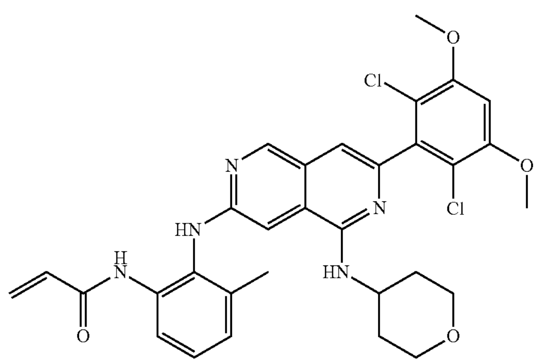 [SMILES: C=CC(=O)Nc1cccc(C)c1Nc1cc2c(NC3CCOCC3)nc(-c3c(Cl)c(OC)cc(OC)c3Cl)cc2cn1] | N-(2-((7-(2,6-dichloro-3,5-dimethoxyphenyl)-5-((tetrahydro-2H-pyran-4-yl)amino)-2,6-naphthyridin-3-yl)amino)-3-methylphenyl)acrylamide | 608 |
| 46 | 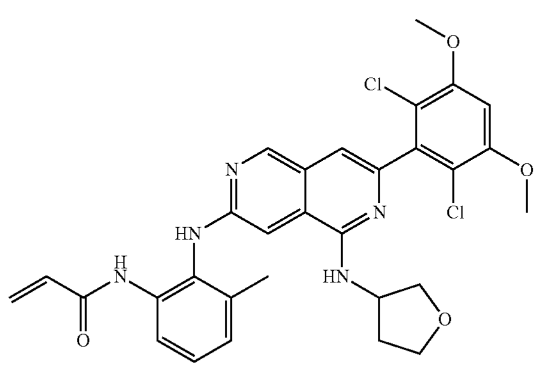 [SMILES: C=CC(=O)Nc1cccc(C)c1Nc1cc2c(NC3CCOC3)nc(-c3c(Cl)c(OC)cc(OC)c3Cl)cc2cn1] | N-(2-((7-(2,6-dichloro-3,5-dimethoxyphenyl)-5-((tetrahydrofuran-3-yl)amino)-2,6-naphthyridin-3-yl)amino)-3 methylphenyl)acrylamide | 594 |

-continued

| Example No. | Compound structure | Compound name | MS: m/z [M + 1]+ |
|---|---|---|---|
| 47 | 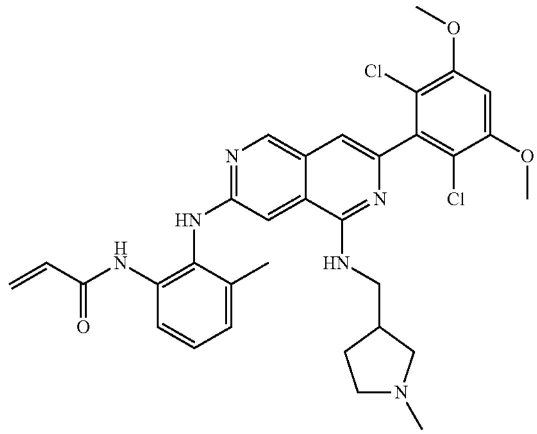 [SMILES: C=CC(=O)Nc1cccc(C)c1Nc1cc2c(NCC3CCN(C)C3)nc(-c3c(Cl)c(OC)cc(OC)c3Cl)cc2cn1] | N-(2-((7-(2,6-dichloro-3,5-dimethoxyphenyl)-5-(((1-methylpyrrolidin-3-yl)methyl)amino)-2,6-naphthyridin-3-yl)amino)-3-methylphenyl)acrylamide | 621 |
| 48 | 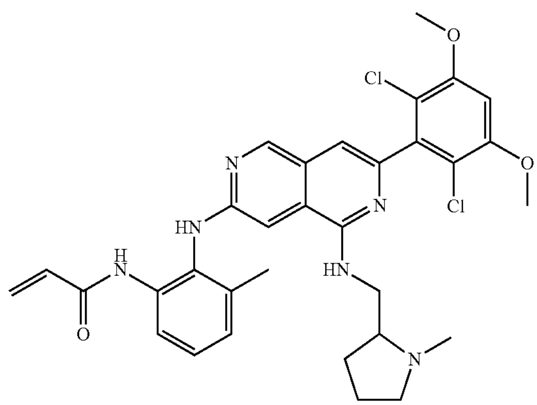 [SMILES: C=CC(=O)Nc1cccc(C)c1Nc1cc2c(NCC3CCCN3C)nc(-c3c(Cl)c(OC)cc(OC)c3Cl)cc2cn1] | N-(2-((7-(2,6-dichloro-3,5-dimethoxyphenyl)-5-(((1-methyl)pyrrolidin-2-yl)methyl)amino)-2,6-naphthyridin-3-yl)amino)-3-methylphenyl)acrylamide | 621 |
| 49 | 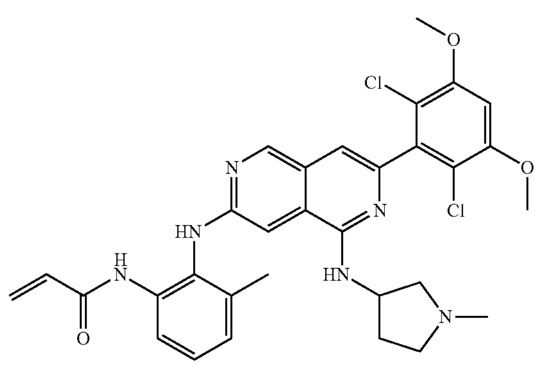 [SMILES: C=CC(=O)Nc1cccc(C)c1Nc1cc2c(NC3CCN(C)C3)nc(-c3c(Cl)c(OC)cc(OC)c3Cl)cc2cn1] | N-(2-((7-(2,6-dichloro-3,5-dimethoxyphenyl)-5-((1-methylpyrrolidin-3-yl)amino)-2,6-naphthyridin-3-yl)amino)-3-methylphenyl)acrylamide | 607 |

-continued

| Example No. | Compound structure | Compound name | MS: m/z [M + 1]+ |
|---|---|---|---|
| 50 | 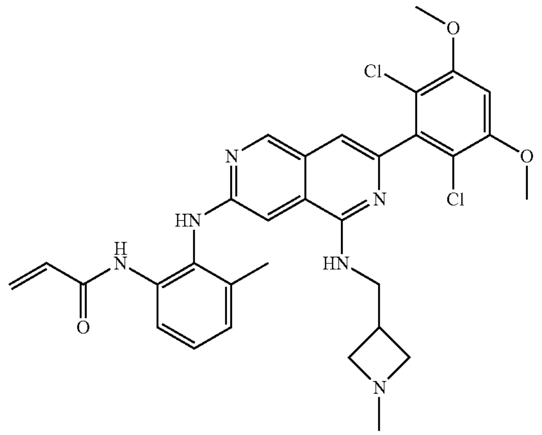 [SMILES: C=CC(=O)Nc1cccc(C)c1Nc1cc2c(NCC3CN(C)C3)nc(-c3c(Cl)c(OC)cc(OC)c3Cl)cc2cn1] | N-(2-((7-(2,6-dichloro-3,5-dimethoxyphenyl)-5-(((1-methylazetidin-3-yl)methyl)amino)-2,6-naphthyridin-3-yl)amino)-3-methylphenyl)acrylamide | 607 |
| 51 | 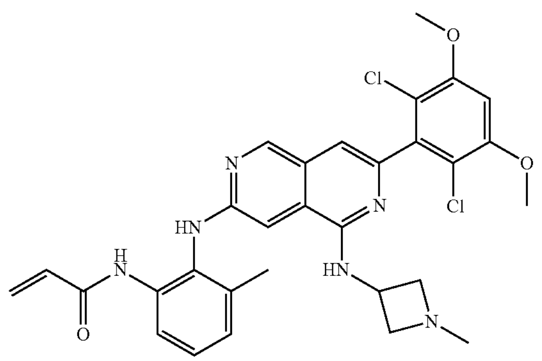 [SMILES: C=CC(=O)Nc1cccc(C)c1Nc1cc2c(NC3CN(C)C3)nc(-c3c(Cl)c(OC)cc(OC)c3Cl)cc2cn1] | N-(2-((7-(2,6-dichloro-3,5-dimethoxyphenyl)-5-((1-methylazetidin-3-yl)amino)-2,6-naphthyridin-3-yl)amino)-3-methylphenyl)acrylamide | 593 |
| 52 | 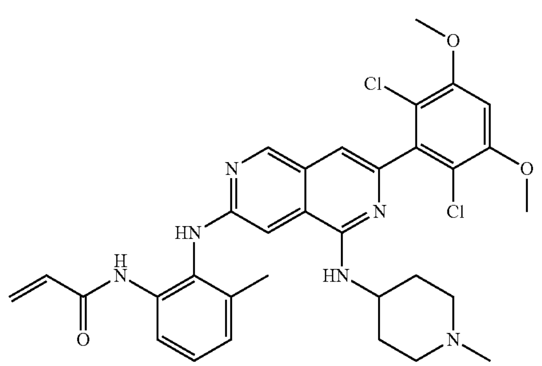 [SMILES: C=CC(=O)Nc1cccc(C)c1Nc1cc2c(NC3CCN(C)CC3)nc(-c3c(Cl)c(OC)cc(OC)c3Cl)cc2cn1] | N-(2-((7-(2,6-dichloro-3,5-dimethoxyphenyl)-5-((1-methylpiperidin-4-yl)amino)-2,6-naphthyridin-3-yl)amino)-3-methylphenyl)acrylamide | 621 |

-continued

| Example No. | Compound structure | Compound name | MS: m/z [M + 1]+ |
|---|---|---|---|
| 53 | 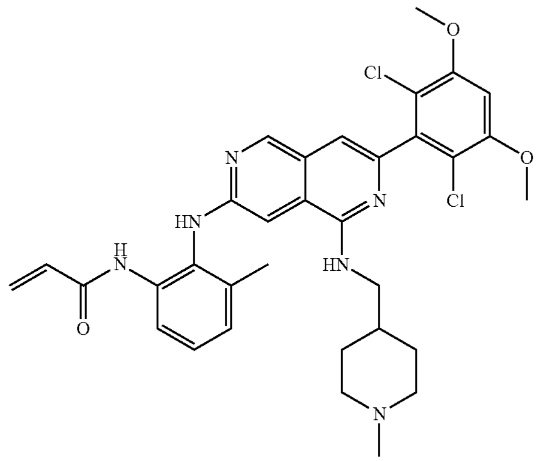 [SMILES: C=CC(=O)Nc1cccc(C)c1Nc1cc2c(NCC3CCN(C)CC3)nc(-c3c(Cl)c(OC)cc(OC)c3Cl)cc2cn1] | N-(2-((7-(2,6-dichloro-3,5-dimethoxyphenyl)-5-(((1-methylpiperidin-4-yl)methyl)amino)-2,6-naphthyridin-3-yl)amino)-3-methylphenyl)acrylamide | 635 |
| 54 | 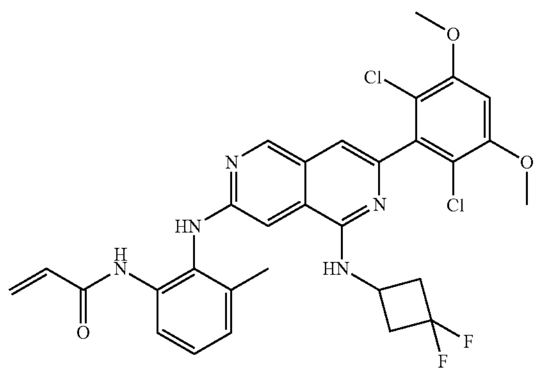 [SMILES: C=CC(=O)Nc1cccc(C)c1Nc1cc2c(NC3CC(F)(F)C3)nc(-c3c(Cl)c(OC)cc(OC)c3Cl)cc2cn1] | N-(2-((7-(2,6-dichloro-3,5-dimethoxyphenyl)-5-((3,3-difluorocyclobutyl)amino)-2,6-naphthyridin-3-yl)amino)-3-methylphenyl)acrylamide | 614 |
| 55 | 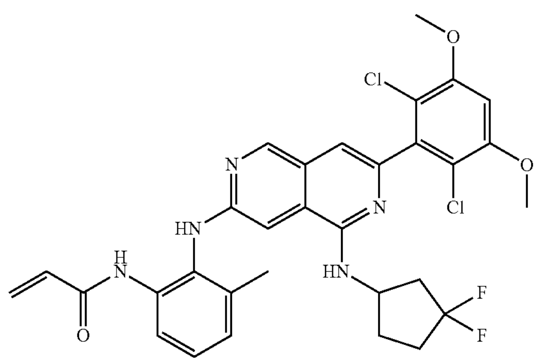 [SMILES: C=CC(=O)Nc1cccc(C)c1Nc1cc2c(NC3CCC(F)(F)C3)nc(-c3c(Cl)c(OC)cc(OC)c3Cl)cc2cn1] | N-(2-((7-(2,6-dichloro-3,5-dimethoxyphenyl)-5-((3,3-difluorocyclopentyl)amino)-2,6-naphthyridin-3-yl)amino)-3-methylphenyl)acrylamide | 628 |
| 56 | 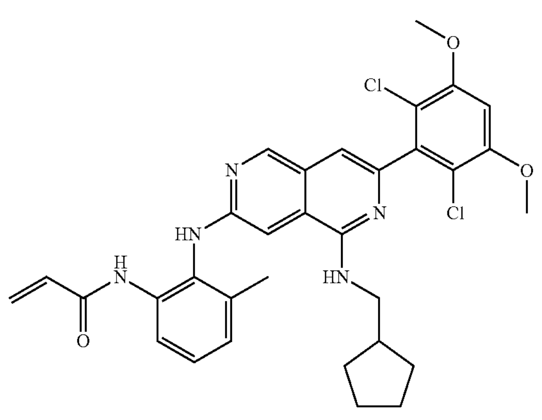 [SMILES: C=CC(=O)Nc1cccc(C)c1Nc1cc2c(NCC3CCCC3)nc(-c3c(Cl)c(OC)cc(OC)c3Cl)cc2cn1] | N-(2-((5-((cyclopentylmethyl)amino)-7-(2,6-dichloro-3,5-dimethoxyphenyl)-2,6-naphthyridin-3-yl)amino)-3-methylphenyl)acrylamide | 606 |

| Example No. | Compound structure | Compound name | MS: m/z [M + 1]+ |
|---|---|---|---|
| 57 | 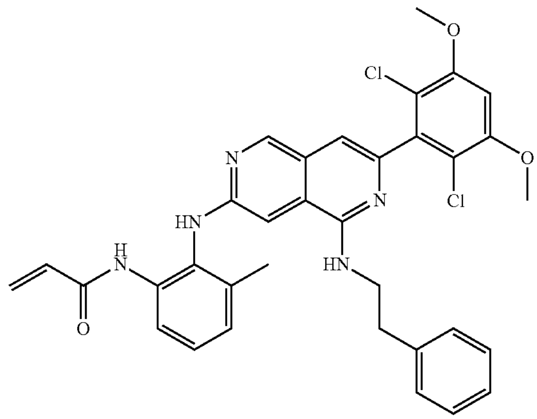 [SMILES: C=CC(=O)Nc1cccc(C)c1Nc1cc2c(NCCc3ccccc3)nc(-c3c(Cl)c(OC)cc(OC)c3Cl)cc2cn1] | N-(2-((7-(2,6-dichloro-3,5-dimethoxyphenyl)-5-(phenethylamino)-2,6-naphthyridin-3-yl)amino)-3-methylphenyl)acrylamide | 628 |
| 58 | 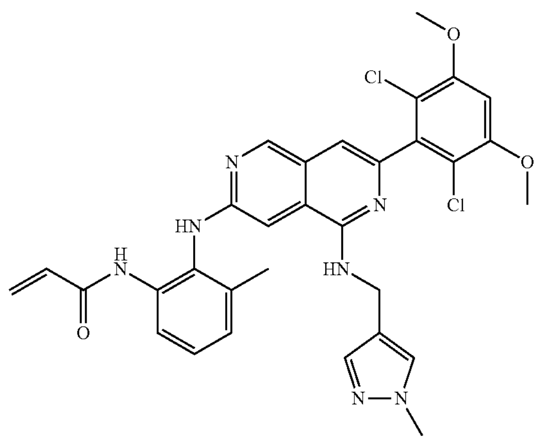 [SMILES: C=CC(=O)Nc1cccc(C)c1Nc1cc2c(NCc3cnn(C)c3)nc(-c3c(Cl)c(OC)cc(OC)c3Cl)cc2cn1] | N-(2-((7-(2,6-dichloro-3,5-dimethoxyphenyl)-5-(((1-methyl-1H-pyrazol-4-yl)methyl)amino)-2,6-naphthyridin-3-yl)amino)-3-methylphenyl)acrylamide | 618 |
| 59 | 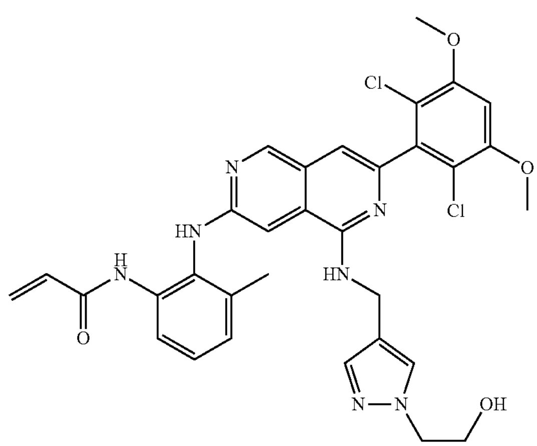 [SMILES: C=CC(=O)Nc1cccc(C)c1Nc1cc2c(NCc3cnn(CCO)c3)nc(-c3c(Cl)c(OC)cc(OC)c3Cl)cc2cn1] | N-(2-((7-(2,6-dichloro-3,5-dimethoxyphenyl)-5-(((1-(2-hydroxyethyl)-1H-pyrazol-4-yl)methyl)amino)-2,6-naphthyridin-3-yl)amino)-3-methylphenyl)acrylamide | 648 |

-continued

| Example No. | Compound structure | Compound name | MS: m/z [M + 1]+ |
|---|---|---|---|
| 60 | 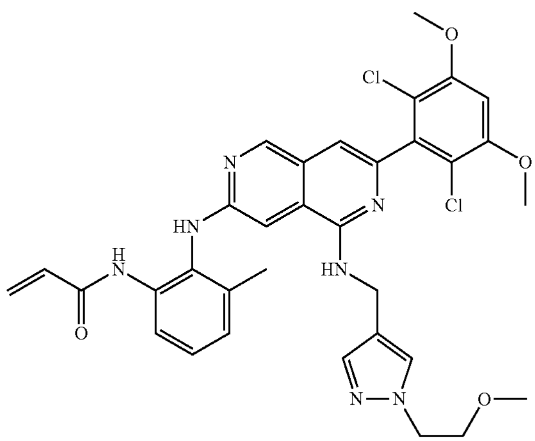 [SMILES: C=CC(=O)Nc1cccc(C)c1Nc1cc2c(NCc3cnn(CCOC)c3)nc(-c3c(Cl)c(OC)cc(OC)c3Cl)cc2cn1] | N-(2-((7-(2,6-dichloro-3,5-dimethoxyphenyl)-5-(((1-(2-dimethoxyethyl)-1H-pyrazol-4-yl)methyl)amino)-2,6-naphthyridin-3-yl)amino)-3-methylphenyl)acrylamide | 662 |
| 61 | 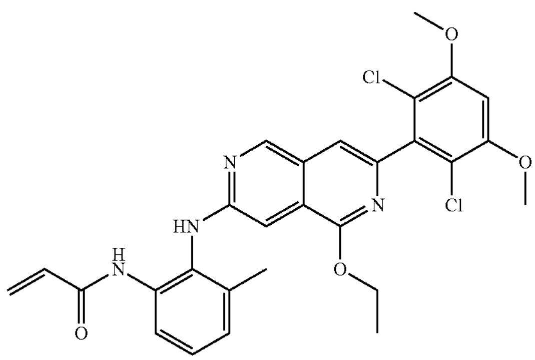 [SMILES: C=CC(=O)Nc1cccc(C)c1Nc1cc2c(OCC)nc(-c3c(Cl)c(OC)cc(OC)c3Cl)cc2cn1] | N-(2-((7-(2,6-dichloro-3,5-dimethoxyphenyl)-5-ethoxy-2,6-naphthyridin-3-yl)amino)-3-methylphenyl)acrylamide | 553 |
| 62 | 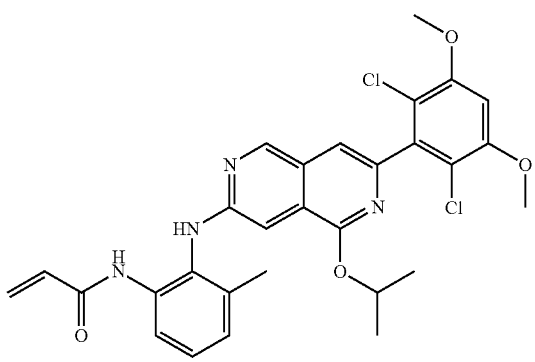 [SMILES: C=CC(=O)Nc1cccc(C)c1Nc1cc2c(OC(C)C)nc(-c3c(Cl)c(OC)cc(OC)c3Cl)cc2cn1] | N-(2-((7-(2,6-dichloro-3,5-dimethoxyphenyl)-5-isopropoxy-2,6-naphthyridin-3-yl)amino)-3-methylphenyl)acrylamide | 567 |
| 63 | 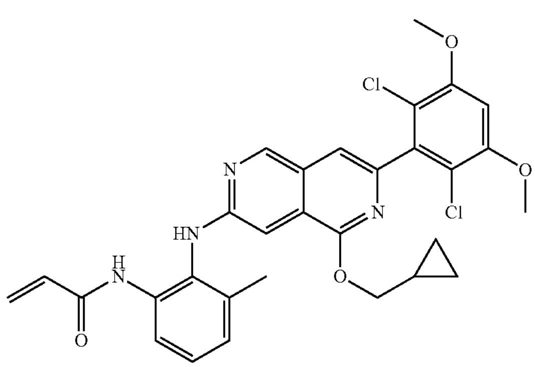 [SMILES: C=CC(=O)Nc1cccc(C)c1Nc1cc2c(OCC3CC3)nc(-c3c(Cl)c(OC)cc(OC)c3Cl)cc2cn1] | N-(2-((5-(cyclopropylmethoxy)-7-(2,6-dichloro-3,5-dimethoxyphenyl)-2,6-naphthyridin-3-yl)amino)-3-methylphenyl)acrylamide | 579 |

-continued

| Example No. | Compound structure | Compound name | MS: m/z [M + 1]+ |
|---|---|---|---|
| 64 | 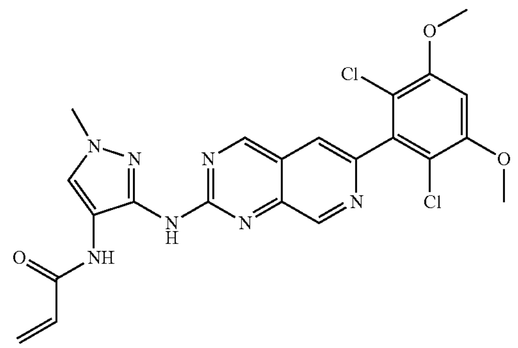 [SMILES: C=CC(=O)Nc1cn(C)nc1Nc1ncc2cc(-c3c(Cl)c(OC)cc(OC)c3Cl)ncc2n1] | N-(3-((6-(2,6-dichloro-3,5-dimethoxyphenyl)pyrido[3,4-d]pyrimidin-2-yl)amino)-1-methyl-1H-pyrazol-4-yl)acrylamide | 500 |
| 65 | 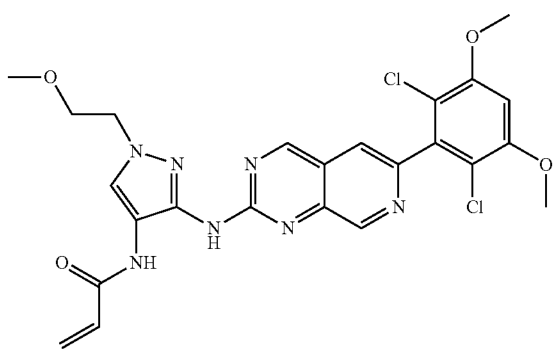 | N-(3-((6-(2,6-dichloro-3,5-dimethoxyphenyl)pyrido[3,4-d]pyrimidin-2-yl)amino-1-(2-dimethoxyethyl)-1H-pyrazol-4-yl)acrylamide | 544 |
| 66 | 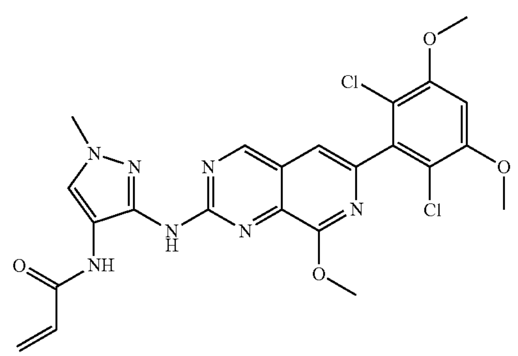 [SMILES: C=CC(=O)Nc1cn(C)nc1Nc1ncc2cc(-c3c(Cl)c(OC)cc(OC)c3Cl)nc(OC)c2n1] | N-(3-((6-(2,6-dichloro-3,5-dimethoxyphenyl)-8-methoxypyrido[3,4-d]pyrimidin-2-yl)amino)-1-methyl-1H-pyrazol-4-yl)acrylamide | 530 |
| 67 | 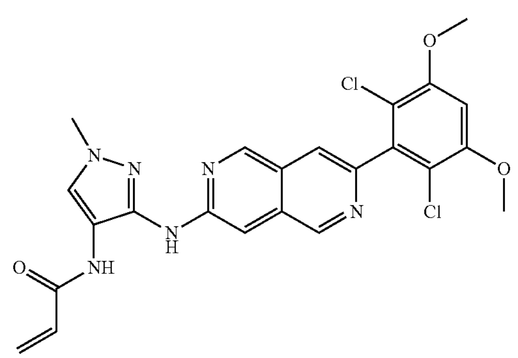 [SMILES: C=CC(=O)Nc1cn(C)nc1Nc1cc2cnc(-c3c(Cl)c(OC)cc(OC)c3Cl)cc2cn1] | N-(3-((7-(2,6-dichloro-3,5-dimethoxyphenyl)-2,6-naphthyridin-3-yl)amino)-1-methyl-1H-pyrazol-4-yl)acrylamide | 499 |

-continued

| Example No. | Compound structure | Compound name | MS: m/z [M + 1]+ |
|---|---|---|---|
| 68 | 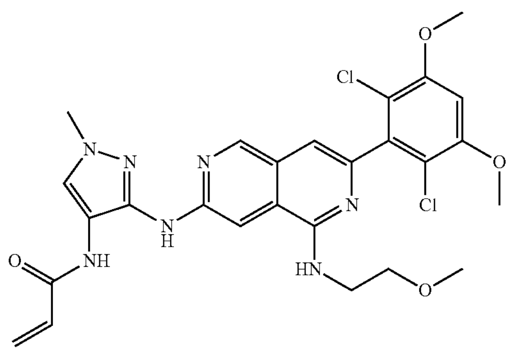 [SMILES: C=CC(=O)Nc1cn(C)nc1Nc1cc2c(NCCOC)nc(-c3c(Cl)c(OC)cc(OC)c3Cl)cc2cn1] | N-(3-((7-(2,6-dichloro-3,5-dimethoxyphenyl)-5-((2-methoxyethyl)amino)-2,6-naphthpyridin-3-yl)amino)-1-methyl-1H-pyrazol-4-yl)acrylamide | 572 |
| 69 | 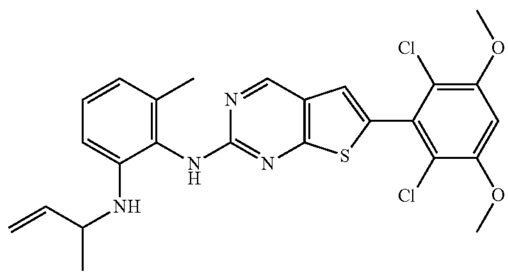 [SMILES: C=CC(C)Nc1cccc(C)c1Nc1ncc2cc(-c3c(Cl)c(OC)cc(OC)c3Cl)sc2n1] | N-(2-((6-(2,6-dichloro-3,5-dimethoxyphenyl)thieno[2,3-d]pyrimidin-2-yl)amino)-3-methylphenyl)acrylamide | 515 |
| 70 | 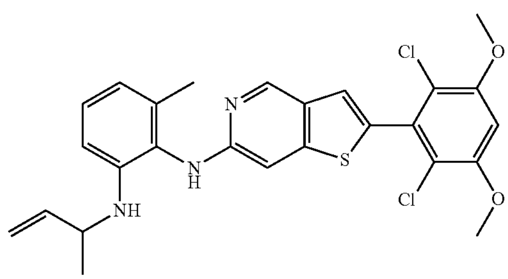 [SMILES: C=CC(C)Nc1cccc(C)c1Nc1cc2sc(-c3c(Cl)c(OC)cc(OC)c3Cl)cc2cn1] | N-(2-((2-(2,6-dichloro-3,5-dimethoxyphenyl)thieno[3,2-c]pyridin-6-yl)amino)-3-methylphenyl)acrylamide | 515 |
| 71 | 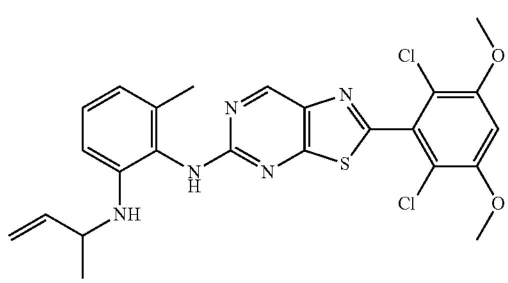 [SMILES: C=CC(C)Nc1cccc(C)c1Nc1ncc2nc(-c3c(Cl)c(OC)cc(OC)c3Cl)sc2n1] | N-(2-((2-(2,6-dichloro-3,5-dimethoxyphenyl)thiazolo[5,4-d]pyrimidin-5-yl)amino)-3-methylphenyl)acrylamide | 516 |
| 72 | 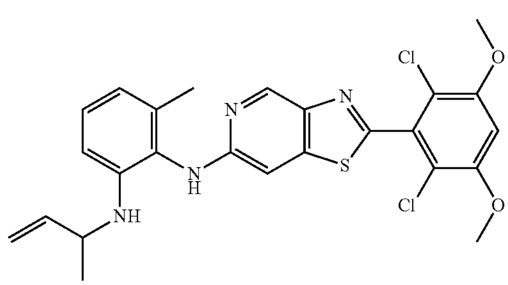 [SMILES: C=CC(C)Nc1cccc(C)c1Nc1cc2sc(-c3c(Cl)c(OC)cc(OC)c3Cl)nc2cn1] | N-(2-((2-(2,6-dichloro-3,5-dimethoxyphenyl)thiazolo[4,5-c]pyridin-6-yl)amino)-3-methylphenyl)acrylamide | 515 |

-continued

| Example No. | Compound structure | Compound name | MS: m/z [M + 1]+ |
|---|---|---|---|
| 73 | 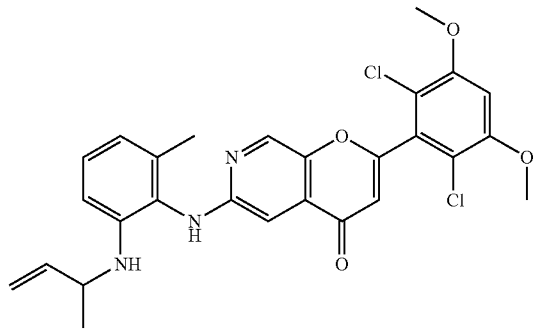 [SMILES: C=CC(C)Nc1cccc(C)c1Nc1cc2c(=O)cc(-c3c(Cl)c(OC)cc(OC)c3Cl)oc2cn1] | N-(2-((2-(2,6-dichloro-3,5-dimethoxyphenyl)-4-oxo-4H-1-pyrano[2,3-c]pyridin-6-yl)amino)-3-methylphenyl)acrylamide | 526 |
| 74 | 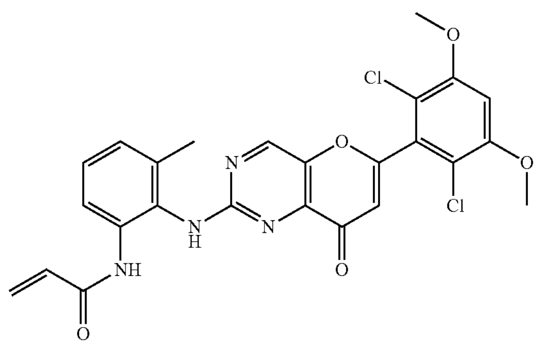 [SMILES: C=CC(=O)Nc1cccc(C)c1Nc1ncc2oc(-c3c(Cl)c(OC)cc(OC)c3Cl)cc(=O)c2n1] | N-(2-((6-(2,6-dichloro-3,5-dimethoxyphenyl)-8-oxo-8H-pyrano[3,2-d]pyrimidin-2-yl)amino)-3-methylphenyl)acrylamide | 527 |
| 75 | 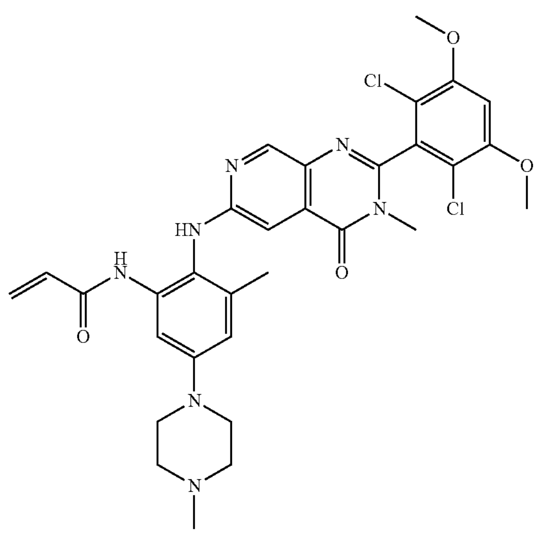 [SMILES: C=CC(=O)Nc1cc(N2CCN(C)CC2)cc(C)c1Nc1cc2c(=O)n(C)c(-c3c(Cl)c(OC)cc(OC)c3Cl)nc2cn1] | N-(2-((2-(2,6-dichloro-3,5-dimethoxyphenyl)-3-methyl-4-oxo-3,4-dihydropyrido[3,4-d]pyrimidin-6-yl)amino)-3-methyl-5-(4-methyl-piperazin-1-yl)phenyl)acrylamide | 638 |

Example 76 Preparation of N-(3-((8-((cyclopropylmethyl)amino)-6-(2,6-dichloro-3,5-dimethoxyphenyl)pyrido[3,4-d]pyrimidin-2-yl)amino)-1-methyl-1H-pyrazol-4-yl)acrylamide

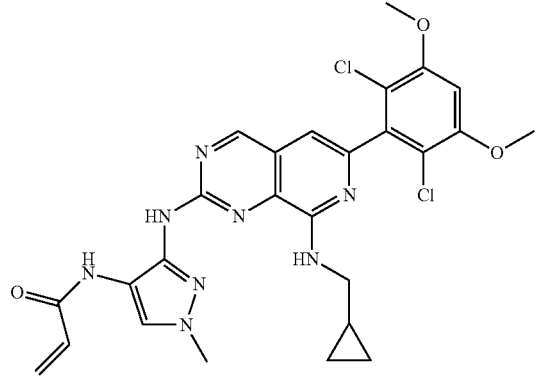 [SMILES: C=CC(=O)Nc1cn(C)nc1Nc1ncc2cc(-c3c(Cl)c(OC)cc(OC)c3Cl)nc(NCC3CC3)c2n1]

Step 1: Preparation of N-(cyclopropylmethyl)-6-(2,6-dichloro-3,5-dimethoxyphenyl)-2-(methylsulfonyl)pyrido[3,4-d]pyrimidine-8-amine

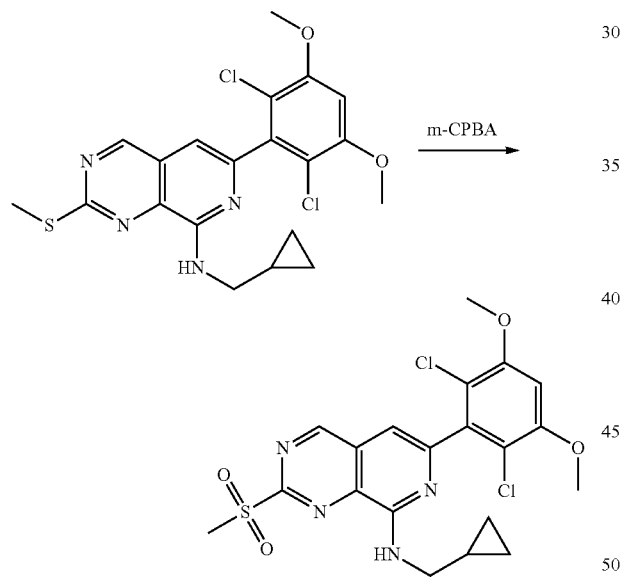

N-(cyclopropylmethyl)-6-(2,6-dichloro-3,5-dimethoxyphenyl)-2-(methylthio)pyrido[3,4-d]pyrimidine-8-amine (210 mg, 0.465 mmol) was dissolved in dichloromethane (6 mL), then m-chloroperoxybenzoic acid (200 mg, 1.163 mmol) was added, and the mixture was stirred at room temperature for 18 h. After the reaction was completed, a saturated sodium sulfite solution (5 mL) was added, and the mixture was stirred for 5 min and extracted with dichloromethane, the organic phase was washed successively with a saturated sodium bicarbonate solution and then saturated brine, dried over anhydrous sodium sulfate, filtrated, concentrated and separated by column chromatography (Eluent: PE/EA=2/1) to obtain compound N-(cyclopropylmethyl)-6-(2,6-dichloro-3,5-dimethoxyphenyl)-2-(methylsulfonyl)pyrido[3,4-d]pyrimidine-8-amine (186 mg, yield: 82.7%). MS m/z (ESI): 483.4 [M+H]⁺.

Step 2: Preparation of $N^8$-(cyclopropylmethyl)-6-(2,6-dichloro-3,5-dimethoxyphenyl)-$N^2$-(1-methy-4-nitro-1H-pyrazol-3-yl)pyrido[3,4-d]pyrimidine-2,8-diamine

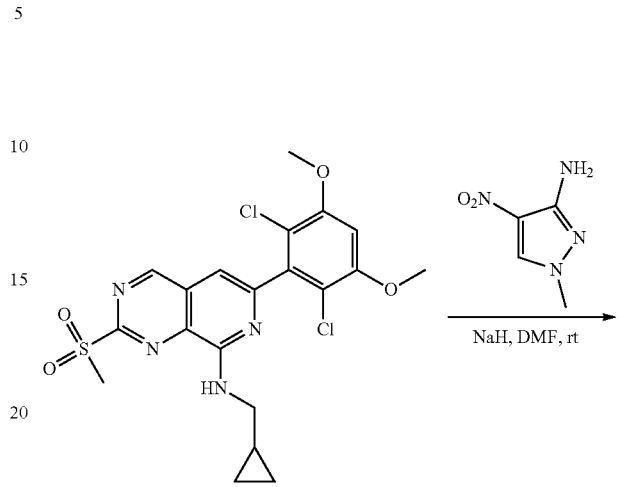

N-(cyclopropylmethyl)-6-(2,6-dichloro-3,5-dimethoxyphenyl)-2-(methylsulfonyl)pyrido[3,4-d]pyrimidine-8-amine (90 mg, 0.186 mmol) was dissolved in dried DMF (5 mL), and NaH (15 mg, 0.372 mmol) was added at 0° C., and the mixture was stirred at room temperature for 10 min. Then 1-methyl-4-nitro-1H-pyrazol-3-amine (32 mg, 0.223 mmol) was added, and the mixture was stirred at room temperature for 3 h. The mixture was quenched with a saturated aqueous ammonium chloride, extracted with ethyl acetate and separated by silica gel column chromatography (PE/EA=1/1) to obtain compound Ne-(cyclopropylmethyl)-6-(2,6-dichloro-3,5-dimethoxyphenyl)-$N^2$-(1-methyl-4-nitro-1H-pyrazol-3-yl)pyrido[3,4-d]p yrimidine-2,8-diamine (100 mg, yield:98%). MS m/z (ESI): 545 [M+H].

Step 3: preparation of N-(4-amino-1-methyl-H-pyrazol-3-yl)-N-(cyclopropylmethyl)-6-(2,6-dichloro-3,5-dimethoxyphenyl)pyrido[3,4-d]imidine-2,8-diamine

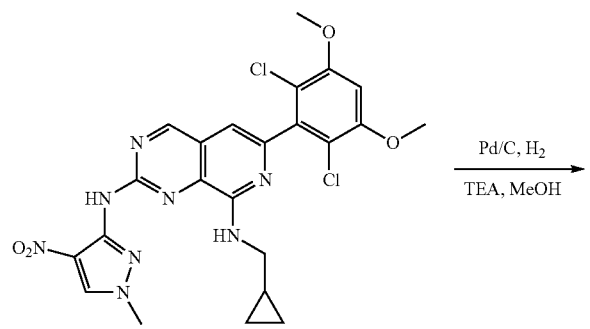

Step 4: Preparation of N-(3-((8-((cyclopropylmethyl)amino)-6-(2,6-dichloro-3,5-dimethoxyphenyl)pyrido[3,4-d]pyrimidin-2-yl)amino)-1-methyl-1H-pyrazol-4-yl)acrylamide

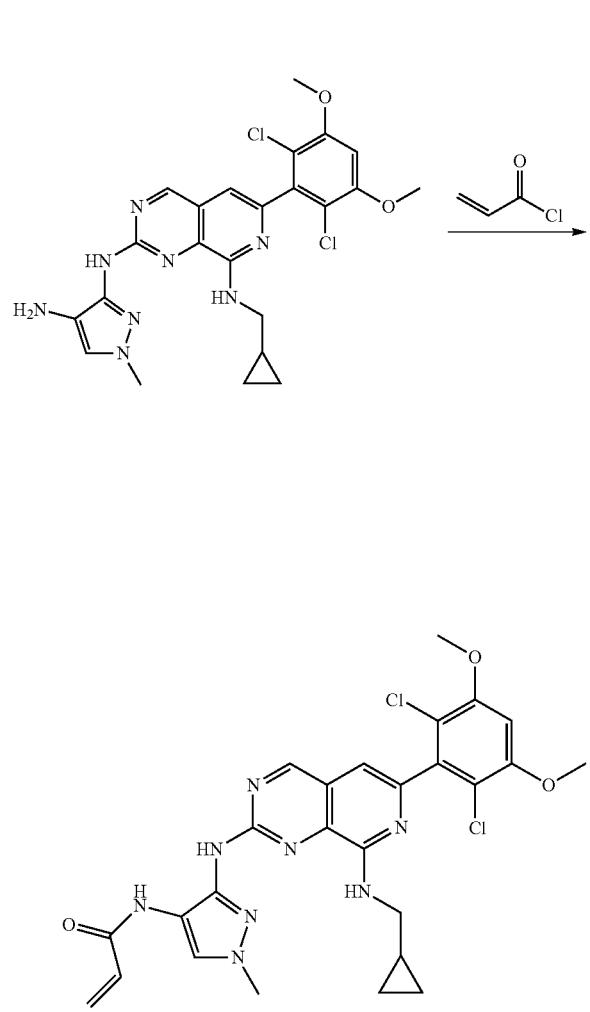

$N^8$-(cyclopropylmethyl)-6-(2,6-dichloro-3,5-dimethoxyphenyl)-$N^2$-(1-methyl-4-nitro-1H-pyrazol-3-yl)pyrido[3,4-d]pyrimidine-2,8-diamine (40 mg, 0.074 mmol) was dissolved in methanol (10 mL), and then triethylamine (3 drops) and Pd/C (20 mg, 10% content) were successively added, and the mixture was stirred at room temperature under $H_2$ for 45 min. The reaction was completed and the mixture was filtrated and separated by silica gel column chromatography (DCM/MeOH) to obtain compound $N^2$-(4-amino-1-methyl-H-pyrazol-3-yl)-$N^8$-(cyclopropylmethyl)-6-(2,6-dichloro-3,5-dimethoxyphenyl)pyrido[3,4-d]pyrimidine-2,8-diamine (30 mg, yield:80%). MS m/z (ESI): 515 [M+H]$^+$.

$N^2$-(4-amino-1-methyl-1H-pyrazol-3-yl)-$N^B$-(cyclopropylmethyl)-6-(2,6-dichloro-3,5-dimeth oxyphenyl)pyrido[3,4-d]pyrimidine-2,8-diamine (30 mg, 0.058 mmol) was dissolved in the mixture of THF and $H_2O$ (8 mL/2 mL), then $NaHCO_3$ (33 mg, 0.39 mmol) was added, and acetyl chloride (7 mg, 0.078 mmol, dissolved in 1 mL of THF) was added dropwise under ice bath, and the mixture was stirred for 10 minutes, a saturated aqueous sodium bi carbonate solution (20 mL) was added, and the mixture was extracted with ethyl acetate and separated by silica gel column chromatography (PE/EA=1/1) to obtain compound N-(3-((8-((cyclopropylmethyl)amino)-6-(2,6-dichloro-3,5-dimethoxyphenyl)pyrido[3,4-d]pyrimidin-2-yl)amino)-1-methyl-H-pyrazol-4-yl)acrylamide (10 mg, yield:22%). MS m/z (ESI): 569 [M+H]$^+$.

$^1$H NMR (400 MHz, $CDCl_3$) δ 9.03 (s, 1H), 8.17 (s, 1H), 6.77 (s, 1H), 6.63 (s, 1H), 6.38 (d, J=16.6 Hz, 2H), 6.33-6.24 (m, 1H), 5.70 (d, J=10.1 Hz, 1H), 3.95 (s, 6H), 3.87 (s, 3H), 3.53-3.36 (m, 2H), 1.19-1.10 (m, 1H), 0.55-0.41 (m, 2H), 0.42-0.29 (m, 2H).

Examples 77-117 were prepared referring to the synthesis method of Example 76.

| Example No. | Compound structure | Compound name | MS: m/z [M + 1]+ |
|---|---|---|---|
| 77 | 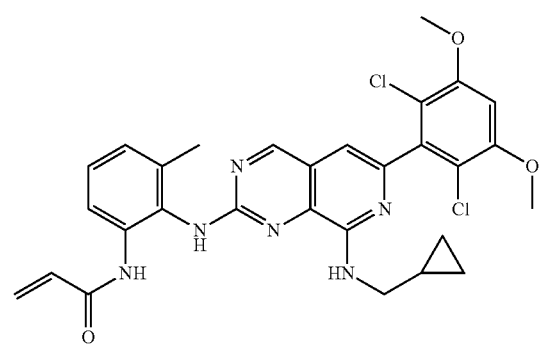 [SMILES: C=CC(=O)Nc1cccc(C)c1Nc1ncc2cc(-c3c(Cl)c(OC)cc(OC)c3Cl)nc(NCC3CC3)c2n1] | N-(2-((8-((cyclopropylmethyl)amino)-6-(2,6-dichloro-3,5-dimethoxyphenyl)pyrido[3,4-d]pyrimidin-2-yl)amino)-3-methylphenyl)acrylamide | 579 |
| 78 | 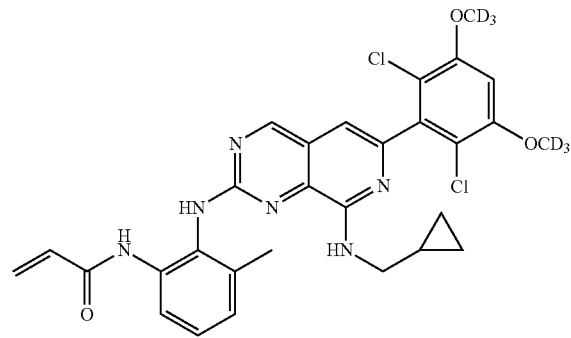 | N-(2-((8-((cyclopropylmethyl)amino)-6-(2,6-dichloro-3,5-bis(dimethoxy-d$_3$)phenyl)pyrido[3,4-d]pyrimidin-2-yl)amino)-3-methylphenyl)acrylamide | 585 |
| 79 | 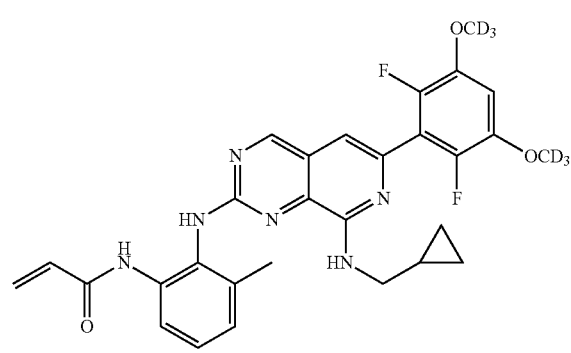 | N-(2-((8-((cyclopropylmethyl)amino)-6-(2,6-difluoro-3,5-bis(methoxy-d$_3$)phenyl)pyrido[3,4-d]pyrimidin-2-yl)amino)-3-methylphenyl)acrylamide | 553 |
| 80 | 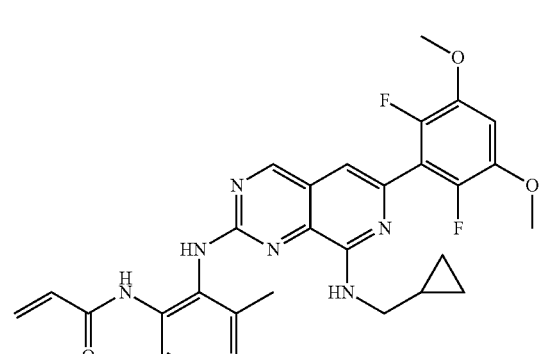 | N-(2-((8-((cyclopropylmethyl)amino)-6-(2,6-difluoro-3,5-dimethoxyphenyl)pyrido[3,4-d]pyrimidin-2-yl)amino)-3-methylphenyl)acrylamide | 547 |

-continued

| Example No. | Compound structure | Compound name | MS: m/z [M + 1]+ |
|---|---|---|---|
| 81 | 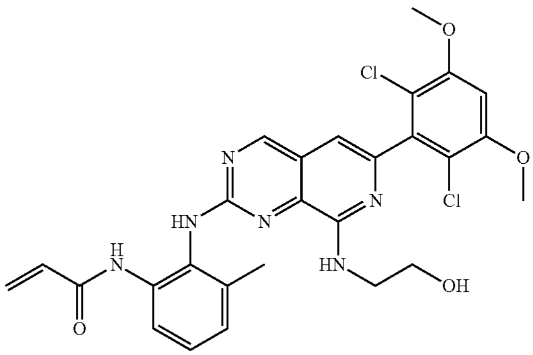 | N-(2-((6-(2,6-dichloro-3,5-dimethoxyphenyl)-8-((2-hydroxyethyl)amino)pyrido[3,4-d]pyrimidin-2-yl-amino)-3-methylphenyl)acrylamide | 569 |
| 82 | 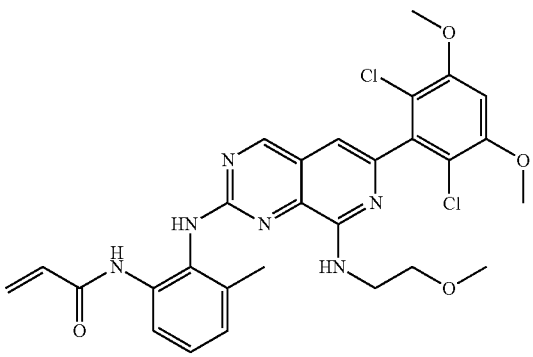 [SMILES: C=CC(=O)Nc1cccc(C)c1Nc1ncc2cc(-c3c(Cl)c(OC)cc(OC)c3Cl)nc(NCCOC)c2n1] | N-(2-((6-(2,6-dichloro-3,5-dimethoxyphenyl))-8-((2-dimethoxyethyl))amino)pyrido[3,4-d]pyrimidin-2-yl)-amino)-3-methylphenyl)acrylamide | 583 |
| 83 | 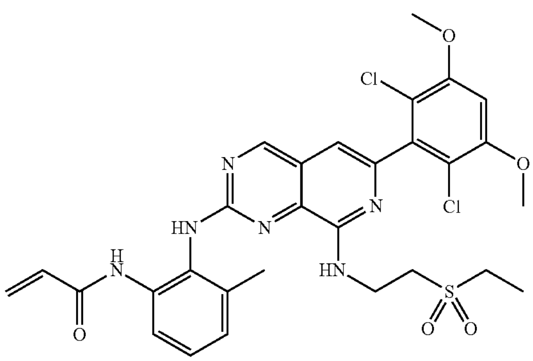 | N-(2-((6-(2,6-dichloro-3,5-dimethoxyphenyl)-8-((2-(ethylsulfonyl)ethyl)amino)pyrido[3,4-d]pyrimidin-2-yl)amino)-3-methylphenyl)acrylamide | 645 |
| 84 | 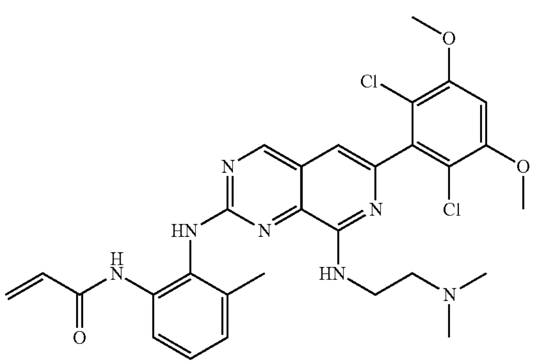 | N-(2-((6-(2,6-dichloro-3,5-dimethoxyphenyl)-8-((2-(dimethylamino)ethyl)amino)pyrido[3,4-d]pyrimidin-2-yl)amino)-3-methylphenyl)acrylamide | 596 |

-continued

| Example No. | Compound structure | Compound name | MS: m/z [M + 1]+ |
|---|---|---|---|
| 85 | 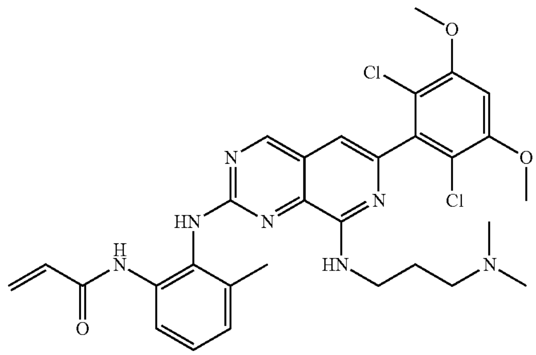 | N-(2-((6-(2,6-dichloro-3,5-dimethoxyphenyl)-8-((3-(dimethylamino)propyl)amino)pyrido[3,4-d]pyrimidin-2-yl)amino)-3-methylphenyl)acrylamide | 610 |
| 86 | 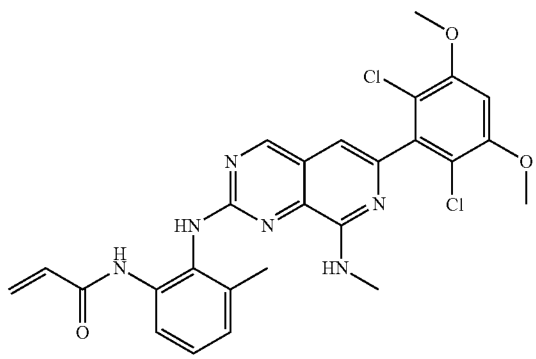 [SMILES: C=CC(=O)Nc1cccc(C)c1Nc1ncc2cc(-c3c(Cl)c(OC)cc(OC)c3Cl)nc(NC)c2n1] | N-(2-((6-(2,6-dichloro-3,5-dimethoxyphenyl)-8-(methylamino)pyrido[3,4-d]pyrimidin-2-yl)amino)-3-methylphenyl)acrylamide | 539 |
| 87 | 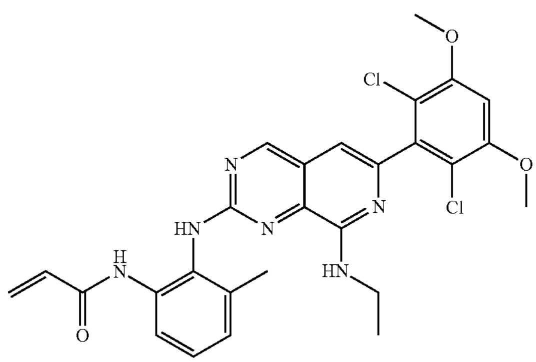 [SMILES: C=CC(=O)Nc1cccc(C)c1Nc1ncc2cc(-c3c(Cl)c(OC)cc(OC)c3Cl)nc(NCC)c2n1] | N-(2-((6-(2,6-dichloro-3,5-dimethoxyphenyl)-8-(ethylamino)pyrido[3,4-d]pyrimidin-2-yl)amino)-3-methylphenyl)acrylamide | 553 |
| 88 | 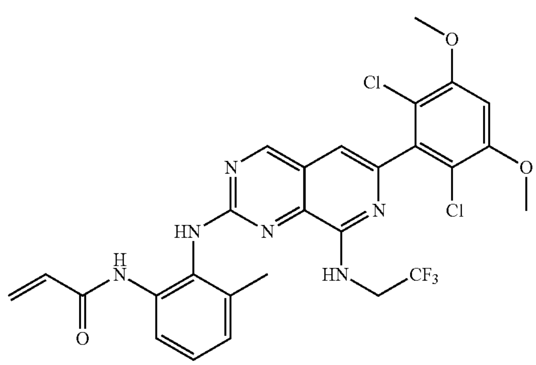 [SMILES: C=CC(=O)Nc1cccc(C)c1Nc1ncc2cc(-c3c(Cl)c(OC)cc(OC)c3Cl)nc(NCC(F)(F)F)c2n1] | N-(2-((6-(2,6-dichloro-3,5-dimethoxyphenyl)-8-(ethylamino)pyrido[3,4-d]pyrimidin-2-yl)amino)-3-methylphenyl)acrylamide | 607 |

-continued

| Example No. | Compound name | MS: m/z [M + 1]+ |
|---|---|---|
| 89 | N-(2-((6-(2,6-dichloro-3,5-dimethoxyphenyl)-8-(dimethylamino)pyrido[3,4-d]pyrimidin-2-yl)amino)-3-methylphenyl)acrylamide | 553 |
| 90 | N-(2-((8-((cyclopropylmethyl)(methyl)amino)-6-(2,6-dichloro-3,5-dimethoxyphenyl)pyrido[3,4-d]pyrimidin-2-yl)amino-3-methylphenyl)acrylamide | 593 |
| 91 | N-(2-((6-(2,6-dichloro-3,5-dimethoxyphenyl)-8-((2-(methylsulfonamido)ethyl)amino)pyrido[3,4-d]pyrimidin-2-yl)amino)-3-methylphenyl)acrylamide | 646 |
| 92 | N-(2-((6-(2,6-dichloro-3,5-dimethoxyphenyl)-8-(((tetrahydrofuran-2-yl)methyl)amino)pyrido[3,4-d]pyrimidin-2-yl)amino)-3-methylphenyl)acrylamide | 609 |

-continued

| Example No. | Compound structure | Compound name | MS: m/z [M + 1]+ |
|---|---|---|---|
| 93 | 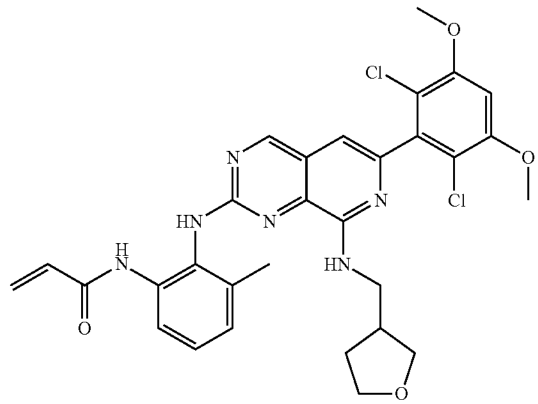 [SMILES: C=CC(=O)Nc1cccc(C)c1Nc1ncc2cc(-c3c(Cl)c(OC)cc(OC)c3Cl)nc(NCC3CCOC3)c2n1] | N-(2-((6-(2,6-dichloro-3,5-dimethoxyphenyl)-8-(((tetrahydrofuran-3-yl)methyl)amino)pyrido[3,4-d]pyrimidin-2-yl)amino)-3-methylphenyl)acrylamide | 609 |
| 94 | 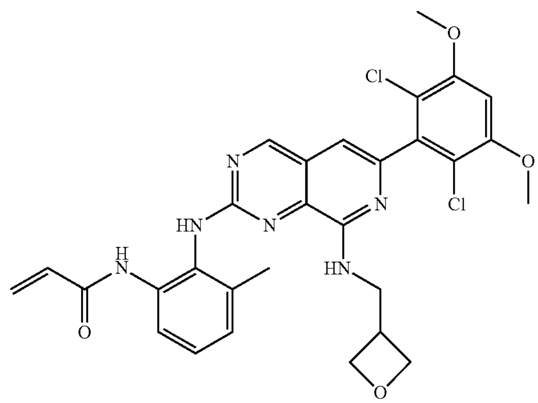 [SMILES: C=CC(=O)Nc1cccc(C)c1Nc1ncc2cc(-c3c(Cl)c(OC)cc(OC)c3Cl)nc(NCC3COC3)c2n1] | N-(2-((6-(2,6-dichloro-3,5-dimethoxyphenyl)-8-((oxetan-3-ylmethyl)amino)pyrido[3,4-d]pyrimidin-2-yl)amino)-3-methylphenyl)acrylamide | 595 |
| 95 | 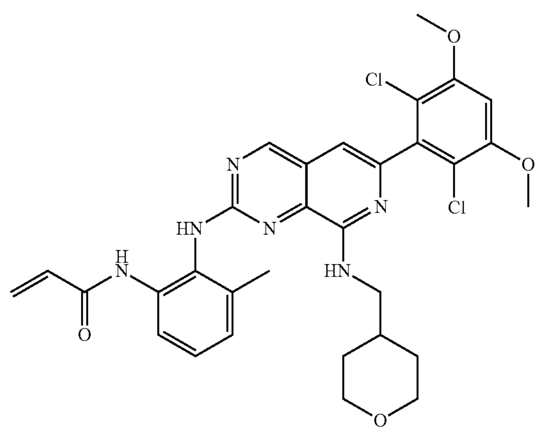 [SMILES: C=CC(=O)Nc1cccc(C)c1Nc1ncc2cc(-c3c(Cl)c(OC)cc(OC)c3Cl)nc(NCC3CCOCC3)c2n1] | N-(2-((6-(2,6-dichloro-3,5-dimethoxyphenyl)-8-(((tetrahydro-2H-pyran-4-yl)methyl)amino)pyrido[3,4-d]pyrimidin-2-yl)amino)-3-methylphenyl)acrylamide | 623 |
| 96 | 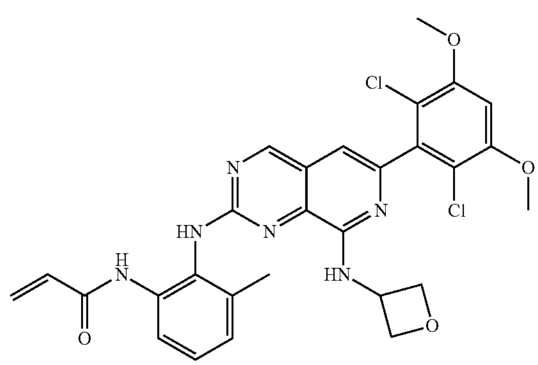 [SMILES: C=CC(=O)Nc1cccc(C)c1Nc1ncc2cc(-c3c(Cl)c(OC)cc(OC)c3Cl)nc(NC3COC3)c2n1] | N-(2-((6-(2,6-dichloro-3,5-dimethoxyphenyl)-8-(oxetan-3-ylamino)pyrido[3,4-d]pyrimidin-2-yl)amino)-3-methylphenyl)acrylamide | 581 |

-continued

| Example No. | Compound structure | Compound name | MS: m/z [M + 1]+ |
|---|---|---|---|
| 97 | 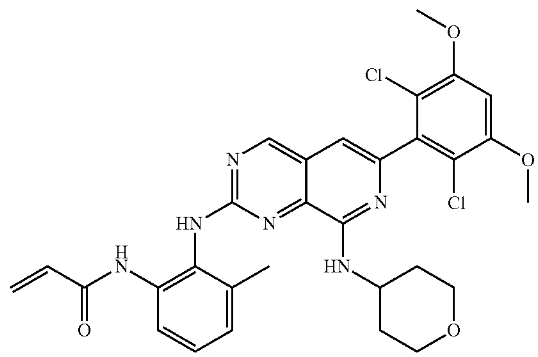 | N-(2-((6-(2,6-dichloro-3,5-dimethoxyphenyl)-8-((tetrahydro-2H-pyran-4-yl)amino)pyrido[3,4-d]pyrimidin-2-yl)amino)-3-methylphenyl)acrylamide | 609 |
| 98 | 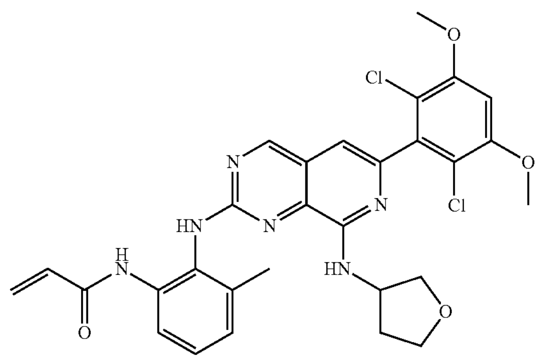 [SMILES: C=CC(=O)Nc1cccc(C)c1Nc1ncc2cc(-c3c(Cl)c(OC)cc(OC)c3Cl)nc(NC3CCOC3)c2n1] | N-(2-((6-(2,6-dichloro-3,5-dimethoxyphenyl)-8-((tetrahydrofuran-3-yl)amino)pyrido[3,4-d]pyrimidin-2-yl)amino)-3-methylphenyl)acrylamide | 595 |
| 99 | 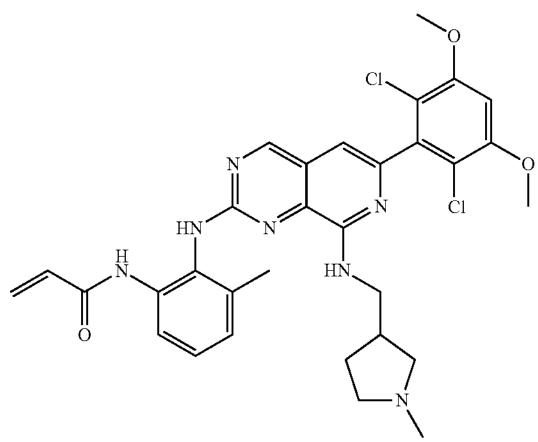 [SMILES: C=CC(=O)Nc1cccc(C)c1Nc1ncc2cc(-c3c(Cl)c(OC)cc(OC)c3Cl)nc(NCC3CCN(C)C3)c2n1] | N-(2-((6-(2,6-dichloro-3,5-dimethoxyphenyl)-8-(((1-methylpyrrolidin-3-yl)methyl)amino)pyrido[3,4-d]pyrimidin-2-yl)amino)-3-methylphenyl)acrylamide | 622 |
| 100 | 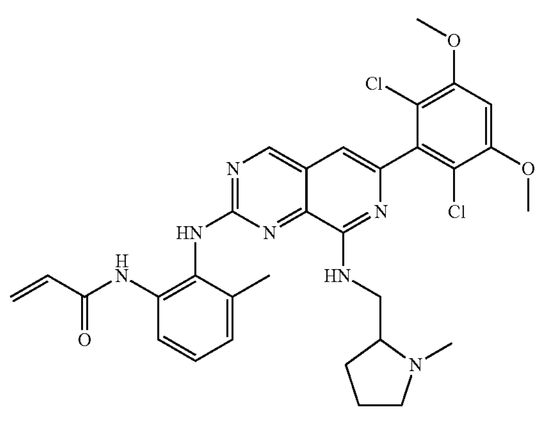 [SMILES: C=CC(=O)Nc1cccc(C)c1Nc1ncc2cc(-c3c(Cl)c(OC)cc(OC)c3Cl)nc(NCC3CCCN3C)c2n1] | N-(2-((6-(2,6-dichloro-3,5-dimethoxyphenyl)-8-(((1-methylpyrrolidin-2-yl)methyl)amino)pyrido[3,4-d]pyrimidin-2-yl)amino)-3-methylphenyl)acrylamide | 622 |

-continued

| Example No. | Compound structure | Compound name | MS: m/z [M + 1]+ |
|---|---|---|---|
| 101 | 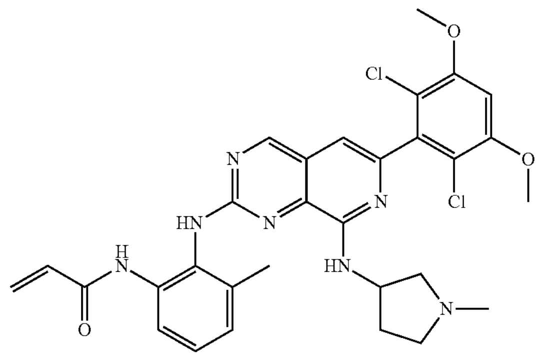 [SMILES: C=CC(=O)Nc1cccc(C)c1Nc1ncc2cc(-c3c(Cl)c(OC)cc(OC)c3Cl)nc(NC3CCN(C)C3)c2n1] | N-(2-((6-(2,6-dichloro-3,5-dimethoxyphenyl)-8-(((1-methylpyrrolidin-3-yl)amino)pyrido[3,4-d]pyrimidin-2-yl)amino)-3-methylphenyl)acrylamide | 608 |
| 102 | 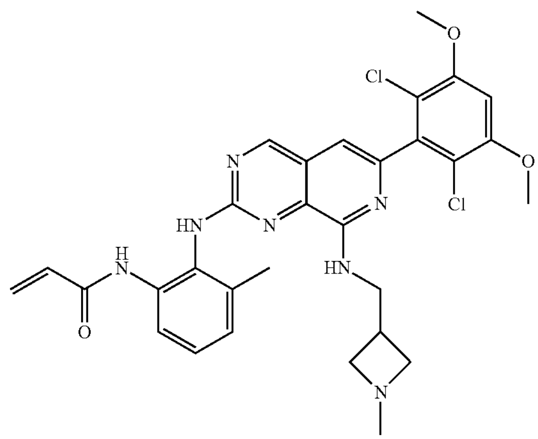 [SMILES: C=CC(=O)Nc1cccc(C)c1Nc1ncc2cc(-c3c(Cl)c(OC)cc(OC)c3Cl)nc(NCC3CN(C)C3)c2n1] | N-(2-((6-(2,6-dichloro-3,5-dimethoxyphenyl)-8-((((1-methylazetidin-3-yl)methyl)amino)pyrido[3,4-d]pyrimidin-2-yl)amino)-3-methylphenyl)acrylamide | 608 |
| 103 | 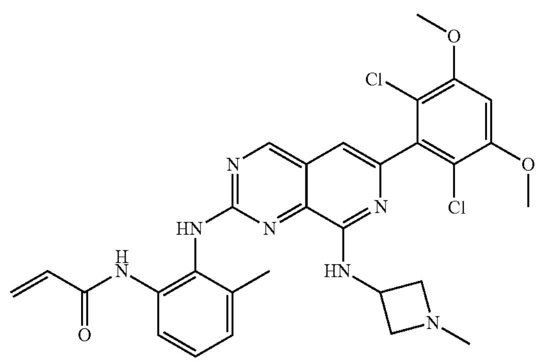 [SMILES: C=CC(=O)Nc1cccc(C)c1Nc1ncc2cc(-c3c(Cl)c(OC)cc(OC)c3Cl)nc(NC3CN(C)C3)c2n1] | N-(2-((6-(2,6-dichloro-3,5-dimethoxyphenyl)-8-((((1-methylazetidin-3-yl)amino)pyrido[3,4-d]pyrimidin-2-yl)amino)-3-methylphenyl)acrylamide | 594 |
| 104 | 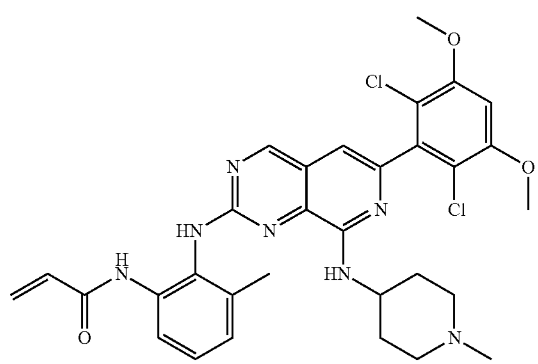 [SMILES: C=CC(=O)Nc1cccc(C)c1Nc1ncc2cc(-c3c(Cl)c(OC)cc(OC)c3Cl)nc(NC3CCN(C)CC3)c2n1] | N-(2-((6-(2,6-dichloro-3,5-dimethoxyphenyl)-8-(((1-methylpiperidin-4-yl)amino)pyrido[3,4-d]pyrimidin-2-yl)amino)-3-methylphenyl)acrylamide | 622 |

-continued

| Example No. | Compound structure | Compound name | MS: m/z [M + 1]+ |
|---|---|---|---|
| 105 | 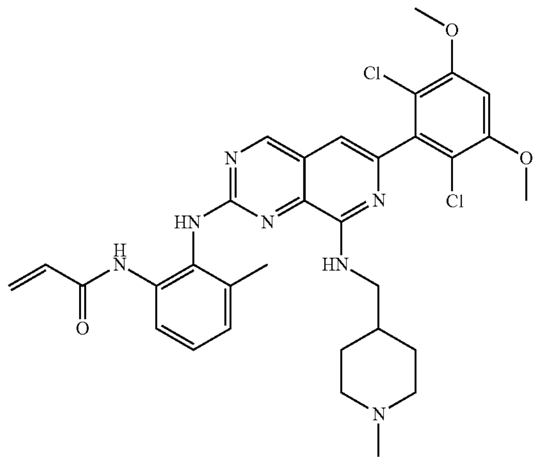 [SMILES: C=CC(=O)Nc1cccc(C)c1Nc1ncc2cc(-c3c(Cl)c(OC)cc(OC)c3Cl)nc(NCC3CCN(C)CC3)c2n1] | N-(2-((6-(2,6-dichloro-3,5-dimethoxyphenyl)-8-(((1-methylpiperidin-4-yl)methyl)amino)pyrido[3,4-d]pyrimidin-2-yl)amino)-3-methylphenyl)acrylamide | 636 |
| 106 | 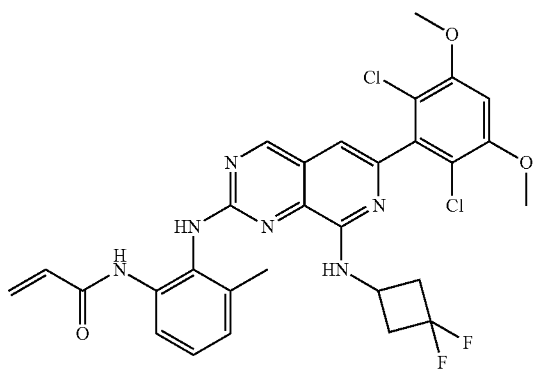 [SMILES: C=CC(=O)Nc1cccc(C)c1Nc1ncc2cc(-c3c(Cl)c(OC)cc(OC)c3Cl)nc(NC3CC(F)(F)C3)c2n1] | N-(2-((6-(2,6-dichloro-3,5-dimethoxyphenyl)-8-((3,3-difluorocyclobutyl)amino)pyrido[3,4-d]pyrimidin-2-yl)amino-3-methylphenyl)acrylamide | 615 |
| 107 | 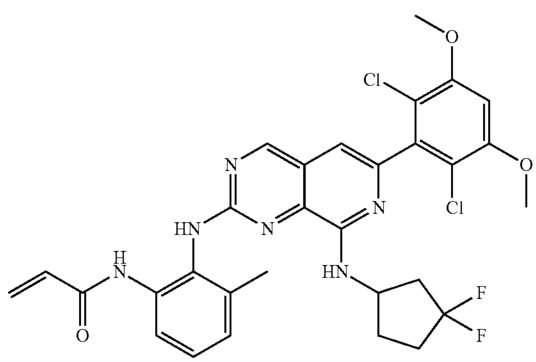 | N-(2-((6-(2,6-dichloro-3,5-dimethoxyphenyl)-8-((3,3-difluorocyclopentyl)amino)pyrido[3,4-d]pyrimidin-2-yl)amino)-3-methylphenyl)acrylamide | 629 |
| 108 | 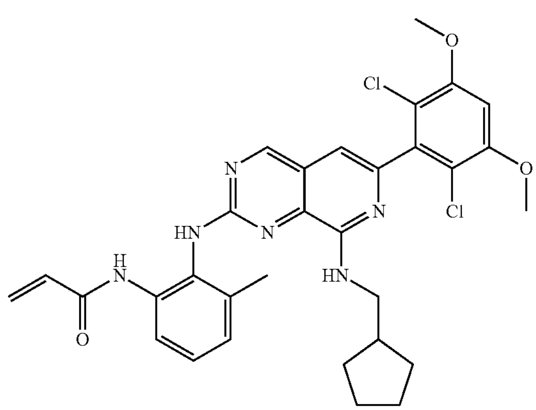 | N-(2-((8-((cyclopentylmethyl)amino)-6-(2,6-dichloro-3,5-dimethoxyphenyl)pyrido[3,4-d]pyrimidin-2-yl)amino)-3-methylphenyl)acrylamide | 607 |

-continued

| Example No. | Compound structure | Compound name | MS: m/z [M + 1]+ |
|---|---|---|---|
| 109 | 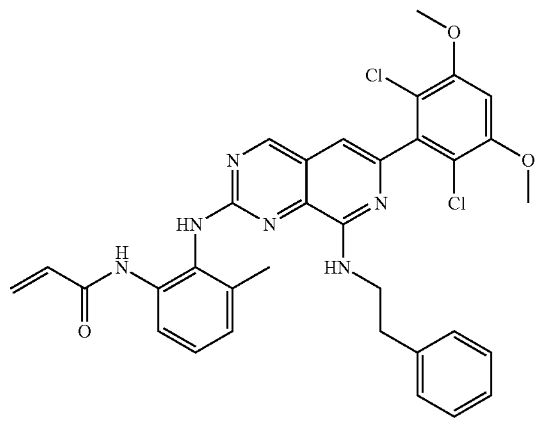 | N-(2-((6-(2,6-dichloro-3,5-dimethoxyphenyl)-8-(phenethylamino)pyrido[3,4-d]pyrimidin-2-yl)amino)-3-methylphenyl)acrylamide | 629 |
| 110 | 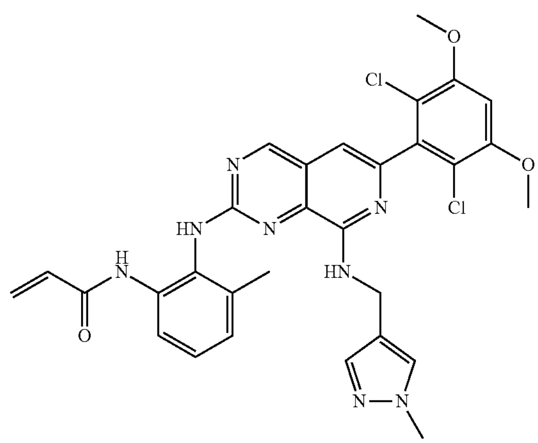 | N-(2-((6-(2,6-dichloro-3,5-dimethoxyphenyl)-8-(((1-methyl-1H-pyrazol-4-yl)methyl)amino)pyrido[3,4-]pyrimidin-2-yl)amino)-3-methylphenyl)acrylamide | 619 |
| 111 | 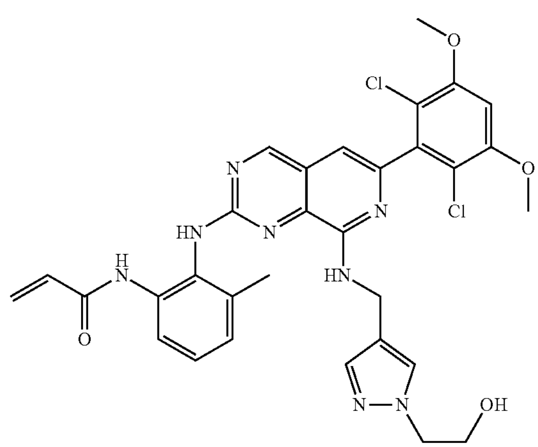 [SMILES: C=CC(=O)Nc1cccc(C)c1Nc1ncc2cc(-c3c(Cl)c(OC)cc(OC)c3Cl)nc(NCc3cnn(CCO)c3)c2n1] | N-(2-((6-(2,6-dichloro-3,5-dimethoxyphenyl)-8-(((1-(2-hydroxyethyl)-1H-pyrazol-4-yl)methyl)amino)pyrido[3,4-d]pyrimidin-2-yl)amino)-3-methylphenyl)acrylamide | 649 |

-continued

| Example No. | Compound structure | Compound name | MS: m/z [M + 1]+ |
|---|---|---|---|
| 112 | 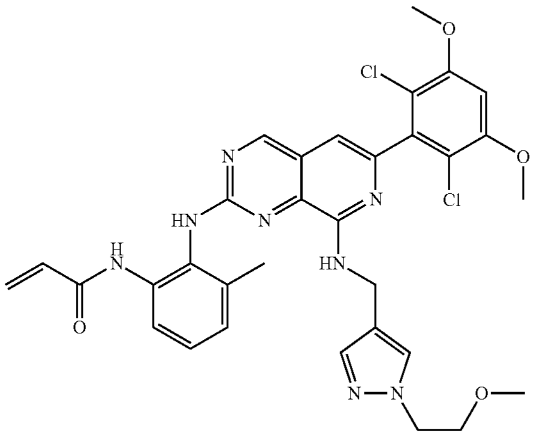 [SMILES: C=CC(=O)Nc1cccc(C)c1Nc1ncc2cc(-c3c(Cl)c(OC)cc(OC)c3Cl)nc(NCc3cnn(CCOC)c3)c2n1] | N-(2-((6-(2,6-dichloro-3,5-dimethoxyphenyl)-8-(((1-(2-dimethoxyethyl)-1H-pyrazol-4-yl)methyl)amino)pyrido[3,4-d]pyrimidin-2-yl)amino)-3-methylphenyl)acrylamide | 663 |
| 113 | 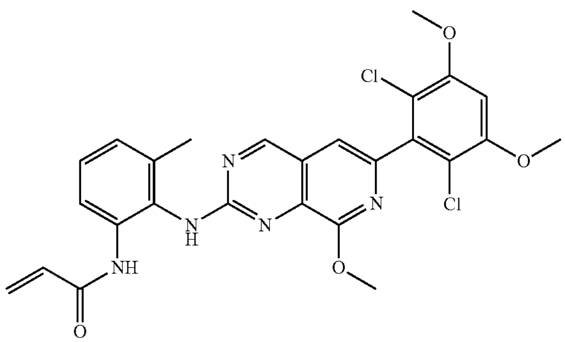 [SMILES: C=CC(=O)Nc1cccc(C)c1Nc1ncc2cc(-c3c(Cl)c(OC)cc(OC)c3Cl)nc(OC)c2n1] | N-(2-((6-(2,6-dichloro-3,5-dimethoxyphenyl)-8-methoxypyrido[3,4-d]pyrimidin-2-yl)amino)-3-methylphenyl)acrylamide | 540 |
| 114 | 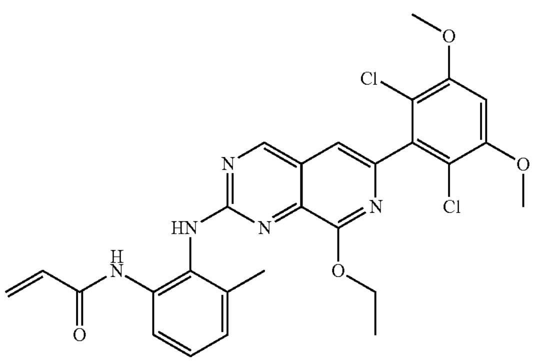 [SMILES: C=CC(=O)Nc1cccc(C)c1Nc1ncc2cc(-c3c(Cl)c(OC)cc(OC)c3Cl)nc(OCC)c2n1] | N-(2-((6-(2,6-dichloro-3,5-dimethoxyphenyl)-8-ethoxypyrido[3,4-d]pyrimidin-2-yl)amino)-3-methylphenyl)acrylamide | 554 |
| 115 | 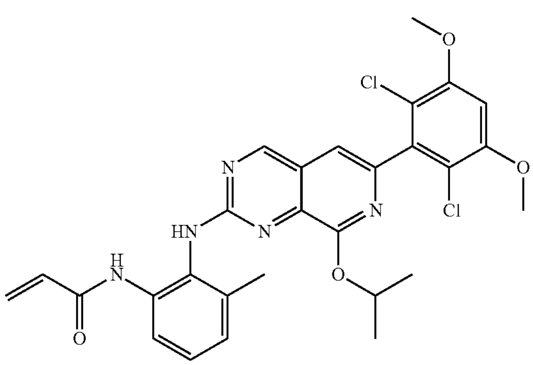 [SMILES: C=CC(=O)Nc1cccc(C)c1Nc1ncc2cc(-c3c(Cl)c(OC)cc(OC)c3Cl)nc(OC(C)C)c2n1] | N-(2-((6-(2,6-dichloro-3,5-dimethoxyphenyl)-8-isopropoxypyrido[3,4-d]pyrimidin-2-yl)amino)-3-methylphenyl)acrylamide | 568 |

| Example No. | Compound structure | Compound name | MS: m/z [M + 1]+ |
|---|---|---|---|
| 116 | 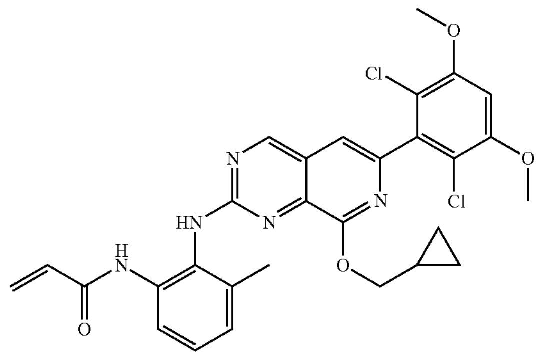 [SMILES: C=CC(=O)Nc1cccc(C)c1Nc1ncc2cc(-c3c(Cl)c(OC)cc(OC)c3Cl)nc(OCC3CC3)c2n1] | N-(2-((8-(cyclopropylmethoxy)-6-(2,6-dichloro-3,5-dimethoxyphenyl)pyrido[3,4-d]pyrimidin-2-yl)amino)-3-methylphenyl)acrylamide | |
| 117 | 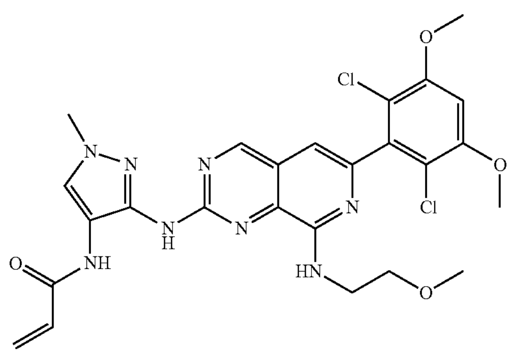 [SMILES: C=CC(=O)Nc1cn(C)nc1Nc1ncc2cc(-c3c(Cl)c(OC)cc(OC)c3Cl)nc(NCCOC)c2n1] | N-(3-((6-(2,6-dichloro-3,5-dimethoxyphenyl)-8-((2-dimethoxyethyl)amino)pyrido[3,4-d]pyrimidin-2-yl)amino)-1-methyl-1H-pyrazol-4-yl)acrylamide | 573 |

Example 118 Preparation of (±)—N-((3R,4S)-4-((6-(2,6-dichloro-3,5-dimethoxyphenyl) pyrido[3,4-d]pyrimidin-2-yl)amino)tetrahydrofuran-3-yl)acrylamide Step 1: Preparation of (±)-(3S,4R)—N³-(6-(2,6-dichloro-3,5-dimethoxyphenyl)pyrido[3,4-d]pyrimidin-2-yl)tetrahydrofuran-3,4-diamine

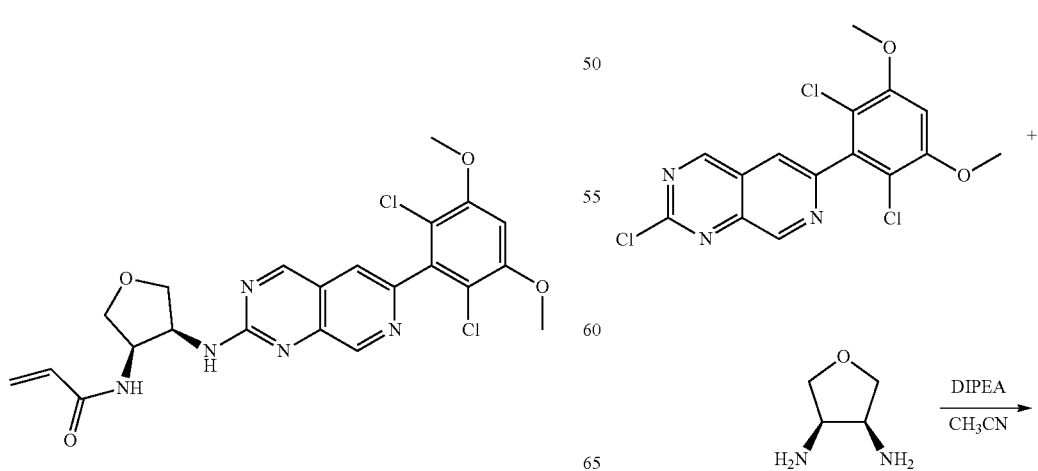

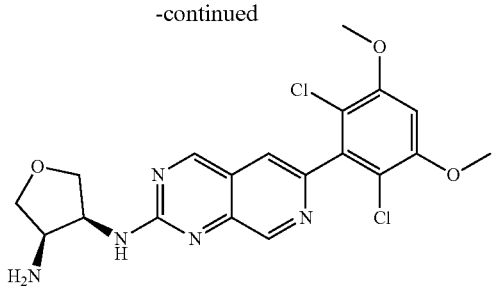

2-chloro-6-(2,6-dichloro-3,5-dimethoxyphenyl)pyrido[3,4-d]pyrimidine (40.0 mg, 0.108 m mol) and trans-tetrahydrofuran-3,4-diamine dihydrochloride (28.3 mg, 0.162 mmol) were dissolved in acetonitrile (2 mL), then N,N-diisopropylethylamine (70 mg, 0.543 mmol) was added, the mixture was heated to reflux for 16 h. After being cooled, the reaction liquid was diluted with EtOAc (10 mL), washed with saturated brine, dried over anhydrous sodium sulfate, filtrated, concentrated and separated by PTLC (Eluent. CH$_2$Cl$_2$/MeOH=10:1) to obtain compound (3S,4R)—N-(6-(2,6-dichloro-3,5-dimethoxyphenyl)pyrido[3,4-d]pyrimidin-2-yl)tetrahydrofuran-3,4-diamine (30 mg, yield: 64%). MS m/z (ESI): 436.1 [M+H]$^+$.

Step 2: Preparation of (±)—N-((3R,4S)-4-((6-(2,6-dichloro-3,5-dimethoxyphenyl)pyrido[3,4-d]pyrimidin-2-yl)amino)tetrahydrofuran-3-yl)acrylamide

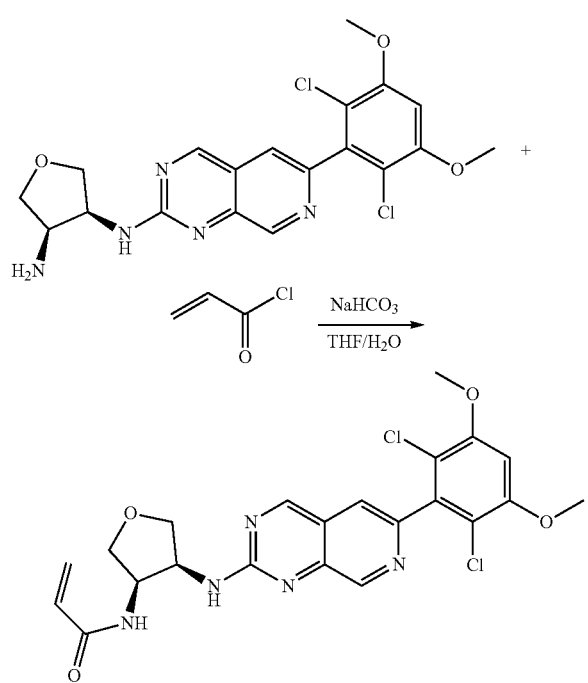

(±)-(3S,4R)—N$^3$-(6-(2,6-dichloro-3,5-dimethoxyphenyl)pyrido[3,4-d]pyrimidin-2-yl)tetrahydrofuran-3,4-diamine (30.0 mg, 0.069 mmol) was dissolved in the mixture THF and H$_2$O (1.2/0.3 mL), NaHCO$_3$ (23.0 mg, 0.276 mmol) was added, and the mixture was cooled under ice water bath, and then acryloyl chloride (6.8 mg, 0.076 mmol) was added. After addition, the mixture was stirred at 0° C. for 10 min. The reaction liquid was diluted with EtOAc (5 mL), washed with saturated brine, dried over anhydrous sodium sulfate, filtrated and concentrated. The crude product was separated by PTLC (Eluent: CH$_2$Cl$_2$/MeOH=10:1) to obtain compound N-((3R,4S)-4-((6-(2,6-dichloro-3,5-dimethoxyphenyl)pyrido[3,4-d]pyrimidin-2-yl)amino)tetrahydrofuran-3-yl)acrylamide (17.4 mg, yield: 52%).

$^1$H NMR (400 MHz, CDCl$_3$) δ 9.21 (s, 1H), 9.16 (s, 1H), 7.55 (s, 1H), 6.68 (s, 1H), 6.45 (d, J=7.3 Hz, 1H), 6.27 (dd, J=17.0, 1.4 Hz, 1H), 6.07 (dd, J=16.9, 10.3 Hz, 1H), 5.63 (dd, J=10.2, 1.4 Hz, 1H), 4.94 (dd, J=11.6, 4.9 Hz, 1H), 4.90-4.79 (m, 1H), 4.34-4.19 (m, 2H), 3.98 (s, 6H), 3.90-3.79 (m, 2H). MS m/z (ESI): 490.1 [M+H]$^+$.

Example 119 Preparation of N-((3S,4S)-3-((6-(2,6-dichloro-3,5-dimethoxyphenyl)pyrido[3,4-d]pyrimidin-2-yl)amino)tetrahydro-2H-pyran-4-yl)acrylamide

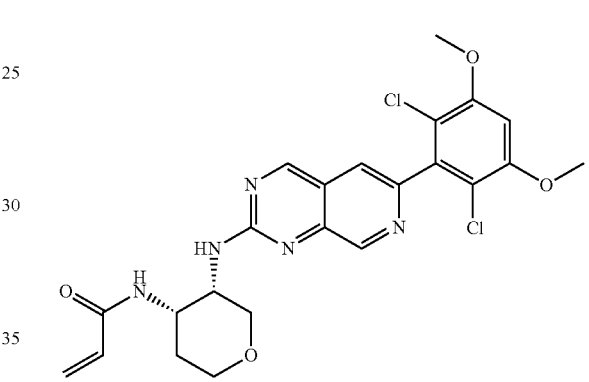

Step 1: Preparation of N-((3S,4S)-4-azidotetrahydro-2H-pyran-3-yl)-6-(2,6-dichloro-3,5-dimethoxyphenyl)pyrido[3,4-d]pyrimidine-2-amine

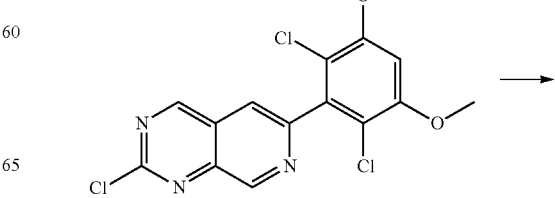

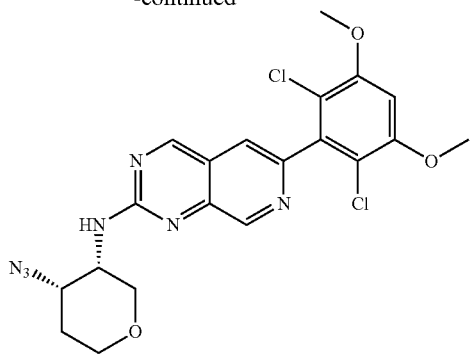

2-chloro-6-(2,6-dichloro-3,5-dimethoxyphenyl)pyrido[3,4-d]pyrimidine (100 mg, 0.27 m mol) was dissolved in NMP (3 mL), and Na₂CO₃ (143 mg, 1.349 mmol) and (3S,4S)-4-azidotetrahydro-2H-pyran-3-amine hydrochloride (72 mg, 0.405 mmol) were added, the mixture was heated to 120° C. for 2 h. The reaction was completed, and the mixture was cooled to room temperature, added with water, and extracted for three times with ethyl acetate. The organic phases were combined, dried over anhydrous sodium sulfate, filtrated, concentrated and separated by column chromatography (Eluent: petroleum ether/ethyl acetate 2:1) to obtain compound N-((3S,4S)-4-azidotetrahydro-2H-pyran-3-yl)-6-(2,6-dichloro-3,5-dimethoxyphenyl)pyrido[3,4-d]pyrimidine-2-amine (38 mg, yield: 29%). MS m/z (ESI): 478.4 [M+H]⁺.

Step 2: Preparation of (3S,4S)—N³-(6-(2,6-dichloro-3,5-dimethoxyphenyl)pyrido[3,4-d]pyrimidin-2-yl)tetrahydro-2H-pyran-3,4-diamine

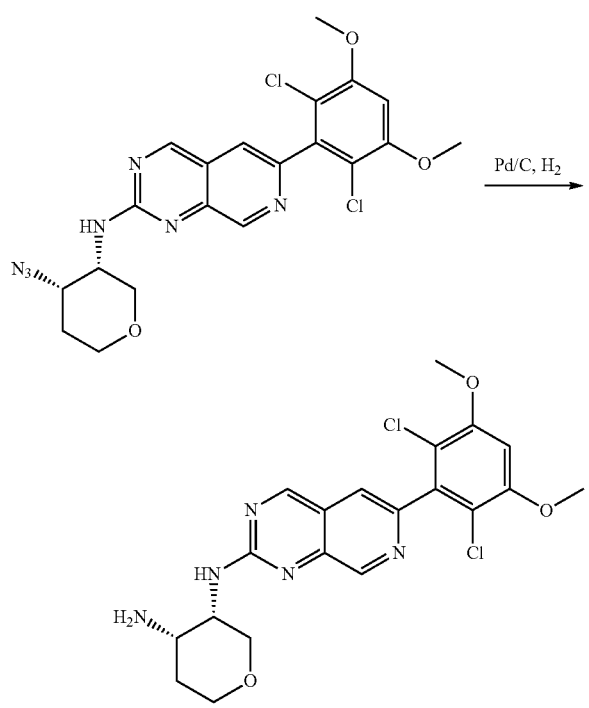

N-((3S,4S)-4-azidotetrahydro-2H-pyran-3-yl)-6-(2,6-dichloro-3,5-dimethoxyphenyl)pyrido[3,4-d]pyrimidine-2-amine (38 mg, 0.08 mmol) was dissolved in MeOH (8 mL), then Pd/C (10 mg) was added, and the mixture was stirred under H₂ at room temperature for 30 min. The reaction was completed, and the mixture was concentrated and separated by column chromatography (Eluent: dichloromethane/methanol 10:1) to obtain compound (3S,4S)—N³-(6-(2,6-dichloro-3,5-dimethoxyphenyl)pyrido[3,4-d]pyrimidin-2-yl)tetrahydro-2H-pyran-3,4-diamine (12 mg, yield: 33%). MS m/z (ESI): 451.2 [M+H]⁺.

Step 3: Preparation of N-((3S,4S)-3-((6-(2,6-dichloro-3,5-dimethoxyphenyl)pyrido[3,4-d]pyrimidin-2-yl)amino)tetrahydro-2H-pyran-4-yl)acrylamide

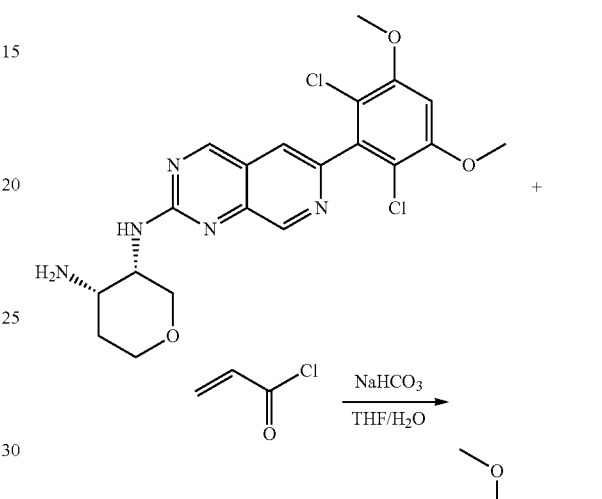

(3S,4S)—N³-(6-(2,6-dichloro-3,5-dimethoxyphenyl)pyrido[3,4-d]pyrimidin-2-yl)tetrahydro-2H-pyran-3,4-diamine (12 mg, 0.027 mmol) was dissolved in the mixture of THF and H₂O (4 mL/1 mL), then NaHCO₃ (12 mg, 0.141 mmol) was added, the mixture was cooled under ice water bath, and a solution of acryloyl chloride (3 mg, 0.027 mmol) in THF (2 mL) was added dropwise, and the mixture was stirred at low temperature for 10 min. After the reaction was completed, the mixture was extracted three times with dichloromethane. The organic phases were combined, washed with saturated brine, dried over anhydrous sodium sulfate, concentrated, and separated by column chromatography (Eluent: dichloromethane/petroleum ether (10:1)) to obtain compound N-((3S,4S)-3-((6-(2,6-dichloro-3,5-dimethoxyphenyl)pyrido[3,4-d]pyrimidin-2-yl)amino)tetrahydro-2H-pyran-4-yl)acrylamide (6.3 mg, yield: 47%).

¹H NMR (400 MHz, CDCl₃) δ 9.17 (s, 2H), 7.56 (s, 1H), 6.68 (s, 1H), 6.25 (dd, J=16.9, 1.4 Hz, 1H), 6.01 (dd, J=17.0, 10.3 Hz, 1H), 5.60 (dd, J=10.3, 1.4 Hz, 1H), 4.55 (s, 1H), 4.35 (s, 1H), 4.11-4.00 (m, 2H), 3.98 (s, 6H), 3.78 (d, J=12.1 Hz, 1H), 3.64 (dd, J=13.4, 10.9 Hz, 1H), 2.24-2.20 (m, 2H), 2.02-1.99 (m, 2H). MS m/z (ESI): 505.4 [M+H]⁺.

Examples 120-420 and 752 were prepared referring to the synthesis method of Example 118 or 119.

| Example No. | Compound structure | Compound name | MS: m/z [M + 1]+ |
|---|---|---|---|
| 120 | 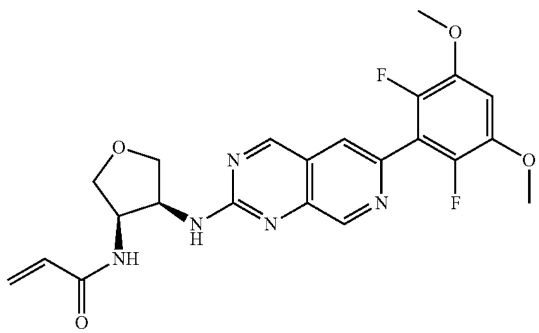 [SMILES: C=CC(=O)N[C@H]1COC[C@H]1Nc1ncc2cc(-c3c(F)c(OC)cc(OC)c3F)ncc2n1] | N-((3R,4S)-4-((6-(2,6-difluoro-3,5-dimethoxyphenyl)pyrido[3,4-d]pyrimidin-2-yl)amino)tetrahydrofuran-3-yl)acrylamide | 458 |
| 121 | 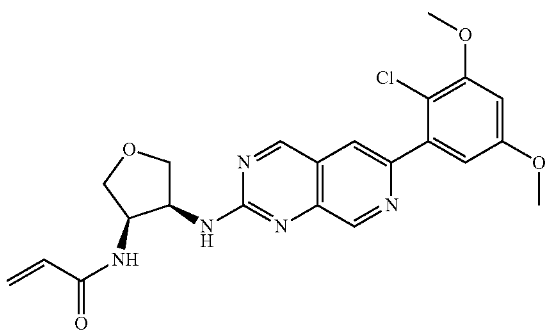 [SMILES: C=CC(=O)N[C@H]1COC[C@H]1Nc1ncc2cc(-c3cc(OC)cc(OC)c3Cl)ncc2n1] | N-((3R,4S)-4-((6-(2-chloro-3,5-dimethoxyphenyl)pyrido[3,4-d]pyrimidin-2-yl)amino)tetrahydrofuran-3-yl)acrylamide | 456 |
| 122 | 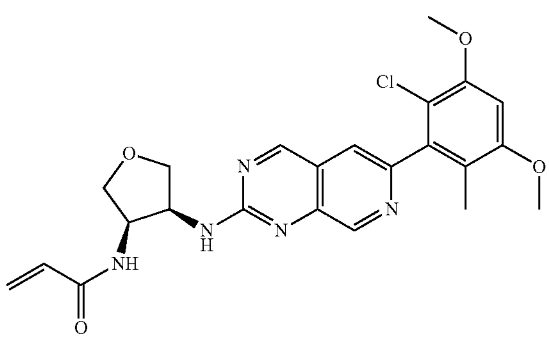 [SMILES: C=CC(=O)N[C@H]1COC[C@H]1Nc1ncc2cc(-c3c(C)c(OC)cc(OC)c3Cl)ncc2n1] | N-((3R,4S)-4-((6-(2-chloro-3,5-dimethoxy-6-methyl)phenyl))pyrido[3,4-d]pyrimidin-2-yl)amino)tetrahydrofuran-3-yl)acrylamide | 470 |
| 123 | 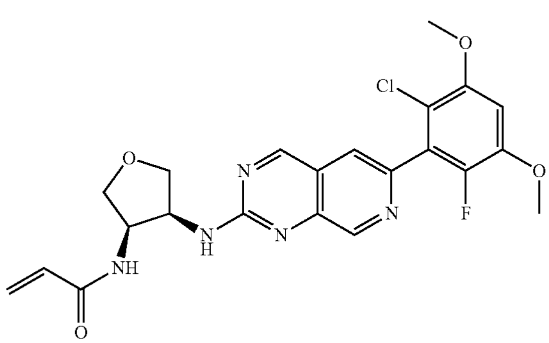 [SMILES: C=CC(=O)N[C@H]1COC[C@H]1Nc1ncc2cc(-c3c(F)c(OC)cc(OC)c3Cl)ncc2n1] | N-((3R,4S)-4-((6-(2-chloro-6-fluoro-3,5-dimethoxyphenyl)pyrido[3,4-d]pyrimidin-2-yl)amino)tetrahydrofuran-3-yl)acrylamide | 474 |

-continued

| Example No. | Compound structure | Compound name | MS: m/z [M + 1]+ |
| --- | --- | --- | --- |
| 124 | 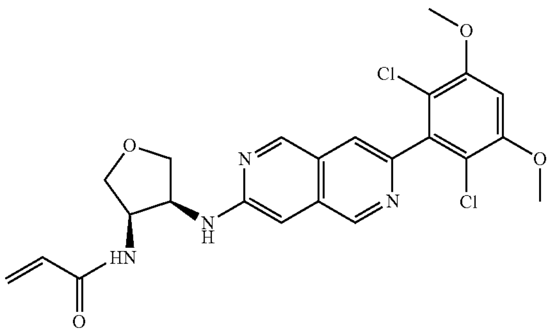 [SMILES: C=CC(=O)N[C@H]1COC[C@H]1Nc1cc2cnc(-c3c(Cl)c(OC)cc(OC)c3Cl)cc2cn1] | N-((3R,4S)-4-((7-(2,6-dichloro-3,5-dimethoxyphenyl)-2,6-naphthyridin-3-yl)amino)tetrahydrofuran-3-yl)acrylamide | 489 |
| 125 | 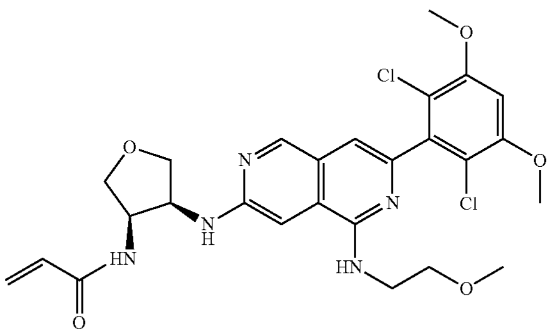 [SMILES: C=CC(=O)N[C@H]1COC[C@H]1Nc1cc2c(NCCOC)nc(-c3c(Cl)c(OC)cc(OC)c3Cl)cc2cn1] | N-((3R,4S)-4-((7-(2,6-dichloro-3,5-dimethoxyphenyl)-5-((2-dimethoxyethyl)amino)-2,6-naphthyridin-3-yl)amino)tetrahydrofuran-3-yl)acrylamide | 562 |
| 126 | 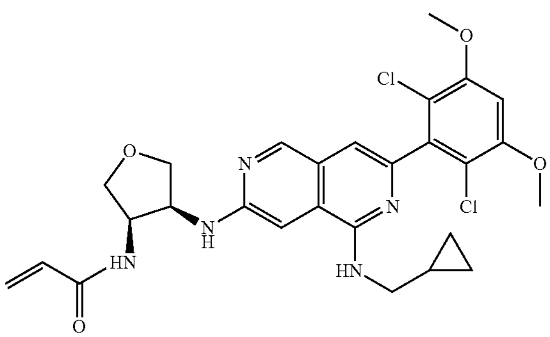 [SMILES: C=CC(=O)N[C@H]1COC[C@H]1Nc1cc2c(NCC3CC3)nc(-c3c(Cl)c(OC)cc(OC)c3Cl)cc2cn1] | N-((3R,4S)-4-((5-((cyclopropylmethyl)amino)-7-(2,6-dichloro-3,5-dimethoxyphenyl)-2,6-naphthyridin-3-yl)amino)tetrahydrofuran-3-yl)acrylamide | 558 |
| 127 | 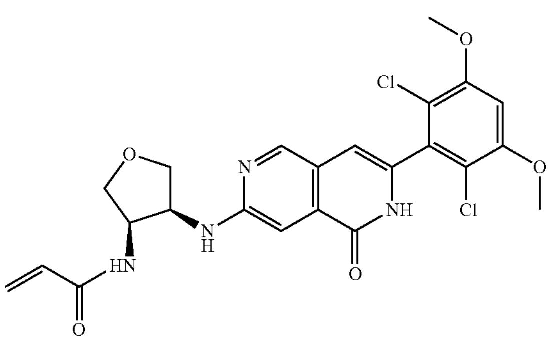 [SMILES: C=CC(=O)N[C@H]1COC[C@H]1Nc1cc2c(=O)[nH]c(-c3c(Cl)c(OC)cc(OC)c3Cl)cc2cn1] | N-((3R,4S)-4-((7-(2,6-dichloro-3,5-dimethoxyphenyl)-5-oxo-5,6-dihydro-2,6-naphthyridin-3-yl)amino)tetrahydrofuran-3-yl)acrylamide | 505 |

-continued

| Example No. | Compound structure | Compound name | MS: m/z [M + 1]+ |
|---|---|---|---|
| 128 | 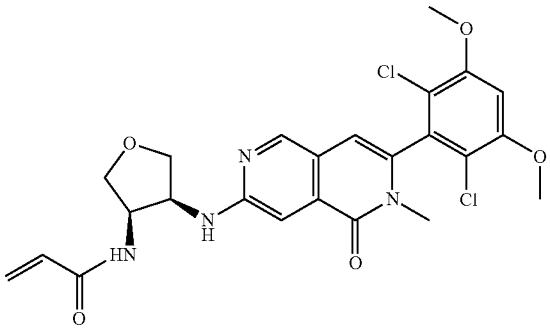 [SMILES: C=CC(=O)N[C@H]1COC[C@H]1Nc1cc2c(=O)n(C)c(-c3c(Cl)c(OC)cc(OC)c3Cl)cc2cn1] | N-((3R,4S)-4-((7-(2,6-dichloro-3,5-dimethoxyphenyl)-6-methyl-5-oxo-5,6-dihydro-2,6-napthyridin-3-yl)amino)tetrahydrofuran-3-yl)acrylamide | 519 |
| 129 | 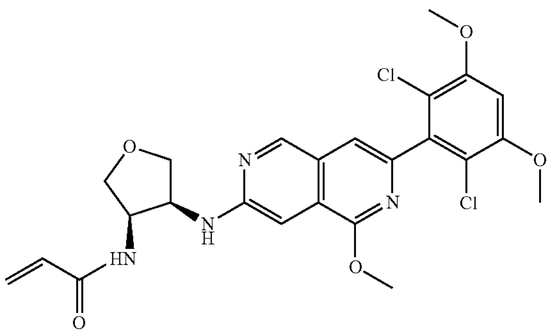 [SMILES: C=CC(=O)N[C@H]1COC[C@H]1Nc1cc2c(OC)nc(-c3c(Cl)c(OC)cc(OC)c3Cl)cc2cn1] | N-((3R,4S)-4-((7-(2,6-dichloro-3,5-dimethoxyphenyl)-5-methoxy-2,6-naphthyridin-3-yl)amino)tetrahydrofuran-3-yl)acrylamide | 519 |
| 130 | 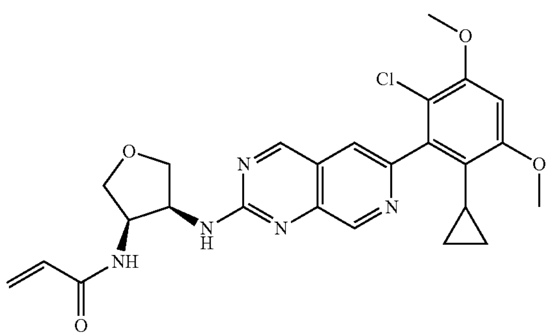 [SMILES: C=CC(=O)N[C@H]1COC[C@H]1Nc1ncc2cc(-c3c(Cl)c(OC)cc(OC)c3C3CC3)ncc2n1] | N-((3R,4S)-4-((6-(2-chloro-6-cyclopropyl-3,5-dimethoxyphenyl)pyrido[3,4-d]pyrimidin-2-yl)amino)tetrahydrofuran-3-yl)acrylamide | 496 |
| 131 | 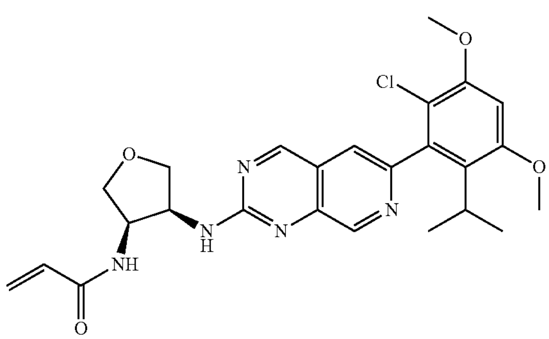 [SMILES: C=CC(=O)N[C@H]1COC[C@H]1Nc1ncc2cc(-c3c(Cl)c(OC)cc(OC)c3C(C)C)ncc2n1] | N-((3R,4S)-4-((6-(2-chloro-6-isopropyl-3,5-dimethoxyphenyl)pyrido[3,4-d]pyrimidin-2-yl)amino)tetrahydrofuran-3-yl)acrylamide | 498 |

-continued

| Example No. | Compound structure | Compound name | MS: m/z [M + 1]+ |
|---|---|---|---|
| 132 | 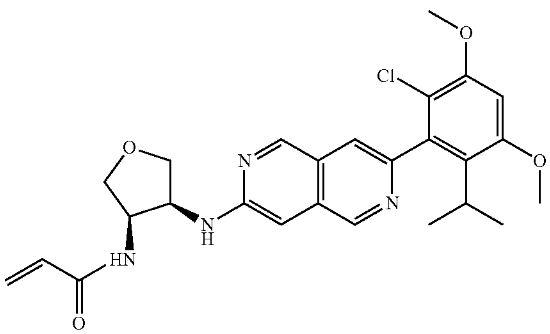 [SMILES: C=CC(=O)N[C@H]1COC[C@H]1Nc1cc2cnc(-c3c(Cl)c(OC)cc(OC)c3C(C)C)cc2cn1] | N-((3R,4S)-4-((7-(2-chloro-6-isopropyl-3,5-dimethoxyphenyl)-2,6-naphthyridin-3-yl)amino)tetrahydrofuran-3-yl)acrylamide | 497 |
| 133 | 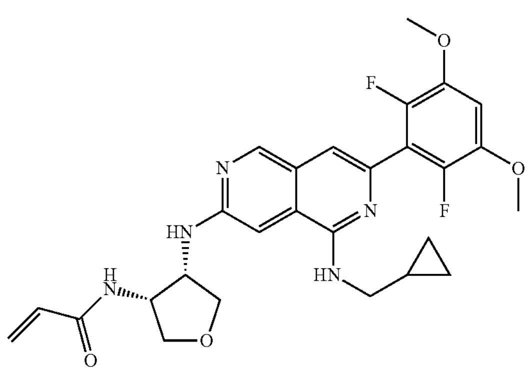 [SMILES: C=CC(=O)N[C@H]1COC[C@H]1Nc1cc2c(NCC3CC3)nc(-c3c(F)c(OC)cc(OC)c3F)cc2cn1] | N-((3R,4S)-4-((5-((cyclopropylmethyl)amino)-7-(2,6-difluoro-3,5-dimethoxyphenyl)-2,6-naphthyridin-3-yl)amino)tetrahydrofuran-3-yl)acrylamide | 526 |
| 134 | 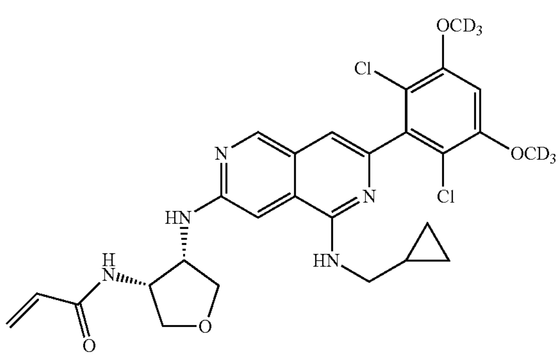 | N-((3R,4S)-4-((5-(cyclopropylmethyl)amino)-7-(2,6-dichloro-3,5-bis(methoxy-d₃)phenyl)-2,6-naphthyridin-3-yl)amino)tetrahydrofuran-3-yl)acrylamide | 564 |
| 135 | 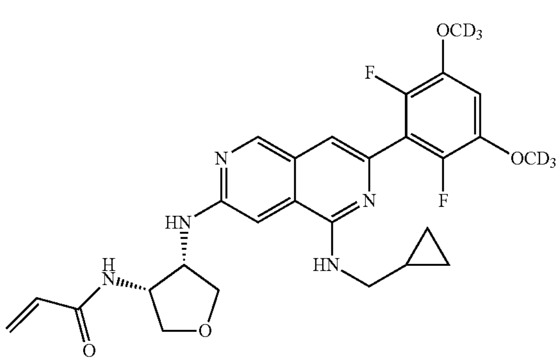 | N-((3R,4S)-4-((5-((cyclopropylmethyl)amino)-7-(2,6-difluoro-3,5-bis(methoxy-d₃)phenyl)-2,6-naphthyridin-3-yl)amino)tetrahydrofuran-3-yl)acrylamide | 532 |

| Example No. | Compound structure | Compound name | MS: m/z [M + 1]+ |
|---|---|---|---|
| 136 | 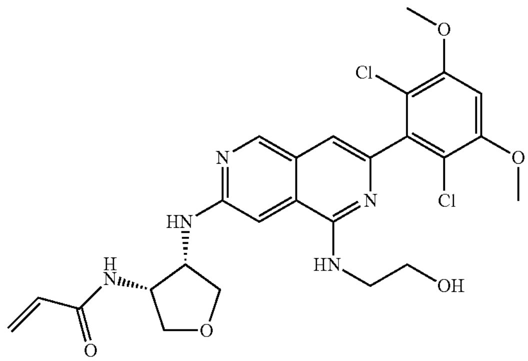 [SMILES: C=CC(=O)N[C@H]1COC[C@H]1Nc1cc2c(NCCO)nc(-c3c(Cl)c(OC)cc(OC)c3Cl)cc2cn1] | N-((3R,4S)-4-((7-(2,6-dichloro-3,5-dimethoxyphenyl)-5-((2-hydroxyethyl)amino)-2,6-naphthyridin-3-yl)amino)tetrahydrofuran-3-yl)acrylamide | 548 |
| 137 | 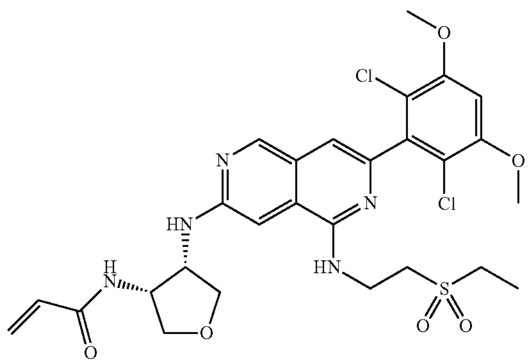 [SMILES: C=CC(=O)N[C@H]1COC[C@H]1Nc1cc2c(NCCS(=O)(=O)CC)nc(-c3c(Cl)c(OC)cc(OC)c3Cl)cc2cn1] | N-((3R,4S)-4-((7-(2,6-dichloro-3,5-dimethoxyphenyl)-5-((2-(ethylsulfonyl)ethyl)amino)-2,6-naphthyridin-3-yl)amino)tetrahydrofuran-3-yl)acrylamide | 624 |
| 138 | 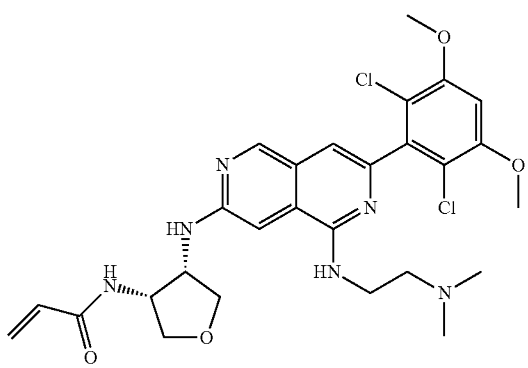 [SMILES: C=CC(=O)N[C@H]1COC[C@H]1Nc1cc2c(NCCN(C)C)nc(-c3c(Cl)c(OC)cc(OC)c3Cl)cc2cn1] | N-((3R,4S)-4-((7-(2,6-dichloro-3,5-dimethoxyphenyl)-5-((2-(dimethylamino)ethyl)amino)-2,6-naphthyridin-3-yl)amino)tetrahydrofuran-3-yl)acrylamide | 575 |
| 139 | 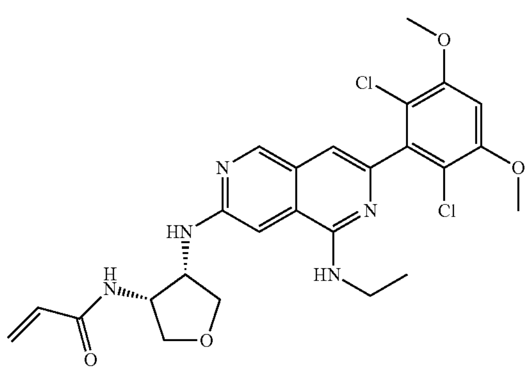 [SMILES: C=CC(=O)N[C@H]1COC[C@H]1Nc1cc2c(NCC)nc(-c3c(Cl)c(OC)cc(OC)c3Cl)cc2cn1] | N-((R,4S)-4-((7-(2,6-dichloro-3,5-dimethoxyphenyl)-5-(ethylamino)-2,6-naphthyridin-3-yl)amino)tetrahydrofuran-3-yl)acrylamide | 532 |

-continued

| Example No. | Compound structure | Compound name | MS: m/z [M + 1]+ |
|---|---|---|---|
| 140 | 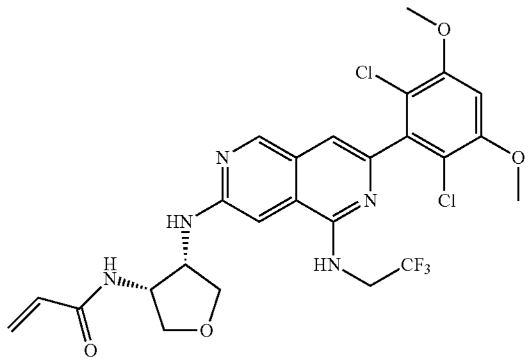 [SMILES: C=CC(=O)N[C@H]1COC[C@H]1Nc1cc2c(NCC(F)(F)F)nc(-c3c(Cl)c(OC)cc(OC)c3Cl)cc2cn1] | N-((3R,4S)-4-((7-(2,6-dichloro-3,5-dimethoxyphenyl)-5-((2,2,2-trifluoroethyl)amino)-2,6-naphthyridin-3-yl)amino)tetrahydrofuran-3-yl)acrylamide | 586 |
| 141 | 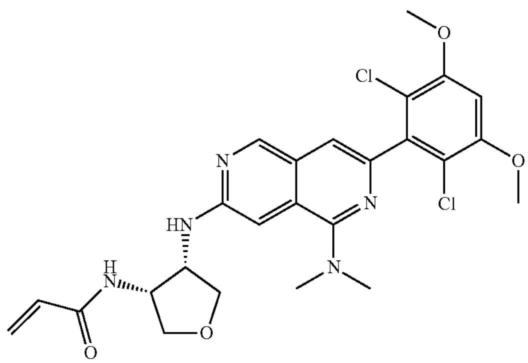 [SMILES: C=CC(=O)N[C@H]1COC[C@H]1Nc1cc2c(N(C)C)nc(-c3c(Cl)c(OC)cc(OC)c3Cl)cc2cn1] | N-((3R,4S)-4-((7-(2,6-dichloro-3,5-dimethoxyphenyl)-5-(dimethylamino)-2,6-naphthyridin-3-yl)amino)tetrahydrofuran-3-yl)acrylamide | 532 |
| 142 | 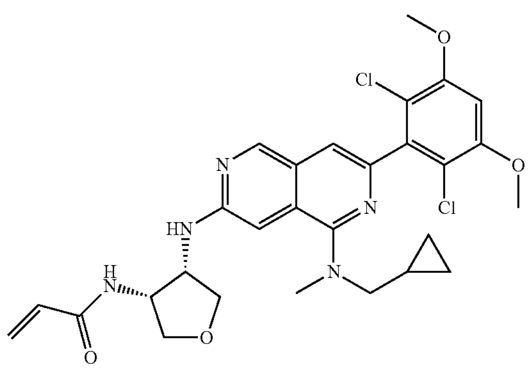 [SMILES: C=CC(=O)N[C@H]1COC[C@H]1Nc1cc2c(N(C)CC3CC3)nc(-c3c(Cl)c(OC)cc(OC)c3Cl)cc2cn1] | N-((3R,4S)-4-((5-((cyclopropylmethyl)methyl)amino)-7-(2,6-dichloro-3,5-dimethoxyphenyl)-2,6-naphthyridin-3-yl)amino)tetrahydrofuran-3-yl)acrylamide | 572 |
| 143 | 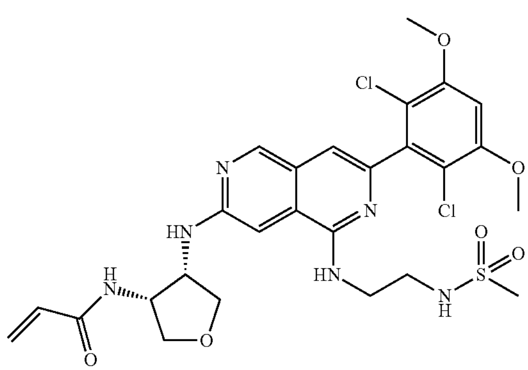 [SMILES: C=CC(=O)N[C@H]1COC[C@H]1Nc1cc2c(NCCNS(C)(=O)=O)nc(-c3c(Cl)c(OC)cc(OC)c3Cl)cc2cn1] | N-((3R,4S)-4-((7-(2,6-dichloro-3,5-dimethoxyphenyl)-5-((2-(methylsulfonamido)ethyl)amino)-2,6-naphthyridin-3-yl)amino)tetrahydrofuran-3-yl)acrylamide | 625 |

-continued

| Example No. | Compound structure | Compound name | MS: m/z [M + 1]+ |
|---|---|---|---|
| 144 | 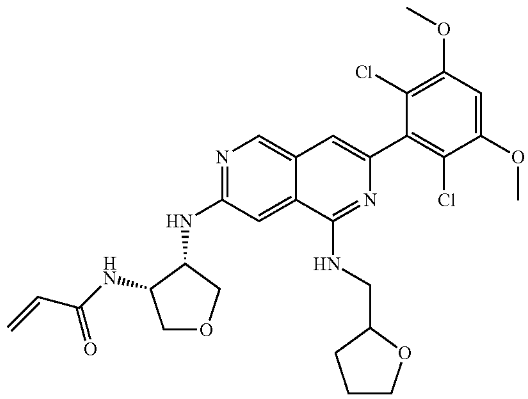 [SMILES: C=CC(=O)N[C@H]1COC[C@H]1Nc1cc2c(NCC3CCCO3)nc(-c3c(Cl)c(OC)cc(OC)c3Cl)cc2cn1] | N-((3R,4S)-4-((7-(2,6-dichloro-3,5-dimethoxyphenyl)-5-(((tetrahydrofuran-2-yl)methyl)amino)-2,6-naphthyridin-3-yl)amino)tetrahydrofuran-3-yl)acrylamide | 588 |
| 145 | 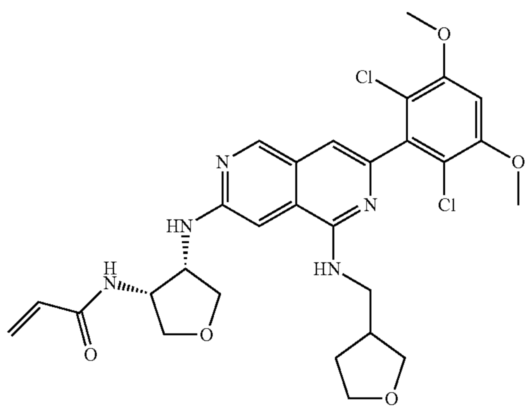 [SMILES: C=CC(=O)N[C@H]1COC[C@H]1Nc1cc2c(NCC3CCOC3)nc(-c3c(Cl)c(OC)cc(OC)c3Cl)cc2cn1] | N-((3R,4S)-4-((7-(2,6-dichloro-3,5-dimethoxyphenyl)-5-(((tetrahydrofuran-3-yl)methyl)amino)-2,6-naphthyridin-3-yl)amino)tetrahydrofuran-3-yl)acrylamide | 588 |
| 146 | 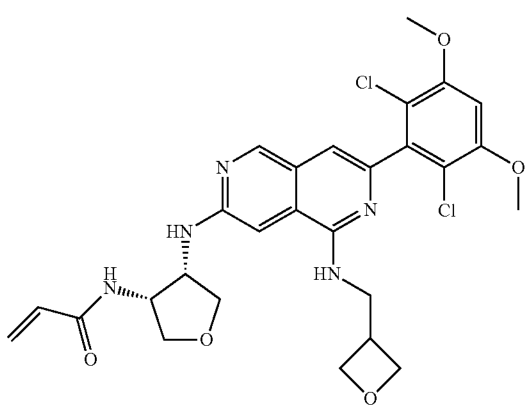 [SMILES: C=CC(=O)N[C@H]1COC[C@H]1Nc1cc2c(NCC3COC3)nc(-c3c(Cl)c(OC)cc(OC)c3Cl)cc2cn1] | N-((3R,4S)-4-((7-(2,6-dichloro-3,5-dimethoxyphenyl)-5-((oxetan-3-ylmethyl)amino)-2,6-naphthyridin-3-yl)amino)tetrahydrofuran-3-yl)acrylamide | 574 |

| Example No. | Compound structure | Compound name | MS: m/z [M + 1]+ |
|---|---|---|---|
| 147 | 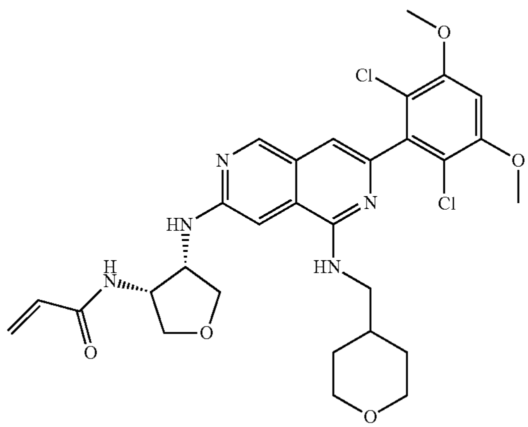 [SMILES: C=CC(=O)N[C@H]1COC[C@H]1Nc1cc2c(NCC3CCOCC3)nc(-c3c(Cl)c(OC)cc(OC)c3Cl)cc2cn1] | N-((3R,4S)-4-((7-(2,6-dichloro-3,5-dimethoxyphenyl)-5-(((tetrahydro-2H-pyran-4-yl)methyl)amino)-2,6-naphthyridin-3-yl)amino)tetrahydrofuran-3-yl)acrylamide | 602 |
| 148 | 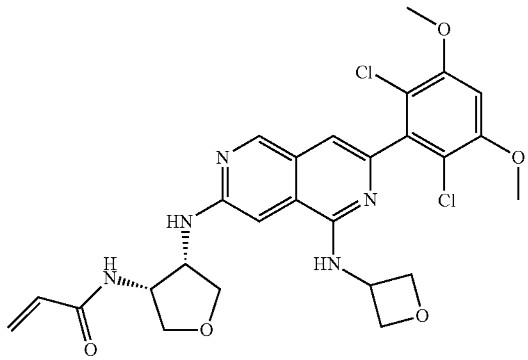 [SMILES: C=CC(=O)N[C@H]1COC[C@H]1Nc1cc2c(NC3COC3)nc(-c3c(Cl)c(OC)cc(OC)c3Cl)cc2cn1] | N-((3R,4S)-4-((7-(2,6-dichloro-3,5-dimethoxyphenyl)-5-(oxetan-3-ylamino)-2,6-naphthyridin-3-yl)amino)tetrahydrofuran-3-yl)acrylamide | 560 |
| 149 | 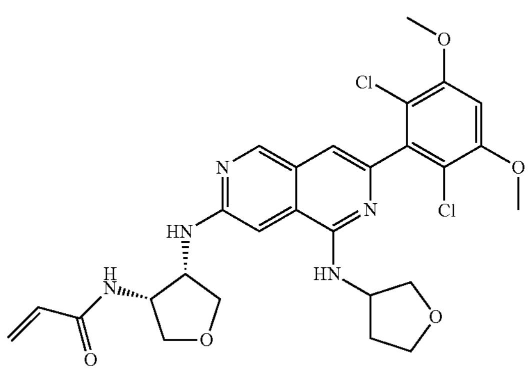 [SMILES: C=CC(=O)N[C@H]1COC[C@H]1Nc1cc2c(NC3CCOC3)nc(-c3c(Cl)c(OC)cc(OC)c3Cl)cc2cn1] | N-((3R,4S)-4-((7-(2,6-dichloro-3,5-dimethoxyphenyl)-5-(((tetrahydrofuran-3-yl)amino)-2,6-naphthyridin-3-yl)amino)tetrahydrofuran-3-yl)acrylamide | 574 |
| 150 | 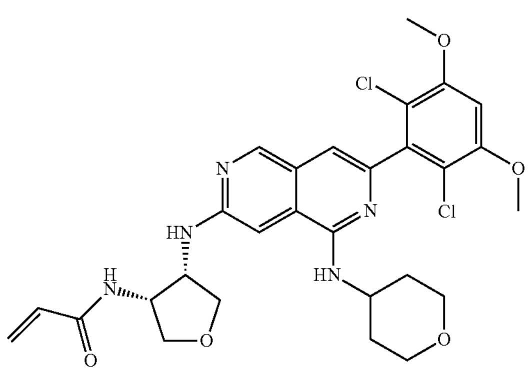 [SMILES: C=CC(=O)N[C@H]1COC[C@H]1Nc1cc2c(NC3CCOCC3)nc(-c3c(Cl)c(OC)cc(OC)c3Cl)cc2cn1] | N-((3R,4S)-4-((7-(2,6-dichloro-3,5-dimethoxyphenyl)-5-(((tetrahydro-2H-pyran-4-yl)amino)-2,6-naphthryridin-3-yl)amino)tetrahydrofuran-3-yl)acrylamide | 588 |

| Example No. | Compound structure | Compound name | MS: m/z [M + 1]+ |
|---|---|---|---|
| 151 | 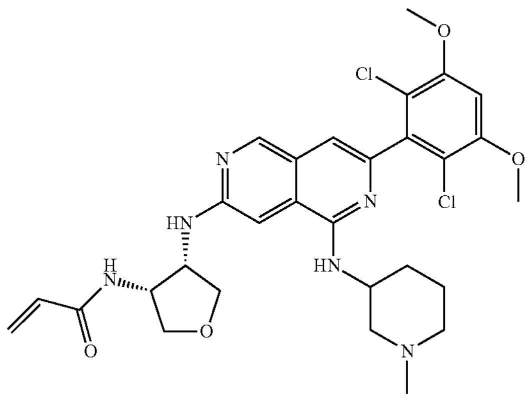 [SMILES: C=CC(=O)N[C@H]1COC[C@H]1Nc1cc2c(NC3CCCN(C)C3)nc(-c3c(Cl)c(OC)cc(OC)c3Cl)cc2cn1] | N-((3R,4S)-4-((7-(2,6-dichloro-3,5-dimethoxyphenyl)-5-(((1-methylpiperidin-4-yl)methyl)amino)-2,6-naphthyridin-3-yl)amino)tetrahydrofuran-3-yl)acrylamide | 615 |
| 152 | 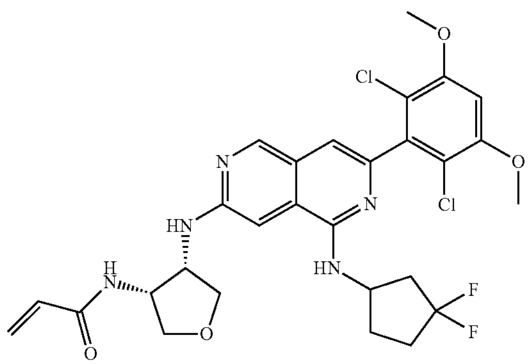 [SMILES: C=CC(=O)N[C@H]1COC[C@H]1Nc1cc2c(NC3CCC(F)(F)C3)nc(-c3c(Cl)c(OC)cc(OC)c3Cl)cc2cn1] | N-((3R,4S)-4-((7-(2,6-dichloro-3,5-dimethoxyphenyl)-5-((3,3-difluorocyclopentyl)amino)-2,6-naphthyridin-3-yl)amino)tetrahydrofuran-3-yl)acrylamide | 608 |
| 153 | 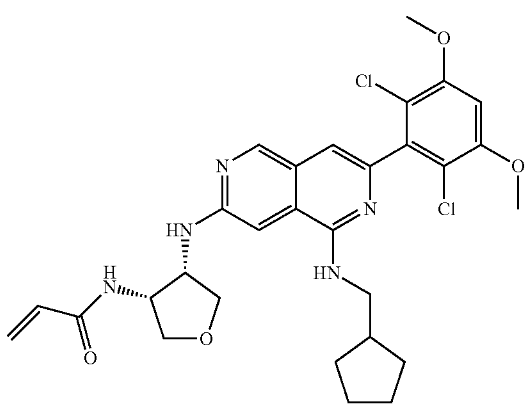 [SMILES: C=CC(=O)N[C@H]1COC[C@H]1Nc1cc2c(NCC3CCCC3)nc(-c3c(Cl)c(OC)cc(OC)c3Cl)cc2cn1] | N-((3R,4S)-4-((5-((cyclopentylmethyl)amino)-7-(2,6-dichloro-3,5-dimethoxyphenyl)-2,6-naphthyridin-3-yl)amino)tetrahydrofuran-3-yl)acrylamide | 586 |
| 154 | 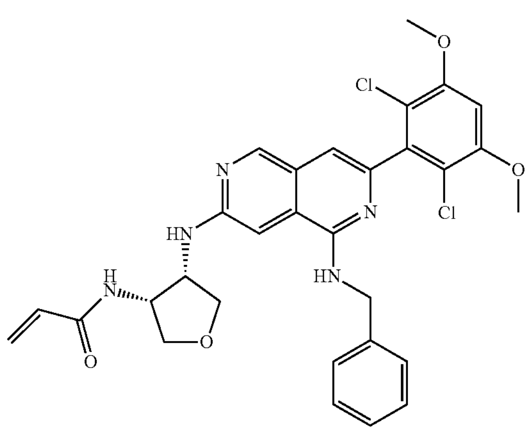 [SMILES: C=CC(=O)N[C@H]1COC[C@H]1Nc1cc2c(NCc3ccccc3)nc(-c3c(Cl)c(OC)cc(OC)c3Cl)cc2cn1] | N-((3R,4S)-4-((5-(benzylamino)-7-(2,6-dichloro-3,5-dimethoxyphenyl)-2,6-naphthyridin-3-yl)amino)tetrahydrofuran-3-yl)acrylamide | 594 |

| Example No. | Compound structure | Compound name | MS: m/z [M + 1]+ |
|---|---|---|---|
| 155 | 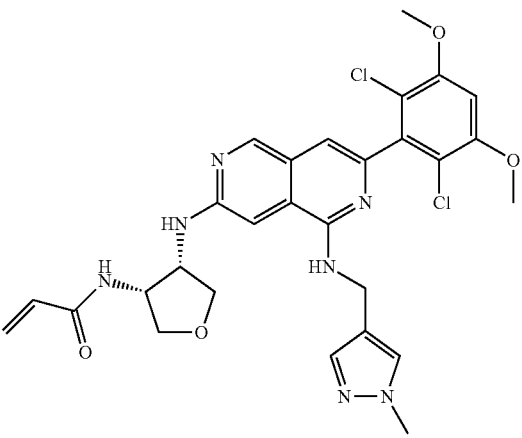 [SMILES: C=CC(=O)N[C@H]1COC[C@H]1Nc1cc2c(NCc3cnn(C)c3)nc(-c3c(Cl)c(OC)cc(OC)c3Cl)cc2cn1] | N-((3R,4S)-4-((7-(2,6-dichloro-3,5-dimethoxyphenyl)-5-(((1-methyl-1H-pyrazol-4-yl)methyl)amino)-2,6-naphthyridin-3-yl)amino)tetrahydrofuran-3-yl)acrylamide | 598 |
| 156 | 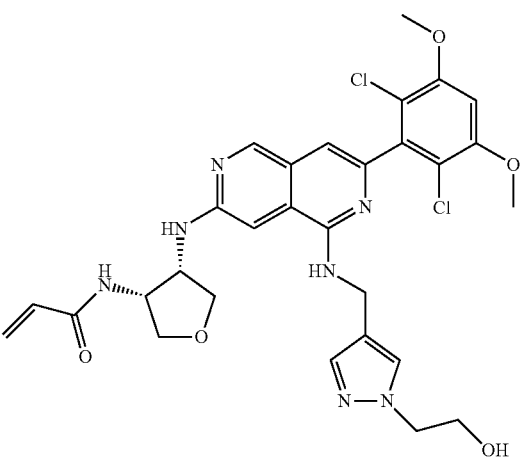 [SMILES: C=CC(=O)N[C@H]1COC[C@H]1Nc1cc2c(NCc3cnn(CCO)c3)nc(-c3c(Cl)c(OC)cc(OC)c3Cl)cc2cn1] | N-((3R,4S)-4-((7-(2,6-dichloro-3,5-dimethoxyphenyl)-5-(((1-(2-hydroxyethyl)-pyrazol-4-yl)methyl)amino)-2,6-naphthyridin-3-yl)amino)tetrahydrafuran-3-yl)acrylamide | 628 |
| 157 | 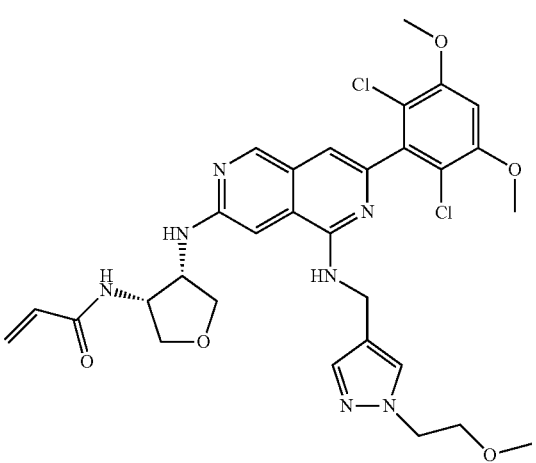 [SMILES: C=CC(=O)N[C@H]1COC[C@H]1Nc1cc2c(NCc3cnn(CCOC)c3)nc(-c3c(Cl)c(OC)cc(OC)c3Cl)cc2cn1] | N-((3R,4S)-4-((7-(2,6-dichloro-3,5-dimethoxyphenyl)-5-(((1-(2-methoxyethyl-)1H-pyrazol-4-yl)methyl)amino)-2,6-naphthyridin-3-yl)amino)tetrahydrofuran-3-yl)acrylamide | 642 |

-continued

| Example No. | Compound structure | Compound name | MS: m/z [M + 1]+ |
|---|---|---|---|
| 158 | 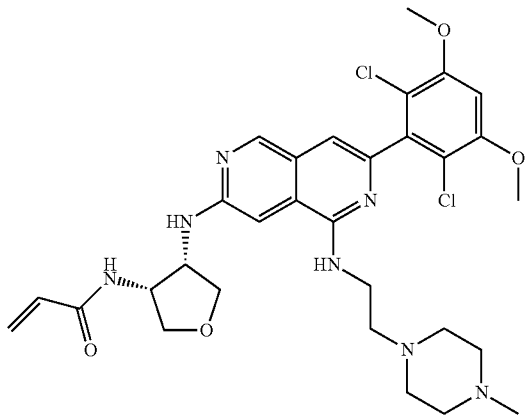 [SMILES: C=CC(=O)N[C@H]1COC[C@H]1Nc1cc2c(NCCN3CCN(C)CC3)nc(-c3c(Cl)c(OC)cc(OC)c3Cl)cc2cn1] | N-((3R,4S)-4-((7-(2,6-dichloro-3,5-dimethoxyphenyl)-5-((2-(4-methylpiperazin-1-yl)ethyl)amino)-2,6-naphthyridin-3-yl amino)tetrahydrofuran-3-yl)acrylamide | 630 |
| 159 | 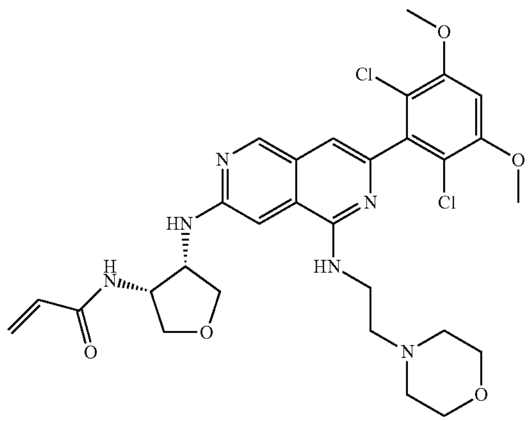 [SMILES: C=CC(=O)N[C@H]1COC[C@H]1Nc1cc2c(NCCN3CCOCC3)nc(-c3c(Cl)c(OC)cc(OC)c3Cl)cc2cn1] | N-((3R,4S)-4-((7-(2,6-dichloro-3,5-dimethoxyphenyl)-5-((2-morpholinoethyl) amino)-2,6-naphthyridin-3-yl)amino) tetrahydrofuran-3-yl)acrylamide | 617 |
| 160 | 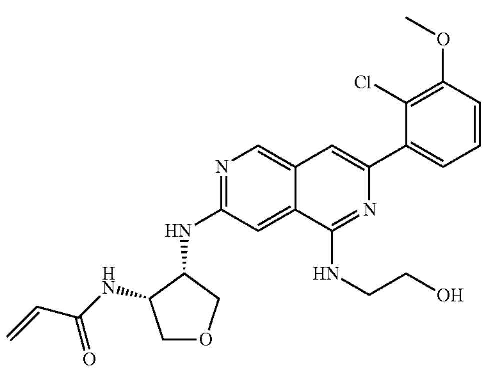 [SMILES: C=CC(=O)N[C@H]1COC[C@H]1Nc1cc2c(NCCO)nc(-c3cccc(OC)c3Cl)cc2cn1] | N-((3R,4S)-4-((7-(2-chloro-3-methoxy-phenyl)-5-((2-hydroxyethyl)amino)-2,6-naphthyridin-3-yl)amino)tetrahydro-furan-3-yl)acrylamide | 484 |
| 161 | 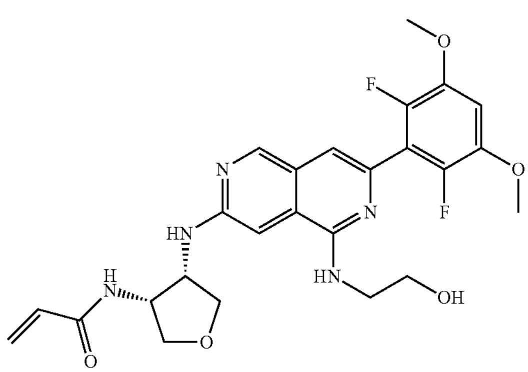 [SMILES: C=CC(=O)N[C@H]1COC[C@H]1Nc1cc2c(NCCO)nc(-c3c(F)c(OC)cc(OC)c3F)cc2cn1] | N-((3R,4S)-4-((7-(2,6-difluoro-3,5-dimethoxyphenyl)-5-((2-hydroxyethyl)ami-no)-2,6-naphthyridin-3-yl)amino)tetra-hydrofuran-3-yl)acrylamide | 516 |

-continued

| Example No. | Compound structure | Compound name | MS: m/z [M + 1]+ |
|---|---|---|---|
| 162 | 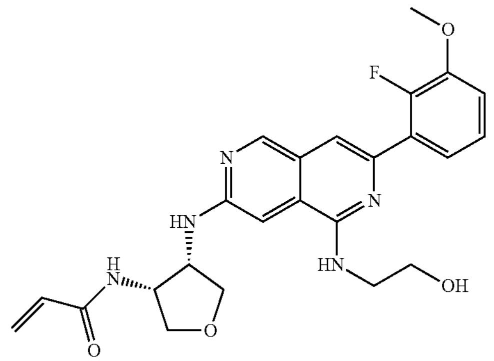 [SMILES: C=CC(=O)N[C@H]1COC[C@H]1Nc1cc2c(NCCO)nc(-c3cccc(OC)c3F)cc2cn1] | N-((3R,4S)-4-((7-(2-fluoro-3-methoxyphenyl)-5-((2-hydroxyethyl)amino)-2,6-naphthyridin-3-yl)amino)tetrahydrofuran-3-yl)acrylamide | 468 |
| 163 | 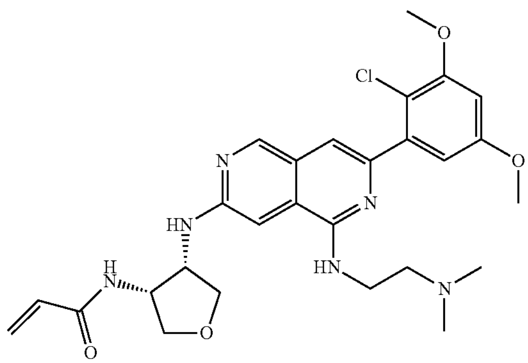 [SMILES: C=CC(=O)N[C@H]1COC[C@H]1Nc1cc2c(NCCN(C)C)nc(-c3cc(OC)cc(OC)c3Cl)cc2cn1] | N-((3R,4S)-4-((7-(2-chloro-3,5-dimethoxyphenyl)-5-((2-(dimethylamino)ethyl)amino)-2,6-naphthyridin-3-yl)amino)tetrahydrofuran-3-yl)acrylamide | 541 |
| 164 | 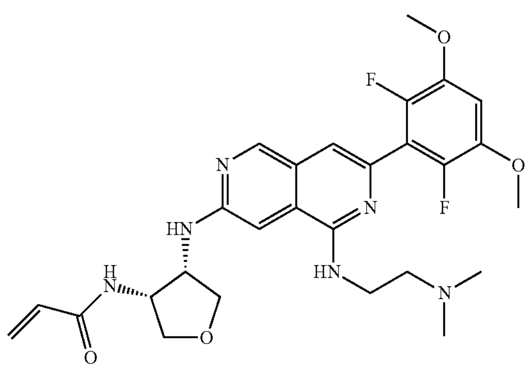 [SMILES: C=CC(=O)N[C@H]1COC[C@H]1Nc1cc2c(NCCN(C)C)nc(-c3c(F)c(OC)cc(OC)c3F)cc2cn1] | N-((3R,4S)-4-((7-(2,6-difluoro-3,5-dimethoxyphenyl)-5-((2-(dimethylamino)ehyl)amino)-2,6-naphthyridin-3-yl)amino)tetrahydrofuran-3-yl)acrylamide | 543 |
| 165 | 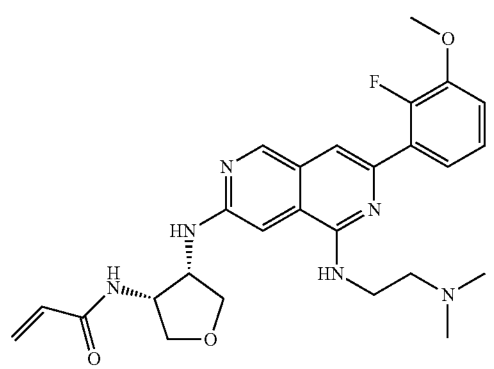 [SMILES: C=CC(=O)N[C@H]1COC[C@H]1Nc1cc2c(NCCN(C)C)nc(-c3cccc(OC)c3F)cc2cn1] | N-((3R,4S)-4-((5-((2-(dimethylamino)ethyl)amino)-7-(2-fluoro-3-dimethoxyphenyl)-2,6-naphthyridin-3-yl)amino)tetrahydrofuran-3-yl)acrylamide | 495 |

-continued

| Example No. | Compound structure | Compound name | MS: m/z [M + 1]+ |
|---|---|---|---|
| 167 | 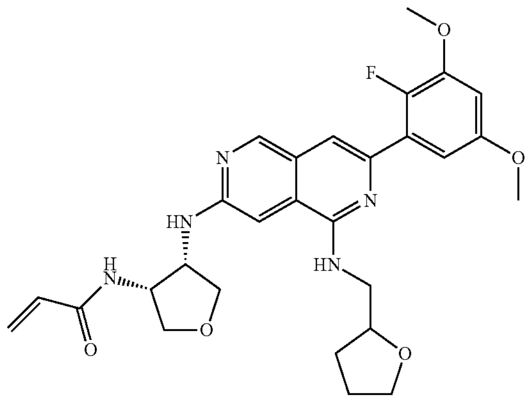 [SMILES: C=CC(=O)N[C@H]1COC[C@H]1Nc1cc2c(NCC3CCCO3)nc(-c3cc(OC)cc(OC)c3F)cc2cn1] | N-((3R,4S)-4-((7-(2-fluoro-3,5-dimethoxyphenyl)-5-((((tetrahydrofuran-2-yl)methyl)amino)-2,6-naphthyridin-3-yl)amino)tetrahydrofuran-3-yl)acrylamide | 538 |
| 168 | 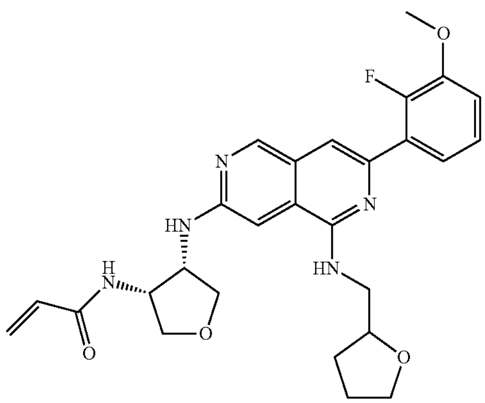 [SMILES: C=CC(=O)N[C@H]1COC[C@H]1Nc1cc2c(NCC3CCCO3)nc(-c3cccc(OC)c3F)cc2cn1] | N-((3R,4S)-4-((7-(2-fluoro-3-methoxyphenyl)-5-((((tetrahydrofuran-2-yl)methylamino)-2,6-naphthyridin-3-yl)amino)tetrahydrofuran-3-yl)acrylamide | 508 |
| 169 | 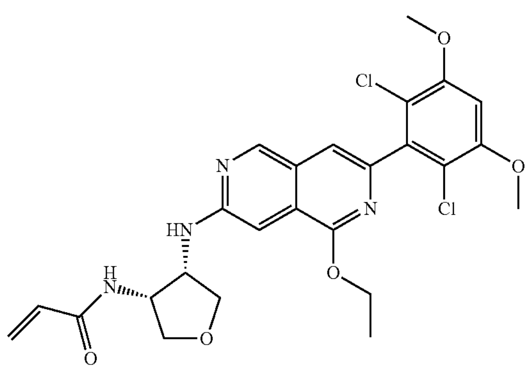 [SMILES: C=CC(=O)N[C@H]1COC[C@H]1Nc1cc2c(OCC)nc(-c3c(Cl)c(OC)cc(OC)c3Cl)cc2cn1] | N-((3R,4S)-4-((7-(2,6-dichloro-3,5-dimethoxyphenyl)-5-ethoxy-2,6-naphthyridin-3-yl)amino)tetrahydrofuran-3-yl)acrylamide | 533 |
| 170 | 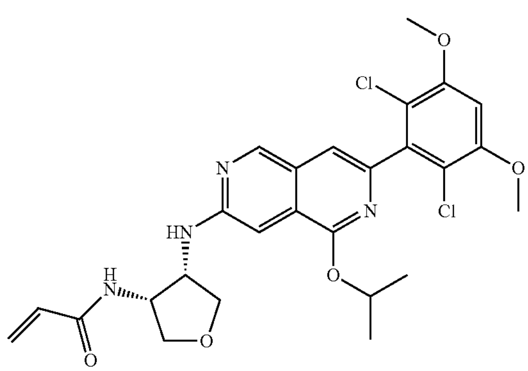 [SMILES: C=CC(=O)N[C@H]1COC[C@H]1Nc1cc2c(OC(C)C)nc(-c3c(Cl)c(OC)cc(OC)c3Cl)cc2cn1] | N-((3R,4S)-4-((7-(2,6-dichloro-3,5-dimethoxyphenyl)-5-isopropoxy-2,6-naphthyridin-3-yl)amino)tetrahydrofuran-3-yl)acrylamide | 547 |

-continued

| Example No. | Compound structure | Compound name | MS: m/z [M + 1]+ |
|---|---|---|---|
| 171 | 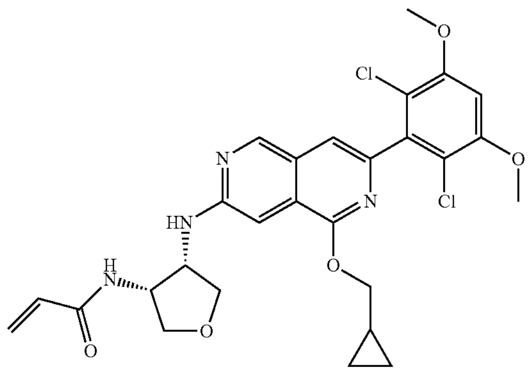 [SMILES: C=CC(=O)N[C@H]1COC[C@H]1Nc1cc2c(OCC3CC3)nc(-c3c(Cl)c(OC)cc(OC)c3Cl)cc2cn1] | N-((3R,4S)-4-((5-(cyclopropylmethoxy)-7-(2,6-dichloro-3,5-dimethoxyphenyl) 2,6-naphthyridin-3-yl)amino)tetrahydro-furan-3-yl)acrylamide | 559 |
| 172 | 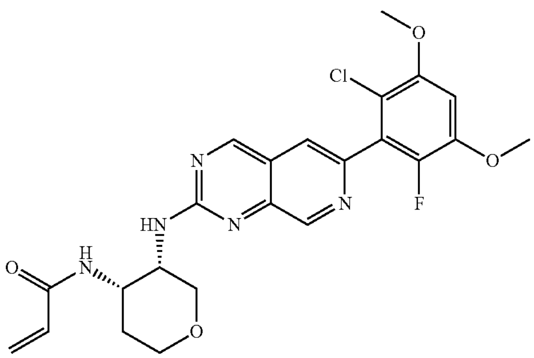 | N-((3S,4S)-3-((6-(2-chloro-6-fluoro-3,5-dimethoxyphenyl)pyrido[3,4-d]pyrimidin-2-yl)amino)tetrahydro-2H-pyran-4-yl)acrylamide | 488 |
| 173 | 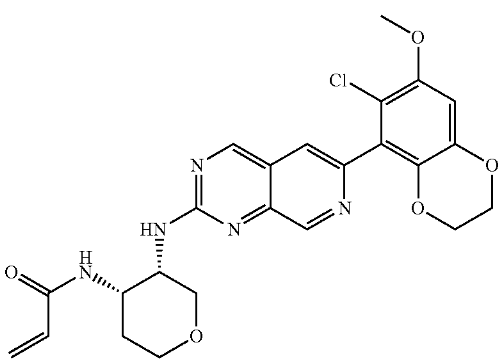 [SMILES: C=CC(=O)N[C@H]1CCOC[C@H]1Nc1ncc2cc(-c3c(Cl)c(OC)cc4c3OCCO4)ncc2n1] | N-((3S,4S)-3-((6-(6-chloro-7-dimethoxy-2,3-dihydrobenzo[b][1,4]dioxin-5-yl)pyrido[3,4-d]pyrimidin-2-yl)amino)tetrahydro-2H-pyran-4-yl)acrylamide | 498 |
| 174 | 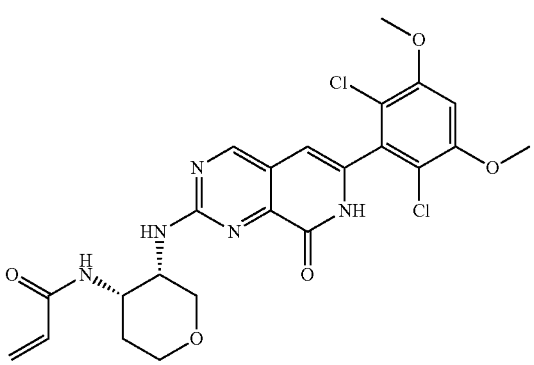 [SMILES: C=CC(=O)N[C@H]1CCOC[C@H]1Nc1ncc2cc(-c3c(Cl)c(OC)cc(OC)c3Cl)[nH]c(=O)c2n1] | N-((3S,4S)-3-((6-(2,6-dichloro-3,5-dimethoxyphenyl)-8-oxo-7,8-dihydropyrido[3,4-d]pyrimidin-2-yl)amino)tetrahydro-2H-pyran-4-yl)acrylamide | 520 |

| Example No. | Compound structure | Compound name | MS: m/z [M + 1]+ |
|---|---|---|---|
| 175 | 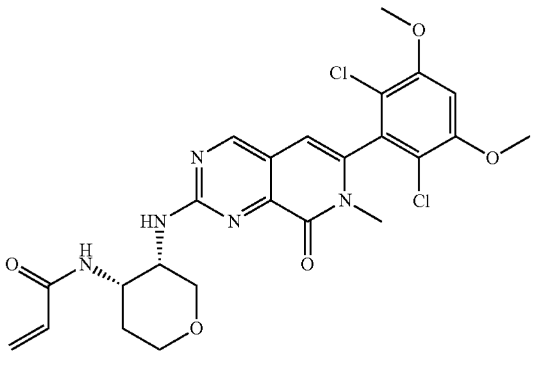 [SMILES: C=CC(=O)N[C@H]1CCOC[C@H]1Nc1ncc2cc(-c3c(Cl)c(OC)cc(OC)c3Cl)n(C)c(=O)c2n1] | N-((3S,4S)-3-((6-(2,6-dichloro-3,5-dimethoxyphenyl)-7-methyl-8-oxo-7,8-dihydropyrido[3,4-d]pyrimidin-2-yl)amino)tetrahydro-2H-pyran-4-yl)acrylamide | 534 |
| 176 | 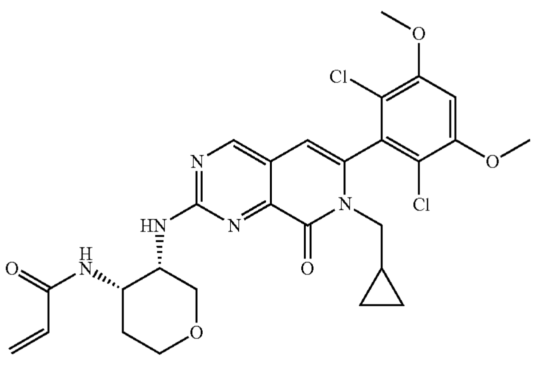 [SMILES: C=CC(=O)N[C@H]1CCOC[C@H]1Nc1ncc2cc(-c3c(Cl)c(OC)cc(OC)c3Cl)n(CC3CC3)c(=O)c2n1] | N-((3S,4S)-3-((7-(cyclopropylmethyl)-6-(2,6-dichloro-3,5-dimethoxyphenyl)-8-oxo-7,8-dihydropyrido[3,4-d]pyrimidin-2-yl)amino)tetrahydro-2H-pyran-4-yl)acrylamide | 574 |
| 177 | 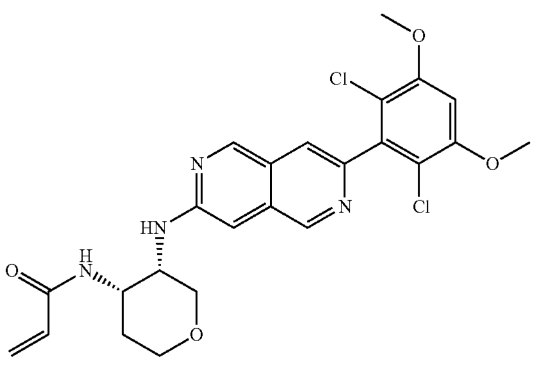 | N-((3S,4S)-3-((7-(2,6-dichloro-3,5-dimethoxyphenyl)-2,6-naphthyridin-3-yl)amino)tetrahydro-2H-pyran-4-yl)acrylamide | 503 |
| 178 | 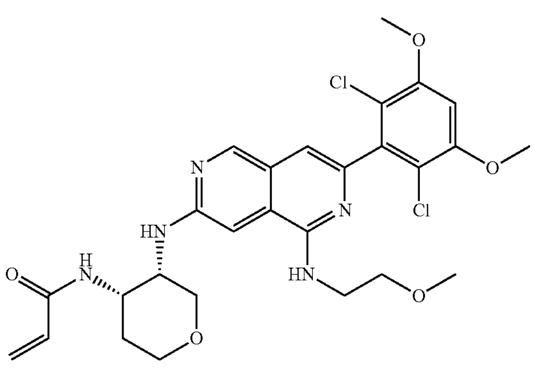 [SMILES: C=CC(=O)N[C@H]1CCOC[C@H]1Nc1cc2c(NCCOC)nc(-c3c(Cl)c(OC)cc(OC)c3Cl)cc2cn1] | N-((3S,4S)-3-((7-(2,6-dichloro-3,5-dimethoxyphenyl)-5-((2-dimethoxyethyl)amino)-2,6-naphthyridin-3-yl)amino)tetrahydro-2H-pyran-4-yl)acrylamide | 576 |

| Example No. | Compound structure | Compound name | MS: m/z [M + 1]+ |
|---|---|---|---|
| 179 | 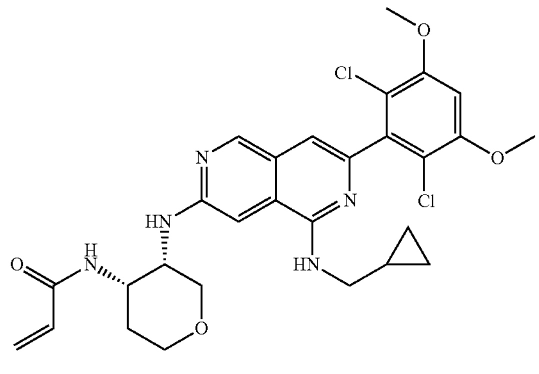 [SMILES: C=CC(=O)N[C@H]1CCOC[C@H]1Nc1cc2c(NCC3CC3)nc(-c3c(Cl)c(OC)cc(OC)c3Cl)cc2cn1] | N-((3S,4S)-3-((5-((cyclopropylmethyl)amino)-7-(2,6-dichloro-3,5-dimethoxyphenyl)-2,6-naphthyridin-3-yl)amino)tetrahydro-2H-pyran-4-yl)acrylamide | 572 |
| 180 | 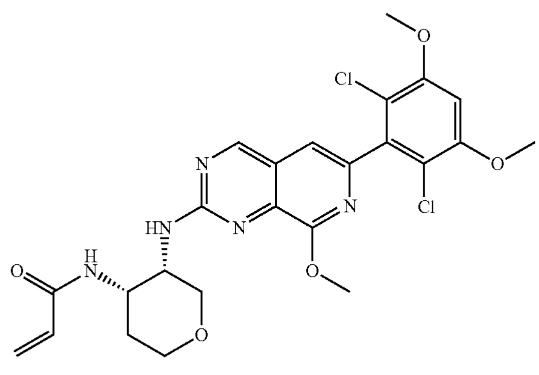 [SMILES: C=CC(=O)N[C@H]1CCOC[C@H]1Nc1ncc2cc(-c3c(Cl)c(OC)cc(OC)c3Cl)nc(OC)c2n1] | N-((3S,4S)-3-((7-(2,6-dichloro-3,5-dimethoxyphenyl)-5-dimethoxy-2,6-naphthyridin-3-yl)amino)tetrahydro-2H-pyran-4-yl)acrylamide | 533 |
| 181 | 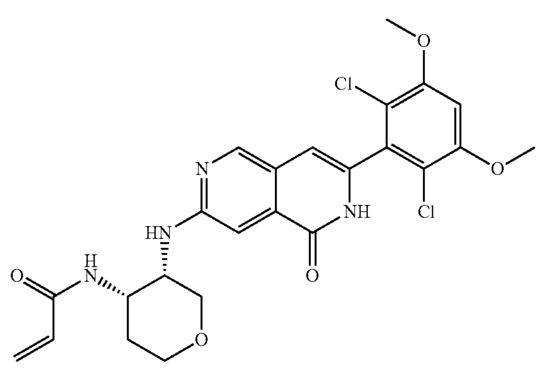 | N-((3S,4S)-3-((7-(2,6-dichloro-3,5-dimethoxyphenyl)-5-oxo-5,6-dihydro-2,6-naphthyridin-3-yl)amino)teahydro-2H-pyran-4-yl)acrylamide | 519 |
| 182 | 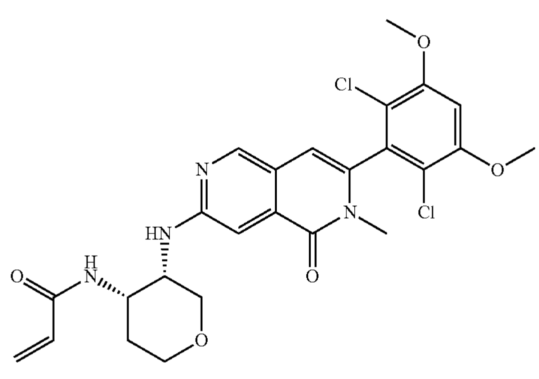 [SMILES: C=CC(=O)N[C@H]1CCOC[C@H]1Nc1cc2c(=O)n(C)c(-c3c(Cl)c(OC)cc(OC)c3Cl)cc2cn1] | N-((3S,4S)-3-((7-(2,6-dichloro-3,5-dimethoxyphenyl)-6-methyl-5-oxo-5,6-dihydro-2,6-naphthyridin-3-yl)amino)tetrahydro-2H-pyran-4-yl)acrylamide | 533 |

| Example No. | Compound structure | Compound name | MS: m/z [M + 1]+ |
|---|---|---|---|
| 183 | 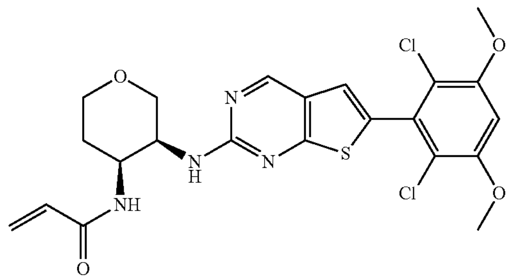 [SMILES: C=CC(=O)N[C@H]1CCOC[C@H]1Nc1ncc2cc(-c3c(Cl)c(OC)cc(OC)c3Cl)sc2n1] | N-((3S,4S)-3-((6-(2,6-dichloro-3,5-dimethoxyphenyl)thieno[2,3-d]pyrimidin-2-yl)amino)tetrahydro-2H-pyran-4-yl)acrylamide | 509 |
| 184 | 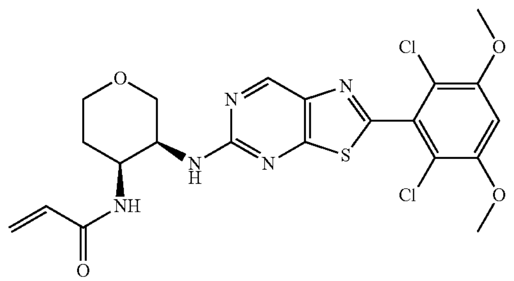 [SMILES: C=CC(=O)N[C@H]1CCOC[C@H]1Nc1ncc2nc(-c3c(Cl)c(OC)cc(OC)c3Cl)sc2n1] | N-((3S,4S)-3-((2-(2,6-dichloro-3,5-dimethoxyphenyl)thiazolo[5,4-d]pyrimidin-5-yl)amino)tetrahydro-2H-pyran-4-yl)acrylamide | 510 |
| 185 | 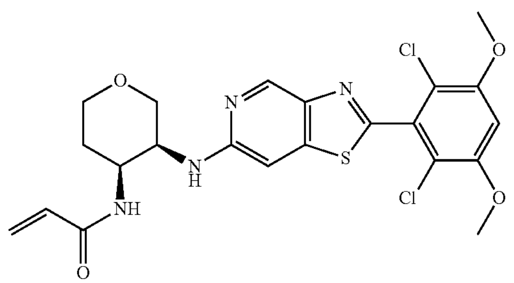 [SMILES: C=CC(=O)N[C@H]1CCOC[C@H]1Nc1cc2sc(-c3c(Cl)c(OC)cc(OC)c3Cl)nc2cn1] | N-((3S,4S)-3-((2-(2,6-dichloro-3,5-dimethoxyphenyl)thiazolo[4,5-c]pyridin-6-yl)amino)tetrahydro-2H-pyran-4-yl)acrylamide | 509 |
| 186 | 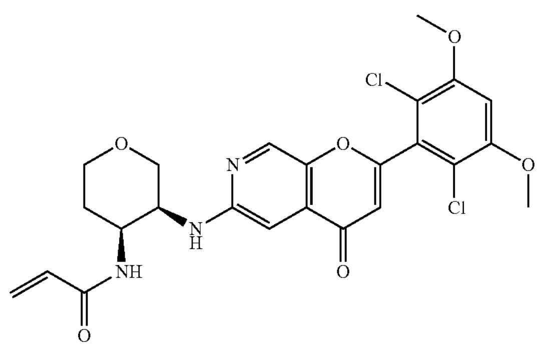 [SMILES: C=CC(=O)N[C@H]1CCOC[C@H]1Nc1cc2c(=O)cc(-c3c(Cl)c(OC)cc(OC)c3Cl)oc2cn1] | N-((3S,4S)-3-((2-(2,6-dichloro-3,5-dimethoxyphenyl)-4-oxo-4H-pyrano[2,3-c]pyridin-6-yl)amino)tetrahydro-2H-pyran-4-yl)acrylamide | 520 |
| 187 | 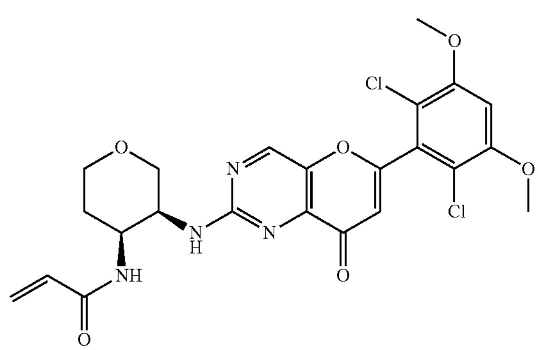 [SMILES: C=CC(=O)N[C@H]1CCOC[C@H]1Nc1ncc2oc(-c3c(Cl)c(OC)cc(OC)c3Cl)cc(=O)c2n1] | N-((3S,4S)-3-((6-(2,6-dichloro-3,5-dimethoxyphenyl)-8-oxo-8H-pyrano[3,2-d]pyrimidin-2-yl)amino)tetrahydro-2H-pyran-4-yl)acrylamide | 521 |

| Example No. | Compound structure | Compound name | MS: m/z [M + 1]+ |
|---|---|---|---|
| 188 | 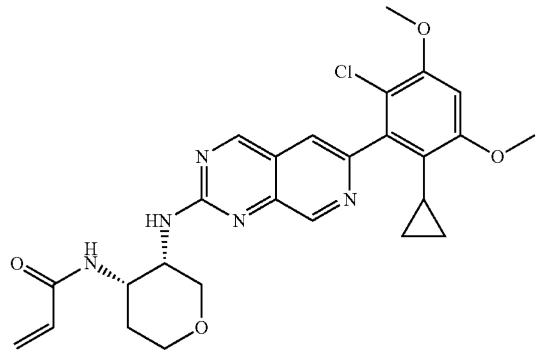 | N-((3S,4S)-3-((6-(2-chloro-6-cyclopropyl-3,5-dimethoxyphenyl)pyrido[3,4-d]pyrimidin-2-yl)amino)tetrahydro-2H-pyran-4-yl)acrylamide | 510 |
| 189 | 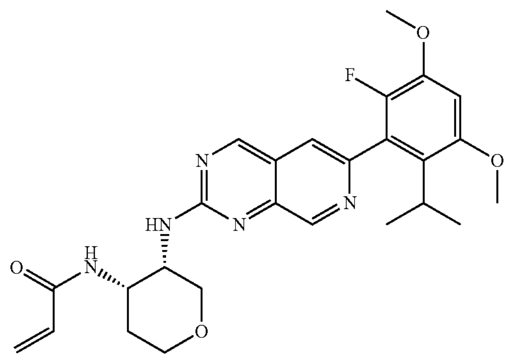 [SMILES: C=CC(=O)N[C@H]1CCOC[C@H]1Nc1ncc2cc(-c3c(F)c(OC)cc(OC)c3C(C)C)ncc2n1] | N-((3S,4S)-3-((6-(2-fluoro-6-isopropyl-3,5-dimethoxyphenyl)pyrido[3,4-d]pyrimidin-2-yl)amino)tetrahydro-2H-pyran-4-yl)acrylamide | 496 |
| 190 | 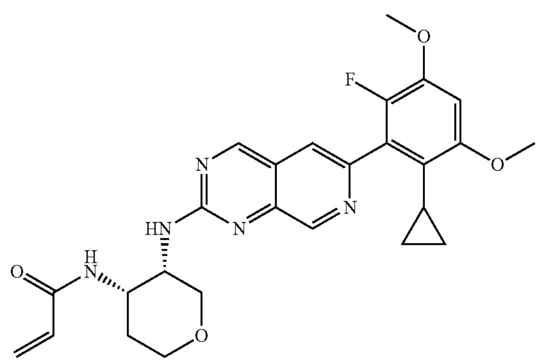 [SMILES: C=CC(=O)N[C@H]1CCOC[C@H]1Nc1ncc2cc(-c3c(F)c(OC)cc(OC)c3C3CC3)ncc2n1] | N-((3S,4S)-3-((6-(2-cyclopropyl-6-fluoro-3,5-dimethoxyphenyl)pyrido[3,4-d]pyrimidin-2-yl)amino)tetrahydro-2H-pyran-4-yl)acrylamide | 493 |
| 191 | 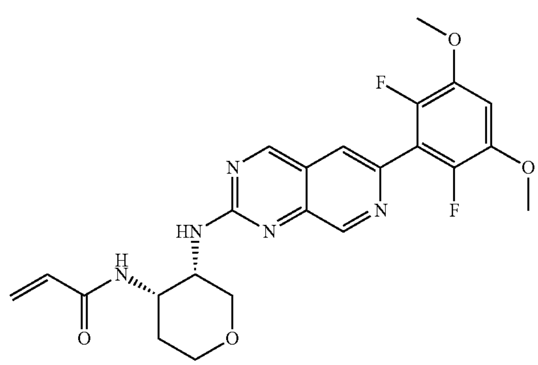 [SMILES: C=CC(=O)N[C@H]1CCOC[C@H]1Nc1ncc2cc(-c3c(F)c(OC)cc(OC)c3F)ncc2n1] | N-((3S,4S)-3-((6-(2,6-difluoro-3,5-dimethoxyphenyl)pyrido[3,4-d]pyrimidin-2-yl)amino)tetrahydro-2H-pyran-4-yl)acrylamide | 472 |

-continued

| Example No. | Compound structure | Compound name | MS: m/z [M + 1]+ |
|---|---|---|---|
| 192 | 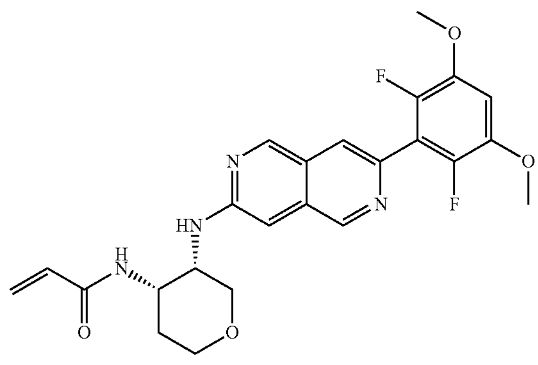 [SMILES: C=CC(=O)N[C@H]1CCOC[C@H]1Nc1cc2cnc(-c3c(F)c(OC)cc(OC)c3F)cc2cn1] | N-((3S,4S)-3-((7-(2,6-difluoro-3,5-dimethoxyphenyl)-2,6-naphthyridin-3-yl)amino)tetrahydro-2H-pyran-4-yl)acrylamide | 471 |
| 193 | 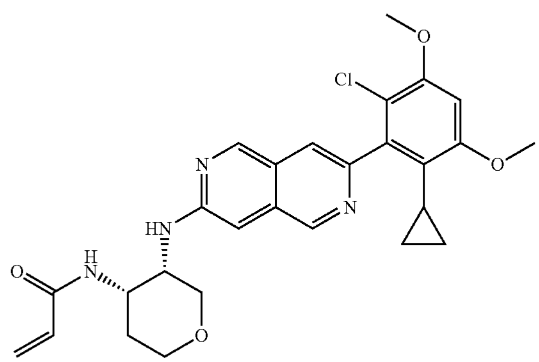 [SMILES: C=CC(=O)N[C@H]1CCOC[C@H]1Nc1cc2cnc(-c3c(Cl)c(OC)cc(OC)c3C3CC3)cc2cn1] | N-((3S,4S)-3-((7-(2-chloro-6-cyclopropyl-3,5-dimethoxyphenyl)-2,6-naphthyridin-3-yl)amino)tetrahydro-2H-pyran-4-yl)acrylamide | 509 |
| 194 | 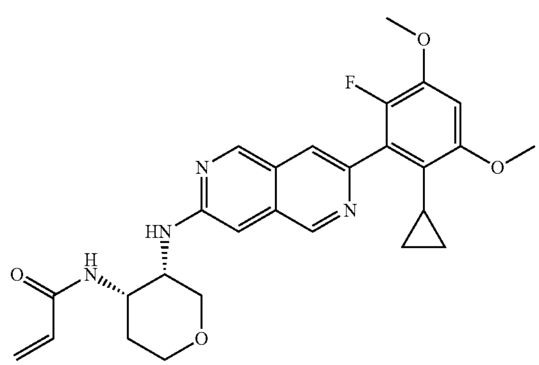 [SMILES: C=CC(=O)N[C@H]1CCOC[C@H]1Nc1cc2cnc(-c3c(F)c(OC)cc(OC)c3C3CC3)cc2cn1] | N-((3S,4S)-3-((7-(2-cyclopropyl-6-fluoro-3,5-dimethoxyphenyl)-2,6-naphthyridin-3-yl)amino)tetrahydro-2H-pyran-4-yl)acrylamide | 493 |
| 195 | 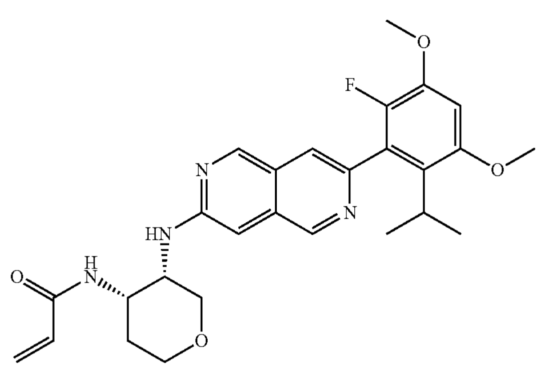 [SMILES: C=CC(=O)N[C@H]1CCOC[C@H]1Nc1cc2cnc(-c3c(F)c(OC)cc(OC)c3C(C)C)cc2cn1] | N-((3S,4S)-3-((7-(2-fluoro-6-isopropyl-3,5-dimethoxyphenyl)-2,6-naphthyridin-3-yl)amino)tetrahydro-2H-pyran-4-yl)acrylamide | 495 |

-continued

| Example No. | Compound structure | Compound name | MS: m/z [M + 1]+ |
|---|---|---|---|
| 196 | 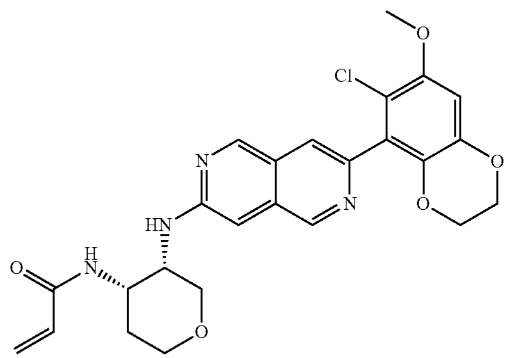 [SMILES: C=CC(=O)N[C@H]1CCOC[C@H]1Nc1cc2cnc(-c3c(Cl)c(OC)cc4c3OCCO4)cc2cn1] | N-((3S,4S)-3-((7-(6-chloro-7-methoxy-2,3-dihydrobenzo[b][1,4]dioxin-5-yl)-2,6-naphthyridin-3-yl)amino)tetrahydro-2H-pyran-4-yl)acrylamide | 496 |
| 197 | 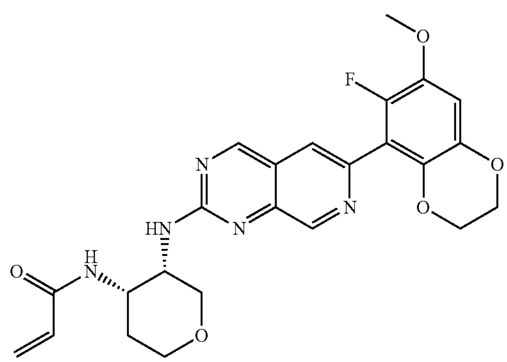 [SMILES: C=CC(=O)N[C@H]1CCOC[C@H]1Nc1ncc2cc(-c3c(F)c(OC)cc4c3OCCO4)ncc2n1] | N-((3S,4S)-3-((7-(6-fluoro-7-methoxy-2,3-dihydrobenzo[b][1,4]dioxin-5-yl)-2,6-naphthyridin-3-yl)amino)tetrahydro-2H-pyrah-4-yl)acrylamide | 481 |
| 198 | 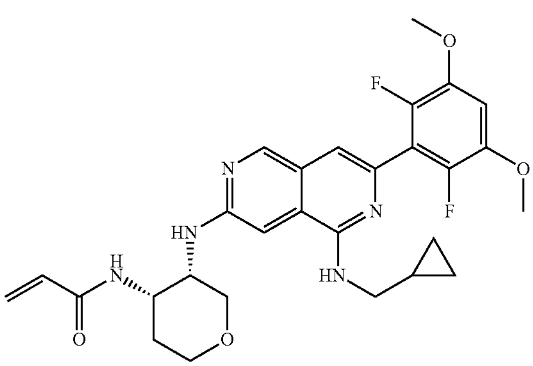 [SMILES: C=CC(=O)N[C@H]1CCOC[C@H]1Nc1cc2c(NCC3CC3)nc(-c3c(F)c(OC)cc(OC)c3F)cc2cn1] | N-((3S,4S)-3-((5-((cyclopropylmethyl)amino)-7-(2,6-difluoro-3,5-dimethoxyphenyl)-2,6-haphthyridin-3-yl)amino)tetrahydro-2H-pyran-4-yl)acrylamide | 540 |
| 199 | 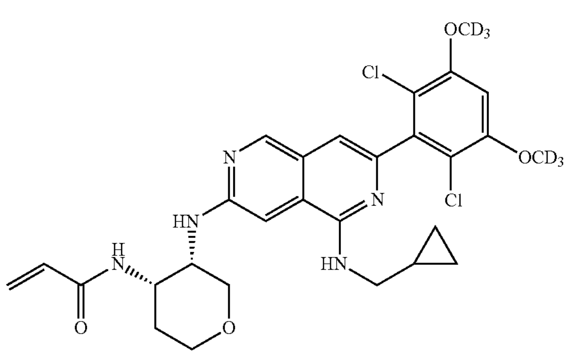 | N-((3S,4S)-3-((5-((cyclopropylmethyl)amino)-7-(2,6-dichloro-3,5-bis(methoxy-d3)phenyl)-2,6-naphthyridin-3-yl)amino)tetrahydro-2H-pyran-4-yl)acrylamide | 578 |

| Example No. | Compound structure | Compound name | MS: m/z [M + 1]+ |
|---|---|---|---|
| 200 | 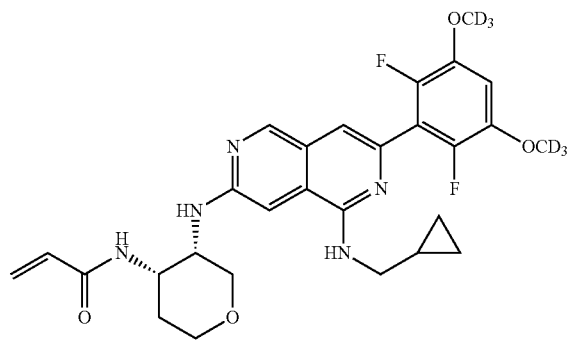 | N-((3S,4S)-3-((5-((cyclopropylmethyl)amino)-7-(2,6-difluoro-3,5-bis(methoxy-d₃)phenyl)-2,6-naphthyridin-3-yl)amino)tetrahydro-2H-pyran-4-yl)acrylamide | 546 |
| 201 | 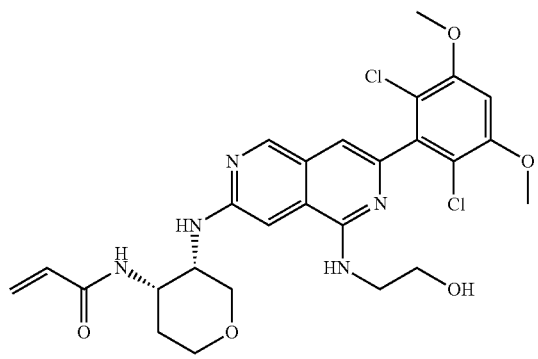 [SMILES: C=CC(=O)N[C@H]1CCOC[C@H]1Nc1cc2c(NCCO)nc(-c3c(Cl)c(OC)cc(OC)c3Cl)cc2cn1] | N-((3S,4S)-3-((7-(2,6-dichloro-3,5-dimethoxyphenyl)-5-((2-hydroxymethyl)amino)-2,6-naphthyridin-3-yl)amino)tetrahydro-2H-pyran-4-yl)acrylamide | 562 |
| 202 | 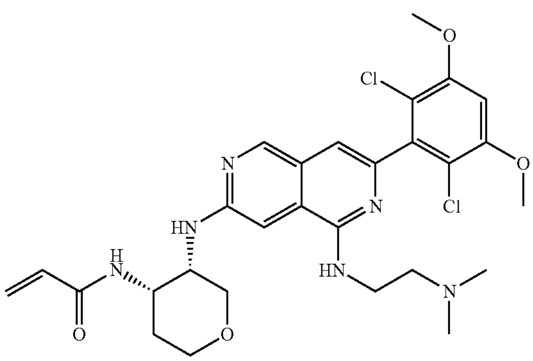 [SMILES: C=CC(=O)N[C@H]1CCOC[C@H]1Nc1cc2c(NCCN(C)C)nc(-c3c(Cl)c(OC)cc(OC)c3Cl)cc2cn1] | N-((3S,4S)-3-((7-(2,6-dichloro-3,5-dimethoxyphenyl)-5-((2-(dimethylamino)ethyl)amino)-2,6-naphthyridin-3-yl)amino)tetrahydro-2H-pyran-4-yl)acrylamide | 589 |
| 203 | 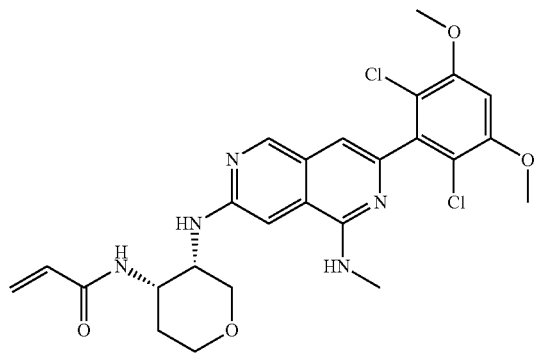 [SMILES: C=CC(=O)N[C@H]1CCOC[C@H]1Nc1cc2c(NC)nc(-c3c(Cl)c(OC)cc(OC)c3Cl)cc2cn1] | N-((3S,4S)-3-((7-(2,6-dichloro-3,5-dimethoxyphenyl)-5-(methylamino)-2,6-naphthyridin-3-yl)amino)tetrahydro-2H-pyran-4-yl)acrylamide | 532 |

-continued

| Example No. | Compound structure | Compound name | MS: m/z [M + 1]+ |
|---|---|---|---|
| 204 | 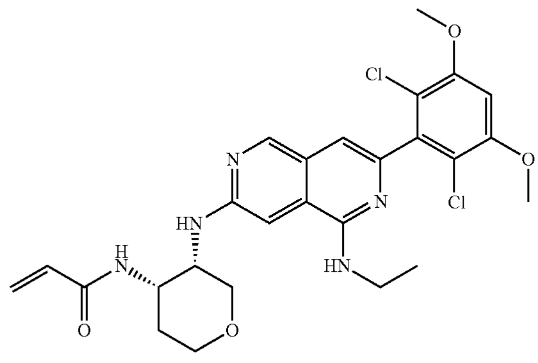 [SMILES: C=CC(=O)N[C@H]1CCOC[C@H]1Nc1cc2c(NCC)nc(-c3c(Cl)c(OC)cc(OC)c3Cl)cc2cn1] | N-((3S,4S)-3-((7-(2,6-dichloro-3,5-dimethoxyphenyl)-5-(ethylamino)-2,6-naphthyridin-3-yl)amino)tetrahydro-2H-pyran-4-yl)acrylamide | 546 |
| 205 | 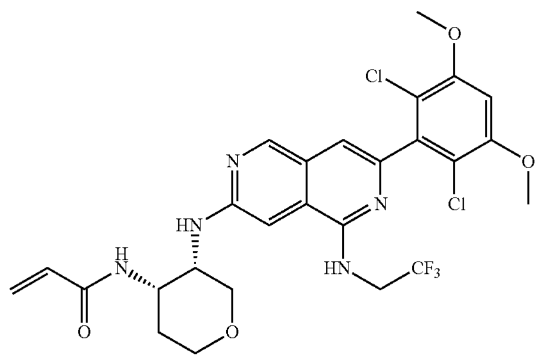 | N-((3S,4S)-3-((7-(2,6-dichloro-3,5-dimethoxyphenyl)-5-((2,2,2-trifluoroethyl)amino)-2,6-naphthyridin-3-yl)amino)tetrahydro-2H-pyran-4-yl)acrylamide | 600 |
| 206 | 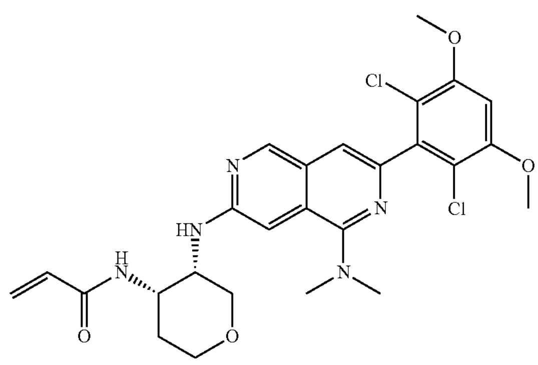 [SMILES: C=CC(=O)N[C@H]1CCOC[C@H]1Nc1cc2c(N(C)C)nc(-c3c(Cl)c(OC)cc(OC)c3Cl)cc2cn1] | N-((3S,4S)-3-((7-(2,6-dichloro-3,5-dimethoxyphenyl)-5-(dimethylamino)-2,6-naphthyridin-3-yl)amino)tetrahydro-2H-pyran-4-yl)acrylamide | 546 |
| 207 | 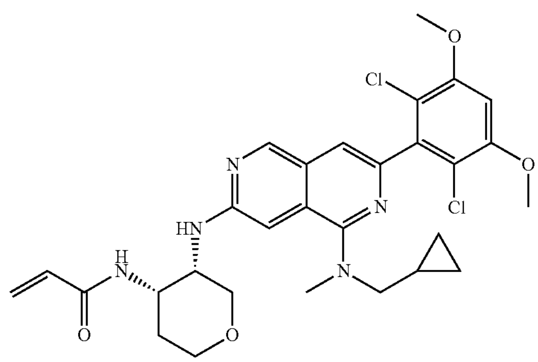 [SMILES: C=CC(=O)N[C@H]1CCOC[C@H]1Nc1cc2c(N(C)CC3CC3)nc(-c3c(Cl)c(OC)cc(OC)c3Cl)cc2cn1] | N-((3S,4S)-3-((5-((cyclopropylmethyl)(methyl)amino)-7-(2,6-dichloro-3,5-dimethoxyphenyl)-2,6-naphthyridin-3-yl)amino)tetrahydro-2H-pyran-4-yl)acrylamide | 586 |

-continued

| Example No. | Compound structure | Compound name | MS: m/z [M + 1]+ |
|---|---|---|---|
| 208 | 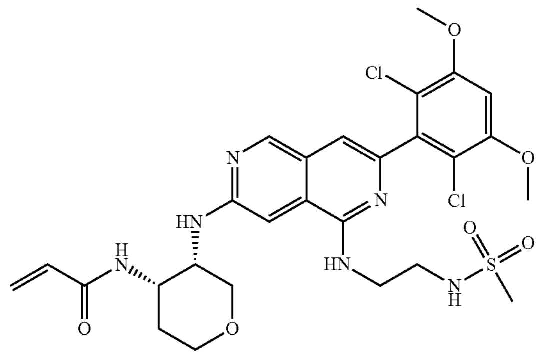 [SMILES: C=CC(=O)N[C@H]1CCOC[C@H]1Nc1cc2c(NCCNS(C)(=O)=O)nc(-c3c(Cl)c(OC)cc(OC)c3Cl)cc2cn1] | N-((3S,4S)-3-((7-(2,6-dichloro-3,5-dimethoxyphenyl)-5-((2-(methylsulfonamido)ethyl)amino)-2,6-naphthyridin-3-yl)amino)tetrahydro-2H-pyran-4-yl)acrylamide | 639 |
| 209 | 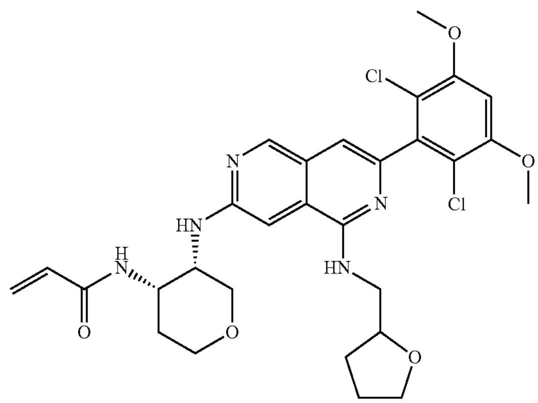 | N-((3S,4S)-3-((7-(2,6-dichloro-3,5-dimethoxyphenyl)-5-(((tetrahydrofuran-2-yl)amino)-2,6-naphthyridin-3-yl)amino)tetrahydro-2H-pyran-4-yl)acrylamide | 602 |
| 210 | 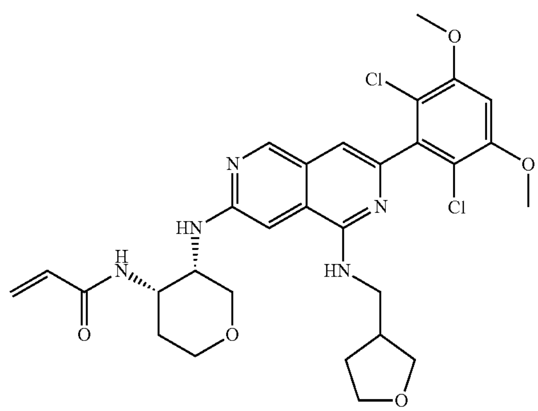 [SMILES: C=CC(=O)N[C@H]1CCOC[C@H]1Nc1cc2c(NCC3CCOC3)nc(-c3c(Cl)c(OC)cc(OC)c3Cl)cc2cn1] | N-((3S,4S)-3-((7-(2,6-dichloro-3,5-dimethoxyphenyl)-5-(((tetrahydrofuran-3-yl)methyl)amino)-2,6-naphthyridin-3-yl)amino)tetrahydro-2H-pyran-4-yl)acrylamide | 602 |
| 211 | 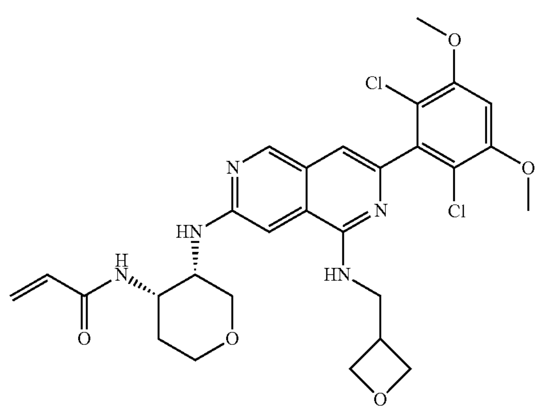 [SMILES: C=CC(=O)N[C@H]1CCOC[C@H]1Nc1cc2c(NCC3COC3)nc(-c3c(Cl)c(OC)cc(OC)c3Cl)cc2cn1] | N-((3S,4S)-3-((7-(2,6-dichloro-3,5-dimethoxyphenyl)-5-((oxetan-3-ylmethyl)amino)-2,6-naphthyridin-3-yl)amino)tetrahydro-2H-pyran-4-yl)acrylamide | 588 |

-continued

| Example No. | Compound structure | Compound name | MS: m/z [M + 1]+ |
|---|---|---|---|
| 212 | 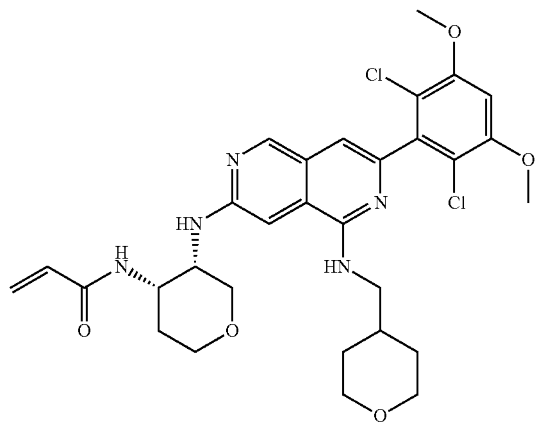 [SMILES: C=CC(=O)N[C@H]1CCOC[C@H]1Nc1cc2c(NCC3CCOCC3)nc(-c3c(Cl)c(OC)cc(OC)c3Cl)cc2cn1] | N-((3S,4S)-3-((7-(2,6-dichloro-3,5-dimethoxyphenyl)-5-(((tetrahydro-2H-pyran-4-yl)methyl)amino)-2,6-naphthyridin-3-yl)amino)tetrahydro-2H-pyran-4-yl)acrylamide | 616 |
| 213 | 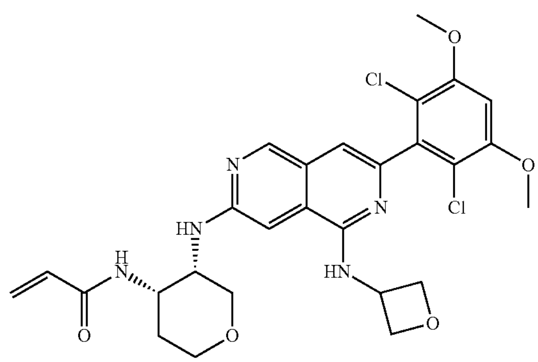 [SMILES: C=CC(=O)N[C@H]1CCOC[C@H]1Nc1cc2c(NC3COC3)nc(-c3c(Cl)c(OC)cc(OC)c3Cl)cc2cn1] | N-((3S,4S)-3-((7-(2,6-dichloro-3,5-dimethoxyphenyl)-5-(oxetan-3-yl)amino)-2,6-naphthyridin-3-yl)amino)tetrahydro-2H-pyran-4-yl)acrylamide | 574 |
| 214 | 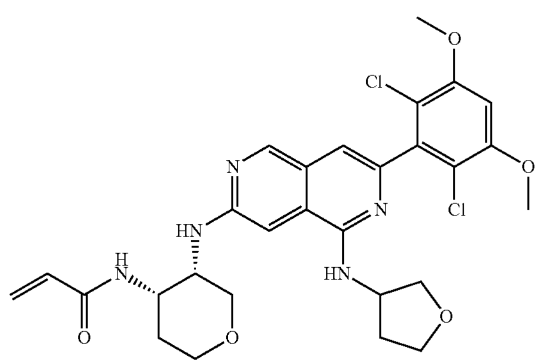 [SMILES: C=CC(=O)N[C@H]1CCOC[C@H]1Nc1cc2c(NC3CCOC3)nc(-c3c(Cl)c(OC)cc(OC)c3Cl)cc2cn1] | N-((3S,4S)-3-((7-(2,6-dichloro-3,5-dimethoxyphenyl)-5-((tetrahydrofuran-3-yl)amino)-2,6-naphthyridin-3-yl)amino)tetrahydro-2H-pyran-4-yl)acrylamide | 588 |
| 215 | 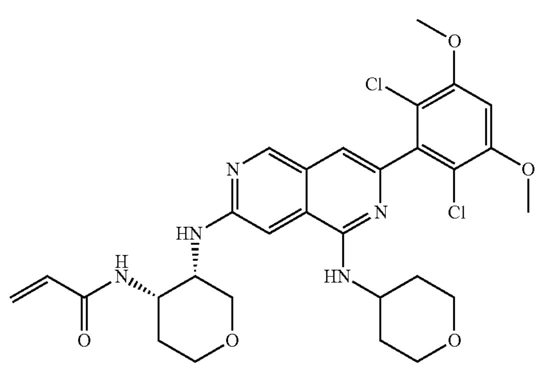 [SMILES: C=CC(=O)N[C@H]1CCOC[C@H]1Nc1cc2c(NC3CCOCC3)nc(-c3c(Cl)c(OC)cc(OC)c3Cl)cc2cn1] | N-((3S,4S)-3-((7-(2,6-dichloro-3,5-dimethoxyphenyl)-5-((tetrahydro-2H-pyran-4-yl)amino)-2,6-naphthyridin-3-yl)amino)tetrahydro-2H-pyran-4-yl)acrylamide | 607 |

-continued

| Example No. | Compound structure | Compound name | MS: m/z [M + 1]+ |
|---|---|---|---|
| 216 | 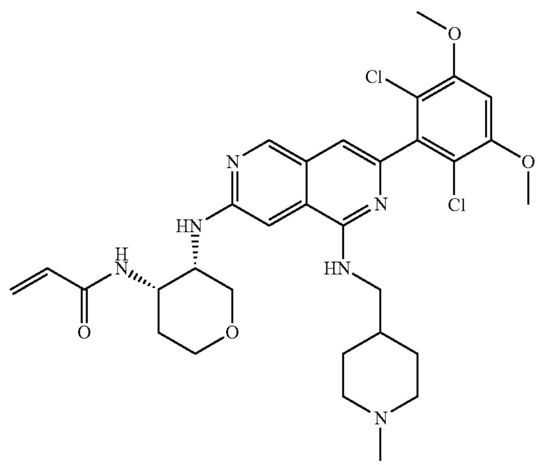 [SMILES: C=CC(=O)N[C@H]1CCOC[C@H]1Nc1cc2c(NCC3CCN(C)CC3)nc(-c3c(Cl)c(OC)cc(OC)c3Cl)cc2cn1] | N-((3S,4S)-3-((7-(2,6-dichloro-3,5-dimethoxyphenyl)-5-(((1-methylpiperidin-4-yl)methyl)amino)-2,6-naphthyridin-3-yl)amino)tetrahydro-2H-pyran-4-yl)acrylamide | 629 |
| 217 | 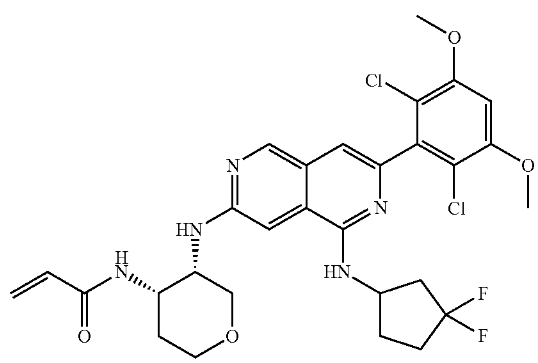 [SMILES: C=CC(=O)N[C@H]1CCOC[C@H]1Nc1cc2c(NC3CCC(F)(F)C3)nc(-c3c(Cl)c(OC)cc(OC)c3Cl)cc2cn1] | N-((3S,4S)-3-((7-(2,6-dichloro-3,5-dimethoxyphenyl)-5-((3,3-difluorocyclopentyl)amino)-2,6-naphthyridin-3-yl)amino)tetrahydro-2H-pyran-4-yl)acrylamide | 622 |
| 218 | 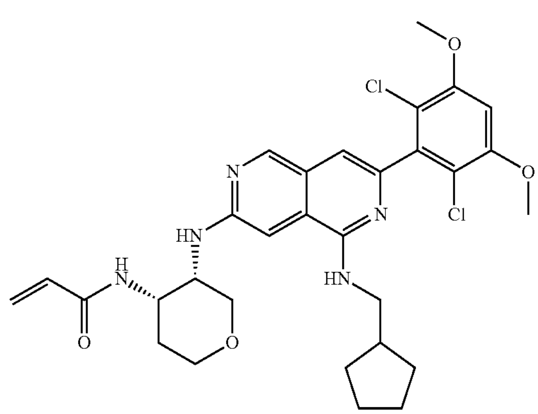 [SMILES: C=CC(=O)N[C@H]1CCOC[C@H]1Nc1cc2c(NCC3CCCC3)nc(-c3c(Cl)c(OC)cc(OC)c3Cl)cc2cn1] | N-((3S,4S)-3-((5-((cyclopentylmethyl)amino)-7-(2,6-dichloro-3,5-dimethoxyphenyl)-2,6-naphthyridin-3-yl)amino)tetrahydro-2H-pyran-4-yl)acrylamide | 600 |

-continued

| Example No. | Compound structure | Compound name | MS: m/z [M + 1]+ |
|---|---|---|---|
| 219 | 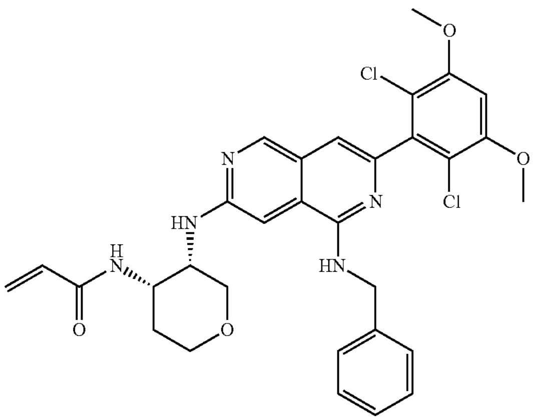 [SMILES: C=CC(=O)N[C@H]1CCOC[C@H]1Nc1cc2c(NCc3ccccc3)nc(-c3c(Cl)c(OC)cc(OC)c3Cl)cc2cn1] | N-((3S,4S)-3-((5-(benzylamino)-7-(2,6-dichloro-3,5-dimethoxyphenyl)-2,6-naphthyridin-3-yl)amino)tetrahydro-2H-pyran-4-yl)acrylamide | 608 |
| 220 | 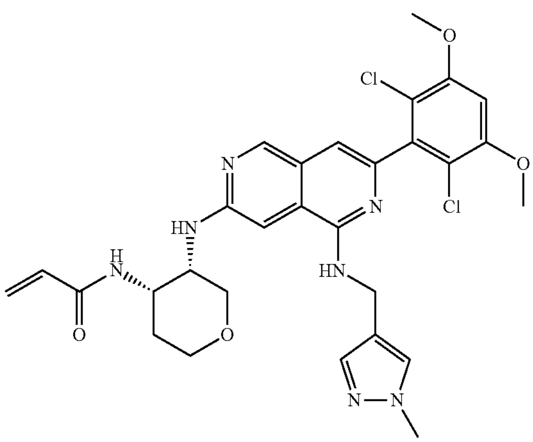 [SMILES: C=CC(=O)N[C@H]1CCOC[C@H]1Nc1cc2c(NCc3cnn(C)c3)nc(-c3c(Cl)c(OC)cc(OC)c3Cl)cc2cn1] | N-((3S,4S)-3-((7-(2,6-dichloro-3,5-dimethoxyphenyl)-5-(((1-methyl-1H-pyrazol-4-yl)methyl)amino)-2,6-naphthyridin-3-yl)amino)tetrahydro-2H-pyran-4-yl)acrylamide | 612 |
| 221 | 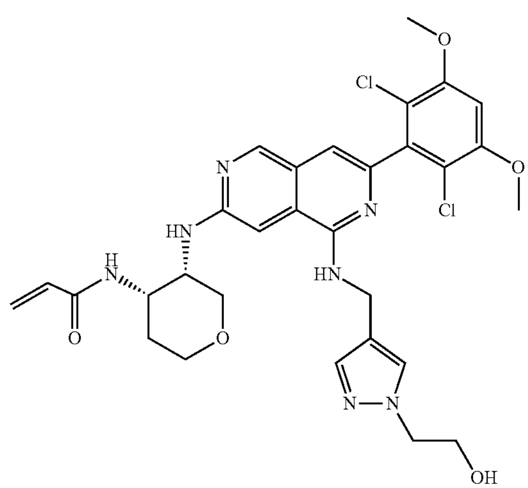 [SMILES: C=CC(=O)N[C@H]1CCOC[C@H]1Nc1cc2c(NCc3cnn(CCO)c3)nc(-c3c(Cl)c(OC)cc(OC)c3Cl)cc2cn1] | N-((3S,4S)-3-((7-(2,6-dichloro-3,5-dimethoxyphenyl)-5-(((1-(2-hydroxyethyl)-1H-pyrazol-4-yl)methyl)amino)-2,6-naphthyridin-3-yl)amino)tetrahydro-2H-pyran-4-yl)acrylamide | 642 |

| Example No. | Compound structure | Compound name | MS: m/z [M + 1]+ |
|---|---|---|---|
| 222 | 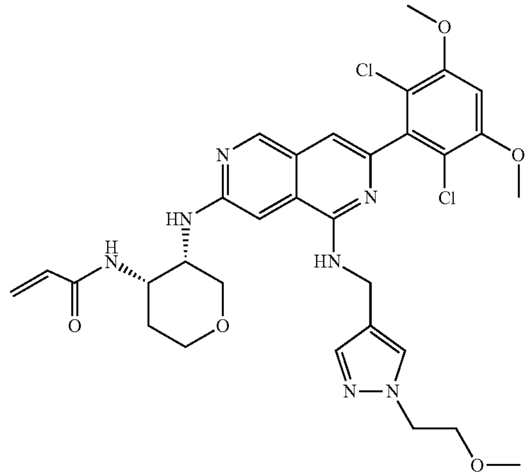 [SMILES: C=CC(=O)N[C@H]1CCOC[C@H]1Nc1cc2c(NCc3cnn(CCOC)c3)nc(-c3c(Cl)c(OC)cc(OC)c3Cl)cc2cn1] | N-((3S,4S)-3-((7-(2,6-dichloro-3,5-dimethoxyphenyl)-5-(((1-(2-dimethoxyethyl)-1H-pyrazol-4-yl)methyl)amino)-2,6-naphthyridin-3-yl)amino)tetrahydro-2H-pyran-4-yl)acrylamide | 656 |
| 223 | 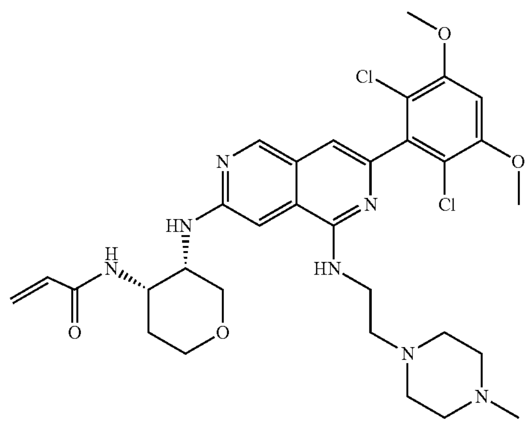 [SMILES: C=CC(=O)N[C@H]1CCOC[C@H]1Nc1cc2c(NCCN3CCN(C)CC3)nc(-c3c(Cl)c(OC)cc(OC)c3Cl)cc2cn1] | N-((3S,4S)-3-((7-(2,6-dichloro-3,5-dimethoxyphenyl)-5-((2-(4-methylpiperazin-1-yl)ethyl)amino)-2,6-naphthyridin-3-yl)amino)tetrahydro-2H-pyran-4-yl)acrylamide | 644 |
| 224 | 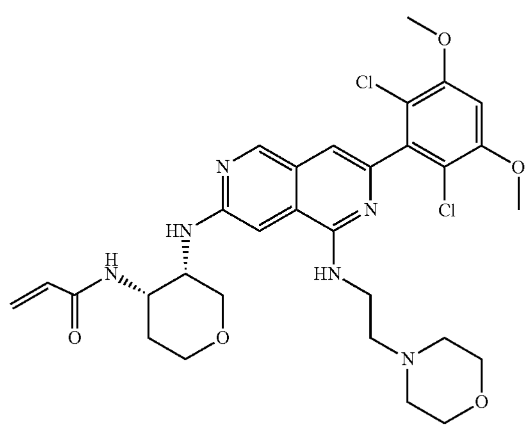 [SMILES: C=CC(=O)N[C@H]1CCOC[C@H]1Nc1cc2c(NCCN3CCOCC3)nc(-c3c(Cl)c(OC)cc(OC)c3Cl)cc2cn1] | N-((3S,4S)-3-((7-(2,6-dichloro-3,5-dimethoxyphenyl)-5-((2-morpholinoethyl)amino)-2,6-naphthyridin-3-yl)amino)tetrahydro-2H-pyran-4-yl)acrylamide | 631 |

| Example No. | Compound structure | Compound name | MS: m/z [M + 1]+ |
|---|---|---|---|
| 225 | 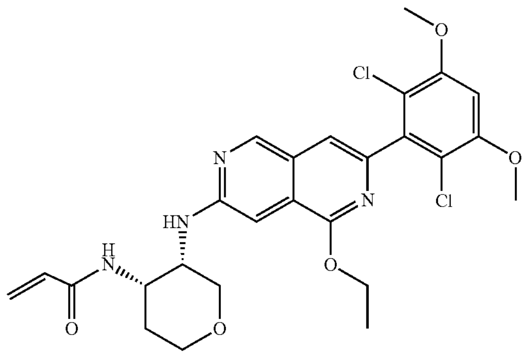 [SMILES: C=CC(=O)N[C@H]1CCOC[C@H]1Nc1cc2c(OCC)nc(-c3c(Cl)c(OC)cc(OC)c3Cl)cc2cn1] | N-((3S,4S)-3-((7-(2,6-dichloro-3,5-dimethoxyphenyl)-5-dimethoxy-2,6-naphthyridin-3-yl)amino)tetrahydro-2H-pyran-4-yl)acrylamide | 547 |
| 226 | 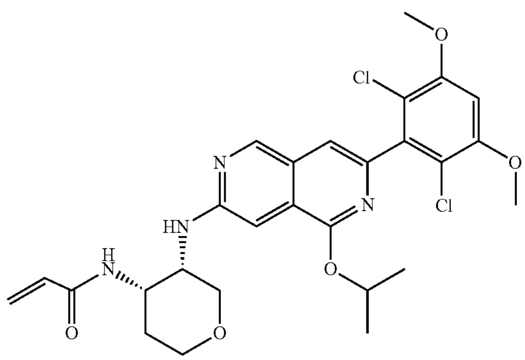 [SMILES: C=CC(=O)N[C@H]1CCOC[C@H]1Nc1cc2c(OC(C)C)nc(-c3c(Cl)c(OC)cc(OC)c3Cl)cc2cn1] | N-((3S,4S)-3-((7-(2,6-dichloro-3,5-dimethoxyphenyl)-5-isopropoxy-2,6-naphthyridin-3-yl)amino)tetrahydro-2H-pyran-4-yl)acrylamide | 561 |
| 227 | 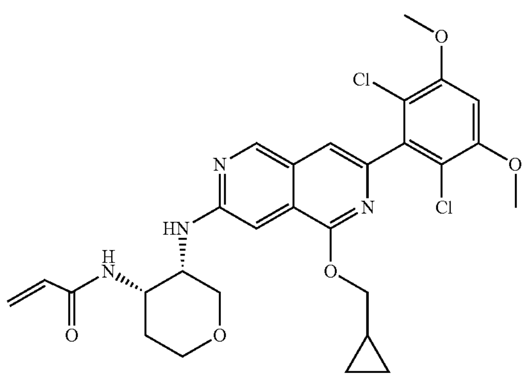 [SMILES: C=CC(=O)N[C@H]1CCOC[C@H]1Nc1cc2c(OCC3CC3)nc(-c3c(Cl)c(OC)cc(OC)c3Cl)cc2cn1] | N-((3S,4S)-3-((5-(cyclopropylmethoxy)-7-(2,6-dichloro-3,5-dimethoxyphenyl)-2,6-naphthyridin-3-yl)amino)tetrahydro-2H-pyran-4-yl)acrylamide | 573 |
| 228 | 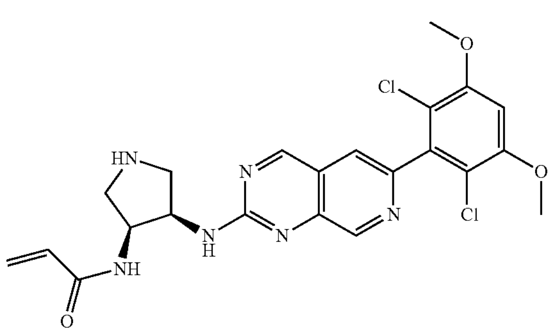 [SMILES: C=CC(=O)N[C@H]1CNC[C@H]1Nc1ncc2cc(-c3c(Cl)c(OC)cc(OC)c3Cl)ncc2n1] | N-((3S,4R)-4-((6-(2,6-dichloro-3,5-dimethoxyphenyl)pyrido[3,4-d]pyrimidin-2-yl)amino)pyrrolidin-3-yl)acrylamide | 489 |

-continued

| Example No. | Compound structure | Compound name | MS: m/z [M + 1]+ |
|---|---|---|---|
| 229 | 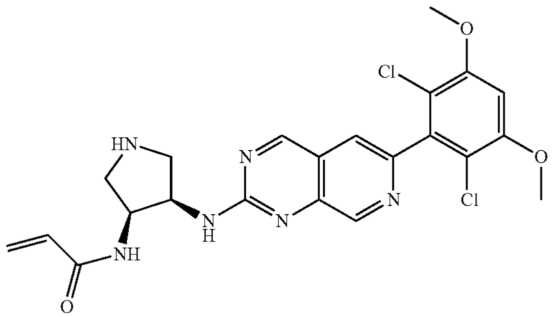 [SMILES: C=CC(=O)N[C@H]1CNC[C@H]1Nc1ncc2cc(-c3c(Cl)c(OC)cc(OC)c3Cl)ncc2n1] | N-((3S,4R)-4-((7-(2,6-dichloro-3,5-dimethoxyphenyl)-2,6-naphthyridin-3-yl)amino)pyrrolidin-3-yl)acrylamide | 488 |
| 230 | 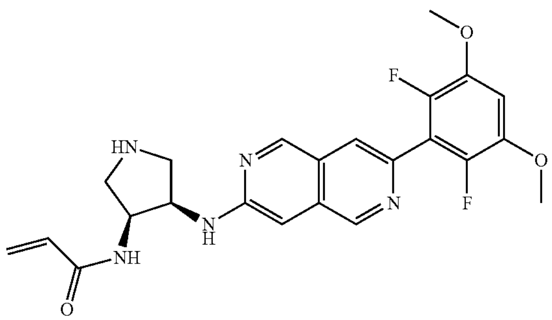 [SMILES: C=CC(=O)N[C@H]1CNC[C@H]1Nc1cc2cnc(-c3c(F)c(OC)cc(OC)c3F)cc2cn1] | N-((3S,4R)-4-((7-(2,6-difluoro-3,5-dimethoxyphenyl)-2,6-naphthyridin-3-yl)amino)pyrrolidin-3-yl)acrylamide | 455 |
| 231 | 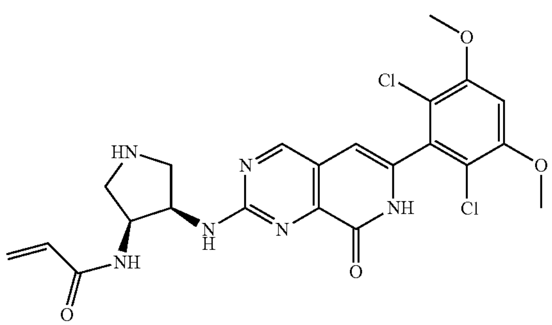 [SMILES: C=CC(=O)N[C@H]1CNC[C@H]1Nc1ncc2cc(-c3c(Cl)c(OC)cc(OC)c3Cl)[nH]c(=O)c2n1] | N-((3S,4R)-4-((6-(2,6-dichloro-3,5-dimethoxyphenyl)-8-oxo-7,8-dihydropyrido[3,4-d]pyrimidin-2-yl)amino)pyrrolidin-3-yl)acrylamide | 505 |
| 232 | 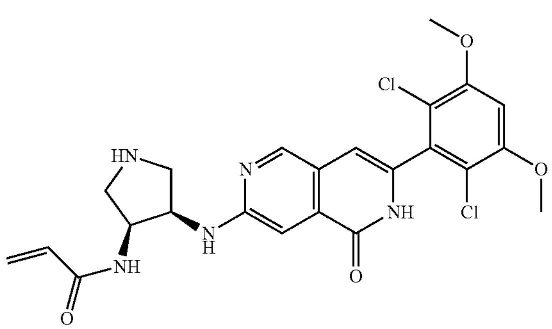 [SMILES: C=CC(=O)N[C@H]1CNC[C@H]1Nc1cc2c(=O)[nH]c(-c3c(Cl)c(OC)cc(OC)c3Cl)cc2cn1] | N-((3S,4R)-4-((7-(2,6-dichloro-3,5-dimethoxyphenyl)-5-oxo-5,6-dihydro-2,6-naphthyridin-3-yl)amino)pyrrolidin-3-yl)acrylamide | 504 |

-continued

| Example No. | Compound structure | Compound name | MS: m/z [M + 1]+ |
|---|---|---|---|
| 233 | 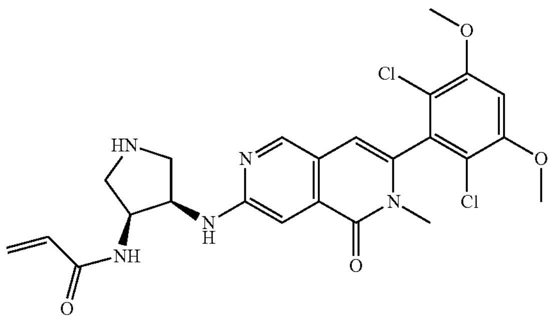 [SMILES: C=CC(=O)N[C@H]1CNC[C@H]1Nc1cc2c(=O)n(C)c(-c3c(Cl)c(OC)cc(OC)c3Cl)cc2cn1] | N-((3S,4R)-4-((7-(2,6-dichloro-3,5-dimethoxyphenyl)-6-methyl-5-oxo-5,6-dihydro-2,6-naphthyridin-3-yl)amino)pyrrolidin-3-yl)acrylamide | 518 |
| 234 | 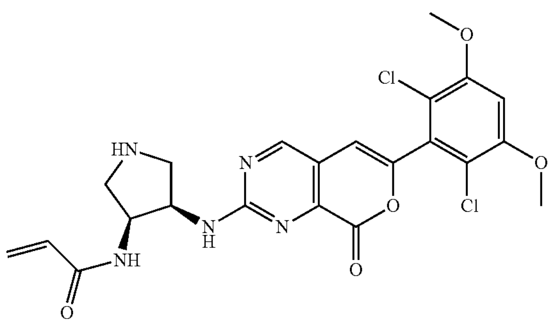 [SMILES: C=CC(=O)N[C@H]1CNC[C@H]1Nc1ncc2cc(-c3c(Cl)c(OC)cc(OC)c3Cl)oc(=O)c2n1] | N-((3S,4R)-4-((6-(2,6-dichloro-3,5-dimethoxyphenyl)-8-oxo-8H-pyrano[3,4-d]pyrimidin-2-yl)amino)pyrrolidin-3-yl)acrylamide | 506 |
| 235 | 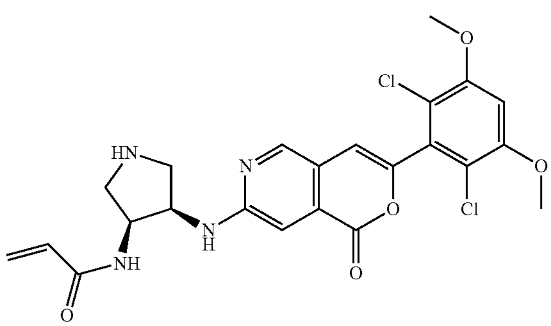 [SMILES: C=CC(=O)N[C@H]1CNC[C@H]1Nc1cc2c(=O)oc(-c3c(Cl)c(OC)cc(OC)c3Cl)cc2cn1] | N-((3S,4R)-4-((3-(2,6-dichloro-3,5-dimethoxyphenyl)-1-oxo-1H-pyrano[4,3-c]pyridin-7-yl)amino)pyrrolidin-3-yl)acrylamide | 505 |
| 236 | 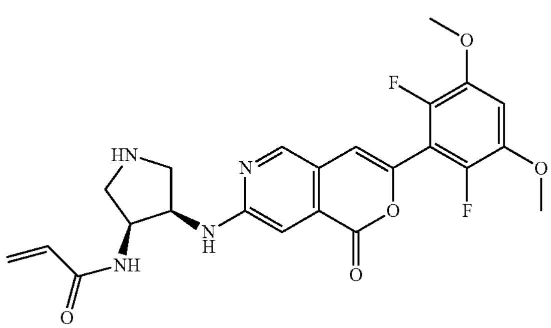 [SMILES: C=CC(=O)N[C@H]1CNC[C@H]1Nc1cc2c(=O)oc(-c3c(F)c(OC)cc(OC)c3F)cc2cn1] | N-((3S,4R)-4-((3-(2,6-difluoro-3,5-dimethoxyphenyl)-1-oxo-1H-pyrano[4,3-c]pyridin-7-yl)amino)pyrrolidin-3-yl)acrylamide | 472 |

| Example No. | Compound structure | Compound name | MS: m/z [M + 1]+ |
|---|---|---|---|
| 237 | 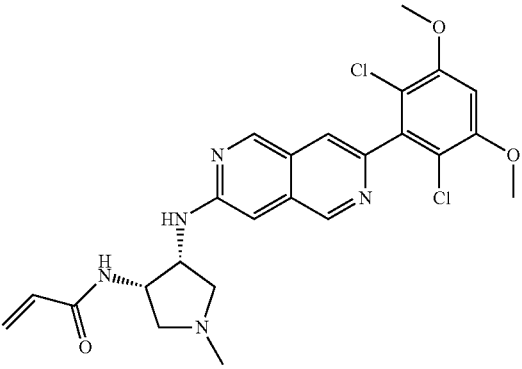 [SMILES: C=CC(=O)N[C@H]1CN(C)C[C@H]1Nc1cc2cnc(-c3c(Cl)c(OC)cc(OC)c3Cl)cc2cn1] | N-((3S,4R)-4-((7-(2,6-dichloro-3,5-dimethoxyphenyl)-2,6-naphthyridin-3-yl)amino)-1-methylpyrrolidin-3-yl)acrylamide | 502 |
| 238 | 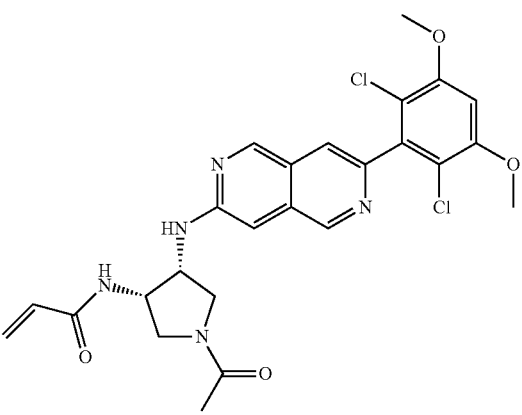 [SMILES: C=CC(=O)N[C@H]1CN(C(C)=O)C[C@H]1Nc1cc2cnc(-c3c(Cl)c(OC)cc(OC)c3Cl)cc2cn1] | N-((3S,4R)-1-acetyl-4-((7-(2,6-dichloro-3,5-dimethoxyphenyl)-2,6-naphthyridin-3-yl)amino)pyrrolidin-3-yl)acrylamide | 530 |
| 239 | 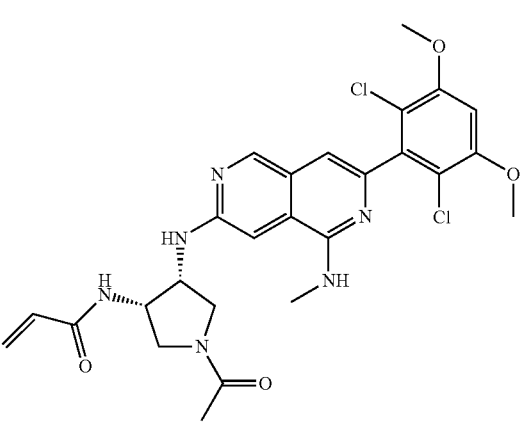 [SMILES: C=CC(=O)N[C@H]1CN(C(C)=O)C[C@H]1Nc1cc2c(NC)nc(-c3c(Cl)c(OC)cc(OC)c3Cl)cc2cn1] | N-((3S,4R)-1-acetyl-4-((7-(2,6-dichloro-3,5-dimethoxyphenyl)-5-(methylamino)-2,6-naphthyridin-3-yl)amino)pyrrolidin-3-yl)acrylamide | 559 |

-continued

| Example No. | Compound structure | Compound name | MS: m/z [M + 1]+ |
|---|---|---|---|
| 240 | 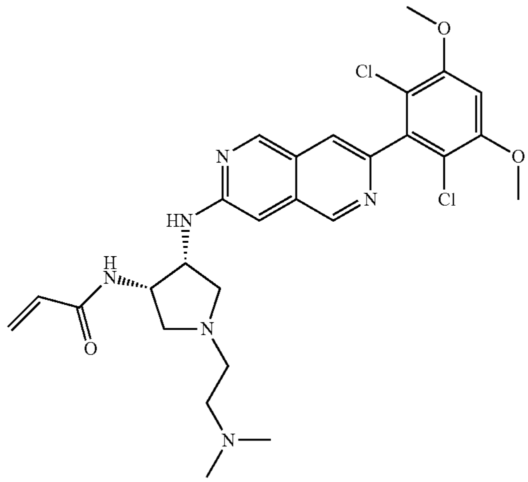 [SMILES: C=CC(=O)N[C@H]1CN(CCN(C)C)C[C@H]1Nc1cc2cnc(-c3c(Cl)c(OC)cc(OC)c3Cl)cc2cn1] | N-((3S,4R)-4-((7-(2,6-dichloro-3,5-dimethoxyphenyl)-2,6-naphthyridin-3-yl)amino)-1-(2-(dimethylamino)ethyl)pyrrolidin-3-yl)acrylamide | 559 |
| 241 | 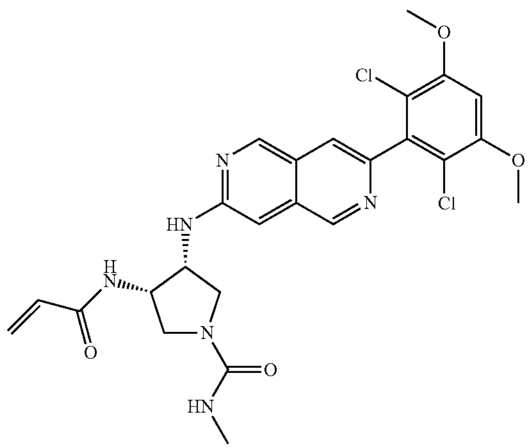 [SMILES: C=CC(=O)N[C@H]1CN(C(=O)NC)C[C@H]1Nc1cc2cnc(-c3c(Cl)c(OC)cc(OC)c3Cl)cc2cn1] | (3S,4R)-3-acrylamido-4-((7-(2,6-dichloro-3,5-dimethoxyphenyl)-2,6-naphthyridin-3-yl)amino)-N-methylpyrrolidine-1-carboxamide | 545 |
| 242 | 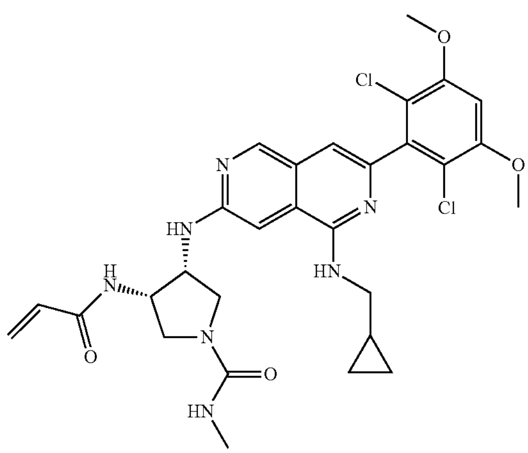 | (3S,4R)-3-acrylamido-4-((5-((cyclopropylmethyl)amino)-7-(2,6-dichloro-3,5-dimethoxyphenyl)-2,6-naphthyridin-3-yl)amino)-N-methylpyrrolidine-1-carboxamide | 614 |

| Example No. | Compound structure | Compound name | MS: m/z [M + 1]+ |
| --- | --- | --- | --- |
| 243 | 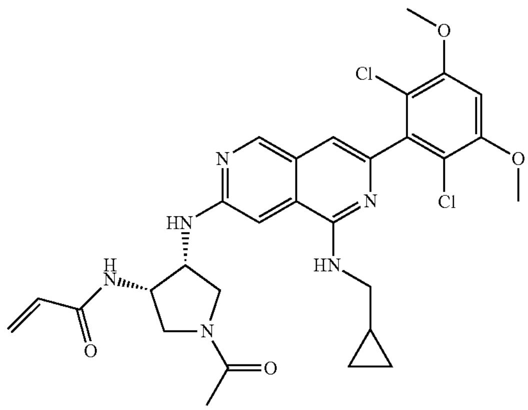 [SMILES: C=CC(=O)N[C@H]1CN(C(C)=O)C[C@H]1Nc1cc2c(NCC3CC3)nc(-c3c(Cl)c(OC)cc(OC)c3Cl)cc2cn1] | N-((3S,4R)-1-acetyl-4-((5-((cyclopropyl-methyl)amino)-7-(2,6-dichloro-3,5-dimethoxyphenyl)-2,6-naphthyridin-3-yl)amino)pyrrolidin-3-yl)acrylamide | 599 |
| 244 | 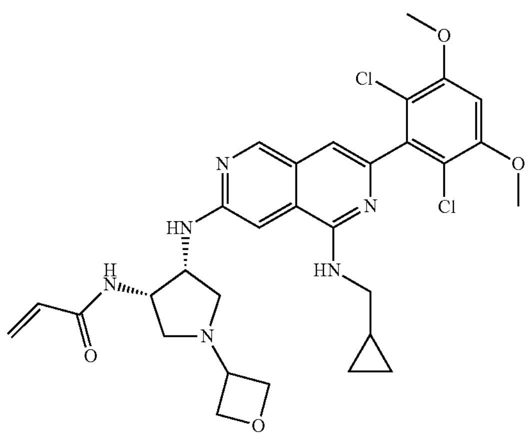 [SMILES: C=CC(=O)N[C@H]1CN(C2COC2)C[C@H]1Nc1cc2c(NCC3CC3)nc(-c3c(Cl)c(OC)cc(OC)c3Cl)cc2cn1] | N-((3S,4R)-4-((5-((cyclopropylmethyl)amino)-7-(2,6-dichloro-3,5-dimethoxyphenyl)-2,6-naphthyridin-3-yl)amino)-1-(oxetan-3-yl)pyrrolidin-3-yl)acrylamide | 613 |
| 245 | 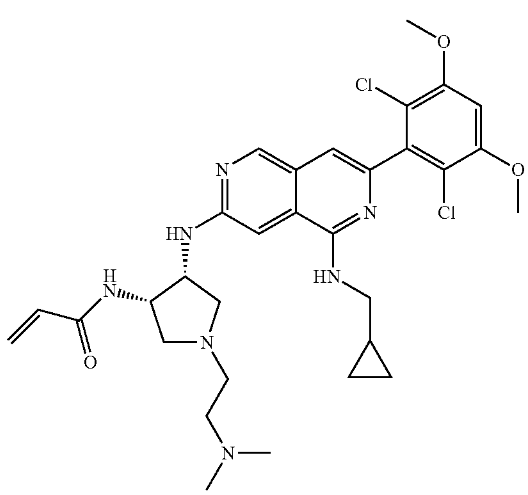 [SMILES: C=CC(=O)N[C@H]1CN(CCN(C)C)C[C@H]1Nc1cc2c(NCC3CC3)nc(-c3c(Cl)c(OC)cc(OC)c3Cl)cc2cn1] | N-((3S,4R)-4-((5-((cyclopropylmethyl)amino)-7-(2,6-dichloro-3,5-dimethoxyphenyl)-2,6-naphthyridin-3-yl)amino-1-(2-(dimethylamino)ethyl)pyrrolidin-3-yl)acrylamide | 628 |

-continued

| Example No. | Compound structure | Compound name | MS: m/z [M + 1]+ |
|---|---|---|---|
| 246 | 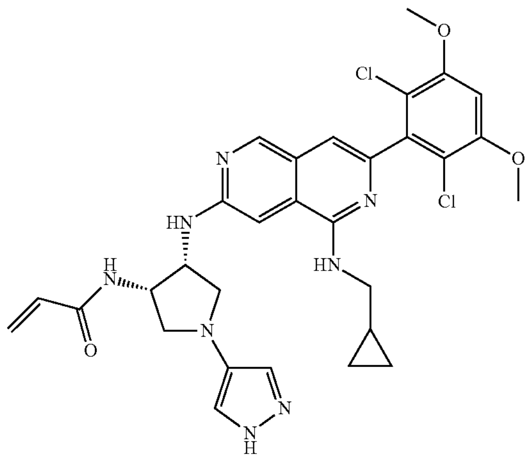 [SMILES: C=CC(=O)N[C@H]1CN(c2cn[nH]c2)C[C@H]1Nc1cc2c(NCC3CC3)nc(-c3c(Cl)c(OC)cc(OC)c3Cl)cc2cn1] | N-((3S,4R)-4-((5-((cyclopropylmethyl)amino)-7-(2,6-dichloro-3,5-dimethoxyphenyl)-2,6-naphthyridin-3-yl)amino)-1-(1H-pyrazol-4-yl)pyrrolidin-3-acrylamide | 623 |
| 247 | 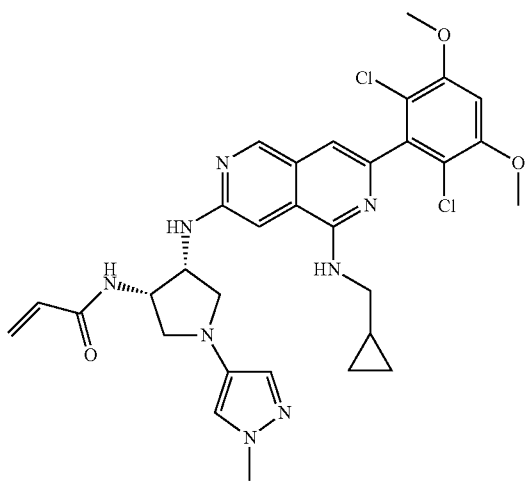 [SMILES: C=CC(=O)N[C@H]1CN(c2cnn(C)c2)C[C@H]1Nc1cc2c(NCC3CC3)nc(-c3c(Cl)c(OC)cc(OC)c3Cl)cc2cn1] | N-((3S,4R)-4-((5-((cyclopropylmethyl)amino)-7-(2,6-dichloro-3,5-dimethoxyphenyl)-2,6-naphthyridin-3-yl)amino)-1-(1-methyl-1H-pyrazol-4-yl)pyrrolidin-3-yl)acrylamide | 637 |
| 248 | 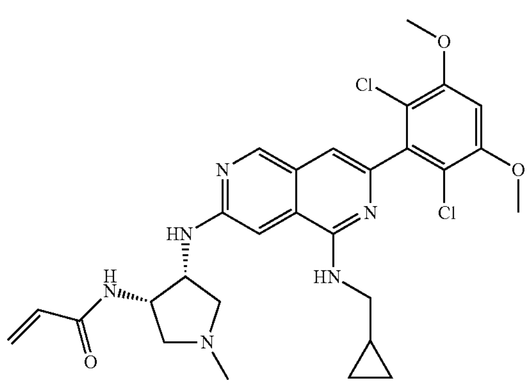 | N-((3S,4R)-4-((5-((cyclopropylmethyl)amino)-7-(2,6-dichloro-3,5-dimethoxyphenyl)-2,6-naphthyridin-3-yl)amino)-1-methylpyrrolidin-3-yl)acrylamide | 571 |

-continued

| Example No. | Compound structure | Compound name | MS: m/z [M + 1]+ |
|---|---|---|---|
| 249 | 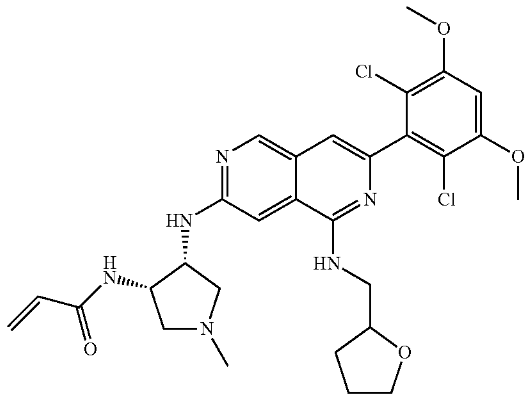 | N-((3S,4R)-4-((7-(2,6-dichloro-3,5-dimethoxyphenyl)-5-(((tetrahydrofuran-2-yl)methyl)amino)-2,6-naphthyridin-3-yl)amino)-1-methylpyrrolidin-3-yl)acrylamide | 601 |
| 250 | 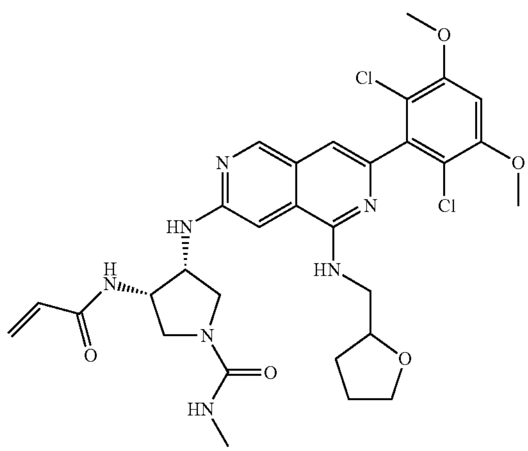 [SMILES: C=CC(=O)N[C@H]1CN(C(=O)NC)C[C@H]1Nc1cc2c(NCC3CCCO3)nc(-c3c(Cl)c(OC)cc(OC)c3Cl)cc2cn1] | (3S,4R)-3-acrylamido-4-((7-(2,6-dichloro-3,5-dimethoxyphenyl)-5-(((tetrahydrofuran-2-yl)methyl)amino)-2,6-naphthyridin-3-yl)amino)-N-methylpyrrolidine-1-carboxamide | 644 |
| 251 | 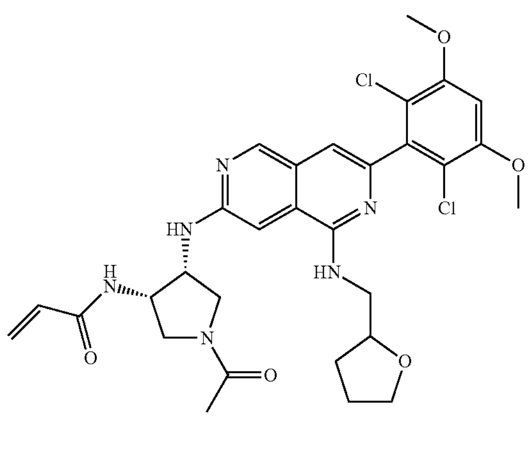 [SMILES: C=CC(=O)N[C@H]1CN(C(C)=O)C[C@H]1Nc1cc2c(NCC3CCCO3)nc(-c3c(Cl)c(OC)cc(OC)c3Cl)cc2cn1] | N-((3S,4R)-1-acetyl-4-((7-(2,6-dichloro-3,5-dimethoxyphenyl)-5-(((tetrahydrofuran-2-yl)methyl)amino)-2,6-naphthyridin-3-yl)amino)pyrrolidin-3-yl)acrylamide | 629 |

| Example No. | Compound structure | Compound name | MS: m/z [M + 1]+ |
| --- | --- | --- | --- |
| 252 | 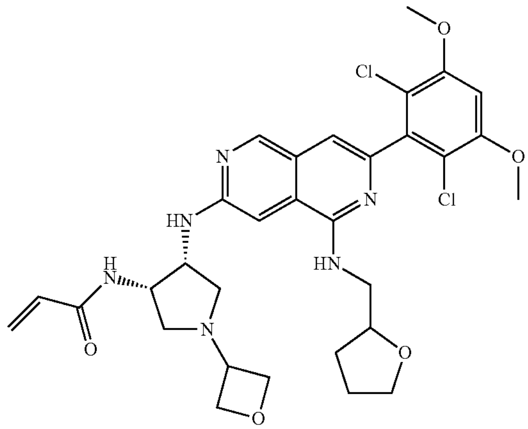 [SMILES: C=CC(=O)N[C@H]1CN(C2COC2)C[C@H]1Nc1cc2c(NCC3CCCO3)nc(-c3c(Cl)c(OC)cc(OC)c3Cl)cc2cn1] | N-((3S,4R)-4-((7-(2,6-dichloro-3,5-dimethoxyphenyl))-5-(((tetrahydrofuran-2-yl)methyl)amino)-2,6-naphthyridin-3-yl)amino)-1-(oxetan-3-yl)pyrrolidin-3-yl)acrylamide | 643 |
| 253 | 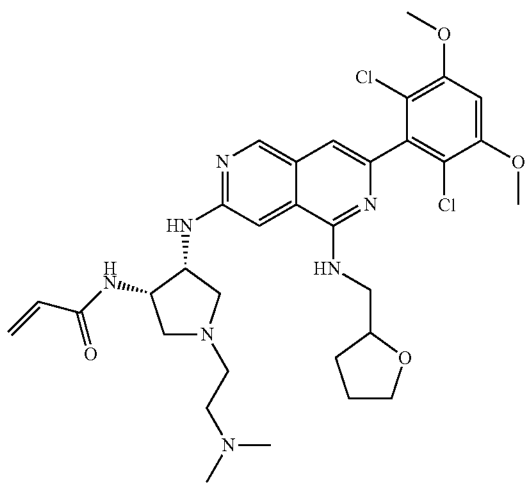 [SMILES: C=CC(=O)N[C@H]1CN(CCN(C)C)C[C@H]1Nc1cc2c(NCC3CCCO3)nc(-c3c(Cl)c(OC)cc(OC)c3Cl)cc2cn1] | N-((3S,4R)-4-((7-(2,6-dichloro-3,5-dimethoxyphenyl)-5-(((tetrahydrofuran-2-yl)methyl)amino)-2,6-naphthyridin-3-yl)amino)-1-(2-(dimethylamino)ethyl)pyrrolidin-3-yl)acrylamide | 658 |
| 254 | 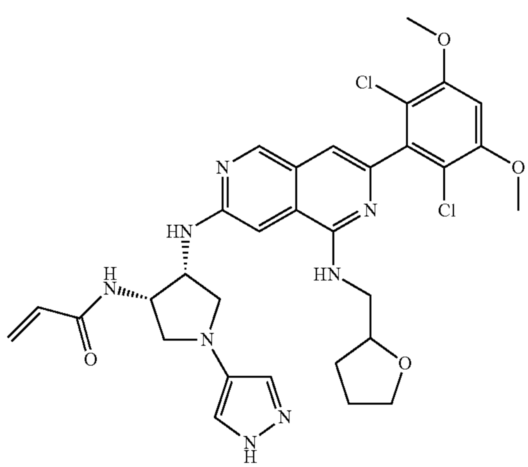 [SMILES: C=CC(=O)N[C@H]1CN(c2cn[nH]c2)C[C@H]1Nc1cc2c(NCC3CCCO3)nc(-c3c(Cl)c(OC)cc(OC)c3Cl)cc2cn1] | N-((3S,4R)-4-((7-(2,6-dichloro-3,5-dimethoxyphenyl)-5-(((tetrahydrofuran-2-yl)methyl)amino)-2,6-naphthyridin-3-yl)amino)-1H-pyrazol-4-yl)pyrrolidin-3-yl)acrylamide | 653 |

| Example No. | Compound structure | Compound name | MS: m/z [M + 1]+ |
| --- | --- | --- | --- |
| 255 | 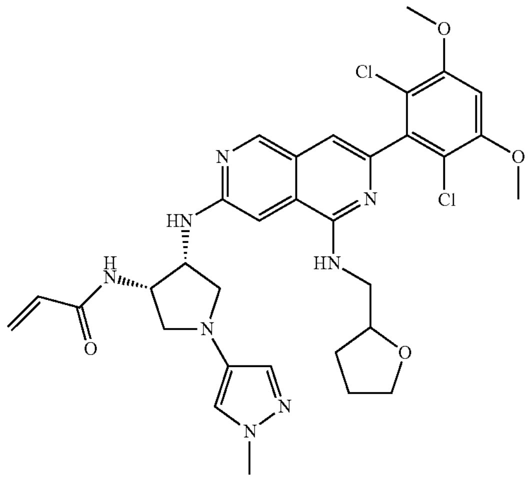 | N-((3S,4R)-4-((7-(2,6-dichloro-3,5-dimethoxyphenyl)-5-(((tetrahydrofuran-2-yl)methyl)amino)-2,6-naphthyridin-3-yl)amino)-1-(1-methyl-1H-pyrazol-4-yl)pyrrolidin-3-yl)acrylamide | 667 |
| 256 | 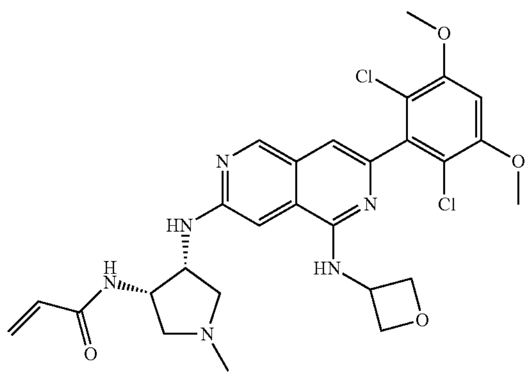 [SMILES: C=CC(=O)N[C@H]1CN(C)C[C@H]1Nc1cc2c(NC3COC3)nc(-c3c(Cl)c(OC)cc(OC)c3Cl)cc2cn1] | N-((3S,4R)-4-((7-(2,6-dichloro-3,5-dimethoxyphenyl)-5-(oxetan-3-ylamino)-2,6-naphthyridin-3-yl)amino)-1-methyl-pyrrolidin-3-yl)acrylamide | 573 |
| 257 | 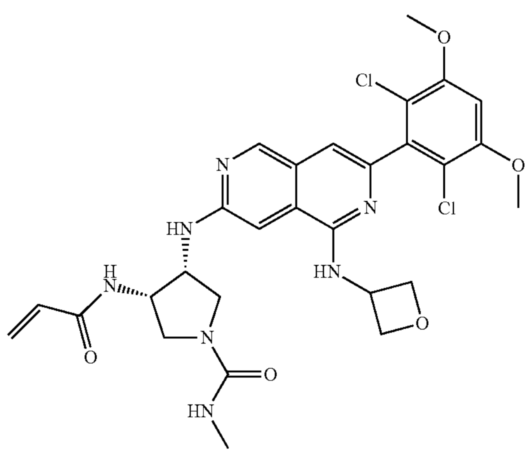 [SMILES: C=CC(=O)N[C@H]1CN(C(=O)NC)C[C@H]1Nc1cc2c(NC3COC3)nc(-c3c(Cl)c(OC)cc(OC)c3Cl)cc2cn1] | (3S,4R)-3-acrylamido-4-((7-(2,6-dichloro-3,5-dimethoxyphenyl)-5-(oxetan-3-yl-amino)-2,6-naphthyridin-3-yl)amino)-N-methylpyrrolidine-1-carboxamide | 616 |

| Example No. | Compound structure | Compound name | MS: m/z [M + 1]+ |
|---|---|---|---|
| 258 | 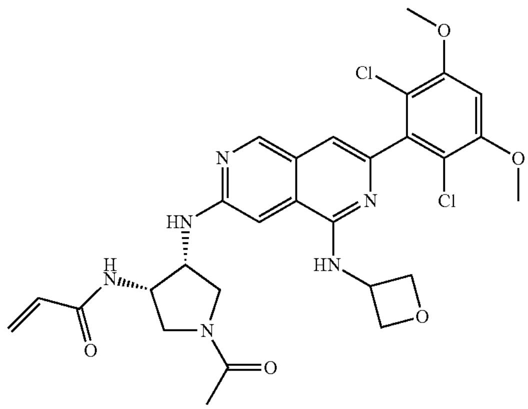 [SMILES: C=CC(=O)N[C@H]1CN(C(C)=O)C[C@H]1Nc1cc2c(NC3COC3)nc(-c3c(Cl)c(OC)cc(OC)c3Cl)cc2cn1] | N-((3S,4R)-1-acetyl-4-((7-(2,6-dichloro-3,5-dimethoxyphenyl)-5-(oxetan-3-yl-amino)-2,6-naphthyridin-3-yl)amino)pyrrolidin-3-yl)acrylamide | 601 |
| 259 | 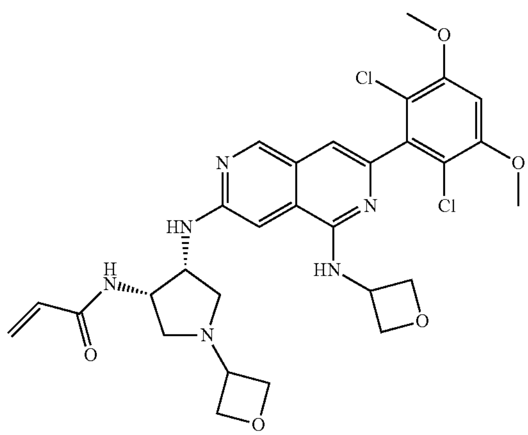 [SMILES: C=CC(=O)N[C@H]1CN(C2COC2)C[C@H]1Nc1cc2c(NC3COC3)nc(-c3c(Cl)c(OC)cc(OC)c3Cl)cc2cn1] | N-((3S,4R)-4-((7-(2,6-dichloro-3,5-dimethoxyphenyl)-5-(oxetan-3-ylamino)-2,6-naphthyridin-3-yl)amino)-1-(oxetan-3-yl)pyrrolidin-3-yl)acrylamide | 615 |
| 260 | 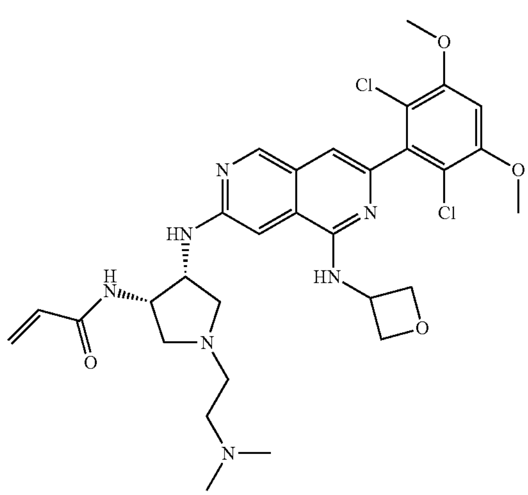 [SMILES: C=CC(=O)N[C@H]1CN(CCN(C)C)C[C@H]1Nc1cc2c(NC3COC3)nc(-c3c(Cl)c(OC)cc(OC)c3Cl)cc2cn1] | N-((3S,4R)-4-((7-(2,6-dichloro-3,5-dimethoxyphenyl)-5-(oxetan-3-ylamino)-2,6-naphthyridin-3-yl)amino)-1-(2-(dimethyl-amino)ethyl)pyrrolidin-3-yl)acrylamide | 630 |

| Example No. | Compound structure | Compound name | MS: m/z [M + 1]⁺ |
|---|---|---|---|
| 261 | 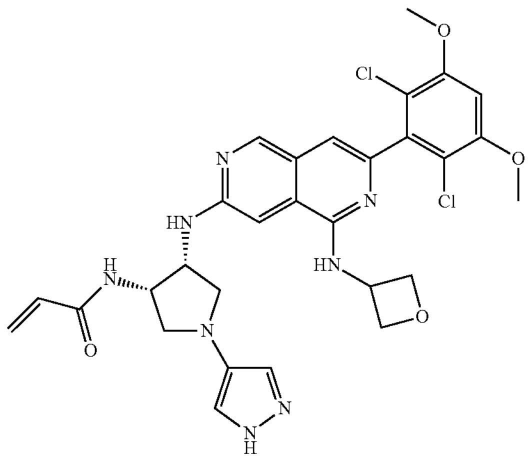 [SMILES: C=CC(=O)N[C@H]1CN(c2cn[nH]c2)C[C@H]1Nc1cc2c(NC3COC3)nc(-c3c(Cl)c(OC)cc(OC)c3Cl)cc2cn1] | N-((3S,4R)-4-((7-(2,6-dichloro-3,5-dimethoxyphenyl)-5-(oxetan-3-ylamino)-2,6-naphthyridin-3-yl)amino)-1-(1H-pyrazol-4-yl)pyrrolidin-3-yl)acrylamide | 625 |
| 262 | 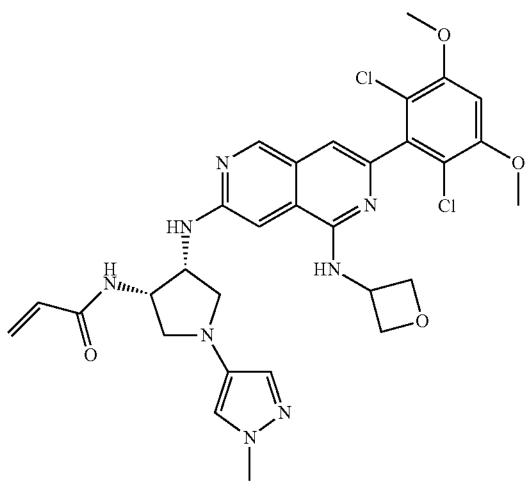 [SMILES: C=CC(=O)N[C@H]1CN(c2cnn(C)c2)C[C@H]1Nc1cc2c(NC3COC3)nc(-c3c(Cl)c(OC)cc(OC)c3Cl)cc2cn1] | N-((3S,4R)-4-((7-(2,6-dichloro-3,5-dimethoxyphenyl)-5-(oxetan-3-ylamino)-2,6-naphthyridin-3-yl)amino)-1-(1-methyl-1H-pyrazol-4-yl)pyrrolidin-3-yl)acrylamide | 639 |
| 263 | 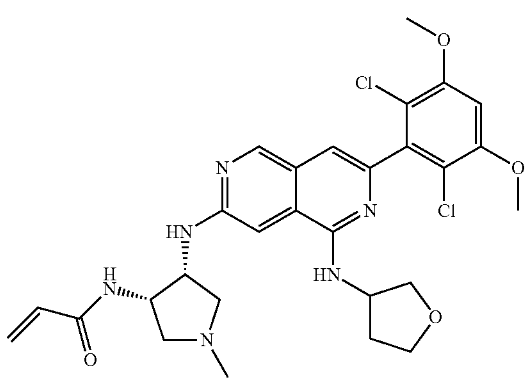 | N-((3S,4R)-4-((7-(2,6-dichloro-3,5-dimethoxyphenyl)-5-((tetrahydrofuran-3-yl)amino)-2,6-naphthyridin-3-yl)amino)-1-methylpyrrolidin-3-yl)acrylamide | 587 |

| Example No. | Compound structure | Compound name | MS: m/z [M + 1]+ |
| --- | --- | --- | --- |
| 264 | 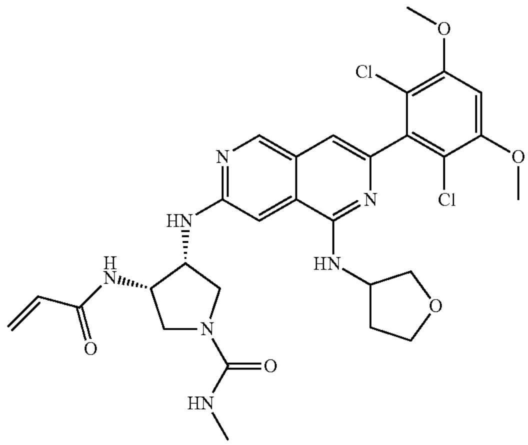 [SMILES: C=CC(=O)N[C@H]1CN(C(=O)NC)C[C@H]1Nc1cc2c(NC3CCOC3)nc(-c3c(Cl)c(OC)cc(OC)c3Cl)cc2cn1] | (3S,4R)-3-acrylamido-4-((7-(2,6-dichloro-3,5-dimethoxyphenyl)-5-(tetrahydrofuran-3-yl)amino)-2,6-naphthyridin-3-yl)amino)-N-methylpyrrolidine-1-carboxamide | 630 |
| 265 | 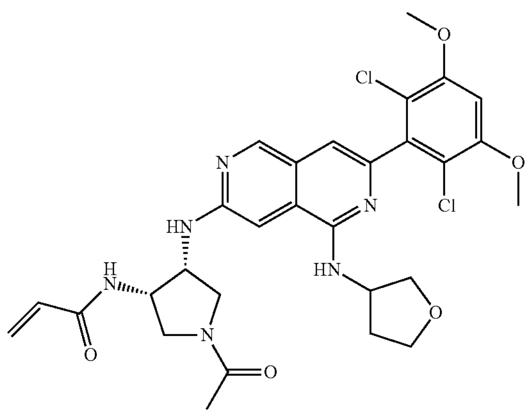 [SMILES: C=CC(=O)N[C@H]1CN(C(C)=O)C[C@H]1Nc1cc2c(NC3CCOC3)nc(-c3c(Cl)c(OC)cc(OC)c3Cl)cc2cn1] | N-((3S,4R)-1-acetyl-4-((7-(2,6-dichloro-3,5-dimethoxyphenyl)-5-(((tetrahydrofuran-3-yl)amino)-2,6-naphthyridin-3-yl)amino)pyrrolidin-3-yl)acrylamide | 615 |
| 266 | 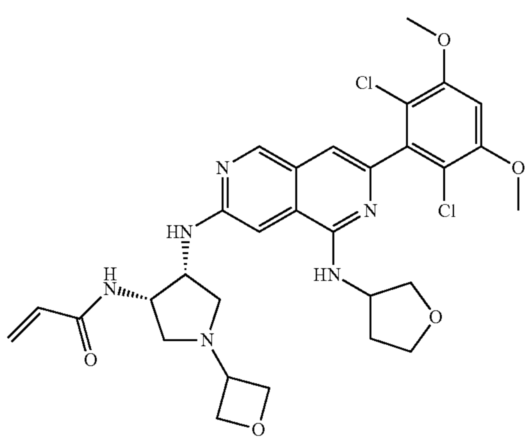 [SMILES: C=CC(=O)N[C@H]1CN(C2COC2)C[C@H]1Nc1cc2c(NC3CCOC3)nc(-c3c(Cl)c(OC)cc(OC)c3Cl)cc2cn1] | N-((3S,4R)-4-((7-(2,6-dichloro-3,5-dimethoxyphenyl)-5-(tetrahydrofuran-3-yl)amino)-2,6-naphthyridin-3-yl)amino)-1-(oxetan-3-yl)pyrrolidin-3-yl)acrylamide | 629 |

-continued

| Example No. | Compound structure | Compound name | MS: m/z [M + 1]+ |
|---|---|---|---|
| 267 | 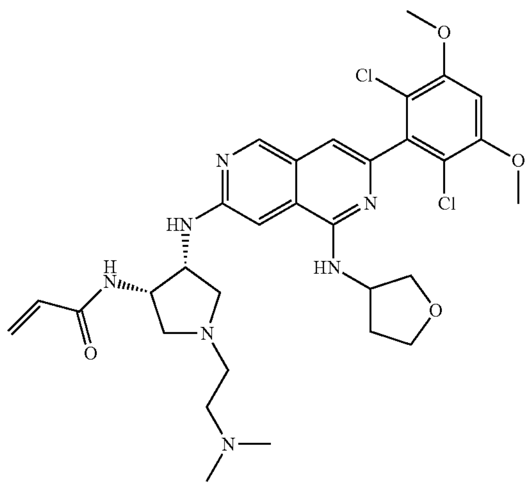 [SMILES: C=CC(=O)N[C@H]1CN(CCN(C)C)C[C@H]1Nc1cc2c(NC3CCOC3)nc(-c3c(Cl)c(OC)cc(OC)c3Cl)cc2cn1] | N-((3S,4R)-4-((7-(2,6-dichloro-3,5-dimethoxyphenyl)-5-((tetrahydrofuran-3-yl)amino)-2,6-naphthyridin-3-yl)amino)-1-(2-(dimethylamino)ethyl)pyrrolidin-3-yl)acrylamide | 644 |
| 268 | 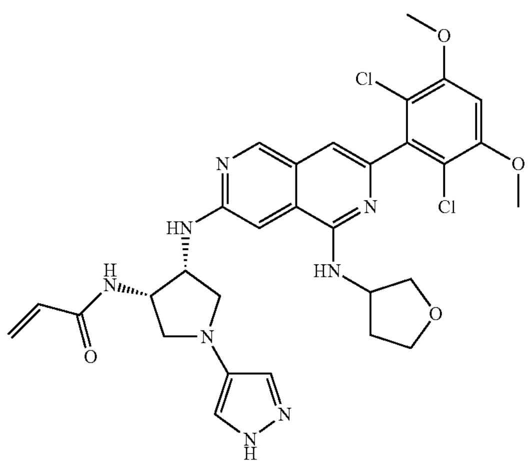 [SMILES: C=CC(=O)N[C@H]1CN(c2cn[nH]c2)C[C@H]1Nc1cc2c(NC3CCOC3)nc(-c3c(Cl)c(OC)cc(OC)c3Cl)cc2cn1] | N-((3S,4R)-4-((7-(2,6-dichloro-3,5-dimethoxyphenyl)-5-((tetrahydrofuran-3-yl amino)-2,6-naphthyridin-3-yl)amino)-1-(1H-pyrazol-4-yl)pyrrolidin-3-yl)acrylamide | 639 |
| 269 | 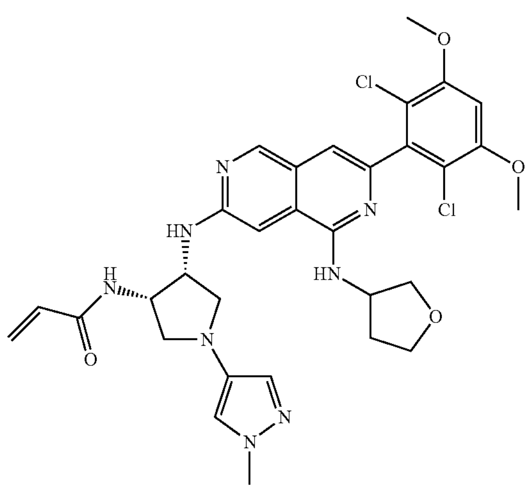 [SMILES: C=CC(=O)N[C@H]1CN(c2cnn(C)c2)C[C@H]1Nc1cc2c(NC3CCOC3)nc(-c3c(Cl)c(OC)cc(OC)c3Cl)cc2cn1] | N-((3S,4R)-4-((7-(2,6-dichloro-3,5-dimethoxyphenyl)-5-((tetrahydrofuran-3-yl amino)-2,6-naphthyridin-3-yl)amino)-1-(1-methyl-1H-pyrazol-4-yl)pyrrolidin-3-yl)acrylamide | 653 |

-continued

| Example No. | Compound structure | Compound name | MS: m/z [M + 1]+ |
|---|---|---|---|
| 270 | 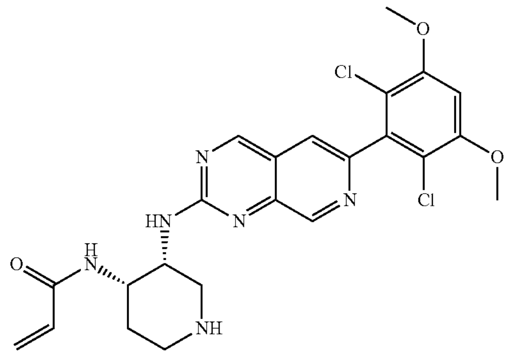 [SMILES: C=CC(=O)N[C@H]1CCNC[C@H]1Nc1ncc2cc(-c3c(Cl)c(OC)cc(OC)c3Cl)ncc2n1] | N-((3R,4S)-3-((6-(2,6-dichloro-3,5-dimethoxyphenyl)pyrido[3,4-d]pyrimidin-2-yl)amino)piperidin-4-yl)acrylamide | 503 |
| 271 | 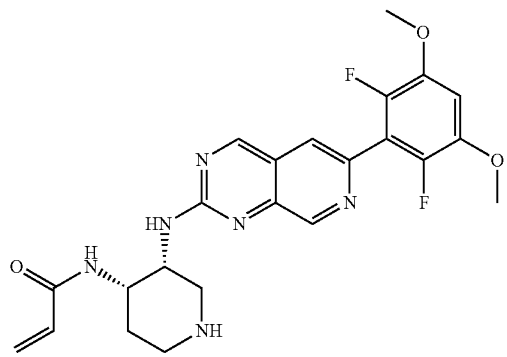 [SMILES: C=CC(=O)N[C@H]1CCNC[C@H]1Nc1ncc2cc(-c3c(F)c(OC)cc(OC)c3F)ncc2n1] | N-((3R,4S)-3-((6-(2,6-difluoro-3,5-dimethoxyphenyl)pyrido[3,4-d]pyrimidin-2-yl)amino)piperidin-4-yl)acrylamide | 470 |
| 272 | 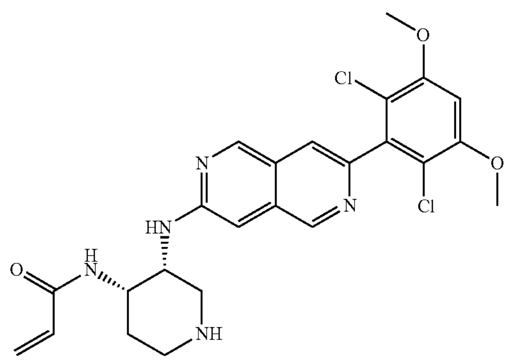 [SMILES: C=CC(=O)N[C@H]1CCNC[C@H]1Nc1cc2cnc(-c3c(Cl)c(OC)cc(OC)c3Cl)cc2cn1] | N-((3R,4S)-3-((7-(2,6-dichloro-3,5-dimethoxyphenyl)-2,6-naphthyridin-3-yl)amino)piperidin-4-yl)acrylamide | 502 |
| 273 | 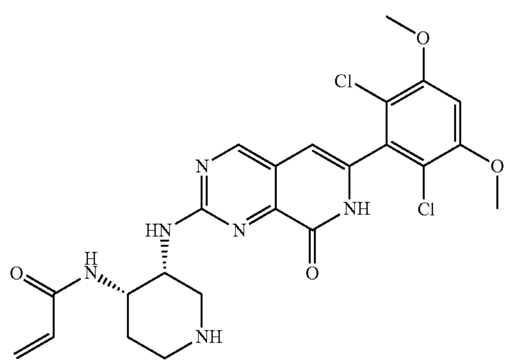 [SMILES: C=CC(=O)N[C@H]1CCNC[C@H]1Nc1ncc2cc(-c3c(Cl)c(OC)cc(OC)c3Cl)[nH]c(=O)c2n1] | N-((3R,4S)-3-((6-(2,6-dichloro-3,5-dimethoxyphenyl)-8-oxo-7,8-dihydropyrido[3,4-d]pyrimidin-2-yl)amino)piperidin-4-yl)acrylamide | 519 |

-continued

| Example No. | Compound structure | Compound name | MS: m/z [M + 1]+ |
|---|---|---|---|
| 274 | 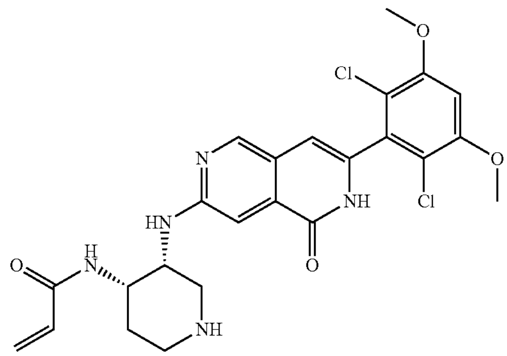 [SMILES: C=CC(=O)N[C@H]1CCNC[C@H]1Nc1cc2c(=O)[nH]c(-c3c(Cl)c(OC)cc(OC)c3Cl)cc2cn1] | N-((3R,4S)-3-((7-(2,6-dichloro-3,5-dimethoxyphenyl)-5-oxo-5,6-dihydro-2,6-naphthyridin-3-yl)amino)piperidin-4-yl)acrylamide | 518 |
| 275 | 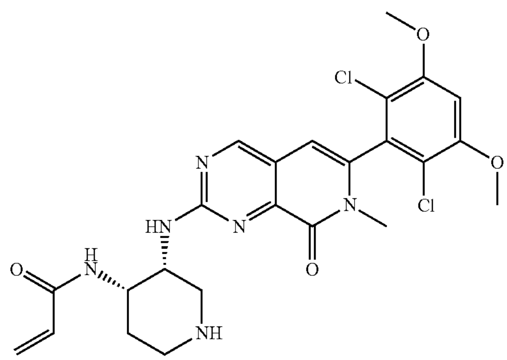 [SMILES: C=CC(=O)N[C@H]1CCNC[C@H]1Nc1ncc2cc(-c3c(Cl)c(OC)cc(OC)c3Cl)n(C)c(=O)c2n1] | N-((3R,4S)-3-((6-(2,6-dichloro-3,5-dimethoxyphenyl)-7-methyl-8-oxo-7,8-hydropyrido[3,4-d]pyrimidin-2-yl)amino)piperidin-4-yl)acrylamide | 533 |
| 276 | 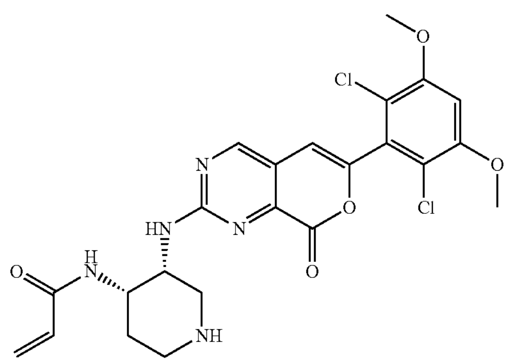 [SMILES: C=CC(=O)N[C@H]1CCNC[C@H]1Nc1ncc2cc(-c3c(Cl)c(OC)cc(OC)c3Cl)oc(=O)c2n1] | N-((3R,4S)-3-((6-(2,6-dichloro-3,5-dimethoxyphenyl)-8-oxo-8H-pyrano[3,4-d]pyrimidin-2-yl)amino)piperidin-4-yl)acrylamide | 520 |
| 277 | 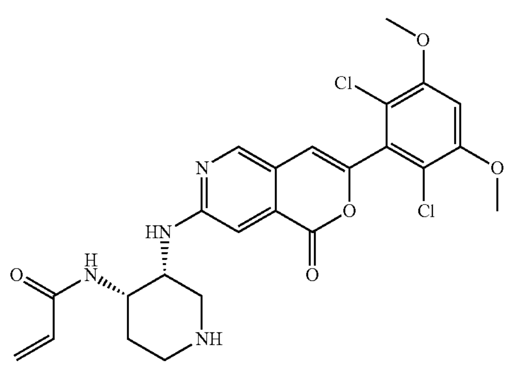 [SMILES: C=CC(=O)N[C@H]1CCNC[C@H]1Nc1cc2c(=O)oc(-c3c(Cl)c(OC)cc(OC)c3Cl)cc2cn1] | N-(3R,4S)-3-((3-(2,6-dichloro-3,5-dimethoxyphenyl)-1-oxo-1H-pyrano[4,3-c]pyridin-7-yl)amino)piperidin-4-yl)acrylamide | 519 |

-continued

| Example No. | Compound structure | Compound name | MS: m/z [M + 1]+ |
| --- | --- | --- | --- |
| 278 | 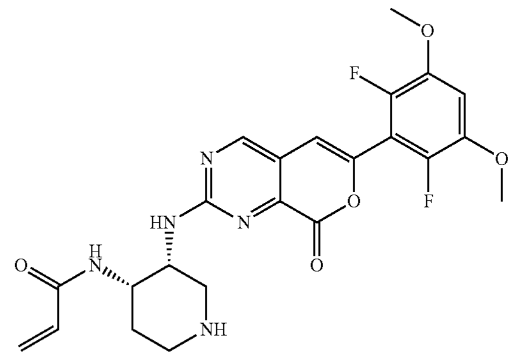 [SMILES: C=CC(=O)N[C@H]1CCNC[C@H]1Nc1ncc2cc(-c3c(F)c(OC)cc(OC)c3F)oc(=O)c2n1] | N-((3R,4S)-3-((6-(2,6-difluoro-3,5-dimethoxyphenyl)-8-oxo-8H-pyrano[3,4-d]pyrimidin-2-yl)amino)piperidin-4-yl)acrylamide | 487 |
| 279 | 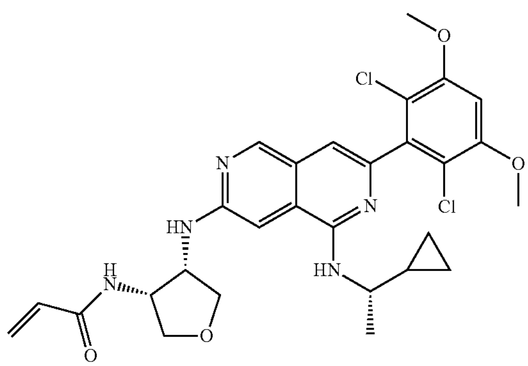 [SMILES: C=CC(=O)N[C@H]1COC[C@H]1Nc1cc2c(N[C@@H](C)C3CC3)nc(-c3c(Cl)c(OC)cc(OC)c3Cl)cc2cn1] | N-((3R,4S)-4-((5-(((S)-1-cyclopropylethyl)amino)-7-(2,6-dichloro-3,5-dimethoxyphenyl)-2,6-naphthyridin-3-yl)amino)tetrahydrofuran-3-yl)acrylamide | 572 |
| 280 | 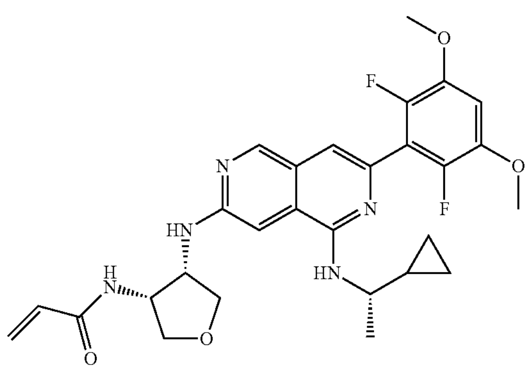 | N-((3R,4S)-4-((5-(((S)-1-cyclopropylethyl)amino)-7-(2,6-difluoro-3,5-dimethoxyphenyl)-2,6-naphthyridin-3-yl)amino)tetrahydrofuran-3-yl)acrylamide | 540 |
| 281 | 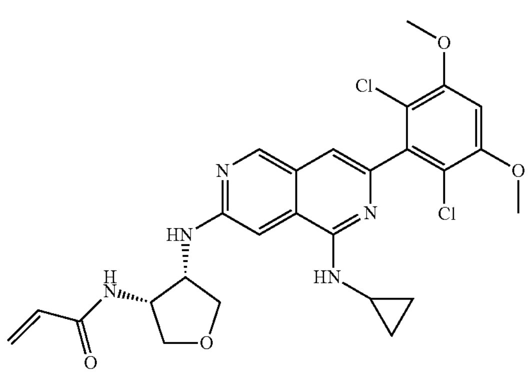 [SMILES: C=CC(=O)N[C@H]1COC[C@H]1Nc1cc2c(NC3CC3)nc(-c3c(Cl)c(OC)cc(OC)c3Cl)cc2cn1] | N-((3R,4S)-4-((5-(cyclopropylamino)-7-(2,6-dichloro-3,5-dimethoxyphenyl)-2,6-naphthyridin-3-yl)amino)tetrahydrofuran-3-yl)acrylamide | 544 |

-continued

| Example No. | Compound structure | Compound name | MS: m/z [M + 1]+ |
|---|---|---|---|
| 282 | 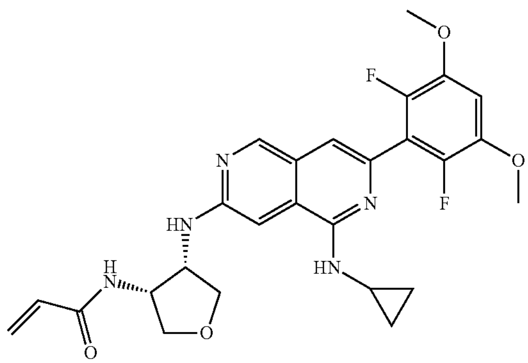 [SMILES: C=CC(=O)N[C@H]1COC[C@H]1Nc1cc2c(NC3CC3)nc(-c3c(F)c(OC)cc(OC)c3F)cc2cn1] | N-((3R,4S)-4-((5-(cyclopropylamino)-7-(2,6-difluoro-3,5-dimethoxyphenyl)-2,6-naphthyridin-3-ylamino)tetrahydrofuran-3-yl)acrylamide | 512 |
| 283 | 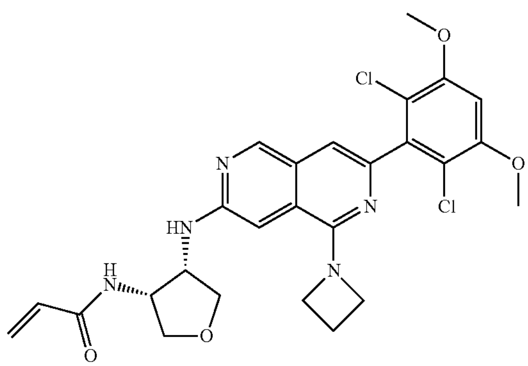 [SMILES: C=CC(=O)N[C@H]1COC[C@H]1Nc1cc2c(N3CCC3)nc(-c3c(Cl)c(OC)cc(OC)c3Cl)cc2cn1] | N-((3R,4S)-4-((5-(azetidin-1-yl)-7-(2,6-dichloro-3,5-dimethoxyphenyl)-2,6-naphthyridin-3-yl)amino)tetrahydrofuran-3-yl)acrylamide | 544 |
| 284 | 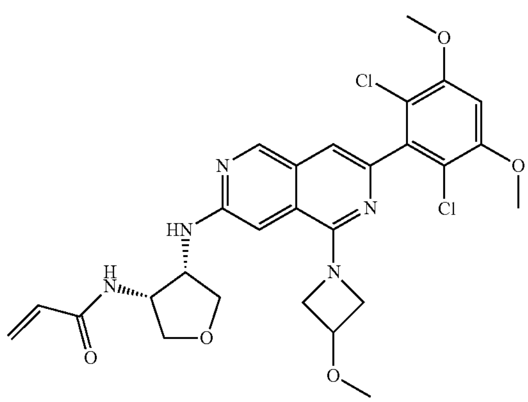 [SMILES: C=CC(=O)N[C@H]1COC[C@H]1Nc1cc2c(N3CC(OC)C3)nc(-c3c(Cl)c(OC)cc(OC)c3Cl)cc2cn1] | N-((3R,4S)-4-((7-(2,6-dichloro-3,5-dimethoxyphenyl)-5-(3-dimethoxyazetidin-1-yl)-2,6-naphthyridin-3-yl)amino)tetrahydrofuran-3-yl)acrylamide | 574 |
| 285 | 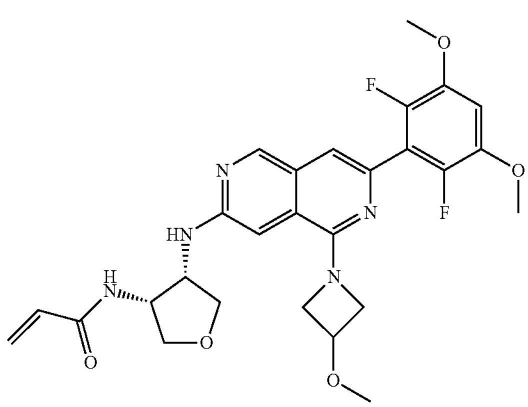 [SMILES: C=CC(=O)N[C@H]1COC[C@H]1Nc1cc2c(N3CC(OC)C3)nc(-c3c(F)c(OC)cc(OC)c3F)cc2cn1] | N-((3R,4S)-4-((7-(2,6-difluoro-3,5-dimethoxyphenyl)-5-(3-methoxyazetidin-1-yl)-2,6-naphthyridin-3-yl)amino)tetrahydrofuran-3-yl)acrylamide | 542 |

-continued

| Example No. | Compound structure | Compound name | MS: m/z [M + 1]+ |
|---|---|---|---|
| 286 | 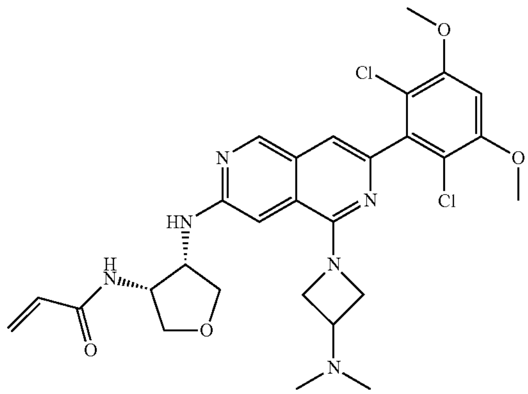 [SMILES: C=CC(=O)N[C@H]1COC[C@H]1Nc1cc2c(N3CC(N(C)C)C3)nc(-c3c(Cl)c(OC)cc(OC)c3Cl)cc2cn1] | N-((3R,4S)-4-((7-(2,6-dichloro-3,5-dimethoxyphenyl)-5-(3-(dimethylamino)azetidin-1-yl)-2,6-naphthyridin-3-yl)amino)tetrahydrofuran-3-yl)acrylamide | 587 |
| 287 | 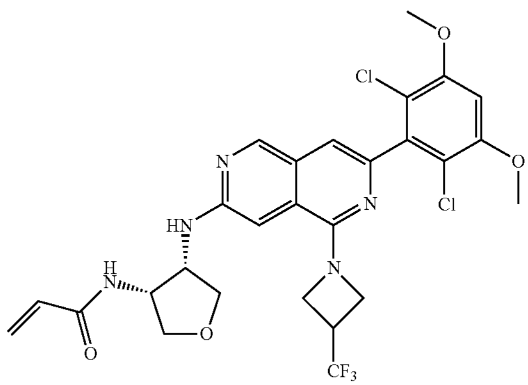 [SMILES: C=CC(=O)N[C@H]1COC[C@H]1Nc1cc2c(N3CC(C(F)(F)F)C3)nc(-c3c(Cl)c(OC)cc(OC)c3Cl)cc2cn1] | N-((3R,4S)-4-((7-(2,6-dichloro-3,5-dimethoxyphenyl)-5-(3-(trifluoromethyl)azetidin-1-yl)-2,6-naphthyridin-3-yl)amino)tetrahydrofuran-3-yl)acrylamide | 612 |
| 288 | 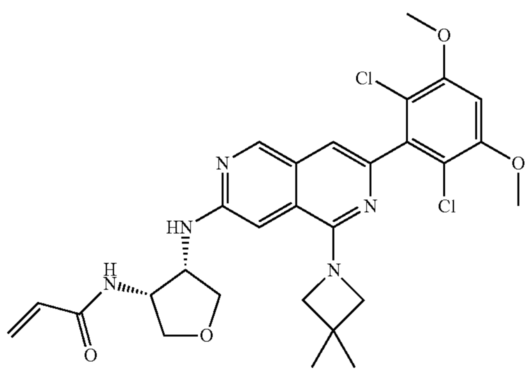 [SMILES: C=CC(=O)N[C@H]1COC[C@H]1Nc1cc2c(N3CC(C)(C)C3)nc(-c3c(Cl)c(OC)cc(OC)c3Cl)cc2cn1] | N-((3R,4S)-4-((7-(2,6-dichloro-3,5-dimethoxyphenyl)-5-(3,3-dimethylazetidin-1-yl)-2,6-naphthyridin-3-yl)amino)tetrahydrofuran-3-yl)acrylamide | 572 |
| 289 | 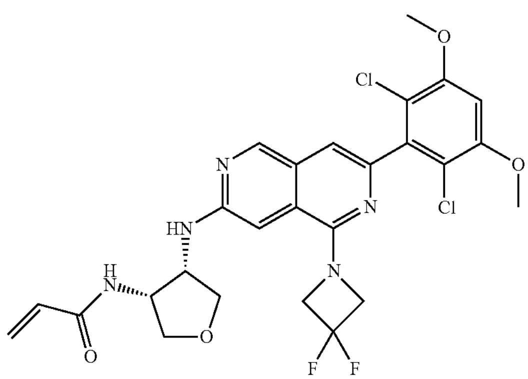 [SMILES: C=CC(=O)N[C@H]1COC[C@H]1Nc1cc2c(N3CC(F)(F)C3)nc(-c3c(Cl)c(OC)cc(OC)c3Cl)cc2cn1] | N-((3R,4S)-4-((7-(2,6-dichloro-3,5-dimethoxyphenyl)-5-(3,3-difluoroazetidin-1-yl)-2,6-naphthyridin-3-yl)amino)tetrahydrofuran-3-yl)acrylamide | 580 |

-continued

| Example No. | Compound structure | Compound name | MS: m/z [M + 1]+ |
|---|---|---|---|
| 290 | 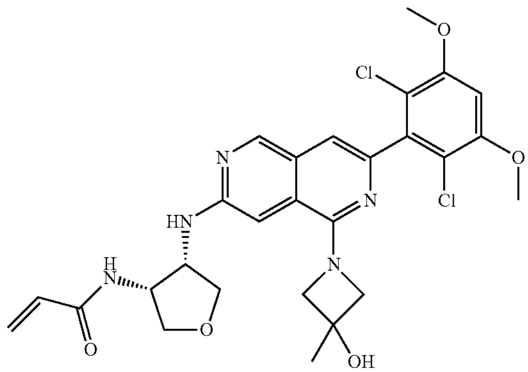 [SMILES: C=CC(=O)N[C@H]1COC[C@H]1Nc1cc2c(N3CC(C)(O)C3)nc(-c3c(Cl)c(OC)cc(OC)c3Cl)cc2cn1] | N-((3R,4S)-4-((7-(2,6-dichloro-3,5-dimethoxyphenyl)-5-(3-hydroxy-3-methyl-azetidin-1-yl)-2,6-naphthyridin-3-yl)amino)tetrahydrofuran-3-yl)acrylamide | 574 |
| 291 | 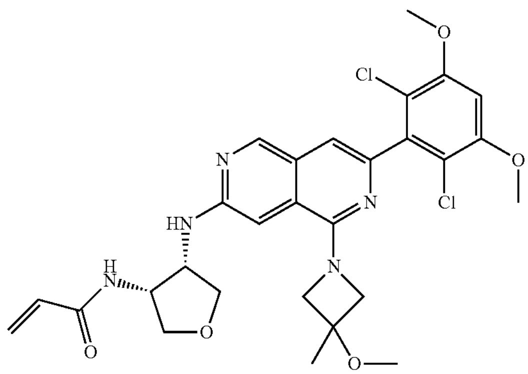 [SMILES: C=CC(=O)N[C@H]1COC[C@H]1Nc1cc2c(N3CC(C)(OC)C3)nc(-c3c(Cl)c(OC)cc(OC)c3Cl)cc2cn1] | N-((3R,4S)-4-((7-(2,6-dichloro-3,5-dimethoxyphenyl)-5-(3-dimethoxy-3-methyl-azetidin-1-yl)-2,6-naphthyridin-3-yl)amino)tetrahydrofuran-3-yl)acrylamide | 588 |
| 292 | 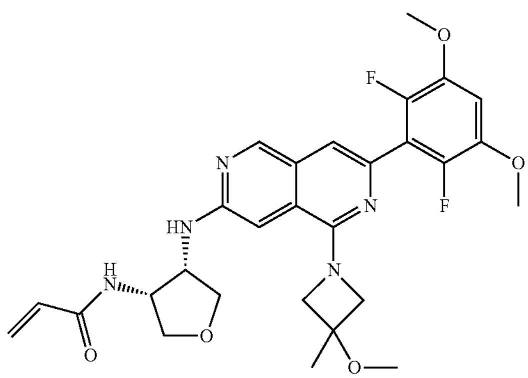 [SMILES: C=CC(=O)N[C@H]1COC[C@H]1Nc1cc2c(N3CC(C)(OC)C3)nc(-c3c(F)c(OC)cc(OC)c3F)cc2cn1] | N-((3R,4S)-4-((7-(2,6-difluoro-3,5-dimethoxyphenyl)-5-(3-dimethoxy-3-methyl-azetidin-1-yl)-2,6-naphthyridin-3-yl)amino)tetrahydrofuran-3-yl)acrylamide | 556 |
| 293 | 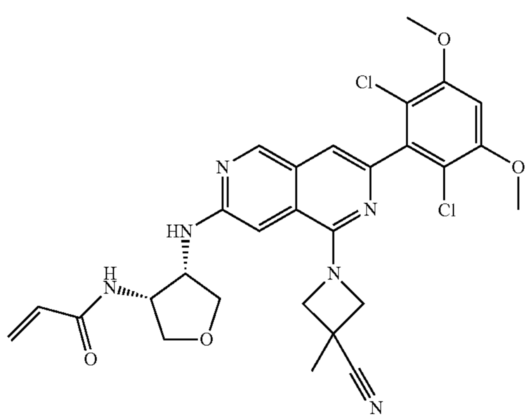 | N-((3R,4S)-4-((5-(3-cyano-3-methyl-azetidin-1-yl)-7-(2,6-dichloro-3,5-dimethoxy-phenyl)-2,6-naphthyridin-3-yl)amino)tetrahydrofuran-3-yl)acrylamide | 583 |

-continued

| Example No. | Compound structure | Compound name | MS: m/z [M + 1]+ |
|---|---|---|---|
| 294 | 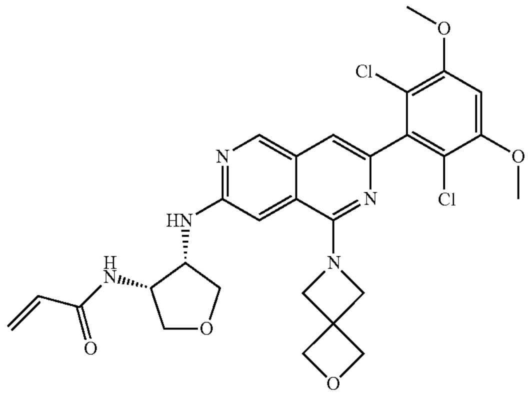 [SMILES: C=CC(=O)N[C@H]1COC[C@H]1Nc1cc2c(N3CC4(COC4)C3)nc(-c3c(Cl)c(OC)cc(OC)c3Cl)cc2cn1] | N-((3R,4S)-4-((7-(2,6-dichloro-3,5-dimethoxyphenyl)-5-(2-oxa-6-azaspiro[3.3]heptan-6-yl)-2,6-naphthyridin-3-yl)amino)tetrahydrofuran-3-yl)acrylamide | 586 |
| 295 | 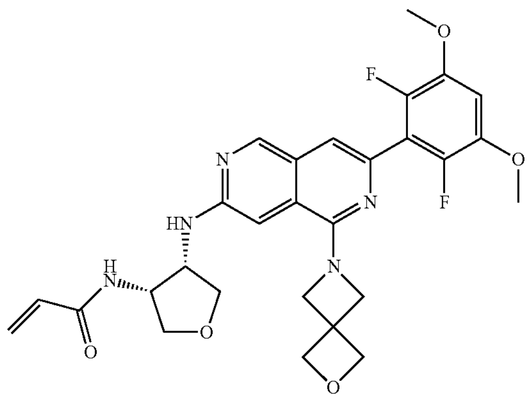 [SMILES: C=CC(=O)N[C@H]1COC[C@H]1Nc1cc2c(N3CC4(COC4)C3)nc(-c3c(F)c(OC)cc(OC)c3F)cc2cn1] | N-(3R,4S)-4-((7-(2,6-difluoro-3,5-dimethoxyphenyl)-5-(2-(2-6-azaspiro[3.3]heptan-6-yl)-2,6-naphthyridin-3-yl)amino)tetrahydrofuran-3-yl)acrylamide | 554 |
| 296 | 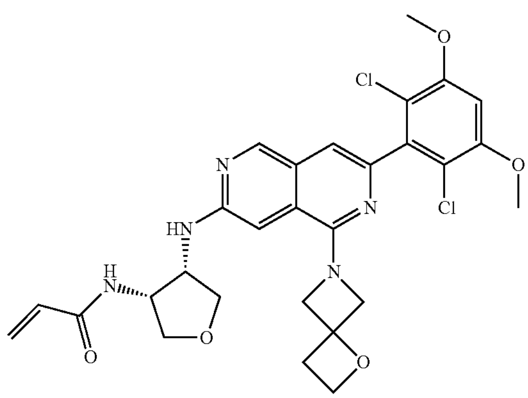 [SMILES: C=CC(=O)N[C@H]1COC[C@H]1Nc1cc2c(N3CC4(CCO4)C3)nc(-c3c(Cl)c(OC)cc(OC)c3Cl)cc2cn1] | N-((3R,4S)-4-((7-(2,6-dichloro-3,5-dimethoxyphenyl)-5-(1-oxa-6-azaspiro[3.3]heptan-6-yl)-2,6-naphthyridin-3-yl)amino)tetrahydrofuran-3-yl)acrylamide | 586 |
| 297 | 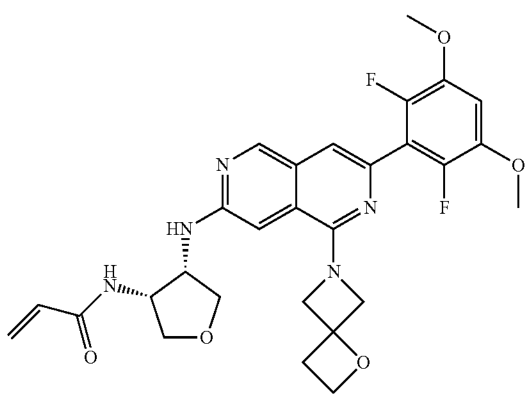 [SMILES: C=CC(=O)N[C@H]1COC[C@H]1Nc1cc2c(N3CC4(CCO4)C3)nc(-c3c(F)c(OC)cc(OC)c3F)cc2cn1] | N-((3R,4S)-4-((7-(2,6-difluoro-3,5-dimethoxyphenyl)-5-(1-oxa-6-azaspiro[3.3]heptan-6-yl)-2,6-naphthyridin-3-yl)amino)tetrahydrofuran-3-yl)acrylamide | 554 |

| Example No. | Compound structure | Compound name | MS: m/z [M + 1]+ |
|---|---|---|---|
| 298 | 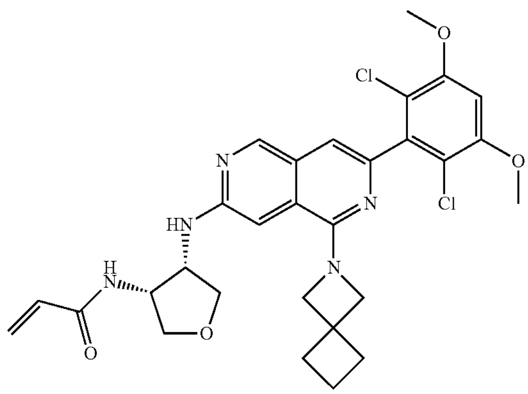 [SMILES: C=CC(=O)N[C@H]1COC[C@H]1Nc1cc2c(N3CC4(CCC4)C3)nc(-c3c(Cl)c(OC)cc(OC)c3Cl)cc2cn1] | N-((3R,4S)-4-((7-(2,6-dichloro-3,5-dimethoxyphenyl)-5-(2-azaspiro[3.3]heptan-2-yl)-2,6-naphthyridin-3-yl)amino)tetrahydrofuran-3-yl)acrylamide | 584 |
| 299 | 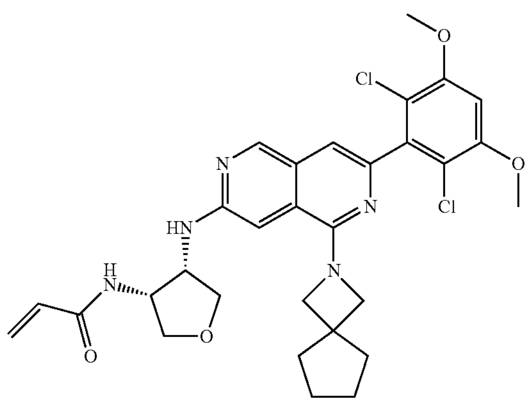 [SMILES: C=CC(=O)N[C@H]1COC[C@H]1Nc1cc2c(N3CC4(CCCC4)C3)nc(-c3c(Cl)c(OC)cc(OC)c3Cl)cc2cn1] | N-((3R,4S)-4-((7-(2,6-dichloro-3,5-dimethoxyphenyl)-5-(2-azaspiro[3.4]octan-2-yl)-2,6-naphthyridin-3-yl)amino)tetrahydrofuran-3-yl)acrylamide | 598 |
| 300 | 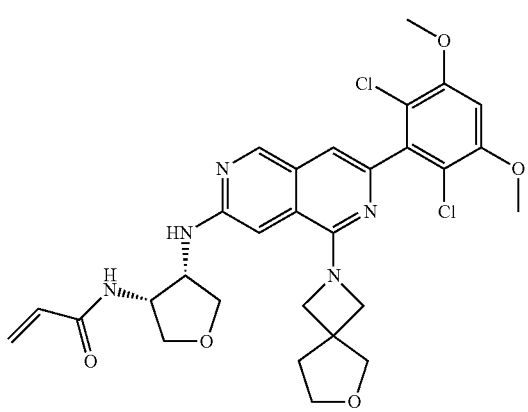 | N-((3R,4S)-4-((7-(2,6-dichloro-3,5-dimethoxyphenyl)-5-(6-oxa-2-azaspiro[3,4]octan-2-yl)-2,6-naphthyridin-3-yl))amino)tetrahydrofuran-3-yl)acrylamide | 600 |

-continued

| Example No. | Compound structure | Compound name | MS: m/z [M + 1]+ |
|---|---|---|---|
| 301 | 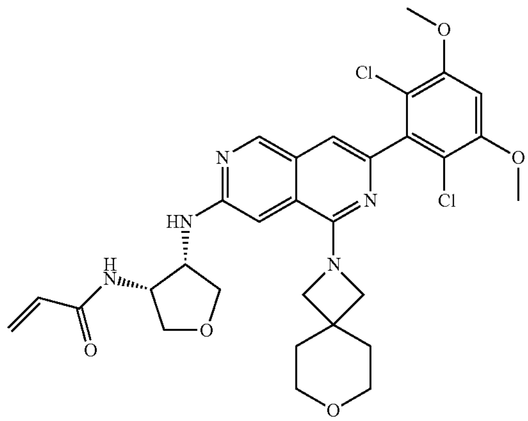 [SMILES: C=CC(=O)N[C@H]1COC[C@H]1Nc1cc2c(N3CC4(CCOCC4)C3)nc(-c3c(Cl)c(OC)cc(OC)c3Cl)cc2cn1] | N-((3R,4S)-4-((7-(2,6-dichloro-3,5-dimethoxyphenyl)-5-(7-oxa-2-azaspiro[3.5]nonan-2-yl)-2,6-naphthyridin-3-yl)amino)tetrahydrofuran-3-yl)acrylamide | 614 |
| 302 | 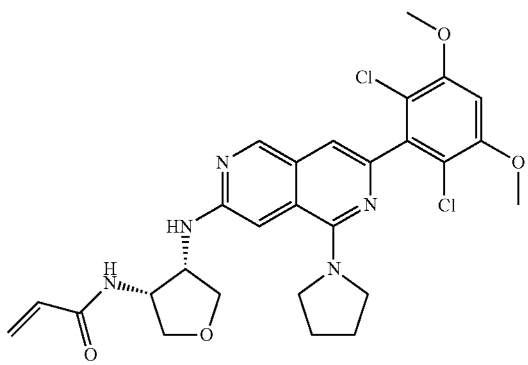 | N-((3R,4S)-4-((7-(2,6-dichloro-3,5-dimethoxyphenyl)-5-(pyrrolidin-1-yl)-2,6-naphthyridin-3-yl)amino)tetrahydrofuran-3-yl)acrylamide | 558 |
| 303 | 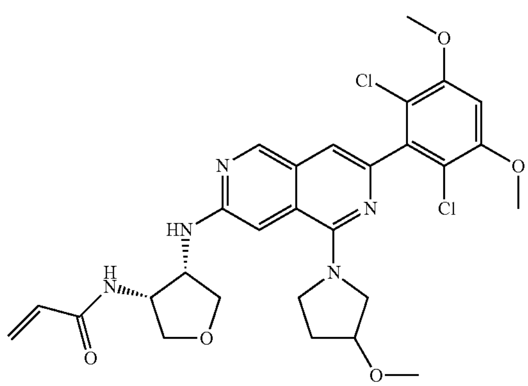 | N-((3R,4S)-4-((7-(2,6-dichloro-3,5-dimethoxyphenyl)-5-(3-methoxypyrrolidin-1-yl)-2,6-naphthyridin-3-yl)amino)tetrahydrofuran-3-yl)acrylamide | 588 |
| 304 | 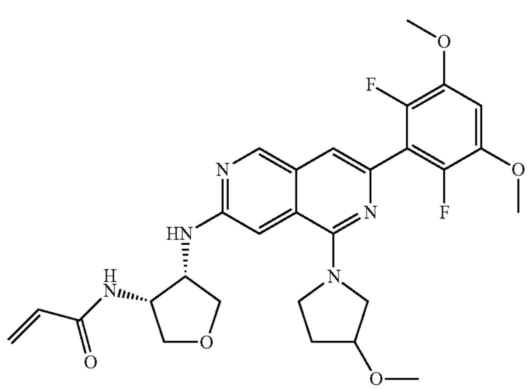 [SMILES: C=CC(=O)N[C@H]1COC[C@H]1Nc1cc2c(N3CCC(OC)C3)nc(-c3c(F)c(OC)cc(OC)c3F)cc2cn1] | N-((3R,4S)-4-((7-(2,6-difluoro-3,5-dimethoxyphenyl)-5-(3-methoxypyrrolidin-1-yl)-2,6-naphthyridin-3-yl)amino)tetrahydrofuran-3-yl)acrylamide | 556 |

-continued

| Example No. | Compound structure | Compound name | MS: m/z [M + 1]+ |
|---|---|---|---|
| 305 | 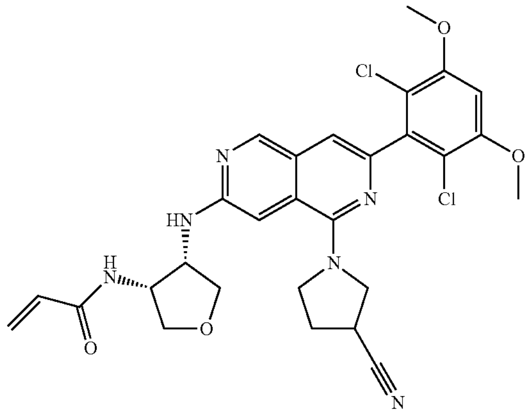 [SMILES: C=CC(=O)N[C@H]1COC[C@H]1Nc1cc2c(N3CCC(C#N)C3)nc(-c3c(Cl)c(OC)cc(OC)c3Cl)cc2cn1] | N-((3R,4S)-4-((5-(3-cyanopyrrolidin-1-yl)-7-(2,6-dichloro-3,5-dimethoxyphenyl)-2,6-naphthyridin-3-yl)amino)tetrahydrofuran-3-yl)acrylamide | 583 |
| 306 | 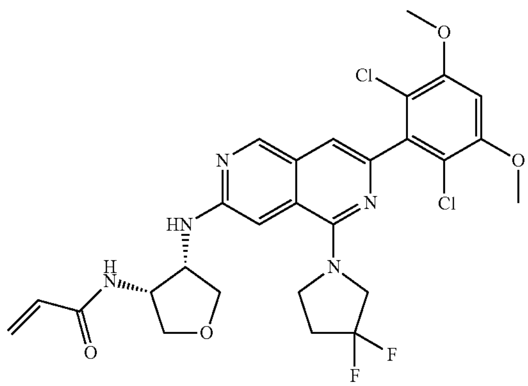 | N-((3R,4S)-4-((7-(2,6-dichloro-3,5-dimethoxyphenyl)-5-(3,3-difluoropyrrolidin-1-yl)-2,6-naphthyridin-3-yl)amino)tetrahydrofuran-3-yl)acrylamide | 594 |
| 307 | 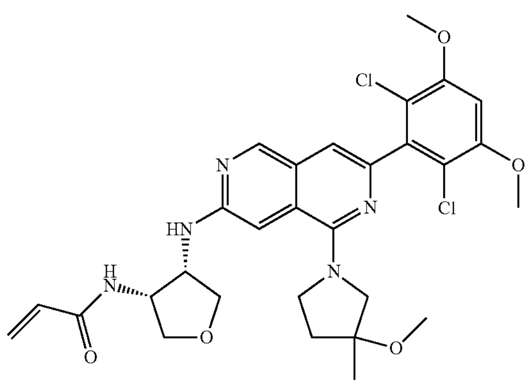 [SMILES: C=CC(=O)N[C@H]1COC[C@H]1Nc1cc2c(N3CCC(C)(OC)C3)nc(-c3c(Cl)c(OC)cc(OC)c3Cl)cc2cn1] | N-(3R,4S)-4-((7-(2,6-dichloro-3,5-dimethoxyphenyl)-5-(3-dimethoxy-3-methyl-pyrrolidin-1-yl)-2,6-naphthyridin-3-yl)amino)tetrahydrofuran-3-yl)acrylamide | 602 |
| 308 | 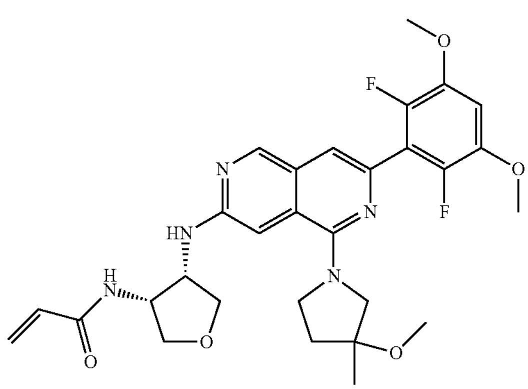 [SMILES: C=CC(=O)N[C@H]1COC[C@H]1Nc1cc2c(N3CCC(C)(OC)C3)nc(-c3c(F)c(OC)cc(OC)c3F)cc2cn1] | N-((3R,4S)-4-((7-(2,6-difluoro-3,5-dimethoxyphenyl)-5-(3-methoxy-3-methyl-pyrrolidin-1-yl)-2,6-naphthyridin-3-yl)amino)tetrahydrofuran-3-yl)acrylamide | 570 |

| Example No. | Compound structure | Compound name | MS: m/z [M + 1]+ |
|---|---|---|---|
| 309 | 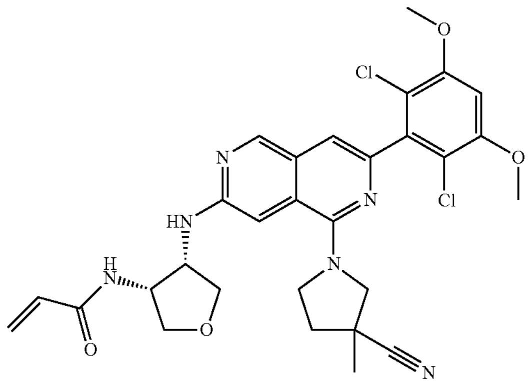 | N-((3R,4S)-4-((5-(3-cyano-3-methyl-pyrrolidin-1-yl)-7-(2,6-dichloro-3,5-dimethoxy-phenyl)-2,6-naphthyridin-3-yl)amino)tetrahydrofuran-3-yl)acrylamide | 597 |
| 310 | 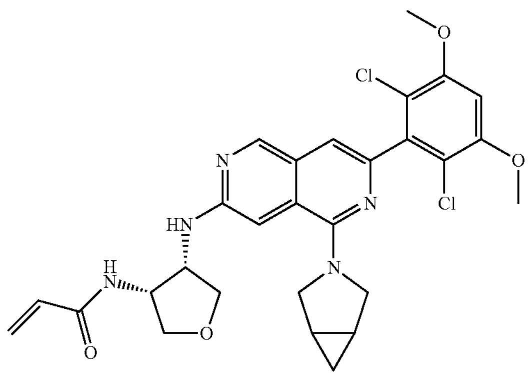 [SMILES: C=CC(=O)N[C@H]1COC[C@H]1Nc1cc2c(N3CC4CC4C3)nc(-c3c(Cl)c(OC)cc(OC)c3Cl)cc2cn1] | N-((3R,4S)-4-((5-(3-azabicyclo[3.1.0]hexan-3-yl)-7-(2,6-dichloro-3,5-dimethoxyphenyl)-2,6-naphthyridin-3-yl)amino)tetrahydrofuran-3-yl)acrylamide | 570 |
| 311 | 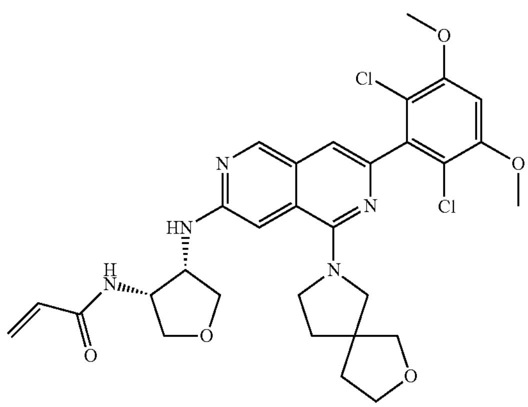 | N-((3R,4S)-4-((7-(2,6-dichloro-3,5-dimethoxyphenyl)-5-(2-oxa-7-azaspiro[4.4]nonan-7-yl)-2,6-naphthyridin-3-yl)amino)tetrahydrofuran-3-yl)acrylamide | 614 |
| 312 | 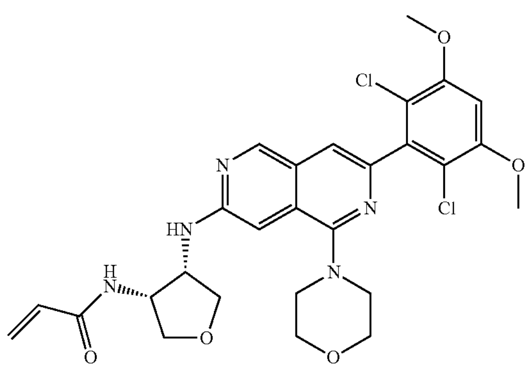 [SMILES: C=CC(=O)N[C@H]1COC[C@H]1Nc1cc2c(N3CCOCC3)nc(-c3c(Cl)c(OC)cc(OC)c3Cl)cc2cn1] | N-((3R,4S)-4-((7-(2,6-dichloro-3,5-dimethoxyphenyl)-5-morpholino-2,6-naphthyridin-3-yl)amino)tetrahydrofuran-3-yl)acrylamide | 574 |

-continued

| Example No. | Compound structure | Compound name | MS: m/z [M + 1]+ |
|---|---|---|---|
| 313 | 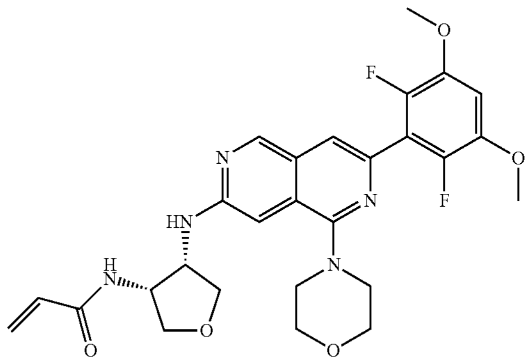 [SMILES: C=CC(=O)N[C@H]1COC[C@H]1Nc1cc2c(N3CCOCC3)nc(-c3c(F)c(OC)cc(OC)c3F)cc2cn1] | N-((3R,4S)-4-((7-(2,6-difluoro-3,5-dimethoxyphenyl)-5-morpholino-2,6-naphthyridin-3-yl)amino)tetrahydrofuran-3-yl)acrylamide | 542 |
| 314 | 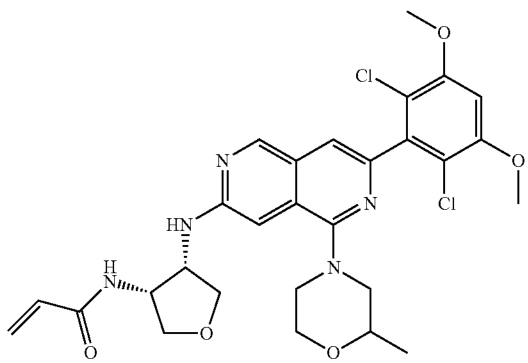 [SMILES: C=CC(=O)N[C@H]1COC[C@H]1Nc1cc2c(N3CCOC(C)C3)nc(-c3c(Cl)c(OC)cc(OC)c3Cl)cc2cn1] | N-((3R,4S)-4-((7-(2,6-dichloro-3,5-dimethoxyphenyl)-5-(2-methylmorpholino)-2,6-naphthyridin-3-yl)amino)tetrahydrofuran-3-yl)acrylamide | 588 |
| 315 | 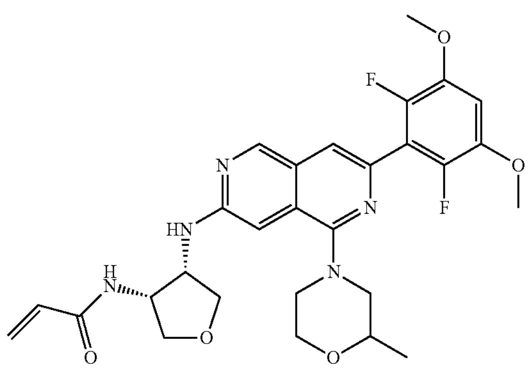 [SMILES: C=CC(=O)N[C@H]1COC[C@H]1Nc1cc2c(N3CCOC(C)C3)nc(-c3c(F)c(OC)cc(OC)c3F)cc2cn1] | N-((3R,4S)-4-((7-(2,6-difluoro-3,5-dimethoxyphenyl)-5-(2-methylmorpholino)-2,6-naphthyridin-3-yl)amino)tetrahydrofuran-3-yl)acrylamide | 556 |
| 316 | 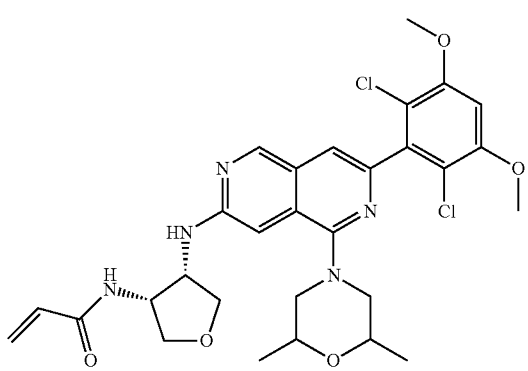 [SMILES: C=CC(=O)N[C@H]1COC[C@H]1Nc1cc2c(N3CC(C)OC(C)C3)nc(-c3c(Cl)c(OC)cc(OC)c3Cl)cc2cn1] | N-((3R,4S)-4-((7-(2,6-dichloro-3,5-dimethoxyphenyl)-5-(2,6-dimethylmorpholino)-2,6-naphthyridin-3-yl)amino)tetrahydrofuran-3-yl)acrylamide | 602 |

| Example No. | Compound structure | Compound name | MS: m/z [M + 1]+ |
|---|---|---|---|
| 317 | 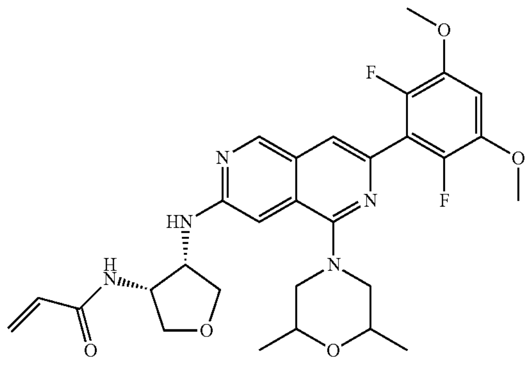 [SMILES: C=CC(=O)N[C@H]1COC[C@H]1Nc1cc2c(N3CC(C)OC(C)C3)nc(-c3c(F)c(OC)cc(OC)c3F)cc2cn1] | N-((3R,4S)-4-((7-(2,6-difluoro-3,5-dimethoxyphenyl)-5-(2,6-dimethylmorpholino)-2,6-naphthyridin-3-yl)amino)tetrahydrofuran-3-yl)acrylamide | 570 |
| 318 | 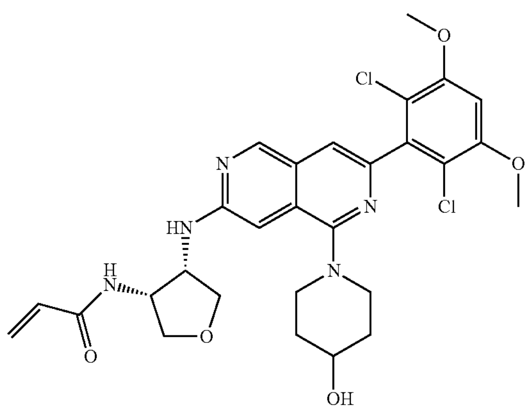 [SMILES: C=CC(=O)N[C@H]1COC[C@H]1Nc1cc2c(N3CCC(O)CC3)nc(-c3c(Cl)c(OC)cc(OC)c3Cl)cc2cn1] | N-((3R,4S)-4-((7-(2,6-dichloro-3,5-dimethoxyphenyl)-5-(4-hydroxypiperidin-1-yl)-2,6-naphthyridin-3-yl)amino)tetrahydrofuran-3-yl)acrylamide | 588 |
| 319 | 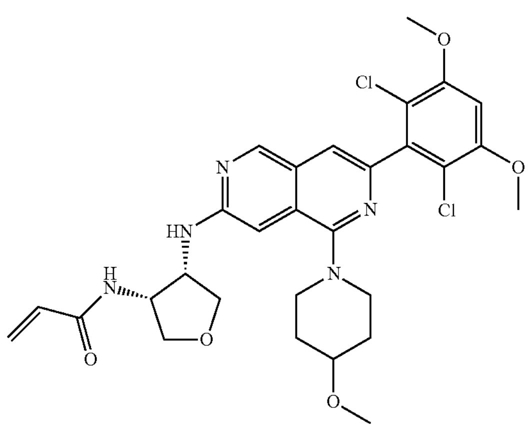 [SMILES: C=CC(=O)N[C@H]1COC[C@H]1Nc1cc2c(N3CCC(OC)CC3)nc(-c3c(Cl)c(OC)cc(OC)c3Cl)cc2cn1] | N-((3R,4S)-4-((7-(2,6-dichloro-3,5-dimethoxyphenyl)-5-(4-dimethoxypiperidin-1-yl)-2,6-naphthyridin-3-yl)amino)tetrahydrofuran-3-yl)acrylamide | 602 |

-continued

| Example No. | Compound structure | Compound name | MS: m/z [M + 1]+ |
|---|---|---|---|
| 320 | 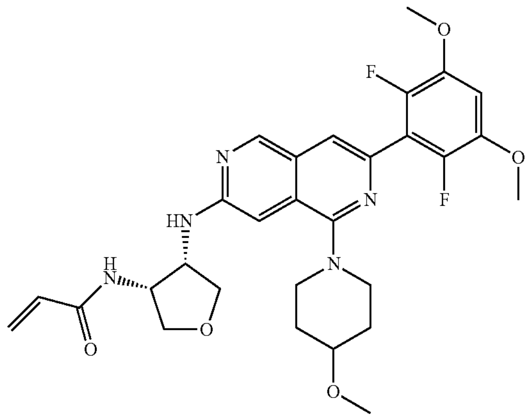 [SMILES: C=CC(=O)N[C@H]1COC[C@H]1Nc1cc2c(N3CCC(OC)CC3)nc(-c3c(F)c(OC)cc(OC)c3F)cc2cn1] | N-((3R,4S)-4-((7-(2,6-difluoro-3,5-dimethoxyphenyl)-5-(4-dimethoxypiperidin-1-yl)-2,6-naphthyridin-3-yl)amino)tetrahydrofuran-3-yl)acrylamide | 570 |
| 321 | 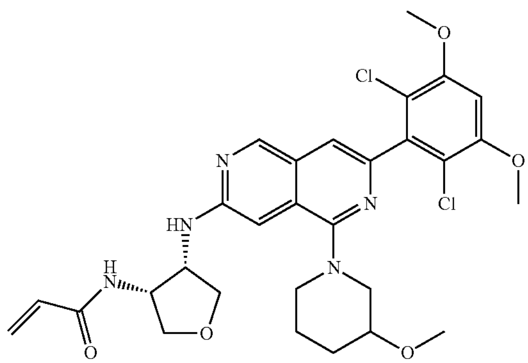 [SMILES: C=CC(=O)N[C@H]1COC[C@H]1Nc1cc2c(N3CCCC(OC)C3)nc(-c3c(Cl)c(OC)cc(OC)c3Cl)cc2cn1] | N-((3R,4S)-4-((7-(2,6-dichloro-3,5-dimethoxyphenyl)-5-(3-methoxypiperidin-1-yl)-2,6-naphthyridin-3-yl)amino)tetrahydrofuran-3-yl)acrylamide | 602 |
| 322 | 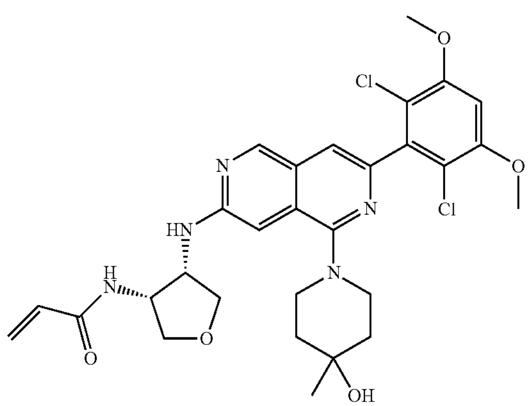 [SMILES: C=CC(=O)N[C@H]1COC[C@H]1Nc1cc2c(N3CCC(C)(O)CC3)nc(-c3c(Cl)c(OC)cc(OC)c3Cl)cc2cn1] | N-((3R,4S)-4-((7-(2,6-dichloro-3,5-dimethoxyphenyl)-5-(4-hydroxy-4-methyl-piperidin-1-yl)-2,6-naphthyridin-3-yl)amino)tetrahydrofuran-3-yl)acrylamide | 602 |
| 323 | 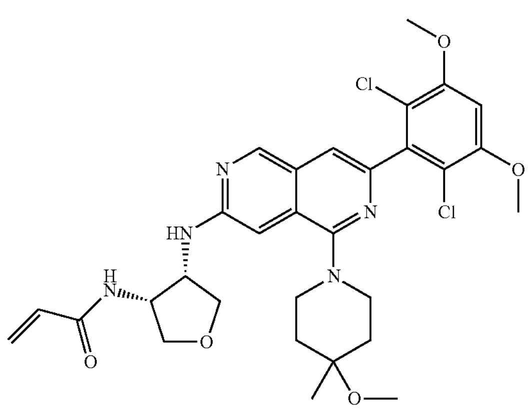 [SMILES: C=CC(=O)N[C@H]1COC[C@H]1Nc1cc2c(N3CCC(C)(OC)CC3)nc(-c3c(Cl)c(OC)cc(OC)c3Cl)cc2cn1] | N-((3R,4S)-4-((7-(2,6-dichloro-3,5-dimethoxyphenyl)-5-(4-methoxy-4-methyl-piperidin-1-yl)-2,6-naphthyridin-3-yl)amino)tetrahydrofuran-3-yl)acrylamide | 616 |

-continued

| Example No. | Compound structure | Compound name | MS: m/z [M + 1]+ |
|---|---|---|---|
| 324 | 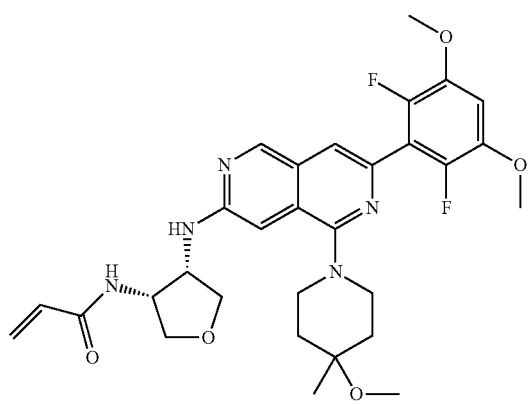 [SMILES: C=CC(=O)N[C@H]1COC[C@H]1Nc1cc2c(N3CCC(C)(OC)CC3)nc(-c3c(F)c(OC)cc(OC)c3F)cc2cn1] | N-((3R,4S)-4-((7-(2,6-difluoro-3,5-dimethoxyphenyl)-5-(4-methoxy-4-methyl-piperidin-1-yl)-2,6-naphthyridin-3-yl)amino)tetrahydrofuran-3-yl)acrylamide | 584 |
| 325 | 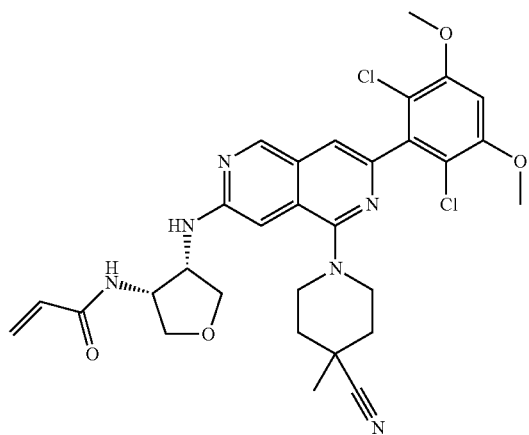 [SMILES: C=CC(=O)N[C@H]1COC[C@H]1Nc1cc2c(N3CCC(C)(C#N)CC3)nc(-c3c(Cl)c(OC)cc(OC)c3Cl)cc2cn1] | N-((3R,4S)-4-((5-(4-cyano-4-methyl-piperidin-1-yl)-7-(2,6-dichloro-3,5-dimethoxy-phenyl)-2,6-naphthyridin-3-yl)amino)tetrahydrofuran-3-yl)acrylamide | 611 |
| 326 | 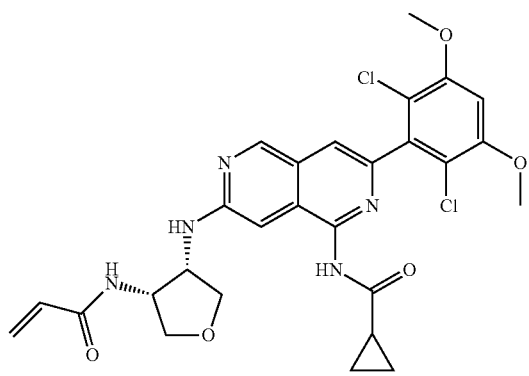 [SMILES: C=CC(=O)N[C@H]1COC[C@H]1Nc1cc2c(NC(=O)C3CC3)nc(-c3c(Cl)c(OC)cc(OC)c3Cl)cc2cn1] | N-(7-(((3S,4R)-4-acrylamidotetrahydro-furan-3-yl)amino)-3-(2,6-dichloro-3,5-dimethoxyphenyl)-2,6-naphthyridin-1-yl)cyclopropanecarboxamide | 572 |

-continued

| Example No. | Compound structure | Compound name | MS: m/z [M + 1]+ |
|---|---|---|---|
| 327 | 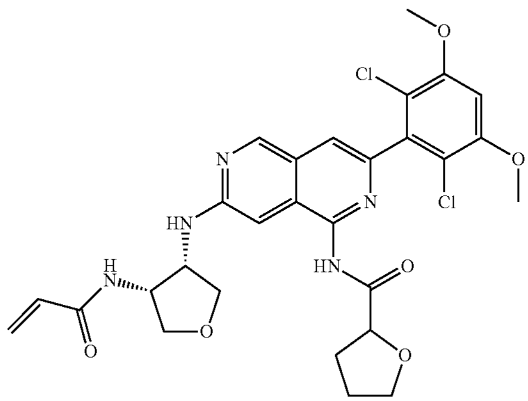 [SMILES: C=CC(=O)N[C@H]1COC[C@H]1Nc1cc2c(NC(=O)C3CCCO3)nc(-c3c(Cl)c(OC)cc(OC)c3Cl)cc2cn1] | N-(7-(((3S,4R)-4-acrylamidotetrahydro-furan-3-yl)-3-(2,6-dichloro-3,5-dimethoxyphenyl)-2,6-naphthyridin-1-yl)tetrahydrofuran-2-carboxamide | 602 |
| 328 | 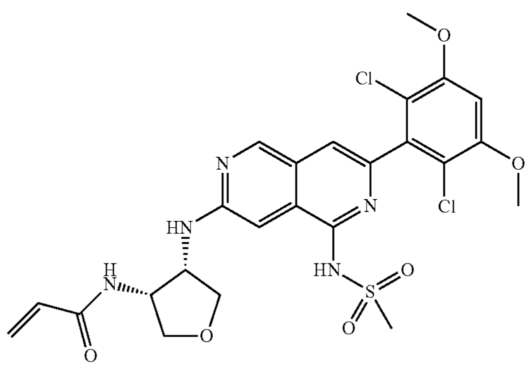 [SMILES: C=CC(=O)N[C@H]1COC[C@H]1Nc1cc2c(NS(C)(=O)=O)nc(-c3c(Cl)c(OC)cc(OC)c3Cl)cc2cn1] | N-((3R,4S)-4-((7-(2,6-dichloro-3,5-dimethoxyphenyl)-5-(methylsulfonamido)-2,6-naphthyridin-3-yl)amino)tetrahydro-furan-3-yl)acrylamide | 582 |
| 329 | 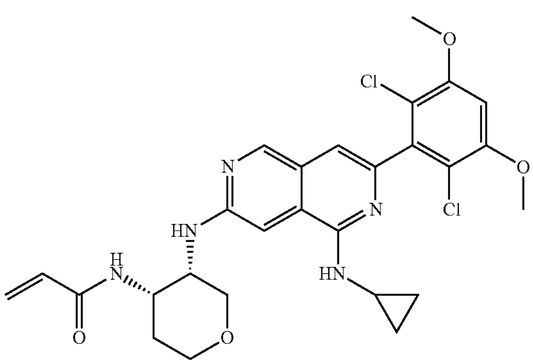 [SMILES: C=CC(=O)N[C@H]1CCOC[C@H]1Nc1cc2c(NC3CC3)nc(-c3c(Cl)c(OC)cc(OC)c3Cl)cc2cn1] | N-((3S,4S)-3-((5-(cyclopropylamino)-7-(2,6-dichloro-3,5-dimethoxyphenyl)-2,6-naphthyridin-3-yl)amino)tetrahydro-2H-pyran-4-yl)acrylamide | 558 |
| 330 | 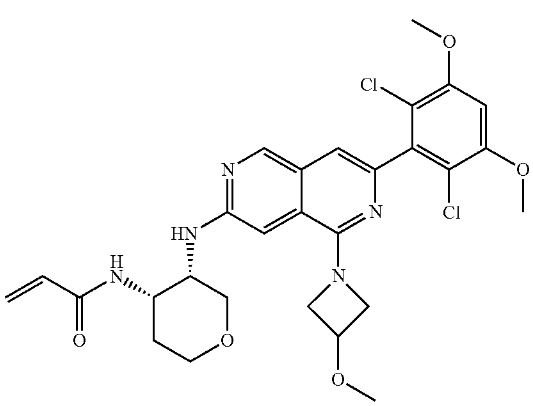 [SMILES: C=CC(=O)N[C@H]1CCOC[C@H]1Nc1cc2c(N3CC(OC)C3)nc(-c3c(Cl)c(OC)cc(OC)c3Cl)cc2cn1] | N-((3S,4S)-3-((7-(2,6-dichloro-3,5-dimethoxyphenyl)-5-(3-methoxyazetidin-1-yl)-2,6-naphthyridin-3-yl)amino)tetra-hydro-2H-pyran-4-yl)acrylamide | 588 |

-continued

| Example No. | Compound structure | Compound name | MS: m/z [M + 1]+ |
|---|---|---|---|
| 331 | 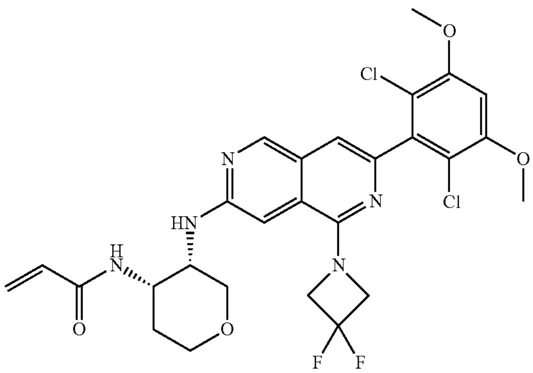 | N-((3S,4S)-3-((7-(2,6-dichloro-3,5-dimethoxyphenyl)-5-(3,3-difluoroazetidin-1-yl)-2,6-naphthyridin-3-yl)amino)tetrahydro-2H-pyran-4-yl)acrylamide | 594 |
| 332 | 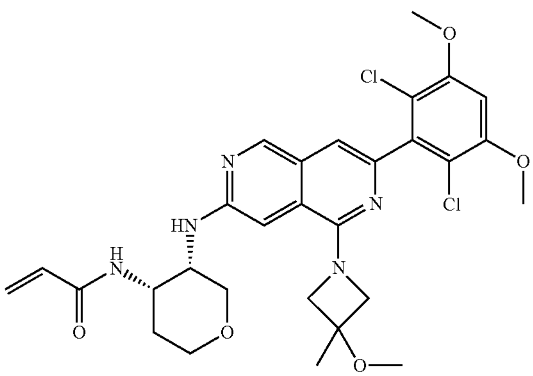 [SMILES: C=CC(=O)N[C@H]1CCOC[C@H]1Nc1cc2c(N3CC(C)(OC)C3)nc(-c3c(Cl)c(OC)cc(OC)c3Cl)cc2cn1] | N-((3S,4S)-3-((7-(2,6-dichloro-3,5-dimethoxyphenyl)-5-(3-dimethoxy-3-methyl-azetidin-1-yl)-2,6-naphthyridin-3-yl)amino)tetrahydro-2H-pyran-4-yl)acrylamide | 602 |
| 333 | 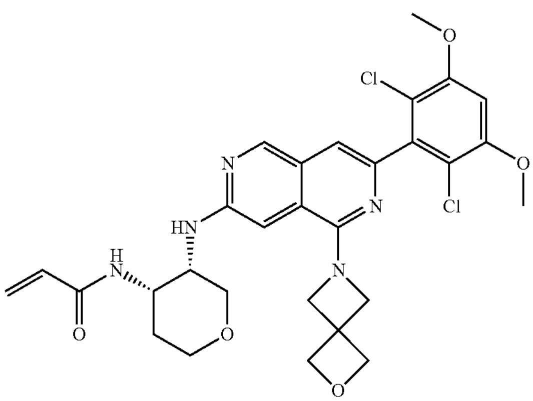 [SMILES: C=CC(=O)N[C@H]1CCOC[C@H]1Nc1cc2c(N3CC4(COC4)C3)nc(-c3c(Cl)c(OC)cc(OC)c3Cl)cc2cn1] | N-((3S,4S)-3-((7-(2,6-dichloro-3,5-dimethoxyphenyl)-5-(2-oxa-6-azaspiro[3.3]heptan-6-yl)-2,6-naphthyridin-3-yl)amino)tetrahydro-2H-pyran-4-yl)acrylamide | 600 |
| 334 | 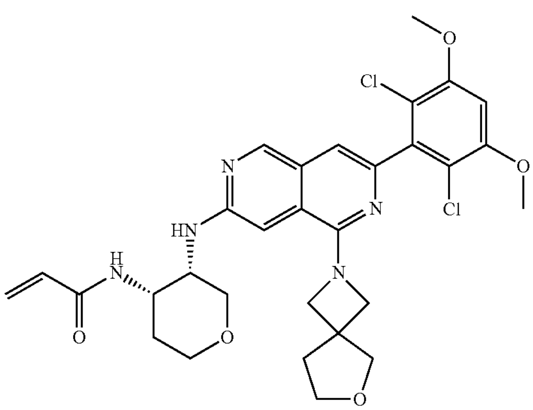 [SMILES: C=CC(=O)N[C@H]1CCOC[C@H]1Nc1cc2c(N3CC4(CCOC4)C3)nc(-c3c(Cl)c(OC)cc(OC)c3Cl)cc2cn1] | N-((3S,4S)-3-((7-(2,6-dichloro-3,5-dimethoxyphenyl)-5-(6-oxa-2-azaspiro[3.4]octan-2-yl)-2,6-naphthyridin-3-yl)amino)tetrahydro-2H-pyran-4-yl)acrylamide | 614 |

-continued

| Example No. | Compound structure | Compound name | MS: m/z [M + 1]+ |
|---|---|---|---|
| 335 | 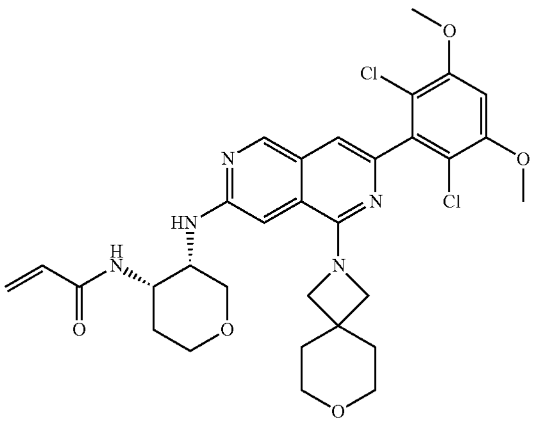 [SMILES: C=CC(=O)N[C@H]1CCOC[C@H]1Nc1cc2c(N3CC4(CCOCC4)C3)nc(-c3c(Cl)c(OC)cc(OC)c3Cl)cc2cn1] | N-((3S,4S)-3-((7-(2,6-dichloro-3,5-dimethoxyphenyl)-5-(7-oxa-2-azaspiro[3.5]nonan-2-yl)-2,6-naphthyridin-3-yl)amino)tetrahydro-2H-pyran-4-yl)acrylamide | 628 |
| 336 | 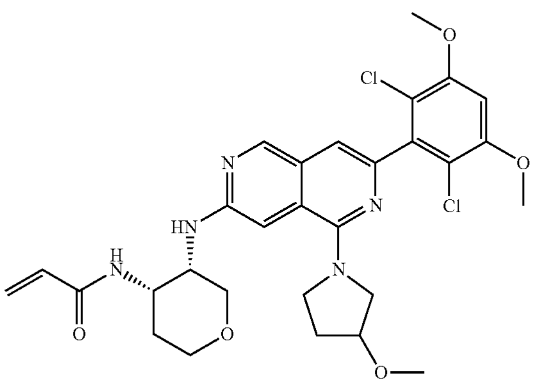 [SMILES: C=CC(=O)N[C@H]1CCOC[C@H]1Nc1cc2c(N3CCC(OC)C3)nc(-c3c(Cl)c(OC)cc(OC)c3Cl)cc2cn1] | N-((3S,4S)-3-((7-(2,6-dichloro-3,5-dimethoxyphenyl)-5-(3-dimethoxypyrrolidin-1-yl)-2,6-naphthyridin-3-yl)amino)tetrahydro-2H-pyran-4-yl)acrylamide | 602 |
| 337 | 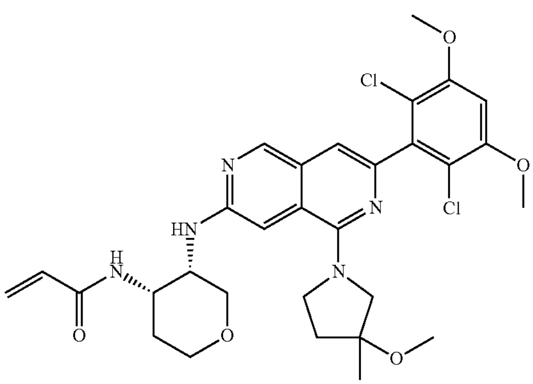 | N-((3S,4S)-3-((7-(2,6-dichloro-3,5-dimethoxyphenyl)-5-(3-dimethoxy-3-methyl-pyrrolidin-1-yl)-2,6-naphthyridin-3-yl)amino)tetrahydro-2H-pyran-4-yl)acrylamide | 616 |
| 338 | 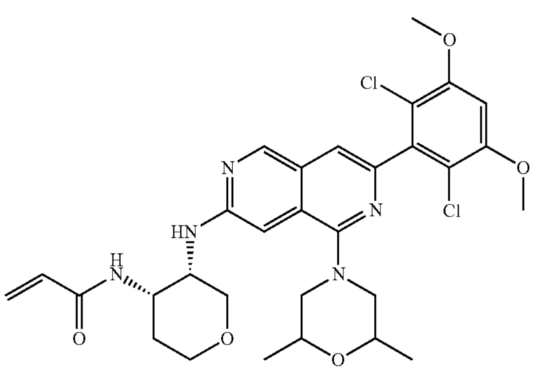 [SMILES: C=CC(=O)N[C@H]1CCOC[C@H]1Nc1cc2c(N3CC(C)OC(C)C3)nc(-c3c(Cl)c(OC)cc(OC)c3Cl)cc2cn1] | N-((3S,4S)-3-((7-(2,6-dichloro-3,5-dimethoxyphenyl)-5-(2,6-dimethylmorpholino)-2,6-naphthyridin-3-yl)amino)tetra-hydro-2H-pyran-4-yl)acrylamide | 616 |

-continued

| Example No. | Compound structure | Compound name | MS: m/z [M + 1]+ |
|---|---|---|---|
| 339 | 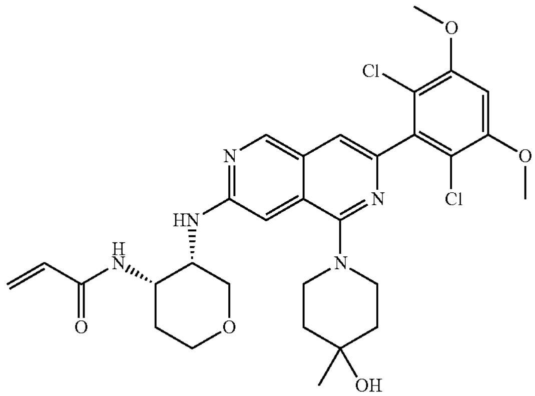 [SMILES: C=CC(=O)N[C@H]1CCOC[C@H]1Nc1cc2c(N3CCC(C)(O)CC3)nc(-c3c(Cl)c(OC)cc(OC)c3Cl)cc2cn1] | N-((3S,4S)-3-((7-(2,6-dichloro-3,5-dimethoxyphenyl)-5-(4-hydroxy-4-methylpiperidin-1-yl)-2,6-naphthyridin-3-yl)amino)tetrahydro-2H-pyran-4-yl)acrylamide | 616 |
| 340 | 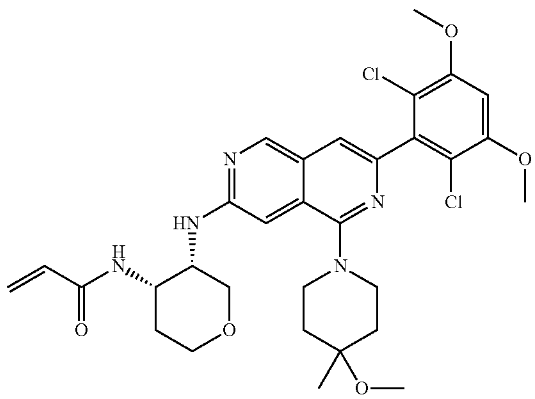 [SMILES: C=CC(=O)N[C@H]1CCOC[C@H]1Nc1cc2c(N3CCC(C)(OC)CC3)nc(-c3c(Cl)c(OC)cc(OC)c3Cl)cc2cn1] | N-((3S,4S)-3-((7-(2,6-dichloro-3,5-dimethoxyphenyl)-5-(4-dimethoxy-4-methyl-piperidin-1-yl)-2,6-naphthyridin-3-yl)amino)tetrahydro-2H-pyran-4-yl)acrylamide | 630 |
| 341 | 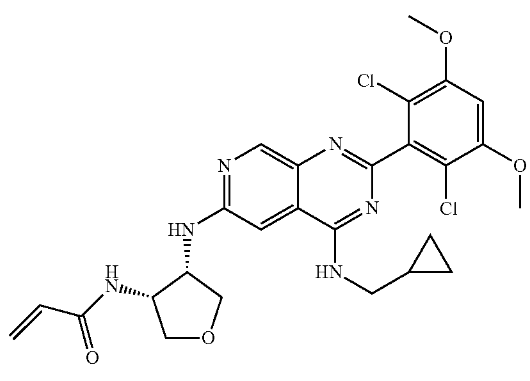 [SMILES: C=CC(=O)N[C@H]1COC[C@H]1Nc1cc2c(NCC3CC3)nc(-c3c(Cl)c(OC)cc(OC)c3Cl)nc2cn1] | N-((3R,4S)-4-((4-((cyclopropylmethyl)amino)-2-(2,6-dichloro-3,5-dimethoxyphenyl)pyrido[3,4-d]pyrimidin-6-yl)amino)tetrahydrofuran-3-yl)acrylamide | 559 |
| 342 | 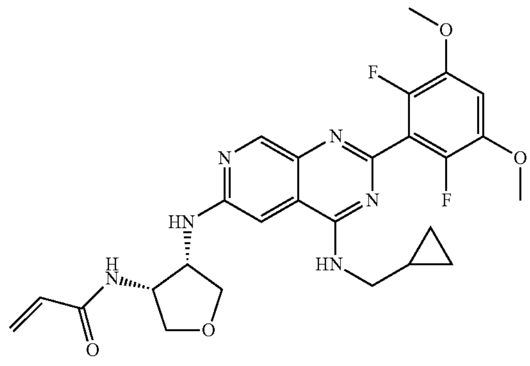 [SMILES: C=CC(=O)N[C@H]1COC[C@H]1Nc1cc2c(NCC3CC3)nc(-c3c(F)c(OC)cc(OC)c3F)nc2cn1] | N-((3R,4S)-4-((4-((cyclopropylmethyl)amino)-2-(2,6-difluoro-3,5-dimethoxyphenyl)pyrido[3,4-d]pyrimidin-6-yl)amino) tetrahydrofuran-3-yl)acrylamide | 527 |

| Example No. | Compound structure | Compound name | MS: m/z [M + 1]+ |
|---|---|---|---|
| 343 | 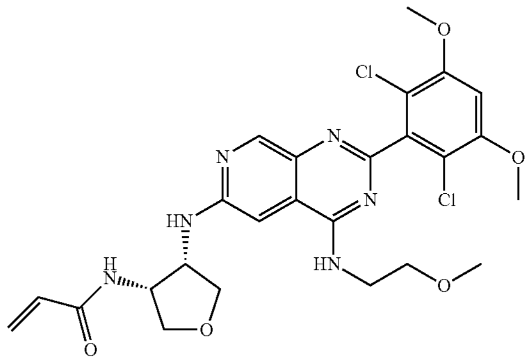 [SMILES: C=CC(=O)N[C@H]1COC[C@H]1Nc1cc2c(NCCOC)nc(-c3c(Cl)c(OC)cc(OC)c3Cl)nc2cn1] | N-((3R,4S)-4-((2-(2,6-dichloro-3,5-dimethoxyphenyl)-4-((2-dimethoxyethyl)amino)pyrido[3,4-d]pyrimidin-6-yl)amino)tetrahydrofuran-3-yl)acrylamide | 563 |
| 344 | 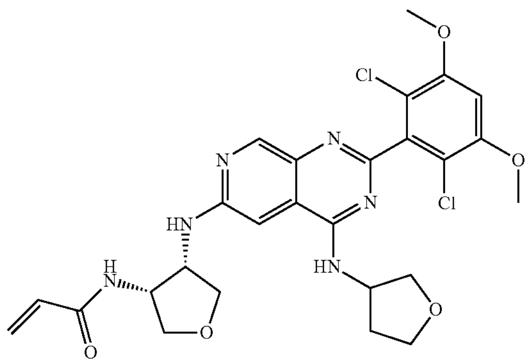 [SMILES: C=CC(=O)N[C@H]1COC[C@H]1Nc1cc2c(NC3CCOC3)nc(-c3c(Cl)c(OC)cc(OC)c3Cl)nc2cn1] | N-((3R,4S)-4-((2-(2,6-dichloro-3,5-dimethoxyphenyl)-4-((tetrahydrofuran-3-yl)amino)pyrido[3,4-d]pyrimidin-6-yl)amino)tetrahydrofuran-3-yl)acrylamide | 575 |
| 345 | 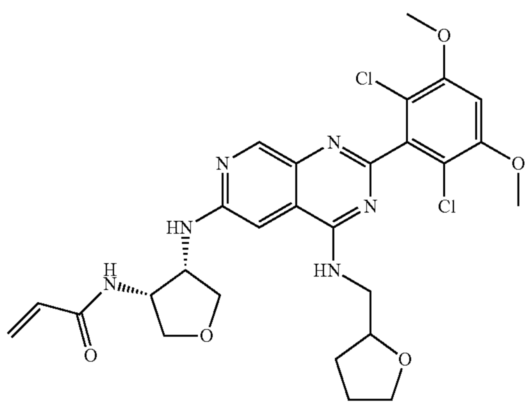 [SMILES: C=CC(=O)N[C@H]1COC[C@H]1Nc1cc2c(NCC3CCCO3)nc(-c3c(Cl)c(OC)cc(OC)c3Cl)nc2cn1] | N-((3R,4S)-4-((2-(2,6-dichloro-3,5-dimethoxyphenyl)-4-((tetrahydrofuran-2-yl)methyl)amino)pyrido[3,4-d]pyrimidin-6-yl)amino)tetrahydrofuran-3-yl)acrylamide | 589 |
| 346 | 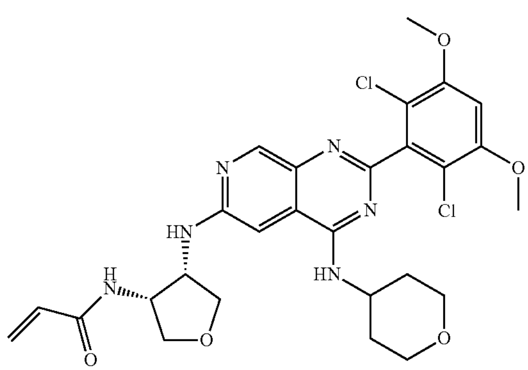 [SMILES: C=CC(=O)N[C@H]1COC[C@H]1Nc1cc2c(NC3CCOCC3)nc(-c3c(Cl)c(OC)cc(OC)c3Cl)nc2cn1] | N-((3R,4S)-4-((2-(2,6-dichloro-3,5-dimethoxyphenyl)-4-((tetrahydro-2H-pyran-4-yl)amino)pyrido[3,4-d]pyrimidin-6-yl)amino)tetrahydrofuran-3-yl)acrylamide | 589 |

-continued

| Example No. | Compound structure | Compound name | MS: m/z [M + 1]+ |
|---|---|---|---|
| 347 | 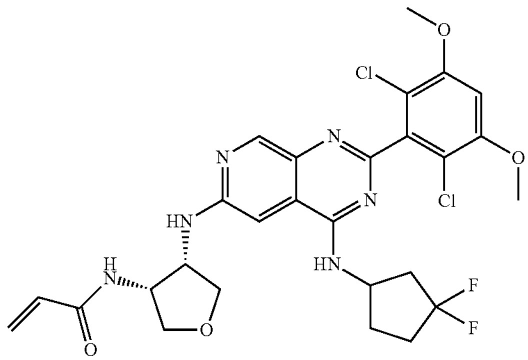 [SMILES: C=CC(=O)N[C@H]1COC[C@H]1Nc1cc2c(NC3CCC(F)(F)C3)nc(-c3c(Cl)c(OC)cc(OC)c3Cl)nc2cn1] | N-((3R,4S)-4-((2-(2,6-dichloro-3,5-dimethoxyphenyl)-4-(3,3-difluorocyclopentyl)amino)pyrido[3,4-d]pyrimidin-6-yl)amino)tetrahydrofuran-3-yl)acrylamide | 609 |
| 348 | 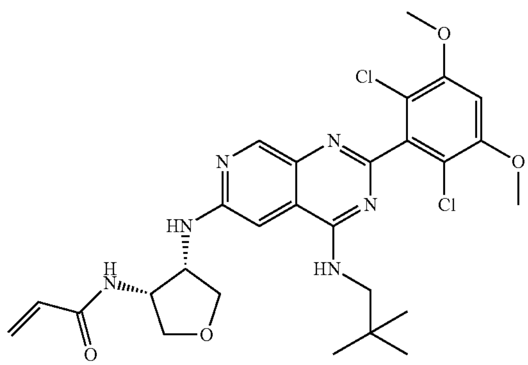 [SMILES: C=CC(=O)N[C@H]1COC[C@H]1Nc1cc2c(NCC(C)(C)C)nc(-c3c(Cl)c(OC)cc(OC)c3Cl)nc2cn1] | N-((3R,4S)-4-((2-(2,6-dichloro-3,5-dimethoxyphenyl)-4-(neopentylamino)pyrido[3,4-d]pyrimidin-6-yl)amino)tetrahydrofuran-3-yl)acrylamide | 575 |
| 349 | 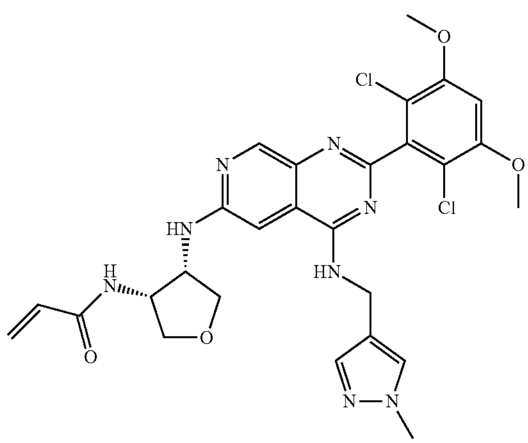 [SMILES: C=CC(=O)N[C@H]1COC[C@H]1Nc1cc2c(NCc3cnn(C)c3)nc(-c3c(Cl)c(OC)cc(OC)c3Cl)nc2cn1] | N-((3R,4S)-4-((2-(2,6-dichloro-3,5-dimethoxyphenyl)-4-(((1-methyl-1H-pyrazol-4-yl)methyl)amino)pyrido[3,4-d]pyrimidin-6-yl)amino)tetrahydrofuran-3-yl)acrylamide | 599 |
| 350 | 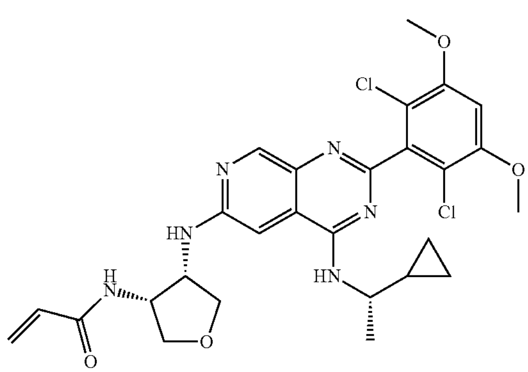 [SMILES: C=CC(=O)N[C@H]1COC[C@H]1Nc1cc2c(N[C@@H](C)C3CC3)nc(-c3c(Cl)c(OC)cc(OC)c3Cl)nc2cn1] | N-((3R,4S)-4-((4-(((S)-1-cyclopropylethyl)amino)-2-(2,6-dichloro-3,5-dimethoxyphenyl)pyrido[3,4-d]pyrimidin-6-yl)amino)tetrahydrofuran-3-yl)acrylamide | 573 |

-continued

| Example No. | Compound structure | Compound name | MS: m/z [M + 1]+ |
|---|---|---|---|
| 351 | 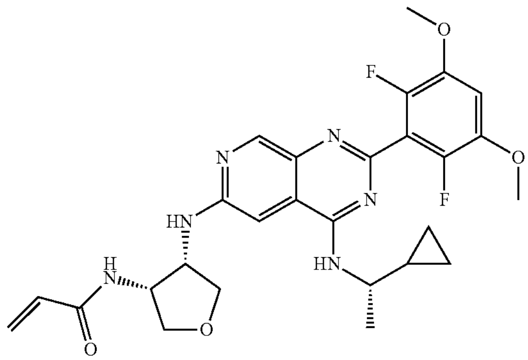 [SMILES: C=CC(=O)N[C@H]1COC[C@H]1Nc1cc2c(N[C@@H](C)C3CC3)nc(-c3c(F)c(OC)cc(OC)c3F)nc2cn1] | N-((3R,4S)-4-((4-(((S)-1-cyclopropyl-ethyl)amino)-2-(2,6-difluoro-3,5-dimethoxy-phenyl)pyrido[3,4-d]pyrimidin-6-yl)amino)tetrahydrofuran-3-yl)acrylamide | 541 |
| 352 | 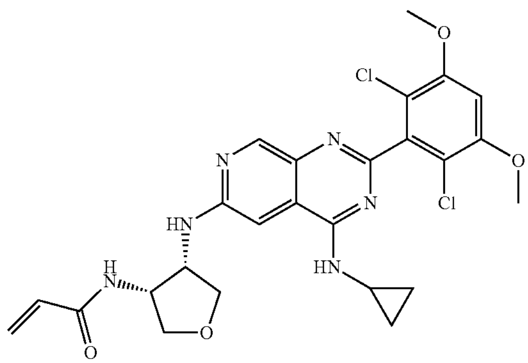 [SMILES: C=CC(=O)N[C@H]1COC[C@H]1Nc1cc2c(NC3CC3)nc(-c3c(Cl)c(OC)cc(OC)c3Cl)nc2cn1] | N-((3R,4S)-4-((4-(cyclopropylamino)-2-(2,6-dichloro-3,5-dimethoxyphenyl)pyrido[3,4-d]pyrimidin-6-yl)amino)tetra-hydrofuran-3-yl)acrylamide | 545 |
| 353 | 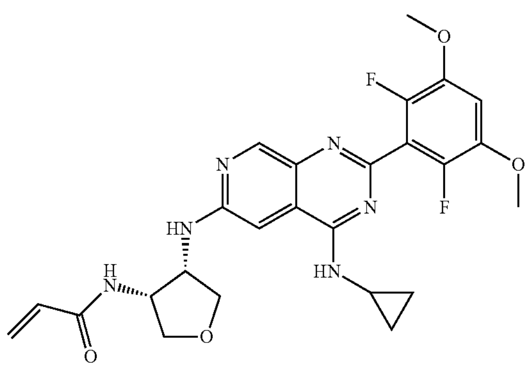 [SMILES: C=CC(=O)N[C@H]1COC[C@H]1Nc1cc2c(NC3CC3)nc(-c3c(F)c(OC)cc(OC)c3F)nc2cn1] | N-((3R,4S)-4-((4-(cyclopropylamino)-2-(2,6-difluoro-3,5-dimethoxyphenyl)pyrido[3,4-d]pyrimidin-6-yl)amino)tetra-hydrofuran-3-yl)acrylamide | 513 |
| 354 | 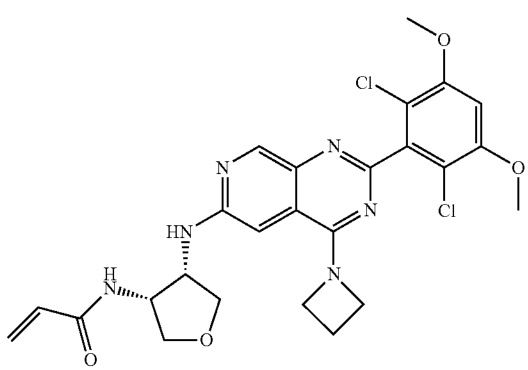 [SMILES: C=CC(=O)N[C@H]1COC[C@H]1Nc1cc2c(N3CCC3)nc(-c3c(Cl)c(OC)cc(OC)c3Cl)nc2cn1] | N-((3R,4S)-4-((4-(azetidin-1-yl)-2-(2,6-dichloro-3,5-dimethoxyphenyl)pyrido[3,4-d]pyrimidin-6-yl)amino)tetrahydrofuran-3-yl)acrylamide | 545 |

-continued

| Example No. | Compound structure | Compound name | MS: m/z [M + 1]+ |
|---|---|---|---|
| 355 | 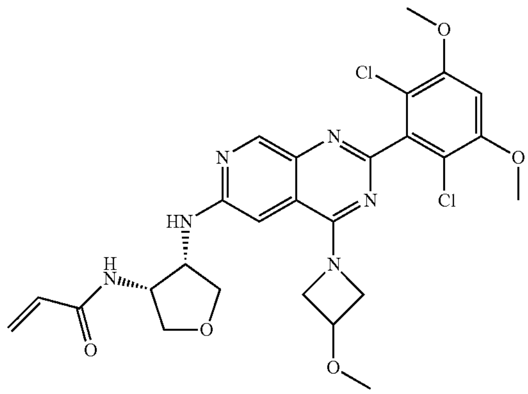 [SMILES: C=CC(=O)N[C@H]1COC[C@H]1Nc1cc2c(N3CC(OC)C3)nc(-c3c(Cl)c(OC)cc(OC)c3Cl)nc2cn1] | N-((3R,4S)-4-((2-(2,6-dichloro-3,5-dimethoxyphenyl)-4-(3-dimethoxyazetidin-1-yl)pyrido[3,4-d]pyrimidin-6-yl)amino)tetrahydrofuran-3-yl)acrylamide | 575 |
| 356 | 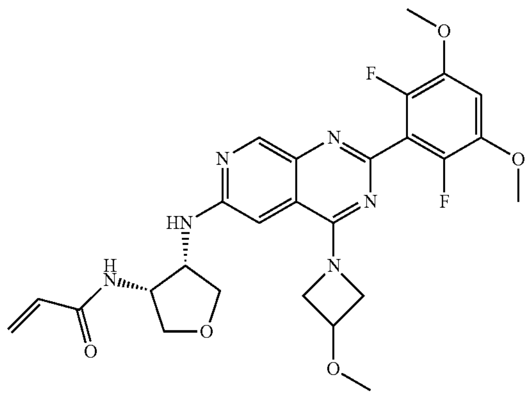 [SMILES: C=CC(=O)N[C@H]1COC[C@H]1Nc1cc2c(N3CC(OC)C3)nc(-c3c(F)c(OC)cc(OC)c3F)nc2cn1] | N-((3R,4S)-4-((2-(2,6-difluoro-3,5-dimethoxyphenyl)-4-(3-dimethoxyazetidin-1-yl)pyrido[3,4-d]pyrimidin-6-yl)amino)tetrahydrofuran-3-yl)acrylamide | 543 |
| 357 | 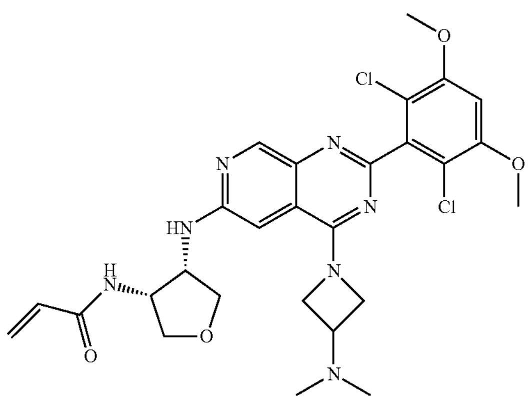 [SMILES: C=CC(=O)N[C@H]1COC[C@H]1Nc1cc2c(N3CC(N(C)C)C3)nc(-c3c(Cl)c(OC)cc(OC)c3Cl)nc2cn1] | N-((3R,4S)-4-((2-(2,6-dichloro-3,5-dimethoxyphenyl)-4-(3-(dimethylamino)azetidin-1-yl)pyrido[3,4-d]pyrimidin-6-yl)amino)tetrahydrofuran-3-yl)acrylamide | 588 |
| 358 | 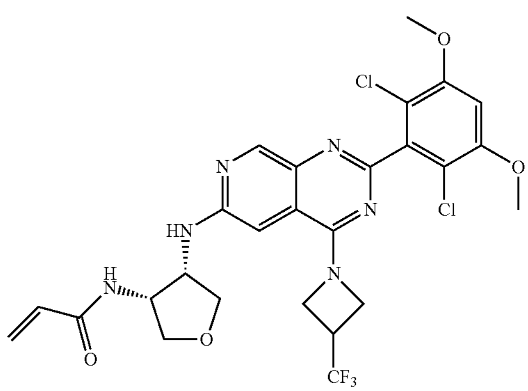 [SMILES: C=CC(=O)N[C@H]1COC[C@H]1Nc1cc2c(N3CC(C(F)(F)F)C3)nc(-c3c(Cl)c(OC)cc(OC)c3Cl)nc2cn1] | N-((3R,4S)-4-((2-(2,6-dichloro-3,5-dimethoxyphenyl)-4-(3-(trifluoromethyl)azetidin-1-yl)pyrido[3,4-d]pyrimidin-6-yl)amino)tetrahydrofuran-3-yl)acrylamide | 613 |

| Example No. | Compound structure | Compound name | MS: m/z [M + 1]+ |
|---|---|---|---|
| 359 | 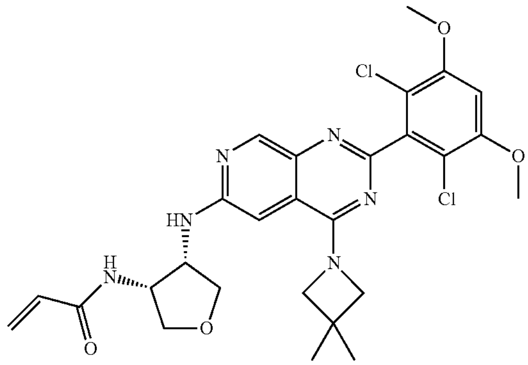 [SMILES: C=CC(=O)N[C@H]1COC[C@H]1Nc1cc2c(N3CC(C)(C)C3)nc(-c3c(Cl)c(OC)cc(OC)c3Cl)nc2cn1] | N-((3R,4S)-4-((2-(2,6-dichloro-3,5-dimethoxyphenyl)-4-(3,3-dimethylazetidin-1-yl)pyrido[3,4-d]pyrimidin-6-yl)amino)tetrahydrofuran-3-yl)acrylamide | 573 |
| 360 | 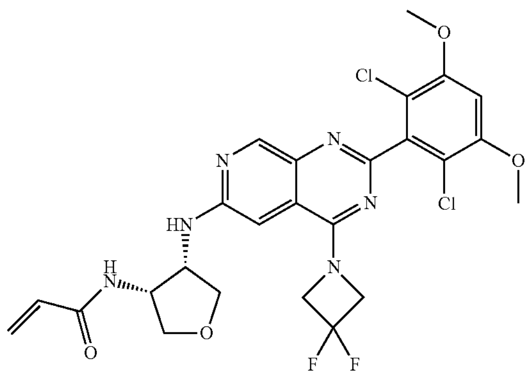 [SMILES: C=CC(=O)N[C@H]1COC[C@H]1Nc1cc2c(N3CC(F)(F)C3)nc(-c3c(Cl)c(OC)cc(OC)c3Cl)nc2cn1] | N-((3R,4S)-4-((2-(2,6-dichloro-3,5-dimethoxyphenyl)-4-(3,3-difluoroazetidin-1-yl)pyrido[3,4-d]pyritnidin-6-yl)amino)tetrahydrofuran-3-yl)acrylamide | 581 |
| 361 | 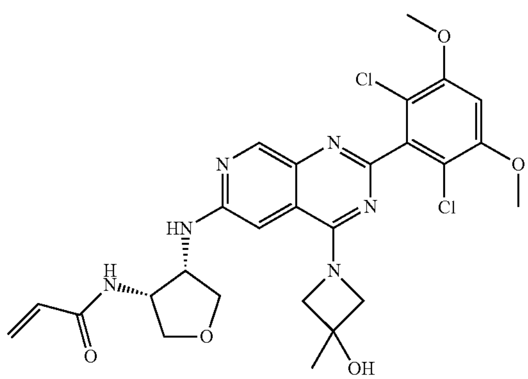 | N-((3R,4S)-4-((2-(2,6-dichloro-3,5-dimethoxyphenyl)-4-(3-hydroxy-3-methyl-azetidin-1-yl)pyrido[3,4-d]pyrimidin-6-yl)amino)tetrahydrofuran-3-yl)acrylamide | 575 |
| 362 | 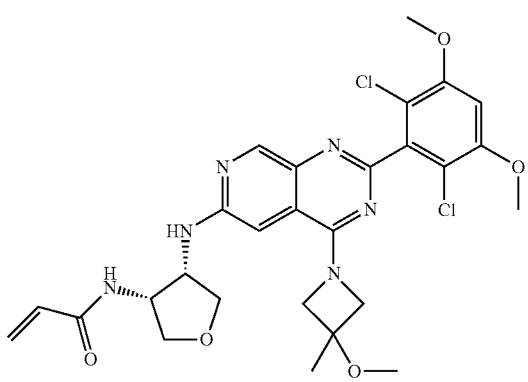 [SMILES: C=CC(=O)N[C@H]1COC[C@H]1Nc1cc2c(N3CC(C)(OC)C3)nc(-c3c(Cl)c(OC)cc(OC)c3Cl)nc2cn1] | N-((3R,4S)-4-((2-(2,6-dichloro-3,5-dimethoxyphenyl)-4-(3-methoxy-3-methyl-azetidin-1-yl)pyrido[3,4-d]pyrimidin-6-yl)amino)tetrahydrofuran-3-yl)acrylamide | 589 |

| Example No. | Compound structure | Compound name | MS: m/z [M + 1]+ |
|---|---|---|---|
| 363 | 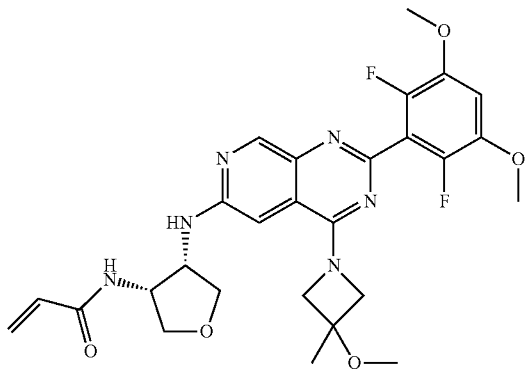 [SMILES: C=CC(=O)N[C@H]1COC[C@H]1Nc1cc2c(N3CC(C)(OC)C3)nc(-c3c(F)c(OC)cc(OC)c3F)nc2cn1] | N-((3R,4S)-4-((2-(2,6-difluoro-3,5-dimethoxyphenyl)-4-(3-dimethoxy-3-methyl-azetidin-1-yl)pyrido[3,4-d]pyrimidin-6-yl)amino)tetrahydrofuran-3-yl)acrylamide | 557 |
| 364 | 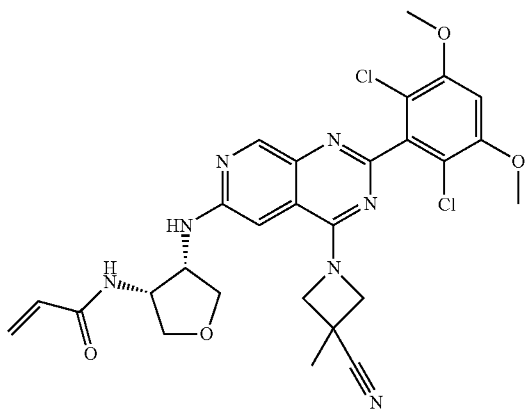 [SMILES: C=CC(=O)N[C@H]1COC[C@H]1Nc1cc2c(N3CC(C)(C#N)C3)nc(-c3c(Cl)c(OC)cc(OC)c3Cl)nc2cn1] | N-((3R,4S)-(4-((4-(3-cyano-3-methyl-azetidin-1-yl)-2-(2,6-dichloro-3,5-dimethoxy-phenyl)pyrido[3,4-d]pyrimidin-6-yl)amino)tetrahydrofuran-3-yl)acrylamide | 584 |
| 365 | 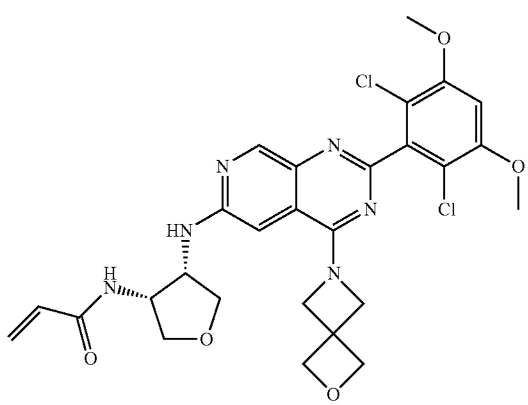 [SMILES: C=CC(=O)N[C@H]1COC[C@H]1Nc1cc2c(N3CC4(COC4)C3)nc(-c3c(Cl)c(OC)cc(OC)c3Cl)nc2cn1] | N-((3R,4S)-4-((2-(2,6-dichloro-3,5-dimethoxyphenyl)-4-(2-oxa-6-azaspiro[3.3]heptan-6-yl)pyrido[3,4-d]pyrimidin-6-yl)amino)tetrahydrofuran-3-yl)acrylamide | 587 |
| 366 | 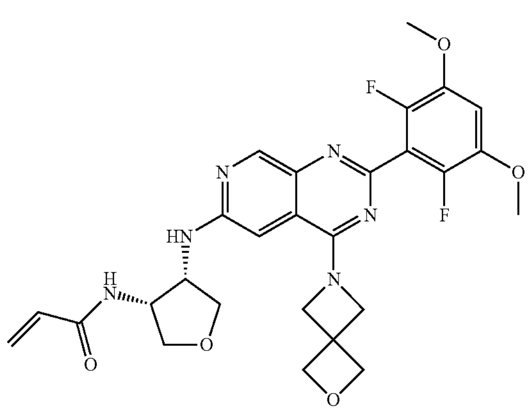 [SMILES: C=CC(=O)N[C@H]1COC[C@H]1Nc1cc2c(N3CC4(COC4)C3)nc(-c3c(F)c(OC)cc(OC)c3F)nc2cn1] | N-((3R,4S)-4-((2-(2,6-difluoro-3,5-dimethoxyphenyl)-4-(2-oxa-6-azaspiro[3.3]heptan-6-yl)pyrido[3,4-d]pyrimidin-6-yl)amino)tetrahydrofuran-3-yl)acrylamide | 555 |

| Example No. | Compound structure | Compound name | MS: m/z [M + 1]+ |
|---|---|---|---|
| 367 | 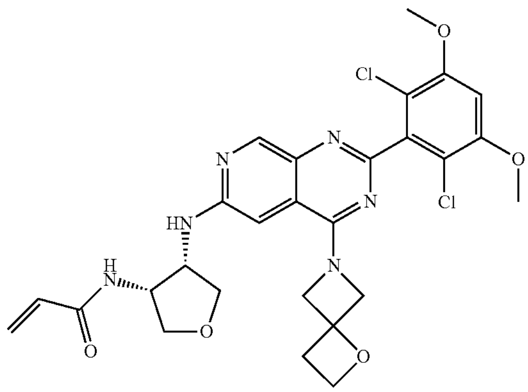 [SMILES: C=CC(=O)N[C@H]1COC[C@H]1Nc1cc2c(N3CC4(CCO4)C3)nc(-c3c(Cl)c(OC)cc(OC)c3Cl)nc2cn1] | N-((3R,4S)-4-((2-(2,6-dichloro-3,5-dimethoxyphenyl)-4-(1-oxa-6-azaspiro[3.3]heptan-6-yl)pyrido[3,4-d]pyrimidin-6-yl)amino)tetrahydrofuran-3-yl)acrylamide | 587 |
| 368 | 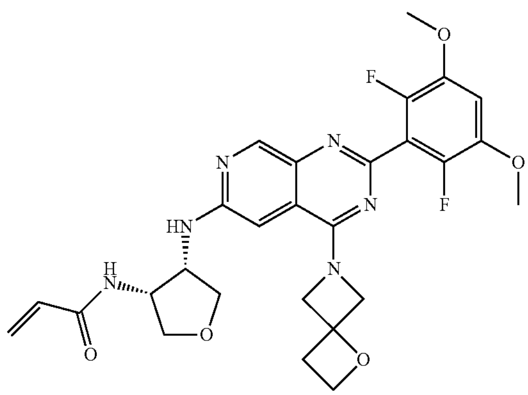 [SMILES: C=CC(=O)N[C@H]1COC[C@H]1Nc1cc2c(N3CC4(CCO4)C3)nc(-c3c(F)c(OC)cc(OC)c3F)nc2cn1] | N-((3R,4S)-4-((2-(2,6-difluoro-3,5-dimethoxyphenyl)-4-(1-oxa-6-azaspiro[3.3]heptan-6-yl)pyrido[3,4-d]pyrimidin-6-yl)amino)tetrahydrofuran-3-yl)acrylamide | 555 |
| 369 | 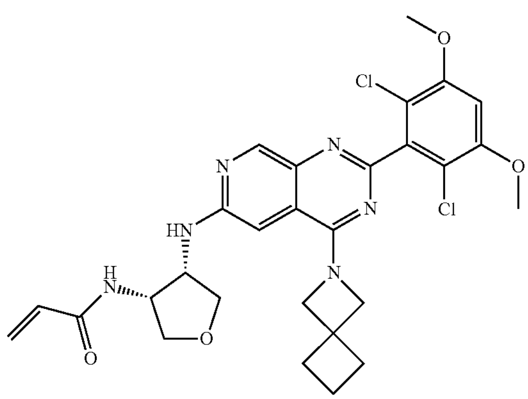 [SMILES: C=CC(=O)N[C@H]1COC[C@H]1Nc1cc2c(N3CC4(CCC4)C3)nc(-c3c(Cl)c(OC)cc(OC)c3Cl)nc2cn1] | N-((3R,4S)-4-((2-(2,6-dichloro-3,5-dimethoxyphenyl)-4-(2-azaspiro[3.3]heptan-2-yl)pyrido[3,4-d]pyrimidin-6-yl)amino)tetrahydrofuran-3-yl)acrylamide | 585 |
| 370 | 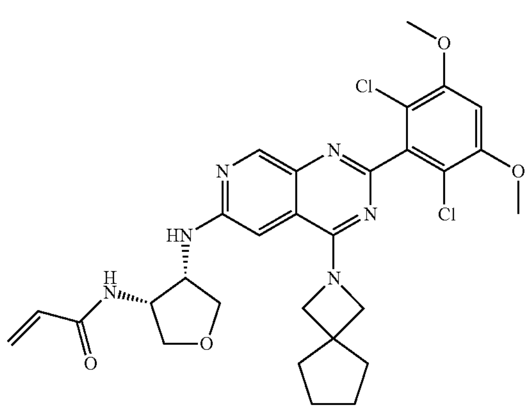 [SMILES: C=CC(=O)N[C@H]1COC[C@H]1Nc1cc2c(N3CC4(CCCC4)C3)nc(-c3c(Cl)c(OC)cc(OC)c3Cl)nc2cn1] | N-((3R,4S)-4-((2-(2,6-dichloro-3,5-dimethoxyphenyl)-4-(2-azaspiro[3.4]octan-2-yl)pyrido[3,4-d]pyrimidin-6-yl)amino)tetrahydrofuran-3-yl)acrylamide | 599 |

-continued

| Example No. | Compound structure | Compound name | MS: m/z [M + 1]+ |
|---|---|---|---|
| 371 | 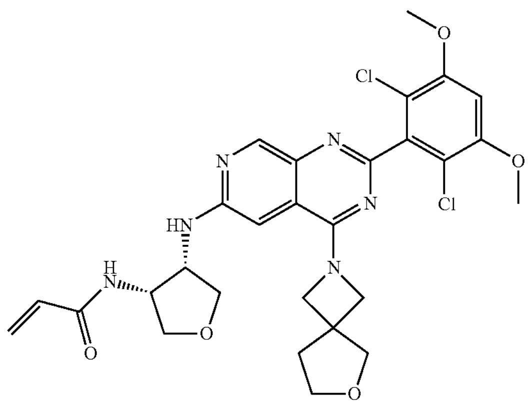 [SMILES: C=CC(=O)N[C@H]1COC[C@H]1Nc1cc2c(N3CC4(CCOC4)C3)nc(-c3c(Cl)c(OC)cc(OC)c3Cl)nc2cn1] | N-((3R,4S)-4-((2-(2,6-dichloro-3,5-dimethoxyphenyl)-4-(6-oxa-2-azaspiro[3.4]octan-2-yl)pyrido[3,4-d]pyrimidin-6-yl)amino)tetrahydrofuran-3-yl)acrylamide | 601 |
| 372 | 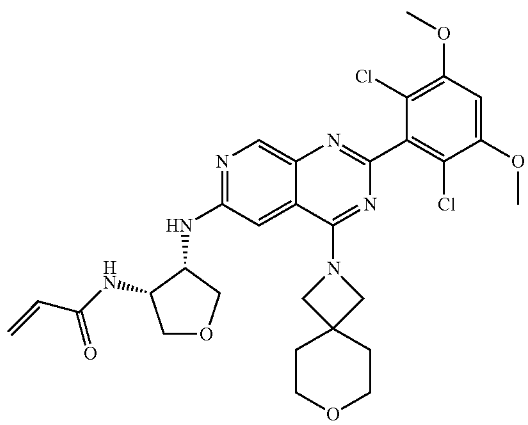 [SMILES: C=CC(=O)N[C@H]1COC[C@H]1Nc1cc2c(N3CC4(CCOCC4)C3)nc(-c3c(Cl)c(OC)cc(OC)c3Cl)nc2cn1] | N-((3R,4S)-4-((2-(2,6-dichloro-3,5-dimethoxyphenyl)-4-(7-oxa-2-azaspiro[3.5]nonan-2-yl)pyrido[3,4-d]pyrimidin-6-yl)amino)tetrahydrofuran-3-yl)acrylamide | 615 |
| 373 | 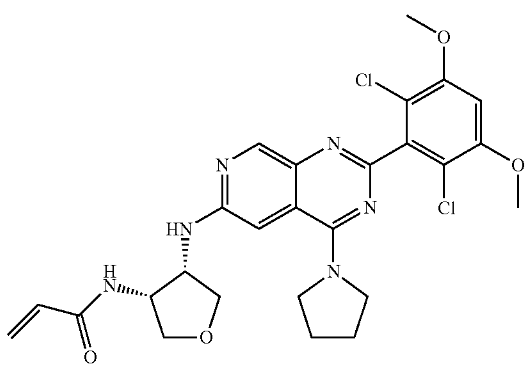 [SMILES: C=CC(=O)N[C@H]1COC[C@H]1Nc1cc2c(N3CCCC3)nc(-c3c(Cl)c(OC)cc(OC)c3Cl)nc2cn1] | N-(3R,4S)-4-((2-(2,6-dichloro-3,5-dimethoxyphenyl)-4-(pyrrolidin-1-yl)pyrido[3,4-d]pyrimidin-6-yl)amino)tetrahydrofuran-3-yl)acrylamide | 559 |
| 374 | 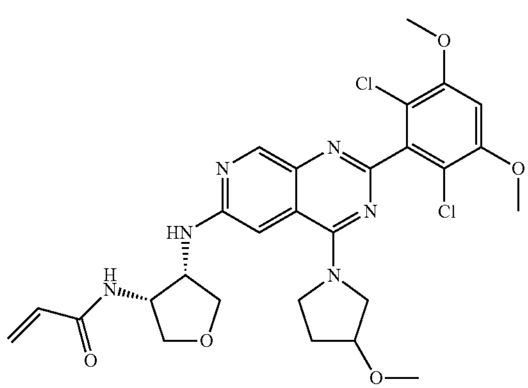 [SMILES: C=CC(=O)N[C@H]1COC[C@H]1Nc1cc2c(N3CCC(OC)C3)nc(-c3c(Cl)c(OC)cc(OC)c3Cl)nc2cn1] | N-((3R,4S)-4-((2-(2,6-dichloro-3,5-dimethoxyphenyl)-4-(3-methoxypyrrolidin-1-yl)pyrido[3,4-d]pyrimidin-6-yl)amino)tetrahydrofuran-3-yl)acrylamide | 589 |

-continued

| Example No. | Compound structure | Compound name | MS: m/z [M + 1]+ |
|---|---|---|---|
| 375 | 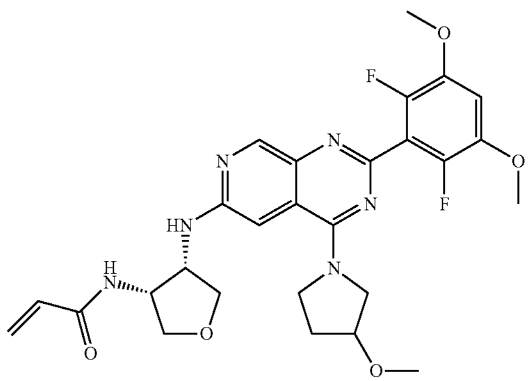 [SMILES: C=CC(=O)N[C@H]1COC[C@H]1Nc1cc2c(N3CCC(OC)C3)nc(-c3c(F)c(OC)cc(OC)c3F)nc2cn1] | N-((3R,4S)-4-((2-(2,6-difluoro-3,5-dimethoxyphenyl)-4-(3-methoxypyrrolidin-1-yl)pyrido[3,4-d]pyrimidin-6-yl)amino)tetrahydrofuran-3-yl)acrylamide | 557 |
| 376 | 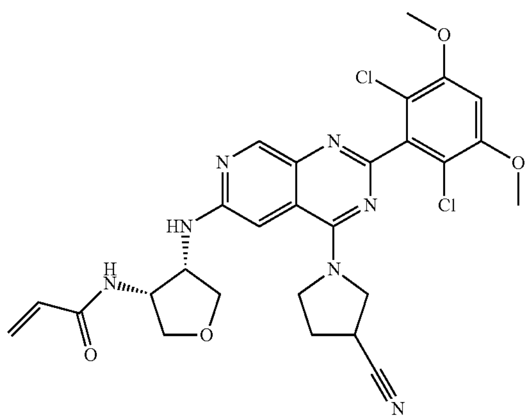 | N-((3R,4S)-4-((4-(3-cyanopyrrolidin-1-yl)-2-(2,6-dichloro-3,5-dimethoxyphenyl)pyrido[3,4-d]pyrimidin-6-yl)amino)tetrahydrofuran-3-yl)acrylamide | 584 |
| 377 | 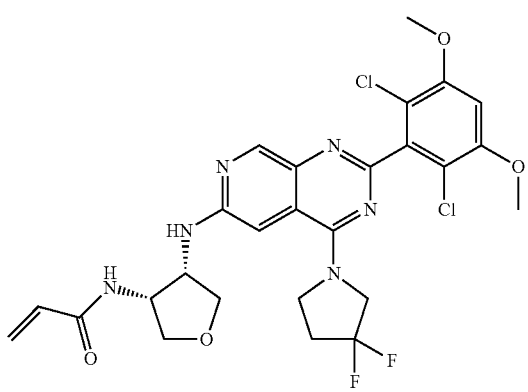 [SMILES: C=CC(=O)N[C@H]1COC[C@H]1Nc1cc2c(N3CCC(F)(F)C3)nc(-c3c(Cl)c(OC)cc(OC)c3Cl)nc2cn1] | N-((3R,4S)-4-((2-(2,6-dichloro-3,5-dimethoxyphenyl)-4-(3,3-difluoropyrrolidin-1-yl)pyrido[3,4-d]pyrimidin-6-yl)amino)tetrahydrofuran-3-yl)acrylamide | 595 |
| 378 | 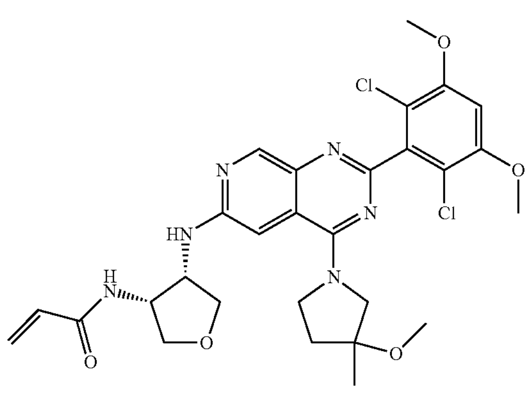 | N-((3R,4S)-4-((2-(2,6-dichloro-3,5-dimethoxyphenyl)-4-(3-dimethoxy-3-methyl-pyrrolidin-1-yl)pyrido[3,4-d]pyrimidin-6-yl)amino)tetrahydrofuran-3-yl)acrylamide | 603 |

| Example No. | Compound structure | Compound name | MS: m/z [M + 1]+ |
|---|---|---|---|
| 379 | 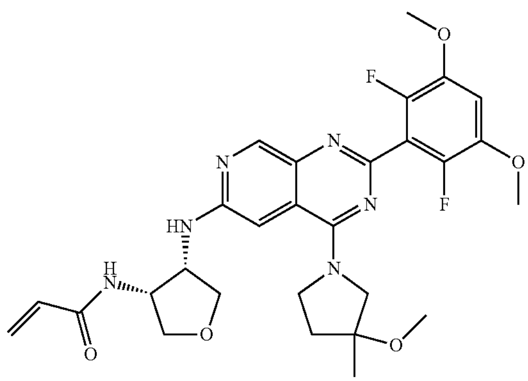 | N-((3R,4S)-4-((2-(2,6-difluoro-3,5-dimethoxyphenyl)-4-(3-methoxy-3-methyl-pyrrolidin-1-yl)pyrido[3,4-d]pyrimidin-6-yl)amino)tetrahydrofuran-3-yl)acrylamide | 571 |
| 380 | 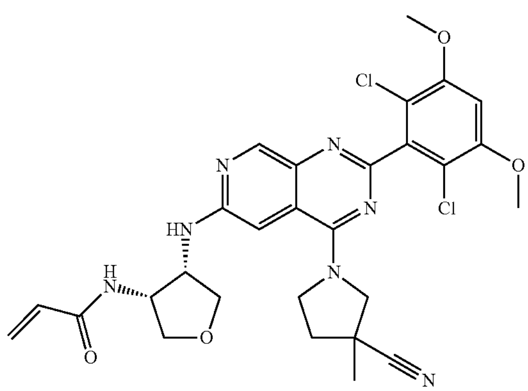 [SMILES: C=CC(=O)N[C@H]1COC[C@H]1Nc1cc2c(N3CCC(C)(C#N)C3)nc(-c3c(Cl)c(OC)cc(OC)c3Cl)nc2cn1] | N-((3R,4S)-4-((4-(3-cyano-3-methyl-pyrrolidin-1-yl)-2-(2,6-dichloro-3,5-dimethoxyphenyl)pyrido[3,4-d]pyrimidin-6-yl)amino)tetrahydrofuran-3-yl)acrylamide | 598 |
| 381 | 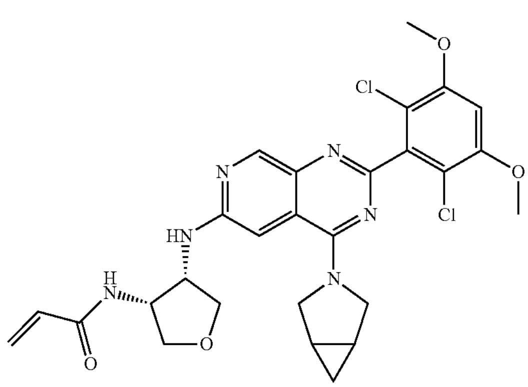 [SMILES: C=CC(=O)N[C@H]1COC[C@H]1Nc1cc2c(N3CC4CC4C3)nc(-c3c(Cl)c(OC)cc(OC)c3Cl)nc2cn1] | N-((3R,4S)-4-((4-(3-azabicyclo[3.1.0]hexan-3-yl)-2-(2,6-dichloro-3,5-dimethoxyphenyl)pyrido[3,4-d]pyrimidin-6-yl)amino)tetrahydrofuran-3-yl)acrylamide | 571 |
| 382 | 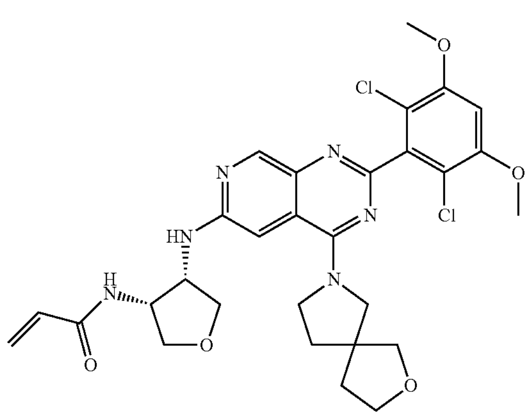 [SMILES: C=CC(=O)N[C@H]1COC[C@H]1Nc1cc2c(N3CCC4(CCOC4)C3)nc(-c3c(Cl)c(OC)cc(OC)c3Cl)nc2cn1] | N-((3R,4S)-4-((2-(2,6-dichloro-3,5-dimethoxyphenyl)-4-(2-oxa-7-azaspiro[4.4]nonan-7-yl)pyrido[3,4-d]pyrimidin-6-yl)amino)tetrahydrofuran-3-yl)acrylamide | 615 |

| Example No. | Compound structure | Compound name | MS: m/z [M + 1]+ |
|---|---|---|---|
| 383 | 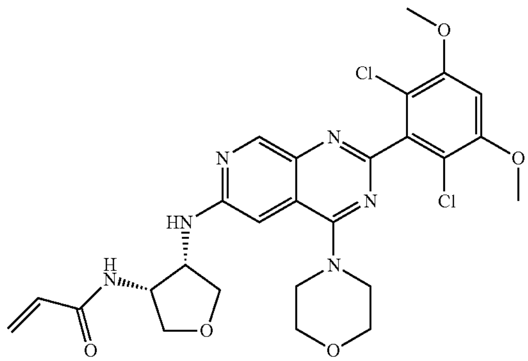 [SMILES: C=CC(=O)N[C@H]1COC[C@H]1Nc1cc2c(N3CCOCC3)nc(-c3c(Cl)c(OC)cc(OC)c3Cl)nc2cn1] | N-(3R,4S)-4-((2-(2,6-dichloro-3,5-dimethoxyphenyl)-4-morpholinopyrido[3,4-d]pyrimidin-6-yl)amino)tetrahydrofuran-3-yl)acrylamide | 573 |
| 384 | 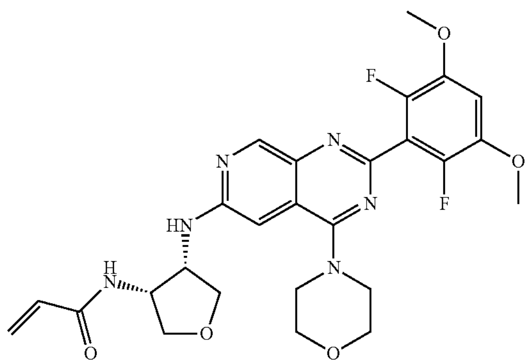 [SMILES: C=CC(=O)N[C@H]1COC[C@H]1Nc1cc2c(N3CCOCC3)nc(-c3c(F)c(OC)cc(OC)c3F)nc2cn1] | N-((3R,4S)-4-((2-(2,6-difluoro-3,5-dimethoxyphenyl)-4-morpholinopyrido[3,4-d]pyrimidin-6-yl)amino)tetrahydrofuran-3-yl)acrylamide | 543 |
| 385 | 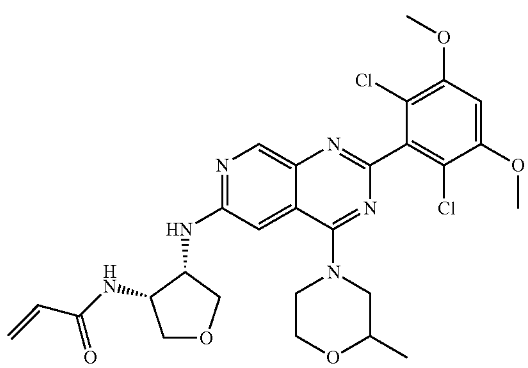 [SMILES: C=CC(=O)N[C@H]1COC[C@H]1Nc1cc2c(N3CCOC(C)C3)nc(-c3c(Cl)c(OC)cc(OC)c3Cl)nc2cn1] | N-((3R,4S)-4-((2-(2,6-dichloro-3,5-dimethoxyphenyl)-4-(2-methylmorpholino)pyrido[3,4-d]pyrimidin-6-yl)amino)tetrahydrofuran-3-yl)acrylamide | 589 |
| 386 | 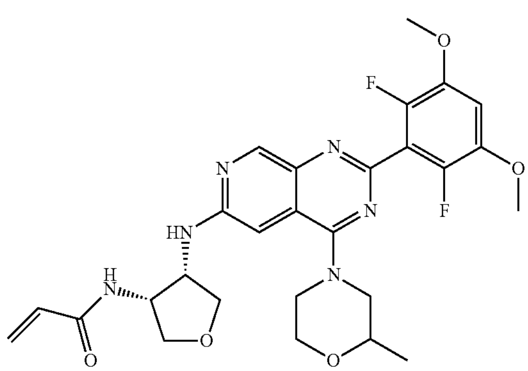 [SMILES: C=CC(=O)N[C@H]1COC[C@H]1Nc1cc2c(N3CCOC(C)C3)nc(-c3c(F)c(OC)cc(OC)c3F)nc2cn1] | N-((3R,4S)-4-((2-(2,6-difluoro-3,5-dimethoxyphenyl)-4-(2-methylmorpholino)pyrido[3,4-d]pyrimidin-6-yl)amino)tetrahydrofuran-3-yl)acrylamide | 557 |

-continued

| Example No. | Compound structure | Compound name | MS: m/z [M + 1]+ |
|---|---|---|---|
| 387 | 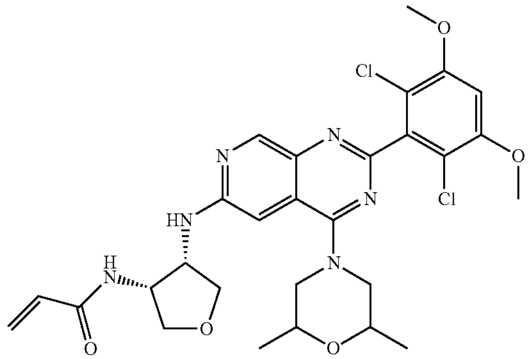 [SMILES: C=CC(=O)N[C@H]1COC[C@H]1Nc1cc2c(N3CC(C)OC(C)C3)nc(-c3c(Cl)c(OC)cc(OC)c3Cl)nc2cn1] | N-((3R,4S)-4-((2-(2,6-dichloro-3,5-dimethoxyphenyl)-4-(2,6-dimethylmorpholino)pyrido[3,4-d]pyrimidin-6-yl)amino)tetrahydrofuran-3-yl)acrylamide | 603 |
| 388 | 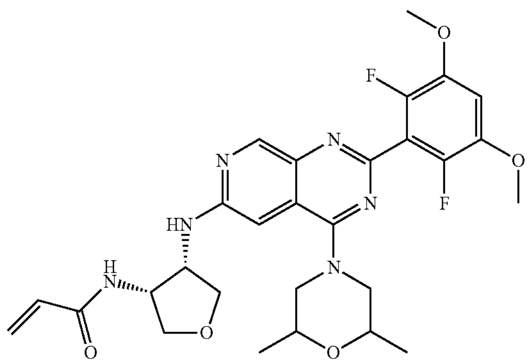 [SMILES: C=CC(=O)N[C@H]1COC[C@H]1Nc1cc2c(N3CC(C)OC(C)C3)nc(-c3c(F)c(OC)cc(OC)c3F)nc2cn1] | N-((3R,4S)-4-((2-(2,6-difluoro-3,5-dimethoxyphenyl)-4-(2,6-dimethylmorpholino)pyrido[3,4-d]pyrimidin-6-yl)amino)tetrahydrofuran-3-yl)acrylamide | 571 |
| 389 | 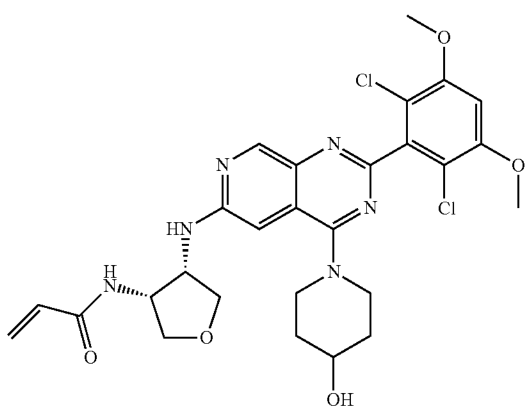 [SMILES: C=CC(=O)N[C@H]1COC[C@H]1Nc1cc2c(N3CCC(O)CC3)nc(-c3c(Cl)c(OC)cc(OC)c3Cl)nc2cn1] | N-((3R,4S)-4-((2-(2,6-dichloro-3,5-dimethoxyphenyl)-4-(4-hydroxypiperidin-yl)pyrido[3,4-d]pyrimidin-6-yl)amino)tetrahydrofuran-3-yl)acrylamide | 589 |
| 390 | 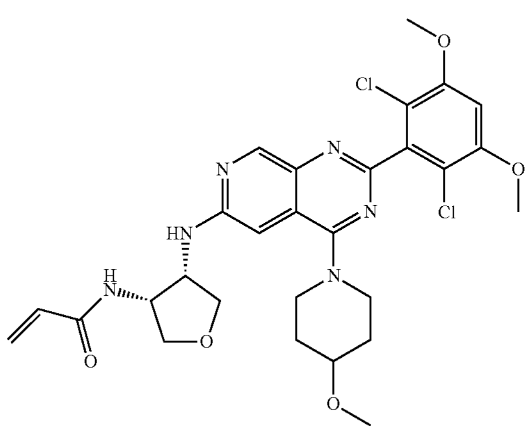 [SMILES: C=CC(=O)N[C@H]1COC[C@H]1Nc1cc2c(N3CCC(OC)CC3)nc(-c3c(Cl)c(OC)cc(OC)c3Cl)nc2cn1] | N-((3R,4S)-4-((2-(2,6-dichloro-3,5-dimethoxyphenyl)-4-(4-methoxypiperidin-1-yl)pyrido[3,4-d]pyrimidin-6-yl)amino)tetrahydrofuran-3-yl)acrylamide | 603 |

-continued

| Example No. | Compound structure | Compound name | MS: m/z [M + 1]+ |
|---|---|---|---|
| 391 | 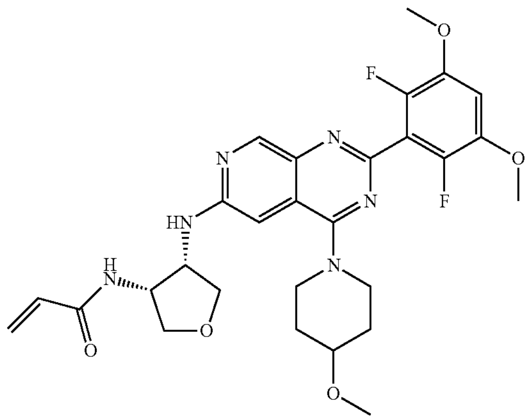 | N-((3R,4S)-4-((2-(2,6-difluoro-3,5-dimethoxyphenyl)-4-(4-methoxypiperidin-1-yl)pyrido[3,4-d]pyrimidin-6-yl)amino) tetrahydrofuran-3-yl)acrylamide | 571 |
| 392 | 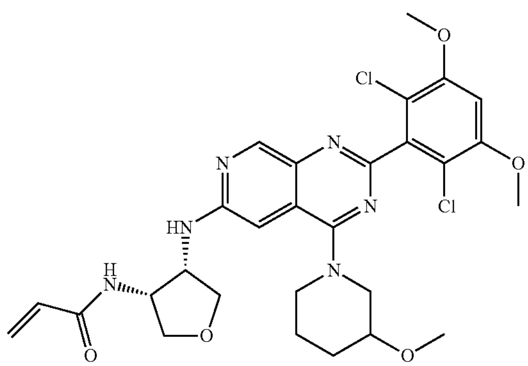 [SMILES: C=CC(=O)N[C@H]1COC[C@H]1Nc1cc2c(N3CCCC(OC)C3)nc(-c3c(Cl)c(OC)cc(OC)c3Cl)nc2cn1] | N-((3R,4S)-4-((2-(2,6-dichloro-3,5-dimethoxyphenyl)-4-(3-dimethoxypiperidin-1-yl)pyrido[3,4-d]pyrimidin-6-yl)amino) tetrahydrofuran-3-yl)acrylamide | 603 |
| 393 | 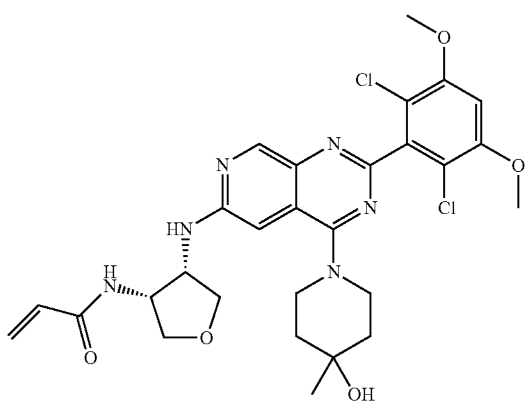 | N-((3R,4S)-4-((2-(2,6-dichloro-3,5-dimethoxyphenyl)-4-(4-hydroxy-4-methyl-piperidin-1-yl)pyrido[3,4-d]pyrimidin-6-yl) amino)tetrahydrofuran-3-yl)acrylamide | 603 |
| 394 | 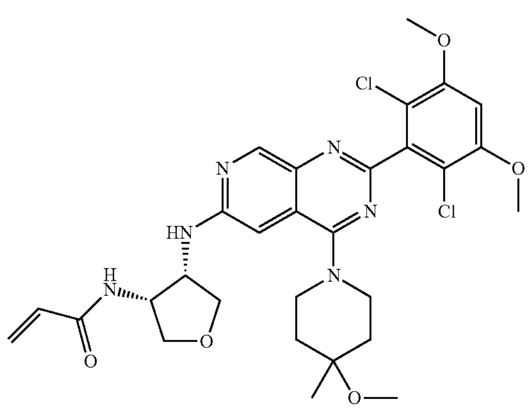 [SMILES: C=CC(=O)N[C@H]1COC[C@H]1Nc1cc2c(N3CCC(C)(OC)CC3)nc(-c3c(Cl)c(OC)cc(OC)c3Cl)nc2cn1] | N-(3R,4S)-4-((2-(2,6-dichloro-3,5-dimethoxyphenyl)-4-(4-dimethoxy-4-methyl-piperidin-1-yl)pyrido[3,4-d]pyrimidin-6-yl amino)tetrahydrofuran-3-yl)acrylamide | 617 |

| Example No. | Compound structure | Compound name | MS: m/z [M + 1]+ |
|---|---|---|---|
| 395 | 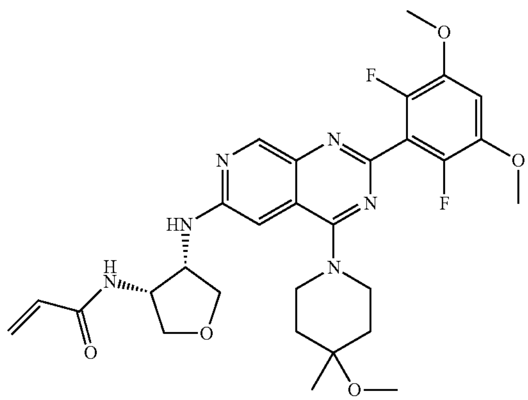 [SMILES: C=CC(=O)N[C@H]1COC[C@H]1Nc1cc2c(N3CCC(C)(OC)CC3)nc(-c3c(F)c(OC)cc(OC)c3F)nc2cn1] | N-((3R,4S)-4-((2-(2,6-difluoro-3,5-dimethoxyphenyl)-4-(4-dimethoxy-4-methyl-piperidin-1-yl)pyrido[3,4-d]pyrimidin-6-yl)amino)tetrahydrofuran-3-yl)acrylamide | 585 |
| 396 | 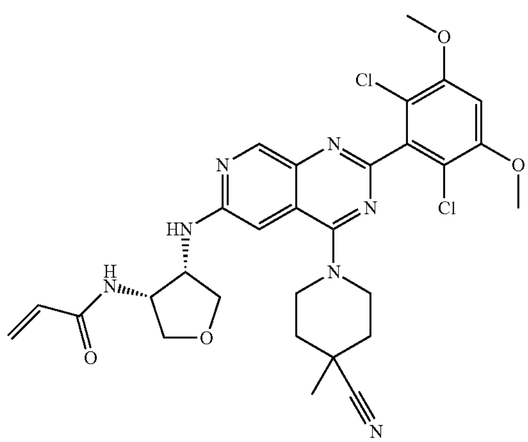 [SMILES: C=CC(=O)N[C@H]1COC[C@H]1Nc1cc2c(N3CCC(C)(C#N)CC3)nc(-c3c(Cl)c(OC)cc(OC)c3Cl)nc2cn1] | N-((3R,4S)-4-((4-(4-cyano-4-methyl-piperidin-1-yl)-2-(2,6-dichloro-3,5-dimethoxy-phenyl)pyrido[3,4-d]pyrimidin-6-yl)amino)tetrahydrofuran-3-yl)acrylamide | 612 |
| 397 | 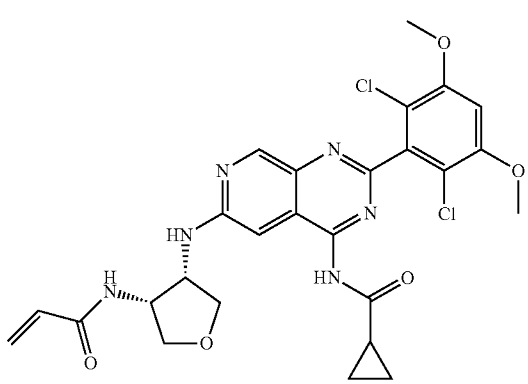 [SMILES: C=CC(=O)N[C@H]1COC[C@H]1Nc1cc2c(NC(=O)C3CC3)nc(-c3c(Cl)c(OC)cc(OC)c3Cl)nc2cn1] | N-(6-(((3S,4R)-4-acrylamidotetrahydro-furan-3-yl)amino)-2-(2,6-dichloro-3,5-dimethoxyphenyl)pyrido[3,4-d]pyrimidin-4-yl)cyclopropanecarboxamide | 573 |

| Example No. | Compound structure | Compound name | MS: m/z [M + 1]+ |
|---|---|---|---|
| 398 | 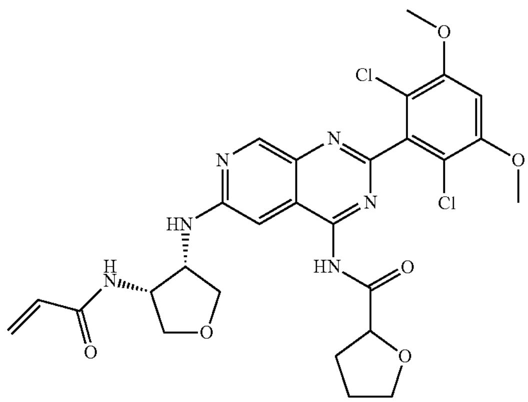 [SMILES: C=CC(=O)N[C@H]1COC[C@H]1Nc1cc2c(NC(=O)C3CCCO3)nc(-c3c(Cl)c(OC)cc(OC)c3Cl)nc2cn1] | N-(6-(((3S,4R)-4-acrylamidotetrahydro-furan-3-yl)amino)-2-(2,6-dichloro-3,5-dimethoxyphenyl)pyrido[3,4-d]pyrimidin-4-yl)tetrahydrofuran-2-carboxamide | 603 |
| 399 | 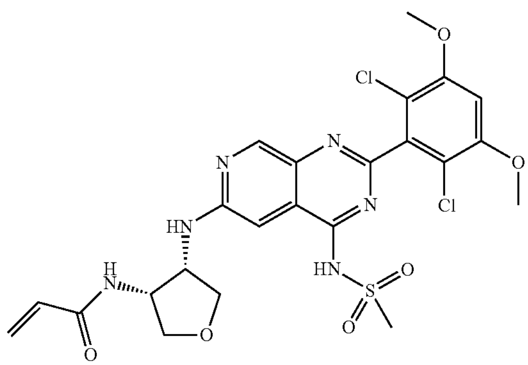 | N-((3R,4S)-4-((2-(2,6-dichloro-3,5-dimethoxyphenyl)-4-(methylsulfonamido)pyrido[3,4-d]pyrimidin-6-yl)amino)tetrahydrofuran-3-yl)acrylamide | 583 |
| 400 | 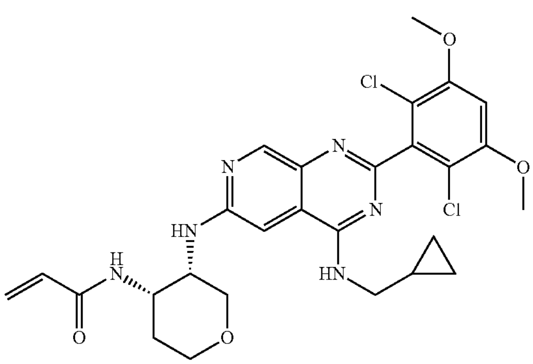 [SMILES: C=CC(=O)N[C@H]1CCOC[C@H]1Nc1cc2c(NCC3CC3)nc(-c3c(Cl)c(OC)cc(OC)c3Cl)nc2cn1] | N-((3S,4S)-3-((4-((cyclopropylmethyl)amino)-2-(2,6-dichloro-3,5-dimethoxyphenyl)pyrido[3,4-d]pyrimidin-6-yl)amino)tetrahydro-2H-pyran-4-yl)acrylamide | 573 |
| 401 | 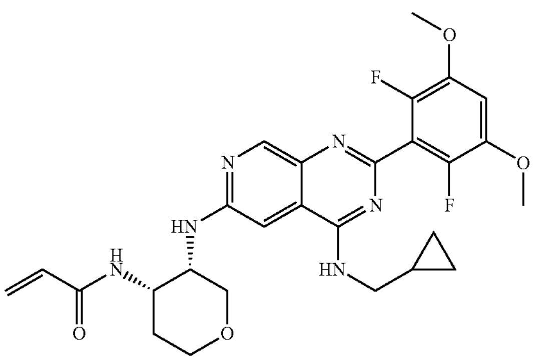 [SMILES: C=CC(=O)N[C@H]1CCOC[C@H]1Nc1cc2c(NCC3CC3)nc(-c3c(F)c(OC)cc(OC)c3F)nc2cn1] | N-((3S,4S)-3-((4-((cyclopropylmethyl)amino)-2-(2,6-difluoro-3,5-dimethoxyphenyl)pyrido[3,4-d]pyrimidin-6-yl)amino)tetrahydro-2H-pyran-4-yl)acrylamide | 541 |

-continued

| Example No. | Compound structure | Compound name | MS: m/z [M + 1]+ |
|---|---|---|---|
| 402 | 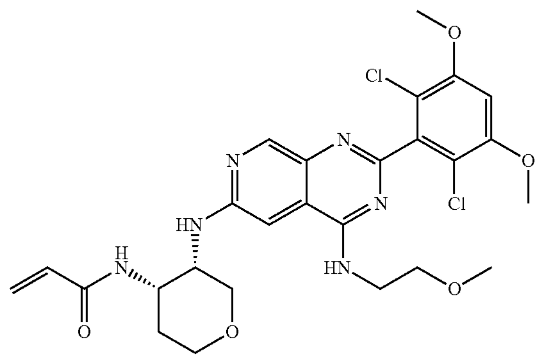 [SMILES: C=CC(=O)N[C@H]1CCOC[C@H]1Nc1cc2c(NCCOC)nc(-c3c(Cl)c(OC)cc(OC)c3Cl)nc2cn1] | N-((3S,4S)-3-((2-(2,6-dichloro-3,5-dimethoxyphenyl)-4-((2-methoxyethyl)amino)pyrido[3,4-d]pyrimidin-6-yl)amino)tetrahydro-2H-pyran-4-yl)acrylamide | 577 |
| 403 | 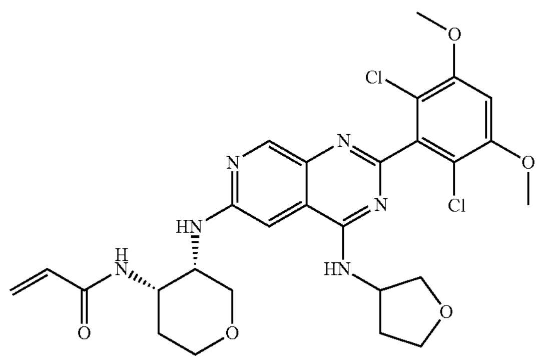 [SMILES: C=CC(=O)N[C@H]1CCOC[C@H]1Nc1cc2c(NC3CCOC3)nc(-c3c(Cl)c(OC)cc(OC)c3Cl)nc2cn1] | N-((3S,4S)-3-((2-(2,6-dichloro-3,5-dimethoxyphenyl)-4-((tetrahydrofuran-3-yl)amino)pyrido[3,4-d]pyrimidin-6-yl)amino)tetrahydro-2H-pyran-4-yl)acrylamide | 589 |
| 404 | 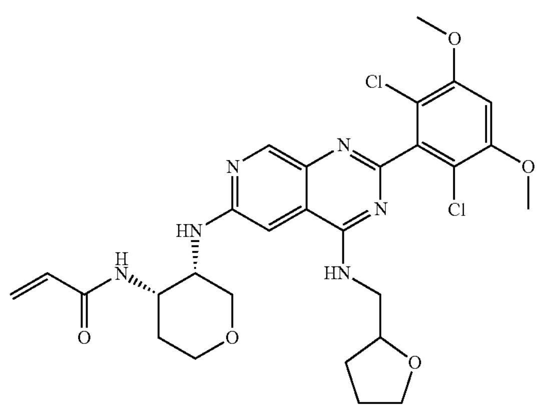 | N-((3S,4S)-3-((2-(2,6-dichloro-3,5-dimethoxyphenyl))-4-(((tetrahydrofuran-2-yl)methyl)amino)pyrido[3,4-d]pyrimidin-6-yl)amino)tetrahydro-2H-pyran-4-yl)acrylamide | 603 |
| 405 | 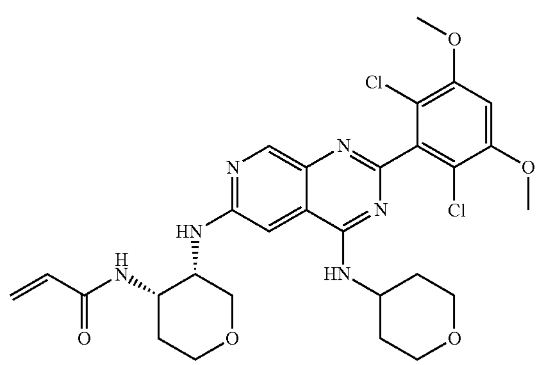 [SMILES: C=CC(=O)N[C@H]1CCOC[C@H]1Nc1cc2c(NC3CCOCC3)nc(-c3c(Cl)c(OC)cc(OC)c3Cl)nc2cn1] | N-((3S,4S)-3-((2-(2,6-dichloro-3,5-dimethoxyphenyl)-4-((tetrahydro-2H-pyran-4-yl)amino)pyrido[3,4-d]pyrimidin-6-yl)amino)tetrahydro-2H-pyran-4-yl)acrylamide | 603 |

| Example No. | Compound structure | Compound name | MS: m/z [M + 1]⁺ |
|---|---|---|---|
| 406 | 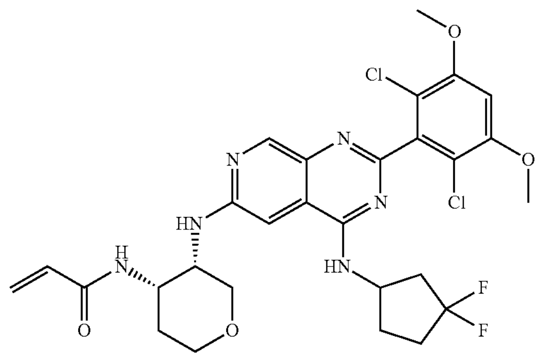 [SMILES: C=CC(=O)N[C@H]1CCOC[C@H]1Nc1cc2c(NC3CCC(F)(F)C3)nc(-c3c(Cl)c(OC)cc(OC)c3Cl)nc2cn1] | N-((3S,4S)-3-((2-(2,6-dichloro-3,5-dimethoxyphenyl)-4-((3,3-difluorocyclopentyl)amino)pyrido[3,4-d]pyrimidin-6-yl)amino)tetrahydro-2H-pyran-4-yl)acrylamide | 623 |
| 407 | 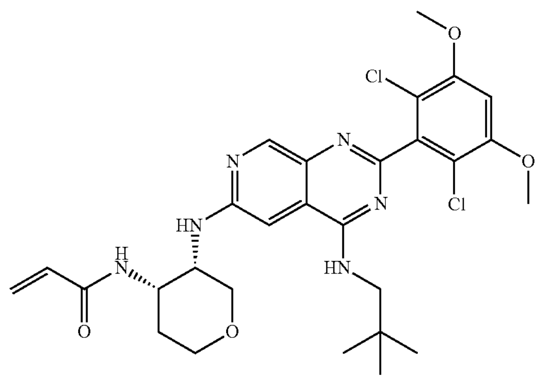 [SMILES: C=CC(=O)N[C@H]1CCOC[C@H]1Nc1cc2c(NCC(C)(C)C)nc(-c3c(Cl)c(OC)cc(OC)c3Cl)nc2cn1] | N-((3S,4S)-3-((2-(2,6-dichloro-3,5-dimethoxyphenyl)-4-(neopentylamino)pyrido[3,4-d]pyrimidin-6-yl)amino)tetrahydro-2H-pyran-4-yl)acrylamide | 589 |
| 408 | 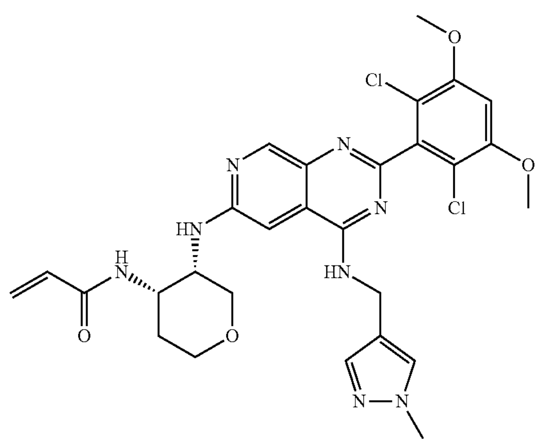 [SMILES: C=CC(=O)N[C@H]1CCOC[C@H]1Nc1cc2c(NCc3cnn(C)c3)nc(-c3c(Cl)c(OC)cc(OC)c3Cl)nc2cn1] | N-((3S,4S)-3-((2-(2,6-dichloro-3,5-dimethoxyphenyl)-4-(((1-methyl-1H-pyrazol-4-yl)methyl)amino)pyrido[3,4-d]pyrimidin-6-yl)amino)tetrahydro-2H-pyran-4-yl)acrylamide | 613 |
| 409 | 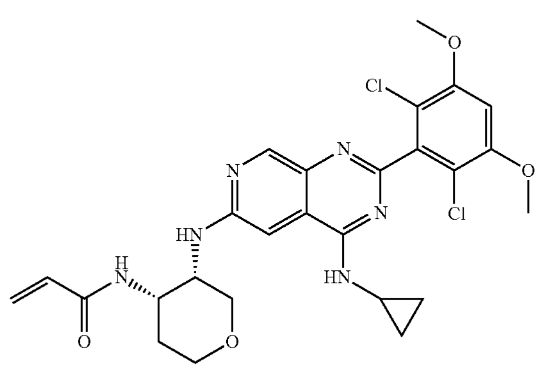 [SMILES: C=CC(=O)N[C@H]1CCOC[C@H]1Nc1cc2c(NC3CC3)nc(-c3c(Cl)c(OC)cc(OC)c3Cl)nc2cn1] | N-((3S,4S)-3-((4-(cyclopropylamino)-2-(2,6-dichloro-3,5-dimethoxyphenyl)pyrido[3,4-d]pyrimidin-6-yl)amino)tetrahydro-2H-pyran-4-yl)acrylamide | 559 |

-continued

| Example No. | Compound structure | Compound name | MS: m/z [M + 1]+ |
|---|---|---|---|
| 410 | 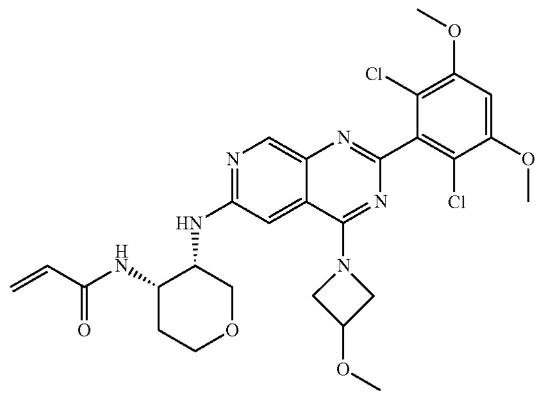 [SMILES: C=CC(=O)N[C@H]1CCOC[C@H]1Nc1cc2c(N3CC(OC)C3)nc(-c3c(Cl)c(OC)cc(OC)c3Cl)nc2cn1] | N-((3S,4S)-3-((2-(2,6-dichloro-3,5-dimethoxyphenyl)-4-(3,3-difluoroazetidin-1-yl)pyrido[3,4-d]pyrimidin-6-yl)amino) tetrahydro-2H-pyran-4-yl)acrylamide | 589 |
| 411 | 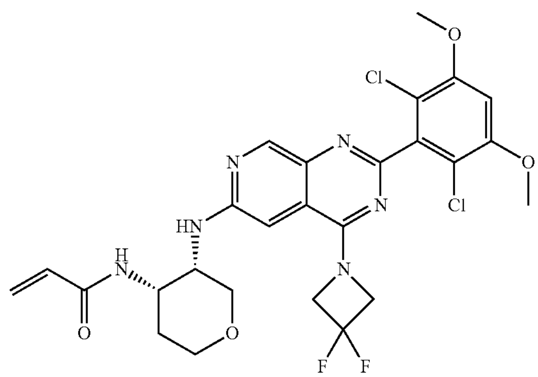 [SMILES: C=CC(=O)N[C@H]1CCOC[C@H]1Nc1cc2c(N3CC(F)(F)C3)nc(-c3c(Cl)c(OC)cc(OC)c3Cl)nc2cn1] | N-((3S,4S)-3-((2-(2,6-dichloro-3,5-dimethoxyphenyl)-4-(3,3-difluoroazetidin-1-yl)pyrido[3,4-d]pyrimidin-6-yl)amino) tetrahydro-2H-pyran-4-yl)acrylamide | 595 |
| 412 | 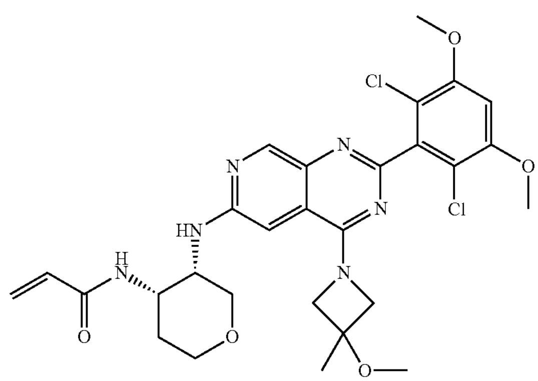 [SMILES: C=CC(=O)N[C@H]1CCOC[C@H]1Nc1cc2c(N3CC(C)(OC)C3)nc(-c3c(Cl)c(OC)cc(OC)c3Cl)nc2cn1] | N-((3S,4S)-3-((2-(2,6-dichloro-3,5-dimethoxyphenyl)-4-(3-dimethoxy-3-methyl-azetidin-1-yl)pyrido[3,4-d]pyrimidin-6-yl-amino)tetrahydro-2H-pyran-4-yl)acrylamide | 603 |
| 413 | 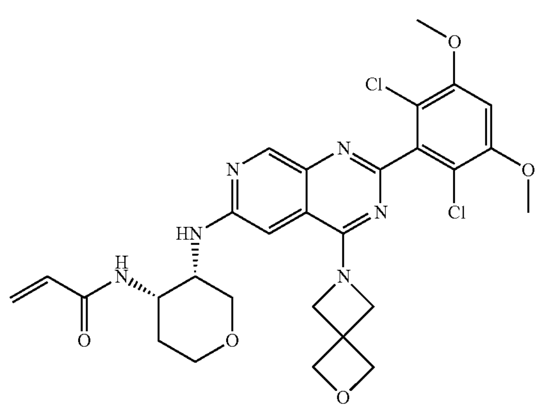 [SMILES: C=CC(=O)N[C@H]1CCOC[C@H]1Nc1cc2c(N3CC4(COC4)C3)nc(-c3c(Cl)c(OC)cc(OC)c3Cl)nc2cn1] | N-((3S,4S)-3-((2-(2,6-dichloro-3,5-dimethoxyphenyl)-4-(2-oxa-6-azaspiro[3.3] heptan-6-yl)pyrido[3,4-d]pyrimidin-6-yl) amino)tetrahydro-2H-pyran-4-yl)acrylamide | 601 |

-continued

| Example No. | Compound structure | Compound name | MS: m/z [M + 1]+ |
|---|---|---|---|
| 414 | 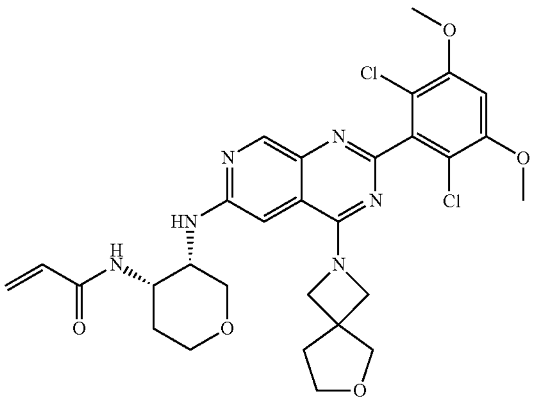 [SMILES: C=CC(=O)N[C@H]1CCOC[C@H]1Nc1cc2c(N3CC4(CCOC4)C3)nc(-c3c(Cl)c(OC)cc(OC)c3Cl)nc2cn1] | N-((3S,4S)-3-((2-(2,6-dichloro-3,5-dimethoxyphenyl)-4-(6-oxa-2-azaspiro[3.4]octan-2-yl)pyrido[3,4-d]pyrimidin-6-yl)amino)tetrahydro-2H-pyran-4-yl)acrylamide | 615 |
| 415 | 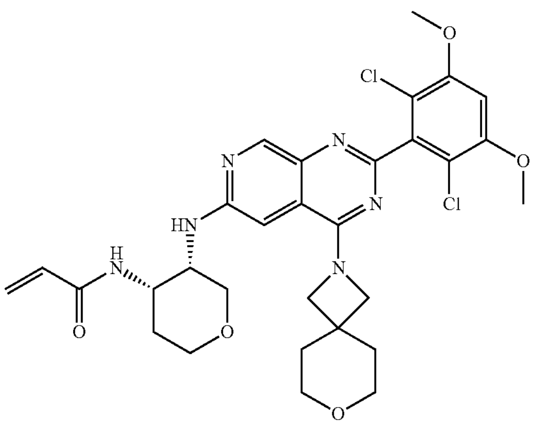 [SMILES: C=CC(=O)N[C@H]1CCOC[C@H]1Nc1cc2c(N3CC4(CCOCC4)C3)nc(-c3c(Cl)c(OC)cc(OC)c3Cl)nc2cn1] | N-((3S,4S)-3-((2-(2,6-dichloro-3,5-dimethoxyphenyl)-4-(7-oxa-2-azaspiro[3.5]nonan-2-yl)pyrido[3,4-d]pyrimidin-6-yl)amino)tetrahydro-2H-pyran-4-yl)acrylamide | 629 |
| 416 | 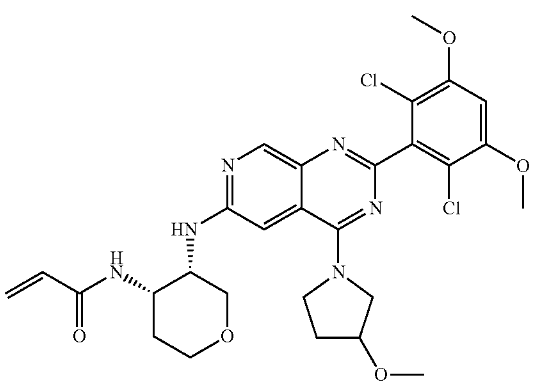 [SMILES: C=CC(=O)N[C@H]1CCOC[C@H]1Nc1cc2c(N3CCC(OC)C3)nc(-c3c(Cl)c(OC)cc(OC)c3Cl)nc2cn1] | N-((3S,4S)-3-((2-(2,6-dichloro-3,5-dimethoxyphenyl)-4-(3-dimethoxypyrrolidin-1-yl)pyrido[3,4-d]pyrimidin-6-yl)amino)tetrahydro-2H-pyran-4-yl)acrylamide | 603 |
| 417 | 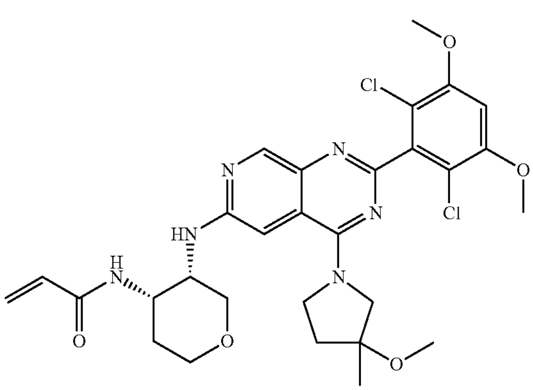 [SMILES: C=CC(=O)N[C@H]1CCOC[C@H]1Nc1cc2c(N3CCC(C)(OC)C3)nc(-c3c(Cl)c(OC)cc(OC)c3Cl)nc2cn1] | N-((3S,4S)-3-((2-(2,6-dichloro-3,5-dimethoxyphenyl)-4-(3-methoxy-3-methyl-pyrrolidin-1-yl)pyrido[3,4-d]pyrimidin-6-yl)amino)tetrahydro-2H-pyran-4-yl)acrylamide | 617 |

| Example No. | Compound structure | Compound name | MS: m/z [M + 1]+ |
|---|---|---|---|
| 418 | 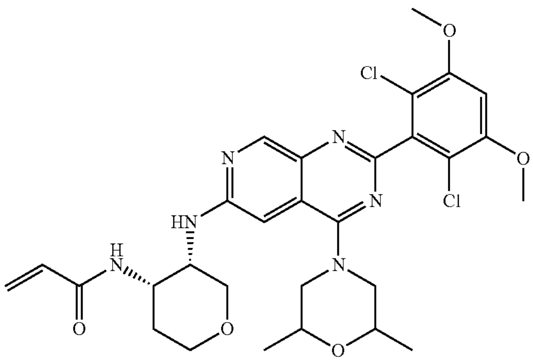 [SMILES: C=CC(=O)N[C@H]1CCOC[C@H]1Nc1cc2c(N3CC(C)OC(C)C3)nc(-c3c(Cl)c(OC)cc(OC)c3Cl)nc2cn1] | N-((3S,4S)-3-((2-(2,6-dichloro-3,5-dimethoxyphenyl)-4-(2,6-dimethylmorpholino) pyrido[3,4-d]pyrimidin-6-yl)amino) tetrahydro-2H-pyran-4-yl)acrylamide | 617 |
| 419 | 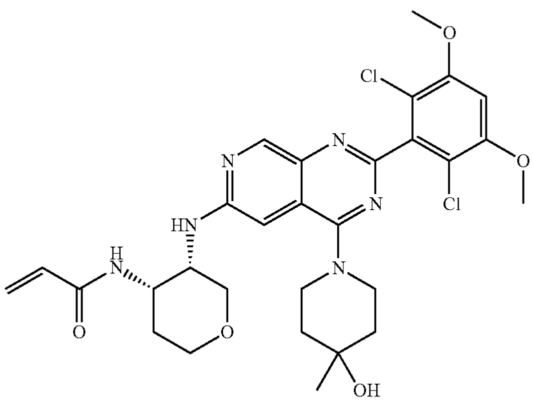 [SMILES: C=CC(=O)N[C@H]1CCOC[C@H]1Nc1cc2c(N3CCC(C)(O)CC3)nc(-c3c(Cl)c(OC)cc(OC)c3Cl)nc2cn1] | N-((3S,4S)-3-((2-(2,6-dichloro-3,5-dimethoxyphenyl)-4-(4-hydroxy-4-methyl-piperidin-1-yl)pyrido[3,4-d]pyrimidin-6-yl)amino)tetrahydro-2H-pyran-4-yl)acrylamide | 617 |
| 420 | 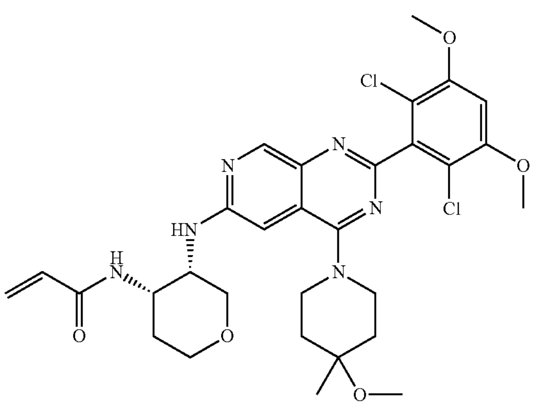 [SMILES: C=CC(=O)N[C@H]1CCOC[C@H]1Nc1cc2c(N3CCC(C)(OC)CC3)nc(-c3c(Cl)c(OC)cc(OC)c3Cl)nc2cn1] | N-((3S,4S)-3-((2-(2,6-dichloro-3,5-dimethoxyphenyl)-4-(4-dimethoxy-4-methyl piperidin-1-yl)pyrido[3,4-d]pyrimidin-6-yl)amino)tetrahydro-2H-pyran-4-yl)acrylamide | 631 |
| 752 | 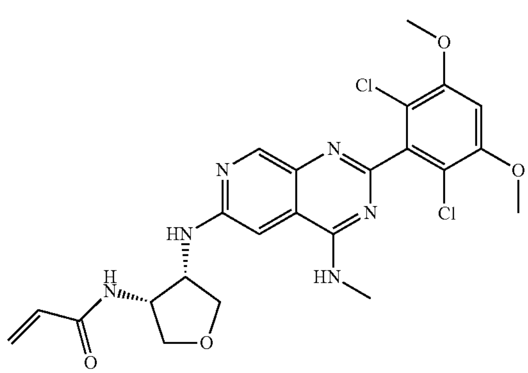 [SMILES: C=CC(=O)N[C@H]1COC[C@H]1Nc1cc2c(NC)nc(-c3c(Cl)c(OC)cc(OC)c3Cl)nc2cn1] | N-((3R,4S)-4-((2-(2,6-dichloro-3,5-dimethoxyphenyl)-4-(methylamino)pyrido [3,4-d]pyrimidin-6-yl)amino)tetrahydro-furan-3-yl)acrylamide | 519 |

Example 421 Preparation of N-((3R,4S)-4-((8-((cyclopropylmethyl)amino)-6-(2,6-dichloro-3,5-dimethoxyphenyl)pyrido[3,4-d]pyrimidin-2-yl)amino)tetrahydrofuran-3-yl)acrylamide Step 2: Preparation of (±)—N²-((3S,4R)-4-aminotetrahydrofuran-3-yl)-N⁸-(cyclopropyl methyl)-6-(2,6-dichloro-3,5-dimethoxyphenyl)pyrido[3,4-d]pyrimidine-2,8-diamine

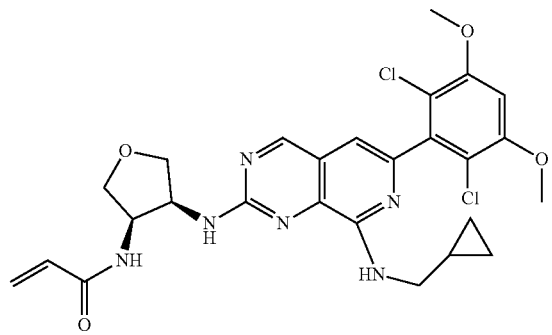 [SMILES: C=CC(=O)N[C@H]1COC[C@H]1Nc1ncc2cc(-c3c(Cl)c(OC)cc(OC)c3Cl)nc(NCC3CC3)c2n1]

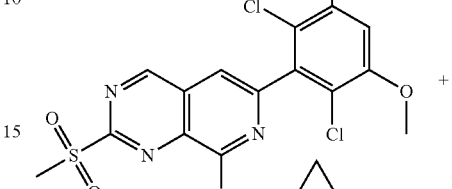

Step 1: preparation of N-(cyclopropylmethyl)-6-(2,6-dichloro-3,5-dimethoxyphenyl)-2-(methylsulfonyl)pyrido[3,4-d]pyrimidine-8-amine

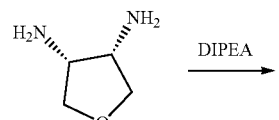

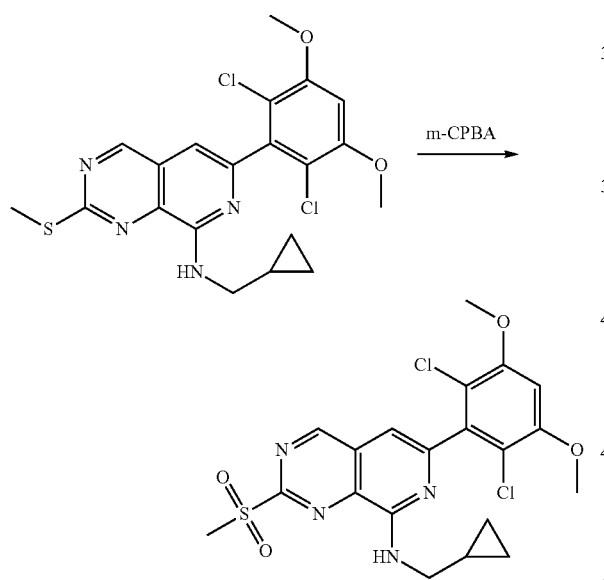

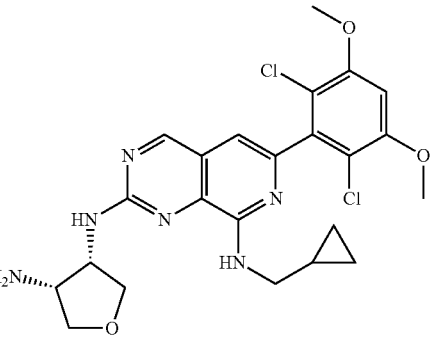

N-(cyclopropylmethyl)-6-(2,6-dichloro-3,5-dimethoxyphenyl)-2-(methylthio)pyrido[3,4-d]pyrimidine-8-amine (210 mg, 0.465 mmol) was dissolved in dichloromethane (6 mL), then m-chloroperoxybenzoic acid (200 mg, 1.163 mmol) was added, and the mixture was stirred at room temperature for 18 h. After the reaction was completed, a saturated sodium sulfite solution was added, and then the mixture was stirred for 5 min and extracted with dichloromethane, the organic phase was washed with a saturated sodium bicarbonate and then saturated brine, dried over anhydrous sodium sulfate, filtrated, concentrated, and separated by column chromatography (Eluent: PE/EA=2/1) to obtain compound N-(cyclopropylmethyl)-6-(2,6-dichloro-3,5-dimethoxyphenyl)-2-(methylsulfonyl)pyrido[3,4-d]pyrimidine-8-amine (186 mg, yield: 82.7%).

MS m/z (ESI): 483.4 [M+H]⁺.

N-(cyclopropylmethyl)-6-(2,6-dichloro-3,5-dimethoxyphenyl)-2-(methylsulfonyl)pyrido[3,4-d]pyrimidine-8-amine (190 mg, 0.393 mmol) and (3R,4S)-tetrahydrofuran-3,4-diamine dihydrochloride (206 mg, 1.179 mmol) were dissolved in acetonitrile (6 mL), then N,N-diisopropylethylamine (507 mg, 3.93 mmol) was added, and the mixture was heated to reflux, an d stirred for 20 h. The reaction was completed, and the mixture was cooled to room temperature. The reaction liquid was diluted with EtOAc (20 mL), washed with saturated brine, dried over anhydrous sodium sulfate, filtrated, concentrated, and separated by TLC (developing agent: CH₂Cl₂/MeOH 10/1) to obtain compound (±)—N²-((3S,4R)-4-aminotetrahydrofuran-3-yl)-N⁸-(cyclopropylmethyl)-6-(2,6-dichloro-3,5-dimethoxyphenyl)pyrido[3,4-d]pyrimidine-2,8-diamine (120 mg, yield: 60%).

MS m/z (ESI): 505.4 [M+H]⁺.

Step 3: Preparation of (±)—N-((3R,4S)-4-((8-((cyclopropylmethyl)amino)-6-(2,6-dichloro-3,5-dimethoxyphenyl)pyrido[3,4-d]pyrimidin-2-yl)amino)tetrahydrofuran-3-yl)acrylamide

Step 4: Preparation of N-((3R,4S)-4-((8-((cyclopropylmethyl)amino)-6-(2,6-dichloro-3,5-dimethoxyphenyl)pyrido[3,4-d]pyrimidin-2-yl)amino)tetrahydrofuran-3-yl)acrylamide

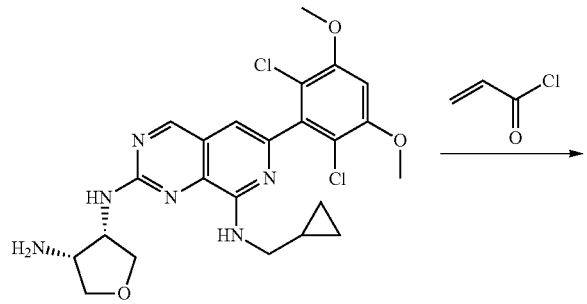

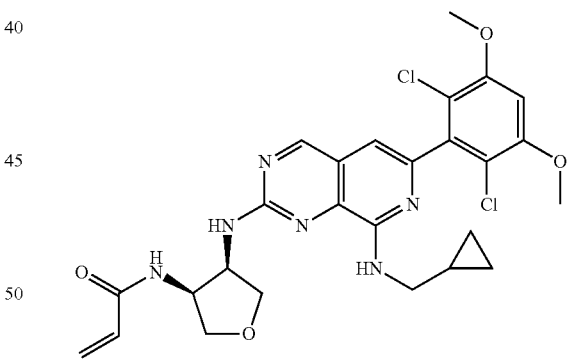

At 0° C., acryloyl chloride (22.6 mg, 0.249 mmol) was added to the solution of (±)—N²-((3S,4R)-4-aminotetrahydrofuran-3-yl)-N⁸-(cyclopropylmethyl)-6-(2,6-dichloro-3,5-dimethoxyphenyl)pyrido[3,4-d]pyrimidine-2,8-diamine (120 mg, 0.237 mmol) and sodium bicarbonate (79.6 mg, 0.948 mmol) in the mixture of tetrahydrofuran (6.4 mL) and water (1.6 mL). After addition, the mixture was stirred at 0° C. for 5 min. The reaction liquid was diluted with EtOAc (10 mL), washed with saturated brine, dried over anhydrous sodium sulfate, filtrated, concentrated and separated by TLC (Eluent: $CH_2Cl_2$/MeOH=20/1) to obtain compound (+)—N-((3R,4S)-4-((8-((cyclopropylmethyl)amino)-6-(2,6-dichloro-3,5-dimethoxyphenyl) pyrido[3,4-d]pyrimidin-2-yl)amino)tetrahydrofuran-3-yl)acrylamide (93 mg, yield: 70%).

$^1$H NMR (400 MHz, $CDCl_3$) δ 8.89 (s, 1H), 6.80 (brs, 1H), 6.68 (s, 1H), 6.62 (s, 1H), 6.38 (brs, 1H), 6.21 (dd, J=17.0, 1.5 Hz, 1H), 6.02 (dd, J=17.0, 10.2 Hz, 1H), 5.56 (dd, J=10.1, 1.5 Hz, 1H), 4.93-4.83 (m, 2H), 4.30-4.18 (m, 2H), 3.96 (s, 6H), 3.90 (dd, J=9.7, 3.2 Hz, 1H), 3.79 (dd, J=9.2, 5.2 Hz, 1H), 3.52-3.37 (m, 2H), 0.88 (t, J=6.0 Hz, 1H), 0.57-0.48 (m, 2H), 0.36-0.26 (m, 2H). MS m/z (ESI): 559.5 [M+H]⁺.

(±)—N-((3R,4S)-4-((8-((cyclopropylmethyl)amino)-6-(2,6-dichloro-3,5-dimethoxyphenyl)pyrido[3,4-d]pyrimidin-2-yl)amino)tetrahydrofuran-3-yl)acrylamide (93 mg, 0.166 mmol) was separated by chiral HPLC to obtain N-((3R,4S)-4-((8-((cyclopropylmethyl)amino)-6-(2,6-dichloro-3,5-dimethoxyphenyl)pyrido[3,4-d]pyrimidin-2-yl)amino)tetrahydrofuran-3-yl)acrylamide(43.5 mg, ee value>98%, yield: 46.8%) and N-((3S,4R)-4-((8-((cyclopropylmethyl)amino)-6-(2,6-dichloro-3,5-dimethoxyphenyl)pyrido[3,4-d]pyrimidin-2-yl)amino)tetrahydrofuran-3-yl)acrylamide (39 mg, ee value>98%, yield: 41.9%).

Example 433 Preparation of N-((3R,4S)-4-((6-(2,6-dichloro-3,5-dimethoxyphenyl)-8-(methylamino)pyrido[3,4-d]pyrimidin-2-yl)amino)tetrahydrofuran-3-yl)acrylamide

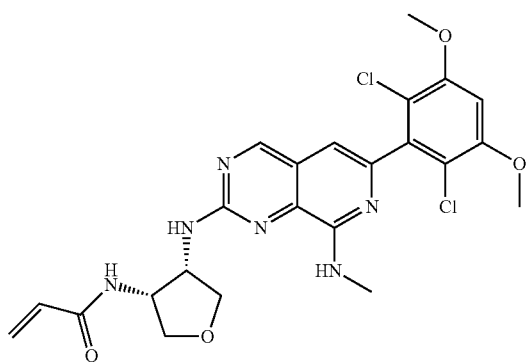

Step 1: Preparation of 8-chloro-6-(2,6-dichloro-3,5-dimethoxyphenyl)-2-(methylsulfonyl)pyrido[3,4-d]pyrimidine

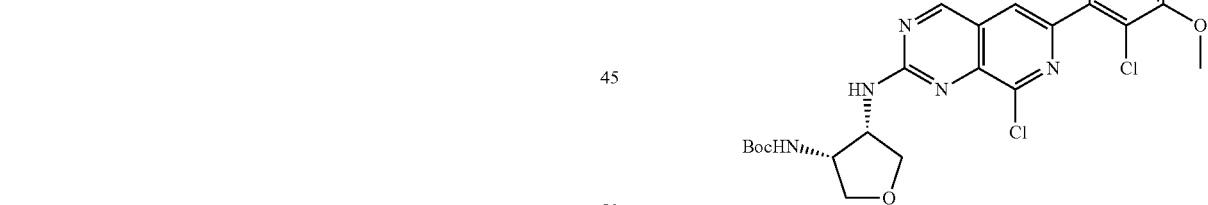

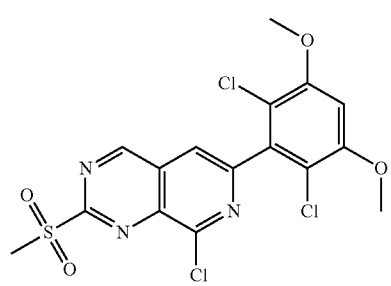

The compound was prepared referring to the synthesis method of step 1 of Example 421.

Step 2: Preparation of Tert-Butyl ((3R,4S)-4-((8-chloro-6-(2,6-dichloro-3,5-dimethoxy phenyl)pyrido[3,4-d]pyrimidin-2-yl)amino)tetrahydrofuran-3-yl) carbamate

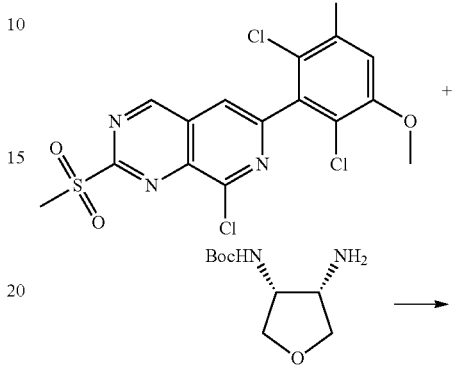

8-chloro-6-(2,6-dichloro-3,5-dimethoxyphenyl)-2-(methylsulfonyl)pyrido[3,4-d]pyrimidine (409 mg, 0.912 mmol) and tert-butyl ((3R,4S)-4-aminotetrahydrofuran-3-yl)carbamate (553 mg, 2.736 mmol) were dissolved in acetonitrile (50 mL), then trifluoroacetic acid (31 mg, 0.274 mmol) was added. The reaction liquid was stirred at 95° C. for 4 h. After being cooled, the mixture was diluted with ethyl acetate (50 mL), washed with a saturated sodium bicarbonate solution and saturated brine, dried over anhydrous sodium sulfate, concentrated and separated by column chromatography (CH$_2$Cl$_2$/MeOH 0-4%) to obtain compound tert-butyl ((3R,4S)-4-((8-chloro-6-(2,6-dichloro-3,5-dimethoxyphenyl)pyrido[3,4-d]pyrimidin-2-yl)amino)tetrahydrofuran-3-yl) carbamate (414 mg, yield: 79.6%). MS m/z (ESI): 570.4, 572.4 [M+H]+.

Step 3: Preparation of Tert-Butyl ((3R,4S)-4-((6-(2,6-dichloro-3,5-dimethoxyphenyl)-8-(methylamino)pyrido[3,4-d]pyrimidin-2-yl)amino)tetrahydrofuran-3-yl)carbamate

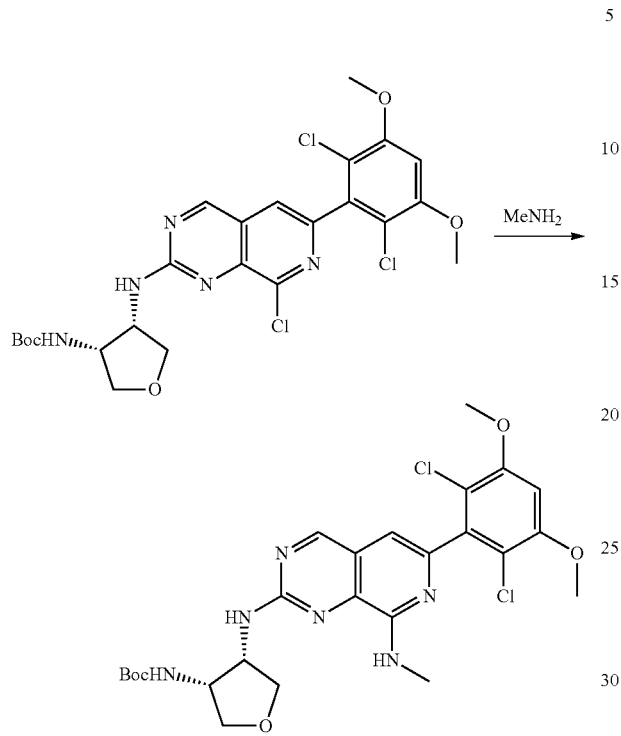

A solution of tert-butyl((3R,4S)-4-((8-chloro-6-(2,6-dichloro-3,5-dimethoxyphenyl)pyrido[3,4-d]pyrimidin-2-yl)amino)tetrahydrofuran-3-yl)carbamate (60 mg, 0.105 mmol) and methylamine (1.5 mL, 33% ethanol solution) in N-methylpyrrolidone (1 mL) was heated to 110° C. and stirred for 18 h. The reaction liquid was diluted with ethyl acetate (5 mL), washed with saturated brine, dried over anhydrous sodium sulfate, concentrated, and separated by using a preparative TLC (PE/EA=1:1) to obtain compound tert-butyl ((3R,4S)-4-((6-(2,6-dichloro-3,5-dimethoxyphenyl)-8-(methylamino)pyrido[3,4-d]pyrimidin-2-yl)amino)tetrahydrofuran-3-yl)carbamate (32 mg, yield: 54%). MS m/z (ESI): 565.4, 567.4 [M+H]+.

Step 4: Preparation of $N^2$-((3S,4R)-4-aminotetrahydrofuran-3-yl)-6-(2,6-dichloro-3,5-dimethoxyphenyl)-$N^8$-methylpyrido[3,4-d]pyrimidine-2,8-diamine Trifluoroacetate

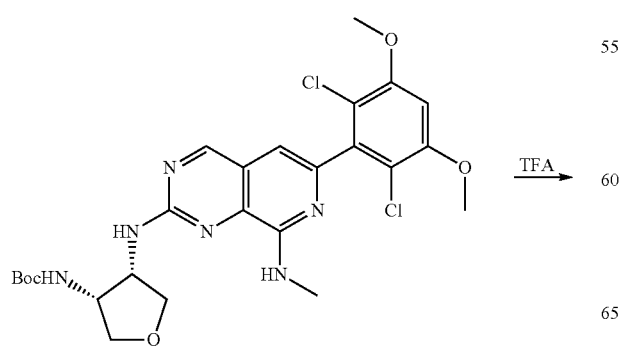

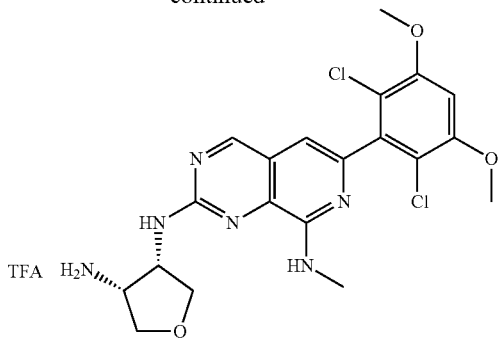

A solution of tert-buty ((3R,4S)-4-((6-(2,6-dichloro-3,5-dimethoxyphenyl)-8-(methylamino)pyrido[3,4-d]pyrimidin-2-yl)amino)tetrahydrofuran-3-yl)carbamate (32 mg, 0.057 mmol) in the solution of trifluoroacetic acid in dichloromethane (2 mL, 20%) was stirred at room temperature for 1 h, and then concentrated to obtain an oil product which was directly use d in the next step. MS m/z (ESI): 465.4, 467.4 [M+H]+.

Step 5: Preparation of N-((3R,4S)-4-((6-(2,6-dichloro-3,5-dimethoxyphenyl)-8-(methylamino)pyrido[3,4-d]pyrimidin-2-yl)amino)tetrahydrofuran-3-yl)acrylamide

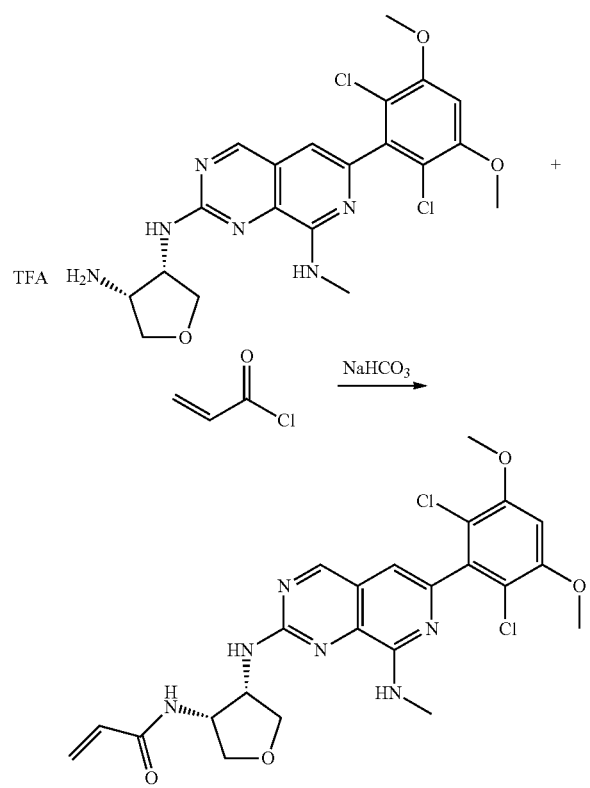

At 0° C., acryloyl chloride (5.7 mg, 0.063 mmol) was added to a solution of $N^2$-((3S,4R)-4-aminotetrahydrofuran-3-yl)-6-(2,6-dichloro-3,5-dimethoxyphenyl)-N-methylpyrido[3,4-d]pyrimidine-2,8-diamine trifluoroacetate (the crude product) and NaHCO3 (57 mg, 0.684 mmol) in the mixture of tetrahydrofuran (3.2 mL) and water (0.8 mL). After addition, the mixture was stirred at 0° C. for 5 min. The reaction liquid was diluted with EtOAc (mL), washed with a saturated sodium bicarbonate and saturated brine, dried over anhydrous sodium sulfate, concentrated and separated by using a preparative TLC ($CH_2Cl_2$/MeOH 20:1) to obtain compound N-((3R,4S)-4-((6-(2,6-dichloro-3,5-dimethoxyphenyl)-8-(methylamino)pyrido[3,4-d]pyrimidin-2-yl)amino)tetrahydrofuran-3-yl)acrylamide (17.6 mg, yield: 59.5%).

$^1$H NMR (400 MHz, $CDCl_3$) δ 8.88 (s, 1H), 6.67 (s, 1H), 6.62 (s, 1H), 6.30 (brs, 1H), 6.19 (d, J=16.9 Hz, 1H), 5.97 (dd, J=17.0, 10.3 Hz, 1H), 5.88 (brs, 1H), 5.54 (d, J=10.4 Hz, 1H), 4.95-4.83 (m, 2H), 4.29-4.18 (m, 2H), 3.95 (s, 6H), 3.89 (dd, J=9.7, 3.0 Hz, 1H), 3.77 (dd, J=9.3, 5.5 Hz, 1H), 3.14 (d, J=4.4 Hz, 3H). MS m/z (ESI): 519.4, 521.4 $[M+H]^+$.

Example 775 N-((3S,4S)-3-((6-(2,6-difluoro-3,5-dimethoxyphenyl)-8-(3-methoxyazetidin-1-yl)pyrido[3,4-d]pyrimidin-2-yl)amino)tetrahydro-2H-pyran-4-yl)acrylamide 8-chloro-6-(2,6-difluoro-3,5-dimethoxyphenyl)-2-(methylthio)pyrido[3,4-d]pyrimidine (930 mg, 2.42 mmol) was dissolved in DCM (50 mL), and m-CPBA (1.23 g, 6.05 mmol) was added, and the mixture was stirred at room temperature for 2 h. The reaction was completed, and sodium thiosulfate was added to quench the reaction. The mixture was extracted with DCM and separated by silica gel column chromatography to obtain compound 8-chloro-6-(2,6-difluoro-3,5-dimethoxyphenyl)-2-(methylsulfonyl)pyrido[3,4-d]pyrimidine (800 mg, yield:79%). MS m/z (ESI): 416 [M+H]+.

Step 2: Preparation of N-((3S,4S)-4-azidotetrahydro-2H-pyran-3-yl)-8-chloro-6-(2,6-difluoro-3,5-dimethoxyphenyl)pyrido[3,4-d]pyrimidine-2-amine

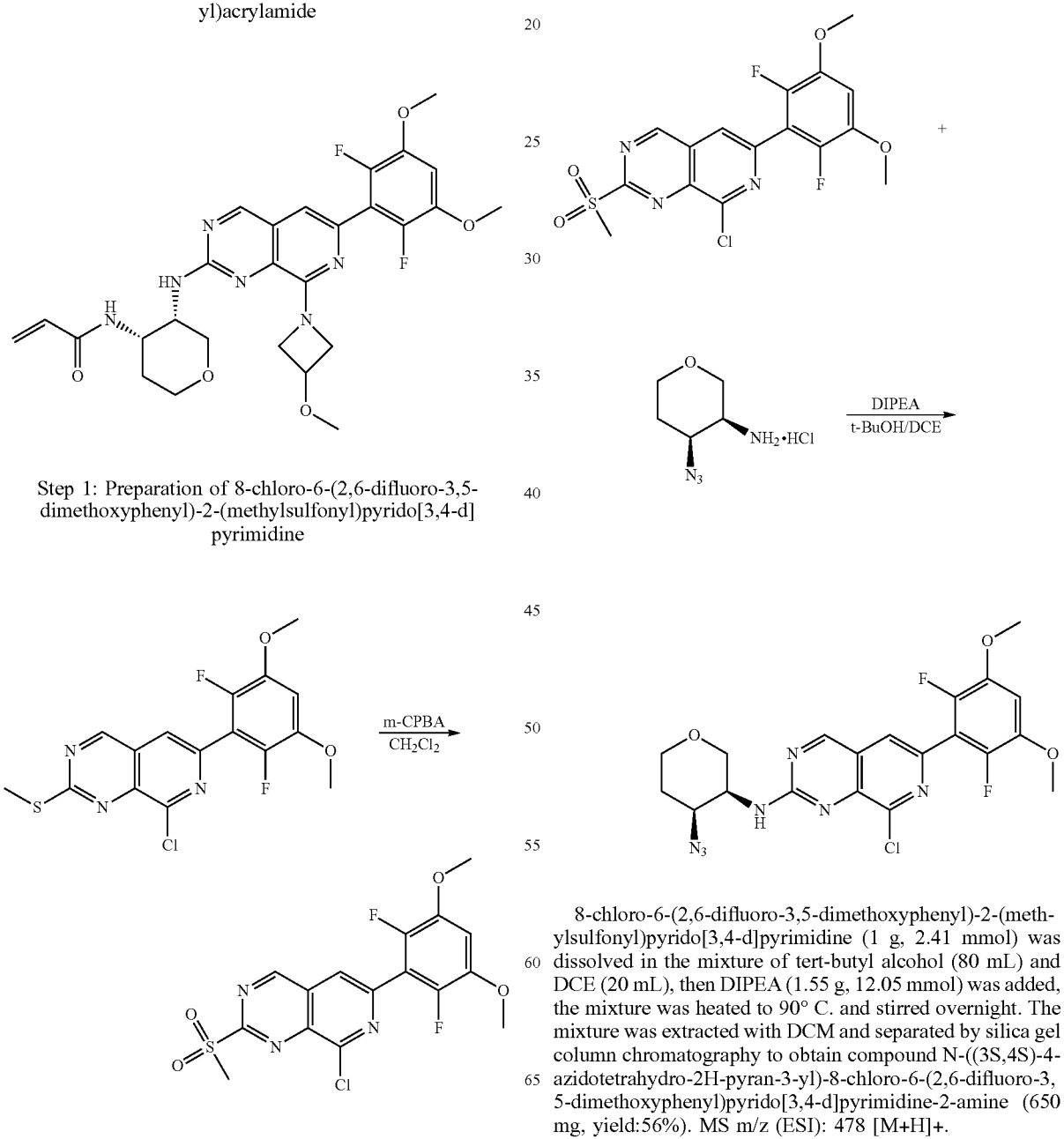

Step 1: Preparation of 8-chloro-6-(2,6-difluoro-3,5-dimethoxyphenyl)-2-(methylsulfonyl)pyrido[3,4-d]pyrimidine 8-chloro-6-(2,6-difluoro-3,5-dimethoxyphenyl)-2-(methylsulfonyl)pyrido[3,4-d]pyrimidine (1 g, 2.41 mmol) was dissolved in the mixture of tert-butyl alcohol (80 mL) and DCE (20 mL), then DIPEA (1.55 g, 12.05 mmol) was added, the mixture was heated to 90° C. and stirred overnight. The mixture was extracted with DCM and separated by silica gel column chromatography to obtain compound N-((3S,4S)-4-azidotetrahydro-2H-pyran-3-yl)-8-chloro-6-(2,6-difluoro-3,5-dimethoxyphenyl)pyrido[3,4-d]pyrimidine-2-amine (650 mg, yield:56%). MS m/z (ESI): 478 [M+H]+.

Step 3: Preparation of N-((3S,4S)-4-azidotetrahydro-2H-pyran-3-yl)-6-(2,6-difluoro-3,5-dimethoxyphenyl)-8-(3-methoxyazetidin-1-yl)pyrido[3,4-d]pyrimidine-2-amine Step 4: Preparation of (3S,4S)—N³-(6-(2,6-difluoro-3,5-dimethoxyphenyl)-8-(3-methoxyazetidin-1-yl)pyrido[3,4-d]pyrimidin-2-yl)tetrahydro-2H-pyran-3,4-diamine

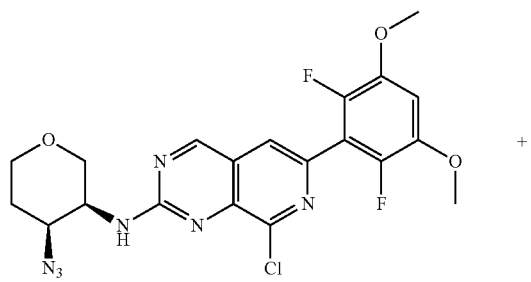

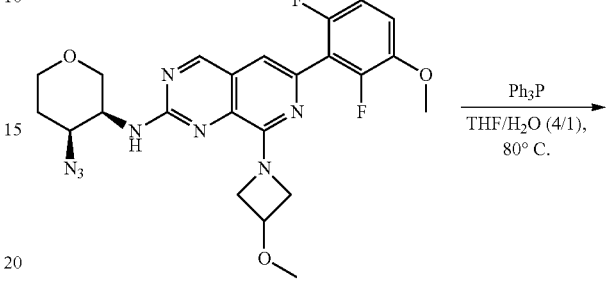

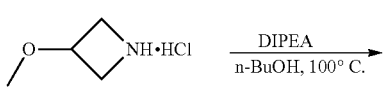

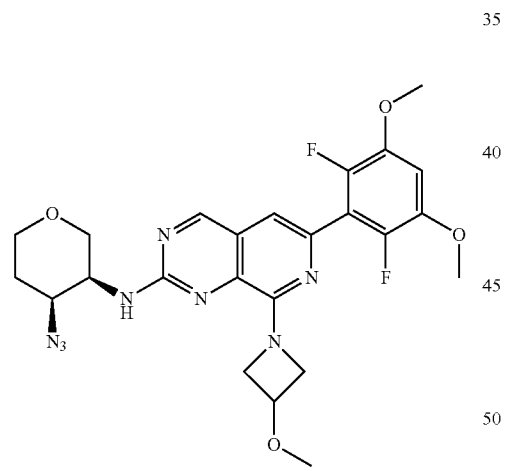

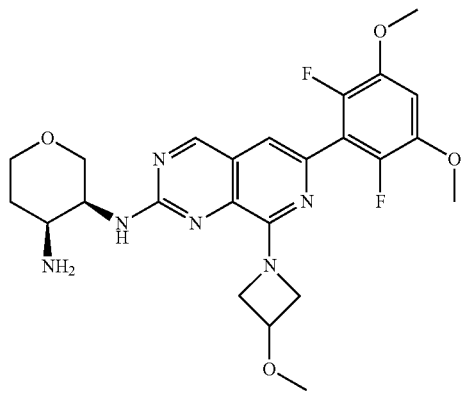

N-((3S,4S)-4-azidotetrahydro-2H-pyran-3-yl)-8-chloro-6-(2,6-difluoro-3,5-dimethoxyphenyl) pyrido[3,4-d]pyrimidine-2-amine (325 mg, 0.68 mmol), 3-methoxyazetidine hydrochloride (25 2 mg, 2.04 mmol) and DIPEA (439 mg, 3.4 mmol) were dissolved in n-butanol (15 mL), the mixture was heated to 100° C. for 4 h, and then the mixture was concentrated, extracted with ethyl acetate and separated by silica gel column chromatography to obtain compound N-((3S,4S)-4-azidotetrahydro-2H-pyran-3-yl)-6-(2,6-difluoro-3,5-dimethoxyphenyl)-8-(3-methoxyazetidin-1-yl)pyrido[3,4-d]pyrimidine-2-amine (350 mg, yield: 97%). MS m/z (ESI): 529 [M+H]+.

N-((3S,4S)-4-azidotetrahydro-2H-pyran-3-yl)-6-(2,6-difluoro-3,5-dimethoxyphenyl)-8-(3-methoxyazetidin-1-yl) pyrido[3,4-d]pyrimidine-2-amine (350 mg, 0.662 mmol) was dissolved in the mixture of THF (10 mL) and water (1 mL), and then triphenylphosphine (521 mg, 1.99 mmol) was added, the mixture was heated to 80° C. and stirred for 16 h. The mixture was cooled, directly dried over anhydrous sodium sulfate, concentrated, and separated by silica gel column chromatography to obtain compound (3S,4S)—N³-(6-(2,6-difluoro-3,5-dimethoxyphenyl)-8-(3-methoxyazetidin-1-yl)pyrido[3,4-d]pyrimidin-2-yl)tetrahydro-2H-pyran-3,4-di amine (290 mg, yield:87%). MS m/z (ESI), 503 [M+H]+.

Step 5: Preparation of N-((3S,4S)-3-((6-(2,6-difluoro-3,5-dimethoxyphenyl)-8-(3-methoxyazetidin-1-yl)pyrido[3,4-d]pyrimidin-2-yl)amino)tetrahydro-2H-pyran-4-yl)acrylamide

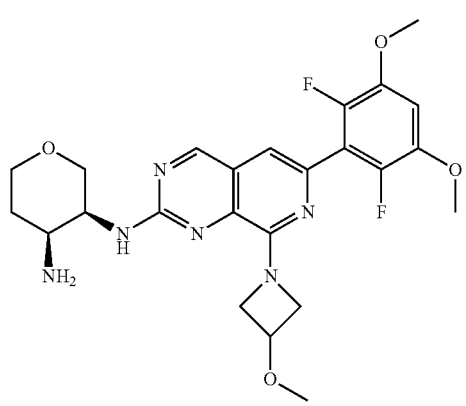

+

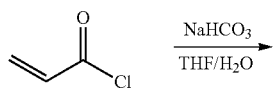

NaHCO₃ / THF/H₂O →

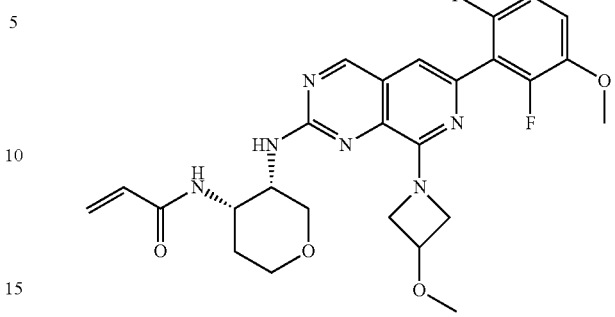

(3S,4S)—N³-(6-(2,6-difluoro-3,5-dimethoxyphenyl)-8-(3-methoxyazetidin-1-yl)pyrido[3,4-d]pyrimidin-2-yl)tetrahydro-2H-pyran-3,4-diamine (290 mg, 0.58 mmol) was dissolved in the mixture of THF (20 mL) and water (5 mL), then NaHCO₃ (243 mg, 2.89 mmol) was added, and acryloyl chloride solution (63 mg, 0.69 mmol, dissolved in 1 mL THF) was added dropwise at room temperature, the mixture was stirred at room temperature for 10 min. The reaction was completed determined by TLC, a saturated aqueous solution of NaHCO₃ was added to quench the reaction, the mixture was extracted with ethyl acetate, concentrated and separated by silica gel column chromatography to obtain compound N-((3S,4S)-3-((6-(2,6-difluoro-3,5-dimethoxyphenyl)-8-(3-methoxyazetidin-1-yl)pyrido[3,4-d]pyrimidin-2-yl)amino)tetrahydro-2H-pyran-4-yl)acrylamide (204 mg, yield:63%). MS m/z (ESI): 557 [M+H]+.

1H NMR (400 MHz, CDCl₃) δ 8.92 (s, 1H), 6.96 (s, 1H), 6.69 (t, J=8.0 Hz, H), 6.65 (s, 1H), 6.25 (dd. J=17.0, 1.4 Hz, 1H), 6.08 (s, 1H), 6.02 (dd. J=16.9, 10.3 Hz, 1H), 5.60 (dd, J=10.3, 1.4 Hz, 1H), 4.73 (brs, 1H), 4.56 (brs, 1H), 4.42 (d, J=8.5 Hz, 1H), 4.39-4.22 (m, 4H), 4.05 (dd. J=12.0, 4.5 Hz, 1H), 3.99 (d, J=11.7 Hz, 1H), 3.92 (s, 6H), 3.75 (dd, J=11.9, 1.6 Hz, 1H), 3.65-3.57 (m, 1H), 3.33 (s, 3H), 2.09-2.02 (m, 1H), 1.91-1.81 (m, 1H).

Examples 422-714 and 753-806 were prepared referring to the synthesis method of Example 33, 421 or 775.

| Example No. | Compound structure | Compound name | MS: m/z [M + 1]+ |
|---|---|---|---|
| 422 | 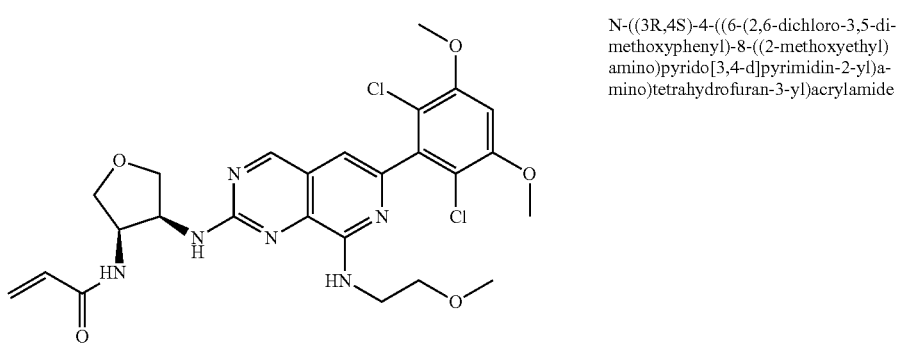 | N-((3R,4S)-4-((6-(2,6-dichloro-3,5-dimethoxyphenyl)-8-((2-methoxyethyl)amino)pyrido[3,4-d]pyrimidin-2-yl)amino)tetrahydrofuran-3-yl)acrylamide | 563 |

-continued

| Example No. | Compound structure | Compound name | MS: m/z [M + 1]+ |
|---|---|---|---|
| 423 | 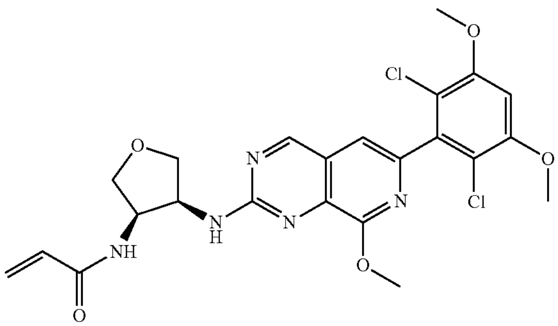 [SMILES: C=CC(=O)N[C@H]1COC[C@H]1Nc1ncc2cc(-c3c(Cl)c(OC)cc(OC)c3Cl)nc(OC)c2n1] | N-((3R,4S)-4-((6-(2,6-dichloro-3,5-dimethoxyphenyl)-8-methoxypyrido[3,4-d]pyrimidin-2-yl)amino)tetrahydrofuran-3-yl)acrylamide | 520 |
| 424 | 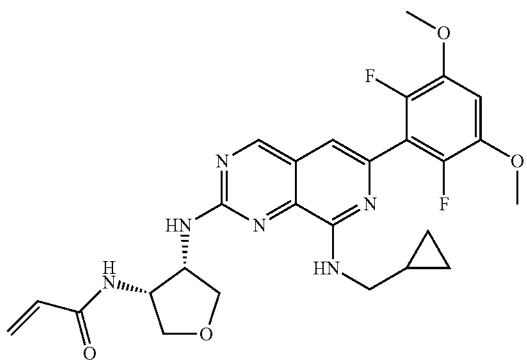 [SMILES: C=CC(=O)N[C@H]1COC[C@H]1Nc1ncc2cc(-c3c(F)c(OC)cc(OC)c3F)nc(NCC3CC3)c2n1] | N-((3R,4S)-4-((8-((cyclopropylmethyl)amino)-6-(2,6-difluoro-3,5-dimethoxyphenyl)pyrido[3,4-d]pyrimidin-2-yl)amino)tetrahydrofuran-3-yl)acrylamide | 527 |
| 425 | 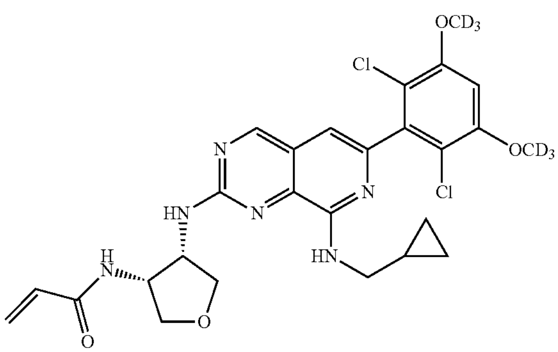 | N-((3R,4S)-4-((8-((cyclopropylmethyl)amino)-6-(2,6-dichloro-3,5-bis(methoxy-$d_3$)phenyl)pyrido[3,4-d]pyrimidin-2-yl)amino)tetrahydrofuran-3-yl)acrylamide | 565 |
| 426 | 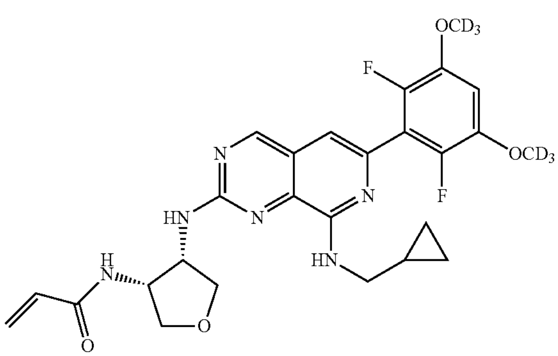 | N-((3R,4S)-4-((8-((cyclopropylmethyl)amino)-6-(2,6-difluoro-3,5-bis(methoxy-$d_3$)phenyl)pyrido[3,4-d]pyrimidin-2-yl)amino)tetrahydrofuran-3-yl)acrylamide | 533 |

| Example No. | Compound structure | Compound name | MS: m/z [M + 1]+ |
| --- | --- | --- | --- |
| 427 | 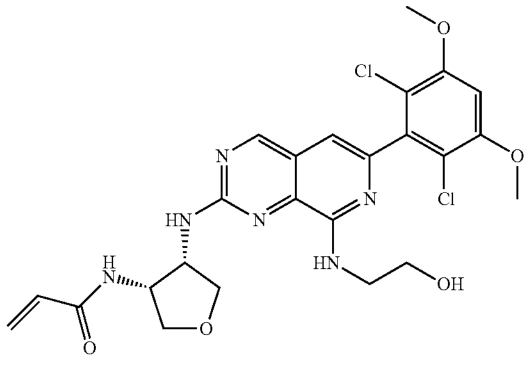 [SMILES: C=CC(=O)N[C@H]1COC[C@H]1Nc1ncc2cc(-c3c(Cl)c(OC)cc(OC)c3Cl)nc(NCCO)c2n1] | N-((3R,4S)-4-((6-(2,6-dichloro-3,5-dimethoxyphenyl)-8-((2-hydroxyethyl)amino)pyrido[3,4-d]pyrimidin-2-yl)amino)tetrahydrofuran-3-yl)acrylamide | 549 |
| 428 | 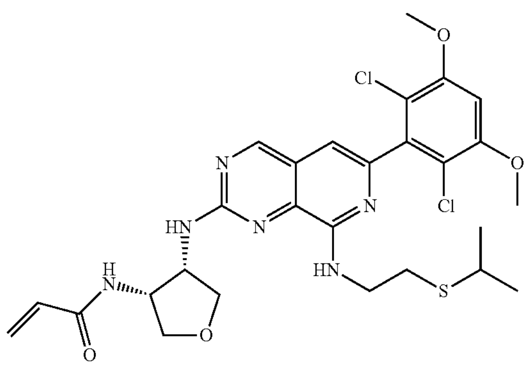 [SMILES: C=CC(=O)N[C@H]1COC[C@H]1Nc1ncc2cc(-c3c(Cl)c(OC)cc(OC)c3Cl)nc(NCCSC(C)C)c2n1] | N-((3R,4S)-4-((6-(2,6-dichloro-3,5-dimethoxyphenyl)-8-((2-(isopropylthio)ethyl)amino)pyrido[3,4-d]pyrimidin-2-yl)amino)tetrahydrofuran-3-yl)acrylamide | 607 |
| 429 | 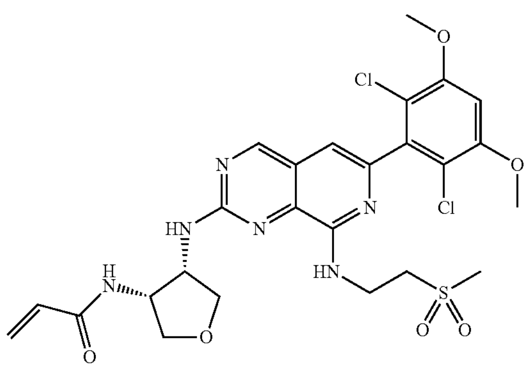 [SMILES: C=CC(=O)N[C@H]1COC[C@H]1Nc1ncc2cc(-c3c(Cl)c(OC)cc(OC)c3Cl)nc(NCCS(C)(=O)=O)c2n1] | N-((3R,4S)-4-((6-(2,6-dichloro-3,5-dimethoxyphenyl)-8-((2-(ethylsulfonyl)ethyl)amino)pyrido[3,4-d]pyrimidin-2-yl)amino)tetrahydrofuran-3-yl)acrylamide | 625 |
| 430 | 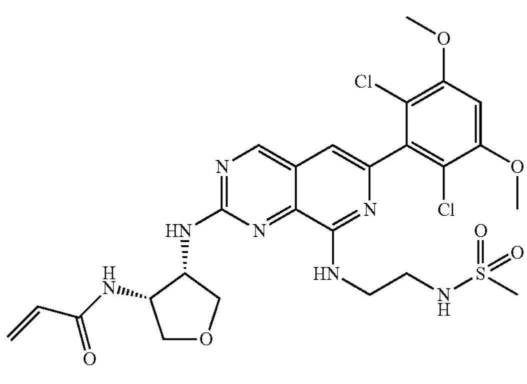 [SMILES: C=CC(=O)N[C@H]1COC[C@H]1Nc1ncc2cc(-c3c(Cl)c(OC)cc(OC)c3Cl)nc(NCCNS(C)(=O)=O)c2n1] | N-((3R,4S)-4-((6-(2,6-dichloro-3,5-dimethoxyphenyl)-8-((2-(methylsulfonamido)ethyl)amino)pyrido[3,4-d]pyrimidin-2-yl)amino)tetrahydrofuran-3-yl)acrylamide | 626 |

-continued

| Example No. | Compound structure | Compound name | MS: m/z [M + 1]+ |
|---|---|---|---|
| 431 | 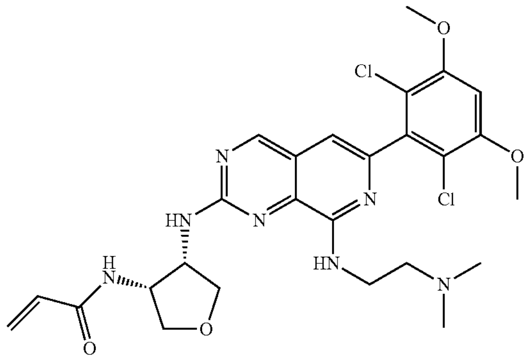 [SMILES: C=CC(=O)N[C@H]1COC[C@H]1Nc1ncc2cc(-c3c(Cl)c(OC)cc(OC)c3Cl)nc(NCCN(C)C)c2n1] | N-((3R,4S)-4-((6-(2,6-dichloro-3,5-dimethoxyphenyl)-8-((2-(dimethylamino)ethyl)amino)pyrido[3,4-d]pyrimidin-2-yl)amino)tetrahydrofuran-3-yl)acrylamide | 576 |
| 432 | 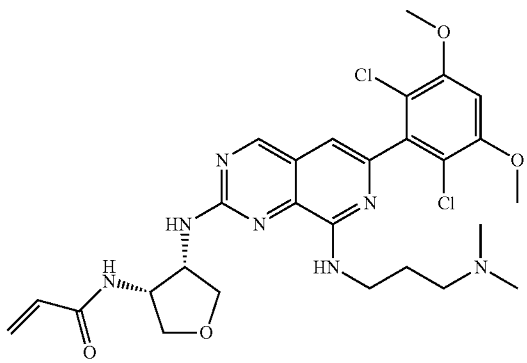 [SMILES: C=CC(=O)N[C@H]1COC[C@H]1Nc1ncc2cc(-c3c(Cl)c(OC)cc(OC)c3Cl)nc(NCCCN(C)C)c2n1] | N-((3R,4S)-4-((6-(2,6-dichloro-3,5-dimethoxyphenyl)-8-((3-(dimethylamino)propyl)amino)pyrido[3,4-d]pyrimidin-2-yl)amino)tetrahydrofuran-3-yl)acrylamide | 590 |
| 434 | 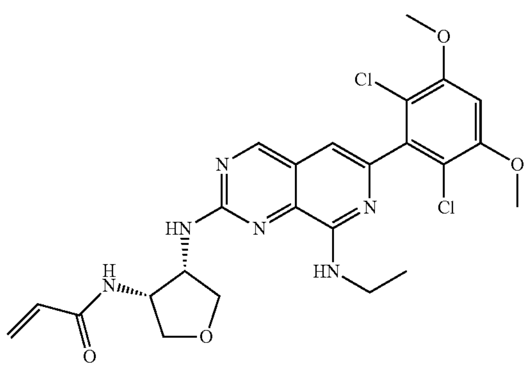 [SMILES: C=CC(=O)N[C@H]1COC[C@H]1Nc1ncc2cc(-c3c(Cl)c(OC)cc(OC)c3Cl)nc(NCC)c2n1] | N-((3R,4S)-4-((6-(2,6-dichloro-3,5-dimethoxyphenyl)-8-(ethylamino)pyrido[3,4-d]pyrimidin-2-yl0amino)tetrahydrofuran-3-yl)acrylamide | 533 |
| 435 | 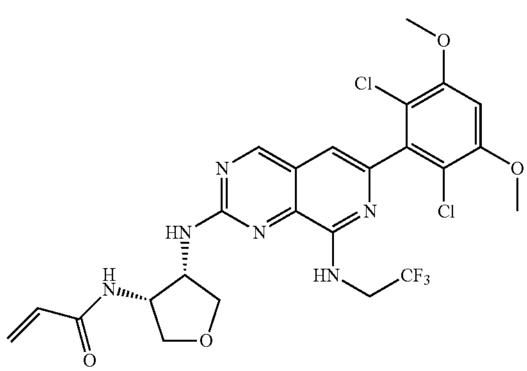 [SMILES: C=CC(=O)N[C@H]1COC[C@H]1Nc1ncc2cc(-c3c(Cl)c(OC)cc(OC)c3Cl)nc(NCC(F)(F)F)c2n1] | N-((3R,4S)-4-((6-(2,6-dichloro-3,5-dimethoxyphenyl)-8-((2,2,2-trifluoroethyl)amino)pyrido[3,4-d]pyrimidin-2-yl)amino)tetrahydrofuran-3-yl)acrylamide | 587 |

-continued

| Example No. | Compound structure | Compound name | MS: m/z [M + 1]+ |
|---|---|---|---|
| 436 | 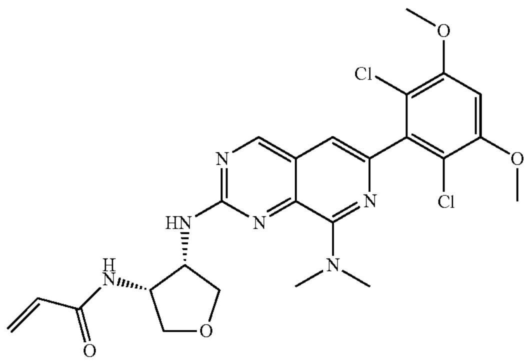 [SMILES: C=CC(=O)N[C@H]1COC[C@H]1Nc1ncc2cc(-c3c(Cl)c(OC)cc(OC)c3Cl)nc(N(C)C)c2n1] | N-((3R,4S)-4-((6-(2,6-dichloro-3,5-dimethoxyphenyl)-8-(dimethylamino)pyrido[3,4-d]pyrimidin-2-yl)amino)tetrahydrofuran-3-yl)acrylamide | 533 |
| 437 | 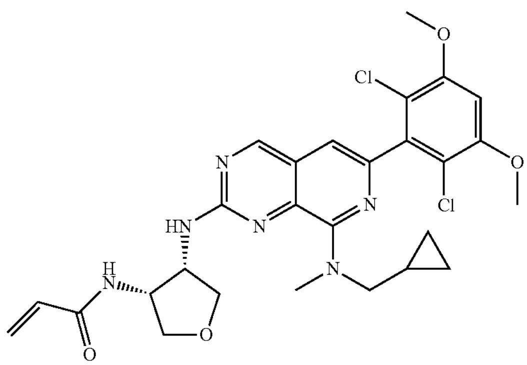 [SMILES: C=CC(=O)N[C@H]1COC[C@H]1Nc1ncc2cc(-c3c(Cl)c(OC)cc(OC)c3Cl)nc(N(C)CC3CC3)c2n1] | N-((3R,4S)-4-((8-((cyclopropylmethyl)(methyl)amino)-6-(2,6-dichloro-3,5-dimethoxyphenyl)pyrido[3,4-d]pyrimidin-2-yl)amino)tetrahydrofuran-3-yl)acrylamide | 573 |
| 438A | 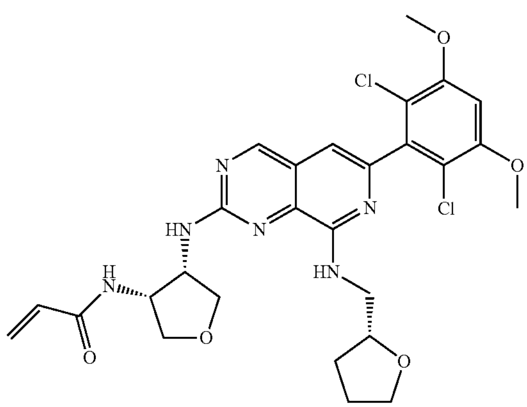 [SMILES: C=CC(=O)N[C@H]1COC[C@H]1Nc1ncc2cc(-c3c(Cl)c(OC)cc(OC)c3Cl)nc(NC[C@H]3CCCO3)c2n1] | N-((3R,4S)-4-((6-(2,6-dichloro-3,5-dimethoxyphenyl)-8-((((R)-tetrahydrofuran-2-yl)methyl)amino)pyrido[3,4-d]pyrimidin-2-yl)amino)tetrahydrofuran-3-yl)acrylamide | 589 |
| 438B | 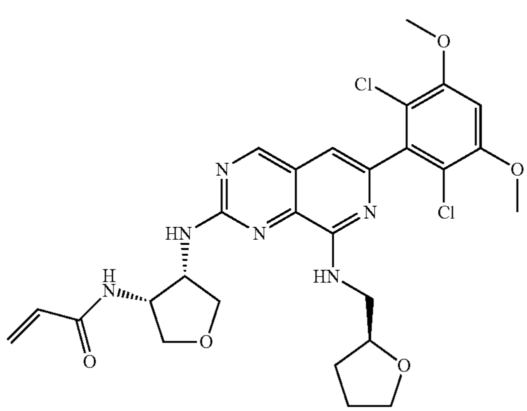 [SMILES: C=CC(=O)N[C@H]1COC[C@H]1Nc1ncc2cc(-c3c(Cl)c(OC)cc(OC)c3Cl)nc(NC[C@@H]3CCCO3)c2n1] | N-((3R,4S)-4-((6-(2,6-dichloro-3,5-dimethoxyphenyl)-8-((((S)-tetrahydrofuran-2-yl)methyl)amino)pyrido[3,4-d]pyrimidin-2-yl)amino)tetrahydrofuran-3-yl)acrylamide | 589 |

-continued

| Example No. | Compound structure | Compound name | MS: m/z [M + 1]+ |
|---|---|---|---|
| 439 | 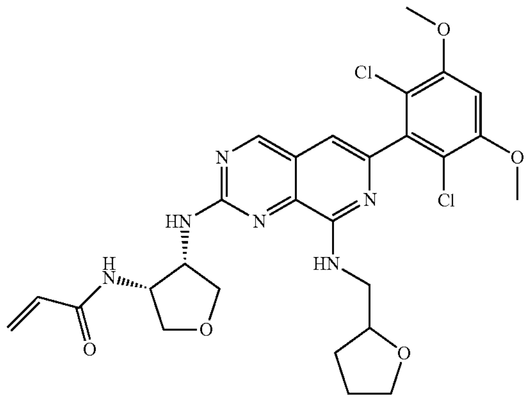 [SMILES: C=CC(=O)N[C@H]1COC[C@H]1Nc1ncc2cc(-c3c(Cl)c(OC)cc(OC)c3Cl)nc(NCC3CCCO3)c2n1] | N-((3R,4S)-4-((6-(2,6-dichloro-3,5-dimethoxyphenyl)-8-(((tetrahydrofuran-3-yl)methyl)amino)pyrido[3,4-d]pyrimidin-2-yl)amino)tetrahydrofuran-3-yl)acrylamide | 589 |
| 440 | 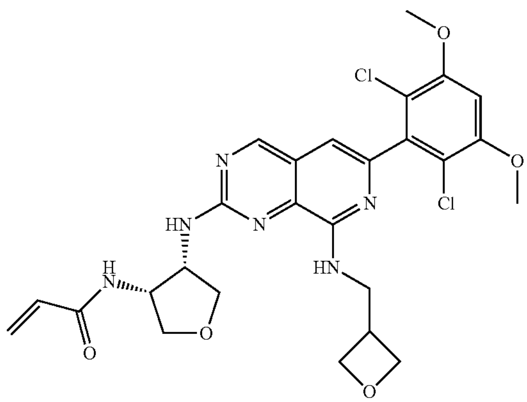 [SMILES: C=CC(=O)N[C@H]1COC[C@H]1Nc1ncc2cc(-c3c(Cl)c(OC)cc(OC)c3Cl)nc(NCC3COC3)c2n1] | N-((3R,4S)-4-((6-(2,6-dichloro-3,5-dimethoxyphenyl)-8-((oxetan-3-ylmethyl)amino)pyrido[3,4-d]pyrimidin-2-yl)amino)tetrahydrofuran-3-yl)acrylamide | 575 |
| 441 | 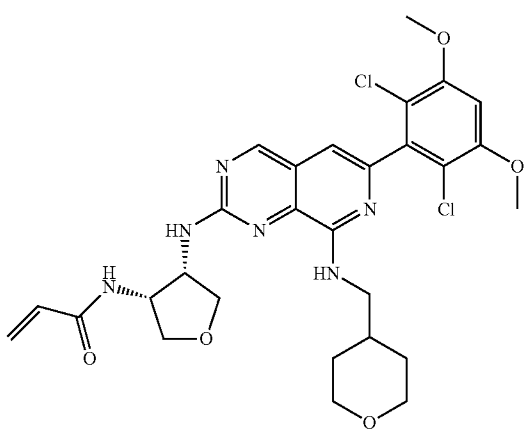 [SMILES: C=CC(=O)N[C@H]1COC[C@H]1Nc1ncc2cc(-c3c(Cl)c(OC)cc(OC)c3Cl)nc(NCC3CCOCC3)c2n1] | N-((3R,4S)-4-((6-(2,6-dichloro-3,5-dimethoxyphenyl)-8-(((tetrahydro-2H-pyran-4-yl)methyl)amino)pyrido[3,4-d]pyrimidin-2-yl)amino)tetrahydrofuran-3-yl)acrylamide | 603 |

-continued

| Example No. | Compound structure | Compound name | MS: m/z [M + 1]+ |
|---|---|---|---|
| 442 | 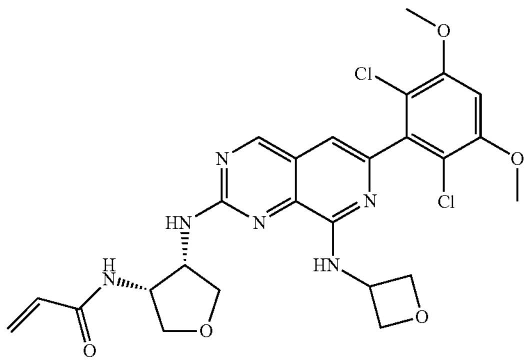 [SMILES: C=CC(=O)N[C@H]1COC[C@H]1Nc1ncc2cc(-c3c(Cl)c(OC)cc(OC)c3Cl)nc(NC3COC3)c2n1] | N-((3R,4S)-4-((6-(2,6-dichloro-3,5-dimethoxyphenyl)-8-(oxetan-3-yl-amino)pyrido[3,4-d]pyrimidin-2-yl)amino)tetrahydrofuran-3-yl)acrylamide | 561 |
| 443 | 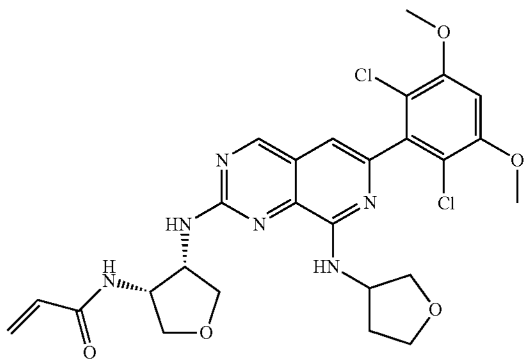 [SMILES: C=CC(=O)N[C@H]1COC[C@H]1Nc1ncc2cc(-c3c(Cl)c(OC)cc(OC)c3Cl)nc(NC3CCOC3)c2n1] | N-((3R,4S)-4-((6-(2,6-dichloro-3,5-dimethoxyphenyl)-8-((tetrahydrofuran-3-yl)amino)pyrido[3,4-d]pyrimidin-2-yl)amino)tetrahydrofuran-3-yl)acrylamide | 575 |
| 444 | 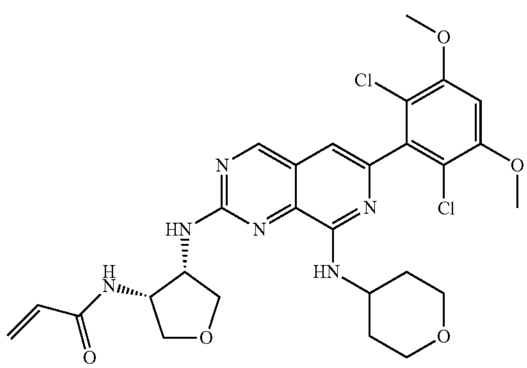 [SMILES: C=CC(=O)N[C@H]1COC[C@H]1Nc1ncc2cc(-c3c(Cl)c(OC)cc(OC)c3Cl)nc(NC3CCOCC3)c2n1] | N-((3R,4S)-4-((6-(2,6-dichloro-3,5-dimethoxyphenyl)-8-((tetrahydro-2H-pyran-4-yl)amino)pyrido[3,4-d]pyrimidin-2-yl)amino)tetrahydrofuran-3-yl)acrylamide | 589 |
| 445 | 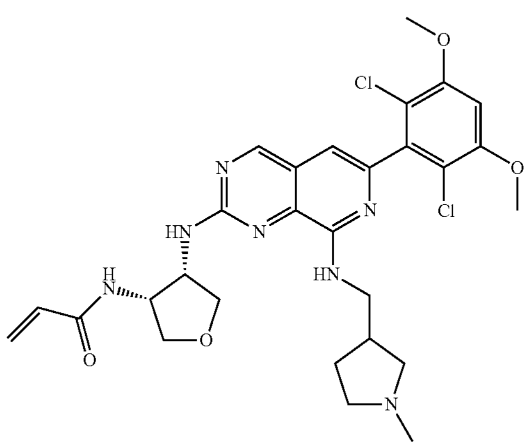 [SMILES: C=CC(=O)N[C@H]1COC[C@H]1Nc1ncc2cc(-c3c(Cl)c(OC)cc(OC)c3Cl)nc(NCC3CCN(C)C3)c2n1] | N-((3R,4S)-4-((6-(2,6-dichloro-3,5-dimethoxyphenyl)-8-(((1-methylpyrrolidin-3-yl)methyl)amino)pyrido[3,4-d]pyrimidin-2-yl)amino)tetrahydrofuran-3-yl)acrylamide | 602 |

-continued

| Example No. | Compound structure | Compound name | MS: m/z [M + 1]+ |
|---|---|---|---|
| 446 | 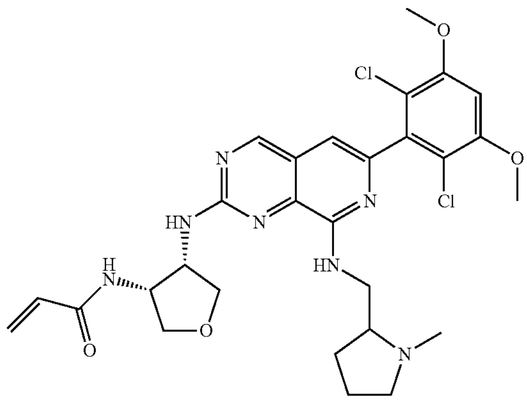 [SMILES: C=CC(=O)N[C@H]1COC[C@H]1Nc1ncc2cc(-c3c(Cl)c(OC)cc(OC)c3Cl)nc(NCC3CCCN3C)c2n1] | N-((3R,4S)-4-((6-(2,6-dichloro-3,5-dimethoxyphenyl)-8-(((1-methylpyrrolidin-2-yl)methyl)amino)pyrido[3,4-d]pyrimidin-2-yl)amino)tetrahydrofuran-3-yl)acrylamide | 602 |
| 447 | 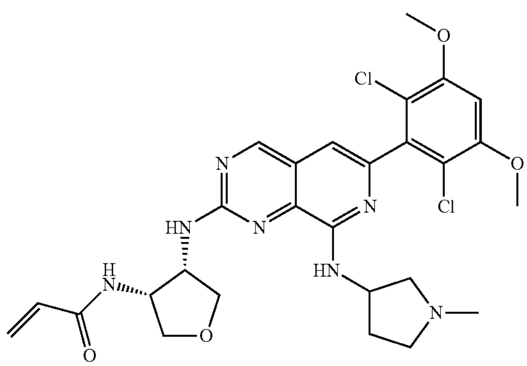 [SMILES: C=CC(=O)N[C@H]1COC[C@H]1Nc1ncc2cc(-c3c(Cl)c(OC)cc(OC)c3Cl)nc(NC3CCN(C)C3)c2n1] | N-((3R,4S)-4-((6-(2,6-dichloro-3,5-dimethoxyphenyl)-8-((1-methylpyrrolidin-3-yl)amino)pyrido[3,4-d]pyrimidin-2-yl)amino)tetrahydrofuran-3-yl)acrylamide | 588 |
| 448 | 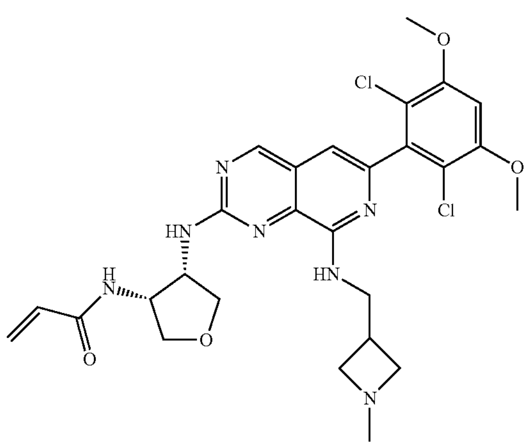 [SMILES: C=CC(=O)N[C@H]1COC[C@H]1Nc1ncc2cc(-c3c(Cl)c(OC)cc(OC)c3Cl)nc(NCC3CN(C)C3)c2n1] | N-((3R,4S)-4-((6-(2,6-dichloro-3,5-dimethoxyphenyl)-8-(((1-methylazetidin-3-yl)methyl)amino)pyrido[3,4-d]pyrimidin-2-yl)amino)tetrahydrofuran-3-yl)acrylamide | 588 |

| Example No. | Compound structure | Compound name | MS: m/z [M + 1]+ |
|---|---|---|---|
| 449 | 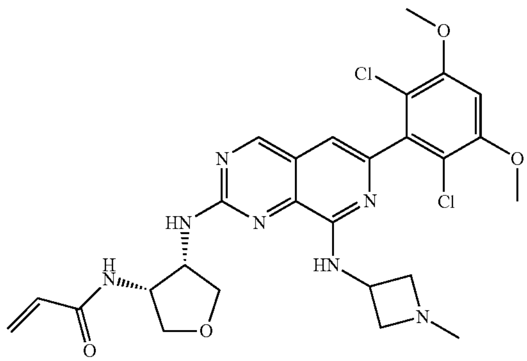 [SMILES: C=CC(=O)N[C@H]1COC[C@H]1Nc1ncc2cc(-c3c(Cl)c(OC)cc(OC)c3Cl)nc(NC3CN(C)C3)c2n1] | N-((3R,4S)-4-((6-(2,6-dichloro-3,5-dimethoxyphenyl)-8-((1-methylazetidin-3-yl)amino)pyrido[3,4-d]pyrimidin-2-yl)amino)tetrahydrofuran-3-yl)acrylamide | 574 |
| 450 | 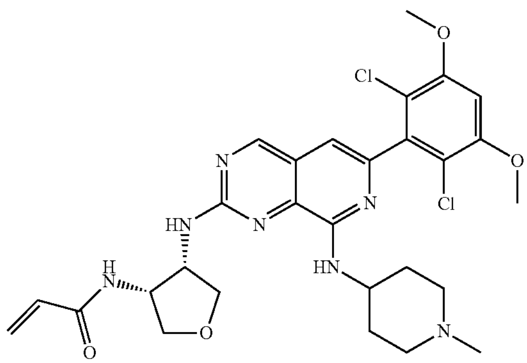 [SMILES: C=CC(=O)N[C@H]1COC[C@H]1Nc1ncc2cc(-c3c(Cl)c(OC)cc(OC)c3Cl)nc(NC3CCN(C)CC3)c2n1] | N-((3R,4S)-4-((6-(2,6-dichloro-3,5-dimethoxyphenyl)-8-((1-methylpiperidin-4-yl)amino)pyrido[3,4-d]pyrimidin-2-yl)amino)tetrahydrofuran-3-yl)acrylamide | 602 |
| 451 | 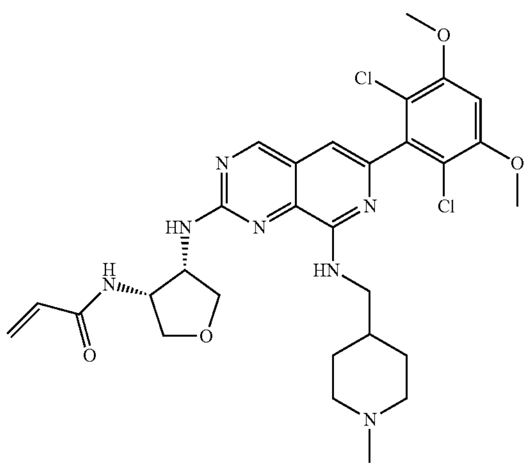 [SMILES: C=CC(=O)N[C@H]1COC[C@H]1Nc1ncc2cc(-c3c(Cl)c(OC)cc(OC)c3Cl)nc(NCC3CCN(C)CC3)c2n1] | N-((3R,4S)-4-((6-(2,6-dichloro-3,5-dimethoxyphenyl)-8-(((1-methylpiperidin-4-yl)methyl)amino)pyrido[3,4-d]pyrimidin-2-yl)amino)tetrahydrofuran-3-yl)acrylamide | 616 |
| 452 | 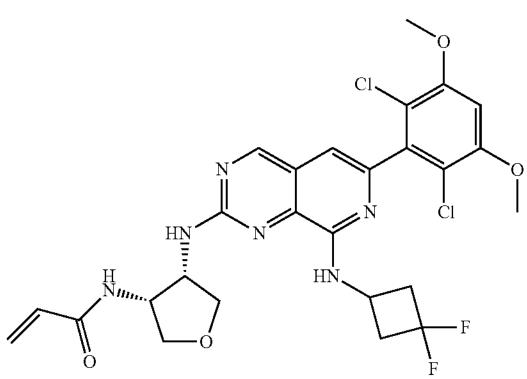 [SMILES: C=CC(=O)N[C@H]1COC[C@H]1Nc1ncc2cc(-c3c(Cl)c(OC)cc(OC)c3Cl)nc(NC3CC(F)(F)C3)c2n1] | N-((3R,4S)-4-((6-(2,6-dichloro-3,5-dimethoxyphenyl)-8-((3,3-difluorocyclobutyl)amino)pyrido[3,4-d]pyrimidin-2-yl)amino)tetrahydrofuran-3-yl)acrylamide | 595 |

-continued

| Example No. | Compound structure | Compound name | MS: m/z [M + 1]+ |
|---|---|---|---|
| 453 | 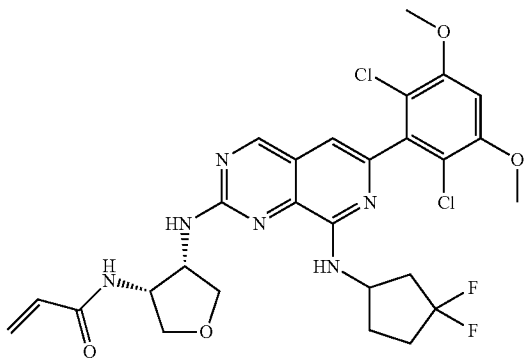 [SMILES: C=CC(=O)N[C@H]1COC[C@H]1Nc1ncc2cc(-c3c(Cl)c(OC)cc(OC)c3Cl)nc(NC3CCC(F)(F)C3)c2n1] | N-((3R,4S)-4-((6-(2,6-dichloro-3,5-dimethoxyphenyl)-8-((3,3-difluorocyclopentyl)amino)pyrido[3,4-d]pyrimidin-2-yl)amino)tetrahydrofuran-3-yl)acrylamide | 609 |
| 454 | 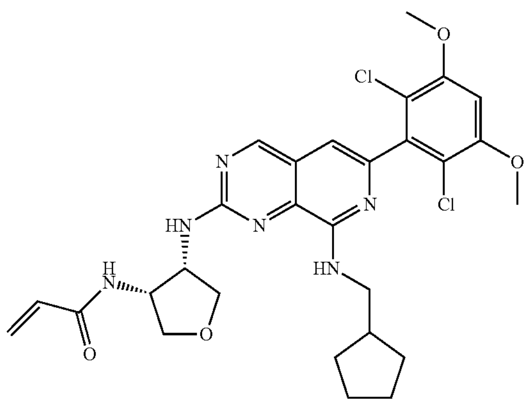 [SMILES: C=CC(=O)N[C@H]1COC[C@H]1Nc1ncc2cc(-c3c(Cl)c(OC)cc(OC)c3Cl)nc(NCC3CCCC3)c2n1] | N-((3R,4S)-4-((8-((cyclopentylmethyl)amino)-6-(2,6-dichloro-3,5-dimethoxyphenyl)pyrido[3,4-d]pyrimidin-2-yl)amino)tetrahydrofuran-3-yl)acrylamide | 587 |
| 455 | 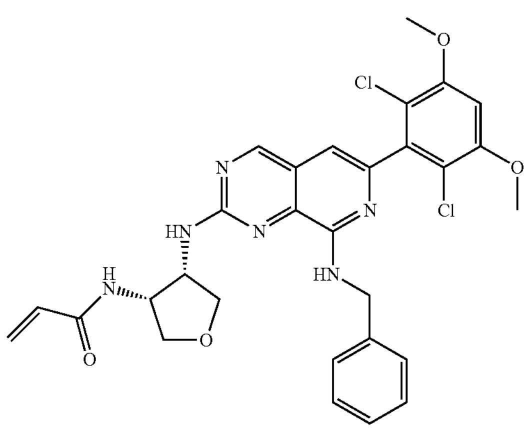 [SMILES: C=CC(=O)N[C@H]1COC[C@H]1Nc1ncc2cc(-c3c(Cl)c(OC)cc(OC)c3Cl)nc(NCc3ccccc3)c2n1] | N-((3R,4S)-4-((8-(benzylamino)-6-(2,6-dichloro-3,5-dimethoxyphenyl)pyrido[3,4-d]pyrimidn-2-yl)amino)tetrahydrofuran-3-yl)acrylamide | 595 |

| Example No. | Compound structure | Compound name | MS: m/z [M + 1]+ |
|---|---|---|---|
| 456 | 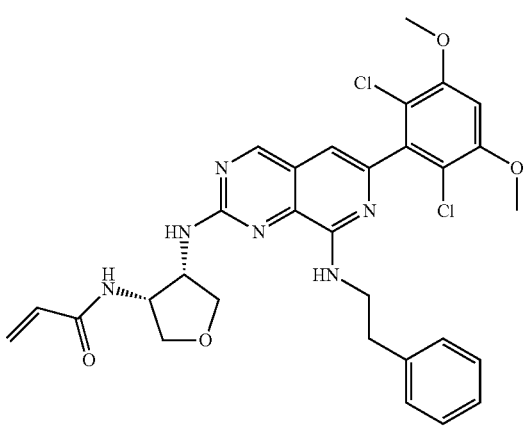 [SMILES: C=CC(=O)N[C@H]1COC[C@H]1Nc1ncc2cc(-c3c(Cl)c(OC)cc(OC)c3Cl)nc(NCCc3ccccc3)c2n1] | N-((3R,4S)-4-((6-(2,6-dichloro-3,5-dimethoxyphenyl)-8-(phenethylamino)pyrido[3,4-d]pyrimidin-2-yl)amino)tetrahydrofuran-3-yl)acrylamide | 609 |
| 457 | 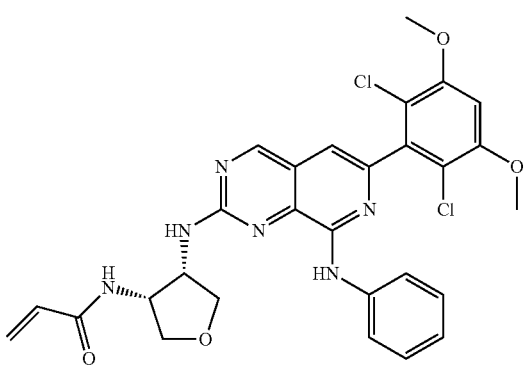 [SMILES: C=CC(=O)N[C@H]1COC[C@H]1Nc1ncc2cc(-c3c(Cl)c(OC)cc(OC)c3Cl)nc(Nc3ccccc3)c2n1] | N-((3R,4S)-4-((6-(2,6-dichloro-3,5-dimethoxyphenyl)-8-(phenylamino)pyrido[3,4-d]pyrimidin-2-yl)amino)tetrahydrofuran-3-yl)acrylamide | 581 |
| 458 | 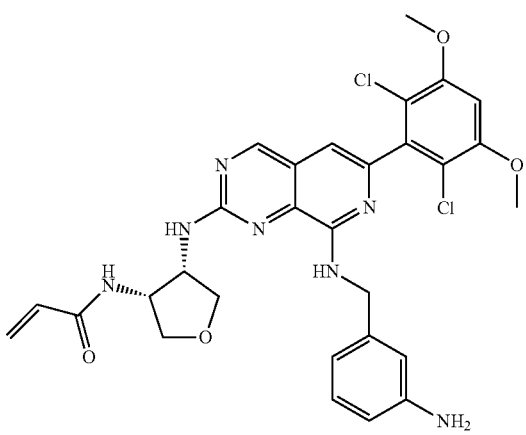 [SMILES: C=CC(=O)N[C@H]1COC[C@H]1Nc1ncc2cc(-c3c(Cl)c(OC)cc(OC)c3Cl)nc(NCc3cccc(N)c3)c2n1] | N-((3R,4S)-4-((8-((3-aminobenzyl)amino)-6-(2,6-dichloro-3,5-dimethoxyphenyl)pyrido[3,4-d]pyrimidin-2-yl)amino)tetrahydrofuran-3-yl)acrylamide | 610 |

-continued

| Example No. | Compound structure | Compound name | MS: m/z [M + 1]+ |
|---|---|---|---|
| 459 | 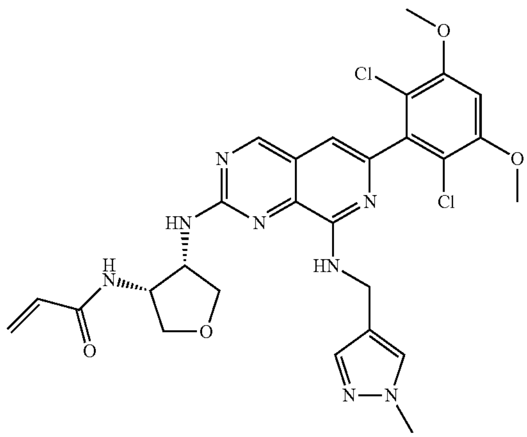 [SMILES: C=CC(=O)N[C@H]1COC[C@H]1Nc1ncc2cc(-c3c(Cl)c(OC)cc(OC)c3Cl)nc(NCc3cnn(C)c3)c2n1] | N-((3R,4S)-4-((6-(2,6-dichloro-3,5-di-methoxyphenyl)-8-(((1-methyl-1H-pyrazol-4-yl)methyl)amino)pyrido[3,4-d]pyrimidin-2-yl)amino)tetrahydro-furan-3-yl)acrylamide | 599 |
| 460 | 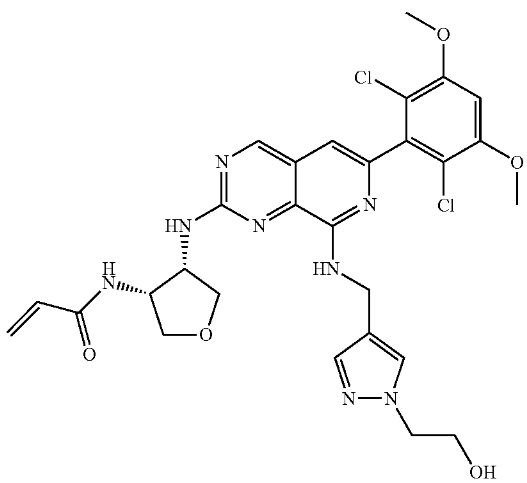 [SMILES: C=CC(=O)N[C@H]1COC[C@H]1Nc1ncc2cc(-c3c(Cl)c(OC)cc(OC)c3Cl)nc(NCc3cnn(CCO)c3)c2n1] | N-((3R,4S)-4-((6-(2,6-dichloro-3,5-di-methoxyphenyl)-8-(((1-(2-hydroxy-ethyl)-1H-pyrazol-4-yl)methyl)amino)pyrido[3,4-d]pyrimidin-2-yl)amino)tetrahydrofuran-3-yl)acrylamide | 629 |
| 461 | 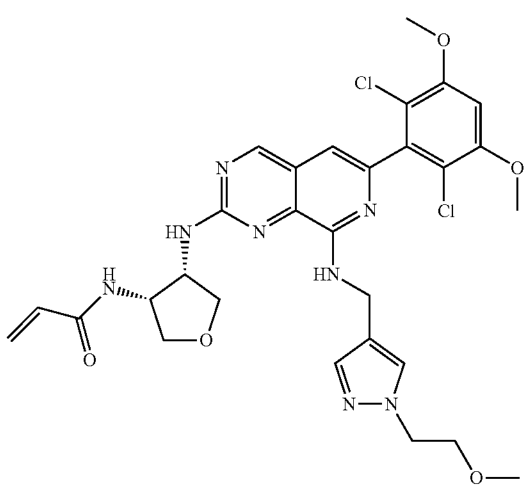 [SMILES: C=CC(=O)N[C@H]1COC[C@H]1Nc1ncc2cc(-c3c(Cl)c(OC)cc(OC)c3Cl)nc(NCc3cnn(CCOC)c3)c2n1] | N-((3R,4S)-4-((6-(2,6-dichloro-3,5-di-methoxyphenyl)-8-(((1-(2-methoxy-ethyl)-1H-pyrazol-4-yl)methyl)amino)pyrido[3,4-d]pyrimidin-2-yl)ami-no)tetrahydrofuran-3-yl)acrylamide | 643 |

-continued

| Example No. | Compound structure | Compound name | MS: m/z [M + 1]+ |
|---|---|---|---|
| 462 | 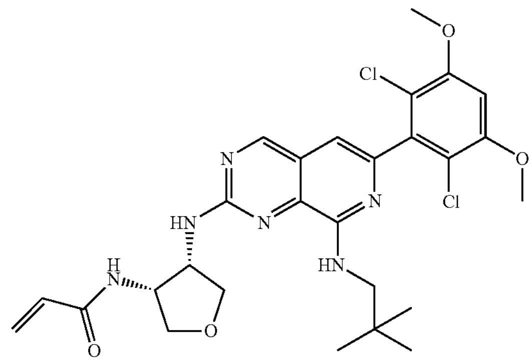 [SMILES: C=CC(=O)N[C@H]1COC[C@H]1Nc1ncc2cc(-c3c(Cl)c(OC)cc(OC)c3Cl)nc(NCC(C)(C)C)c2n1] | N-((3R,4S)-4-((6-(2,6-dichloro-3,5-dimethoxyphenyl)-8-(neopentylamino)pyrido[3,4-d]pyrimidin-2-yl)amino)tetrahydrofuran-3-yl)acrylamide | 575 |
| 463 | 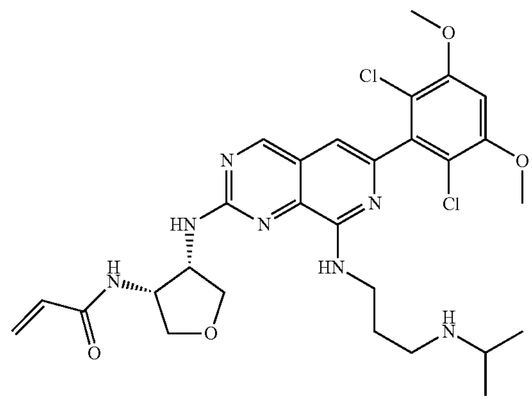 [SMILES: C=CC(=O)N[C@H]1COC[C@H]1Nc1ncc2cc(-c3c(Cl)c(OC)cc(OC)c3Cl)nc(NCCCNC(C)C)c2n1] | N-((3R,4S)-4-((6-(2,6-dichloro-3,5-dimethoxyphenyl)-8-((3-(isopropylamino)propyl)amino)pyrido[3,4-d]pyrimidin-2-yl)amino)tetrahydrofuran-3-yl)acrylamide | 604 |
| 464 | 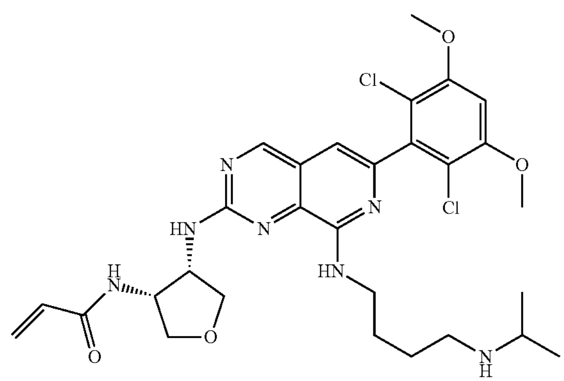 [SMILES: C=CC(=O)N[C@H]1COC[C@H]1Nc1ncc2cc(-c3c(Cl)c(OC)cc(OC)c3Cl)nc(NCCCCNC(C)C)c2n1] | N-((3R,4S)-4-((6-(2,6-dichloro-3,5-dimethoxyphenyl)-8-((4-(isopropylamino)butyl)amino)pyrido[3,4-d]pyrimidin-2-yl)amino)tetrahydrofuran-3-yl)acrylamide | 618 |
| 465 | 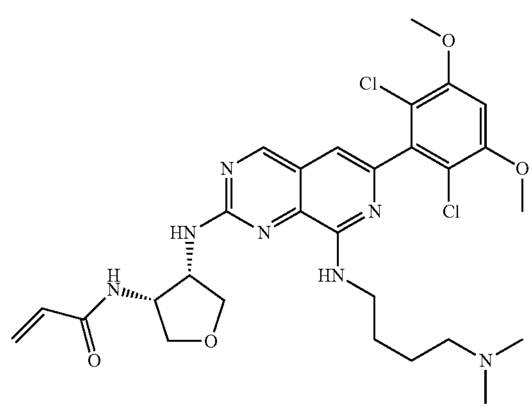 [SMILES: C=CC(=O)N[C@H]1COC[C@H]1Nc1ncc2cc(-c3c(Cl)c(OC)cc(OC)c3Cl)nc(NCCCCN(C)C)c2n1] | N-((3R,4S)-4-((6-(2,6-dichloro-3,5-dimethoxyphenyl)-8-((4-(dimethylamino)butyl)amino)pyrido[3,4-d]pyrimidin-2-yl)amino)tetrahydrofuran-3-yl)acrylamide | 604 |

-continued

| Example No. | Compound structure | Compound name | MS: m/z [M + 1]+ |
|---|---|---|---|
| 466 | 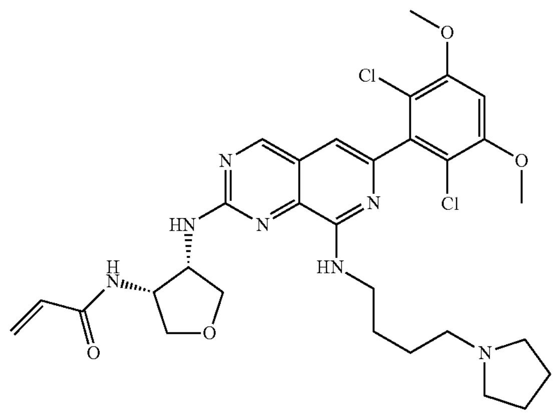 [SMILES: C=CC(=O)N[C@H]1COC[C@H]1Nc1ncc2cc(-c3c(Cl)c(OC)cc(OC)c3Cl)nc(NCCCCN3CCCC3)c2n1] | N-((3R,4S)-4-((6-(2,6-dichloro-3,5-dimethoxyphenyl)-8-((4-(pyrrolidin-1-yl)butyl)amino)pyrido[3,4-d]pyrimidin-2-yl)amino)tetrahydrofuran-3-yl)acrylamide | 630 |
| 467 | 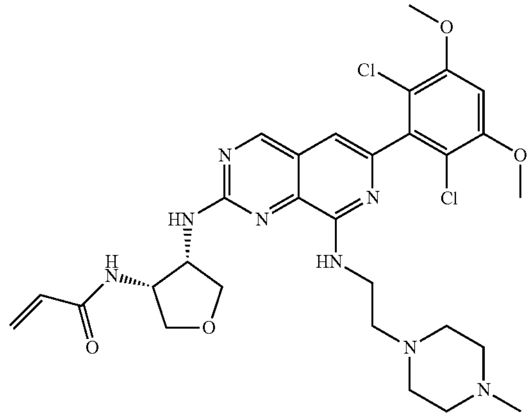 [SMILES: C=CC(=O)N[C@H]1COC[C@H]1Nc1ncc2cc(-c3c(Cl)c(OC)cc(OC)c3Cl)nc(NCCN3CCN(C)CC3)c2n1] | N-((3R,4S)-4-((6-(2,6-dichloro-3,5-dimethoxyphenyl)-8-((2-(4-methylpiperazin-1-yl)ethyl)amino)pyrido[3,4-d]pyrimidin-2-yl)amino)tetrahydrofuran-3-yl)acrylamide | 631 |
| 468 | 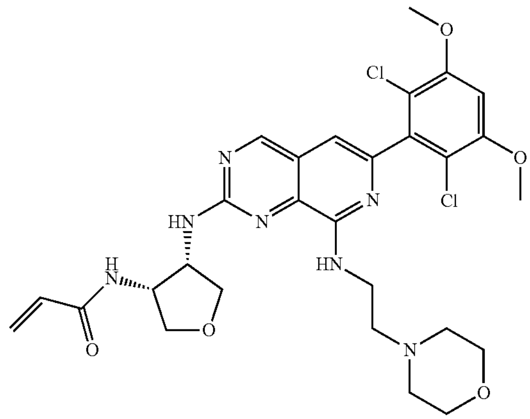 [SMILES: C=CC(=O)N[C@H]1COC[C@H]1Nc1ncc2cc(-c3c(Cl)c(OC)cc(OC)c3Cl)nc(NCCN3CCOCC3)c2n1] | N-((3R,4S)-4-((6-(2,6-dichloro-3,5-dimethoxyphenyl)-8-((2-morpholinoethyl)amino)pyrido[3,4-d]pyrimidin-2-yl)amino)tetrahydrofuran-3-yl)acrylamide | 618 |

-continued

| Example No. | Compound structure | Compound name | MS: m/z [M + 1]+ |
|---|---|---|---|
| 469 | 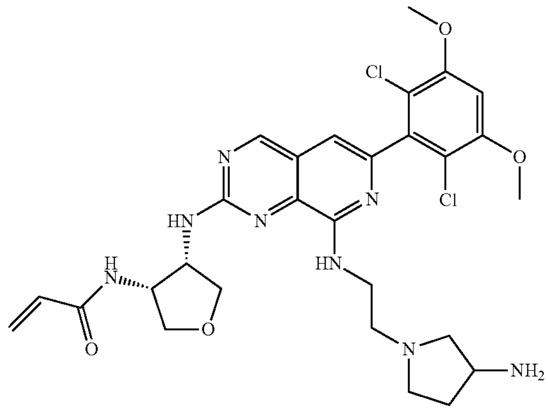 [SMILES: C=CC(=O)N[C@H]1COC[C@H]1Nc1ncc2cc(-c3c(Cl)c(OC)cc(OC)c3Cl)nc(NCCN3CCC(N)C3)c2n1] | N-((3R,4S)-4-((8-((2-(3-amino-pyrrolidin-1-yl)ethyl)amino)-6-(2,6-dichloro-3,5-dimethoxy-phenyl)pyrido[3,4-d]pyrimidin-2-yl)amino)tetrahydrofuran-3-yl)acrylamide | 617 |
| 470 | 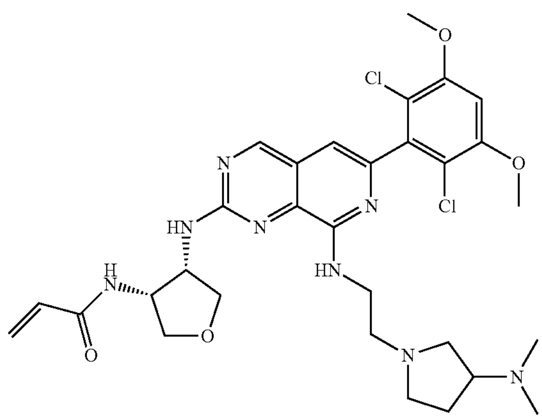 [SMILES: C=CC(=O)N[C@H]1COC[C@H]1Nc1ncc2cc(-c3c(Cl)c(OC)cc(OC)c3Cl)nc(NCCN3CCC(N(C)C)C3)c2n1] | N-((3R,4S)-4-((6-(2,6-dichloro-3,5-dimethoxyphenyl)-8-((2-(3-(dimethyl-amino)pyrrolidin-1-yl)ethyl)amino)pyrido[3,4-d]pyrimidin-2-yl)amino)tetrahydrofuran-3-yl)acrylamide | 645 |
| 471 | 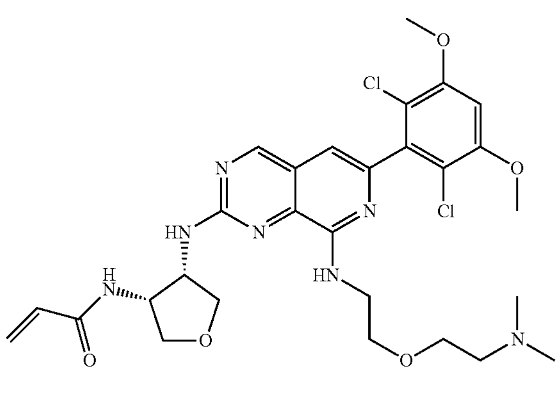 [SMILES: C=CC(=O)N[C@H]1COC[C@H]1Nc1ncc2cc(-c3c(Cl)c(OC)cc(OC)c3Cl)nc(NCCOCCN(C)C)c2n1] | N-((3R,4S)-4-((6-(2,6-dichloro-3,5-dimethoxyphenyl)-8-((2-(2-(dimethyl-amino)ethoxy)ethyl)amino)pyrido[3,4-d]pyrimidin-2-yl)amino)tetrahydro-furan-3-yl)acrylamide | 620 |

-continued

| Example No. | Compound structure | Compound name | MS: m/z [M + 1]+ |
|---|---|---|---|
| 472 | 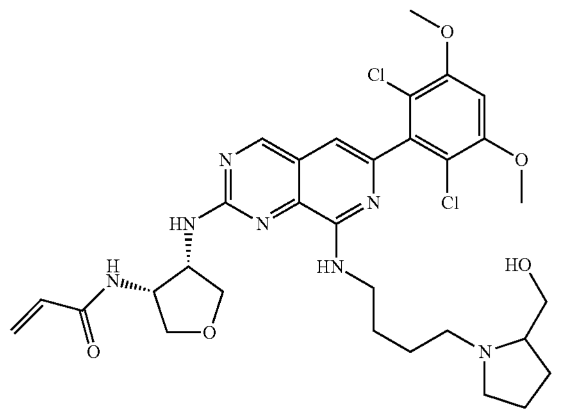 [SMILES: C=CC(=O)N[C@H]1COC[C@H]1Nc1ncc2cc(-c3c(Cl)c(OC)cc(OC)c3Cl)nc(NCCCCN3CCCC3CO)c2n1] | N-((3R,4S)-4-((6-(2,6-dichloro-3,5-di-methoxyphenyl)-8-((4-(2-(hydroxy-methyl)pyrrolidin-1-yl)butyl)amino)pyrido[3,4-d]pyrimidni-2-yl)amino)tetrahydrofuran-3-yl)acrylamide | 660 |
| 473 | 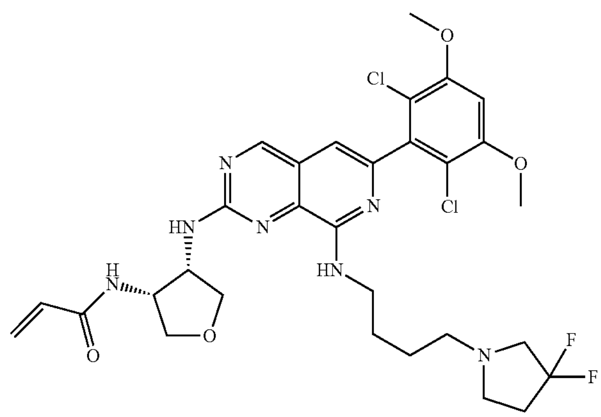 [SMILES: C=CC(=O)N[C@H]1COC[C@H]1Nc1ncc2cc(-c3c(Cl)c(OC)cc(OC)c3Cl)nc(NCCCCN3CCC(F)(F)C3)c2n1] | N-((3R,4S)-4-((6-(2,6-dichloro-3,5-di-methoxyphenyl)-8-((4-(3,3-difluoro-pyrrolidin-1-yl)butyl)amino)pyrido[3,4-d]pyrimidin-2-yl)amino)tetra-hydrofuran-3-yl)acrylamide | 666 |
| 474 | 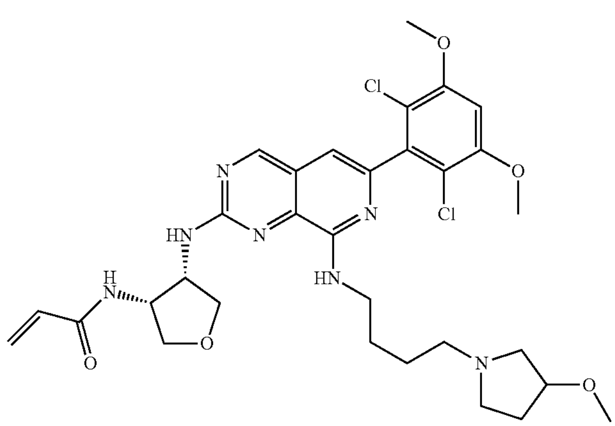 [SMILES: C=CC(=O)N[C@H]1COC[C@H]1Nc1ncc2cc(-c3c(Cl)c(OC)cc(OC)c3Cl)nc(NCCCCN3CCC(OC)C3)c2n1] | N-((3R,4S)-4-((6-(2,6-dichloro-3,5-di-methoxyphenyl)-8-((4-(3-methoxy-pyrrolidin-1-yl)butyl)amino)pyrido[3,4-d]pyrimidin-2-yl)amino)tetrahydro-furan-3-yl)acrylamide | 660 |

-continued

| Example No. | Compound structure | Compound name | MS: m/z [M + 1]+ |
|---|---|---|---|
| 475 | 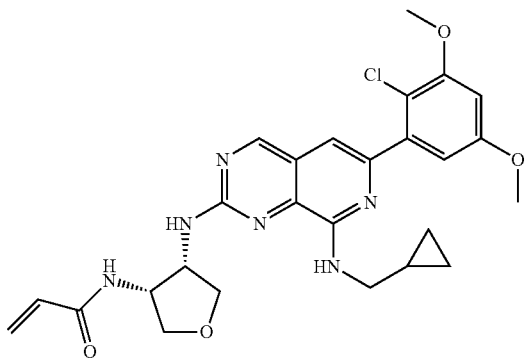 [SMILES: C=CC(=O)N[C@H]1COC[C@H]1Nc1ncc2cc(-c3cc(OC)cc(OC)c3Cl)nc(NCC3CC3)c2n1] | N-((3R,4S)-4-((6-(2-chloro-3,5-dimethoxyphenyl)-8-((cyclopropylmethyl)amino)pyrido[3,4-d]pyrimidin-2-yl)amino)tetrahydrofuran-3-yl)acrylamide | 525 |
| 476 | 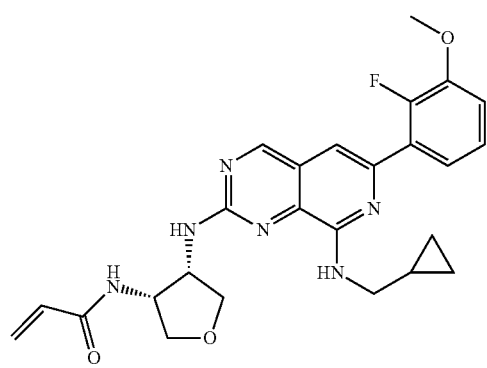 [SMILES: C=CC(=O)N[C@H]1COC[C@H]1Nc1ncc2cc(-c3cccc(OC)c3F)nc(NCC3CC3)c2n1] | N-((3R,4S)-4-((8-((cyclopropylmethyl)amino)-6-(2-fluoro-3-methoxyphenyl)pyrido[3,4-d]pyrimidin-2-yl)amino)tetrahydrofuran-3-yl)acrylamide | 479 |
| 477 | 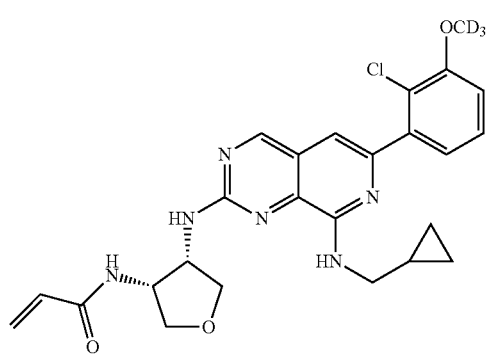 | N-((3R,4S)-4-((6-(2-chloro-3-(methoxy-$d_3$)phenyl)-8-((cyclopropylmethyl)amino)pyrido[3,4-d]pyrimidin-2-yl)amino)tetrahydrofuran-3-yl)acrylamide | 498 |
| 478 | 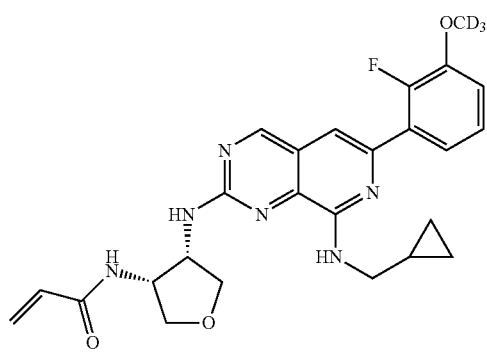 | N-((3R,4S)-4-((8-((cyclopropylmethyl)amino)-6-(2-fluoro-3-(methoxy-d3)phenyl)pyrido[3,4-d]pyrimidin-2-yl)amino)tetrahydrofuran-3-yl)acrylamide | 482 |

-continued

| Example No. | Compound structure | Compound name | MS: m/z [M + 1]+ |
|---|---|---|---|
| 479 | 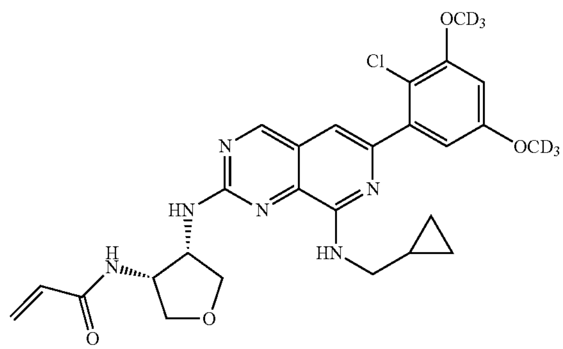 | N-((3R,4S)-4-((6-(2-chloro-3,5-bis(methoxy-d₃)phenyl)-8-((cylcopropyl-methyl)amino)pyrido[3,4-d]pyrimidin-2-yl)amino)tetrahydrofuran-3-yl)acrylamide | 531 |
| 480 | 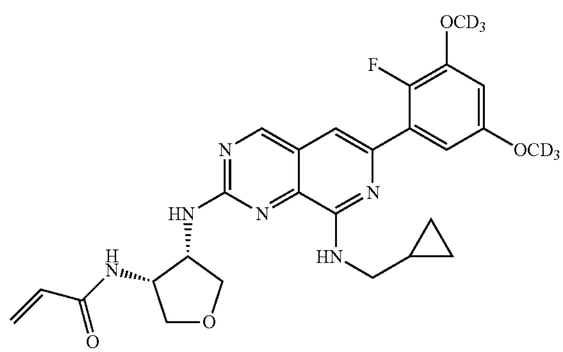 | N-((3R,4S)-4-((8-((cyclopropylmethyl)amino)-6-(2-fluoro-3,5-bis(methoxy-d₃)phenyl)pyrido[3,4-d]pyrimidin-2-yl)amino)tetrahydrofuran-3-yl)acrylamide | 515 |
| 481 | 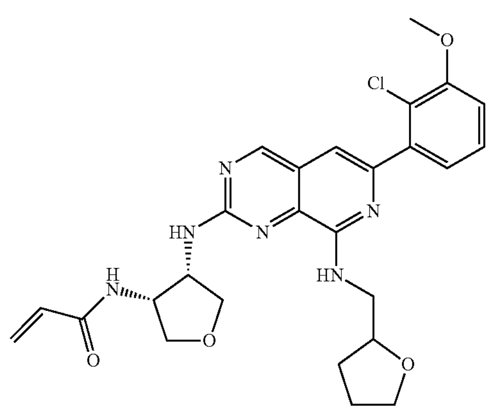 [SMILES: C=CC(=O)N[C@H]1COC[C@H]1Nc1ncc2cc(-c3cccc(OC)c3Cl)nc(NCC3CCCO3)c2n1] | N-((3R,4S)-4-((6-(2-chloro-3-methoxyphenyl)-8-(((tetrahydrofuran-2-yl)methyl)amino)pyrido[3,4-d]pyrimidin-2-yl)amino)tetrahydrofuran-3-yl)acrylamide | 525 |
| 482 | 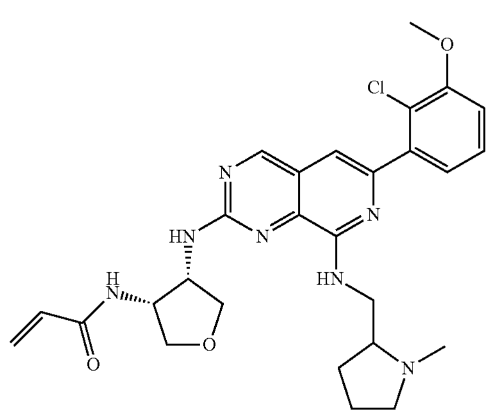 [SMILES: C=CC(=O)N[C@H]1COC[C@H]1Nc1ncc2cc(-c3cccc(OC)c3Cl)nc(NCC3CCCN3C)c2n1] | N-((3R,4S)-4-((6-(2-chloro-3-methoxyphenyl)-8-(((1-methylpyrrolidin-2-yl)methyl)amino)pyrido[3,4-d]pyrimidin-2-yl)amino)tetrahydrofuran-3-yl)acrylamide | 538 |

-continued

| Example No. | Compound structure | Compound name | MS: m/z [M + 1]+ |
| --- | --- | --- | --- |
| 483 | 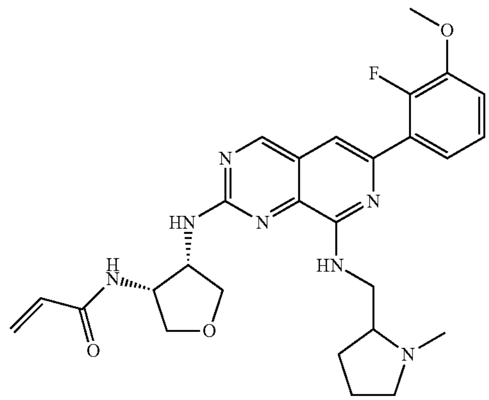 [SMILES: C=CC(=O)N[C@H]1COC[C@H]1Nc1ncc2cc(-c3cccc(OC)c3F)nc(NCC3CCCN3C)c2n1] | N-((3R,4S)-4-((6-(2-fluoro-3-methoxyphenyl)-8-(((1-methylpyrrolidin-2-yl)methyl)amino)pyrido[3,4-d]pyrimidin-2-yl)amino)tetrahydrofuran-3-yl)acrylamide | 522 |
| 484 | 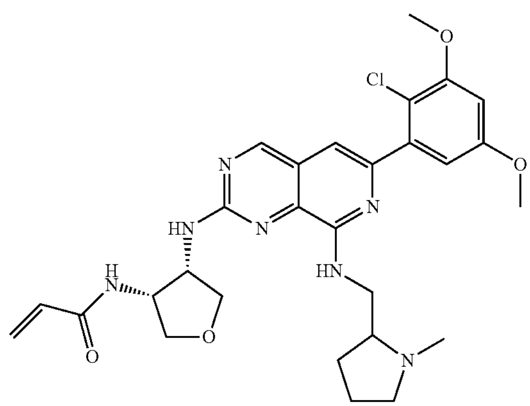 [SMILES: C=CC(=O)N[C@H]1COC[C@H]1Nc1ncc2cc(-c3cc(OC)cc(OC)c3Cl)nc(NCC3CCCN3C)c2n1] | N-((3R,4S)-4-((6-(2-chloro-3,5-dimethoxyphenyl)-8-(((1-methylpyrrolidin-2-yl)methyl)amino)pyrido[3,4-d]pyrimidin-2-yl)amino)tetrahydrofuran-3-yl)acrylamide | 568 |
| 485 | 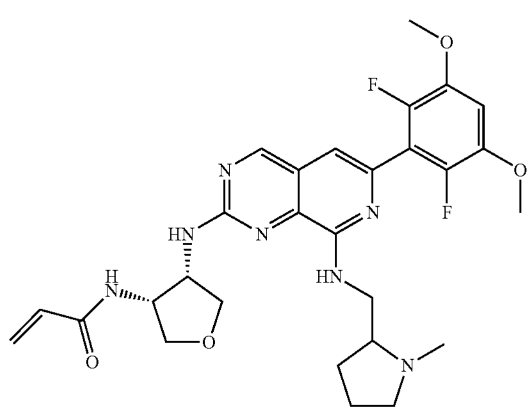 [SMILES: C=CC(=O)N[C@H]1COC[C@H]1Nc1ncc2cc(-c3c(F)c(OC)cc(OC)c3F)nc(NCC3CCCN3C)c2n1] | N-((3R,4S)-4-((6-(2,6-difluoro-3,5-dimethoxyphenyl)-8-(((1-methylpyrrolidin-2-yl)methyl)amino)pyrido[3,4-d]pyrimidin-2-yl)amino)tetrahydrofuran-3-yl)acrylamide | 570 |

-continued

| Example No. | Compound structure | Compound name | MS: m/z [M + 1]+ |
|---|---|---|---|
| 486 | 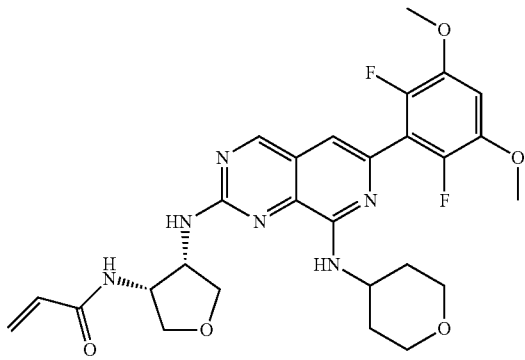 [SMILES: C=CC(=O)N[C@H]1COC[C@H]1Nc1ncc2cc(-c3c(F)c(OC)cc(OC)c3F)nc(NC3CCOCC3)c2n1] | N-((3R,4S)-4-((6-(2,6-difluoro-3,5-di-methoxyphenyl)-8-((tetrahydro-2H-pyran-4-yl)amino)pyrido[3,4-d]pyrimidin-2-yl)amino)tetrahydrofuran-3-yl)acrylamide | 557 |
| 487 | 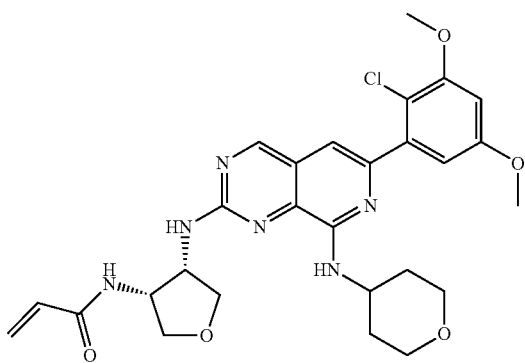 [SMILES: C=CC(=O)N[C@H]1COC[C@H]1Nc1ncc2cc(-c3cc(OC)cc(OC)c3Cl)nc(NC3CCOCC3)c2n1] | N-((3R,4S)-4-((6-(2-chloro-3,5-dimethoxyphenyl)-8-((tetrahydro-2H-pyran-4-yl)amino)pyrido[3,4-d]pyrimidin-2-yl)amino)tetrahydrofuran-3-yl)acrylamide | 555 |
| 488 | 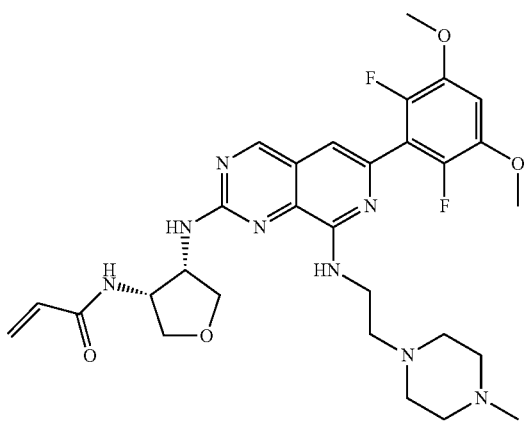 [SMILES: C=CC(=O)N[C@H]1COC[C@H]1Nc1ncc2cc(-c3c(F)c(OC)cc(OC)c3F)nc(NCCN3CCN(C)CC3)c2n1] | N-((3R,4S)-4-((6-(2,6-difluoro-3,5-di-methoxyphenyl)-8-((2-(4-methylpiperazin-1-yl)ethyl)amino)pyrido[3,4-d]pyrimidin-2-yl)amino)tetrahydrofuran-3-yl)acrylamide | 599 |

-continued

| Example No. | Compound structure | Compound name | MS: m/z [M + 1]+ |
|---|---|---|---|
| 489 | 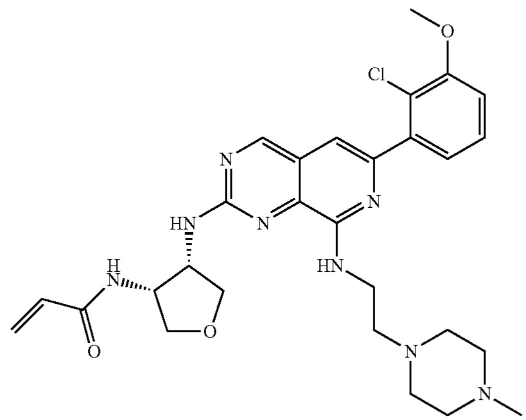 [SMILES: C=CC(=O)N[C@H]1COC[C@H]1Nc1ncc2cc(-c3cccc(OC)c3Cl)nc(NCCN3CCN(C)CC3)c2n1] | N-((3R,4S)-4-((6-(2-chloro-3-methoxyphenyl)-8-((2-(4-methylpiperazin-1-yl)ethyl)amino)pyrido[3,4-d]pyrimidin-2-yl)amino)tetrahydrofuran-3-yl)acrylamide | 567 |
| 490 | 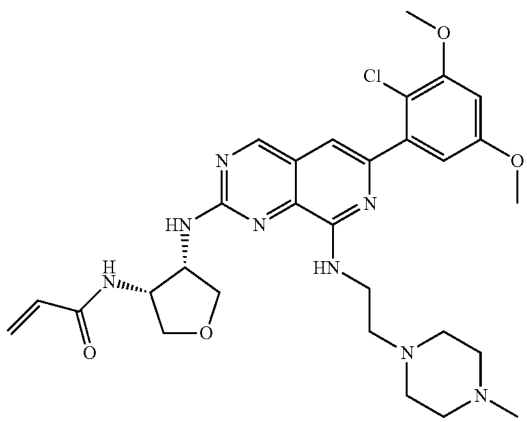 [SMILES: C=CC(=O)N[C@H]1COC[C@H]1Nc1ncc2cc(-c3cc(OC)cc(OC)c3Cl)nc(NCCN3CCN(C)CC3)c2n1] | N-((3R,4S)-4-((6-(2-chloro-3,5-dimethoxyphenyl)-8-((2-(4-methylpiperazin-1-yl)ethyl)amino)pyrido[3,4-d]pyrimidin-2-yl)amino)tetrahydrofuran-3-yl)acrylamide | 597 |
| 491 | 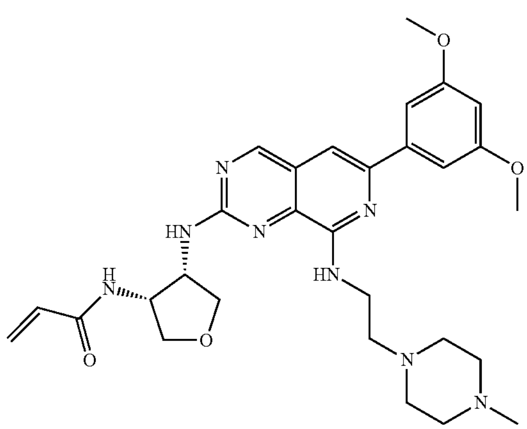 [SMILES: C=CC(=O)N[C@H]1COC[C@H]1Nc1ncc2cc(-c3cc(OC)cc(OC)c3)nc(NCCN3CCN(C)CC3)c2n1] | N-((3R,4S)-4-((6-(3,5-dimethoxyphenyl)-8-((2-(4-methylpiperazin-1-yl)ethyl)amino)pyrido[3,4-d]pyrimidin-2-yl)amino)tetrahydrofuran-3-yl)acrylamide | 563 |

-continued

| Example No. | Compound structure | Compound name | MS: m/z [M + 1]+ |
|---|---|---|---|
| 492 | 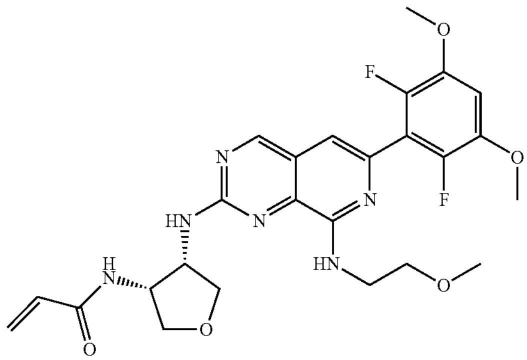 [SMILES: C=CC(=O)N[C@H]1COC[C@H]1Nc1ncc2cc(-c3c(F)c(OC)cc(OC)c3F)nc(NCCOC)c2n1] | N-((3R,4S)-4-((6-(2,6-difluoro-3,5-dimethoxyphenyl)-8-((2-methoxyethyl)amino)pyrido[3,4-d]pyrimidin-2-yl)amino)tetrahydrofuran-3-yl)acrylamide | 531 |
| 493 | 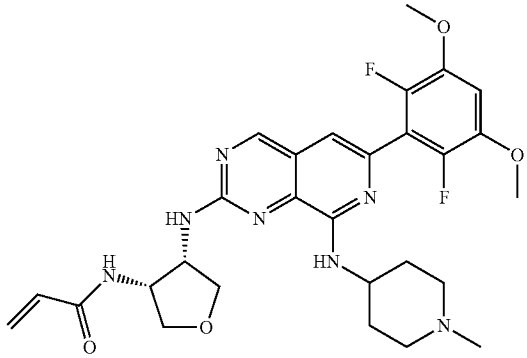 [SMILES: C=CC(=O)N[C@H]1COC[C@H]1Nc1ncc2cc(-c3c(F)c(OC)cc(OC)c3F)nc(NC3CCN(C)CC3)c2n1] | N-((3R,4S)-4-((6-(2,6-difluoro-3,5-dimethoxyphenyl)-8-((1-methylpiperidin-4-yl)amino)pyrido[3,4-d]pyrimidin-2-yl)amino)tetrahydrofuran-3-yl)acrylamide | 570 |
| 494 | 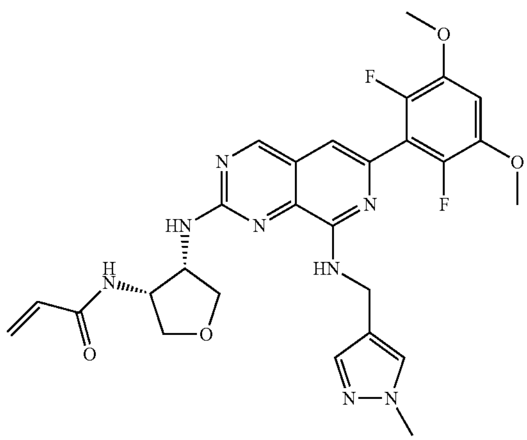 [SMILES: C=CC(=O)N[C@H]1COC[C@H]1Nc1ncc2cc(-c3c(F)c(OC)cc(OC)c3F)nc(NCc3cnn(C)c3)c2n1] | N-((3R,4S)-4-((6-(2,6-difluoro-3,5-dimethoxyphenyl)-8-(((1-methyl-1H-pyrazol-4-yl)methyl)amino)pyrido[3,4-d]pyrimidin-2-yl)amino)tetrahydrofuran-3-yl)acrylamide | 567 |
| 495 | 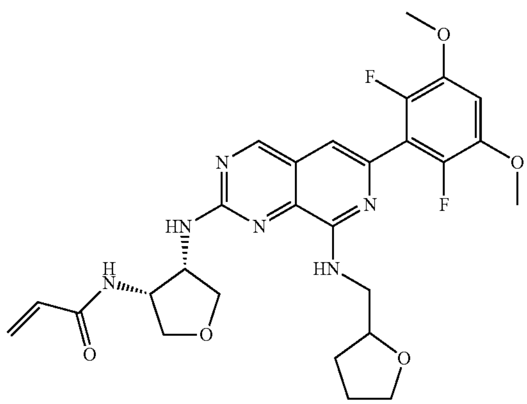 [SMILES: C=CC(=O)N[C@H]1COC[C@H]1Nc1ncc2cc(-c3c(F)c(OC)cc(OC)c3F)nc(NCC3CCCO3)c2n1] | N-((3R,4S)-4-((6-(2,6-difluoro-3,5-dimethoxyphenyl)-8-(((tetrahydrofuran-2-yl)methyl)amino)pyrido[3,4-d]pyrimidin-2-yl)amino)tetrahydrofuran-3-yl)acrylamide | 557 |

-continued

| Example No. | Compound structure | Compound name | MS: m/z [M + 1]+ |
|---|---|---|---|
| 496 | 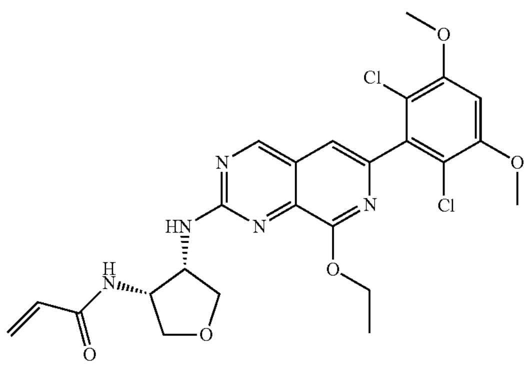 [SMILES: C=CC(=O)N[C@H]1COC[C@H]1Nc1ncc2cc(-c3c(Cl)c(OC)cc(OC)c3Cl)nc(OCC)c2n1] | N-((3R,4S)-4-((6-(2,6-dichloro-3,5-di-methoxyphenyl)-8-ethoxypyrido[3,4-d]pyrimidin-2-yl)amino)tetrahydro-furan-3-yl)acrylamide | 534 |
| 497 | 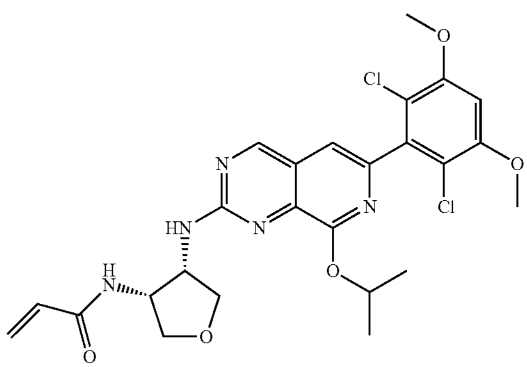 [SMILES: C=CC(=O)N[C@H]1COC[C@H]1Nc1ncc2cc(-c3c(Cl)c(OC)cc(OC)c3Cl)nc(OC(C)C)c2n1] | N-((3R,4S)-4-((6-(2,6-dichloro-3,5-di-methoxyphenyl)-8-isopropoxy-pyrido[3,4-d]pyrimidin-2-yl)amino)tetra-hydrofuran-3-yl)acryl-amide | 548 |
| 498 | 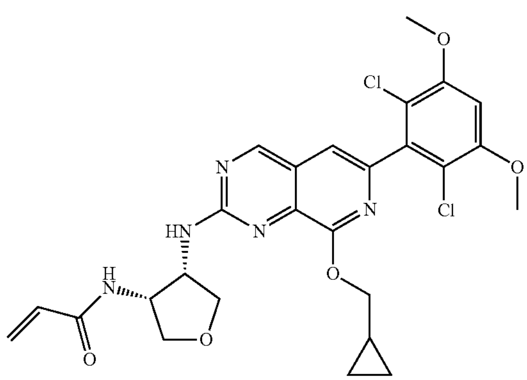 [SMILES: C=CC(=O)N[C@H]1COC[C@H]1Nc1ncc2cc(-c3c(Cl)c(OC)cc(OC)c3Cl)nc(OCC3CC3)c2n1] | N-((3R,4S)-4-((8-(cyclopropylmethoxy)-6-(2,6-dichloro-3,5-dimethoxyphen-nyl)pyrido[3,4-d]pyrimidin-2-yl)amino)tetrahydrofuran-3-yl)acrylamide | 560 |
| 499 | 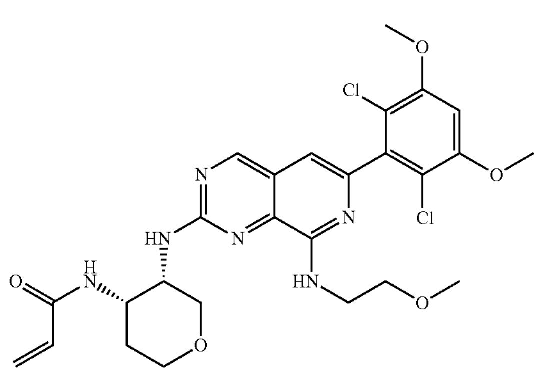 [SMILES: C=CC(=O)N[C@H]1CCOC[C@H]1Nc1ncc2cc(-c3c(Cl)c(OC)cc(OC)c3Cl)nc(NCCOC)c2n1] | N-((3S,4S)-3-((6-(2,6-dichloro-3,5-di-methoxyphenyl)-8-((2-methoxyeth-yl)amino)pyrido[3,4-d]pyrimidin-2-yl)amino)tetrahydro-2H-pyran-4-yl)acrylamide | 577 |

-continued

| Example No. | Compound structure | Compound name | MS: m/z [M + 1]+ |
|---|---|---|---|
| 500 | 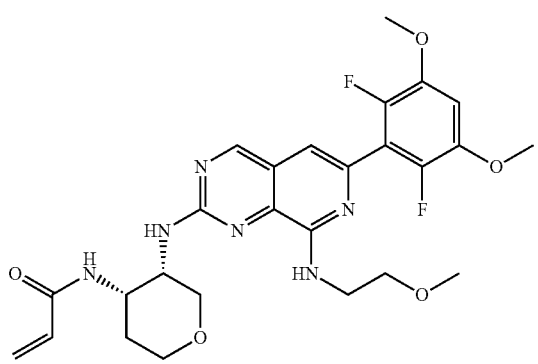 [SMILES: C=CC(=O)N[C@H]1CCOC[C@H]1Nc1ncc2cc(-c3c(F)c(OC)cc(OC)c3F)nc(NCCOC)c2n1] | N-((3S,4S)-3-((6-(2,6-difluoro-3,5-di-methoxyphenyl)-8-((2-methoxyeth-yl)amino)pyrido[3,4-d]pyrimidin-2-yl)amino)tetrahydro-2H-pyran-4-yl)acryl-amide | 545 |
| 501 | 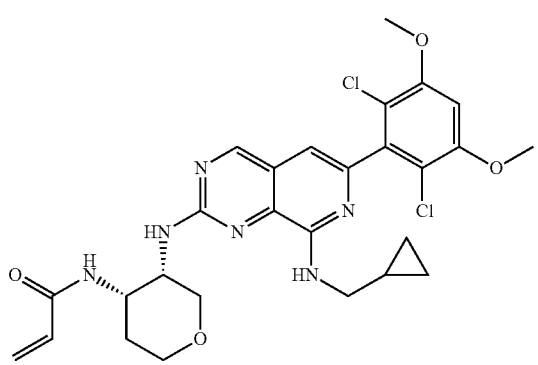 [SMILES: C=CC(=O)N[C@H]1CCOC[C@H]1Nc1ncc2cc(-c3c(Cl)c(OC)cc(OC)c3Cl)nc(NCC3CC3)c2n1] | N-((3S,4S)-3-((8-((cyclopropylmeth-yl)amino)-6-(2,6-dichloro-3,5-dimeth-oxyphenyl)pyrido[3,4-d]pyrimidin-2-yl)amino)tetrahydro-2H-pyran-4-yl)acrylamide | 573 |
| 502 | 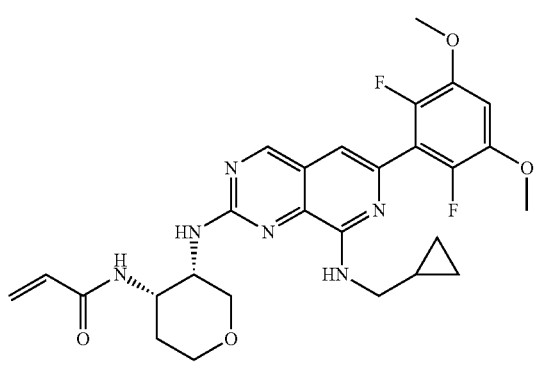 [SMILES: C=CC(=O)N[C@H]1CCOC[C@H]1Nc1ncc2cc(-c3c(F)c(OC)cc(OC)c3F)nc(NCC3CC3)c2n1] | N-((3S,4S)-3-((8-((cyclopropylmeth-yl)amino)-6-(2,6-difluoro-3,5-dimeth-oxyphenyl)pyrido[3,4-d]pyrimidin-2-yl)amino)tetrahydro-2H-pyran-4-yl)acrylamide | 541 |
| 503 | 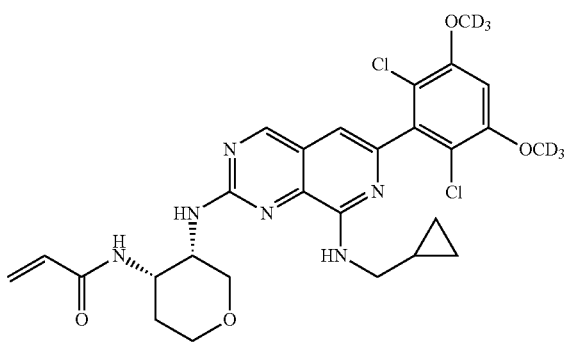 | N-((3S,4S)-3-((8-((cyclopropylmeth-yl)amino)-6-(2,6-dichloro-3,5-bis(meth-oxy-$d_3$)phenyl)pyrido[3,4-d]pyrimi-din-2-yl)amino)tetrahydro-2H-pyran-4-yl)acrylamide | 579 |

| Example No. | Compound structure | Compound name | MS: m/z [M + 1]+ |
|---|---|---|---|
| 504 | 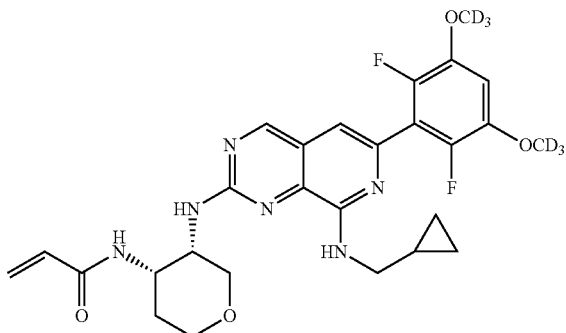 | N-((3S,4S)-3-((8-((cyclopropylmethyl)amino)-6-(2,6-difluoro-3,5-bis(methoxy-d₃)phenyl)pyrido[3,4-d]pyrimidin-2-yl)amino)tetrahydro-2H-pyran-4-yl)acrylamide | 547 |
| 505 | 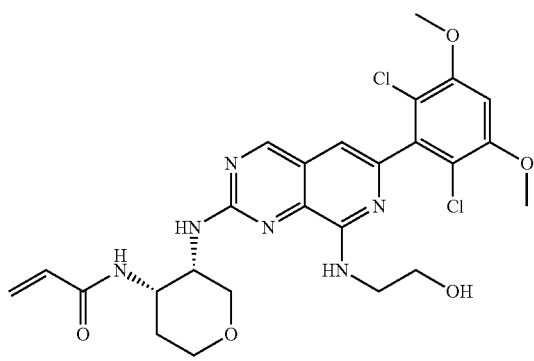 [SMILES: C=CC(=O)N[C@H]1CCOC[C@H]1Nc1ncc2cc(-c3c(Cl)c(OC)cc(OC)c3Cl)nc(NCCO)c2n1] | N-((3S,4S)-3-((6-(2,6-dichloro-3,5-dimethoxyphenyl)-8-((2-hydroxyethyl)amino)pyrido[3,4-d]pyrimidin-2-yl)amino)tetrahydro-2H-pyran-4-yl)acrylamide | 563 |
| 506 | 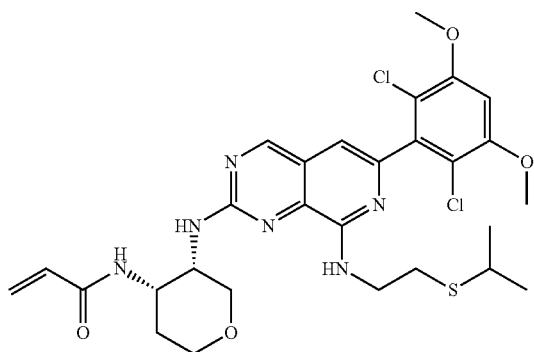 | N-((3S,4S)-3-((6-(2,6-dichloro-3,5-dimethoxyphenyl)-8-((2-(isopropylthio)ethyl)amino)pyrido[3,4-d]pyrimidin-2-yl)amino)tetrahydro-2H-pyran-4-yl)acrylamide | 621 |
| 507 | 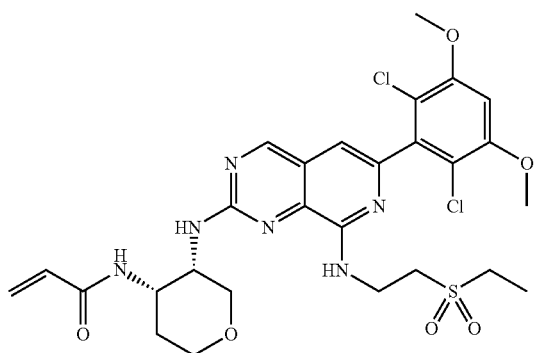 | N-((3S,4S)-3-((6-(2,6-dichloro-3,5-dimethoxyphenyl)-8-((2-(ethylsulfonyl)ethyl)amino)pyrido[3,4-d]pyrimidin-2-yl)amino)tetrahydro-2H-pyran-4-yl)acrylamide | 639 |

-continued

| Example No. | Compound structure | Compound name | MS: m/z [M + 1]+ |
|---|---|---|---|
| 508 | 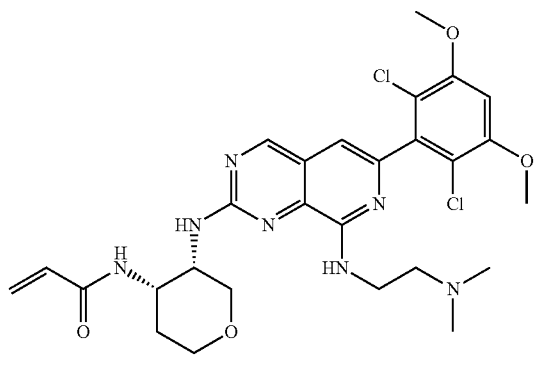 [SMILES: C=CC(=O)N[C@H]1CCOC[C@H]1Nc1ncc2cc(-c3c(Cl)c(OC)cc(OC)c3Cl)nc(NCCN(C)C)c2n1] | N-((3S,4S)-3-((6-(2,6-dichloro-3,5-dimethoxyphenyl)-8-((2-(dimethylamino)ethyl)amino)pyrido[3,4-d]pyrimidin-2-yl)amino)tetrahydro-2H-pyran-4-yl)acrylamide | 590 |
| 509 | 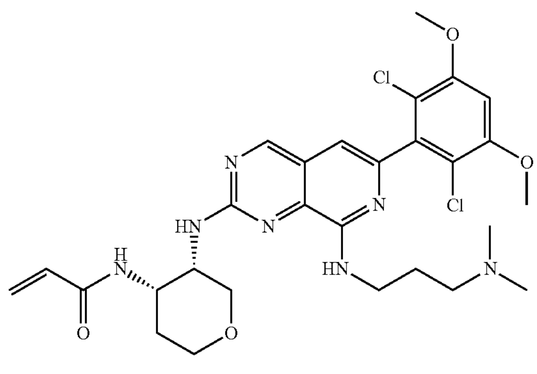 [SMILES: C=CC(=O)N[C@H]1CCOC[C@H]1Nc1ncc2cc(-c3c(Cl)c(OC)cc(OC)c3Cl)nc(NCCCN(C)C)c2n1] | N-((3S,4S)-3-((6-(2,6-dichloro-3,5-dimethoxyphenyl)-8-((3-(dimethylamino)propyl)amino)pyrido[3,4-d]pyrimidin-2-yl)amino)tetrahydro-2H-pyran-4-yl)acrylamide | 604 |
| 510 | 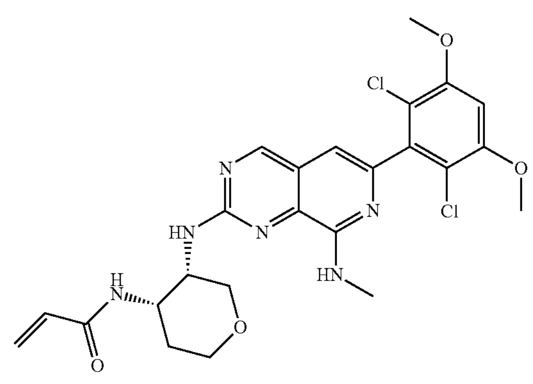 [SMILES: C=CC(=O)N[C@H]1CCOC[C@H]1Nc1ncc2cc(-c3c(Cl)c(OC)cc(OC)c3Cl)nc(NC)c2n1] | N-((3S,4S)-3-((6-(2,6-dichloro-3,5-dimethoxyphenyl)-8-(methylamino)pyrido[3,4-d]pyrimidin-2-yl)amino)tetrahydro-2H-pyran-4-yl)acrylamide | 549 |
| 511 | 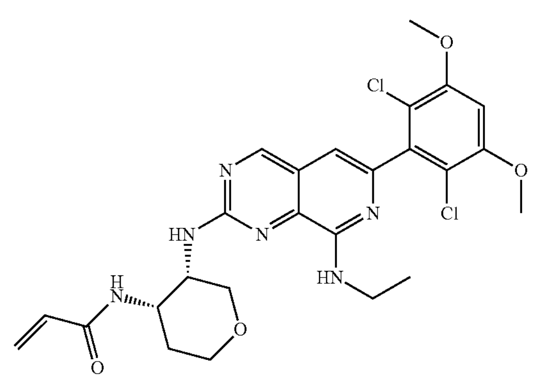 [SMILES: C=CC(=O)N[C@H]1CCOC[C@H]1Nc1ncc2cc(-c3c(Cl)c(OC)cc(OC)c3Cl)nc(NCC)c2n1] | N-((3S,4S)-3-((6-(2,6-dichloro-3,5-dimethoxyphenyl)-8-(ethylamino)pyrido[3,4-d]pyrimidin-2-yl)amino)tetrahydro-2H-pyran-4-yl)acrylamide | 547 |

-continued

| Example No. | Compound structure | Compound name | MS: m/z [M + 1]+ |
|---|---|---|---|
| 512 | 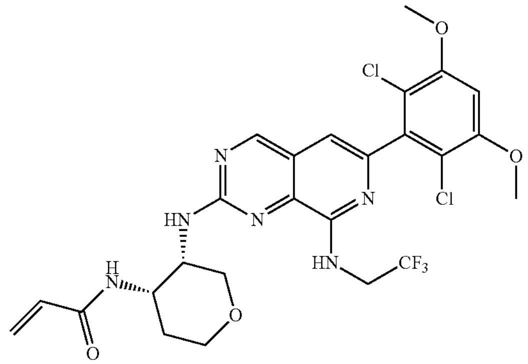 [SMILES: C=CC(=O)N[C@H]1CCOC[C@H]1Nc1ncc2cc(-c3c(Cl)c(OC)cc(OC)c3Cl)nc(NCC(F)(F)F)c2n1] | N-((3S,4S)-3-((6-(2,6-dichloro-3,5-di-methoxyphenyl)-8-((2,2,2-trifluoroeth-yl)amino)pyrido[3,4-d]pyrimidin-2-yl)amino)tetrahydro-2H-pyran-4-yl)acrylamide | 601 |
| 513 | 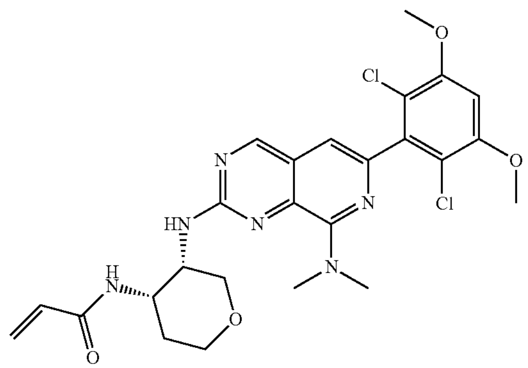 [SMILES: C=CC(=O)N[C@H]1CCOC[C@H]1Nc1ncc2cc(-c3c(Cl)c(OC)cc(OC)c3Cl)nc(N(C)C)c2n1] | N-((3S,4S)-3-((6-(2,6-dichloro-3,5-di-methoxyphenyl)-8-(dimethylamino)pyrido[3,4-d]pyrimidin-2-yl)amino)tetrahydro-2H-pyran-4-yl)acrylamide | 547 |
| 514 | 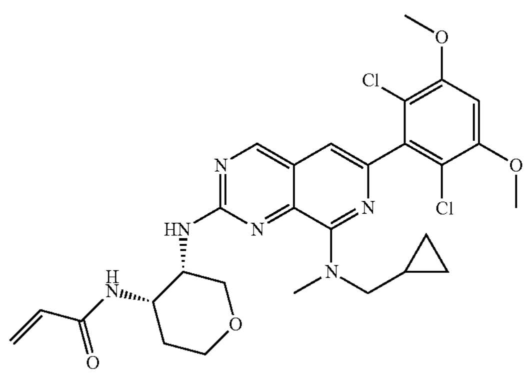 [SMILES: C=CC(=O)N[C@H]1CCOC[C@H]1Nc1ncc2cc(-c3c(Cl)c(OC)cc(OC)c3Cl)nc(N(C)CC3CC3)c2n1] | N-((3S,4S)-3-((8-((cyclopropylmeth-yl)(methyl)amino)-6-(2,6-dichloro-3,5-dimethoxyphenyl)pyrido[3,4-d]pyrimidin-2-yl)amino)tetrahydro-2H-pyran-4-yl)acrylamide | 587 |
| 515 | 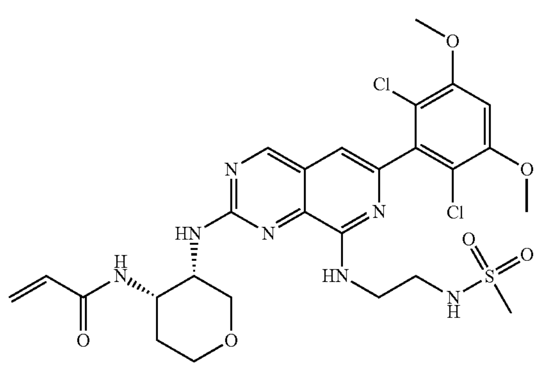 [SMILES: C=CC(=O)N[C@H]1CCOC[C@H]1Nc1ncc2cc(-c3c(Cl)c(OC)cc(OC)c3Cl)nc(NCCNS(C)(=O)=O)c2n1] | N-((3S,4S)-3-((6-(2,6-dichloro-3,5-di-methoxyphenyl)-8-((2-(methyl-sulfonamido)ethyl)amino)pyrido[3,4-d]pyrimidin-2-yl)amino)tetrahydro-2H-pyran-4-yl)acrylamide | 640 |

-continued

| Example No. | Compound structure | Compound name | MS: m/z [M + 1]+ |
|---|---|---|---|
| 516 | 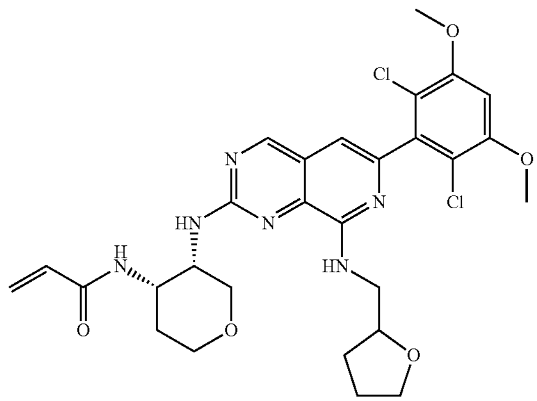 [SMILES: C=CC(=O)N[C@H]1CCOC[C@H]1Nc1ncc2cc(-c3c(Cl)c(OC)cc(OC)c3Cl)nc(NCC3CCCO3)c2n1] | N-((3S,4S)-3-((6-(2,6-dichloro-3,5-dimethoxyphenyl)-8-(((tetrahydrofuran-2-yl)methyl)amino)pyrido[3,4-d]pyrimidin-2-yl)amino)tetrahydro-2H-pyran-4-yl)acrylamide | 603 |
| 517 | 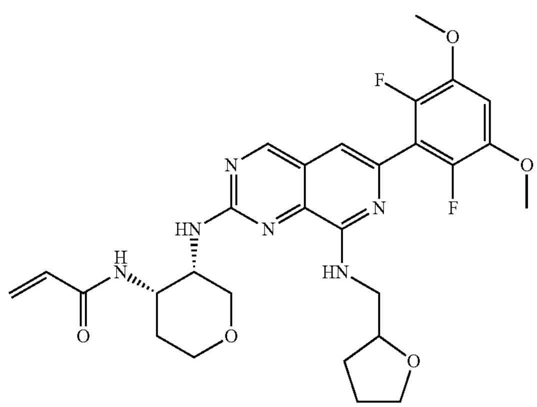 [SMILES: C=CC(=O)N[C@H]1CCOC[C@H]1Nc1ncc2cc(-c3c(F)c(OC)cc(OC)c3F)nc(NCC3CCCO3)c2n1] | N-((3S,4S)-3-((6-(2,6-difluoro-3,5-dimethoxyphenyl)-8-(((tetrahydrofuran-2-yl)methyl)amino)pyrido[3,4-d]pyrimidin-2-yl)amino)tetrahydro-2H-pyran-4-yl)acrylamide | 571 |
| 518 | 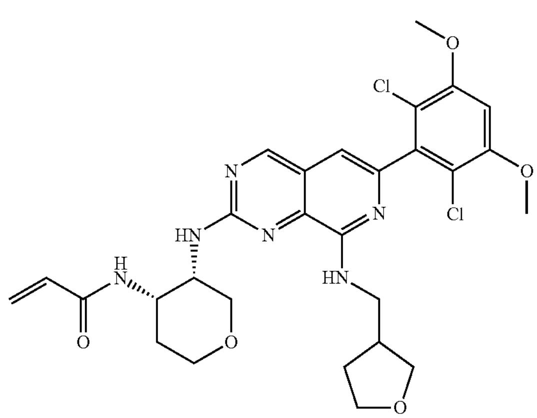 [SMILES: C=CC(=O)N[C@H]1CCOC[C@H]1Nc1ncc2cc(-c3c(Cl)c(OC)cc(OC)c3Cl)nc(NCC3CCOC3)c2n1] | N-((3S,4S)-3-((6-(2,6-dichloro-3,5-dimethoxyphenyl)-8-(((tetrahydrofuran-3-yl)methyl)amino)pyrido[3,4-d]pyrimidin-2-yl)amino)tetrahydro-2H-pyran-4-yl)acrylamide | 603 |

-continued

| Example No. | Compound structure | Compound name | MS: m/z [M + 1]+ |
|---|---|---|---|
| 519 | 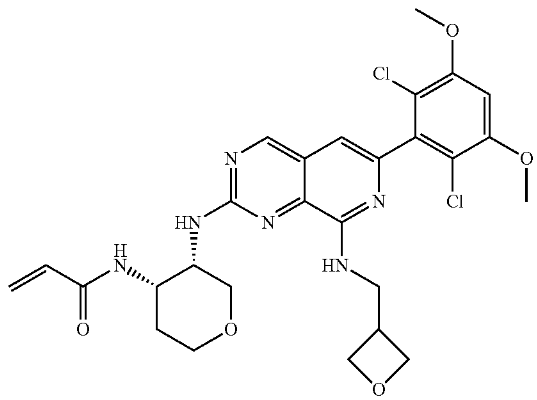 [SMILES: C=CC(=O)N[C@H]1CCOC[C@H]1Nc1ncc2cc(-c3c(Cl)c(OC)cc(OC)c3Cl)nc(NCC3COC3)c2n1] | N-((3S,4S)-3-((6-(2,6-dichloro-3,5-dimethoxyphenyl)-8-((oxetan-3-ylmethyl)amino)pyrido[3,4-d]pyrimidin-2-yl)amino)tetrahydro-2H-pyran-4-yl)acrylamide | 589 |
| 520 | 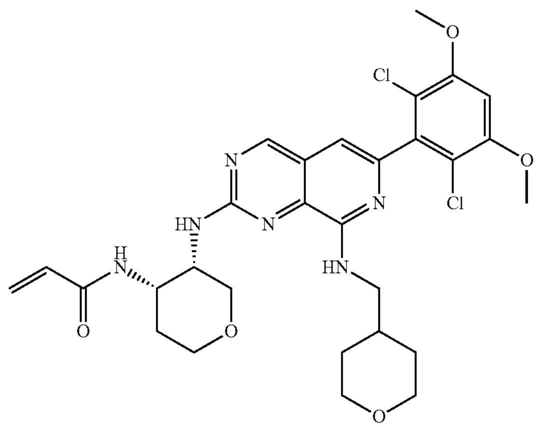 [SMILES: C=CC(=O)N[C@H]1CCOC[C@H]1Nc1ncc2cc(-c3c(Cl)c(OC)cc(OC)c3Cl)nc(NCC3CCOCC3)c2n1] | N-((3S,4S)-3-((6-(2,6-dichloro-3,5-dimethoxyphenyl)-8-(((tetrahydro-2H-pyran-4-yl)methyl)amino)pyrido[3,4-d]pyrimidin-2-yl)amino)tetrahydro-2H-pyran-4-yl)acrylamide | 617 |
| 521 | 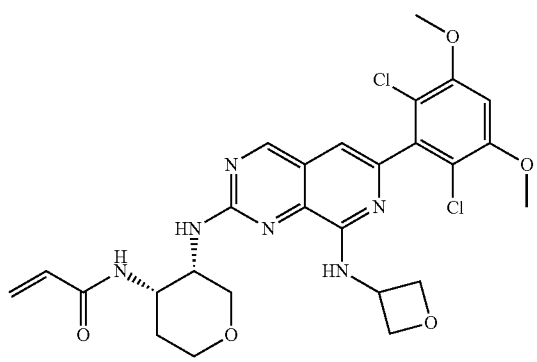 [SMILES: C=CC(=O)N[C@H]1CCOC[C@H]1Nc1ncc2cc(-c3c(Cl)c(OC)cc(OC)c3Cl)nc(NC3COC3)c2n1] | N-((3S,4S)-3-((6-(2,6-dichloro-3,5-dimethoxyphenyl)-8-(oxetan-3-ylamino)pyrido[3,4-d]pyrimidin-2-yl)amino)tetrahydro-2H-pyran-4-yl)acrylamide | 575 |
| 522 | 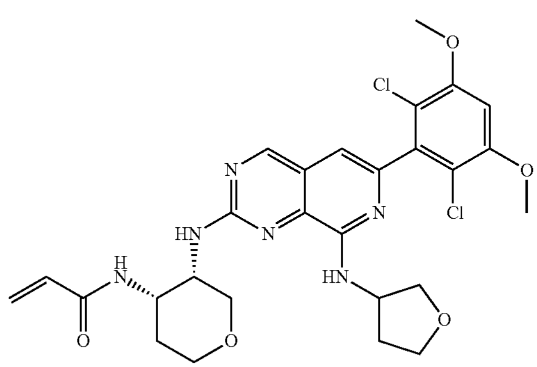 [SMILES: C=CC(=O)N[C@H]1CCOC[C@H]1Nc1ncc2cc(-c3c(Cl)c(OC)cc(OC)c3Cl)nc(NC3CCOC3)c2n1] | N-((3S,4S)-3-((6-(2,6-dichloro-3,5-dimethoxyphennyl)-8-((tetrahydrofuran-3-yl)amino)pyrido[3,4-d]pyrimidin-2-yl)amino)tetrahydro-2H-pyran-4-yl)acrylamide | 589 |

-continued

| Example No. | Compound structure | Compound name | MS: m/z [M + 1]+ |
|---|---|---|---|
| 523 | 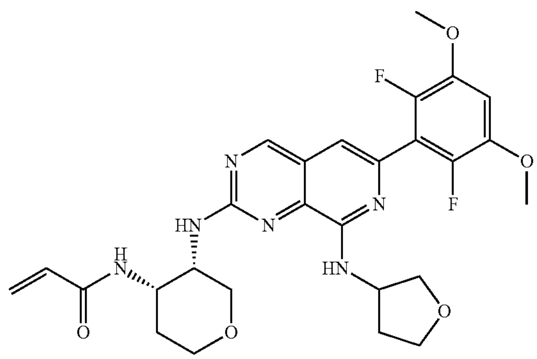 [SMILES: C=CC(=O)N[C@H]1CCOC[C@H]1Nc1ncc2cc(-c3c(F)c(OC)cc(OC)c3F)nc(NC3CCOC3)c2n1] | N-((3S,4S)-3-((6-(2,6-difluoro-3,5-dimethoxyphenyl)-8-(((tetrahydrofuran-3-yl)amino)pyrido[3,4-d]pyrimidin-2-yl)amino)tetrahydro-2H-pyran-4-yl)acrylamide | 557 |
| 524 | 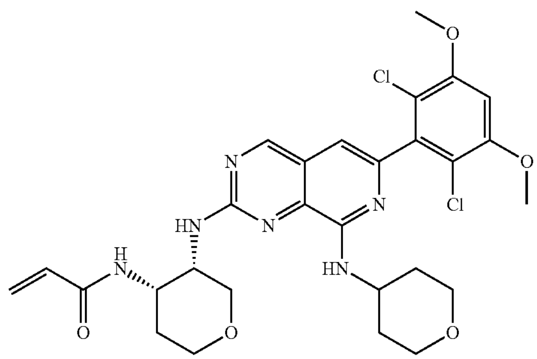 [SMILES: C=CC(=O)N[C@H]1CCOC[C@H]1Nc1ncc2cc(-c3c(Cl)c(OC)cc(OC)c3Cl)nc(NC3CCOCC3)c2n1] | N-((3S,4S)-3-((6-(2,6-dichloro-3,5-dimethoxyphenyl)-8-(((tetrahydro-2H-pyran-4-yl)amino)pyrido[3,4-d]pyrimidin-2-yl)amino)tetrahydro-2H-pyran-4-yl)acrylamide | 603 |
| 525 | 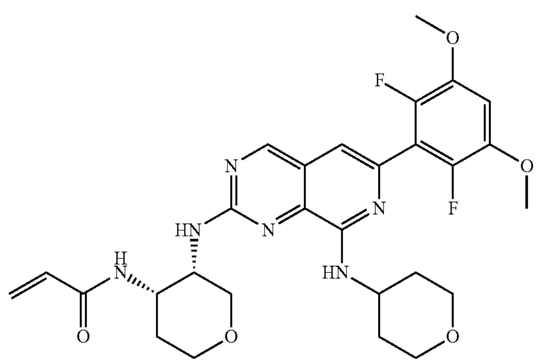 [SMILES: C=CC(=O)N[C@H]1CCOC[C@H]1Nc1ncc2cc(-c3c(F)c(OC)cc(OC)c3F)nc(NC3CCOCC3)c2n1] | N-((3S,4S)-3-((6-(2,6-difluoro-3,5-dimethoxyphenyl)-8-(((tetrahydro-2H-pyran-4-yl)amino)pyrido[3,4-d]pyrimidin-2-yl)amino)tetrahydro-2H-pyran-4-yl)acrylamide | 571 |
| 526 | 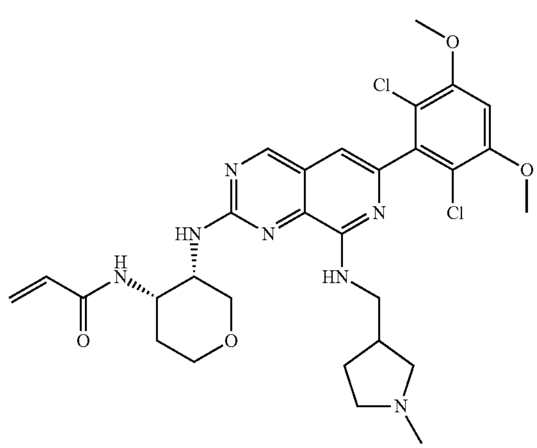 [SMILES: C=CC(=O)N[C@H]1CCOC[C@H]1Nc1ncc2cc(-c3c(Cl)c(OC)cc(OC)c3Cl)nc(NCC3CCN(C)C3)c2n1] | N-((3S,4S)-3-((6-(2,6-dichloro-3,5-dimethoxyphenyl)-8-(((1-methylpyrrolidin-3-yl)methyl)amino)pyrido[3,4-d]pyrimidin-2-yl)amino)tetrahydro-2H-pyran-4-yl)acrylamide | 616 |

| Example No. | Compound structure | Compound name | MS: m/z [M + 1]+ |
|---|---|---|---|
| 527 | 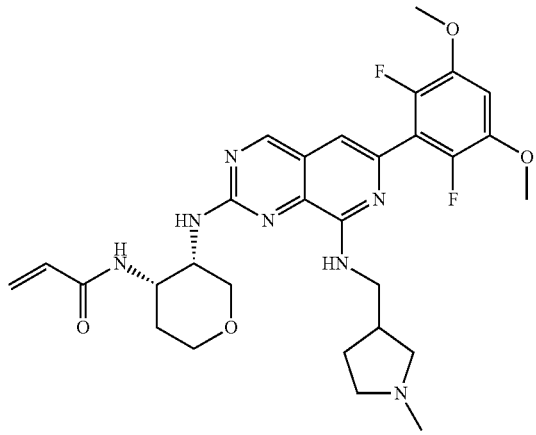 [SMILES: C=CC(=O)N[C@H]1CCOC[C@H]1Nc1ncc2cc(-c3c(F)c(OC)cc(OC)c3F)nc(NCC3CCN(C)C3)c2n1] | N-((3S,4S)-3-((6-(2,6-difluoro-3,5-di-methoxyphenyl)-8-(((1-methylpyrroli-din-3-yl)methyl)amino)pyrido[3,4-d]pyrimidin-2-yl)amino)tetrahydro-2H-pyran-4-yl)acrylamide | 584 |
| 528 | 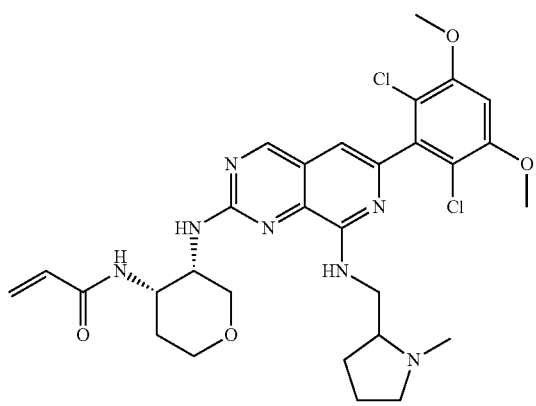 | N-((3S,4S)-3-((6-(2,6-dichloro-3,5-di-methoxyphenyl)-8-(((1-methylpyrroli-din-2-yl)methyl)amino)pyrido[3,4-d]pyrimidin-2-yl)amino)tetrahydro-2H-pyran-4-yl)acrylamide | 616 |
| 529 | 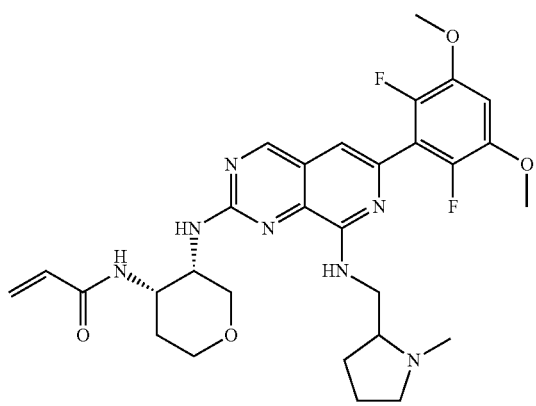 [SMILES: C=CC(=O)N[C@H]1CCOC[C@H]1Nc1ncc2cc(-c3c(F)c(OC)cc(OC)c3F)nc(NCC3CCCN3C)c2n1] | N-((3S,4S)-3-((6-(2,6-difluoro-3,5-di-methoxyphenyl)-8-(((1-methylpyrroli-din-2-yl)methyl)amino)pyrido[3,4-d]pyrimidin-2-yl)amino)tetrahydro-2H-pyran-4-yl)acrylamide | 584 |

| Example No. | Compound structure | Compound name | MS: m/z [M + 1]+ |
|---|---|---|---|
| 530 | 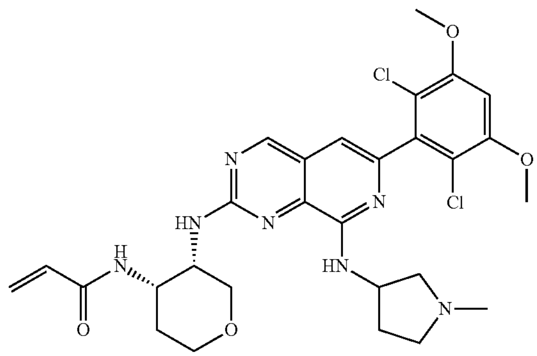 [SMILES: C=CC(=O)N[C@H]1CCOC[C@H]1Nc1ncc2cc(-c3c(Cl)c(OC)cc(OC)c3Cl)nc(NC3CCN(C)C3)c2n1] | N-((3S,4S)-3-((6-(2,6-dichloro-3,5-dimethoxyphenyl)-8-((1-methylpyrrolidin-3-yl)amino)pyrido[3,4-d]pyrimidin-2-yl)amino)tetrahydro-2H-pyran-4-yl)acrylamide | 602 |
| 531 | 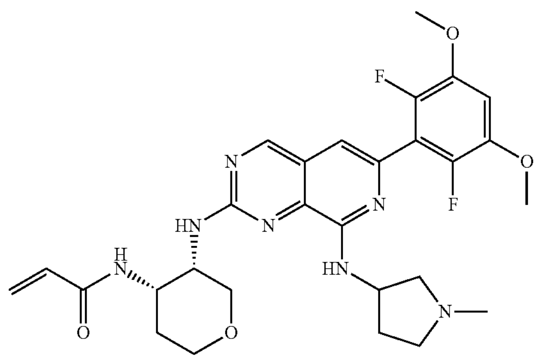 [SMILES: C=CC(=O)N[C@H]1CCOC[C@H]1Nc1ncc2cc(-c3c(F)c(OC)cc(OC)c3F)nc(NC3CCN(C)C3)c2n1] | N-((3S,4S)-3-((6-(2,6-difluoro-3,5-dimethoxyphenyl)-8-((1-methylpyrrolidin-3-yl)amino)pyrido[3,4-d]pyrimidin-2-yl)amino)tetrahydro-2H-pyran-4-yl)acrylamide | 570 |
| 532 | 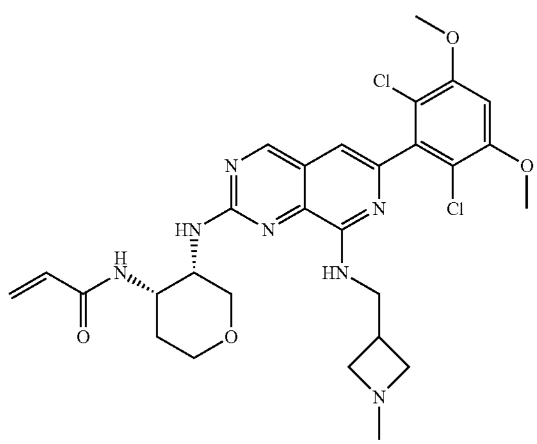 [SMILES: C=CC(=O)N[C@H]1CCOC[C@H]1Nc1ncc2cc(-c3c(Cl)c(OC)cc(OC)c3Cl)nc(NCC3CN(C)C3)c2n1] | N-((3S,4S)-3-((6-(2,6-dichloro-3,5-dimethoxyphenyl)-8-(((1-methylazetidin-3-yl)methyl)amino)pyrido[3,4-d]pyrimidin-2-yl)amino)tetrahydro-2H-pyran-4-yl)acrylamide | 602 |
| 533 | 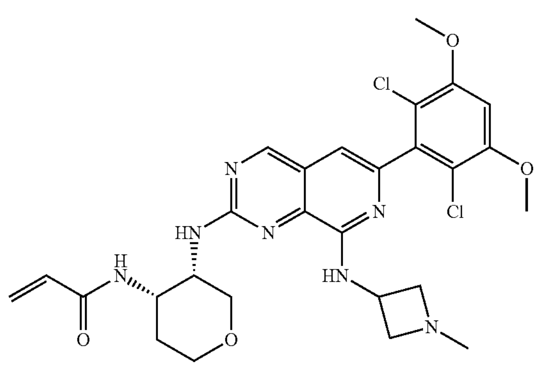 [SMILES: C=CC(=O)N[C@H]1CCOC[C@H]1Nc1ncc2cc(-c3c(Cl)c(OC)cc(OC)c3Cl)nc(NC3CN(C)C3)c2n1] | N-((3S,4S)-3-((6-(2,6-dichloro-3,5-dimethoxyphenyl)-8-((1-methylazetidin-3-yl)amino)pyrido[3,4-d]pyrimidin-2-yl)amino)tetrahydro-2H-pyran-4-yl)acrylamide | 588 |

-continued

| Example No. | Compound structure | Compound name | MS: m/z [M + 1]+ |
|---|---|---|---|
| 534 | 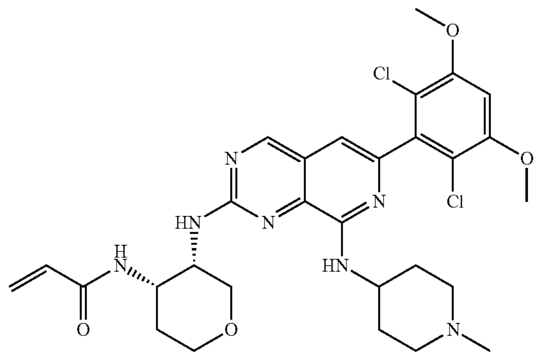 [SMILES: C=CC(=O)N[C@H]1CCOC[C@H]1Nc1ncc2cc(-c3c(Cl)c(OC)cc(OC)c3Cl)nc(NC3CCN(C)CC3)c2n1] | N-((3S,4S)-3-((6-(2,6-dichloro-3,5-dimethoxyphenyl)-8-((1-methylpiperidin-4-yl)amino)pyrido[3,4-d]pyrimidin-2-yl)amino)tetrahydro-2H-pyran-4-yl)acrylamide | 616 |
| 535 | 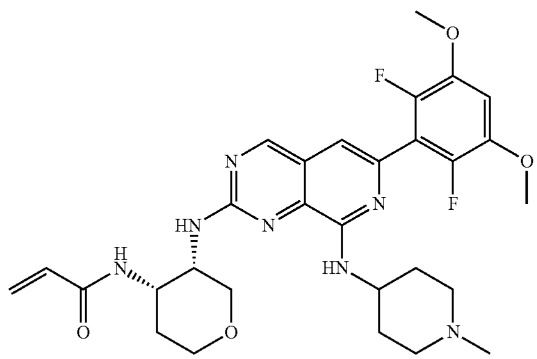 [SMILES: C=CC(=O)N[C@H]1CCOC[C@H]1Nc1ncc2cc(-c3c(F)c(OC)cc(OC)c3F)nc(NC3CCN(C)CC3)c2n1] | N-((3S,4S)-3-((6-(2,6-difluoro-3,5-dimethoxyphenyl)-8-((1-methylpiperidin-4-yl)amino)pyrido[3,4-d]pyrimidin-2-yl)amino)tetrahydro-2H-pyran-4-yl)acrylamide | 584 |
| 536 | 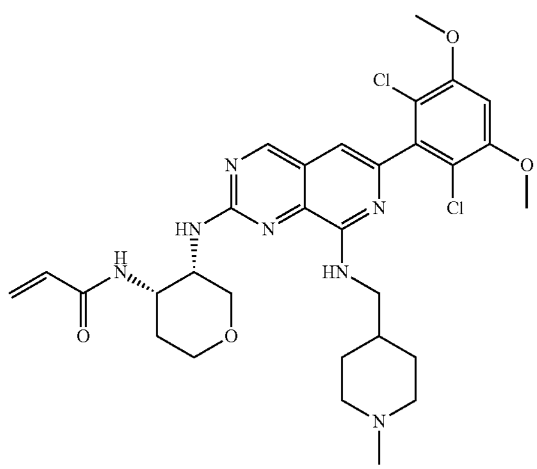 [SMILES: C=CC(=O)N[C@H]1CCOC[C@H]1Nc1ncc2cc(-c3c(Cl)c(OC)cc(OC)c3Cl)nc(NCC3CCN(C)CC3)c2n1] | N-((3S,4S)-3-((6-(2,6-dichloro-3,5-dimethoxyphenyl)-8-(((1-methylpiperidin-4-yl)methyl)amino)pyrido[3,4-d]pyrimidin-2-yl)amino)tetrahydro-2H-pyran-4-yl)acrylamide | 630 |
| 537 | 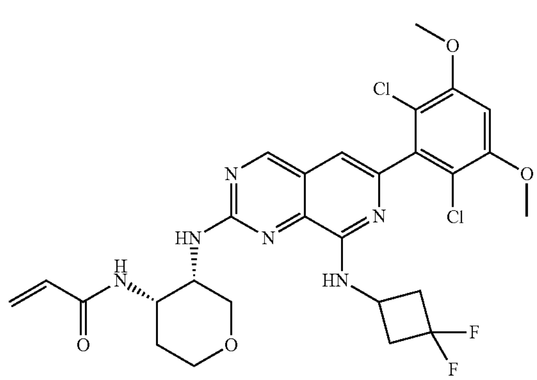 [SMILES: C=CC(=O)N[C@H]1CCOC[C@H]1Nc1ncc2cc(-c3c(Cl)c(OC)cc(OC)c3Cl)nc(NC3CC(F)(F)C3)c2n1] | N-((3S,4S)-3-(((6-(2,6-dichloro-3,5-dimethoxyphenyl)-8-((3,3-difluorocyclobutyl)amino)pyrido[3,4-d]pyrimidin-2-yl)amino)tetrahydro-2H-pyran-4-yl)acrylamide | 609 |

| Example No. | Compound structure | Compound name | MS: m/z [M + 1]+ |
|---|---|---|---|
| 538 | 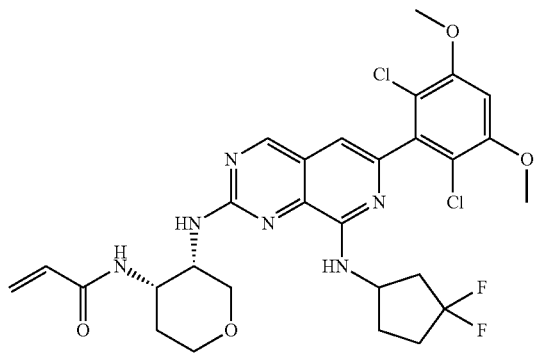 [SMILES: C=CC(=O)N[C@H]1CCOC[C@H]1Nc1ncc2cc(-c3c(Cl)c(OC)cc(OC)c3Cl)nc(NC3CCC(F)(F)C3)c2n1] | N-((3S,4S)-3-((6-(2,6-dichloro-3,5-di-methoxyphenyl)-8-((3,3-difluorocyclo-pentyl)amino)pyrido[3,4-d]pyrimi-din-2-yl)amino)tetrahydro-2H-pyran-4-yl)acrylamide | 623 |
| 539 | 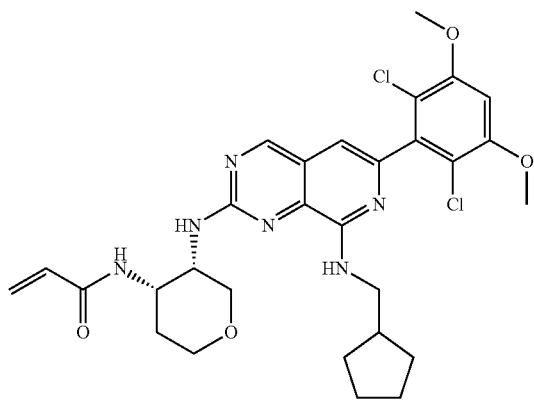 [SMILES: C=CC(=O)N[C@H]1CCOC[C@H]1Nc1ncc2cc(-c3c(Cl)c(OC)cc(OC)c3Cl)nc(NCC3CCCC3)c2n1] | N-((3S,4S)-3-((8-((cyclopentylmeth-yl)amino)-6-(2,6-dichloro-3,5-dimeth-oxyphenyl)pyrido[3,4-d]pyrimidin-2-yl)amino)tetrahydro-2H-pyran-4-yl)acrylamide | 601 |
| 540 | 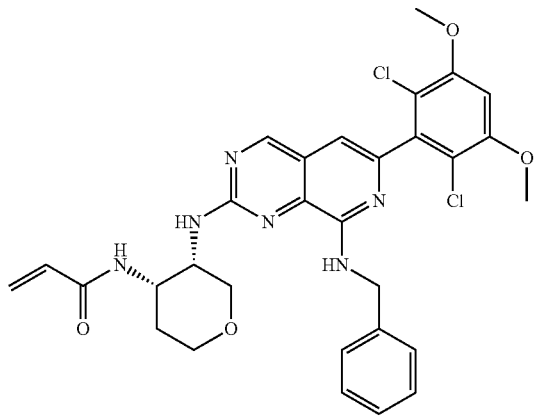 [SMILES: C=CC(=O)N[C@H]1CCOC[C@H]1Nc1ncc2cc(-c3c(Cl)c(OC)cc(OC)c3Cl)nc(NCc3ccccc3)c2n1] | N-((3S,4S)-3-((8-(benzylamino)-6-(2,6-dichloro-3,5-dimethoxyphenyl)py-rido[3,4-d]pyrimidin-2-yl)amino)tetra-hydro-2H-pyran-4-yl)acrylamide | 609 |

| Example No. | Compound structure | Compound name | MS: m/z [M + 1]+ |
|---|---|---|---|
| 541 | 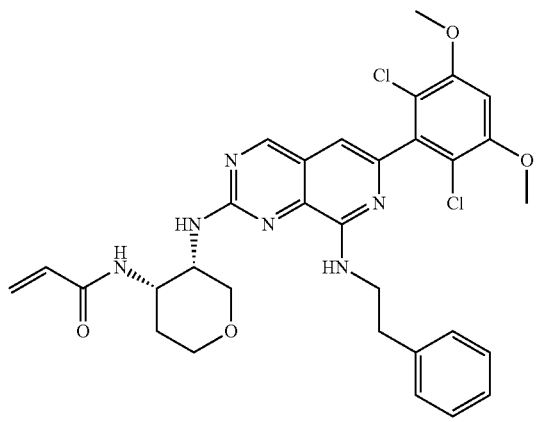 [SMILES: C=CC(=O)N[C@H]1CCOC[C@H]1Nc1ncc2cc(-c3c(Cl)c(OC)cc(OC)c3Cl)nc(NCCc3ccccc3)c2n1] | N-((3S,4S)-3-((6-(2,6-dichloro-3,5-dimethoxyphenyl)-8-(phenethylamino)pyrido[3,4-d]pyrimidin-2-yl)amino)tetrahydro-2H-pyran-4-yl)acrylamide | 623 |
| 542 | 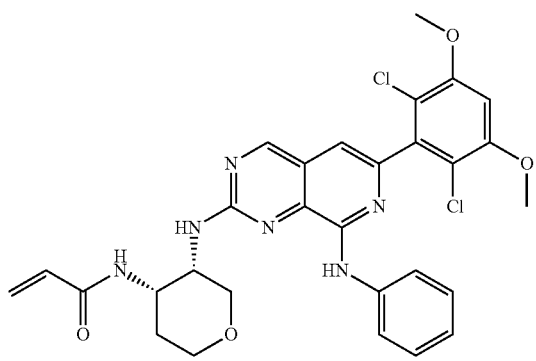 [SMILES: C=CC(=O)N[C@H]1CCOC[C@H]1Nc1ncc2cc(-c3c(Cl)c(OC)cc(OC)c3Cl)nc(Nc3ccccc3)c2n1] | N-((3S,4S)-3-((6-(2,6-dichloro-3,5-dimethoxyphenyl)-8-(phenylamino)pyrido[3,4-d]pyrimidin-2-yl)amino)tetrahydro-2H-pyran-4-yl)acrylamide | 595 |
| 543 | 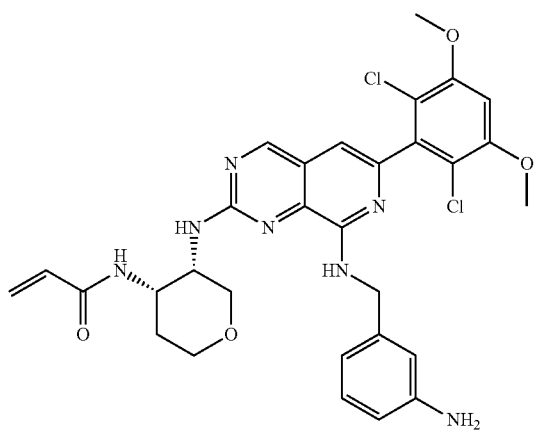 [SMILES: C=CC(=O)N[C@H]1CCOC[C@H]1Nc1ncc2cc(-c3c(Cl)c(OC)cc(OC)c3Cl)nc(NCc3cccc(N)c3)c2n1] | N-((3S,4S)-3-((8-((3-aminobenzyl)amino)-6-(2,6-dichloro-3,5-dimethoxyphenyl))pyrido[3,4-d]pyrimidin-2-yl)amino)tetrahydro-2H-pyran-4-yl)acrylamide | 624 |

| Example No. | Compound structure | Compound name | MS: m/z [M + 1]+ |
|---|---|---|---|
| 544 | 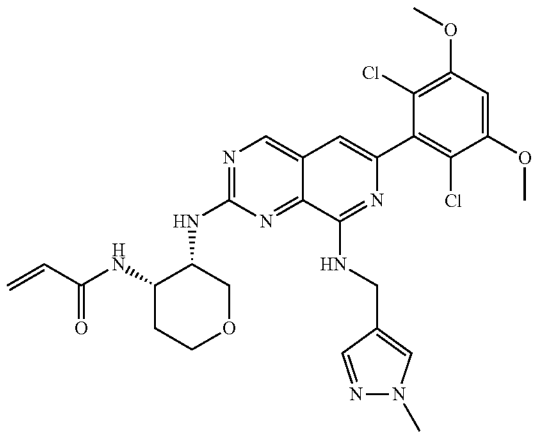 | N-((3S,4S)-3-((6-(2,6-dichloro-3,5-dimethoxyphenyl)-8-(((1-methyl-1H-pyrazol-4-yl)methyl)amino)pyrido[3,4-d]pyrimidin-2-yl)amino)tetrahydro-2H-pyran-4-yl)acrylamide | 613 |
| 545 | 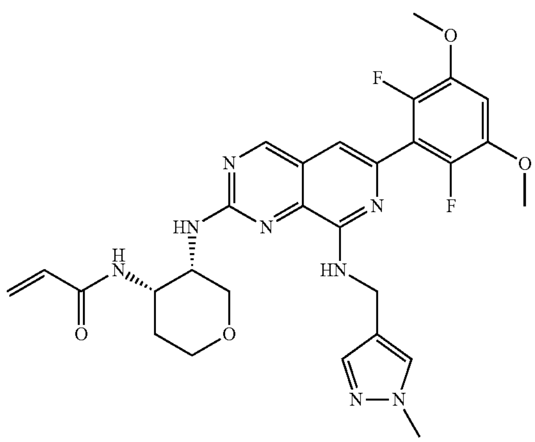 [SMILES: C=CC(=O)N[C@H]1CCOC[C@H]1Nc1ncc2cc(-c3c(F)c(OC)cc(OC)c3F)nc(NCc3cnn(C)c3)c2n1] | N-((3S,4S)-3-((6-(2,6-difluoro-3,5-dimethoxyphenyl)-8-(((1-methyl-1H-pyrazol-4-yl)methyl)amino)pyrido[3,4-d]pyrimidin-2-yl)amino)tetrahydro-2H-pyran-4-yl)acrylamide | 581 |
| 546 | 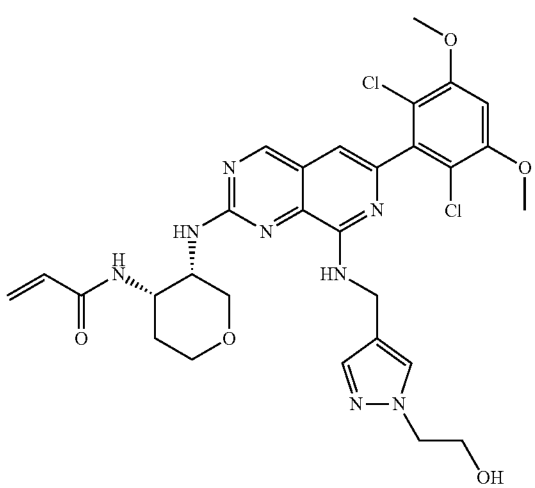 [SMILES: C=CC(=O)N[C@H]1CCOC[C@H]1Nc1ncc2cc(-c3c(Cl)c(OC)cc(OC)c3Cl)nc(NCc3cnn(CCO)c3)c2n1] | N-((3S,4S)-3-((6-(2,6-dichloro-3,5-dimethoxyphenyl)-8-(((1-(2-hydroxyethyl)-1H-pyrazol-4-yl)methyl)amino)pyrido[3,4-d]pyrimidin-2-yl)amino)tetrahydro-2H-pyran-4-yl)acrylamide | 643 |

-continued

| Example No. | Compound structure | Compound name | MS: m/z [M + 1]+ |
|---|---|---|---|
| 547 | 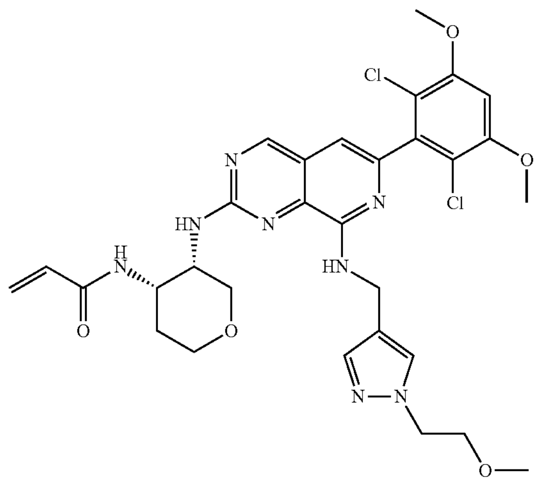 [SMILES: C=CC(=O)N[C@H]1CCOC[C@H]1Nc1ncc2cc(-c3c(Cl)c(OC)cc(OC)c3Cl)nc(NCc3cnn(CCOC)c3)c2n1] | N-((3S,4S)-3-((6-(2,6-dichloro-3,5-dimethoxyphenyl)-8-(((1-(2-methoxyethyl)-1H-pyrazol-4-yl)methyl)amino)pyrido[3,4-d]pyrimidin-2-yl)amino)tetrahydroxy-2H-pyran-4-yl)acrylamide | 657 |
| 548 | 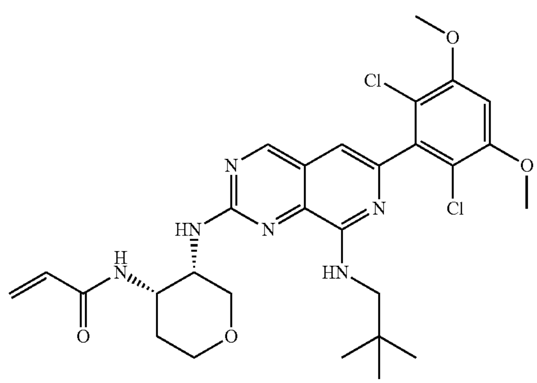 [SMILES: C=CC(=O)N[C@H]1CCOC[C@H]1Nc1ncc2cc(-c3c(Cl)c(OC)cc(OC)c3Cl)nc(NCC(C)(C)C)c2n1] | N-((3S,4S)-3-((6-(2,6-dichloro-3,5-dimethoxyphenyl)-8-(neopentylamino)pyrido[3,4-d]pyrimidin-2-yl)amino)tetrahydro-2H-pyran-4-yl)acrylamide | 589 |
| 549 | 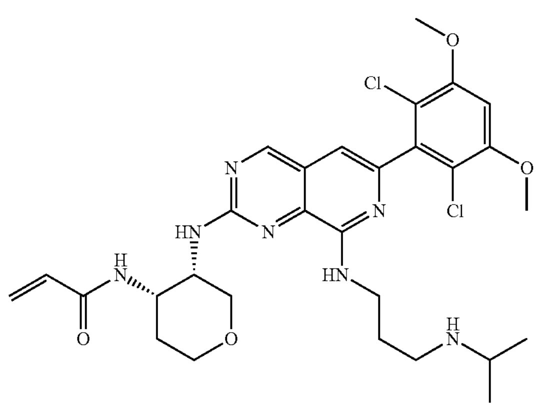 [SMILES: C=CC(=O)N[C@H]1CCOC[C@H]1Nc1ncc2cc(-c3c(Cl)c(OC)cc(OC)c3Cl)nc(NCCCNC(C)C)c2n1] | N-((3S,4S)-3-((6-(2,6-dichloro-3,5-dimethoxyphenyl)-8-((3-(isopropylamino)propyl)amino)pyrido[3,4-d]pyrimidin-2-yl)amino)tetrahydro-2H-pyran-4-yl)acrylamide | 618 |

-continued

| Example No. | Compound structure | Compound name | MS: m/z [M + 1]+ |
|---|---|---|---|
| 550 | 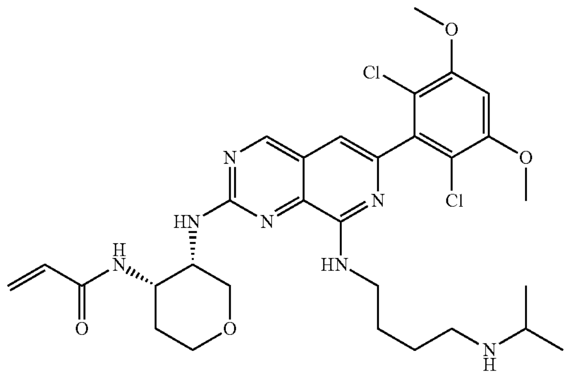 [SMILES: C=CC(=O)N[C@H]1CCOC[C@H]1Nc1ncc2cc(-c3c(Cl)c(OC)cc(OC)c3Cl)nc(NCCCCNC(C)C)c2n1] | N-((3S,4S)-3-((6-(2,6-dichloro-3,5-di-methoxyphenyl)-8-((4-(isopropyl-amino)butyl)amino)pyrido[3,4-d]pyrimi-din-2-yl)amino)tetrahydro-2H-pyran-4-yl)acrylamide | 632 |
| 551 | 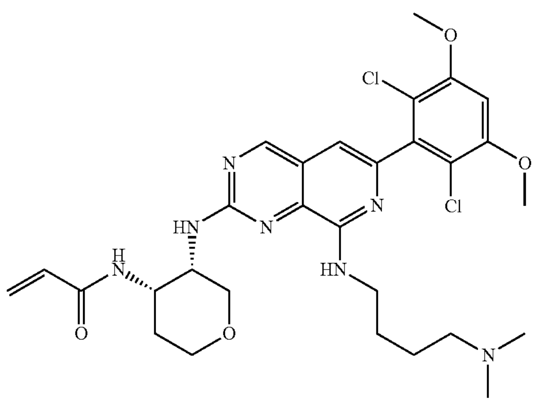 [SMILES: C=CC(=O)N[C@H]1CCOC[C@H]1Nc1ncc2cc(-c3c(Cl)c(OC)cc(OC)c3Cl)nc(NCCCCN(C)C)c2n1] | N-((3S,4S)-3-((6-(2,6-dichloro-3,5-di-methoxyphenyl)-8-((4-(dimethyl-amino)butyl)amino)pyrido[3,4-d]pyrimi-din-2-yl)amino)tetrahydro-2H-pyran-4-yl)acrylamide | 618 |
| 552 | 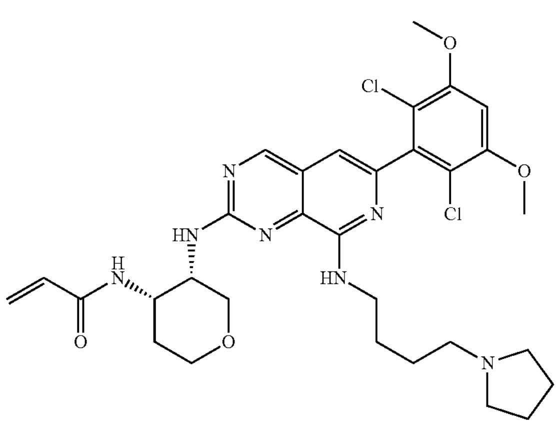 [SMILES: C=CC(=O)N[C@H]1CCOC[C@H]1Nc1ncc2cc(-c3c(Cl)c(OC)cc(OC)c3Cl)nc(NCCCCN3CCCC3)c2n1] | N-((3S,4S)-3-((6-(2,6-dichloro-3,5-di-methoxyphenyl)-8-((4-(pyrrolidin-1-yl)butyl)amino)pyrido[3,4-d]pyrimi-din-2-yl)amino)tetrahydro-2H-pyran-4-yl)acrylamide | 644 |

-continued

| Example No. | Compound structure | Compound name | MS: m/z [M + 1]+ |
|---|---|---|---|
| 553 | 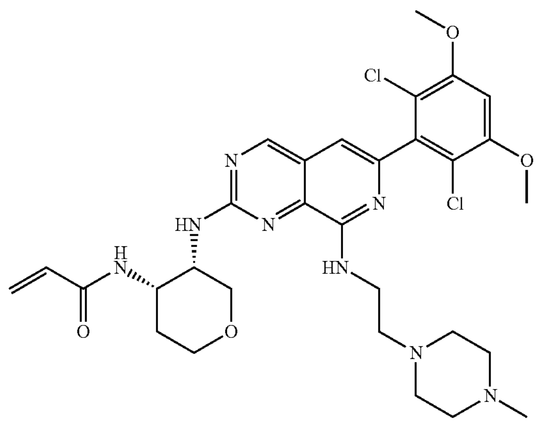 [SMILES: C=CC(=O)N[C@H]1CCOC[C@H]1Nc1ncc2cc(-c3c(Cl)c(OC)cc(OC)c3Cl)nc(NCCN3CCN(C)CC3)c2n1] | N-((3S,4S)-3-((6-(2,6-dichloro-3,5-dimethoxyphenyl)-8-((2-(4-methyl-piperazin-1-yl)ethyl)amino)pyrido[3,4-d]pyrimidin-2-yl)amino)tetrahydro-2H-pyran-4-yl)acrylamide | 645 |
| 554 | 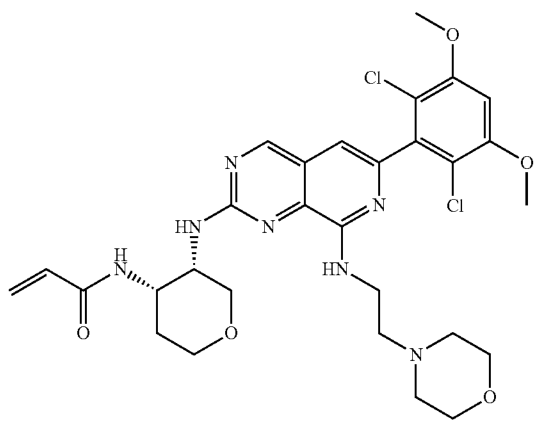 [SMILES: C=CC(=O)N[C@H]1CCOC[C@H]1Nc1ncc2cc(-c3c(Cl)c(OC)cc(OC)c3Cl)nc(NCCN3CCOCC3)c2n1] | N-((3S,4S)-3-((6-(2,6-dichloro-3,5-dimethoxyphenyl)-8-((2-morpholinoethyl)amino)pyrido[3,4-d]pyrimidin-2-yl)amino)tetrahydro-2H-pyran-4-yl)acrylamide | 632 |
| 555 | 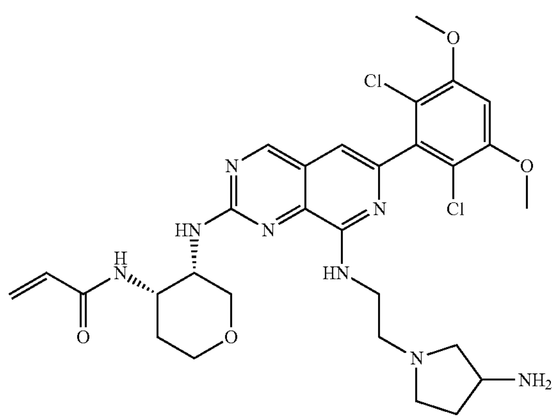 [SMILES: C=CC(=O)N[C@H]1CCOC[C@H]1Nc1ncc2cc(-c3c(Cl)c(OC)cc(OC)c3Cl)nc(NCCN3CCC(N)C3)c2n1] | N-((3S,4S)-3-((8-((2-(3-aminopyrrolidin-1-yl)ethyl)amino)-6-(2,6-dichloro-3,5-dimethoxyphenyl)pyrido[3,4-d]pyrimidin-2-yl)amino)tetrahydro-2H-pyran-4-yl)acrylamide | 631 |

-continued

| Example No. | Compound structure | Compound name | MS: m/z [M + 1]+ |
|---|---|---|---|
| 556 | 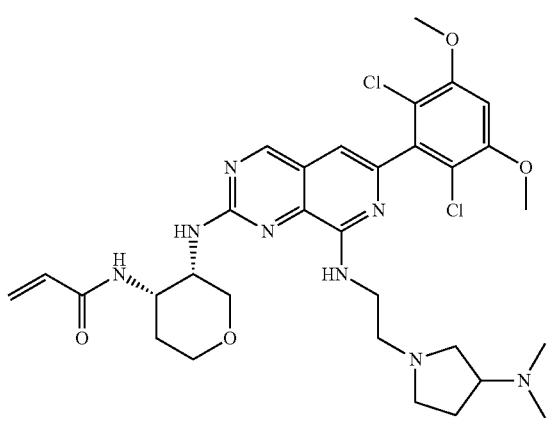 [SMILES: C=CC(=O)N[C@H]1CCOC[C@H]1Nc1ncc2cc(-c3c(Cl)c(OC)cc(OC)c3Cl)nc(NCCN3CCC(N(C)C)C3)c2n1] | N-((3S,4S)-3-((6-(2,6-dichloro-3,5-di-methoxyphenyl)-8-((2-(3-(dimethyl-amino)pyrrolidin-1-yl)ethyl)amino)pyrido[3,4-d]pyrimidin-2-yl)a-mino)tetrahydro-2H-pyran-4-yl)acrylamide | 659 |
| 557 | 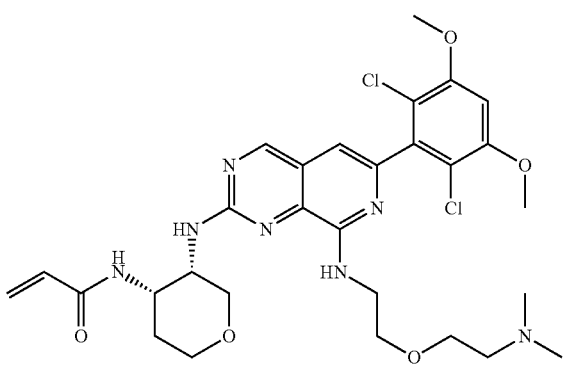 [SMILES: C=CC(=O)N[C@H]1CCOC[C@H]1Nc1ncc2cc(-c3c(Cl)c(OC)cc(OC)c3Cl)nc(NCCOCCN(C)C)c2n1] | N-((3S,4S)-3-((6-(2,6-dichloro-3,5-di-methoxypehnyl)-8-((2-(2-(dimethyl-amino)ethoxy)ethyl)amino)pyrido[3,4-d]pyrimidin-2-yl)amino)tetrahydro-2H-pyran-4-yl)acrylamide | 634 |
| 558 | 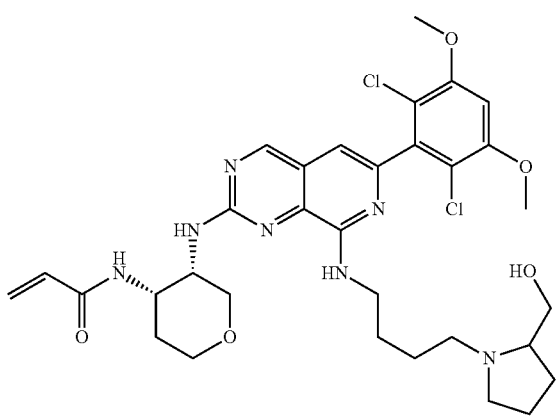 [SMILES: C=CC(=O)N[C@H]1CCOC[C@H]1Nc1ncc2cc(-c3c(Cl)c(OC)cc(OC)c3Cl)nc(NCCCCN3CCCC3CO)c2n1] | N-((3S,4S)-3-((6-(2,6-dichloro-3,5-di-methoxyphenyl)-8-((4-(2-(hydroxy-methyl)pyrrolidin-1-yl)butyl)amino)py-rido[3,4-d]pyrimidin-2-yl)amino)tetra-hydro-2H-pyran-4-yl)acrylamide | 674 |

| Example No. | Compound structure | Compound name | MS: m/z [M + 1]+ |
|---|---|---|---|
| 559 | 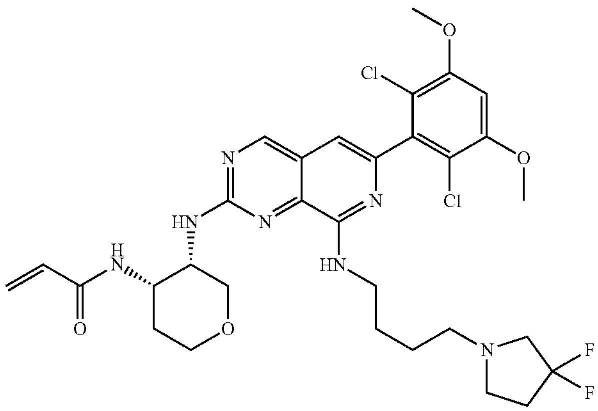 [SMILES: C=CC(=O)N[C@H]1CCOC[C@H]1Nc1ncc2cc(-c3c(Cl)c(OC)cc(OC)c3Cl)nc(NCCCCN3CCC(F)(F)C3)c2n1] | N-((3S,4S)-3-((6-(2,6-dichloro-3,5-di-methoxyphenyl)-8-((4-(3,3-difluoro-pyrrolidin-1-yl)butyl)amino)pyrido[3,4-d]pyrimidin-2-yl)amino)tetrahydro-2H-pyran-4-yl)acrylamide | 680 |
| 560 | 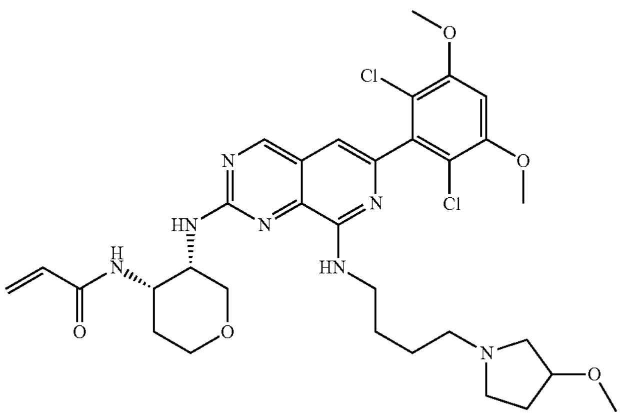 [SMILES: C=CC(=O)N[C@H]1CCOC[C@H]1Nc1ncc2cc(-c3c(Cl)c(OC)cc(OC)c3Cl)nc(NCCCCN3CCC(OC)C3)c2n1] | N-((3S,4S)-3-((6-(2,6-dichloro-3,5-di-methoxyphenyl)-8-((4-(3-methoxy-pyrrolidin-1-yl)butyl)amino)pyrido[3,4-d]pyrimidin-2-yl)amino)tetrahydro-2H-pyran-4-yl)acrylamide | 674 |
| 561 | 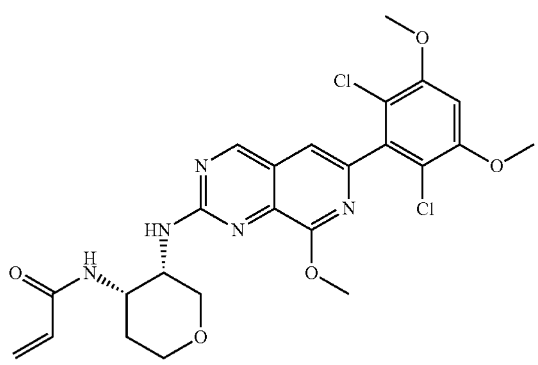 [SMILES: C=CC(=O)N[C@H]1CCOC[C@H]1Nc1ncc2cc(-c3c(Cl)c(OC)cc(OC)c3Cl)nc(OC)c2n1] | N-((3S,4S)-3-((6-(2,6-dichloro-3,5-di-methoxyphenyl)-8-methoxypyrido[3,4-d]pyrimidin-2-yl)amino)tetra-hydro-2H-pyran-4-yl)acrylamide | 534 |
| 562 | 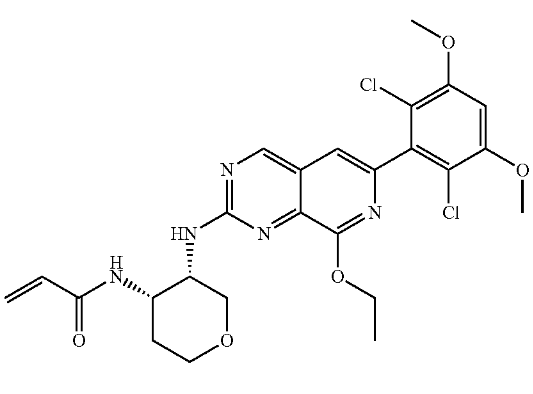 [SMILES: C=CC(=O)N[C@H]1CCOC[C@H]1Nc1ncc2cc(-c3c(Cl)c(OC)cc(OC)c3Cl)nc(OCC)c2n1] | N-((3S,4S)-3-((6-(2,6-dichloro-3,5-di-methoxyphenyl)-8-ethoxypyrido[3,4-d]pyrimidin-2-yl)amino)tetra-hydro-2H-pyran-4-yl)acrylamide | 548 |

-continued

| Example No. | Compound structure | Compound name | MS: m/z [M + 1]+ |
|---|---|---|---|
| 563 | 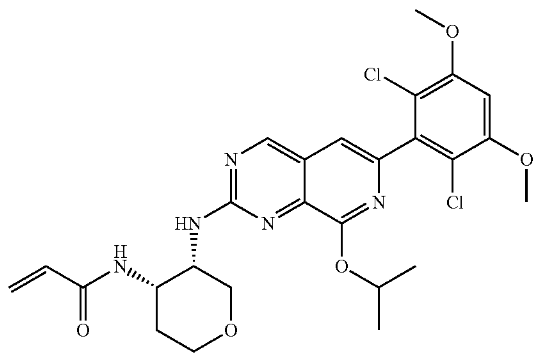 [SMILES: C=CC(=O)N[C@H]1CCOC[C@H]1Nc1ncc2cc(-c3c(Cl)c(OC)cc(OC)c3Cl)nc(OC(C)C)c2n1] | N-((3S,4S)-3-((6-(2,6-dichloro-3,5-di-methoxyphenyl)-8-isopropoxypyrdo[3,4-d]pyrimidin-2-yl)amino)tetra-hydro-2H-pyran-4-yl)acrylamide | 562 |
| 564 | 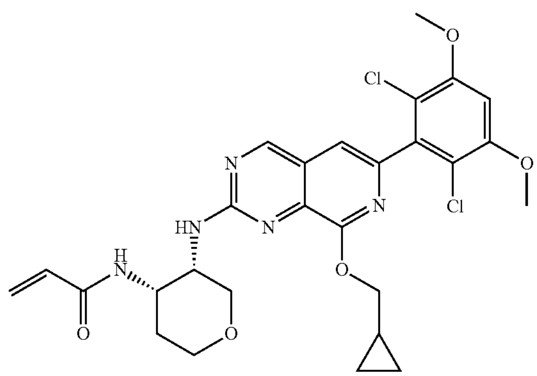 [SMILES: C=CC(=O)N[C@H]1CCOC[C@H]1Nc1ncc2cc(-c3c(Cl)c(OC)cc(OC)c3Cl)nc(OCC3CC3)c2n1] | N-((3S,4S)-3-((8-(cyclopropylmeth-oxy)-6-(2,6-dichloro-3,5-dimethoxy-phenyl)pyrido[3,4-d]pyrimidin-2-yl)a-mino)tetrahydro-2H-pyran-4-yl)acryl-amide | 574 |
| 565 | 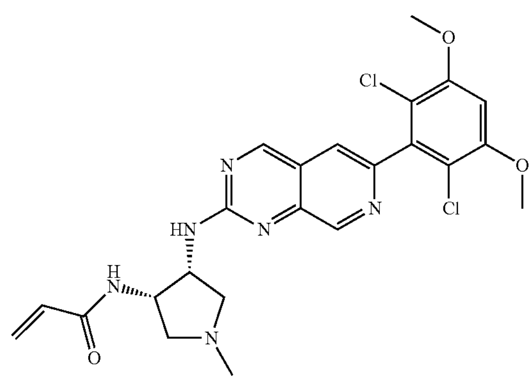 [SMILES: C=CC(=O)N[C@H]1CN(C)C[C@H]1Nc1ncc2cc(-c3c(Cl)c(OC)cc(OC)c3Cl)ncc2n1] | N-((3S,4R)-4-((6-(2,6-dichloro-3,5-dimethoxyphenyl)pyrido[3,4-d]pyrimi-din-2-yl)amino)-1-methylpyrrolidin-3-yl)acrylamide | 503 |
| 566 | 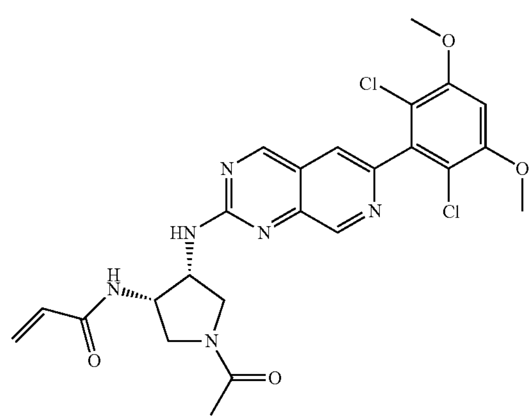 [SMILES: C=CC(=O)N[C@H]1CN(C(C)=O)C[C@H]1Nc1ncc2cc(-c3c(Cl)c(OC)cc(OC)c3Cl)ncc2n1] | N-((3S,4R)-1-acetyl-4-((6-(2,6-di-chloro-3,5-dimethoxyphenyl)pyrido[3,4-d]pyrimidin-2-yl)amino)pyrrolidin-3-yl)acrylamide | 531 |

-continued

| Example No. | Compound structure | Compound name | MS: m/z [M + 1]+ |
| --- | --- | --- | --- |
| 567 | 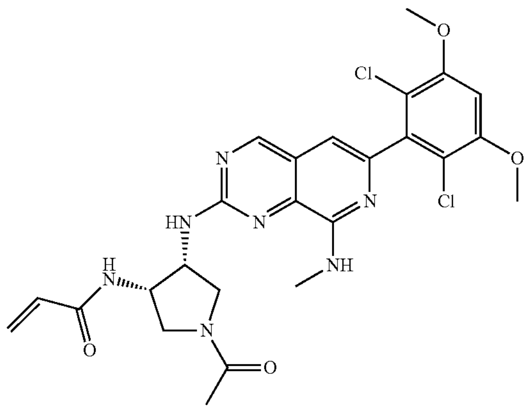 [SMILES: C=CC(=O)N[C@H]1CN(C(C)=O)C[C@H]1Nc1ncc2cc(-c3c(Cl)c(OC)cc(OC)c3Cl)nc(NC)c2n1] | N-((3S,4R)-1-acetyl-4-((6-(2,6-dichloro-3,5-dimethoxyphenyl)-8-(methylamino)pyrido[3,4-d]pyrimidin-2-yl)amino)pyrrolidin-3-yl)acrylamide | 560 |
| 568 | 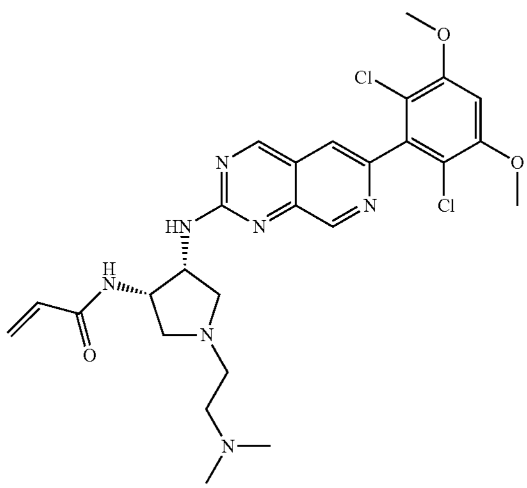 [SMILES: C=CC(=O)N[C@H]1CN(CCN(C)C)C[C@H]1Nc1ncc2cc(-c3c(Cl)c(OC)cc(OC)c3Cl)ncc2n1] | N-((3S,4R)-4-((6-(2,6-dichloro-3,5-dimethoxyphenyl)pyrido[3,4-d]pyrimidin-2-yl)amino)-1-(2-(dimethylamino)ethyl)pyrrolidin-3-yl)acrylamide | 560 |
| 569 | 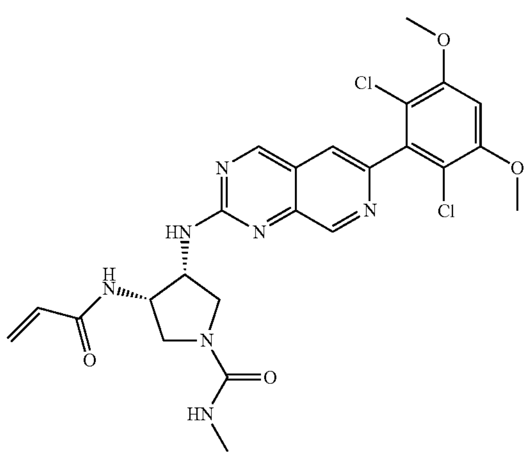 [SMILES: C=CC(=O)N[C@H]1CN(C(=O)NC)C[C@H]1Nc1ncc2cc(-c3c(Cl)c(OC)cc(OC)c3Cl)ncc2n1] | (3S,4R)-3-acrylamido-4-((6-(2,6-dichloro-3,5-dimethoxyphenyl)pyrido[3,4-d]pyrimidin-2-yl)amino)-N-methylpyrrolidine-1-carboxamide | 546 |

-continued

| Example No. | Compound structure | Compound name | MS: m/z [M + 1]+ |
|---|---|---|---|
| 570 | 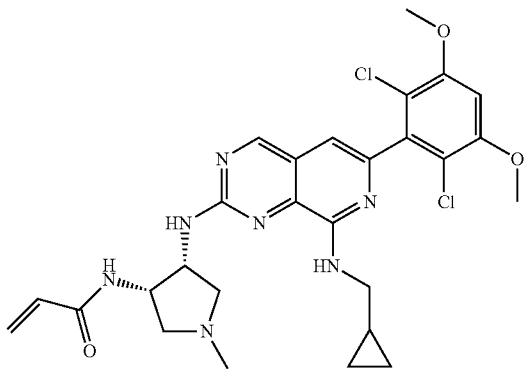 [SMILES: C=CC(=O)N[C@H]1CN(C)C[C@H]1Nc1ncc2cc(-c3c(Cl)c(OC)cc(OC)c3Cl)nc(NCC3CC3)c2n1] | N-((3S,4R)-4-((8-((cyclopropylmethyl)amino)-6-(2,6-dichloro-3,5-dimethoxyphenyl)pyrido[3,4-d]pyrimidin-2-yl)amino)-1-methylpyrrolidin-3-yl)acrylamide | 572 |
| 571 | 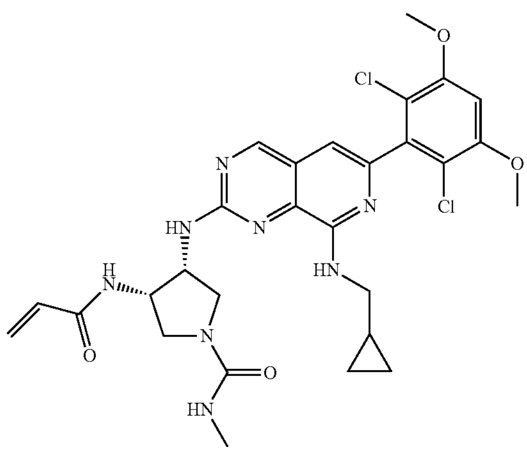 [SMILES: C=CC(=O)N[C@H]1CN(C(=O)NC)C[C@H]1Nc1ncc2cc(-c3c(Cl)c(OC)cc(OC)c3Cl)nc(NCC3CC3)c2n1] | (3S,4R)-3-acrylamido-4-((8-((cyclopropylmethyl)amino)-6-(2,6-dichloro-3,5-dimethoxyphenyl)pyrido[3,4-d]pyrimidin-2-yl)amino)-N-methyl-pyrrolidine-1-carboxamide | 615 |
| 572 | 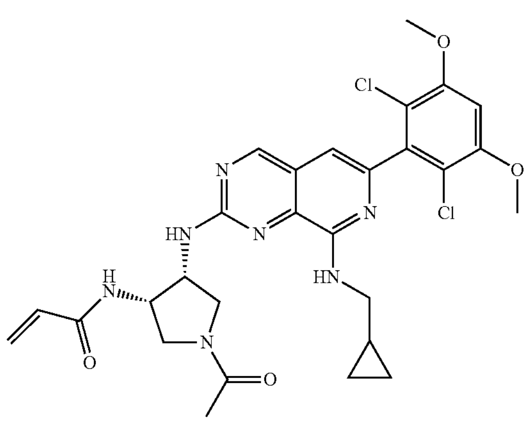 [SMILES: C=CC(=O)N[C@H]1CN(C(C)=O)C[C@H]1Nc1ncc2cc(-c3c(Cl)c(OC)cc(OC)c3Cl)nc(NCC3CC3)c2n1] | N-((3S,4R)-1-acetyl-4-((8-((cyclopropylmethyl)amino)-6-(2,6-dichloro-3,5-dimethoxyphenyl)pyrido[3,4-d]pyrimidin-2-yl)amino)pyrrolidin-3-yl)acrylamide | 600 |

-continued

| Example No. | Compound structure | Compound name | MS: m/z [M + 1]+ |
|---|---|---|---|
| 573 | 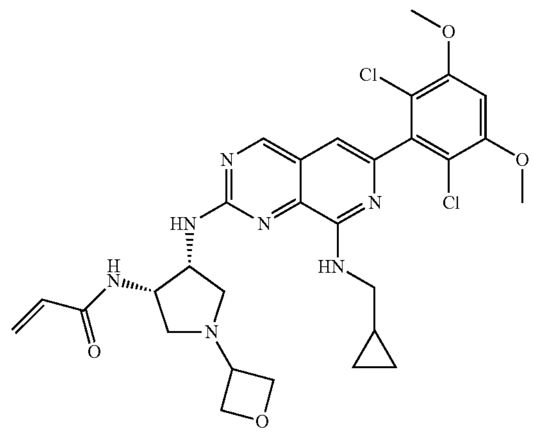 [SMILES: C=CC(=O)N[C@H]1CN(C2COC2)C[C@H]1Nc1ncc2cc(-c3c(Cl)c(OC)cc(OC)c3Cl)nc(NCC3CC3)c2n1] | N-((3S,4R)-4-((8-((cyclopropylmethyl)amino)-6-(2,6-dichloro-3,5-dimethoxyphenyl)pyrido[3,4-d]pyrimidin-2-yl)amino)-1-(oxetan-3-yl)pyrrolidin-3-yl)acrylamide | 614 |
| 574 | 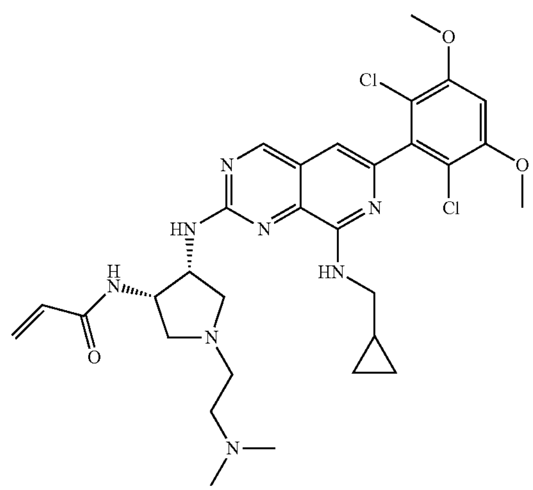 [SMILES: C=CC(=O)N[C@H]1CN(CCN(C)C)C[C@H]1Nc1ncc2cc(-c3c(Cl)c(OC)cc(OC)c3Cl)nc(NCC3CC3)c2n1] | N-((3S,4R)-4-((8-((cyclopropylmethyl)amino)-6-(2,6-dichloro-3,5-dimethoxyphenyl)pyrido[3,4-d]pyrimidin-2-yl)amino)-1-(2-(dimethylamino)ethyl)pyrrolidin-3-yl)acrylamide | 629 |
| 575 | 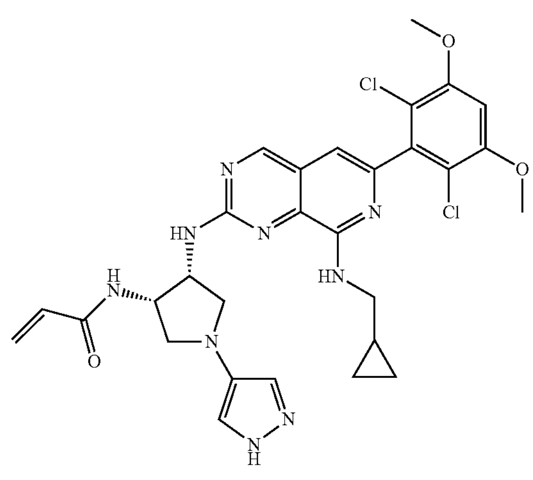 [SMILES: C=CC(=O)N[C@H]1CN(c2cn[nH]c2)C[C@H]1Nc1ncc2cc(-c3c(Cl)c(OC)cc(OC)c3Cl)nc(NCC3CC3)c2n1] | N-((3S,4R)-4-((8-((cyclopropylmethyl)amino)-6-(2,6-dichloro-3,5-dimethoxyphenyl)pyrido[3,4-d]pyrimidin-2-yl)amino)-1-(1H-pyrazol-4-yl)pyrrolidin-3-yl)acrylamide | 624 |

-continued

| Example No. | Compound structure | Compound name | MS: m/z [M + 1]+ |
| --- | --- | --- | --- |
| 576 | 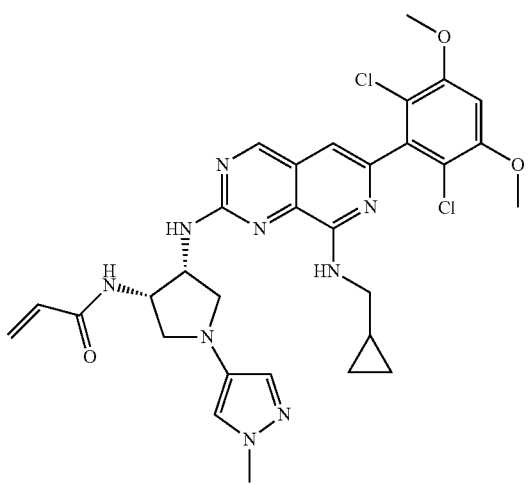 [SMILES: C=CC(=O)N[C@H]1CN(c2cnn(C)c2)C[C@H]1Nc1ncc2cc(-c3c(Cl)c(OC)cc(OC)c3Cl)nc(NCC3CC3)c2n1] | N-((3S,4R)-4-((8-((cyclopropylmethyl)amino)-6-(2,6-dichloro-3,5-dimethoxyphenyl)pyrido[3,4-d]pyrimidin-2-yl)amino)-1-(1-methyl-1H-pyrazol-4-yl)pyrrolidin-3-yl)acrylamide | 638 |
| 577 | 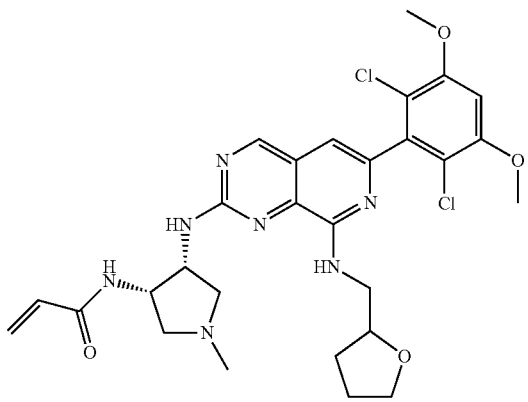 [SMILES: C=CC(=O)N[C@H]1CN(C)C[C@H]1Nc1ncc2cc(-c3c(Cl)c(OC)cc(OC)c3Cl)nc(NCC3CCCO3)c2n1] | N-((3S,4R)-4-((6-(2,6-dichloro-3,5-dimethoxyphenyl)-8-(((tetrahydrofuran-2-yl)methyl)amino)pyrido[3,4-d]pyrimidin-2-yl)amino)-1-methylpyrrolidin-3-yl)acrylamide | 602 |
| 578 | 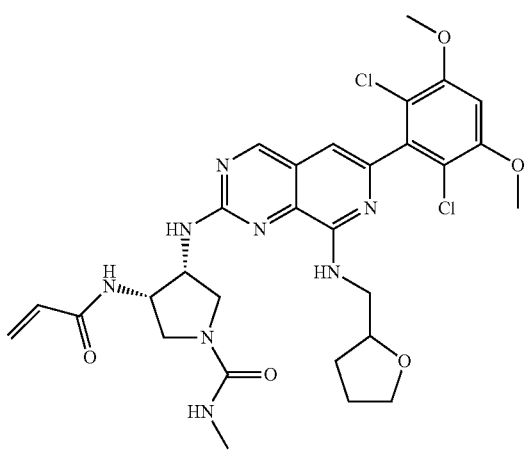 [SMILES: C=CC(=O)N[C@H]1CN(C(=O)NC)C[C@H]1Nc1ncc2cc(-c3c(Cl)c(OC)cc(OC)c3Cl)nc(NCC3CCCO3)c2n1] | (3S,4R)-3-acrylamido-4-((6-(2,6-dichloro-3,5-dimethoxyphenyl)-8-(((tetrahydrofuran-2-yl)methyl)amino)pyrido[3,4-d]pyrimidin-2-yl)amino)-N-methylpyrrolidine-1-carboxamide | 645 |

| Example No. | Compound structure | Compound name | MS: m/z [M + 1]+ |
| --- | --- | --- | --- |
| 579 | 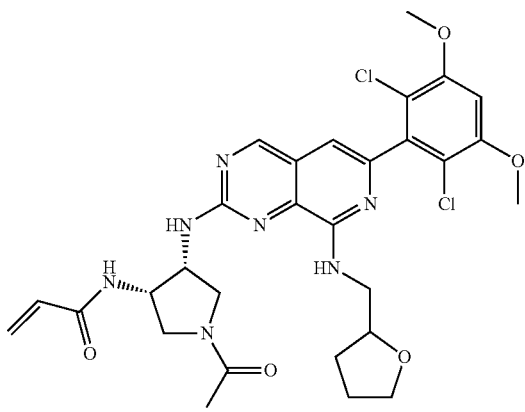 [SMILES: C=CC(=O)N[C@H]1CN(C(C)=O)C[C@H]1Nc1ncc2cc(-c3c(Cl)c(OC)cc(OC)c3Cl)nc(NCC3CCCO3)c2n1] | N-((3S,4R)-1-acetyl-4-(((6-(2,6-dichloro-3,5-dimethoxyphenyl)-8-(((tetrahydrofuran-2-yl)methyl)amino)pyrido[3,4-d]pyrimidin-2-yl)amino)pyrrolidin-3-yl)acrylamide | 630 |
| 580 | 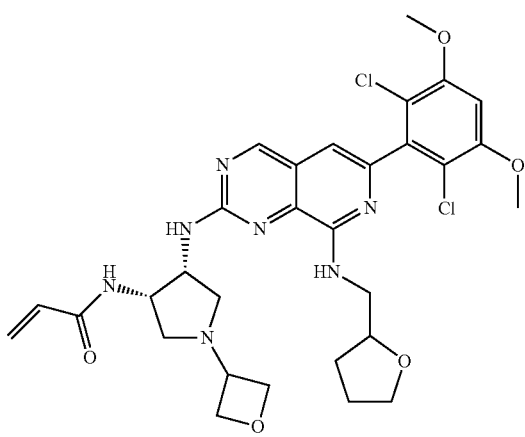 [SMILES: C=CC(=O)N[C@H]1CN(C2COC2)C[C@H]1Nc1ncc2cc(-c3c(Cl)c(OC)cc(OC)c3Cl)nc(NCC3CCCO3)c2n1] | N-((3S,4R)-4-((6-(2,6-dichloro-3,5-dimethoxyphenyl)-8-(((tetrahydrofuran-2-yl)methyl)amino)pyrido[3,4-d]pyrimidin-2-yl)amino)-1-(oxetan-3-yl)pyrrolidin-3-yl)acrylamide | 644 |
| 581 | 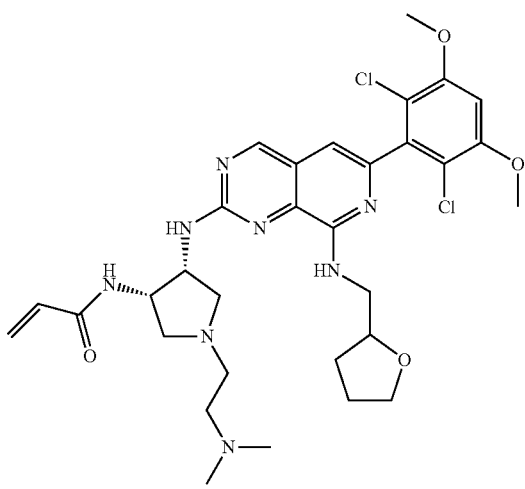 [SMILES: C=CC(=O)N[C@H]1CN(CCN(C)C)C[C@H]1Nc1ncc2cc(-c3c(Cl)c(OC)cc(OC)c3Cl)nc(NCC3CCCO3)c2n1] | N-((3S,4R)-4-((6-(2,6-dichloro-3,5-dimethoxyphenyl)-8-(((tetrahydrofuran-2-yl)methyl)amino)pyrido[3,4-d]pyrimidin-2-yl)amino)-1-(2-(dimethylamino)ethyl)pyrrolidin-3-yl)acrylamide | 659 |

-continued

| Example No. | Compound structure | Compound name | MS: m/z [M + 1]+ |
| --- | --- | --- | --- |
| 582 | 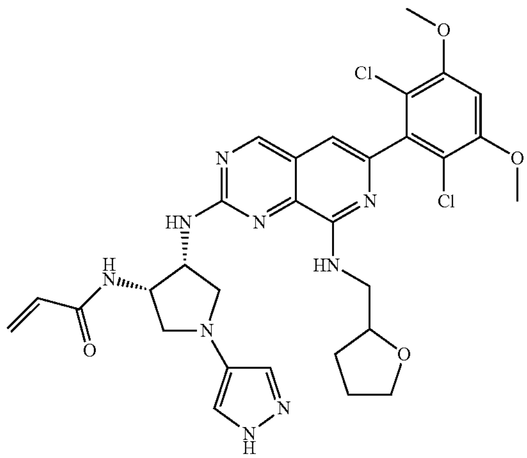 [SMILES: C=CC(=O)N[C@H]1CN(c2cn[nH]c2)C[C@H]1Nc1ncc2cc(-c3c(Cl)c(OC)cc(OC)c3Cl)nc(NCC3CCCO3)c2n1] | N-((3S,4R)-4-((6-(2,6-dichloro-3,5-di-methoxyphenyl)-8-(((tetrahydrofuran-2-yl)methyl)amino)pyrido[3,4-d]py-rimidin-2-yl)amino)-1-(1H-pyrazol-4-yl)pyrrolidin-3-yl)acrylamide | 654 |
| 583 | 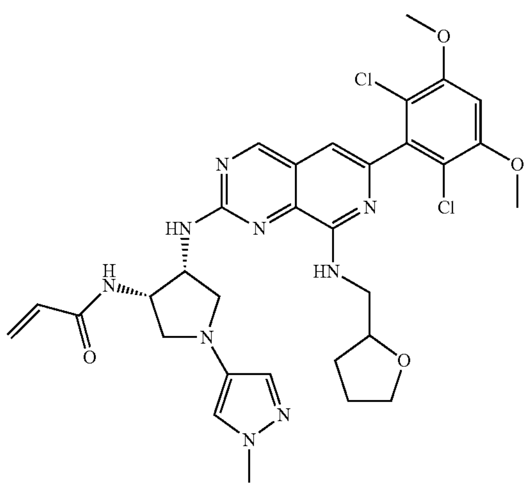 [SMILES: C=CC(=O)N[C@H]1CN(c2cnn(C)c2)C[C@H]1Nc1ncc2cc(-c3c(Cl)c(OC)cc(OC)c3Cl)nc(NCC3CCCO3)c2n1] | N-((3S,4R)-4-((6-(2,6-dichloro-3,5-di-methoxyphenyl)-8-(((tetrahydrofuran-2-yl)methyl)amino)pyrido[3,4-d]py-rimidin-2-yl)amino)-1-(1-methyl-1H-pyrazol-4-yl)pyrrolidin-3-yl)acryl-amide | 668 |
| 584 | 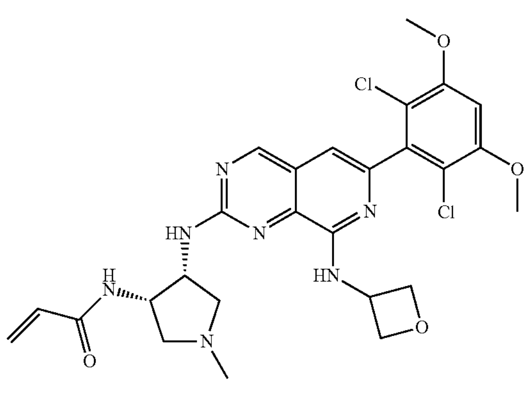 [SMILES: C=CC(=O)N[C@H]1CN(C)C[C@H]1Nc1ncc2cc(-c3c(Cl)c(OC)cc(OC)c3Cl)nc(NC3COC3)c2n1] | N-((3S,4R)-4-((6-(2,6-dichloro-3,5-di-methoxyphenyl)-8-(oxetan-3-ylamino)py-rido[3,4-d]pyrimidin-2-yl)amino)-1-methylpyrrolidin-3-yl)acrylamide | 574 |

-continued

| Example No. | Compound structure | Compound name | MS: m/z [M + 1]+ |
| --- | --- | --- | --- |
| 585 | 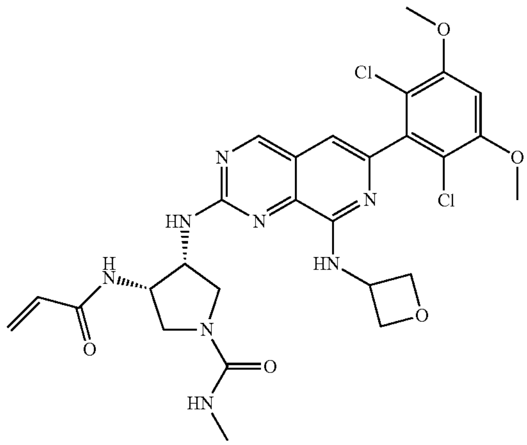 [SMILES: C=CC(=O)N[C@H]1CN(C(=O)NC)C[C@H]1Nc1ncc2cc(-c3c(Cl)c(OC)cc(OC)c3Cl)nc(NC3COC3)c2n1] | (3S,4R)-3-acrylamido-4-((6-(2,6-dichloro-3,5-dimethoxyphenyl)-8-(oxetan-3-ylamino)pyrido[3,4-d]pyrimidin-2-yl)amino)-N-methylpyrrolidine-1-carboxamide | 617 |
| 586 | 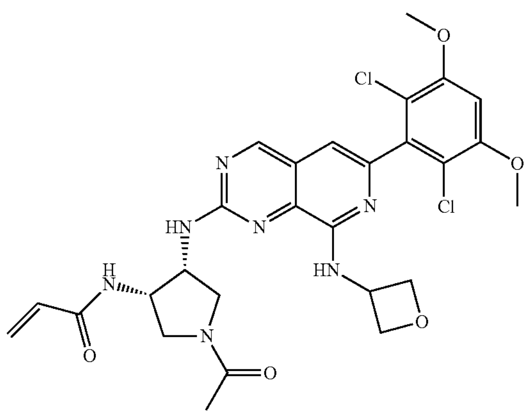 [SMILES: C=CC(=O)N[C@H]1CN(C(C)=O)C[C@H]1Nc1ncc2cc(-c3c(Cl)c(OC)cc(OC)c3Cl)nc(NC3COC3)c2n1] | N-((3S,4R)-1-acetyl-4-((6-(2,6-dichloro-3,5-dimethoxyphenyl)-8-(oxetan-3-ylamino)pyrido[3,4-d]pyrimidin-2-yl)amino)pyrrolidin-3-yl)acrylamide | 602 |
| 587 | 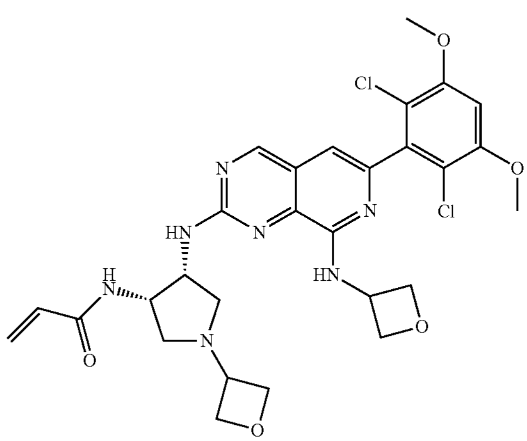 [SMILES: C=CC(=O)N[C@H]1CN(C2COC2)C[C@H]1Nc1ncc2cc(-c3c(Cl)c(OC)cc(OC)c3Cl)nc(NC3COC3)c2n1] | N-((3S,4R)-4-((6-(2,6-dichloro-3,5-dimethoxyphenyl)-8-(oxetan-3-ylamino)pyrido[3,4-d]pyrimidin-2-yl)amino)-1-(oxetan-3-yl)pyrrolidin-3-yl)acrylamide | 616 |

| Example No. | Compound structure | Compound name | MS: m/z [M + 1]+ |
|---|---|---|---|
| 588 | 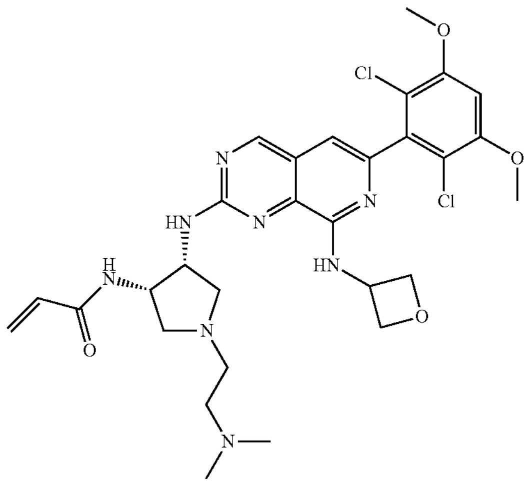 [SMILES: C=CC(=O)N[C@H]1CN(CCN(C)C)C[C@H]1Nc1ncc2cc(-c3c(Cl)c(OC)cc(OC)c3Cl)nc(NC3COC3)c2n1] | N-((3S,4R)-4-((6-(2,6-dichloro-3,5-dimethoxyphenyl)-8-(oxetan-3-yl-amino)pyrido[3,4-d]pyrimidin-2-yl)amino)-1-(2-dimethylamino)ethyl)pyrrolidin-3-yl)acrylamide | 631 |
| 589 | 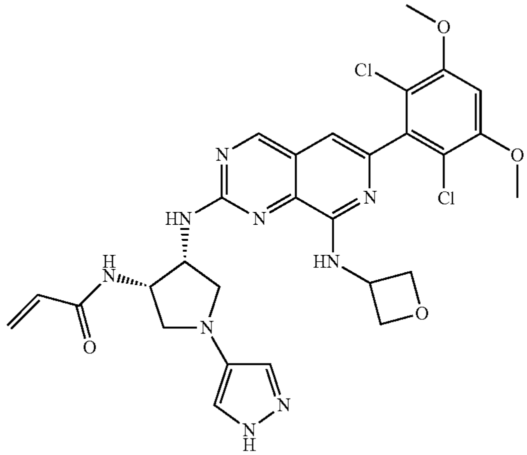 [SMILES: C=CC(=O)N[C@H]1CN(c2cn[nH]c2)C[C@H]1Nc1ncc2cc(-c3c(Cl)c(OC)cc(OC)c3Cl)nc(NC3COC3)c2n1] | N-((3S,4R)-4-((6-(2,6-dichloro-3,5-dimethoxyphenyl)-8-(oxetan-3-yl-amino)pyrido[3,4-d]pyrimidin-2-yl)amino)-1-(1H-pyrazol-4-yl)pyrrolidin-3-yl)acrylamide | 626 |
| 590 | 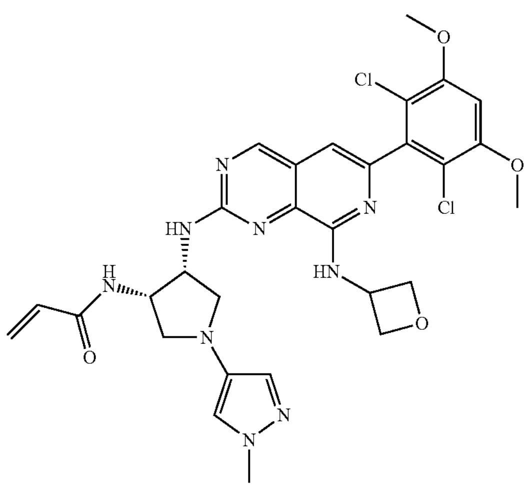 [SMILES: C=CC(=O)N[C@H]1CN(c2cnn(C)c2)C[C@H]1Nc1ncc2cc(-c3c(Cl)c(OC)cc(OC)c3Cl)nc(NC3COC3)c2n1] | N-((3S,4R)-4-((6-(2,6-dichloro-3,5-dimethoxyphenyl)-8-(oxetan-3-yl-amino)pyrido[3,4-d]pyrimidin-2-yl)amino)-1-(1-methyl-1H-pyrazol-4-yl)pyrrolidin-3-yl)acrylamide | 640 |

-continued

| Example No. | Compound structure | Compound name | MS: m/z [M + 1]+ |
| --- | --- | --- | --- |
| 591 | 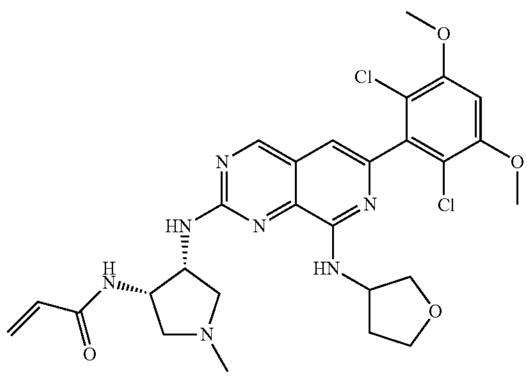 [SMILES: C=CC(=O)N[C@H]1CN(C)C[C@H]1Nc1ncc2cc(-c3c(Cl)c(OC)cc(OC)c3Cl)nc(NC3CCOC3)c2n1] | N-((3S,4R)-4-((6-(2,6-dichloro-3,5-dimethoxyphenyl)-8-((tetrahydrofuran-3-yl)amino)pyrido[3,4-d]pyrimidin-2-yl)amino)-1-methylpyrrolidin-3-yl)acrylamide | 588 |
| 592 | 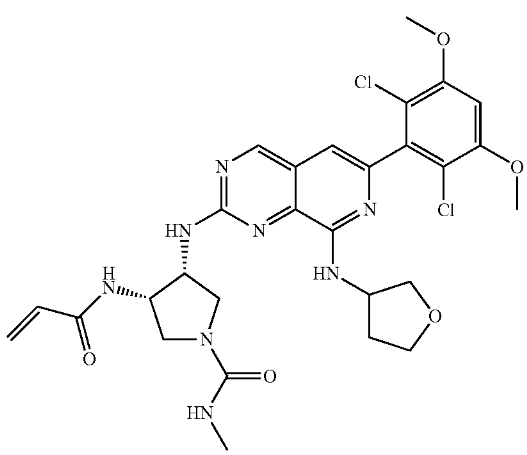 [SMILES: C=CC(=O)N[C@H]1CN(C(=O)NC)C[C@H]1Nc1ncc2cc(-c3c(Cl)c(OC)cc(OC)c3Cl)nc(NC3CCOC3)c2n1] | (3S,4R)-3-acrylamido-4-((6-(2,6-dichloro-3,5-dimethoxyphenyl)-8-((tetrahydrofuran-3-yl)amino)pyrido[3,4-d]pyrimidin-2-yl)amino)-N-methyl-pyrrolidine-1-carboxamide | 631 |
| 593 | 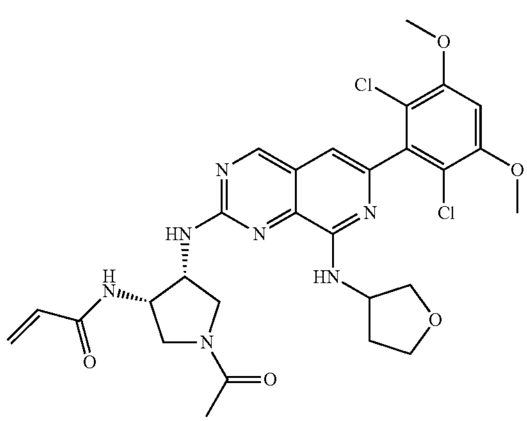 [SMILES: C=CC(=O)N[C@H]1CN(C(C)=O)C[C@H]1Nc1ncc2cc(-c3c(Cl)c(OC)cc(OC)c3Cl)nc(NC3CCOC3)c2n1] | N-((3S,4R)-1-acetyl-4-((6-(2,6-dichloro-3,5-dimethoxyphenyl)-8-((tetrahydrofuran-3-yl)amino)pyrido[3,4-d]pyrimidin-2-yl)amino)pyrrolidin-3-yl)acrylamide | 616 |

-continued

| Example No. | Compound structure | Compound name | MS: m/z [M + 1]+ |
|---|---|---|---|
| 594 | 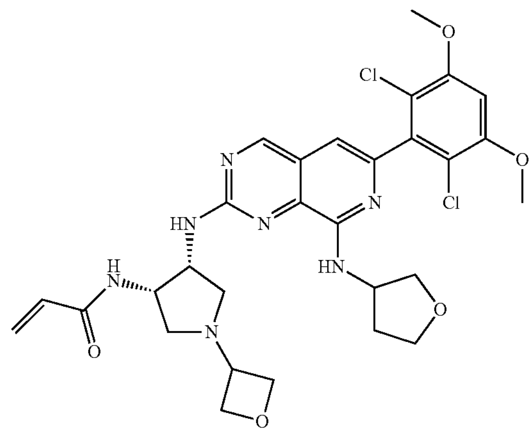 [SMILES: C=CC(=O)N[C@H]1CN(C2COC2)C[C@H]1Nc1ncc2cc(-c3c(Cl)c(OC)cc(OC)c3Cl)nc(NC3CCOC3)c2n1] | N-((3S,4R)-4-((6-(2,6-dichloro-3,5-dimethoxyphenyl)-8-((tetrahydrofuran-3-yl)amino)pyrido[3,4-d]pyrimidin-2-yl)amino)-1-(oxetan-3-yl)pyrrolidine-3-yl)acrylamide | 630 |
| 595 | 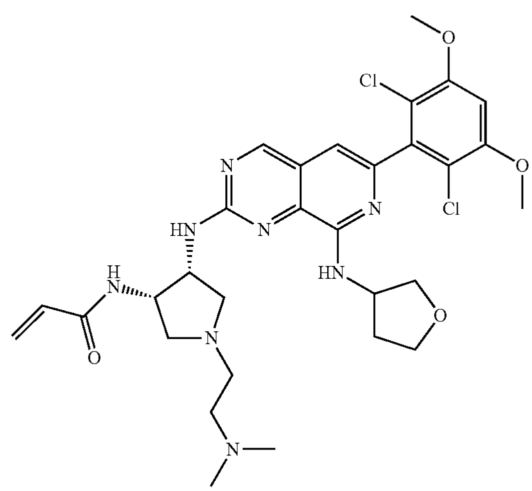 [SMILES: C=CC(=O)N[C@H]1CN(CCN(C)C)C[C@H]1Nc1ncc2cc(-c3c(Cl)c(OC)cc(OC)c3Cl)nc(NC3CCOC3)c2n1] | N-((3S,4R)-4-((6-(2,6-dichloro-3,5-dimethoxyphenyl)-8-((tetrahydrofuran-3-yl)amino)pyrido[3,4-d]pyrimidin-2-yl)amino)-1-(2-(dimethylamino)ethyl)pyrrolidin-3-yl)acrylamide | 645 |
| 596 | 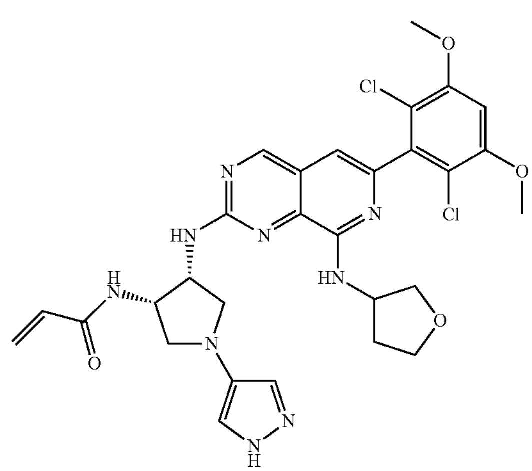 [SMILES: C=CC(=O)N[C@H]1CN(c2cn[nH]c2)C[C@H]1Nc1ncc2cc(-c3c(Cl)c(OC)cc(OC)c3Cl)nc(NC3CCOC3)c2n1] | N-((3S,4R)-4-((6-(2,6-dichloro-3,5-dimethoxyphenyl)-8-((tetrahydrofuran-3-yl)amino)pyrido[3,4-d]pyrimidin-2-yl)amino)-1-(1H-pyrazol-4-yl)pyrrolidine-3-yl)acrylamide | 640 |

-continued

| Example No. | Compound structure | Compound name | MS: m/z [M + 1]+ |
|---|---|---|---|
| 597 | 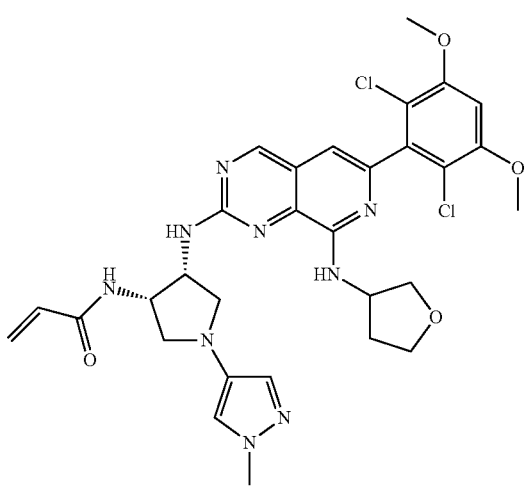 [SMILES: C=CC(=O)N[C@H]1CN(c2cnn(C)c2)C[C@H]1Nc1ncc2cc(-c3c(Cl)c(OC)cc(OC)c3Cl)nc(NC3CCOC3)c2n1] | N-((3S,4R)-4-((6-(2,6-dichloro-3,5-di-methoxyphenyl)-8-(((tetrahydrofuran-3-yl)amino)pyrido[3,4-d]pyrimidin-2-yl)amino)-1-(1-methyl-1H-pyrazol-4-yl)pyrrolidin-3-yl)acrylamide | 654 |
| 598 | 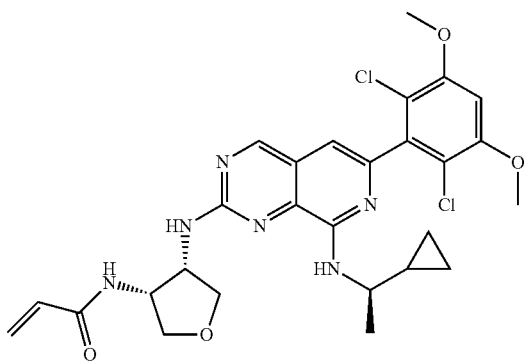 [SMILES: C=CC(=O)N[C@H]1COC[C@H]1Nc1ncc2cc(-c3c(Cl)c(OC)cc(OC)c3Cl)nc(N[C@H](C)C3CC3)c2n1] | N-((3R,4S)-4-((8-(((R)-1-cyclopropopyl-ethyl)amino)-6-(2,6-dichloro-3,5-di-methoxyphenyl)pyrido[3,4-d]pyrimidin-2-yl)amino)tetrahydrofuran-3-yl)acrylamide | 573 |
| 599 | 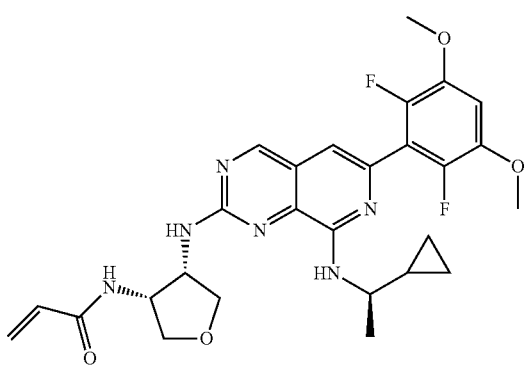 [SMILES: C=CC(=O)N[C@H]1COC[C@H]1Nc1ncc2cc(-c3c(F)c(OC)cc(OC)c3F)nc(N[C@H](C)C3CC3)c2n1] | N-((3R,4S)-4-((8-(((R)-1-cylopropyl-ethyl)amino)-6-(2,6-difluoro-3,5-di-methoxyphenyl)pyrido[3,4-d]pyrimidin-2-yl)amino)tetrahydrofuran-3-yl)acrylamide | 541 |

-continued

| Example No. | Compound structure | Compound name | MS: m/z [M + 1]+ |
|---|---|---|---|
| 600 | 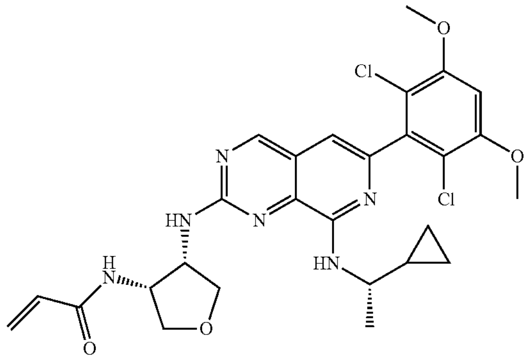 [SMILES: C=CC(=O)N[C@H]1COC[C@H]1Nc1ncc2cc(-c3c(Cl)c(OC)cc(OC)c3Cl)nc(N[C@@H](C)C3CC3)c2n1] | N-((3R,4S)-4-((8-(((S)-1-cyclopropyl-ethyl)amino)-6-(2,6-dichloro-3,5-di-methoxyphenyl)pyrido[3,4-d]pyrimi-din-2-yl)amino)tetrahydrofuran-3-yl)acrylamide | 573 |
| 601 | 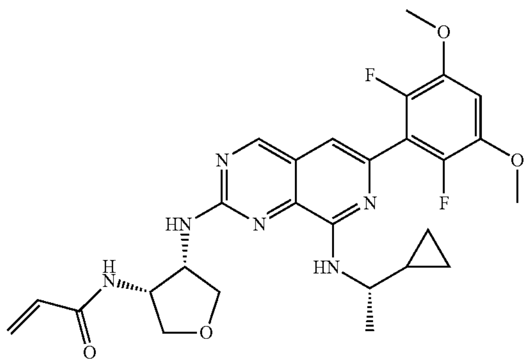 [SMILES: C=CC(=O)N[C@H]1COC[C@H]1Nc1ncc2cc(-c3c(F)c(OC)cc(OC)c3F)nc(N[C@@H](C)C3CC3)c2n1] | N-((3R,4S)-4-((8-(((S)-1-cyclopropyl-ethyl)amino)-6-(2,6-difluoro-3,5-di-methoxyphenyl)pyrido[3,4-d]pyrimi-din-2-yl)amino)tetrahydrofuran-3-yl)acrylamide | 541 |
| 602 | 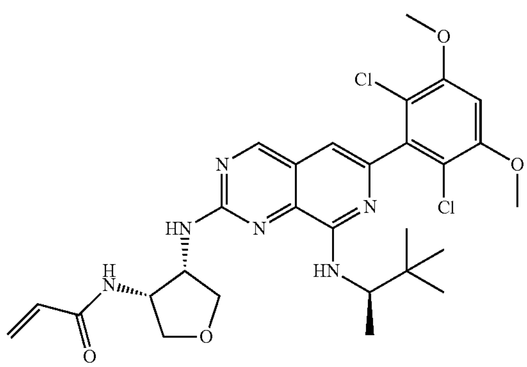 [SMILES: C=CC(=O)N[C@H]1COC[C@H]1Nc1ncc2cc(-c3c(Cl)c(OC)cc(OC)c3Cl)nc(N[C@H](C)C(C)(C)C)c2n1] | N-((3R,4S)-4-((6-(26-dichloro-3,5-di-methoxyphenyl)-8-(((R)-3,3-dimeth-ylbutan-2-yl)amino)pyrido[3,4-d]pyrimi-din-2-yl)amino)tetrahydrofuran-3-yl)acrylamide | 589 |
| 603 | 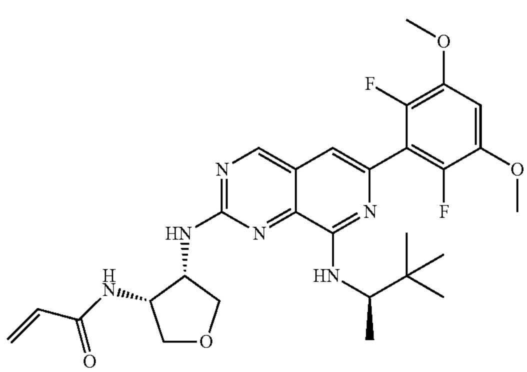 [SMILES: C=CC(=O)N[C@H]1COC[C@H]1Nc1ncc2cc(-c3c(F)c(OC)cc(OC)c3F)nc(N[C@H](C)C(C)(C)C)c2n1] | N-((3R,4S)-4-((6-(2,6-difluoro-3,5-di-methoxyphenyl)-8-(((R)-3,3-dimeth-ylbutan-2-yl)amino)pyrido[3,4-d]pyrimi-din-2-yl)amino)tetrahydrofuran-3-yl)acrylamide | 557 |

-continued

| Example No. | Compound structure | Compound name | MS: m/z [M + 1]+ |
|---|---|---|---|
| 604 | 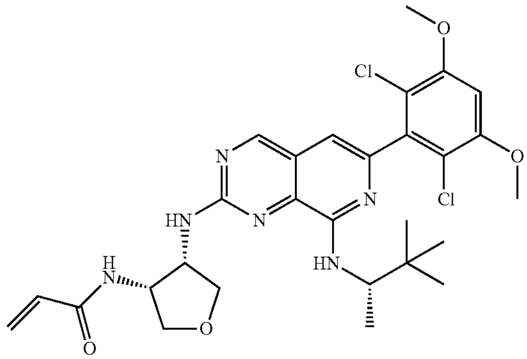 [SMILES: C=CC(=O)N[C@H]1COC[C@H]1Nc1ncc2cc(-c3c(Cl)c(OC)cc(OC)c3Cl)nc(N[C@@H](C)C(C)(C)C)c2n1] | N-((3R,4S)-4-((6-(2,6-dichloro-3,5-dimethoxyphenyl)-8-(((S)-3,3-dimethylbutan-2-yl)amino)pyrido[3,4-d]pyrimidin-2-yl)amino)tetrahydrofuran-3-yl)acrylamide | 589 |
| 605 | 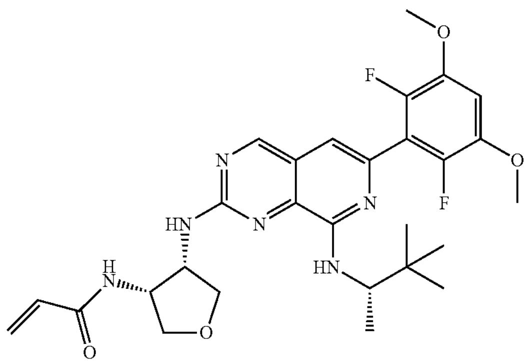 [SMILES: C=CC(=O)N[C@H]1COC[C@H]1Nc1ncc2cc(-c3c(F)c(OC)cc(OC)c3F)nc(N[C@@H](C)C(C)(C)C)c2n1] | N-((3R,4S)-4-((6-(2,6-difluoro-3,5-dimethoxyphenyl)-8-(((S)-3,3-dimethylbutan-2-yl)amino)pyrido[3,4-d]pyrimidin-2-yl)amino)tetrahydrofuran-3-yl)acrylamide | 557 |
| 606 | 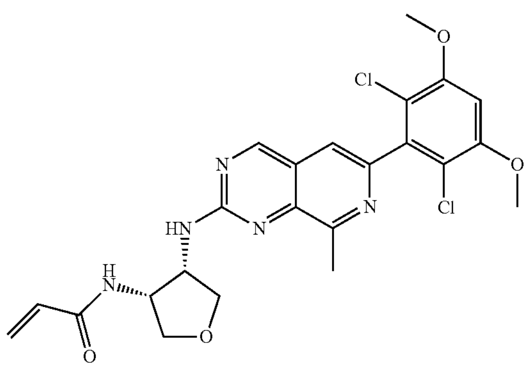 [SMILES: C=CC(=O)N[C@H]1COC[C@H]1Nc1ncc2cc(-c3c(Cl)c(OC)cc(OC)c3Cl)nc(C)c2n1] | N-((3R,4S)-4-((6-(2,6-dichloro-3,5-dimethoxyphenyl)-8-methylpyrido[3,4-d]pyrimidin-2-yl)amino)tetrahydrofuran-3-yl)acrylamide | 504 |
| 607 | 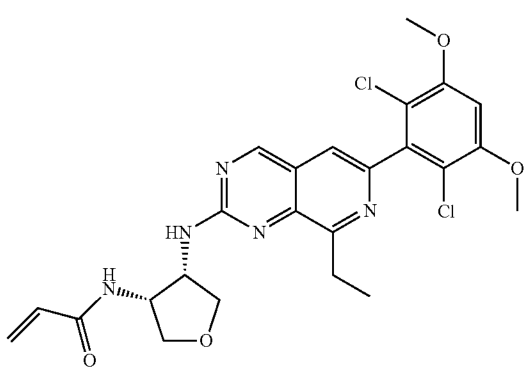 [SMILES: C=CC(=O)N[C@H]1COC[C@H]1Nc1ncc2cc(-c3c(Cl)c(OC)cc(OC)c3Cl)nc(CC)c2n1] | N-((3R,4)S-4-((6-(2,6-dichloro-3,5-dimethoxyphenyl)-8-ethylpyrido[3,4-d]pyrimidin-2-yl)amino)tetrahydrofuran-3-yl)acrylamide | 518 |

-continued

| Example No. | Compound structure | Compound name | MS: m/z [M + 1]+ |
|---|---|---|---|
| 608 | 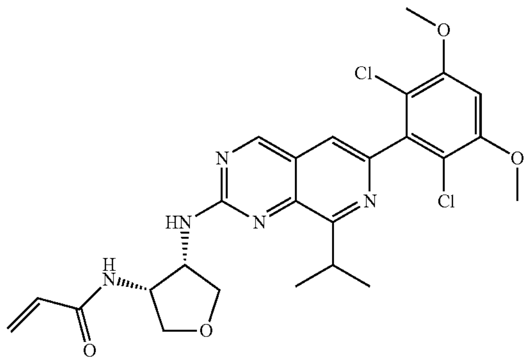 [SMILES: C=CC(=O)N[C@H]1COC[C@H]1Nc1ncc2cc(-c3c(Cl)c(OC)cc(OC)c3Cl)nc(C(C)C)c2n1] | N-((3R,4S)-4-((6-(2,6-dichloro-3,5-dimethoxyphenyl)-8-isopropylpyrido[3,4-d]pyrimidin-2-yl)amino)tetrahydrofuran-3-yl)acrylamide | 532 |
| 609 | 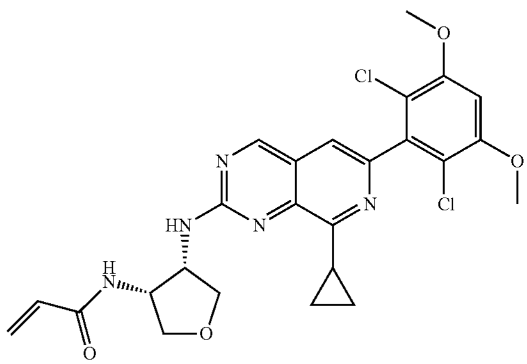 [SMILES: C=CC(=O)N[C@H]1COC[C@H]1Nc1ncc2cc(-c3c(Cl)c(OC)cc(OC)c3Cl)nc(C3CC3)c2n1] | N-((3R,4S)-4-((8-cyclopropyl-6-(2,6-dichloro-3,5-dimethoxyphenyl)pyrido[3,4-d]pyrimidin-2-yl)amino)tetrahydrofuran-3-yl)acrylamide | 530 |
| 610 | 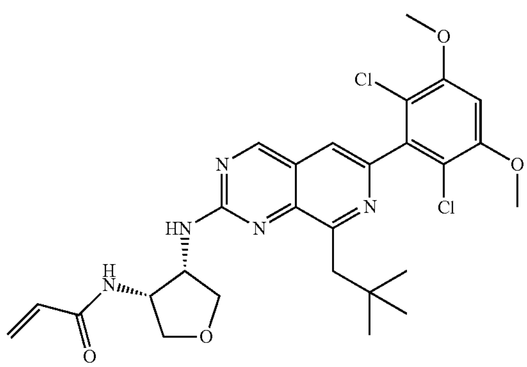 [SMILES: C=CC(=O)N[C@H]1COC[C@H]1Nc1ncc2cc(-c3c(Cl)c(OC)cc(OC)c3Cl)nc(CC(C)(C)C)c2n1] | N-((3R,4S)-4-((6-(2,6-dichloro-3,5-dimethoxyphenyl)-8-neopentylpyrido[3,4-d]pyrimidin-2-yl)amino)tetrahydrofuran-3-yl)acrylamide | 560 |
| 611 | 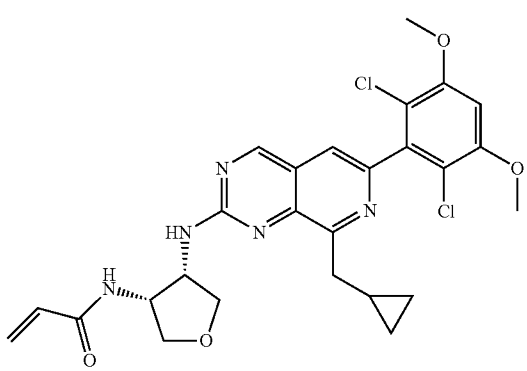 [SMILES: C=CC(=O)N[C@H]1COC[C@H]1Nc1ncc2cc(-c3c(Cl)c(OC)cc(OC)c3Cl)nc(CC3CC3)c2n1] | N-((3R,4S)-4-((8-(cyclopropylmethyl)-6-(2,6-dichloro-3,5-dimethoxyphenyl)pyrido[3,4-d]pyrimidin-2-yl)amino)tetrahydrofuran-3-yl)acrylamide | 544 |

| Example No. | Compound structure | Compound name | MS: m/z [M + 1]+ |
|---|---|---|---|
| 612 | 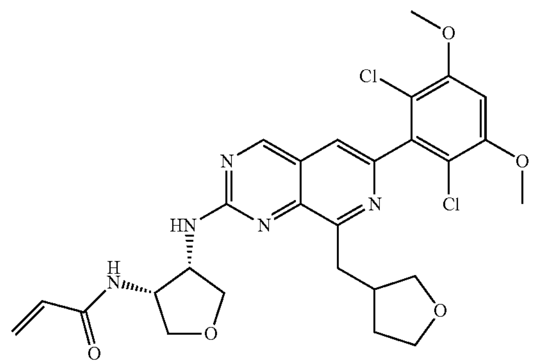 [SMILES: C=CC(=O)N[C@H]1COC[C@H]1Nc1ncc2cc(-c3c(Cl)c(OC)cc(OC)c3Cl)nc(CC3CCOC3)c2n1] | N-((3R,4S)-4-((6-(2,6-dichloro-3,5-dimethoxyphenyl)-8-((tetrahydrofuran-3-yl)methyl)pyrido[3,4-d]pyrimidin-2-yl)amino)tetrahydrofuran-3-yl)acrylamide | 574 |
| 613 | 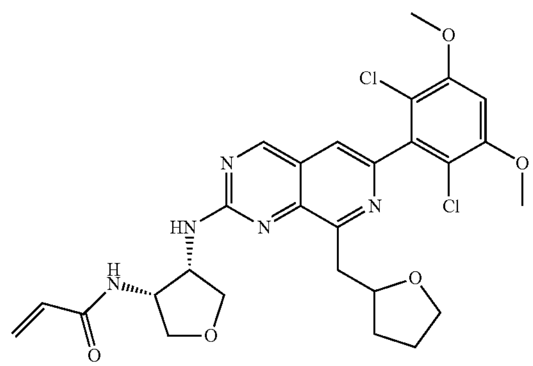 [SMILES: C=CC(=O)N[C@H]1COC[C@H]1Nc1ncc2cc(-c3c(Cl)c(OC)cc(OC)c3Cl)nc(CC3CCCO3)c2n1] | N-((3R,4S)-4-((6-(2,6-dichloro-3,5-dimethoxyphenyl)-8-((tetrahydrofuran-2-yl)methyl)pyrido[3,4-d]pyrimidin-2-yl)amino)tetrahydrofuran-3-yl)acrylamide | 574 |
| 614 | 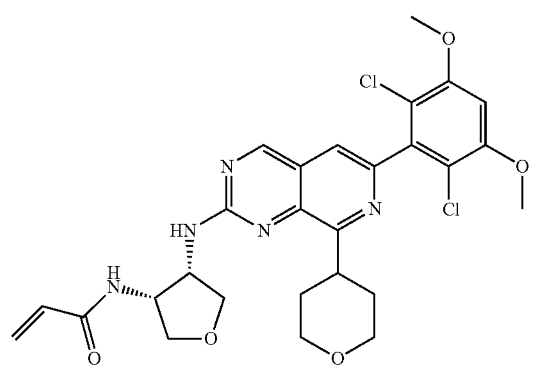 | N-((3R,4S)-4-((6-(2,6-dichloro-3,5-dimethoxyphenyl)-8-(tetrahydro-2H-pyran-4-yl)pyrido[3,4-d]pyrimidin-2-yl)amino)tetrahydrofuran-3-yl)acrylamide | 574 |
| 615 | 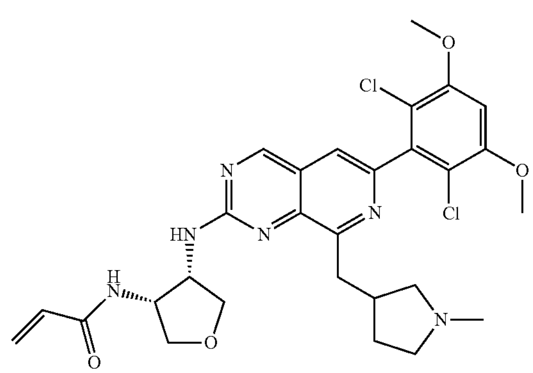 [SMILES: C=CC(=O)N[C@H]1COC[C@H]1Nc1ncc2cc(-c3c(Cl)c(OC)cc(OC)c3Cl)nc(CC3CCN(C)C3)c2n1] | N-((3R,4S)-4-((6-(2,6-dichloro-3,5-dimethoxyphenyl)-8-((1-methylpyrrolidin-3-yl)methyl)pyrido[3,4-d]pyrimidin-2-yl)amino)tetrahydrofuran-3-yl)acrylamide | 587 |

-continued

| Example No. | Compound structure | Compound name | MS: m/z [M + 1]+ |
|---|---|---|---|
| 616 | 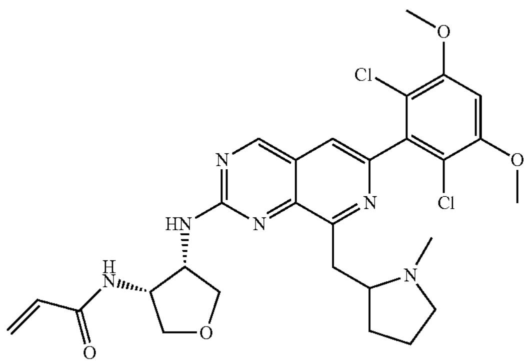 [SMILES: C=CC(=O)N[C@H]1COC[C@H]1Nc1ncc2cc(-c3c(Cl)c(OC)cc(OC)c3Cl)nc(CC3CCCN3C)c2n1] | N-((3R,4S)-4-((6-(2,6-dichloro-3,5-dimethoxyphenyl)-8-((1-methylpyrrolidin-2-yl)methyl)pyrido[3,4-d]pyrimidin-2-yl)amino)tetrahydrofuran-3-yl)acrylamide | 587 |
| 617 | 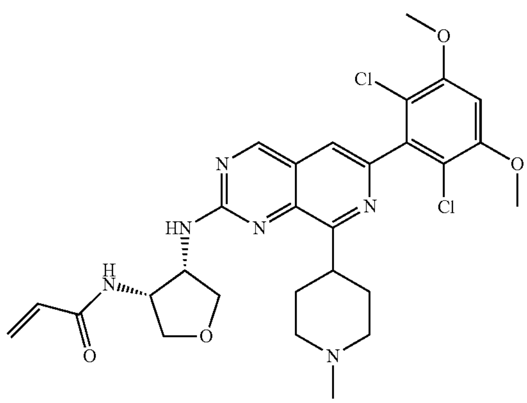 [SMILES: C=CC(=O)N[C@H]1COC[C@H]1Nc1ncc2cc(-c3c(Cl)c(OC)cc(OC)c3Cl)nc(C3CCN(C)CC3)c2n1] | N-((3R,4S)-4-((6-(2,6-dichloro-3,5-dimethoxyphenyl)-8-(1-methylpiperidin-4-yl)pyrido[3,4-d]pyrimidin-2-yl)amino)tetrahydrofuran-3-yl)acrylamide | 587 |
| 618 | 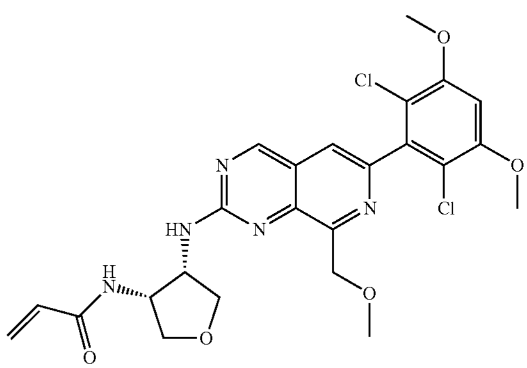 [SMILES: C=CC(=O)N[C@H]1COC[C@H]1Nc1ncc2cc(-c3c(Cl)c(OC)cc(OC)c3Cl)nc(COC)c2n1] | N-((3R,4S)-4-((6-(2,6-dichloro-3,5-dimethoxyphenyl)-8-(methoxymethyl)pyrido[3,4-d]pyrimidin-2-yl)amino)tetrahydrofuran-3-yl)acrylamide | 534 |
| 619 | 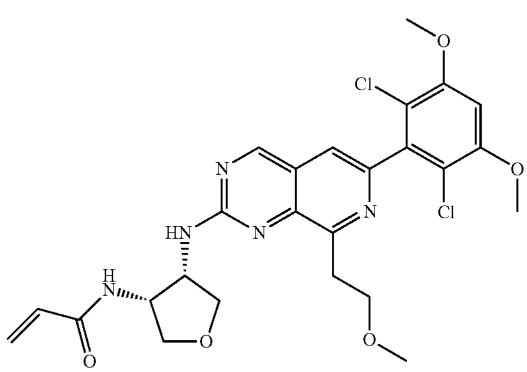 [SMILES: C=CC(=O)N[C@H]1COC[C@H]1Nc1ncc2cc(-c3c(Cl)c(OC)cc(OC)c3Cl)nc(CCOC)c2n1] | N-((3R,4S)-4-((6-(2,6-dichloro-3,5-dimethoxyphenyl)-8-(2-methoxyethyl)pyrido[3,4-d]pyrimidin-2-yl)amino)tetrahydrofuran-3-yl)acrylamide | 548 |

-continued

| Example No. | Compound structure | Compound name | MS: m/z [M + 1]+ |
|---|---|---|---|
| 620 | 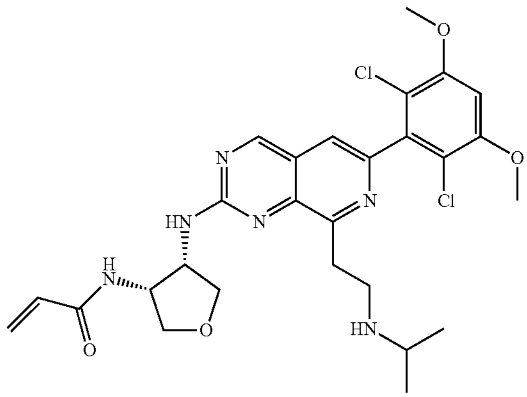 [SMILES: C=CC(=O)N[C@H]1COC[C@H]1Nc1ncc2cc(-c3c(Cl)c(OC)cc(OC)c3Cl)nc(CCNC(C)C)c2n1] | N-((3R,4S)-4-((6-(2,6-dichloro-3,5-dimethoxyphenyl)-8-(2-(isopropylamino)ethyl)pyrido[3,4-d]pyrimidin-2-yl)amino)tetrahydrofuran-3-yl)acrylamide | 575 |
| 621 | 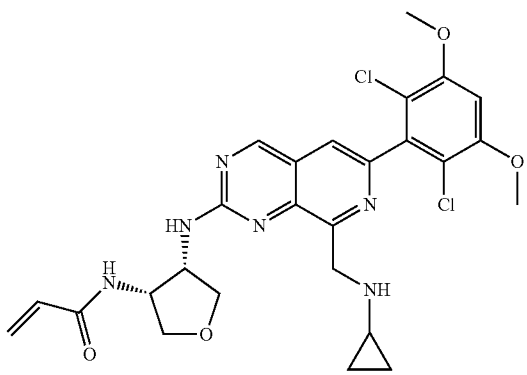 [SMILES: C=CC(=O)N[C@H]1COC[C@H]1Nc1ncc2cc(-c3c(Cl)c(OC)cc(OC)c3Cl)nc(CNC3CC3)c2n1] | N-((3R,4S)-4-((8-((cyclopropylamino)methyl)-6-(2,6-dichloro-3,5-dimethoxyphenyl)pyrido[3,4-d]pyrimidin-2-yl)amino)tetrahydrofuran-3-yl)acrylamide | 559 |
| 622 | 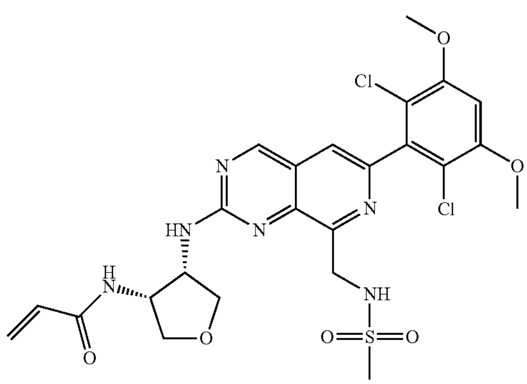 [SMILES: C=CC(=O)N[C@H]1COC[C@H]1Nc1ncc2cc(-c3c(Cl)c(OC)cc(OC)c3Cl)nc(CNS(C)(=O)=O)c2n1] | N-((3R,4S)-4-((6-(2,6-dichloro-3,5-dimethoxyphenyl)-8-(methylsulfonamidomethyl)pyrido[3,4-d]pyrimidin-2-yl)amino)tetrahydrofuran-3-yl)acrylamide | 597 |
| 623 | 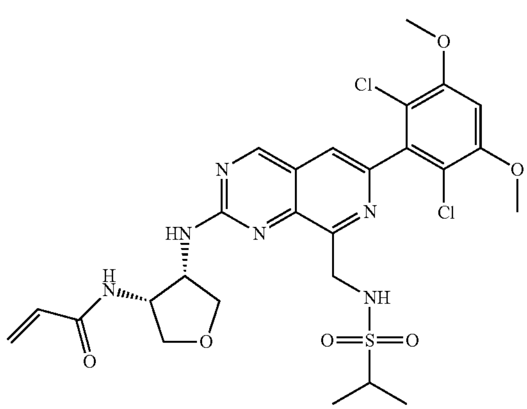 [SMILES: C=CC(=O)N[C@H]1COC[C@H]1Nc1ncc2cc(-c3c(Cl)c(OC)cc(OC)c3Cl)nc(CNS(=O)(=O)C(C)C)c2n1] | N-((3R,4S)-4-((6-(2,6-dichloro-3,5-dimethoxyphenyl)-8-(((1-methylethyl)sulfonamido)methyl)pyrido[3,4-d]pyrimidin-2-yl)amino)tetrahydrofuran-3-yl)acrylamide | 625 |

-continued

| Example No. | Compound structure | Compound name | MS: m/z [M + 1]+ |
|---|---|---|---|
| 624 | 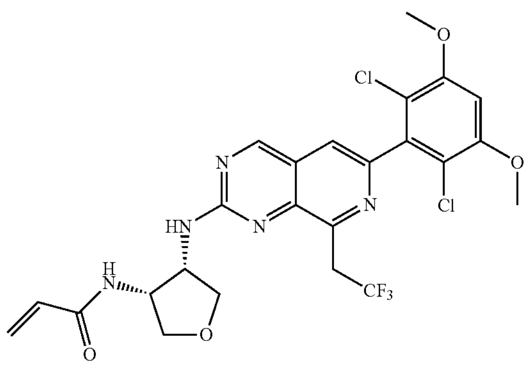 [SMILES: C=CC(=O)N[C@H]1COC[C@H]1Nc1ncc2cc(-c3c(Cl)c(OC)cc(OC)c3Cl)nc(CC(F)(F)F)c2n1] | N-((3R,4S)-4-((6-(2,6-dichloro-3,5-di-methoxyphenyl)-8-(2,2,2-trifluoroeth-yl)pyrido[3,4-d]pyrimidin-2-yl)ami-no)tetrahydrofuran-3-yl)acrylamide | 572 |
| 625 | 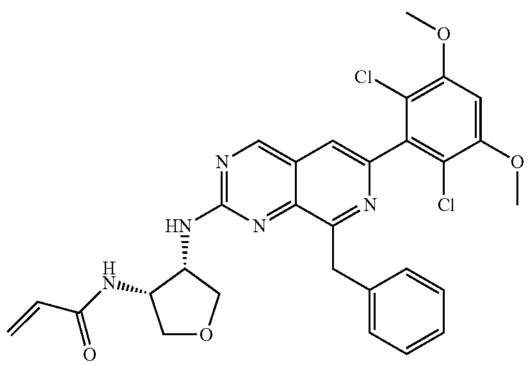 [SMILES: C=CC(=O)N[C@H]1COC[C@H]1Nc1ncc2cc(-c3c(Cl)c(OC)cc(OC)c3Cl)nc(Cc3ccccc3)c2n1] | N-((3R,4S)-4-((8-benzyl-6-(2,6-di-chloro-3,5-dimethoxyphenyl)pyrido[3,4-d]pyrimidin-2-yl)amino)tetrahydro-furan-3-yl)acrylamide | 580 |
| 626 | 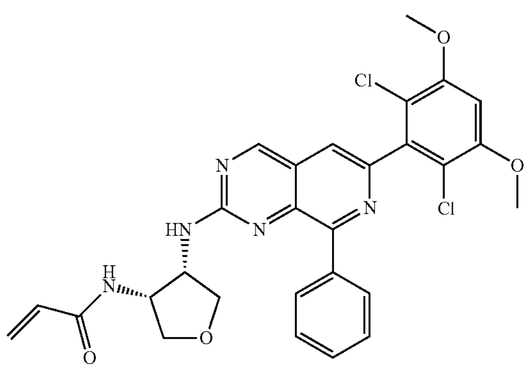 [SMILES: C=CC(=O)N[C@H]1COC[C@H]1Nc1ncc2cc(-c3c(Cl)c(OC)cc(OC)c3Cl)nc(-c3ccccc3)c2n1] | N-((3R,4S)-4-((6-(2,6-dichloro-3,5-di-methoxyphenyl)-8-phenylpyrido[3,4-d]pyrimidin-2-yl)amino)tetrahydro-furan-3-yl)acrylamide | 566 |
| 627 | 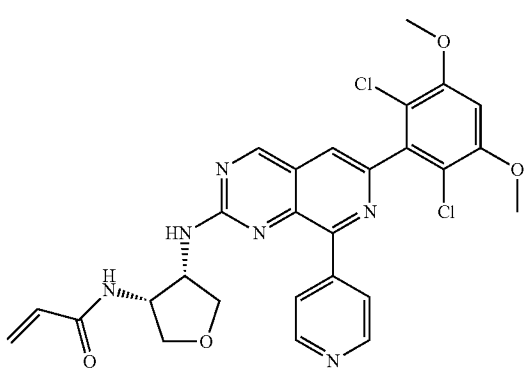 [SMILES: C=CC(=O)N[C@H]1COC[C@H]1Nc1ncc2cc(-c3c(Cl)c(OC)cc(OC)c3Cl)nc(-c3ccncc3)c2n1] | N-((3R,4S)-4-((6-(2,6-dichloro-3,5-di-methoxyphenyl)-8-(pyridin-4-yl)py-rido[3,4-d]pyrimidin-2-yl)amino)tetra-hydrofuran-3-yl)acrylamide | 567 |

-continued

| Example No. | Compound structure | Compound name | MS: m/z [M + 1]+ |
|---|---|---|---|
| 628 | 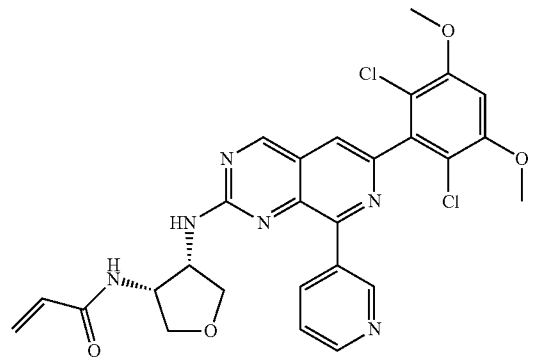 [SMILES: C=CC(=O)N[C@H]1COC[C@H]1Nc1ncc2cc(-c3c(Cl)c(OC)cc(OC)c3Cl)nc(-c3cccnc3)c2n1] | N-((3R,4S)-4-((6-(2,6-dichloro-3,5-dimethoxyphenyl)-8-(pyridin-3-yl)pyrido[3,4-d]pyrimidin-2-yl)amino)tetrahydrofuran-3-yl)acrylamide | 567 |
| 629 | 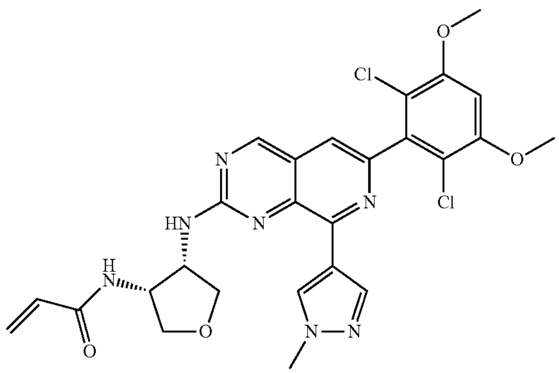 [SMILES: C=CC(=O)N[C@H]1COC[C@H]1Nc1ncc2cc(-c3c(Cl)c(OC)cc(OC)c3Cl)nc(-c3cnn(C)c3)c2n1] | N-((3R,4S)-4-((6-(2,6-dichloro-3,5-dimethoxyphenyl)-8-(1-methyl-1H-pyrazol-4-yl)pyrido[3,4-d]pyrimidin-2-yl)amino)tetrahydrofuran-3-yl)acrylamide | 570 |
| 630 | 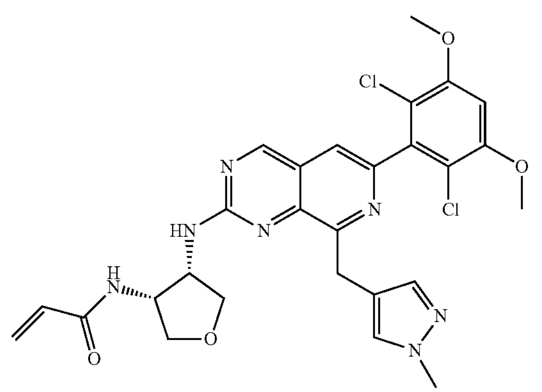 [SMILES: C=CC(=O)N[C@H]1COC[C@H]1Nc1ncc2cc(-c3c(Cl)c(OC)cc(OC)c3Cl)nc(Cc3cnn(C)c3)c2n1] | N-((3R,4S)-4-((6-(2,6-dichloro-3,5-dimethoxyphenyl)-8-((1-methyl-1H-pyrazol-4-yl)methyl)pyrido[3,4-d]pyrimidin-2-yl)amino)tetrahydrofuran-3-yl)acrylamide | 584 |
| 631 | 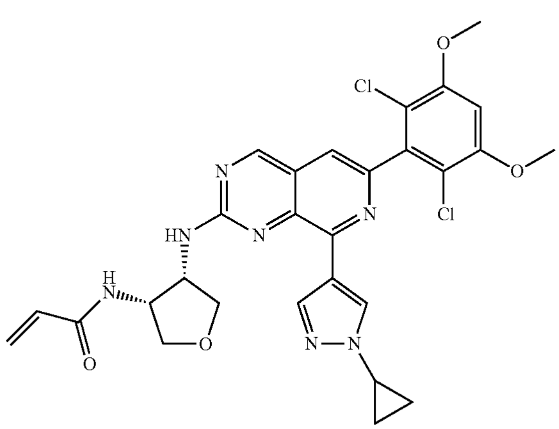 [SMILES: C=CC(=O)N[C@H]1COC[C@H]1Nc1ncc2cc(-c3c(Cl)c(OC)cc(OC)c3Cl)nc(-c3cnn(C4CC4)c3)c2n1] | N-((3R,4S)-4-((8-(1-cyclopropyl-1H-pyrazol-4-yl)-6-(2,6-dichloro-3,5-dimethoxyphenyl)pyrido[3,4-d]pyrimidin-2-yl)amino)tetrahydrofuran-3-yl)acrylamide | 596 |

-continued

| Example No. | Compound structure | Compound name | MS: m/z [M + 1]+ |
|---|---|---|---|
| 632 | 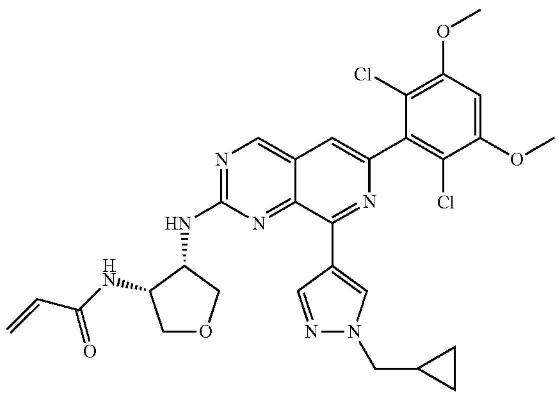 [SMILES: C=CC(=O)N[C@H]1COC[C@H]1Nc1ncc2cc(-c3c(Cl)c(OC)cc(OC)c3Cl)nc(-c3cnn(CC4CC4)c3)c2n1] | N-((3R,4S)-4-((8-(1-(cyclopropyl-methyl)-1H-pyrazol-4-yl)-6-(2,6-dichloro-3,5-dimethoxyphenyl)pyrido[3,4-d]pyrimidin-2-yl)amino)tetrahydro-furan-3-yl)acrylamide | 610 |
| 633 | 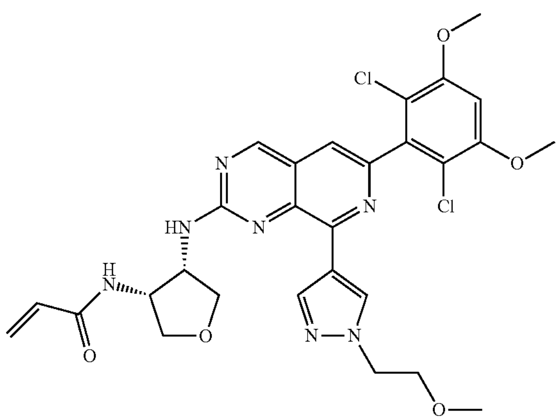 [SMILES: C=CC(=O)N[C@H]1COC[C@H]1Nc1ncc2cc(-c3c(Cl)c(OC)cc(OC)c3Cl)nc(-c3cnn(CCOC)c3)c2n1] | N-((3R,4S)-4-((6-(2,6-dichloro-3,5-dimethoxyphenyl)-8-(1-(2-methoxyeth-yl)-1H-pyrazol-4-yl)pyrido[3,4-d]py-rimidin-2-yl)amino)tetrahydro-furan-3-yl)acrylamide | 614 |
| 634 | 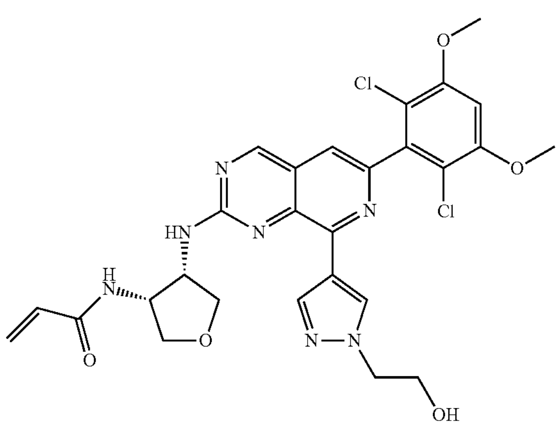 [SMILES: C=CC(=O)N[C@H]1COC[C@H]1Nc1ncc2cc(-c3c(Cl)c(OC)cc(OC)c3Cl)nc(-c3cnn(CCO)c3)c2n1] | N-((3R,4S)-4-((6-(2,6-dichloro-3,5-di-methoxyphenyl)-8-(1-(2-hydroxy-ethyl)-1H-pyrazol-4-yl)pyrido[3,4-d]py-rimidin-2-yl)amio)tetrahydro-furan-3-yl)acrylamide | 600 |

| Example No. | Compound structure | Compound name | MS: m/z [M + 1]+ |
| --- | --- | --- | --- |
| 635 | 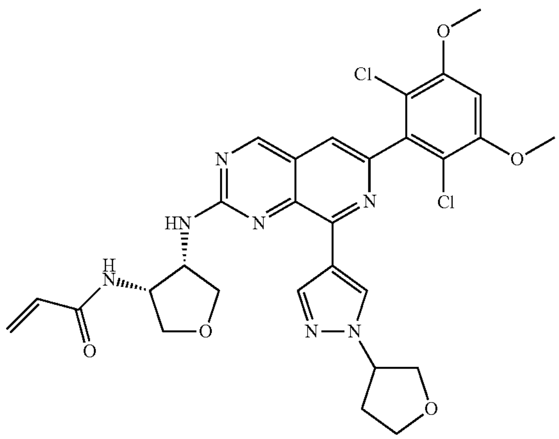 [SMILES: C=CC(=O)N[C@H]1COC[C@H]1Nc1ncc2cc(-c3c(Cl)c(OC)cc(OC)c3Cl)nc(-c3cnn(C4CCOC4)c3)c2n1] | N-((3R,4S)-4-((6-(2,6-dichloro-3,5-di-methoxphenyl)-8-(1-(tetrahydrofuran-3-yl)-1H-pyrazol-4-yl)pyrido[3,4-d]pyrimidin-2-yl)amino)tetrahydro-furan-3-yl)acrylamide | 626 |
| 636 | 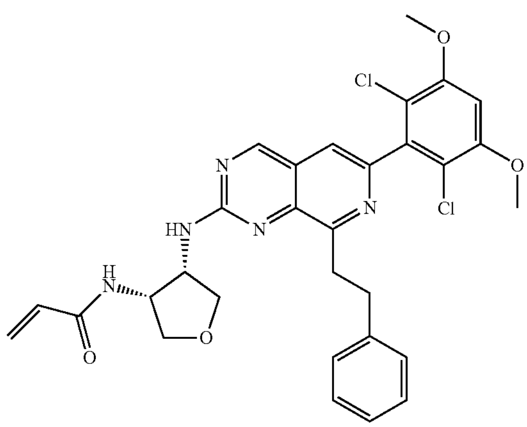 [SMILES: C=CC(=O)N[C@H]1COC[C@H]1Nc1ncc2cc(-c3c(Cl)c(OC)cc(OC)c3Cl)nc(CCc3ccccc3)c2n1] | N-((3R,4S)-4-((6-(2,6-dichloro-3,5-dimethoxyphenyl)-8-phenethylpyrido[3,4-d]pyrimidin-2-yl)amino)tetra-hydrofuran-3-yl)acrylamide | 594 |
| 637 | 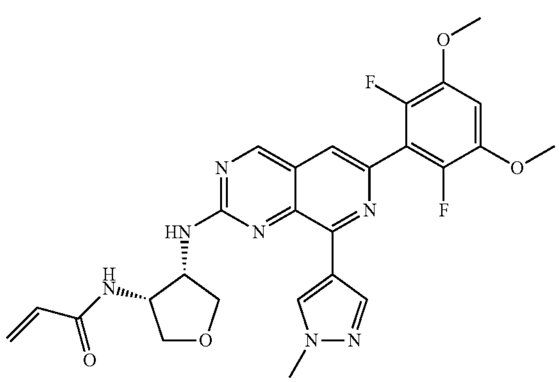 [SMILES: C=CC(=O)N[C@H]1COC[C@H]1Nc1ncc2cc(-c3c(F)c(OC)cc(OC)c3F)nc(-c3cnn(C)c3)c2n1] | N-((3R,4S)-4-((6-(2,6-difluoro-3,5-dimethoxyphenyl)-8-(1-methyl-1H-py-razol-4-yl)pyrido[3,4-d]pyrimidin-2-yl)amino)tetrahydrofuran-3-yl)acryl-amide | 538 |

-continued

| Example No. | Compound structure | Compound name | MS: m/z [M + 1]+ |
|---|---|---|---|
| 638 | 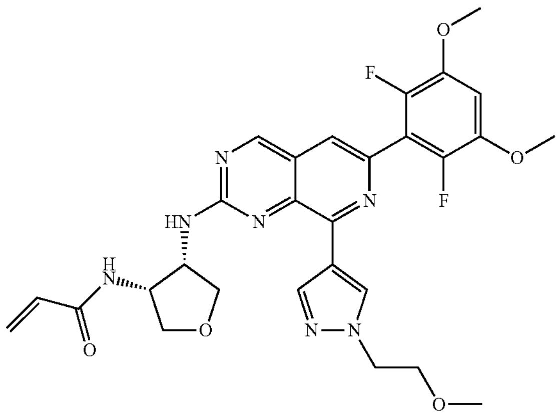 [SMILES: C=CC(=O)N[C@H]1COC[C@H]1Nc1ncc2cc(-c3c(F)c(OC)cc(OC)c3F)nc(-c3cnn(CCOC)c3)c2n1] | N-((3R,4S)-4-((6-(2,6-difluoro-3,5-dimethoxyphenyl)-8-(1-(2-methoxyethyl)-1H-pyrazol-4-yl)pyrido[3,4-d]pyrimidin-2-yl)amino)tetrahydrofuran-3-yl)acrylamide | 582 |
| 639 | 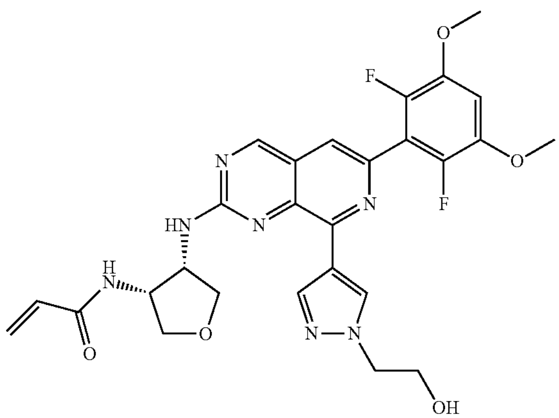 [SMILES: C=CC(=O)N[C@H]1COC[C@H]1Nc1ncc2cc(-c3c(F)c(OC)cc(OC)c3F)nc(-c3cnn(CCO)c3)c2n1] | N-((3R,4S)-4-((6-(2,6-difluoro-3,5-dimethoxyphenyl)-8-(1-(2-hydroxyethyl)-1H-pyrazol-4-yl)pyrido[3,4-d]pyrimidin-2-yl)amino)tetrahydrofuran-3-yl)acrylamide | 568 |
| 640 | 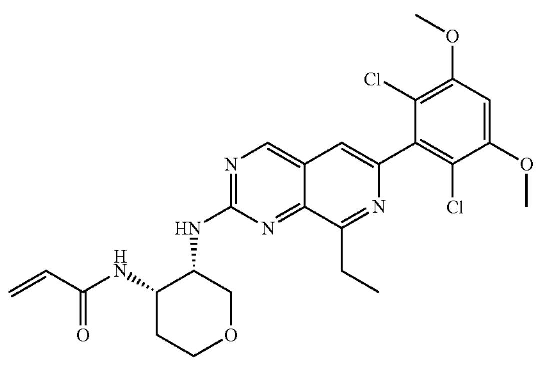 | N-((3S,4S)-3-((6-(2,6-dichloro-3,5-methoxyphenyl)-8-ethylpyrido[3,4-d]pyrimidin-2-yl)amino)tetrahydro-2H-pyran-4-yl)acrylamide | 532 |
| 641 | 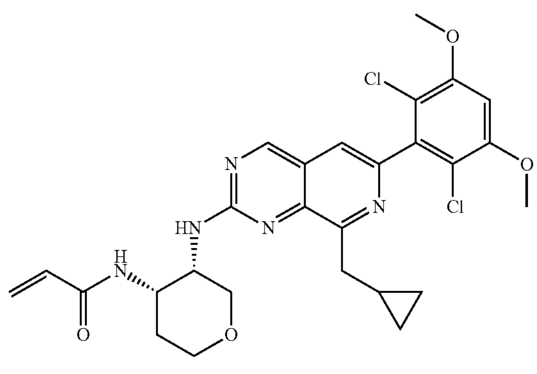 | N-((3S,4S)-3-((8-(cyclopropylmethyl)-6-(2,6-dichloro-3,5-dimethoxyphenyl)pyrido[3,4-d]pyrimidin-2-yl)amino)tetrahydro-2H-pyran-4-yl)acrylamide | 558 |

| Example No. | Compound structure | Compound name | MS: m/z [M + 1]+ |
|---|---|---|---|
| 642 | 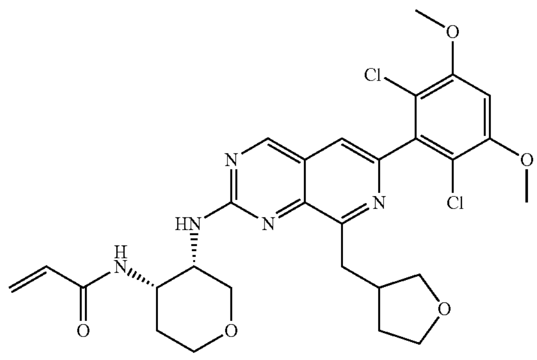 | N-((3S,4S)-3-((6-(2,6-dichloro-3,5-dimethoxyphenyl)-8-((tetrahydrofuran-3-yl)methyl)pyrido[3,4-d]pyrimidin-2-yl)amino)tetrahydro-2H-pyran-4-yl)acrylamide | 588 |
| 643 | 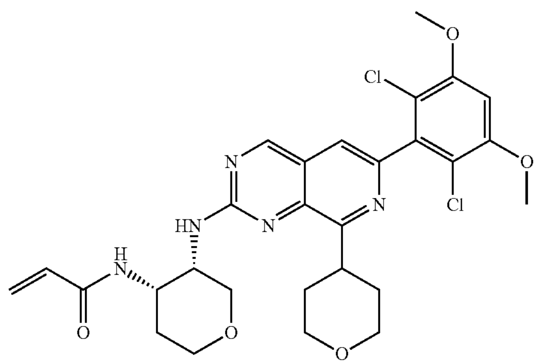 | N-((3S,4S)-3-((6-(2,6-dichloro-3,5-dimethoxyphenyl)-8-(tetrahydro-2H-pyran-4-yl)pyrido[3,4-d]pyrimidin-2-yl)amino)tetrahydro-2H-pyran-4-yl)acrylamide | 588 |
| 644 | 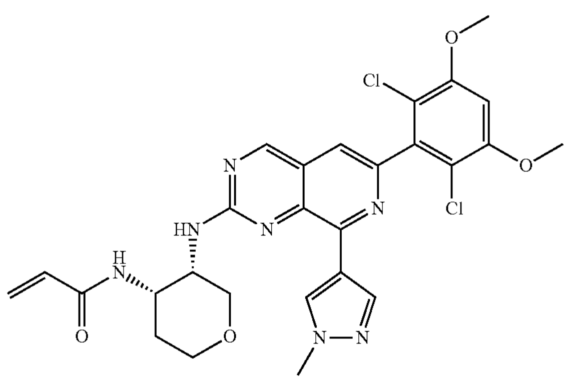 | N-((3S,4S)-3-((6-(2,6-dichloro-3,5-dimethoxyphenyl)-8-(1-methyl-1H-pyrazol-4-yl)pyrido[3,4-d]pyrimidin-2-yl)amino)tetrahydro-2H-pyran-4-yl)acrylamide | 584 |
| 645 | 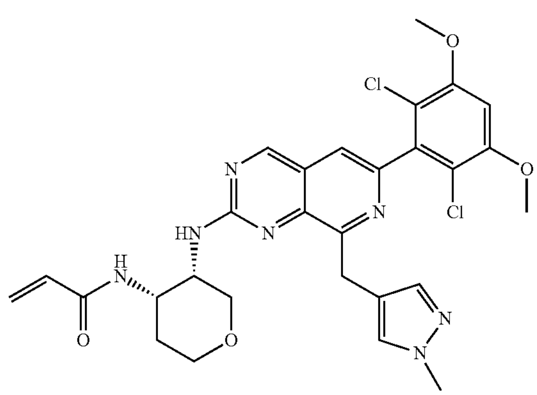 [SMILES: C=CC(=O)N[C@H]1CCOC[C@H]1Nc1ncc2cc(-c3c(Cl)c(OC)cc(OC)c3Cl)nc(Cc3cnn(C)c3)c2n1] | N-((3S,4S)-3-((6-(2,6-dichloro-3,5-dimethoxyphenyl)-8-((1-methyl-1H-pyrazol-4-yl)methyl)pyrido[3,4-d]pyrimidin-2-yl)amino)tetrahydro-2H-pyran-4-yl)acrylamide | 598 |

| Example No. | Compound structure | Compound name | MS: m/z [M + 1]+ |
|---|---|---|---|
| 646 | 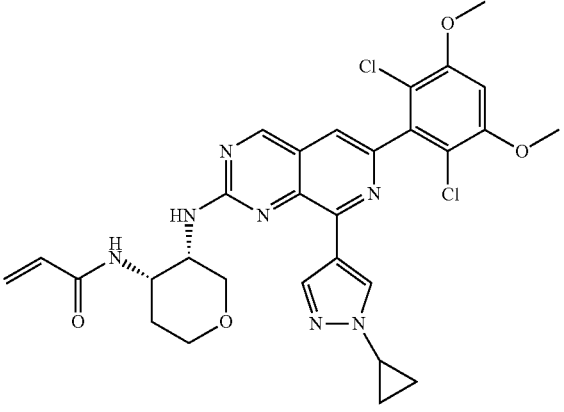 [SMILES: C=CC(=O)N[C@H]1CCOC[C@H]1Nc1ncc2cc(-c3c(Cl)c(OC)cc(OC)c3Cl)nc(-c3cnn(C4CC4)c3)c2n1] | N-((3S,4S)-3-((8-(1-cyclopropyl-1H-pyrazol-4-yl)-6-(2,6-dichloro-3,5-dimethoxyphenyl)pyrido[3,4-d]pyrimidin-2-yl)amino)tetrahydro-2H-pyran-4-yl)acrylamide | 610 |
| 647 | 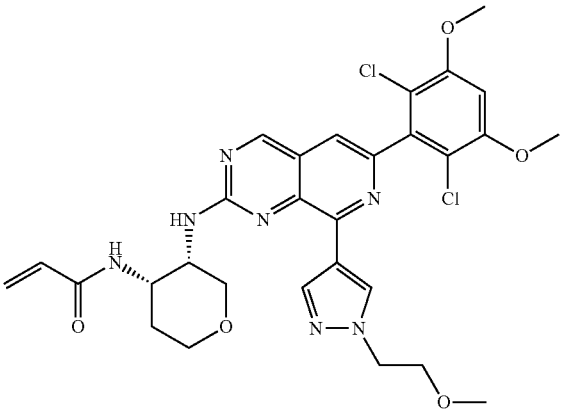 [SMILES: C=CC(=O)N[C@H]1CCOC[C@H]1Nc1ncc2cc(-c3c(Cl)c(OC)cc(OC)c3Cl)nc(-c3cnn(CCOC)c3)c2n1] | N-((3S,4S)-3-((6-(2,6-dichloro-3,5-dimethoxyphenyl)-8-(1-(2-methoxyethyl)-1H-pyrazol-4-yl)pyrido[3,4-d]pyrimidin-2-yl)amino)tetrahydro-2H-pyran-4-yl)acrylamide | 628 |
| 648 | 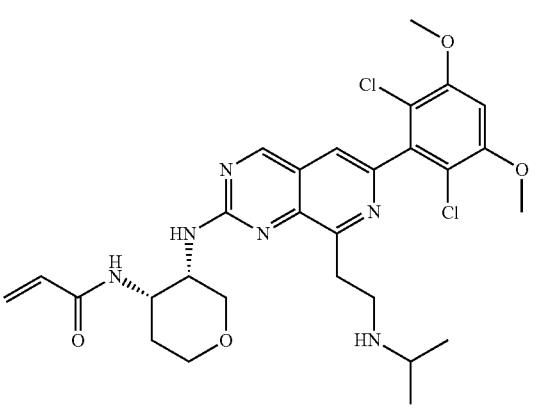 [SMILES: C=CC(=O)N[C@H]1CCOC[C@H]1Nc1ncc2cc(-c3c(Cl)c(OC)cc(OC)c3Cl)nc(CCNC(C)C)c2n1] | N-((3S,4S)-3-((6-(2,6-dichloro-3,5-dimethoxyphenyl)-8-(2-(isopropylamino)ethyl)pyrido[3,4-d]pyrimidin-2-yl)amino)tetrahydro-2H-pyran-4-yl)acrylamide | 589 |

-continued

| Example No. | Compound structure | Compound name | MS: m/z [M + 1]+ |
|---|---|---|---|
| 649 | 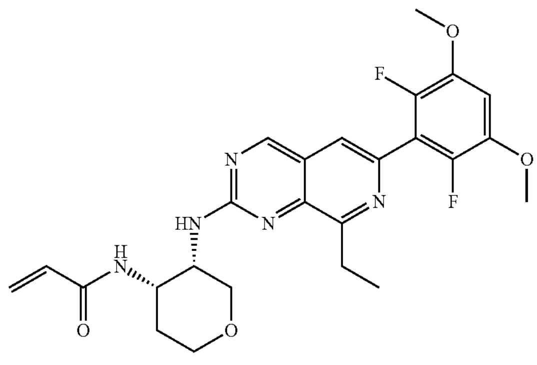 [SMILES: C=CC(=O)N[C@H]1CCOC[C@H]1Nc1ncc2cc(-c3c(F)c(OC)cc(OC)c3F)nc(CC)c2n1] | N-((3S,4S)-3-((6-(2,6-difluoro-3,5-dimethoxyphenyl)-8-ethylpyrido[3,4-d]pyrimidin-2-yl)amino)tetrahydro-2H-pyran-4-yl)acrylamide | 500 |
| 650 | 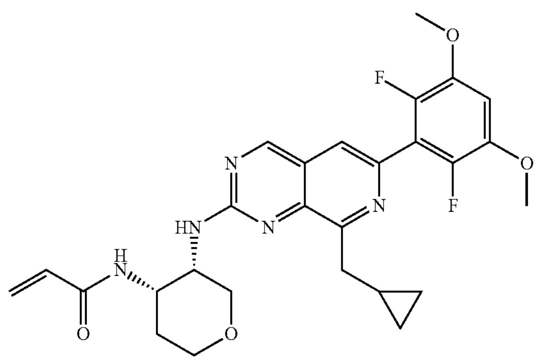 [SMILES: C=CC(=O)N[C@H]1CCOC[C@H]1Nc1ncc2cc(-c3c(F)c(OC)cc(OC)c3F)nc(CC3CC3)c2n1] | N-((3S,4S)-3-((8-(cyclopropylmethyl)-6-(2,6-difluoro-3,5-dimethoxyphenyl)pyrido[3,4-d]pyrimidin-2-yl)amino)tetrahydro-2H-pyran-4-yl)acrylamide | 526 |
| 651 | 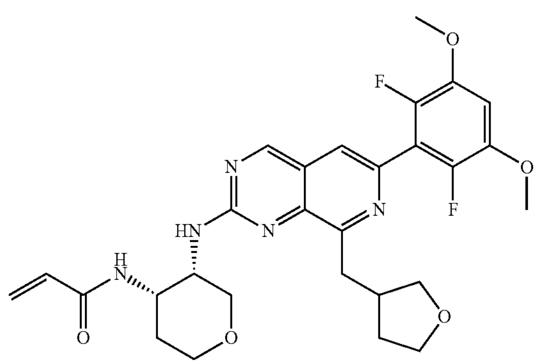 [SMILES: C=CC(=O)N[C@H]1CCOC[C@H]1Nc1ncc2cc(-c3c(F)c(OC)cc(OC)c3F)nc(CC3CCOC3)c2n1] | N-((3S,4S)-3-((6-(2,6-difluoro-3,5-dimethoxyphenyl)-8-((tetrahydrofuran-3-yl)methyl)pyrido[3,4-d]pyrimidin-2-yl)amino)tetrahydro-2H-pyran-4-yl)acrylamide | 556 |
| 652 | 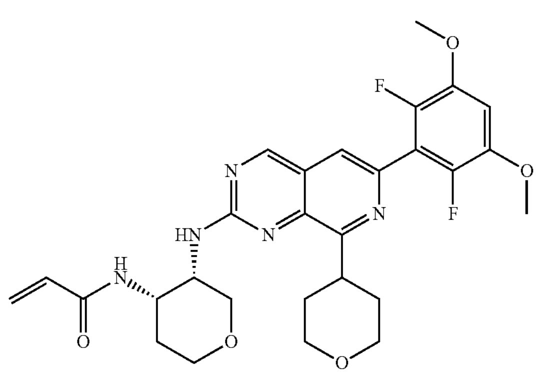 [SMILES: C=CC(=O)N[C@H]1CCOC[C@H]1Nc1ncc2cc(-c3c(F)c(OC)cc(OC)c3F)nc(C3CCOCC3)c2n1] | N-((3S,4S)-3-((6-(2,6-difluoro-3,5-dimethoxyphenyl)-8-(tetrahydro-2H-pyran-4-yl)pyrido[3,4-d]pyrimidin-2-yl)amino)tetrahydro-2H-pyran-4-yl)acrylamide | 556 |

-continued

| Example No. | Compound structure | Compound name | MS: m/z [M + 1]+ |
|---|---|---|---|
| 653 | 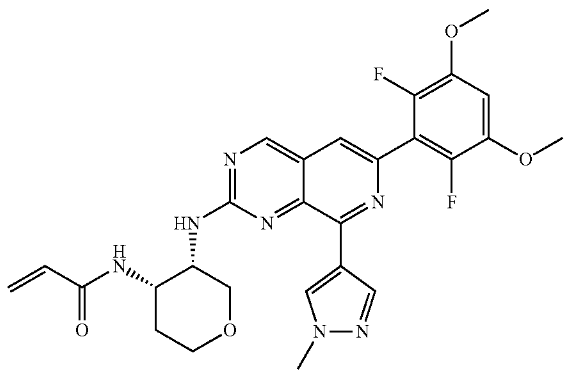 [SMILES: C=CC(=O)N[C@H]1CCOC[C@H]1Nc1ncc2cc(-c3c(F)c(OC)cc(OC)c3F)nc(-c3cnn(C)c3)c2n1] | N-((3S,4S)-3-((6-(2,6-difluoro-3,5-dimethoxypehnyl)-8-(1-methyl-1H-pyrazol-4-yl)pyrido[3,4-d]pyrimidin-2-yl)amino)tetrahydro-2H-pyran-4-yl)acrylamide | 552 |
| 654 | 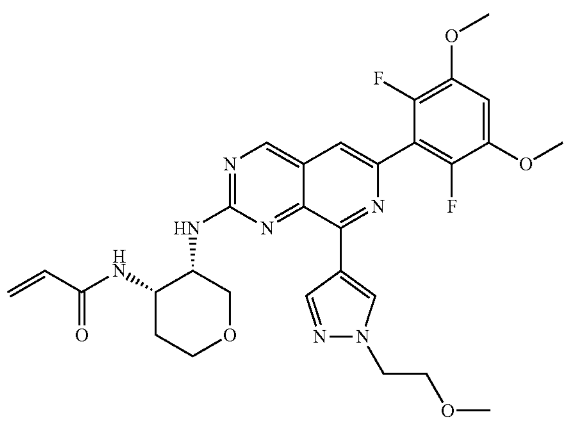 [SMILES: C=CC(=O)N[C@H]1CCOC[C@H]1Nc1ncc2cc(-c3c(F)c(OC)cc(OC)c3F)nc(-c3cnn(CCOC)c3)c2n1] | N-((3S,4S)-3-((6-(2,6-difluoro-3,5-dimethoxyphenyl)-8-(1-(2-methoxyethyl)-1H-pyrazol-4-yl)pyrido[3,4-d]pyrimidin-2-yl)amino)tetrahydro-2H-pyran-4-yl)acrylamide | 596 |
| 655 | 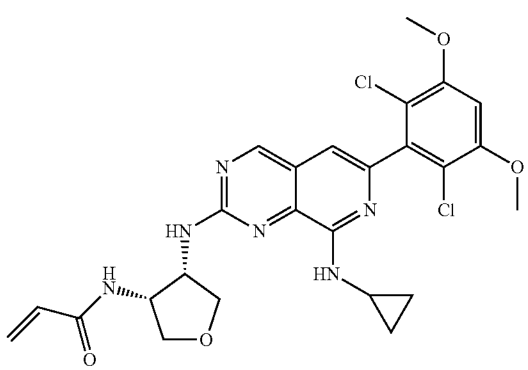 | N-((3R,4S)-4-((8-(cyclopropylamino)-6-(2,6-dichloro-3,5-dimethoxyphenyl)pyrido[3,4-d]pyrimidin-2-yl)amino)tetrahydrofuran-3-yl)acrylamide | 545 |
| 656 | 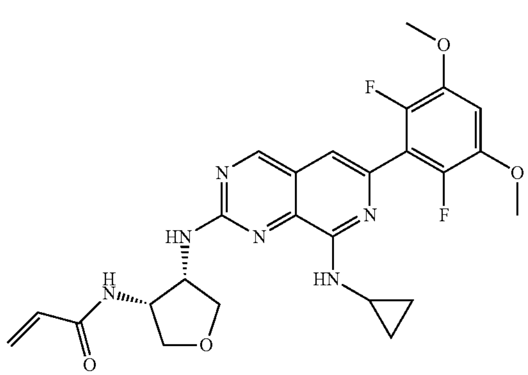 [SMILES: C=CC(=O)N[C@H]1COC[C@H]1Nc1ncc2cc(-c3c(F)c(OC)cc(OC)c3F)nc(NC3CC3)c2n1] | N-((3R,4S)-4-((8-(cyclopropylamino)-6-(2,6-difluoro-3,5-dimethoxyphenyl)pyrido[3,4-d]pyrimidin-2-yl)amino)tetrahydrofuran-3-yl)acrylamide | 513 |

| Example No. | Compound structure | Compound name | MS: m/z [M + 1]+ |
|---|---|---|---|
| 657 | 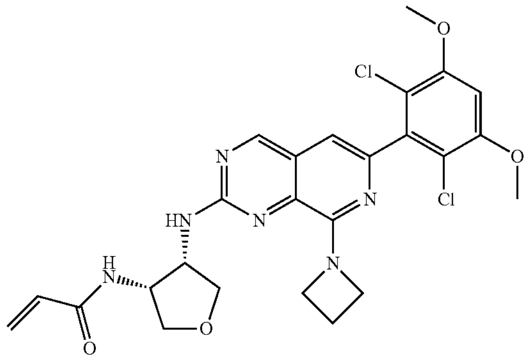 [SMILES: C=CC(=O)N[C@H]1COC[C@H]1Nc1ncc2cc(-c3c(Cl)c(OC)cc(OC)c3Cl)nc(N3CCC3)c2n1] | N-((3R,4S)-4-((8-(azetidin-1-yl)-6-(2,6-dichloro-3,5-dimethoxyphenyl)pyrido[3,4-d]pyrimidin-2-yl)amino)tetrahydrofuran-3-yl)acrylamide | 545 |
| 658 | 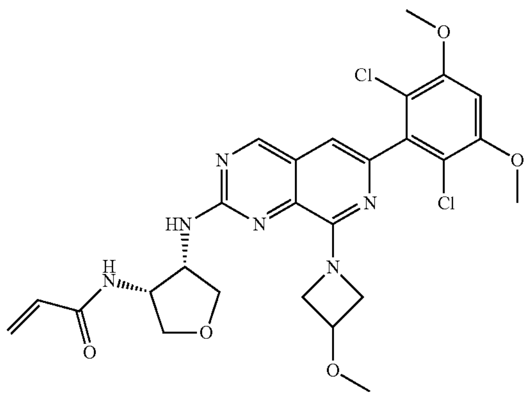 [SMILES: C=CC(=O)N[C@H]1COC[C@H]1Nc1ncc2cc(-c3c(Cl)c(OC)cc(OC)c3Cl)nc(N3CC(OC)C3)c2n1] | N-((3R,4S)-4-((6-(2,6-dichloro-3,5-dimethoxyphenyl)-8-(3-methoxyazetidin-1-yl)pyrido[3,4-d]pyrimidin-2-yl)amino)tetrahydrofuran-3-yl)acrylamide | 575 |
| 659 | 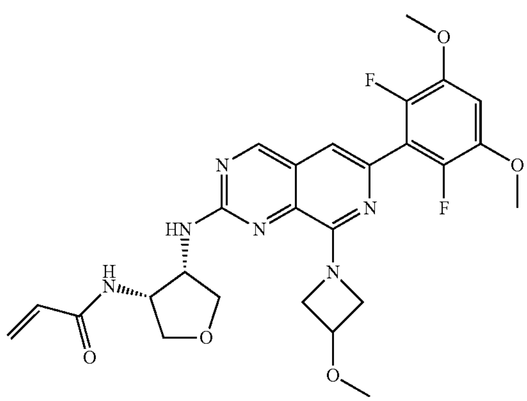 [SMILES: C=CC(=O)N[C@H]1COC[C@H]1Nc1ncc2cc(-c3c(F)c(OC)cc(OC)c3F)nc(N3CC(OC)C3)c2n1] | N-((3R,4S)-4-((6-(2,6-difluoro-3,5-dimethoxyphenyl)-8-(3-methoxyazetidin-1-yl)pyrido[3,4-d]pyrimidin-2-yl)amino)tetrahydrofuran-3-yl)acrylamide | 543 |
| 660 | 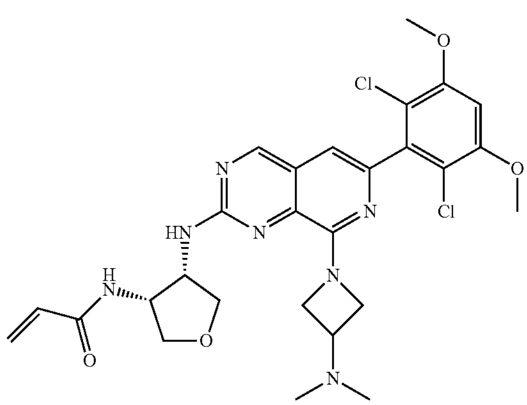 [SMILES: C=CC(=O)N[C@H]1COC[C@H]1Nc1ncc2cc(-c3c(Cl)c(OC)cc(OC)c3Cl)nc(N3CC(N(C)C)C3)c2n1] | N-((3R,4S)-4-((6-(2,6-dichloro-3,5-dimethoxyphenyl)-8-(3-(dimethylamino)azetidin-1-yl)pyrido[3,4-d]pyrimidin-2-yl)amino)tetrahydrofuran-3-yl)acrylamide | 588 |

-continued

| Example No. | Compound structure | Compound name | MS: m/z [M + 1]+ |
|---|---|---|---|
| 661 | 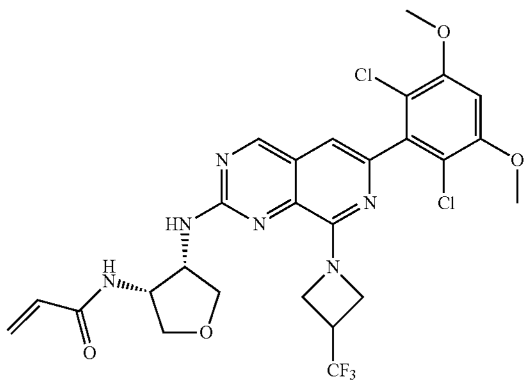 | N-((3R,4S)-4-((6-(2,6-dichloro-3,5-dimethoxyphenyl)-8-(3-(trifluoromethyl)azetidin-1-yl)pyrido[3,4-d]pyrimidin-2-yl)amino)tetrahydrofuran-3-yl)acrylamide | 613 |
| 662 | 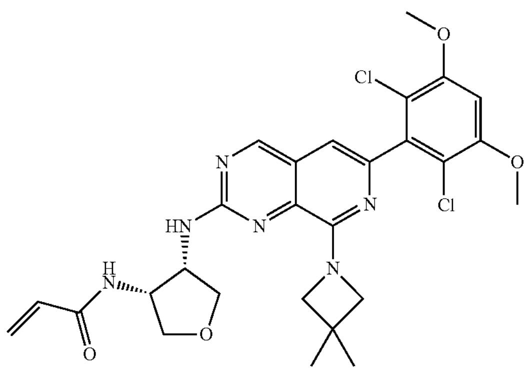 [SMILES: C=CC(=O)N[C@H]1COC[C@H]1Nc1ncc2cc(-c3c(Cl)c(OC)cc(OC)c3Cl)nc(N3CC(C)(C)C3)c2n1] | N-((3R,4S)-4-((6-(2,6-dichloro-3,5-dimethoxyphenyl)-8-(3,3-dimethylazetidin-1-yl)pyrido[3,4-d]pyrimidin-2-yl)amino)tetrahydrofuran-3-yl)acrylamide | 573 |
| 663 | 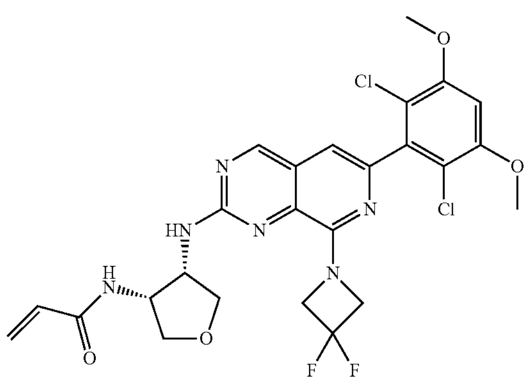 | N-((3R,4S)-4-((6-(2,6-dichloro-3,5-dimethoxyphenyl)-8-(3,3-difluoroazetidin-1-yl)pyrido[3,4-d]pyrimidin-2-yl)amino)tetrahydrofuran-3-yl)acrylamide | 581 |
| 664 | 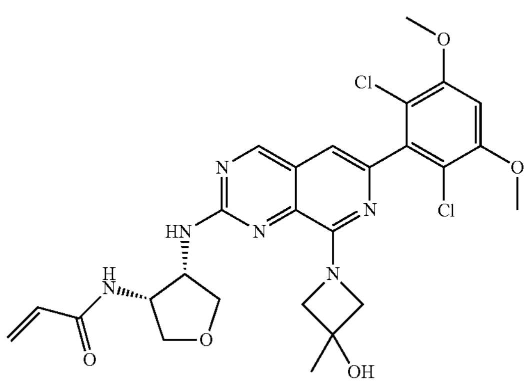 [SMILES: C=CC(=O)N[C@H]1COC[C@H]1Nc1ncc2cc(-c3c(Cl)c(OC)cc(OC)c3Cl)nc(N3CC(C)(O)C3)c2n1] | N-((3R,4S)-4-((6-(2,6-dichloro-3,5-dimethoxyphenyl)-8-(3-hydroxy-3-methylazetidin-1-yl)pyrido[3,4-d]pyrimidin-2-yl)amino)tetrahydrofuran-3-yl)acrylamide | 575 |

-continued

| Example No. | Compound structure | Compound name | MS: m/z [M + 1]+ |
| --- | --- | --- | --- |
| 665 | 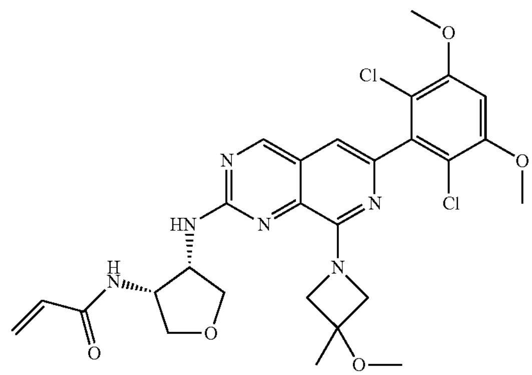 [SMILES: C=CC(=O)N[C@H]1COC[C@H]1Nc1ncc2cc(-c3c(Cl)c(OC)cc(OC)c3Cl)nc(N3CC(C)(OC)C3)c2n1] | N-((3R,4S)-4-((6-(2,6-dichloro-3,5-dimethoxyphenyl)-8-(3-methoxy-3-methylazetidin-1-yl)pyrido[3,4-d]pyrimidin-2-yl)amino)tetrahydrofuran-3-yl)acrylamide | 589 |
| 666 | 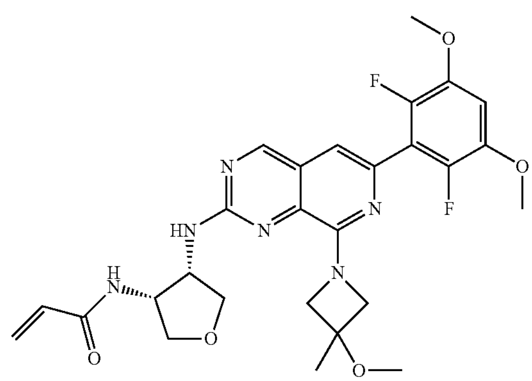 [SMILES: C=CC(=O)N[C@H]1COC[C@H]1Nc1ncc2cc(-c3c(F)c(OC)cc(OC)c3F)nc(N3CC(C)(OC)C3)c2n1] | N-((3R,4S)-4-((6-(2,6-difluoro-3,5-dimethoxyphenyl)-8-(3-methoxy-3-methylazetidin-1-yl)pyrido[3,4-d]pyrimidin-2-yl)amino)tetrahydrofuran-3-yl)acrylamide | 557 |
| 667 | 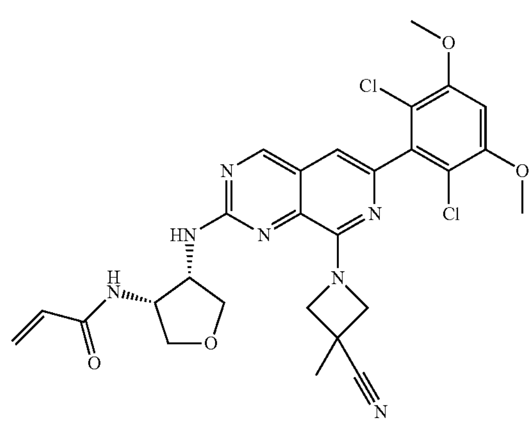 [SMILES: C=CC(=O)N[C@H]1COC[C@H]1Nc1ncc2cc(-c3c(Cl)c(OC)cc(OC)c3Cl)nc(N3CC(C)(C#N)C3)c2n1] | N-((3R,4S)-4-((8-(3-cyano-3-methylazetidin-1-yl)-6-(2,6-dichloro-3,5-dimethoxyphenyl)pyrido[3,4-d]pyrimidin-2-yl)amino)tetrahydrofuran-3-yl)acrylamide | 584 |

-continued

| Example No. | Compound structure | Compound name | MS: m/z [M + 1]+ |
|---|---|---|---|
| 668 | 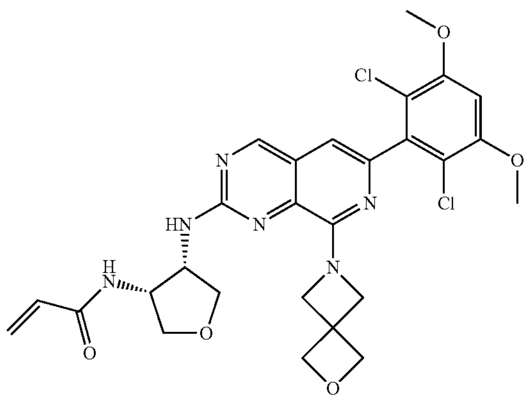 [SMILES: C=CC(=O)N[C@H]1COC[C@H]1Nc1ncc2cc(-c3c(Cl)c(OC)cc(OC)c3Cl)nc(N3CC4(COC4)C3)c2n1] | N-((3R,4S)-4-((6-(2,6-dichloro-3,5-dimethoxyphenyl)-8-(2-oxa-6-azaspiro[3.3]heptan-6-yl)pyrido[3,4-d]pyrimidin-2-yl)amino)tetrahydrofuran-3-yl)acrylamide | 587 |
| 669 | 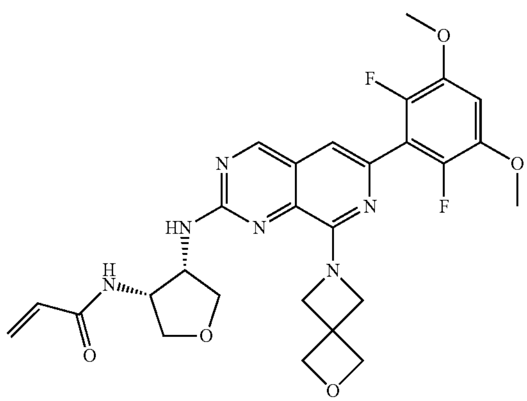 [SMILES: C=CC(=O)N[C@H]1COC[C@H]1Nc1ncc2cc(-c3c(F)c(OC)cc(OC)c3F)nc(N3CC4(COC4)C3)c2n1] | N-((3R,4S)-4-((6-(2,6-difluoro-3,5-dimethoxyphenyl)-8-(2-oxa-6-azaspiro[3.3]heptan-6-yl)pyrido[3,4-d]pyrimidin-2-yl)amino)tetrahydrofuran-3-yl)acrylamide | 555 |
| 670 | 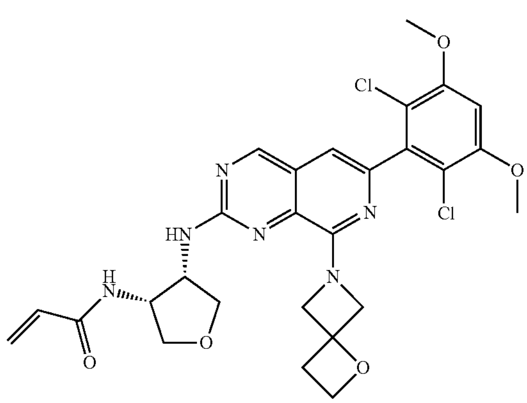 [SMILES: C=CC(=O)N[C@H]1COC[C@H]1Nc1ncc2cc(-c3c(Cl)c(OC)cc(OC)c3Cl)nc(N3CC4(CCO4)C3)c2n1] | N-((3R,4S)-4-((6-(2,6-dichloro-3,5-dimethoxyphenyl)-8-(1-oxa-6-azaspiro[3.3]heptan-6-yl)pyrido[3,4-d]pyrimidin-2-yl)amino)tetrahydrofuran-3-yl)acrylamide | 587 |

-continued

| Example No. | Compound structure | Compound name | MS: m/z [M + 1]+ |
| --- | --- | --- | --- |
| 671 | 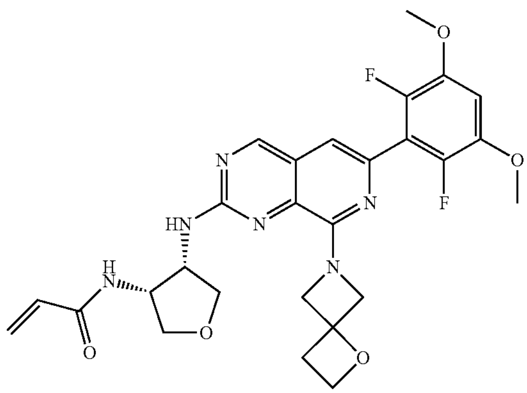 [SMILES: C=CC(=O)N[C@H]1COC[C@H]1Nc1ncc2cc(-c3c(F)c(OC)cc(OC)c3F)nc(N3CC4(CCO4)C3)c2n1] | N-((3R,4S)-4-((6-(2,6-difluoro-3,5-dimethoxyphenyl)-8-(1-oxa-6-azaspiro[3.3]heptan-6-yl)pyrido[3,4-d]pyrimidin-2-yl)amino)tetrahydrofuran-3-yl)acrylamide | 555 |
| 672 | 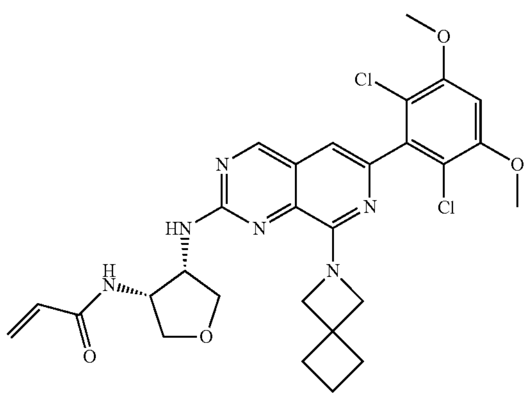 [SMILES: C=CC(=O)N[C@H]1COC[C@H]1Nc1ncc2cc(-c3c(Cl)c(OC)cc(OC)c3Cl)nc(N3CC4(CCC4)C3)c2n1] | N-((3R,4S)-4-((6-(2,6-dichloro-3,5-dimethoxyphenyl)-8-(2-azaspiro[3.3]heptan-2-yl)pyrido[3,4-d]pyrimidin-2-yl)amino)tetrahydrofuran-3-yl)acrylamide | 585 |
| 673 | 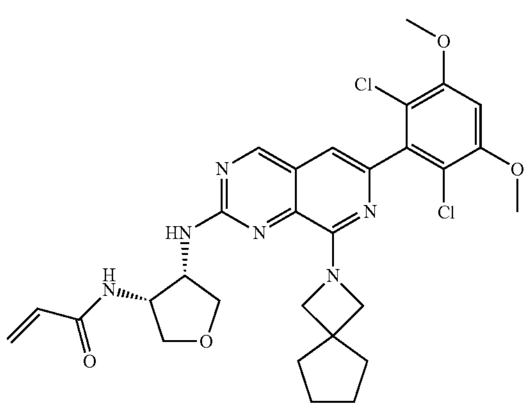 [SMILES: C=CC(=O)N[C@H]1COC[C@H]1Nc1ncc2cc(-c3c(Cl)c(OC)cc(OC)c3Cl)nc(N3CC4(CCCC4)C3)c2n1] | N-((3R,4S)-4-((6-(2,6-dichloro-3,5-dimethoxyphenyl)-8-(2-azaspiro[3.4]octan-2-yl)pyrido[3,4-d]pyrimidin-2-yl)amino)tetrahydrofuran-3-yl)acrylamide | 599 |

-continued

| Example No. | Compound structure | Compound name | MS: m/z [M + 1]+ |
| --- | --- | --- | --- |
| 674 | 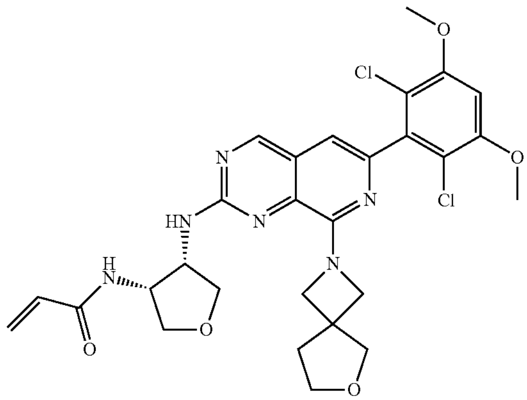 [SMILES: C=CC(=O)N[C@H]1COC[C@H]1Nc1ncc2cc(-c3c(Cl)c(OC)cc(OC)c3Cl)nc(N3CC4(CCOC4)C3)c2n1] | N-((3R,4S)-4-((6-(2,6-dichloro-3,5-dimethoxyphenyl)-8-(6-oxa-2-azaspiro[3.4]octan-2-yl)pyrido[3,4-d]pyrimidin-2-yl)amino)tetrahydrofuran-3-yl)acrylamide | 601 |
| 675 | 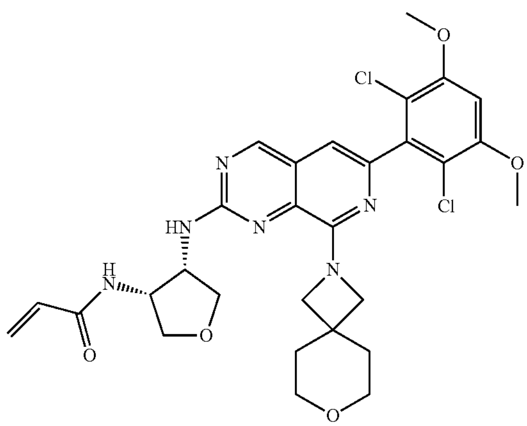 [SMILES: C=CC(=O)N[C@H]1COC[C@H]1Nc1ncc2cc(-c3c(Cl)c(OC)cc(OC)c3Cl)nc(N3CC4(CCOCC4)C3)c2n1] | N-((3R,4S)-4-((6-(2,6-dichloro-3,5-dimethoxyphenyl)-8-(7-oxa-2-azaspiro[3.5]nonan-2-yl)pyrido[3,4-d]pyrimidin-2-yl)amino)tetrahydrofuran-3-yl)acrylamide | 615 |
| 676 | 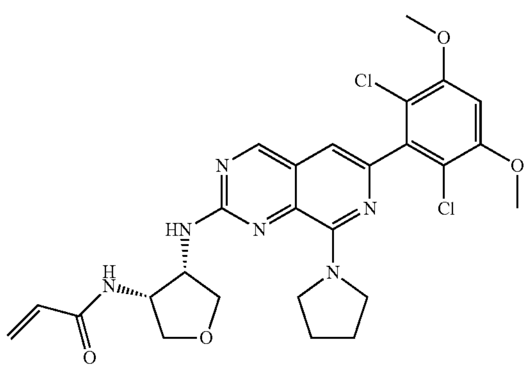 [SMILES: C=CC(=O)N[C@H]1COC[C@H]1Nc1ncc2cc(-c3c(Cl)c(OC)cc(OC)c3Cl)nc(N3CCCC3)c2n1] | N-((3R,4S)-4-((6-(2,6-dichloro-3,5-dimethoxyphenyl)-8-(pyrrolidin-1-yl)pyrido[3,4-d]pyrimidin-2-yl)amino)tetrahydrofuran-3-yl)acrylamide | 559 |

-continued

| Example No. | Compound structure | Compound name | MS: m/z [M + 1]+ |
|---|---|---|---|
| 677 | 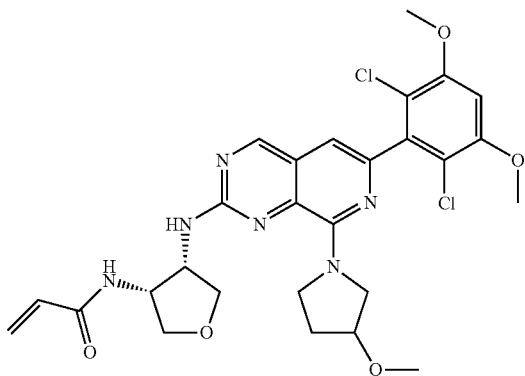 [SMILES: C=CC(=O)N[C@H]1COC[C@H]1Nc1ncc2cc(-c3c(Cl)c(OC)cc(OC)c3Cl)nc(N3CCC(OC)C3)c2n1] | N-((3R,4S)-4-((6-(2,6-dichloro-3,5-dimethoxyphenyl)-8-(3-methoxypyrrolidin-1-yl)pyrido[3,4-d]pyrimidin-2-yl)amino)tetrahydrofuran-3-yl)acrylamide | 589 |
| 678 | 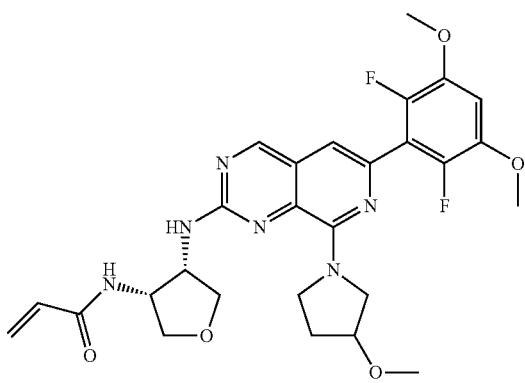 [SMILES: C=CC(=O)N[C@H]1COC[C@H]1Nc1ncc2cc(-c3c(F)c(OC)cc(OC)c3F)nc(N3CCC(OC)C3)c2n1] | N-((3R,4S)-4-((6-(2,6-difluoro-3,5-dimethoxyphenyl)-8-(3-methoxypyrrolidin-1-yl)pyrido[3,4-d]pyrimidin-2-yl)amino)tetrahydrofuran-3-yl)acrylamide | 557 |
| 679 | 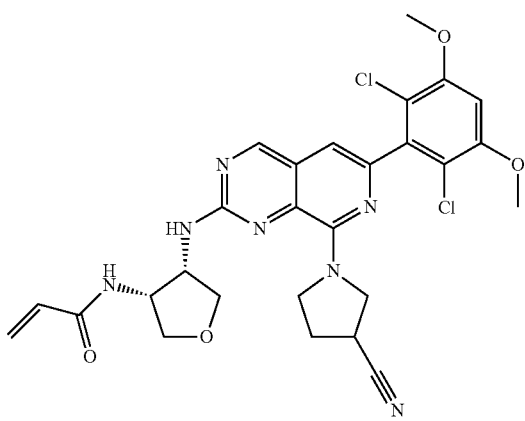 [SMILES: C=CC(=O)N[C@H]1COC[C@H]1Nc1ncc2cc(-c3c(Cl)c(OC)cc(OC)c3Cl)nc(N3CCC(C#N)C3)c2n1] | N-((3R,4S)-4-((8-(3-cyanopyrrolidin-1-yl)-6-(2,6-dichloro-3,5-dimethoxyphenyl)pyrido[3,4-d]pyrimidin-2-yl)amino)tetrahydrofuran-3-yl)acrylamide | 584 |

-continued

| Example No. | Compound structure | Compound name | MS: m/z [M + 1]+ |
|---|---|---|---|
| 680 | 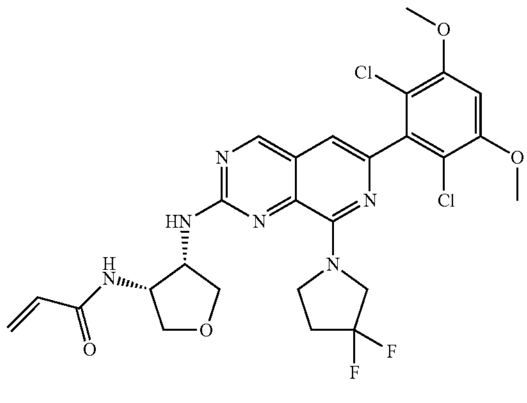 [SMILES: C=CC(=O)N[C@H]1COC[C@H]1Nc1ncc2cc(-c3c(Cl)c(OC)cc(OC)c3Cl)nc(N3CCC(F)(F)C3)c2n1] | N-((3R,4S)-4-((6-(2,6-dichloro-3,5-dimethoxyphenyl)-8-(3,3-difluoropyrrolidin-1-yl)pyrido[3,4-d]pyrimidin-2-yl)amino)tetrahydrofuran-3-yl)acrylamide | 595 |
| 681 | 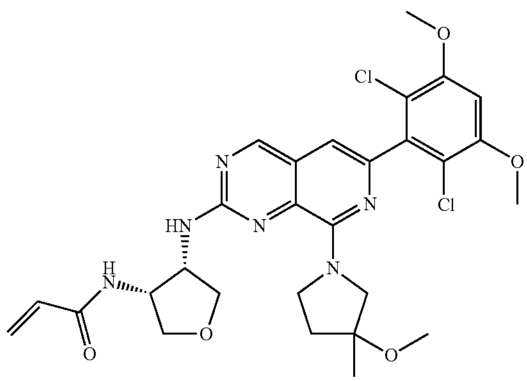 [SMILES: C=CC(=O)N[C@H]1COC[C@H]1Nc1ncc2cc(-c3c(Cl)c(OC)cc(OC)c3Cl)nc(N3CCC(C)(OC)C3)c2n1] | N-((3R,4S)-4-((6-(2,6-dichloro-3,5-dimethoxyphenyl)-8-(3-methoxy-3-methylpyrrolidin-1-yl)pyrido[3,4-d]pyrimidn-2-yl)amino)tetrahydrofuran-3-yl)acrylamide | 603 |
| 682 | 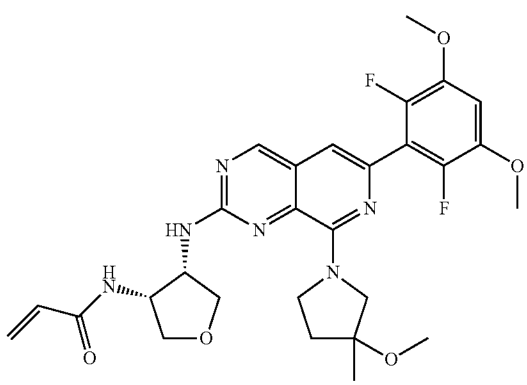 [SMILES: C=CC(=O)N[C@H]1COC[C@H]1Nc1ncc2cc(-c3c(F)c(OC)cc(OC)c3F)nc(N3CCC(C)(OC)C3)c2n1] | N-((3R,4S)-4-((6-(2,6-difluoro-3,5-dimethoxyphenyl)-8-(3-methoxy-3-methylpyrrolidin-1-yl)pyrido[3,4-d]pyrimidin-2-yl)amino)tetrahydrofuran-3-yl)acrylamide | 571 |
| 683 | 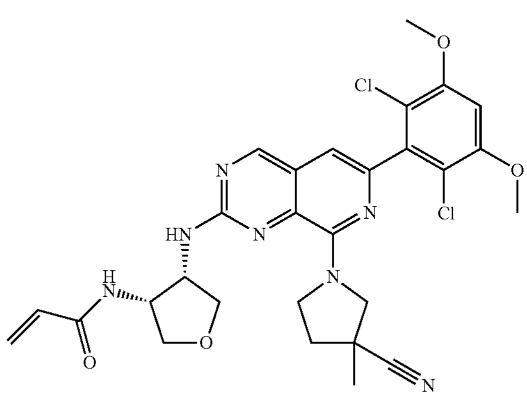 [SMILES: C=CC(=O)N[C@H]1COC[C@H]1Nc1ncc2cc(-c3c(Cl)c(OC)cc(OC)c3Cl)nc(N3CCC(C)(C#N)C3)c2n1] | N-((3R,4S)-4-((8-(3-cyano-3-methylpyrrolidin-1-yl)-6-(2,6-dichloro-3,5-dimethoxyphenyl)pyrido[3,4-d]pyrimidin-2-yl)amino)tetrahydrofuran-3-yl)acrylamide | 598 |

-continued

| Example No. | Compound structure | Compound name | MS: m/z [M + 1]+ |
|---|---|---|---|
| 684 | 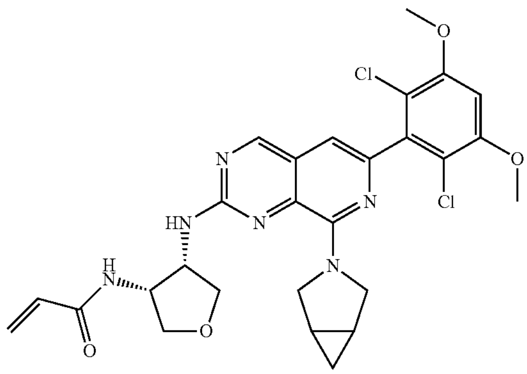 [SMILES: C=CC(=O)N[C@H]1COC[C@H]1Nc1ncc2cc(-c3c(Cl)c(OC)cc(OC)c3Cl)nc(N3CC4CC4C3)c2n1] | N-((3R,4S)-4-((8-(3-aza-bicyclo[3.1.0]hexan-3-yl)-6-(2,6-dichloro-3,5-dimethoxyphen-yl)pyrido[3,4-d]pyrimidin-2-yl)a-mino)tetrahydrofuran-3-yl)acrylamide | 571 |
| 685 | 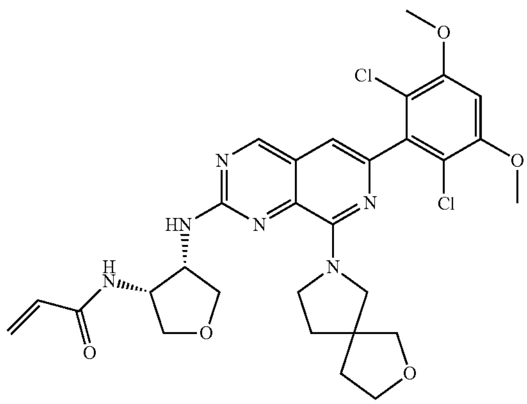 [SMILES: C=CC(=O)N[C@H]1COC[C@H]1Nc1ncc2cc(-c3c(Cl)c(OC)cc(OC)c3Cl)nc(N3CCC4(CCOC4)C3)c2n1] | N-((3R,4S)-4-((6-(2,6-dichloro-3,5-di-methoxyphenyl)-8-(2-oxa-7-azaspiro[4.4]nonan-7-yl)pyrido[3,4-d]pyrimidin-2-yl)amino)tetrahydro-furan-3-yl)acrylamide | 615 |
| 686 | 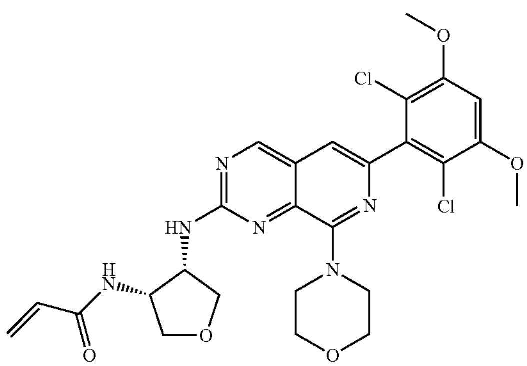 [SMILES: C=CC(=O)N[C@H]1COC[C@H]1Nc1ncc2cc(-c3c(Cl)c(OC)cc(OC)c3Cl)nc(N3CCOCC3)c2n1] | N-((3R,4S)-4-((6-(2,6-dichloro-3,5-dimethoxyphenyl)-8-morpholino-pyrido[3,4-d]pyrimidin-2-yl)amino)tetra-hydrofuran-3-yl)acrylamide | 575 |
| 687 | 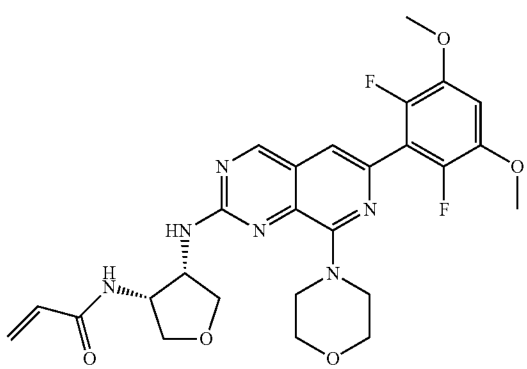 [SMILES: C=CC(=O)N[C@H]1COC[C@H]1Nc1ncc2cc(-c3c(F)c(OC)cc(OC)c3F)nc(N3CCOCC3)c2n1] | N-((3R,4S)-4-((6-(2,6-difluoro-3,5-dimethoxyphenyl)-8-morpholino-pyrido[3,4-d]pyrimidin-2-yl)a-mino)tetrahydrofuran-3-yl)acrylamide | 543 |

-continued

| Example No. | Compound structure | Compound name | MS: m/z [M + 1]+ |
|---|---|---|---|
| 688 | 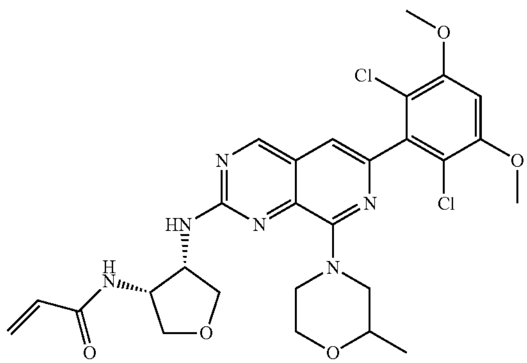 [SMILES: C=CC(=O)N[C@H]1COC[C@H]1Nc1ncc2cc(-c3c(Cl)c(OC)cc(OC)c3Cl)nc(N3CCOC(C)C3)c2n1] | N-((3R,4S)-4-((6-(2,6-dichloro-3,5-dimethoxyphenyl)-8-(2-methyl-morpholino)pyrido[3,4-d]pyrimidin-2-yl)amino)tetrahydrofuran-3-yl)acrylamide | 589 |
| 689 | 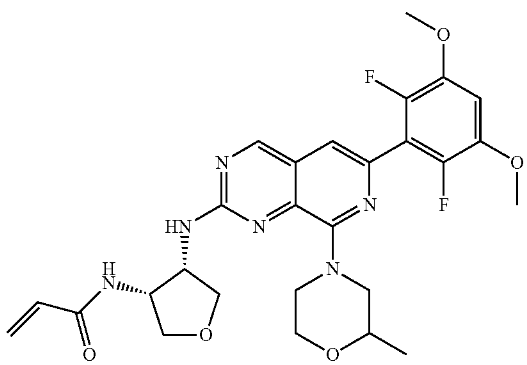 [SMILES: C=CC(=O)N[C@H]1COC[C@H]1Nc1ncc2cc(-c3c(F)c(OC)cc(OC)c3F)nc(N3CCOC(C)C3)c2n1] | N-((3R,4S)-4-((6-(2,6-difluoro-3,5-dimethoxyphenyl)-8-(2-methyl-morpholino)pyrido[3,4-d]pyrimidin-2-yl)amino)tetrahydrofuran-3-yl)acrylamide | 557 |
| 690 | 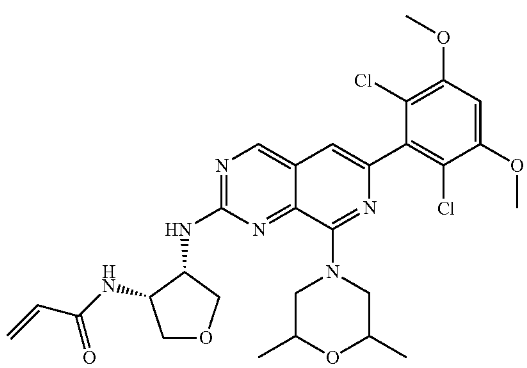 [SMILES: C=CC(=O)N[C@H]1COC[C@H]1Nc1ncc2cc(-c3c(Cl)c(OC)cc(OC)c3Cl)nc(N3CC(C)OC(C)C3)c2n1] | N-((3R,4S)-4-((6-(2,6-dichloro-3,5-dimethoxyphenyl)-8-(2,6-dimethyl-morpholino)pyrido[3,4-d]pyrimidin-2-yl)amino)tetrahydrofuran-3-yl)acrylamide | 603 |
| 691 | 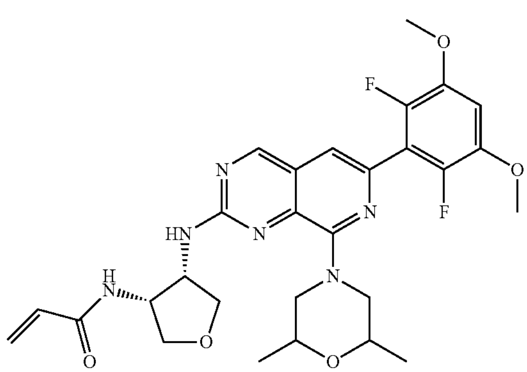 [SMILES: C=CC(=O)N[C@H]1COC[C@H]1Nc1ncc2cc(-c3c(F)c(OC)cc(OC)c3F)nc(N3CC(C)OC(C)C3)c2n1] | N-((3R,4S)-4-((6-(2,6-difluoro-3,5-dimethoxyphenyl)-8-(2,6-dimethyl-morpholino)pyrido[3,4-d]pyrimidin-2-yl)amino)tetrahydrofuran-3-yl)acrylamide | 571 |

| Example No. | Compound structure | Compound name | MS: m/z [M + 1]+ |
| --- | --- | --- | --- |
| 692 | 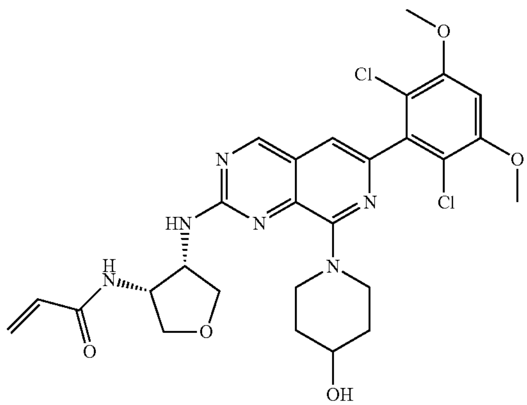 [SMILES: C=CC(=O)N[C@H]1COC[C@H]1Nc1ncc2cc(-c3c(Cl)c(OC)cc(OC)c3Cl)nc(N3CCC(O)CC3)c2n1] | N-((3R,4S)-4-((6-(2,6-dichloro-3,5-dimethoxyphenyl)-8-(4-hydroxypiperidin-1-yl)pyrido[3,4-d]pyrimidin-2-yl)amino)tetrahydrofuran-3-yl)acrylamide | 589 |
| 693 | 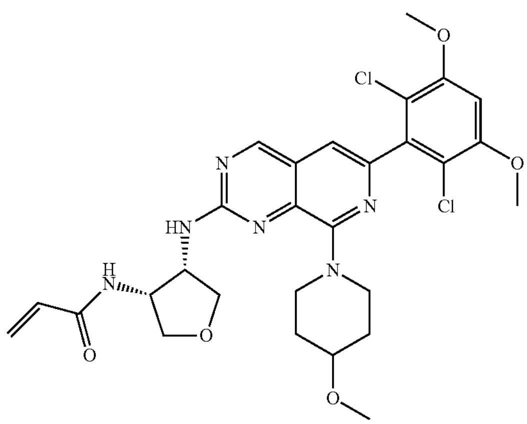 [SMILES: C=CC(=O)N[C@H]1COC[C@H]1Nc1ncc2cc(-c3c(Cl)c(OC)cc(OC)c3Cl)nc(N3CCC(OC)CC3)c2n1] | N-((3R,4S)-4-((6-(2,6-dichloro-3,5-dimethoxyphenyl)-8-(4-methoxypiperidin-1-l)pyrido[3,4-d]pyrimidin-2-yl)amino)tetrahydrofuran-3-yl)acrylamide | 603 |
| 694 | 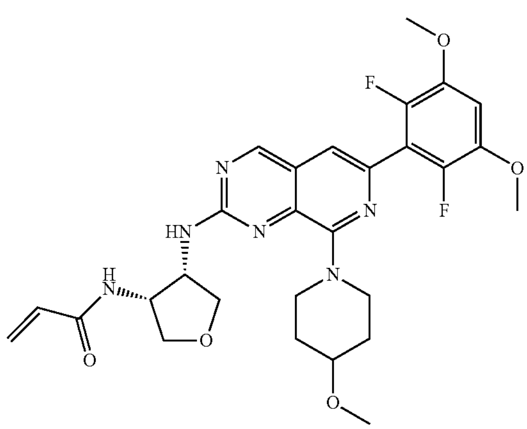 [SMILES: C=CC(=O)N[C@H]1COC[C@H]1Nc1ncc2cc(-c3c(F)c(OC)cc(OC)c3F)nc(N3CCC(OC)CC3)c2n1] | N-((3R,4S)-4-((6-(2,6-difluoro-3,5-dimethoxyphenyl)-8-(4-methoxypiperidin-1-yl)pyrido[3,4-d]pyrimidin-2-yl)amino)tetrahydrofuran-3-yl)acrylamide | 571 |

-continued

| Example No. | Compound structure | Compound name | MS: m/z [M + 1]+ |
|---|---|---|---|
| 695 | 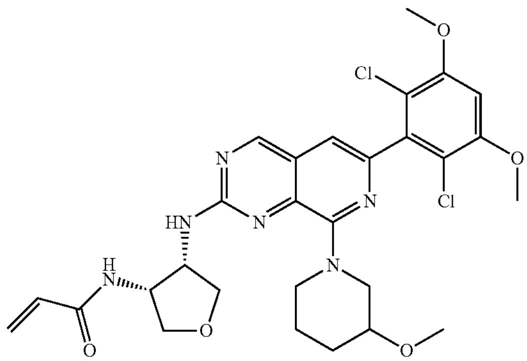 [SMILES: C=CC(=O)N[C@H]1COC[C@H]1Nc1ncc2cc(-c3c(Cl)c(OC)cc(OC)c3Cl)nc(N3CCCC(OC)C3)c2n1] | N-((3R,4S)-4-((6-(2,6-dichloro-3,5-dimethoxyphenyl)-8-(3-methoxypiperidin-1-yl)pyrido[3,4-d]pyrimidin-2-yl)amino)tetrahydrofuran-3-yl)acrylamide | 603 |
| 696 | 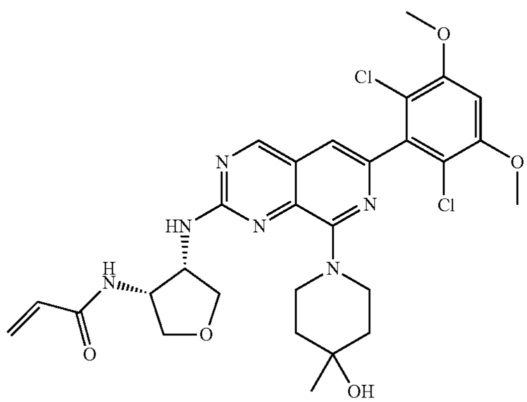 [SMILES: C=CC(=O)N[C@H]1COC[C@H]1Nc1ncc2cc(-c3c(Cl)c(OC)cc(OC)c3Cl)nc(N3CCC(C)(O)CC3)c2n1] | N-((3R,4S)-4-((6-(2,6-dichloro-3,5-dimethoxyphenyl)-8-(4-hydroxy-4-methylpiperidin-1-yl)pyrido[3,4-d]pyrimidin-2-yl)amino)tetrahydrofuran-3-yl)acrylamide | 603 |
| 697 | 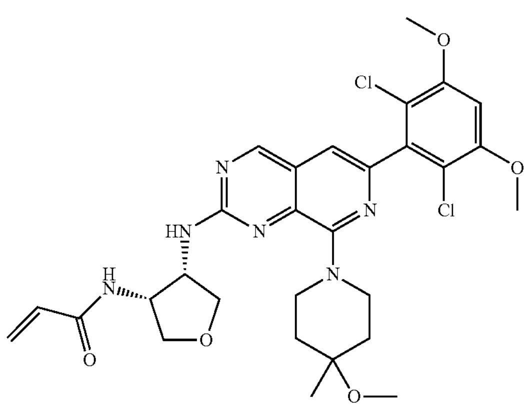 [SMILES: C=CC(=O)N[C@H]1COC[C@H]1Nc1ncc2cc(-c3c(Cl)c(OC)cc(OC)c3Cl)nc(N3CCC(C)(OC)CC3)c2n1] | N-((3R,4S)-4-((6-(2,6-dichloro-3,5-dimethoxyphenyl)-8-(4-methoxy-4-methylpiperidin-1-yl)pyrido[3,4-d]pyrimidin-2-yl)amino)tetrahydrofuran-3-yl)acrylamide | 617 |

| Example No. | Compound structure | Compound name | MS: m/z [M + 1]+ |
|---|---|---|---|
| 698 | 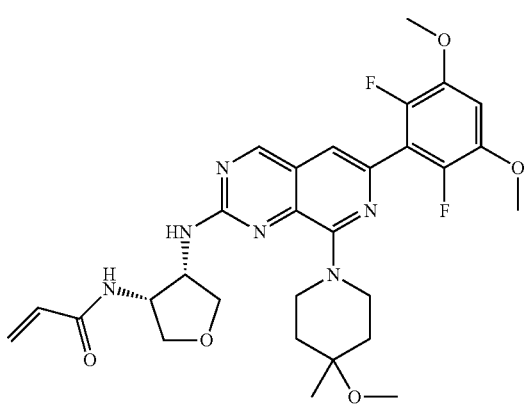 [SMILES: C=CC(=O)N[C@H]1COC[C@H]1Nc1ncc2cc(-c3c(F)c(OC)cc(OC)c3F)nc(N3CCC(C)(OC)CC3)c2n1] | N-((3R,4S)-4-((6-(2,6-difluoro-3,5-di-methoxyphenyl)-8-(4-methoxy-4-methylpiperidin-1-yl)pyrido[3,4-d]py-rimidin-2-yl)amino)tetrahydrofuran-3-yl)acrylamide | 585 |
| 699 | 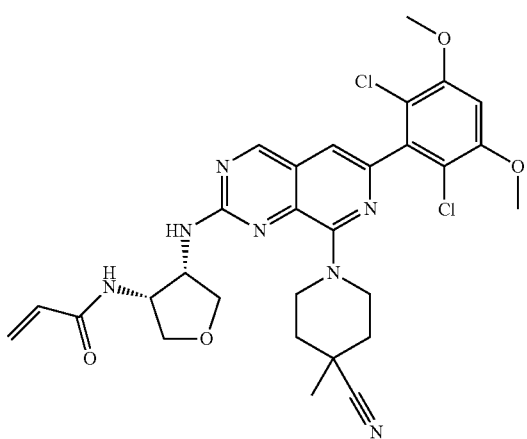 [SMILES: C=CC(=O)N[C@H]1COC[C@H]1Nc1ncc2cc(-c3c(Cl)c(OC)cc(OC)c3Cl)nc(N3CCC(C)(C#N)CC3)c2n1] | N-((3R,4S)-4-((8-(4-cyano-4-methyl-piperidin-1-yl)-6-(2,6-dichloro-3,5-di-methoxyphenyl)pyrido[3,4-d]pyrimi-din-2-yl)amino)tetrahydrofurna-3-yl) acrylamide | 612 |
| 700 | 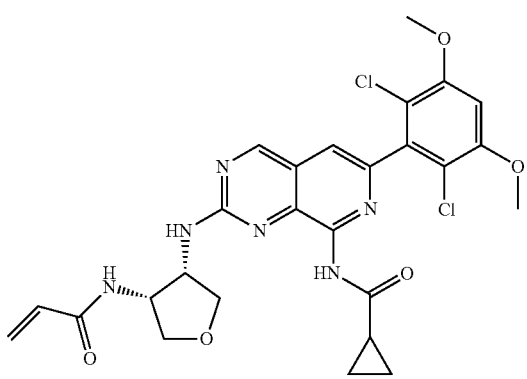 [SMILES: C=CC(=O)N[C@H]1COC[C@H]1Nc1ncc2cc(-c3c(Cl)c(OC)cc(OC)c3Cl)nc(NC(=O)C3CC3)c2n1] | N-(2-(((3S,4R)-4-acrylamidotetrahy-drofuran-3-yl)amino)-6-(2,6-dichloro-3,5-dimethoxyphenyl)pyrido[3,4-d]pyrimidin-4-8-yl)cyclopropanecarbox-amide | 573 |

-continued

| Example No. | Compound structure | Compound name | MS: m/z [M + 1]+ |
|---|---|---|---|
| 701 | 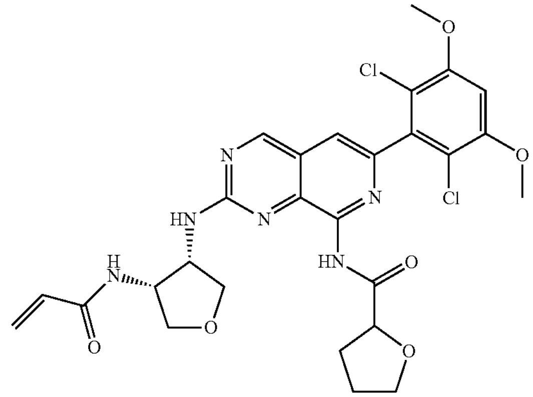 [SMILES: C=CC(=O)N[C@H]1COC[C@H]1Nc1ncc2cc(-c3c(Cl)c(OC)cc(OC)c3Cl)nc(NC(=O)C3CCCO3)c2n1] | N-(2-(((3S,4R)-4-acrylamidotetra-hydrofuran-3-yl)amino)-6-(2,6-dichloro-3,5-dimethoxyphenyl)pyrido[3,4-d]pyrimidin-8-yl)tetrahydrofuran-2-carboxamide | 603 |
| 702 | 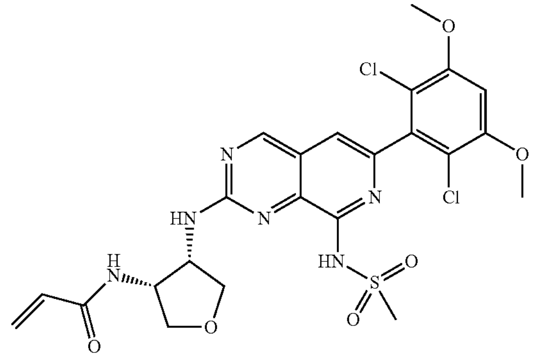 [SMILES: C=CC(=O)N[C@H]1COC[C@H]1Nc1ncc2cc(-c3c(Cl)c(OC)cc(OC)c3Cl)nc(NS(C)(=O)=O)c2n1] | N-((3R,4S)-4-((6-(2,6-dichloro-3,5-dimethoxyphenyl)-8-(methylsulfonamido)pyrido[3,4-d]pyrimidin-2-yl)amino)tetrahydrofuran-3-yl)acrylamide | 583 |
| 703 | 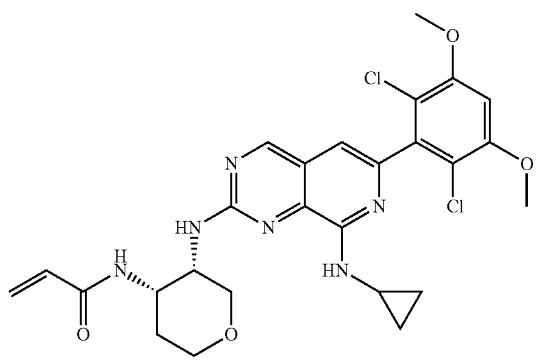 [SMILES: C=CC(=O)N[C@H]1CCOC[C@H]1Nc1ncc2cc(-c3c(Cl)c(OC)cc(OC)c3Cl)nc(NC3CC3)c2n1] | N-((3S,4S)-3-((8-(cyclopropylamino)-6-(2,6-dichloro-3,5-dimethoxyphenyl)pyrido[3,4-d]pyrimidin-2-yl)amino)tetrahydro-2H-pyran-4-yl)acrylamide | 559 |
| 704 | 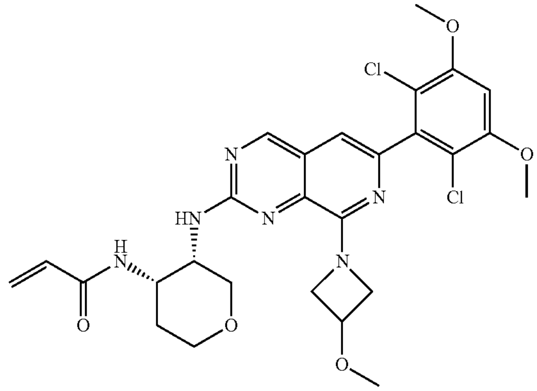 [SMILES: C=CC(=O)N[C@H]1CCOC[C@H]1Nc1ncc2cc(-c3c(Cl)c(OC)cc(OC)c3Cl)nc(N3CC(OC)C3)c2n1] | N-((3S,4S)-3-((6-(2,6-dichloro-3,5-dimethoxyphenyl)-8-(3-methoxyazetidin-1-yl)pyrido[3,4-d]pyrimidin-2-yl)amino)tetrahydro-2H-pyran-4-yl)acrylamide | 589 |

| Example No. | Compound structure | Compound name | MS: m/z [M + 1]+ |
|---|---|---|---|
| 705 | 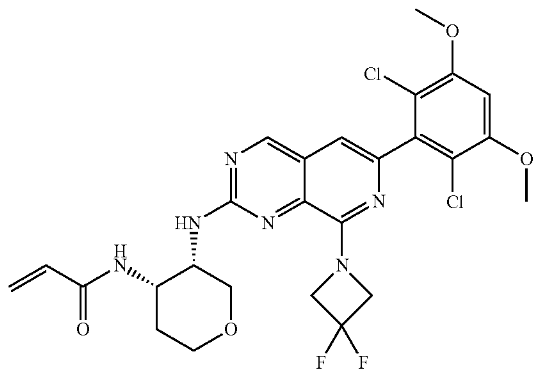 [SMILES: C=CC(=O)N[C@H]1CCOC[C@H]1Nc1ncc2cc(-c3c(Cl)c(OC)cc(OC)c3Cl)nc(N3CC(F)(F)C3)c2n1] | N-((3S,4S)-3-((6-(2,6-dichloro-3,5-dimethoxyphenyl)-8-(3,3-difluoroazetidin-1-yl)pyrido[3,4-d]pyrimidin-2-yl)amino)tetrahydro-2H-pyran-4-yl)acrylamide | 595 |
| 706 | 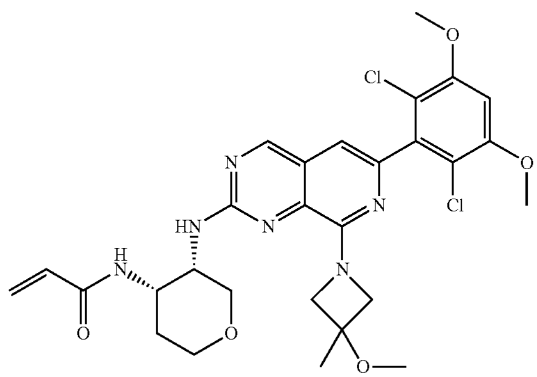 [SMILES: C=CC(=O)N[C@H]1CCOC[C@H]1Nc1ncc2cc(-c3c(Cl)c(OC)cc(OC)c3Cl)nc(N3CC(C)(OC)C3)c2n1] | N-((3S,4S)-3-((6-(2,6-dichloro-3,5-dimethoxyphenyl)-8-(3-methoxy-3-methylazetidin-1-yl)pyrido[3,4-d]pyrimidin-2-yl)amino)tetrahydro-2H-pyran-4-yl)acrylamide | 603 |
| 707 | 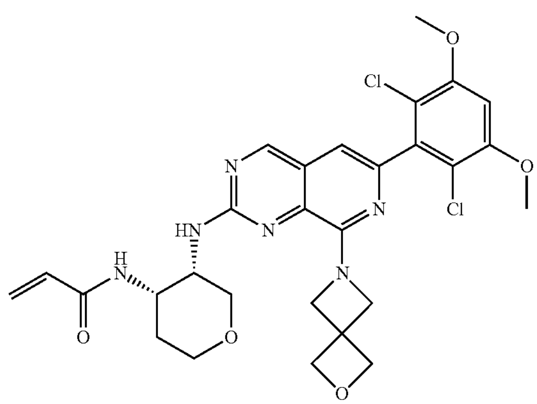 [SMILES: C=CC(=O)N[C@H]1CCOC[C@H]1Nc1ncc2cc(-c3c(Cl)c(OC)cc(OC)c3Cl)nc(N3CC4(COC4)C3)c2n1] | N-((3S,4S)-3-((6-(2,6-dichloro-3,5-dimethoxyphenyl)-8-(2-oxa-6-azaspiro[3.3]heptan-6-yl)pyrido[3,4-d]pyrimidin-2-yl)amino)tetrahydro-2H-pyran-4-yl)acrylamide | 601 |
| 708 | 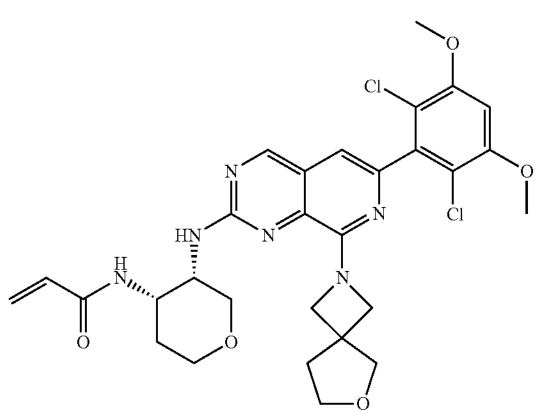 [SMILES: C=CC(=O)N[C@H]1CCOC[C@H]1Nc1ncc2cc(-c3c(Cl)c(OC)cc(OC)c3Cl)nc(N3CC4(CCOC4)C3)c2n1] | N-((3S,4S)-3-((6-(2,6-dichloro-3,5-dimethoxyphenyl)-8-(6-oxa-2-azaspiro[3.4]octan-2-yl)pyrido[3,4-d]pyrimidin-2-yl)amino)tetrahydro-2H-pyran-4-yl)acrylamide | 615 |

| Example No. | Compound structure | Compound name | MS: m/z [M + 1]+ |
|---|---|---|---|
| 709 | 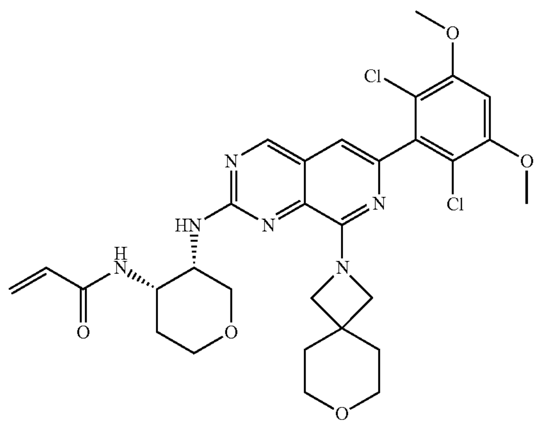 [SMILES: C=CC(=O)N[C@H]1CCOC[C@H]1Nc1ncc2cc(-c3c(Cl)c(OC)cc(OC)c3Cl)nc(N3CC4(CCOCC4)C3)c2n1] | N-((3S,4S)-3-((6-(2,6-dichloro-3,5-dimethoxyphenyl)-8-(7-oxa-2-azaspiro[3.5]nonan-2-yl)pyrido[3,4-d]pyrimidin-2-yl)amino)tetrahydro-2H-pyran-4-yl)acrylamide | 629 |
| 710 | 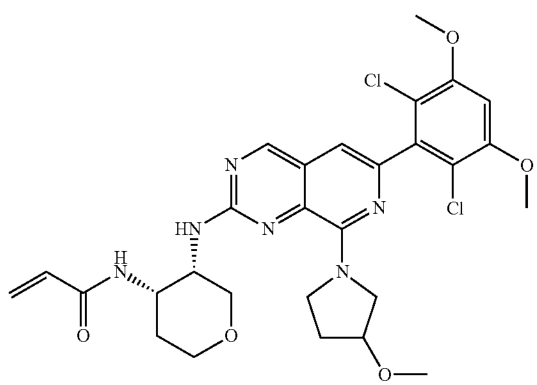 [SMILES: C=CC(=O)N[C@H]1CCOC[C@H]1Nc1ncc2cc(-c3c(Cl)c(OC)cc(OC)c3Cl)nc(N3CCC(OC)C3)c2n1] | N-((3S,4S)-3-((6-(2,6-dichloro-3,5-dimethoxyphenyl)-8-(3-methoxypyrrolidin-1-yl)pyrido[3,4-d]pyrimidin-2-yl)amino)tetrahydro-2H-pyran-4-yl)acrylamide | 603 |
| 711 | 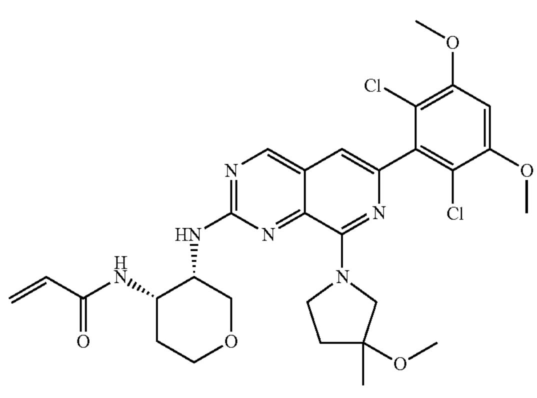 [SMILES: C=CC(=O)N[C@H]1CCOC[C@H]1Nc1ncc2cc(-c3c(Cl)c(OC)cc(OC)c3Cl)nc(N3CCC(C)(OC)C3)c2n1] | N-((3S,4S)-3-((6-(2,6-dichloro-3,5-dimethoxyphenyl)-8-(3-methoxy-3-methylpyrrolidin-1-yl)pyrido[3,4-d]pyrimidin-2-yl)amino)tetrahydro-2H-pyran-4-yl)acrylamide | 617 |

-continued

| Example No. | Compound structure | Compound name | MS: m/z [M + 1]+ |
|---|---|---|---|
| 712 | 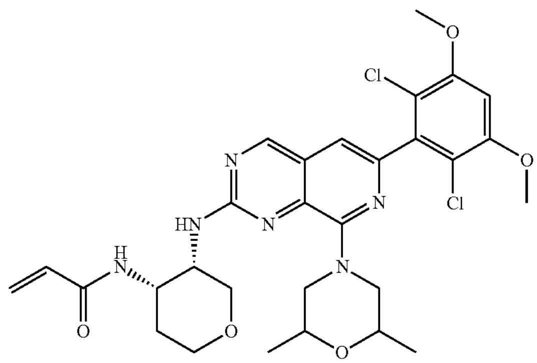 [SMILES: C=CC(=O)N[C@H]1CCOC[C@H]1Nc1ncc2cc(-c3c(Cl)c(OC)cc(OC)c3Cl)nc(N3CC(C)OC(C)C3)c2n1] | N-((3S,4S)-3-((6-(2,6-dichloro-3,5-dimethoxyphenyl)-8-(2,6-dimethyl-morpholino)pyrido[3,4-d]pyrimidin-2-yl)amino)tetrahydro-2H-pyran-4-yl)acrylamide | 617 |
| 713 | 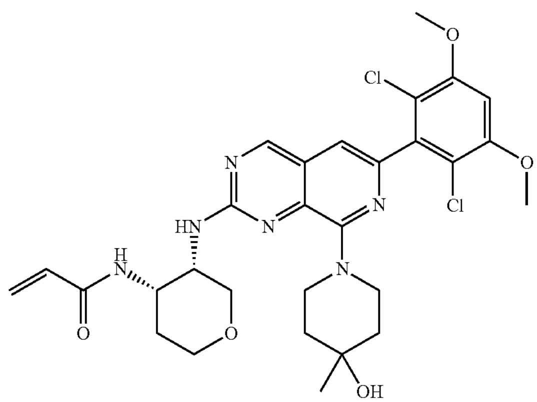 [SMILES: C=CC(=O)N[C@H]1CCOC[C@H]1Nc1ncc2cc(-c3c(Cl)c(OC)cc(OC)c3Cl)nc(N3CCC(C)(O)CC3)c2n1] | N-((3S,4S)-3-((6-(2,6-dichloro-3,5-dimethoxyphenyl)-8-(4-hydroxy-4-methylpiperidin-1-yl)pyrido[3,4-d]pyrimidin-2-yl)amino)tetrahydro-2H-pyran-4-yl)acrylamide | 617 |
| 714 | 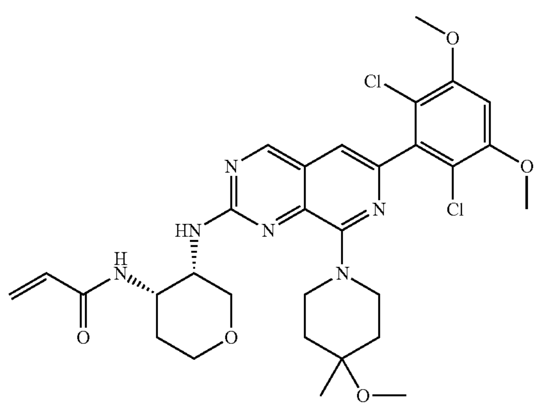 [SMILES: C=CC(=O)N[C@H]1CCOC[C@H]1Nc1ncc2cc(-c3c(Cl)c(OC)cc(OC)c3Cl)nc(N3CCC(C)(OC)CC3)c2n1] | N-((3S,4S)-3-((6-(2,6-dichloro-3,5-dimethoxyphenyl)-8-(4-methoxy-4-methylpiperidin-1-yl)pyrido[3,4-d]pyrimidin-2-yl)amino)tetrahydro-2H-pyran-4-yl)acrylamide | 631 |
| 753 | 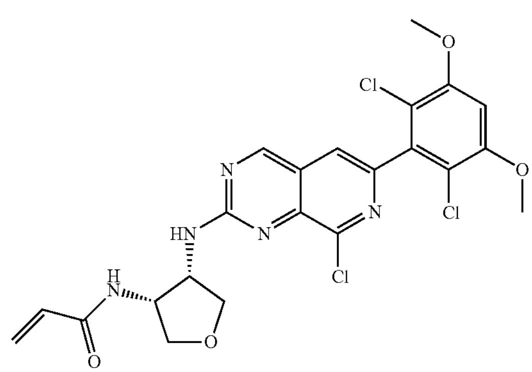 [SMILES: C=CC(=O)N[C@H]1COC[C@H]1Nc1ncc2cc(-c3c(Cl)c(OC)cc(OC)c3Cl)nc(Cl)c2n1] | N-((3R,4S)-4-((8-chloro-6-(2,6-dichloro-3,5-dimethoxyphenyl)pyrido[3,4-d]pyrimidin-2-yl)amino)tetrahydrofuran-3-yl)acrylamide | 524 |

-continued

| Example No. | Compound structure | Compound name | MS: m/z [M + 1]+ |
|---|---|---|---|
| 754 | 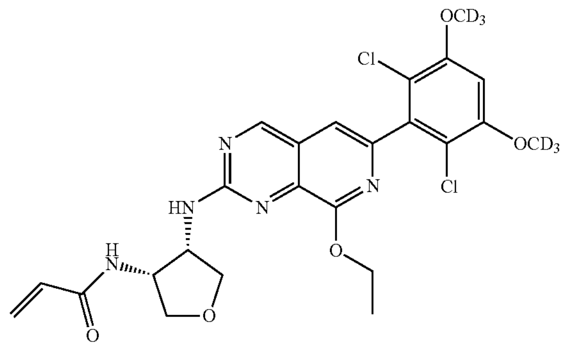 | N-((3R,4S)-4-((6-(2,6-dichloro-3,5-bis(methoxy-d₃)phenyl)-8-ethoxy-pyrido[3,4-d]pyrimidin-2-yl)amino)tetra-hydrofuran-3-yl)acrylamide | 540 |
| 755 | 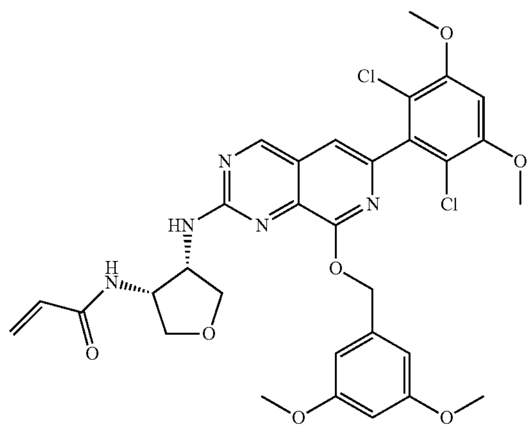 [SMILES: C=CC(=O)N[C@H]1COC[C@H]1Nc1ncc2cc(-c3c(Cl)c(OC)cc(OC)c3Cl)nc(OCc3cc(OC)cc(OC)c3)c2n1] | N-((3R,4S)-4-((6-(2,6-dichloro-3,5-dimethoxyphenyl)-8-((3,5-dimethoxy-benzyl)oxy)pyrido[3,4-d]pyrimidin-2-yl)amino)tetrahydrofuran-3-yl)acrylamide | 656 |
| 756 | 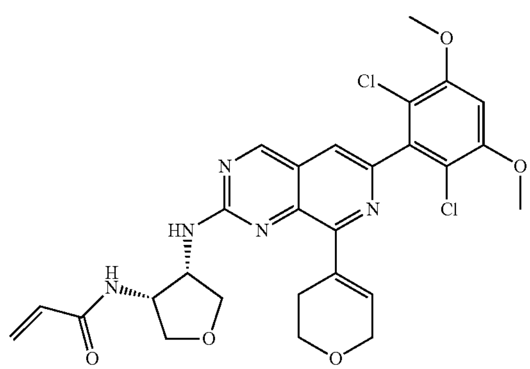 [SMILES: C=CC(=O)N[C@H]1COC[C@H]1Nc1ncc2cc(-c3c(Cl)c(OC)cc(OC)c3Cl)nc(C3=CCOCC3)c2n1] | N-((3R,4S)-4-((6-(2,6-dichloro-3,5-dimethoxyphenyl)-8-(3,6-dihydro-2H-pyran-4-yl)pyrido[3,4-d]pyrimidin-2-yl)amino)tetrahydrofuran-3-yl)acryl-amide | 572 |
| 758 | 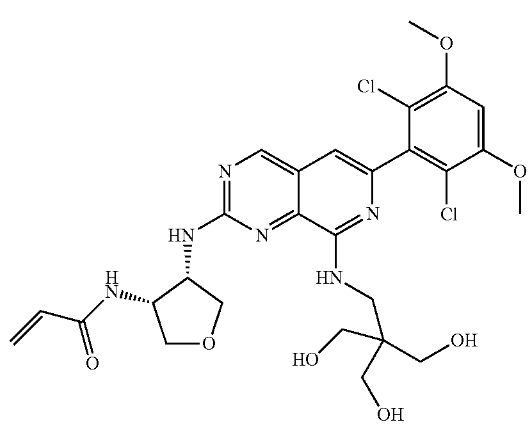 [SMILES: C=CC(=O)N[C@H]1COC[C@H]1Nc1ncc2cc(-c3c(Cl)c(OC)cc(OC)c3Cl)nc(NCC(CO)(CO)CO)c2n1] | N-((3R,4S)-4-((6-(2,6-dichloro-3,5-dimethoxypehnyl)-8-((3-hydroxy-2,2-bis(hydroxymethyl)propyl)amino)py-rido[3,4-d]pyrimidin-2-yl)amino)tetra-hydrofuran-3-yl)acrylamide | 623 |

| Example No. | Compound structure | Compound name | MS: m/z [M + 1]+ |
|---|---|---|---|
| 759 | 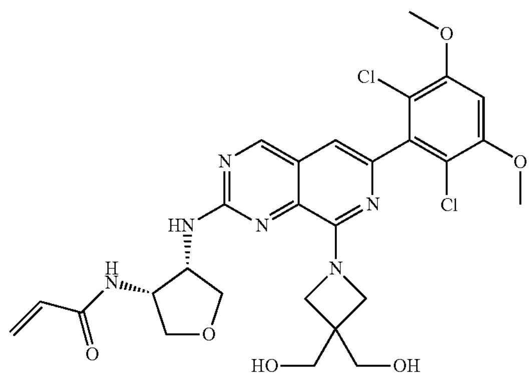 [SMILES: C=CC(=O)N[C@H]1COC[C@H]1Nc1ncc2cc(-c3c(Cl)c(OC)cc(OC)c3Cl)nc(N3CC(CO)(CO)C3)c2n1] | N-((3R,4S)-4-((8-(3,3-bis(hydroxymethyl)azetidin-1-yl)-6-(2,6-dichloro-3,5-dimethoxyphenyl)pyrido[3,4-d]pyrimidin-2-yl)amino)tetrahydrofuran-3-yl)acrylamide | 605 |
| 760 | 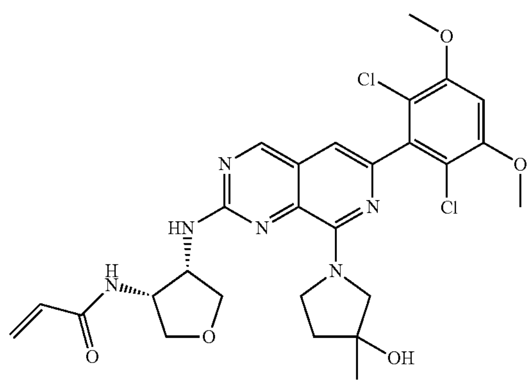 | N-((3R,4S)-4-((6-(2,6-dichloro-3,5-dimethoxyphenyl)-8-(3-hydroxy-3-methylpyrrolidin-1-yl)pyrido[3,4-d]pyrimidin-2-yl)amino)tetarhydrofuran-3-yl)acrylamide | 589 |
| 761 | 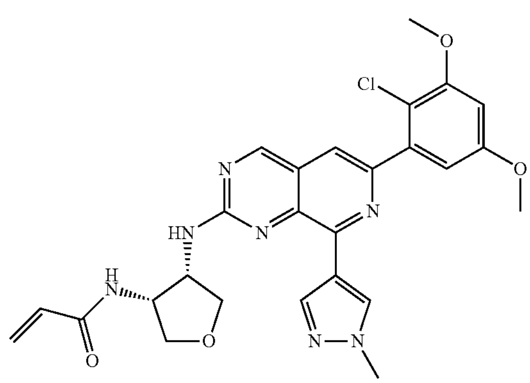 [SMILES: C=CC(=O)N[C@H]1COC[C@H]1Nc1ncc2cc(-c3cc(OC)cc(OC)c3Cl)nc(-c3cnn(C)c3)c2n1] | N-((3R,4S)-4-((6-(2-chloro-3,5-dimethoxyphenyl)-8-(1-methyl-1H-pyrazol-4-yl)pyrido[3,4-d]pyrimidin-2-yl)amino)tetrahydrofuran-3-yl)acrylamide | 536 |
| 762 | 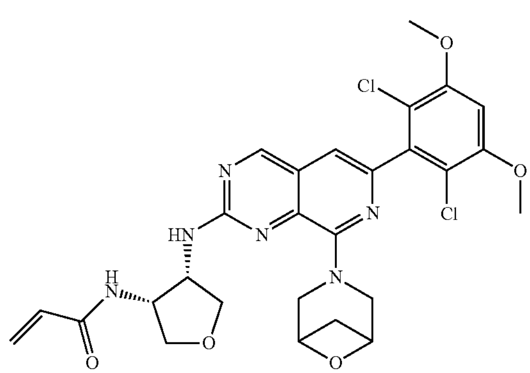 [SMILES: C=CC(=O)N[C@H]1COC[C@H]1Nc1ncc2cc(-c3c(Cl)c(OC)cc(OC)c3Cl)nc(N3CC4CC(C3)O4)c2n1] | N-((3R,4S)-4-((8-(6-oxa-3-azabicyclo[3.1.1]heptan-3-yl)-6-(2,6-dichloro-3,5-dimethoxyphenyl)pyrido[3,4-d]pyrimidin-2-yl)amino)tetrahydrofuran-3-yl)acrylamide | 587 |

-continued

| Example No. | Compound structure | Compound name | MS: m/z [M + 1]+ |
|---|---|---|---|
| 763 | 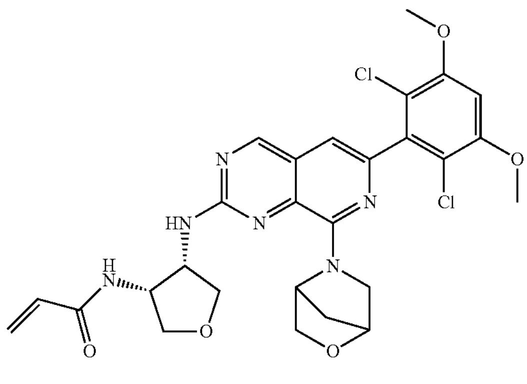 [SMILES: C=CC(=O)N[C@H]1COC[C@H]1Nc1ncc2cc(-c3c(Cl)c(OC)cc(OC)c3Cl)nc(N3CC4CC3CO4)c2n1] | N-((3R,4S)-4-((8-(2-oxa-5-azabicyclo[2.2.1]heptan-5-yl)-6-(2,6-dichloro-3,5-dimethoxyphenyl)pyrido[3,4-d]pyrimidin-2-yl)amino)tetrahydrofuran-3-yl)acrylamide | 587 |
| 764 | 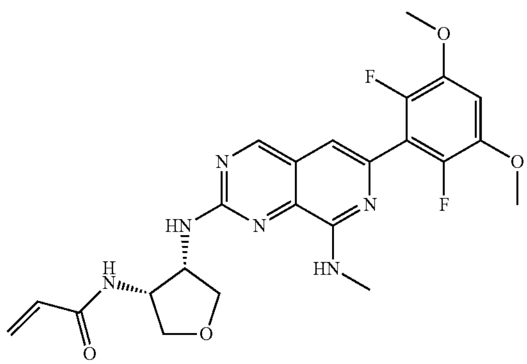 [SMILES: C=CC(=O)N[C@H]1COC[C@H]1Nc1ncc2cc(-c3c(F)c(OC)cc(OC)c3F)nc(NC)c2n1] | N-((3R,4S)-4-((6-(2,6-difluoro-3,5-dimethoxyphenyl)-8-(methylamino)pyrido[3,4-d]pyrimidin-2-yl)amino)tetrahydrofuran-3-yl)acrylamide | 487 |
| 765 | 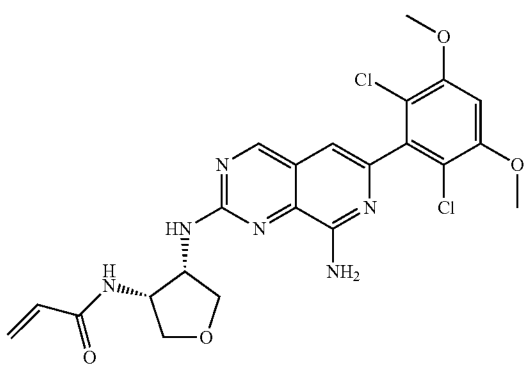 [SMILES: C=CC(=O)N[C@H]1COC[C@H]1Nc1ncc2cc(-c3c(Cl)c(OC)cc(OC)c3Cl)nc(N)c2n1] | N-((3R,4S)-4-((8-amino-6-(2,6-dichloro-3,5-dimethoxyphenyl)pyrido[3,4-d]pyrimidin-2-yl)amino)tetrahydrofuran-3-yl)acrylamide | 505 |
| 766 | 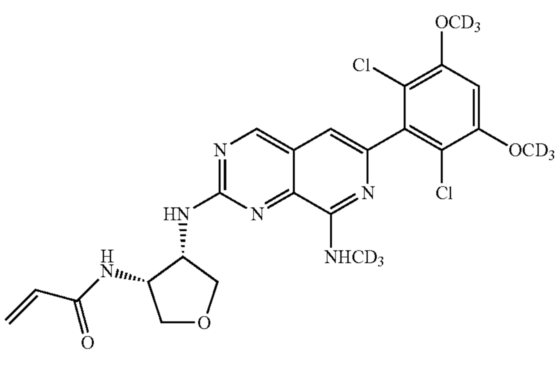 | N-((3R,4S)-4-((6-(2,6-dichloro-3,5-bis(methoxy-d3)phenyl)-8-((methyl-d3)amino)pyrido[3,4-d]pyrimidin-2-yl)amino)tetrahydrofuran-3-yl)acrylamide | 528 |

-continued

| Example No. | Compound structure | Compound name | MS: m/z [M + 1]+ |
|---|---|---|---|
| 767 | 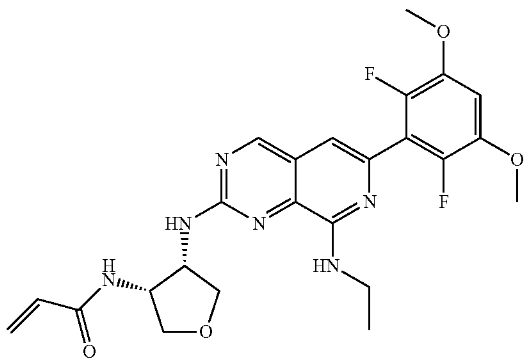 [SMILES: C=CC(=O)N[C@H]1COC[C@H]1Nc1ncc2cc(-c3c(F)c(OC)cc(OC)c3F)nc(NCC)c2n1] | N-((3R,4S)-4-((6-(2,6-difluoro-3,5-dimethoxyphenyl)-8-(ethylamino)pyrido[3,4-d]pyrimidin-2-yl)amino)tetrahydrofuran-3-yl)acrylamide | 501 |
| 768 | 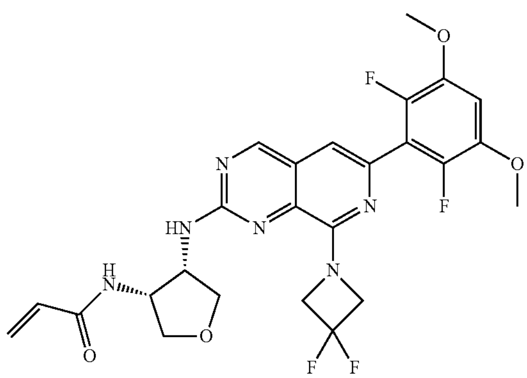 [SMILES: C=CC(=O)N[C@H]1COC[C@H]1Nc1ncc2cc(-c3c(F)c(OC)cc(OC)c3F)nc(N3CC(F)(F)C3)c2n1] | N-((3R,4S)-4-((6-(2,6-difluoro-3,5-dimethoxyphenyl)-8-(3,3-difluoroazetidin-1-yl)pyrido[3,4-d]pyrimidin-2-yl)amino)tetrahydrofuran-3-yl)acrylamide | 549 |
| 769 | 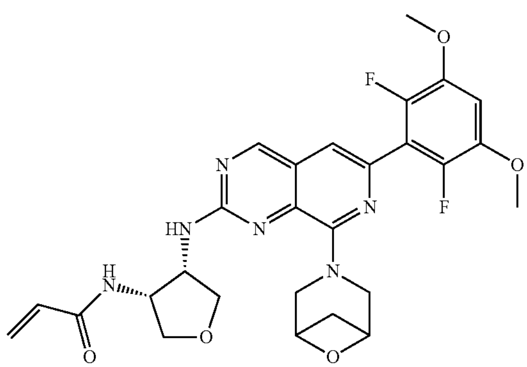 [SMILES: C=CC(=O)N[C@H]1COC[C@H]1Nc1ncc2cc(-c3c(F)c(OC)cc(OC)c3F)nc(N3CC4CC(C3)O4)c2n1] | N-((3R,4S)-4-((8-(6-oxa-3-azabicyclo[3.1.1]heptan-3-yl)-6-(2,6-difluoro-3,5-dimethoxyphenyl)pyrido[3,4-d]pyrimidin-2-yl)amino)tetrahydrofuran-3-yl)acrylamide | 555 |
| 770 | 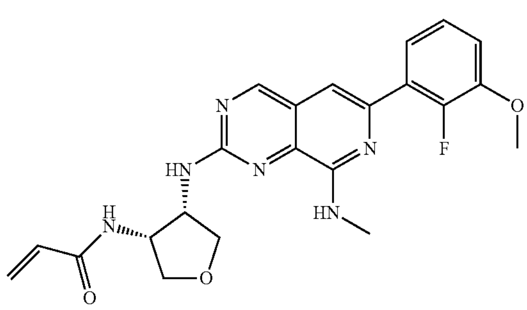 [SMILES: C=CC(=O)N[C@H]1COC[C@H]1Nc1ncc2cc(-c3cccc(OC)c3F)nc(NC)c2n1] | N-((3R,4S)-4-((6-(2-fluoro-3-methoxyphenyl)-8-(methylamino)pyrido[3,4-d]pyrimidin-2-yl)amino)tetrahydrofuran-3-yl)acrylamide | 439 |

-continued

| Example No. | Compound structure | Compound name | MS: m/z [M + 1]+ |
|---|---|---|---|
| 771 | 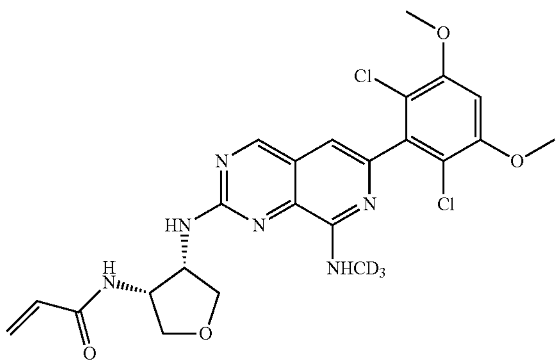 | N-((3R,4S)-4-((6-(2,6-dichloro-3,5-dimethoxyphenyl)-8-((methyl-d$_3$)amino)pyrido[3,4-d]pyrimidin-2-yl)amino)tetrahydrofuran-3-yl)acrylamide | 522 |
| 772 | 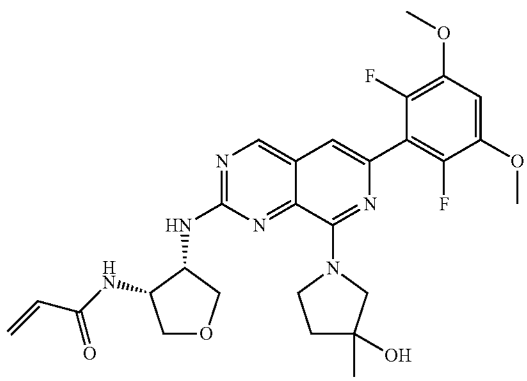 [SMILES: C=CC(=O)N[C@H]1COC[C@H]1Nc1ncc2cc(-c3c(F)c(OC)cc(OC)c3F)nc(N3CCC(C)(O)C3)c2n1] | N-((3R,4S)-4-((6-(2,6-difluoro-3,5-dimethoxyphenyl)-8-(3-hydroxy-3-methylpyrrolidin-1-yl)pyrido[3,4-d]pyrimidin-2-l)amino)tetrahydrofuran-3-yl)acrylamide | 557 |
| 773 | 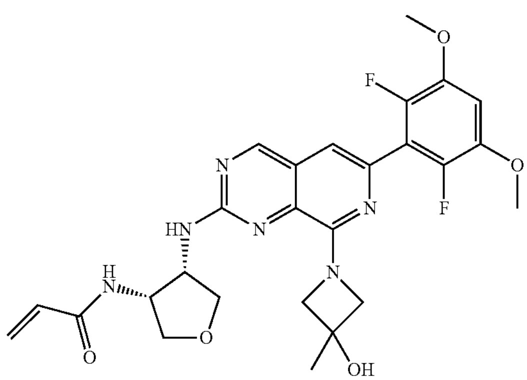 [SMILES: C=CC(=O)N[C@H]1COC[C@H]1Nc1ncc2cc(-c3c(F)c(OC)cc(OC)c3F)nc(N3CC(C)(O)C3)c2n1] | N-((3R,4S)-4-((6-(2,6-difluoro-3,5-dimethoxyphenyl)-8-(3-hydroxy-3-methylazetidin-1-yl)pyrido[3,4-d]pyrimidin-2-yl)amino)tetrahydrofuran-3-yl)acrylamide | 543 |
| 774 | 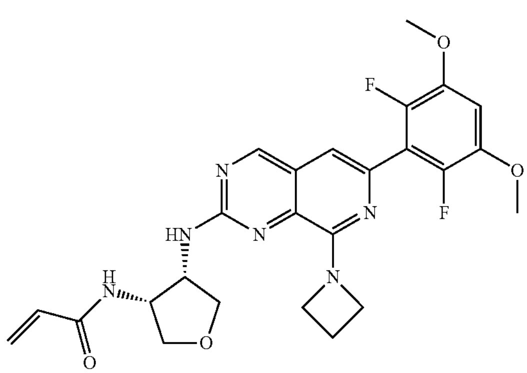 [SMILES: C=CC(=O)N[C@H]1COC[C@H]1Nc1ncc2cc(-c3c(F)c(OC)cc(OC)c3F)nc(N3CCC3)c2n1] | N-((3R,4S)-4-((8-(azetidin-1-yl)-6-(2,6-difluoro-3,5-dimethoxyphenyl)pyrido[3,4-d]pyrimidin-2-yl)amino)tetrahydrofuran-3-yl)acrylamide | 513 |

-continued

| Example No. | Compound structure | Compound name | MS: m/z [M + 1]+ |
|---|---|---|---|
| 775 | 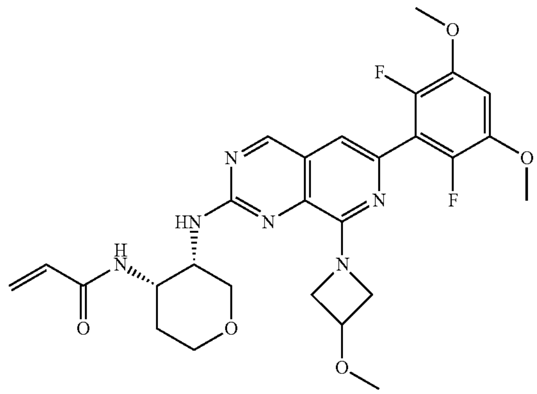 [SMILES: C=CC(=O)N[C@H]1CCOC[C@H]1Nc1ncc2cc(-c3c(F)c(OC)cc(OC)c3F)nc(N3CC(OC)C3)c2n1] | N-((3S,4S)-3-((6-(2,6-difluoro-3,5-dimethoxyphenyl)-8-(3-methoxyazetidin-1-yl)pyrido[3,4-d]pyrimidin-2-yl)amino)tetrahydro-2H-pyran-4-yl)acrylamide | 557 |
| 776 | 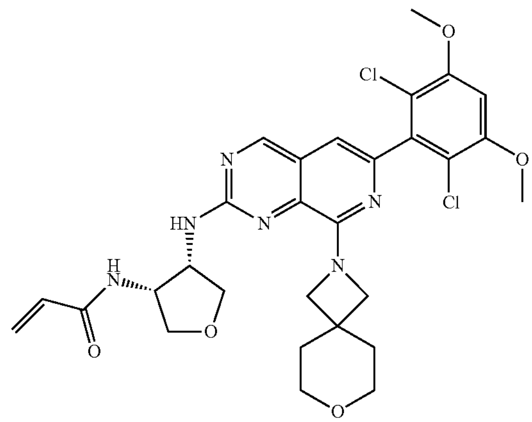 [SMILES: C=CC(=O)N[C@H]1COC[C@H]1Nc1ncc2cc(-c3c(Cl)c(OC)cc(OC)c3Cl)nc(N3CC4(CCOCC4)C3)c2n1] | N-((3R,4S)-4-((6-(2,6-dichloro-3,5-dimethoxyphenyl)-8-(7-oxa-2-azaspiro[3.5]nonan-2-yl)pyrido[3,4-d]pyrimidin-2-yl)amino)tetrahydrofuran-3-yl)acrylamide | 615 |
| 777 | 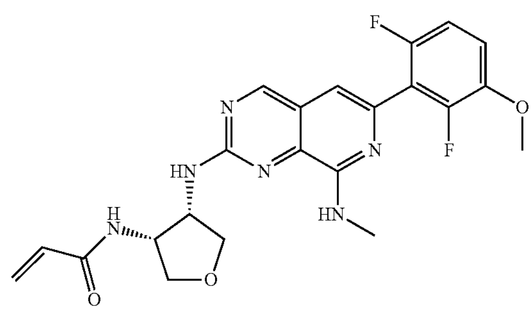 [SMILES: C=CC(=O)N[C@H]1COC[C@H]1Nc1ncc2cc(-c3c(F)ccc(OC)c3F)nc(NC)c2n1] | N-((3R,4S)-4-((6-(2,6-difluoro-3-methoxyphenyl)-8-(methylamino)pyrido[3,4-d]pyrimidin-2-yl)amino)tetrahydrofuran-3-yl)acrylamide | 457 |
| 778 | 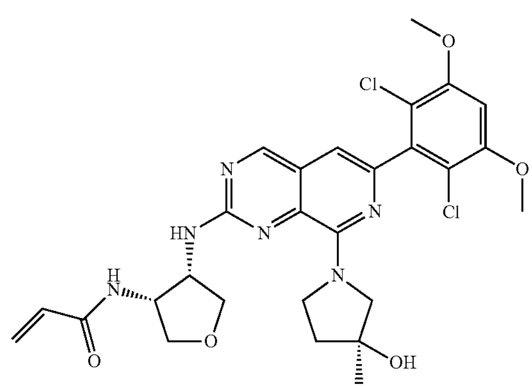 [SMILES: C=CC(=O)N[C@H]1COC[C@H]1Nc1ncc2cc(-c3c(Cl)c(OC)cc(OC)c3Cl)nc(N3CC[C@](C)(O)C3)c2n1] | N-((3R,4S)-4-((6-(2,6-dichloro-3,5-dimethoxyphenyl)-8-((S)-3-hydroxy-3-methylpyrrolidin-1-yl)pyrido[3,4-d]pyrimidin-2-yl)amino)tetrahydrofuran-3-yl)acrylamide | 589 |

-continued

| Example No. | Compound structure | Compound name | MS: m/z [M + 1]+ |
|---|---|---|---|
| 779 | 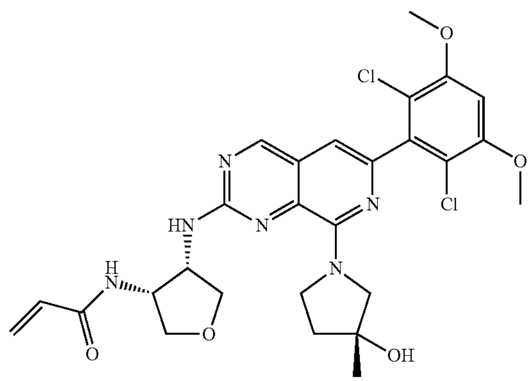 [SMILES: C=CC(=O)N[C@H]1COC[C@H]1Nc1ncc2cc(-c3c(Cl)c(OC)cc(OC)c3Cl)nc(N3CC[C@@](C)(O)C3)c2n1] | N-((3R,4S)-4-((6-(2,6-dichloro-3,5-dimethoxyphenyl)-8-((R)-3-hydroxy-3-methylpyrrolidin-1-yl)pyrido[3,4-d]pyrimidin-2-yl)amino)tetrahydrofuran-3-yl)acrylamide | 589 |
| 780 | 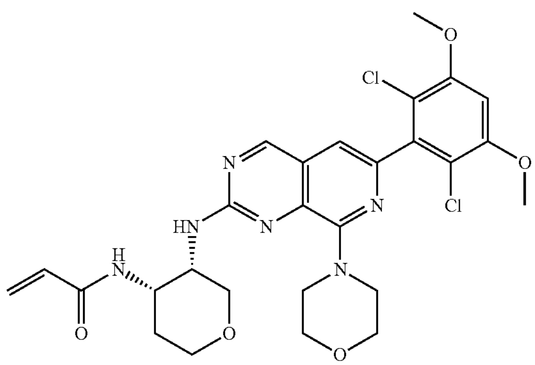 [SMILES: C=CC(=O)N[C@H]1CCOC[C@H]1Nc1ncc2cc(-c3c(Cl)c(OC)cc(OC)c3Cl)nc(N3CCOCC3)c2n1] | N-((3S,4S)-3-((6-(2,6-dichloro-3,5-dimethoxyphenyl)-8-morpholino-pyrido[3,4-d]pyrimidin-2-yl)amino)tetrahydro-2H-pyran-4-yl)acrylamide | 589 |
| 781 | 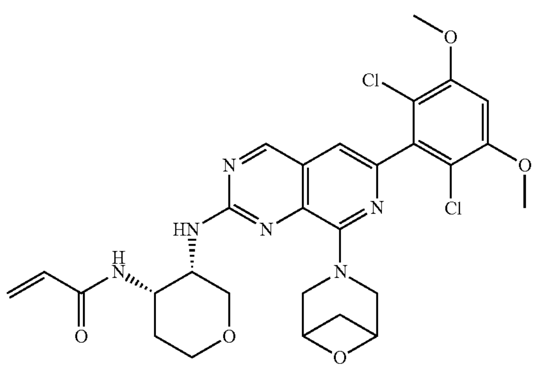 [SMILES: C=CC(=O)N[C@H]1CCOC[C@H]1Nc1ncc2cc(-c3c(Cl)c(OC)cc(OC)c3Cl)nc(N3CC4CC(C3)O4)c2n1] | N-((3S,4S)-3-((8-(6-oxa-3-azabicyclo[3.1.1]heptan-3-yl)-6-(2,6-dichloro-3,5-dimethoxyphenyl)pyrido[3,4-d]pyrimidin-2-yl)amino)tetrahydro-2H-pyran-4-yl)acrylamide | 601 |
| 782 | 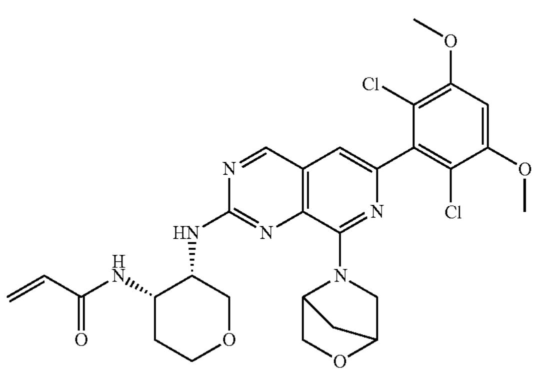 [SMILES: C=CC(=O)N[C@H]1CCOC[C@H]1Nc1ncc2cc(-c3c(Cl)c(OC)cc(OC)c3Cl)nc(N3CC4CC3CO4)c2n1] | N-((3S,4S)-3-((8-(2-oxa-5-azabicyclo[2.2.1]heptan-5-yl)-6-(2,6-dichloro-3,5-dimethoxyphenyl)pyrido[3,4-d]pyrimidin-2-yl)amino)tetrahydro-2H-pyran-4-yl)acrylamide | 601 |

-continued

| Example No. | Compound structure | Compound name | MS: m/z [M + 1]+ |
|---|---|---|---|
| 783 | 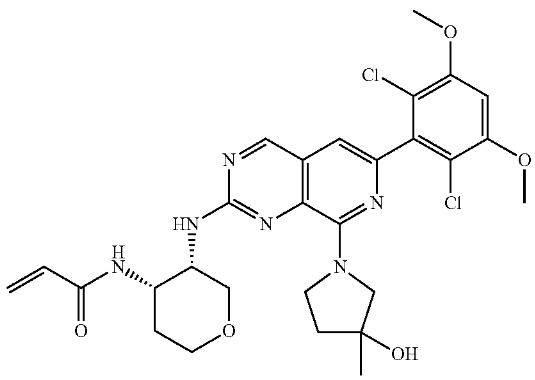 [SMILES: C=CC(=O)N[C@H]1CCOC[C@H]1Nc1ncc2cc(-c3c(Cl)c(OC)cc(OC)c3Cl)nc(N3CCC(C)(O)C3)c2n1] | N-((3S,4S)-3-((6-(2,6-dichloro-3,5-dimethoxyphenyl)-8-(3-hydroxy-3-methylpyrrolidin-1-yl)pyrido[3,4-d]pyrimidin-2-yl)amino)tetrahydro-2H-pyran-4-yl)acrylamide | 603 |
| 784 | 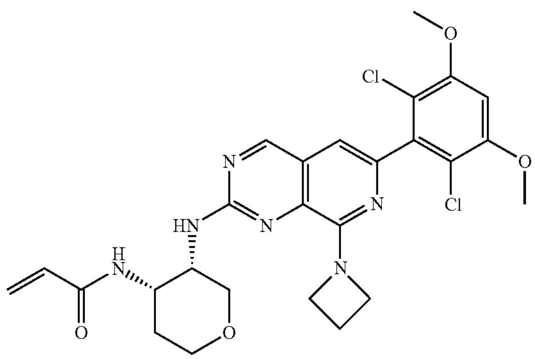 [SMILES: C=CC(=O)N[C@H]1CCOC[C@H]1Nc1ncc2cc(-c3c(Cl)c(OC)cc(OC)c3Cl)nc(N3CCC3)c2n1] | N-((3S,4S)-3-((8-(azetidin-1-yl)-6-(2,6-dichloro-3,5-dimethoxyphenyl)pyrido[3,4-d]pyrimidin-2-yl)amino)tetrahydro-2H-pyran-4-yl)acrylamide | 559 |
| 785 | 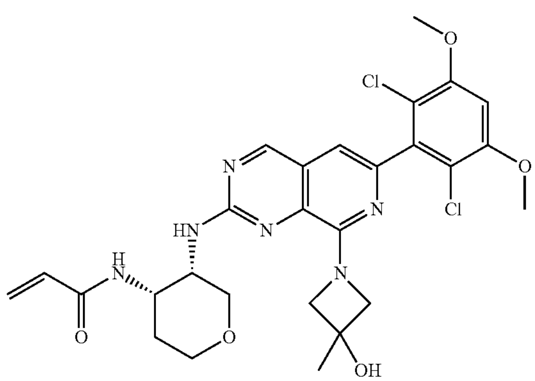 [SMILES: C=CC(=O)N[C@H]1CCOC[C@H]1Nc1ncc2cc(-c3c(Cl)c(OC)cc(OC)c3Cl)nc(N3CC(C)(O)C3)c2n1] | N-((3S,4S)-3-((6-(2,6-dichloro-3,5-dimethoxyphenyl)-8-(3-hydroxy-3-methylazetidin-1-yl)pyrido[3,4-d]pyrimidin-2-yl)amino)tetrahydro-2H-pyran-4-yl)acrylamide | 589 |
| 786 | 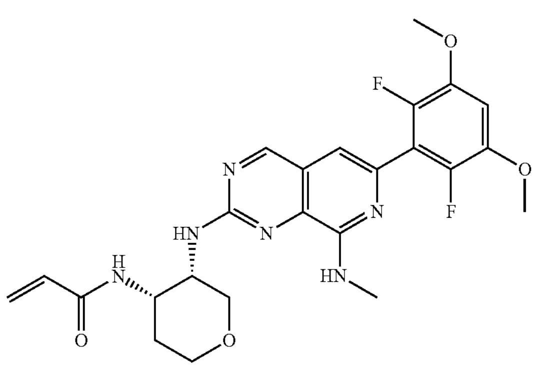 [SMILES: C=CC(=O)N[C@H]1CCOC[C@H]1Nc1ncc2cc(-c3c(F)c(OC)cc(OC)c3F)nc(NC)c2n1] | N-((3S,4S)-3-((6-(2,6-difluoro-3,5-dimethoxyphenyl)-8-(methylamino)pyrido[3,4-d]pyrimidin-2-yl)amino)tetrahydro-2H-pyran-4-yl)acrylamide | 501 |

| Example No. | Compound structure | Compound name | MS: m/z [M + 1]+ |
|---|---|---|---|
| 787 | 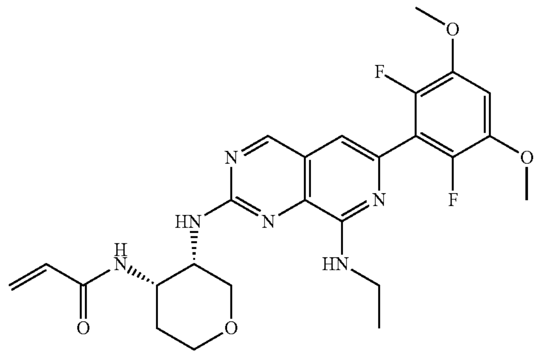 [SMILES: C=CC(=O)N[C@H]1CCOC[C@H]1Nc1ncc2cc(-c3c(F)c(OC)cc(OC)c3F)nc(NCC)c2n1] | N-((3S,4S)-3-((6-(2,6-difluoro-3,5-dimethoxyphenyl)-8-(ethylamino)pyrido[3,4-d]pyrimidin-2-yl)amino)tetrahydro-2H-pyran-4-yl)acrylamide | 515 |
| 788 | 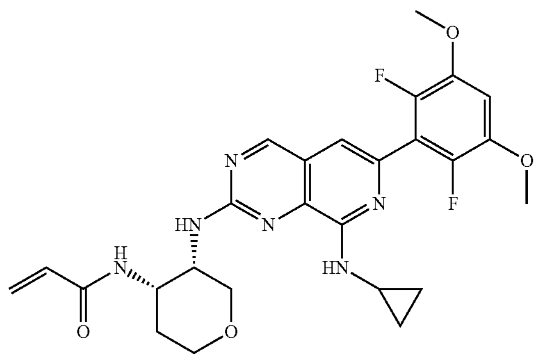 [SMILES: C=CC(=O)N[C@H]1CCOC[C@H]1Nc1ncc2cc(-c3c(F)c(OC)cc(OC)c3F)nc(NC3CC3)c2n1] | N-((3S,4S)-3-((8-(cyclopropylamino)-6-(2,6-difluoro-3,5-dimethoxyphenyl)pyrido[3,4-d]pyrimidin-2-yl)amino)tetrahydro-2H-pyran-4-yl)acrylamide | 527 |
| 789 | 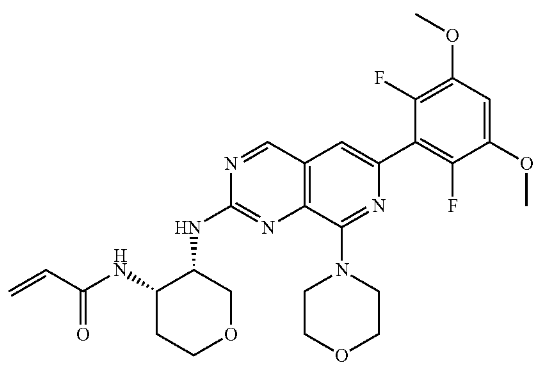 [SMILES: C=CC(=O)N[C@H]1CCOC[C@H]1Nc1ncc2cc(-c3c(F)c(OC)cc(OC)c3F)nc(N3CCOCC3)c2n1] | N-((3S,4)S-3-((6-(2,6-difluoro-3,5-dimethoxyphenyl)-8-morpholinopyrido[3,4-d]pyrimidin-2-yl)amino)tetrahydro-2H-pyran-4-yl)acrylamide | 557 |
| 790 | 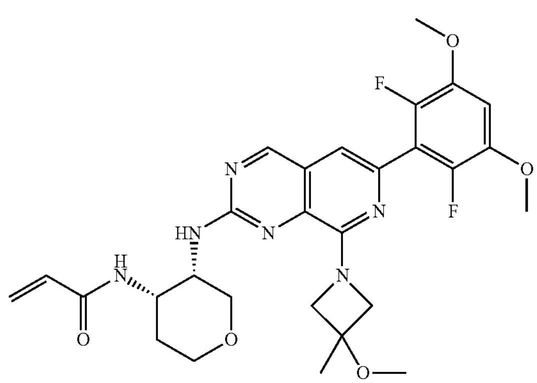 [SMILES: C=CC(=O)N[C@H]1CCOC[C@H]1Nc1ncc2cc(-c3c(F)c(OC)cc(OC)c3F)nc(N3CC(C)(OC)C3)c2n1] | N-((3S,4S)-3-((6-(2,6-difluoro-3,5-dimethoxyphenyl)-8-(3-methoxy-3-methylazetidin-1-yl)pyrido[3,4-d]pyrimidin-2-yl)amino)tetrahydro-2H-pyran-4-yl)acrylamide | 571 |

-continued

| Example No. | Compound structure | Compound name | MS: m/z [M + 1]+ |
|---|---|---|---|
| 791 | 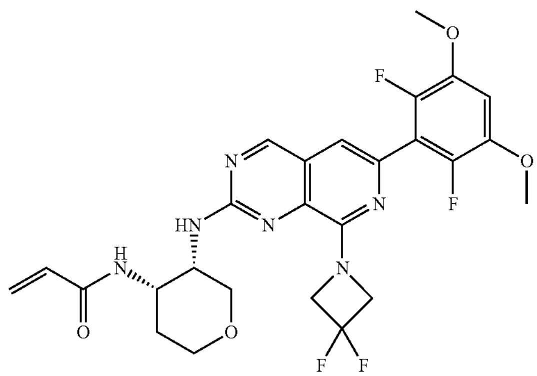 [SMILES: C=CC(=O)N[C@H]1CCOC[C@H]1Nc1ncc2cc(-c3c(F)c(OC)cc(OC)c3F)nc(N3CC(F)(F)C3)c2n1] | N-((3S,4S)-3-((6-(2,6-difluoro-3,5-dimethoxyphenyl)-8-(3,3-difluoroazetidin-1-yl)pyrido[3,4-d]pyrimidin-2-yl)amino)tetrahydro-2H-pyran-4-yl)acrylamide | 563 |
| 792 | 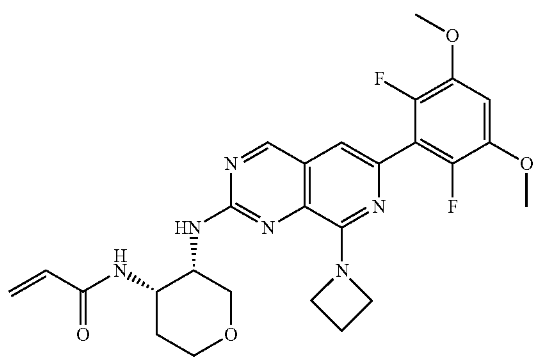 [SMILES: C=CC(=O)N[C@H]1CCOC[C@H]1Nc1ncc2cc(-c3c(F)c(OC)cc(OC)c3F)nc(N3CCC3)c2n1] | N-((3S,4S)-3-((8-(azetidin-1-yl)-6-(2,6-difluoro-3,5-dimethoxyphenyl)pyrido[3,4-d]pyrimidin-2-yl)amino)tetrahydro-2H-pyran-4-yl)acrylamide | 527 |
| 793 | 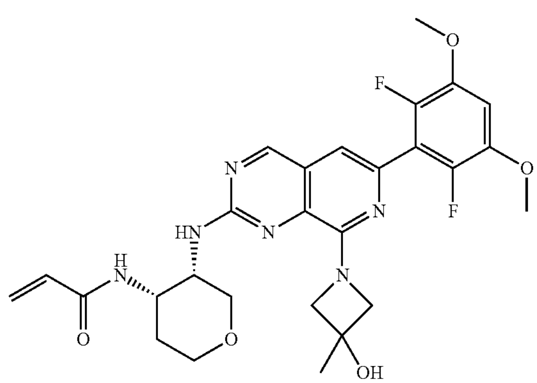 [SMILES: C=CC(=O)N[C@H]1CCOC[C@H]1Nc1ncc2cc(-c3c(F)c(OC)cc(OC)c3F)nc(N3CC(C)(O)C3)c2n1] | N-((3S,4S)-3-((6-(2,6-difluoro-3,5-dimethoxyphenyl)-8-(3-hydroxy-3-methylazetidin-1-yl)pyrido[3,4-d]pyrimidin-2-yl)amino)tetrahydro-2H-pyran-4-yl)acrylamide | 557 |
| 794 | 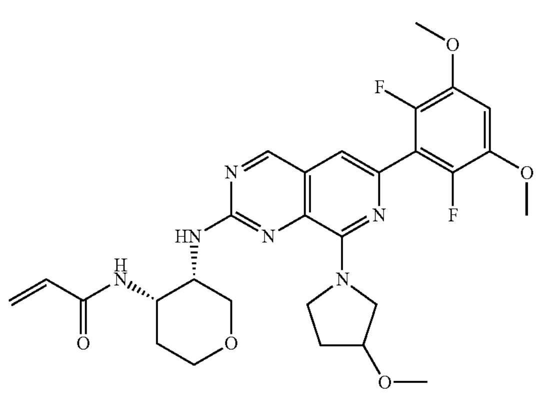 [SMILES: C=CC(=O)N[C@H]1CCOC[C@H]1Nc1ncc2cc(-c3c(F)c(OC)cc(OC)c3F)nc(N3CCC(OC)C3)c2n1] | N-((3S,4S)-3-((6-(2,6-difluoro-3,5-dimethoxyphenyl)-8-(3-methoxypyrrolidin-1-yl)pyrido[3,4-d]pyrimidin-2-yl)amino)tetrahydro-2H-pyran-4-yl)acrylamide | 571 |

-continued

| Example No. | Compound structure | Compound name | MS: m/z [M + 1]+ |
|---|---|---|---|
| 795 | 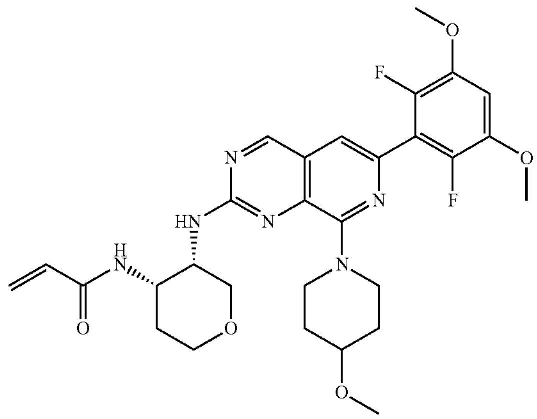 [SMILES: C=CC(=O)N[C@H]1CCOC[C@H]1Nc1ncc2cc(-c3c(F)c(OC)cc(OC)c3F)nc(N3CCC(OC)CC3)c2n1] | N-((3S,4S)-3-((6-(2,6-difluoro-3,5-dimethoxyphenyl)-8-(4-methoxy-piperidin-1-yl)pyrido[3,4-d]pyrimidin-2-yl)amino)tetrahydro-2H-pyran-4-yl)acrylamide | 585 |
| 796 | 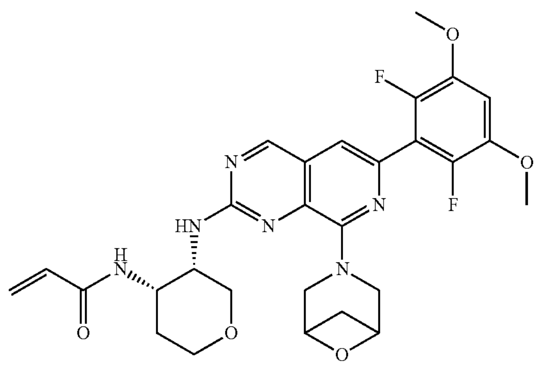 [SMILES: C=CC(=O)N[C@H]1CCOC[C@H]1Nc1ncc2cc(-c3c(F)c(OC)cc(OC)c3F)nc(N3CC4CC(C3)O4)c2n1] | N-((3S,4S)-3-((8-(6-oxa-3-aza-bicyclo[3.1.1]heptan-3-yl)-6-(2,6-difluoro-3,5-dimethoxyphenyl)pyrido[3,4-d]pyrimidin-2-yl)amino)tetrahydro-2H-pyran-4-yl)acrylamide | 569 |
| 797 | 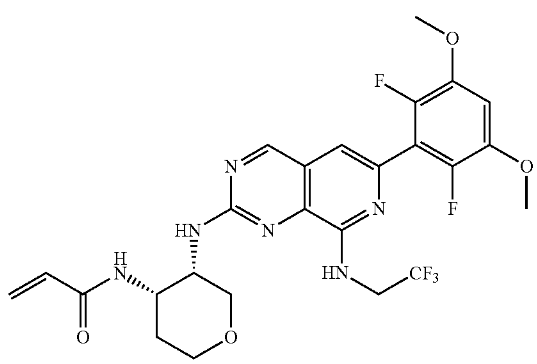 [SMILES: C=CC(=O)N[C@H]1CCOC[C@H]1Nc1ncc2cc(-c3c(F)c(OC)cc(OC)c3F)nc(NCC(F)(F)F)c2n1] | N-((3S,4S)-3-((6-(2,6-difluoro-3,5-dimethoxyphenyl)-8-((2,2,2-trifluoroethyl)amino)pyrido[3,4-d]pyrimidin-2-yl)amino)tetrahydro-2H-pyran-4-yl)acrylamide | 569 |
| 798 | 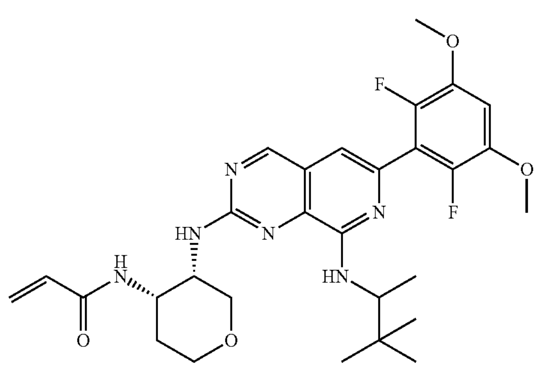 [SMILES: C=CC(=O)N[C@H]1CCOC[C@H]1Nc1ncc2cc(-c3c(F)c(OC)cc(OC)c3F)nc(NC(C)C(C)(C)C)c2n1] | N-((3S,4S)-3-((6-(2,6-difluoro-3,5-dimethoxyphenyl)-8-((3,3-dimethylbutan-2-yl)amino)pyrido[3,4-d]pyrimidin-2-yl)amino)tetrahydro-2H-pyran-4-yl)acrylamide | 571 |

-continued

| Example No. | Compound structure | Compound name | MS: m/z [M + 1]+ |
|---|---|---|---|
| 799 | 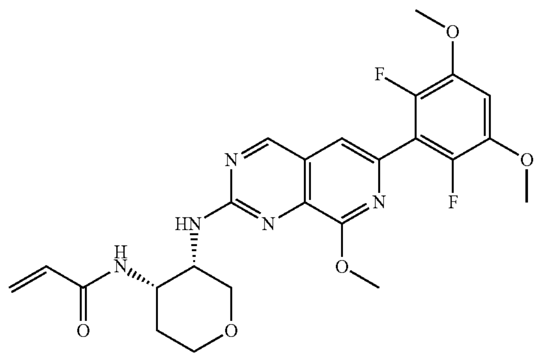 [SMILES: C=CC(=O)N[C@H]1CCOC[C@H]1Nc1ncc2cc(-c3c(F)c(OC)cc(OC)c3F)nc(OC)c2n1] | N-((3S,4S)-3-((6-(2,6-difluoro-3,5-dimethoxyphenyl)-8-methoxypyrido[3,4-d]pyrimidin-2-yl)amino)tetrahydro-2H-pyran-4-yl)acrylamide | 502 |
| 800 | 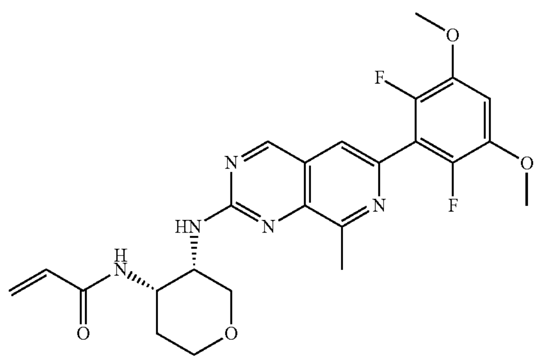 [SMILES: C=CC(=O)N[C@H]1CCOC[C@H]1Nc1ncc2cc(-c3c(F)c(OC)cc(OC)c3F)nc(C)c2n1] | N-((3S,4S)-3-((6-(2,6-difluoro-3,5-dimethoxyphenyl)-8-methylpyrido[3,4-d]pyrimidin-2-yl)amino)tetrahydro-2H-pyran-4-yl)acrylamide | 486 |
| 801 | 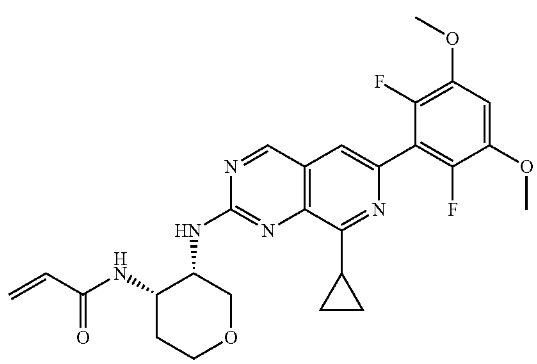 [SMILES: C=CC(=O)N[C@H]1CCOC[C@H]1Nc1ncc2cc(-c3c(F)c(OC)cc(OC)c3F)nc(C3CC3)c2n1] | N-((3S,4)S-3-((8-cyclopropyl-6-(2,6-difluoro-3,5-dimethoxyphenyl)pyrido[3,4-d]pyrimidin-2-yl)amino)tetrahydro-2H-pyran-4-yl)acrylamide | 512 |
| 802 | 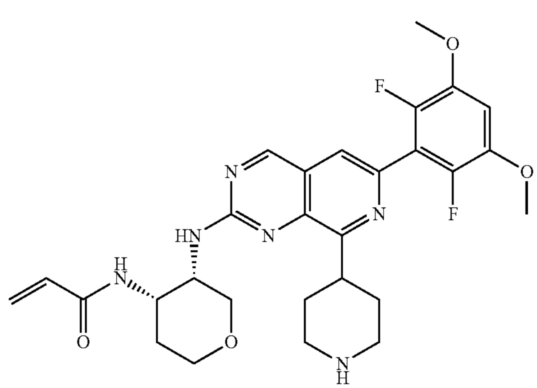 [SMILES: C=CC(=O)N[C@H]1CCOC[C@H]1Nc1ncc2cc(-c3c(F)c(OC)cc(OC)c3F)nc(C3CCNCC3)c2n1] | N-((3S,4S)-3-((6-(2,6-difluoro-3,5-dimethoxyphenyl)-8-(piperidin-4-yl)pyrido[3,4-d]pyrimidin-2-yl)amino)tetrahydro-2H-pyran-4-yl)acrylamide | 555 |

| Example No. | Compound structure | Compound name | MS: m/z [M + 1]+ |
|---|---|---|---|
| 803 | 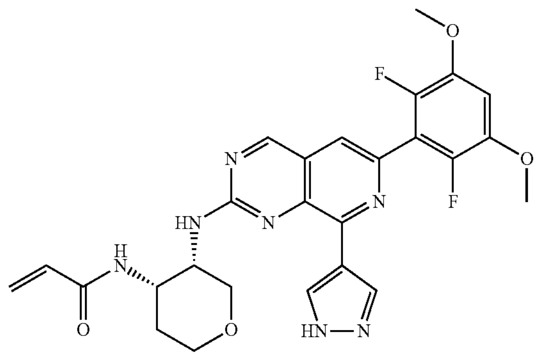 [SMILES: C=CC(=O)N[C@H]1CCOC[C@H]1Nc1ncc2cc(-c3c(F)c(OC)cc(OC)c3F)nc(-c3cn[nH]c3)c2n1] | N-((3S,4S)-3-((6-(2,6-difluoro-3,5-dimethoxyphenyl)-8-(1H-pyrazol-4-yl)pyrido[3,4-d]pyrimidin-2-yl)amino)tetrahydro-2H-pyran-4-yl)acrylamide | 538 |
| 804 | 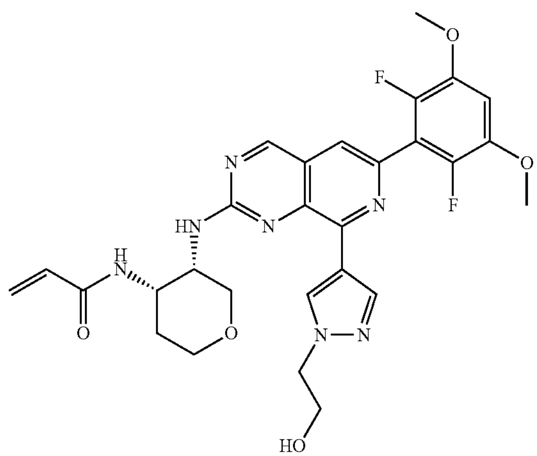 [SMILES: C=CC(=O)N[C@H]1CCOC[C@H]1Nc1ncc2cc(-c3c(F)c(OC)cc(OC)c3F)nc(-c3cnn(CCO)c3)c2n1] | N-((3S,4S)-3-((6-(2,6-difluoro-3,5-dimethoxyphenyl)-8-(1-(2-hydroxyethyl)-1H-pyrazol-4-yl)pyrido[3,4-d]pyrimidin-2-yl)amino)tetrahydro-2H-pyran-4-yl)acrylamide | 582 |
| 805 | 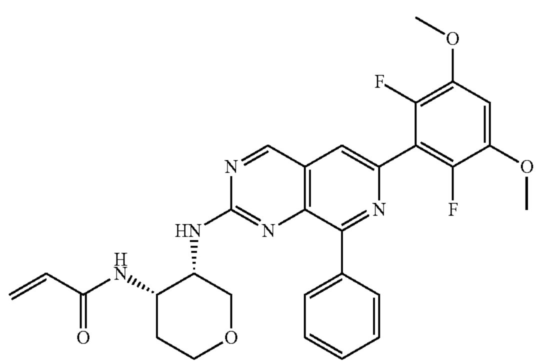 [SMILES: C=CC(=O)N[C@H]1CCOC[C@H]1Nc1ncc2cc(-c3c(F)c(OC)cc(OC)c3F)nc(-c3ccccc3)c2n1] | N-((3S,4S)-3-((6-(2,6-difluoro-3,5-dimethoxyphenyl)-8-phenylpyrido[3,4-d]pyrimidin-2-yl)amino)tetrahydro-2H-pyran-4-yl)acrylamide | 548 |
| 806 | 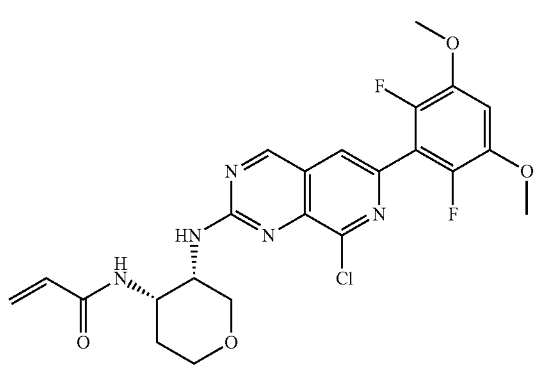 [SMILES: C=CC(=O)N[C@H]1CCOC[C@H]1Nc1ncc2cc(-c3c(F)c(OC)cc(OC)c3F)nc(Cl)c2n1] | N-((3S,4S)-3-((8-chloro-6-(2,6-difluoro-3,5-dimethoxyphenyl)pyrido[3,4-d]pyrimidin-2-yL)amino)tetrahydro-2H-pyran-4-yl)acrylamide | 506 |

Example 715 Preparation of N-(5-(6-(2,6-dichloro-3,5-dimethoxyphenyl)pyrido[3,4-d]pyrimidin-2-yl)-1-(2-methoxyethyl)-1H-pyrazol-4-yl)acrylamide

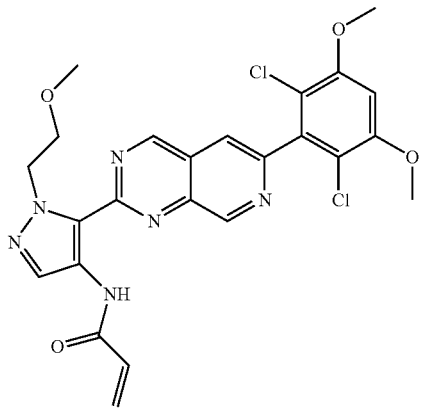 [SMILES: C=CC(=O)Nc1cnn(CCOC)c1-c1ncc2cc(-c3c(Cl)c(OC)cc(OC)c3Cl)ncc2n1]

Step 1: Preparation of 6-(2,6-dichloro-3,5-dimethoxyphenyl)-2-(1-(2-methoxyethyl)-4-nitro-1H-pyrazol-5-yl)pyrido[3,4-d]pyrimidine

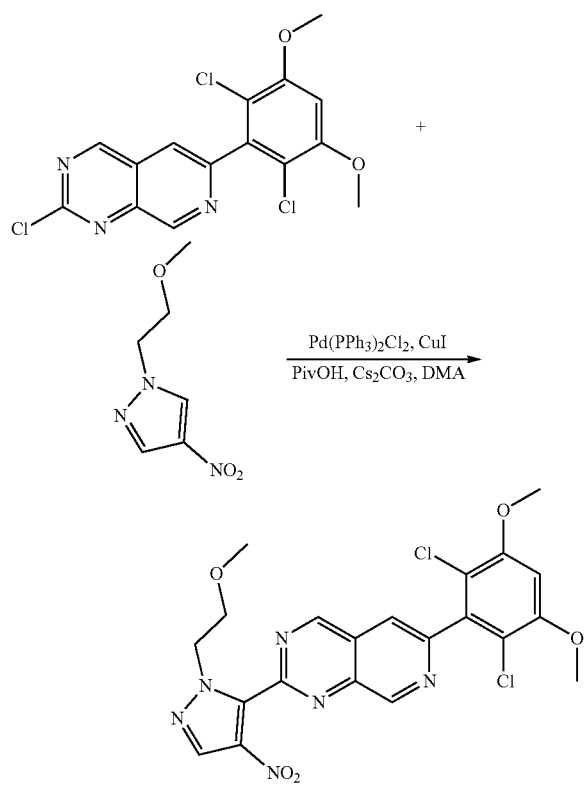

1-(2-methoxyethyl)-4-nitro-H-pyrazole (84 mg, 0.49 mmol) and 2-chloro-6-(2,6-dichloro-3,5-dimethoxyphenyl)pyrido[3,4-d]pyrimidine (200 mg, 0.54 mmol) were dissolved into DMA (15 mL), then CuI (112 mg, 0.59 mmol), PivOH (15 mg, 0.15 mmol), K₂CO₃ (88 mg, 0.64 mmol) and Pd(PPh₃)₂Cl₂ (34 mg, 0.05 mmol) were added, the mixture was heated to 140° C. under N₂ and stirred for 1 h. The reaction was completed, and the mixture was concentrated to remove the solvent by reduced pressure and separated by fast silica gel column (PE/EA 2:1) to obtain compound 6-(2,6-dichloro-3,5-dimethoxyphenyl)-2-(1-(2-methoxyethyl)-4-nitro-1H-pyrazol-5-yl)pyrido[3,4-d]pyrimidine (103 mg, yield 42%). MS m/z (ESI): 505 [M+1]⁺.

Step 2: Preparation of 5-(6-(2,6-dichloro-3,5-dimethoxyphenyl)pyrido[3,4-d]pyrimidin-2-yl)-1-(2-methoxyethyl)-1H-pyrazolyl-4-amine

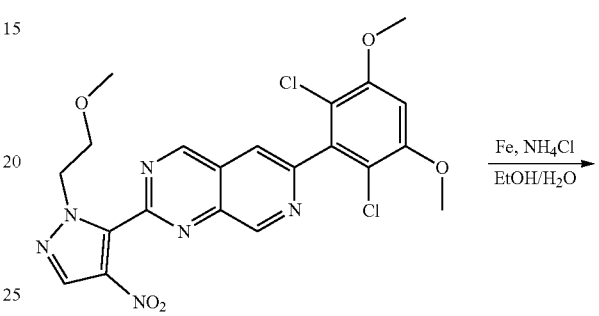

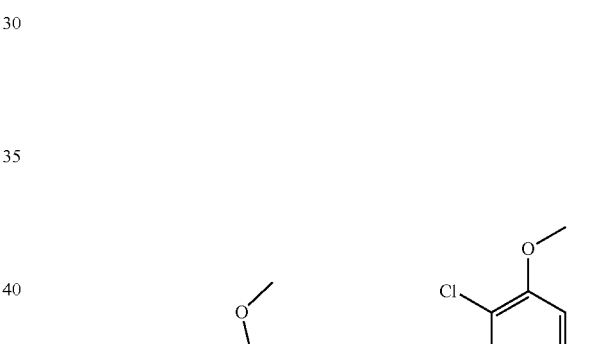

6-(2,6-dichloro-3,5-dimethoxyphenyl)-2-(1-(2-methoxyethyl)-4-nitro-1H-pyrazol-5-yl)pyrido[3,4-d]pyrimidine (103 mg, 0.20 mmol) was dissolved in the mixture of EtOH and H₂O (10/3 mL), then Fe powder (114 mg, 2.04 mmol) and NH₄Cl (109 mg, 2.04 mmol) were added, the mixture was heated to reflux and stirred for 2 h. After the reaction was completed, the reaction liquid was extracted for three times with dichloromethane. The organic phases were combined, washed with water, then a saturated aqueous sodium chloride solution, dried over anhydrous sodium sulfate, filtrated and concentrated. The crude product was separated by fast silica gel column chromatography (CH₂Cl₂/MeOH 10:1) to obtain compound 5-(6-(2,6-dichloro-3,5-dimethoxyphenyl)pyrido[3,4-d]pyrimidin-2-yl)-1-(2-methoxyethyl)-1H-pyrazolyl-4-amine (12 mg, yield 12%). MS m/z (ESI): 476 [M+1]⁺.

895

Step 3: Preparation of N-(5-(6-(2,6-dichloro-3,5-dimethoxyphenyl)pyrido[3,4-d]pyrimidin-2-yl)1-2-methoxyethyl)-1H-pyrazol-4-yl)acrylamide

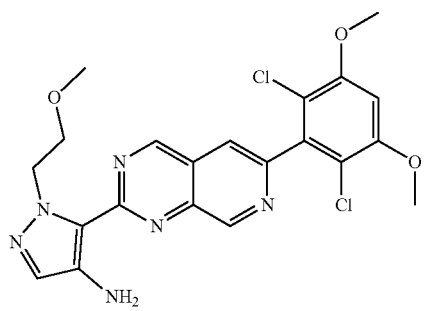

+

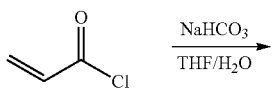

896

-continued

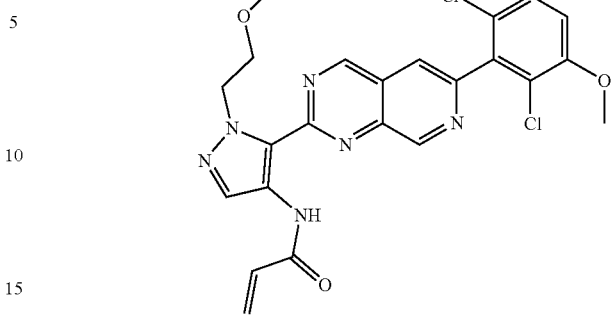

5-(6-(2,6-dichloro-3,5-dimethoxyphenyl)pyrido[3,4-d]pyrimidin-2-yl)-1-(2-methoxyethyl)-1H-pyrazolyl-4-amine (12 mg, 0.025 mmol) was dissolved in the mixture of THF and H$_2$O (4:1, 4 mL), then NaHCO$_3$ (11 mg, 0.13 mmol) was added, the mixture was cooled under ice water bath, Acryloyl chloride (2.3 mg, 0.025 mmol) as added, and the mixture was stirred at 0° C. for 10 min. After the reaction was completed, the reaction liquid w as concentrated by reduced pressure, separated by silica gel column chromatography (CH$_2$Cl$_2$/MeOH 10:1) to obtain compound N-(5-(6-(2,6-dichloro-3,5-dimethoxyphenyl)pyrido[3,4-d]pyrimidin-2-yl)-1-(2-methoxyethyl)-1H-pyrazol-4-yl)acrylamide (4.8 mg, yield 36%). MS m/z (ESI): 529 [M+1]$^+$.

$^1$H NMR (400 MH-z, CDCl$_3$) δ 10.71 (s, 1H), 9.63 (s, 1H) 9.60 (s, 1H), 8.61 (s, 1H), 7.80 (s, 1H), 6.72 (s, 1H), 6.49 (d, J=16.7 Hz, 1H), 6.40 (dd, J=16.9, 9.7 Hz, 1H), 5.84 (d, J=9.7 Hz 1H), 5.21 (t, J=6.0 Hz, 2H), 4.00 (s, 7H), 3.89 (t, J=5.9 Hz, 2H), 3.35 (s, 3H).

Examples 716-729 were prepared by referring to the synthesis method of Example 715.

| Example No. | Compound structure | Compound name | MS: m/z [M + 1]$^+$ |
|---|---|---|---|
| 716 | 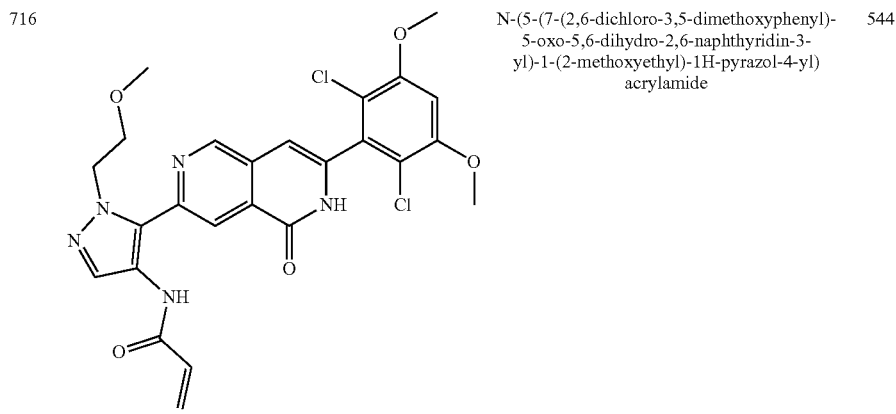 | N-(5-(7-(2,6-dichloro-3,5-dimethoxyphenyl)-5-oxo-5,6-dihydro-2,6-naphthyridin-3-yl)-1-(2-methoxyethyl)-1H-pyrazol-4-yl)acrylamide | 544 |

-continued

| Example No. | Compound structure | Compound name | MS: m/z [M + 1]+ |
|---|---|---|---|
| 717 | 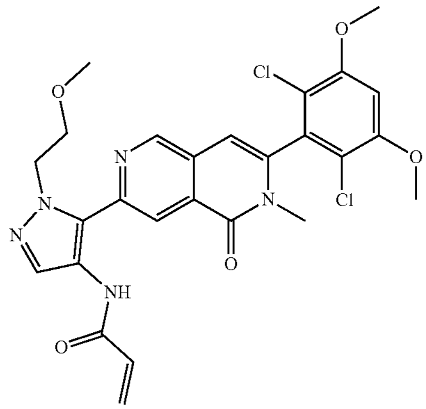 [SMILES: C=CC(=O)Nc1cnn(CCOC)c1-c1cc2c(=O)n(C)c(-c3c(Cl)c(OC)cc(OC)c3Cl)cc2cn1] | N-(5-(7-(2,6-dichloro-3,5-dimethoxyphenyl)-6-methyl-5-oxo-5,6-dihydro-2,6-naphthyridin-3-yl)-1-(2-methoxyethyl)-1H-pyrazol-4-yl)acrylamide | 558 |
| 718 | 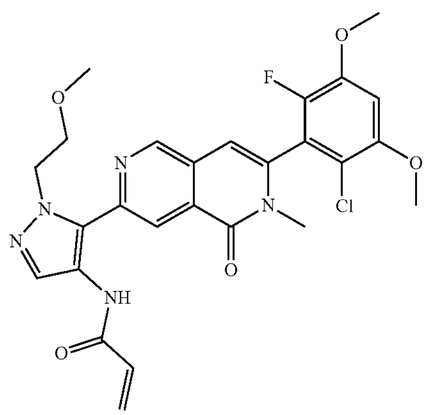 [SMILES: C=CC(=O)Nc1cnn(CCOC)c1-c1cc2c(=O)n(C)c(-c3c(F)c(OC)cc(OC)c3Cl)cc2cn1] | N-(5-(7-(2-chloro-6-fluoro-3,5-dimethoxyphenyl)-6-methyl-5-oxo-5,6-dihydro-2,6-naphthyridin-3-yl)-1-(2-methoxyethyl)-1H-pyrazol-4-yl)acrylamide | 542 |
| 719 | 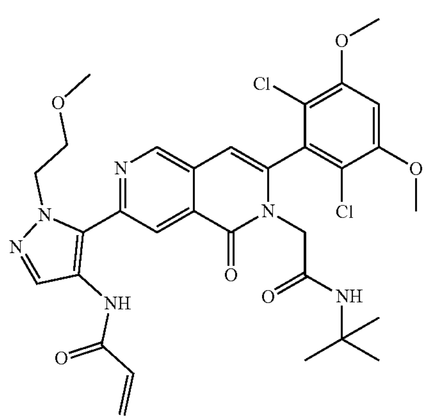 [SMILES: C=CC(=O)Nc1cnn(CCOC)c1-c1cc2c(=O)n(CC(=O)NC(C)(C)C)c(-c3c(Cl)c(OC)cc(OC)c3Cl)cc2cn1] | N-(5-(6-(2-(tert-butylamino)-2-oxoethyl)-7-(2,6-dichloro-3,5-dimethoxyphenyl)-5-oxo-5,6-dihydro-2,6-naphthyridin-3-yl)-1-(2-methoxyethyl)-1H-pyazol-4-yl)acrylamide | 657 |

-continued

| Example No. | Compound structure | Compound name | MS: m/z [M + 1]+ |
|---|---|---|---|
| 720 | 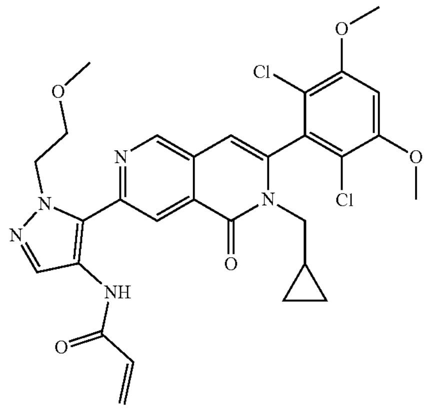 [SMILES: C=CC(=O)Nc1cnn(CCOC)c1-c1cc2c(=O)n(CC3CC3)c(-c3c(Cl)c(OC)cc(OC)c3Cl)cc2cn1] | N-(5-(6-(cyclopropylmethyl)-7-(2,6-dichloro-3,5-dimethoxyphenyl)-5-oxo-5,6-dihydro-2,6-naphthyridin-3-yl)-1-(2-methoxyethyl)-1H-pyrazol-4-yl)acrylamide | 598 |
| 721 | 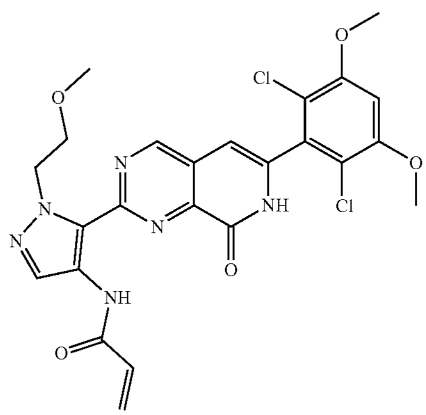 [SMILES: C=CC(=O)Nc1cnn(CCOC)c1-c1ncc2cc(-c3c(Cl)c(OC)cc(OC)c3Cl)[nH]c(=O)c2n1] | N-(5-(6-(2,6-dichloro-3,5-dimethoxyphenyl)-8-oxo-7,8-dihydropyrido[3,4-d]pyrimidin-2-yl)-1-(2-methoxyethyl)-1H-pyrazol-4-yl)acrylamide | 545 |
| 722 | 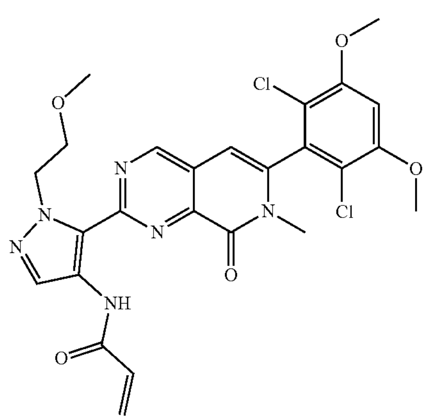 [SMILES: C=CC(=O)Nc1cnn(CCOC)c1-c1ncc2cc(-c3c(Cl)c(OC)cc(OC)c3Cl)n(C)c(=O)c2n1] | N-(5-(6-(2,6-dichloro-3,5-dimethoxyphenyl)-7-methyl-8-oxo-7,8-dihydropyrido[3,4-d]pyrimidin-2-yl)-1-(2-methoxyethyl)-1H-pyrazol-4-yl)acrylamide | 559 |

-continued

| Example No. | Compound structure | Compound name | MS: m/z [M + 1]+ |
|---|---|---|---|
| 723 | 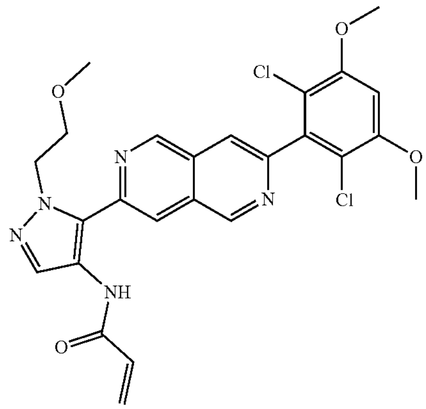 [SMILES: C=CC(=O)Nc1cnn(CCOC)c1-c1cc2cnc(-c3c(Cl)c(OC)cc(OC)c3Cl)cc2cn1] | N-(5-(7-(2,6-dichloro-3,5-dimethoxyphenyl)-2,6-naphthyridin-3-yl)-1-(2-methoxyethyl)-1H-pyrazol-4-yl)acrylamide | 528 |
| 724 | 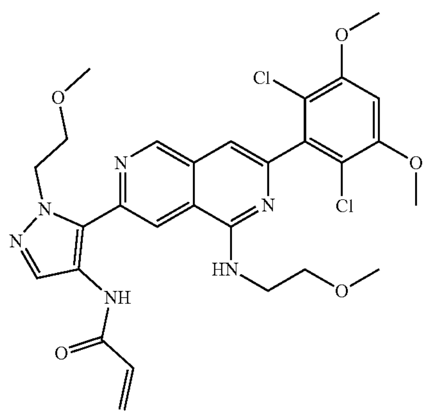 [SMILES: C=CC(=O)Nc1cnn(CCOC)c1-c1cc2c(NCCOC)nc(-c3c(Cl)c(OC)cc(OC)c3Cl)cc2cn1] | N-(5-(7-(2,6-dichloro-3,5-dimethoxyphenyl)-2,6-naphthyridin-3-yl)-1-(2-methoxyethyl)-1H-pyrazol-4-yl)acrylamide | 601 |
| 725 | 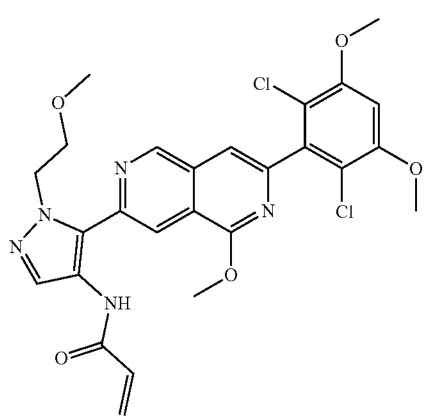 [SMILES: C=CC(=O)Nc1cnn(CCOC)c1-c1cc2c(OC)nc(-c3c(Cl)c(OC)cc(OC)c3Cl)cc2cn1] | N-(5-(7-(2,6-dichloro-3,5-dimethoxyphenyl)-5-methoxy-2,6-naphthyridin-3-yl)-1-(2-methoxyethyl)-1H-pyrazol-4-yl)acrylamide | 558 |

-continued

| Example No. | Compound structure | Compound name | MS: m/z [M + 1]+ |
|---|---|---|---|
| 726 | 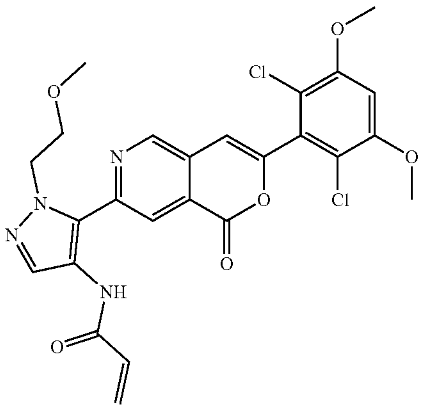 [SMILES: C=CC(=O)Nc1cnn(CCOC)c1-c1cc2c(=O)oc(-c3c(Cl)c(OC)cc(OC)c3Cl)cc2cn1] | N-(5-(3-(2,6-dichloro-3,5-dimethoxyphenyl)-1-oxo-1H-pyrano[4,3-c]pyridin-7-yl)-1-(2-methoxyethyl)-1H-pyrazol-4-yl)acrylamide | 545 |
| 727 | 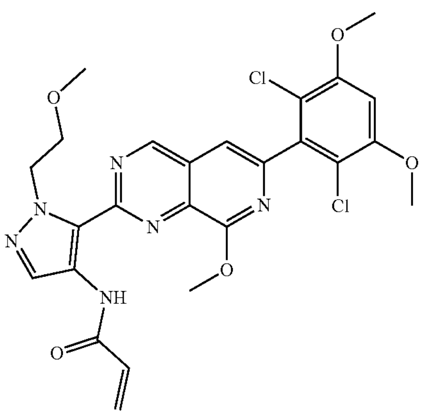 [SMILES: C=CC(=O)Nc1cnn(CCOC)c1-c1ncc2cc(-c3c(Cl)c(OC)cc(OC)c3Cl)nc(OC)c2n1] | N-(5-(6-(2,6-dichloro-3,5-dimethoxyphenyl)-8-methoxypyrido[3,4-d]pyrimidin-2-yl)-1-(2-methoxyethyl)-1H-pyrazol-4-yl)acrylamide | 560 |
| 728 | 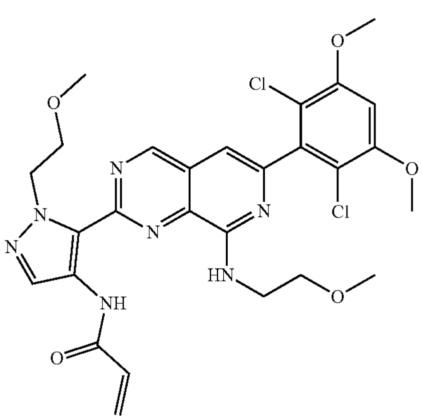 [SMILES: C=CC(=O)Nc1cnn(CCOC)c1-c1ncc2cc(-c3c(Cl)c(OC)cc(OC)c3Cl)nc(NCCOC)c2n1] | N-(5-(6-(2,6-dichloro-3,5-dimethoxyphenyl)-8-((2-methoxyethyl)amino)pyrido[3,4-d]pyrimidin-2-yl)-1-(2-methoxyethyl)-1H-pyrazol-4-yl)acrylamide | 602 |

| Example No. | Compound structure | Compound name | MS: m/z [M + 1]+ |
|---|---|---|---|
| 729 | 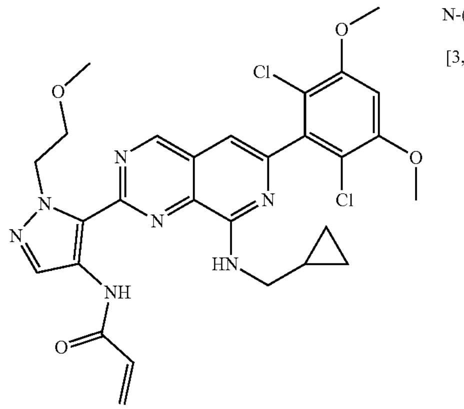 | N-(5-(8-((cyclopropylmethyl)amino)-6-(2,6-dichloro-3,5-dimethoxyphenyl)pyrido[3,4-d]pyrimidin-2-yl)-1-(2-methoxyethyl)-1H-pyrazol-4-yl)acrylamide | 598 |

Example 730 Preparation of N-((3-(2,6-dichloro-3,5-dimethoxyphenyl)-1-methyl-2-oxo-1,2-dihydro-1,6-naphthyridin-7-yl)methyl)acrylamide

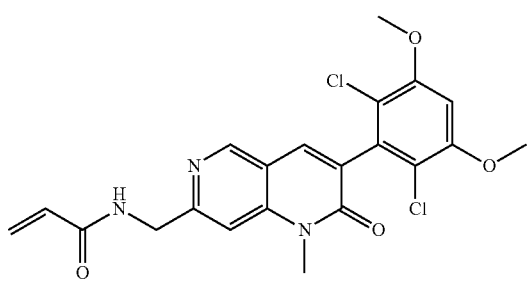 [SMILES: C=CC(=O)NCc1cc2c(cn1)cc(-c1c(Cl)c(OC)cc(OC)c1Cl)c(=O)n2C]

Step 1: Preparation of 3-(2,6-dichloro-3,5-dimethoxyphenyl)-1-methyl-2-oxo-1,2-dihydro-1,6-naphthyridin-7-carbonitrile 7-chloro-3-(2,6-dichloro-3,5-dimethoxyphenyl)-1-methyl-1,6-naphthyridin-2(1H)-one (250.0 mg, 0.626 mmol), Zn(CN)$_2$ (110 mg, 0.938 mmol) and 1,1'-bis(diphenylphosphino)ferrocene (34.7 mg, 0.063 mmol) were added to the mixture of DMF and H$_2$O (5 mL, 100:1), then Pd$_2$(dba)$_3$ (28.7 mg, 0.031 mmol) was added under N$_2$, the mixture was heated to 12 0° C. and stirred for 20 h. The reaction was completed, and the mixture was cooled to room temperature, diluted with water and extracted with EtOAc. The organic phase was washed with saturated brine, dried over anhydrous sodium sulfate, filtrated, concentrated and separated by silica gel column chromatography (Eluent: PE/EtOAc=10-25%) to obtain compound 3-(2,6-dichloro-3,5-dimethoxyphenyl)-1-methyl-2-oxo-1,2-dihydro-1,6-naphthyridin-7-carbonitrile (75 mg, yield: 28%). MS m/z (ESI): 390.0 [M+H]+.

Step 2: Preparation of 7-(aminomethyl)-3-(2,6-dichloro-3,5-dimethoxyphenyl)-1-methyl-1,6-naphthyridin-2(1H)-one

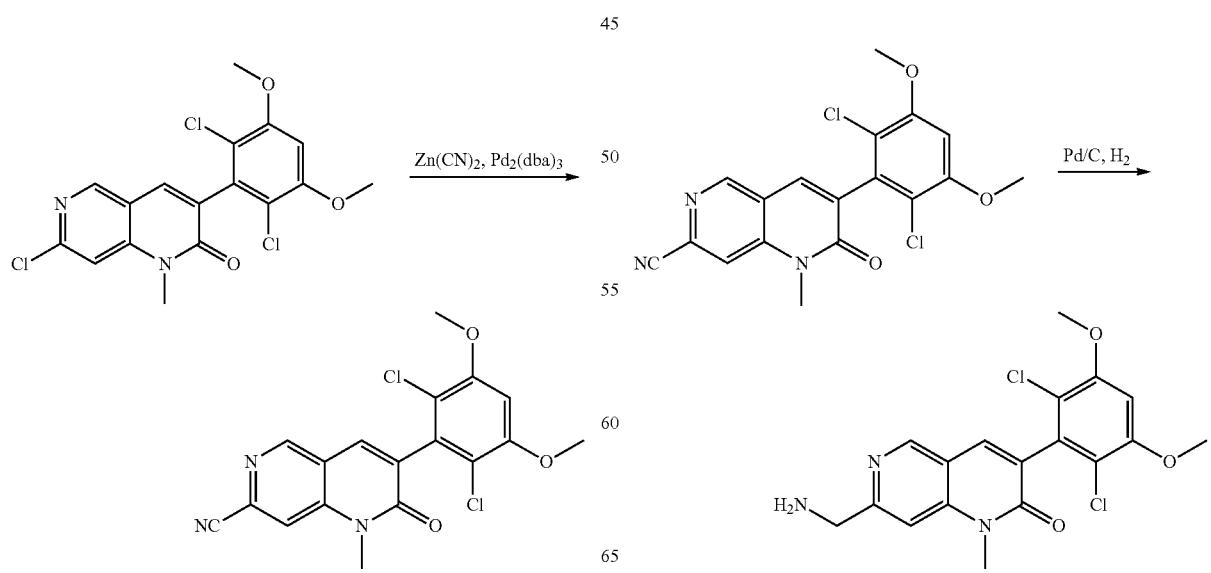

3-(2,6-dichloro-3,5-dimethoxyphenyl)-1-methyl-2-carbonyl-1,2-dihydro-1,6-naphthyridin-7-carbonitrile (15 mg, 0.038 mmol) was dissolved in methanol (3 mL) and concentrated hydrochloric acid (15 mL) and 10% Pd/C (catalytic amount) were added, the mixture was stirred at room temperature for 2 h under H₂, the reaction was completed. The reaction liquid was filtrated and evaporated in vacuo to obtain the crude product 7-(aminomethyl)-3-(2,6-dichloro-3,5-dimethoxyphenyl)-1-methyl-1,6-naphthyridin-2(1H)-one, which can be directly used in the next reaction. MS m/z (ESI): 394.0 [M+H]⁺.

Step 3: Preparation of N-((3-(2,6-dichloro-3,5-dimethoxyphenyl)-1-methyl-2-oxo-1,2-dihydro-1,6-naphthyridin-7-yl)methyl)acrylamide

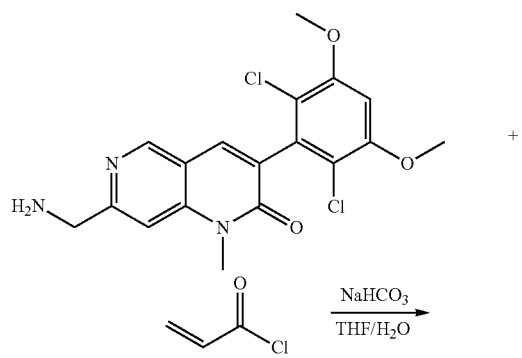

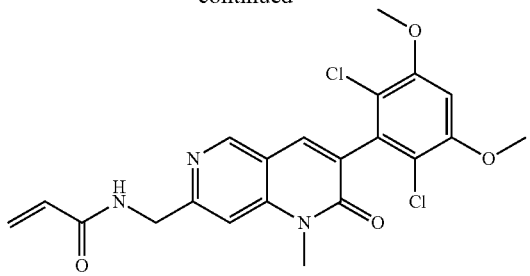

At 0° C., acryloyl chloride (3.8 mg, 0.042 mmol) was added to a solution of 7-(aminomethyl)-3-(2,6-dichloro-3,5-dimethoxyphenyl)-1-methyl-, 6-naphthyridin-2(1H)-one (the crude product, 0.038 mmol) and NaHCO₃ (19.0 mg, 0.230 mmol) in the mixture of THF and H₂O (0.8 mL/0.2 mL), the mixture was stirred for 10 min At 0° C. The reaction liquid was diluted with EtOAc (5 mL), washed with saturated brine, dried over anhydrous sodium sulfate, filtrated, concentrated and separated by a preparative TLC (Eluent: CH₂Cl₂/MeOH=10:1) to obtain compound N-((3-(2,6-dichloro-3,5-dimethoxyphenyl)-1-methyl-2-oxo-1,2-dihydro-1,6-naphthyridin-7-yl)methyl)acrylamide (1.1 mg, two-step yield: 6%).

¹H NMR (400 MHz, Chloroform-d) δ 8.75 (s, 1H), 7.68 (s, 1H), 7.40 (s, 1H), 6.65 (s, 1H), 6.38-6.32 (m, 1H), 6.27-6.21 (m, 1H), 5.73-5.69 (m, 1H), 5.30 (s, 1H), 4.81 (d, J=5.6 Hz, 2H), 3.96 (s, 6H), 3.78 (s, 3H):

MS m/z (ESI): 448.0 [M+H]⁺.

Examples 731-751 were prepared referring to the synthesis method of Example 730.

| Example No. | Compound structure | Compound name | MS: m/z [M + 1]⁺ |
|---|---|---|---|
| 731 | 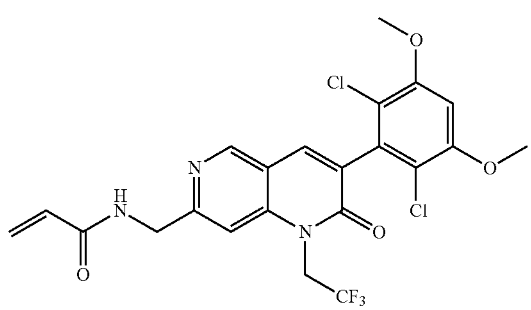 [SMILES: C=CC(=O)NCc1cc2c(cn1)cc(-c1c(Cl)c(OC)cc(OC)c1Cl)c(=O)n2CC(F)(F)F] | N-((3-(2,6-dichloro-3,5-dimethoxyphenyl)-2-oxo-1-(2,2,2-trifluoroethyl)-1,2-dihydro-1,6-naphthyridin-7-yl)methyl)acrylamide | 516 |
| 732 | 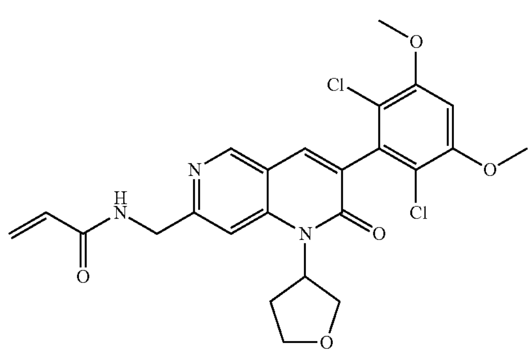 [SMILES: C=CC(=O)NCc1cc2c(cn1)cc(-c1c(Cl)c(OC)cc(OC)c1Cl)c(=O)n2C1CCOC1] | N-((3-(2,6-dichloro-3,5-dimethoxyphenyl)-2-oxo-1-(tetrahydrofuran-3-yl)-1,2-dihydro-1,6-naphthyridin-7-yl)methyl)acrylamide | 504 |

-continued

| Example No. | Compound structure | Compound name | MS: m/z [M + 1]+ |
|---|---|---|---|
| 733 | 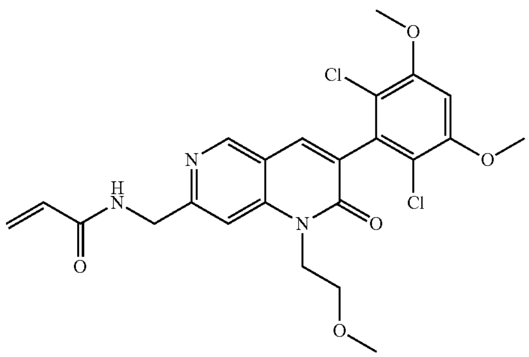 [SMILES: C=CC(=O)NCc1cc2c(cn1)cc(-c1c(Cl)c(OC)cc(OC)c1Cl)c(=O)n2CCOC] | N-((3-(2,6-dichloro-3,5-dimethoxyphenyl)-1-(2-methoxyethyl)-2-oxo-1,2-dihydro-1,6-naphthyridin-7-yl)methyl)acrylamide | 492 |
| 734 | 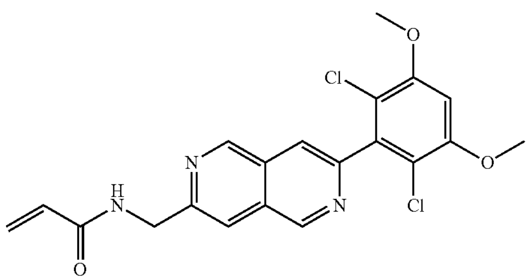 [SMILES: C=CC(=O)NCc1cc2cnc(-c3c(Cl)c(OC)cc(OC)c3Cl)cc2cn1] | N-((7-(2,6-dichloro-3,5-dimethoxyphenyl)-2,6-naphthyridin-3-yl)methyl)acrylamide | 418 |
| 735 | 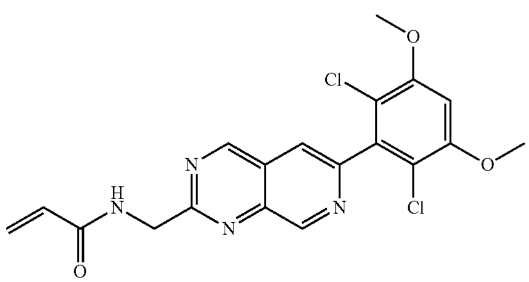 [SMILES: C=CC(=O)NCc1ncc2cc(-c3c(Cl)c(OC)cc(OC)c3Cl)ncc2n1] | N-((6-(2,6-dichloro-3,5-dimethoxyphenyl)pyrido[3,4-d]pyrimidin-2-yl)methyl)acrylamide | 419 |
| 736 | 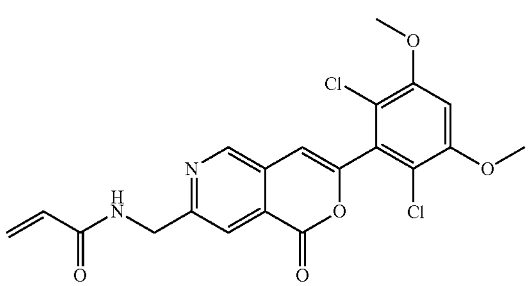 [SMILES: C=CC(=O)NCc1cc2c(=O)oc(-c3c(Cl)c(OC)cc(OC)c3Cl)cc2cn1] | N-((3-(2,6-dichloro-3,5-dimethoxyphenyl)-1-oxo-1H-pyrano[4,3-c]pyridin-7-yl)methyl)acrylamide | 435 |
| 737 | 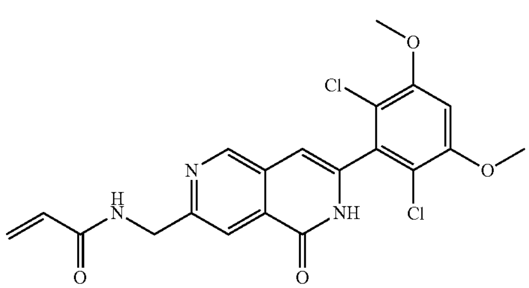 [SMILES: C=CC(=O)NCc1cc2c(=O)[nH]c(-c3c(Cl)c(OC)cc(OC)c3Cl)cc2cn1] | N-((7-(2,6-dichloro-3,5-dimethoxyphenyl)-5-oxo-5,6-dihydro-2,6-naphthyridin-3-yl)methyl)acrylamide | 434 |

-continued

| Example No. | Compound structure | Compound name | MS: m/z [M + 1]+ |
|---|---|---|---|
| 738 | 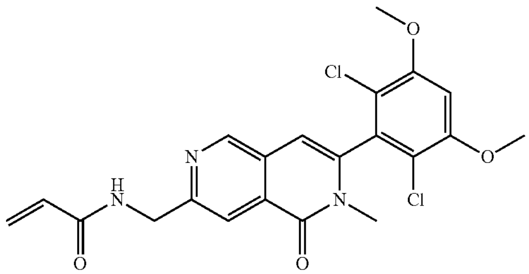 [SMILES: C=CC(=O)NCc1cc2c(=O)n(C)c(-c3c(Cl)c(OC)cc(OC)c3Cl)cc2cn1] | N-((7-(2,6-dichloro-3,5-dimethoxyphenyl)-6-methyl-5-oxo-5,6-dihydro-2,6-napthyridin-3-yl)methyl)acrylamide | 448 |
| 739 | 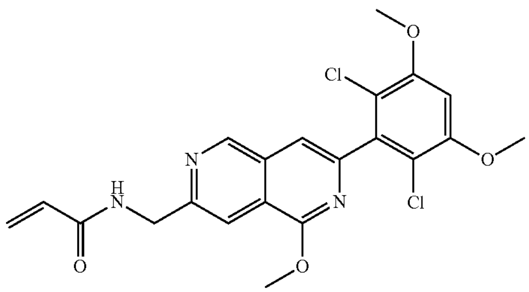 [SMILES: C=CC(=O)NCc1cc2c(OC)nc(-c3c(Cl)c(OC)cc(OC)c3Cl)cc2cn1] | N-((7-(2,6-dichloro-3,5-dimethoxyphenyl)-5-methoxy-2,6-naphthyridin-3-yl)methyl)acrylamide | 448 |
| 740 | 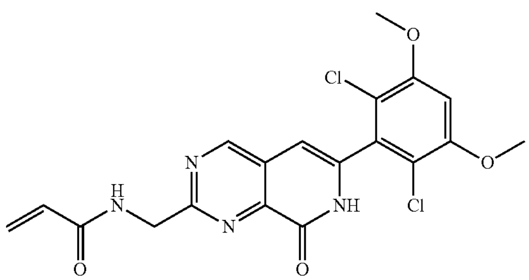 [SMILES: C=CC(=O)NCc1ncc2cc(-c3c(Cl)c(OC)cc(OC)c3Cl)[nH]c(=O)c2n1] | N-((6-(2,6-dichloro-3,5-dimethoxyphenyl)-8-oxo-7,8-dihydropyrido[3,4-d]pyrimidin-2-yl)methyl)acrylamide | 435 |
| 741 | 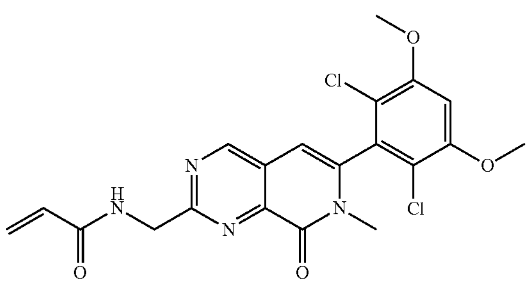 [SMILES: C=CC(=O)NCc1ncc2cc(-c3c(Cl)c(OC)cc(OC)c3Cl)n(C)c(=O)c2n1] | N-((6-(2,6-dichloro-3,5-dimethoxyphenyl)-7-methyl-8-oxo-7,8-dihydropyrido[3,4-d]pyrimidin-2-yl)methyl)acrylamide | 449 |
| 742 | 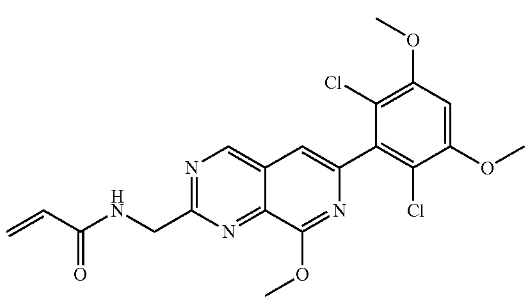 [SMILES: C=CC(=O)NCc1ncc2cc(-c3c(Cl)c(OC)cc(OC)c3Cl)nc(OC)c2n1] | N-((6-(2,6-dichloro-3,5-dimethoxyphenyl)-8-methoxypyrido[3,4-d]pyrimidin-2-yl)methyl)acrylamide | 449 |

| Example No. | Compound structure | Compound name | MS: m/z [M + 1]+ |
|---|---|---|---|
| 743 | 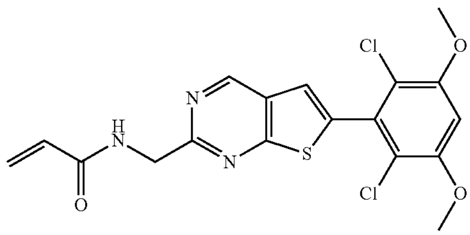 [SMILES: C=CC(=O)NCc1ncc2cc(-c3c(Cl)c(OC)cc(OC)c3Cl)sc2n1] | N-((6-(2,6-dichloro-3,5-dimethoxyphenyl) thieno[2,3-d]pyrimidin-2-yl) methyl)acrylamide | 424 |
| 744 | 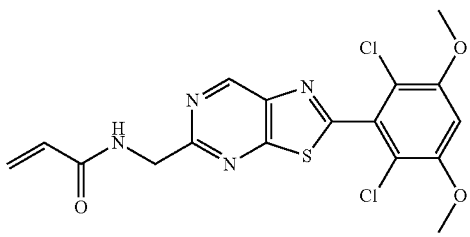 [SMILES: C=CC(=O)NCc1ncc2nc(-c3c(Cl)c(OC)cc(OC)c3Cl)sc2n1] | N-((2-(2,6-dichloro-3,5-dimethoxyphenyl) thiazolo[5,4-d]pyrimidin-5-yl)methyl)acrylamide | 425 |
| 745 | 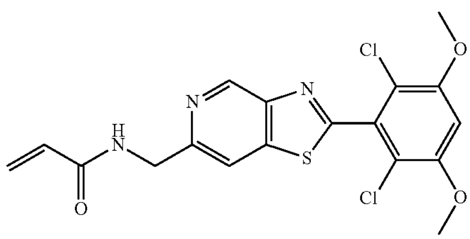 [SMILES: C=CC(=O)NCc1cc2sc(-c3c(Cl)c(OC)cc(OC)c3Cl)nc2cn1] | N-((2-(2,6-dichloro-3,5-dimethoxyphenyl) thiazolo[4,5-c]pyridin-6-yl) methyl)acrylamide | 424 |
| 746 | 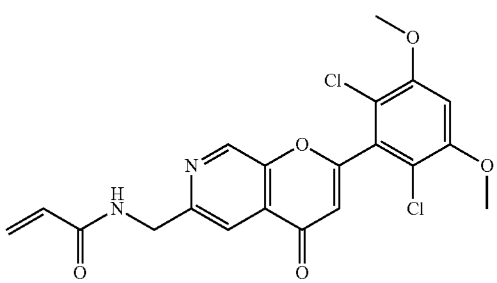 [SMILES: C=CC(=O)NCc1cc2c(=O)cc(-c3c(Cl)c(OC)cc(OC)c3Cl)oc2cn1] | N-((2-(2,6-dichloro-3,5-dimethoxyphenyl)-4-oxo-4H-pyrano[2,3-c] pyridin-6-yl)methyl)acrylamide | 435 |
| 747 | 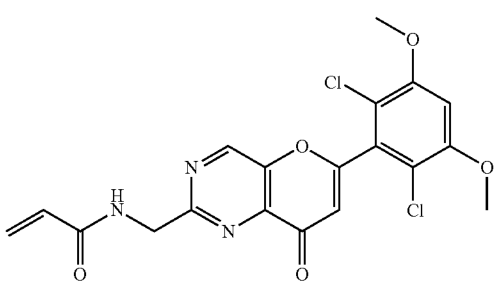 [SMILES: C=CC(=O)NCc1ncc2oc(-c3c(Cl)c(OC)cc(OC)c3Cl)cc(=O)c2n1] | N-((6-(2,6-dichloro-3,5-dimethoxyphenyl)-8-oxo-8H-pyrano[3,2-d] pyrimidin-2-yl)methyl)acrylamide | 436 |
| 748 | 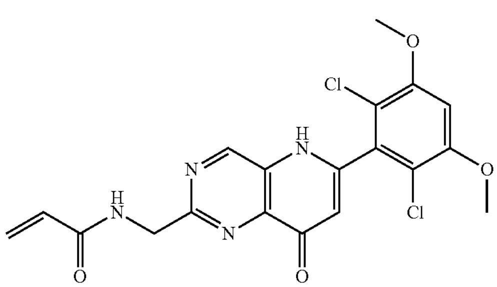 [SMILES: C=CC(=O)NCc1ncc2[nH]c(-c3c(Cl)c(OC)cc(OC)c3Cl)cc(=O)c2n1] | N-((6-(2,6-dichloro-3,5-dimethoxyphenyl)-8-oxo-5,8-dihydropyrido [3,2-d]pyrimidin-2-yl)methyl) acrylamide | 435 |

-continued

| Example No. | Compound structure | Compound name | MS: m/z [M + 1]+ |
|---|---|---|---|
| 749 | 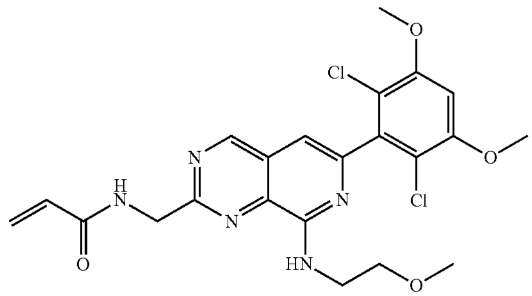 [SMILES: C=CC(=O)NCc1ncc2cc(-c3c(Cl)c(OC)cc(OC)c3Cl)nc(NCCOC)c2n1] | N-((6-(2,6-dichloro-3,5-dimethoxyphenyl)-8-((2-methoxyethyl)amino)pyrido[3,4-d]pyrimidin-2-yl)methyl)acrylamide | 492 |
| 750 | 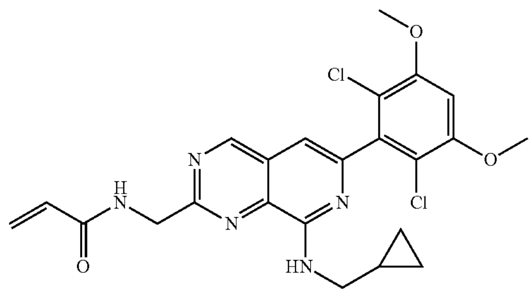 [SMILES: C=CC(=O)NCc1ncc2cc(-c3c(Cl)c(OC)cc(OC)c3Cl)nc(NCC3CC3)c2n1] | N-((8-((cyclopropylmethyl)amino)-6-(2,6-dichloro-3,5-dimethoxyphenyl)pyrido[3,4-d]pyrimidin-2-yl)methyl)acrylamide | 488 |
| 751 | 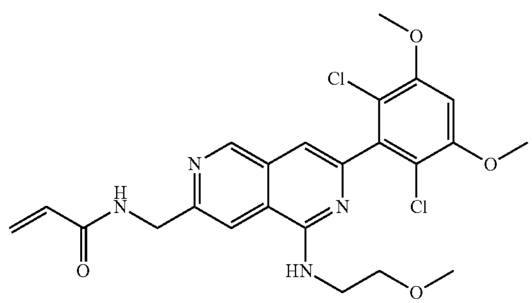 [SMILES: C=CC(=O)NCc1cc2c(NCCOC)nc(-c3c(Cl)c(OC)cc(OC)c3Cl)cc2cn1] | N-((7-(2,6-dichloro-3,5-dimethoxyphenyl)-5-((2-methoxyethyl)amino)-2,6-naphthyridin-3-yl)methyl)acrylamide | 491 |

Biological Test and Evaluation

I. In Vitro Biochemical Kinase Analysis of FGFR4

FGFR4 Caliper Assay was used in the present invention to determine the inhibitory activities of the compounds against FGFR4. The detailed experimental procedure was as follows.

1. The kinase reaction in the present invention was carried out in a 384-well plate, and 12.5 μM of FGFR4, 65 μM of ATP and 1 μM of peptide (5 Fluo Ahx KKKKEEIYFFFG NH2) were respectively added into the following reaction system.

2. A reaction system is a mixture solution of 50 mM HEPES, pH 7.5, 1 mM DTT, 0.02% Tween 20, 0.02% BSA, 0.6% DMSO, 10 mM beta glycerol phosphate and 10 μM sodium orthovanadate and 16 mM $MgCl_2$.

3. The reaction system was incubated at 30° C. for 40 minutes.

4. The reaction was terminated by adding a stop solution (100 mM HEPES, pH 7.5, 5% DMSO, 0.1% Caliper coating reagent, 10 mM EDTA and 0.015% Brij35).

5. The culture plate with the terminated kinase reaction was transferred to the Caliper LC 3000 workstation to read the data, the phosphorylated and unphosphorylated peptides were separated by using the Caliper microfluid migration shift technique, and the analyte was transferred by allowing a constant buffer flow through the chip, the migration of the substrate peptide was monitored by the labeled fluorescent signal, and the kinase activity was calculated by using the amount of the phosphate-based peptide formed.

6. Finally, $IC_{50}$ values were determined by non-linear regression analysis of percent inhibition at different compound concentrations. The test results for the enzymatic activities of the compounds of the specific examples were shown in Table 1.

II. FGFR4 Cell Proliferation Experiment

Cell Titer Glo (CTG) experiment was used in the present invention to evaluate the functional effects of the compounds on cell proliferation. Huh7 hepatocellular carcinoma cells (Catalog No. TChU182) from the Chinese Academy of Sciences cell bank were cultured in DMEM with high glucose (Gibco, cat. No. 1773536), 10% fetal bovine serum (Gibco, 10099-141) at 37° C., in a 5% $CO_2$ incubator. Compound-mediated inhibition of cell proliferation/survival was assessed by quantification of cellular ATP levels using CTG reagent (Promega, #G7573). The specific experimental procedure was as follows:

1. The cells were seeded into a tissue culture medium-treated 96-well plate (Costar #3904) at 3500 cells/well/90 μL of fresh medium:

2. 10 μL of medium containing a compound concentration of 10 fold of its final test concentration was added;
3. The dose effect was evaluated by a 5-fold serial dilution of the test compound, starting from 10 μM.
4. After cells incubation for 3 days at 37° C. under 5% $CO_2$, the effect of the inhibitor on cell proliferation was quantified after adding 50 μL of CTG and testing with luminescence.

5. The concentration of the compound ($EC_{50}$) leading to half maximal growth inhibition and the concentration of compound (Absolute $IC_{50}$) leading to absolute half growth inhibition were determined using a four-parameter curve fit in Graphpad Prism in a plate reader (M1000, Tecan). The test results of cell activities for the compounds of specific examples were shown in Table 1.

TABLE 1

The results of enzymatic activity and cell activity tests

| Example No. | Enzymatic activity FGFR4 $IC_{50}$ (nM) | Cell activity HuH-7 $EC_{50}$ (nM) | HuH-7 Absolute $IC_{50}$ (nM) | $^1$H-NMR |
|---|---|---|---|---|
| Example 1 | 13.9 | 1527 | 2446 | $^1$H NMR (400 MHz, $CDCl_3$) δ 8.60 (s, 1H), 8.30 (d, J = 8.1 Hz, 1H), 7.31 (s, 1H), 7.10-7.05 (m, 2H), 6.68 (s, 1H), 6.52-6.48 (m, 1H), 6.44 (s, 1H), 6.39 (s, 1H), 6.33 (d, J = 1.4 Hz, 1H), 6.19 (d, J = 10.2 Hz, 1H), 5.68 (dd, J = 10.2, 1.4 Hz, 1H), 3.99 (s, 6H), 3.25 (s, 3H), 2.21 (s, 3H). |
| Example 5 | 26.1 | >10000 | >10000 | $^1$H NMR (400 MHz, $CDCl_3$) δ 9.21 (s, 1H), 8.72 (s, 1H), 8.23 (s, 3H), 7.34 (t, J = 7.8 Hz, 1H), 7.12 (d, J = 7.7 Hz, 1H), 7.02 (s, 1H), 6.70 (s, 1H), 6.42-6.25 (m, 2H), 5.71 (d, J = 9.8 Hz, 1H), 3.97 (s, 6H), 2.25 (s, 3H). |
| Example 7 | 28.9 | >10000 | >10000 | $^1$H NMR (400 MHz, $CDCl_3$) δ 8.53 (s, 1H), 8.13 (s, 1H), 7.92 (s, 1H), 7.32 (t, J = 8.0 Hz, 1H), 7.13 (d, J = 7.6 Hz, 1H), 6.94 (s, 1H), 6.75 (s, 1H), 6.67 (s, 1H), 6.54 (s, 1H), 6.39 (d, J = 16.7 Hz, 1H), 6.25-6.13 (m, 1H), 5.73 (d, J = 10.0 Hz, 1H), 3.96 (s, 6H), 2.22 (s, 3H). |
| Example 9 | 138 | 89 | 1049 | $^1$H NMR (400 MHz, $CDCl_3$) δ 8.91 (s, 1H), 8.42 (s, 1H), 8.20 (s, 1H), 7.34 (t, J = 7.9 Hz, 1H), 7.20 (s, 1H), 7.12 (d, J = 7.6 Hz, 1H), 6.65 (s, 2H), 6.35 (d, J = 15.3 Hz, 2H), 6.16 (dd, J = 17.2, 9.9 Hz, 1H), 5.68 (d, J = 10.2 Hz, 1H), 3.97 (s, 9H), 2.23 (s, 3H). |
| Example 10 | 105.3 | 3515 | 4817 | $^1$H NMR (400 MHz, $CDCl_3$) δ 9.16 (s, 1H), 8.38 (d, J = 8.2 Hz, 1H), 8.17 (s, 1H), 7.36 (t, J = 7.9 Hz, 1H), 7.13 (d, J = 7.7 Hz, 1H), 6.98 (s, 1H), 6.64 (s, 1H), 6.56 (s, 1H), 6.37 (d, J = 16.8 Hz, 1H), 6.20 (dd, J = 16.9, 10.2 Hz, 1H), 5.70 (d, J = 10.2 Hz, 1H), 4.07 (s, 3H), 3.96 (s, 6H), 2.25 (s, 3H). |
| Example 11 | 100.7 | 4717 | 4717 | $^1$H NMR (400 MHz, $CDCl_3$) δ 8.76 (s, 1H), 8.27 (d, J = 8.2 Hz, 1H), 8.14 (s, 1H), 7.49 (s, 1H), 7.33 (t, J = 7.9 Hz, 1H), 7.11 (d, J = 7.6 Hz, 1H) 6.94 (s, 1H), 6.69 (s, 1H), 6.43-6.34 (m, 1H), 6.26 (dd, J = 16.9, 10.1 Hz, 1H), 5.72 (dd, J = 10.1, 1.4 Hz, 1H), 3.98 (s, 6H), 3.51 (t, J = 6.4 Hz, 2H), 3.22 (s, 3H), 2.24 (s, 3H), 1.27 (d, J = 7.0 Hz, 2H). |
| Example 12 | 43.8 | 3352 | 3352 | $^1$H NMR (400 MHz, $CDCl_3$) δ 8.38 (s, 1H), 8.02 (s, 1H), 7.57 (s, 1H), 7.33 (t, J = 7.9 Hz, 1H), 7.14 (d, J = 7.6 Hz, 1H), 6.64 (s, 1H), 6.41 (d, J = 16.6 Hz, 1H), 6.26 (dd, J = 16.6, 9.8 Hz, 1H), 6.07 (s, 1H), 5.74 (d, J = 9.8 Hz, 1H), 3.95 (s, 6H), 2.08 (s, 3H). |
| Example 13 | 8.0 | 181.5 | 513.1 | $^1$H NMR (400 MHz, Methanol-$d_4$) δ 9.05 (s, 1H), 8.98 (s, 1H), 7.72 (s, 1H), 7.68-7.66 (d, J = 8.0 Hz, 1H), 7.32-7.24 (m, 2H), 6.91 (s, 1H), 6.47(s, 1H), 6.35-6.23 (m, 2H), 5.66-5.63 (dd, J = 8 Hz, 1H), 3.97(s, 6H), 2.30(s, 3H). |
| Example 64 | 53.3 | 54.2 | 268.5 | $^1$H NMR (400 MHz, $CDCl_3$) δ 10.72 (s, 1H), 9.31-9.24 (m, 2H), 8.24 (s, 1H), 7.64 (s, 1H), 6.70 (s, 1H), 6.42-6.33 (m, 2H), 5.75 (dd, J = 9.0, 2.6 Hz, 1H), 5.38-5.32 (m, 1H), 3.99 (s, 6H), 3.87 (s, 3H). |
| Example 75 | 246.6 | >10000 | >10000 | $^1$H NMR (400 MHz, $CDCl_3$) δ 8.77 (s, 1H), 8.08 (s, 1H), 7.97 (s, 1H), 6.89 (s, 1H), 6.75 (s, 1H), 6.62 (s, 1H), 6.54-6.50 (m, 1H), 6.28 (d, J = 16.6 Hz, 1H), 6.13-6.03 (m, 1H), 5.70-5.57 (m, 1H), 3.91 (s, 61H), 3.49-3.38 (m, 4H), 3.25 (s, 3H), 2.54-2.39 (m, 4H), 2.08 (s, 3H), 1.31 (s, 3H). |
| Example 76 | 24.0 | 23.8 | 62.6 | $^1$H NMR (400 MHz, $CDCl_3$) δ 9.03 (s, 1H), 8.17 (s, 1H) 6.77 (s, 1H), 6.63 (s, 1H), 6.38 (d, J = 16.6 Hz, 2H), 6.33-6.24 (m, 1H), 5.70 (d, J = 10.1 Hz, 1H), 3.95 (s, 6H), 3.87 (s, 3H), 3.53-3.36 (m, 2H), 1.19-1.10 (m, 1H), 0.55-0.41(m, 2H), 0.42-0.29 (m, 2H). |
| Example 118 | 80.5 | 179.4 | 332.8 | $^1$H NMR (400 MHz, $CDCl_3$) δ 9.21 (s, 1H), 9.16 (s, 1H), 7.55 (s, 1H), 6.68 (s, 1H), 6.45 (d, J = 7.3 Hz, 1H), 6.27 (dd, J = 17.0, 1.4 Hz, 1H), 6.07 (dd, J = 16.9, 10.3 Hz, 1H), 5.63 (dd, J = 10.2, 1.4 Hz, 1H), 4.94 (dd, J = 11.6, 4.9 Hz, 1H), 4.90-4.79 (m, 1H), 4.34-4.19 (m, 2H), 3.98 (s, 6H), 3.90-3.79 (m, 2H). |

TABLE 1-continued

The results of enzymatic activity and cell activity tests

| Example No. | Enzymatic activity FGFR4 IC$_{50}$ (nM) | Cell activity HuH-7 EC$_{50}$ (nM) | HuH-7 Absolute IC$_{50}$ (nM) | $^1$H-NMR |
|---|---|---|---|---|
| Example 119 | 166.0 | 78.1 | 457.1 | $^1$H NMR (400 MHz, CDCl$_3$) δ 9.17 (s, 2H), 7.56 (s, 1H), 6.68 (s, 1H), 6.25 (dd, J = 16.9, 1.4 Hz, 1H), 6.01 (dd, J = 17.0, 10.3 Hz, 1H), 5.60 (dd, J = 10.3, 1.4 Hz, 1H), 4.55 (s, 1H), 4.35 (s, 1H), 4.11-4.00 (m, 2H), 3.98 (s, 6H), 3.78 (d, J = 12.1 Hz, 1H), 3.64 (dd, J = 3.4, 10.9 Hz, 1H), 2.24-2.20 (m, 2H), 2.02-1.99 (m, 2H). |
| Example 120 | 303.0 | 155.6 | 754.2 | 1H NMR (400 MHz, CDCl$_3$) δ 9.20 (s, 1H), 9.14 (s, 1H), 7.71 (s, 1H), 6.73 (t, J = 8.0 Hz, 1H), 6.46 (d, J = 7.0 Hz, 1H), 6.26 (d, J = 16.9 Hz, 2H), 6.04 (dd, J = 17.0, 10.3 Hz, 1H), 5.62 (d, J = 10.2 Hz, 1H), 4.93 (d, J = 6.0 Hz, 1H), 4.86 (t, J = 6.2 Hz, 1H), 4.28 (ddd, J = 18.7, 9.4, 6.2 Hz, 2H), 3.93 (s, 6H), 3.85 (ddd, J = 15.4, 9.5, 4.9 Hz, 2H). |
| Example 121 | 182.6 | 171.9 | 401.4 | $^1$H NMR (400 MHz, CDCl$_3$) δ 9.20 (d, J = 9.2 Hz, 2H), 7.94 (s, 1H), 6.82 (d, J = 2.8 Hz, 1H), 6.60 (d = 2.7 Hz, 1H), 6.48-6.43 (m, 1H), 6.24 (t, J = 1.9 Hz, 1H), 6.18 (dd, J = 17.3, 10.4 Hz, 1H), 6.12-6.04 (m, 1H), 5.63 (dt, J = 10.3, 1.6 Hz, 1H), 4.97-4.85 (m, 3H), 4.28 (ddd, J = 20.2, 9.5, 6.3 Hz, 3H), 3.98 (s, 3H), 3.94 (s, 3H). |
| Example 124 | 61.6 | 302.7 | 556 | $^1$H NMR (400 MHz, DMSO-d$_6$) δ 9.12 (s, 1H), 9.02 (s, 1H), 8.11-8.09 (d, J = 8.0 Hz, 1H), 7.67 (s, 1H), 7.03 (s, 1H), 6.92 (s, 1H), 6.70-6.68 (dd, J = 8 Hz, 1H), 6.23-6.16 (dd, J = 16 Hz, 1H), 6.01-5.97 (dd, J = 16 Hz, 1H), 5.52-5.48 (dd, J = 16 Hz, 1H), 4.75-4.68 (m, 1H), 4.59-4.52 (m, 1H), 4.15-4.11 (m, 1H), 4.06-4.03 (m, 1H), 3.98 (s, 6H), 3.74-3.67 (m, 2H). |
| Example 126 | 22.0 | 31.5 | 53.7 | $^1$H NMR (400 MHz, CDCl$_3$) δ 8.68(s, 1H), 6.82 (s, 1H), 6.76 (s, 1H), 6.62(s, 1H), 6.44 (s, 1H), 6.22-6.18 (dd, J = 16 Hz, 1H), 6.00-5.94 (dd, J = 16 Hz, 1H), 5.55-5.52(dd, J = 8 Hz, 1H), 4.92-4.85 (m, 1H), 4.56-4.50 (m, 1H), 4.30-4.21 (m, 2H), 3.98 (s, 6H), 3.87-3.84 (dd, J = 12 Hz, 1H), 3.77-3.74 (dd, J = 12 Hz, 1H), 4.42-4.39 (m, 2H), 1.23-1.19 (m, 1H), 0.59-0.53 (m, 2H), 0.33-0.29 (m, 2H), |
| Example 421 | 12.4 | 5.4 | 10.0 | $^1$H NMR (400 MHz, CDCl$_3$) δ 8.89 (s, 1H), 6.80 (brs, 1H), 6.68 (s, 1H), 6.62 (s, 1H), 6.38 (brs, 1H), 6.21 (dd, J = 17.0, 1.5 Hz, 1H), 6.02 (dd, J = 17.0, 10.2 Hz, 1H),, 5.56 (dd, J = 10.1, 1.5 Hz, 1H), 4.93-4.83 (m, 2H), 4.30-4.18(m, 2H), 3.96 (s, 6H), 3.90 (dd, J = 9.7, 3.2 Hz, 1H), 3.79 (dd, J = 9.2, 5.2 Hz, 2H), 3.52-3.37 (m, 2H), 0.88 (t, J = 6.0 Hz, 1H), 0.57-0.48 (m, 2H), 0.36-0.26 (m, 2H). |
| Example 422 | 22.5 | 47.0 | 238.5 | $^1$H NMR (400 MHz, CDCl$_3$) δ 8.92 (s, 1H), 6.74 (s, 1H), 6.67 (s, 2H), 6.22 (d, J = 15.4 Hz, 1H), 5.56 (d, J = 10.4 Hz, 1H), 4.89 (s, 2H), 4.29-4.17 (m, 2H), 3.98 (s, 6H), 3.96-3.80 (m, 4H), 3.76-3.65 (m, 2H), 3.35 (s, 3H). |
| Example 423 | 31.7 | 98.0 | 347.6 | $^1$H NMR (400 MHz, CDCl$_3$) δ 9.13 (s, 1H), 7.17 (s, 1H), 6.75 (s, 1H), 6.66 (s, 1H), 6.26 4 J = 16.9 Hz, 1H), 6.12 (dd, J = 17.0, 10.2 Hz, 1H), 5.61 (d, J = 10.2 Hz, 1H), 5.03-4.93 (m, 1H), 4.93-4.85 (m, 1H), 4.31-4.20 (m, 2H), 4.14 (s, 3H), 3.98 (s, 6H), 3.88 (dd, J = 9.8, 4.0 Hz, 1H), 3.82 (dd, J = 9.3, 6.5 Hz, 1H). |
| Example 424 | 11.0 | 18.5 | 37.2 | $^1$H NMR (400 MHz, CDCl$_3$) δ 8.89 (s, 1H), 6.85 (s, 1H), 6.82 (t, J = 8.0 Hz, 1H), 6.15 (dd, J = 17.1, 2.5 Hz, 1H), 6.12-6.02 (m, 1H), 5.53 (dd, J = 9.5, 2.5 Hz, 1H), 4.99 (td, J = 6.3, 4.8 Hz, 1H), 4.87 (q, J = 6.5 Hz, 1H), 4.27 (dd, J = 9.4, 6.3 Hz, 1H), 4.16 (dd, J = 9.0, 6.9 Hz, 1H), 3.92 (m, 7H), 3.80 (dd, J = 9.0, 6.5 Hz, 1H), 3.45 (dd, J = 13.7, 7.0 Hz, 1H), 3.37 (d, J = 6.8 Hz, 1H), 1.33-1.24 (m, 1H), 0.55-0.41 (m, 2H), 0.42-0.29 (m, 2H). |
| Example 425 | 7.7 | NT | NT | $^1$H NMR (400 MHz, CDCl$_3$) δ 8.93 (s, 1H), 6.68 (s, 1H), 6.61 (s, 1H), 6.22 (d, J = 16.6 Hz, 2H), 6.00 (dd, J = 16.9, 10.2 Hz, 1H), 5.89 (s 1H), 5.57 (d, J = 10.2 Hz, 1H), 4.89 (s, 2H), 4.30-4.20 (m, 2H), 3.90 (d, J = 9.8 Hz, 1H), 3.82-3.72 (m, 1H), 3.42 (s, 2H), 1.26-1.21 (m, 1H), 0.58-0.47 (m, 2H), 0.36-0.27 (m, 2H). |
| Example 429 | 22.4 | 63.2 | 184.5 | $^1$H NMR (400 MHz, CDCl$_3$) δ 8.90 (s, 1H), 7.06 (s, 1H), 6.78 (s, 1H), 6.64 (s, 1H), 6.18 (d, J = 17.0 Hz, 1H), 6.11 (d, J = 7.2 Hz, 1H), 5.98 (dd, J = 17.0, 10.2 Hz, 1H), 5.81 (s, 1H), 5.56 (d, J = 10.3 Hz, 1H), 4.94-4.83 (m, 2H), 4.27 (dd, J = 9.6, 5.8 Hz, 1H), 4.20 (dd, J = 9.4, 6.1 Hz, 1H), 4.10 (s, 2H), 3.97 (s, 6H), 3.87 (dd, J = 9.6, 3.9 Hz, 1H), 3.81 (dd, J = 9.5, 5.0 Hz, 1H), 3.49-3.38 (m, 2H), 3.01 (q, J = 7.5 Hz, 2H), 1.27 (t, J = 7.4 Hz, 3H). |

TABLE 1-continued

The results of enzymatic activity and cell activity tests

| Example No. | Enzymatic activity FGFR4 IC$_{50}$ (nM) | Cell activity HuH-7 EC$_{50}$ (nM) | HuH-7 Absolute IC$_{50}$ (nM) | $^1$H-NMR |
|---|---|---|---|---|
| Example 430 | 19.1 | 32.0 | 93.5 | $^1$H NMR (400 MHz, CDCl$_3$) δ 8.60 (s, 1H), 7.24 (s, 1H), 6.81 (brs, 1H), 6.63 (s, 1H), 6.57 (s, 1H), 6.26 (brs, 1H), 6.16-6.03 (m, 2H), 5.53 (d, J = 9.6 Hz, 1H), 5.08 (s, 1H), 4.88 (s, 1H), 4.26-4.12 (m, 2H), 3.96 (d, J = 6.0 Hz, 6H), 3.93-3.88 (m, 2H), 3.81 (d, J = 10.1 Hz, 2H), 3.60 (d, J = 11.3 Hz, 2H), 3.42 (s, 1H), 2.94 (s, 3H). |
| Example 431 | 519.1 | NT | NT | $^1$H NMR (400 MHz, CDCl$_3$) δ 12.21 (s, 1H), 8.90 (s, 1H), 7.72 (s, 1H), 7.52 (s, 1H), 6.78 (s, 1H), 6.67 (s, 1H), 6.22-6.12 (m, 2H), 5.53 (d, J = 9.9 Hz, 1H), 5.00-4.88 (m, 2H), 4.33-4.27 (m, 2H), 4.26-4.19(m, 2H), 3.97 (s, 6H), 3.94-3.87 (m, 2H), 3.49 (s, 2H), 2.87 (s, 6H). |
| Example 432 | 105.8 | 395.8 | 934.2 | $^1$H NMR (400 MHz, CDCl$_3$) δ8.66 (s, 1H), 6.99 (s, 1H), 6.91 (s, 1H), 6.63 (s, 1H), 6.59 (s, 1H), 6.33 (d, J = 6.4 Hz, 1H), 6.18 (d, J = 5.9 Hz, 2H), 5.59-5.49 (m, 1H), 4.99 (s, 2H), 4.30-4.23(m, 2H), 3.97 (s, 6H), 3.92-3.87 (m, 1H), 3.77-3.71 (m, 1H), 3.25 (s, 2H), 2.77 (s, 6H), 2.25 (s, 2H), 1.70 (s, 2H). |
| Example 433 | 7.6 | 19.3 | 26.1 | $^1$H NMR (400 MHz, CDCl$_3$) δ 8.88 (s, 1H), 6.67 (s, 1H), 6.62 (s, 1H), 6.30 (brs, 1H), 6.19 (d, J = 16.9 Hz, 1H), 5.97 (dd, J = 17.0, 10.3 Hz, 1H), 5.88 (brs, 1H), 5.54 (d, J = 10.4 Hz, 1H), 4.95-4.83 (m, 2H), 4.29-4.18 (m, 2H), 3.95 (s, 6H), 3.89 (dd, J = 9.7, 3.0 Hz, 1H), 3.77 (dd, J = 9.3, 5.5 Hz, 1H), 3.14 (d, J = 4.4 Hz, 3H). |
| Example 434 | 8.4 | 9.6 | 18.2 | $^1$H NMR (400 MHz, CDCl$_3$) δ 8.87 (s, 1H), 6.67 (s, 1H), 6.62 (s, 1H), 6.51 (s, 1H), 6.27-6.15 (m, 2H), 5.97 (dd, J = 16.9, 10.3 Hz, 1H), 5.79 (s, 1H), 5.56 (dd, J = 10.3, 1.4 Hz, 1H), 4.97-4.82 (m, 2H), 4.29-4.18 (M, 2H), 3.96 (s, 6H), 3.89 (dd, J = 9.6, 3.2 Hz, 1H), 3.76 (dd, J = 9.2, 5.5 Hz, 1H), 3.65-3.50 (m, 2H), 1.32 (t, J = 7.2 Hz, 3H). |
| Example 435 | 67.0 | 80 | 148.5 | $^1$H NMR (400 MHz, CDCl$_3$) δ 8.96 (s, 1H), 6.85 (s, 1H), 6.79 (s, 1H), 6.64 (s, 1H), 6.19 (d, J = 16.9 Hz, 1H), 6.13 (s, 1H), 6.06 (s, 1H), 5.98 (dd, J = 17.0, 10.3 Hz, 1H), 5.56 (d, J = 10.2 Hz, 1H), 4.93 (dd, J = 11.7, 4.8 Hz, 2H), 4.51-4.37 (m, 1H), 4.30-4.17 (m, 3H), 3.97 (s, 6H), 3.90 (dd, J = 9.7, 2.8 Hz, 1H), 3.78 (dd, J = 9.4, 5.0 Hz, 1H). |
| Example 436 | >10000 | NT | NT | $^1$H NMR (400 MHz, CDCl$_3$) δ 9.33 (s, 1H), 6.59 (s, 1H), 6.56 (s, 1H), 6.45 (s, 1H), 6.22 (s, 1H), 6.14-6.00 (m, 1H), 5.62 (d, J = 10.2 Hz, 1H), 4.86 (s, 2H), 4.24 (s, 2H), 3.98-3.94 (m, 2H), 3.83 (s, 6H), 3.38 (s, 6H). |
| Example 438A | 3.5 | 9.9 | 17.8 | $^1$H NMR (400 MHz, CDCl$_3$) δ 8.89 (s, 1H), 6.84 (brs, 1H), 6.70 (s, 1H), 6.63 (s, 1H), 6.42 (brs, 1H), 6.22 (dd, J = 17.0, 1.5 Hz, 1H), 6.11-6.01 (m, 1H), 5.85 (s, 1H), 5.57 (dd, J = 10.1, 1.5 Hz, 1H), 4.93-4.81 (m, 2H), 4.30-4.16 (m, 3H), 3.96 (s, 6H), 3.92-3.82 (m, 3H), 3.82-3.74 (m, 2H), 3.58-3.45 (m, 1H), 1.95-1.85 (m, 2H), 1.70-1.64 (m, 2H). |
| Example 438B | 9.1 | 15.8 | 35.1 | $^1$H NMR (400 MHz, CDCl$_3$) δ 8.89 (s, 1H), 6.74 (s, 1H), 6.69 (s, 1H), 6.62 (s, 1H), 6.25 (dd, J = 16.9, 1.4 Hz, 1H), 6.20 (s, 1H), 6.03 (dd, J = 16.9, 10.3 Hz, 1H), 5.81 (s, 1H), 5.61 (d, J = 10.4 Hz, 1H), 4.93-4.81 (m, 2H), 4.31-4.16 (m, 3H), 3.96 (s, 6H), 3.93-3.84 (m, 2H), 3.82-3.72 (m, 3H), 3.59 (dd, J = 13.3, 6.7 Hz, 1H), 1.91-1.85 (m, 2H), 1.70-1.63 (m, 2H). |
| Example 439 | 4.6 | NT | NT | $^1$H NMR (400 MHz, CDCl$_3$) δ 8.88 (s, 1H), 6.72 (brs, 1H), 6.69 (s, 1H), 6.63 (s, 1H), 6.35 (brs, 1H), 6.19 (d, J = 17.1 Hz, 1H), 6.00 (dd, J = 17.0, 10.2 Hz, 1H), 5.89 (s, 1H), 5.55 (dd, J = 10.3, 1.5 Hz, 1H), 4.96-4.82 (m, 2H), 4.31-4.17 (m, 2H), 3.96 (s, 6H), 3.93-3.82 (m, 2H), 3.81-3.71 (m, 2H), 3.66 (dd, J = 8.9, 5.3 Hz, 1H), 3.63-3.51 (m, 2H), 2.82-2.69 (m, 1H), 2.13-2.00 (m, 1H), 1.77-1.72 (m, 1H). |
| Example 443 | 8.2 | 15.9 | 70.8 | $^1$H NMR (400 MHz, CDCl$_3$) δ 8.89 (s, 1H), 6.73 (s, 1H), 6.63 (s, 1H), 6.24-6.16 (m, 1H), 6.13 (brs, 1H), 5.96 (dd, J = 17.2, 10.3 Hz, 1H), 5.79 (brs, 1H), 5.59-5.51 (m, 1H), 4.95-4.84 (m, 2H), 4.71 (s, 1H), 4.30-4.15 (m, 2H), 4.13-4.04 (m, 1H), 4.05-3.98 (m, 1H), 3.97 (s, 6H), 3.92-3.82 (m, 3H), 3.76 (dd, J = 9.3, 5.7 Hz, 1H), 2.45-2.31 (m, 1H), 2.18-2.05 (m, 1H). |
| Example 444 | 7.0 | NT | NT | $^1$H NMR (400 MHz, CDCl$_3$) δ 8.89 (s, 1H), 6.70 (s, 1H), 6.63 (s, 1H), 6.42-6.33 (m, 1H), 6.20 (dd, J = 17.0, 1.4 Hz, 1H), 6.17-6.13 (m, 1H), 5.97 (dd, J = 17.0, 10.3 Hz, 1H), 5.75 (d, J = 6.5 Hz, 1H), 5.57 (dd, J = 10.4, 1.4 Hz, |

TABLE 1-continued

The results of enzymatic activity and cell activity tests

| Example No. | Enzymatic activity FGFR4 IC$_{50}$ (nM) | Cell activity HuH-7 EC$_{50}$ (nM) | HuH-7 Absolute IC$_{50}$ (nM) | $^1$H-NMR |
|---|---|---|---|---|
| | | | | 1H), 4.95-4.82 (m, 2H), 4.29-4.18 (m, 3H), 4.03-3.98 (m, 2H), 3.97 (s, 6H), 3.89 (dd, J = 9.6, 3.6 Hz, 1H), 3.76 (dd, J = 9.3, 5.8 Hz, 1H), 3.58-3.48 (m, 2H), 2.24-2.10 (m, 2H), 1.73-1.64 (m, 2H). |
| Example 452 | 42.2 | 20.3 | 53.3 | $^1$H NMR (400 MHz, CDCl$_3$) δ 8.92 (s, 1H), 6.88 (brs, 1H), 6.77 (s, 1H), 6.64 (s, 1H), 6.17 (d, J = 16.8 Hz, 1H), 5.95 (m, 2H), 5.55 (d, J = 10.2 Hz, 1H), 5.02-4.94 (m, 1H), 4.90 (s, 1H), 4.46 (s, 1H), 4.31-4.18 (m, 2H), 3.97 (s, 6H), 3.91 (d, J = 10.8 Hz, 1H), 3.73 (t, J = 8.1 Hz, 1H), 3.11 (s, 2H), 2.80 (s, 1H), 2.69 (s, 1H). |
| Example 454 | 66.9 | 40.8 | 89.2 | $^1$H NMR (400 MHz, CDCl$_3$) δ 8.88 (s, 1H), 6.67 (s, 1H), 6.63 (s, 1H), 6.21 (d, J = 17.0 Hz, 1H), 6.09-5.97 (m, 1H), 5.57 (d, J = 10.2 Hz, 1H), 4.89-4.81 (m, 2H), 4.27-4.20 (m, 2H), 3.96 (s, 6H), 3.92-3.90 (m, 1H), 3.81-3.77 (m, 1H), 3.59-3.48 (m, 2H), 2.30 (dd, J = 15.2, 7.9 Hz, 1H), 1.83-1.76 (m, 2H), 1.59 (brd, J = 31.7 Hz, 4H), 1.28 (brs, 3H). |
| Example 456 | 82.4 | 163 | 299 | $^1$H NMR (400 MHz, CDCl$_3$) δ 8.87 (s, 1H), 7.47-7.11 (m, 6H), 6.70 (s, 1H), 6.63 (s, 1H), 6.22 (d, J = 17.1 Hz, 2H), 6.09-5.75 (m, 2H), 5.58 (d, J = 10.3 Hz, 1H), 4.89-4.60 (m, 2H), 4.22-4.15 (m, 2H), 3.96 (s, 6H), 3.83-3.75 (m, 3H), 3.03 (q, J = 6.8 Hz, 2H). |
| Example 459 | 17.3 | 23.8 | 58.0 | $^1$H NMR (400 MHz, DMSO-d$_6$) δ 9.02 (s, 1H), 7.58 (s, 1H), 7.38 (s, 1H), 6.98 (s, 1H), 6.71 (s, 1H), 6.14 (dd, J = 17.1, 10.2 Hz, 1H), 5.94 (dd, J = 17.2, 2.2 Hz, 1H), 5.47 (dd, J = 10.4, 2.0 Hz, 1H), 4.86 (s, 1H), 4.67 (q, J = 6.1 Hz, 1H), 4.39 (td, J = 14.6, 13.6, 5.3 Hz, 2H), 4.12 (t, J = 7.9 Hz, 1H), 4.02 (dd, J = 8.8, 6.5 Hz, 1H), 3.97 (s, 6H), 3.81-3.68 (m, 4H), 3.66 (dd, J = 8.8, 5.9 Hz, 1H), 3.33 (s, 3H). |
| Example 462 | 14.5 | 24.6 | 38.3 | $^1$H NMR (400 MHz, CDCl$_3$) δ 8.89 (s, 1H), 6.66 (s, 1H), 6.64 (s, 1H), 6.62 (s, 1H), 6.30 (s, 1H), 6.23 (dd, J = 16.9, 1.4 Hz, 1H), 6.01 (dd, J = 16.9, 10.3 Hz, 1H), 5.84 (s, 1H), 5.59 (dd, J = 10.3, 1.4 Hz, 1H), 4.93-4.77 (m, 2H), 4.29-4.19 (m, 2H), 3.96 (s, 6H), 3.91 (dd, J = 9.5, 4.0 Hz, 1H), 3.79 (dd, J = 9.3, 5.5 Hz, 1H), 3.51 (dd, J = 13.1, 6.5 Hz, 1H), 3.36 (dd, J = 13.2, 5.9 Hz, 1H), 0.99 (s, 9H). |
| Example 465 | 46.4 | NT | NT | $^1$H NMR (400 MHz, CDCl$_3$) δ 8.87 (s, 1H), 6.67 (s, 1H), 6.62 (s, 1H), 6.18 (d, J = 17.1 Hz, 1H), 6.06 (d, J = 10.1 Hz, 1H), 5.86 (s, 1H), 5.54 (d, J = 10.1 Hz, 1H), 4.96-4.83(m, 2H), 4.30-4.19 (m, 2H), 3.96 (s, 6H), 3.89 (dd, J = 9.6, 3.7 Hz, 1H), 3.81 (dd, J = 9.2, 5.6 Hz, 1H), 3.59 (s, 2H), 2.76 (s, 2H), 2.53 (s, 6H), 1.26 (s, 4H). |
| Example 475 | 62.0 | 131.9 | 677.8 | $^1$H NMR (400 MHz, CDCl$_3$) δ 8.89 (s, 1H), 7.03 (s, 1H), 6.83 (d, J = 2.8 Hz, 1H), 6.54 (d, J = 2.8 Hz, 1H), 6.30 (s, 1H), 6.22 (dd, J = 16.8, 1.4 Hz, 1H), 6.00 (dd, J = 16.9, 10.3 Hz, 1H), 5.82 (s, 1H), 5.61-5.53 (m, 1H), 4.88 (q, J = 6.5, 6.0 Hz, 2H), 4.33-4.18 (m, 2H), 3.92 (s, 3H), 3.89 (s, 1H), 3.84 (s, 3H), 3.81-3.73 (m, 1H), 3.58-3.40 (m, 2H), 1.26 (s, 1H), 0.66-0.46 (m, 2H), 0.42-0.24 (m, 2H). |
| Example 498 | 8797 | 2393 | >10000 | $^1$H NMR (400 MHz, CDCl$_3$) δ 9.18 (s, 1H), 7.71 (d, J = 4.2 Hz, 1H), 7.53 (d, J = 8.4 Hz, 1H), 6.93 (s, 1H), 6.67 (s, 1H), 6.17 (d, J = 16.9 Hz, 1H), 6.06 (d, J = 11.2 Hz, 1H), 5.55 (d, J = 10.1 Hz, 1H), 4.95 (s, 1H), 4.63 (s, 1H), 4.39 (s, 2H), 4.31 (t, J = 6.7 Hz, 1H), 4.24 (s, 2H), 3.98 (s, 6H), 3.92 (s, 1H), 0.88 (t, J = 7.0 Hz, 1H), 0.76-0.65 (m, 2H), 0.47 (s, 2H). |
| Example 501 | 15.7 | 17.8 | 49.9 | $^1$H NMR (400 MHz, CDCl$_3$) δ 8.89 (s, 1H), 6.68 (s, 1H), 6.64 (s, 1H), 6.17 (d, J = 16.7 Hz, 1H), 5.96 (d, J = 12.1 Hz, 1H), 5.55 (d, J = 10.5 Hz, 1H), 4.75-4.60 (m, 1H), 4.40-4.25 (m, 1H), 4.10-4.02 (m, 1H), 4.01-3.90 (m, 3H), 3.96 (s, 6H), 3.77 (d, J = 11.9 Hz, 1H), 3.62 (t, J = 12.2 Hz, 2H), 1.98-1.86 (m, 2H), 0.88 (s, 1H), 0.55 (s, 2H), 0.35 (s, 2H). |
| Example 510 | 29 | 75.2 | 115.9 | $^1$H NMR (400 MHz, CDCl$_3$) δ 8.87 (s, 1H), 6.67 (s, 1H), 6.62 (s, 1H), 6.48 (s, 1H), 6.20 (dd, J = 16.9, 1.4 Hz, 2H), 6.05 (d, J = 8.5 Hz, 1H), 5.91 (dd, J = 16.9, 10.3 Hz, 1H), 5.54 (d, J = 10.4, 1.4 Hz, 1H), 4.70 (d, J = 8.7 Hz, 1H), 4.38-4.27 (m, 1H), 4.12-4.05 (m, 1H), 3.99 (d, J = 11.2 Hz, 1H), 3.96 (s, 6H), 3.75 (dd, J = 12.0, 1.7 Hz, 1H), 3.65- |

TABLE 1-continued

The results of enzymatic activity and cell activity tests

| Example No. | Enzymatic activity FGFR4 IC$_{50}$ (nM) | Cell activity HuH-7 EC$_{50}$ (nM) | HuH-7 Absolute IC$_{50}$ (nM) | $^1$H-NMR |
|---|---|---|---|---|
| | | | | 3.57 (m, 1H), 3.09 (d, J = 5.0 Hz, 3H), 1.97-1.86 (m, 2H). |
| Example 606 | 23.4 | 25.7 | 41.1 | $^1$H NMR (400 MHz, CDCl$_3$) δ 9.18 (s, 1H), 7.44 (s, 1H), 6.67 (s, 1H), 6.30-6.24 (m, 1H), 6.17-6.08 (m, 1H), 5.63 (d, J = 10.7 Hz, 1H), 4.93 (s, 2H), 4.35-4.30 (m 1H), 4.25 (dd, J = 9.4, 6.1 Hz, 1H), 3.97 (s, 6H), 3.92 (dd, J = 9.6, 3.1 Hz, 1H), 3.87-3.82 (m, 1H), 2.98 (s, 3H). |
| Example 609 | NT | 36.6 | 56.1 | $^1$H NMR (400 MHz, CDCl$_3$) δ 9.07 (s, 1H), 6.64 (s, 1H), 6.55 (s, 1H), 6.25 (d, J = 16.8 Hz, 1H), 6.05 (dd, J = 16.9, 10.3 Hz, 1H), 5.86 (brs, 1H), 5.62 (dd, J = 10.3, 1.4 Hz, 1H), 4.90-4.87 (m, 2H), 4.82-4.78 (m, 1H), 4.31 (td, J = 10.3, 6.2 Hz, 2H), 3.97 (s, 6H), 3.95-3.68 (m, 2H), 3.28-3.24 (m, 1H), 1.27-1.21 (m, 2H), 1.10 (dd, J = 8.3, 3.0 Hz, 2H). |
| Example 629 | 2.9 | 2.6 | 4.0 | $^1$H NMR (400 MHz, CDCl$_3$) δ 9.10 (s, 1H), 8.53 (s, 1H), 8.49 (s, 1H), 7.37 (s, 1H), 6.68 (s, 1H), 6.43 (d, J = 6.2 Hz, 1H), 6.20 (d, J = 16.9 Hz, 1H), 6.09 (s, 1H), 5.98 (dd, J = 17.0, 10.2 Hz, 1H), 5.57 (d, J = 10.3 Hz, 1H), 4.97-4.90 (m, 2H), 4.33-4.23 (m, 2H), 3.98 (s, 9H), 3.94 (dd, J = 9.8, 3.2 Hz, 1H), 3.82 (dd, J = 9.5, 4.8 Hz, 1H). |
| Example 637 | 4.2 | 10.1 | 17.3 | $^1$H NMR (400 MHz, Methanol-d$_4$) δ 9.03 (s, 1H), 8.56 (s, 1H), 8.40 (s, 1H), 7.49 (s, 1H), 6.74 (t, J = 8.0 Hz, 1H), 6.03 (d, J = 5.9 Hz, 2H), 5.46 (t, J = 5.9 Hz, 1H), 4,87 (s, 2H), 4.20 (4, J = 7.8 Hz, 1H), 4.12 (dd, J = 9.1, 6.6 Hz, 1H), 3.93 (s, 3H), 3.86 (s, 6H), 3.83 (d, J = 4.0 Hz, 1H), 3.74 (dd, J = 9.2, 5.4 Hz, 1H). |
| Example 655 | 8.0 | 28.0 | 68.4 | $^1$H NMR (400 MHz, CDCl$_3$) δ 8.88 (s, 1H), 6.74 (s, 1H), 6.70 (s, 1H), 6.62 (s, 1H), 6.19 (dd, J = 16.9, 1.4 Hz 2H), 5.95 (dd, J = 16.9, 10.3 Hz, 1H), 5.79 (s, 1H), 5.55 (dd, J = 10.3, 1.4 Hz, 1H), 4.93-4.81 (m, 2H), 4.29-4.17 (m, 2H), 3.96 (s, 6H), 3.88 (dd, J = 9.7, 3.3 Hz, 1H), 3.75 (dd, J = 9.2, 5.9 Hz, 1H), 3.01-2.84 (m, 1H), 0.87-0.79 (m, 2H), 0.76-0.69 (m, 1H), 0.68-0.58 (m, 1H). |
| Example 657 | 6.5 | 9.6 | 13.3 | $^1$H NMR (400 MHz, CDCl$_3$) δ 8.87 (s, 1H), 6.69 (s, 1H), 6.62 (s, 1H), 6.26 (dd-J = 16.8, 1.3 Hz, 2H), 6.06 (dd, J = 17.0, 10.3 Hz, 1H), 5.70-5.60 (n, 2H), 4.80-4.70 (m, 31-1), 4.60-4.45 (m, 3H), 4.29-4.15 (m, 2H), 3.95 (s, 6H), 3.87-3.73 (m, 2H), 2.42 (q, J = 7.6 Hz). |
| Example 658 | 4.8 | 11.4 | 15.1 | $^1$H NMR (400 MHz, CDCl$_3$) δ 8.89 (s, 1H), 6.73 (s, 1H), 6.63 (s, 1H), 6.24 (d, J = 16.8 Hz, 1H), 6.13 (d, J = 10.9 Hz, 1H), 5.61 (d, J = 10.1 Hz, 1H), 4.84-4.57 (m, 4H), 4.54-4.07 (m, 5H), 3.95 (s, 6H), 3.89-3.72 (m, 2H), 3.30 (s, 3H). |
| Example 659 | 6.6 | 18.0 | 24.3 | $^1$H NMR (400 MHz, CDCl$_3$) δ 8.90 (s, 1H), 6.93 (s, 1H), 6.68 (t, J = 7.9 Hz, 1H), 6.34 (brs, 1H), 6.24 (dd, J = 16.8, 1.4 Hz, 1H), 6.05 (dd, J = 16.9, 10.3 Hz, 1H), 5.74 (brs, 1H), 5.62 (dd, J = 10.2, 1.4 Hz, 1H), 4.88-4.61 (m, 4H), 4.45-4.37 (m, 3H), 4.28-4.15 (m, 2H), 3.91 (s, 6H), 3.84 (dd, J = 9.5, 3.6 Hz, 1H), 3.77 (dd, J = 9.5, 5.1 Hz, 1H), 3.33 (s, 3H). |
| Example 663 | 4.5 | 2.3 | 3.5 | $^1$H NMR (400 MHz, CDCl$_3$) δ 8.95 (s, 1H), 6.88 (s, 1H), 6.64 (s, 1H), 6.25 (d, J = 16.9 Hz, 2H), 6.06 (dd, J = 17.0, 10.3 Hz, 1H), 5.93 (s, 1H), 5.63 (d, J = 10.3 Hz, 1H), 4.88-4.77 (m, 6H), 4.22 (dd, J = 9.5, 6.2 Hz, 2H), 3.96 (s, 6H), 3.82 (ddd, J = 17.2, 9.6, 5.0 Hz, 2H). |
| Example 664 | 4.9 | 3.7 | 4.9 | $^1$H NMR (400 MHz, DMSO-d$_6$) δ 9.04 (s, 1H), 8.06 (d, J = 8.1 Hz, 1H), 7.23 (brs, 1H), 6.97 (s, 1H), 6.77 (s, 1H), 6.23 (dd, J = 17.1, 10.2 Hz, 1H), 6.02 (dd, J = 17.1, 2.1 Hz, 1H), 5.57 (d, J = 10.7 Hz, 1H), 5.55 (m, 1H), 4.74-4.58 (m, 2H), 4.21 (brs, 4H), 4.12-4.01 (m, 2H), 3.95 (s, 6H), 3.78-3.66 (m, 2H), 1.46 (s, 3H). |
| Example 665 | 5.7 | 9.9 | 11.8 | $^1$H NMR (400 MHz, DMSO-d$_6$) δ 9.06 (s, 1H), 8.06 (d, J = 8.3 Hz, 1H), 7.28 (s, 1H), 6.97 (s, 1H), 6.81 (s, 1H), 6.21 (dd, J = 17.1, 10.2 Hz, 1H), 6.00 (dd, J = 17.1, 2.2 Hz, 1H), 5.54 (dd, J = 10.1, 2.2 Hz, 1H), 4.76-4.60 (m, 2H), 4.17 (br s, 4H), 4.09 (d, J = 7.4 Hz, 1H), 4.05-4.00 (m, 1H), 3.95 (s, 6H), 3.75 (dd, J = 8.7, 5.9 Hz, 1H), 3.67 (dd, J = 9.0, 5.2 Hz, 1H), 3.21 (s, 3H), 1.49 (s, 3H). |
| Example 666 | 4.5 | 3.2 | 4.6 | $^1$H NMR (400 MHz, CDCl$_3$) δ 8.90 (s, 1H), 6.93 (s, 1H), 6.68 (t, J = 7.9 Hz, 1H), 6.37 (s, 1H), 6.24 (d, J = 16.9 Hz, 1H), 6.04 (dd, J = 17.0, 10.3 Hz, 1H), 5.78 (s, 1H), 5.61 (d, J = 10.3 Hz, 1H), 4.84-4.73 (m, 2H), 4.56-4.41 (m, 2H), |

TABLE 1-continued

The results of enzymatic activity and cell activity tests

| Example No. | Enzymatic activity FGFR4 IC$_{50}$ (nM) | Cell activity HuH-7 EC$_{50}$ (nM) | HuH-7 Absolute IC$_{50}$ (nM) | $^1$H-NMR |
|---|---|---|---|---|
| Example 668 | 14.7 | 16 | 22.6 | 4.41-4.26 (m, 2H), 4.26-4.17 (m, 2H), 3.91 (s, 6H), 3.85 (dd, J = 9.6, 3.5 Hz, 1H), 3.76 (dd, J = 9.4, 5.1 Hz, 1H), 3.30 (s, 3H), 1.56 (s, 3H).<br>$^1$H NMR (400 MHz, CDCl$_3$) δ 8.82 (s, 1H), 6.70 (s, 1H), 6.66 (s, 1H), 6.56 (s, 1H), 6.16 (d, J = 17.0 Hz, 1H), 6.01 (dd, J = 17.1, 10.2 Hz, 1H), 5.53 (d, J = 10.0 Hz, 1H), 4.80-4.55(m, 8H), 4.18-4.15 (m, 2H), 3.88 (s, 6H), 3.84-3.70 (m, 4H). |
| Example 675 | 11.0 | 6.2 | 8.7 | $^1$H NMR (400 MHz, CDCl$_3$) δ 8.89 (s, 1H), 6.71 (s, 1H), 6.63 (s, 1H), 6.38 (brs, 1H), 6.24 (d, J = 16.9 Hz, 1H), 6.05 (dd, J = 16.9, 10.2 Hz, 1H), 5.78 (brs, 1H), 5.61 (dd, J = 10.2, 1.3 Hz, 1H), 4.87-4.75 (m, 2H), 4.42-4.15 (m, 6H), 3.95 (s, 6H), 3.86 (dd, J = 9.5, 3.9 Hz, 1H), 3.78 (dd, J = 9.4, 5.4 Hz, 1H), 3.72-3.60 (m, 4H), 1.86 (t, J = 5.2 Hz, 4H). |
| Example 677 | 7.4 | 3.7 | 5.3 | $^1$H NMR (400 MHz, CDCl$_3$) δ 8.80 (s, 1H), 6.63 (s, 1H), 6.54 (s, 1H), 6.41 (brs, 1H), 6.21 (d, J = 17.0 Hz, 1H), 5.99 (dd, J = 16.6, 10.2 Hz, 1H), 5.71 (brs, 1H), 5.53 (dd, J = 10.3, 3.5 Hz, 1H), 4.85-4.70 (m, 2H), 4.28-3.96 (m, 7H), 3.88 (s, 6H), 3.90-3.82 (m, 1H), 3.80-3.72 (m, 1H), 3.29 (d, J = 2.8 Hz, 3H), 2.07-1.94 (m, 2H). |
| Example 678 | 6.5 | 13.3 | 16.5 | $^1$H NMR (400 MHz, CDCl$_3$) δ 8.92 (s, 1H), 6.94 (s, 1H), 6.56 (s, 1H), 6.50 (d, J = 7.4 Hz, 1H), 6.18 (d, J = 16.9 Hz, 1H) 5.98 (dd, J = 16.9, 10.3 Hz, 2H), 5.54 (d, J = 9.7 Hz, 1H), 4.82-4.69 (m, 2H), 4.74-4.64 (m, 2H), 4.19-4.12 (m, 2H), 3.89 (s, 6H), 3.87-3.76 (m, 7H), 3.76-3.67 (m, 1H), 2.20-2.10 (m, 1H), 2.08-1.95 (m, 1H). |
| Example 686 | 8.2 | 5.4 | 8.8 | $^1$H NMR (400 MHz, CDCl$_3$) δ 8.92 (s, 1H), 6.94 (s, 1H), 6.56 (s, 1H), 6.50 (d, J = 7.4 Hz, 1H), 6.18 (d, J = 16.9 Hz, 1H), 5.98 (dd, J = 16.9, 10.3 Hz, 1H), 5.54 (d, J = 10.2 Hz, 1H), 4.81-4.73 (m, 1H), 4.70-4.67 (m, 1H), 4.20-4.12 (m, 2H), 3.89 (s, 6H), 3.88-3.67 (m, 10H), |
| Example 687 | 6.3 | 6.9 | 10.0 | $^1$H NMR (400 MHz, CDCl$_3$) δ 9.03 (s, 1H), 7.25 (s, 1H), 6.70 (t, J = 7.9 Hz, 1H), 6.47 (brs, 1H), 6.25 (d, J = 16.9 Hz 1H), 6.06 (dd, J = 16.9, 10.2 Hz, 1H), 5.62 (d, J = 10.3 Hz, 1H), 4.88-4.81 (m, 1H), 4.78 (brs, 1H), 4.23 (dd, J = 9.5, 6.2 Hz, 2H), 3.93 (s, 6H), 3.92-3.81 (m, 9H), 3.81-3.77 (m, 1H). |
| Example 690 | 8.0 | 8.4 | 12.1 | $^1$H NMR (400 MHz, CDCl$_3$) δ 8.98 (s, 1H), 6.99 (s, 1H), 6.64 (s, 1H), 6.55 (d, J = 7.1 Hz, 1H), 6.26 (dd, J = 17.1, 1.3 Hz, 1H), 6.11-6.04 (m, 1H), 6.04 (s, 1H), 5.63 (d, J = 10.2 Hz, 1H), 4.86-4.73 (m, 2H), 4.68 (d, J = 12.8 Hz, 1H), 4.61 (d, J = 12.8 Hz, 1H), 4.29-4.20 (m, 2H), 3.97 (s, 6H), 3.94-3.85 (m, 3H), 3.82 (dd, J = 9.4, 5.0 Hz, 1H), 2.79-2.68 (m, 2H), 1.23 (dd, J = 6.3, 2.2 Hz, 6H). |
| Example 693 | 5.6 | 1.3 | 2.1 | $^1$H NMR (400 MHz, CDCl$_3$) δ 8.99 (s, 1H), 6.99 (s, 1H) 6.63 (s, 1H), 6.53 (s, 1H), 6.23 (d, J = 16.9 Hz, 1H), 6.06 (dd, J = 17.0, 10.2 Hz, 1H), 5.94 (s, 1H), 5.60 (d, J = 10.2 Hz, 1H), 4,87-4.77 (m, 2H), 4.39 (d, J = 8.3 Hz, 1H), 4.30 (d, J = 13.2 Hz, 1H), 4.27-4.20 (m, 2H), 3.96 (s, 6H), 3.88 (dd, J = 9.5, 3.5 Hz, 1H), 3.81 (dd, J = 14.4, 5.1 Hz, 1H), 3.51-3.39 (m, 3H), 3.38 (s, 3H), 2.15-2.01 (m, 2H), 1.79-1.74 (m, 2H). |
| Example 694 | 4.8 | 10.0 | 12.0 | $^1$H NMR (400 MHz, CDCl$_3$) δ 9.01 (s, 1H), 6.70 (t, J = 7.9 Hz, 1H), 6.22 (d, J = 16.8 Hz, 1H), 6.07 (dd, J = 17.0, 10.2 Hz, 1H), 5.59 (d, J = 10.2 Hz, 1H), 4.86-4.80 (m, 2H), 4.38-4.21 (m, 4H), 3.93 (s, 6H) 3.91-3.82 (m, 2H), 3.52-3.43 (m, 3H), 3.39 (s, 3H), 2.21-2.11 (m, 2H). |
| Example 704 | 8.5 | 17.2 | 20.2 | 1H NMR (400 MHz, CDCl$_3$) δ 8.92 (s, 1H), 6.76 (s, 1H), 6.65 (brs, 1H), 6.62 (s, 1H), 6.25 (d, J = 16.9 Hz, 1H), 6.05 (dd, J = 16.8, 10.4 Hz, 1H), 5.61 (d, J = 10.3 Hz, 1H), 4.69 (brs, 1H), 4.55 (brs, 1H), 4.46-4.23 (m, 5H), 4.10-3.99 (m, 2H), 3.95 (s, 6H), 3.74 (d, J = 11.9 Hz, 1H), 3.61 (t, J = 11.8 Hz, 1H), 3.32 (s, 3H), 2.10-1.98 (m, 1H), 1.90-1.80 (m, 1H). |
| Example 715 | 62.7 | 1917.5 | 1917.5 | $^1$H NMR (400 MHz, CDCl$_3$) δ 10.71 (s, 1H), 9.63 (s, 1H), 9.60 (s, 1H), 8.61 (s, 1H), 7.80 (s, 1H), 6.72 (s, 1H), 6.49 (d, J = 16.7 Hz, 1H), 6.40 (dd, J = 16.9, 9.7 Hz, 1H), 5.84 (d-J = 9.7 Hz, 1H), 5.21 (t, J = 6.0 Hz, 2H), 4.00 (s, 7H), 3.89 (t, J = 5.9 Hz, 2H), 3.35 (s, 3H). |
| Example 723 | 78.5 | 338.1 | 1211.5 | $^1$H NMR (400 MHz, DMSO-d$_6$) δ 9.75 (s, 1H), 9.71 (s, 1H), 9.68 (s, 1H), 8.37 (s, 1H), 8.21 (s, 1H), 8.05 (s, 1H), |

TABLE 1-continued

The results of enzymatic activity and cell activity tests

| Example No. | Enzymatic activity FGFR4 IC$_{50}$ (nM) | Cell activity HuH-7 EC$_{50}$ (nM) | HuH-7 Absolute IC$_{50}$ (nM) | $^1$H-NMR |
|---|---|---|---|---|
| | | | | 7.15 (s, 1H), 6.51 (dd, J = 17.0, 10.2 Hz, 1H), 6.26 (dd, J = 17.1, 2.2 Hz, 1H), 5.75 (dd, J = 10.1, 2.1 Hz, 1H), 4.56 (t, J = 5.6 Hz, 2H), 4.06 (s, 6H), 3.70 (t, J = 5.6 Hz, 2H), 3.14 (s, 3H), |
| Example 730 | 115.0 | 164 | 194 | $^1$H NMR (400 MHz, CDCl$_3$) δ 8.75 (s, 1H), 7.68 (s, 1H), 7.40 (s, 1H), 6.65 (s, 1H), 6.38-6.32 (m, 1H), 6.27-6.21 (m, 1H), 5.73-5.69 (m, 1H), 5.30 (s, 1H), 4.81 (d, J = 5.6 Hz, 2H), 3.96 (s, 6H), 3.78 (s, 3H). |
| Example 752 | 990.9 | 1712 | 2631 | $^1$H NMR (400 MHz, CDCl$_3$) δ 8.82 (s, 1H), 6.68 (s, 1H), 6.66 (s, 1H), 6.59 (s, 1H), 6.13 (dd, J = 16.8, 1.4 Hz, 1H), 5.94 (dd, J = 17.0, 10.2 Hz, 1H), 5.51 (d, J = 10.3, 1.4 Hz, 1H), 5.30 (s, 1H), 4.96-4.82 (m, 1H), 4.42 (s, 1H), 4.26 (dd, J = 9.8, 6.0 Hz, 1H), 4.18 (dd, J = 9.3, 7.4 Hz, 1H), 3.92 (s, 6H), 3.88-3.81 (m, 1H), 3.74 (d, J = 9.2, 6.9 Hz, 1H), 3.13 (d, J = 4.6 Hz, 3H). |
| Example 753 | 19 | 130 | 212 | $^1$H NMR (400 MHz, Methanol-d$_4$) δ 9.22 (s, 1H), 7.65 (s, 1H), 6.94 (s, 1H), 6.19 (dd, J = 17.1, 9.9 Hz, 1H), 6.10 (d, J = 17.1, 2.2 Hz, 1H), 5.56 (dd, J = 9.9, 2.1 Hz, 1H), 5.01 (s, 2H), 4.29 (s, 1H), 4.17 (dd, J = 9.3, 6.2 Hz, 1H), 3.98 (s, 6H), 3.93-3.85 (m, 1H), 3.85-3.79 (m, 1H). |
| Example 754 | 13.6 | 18.0 | 54.0 | $^1$H NMR (400 MHz, CDCl$_3$) δ 9.06 (d, J = 6.5 Hz, 1H), 7.11 (s, 1H), 6.64 (s, 1H), 6.25 (dd, J = 16.9, 1.5 Hz, 1H), 6.05 (dd, J = 17.0, 10.4 Hz, 1H), 5.60 (dd, J = 10.3, 1.5 Hz, 1H), 4.91 (brs, 1H), 4.79 (t, J = 6.5, 1H), 4.59 (q, J = 7.0, 2H), 4.35-4.19 (m, 2H), 3.93-3.68 (m, 2H) 1.48 (t, J = 7.1 Hz, 3H). |
| Example 755 | 43.0 | NT | NT | $^1$H NMR (400 MHz, CDCl$_3$) δ 8.84 (s, 1H), 6.84 (s, 1H), 6.67 (s, 1H), 6.58-6.49 (m, 3H), 6.30 (d, J = 8.5 Hz, 2H), 6.10 (d, J = 17.0 Hz, 2H), 6.04-5.83 (m, 2H), 5.48 (d, J = 10.1 Hz, 1H), 4.72 (s, 3H), 4.63 (d, J = 14.8 Hz, 1H), 4.17-4.04 (m, 2H), 3.89 (s, 6H), 3.78 (d, J = 6.2 Hz, 1H), 3.71 (s, 2H), 3.68 (s, 7H). |
| Example 756 | 20.2 | 19 | 31 | $^1$H NMR (400 MHz, CDCl$_3$) δ 9.10 (s, 1H), 7.43 (s, 1H), 7.13 (s, 1H), 6.66 (s, 1H), 6.36 (s, 1H), 6.26 (dd, J = 16.9, 1.4 Hz, 1H), 6.04 (dd, J = 16.9, 10.3 Hz, 1H), 5.94 (s, 1H), 5.63 (dd, J = 10.3, 1.4 Hz, 1H), 4.89-4.78 (m, 2H), 4.45 (d, J = 2.8 Hz, 2H), 4.31-4.21 (m, 2H), 3.97 (s, 6H), 3.95-3.92 (m, 2H), 3.90-3.87 (m, 1H), 3.81 (dd, J = 9.5, 4.8 Hz, 1H), 2.94-2.77 (m, 2H). |
| Example 758 | 5.9 | 5.8 | 9.2 | $^1$H NMR (400 MHz, CDCl$_3$) δ 8.89 (s, 1H), 6.71 (s, 1H), 6.62 (s, 1H), 6.42 (s, 1H), 6.20 (d, J = 17.0 Hz, 1H), 6.03-5.91 (m 2H), 5.56 (d J = 10.3 Hz, 1H), 4.93 (d, J = 7.1 Hz, 1H), 4.81 (s, 1H), 4.67 (s, 1H), 4.41 (s, 1H), 4.25-4.05 (m, 3H), 4.25-4.12 (m, 3H), 3.97-3.80 (m, 10H), 3.68 (s, 3H). |
| Example 759 | 5.7 | 42.2 | 61.1 | $^1$H NMR (400 MHz, CDCl$_3$) δ 8.89 (d, J = 11.1 Hz, 1H), 6.69 (s, 1H), 6.61 (s, 1H), 6.35-6.09 (m, 2H), 5.94 (dd, J = 17.0, 10.3 Hz, 1H), 5.59 (d, J = 10.1 Hz, 2H), 5.00 (p, J = 7.5 Hz, 1H), 4.83 (s, 1H), 4.31-4.18 (m, 1H), 4.16 (d, J = 8.1 Hz, 1H), 4.01-3.85 (m, 12H), 3.67 (d, J = 14.5 Hz, 2H). |
| Example 760 | 2.9 | 5.5 | 6.7 | $^1$H NMR (400 MHz, CDCl$_3$) δ 8.86 (d, J = 5.2 Hz, 1H), 6.68 (d, J = 10.6 Hz, 1H), 6.61 (s, 1H), 6.42-6.21 (m, 1H), 6.14 (t, J = 18.1 Hz, 1H), 6.00-5.78 (m, 1H), 5.74 (s, 1H), 5.49 (dd, J = 29.1, 10.3 Hz, 1H), 4.91 (t, J = 7.6 Hz, 1H), 4.87-4.78 (m, 1H), 4.52-4.40 (m, 1H), 4.24-4.14 (m, 2H), 4.08 (d, J = 8.7 Hz, 1H), 3.95 (s, 6H), 3.92-3.83 (m, 2H), 3.80-3.70 (m, 2H), 2.03-1.89 (m, 2H), 1.54-1.43 (m, 3H). |
| Example 761 | 14.3 | 20.7 | 51.8 | $^1$H NMR (400 MHz, CDCl$_3$) δ 9.14 (s, 1H), 8.64 (s, 1H), 8.53 (s, 1H), 7.74 (s, 1H), 6.88 (d, J = 2.7 Hz, 1H), 6.61 (d, J = 2.7 Hz, 1H), 6.20 (d J = 16.9 Hz, 1H), 6.01 (s, 1H), 5.56 (d, J = 10.3 Hz, 1H), 5.01-4.91 (m, 2H), 4.32-4.23 (m, 2H), 4.02 (s, 3H), 3.99-3.95 (m, 1H), 3.95 (s, 3H), 3.87 (s, 3H), 3.84-3.82 (m, 1H). |
| Example 762 | 5.2 | 3.2 | 4.2 | $^1$H NMR (400 MHz, CDCl$_3$) δ 8.94 (s, 1H), 6.83 (s, 1H), 6.63 (s, 1H), 6.30 (s, 1H), 6.22 (d, J = 17.1 Hz, 1H), 6.04 (dd, J = 16.9, 10.2 Hz, 1H), 5.81 (s, 1H), 5.60 (d, J = 10.2 Hz, 1H), 4.87-4.80 (m, 1H), 4.80-4.73 (m, 1H), 4.70 (d, J = 6.4 Hz, 2H), 4.60 (d, J = 13.8 Hz, 2H), 4.27 (d, J = 13.6 Hz, 1H), 4.23-4.15 (m, 2H), 4.10 (d, J = 13.7 Hz, 1H), 3.96 (s, 6H), 3.86 (dd, J = 9.6, 4.0 Hz, 1H), 3.75 (dd, J = |

TABLE 1-continued

The results of enzymatic activity and cell activity tests

| Example No. | Enzymatic activity FGFR4 IC$_{50}$ (nM) | Cell activity HuH-7 EC$_{50}$ (nM) | HuH-7 Absolute IC$_{50}$ (nM) | $^1$H-NMR |
|---|---|---|---|---|
| Example 763 | 7.9 | 7.8 | 11.1 | 9.4, 5.8 Hz, 1H), 3.23 (q, J = 7.2 Hz, 1H), 2.08 (d, J = 8.6 Hz, 1H). $^1$H NMR (400 MHz, CDCl$_3$) δ 8.91 (s, 1H), 6.79 (s, 1H), 6.63 (s, 1H), 6.25 (dd, J = 23.9, 17.1 Hz, 2H), 5.63 (dd, J = 19.8, 10.3 Hz, 2H) 4.76 (s, 2H) 4.66 (s, 1H), 4.22 (dd, J = 15.1, 7.2 Hz, 3H), 4.4-4.10 (m, 1H), 3.97 (d, J = 2.0 Hz, 8H), 3.85 (d, J = 10.5 Hz, 3H), 3.75 (s, 1H), 2.00 (d, J = 9.2 Hz, 1H), 1.93 (s, 1H). |
| Example 764 | 7.0 | 49.4 | 60.4 | $^1$H NMR (400 MHz, CDCl$_3$) δ 8.78 (s, 1H), 6.84 (brs, 2H), 6.76 (s, 1H), 6.58 (t J = 7.9 Hz, 1H), 6.39 (brs, 1H), 6.08 (d J = 16.9 Hz, 1H), 5.93 (dd, J = 17.0, 10.2 Hz, 1H), 5.39 (d, J = 10.2 Hz, 1H), 4.81 (p, J = 6.6, 5.6 Hz, 2H), 4.15-4.05 (m, 2H), 3.85-3.81 (m, 1H), 3.81 (s, 6H), 3.71 (dd, J = 9.2, 5.8 Hz, 1H), 3.08 (s, 3H). |
| Example 765 | 158 | 420.8 | 656.5 | $^1$H NMR (400 MHz, CDCl$_3$) δ 8.93 (s, 1H), 6.80 (s, 1H), 6.64 (s, 1H), 6.23 (d, J = 16.9 Hz, 1H), 6.08-5.91 (m, 4H), 5.75 (s, 1H), 5.58 (d, J = 10.4 Hz, 1H), 4.89 (s, 2H), 4.24 (ddd, J = 23.7, 9.4, 5.9 Hz, 2H), 3.96 (s, 6H), 3.88 (dd, J = 9.8, 3.4 Hz, 1H), 3.76 (dd, J = 9.2, 5.5 Hz, 1H). |
| Example 766 | 8.3 | 19.8 | 27.9 | $^1$H NMR (400 MHz, CDCl$_3$) δ 8.80 (s, 1H), 6.60 (s, 1H), 6.54 (s, 1H), 6.33 (brs, 1H), 6.12 (d, J = 16.9 Hz, 1H), 5.96 (dd, J = 17.0, 10.3 Hz, 1H), 5.48 (dd, J = 10.3, 1.4 Hz, 1H), 4.83-4.78 (m, 2H), 4.17-4.06 (m, 2H), 3.84-3.81 (m,1H), 3.71-3.68 (m, 1H). |
| Example 767 | 7 | 23.9 | 45.1 | $^1$H NMR (400 MHz, CDCl$_3$) δ 8.87 (s, 1H), 6.87 (s, 1H), 6.68 (t, J = 7.9 Hz, 1H), 6.60 (brs, 1H), 6.22 (s, 1H), 6.17 (s, 1H), 5.96 (dd, J = 16.9, 10.3 Hz, 1H), 5.80 (brs, 1H), 5.56 (d, J = 10.3 Hz, 1H), 4.94-4.83 (m, 2H), 4.30-4.18 (m, 2H), 3.91 (s, 6H), 3.88 (s, 1H), 3.75 (dd, J = 9.3, 5.9 Hz, 1H), 3.65 (s, 2H), 1.36 (t, J = 7.2 Hz, 3H). |
| Example 768 | 4 | 9.9 | 12.5 | $^1$H NMR (400 MHz, CDCl$_3$) δ 8.95 (s, 1H), 7.09 (s, 1H), 6.69 (t, J = 7.9 Hz, 1H), 6.26 (dd, J = 17.0, 1.3 Hz, 1H), 6.14 (d, J = 7.4 Hz, 1H), 6.03 (dd, J = 17.0, 10.3 Hz, 1H), 5.75 (d, J = 7.1 Hz, 1H), 5.63 (dd, J = 10.3, 1.3 Hz, 1H), 4.89-4.83 (m, 1H), 4.82-4.72 (m, 5H), 4.23 (dd, J = 9.5, 6.2 Hz, 2H), 3.92 (s, 6H), 3.81 (ddd, J = 19.8, 9.5, 4.8 Hz, 2H). |
| Example 769 | 3.7 | 8.4 | 10.0 | $^1$H NMR (400 MHz, CDCl$_3$) δ 8.94 (s, 1H), 7.04 (s, 1H), 6.69 (t, J = 7.8 Hz, 1H), 6.34 (brs, 1H), 6.22 (d, J = 16.9 Hz, 1H), 6.04 (dd, J = 17.1, 10.1 Hz, 1H), 5.60 (d, J = 10.2 Hz, 1H), 4.87-4.70 (m, 4H), 4.63 (d, J = 13.5 Hz, 2H), 4.30 (d, J = 13.6 Hz, 1H), 4.23-4.10 (m, 3H), 3.92 (s, 6H), 3.90-3.85 (m, 1H), 3.79-3.73 (m, 1H), 3.29-3.24 (m, 1H), 2.08-2.01 (m, 2H). |
| Example 770 | 2413.9 | >10000 | >10000 | $^1$H NMR (400 MHz, CDCl$_3$) δ 8.90 (s, 1H), 7.78 (t, J = 7.5, 1H), 7.31 (s, 1H), 7.17 (t, J = 8.0 Hz, 1H), 6.96 (s, J = 8.0 Hz, 1H), 6.49 (m, 1H), 6.27 (brs, 1H), 6.18 (d, J = 16.9 Hz, 1H), 5.93 (dd, J = 17.0, 10.3 Hz, 1H), 5.84, (brs, 1H), 5.53 (d, J = 10.3 Hz, 1H), 4.91-4.88 (m, 2H), 4.31-4.13 (m, 2H), 3.94 (s, 3H), 3.94-3.88(m, 1H), 3.82-3.70 (m, 1H), 3.21 (t, J = 4.8 Hz, 3H). |
| Example 771 | 7.9 | 25.5 | 32.3 | $^1$H NMR (400 MHz, CDCl$_3$) δ 8.88 (s, 1H), 6.67 (s, 1H), 6.63 (s, 1H), 6.22 (brs, 1H), 6.20 (dd, J = 17.0, 1.4 Hz, 1H), 5.97 (dd, J = 17.0, 10.3 Hz, 1H), 5.79 (brs, 1H), 5.55 (dd, J = 10.3, 1.5 Hz, 1H), 4.94-4.86 (m, 2H), 4.26-4.18 (m, 2H), 3.96 (s, 6H), 3.88 (dd, J = 9.8, 3.2 Hz, 1H), 3.81-3.72 (m, 1H). |
| Example 772 | 2.9 | 6.8 | 8.1 | $^1$H NMR (400 MHz, CDCl$_3$) δ 8.77 (s, 1H), 6.81 (s, 1H), 6.59 (s, 1H), 6.57(brs, 1H), 6.14 (d, J = 16.6 Hz, 1H), 5.96 (m, 1H), 5.85 (brs, 1H), 5.53 (d, J = 10.4 Hz, 1H), 4.87-4.66 (m, 2H), 4.53-4.23 (m, 4H), 4.18-4.08 (m, 2H), 3.83 (s, 6H), 3.82-3.69 (m, 2H), 1.95-1.75 (m, 2H), 1.51 (s, 3H). |
| Example 773 | 1.8 | 2.0 | 2.3 | $^1$H NMR (400 MHz, CDCl$_3$) δ 8.84 (s, 1H), 6.87 (d, J = 5.2 Hz, 1H), 6.66 (t, J = 8.1 Hz, 1H), 6.45 (brs, 1H), 6.14 (dd, J = 16.9, 12.4 Hz, 1H), 5.96 (dd, J = 16.9, 10.3 Hz, 1H), 5.82 (brs, 1H), 5.50 (d, J = 20.2, 10.3 Hz, 1H), 4.93-4.85 (m, 1H), 4.84-4.78 (m, 1H), 4.43-4.34 (m, 2H), 4.19-3.77 (m, 5H), 3.90 (s, 6H), 3.72-3.69 (m, 1H), 1.49 (d, J = 23.8 Hz, 3H). |
| Example 774 | 3.2 | 6.9 | 8.8 | $^1$H NMR (400 MHz, CDCl$_3$) δ 8.87 (s, 1H), 6.88 (s, 1H), 6.67 (t, J = 7.9 Hz, 1H), 6.52 (brs, 1H), 6.24 (dd, J = 17.0, 1.5 Hz, 1H), 6.08 (dd, J = 17.0, 10.2 Hz, 1H), 5.96 (brs, |

TABLE 1-continued

The results of enzymatic activity and cell activity tests

| Example No. | Enzymatic activity FGFR4 IC$_{50}$ (nM) | Cell activity HuH-7 EC$_{50}$ (nM) | HuH-7 Absolute IC$_{50}$ (nM) | $^1$H-NMR |
|---|---|---|---|---|
| | | | | 1H), 5.61 (dd, J = 10.2, 1.4 Hz, 1H), 4.82-4.72 (m, 2H), 4.57 (brs, 4H), 4.26-4.16 (m, 2H), 3.91 (s, 6H), 3.85 (dd, J = 9.4, 3.9 Hz, 1H), 3.78 (dd, J = 9.4, 5.0 Hz, 1H), 2.42 (p, J = 7.6 Hz, 2H). |
| Example 775 | 8.9 | 20.8 | 27.8 | $^1$H NMR (400 MHz, CDCl$_3$) δ 8.92 (s, 1H), 6.96 (s, 1H), 6.69 (t, J = 8.0 Hz, 1H), 6.65 (s, 1H), 6.25 (dd, J = 17.0, 1.4 Hz, 1H), 6.08 (s, 1H), 6.02 (dd, J = 16.9, 10.3 Hz, 1H), 5.60 (dd, J = 10.3, 1.4 Hz, 1H), 4.73 (brs, 1H, 4.56 (brs, 1H), 4.42 (d, J = 8.5 Hz, 1H), 4.39-4.22 (m, 4H), 4.05 (dd, J = 12.0, 4.5 Hz, 1H), 3.99 (d, J = 11.7 Hz, 1H), 3.92 (s, 6H), 3.75 (dd, J = 11.9, 1.6 Hz, 1H), 3.65-3.57 (m, 1H), 3.33 (s, 3H), 2.09-2.02 (m, 1H), 1.91-1.81 (m, 1H). |
| Example 776 | 4.9 | 7.9 | 9.4 | $^1$H NMR (400 MHz, CDCl$_3$) δ 8.89 (s, 1H), 6.92 (s, 1H), 6.67 (t, J = 7.9 Hz, 1H), 6.38 (brs, 1H), 6.23 (dd, J = 17.0, 1.4 Hz, 1H), 6.03 (dd, J = 16.9, 10.3 Hz, 1H), 5.80 (brs, 1H), 5.61 (dd, J = 10.3, 1.4 Hz, 1H), 4.86-4.77 (m, 2H), 4.27-4.19 (m, 6H), 3.91 (s, 6H), 3.89-3.86 (m, 1H), 3.76 (dd, J = 9.3, 5.7 Hz, 1H), 3.69-3.66 (m, 4H), 1.86 (t, J = 5.2 Hz, 4H). |
| Example 777 | NT | 650.8 | 660 | $^1$H NMR (400 MHz, CDCl$_3$) δ 8.80 (s, 1H), 6.86-6.81 (m, 3H), 6.45 (brs, 1H), 6.13 (d, J = 16.9 Hz, 1H), 6.06 (brs, 1H), 5.86 (dd J = 16.9 10.3 Hz, 1H), 5.67 (brs, 1H), 5.49 (d, J = 10.4 Hz, 1H), 4.98-4.68 (m, 2H), 4.28-4,07 (m, 2H), 3.84 (s, 3H), 3.84-3.71 (m, 1H), 3.67 (dd, J = 9.2, 6.0 Hz, 1H), 3.08 (d, J = 4.8 Hz, 3H). |
| Example 778 | NT | 9.5 | 11.2 | $^1$H NMR (400 MHz, CDCl$_3$) δ 8.87 (s, 1H), 6.70 (s, 1H), 6.61 (s, 1H), 6.29 (brs, 1H), 6.11 (d, J = 17.1 Hz, 1H), 5.81 (m, 2H), 5.45 (d, J = 10.2 Hz, 1H), 5.07-4.84 (m, 2H), 4.55-4.40 (m, 1H), 4.22-4.15 (m, 2H), 4.05-3.75 (m, 3H), 3.95 (s, 6H), 3.91-3.71 (m, 2H), 2.05-1.96 (m, 2H), 1.44 (s, 3H). |
| Example 779 | NT | 7.5 | 8.6 | $^1$H NMR (400 MHz, CDCl$_3$) δ 8.87 (s, 1H), 6.70 (s, 1H), 6.61 (s, 1H), 6.43 (brs, 1H), 6.11 (d, J = 17.1 Hz, 1H), 5.97 (dd, J = 16.9, 10.3 Hz, 1H,), 5.79 (brs, 1H), 5.45 (d, J = 10.2 Hz, 1H), 5.01-4.75 (m, 2H), 4.55-4.40 (m, 1H), 4.25-4.00 (m, 4H), 3.95 (s, 6H), 3.94-4.80 (m, 2H), 3.79-3.72 (m, 1H), 2.03-1.93 (m, 2H), 1.53 (s, 3H). |
| Example 786 | 17.0 | 38.4 | 47.6 | $^1$H NMR (400 MHz, CDCl$_3$) δ 8.87 (s, 1H), 6.86 (s, 1H), 6.68 (t, J = 7.9 Hz, 1H), 6.49 (s, 1H), 6.20 (dd, J = 16.9, 1.3 Hz, 1H), 6.11 (s, 1H), 6.02 (d, J = 8.6 Hz, 1H), 5.88 (dd, J = 17.0, 10.3 Hz 1H) 5.53 (dd, J = 10.4, 1.4 Hz, 1H), 4.73 (d, J = 8.5 Hz, 1H), 4.38-4.26 (m, 1H), 4.08 (d, J = 12.1 Hz, 1H), 3.99 (d, J = 12.1 Hz, 1H), 3.92 (s, 6H), 3.75 (dd, J = 12.0, 1.7 Hz, 1H), 3.61 (m, 1H), 3.13 (s, 3H), 1.91 (m, 2H). |
| Example 787 | 45.0 | 86.0 | 102.8 | $^1$H NMR (400 MHz, Methanol-d$_4$) δ 8.89 (s, 1H), 6.90 (t, J = 8.1 Hz, 1H), 6.81 (s, 1H), 6.13 (dd, J = 17.1, 1.9 Hz, 1H), 5.96 (dd, J = 17.0, 10.3 Hz, 1H), 5.47 (dd, J = 10.2, 1.9 Hz, 1H), 4.24 (dt, J = 12.4, 4.2 Hz, 1H), 4.07 (dd, J = 11.9, 4.4 Hz, 1H), 3.99-3.93 (m, 1H), 3.90 (s, 6H), 3.78 (dd, J = 12.0, 2.0 Hz, 1H), 3.67-3.52 (m, 2H), 3.47-3.33 (m, 1H), 2.06 (qd, J = 12.5, 4.8 Hz, 1H), 1.77-1.66 (m, 1H), 1.46-1.26 (m, 5H). |
| Example 789 | 7.8 | 12.6 | 15.9 | $^1$H NMR (400 MHz, CDCl$_3$) δ 9.02 (s, 1H), 7.24 (s, 1H), 7.00 (brs, 1H), 6.70 (t, J = 8.0 Hz, 1H), 6.25 (dd, J = 16.9, 1.3 Hz, 1H), 6.02 (dd, J = 17.0, 10.3 Hz, 1H), 5.57 (d, J = 10.3 Hz, 1H), 4.50-4.30 (m, 2H), 4.19-3.76 (m, 11H), 3.97 (s, 6H), 3.63 (t, J = 10.2 Hz, 1H), 2.32-1.75 (m, 2H). |
| Example 790 | 8.5 | 11.4 | 13.6 | $^1$H NMR (400 MHz, CDCl$_3$) δ 8.93 (s, 1H), 6.97 (s, 1H), 6.68 (t, J = 7.9 Hz, 1H), 6.24 (dd, J = 17.1, 1.4 Hz, 1H), 6.04 (brs, 1H), 6.01 (dd, J = 16.9, 10.3 Hz, 1H), 5.63-5.53 (m, 1H), 4.62-4.31 (m, 4H), 4.22-3.95 (m, 4H), 3.92 (s, 6H), 3.78-3.72 (m, 1H), 3.66-3.57 (m, 1H), 3.28 (s, 3H), 1.13-2.05 (m, 1H), 1.90-1.78 (m, 1H), 1.53 (s, 3H). |
| Example 791 | 3.7 | 6.4 | 8.4 | $^1$H NMR (400 MHz, CDCl$_3$) δ 8.97 (s, 1H), 7.10 (s, 1H), 6.70 (t, J = 7.9 Hz, 1H), 6.48 (d, J = 7.2 Hz, 1H), 6.27 (dd, J = 17.0, 1.4 Hz, 1H), 6.18-6.08 (m, 1H), 5.98 (dd, J = 16.9, 10.3 Hz, 1H), 5.59 (dd, J = 10.3, 1.3 Hz, 1H), 4.80 (q, J = 12.0 Hz, 2H), 4.68 (q, J = 11.9 Hz, 2H), 4.44 (d, J = 10.0 Hz, 1H), 4.41-4.34 (m, 1H), 4.06 (dd, J = 11.9, 4.6 |

TABLE 1-continued

The results of enzymatic activity and cell activity tests

| Example No. | Enzymatic activity FGFR4 IC$_{50}$ (nM) | Cell activity HuH-7 EC$_{50}$ (nM) | HuH-7 Absolute IC$_{50}$ (nM) | $^1$H-NMR |
|---|---|---|---|---|
| | | | | Hz, 1H), 3.99 (d, J = 11.8 Hz, 1H), 3.92 (s, 6H), 3.76 (dd, J = 11.9, 1.6 Hz, 1H), 3.62 (td, J = 12.0, 2.5 Hz, 1H), 2.02 (s, 1H), 1.92-1.81 (m, 1H). |
| Example 792 | 3.1 | 4.8 | 6.2 | $^1$H NMR (400 MHz, CDCl$_3$) δ 8.91 (s, 1H), 6.92 (s, 1H), 6.83 (d, J = 6.8 Hz, 1H), 6.68 (t, J = 7.9 Hz, 1H), 6.26 (dd, J = 16.9, 1.5 Hz, 1H), 6.07 (dd, J = 17.0, 10.2 Hz, 1H), 6.02 (brs, 1H),, 5.61 (dd, J = 10.3, 1.5 Hz, 1H), 4.53 (s, 2H), 4.48-4.36 (m, 3H), 4.35-4.29 (m, 1H), 4.05 (dd, J = 11.9, 4.6 Hz, 1H), 3.99 (d, J = 11.7 Hz, 1H), 3.91 (s, 6H), 3.74 (dd, J = 11.8, 1.6 Hz, 1H), 3.61 (td, J = 12.0, 2.5 Hz, 1H), 2.41-2.32 (m, 2H), 2.12-2.04 (m, 1H), 1.91-1.80 (m, 1H). |
| Example 793 | 5.3 | 7.9 | 9.9 | $^1$H NMR (400 MHz, CDCl$_3$) δ 8.92 (s, 1H), 6.97 (s, 1H), 6.67 (t, J = 7.9 Hz, 1H), 6.63 (brs, 1H), 6.23 (dd, J = 17.0, 1.3 Hz, 1H), 6.04 (d, J = 8.8 Hz, 1H), 5.99 (dd, J = 17.1, 10.4 Hz, 1H), 5.57 (dd, J = 10.2, 1.4 Hz, 1H), 4.51-4.39 (m, 3H), 4.38-4.31 (m, 1H), 4.30-4.20 (m, 2H), 4.07-3.96 (m, 2H), 3.91 (s, 6H), 3.75 (dd, J = 11.8, 1.6 Hz, 1H), 3.65-3.56 (m, 1H), 2.05-1.98 (m, 1H), 1.91-1.80 (m, 1H), 1.56 (s, 3H). |
| Example 794 | 4.8 | 5.5 | 6.9 | $^1$H NMR (400 MHz, CDCl$_3$) δ 8.90 (d, J = 3.0 Hz, 1H), 6.93 (d, J = 4.0 Hz, 1H), 6.68 (t, J = 7.9 Hz, 1H), 6.36 (brs, 1H), 6.26-6.15 (m, 1H), 6.05-5.90 (m, 2H), 5.60-5.50 (m, 1H), 4.50-4.30 (m, 2H), 3.92 (s, 6H), 4.23-3.80 (m, 7H), 3.70-3.65 (m, 1H), 3.60-3.55 (m, 1H), 3.34 (d, J = 7.0 Hz, 3H), 2.02-1.90 (m, 2H), 1.87-1.78 (m, 2H). |
| Example 795 | 7.5 | 9.5 | 11.8 | $^1$H NMR (400 MHz, CDCl$_3$) δ 9.00 (s, 1H), 7.20 (s, 1H), 6.69 (t, J = 7.9 Hz, 1H), 6.22 (dd, J = 17.0, 1.5 Hz, 1H), 6.02 (dd, J = 17.0, 10.3 Hz, 1H), 5.55 (d, J = 10.8 Hz, 1H), 4.54-4.15 (m, 4H), 4.13-4.00 (m, 2H), 3.93 (s, 6H), 3.77 (d, J = 12.0 Hz, 1H), 3.70-3.57 (m, 1H), 3.52-3.38 (m, 3H), 3.37 (s, 3H), 2.07-1.85 (m, 2H), 1.65-1.46 (m, 4H). |
| Example 796 | 23.0 | 38.0 | 47.8 | $^1$H NMR (400 MHz, CDCl$_3$) δ 8.95 (s, 1H), 7.04 (s, 1H), 6.68 (t, J = 7.9 Hz, 1H), 6.25 (s, 1H), 6.20 (dd, J = 17.0, 1.4 Hz, 1H), 6.07 (s, 1H), 5.93 (dd, J = 16.9, 10.3 Hz, 1H), 5.56 (dd, J = 10.2, 1.4 Hz, 1H), 4.71 (d, J = 6.4 Hz, 2H), 4.61 (d, J = 13.6 Hz, 1H), 4.55 (d, J = 13.6 Hz, 1H), 4.45 (d, J = 8.9 Hz, 1H), 4.41-4.34 (m, 1H), 4.17 (d, J = 13.7 Hz, 1H), 4.07 (d, J = 13.5 Hz, 2H), 3.99 (d, J = 11.9 Hz, 1H), 3.92 (s, 6H), 3.73 (d, J = 11.6 Hz, 1H), 3.67-3.64 (m, 1H), 3.59 (td, J = 11.9, 2.6 Hz, 1H), 3.22 (q, J = 7.1 Hz, 1H), 1.97 (d, J = 13.7 Hz, 1H), 1.92-1.81 (m, 1H). |
| BLU-9931 | 24.7 | 549 | 1362 | |
| BLU-554 | 18.0 | 27 | 126 | |

Note
"NT", i.e., "Not Tested", means that the compound is not tested. BLU-9931 and BLU-554 are positive compounds.

It can be seen from the enzymatic activity data of the compounds of specific examples that the compounds of the present invention have a strong inhibitory effect on FGFR4 kinase activity. It can be seen from the cell activity data of the compounds of specific examples that the compounds of the present invention have a strong inhibitory effect on the proliferation activity of HuH-7 cells highly expressing FGFR4.

All documents mentioned in the present application are hereby incorporated by reference in their entirety, just as each document is cited separately as a reference. In addition, it should be understood that various modifications and changes may be made by those skilled in the art after reading the above teachings of the present invention and these equivalent forms also fall within the scope defined by the claims appended hereto.

The invention claimed is:

1. A method for treating FGFR4 related cancer comprising administering to a patient in need thereof a therapeutically effective amount of a compound of formula (IVa-1), a stereoisomer or pharmaceutically acceptable salt thereof:

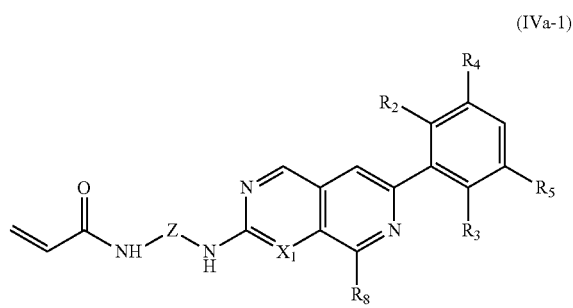

(IVa-1)

wherein
Z is

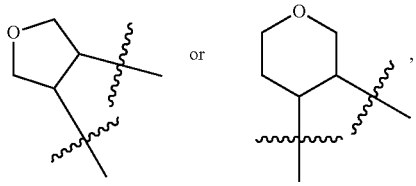 [SMILES: *C1COCC1* ; *C1CCOCC1*]

$R_2$, $R_3$, $R_4$ and $R_5$ are each independently selected from the group consisting of H, deuterium, Cl, F, hydroxyl, methyl, isopropyl, cyclopropyl, 3-oxacyclobutyl, trifluoromethyl, trideuteromethyl and —O—$R_{11}$, or $R_2$ and $R_4$, $R_3$ and $R_5$ are taken together with the directly attached carbon atoms to form a 5-8 membered heterocyclyl, the heteroatom is N or 0;

$R_8$ is selected from the group consisting of H, deuterium, halogen, cyano, nitro, azido, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—S(O)$_r$$R_{10}$, —$C_{0-8}$—P(O)($R_{10}$)$_2$, —$C_{0-8}$—O—$R_{11}$, —$C_{0-8}$—C(O)O$R_{11}$, —$C_{0-8}$—C(O)$R_{12}$, —$C_{0-8}$—O—C(O)$R_{12}$, —$C_{0-8}$—N$R_{13}R_{14}$, —$C_{0-8}$—C(O)N$R_{13}R_{14}$, —$C_{0-8}$—N($R_{13}$)—C(O)$R_{12}$ and —$C_{0-8}$—N($R_{13}$)—C(O)O$R_{11}$, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—S(O)$_r$$R_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-4}$—C(O)N$R_{13}R_{14}$, —$C_{0-4}$—N($R_{13}$)—C(O)$R_{12}$ and —$C_{0-4}$—N($R_{13}$)—C(O)O$R_{11}$, above groups are further more optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—S(O)$_r$$R_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-4}$—C(O)N$R_{13}R_{14}$, —$C_{0-4}$—N($R_{13}$)—C(O)$R_{12}$ and —$C_{0-4}$—N($R_{13}$)—C(O)O$R_{11}$;

$X_1$ is —CH— or N;

$R_{10}$ is selected from the group consisting of H, deuterium, $C_{1-8}$ alkyl, $C_{2-8}$ alkenyl, $C_{3-8}$ cycloalkyl, 3-10 membered heterocyclyl, $C_{1-8}$ haloalkyl, $C_{5-10}$ aryl, 5-10 membered heteroaryl, amino, mono-$C_{1-8}$ alkylamino, di-$C_{1-8}$ alkylamino and $C_{1-8}$ alkanoylamino;

$R_{11}$ is selected from the group consisting of H, deuterium, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl and 5-10 membered heteroaryl, above groups are unsubstituted or substituted by one or more substituents selected from the group consisting of deuterium, halogen, cyano, $C_{1-8}$ alkyl, $C_{1-8}$ alkoxy, $C_{1-8}$ alkylthio, $C_{3-8}$ cycloalkyl, 3-10 membered heterocyclyl, $C_{5-10}$ aryl, 5-10 membered heteroaryl, $C_{1-8}$ alkylsulfonyl, $C_{1-8}$ alkylsulfonylamino, amino, mono-$C_{1-8}$ alkylamino, di-$C_{1-8}$ alkylamino, =O or hydroxyl;

$R_{12}$ is selected from the group consisting of H, deuterium, $C_{1-8}$ alkyl, $C_{2-8}$ alkenyl, $C_{2-8}$ alkynyl, $C_{1-8}$ alkoxy, $C_{3-8}$ cycloalkyl, $C_{3-8}$ cycloalkyloxy, 3-10 membered heterocyclyl, 3-10 membered heterocyclyloxy, $C_{5-10}$ aryl, 5-10 membered heteroaryl, $C_{5-10}$ aryloxy and 5-10 membered heteroaryloxy, above groups are unsubstituted or substituted by one or more substituents selected from the group consisting of deuterium, halogen, cyano, $C_{1-8}$ alkyl, $C_{1-8}$ alkoxy, $C_{1-8}$ alkylthio, $C_{3-8}$ cycloalkyl, 3-10 membered heterocyclyl, $C_{5-10}$ aryl, 5-10 membered heteroaryl, $C_{1-8}$ alkylsulfonyl, $C_{1-8}$ alkylsulfonylamino, amino, mono-$C_{1-8}$ alkylamino, di-$C_{1-8}$ alkylamino, =O or hydroxyl;

$R_{13}$ and $R_{14}$ are each independently selected from the group consisting of H, deuterium, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, $C_{1-8}$ alkylsulfonyl and $C_{1-8}$ alkanoyl, or $R_{13}$ and $R_{14}$ are taken together with the directly attached nitrogen atom to form a 4-10 membered heterocyclyl, above groups are unsubstituted or substituted by one or more substituents selected from the group consisting of deuterium, halogen, $C_{1-8}$ alkyl, $C_{1-8}$ alkoxy, $C_{1-8}$ alkylthio, $C_{3-8}$ cycloalkyl, 3-10 membered heterocyclyl, $C_{5-10}$ aryl, 5-10 membered heteroaryl, $C_{1-8}$ alkylsulfonyl, $C_{1-8}$ alkylsulfonylamino, amino, mono-$C_{1-8}$ alkylamino, di-$C_{1-8}$ alkylamino, =O or hydroxyl;

r is 0, 1 or 2;

wherein unless otherwise defined, the heterocyclyl is a saturated or partially unsaturated monocyclic or polycyclic cyclic hydrocarbon substituent containing 1 to 2 heteroatoms selected from nitrogen, oxygen or sulfur, and the polycyclic cycloalkyl is a spiro, fused or bridged cycloalkyl, and the heteroaryl is a heteroaromatic system containing 1 to 2 heteroatoms selected from nitrogen, oxygen or sulfur;

and wherein the FGFR4 related cancer is prostate cancer, liver cancer, pancreatic cancer, esophageal cancer, gastric cancer, lung cancer, breast cancer, ovarian cancer, colon cancer, skin cancer, glioblastoma or rhabdomyosarcoma.

2. The method of claim 1, wherein $R_8$ is selected from the group consisting of H, deuterium, halogen, cyano, $C_{1-8}$ alkyl, $C_{2-8}$ alkenyl, $C_{2-8}$ alkynyl, $C_{3-8}$ cycloalkyl, 3-10 membered heterocyclyl, $C_{5-10}$ aryl, 5-10 membered heteroaryl, —$C_{0-8}$—O—$R_{11}$, —$C_{0-8}$—N$R_{13}R_{14}$, —$C_{0-8}$—N($R_{13}$)—C(O)$R_{12}$ and —$C_{0-8}$—N($R_{13}$)—C(O)O$R_{11}$, above groups are further optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—S(O)$_r$$R_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-4}$—C(O)N$R_{13}R_{14}$, —$C_{0-4}$—N($R_{13}$)—C(O)$R_{12}$ and —$C_{0-4}$—N($R_{13}$)—C(O)O$R_{11}$, above groups are further more optionally substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-6}$ cycloalkyl, 3-8 membered heterocyclyl, $C_{5-8}$ aryl, 5-8 membered heteroaryl, —$C_{0-4}$—S(O)$_r$$R_{10}$, —$C_{0-4}$—O—$R_{11}$, —$C_{0-4}$—C(O)O$R_{11}$, —$C_{0-4}$—C(O)$R_{12}$, —$C_{0-4}$—O—C(O)$R_{12}$, —$C_{0-4}$—N$R_{13}R_{14}$, —$C_{0-}$ —C(O)NR₁₃R₁₄, —C₀₋₄—N(R₁₃)—C(O)R₁₂ and —C₀₋₄—N(R₁₃)—C(O)OR₁₁.
3. The method of claim 1, wherein the compound is selected from the group consisting of:
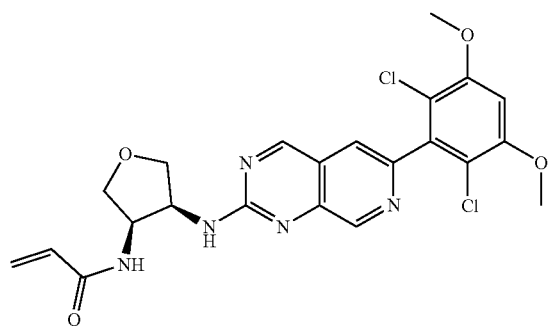
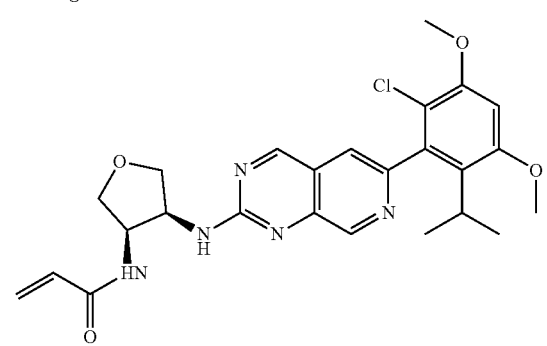
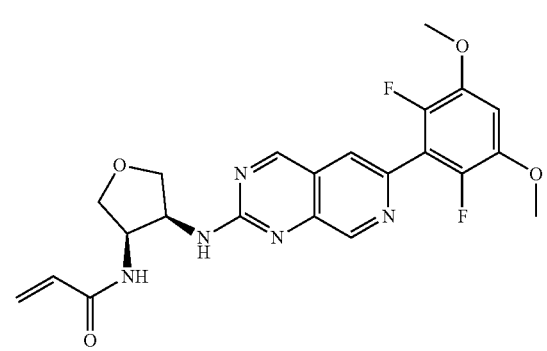
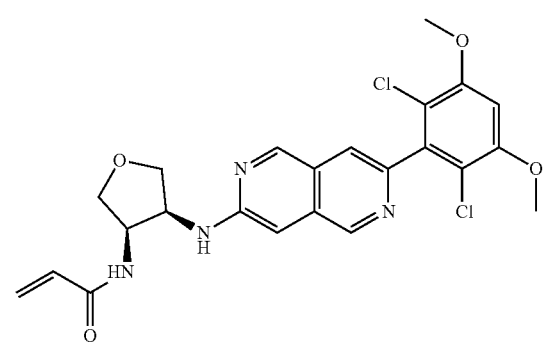
-continued
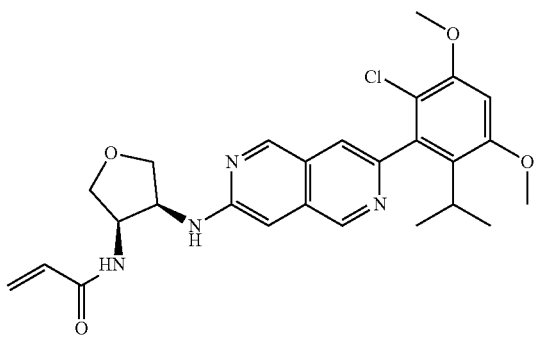
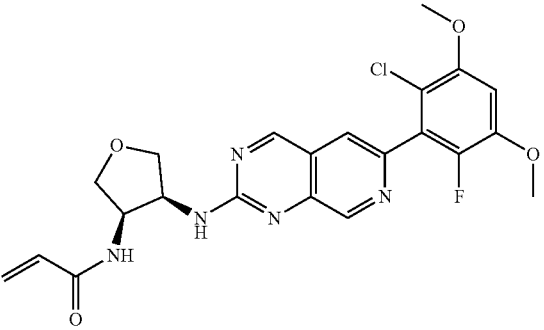
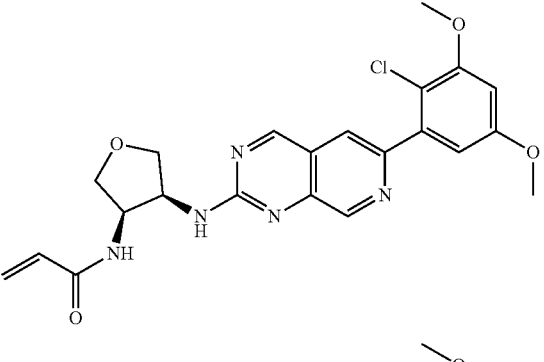
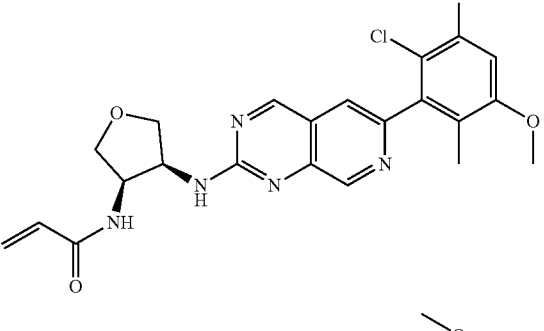
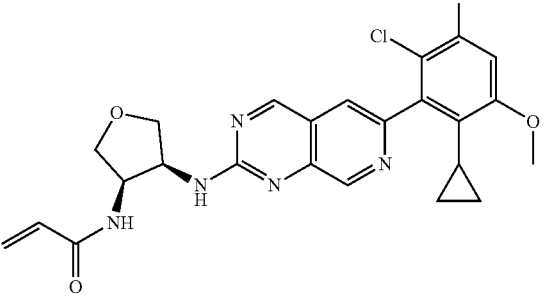

941
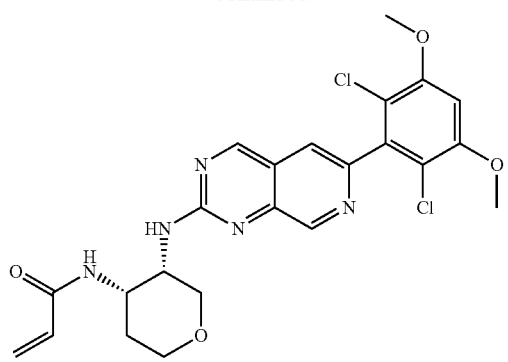
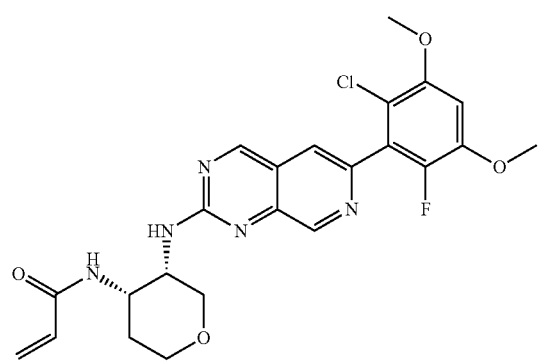
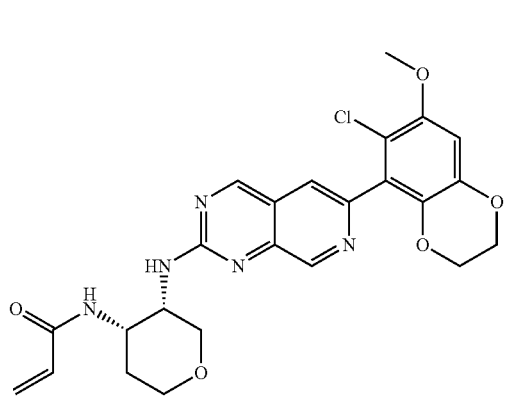
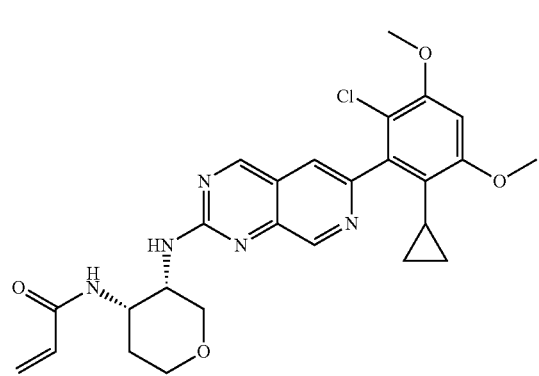
942
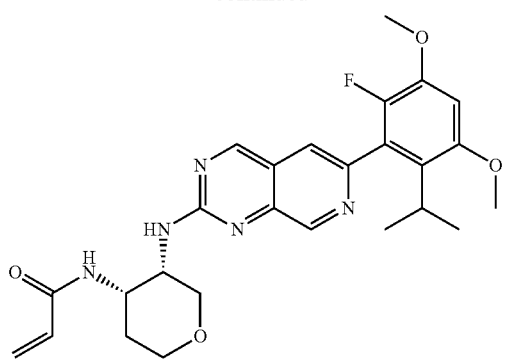
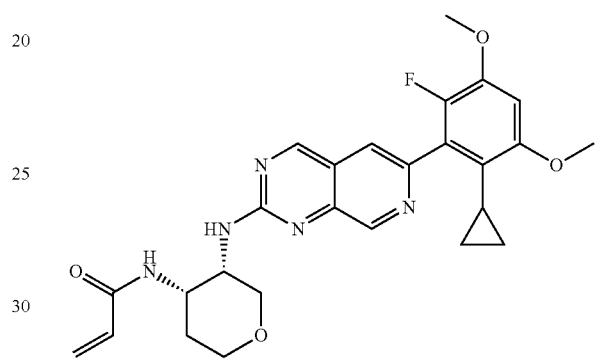
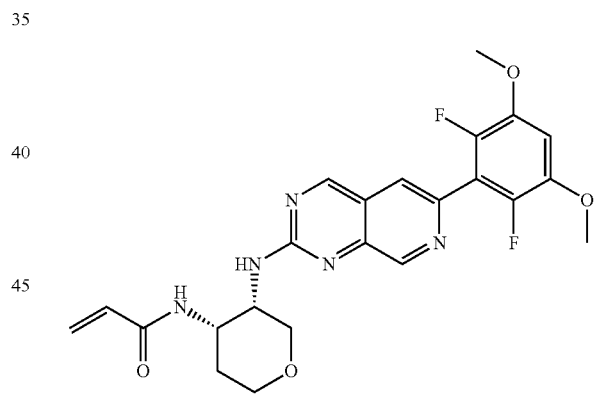
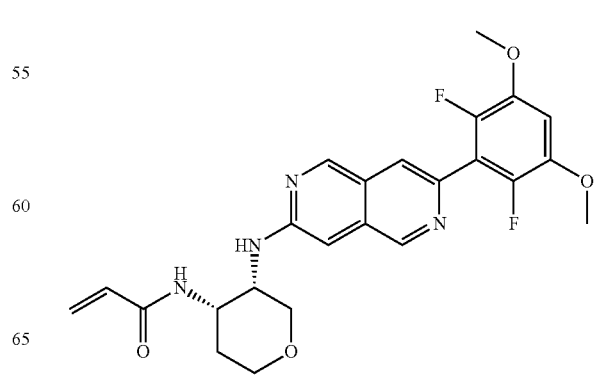

943
-continued
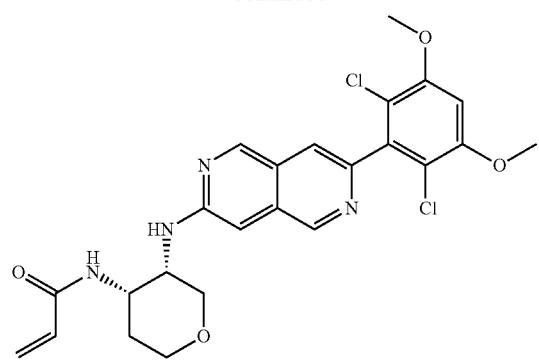
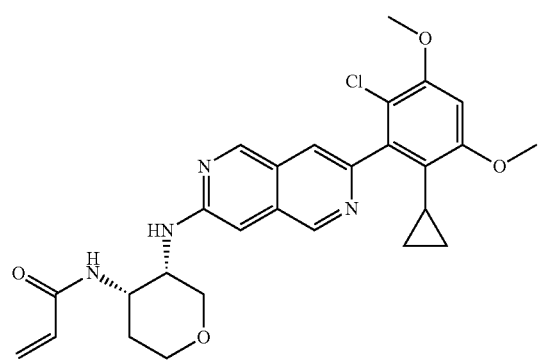
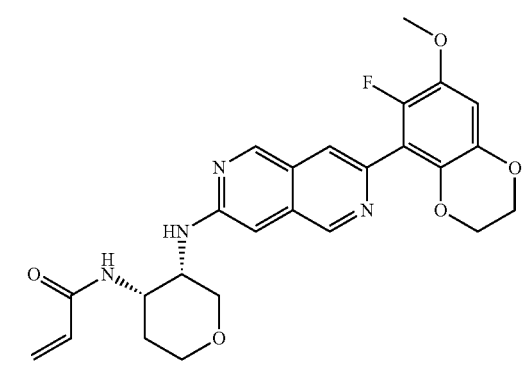
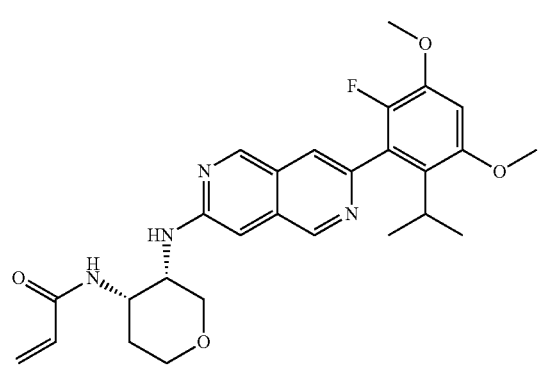
944
-continued
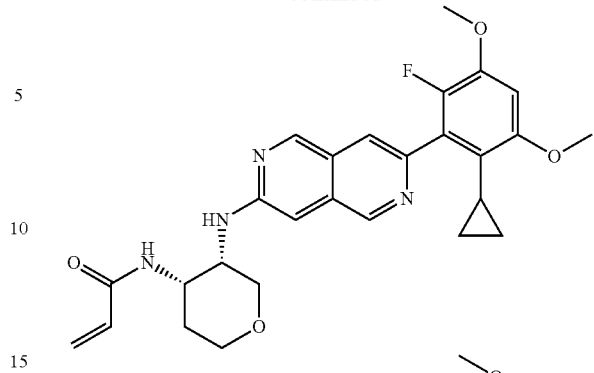
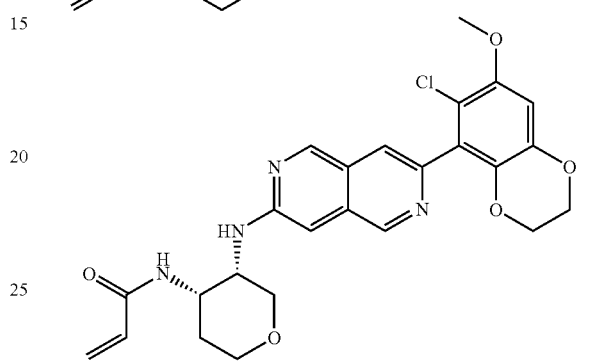
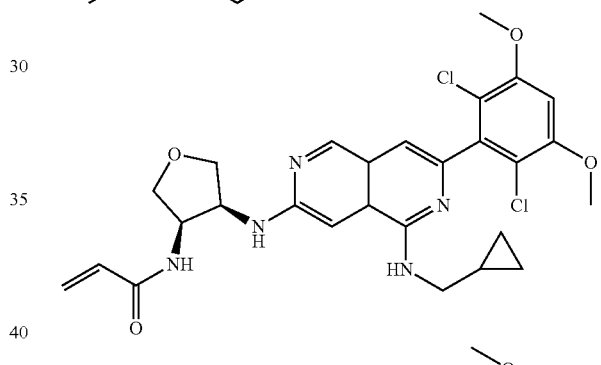
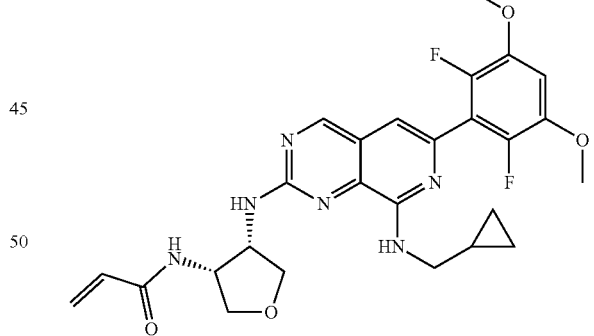
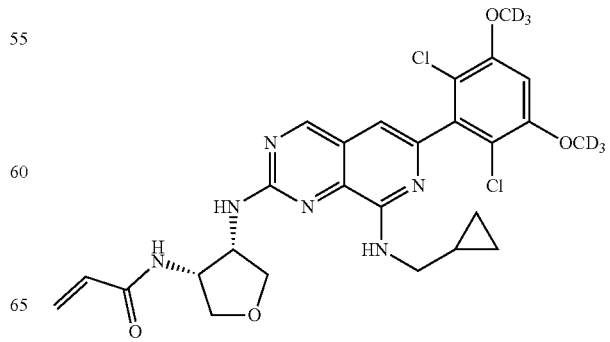

945
-continued
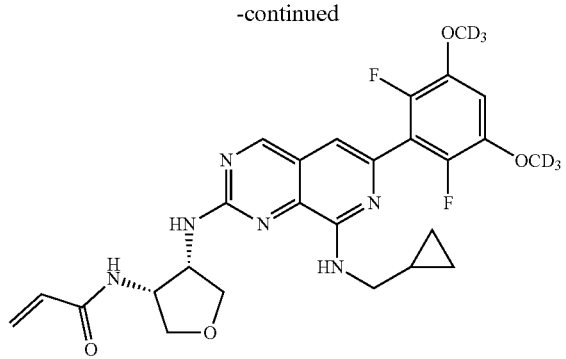
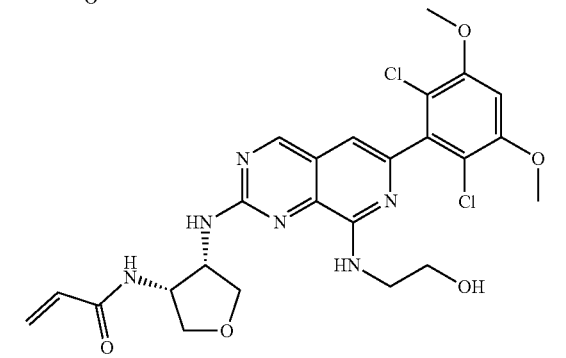
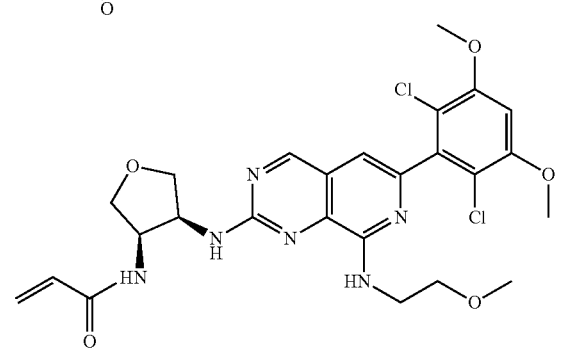
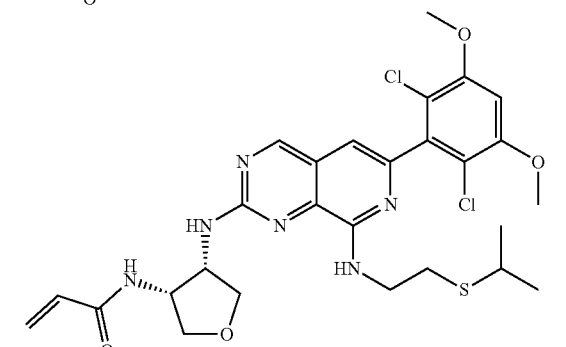
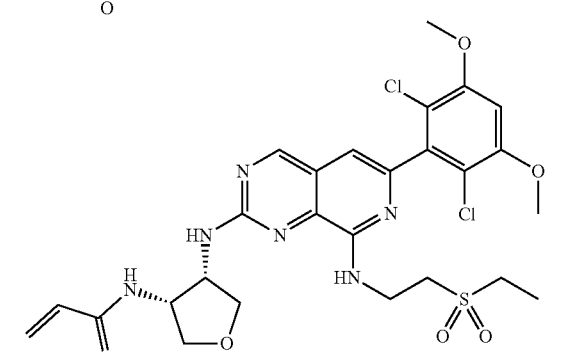
946
-continued
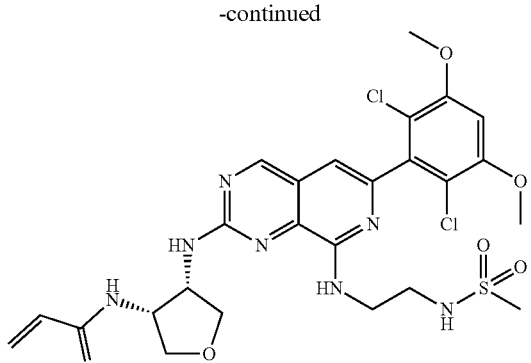
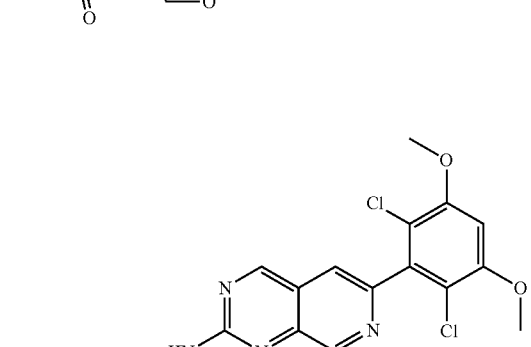
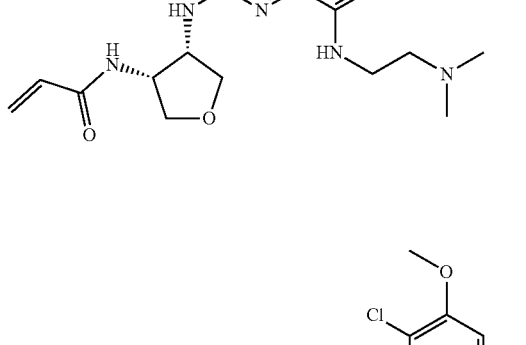
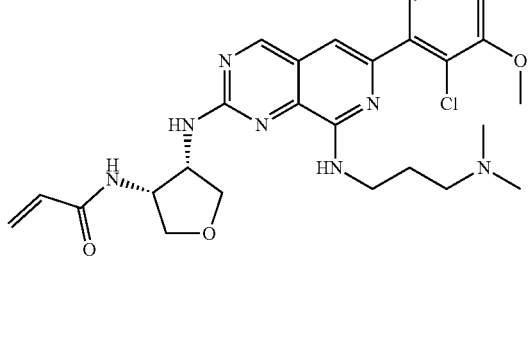
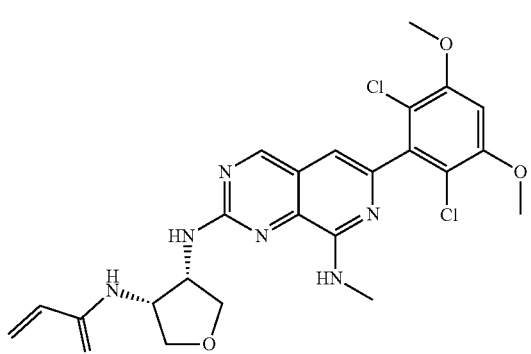

947
-continued
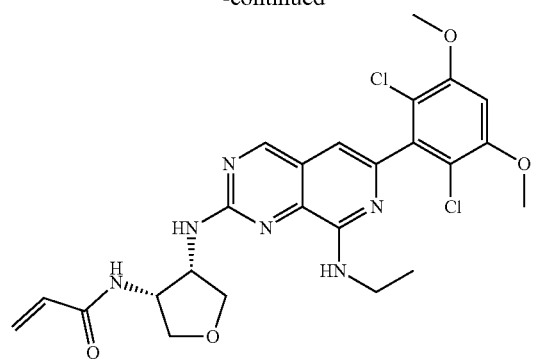
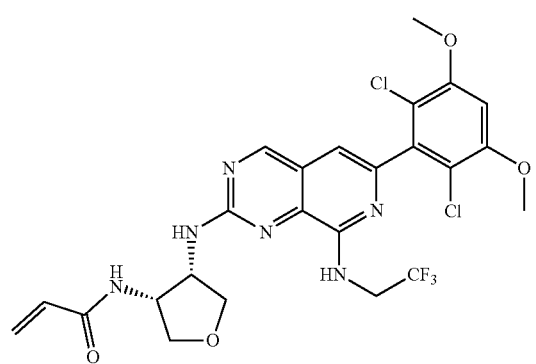
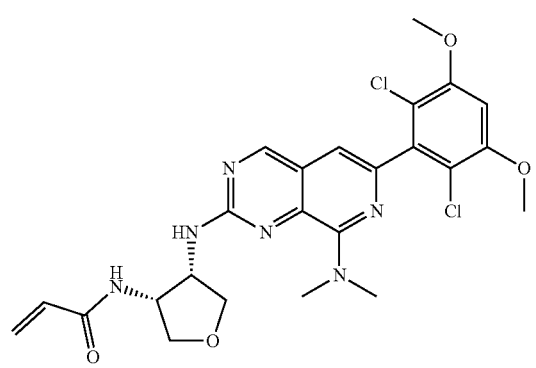
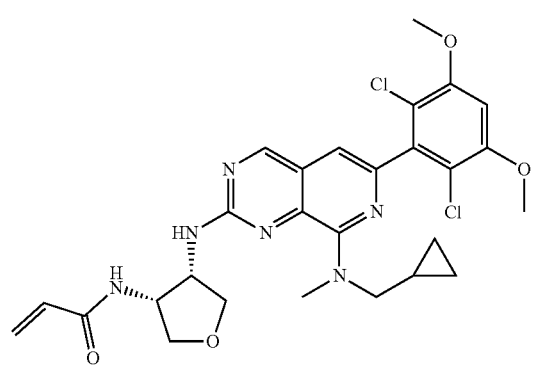
948
-continued
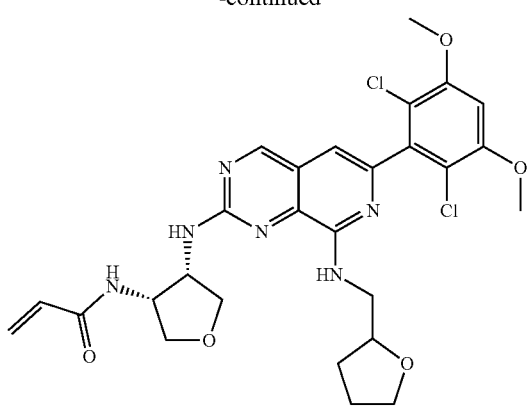
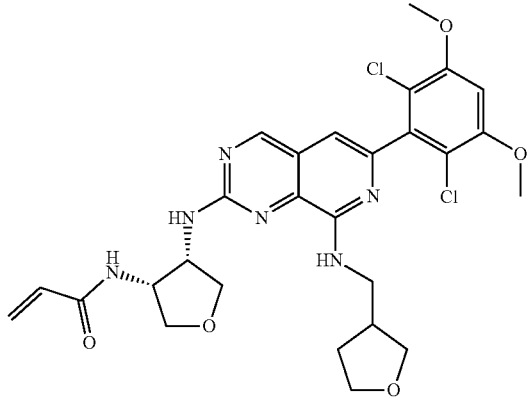
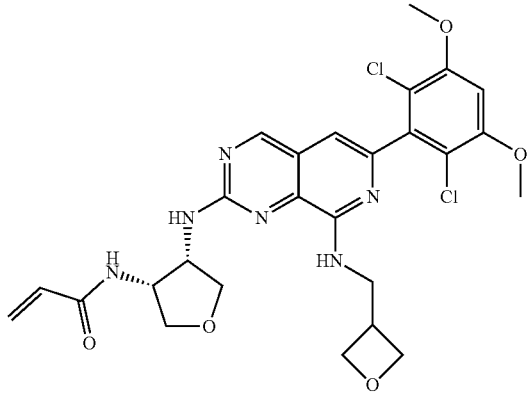
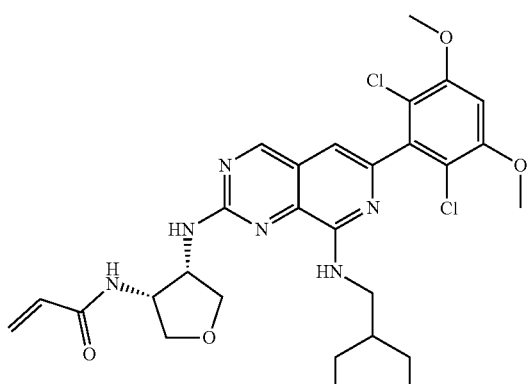

949
-continued
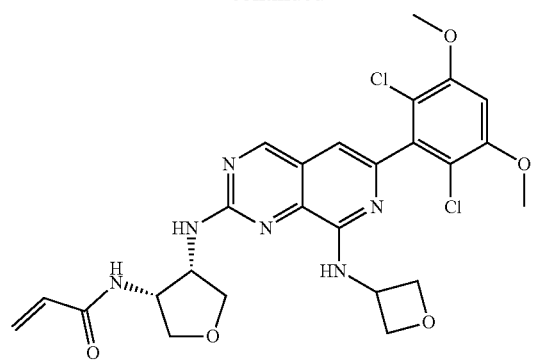
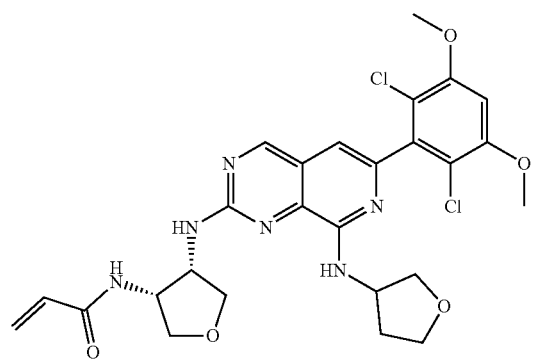
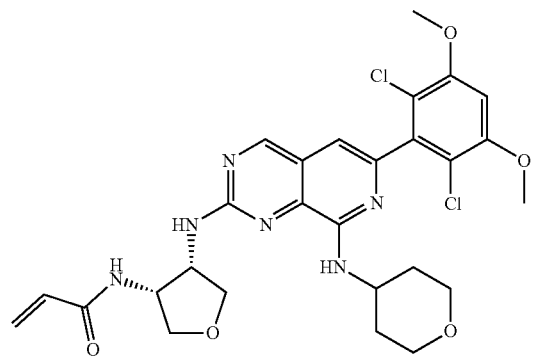
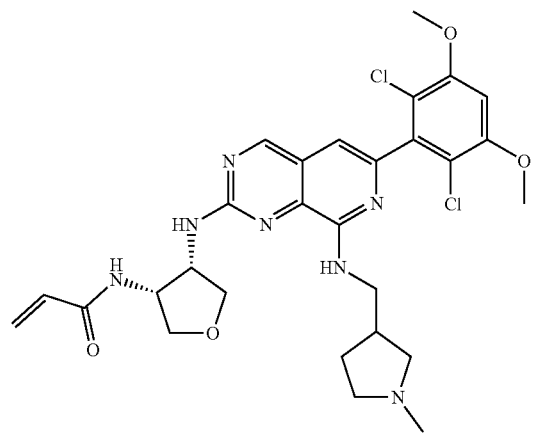
950
-continued
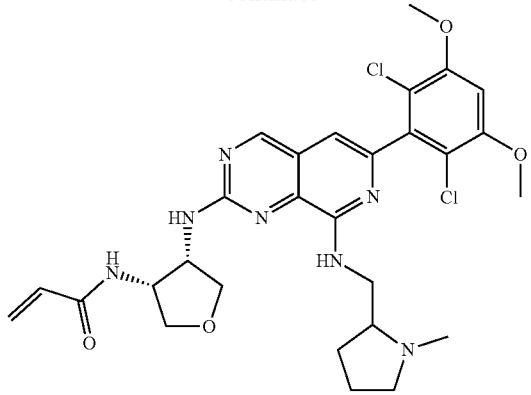
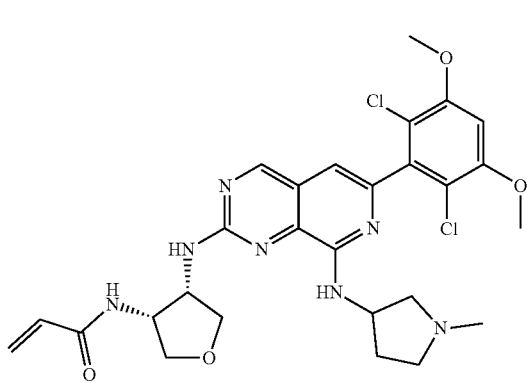
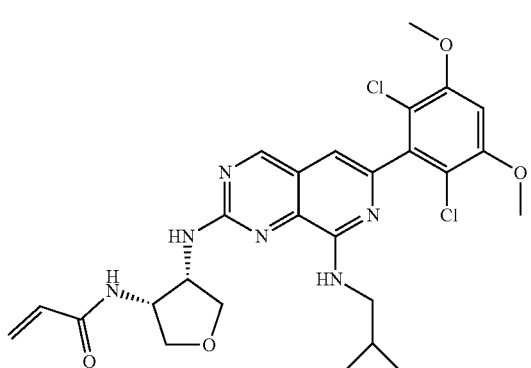
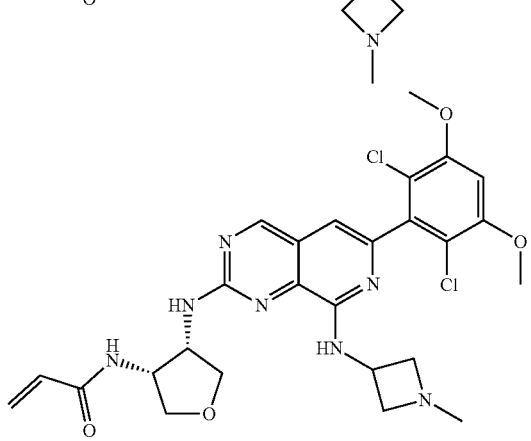

951
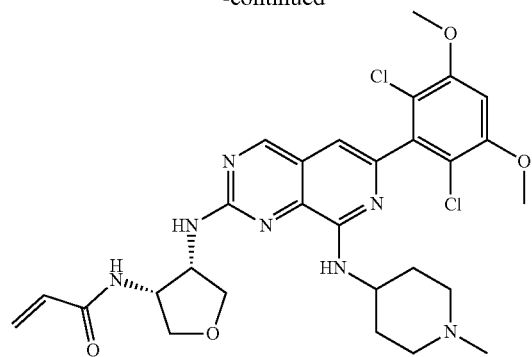
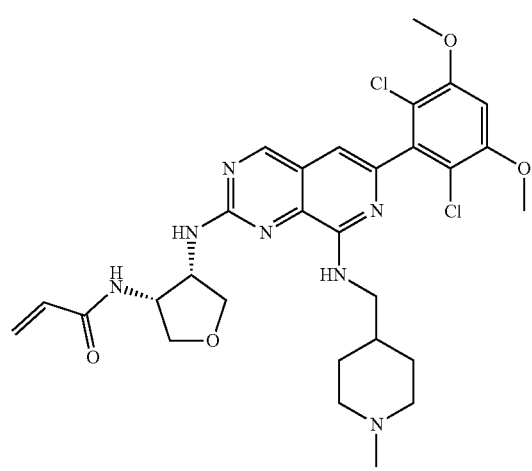
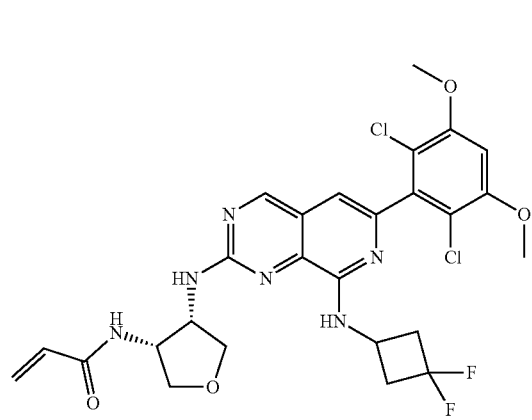
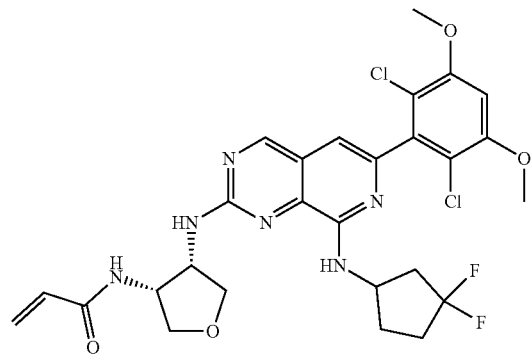
952
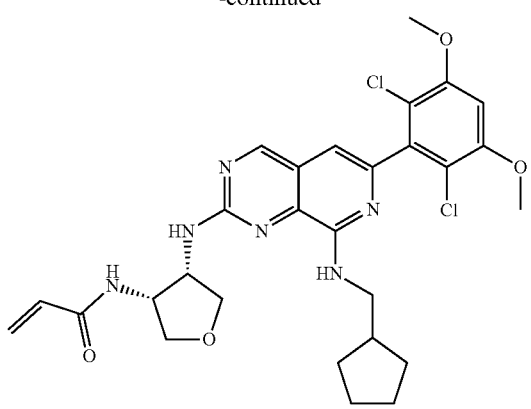
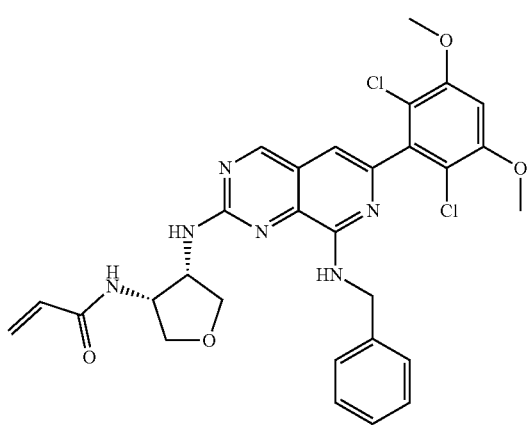
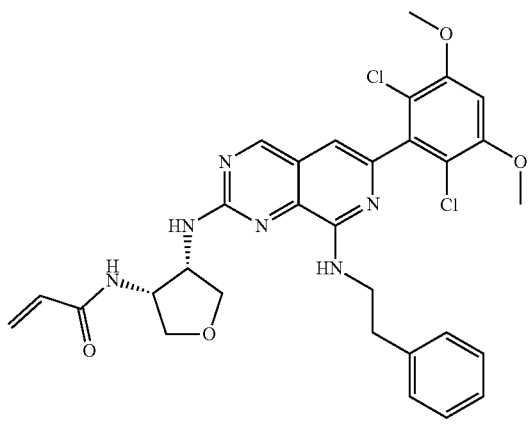
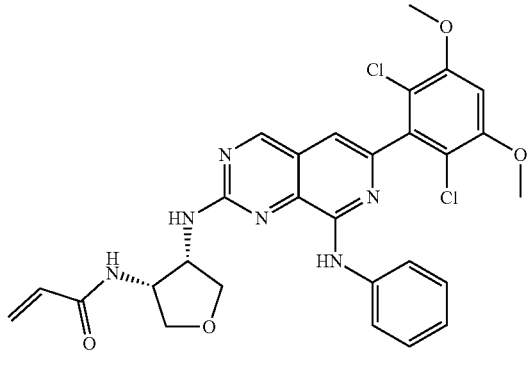

953
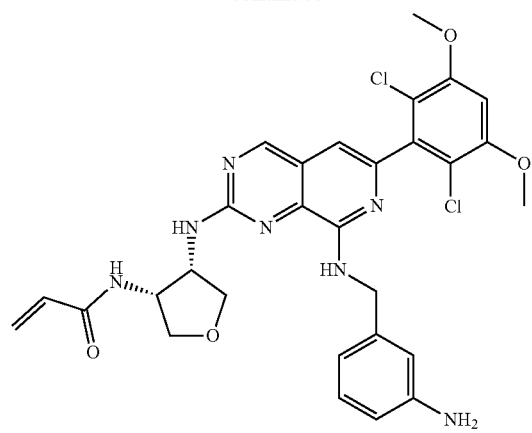
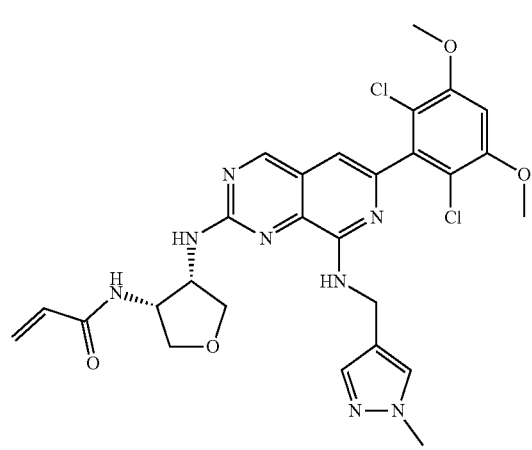
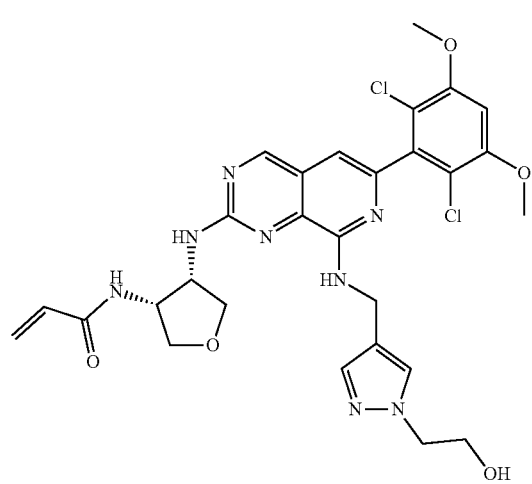
954
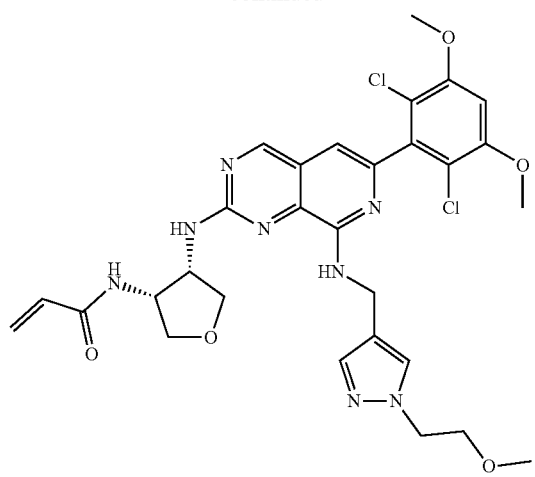
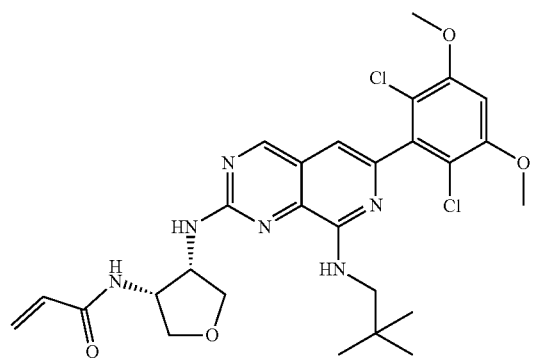
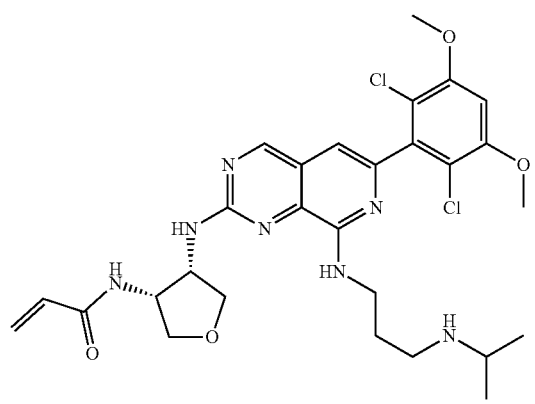
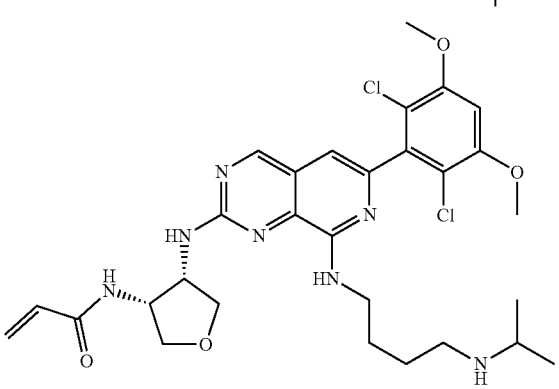

955
-continued
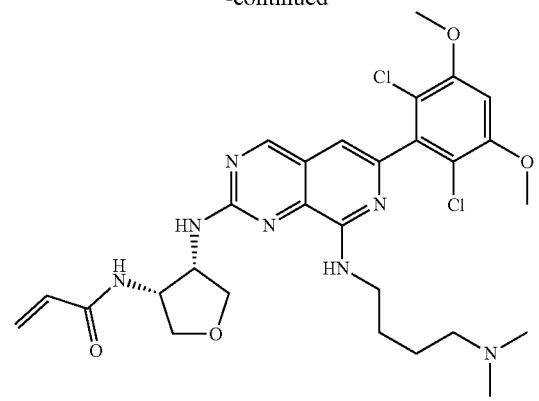
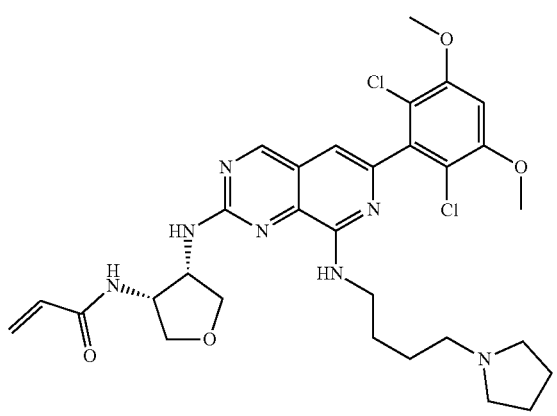
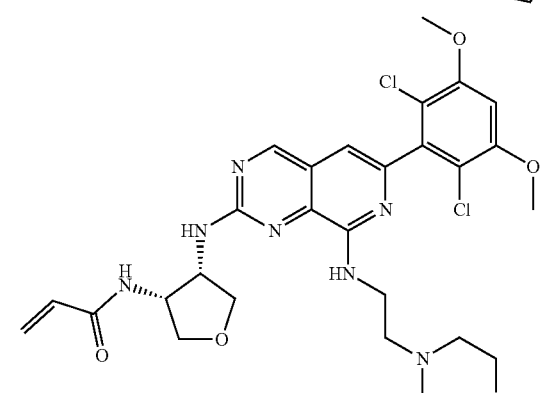
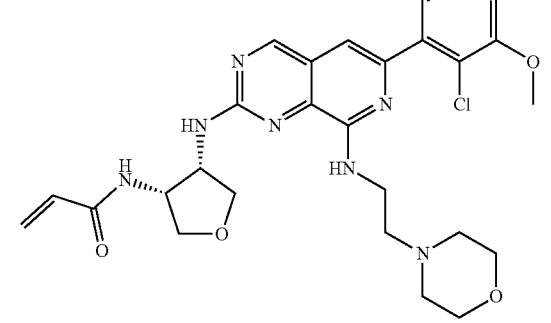
956
-continued
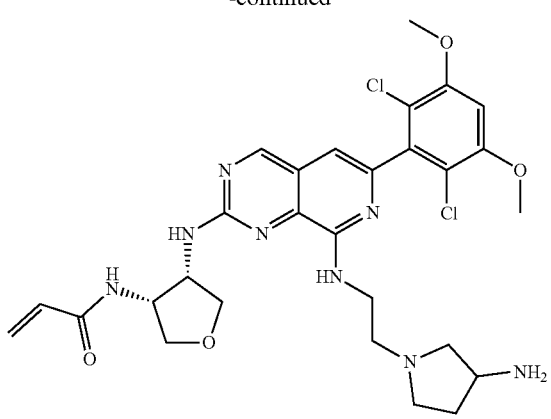
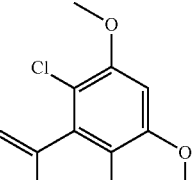
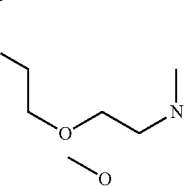
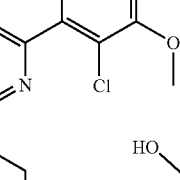

957
-continued
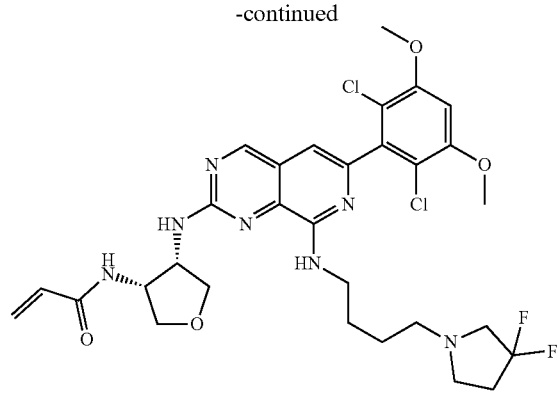
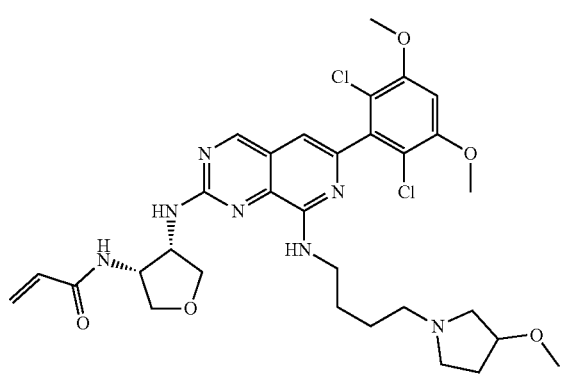
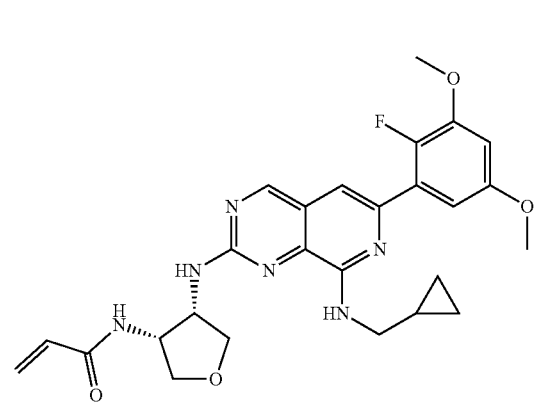
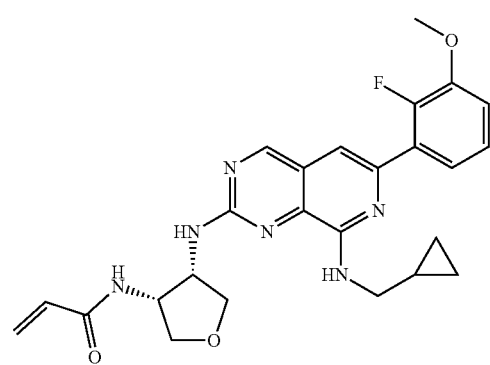
958
-continued
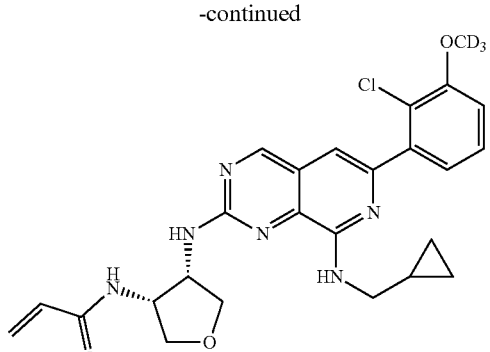
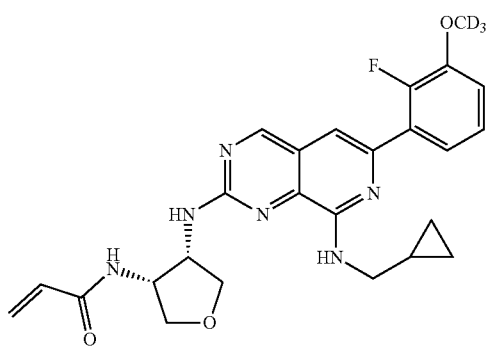
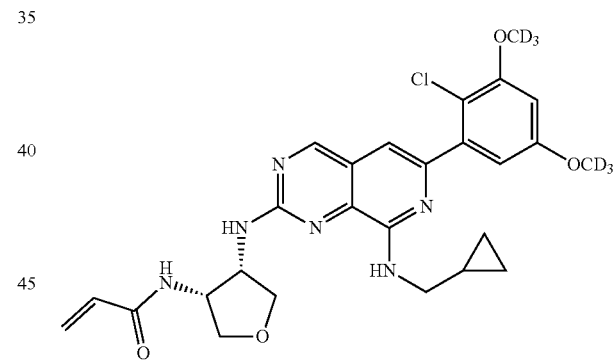
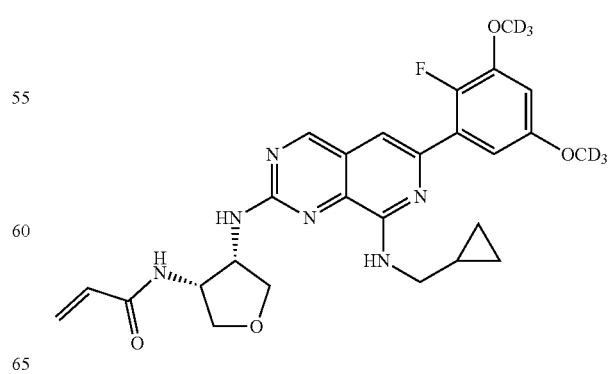

959
-continued
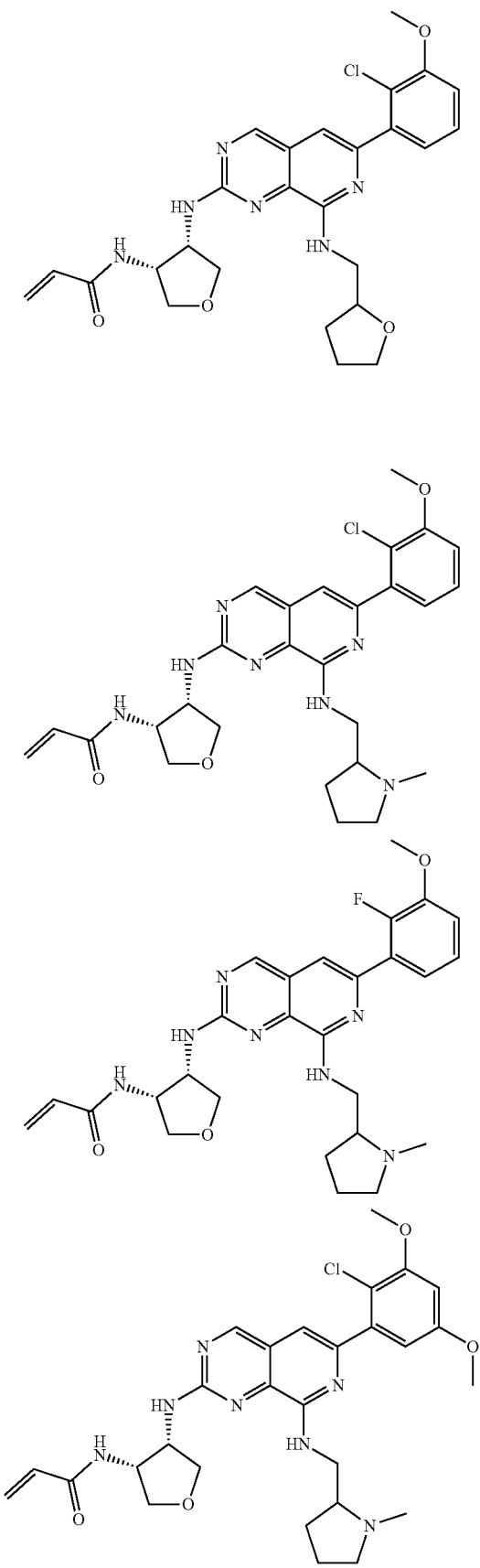
960
-continued
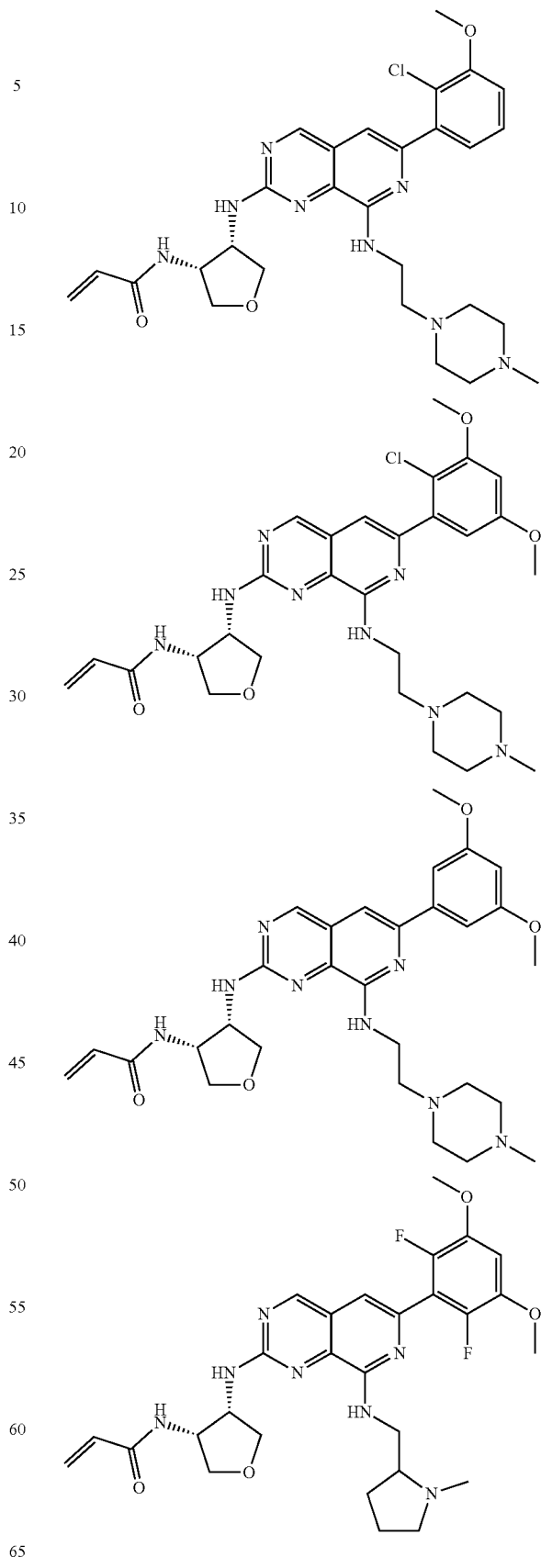

961 -continued
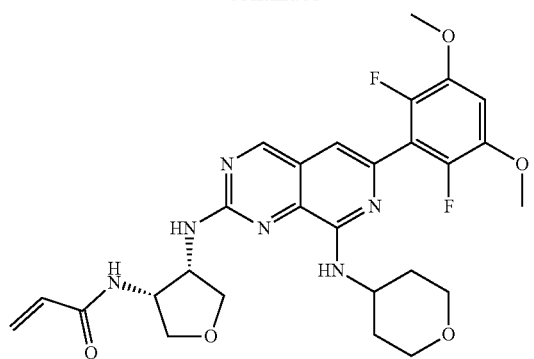
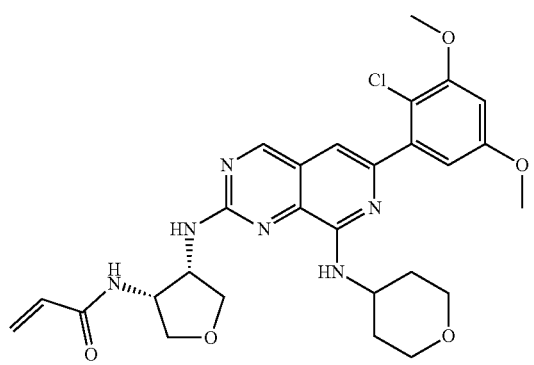
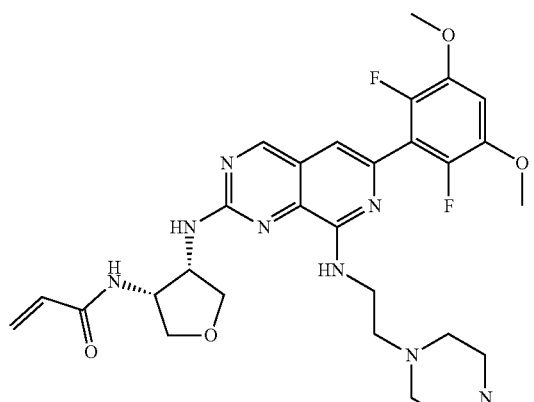
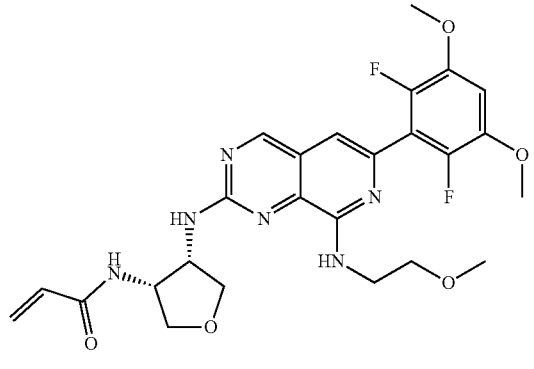
962 -continued
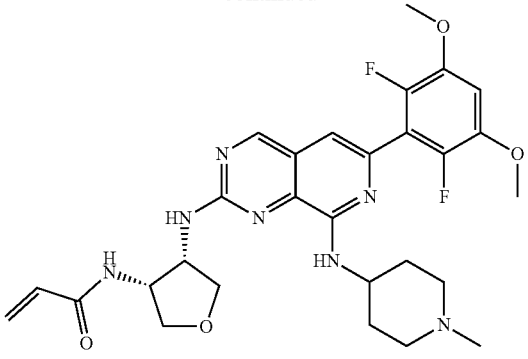
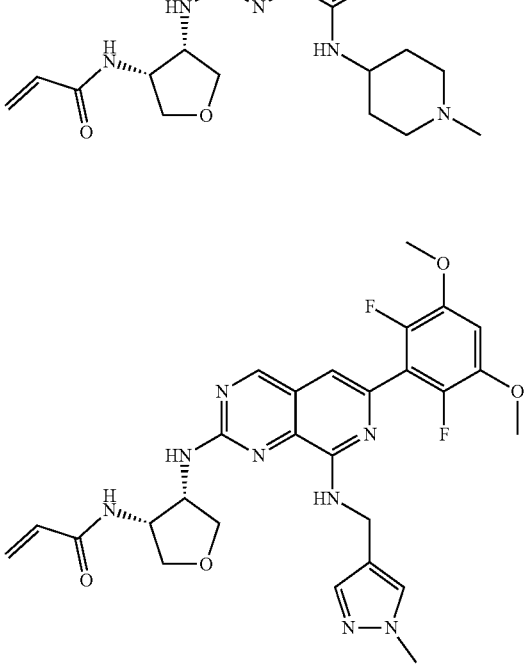
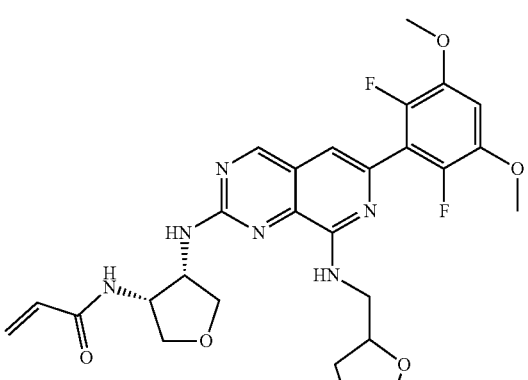
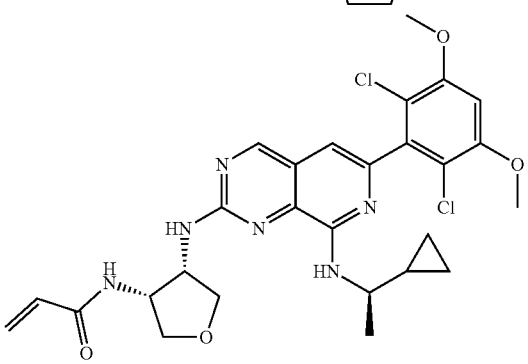

963
-continued
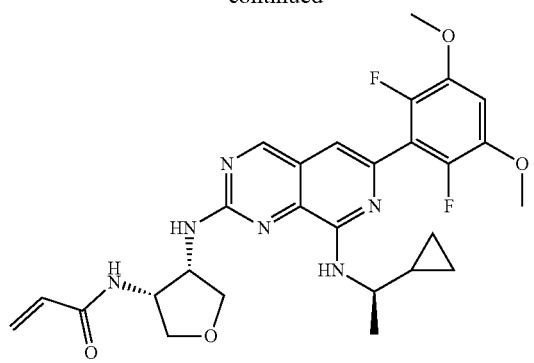
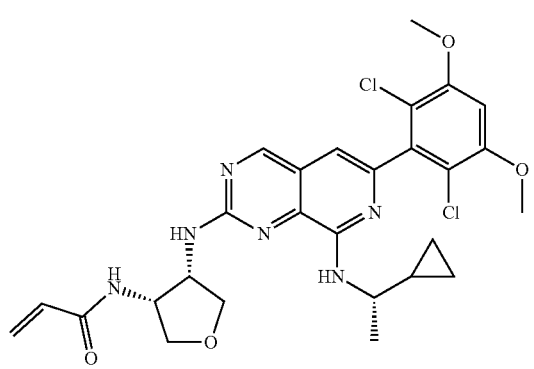
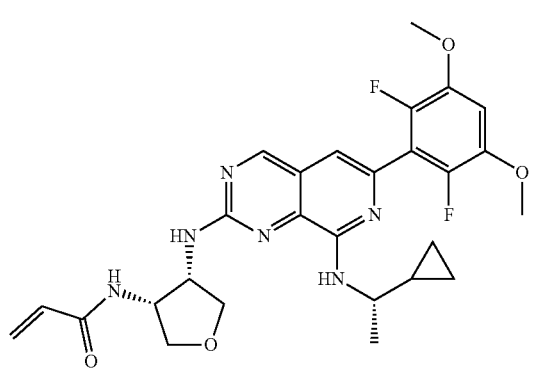
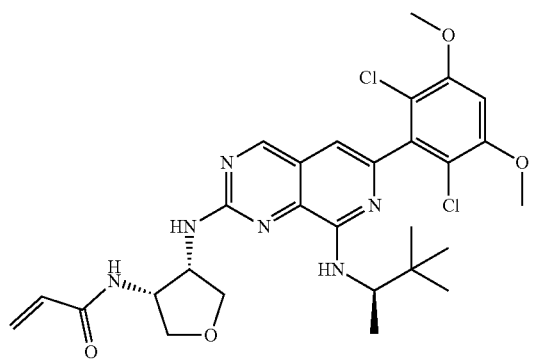
964
-continued
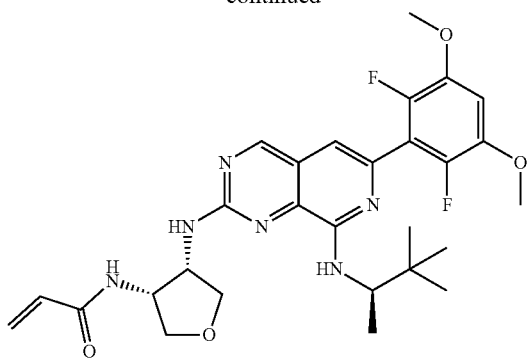
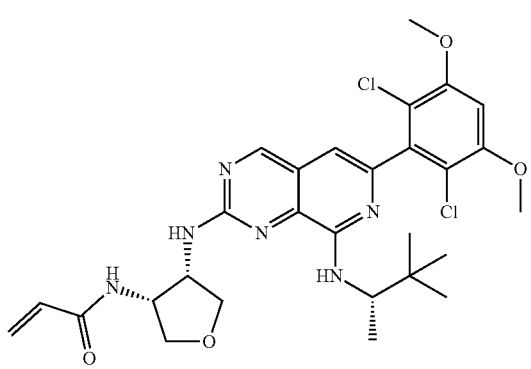
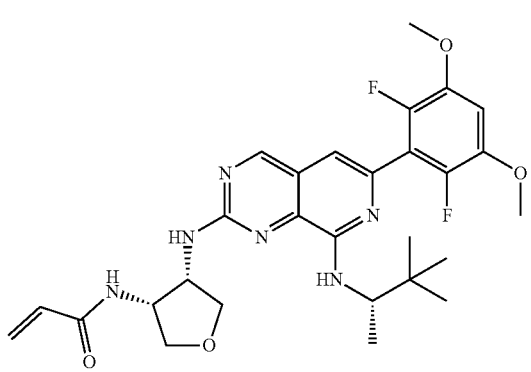
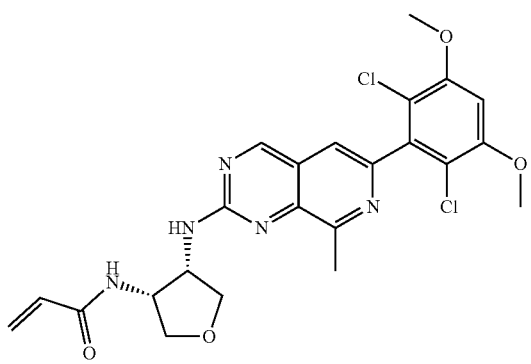

965
-continued
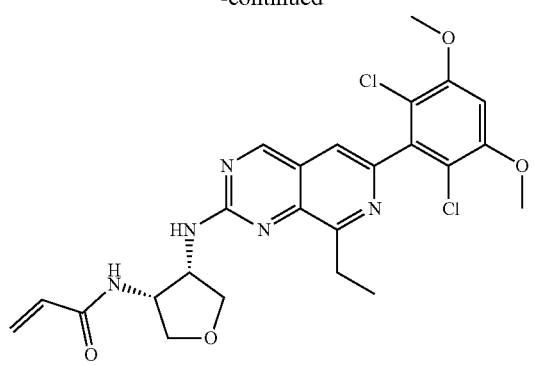
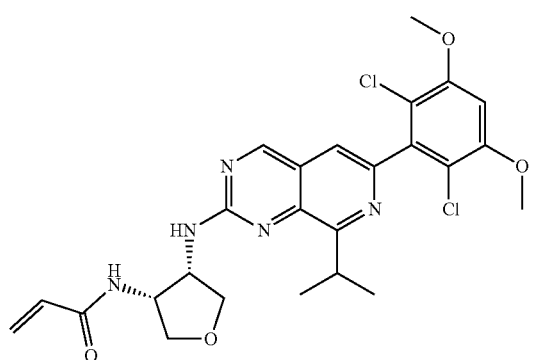
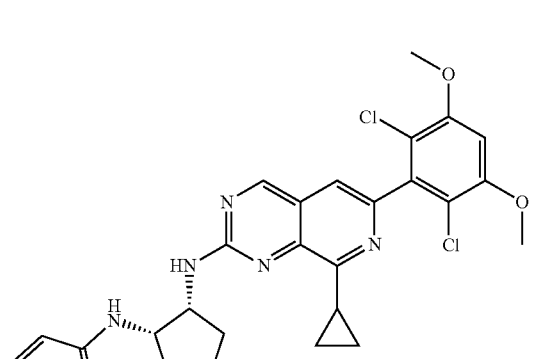
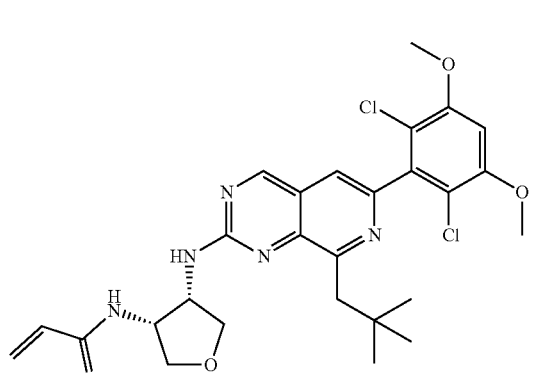
966
-continued
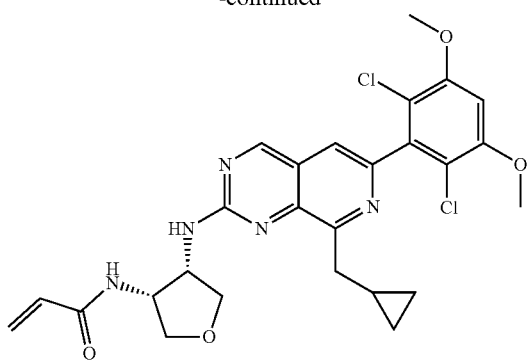
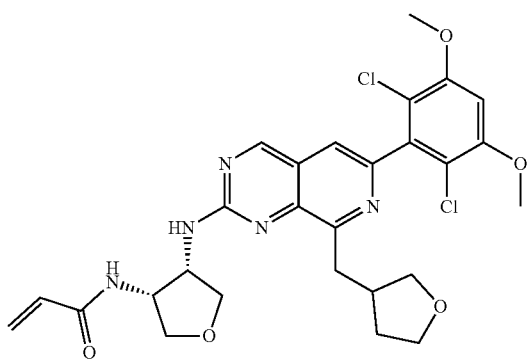
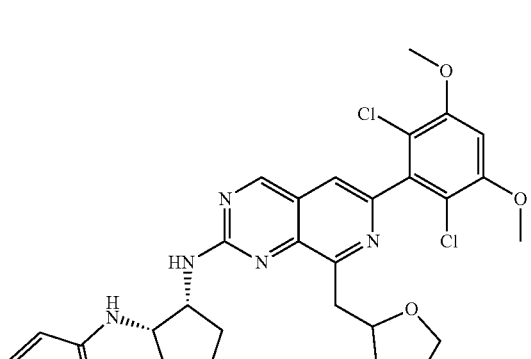
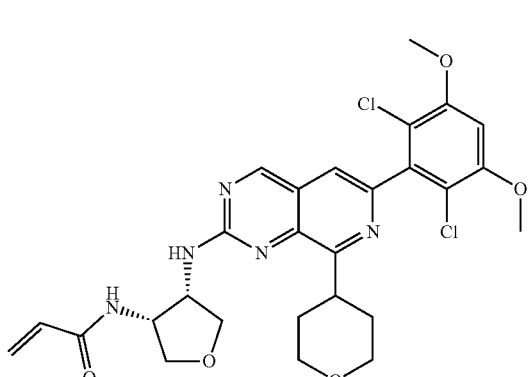

967
-continued
968
-continued
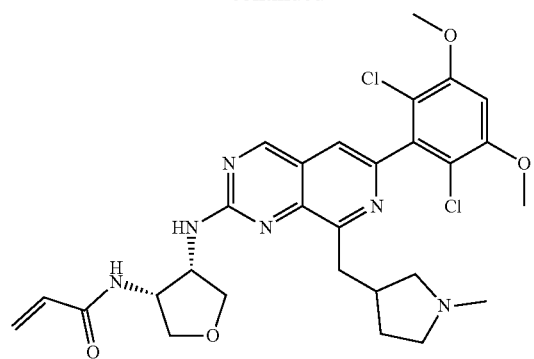
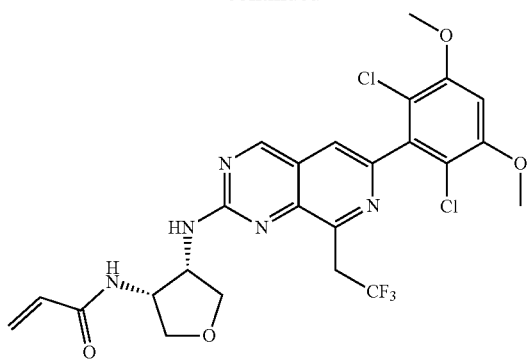
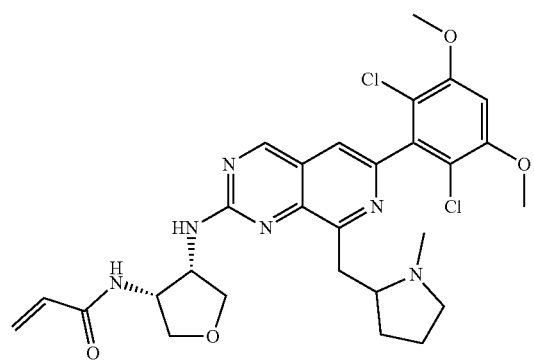
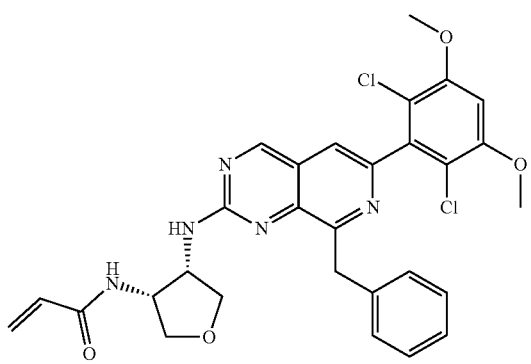
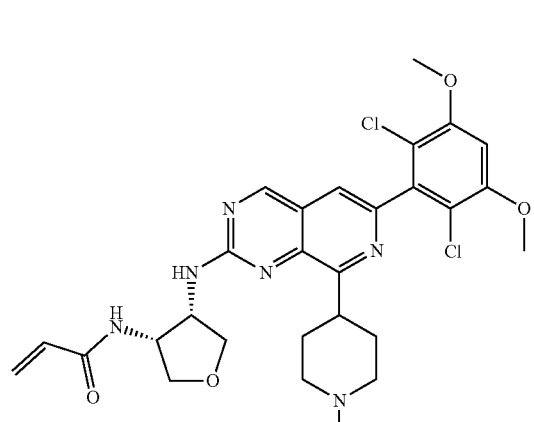
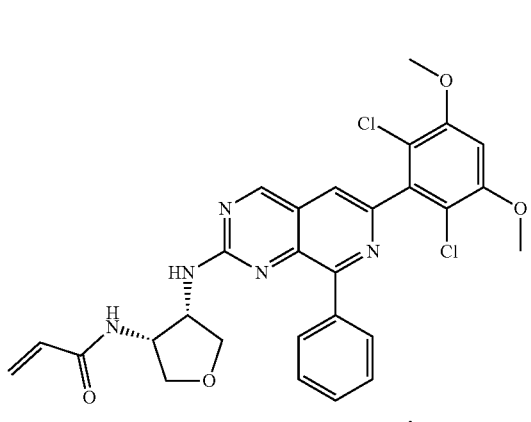
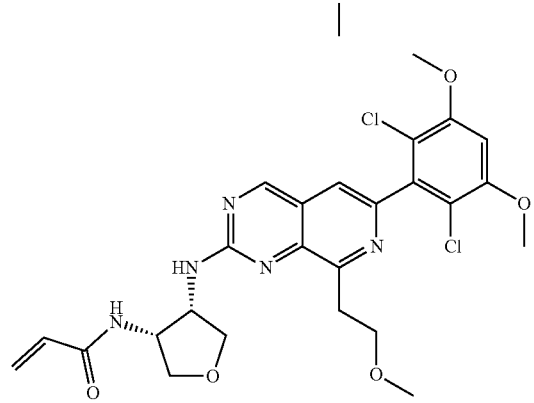
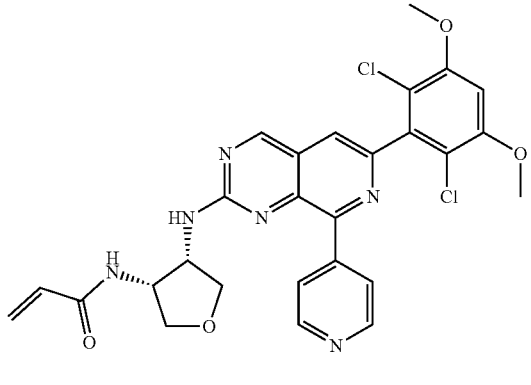

969
-continued
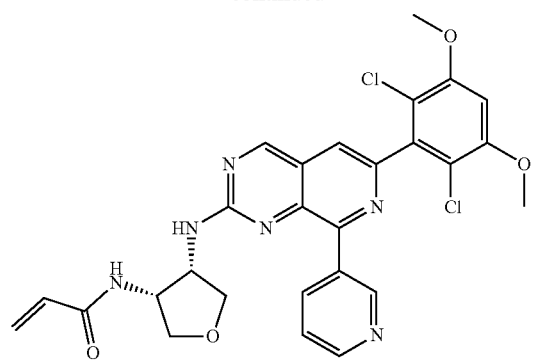
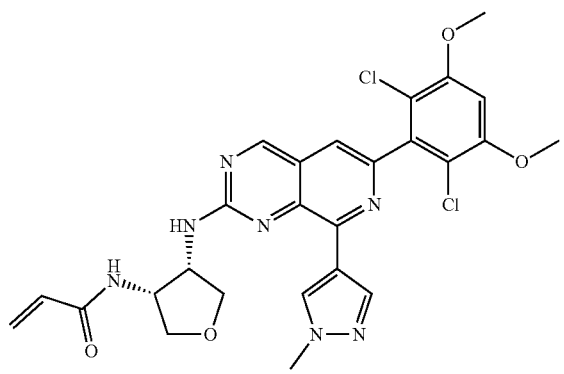
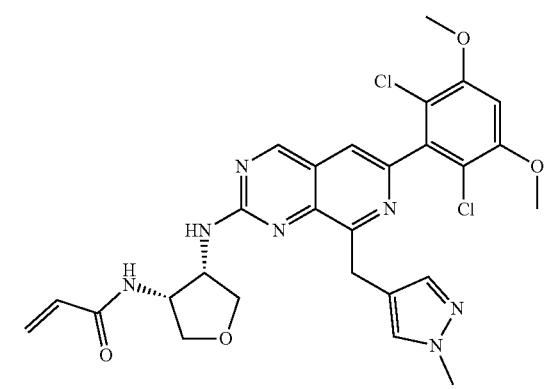
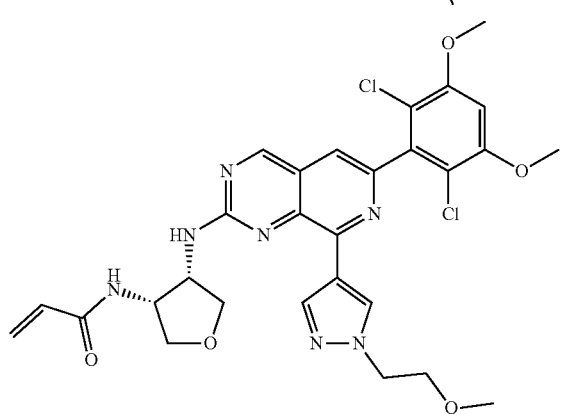
970
-continued
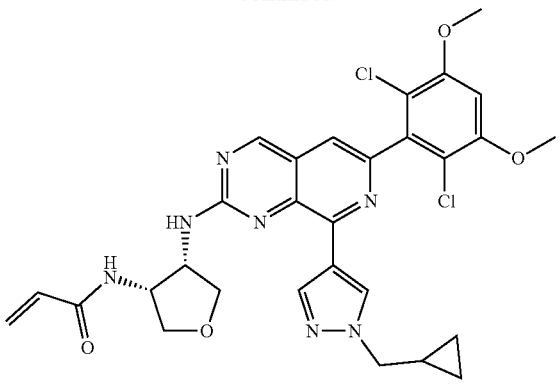
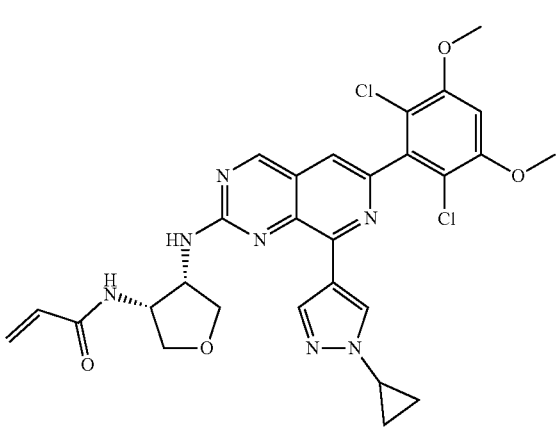
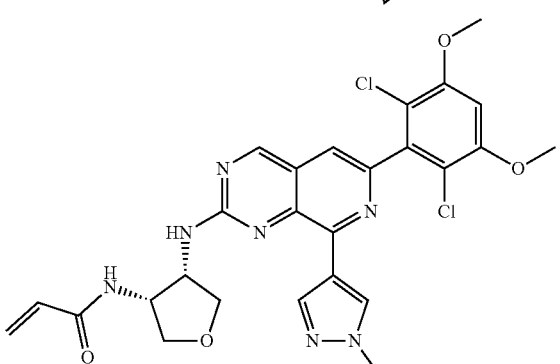
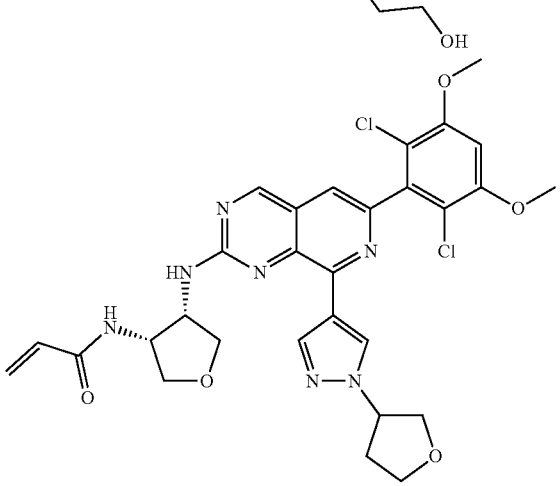

971
-continued
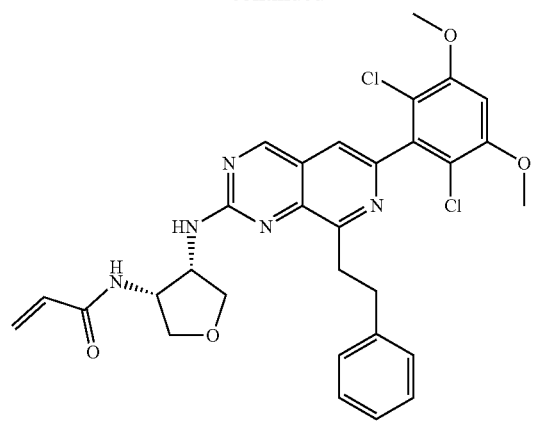
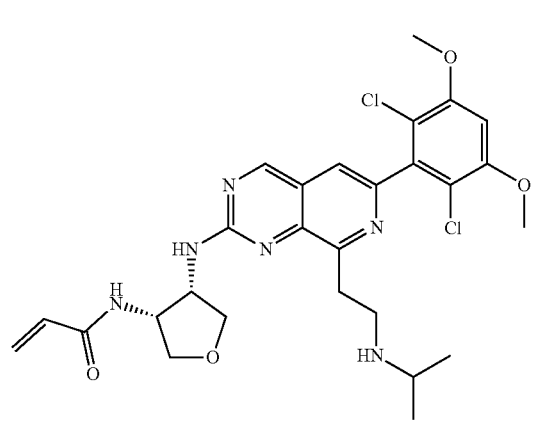
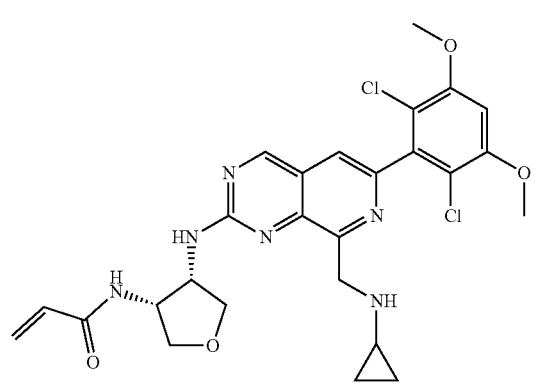
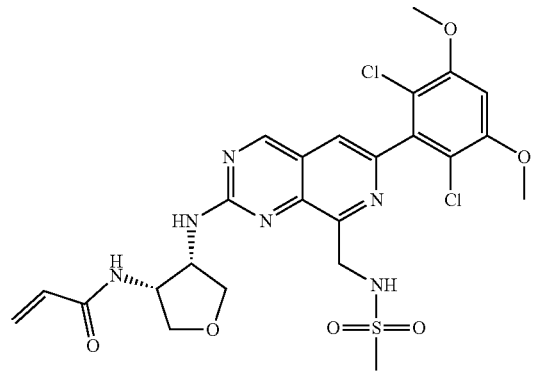
972
-continued
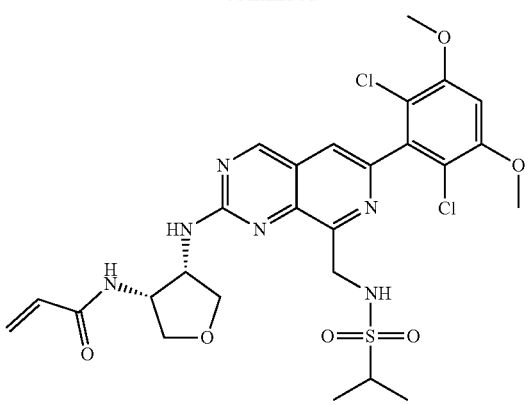
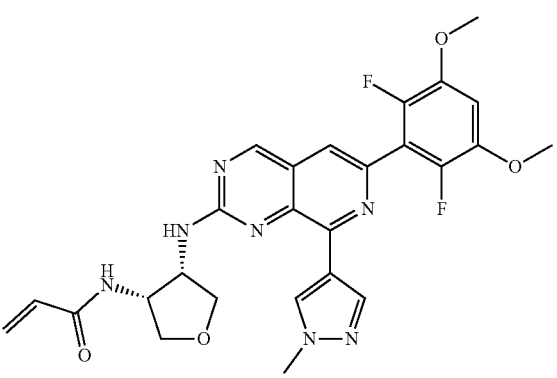
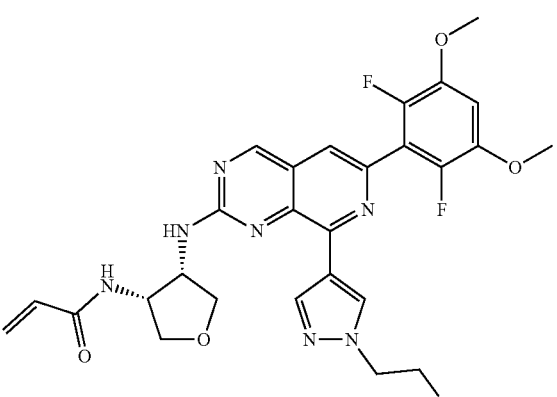
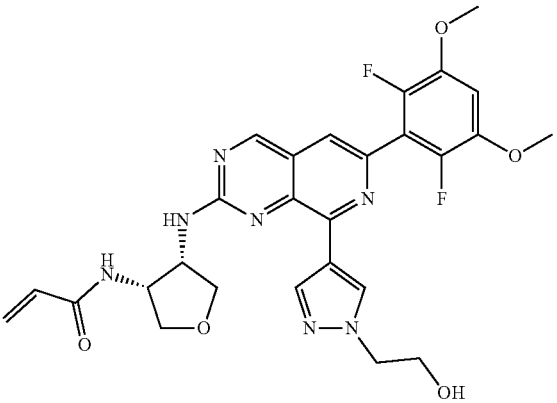

973 -continued
974 -continued
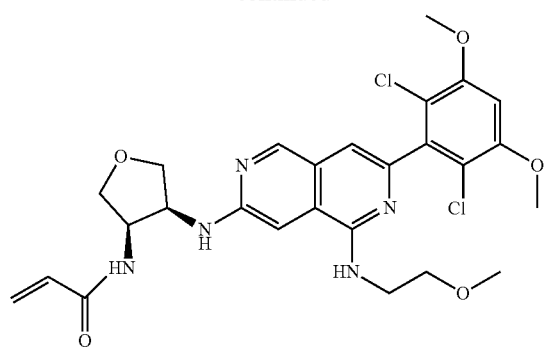
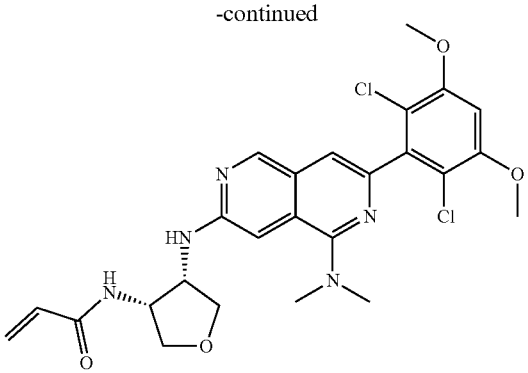

975
-continued
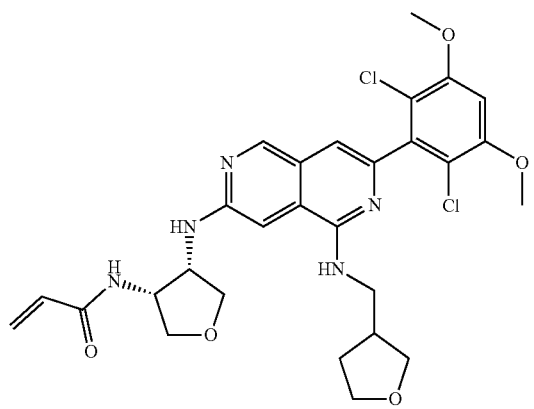
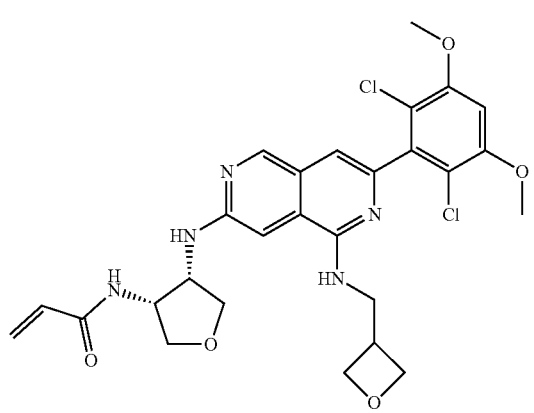
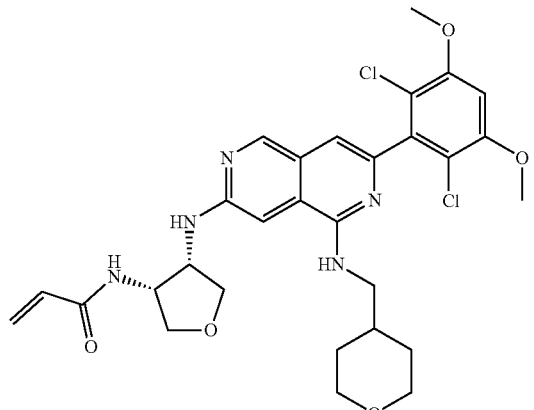
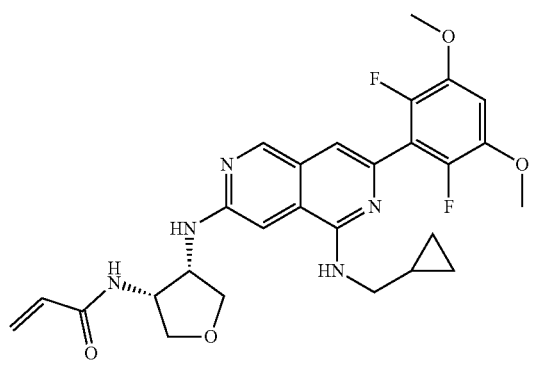
976
-continued
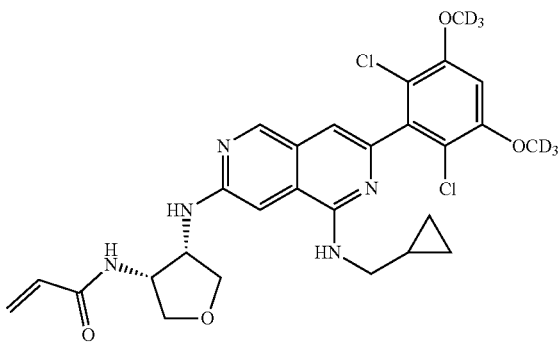
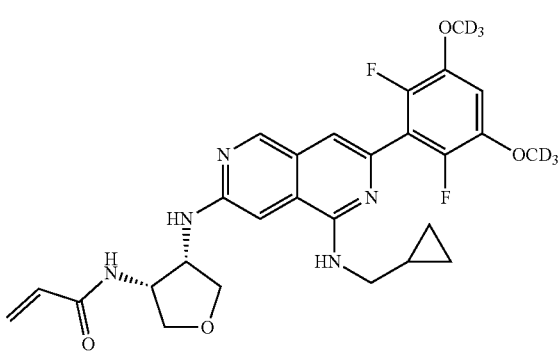
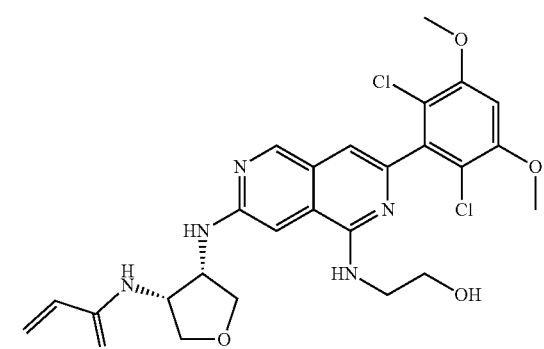
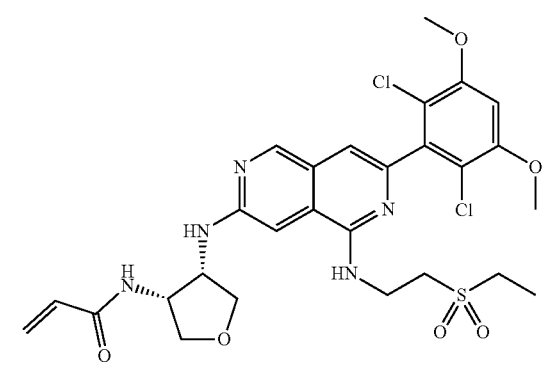

| 977 | 978 |
|---|---|
| -continued | -continued |
| 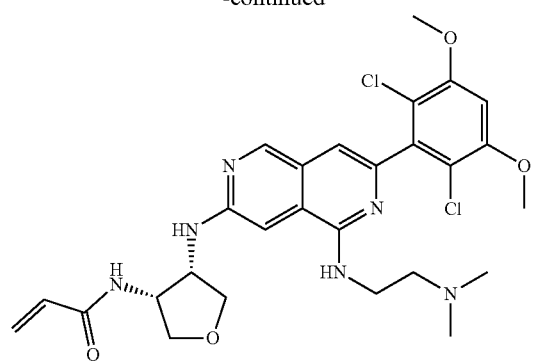 | 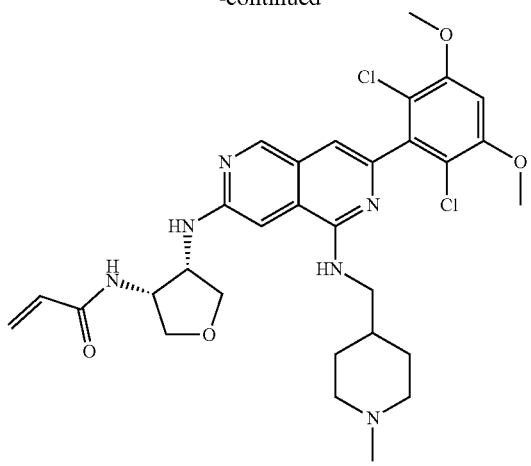 |
| 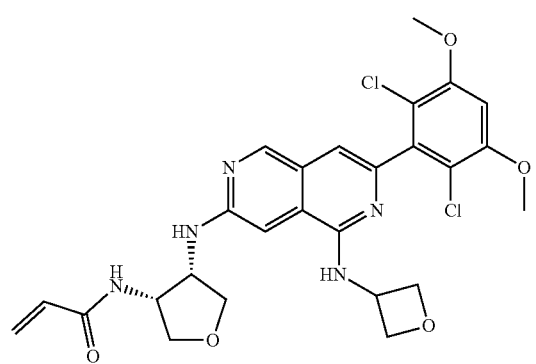 | 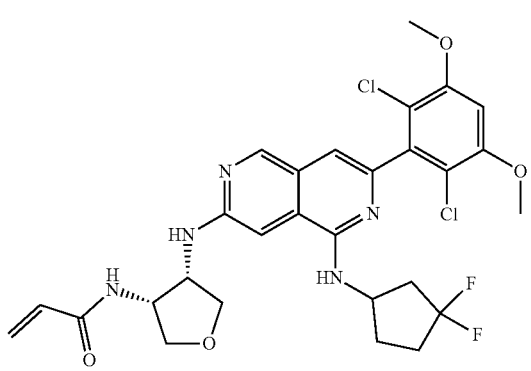 |
| 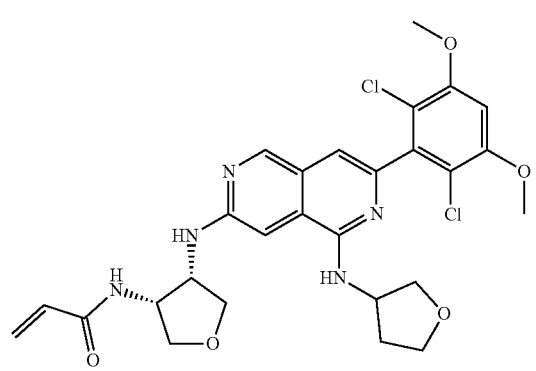 | 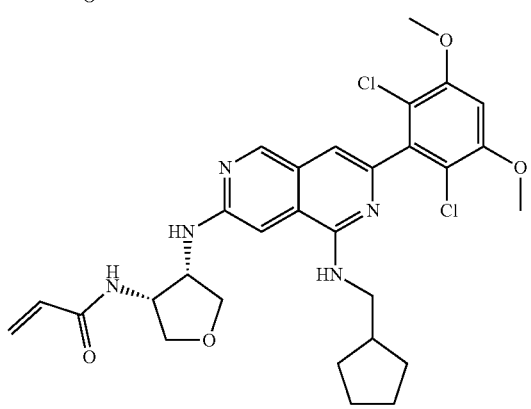 |
| 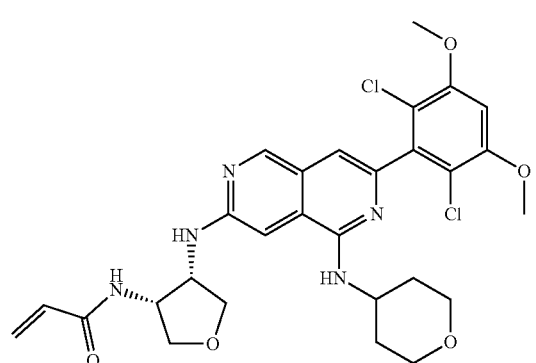 | 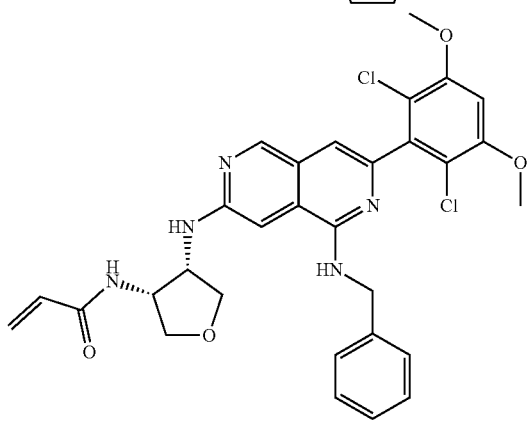 |

979
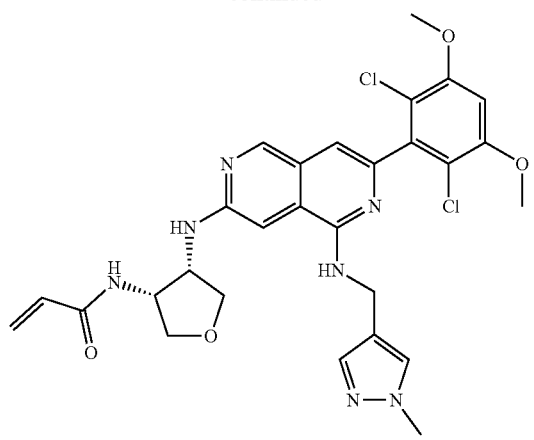
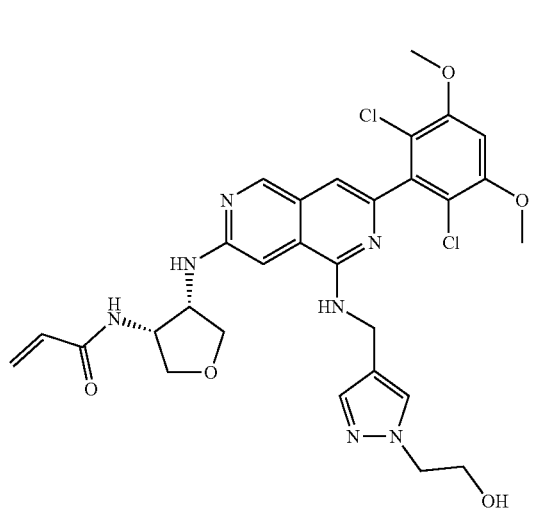
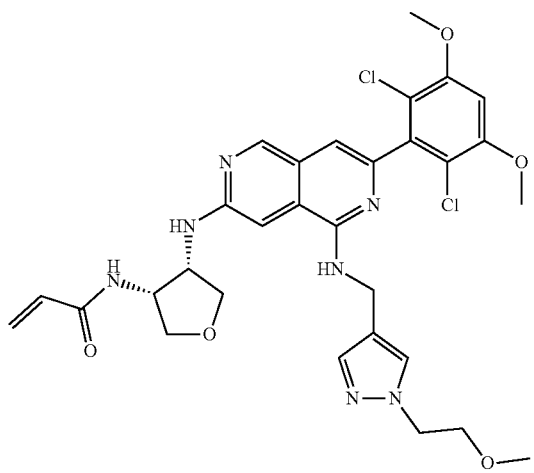
980
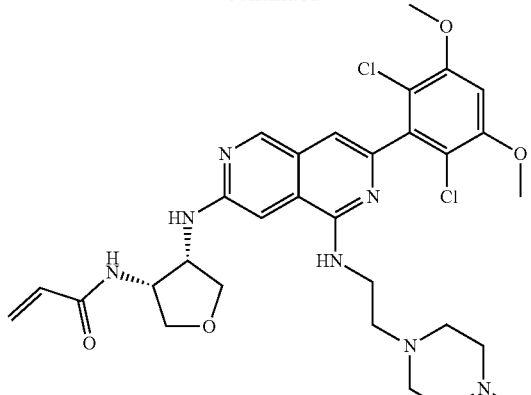
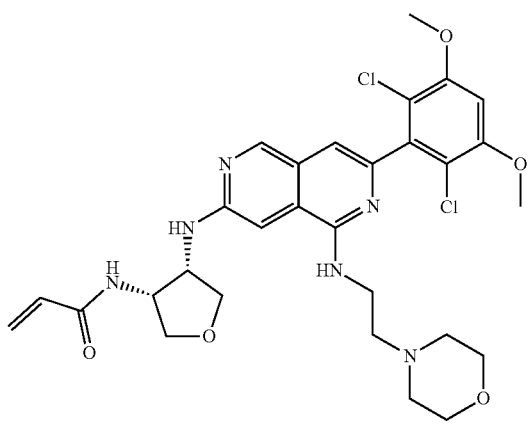
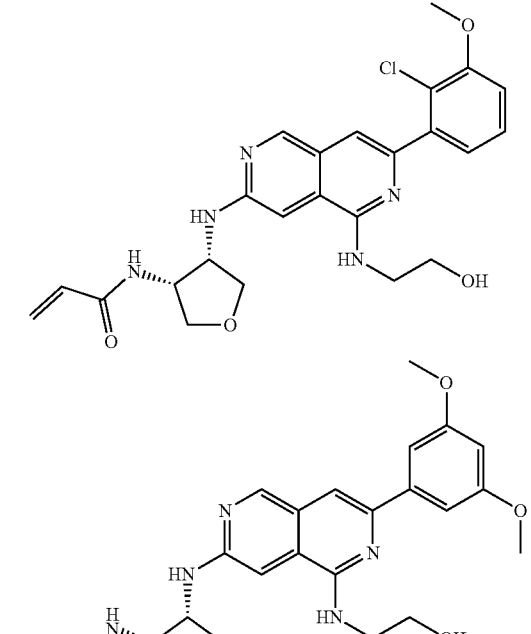
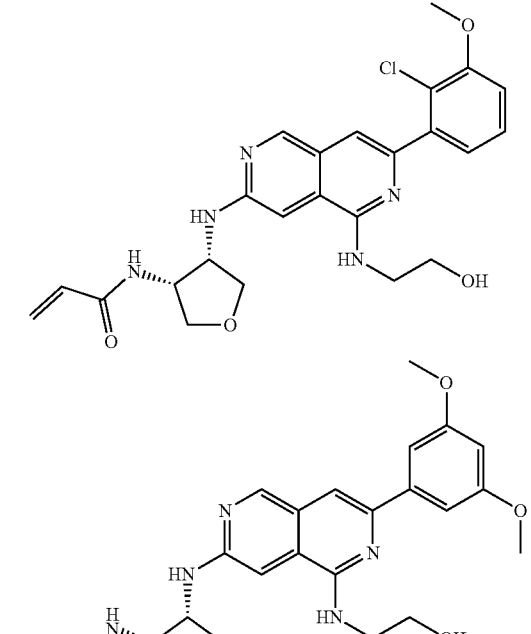

981 982
-continued -continued
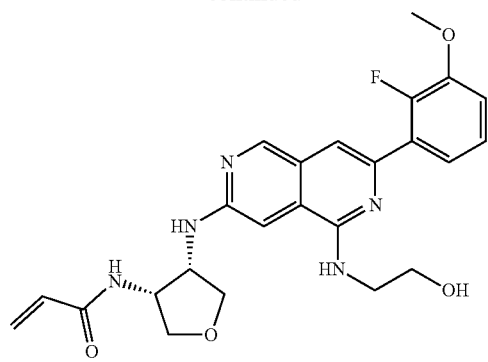
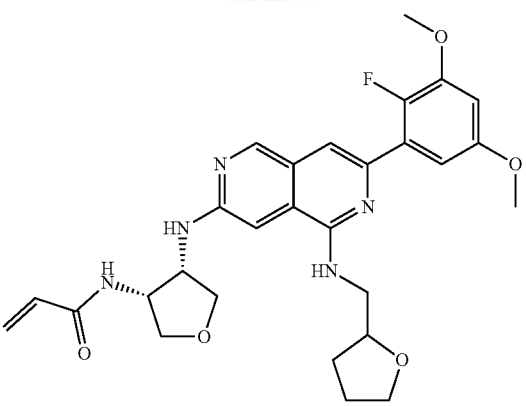

983
-continued
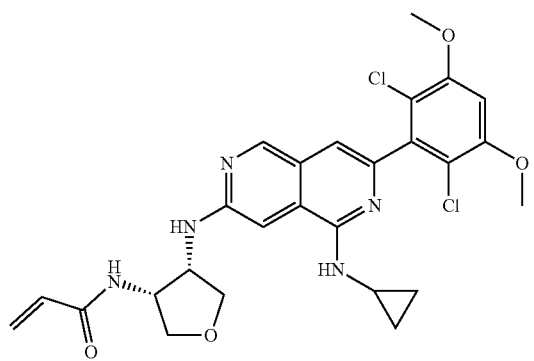
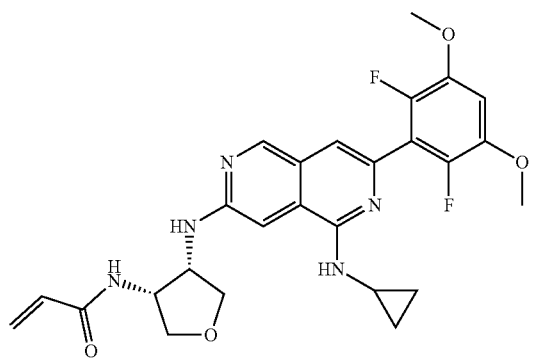
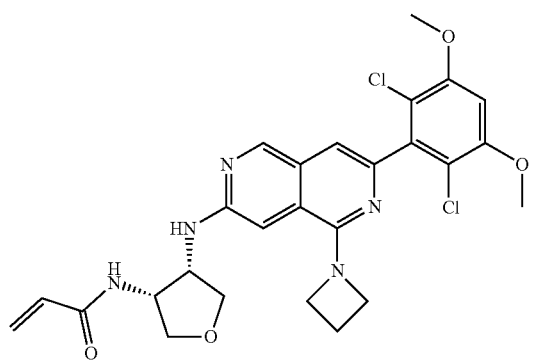
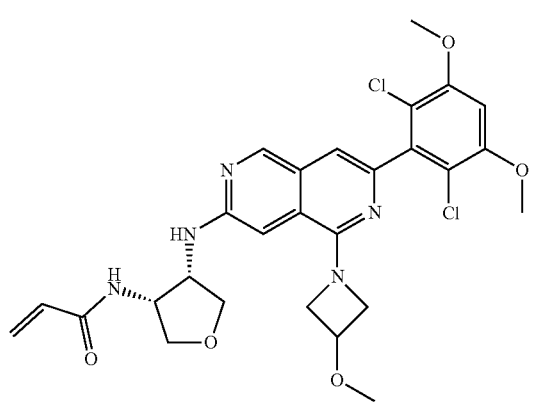
984
-continued
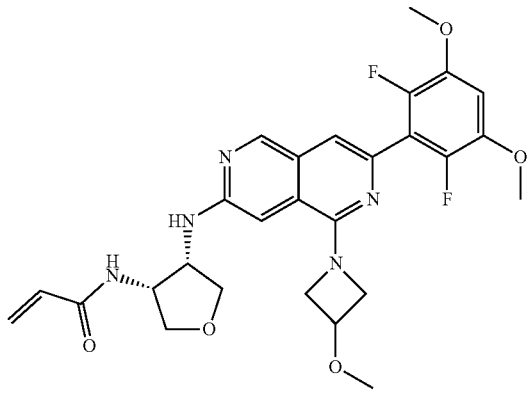
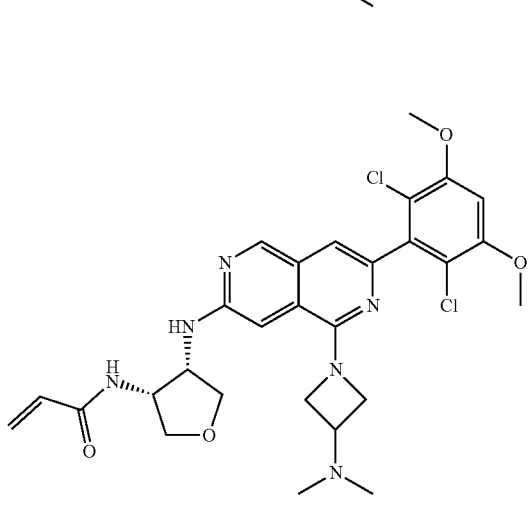
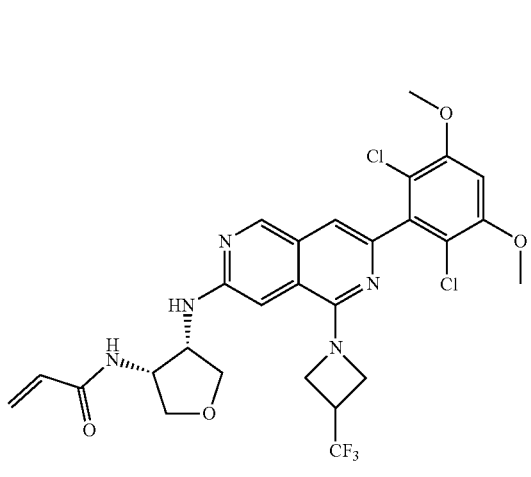
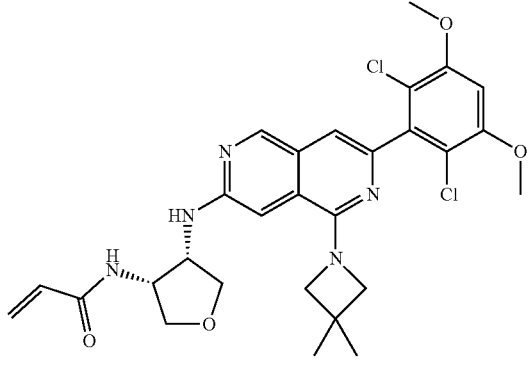

985
-continued
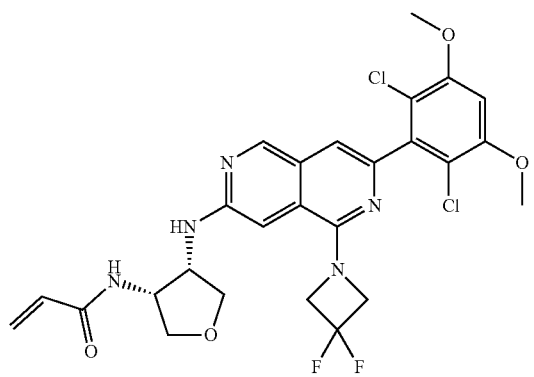
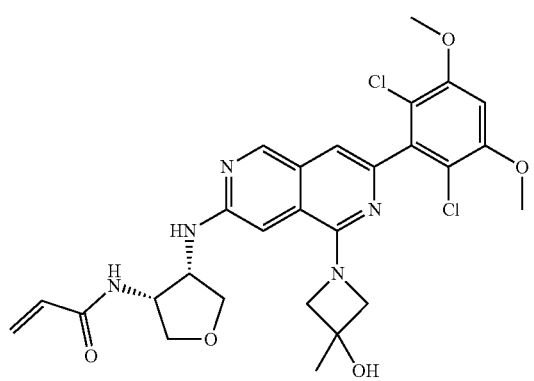
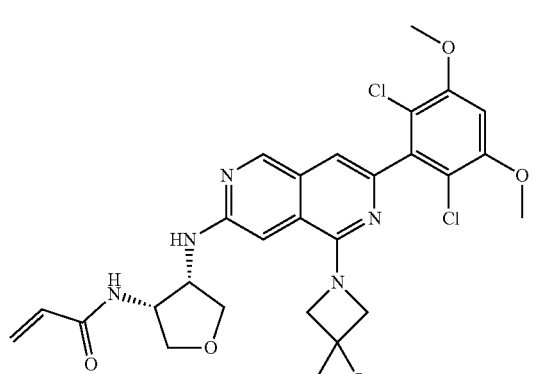
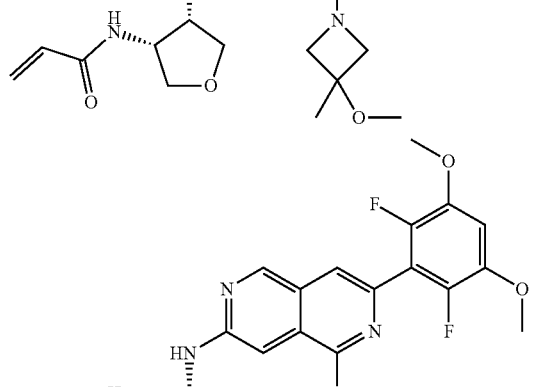
986
-continued
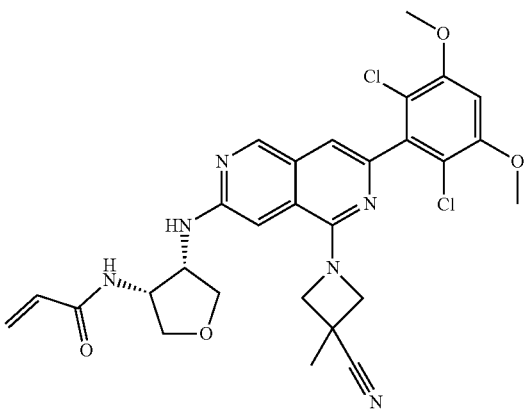
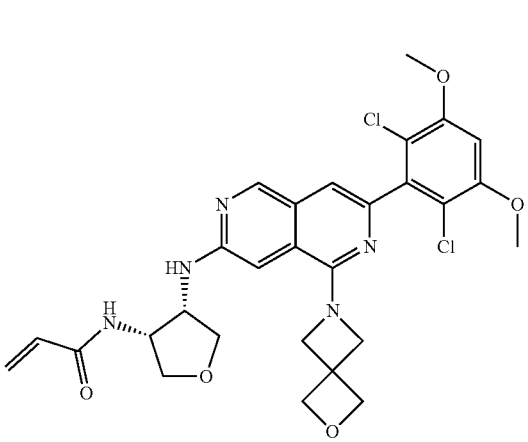
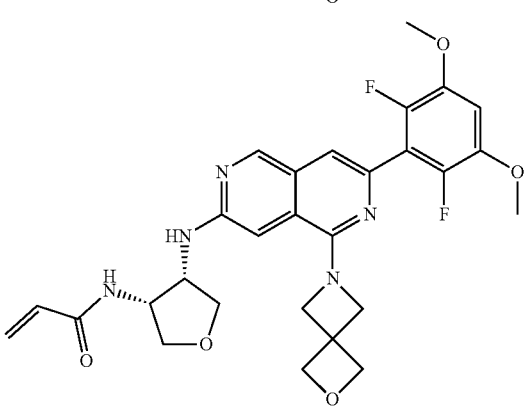
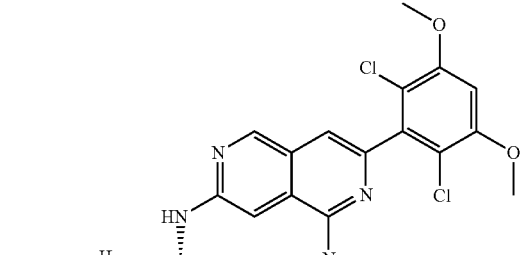

987
-continued
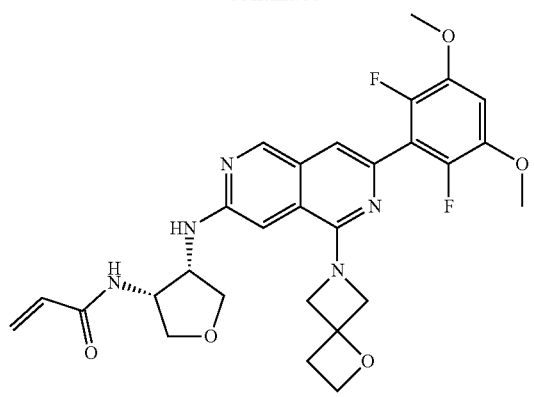
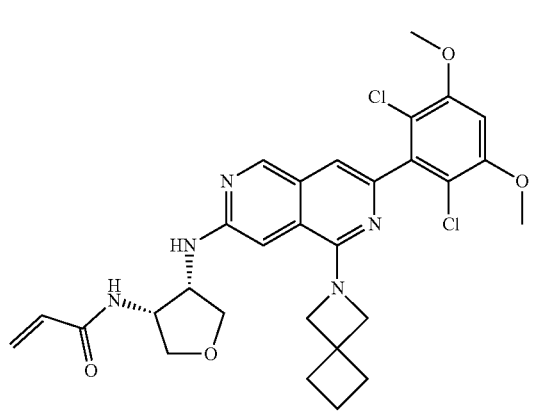
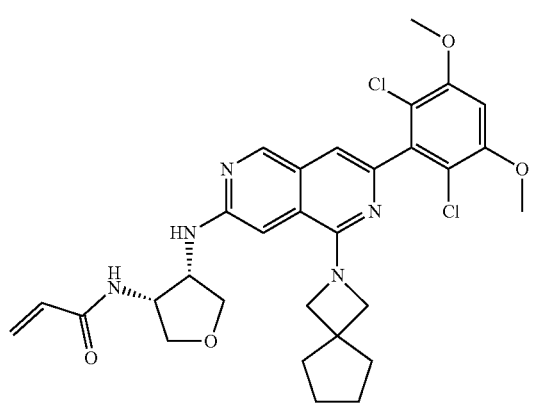
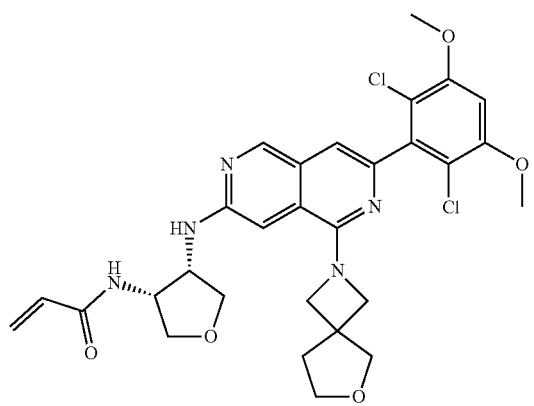
988
-continued
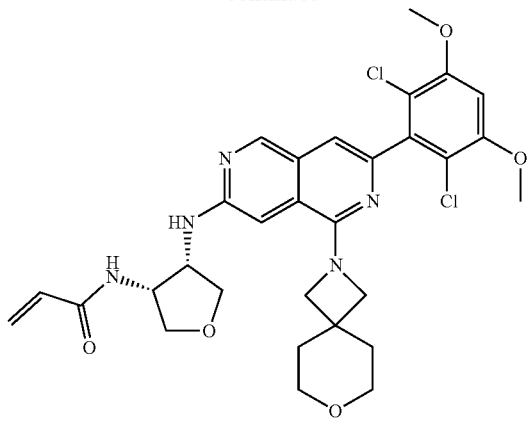
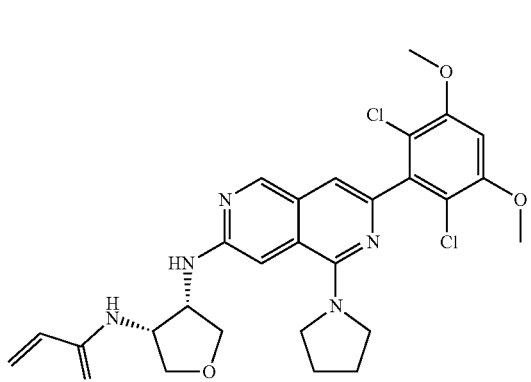
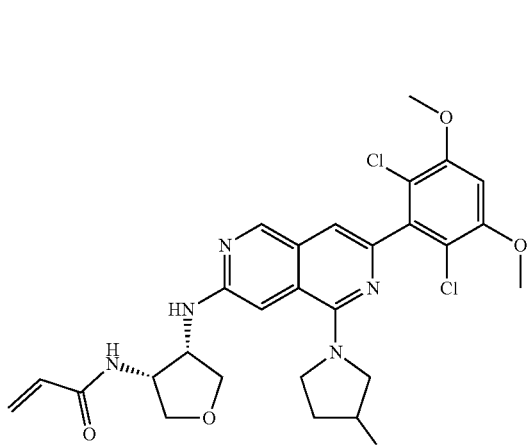
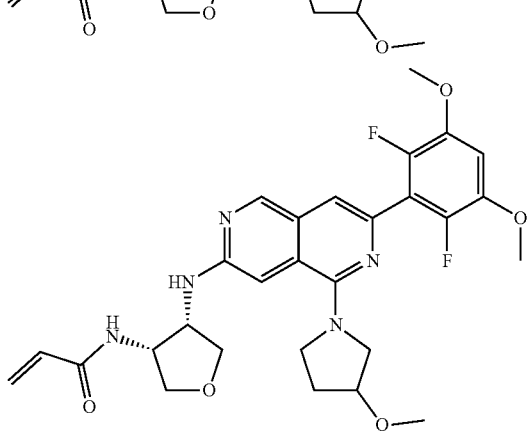

989
-continued
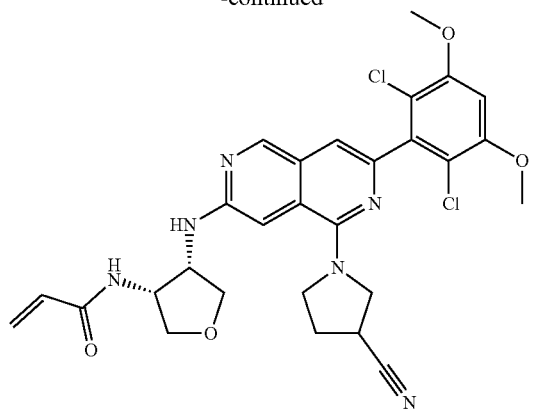
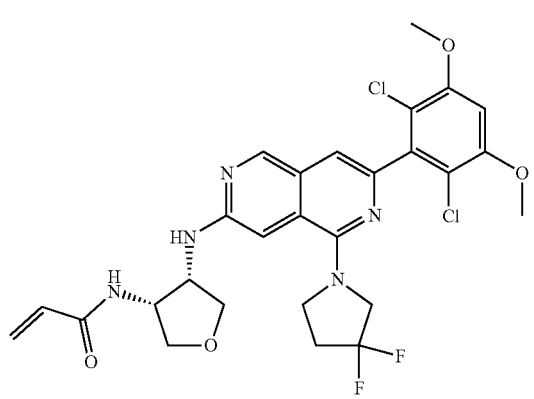
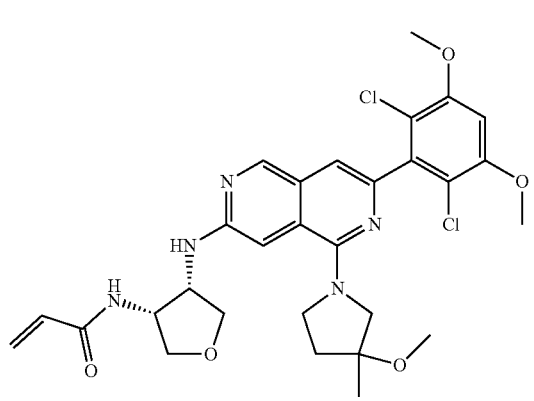
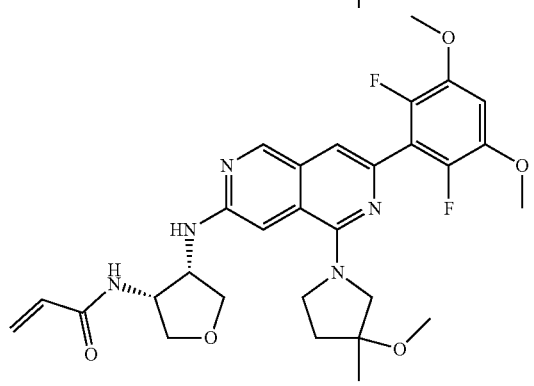
990
-continued
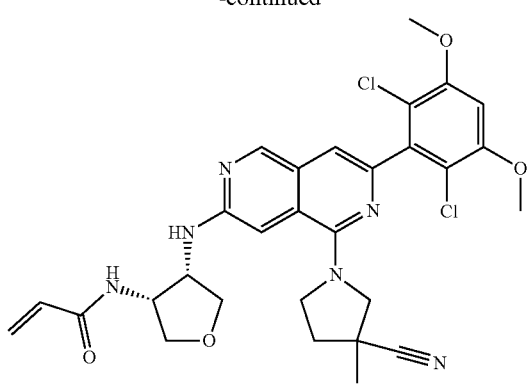
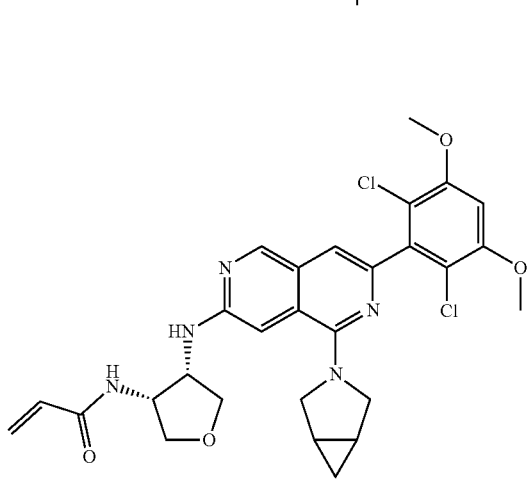
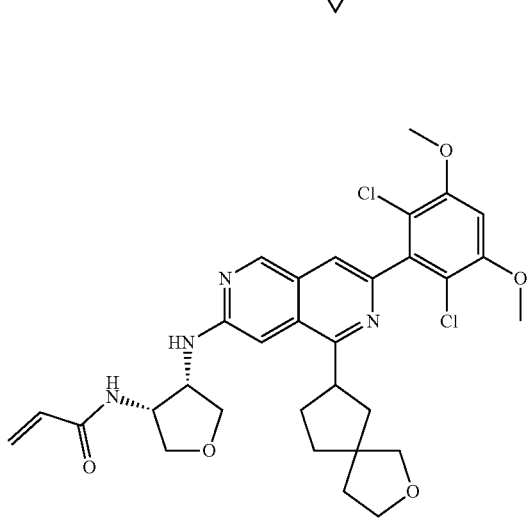
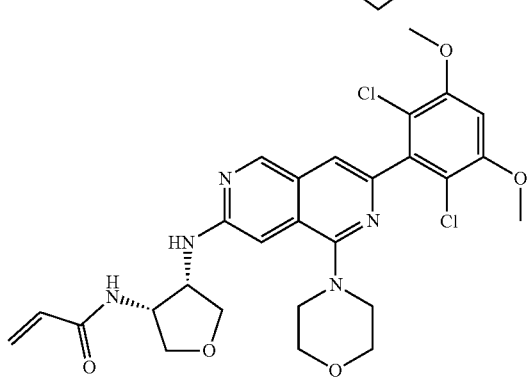

991
-continued
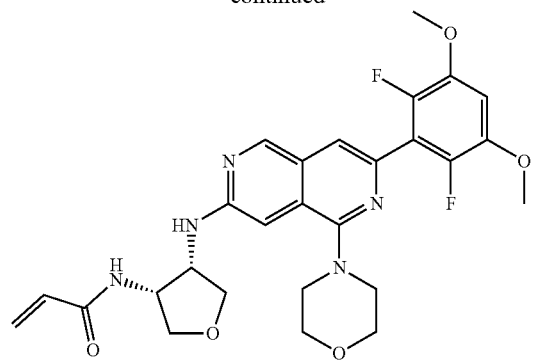
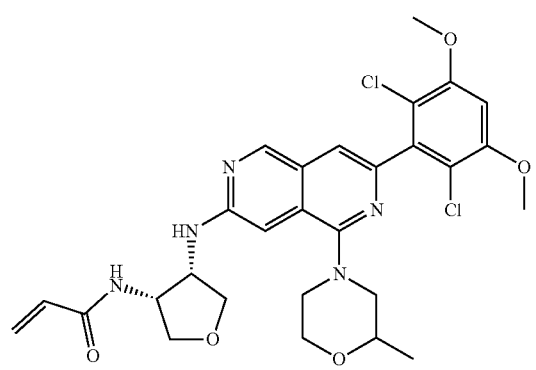
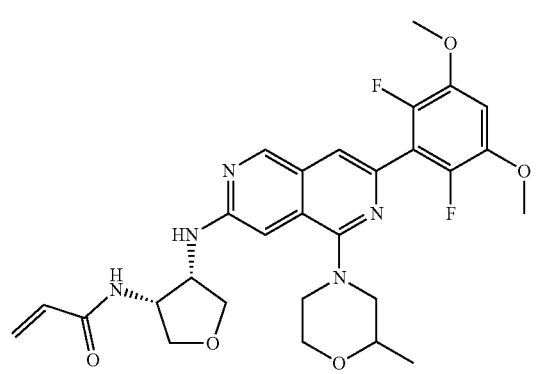
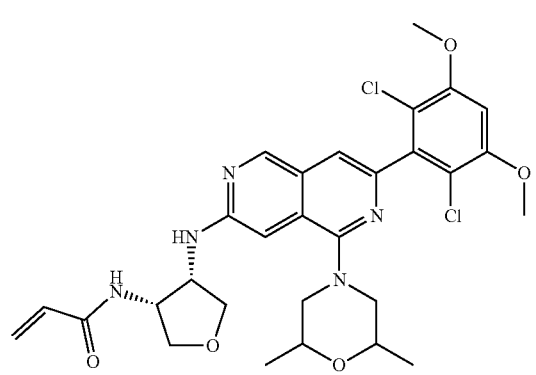
992
-continued
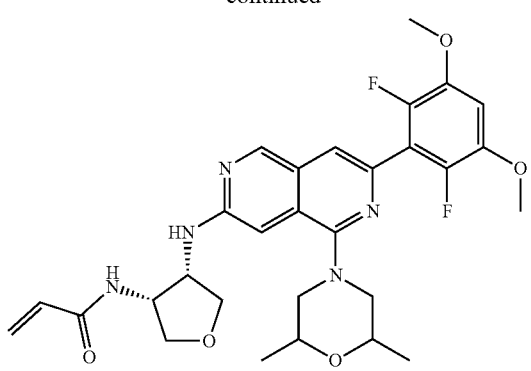
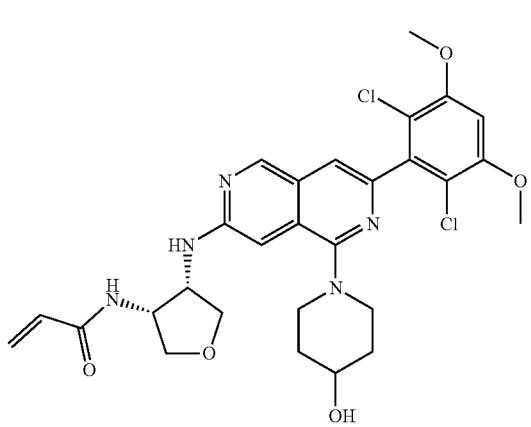
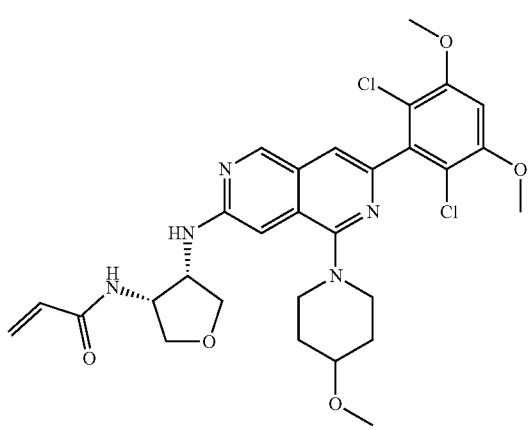
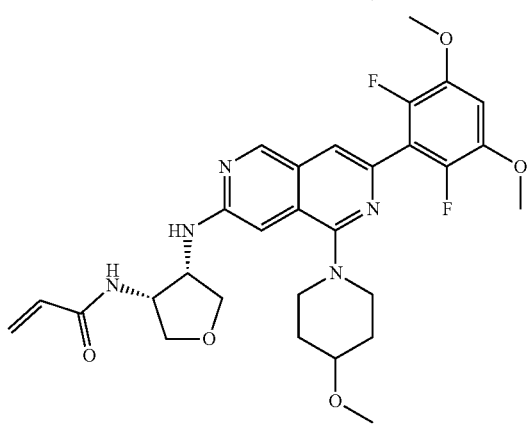

993
-continued
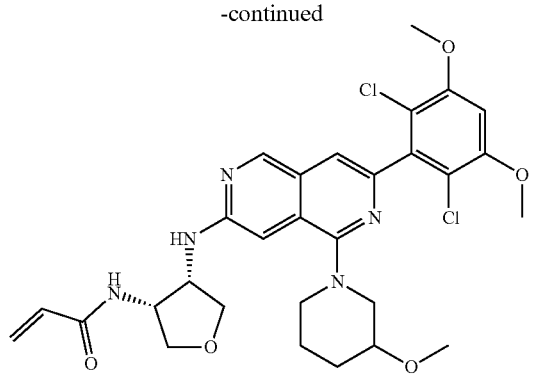
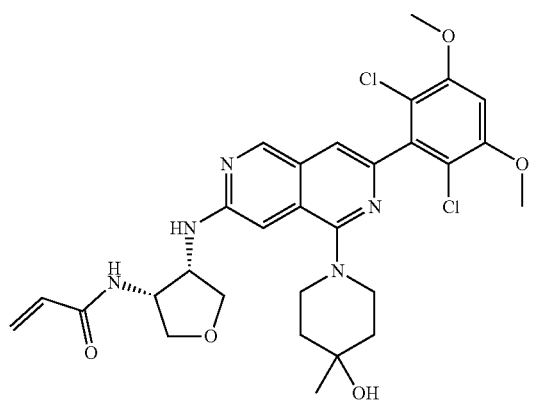
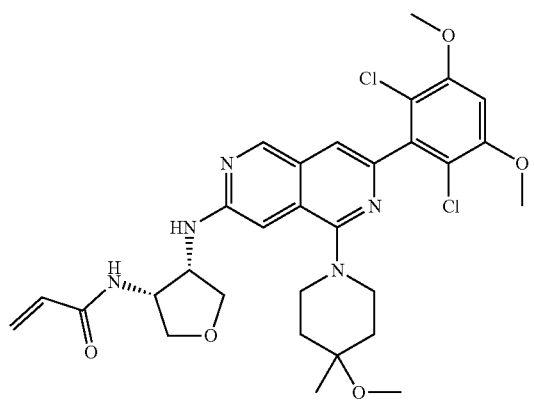
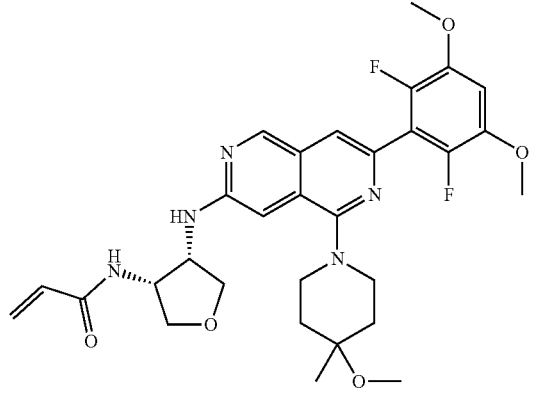
994
-continued
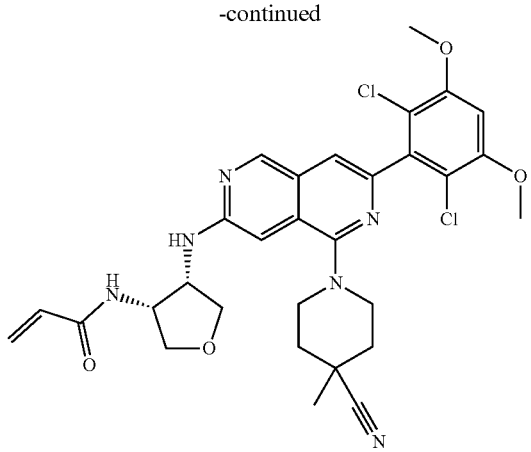
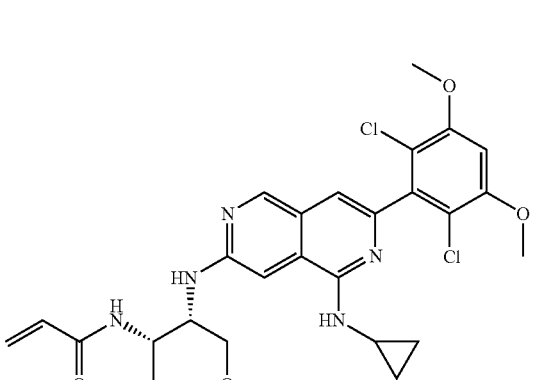
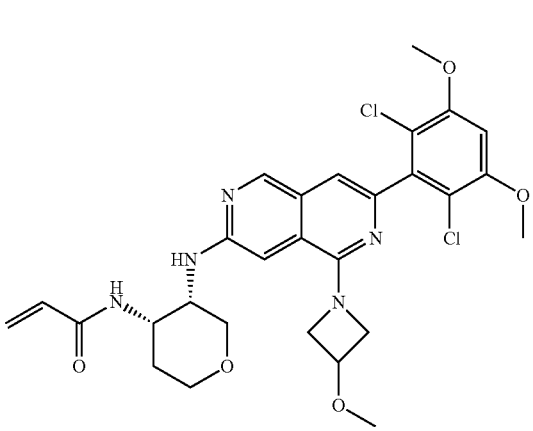
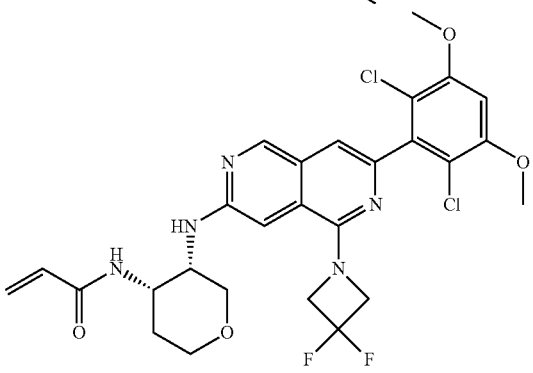

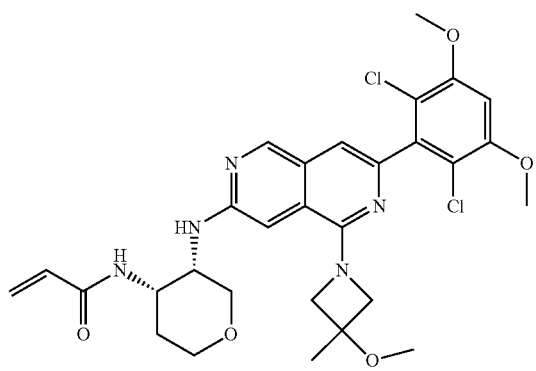
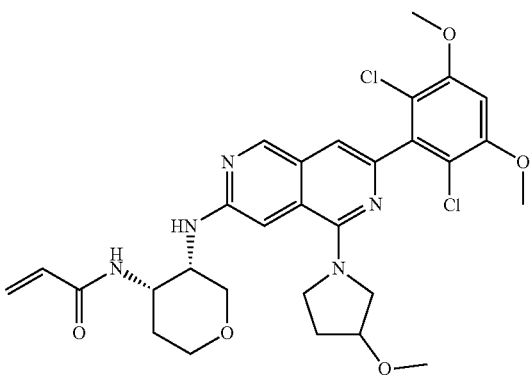
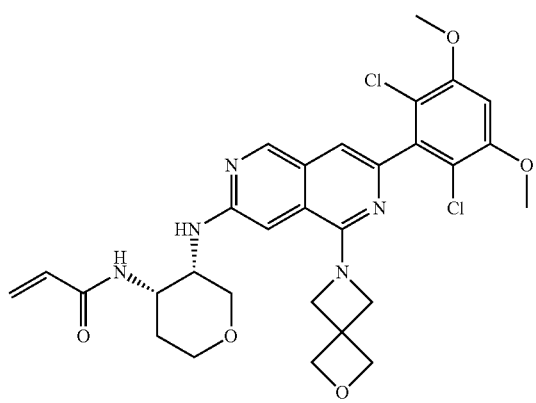
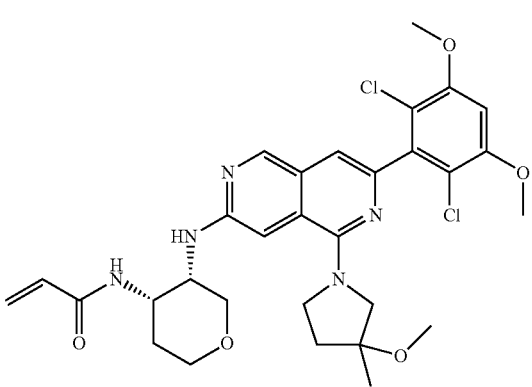
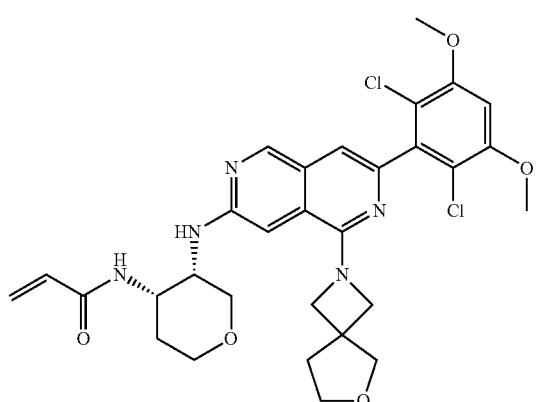
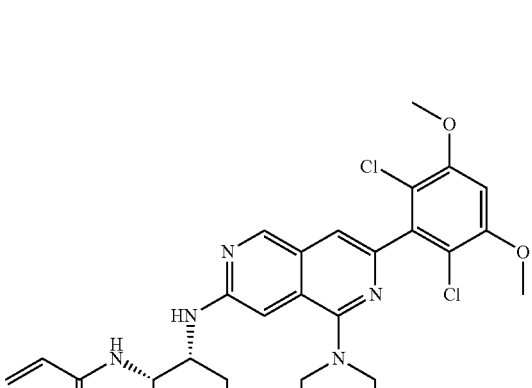
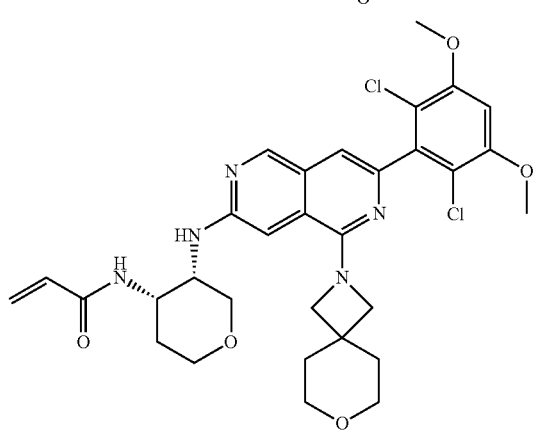
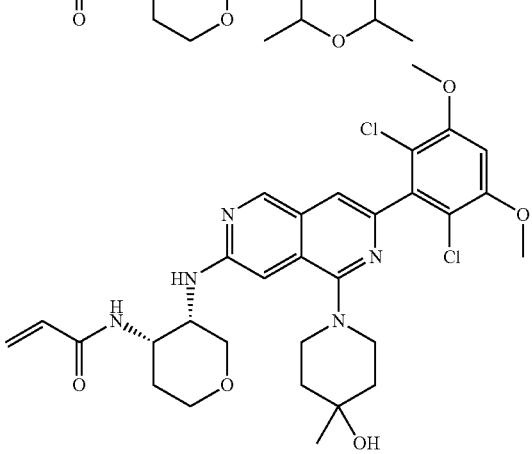

997 -continued
998 -continued
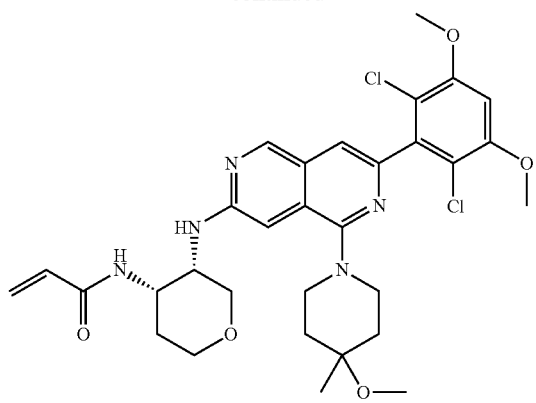
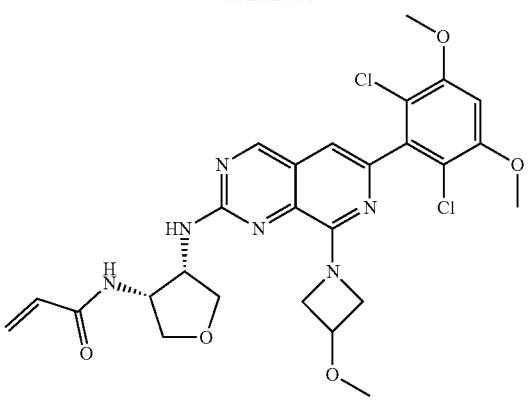

999
-continued
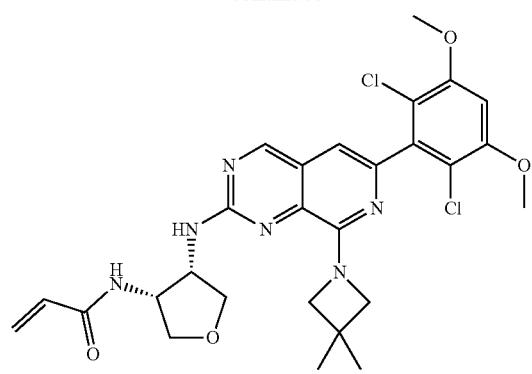
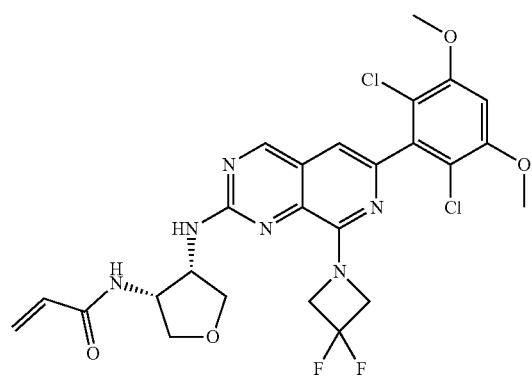
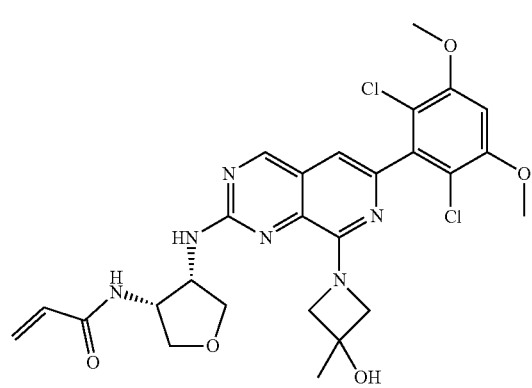
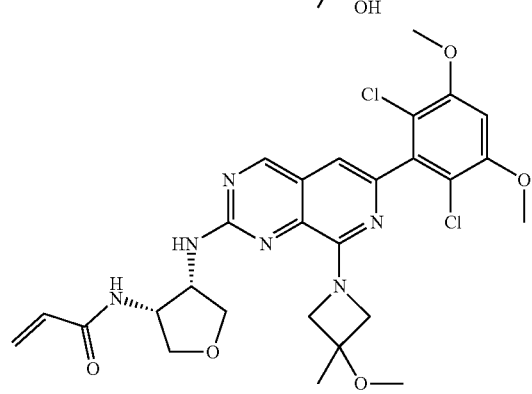
1000
-continued
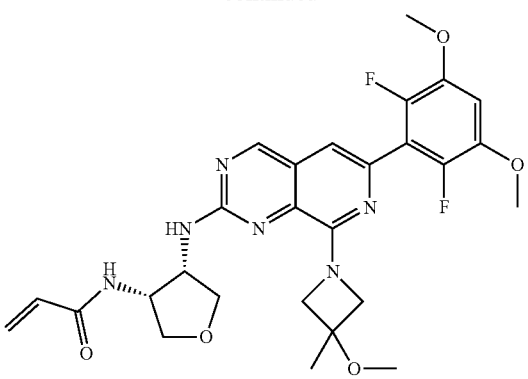

1001
-continued
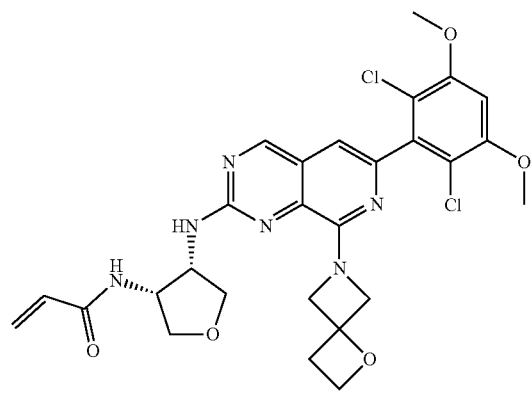
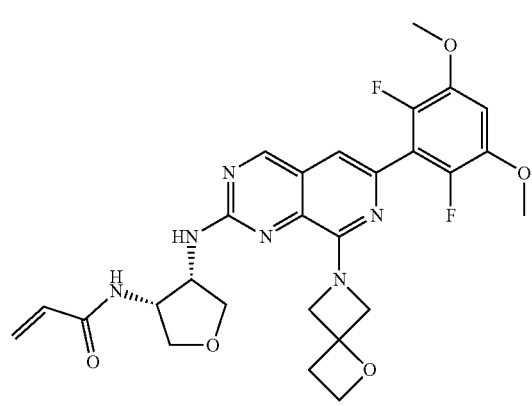
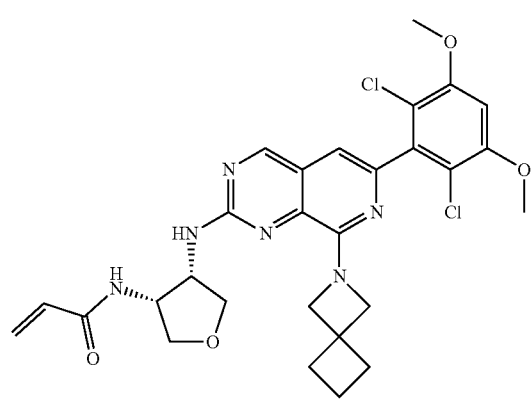
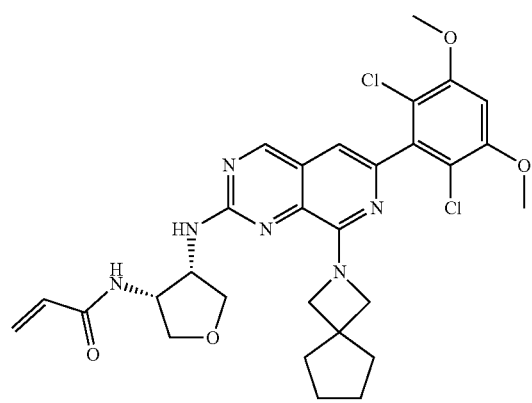
1002
-continued
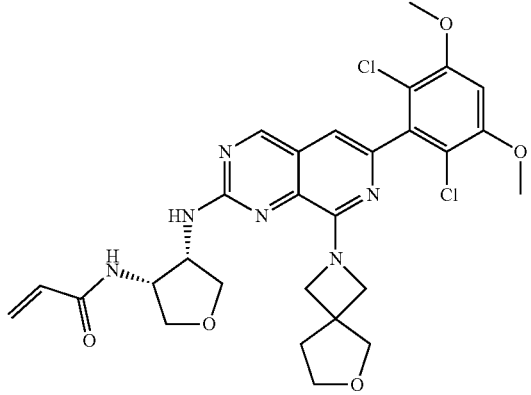
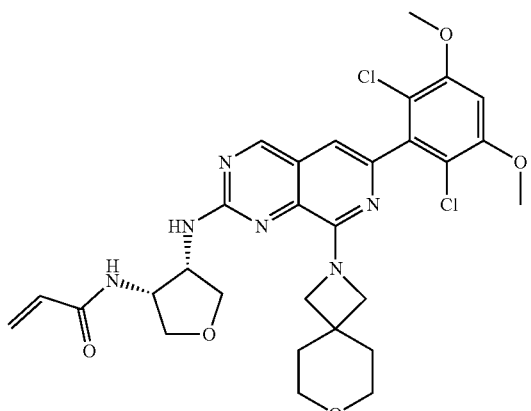
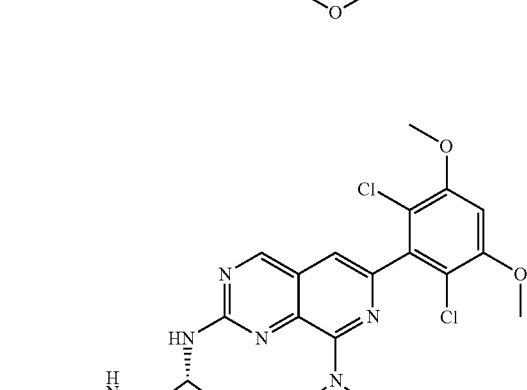
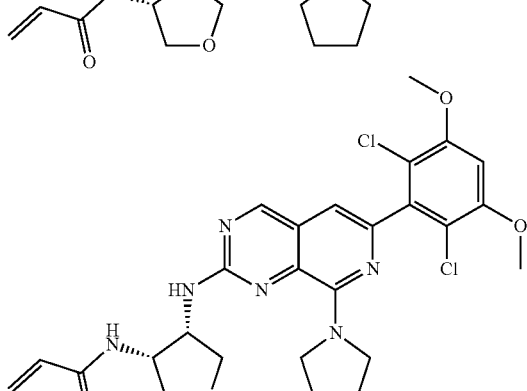

1003
-continued
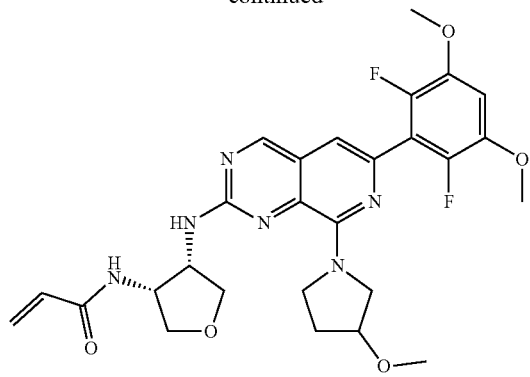
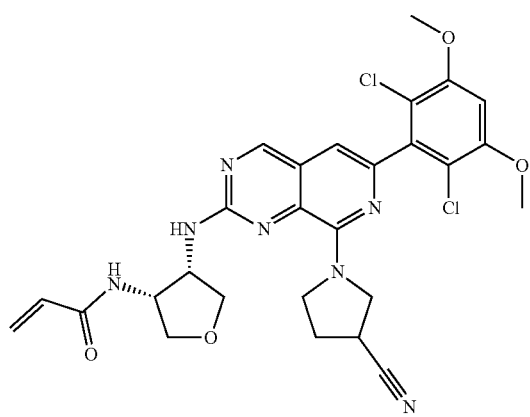
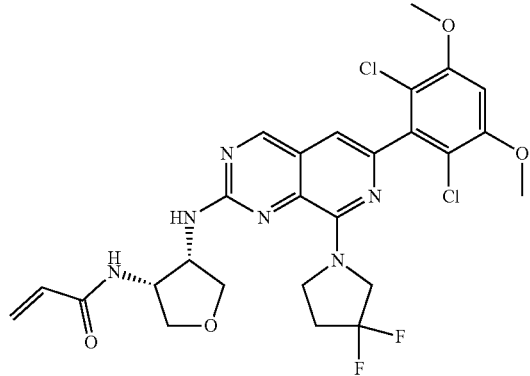
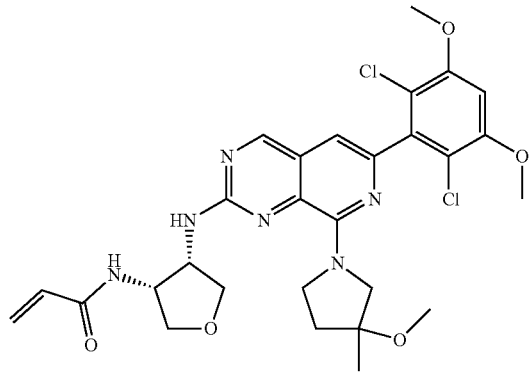
1004
-continued
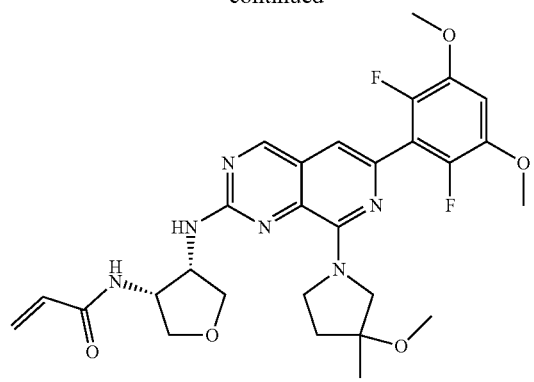
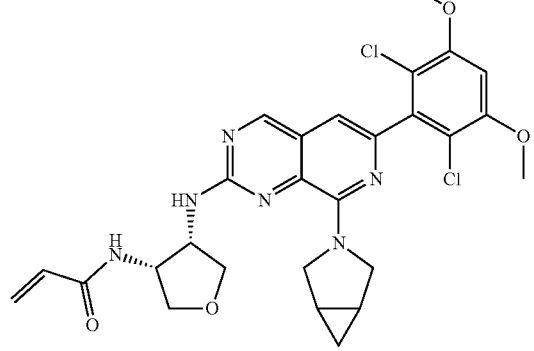
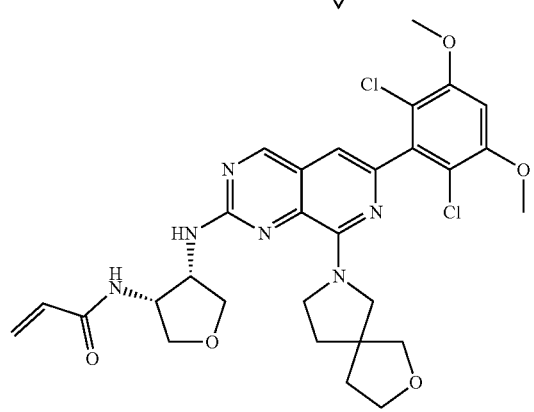

1005
-continued
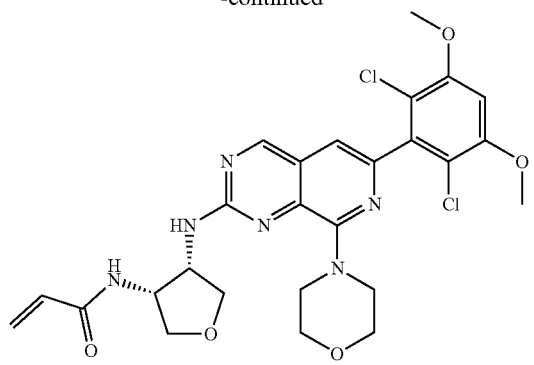
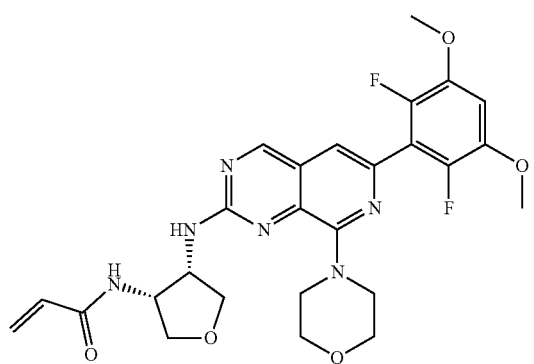
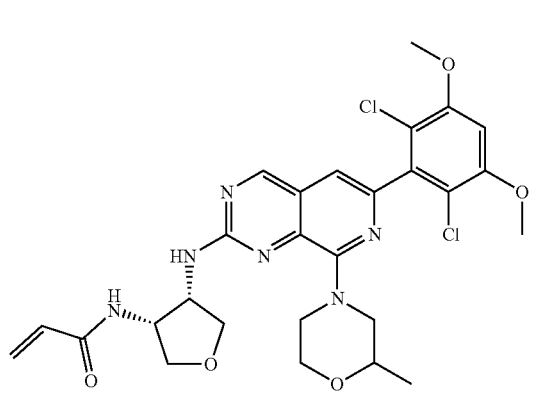
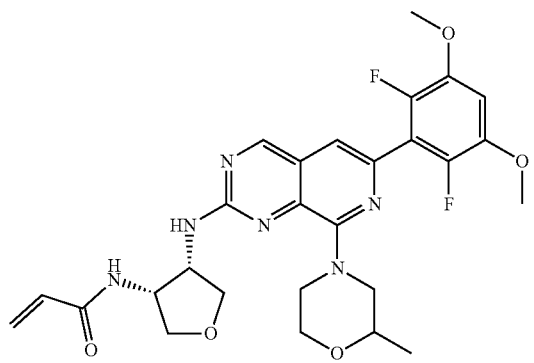
1006
-continued
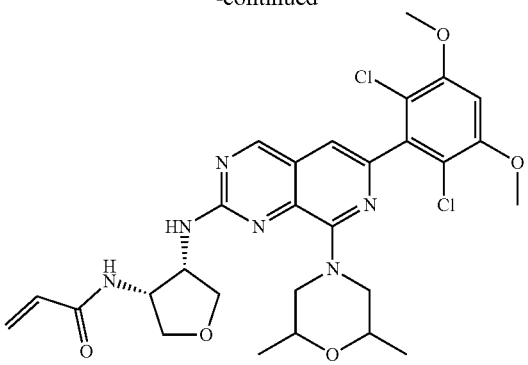
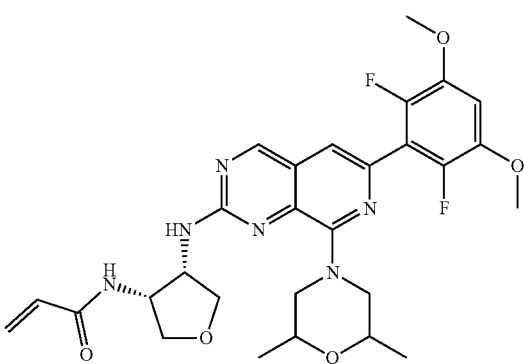
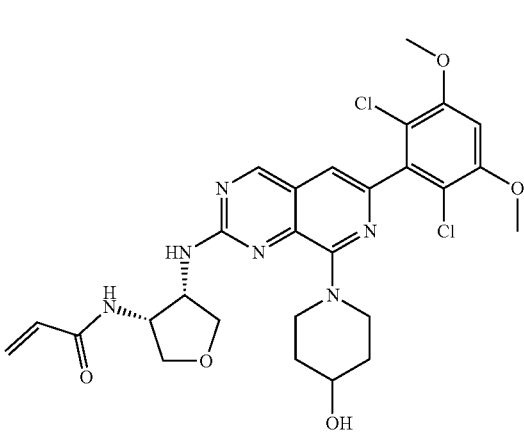
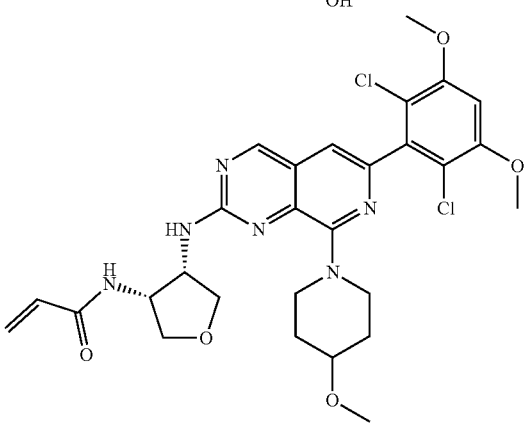

1007
-continued
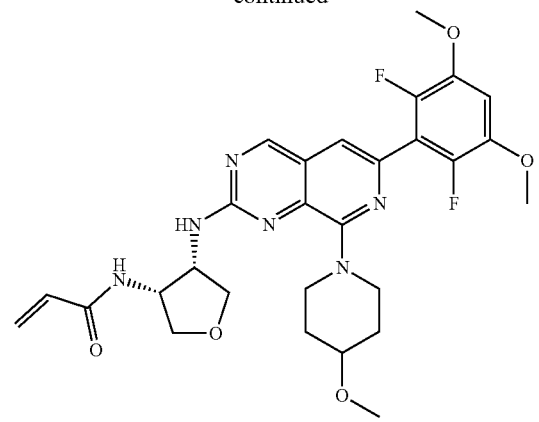
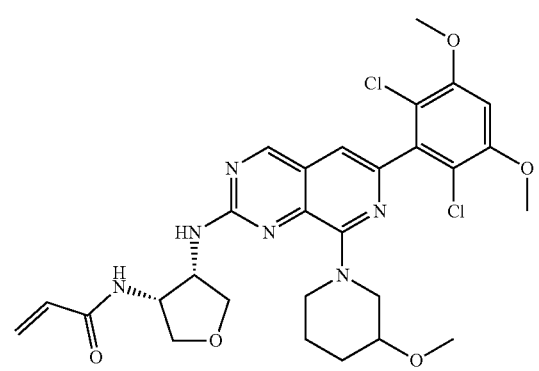
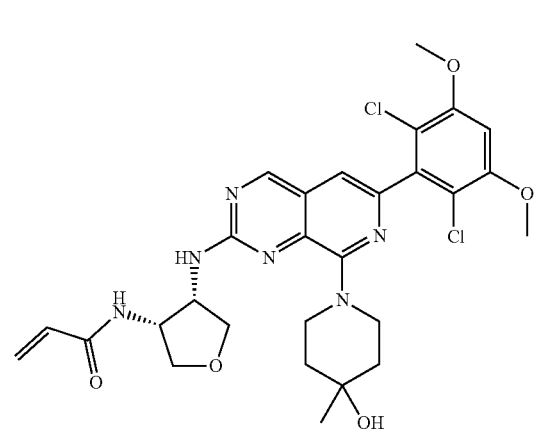
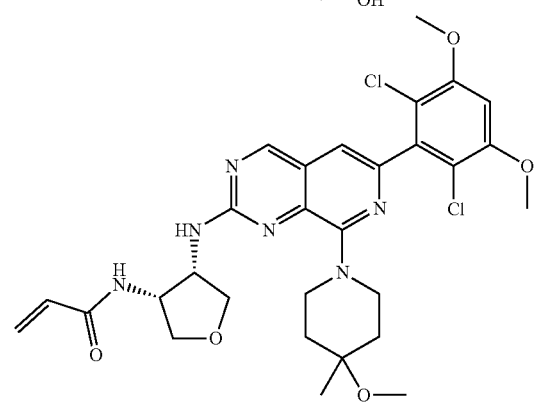
1008
-continued
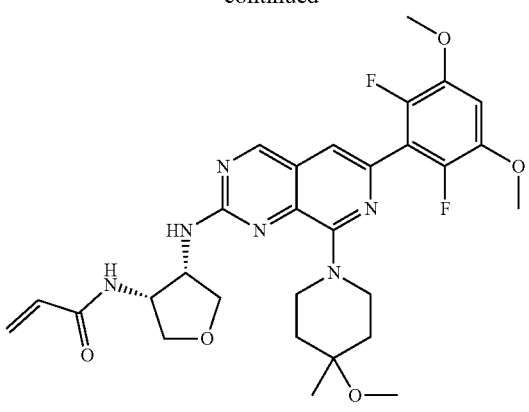
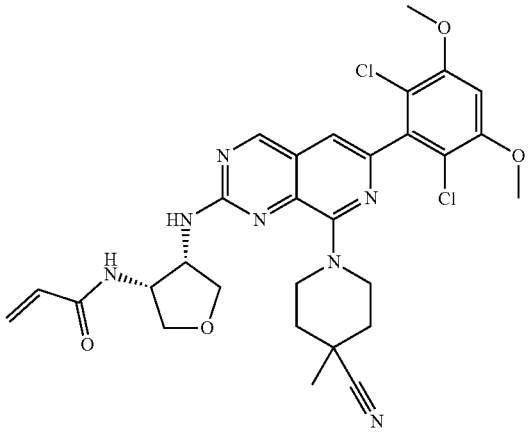
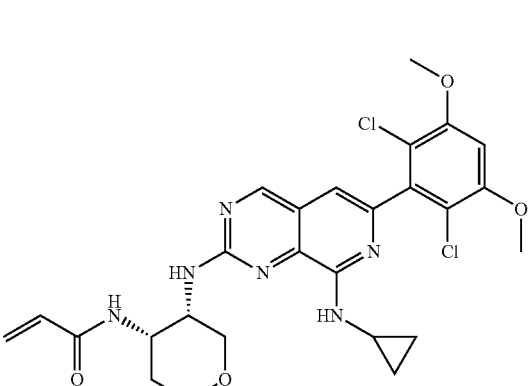
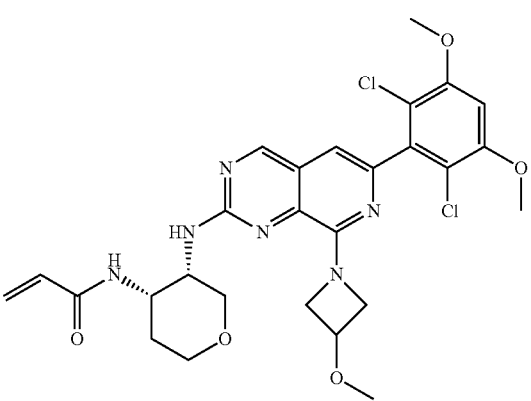

1009
-continued
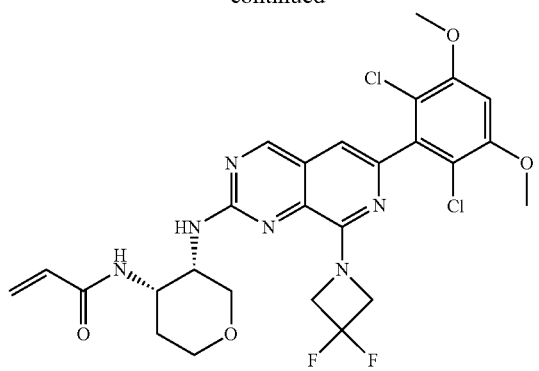
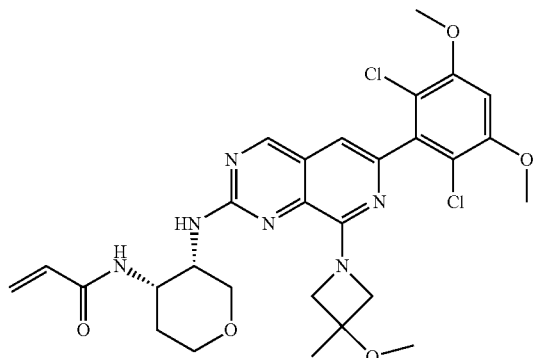
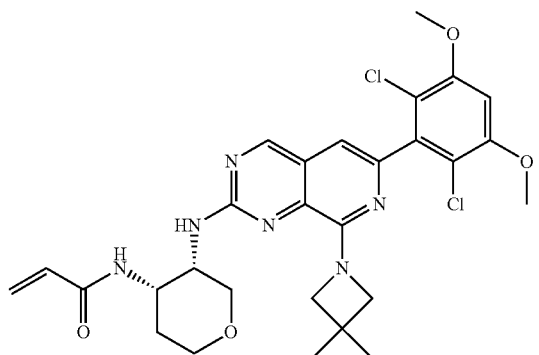
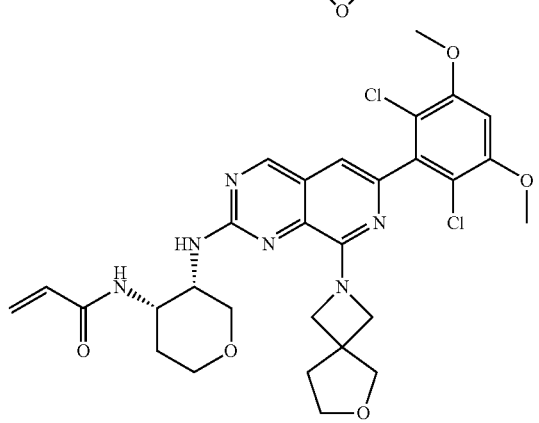
1010
-continued
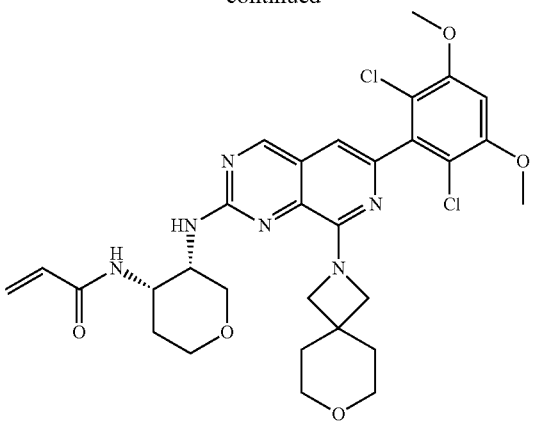
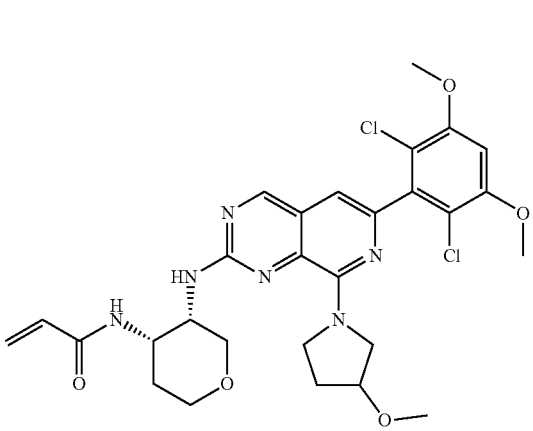
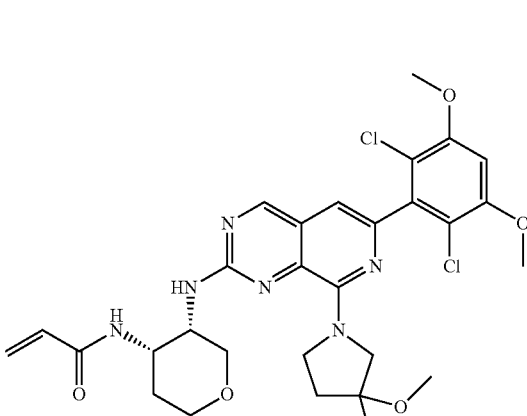
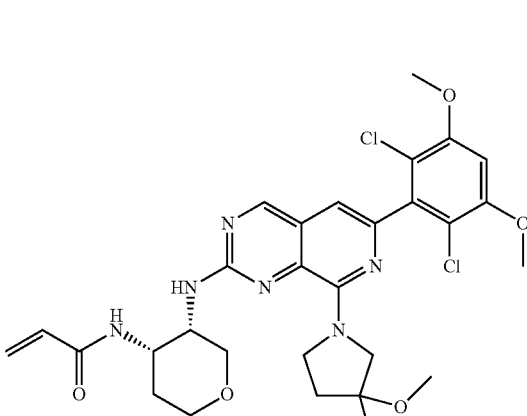

1011
-continued
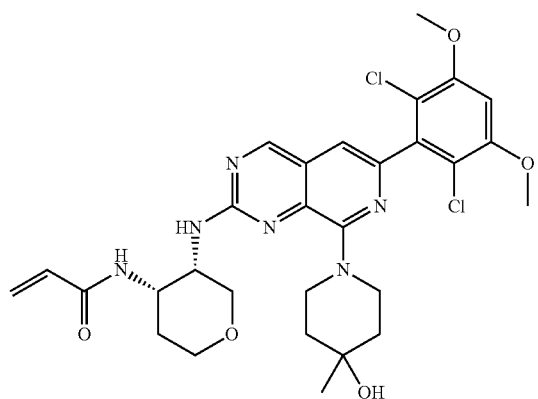
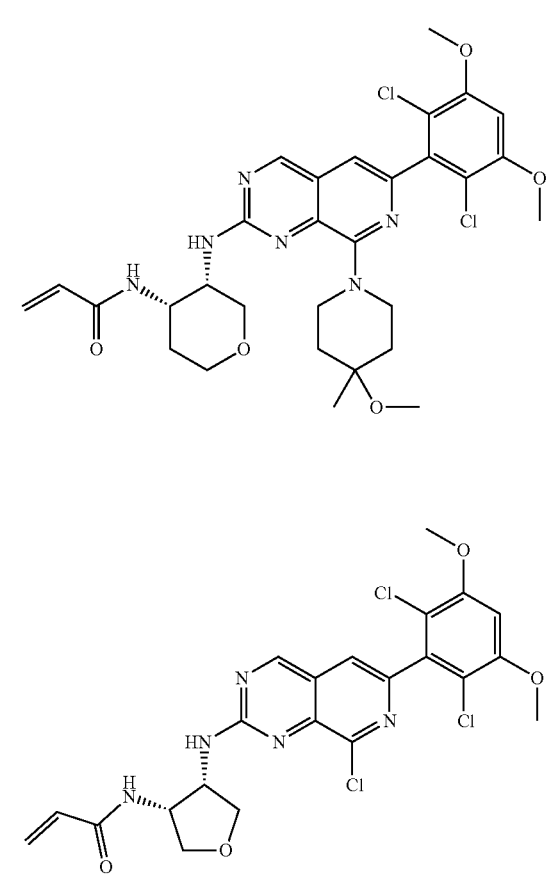
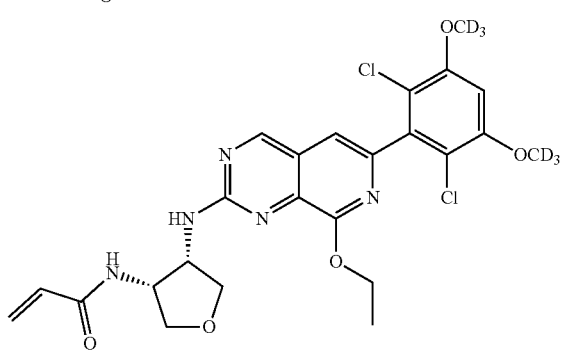
1012
-continued
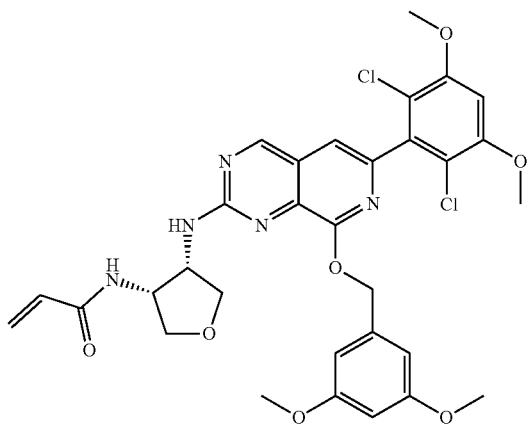
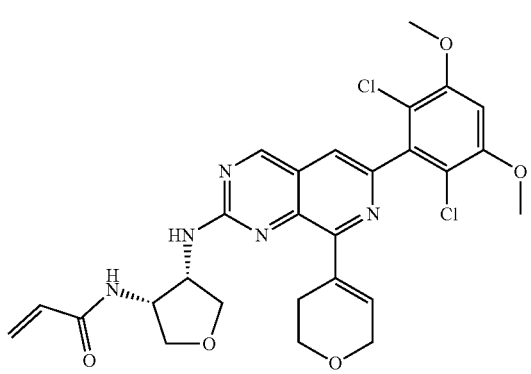
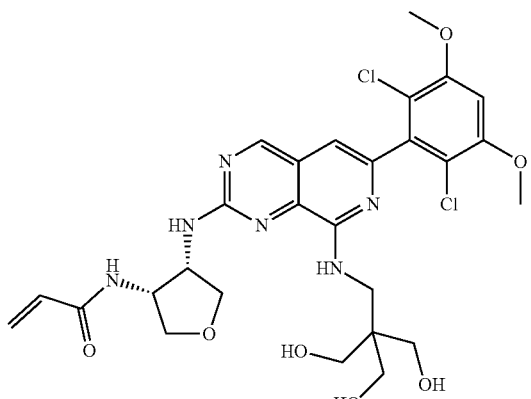
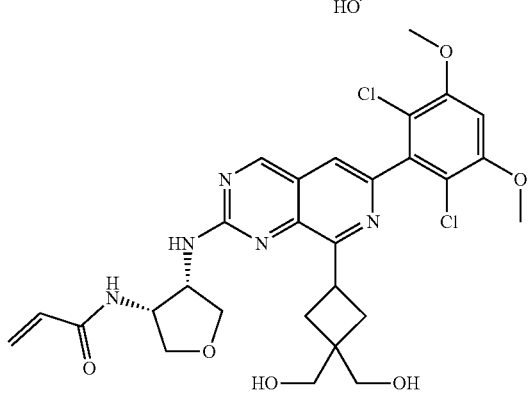

1013
-continued
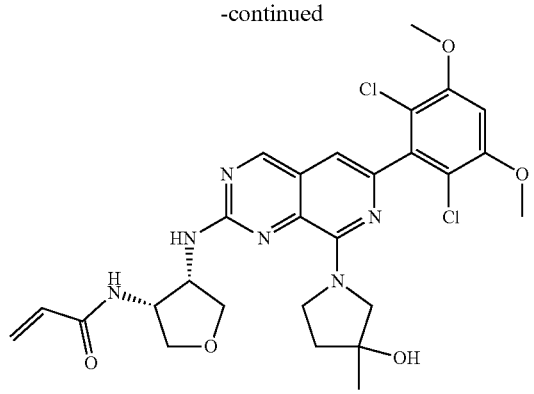
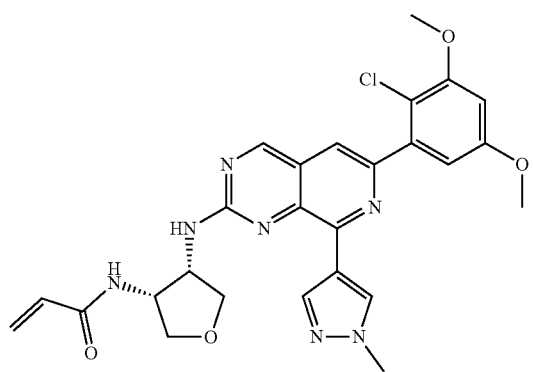
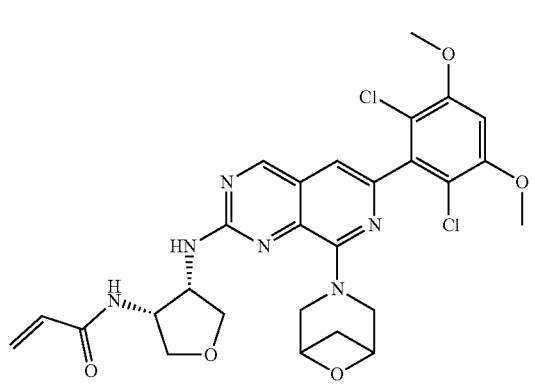
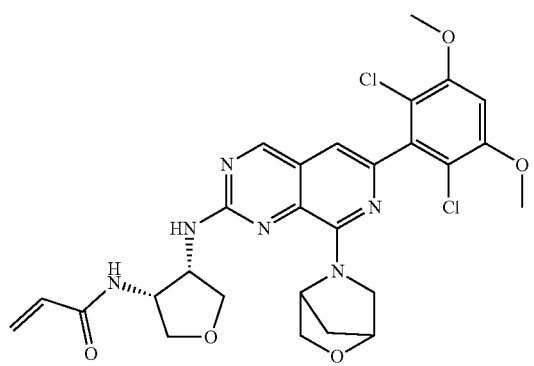
1014
-continued
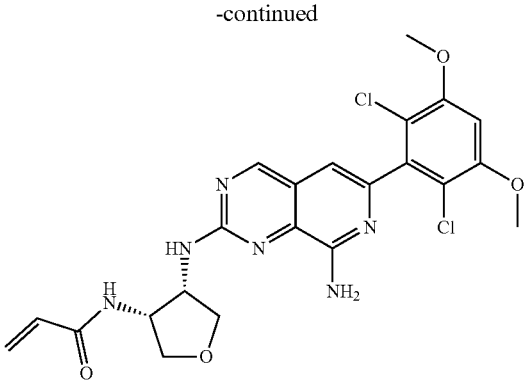
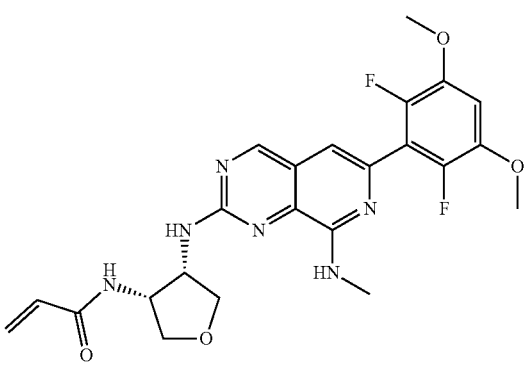
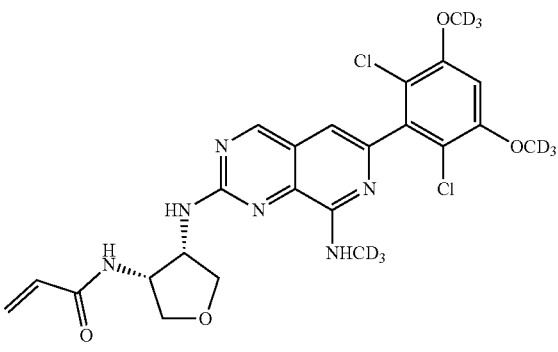
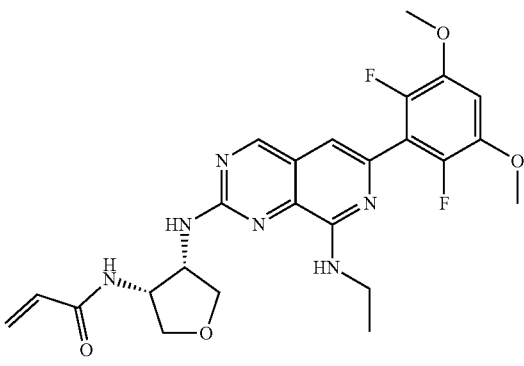

1015
-continued

1016
-continued

1017
-continued
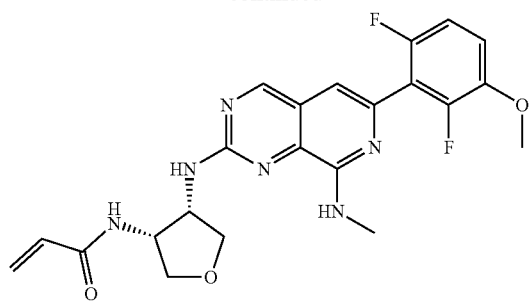
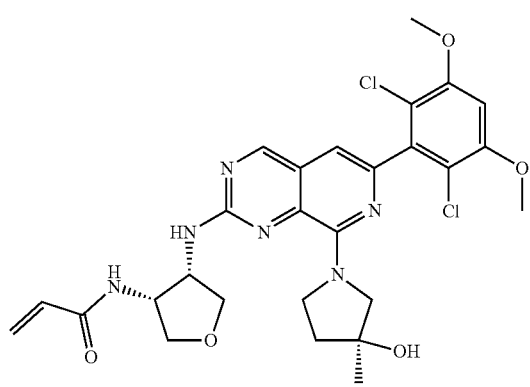
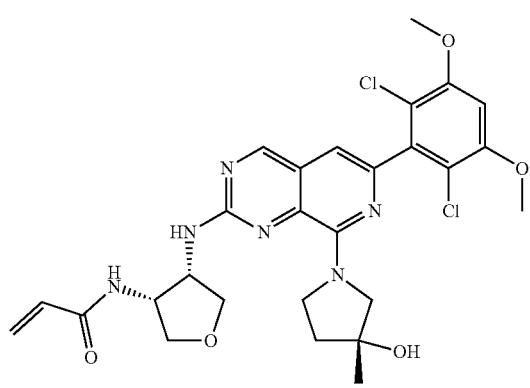
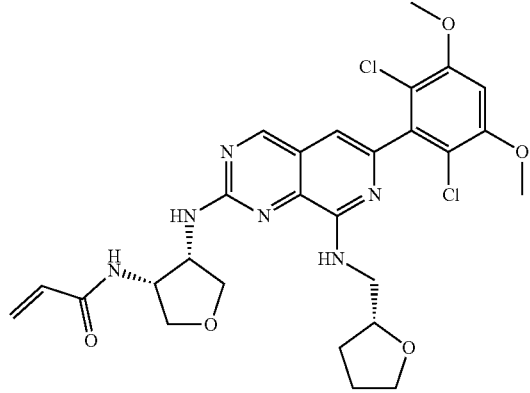
1018
-continued
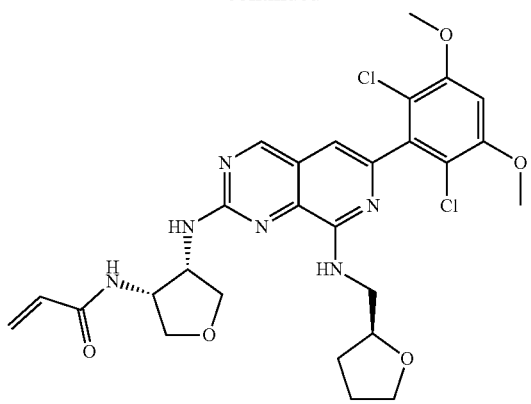
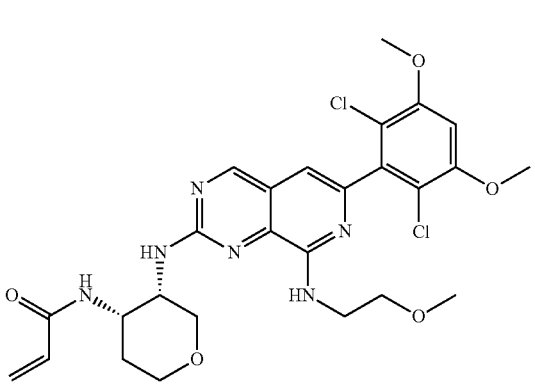
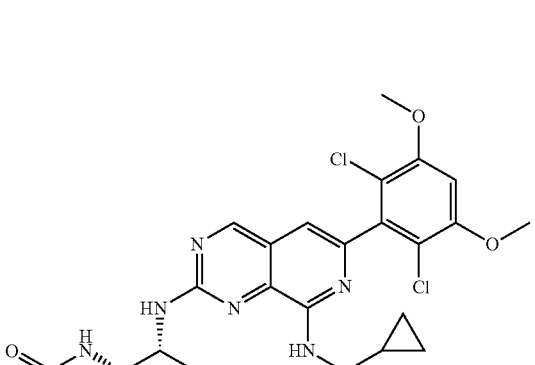
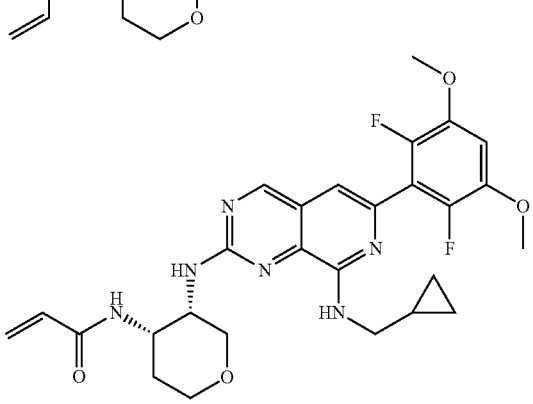

1019
-continued
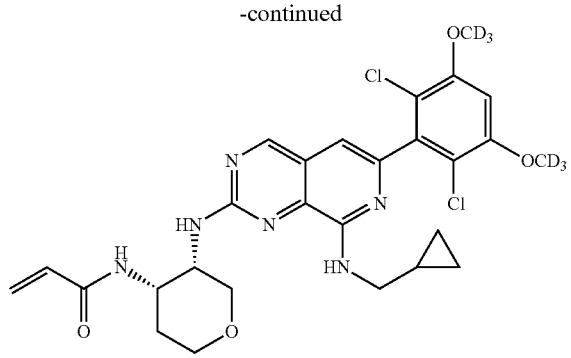
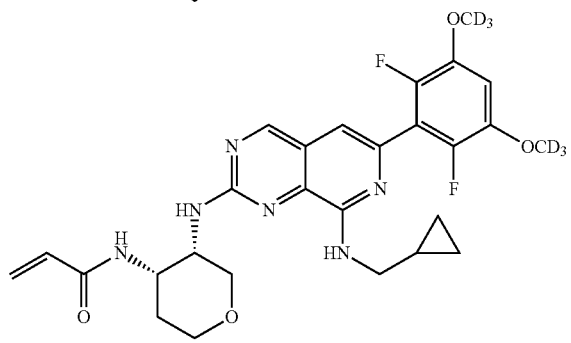
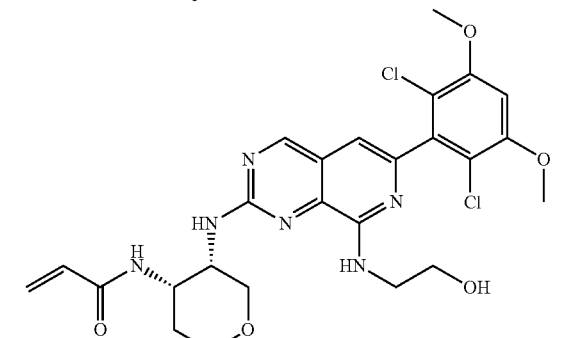
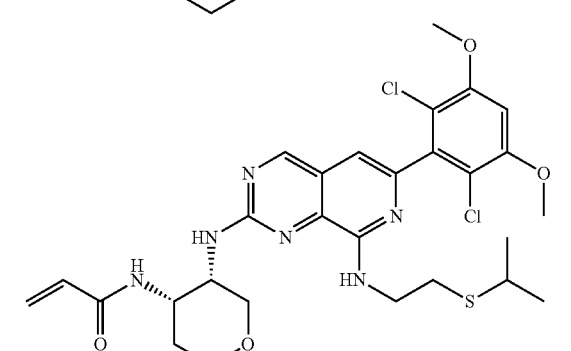
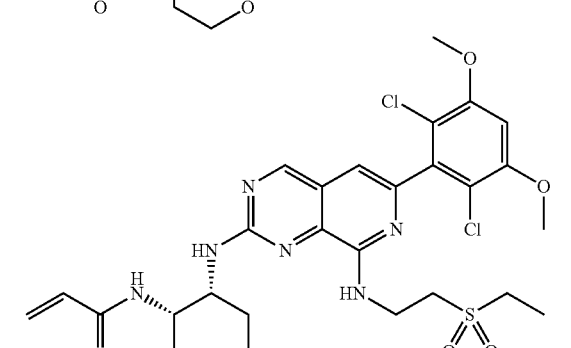
1020
-continued
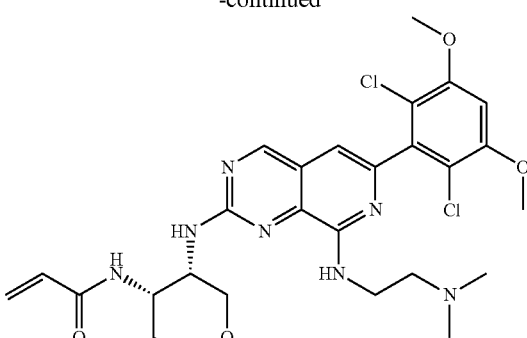
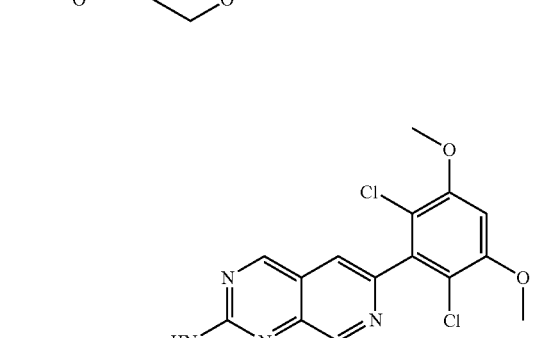
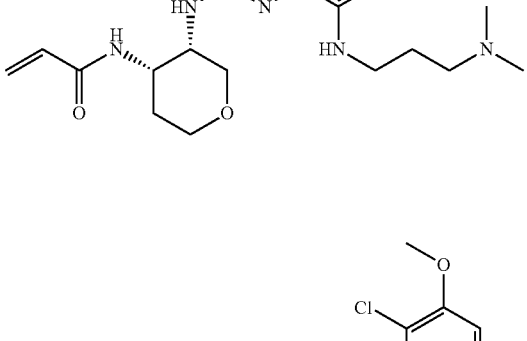
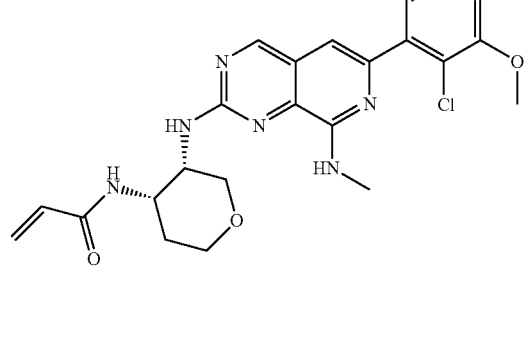
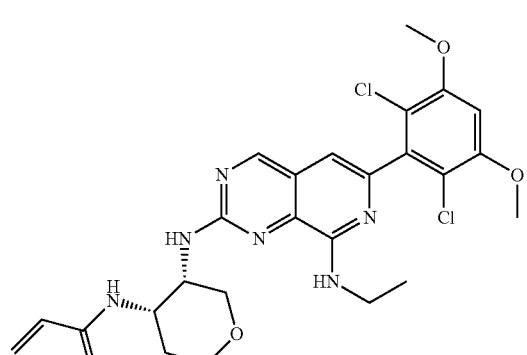

1021
-continued
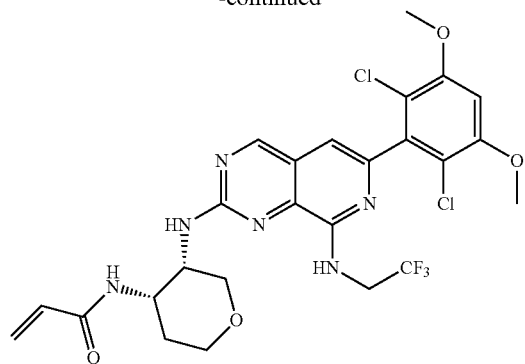
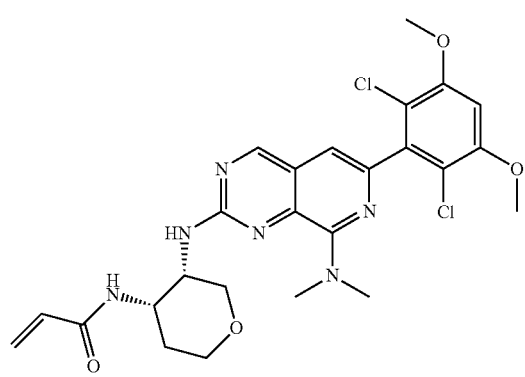
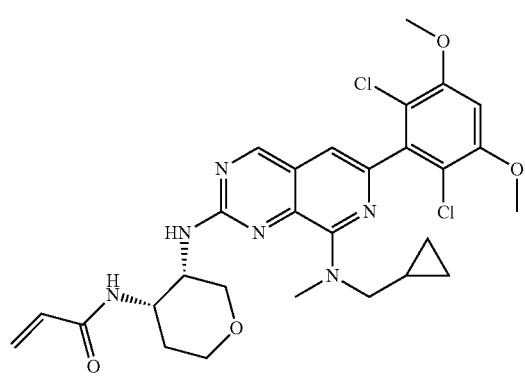
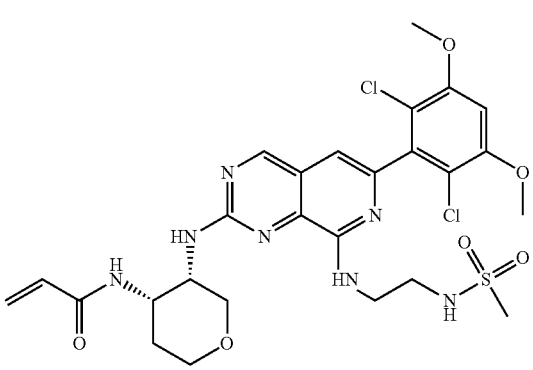
1022
-continued
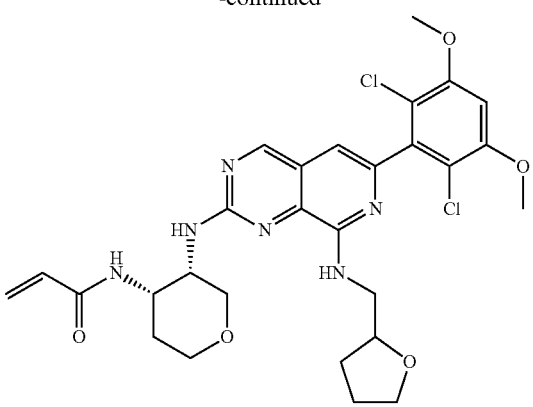
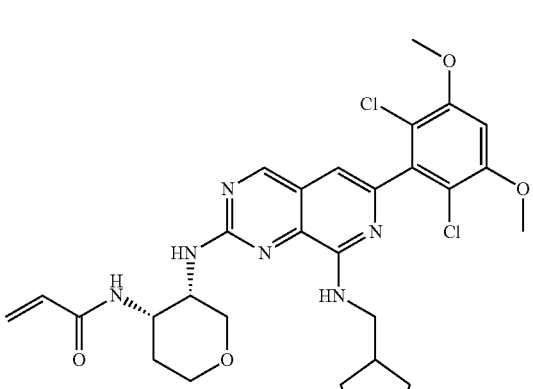
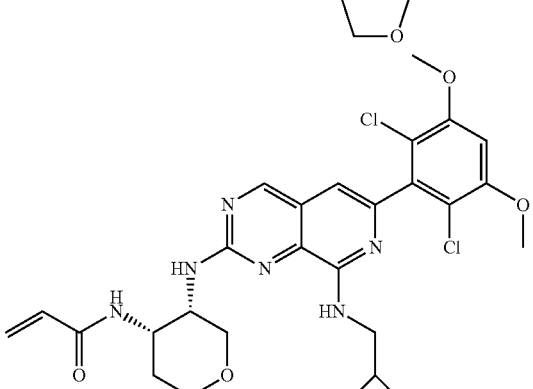
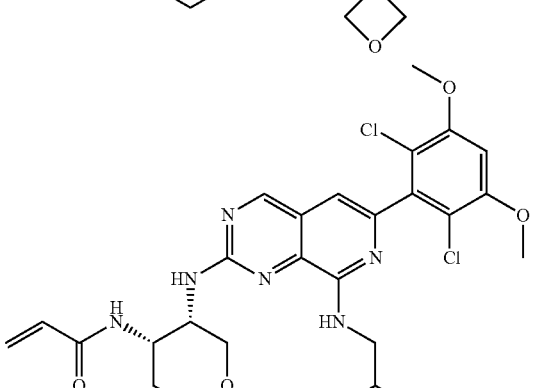

1023
-continued
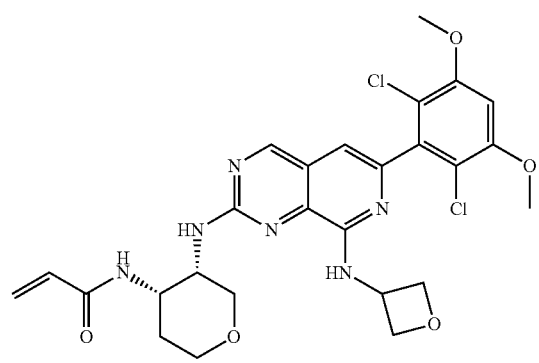
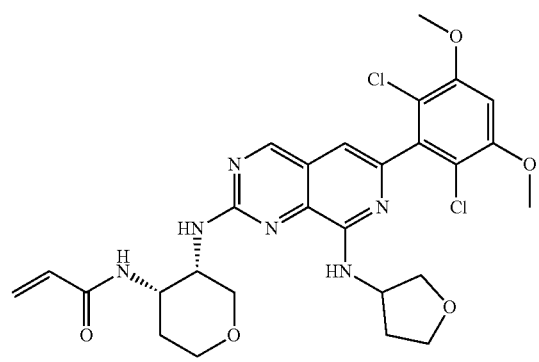
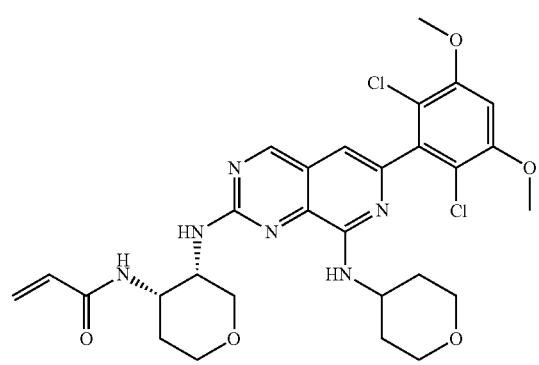
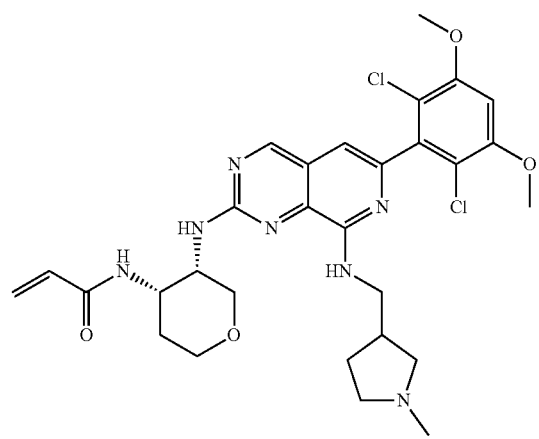
1024
-continued
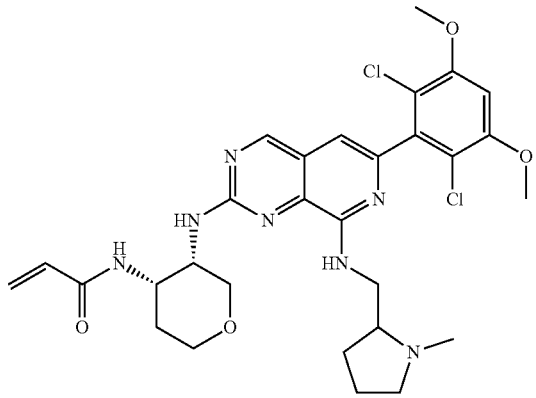
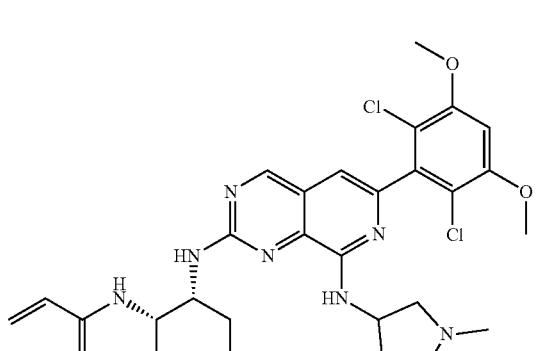
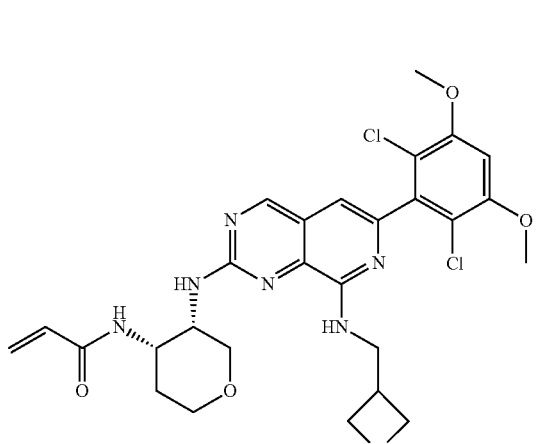
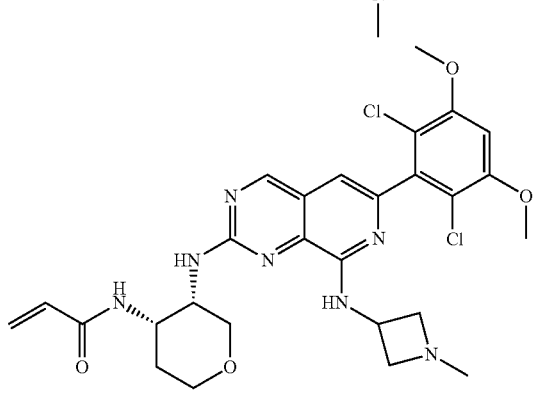

1025
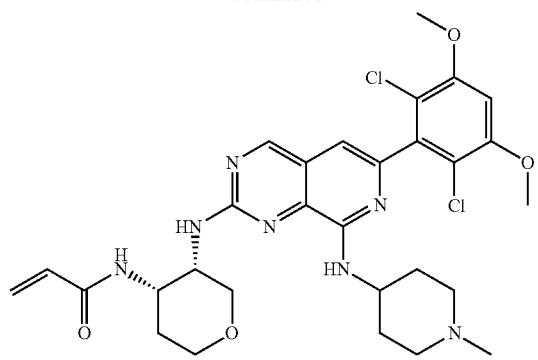
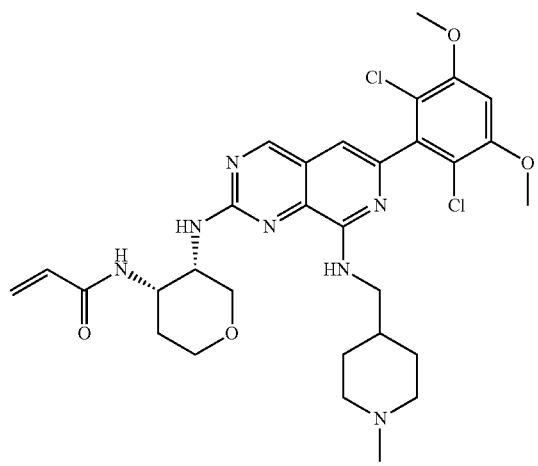
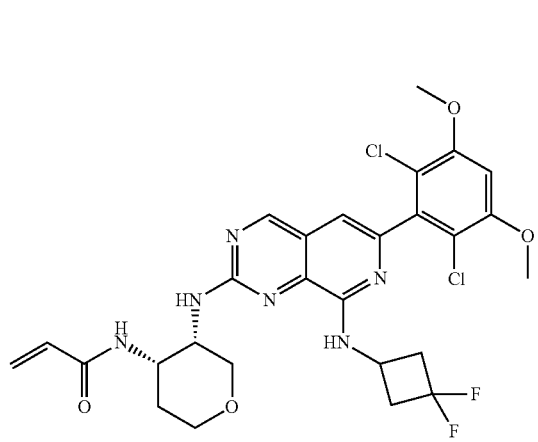
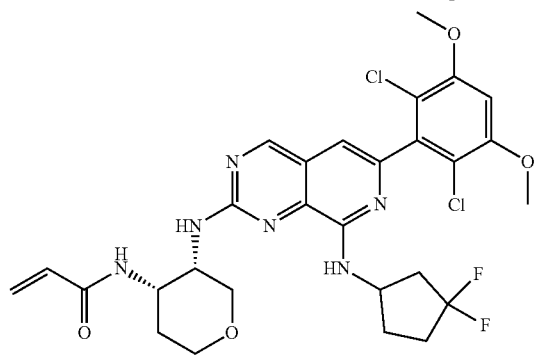
1026
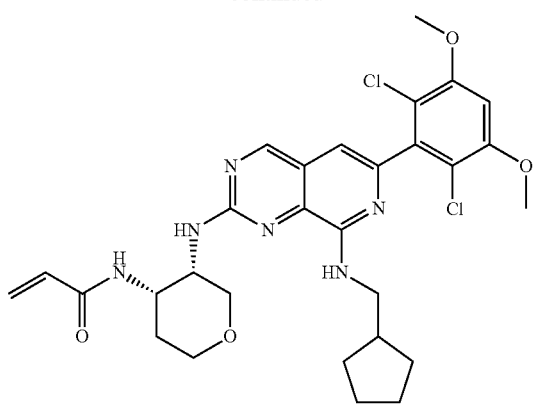
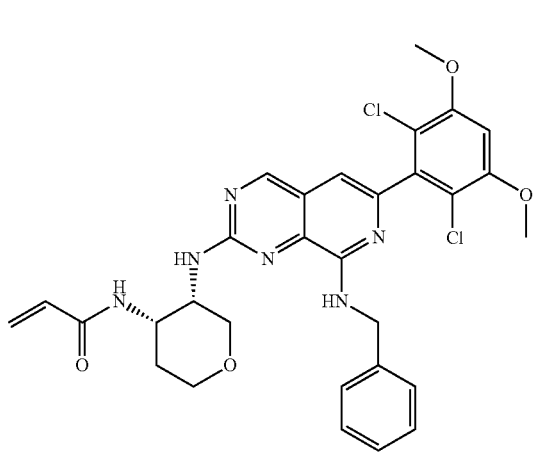
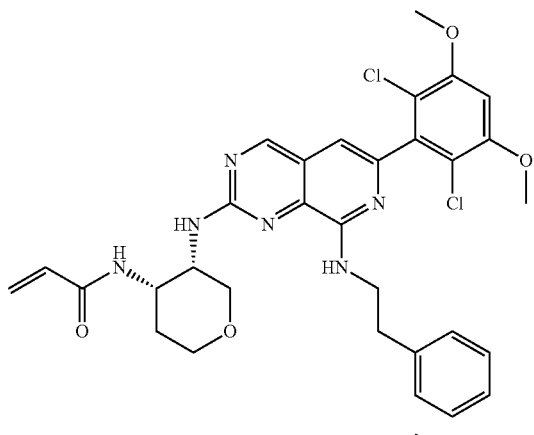
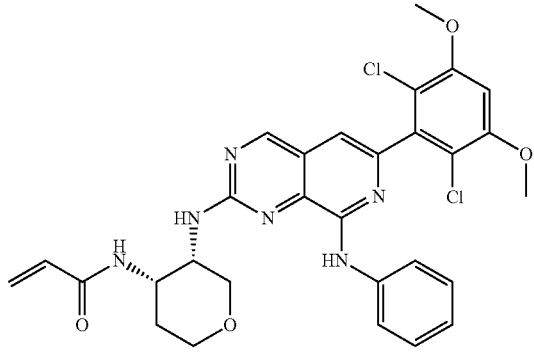

1027
-continued
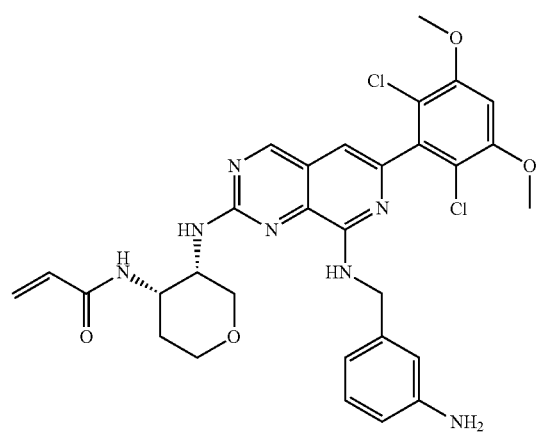
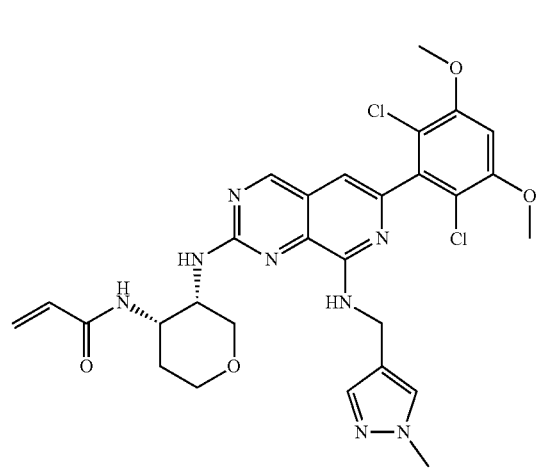
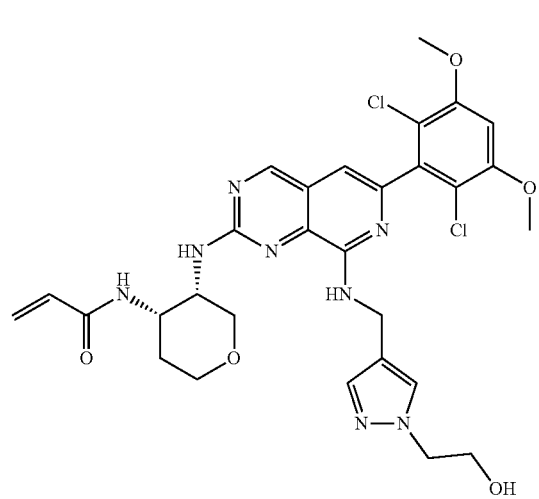
1028
-continued
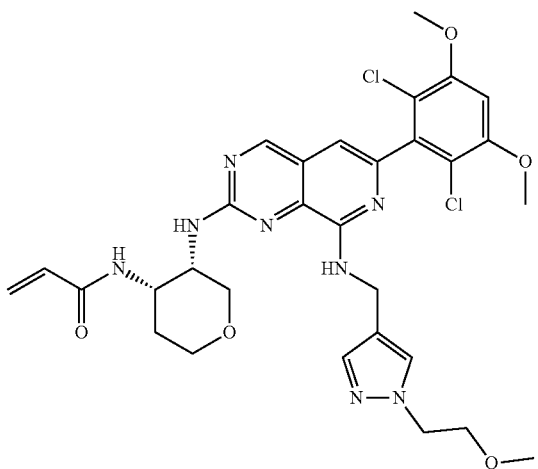
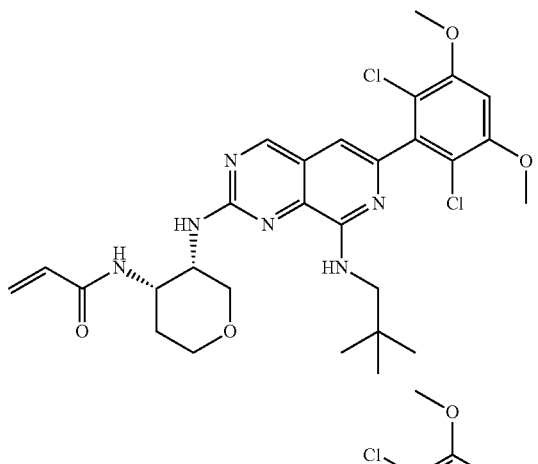
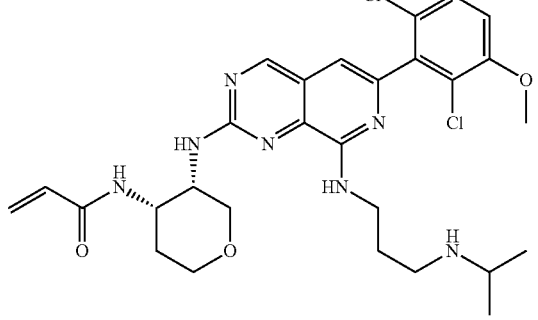
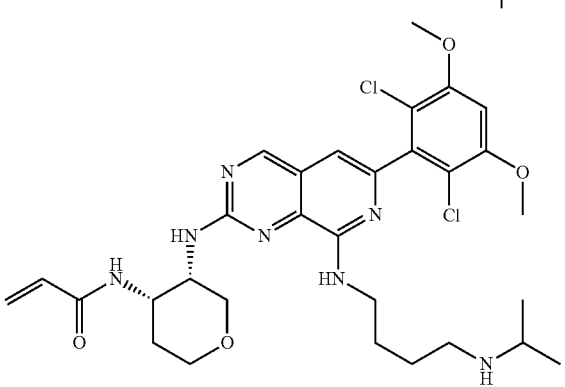

1029
-continued
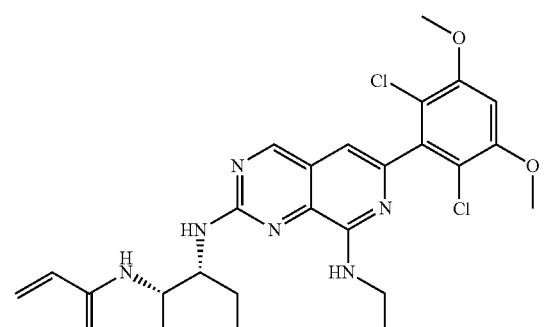
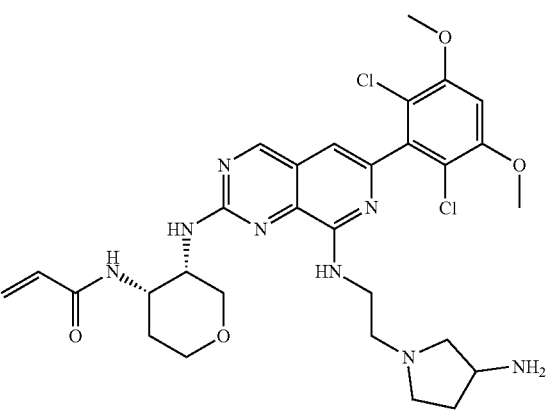
1030
-continued
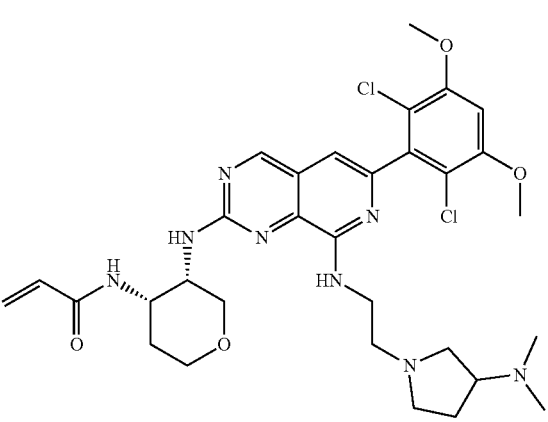
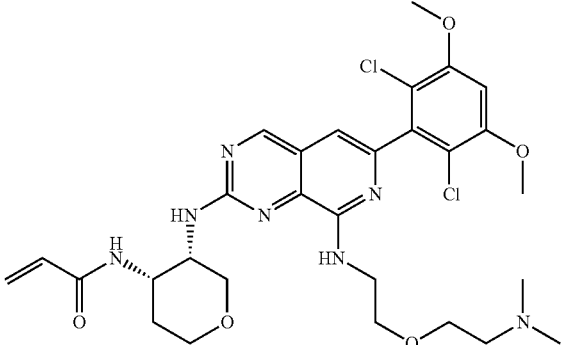
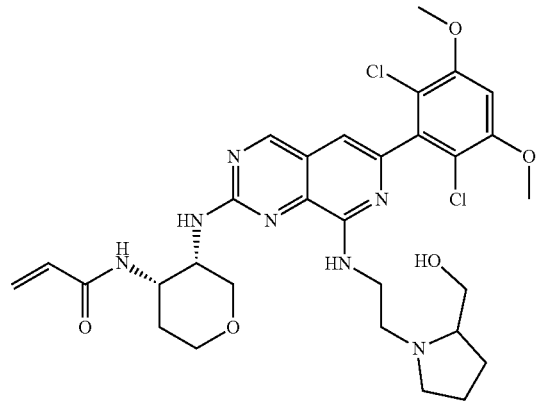

1031
-continued
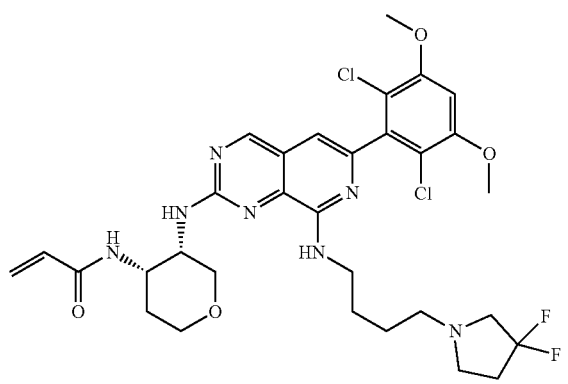
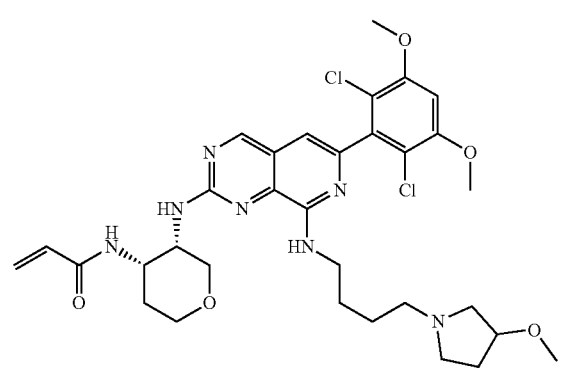
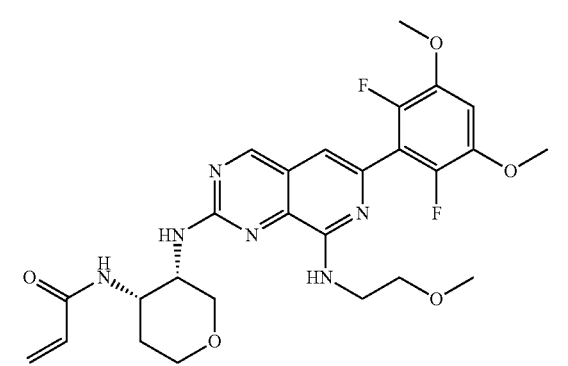
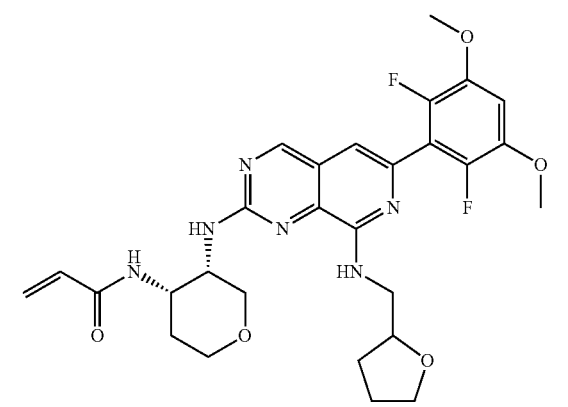
1032
-continued
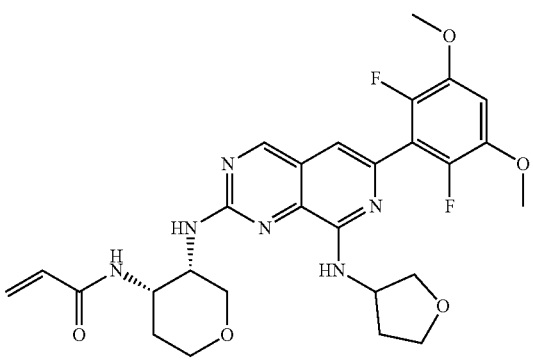
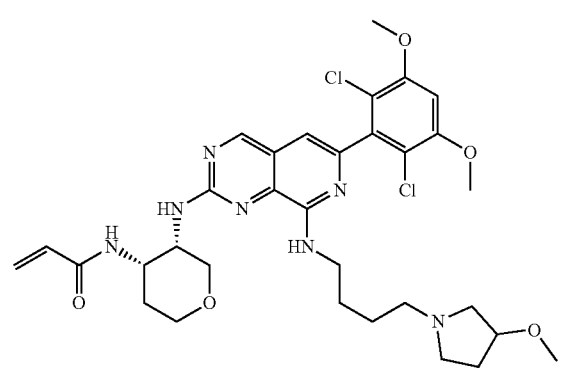
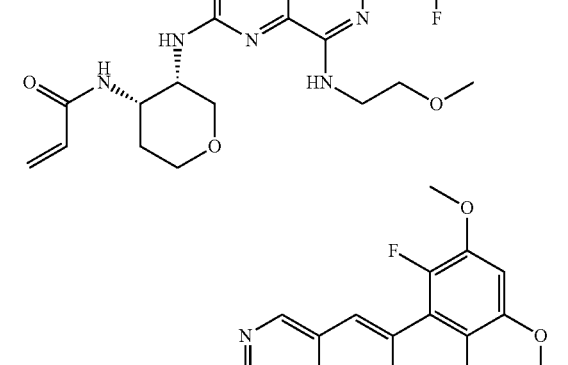
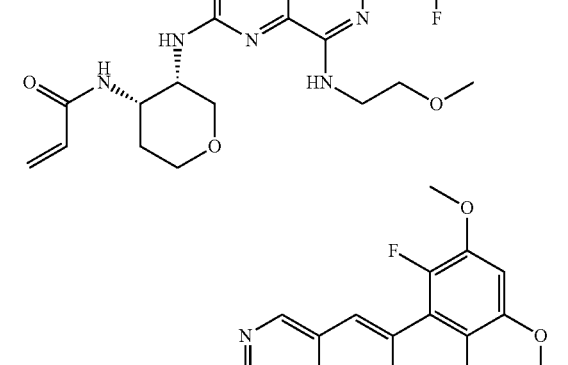
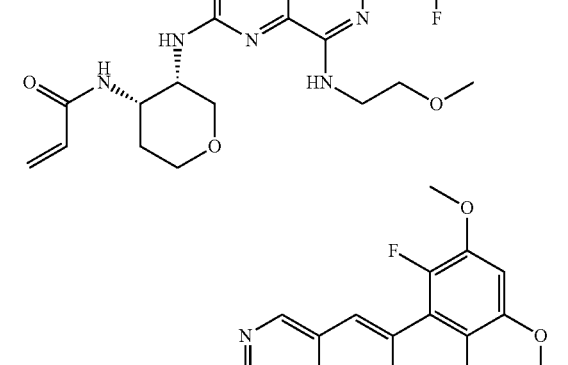

1033
-continued
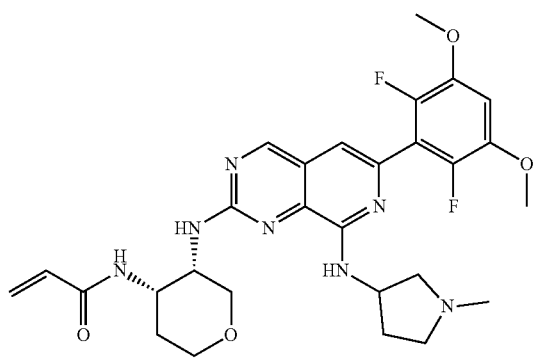
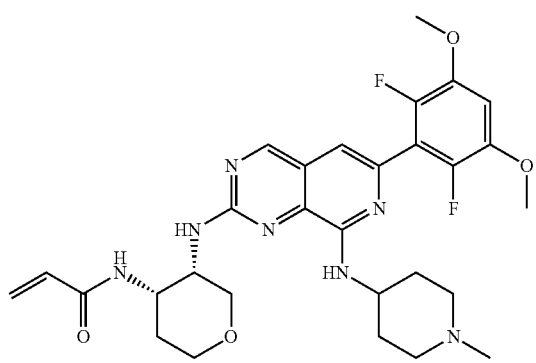
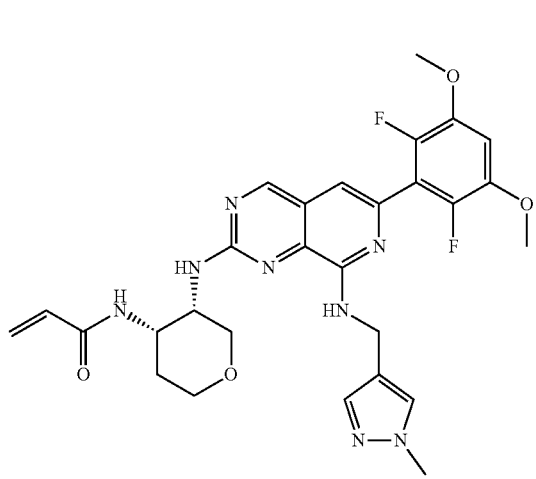
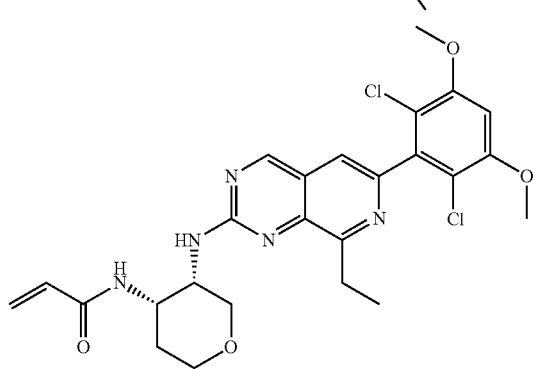
1034
-continued
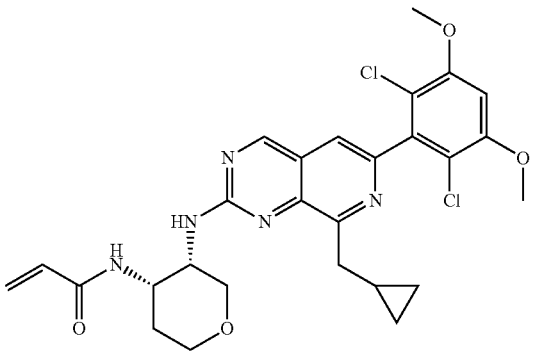
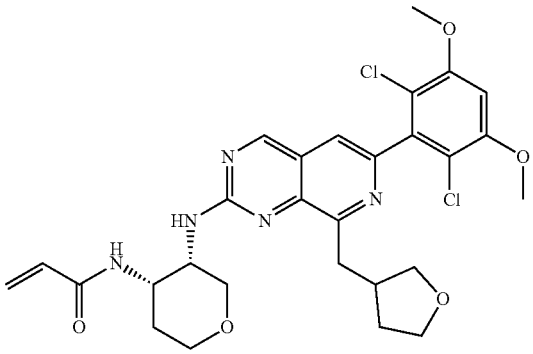
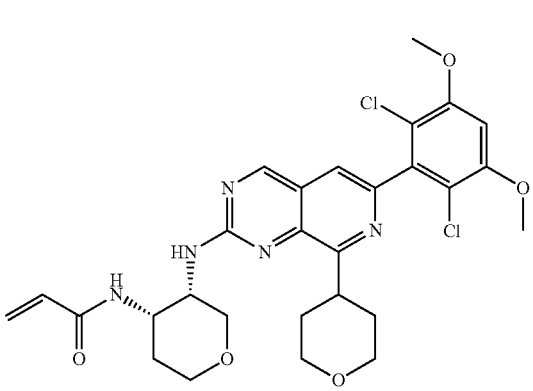
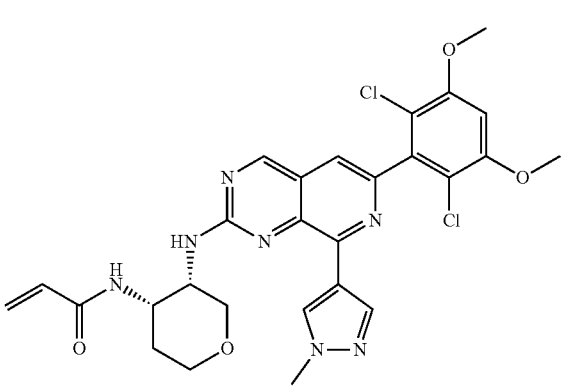

1035
-continued
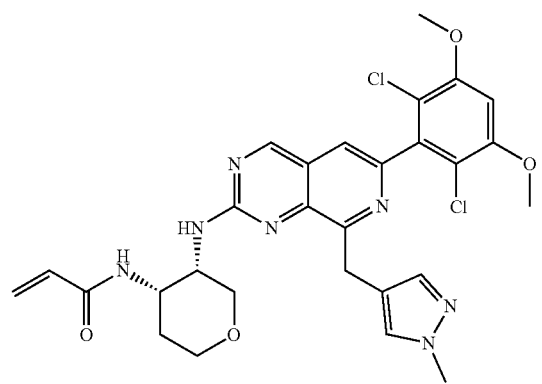
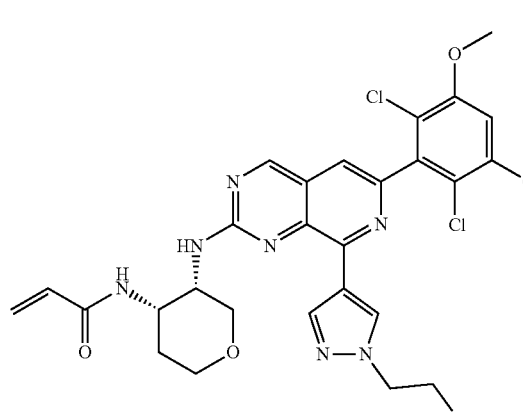
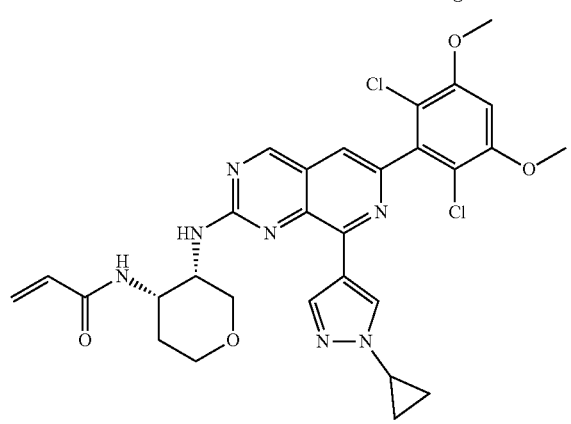
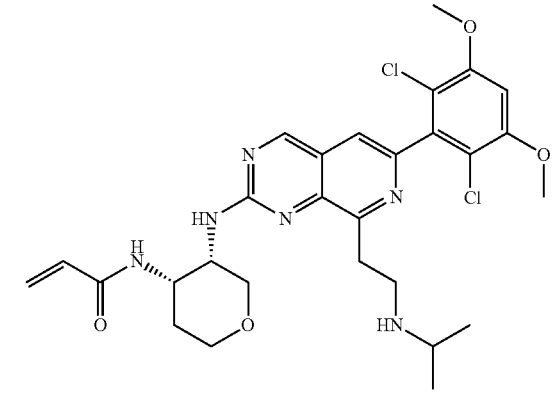
1036
-continued
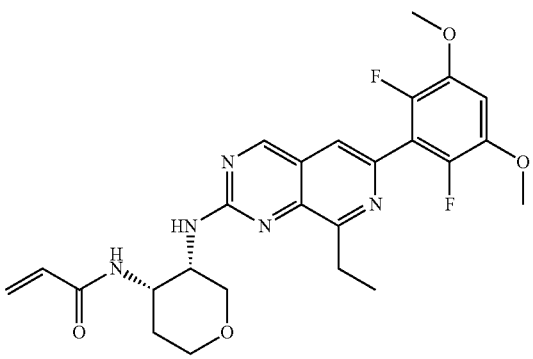
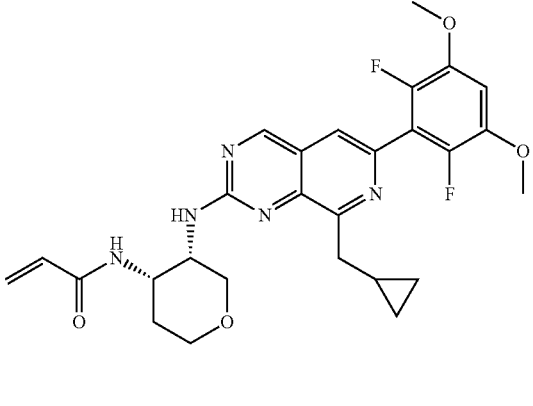
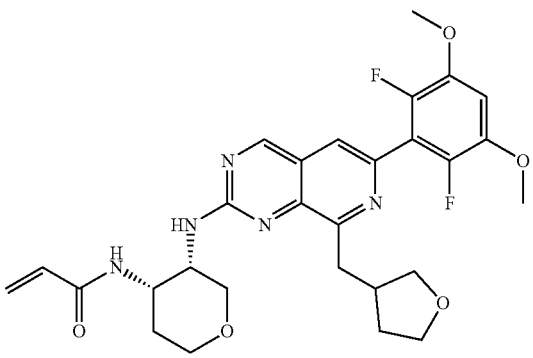
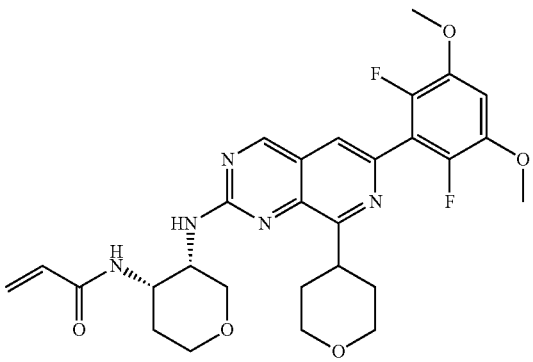

1037
-continued
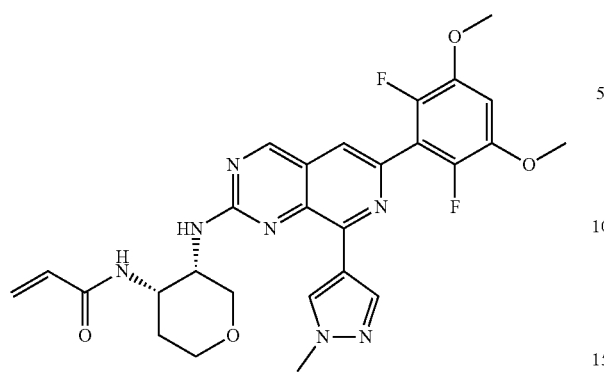
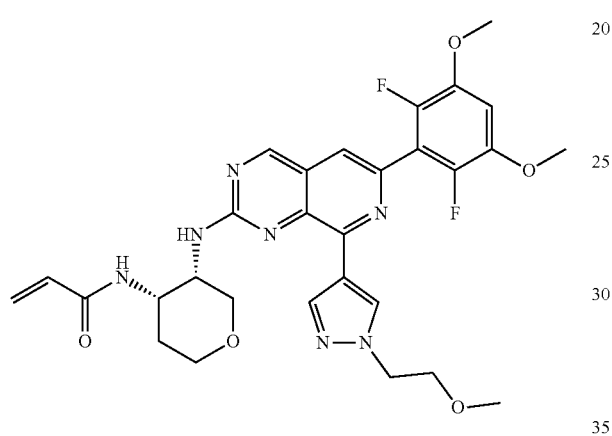
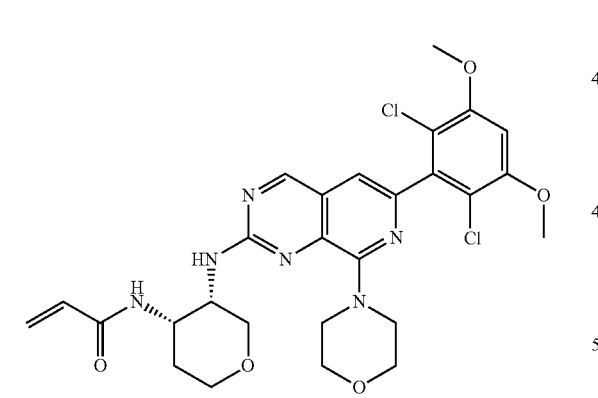
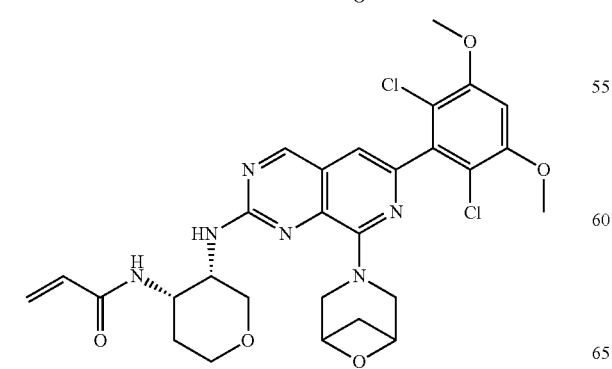
1038
-continued
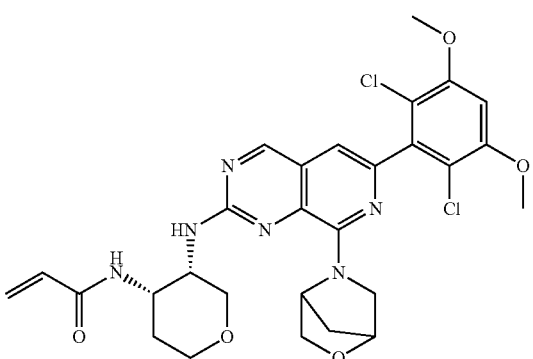
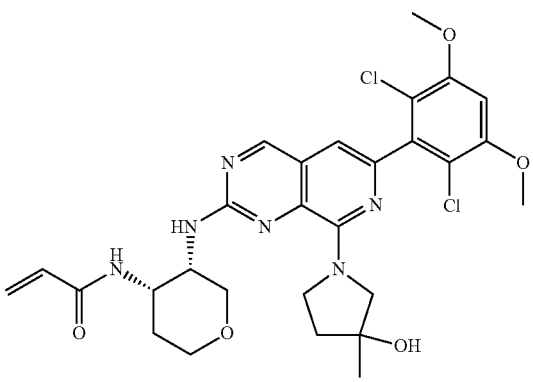
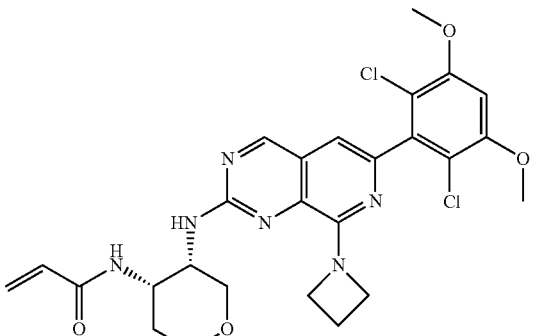
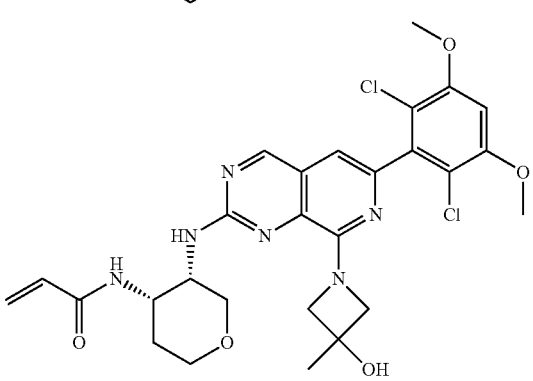

1039
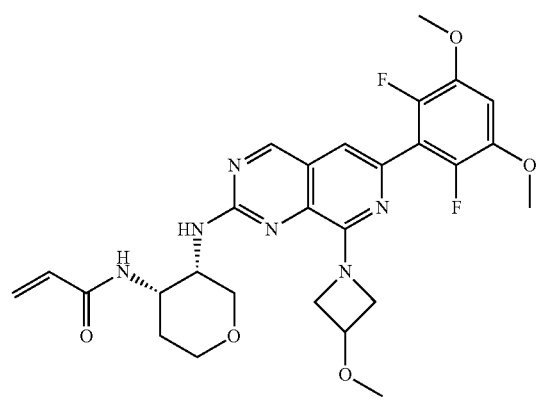
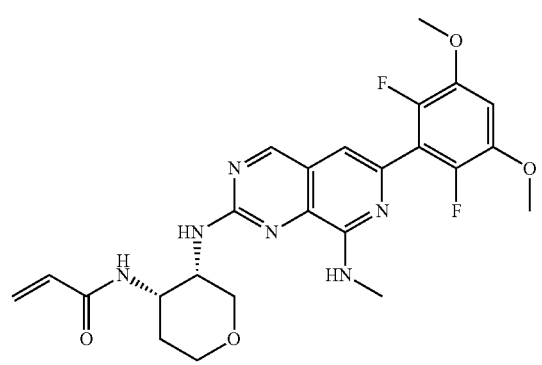
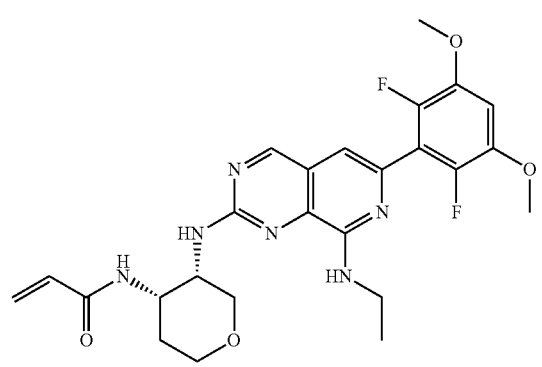
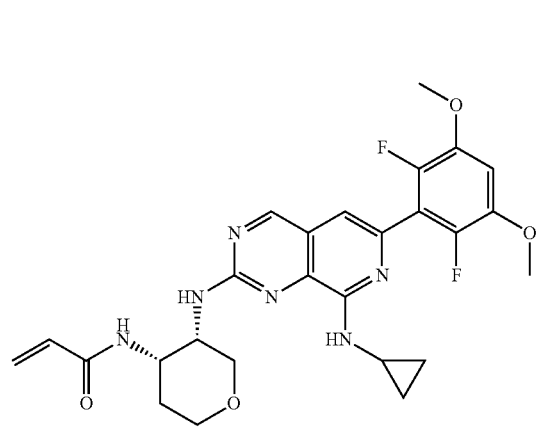
1040
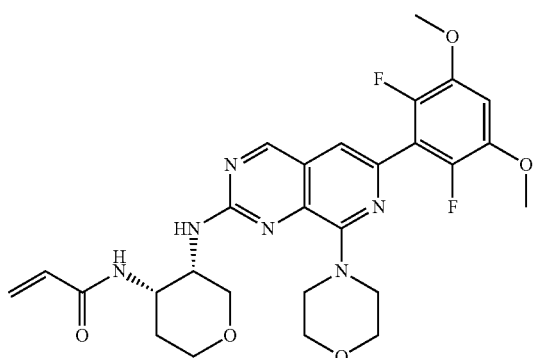
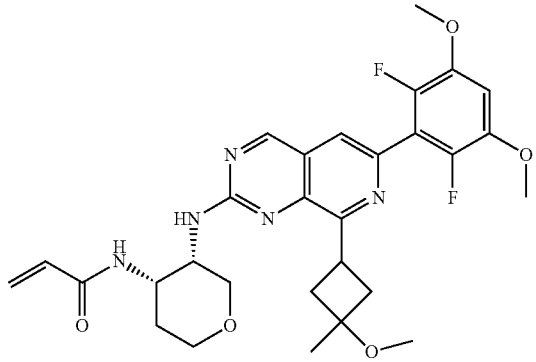
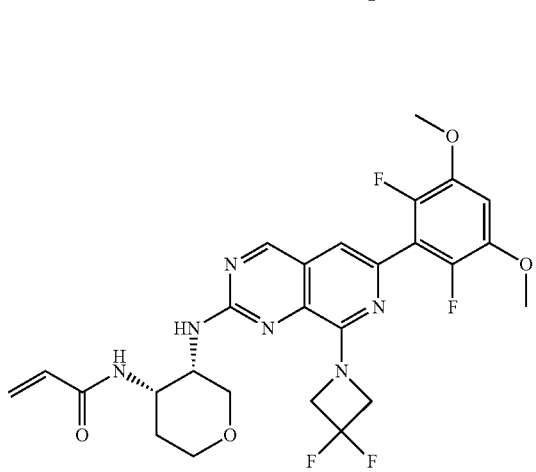
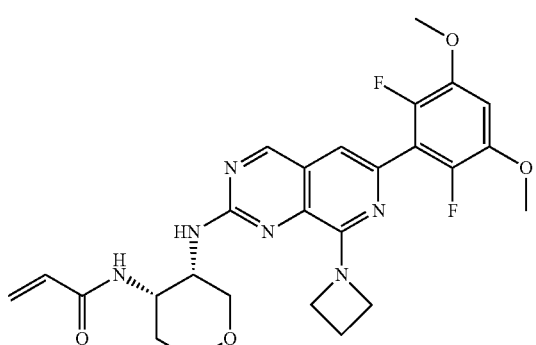

-continued
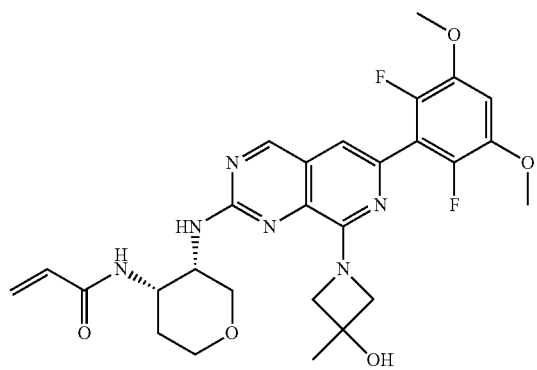
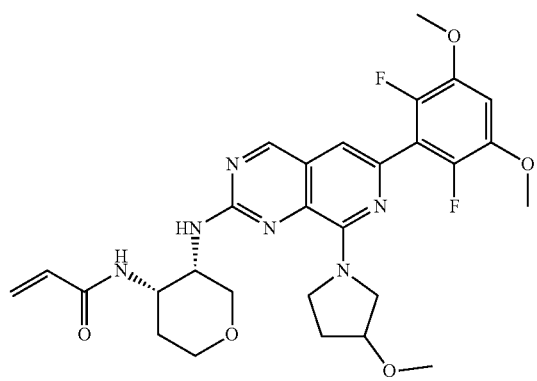
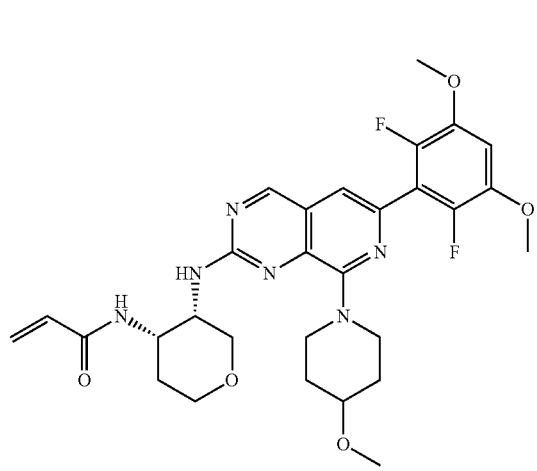
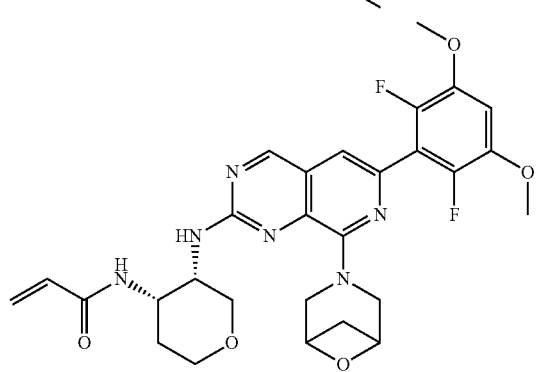
-continued
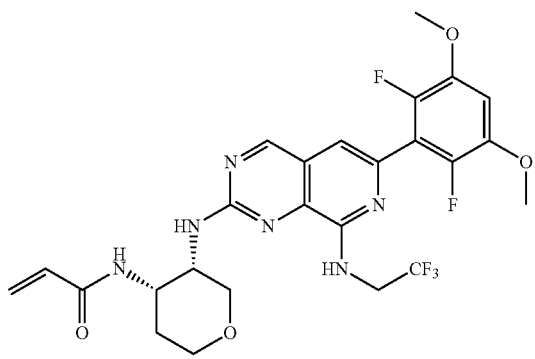
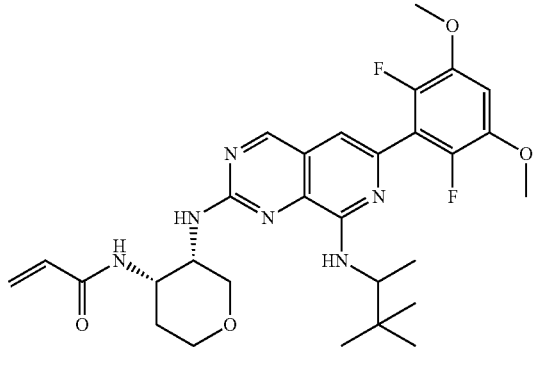
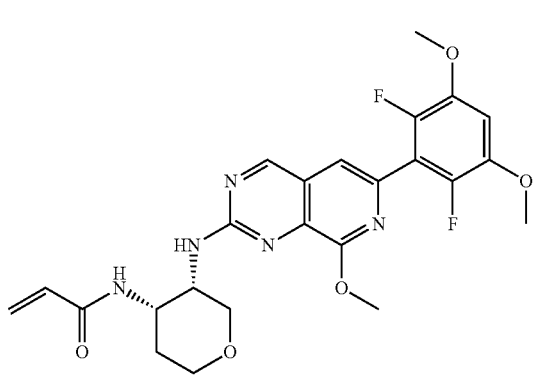
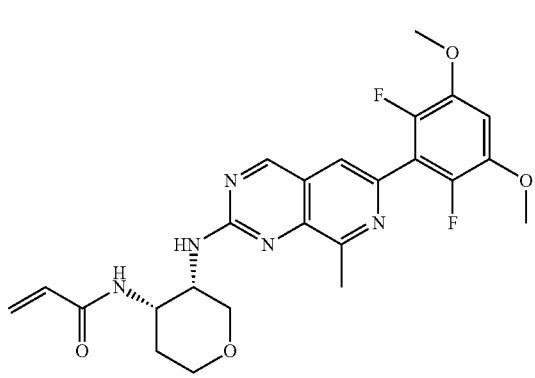

1043
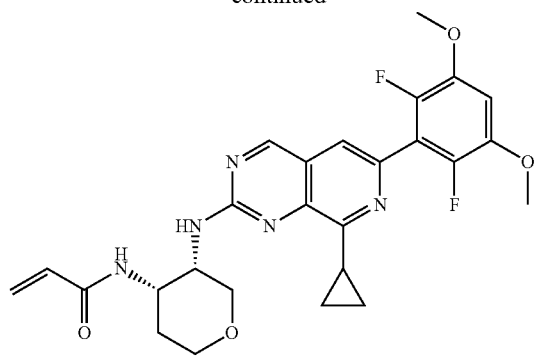
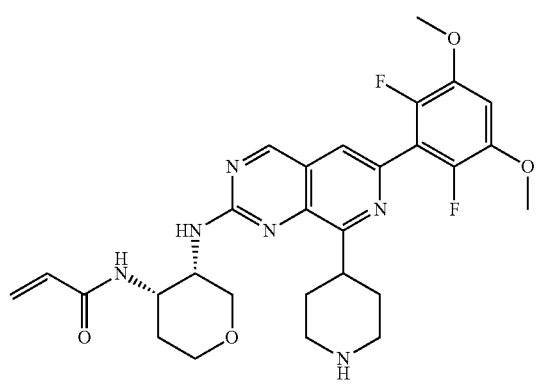
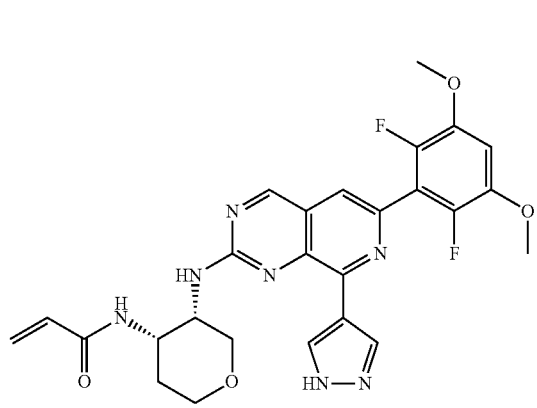
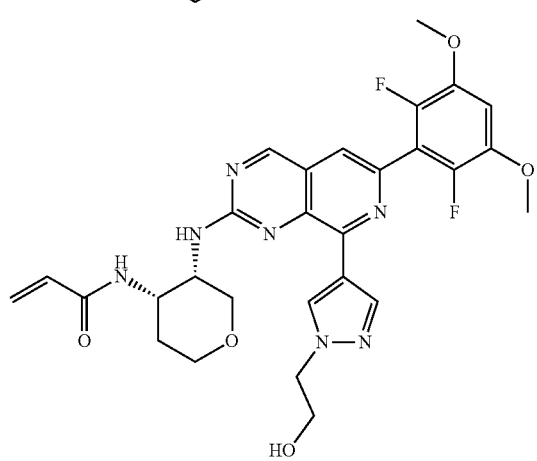
1044
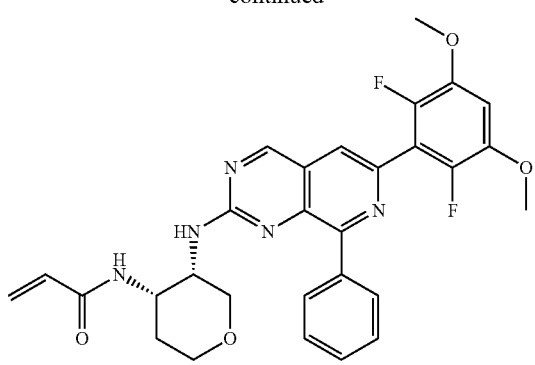
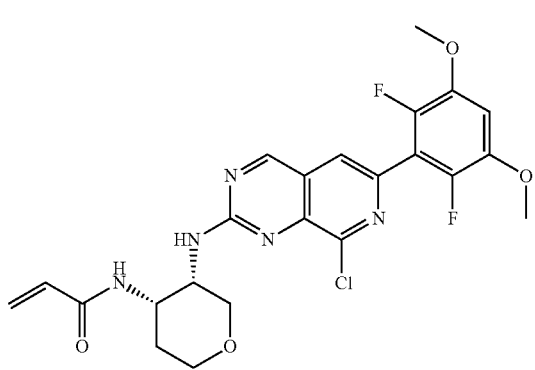
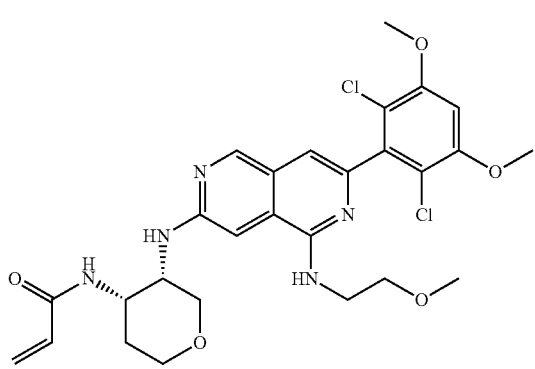
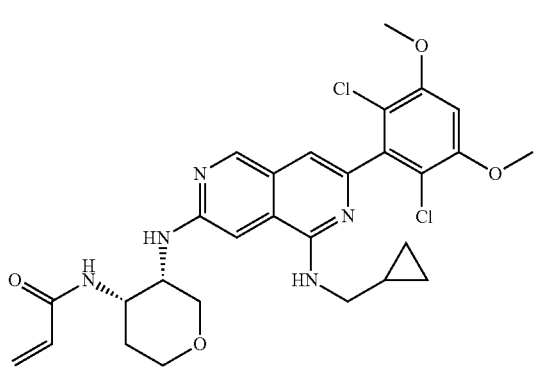

1045
-continued
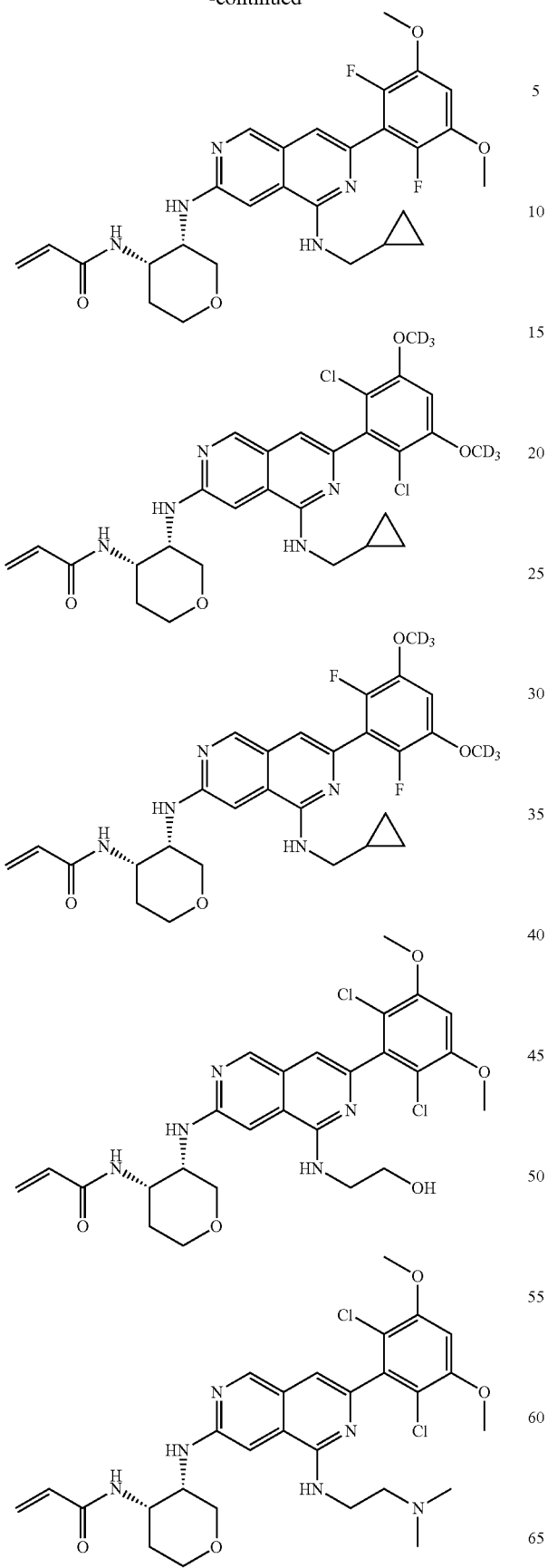
1046
-continued
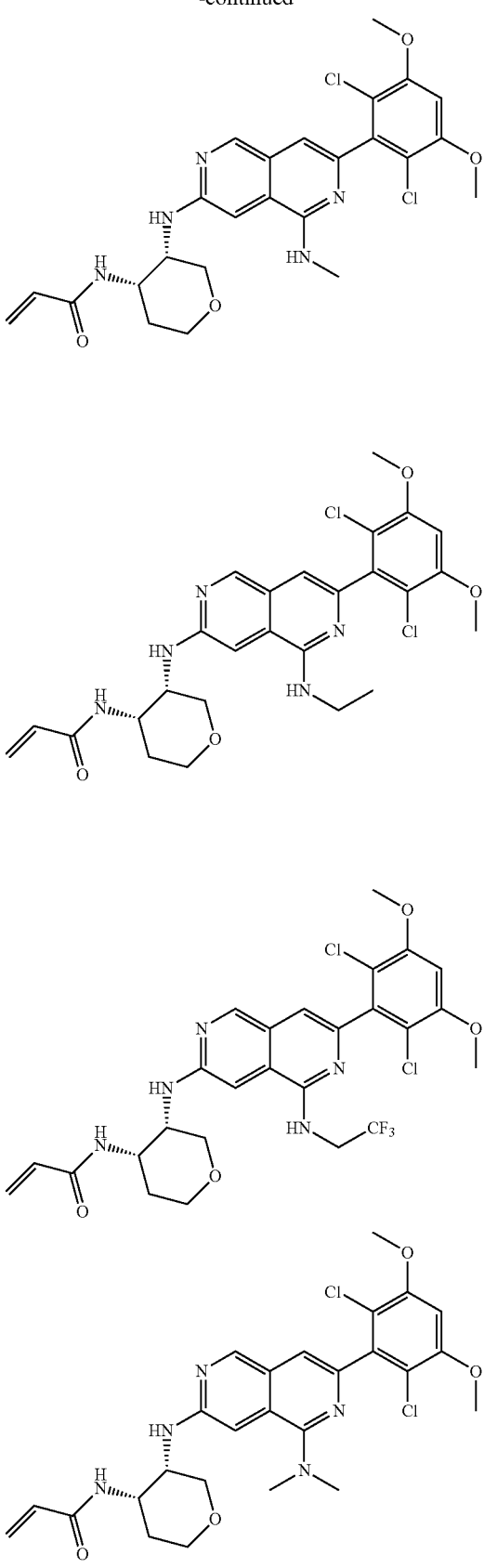

1047
-continued
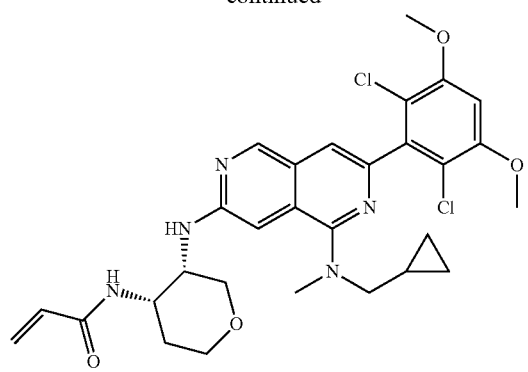
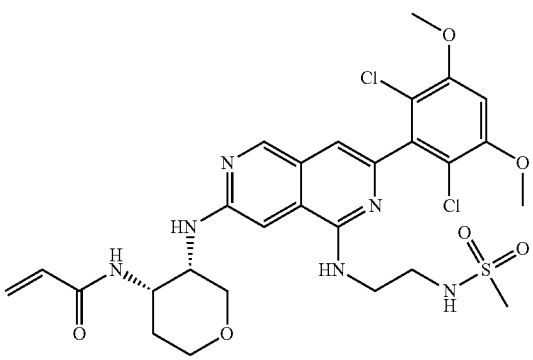
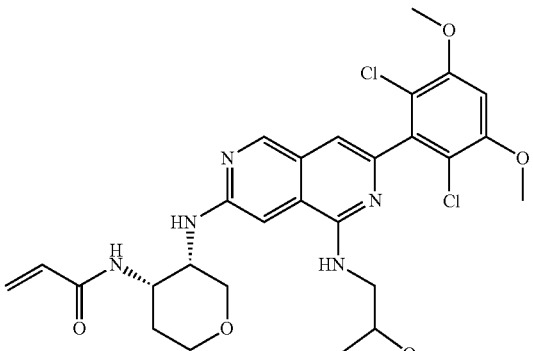
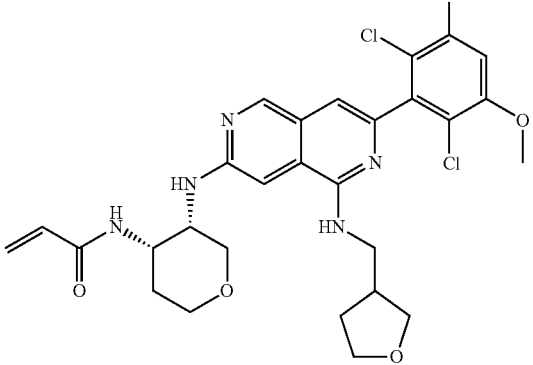
1048
-continued
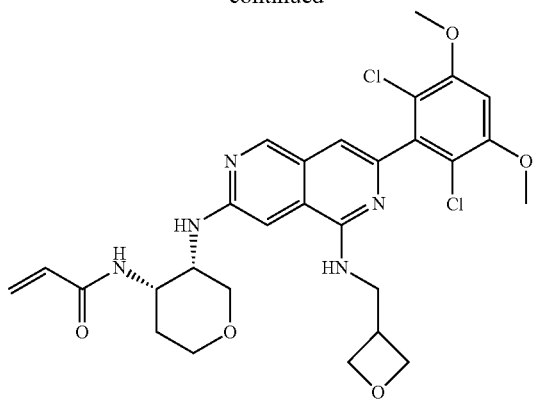
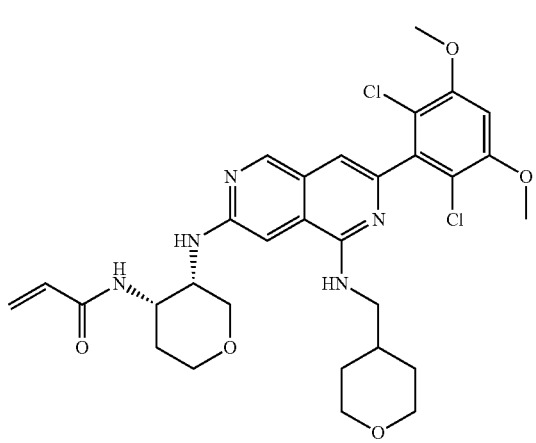
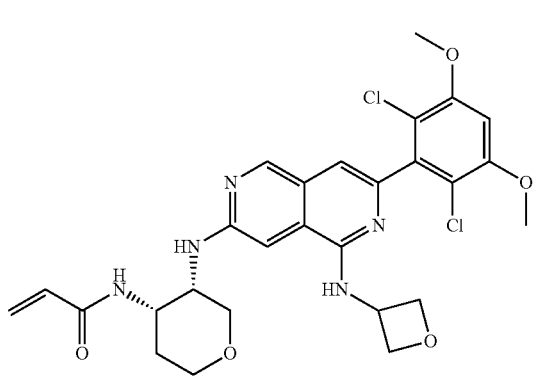
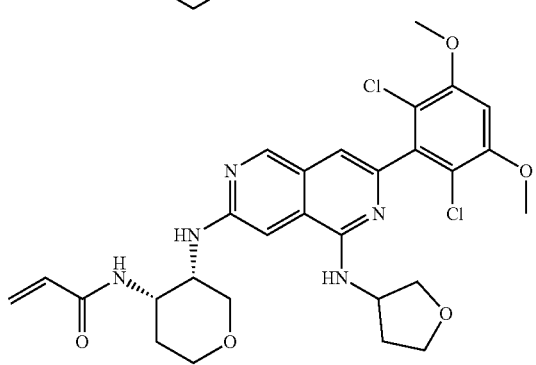

1049
-continued
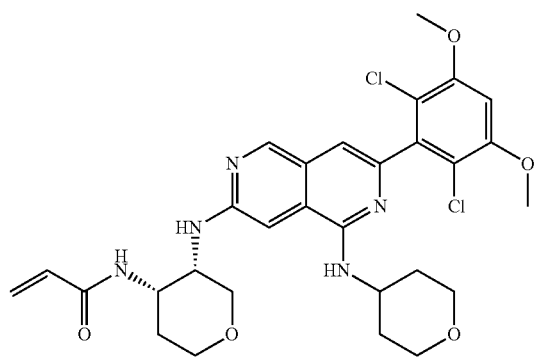
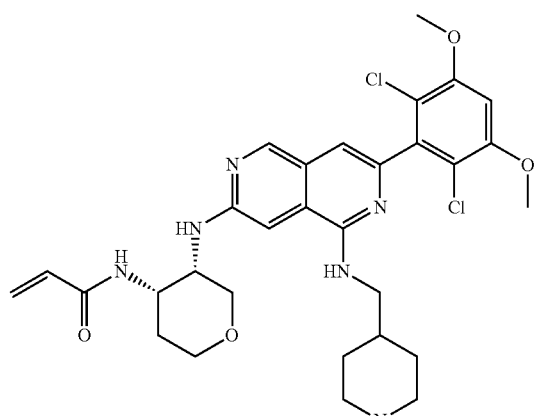
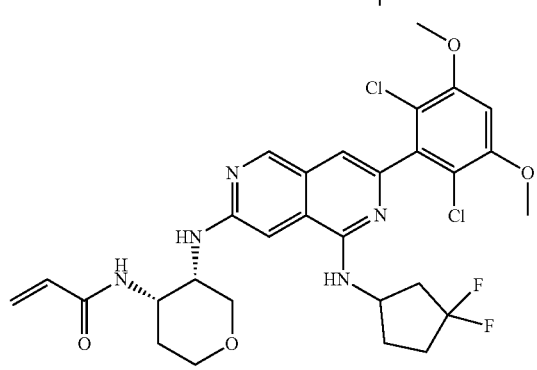
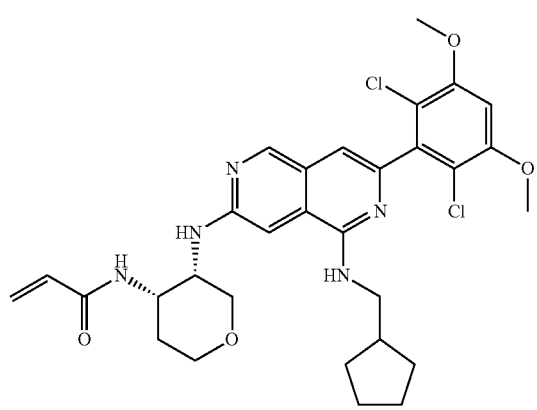
1050
-continued
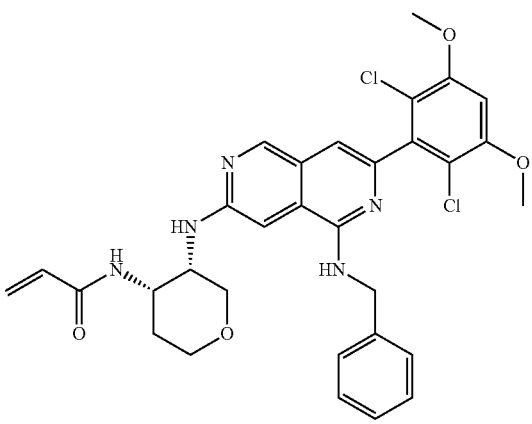
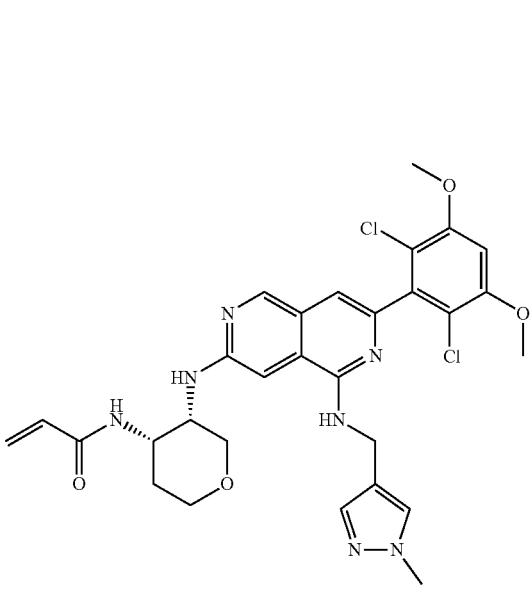
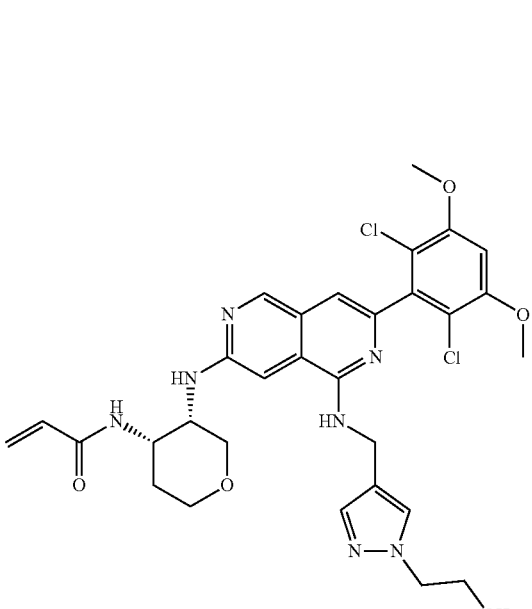

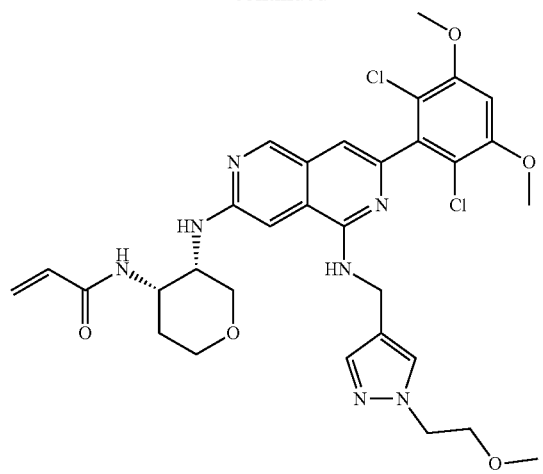
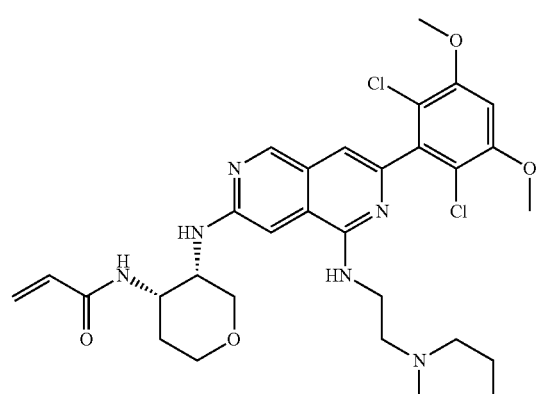
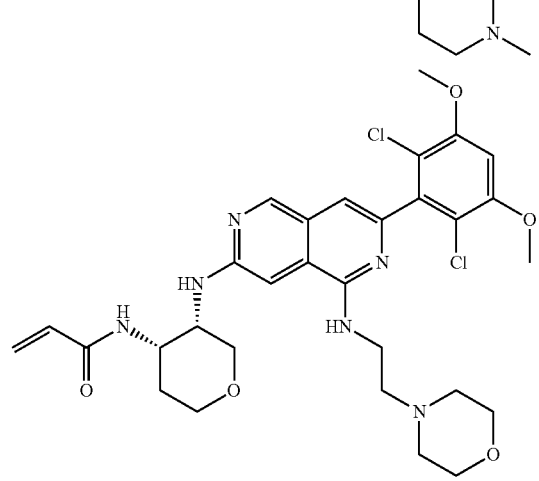
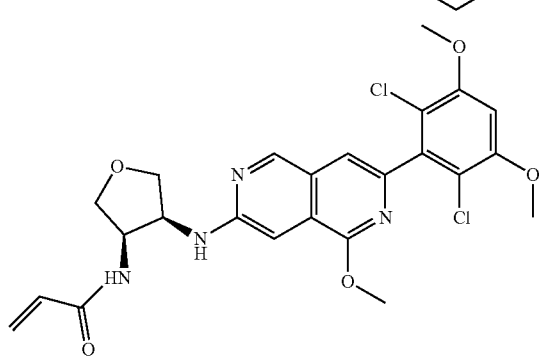
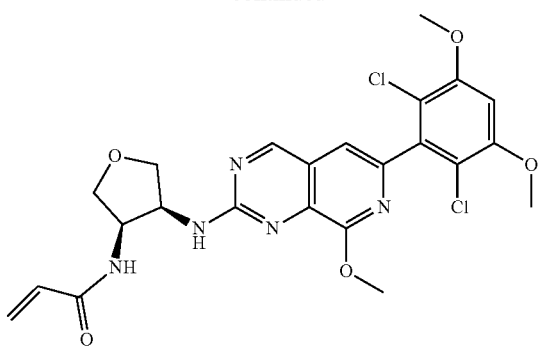
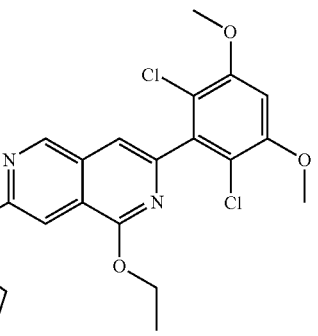
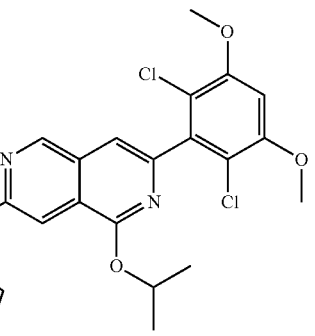
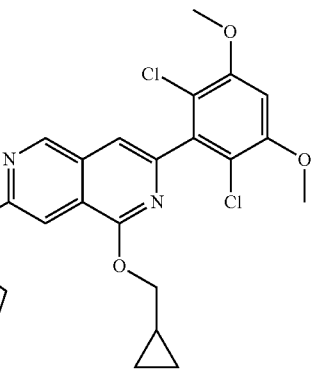

| 1053 | 1054 |
|---|---|
| -continued | -continued |
| 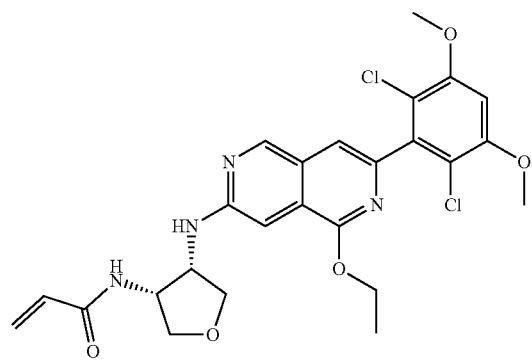 | 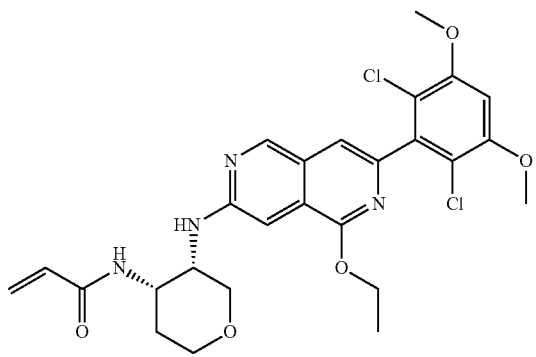 |
| 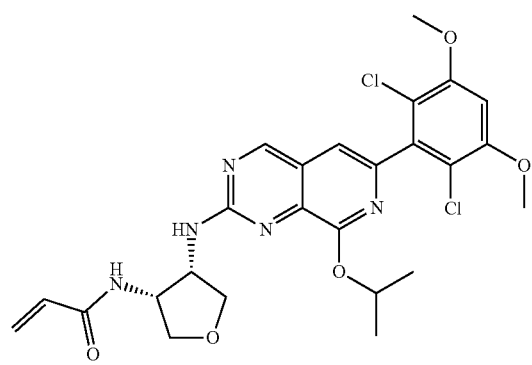 | 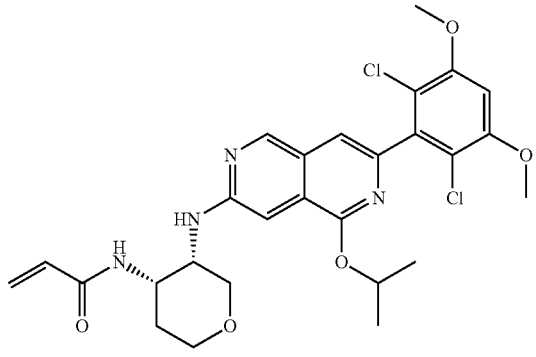 |
| 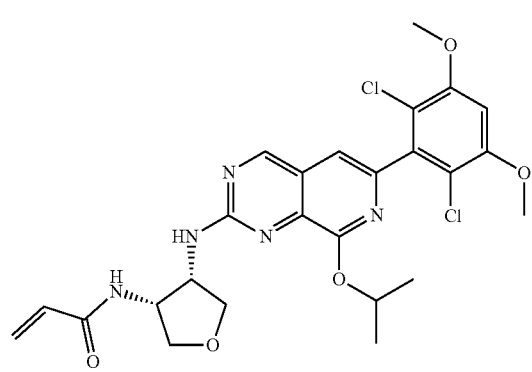 | 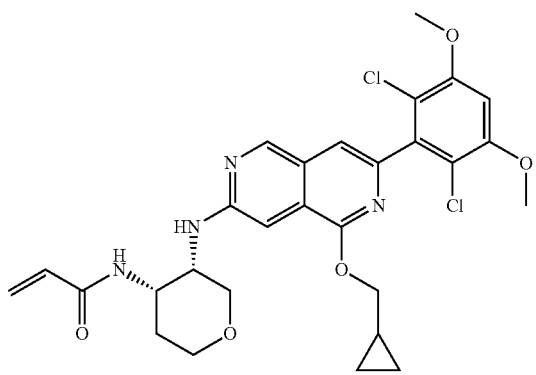 |
| 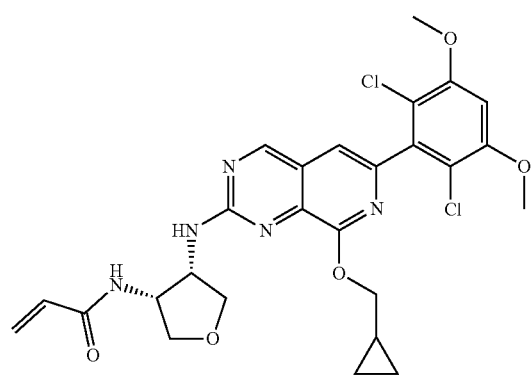 | 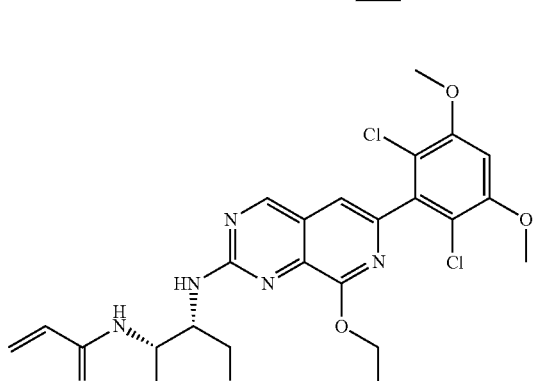 |

1055
-continued
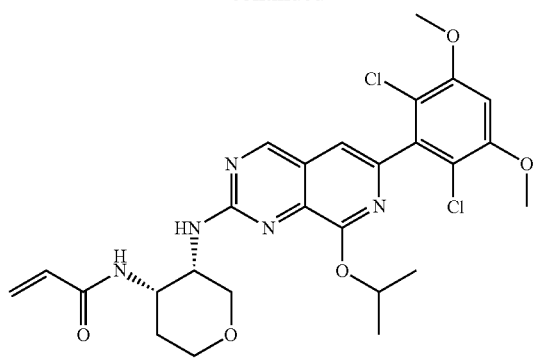
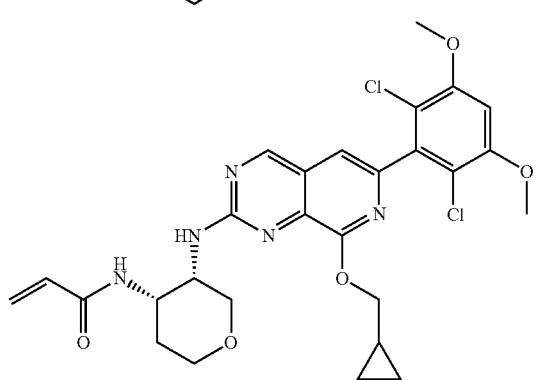
1056
-continued
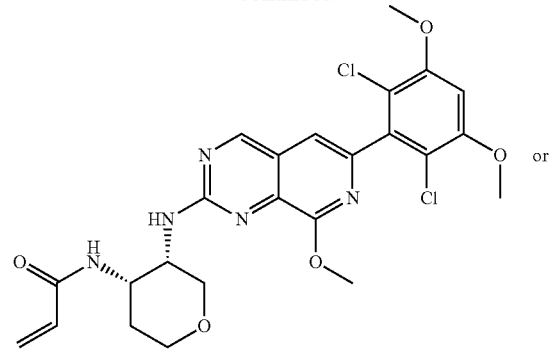 [SMILES: C=CC(=O)N[C@H]1CCOC[C@H]1Nc1cc2c(OC)nc(-c3c(Cl)c(OC)cc(OC)c3Cl)cc2cn1]
or
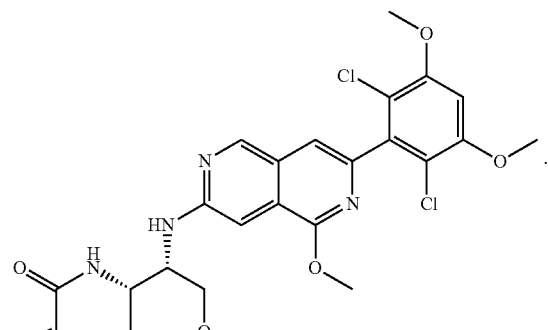
* * * * *